US009763922B2

(12) United States Patent
Adler et al.

(10) Patent No.: US 9,763,922 B2
(45) Date of Patent: Sep. 19, 2017

(54) THERAPEUTIC COMPOUNDS AND USES THEREOF

(71) Applicants: Genentech, Inc., South San Francisco, CA (US); Constellation Pharmaceuticals, Inc., Cambridge, MA (US)

(72) Inventors: Marc Adler, South San Francisco, CA (US); Brian K. Albrecht, Cambridge, MA (US); Sarah Bronner, South San Francisco, CA (US); Kevin X. Chen, Shanghai (CN); Alexandre Côté, Cambridge, MA (US); Terry Crawford, South San Francisco, CA (US); Patrick Cyr, South San Francisco, CA (US); Jackson Egen, South San Francisco, CA (US); Steven Kauder, South San Francisco, CA (US); Kwong Wah Lai, Shanghai (CN); Jiangpeng Liao, Shanghai (CN); Steven Magnuson, South San Francisco, CA (US); Jeremy Murray, South San Francisco, CA (US); Richard Pastor, South San Francisco, CA (US); F. Anthony Romero, South San Francisco, CA (US); Alexander M. Taylor, Cambridge, MA (US); Vickie Hsiao-Wei Tsui, South San Francisco, CA (US); Fei Wang, Shanghai (CN); Bing-Yan Zhu, South San Francisco, CA (US)

(73) Assignees: GENENTECH, INC., South San Francisco, CA (US); CONSTELLATION PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 14/952,821

(22) Filed: Nov. 25, 2015

(65) Prior Publication Data
US 2016/0158207 A1    Jun. 9, 2016

(30) Foreign Application Priority Data

Nov. 27, 2014   (WO) ................ PCT/CN2014/092380
Oct. 27, 2015   (WO) ................ PCT/CN2015/092965

(51) Int. Cl.
*A61K 31/437*     (2006.01)
*A61K 31/4375*    (2006.01)
(Continued)

(52) U.S. Cl.
CPC ........ *A61K 31/437* (2013.01); *A61K 31/4375* (2013.01); *A61K 31/4709* (2013.01);
(Continued)

(58) Field of Classification Search
None
See application file for complete search history.

(56) References Cited

U.S. PATENT DOCUMENTS

2015/0366939 A1* 12/2015 Pendurthi ............ A61K 48/005
424/85.5

FOREIGN PATENT DOCUMENTS

CN          101812063 A        8/2010
EP          2239264 A1        10/2010
(Continued)

OTHER PUBLICATIONS

Filippakopoulos, et al., "Selective inhibition of BET bromodomain", Nature, vol. 468, No. 7327, pp. 1067-1073, XP055104608, (2010).

(Continued)

*Primary Examiner* — Samantha Shterengarts
(74) *Attorney, Agent, or Firm* — Viksnins Harris Padys Maien LLP

(57) ABSTRACT

The present invention relates to compounds of formula (I) or formula (II):

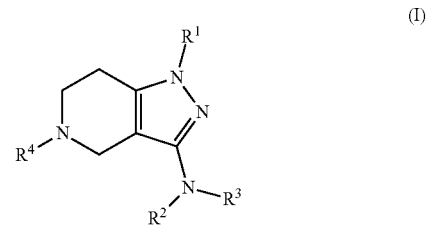

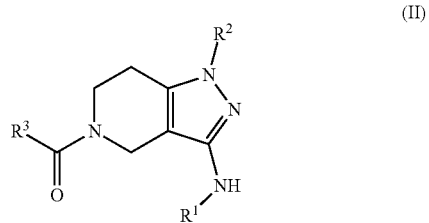

and to salts thereof, wherein $R^1$-$R^4$ of formula (I) and $R^1$-$R^3$ of formula (II) have any of the values defined herein, and compositions and uses thereof. The compounds are useful as inhibitors of CBP and/or EP300. Also included are pharmaceutical compositions comprising a compound of formula (I) of formula (II) or a pharmaceutically acceptable salt thereof, and methods of using such compounds and salts in the treatment of various CBP and/or EP300-mediated disorders.

20 Claims, 14 Drawing Sheets

(51) Int. Cl.
| | |
|---|---|
| A61K 31/4709 | (2006.01) |
| A61K 31/4725 | (2006.01) |
| A61K 31/496 | (2006.01) |
| A61K 31/498 | (2006.01) |
| A61K 31/506 | (2006.01) |
| A61K 31/5377 | (2006.01) |
| A61K 31/538 | (2006.01) |
| A61K 31/5415 | (2006.01) |
| A61K 31/55 | (2006.01) |
| C07D 471/04 | (2006.01) |
| C07D 519/00 | (2006.01) |
| A61K 45/06 | (2006.01) |

(52) U.S. Cl.
CPC ........ *A61K 31/4725* (2013.01); *A61K 31/496* (2013.01); *A61K 31/498* (2013.01); *A61K 31/506* (2013.01); *A61K 31/538* (2013.01); *A61K 31/5377* (2013.01); *A61K 31/5415* (2013.01); *A61K 31/55* (2013.01); *A61K 45/06* (2013.01); *C07D 471/04* (2013.01); *C07D 519/00* (2013.01)

(56) References Cited

FOREIGN PATENT DOCUMENTS

| | | |
|---|---|---|
| WO | 2004013144 A1 | 2/2004 |
| WO | 2004014374 A1 | 2/2004 |
| WO | 2004080457 A1 | 9/2004 |
| WO | 2007068619 A1 | 6/2007 |
| WO | 2007099166 A1 | 9/2007 |
| WO | 2009138440 A1 | 11/2009 |
| WO | 2013097052 A1 | 7/2013 |
| WO | 2013148114 A1 | 10/2013 |

OTHER PUBLICATIONS

Hay, et al., "Discovery and Optimization of Small-Molecule Ligands for the CBP/p300 Bromodomain", Journal of the American Chemical Society, vol. 136, No. 26, pp. 9308-9319, XP055135823 (Jul. 2, 2014).

Jeanmougin, "The bromodomain revisited", Trends Biochem Sci 22(5), 151-153 (1997).

Muller, et al., "Bromodomains as therapeutic targets", Expert Rev Mol Med 13 (29), 1-21 (2011).

Patent Cooperation Treaty, International Searching Authority, Search Report and Written Opinion for PCT/US2015/062794, 18 pages, May 17, 2016.

Prinjha, et al., "Place your BETs: the therapeutic potential of bromodomains", Trends Pharm Sci 33(3), 146-153 (2012).

Struhl, "Histone acetylation and transcriptional regulatory mechanisms", Genes Dev 12 (5), 599-606 (1989).

Tamkun, et al., "brahma: a regulator of Drosophila homeotic genes structurally related to the yeast transcriptional activator SNF2/SWI2", Cell 68, 561-572 (1992).

* cited by examiner

Primary human fibroblasts in 384 well format

↓ O/N

SMI
8X dilutions, duplicate

↓ 1h

TGFβ

↓ O/N

Isolate RNA in 384 well format

↓

Fluidigm qPCR
192 sample x 24 assay

Figure 2A-E.
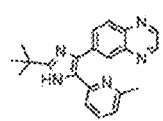
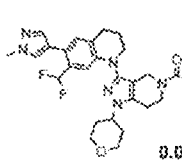
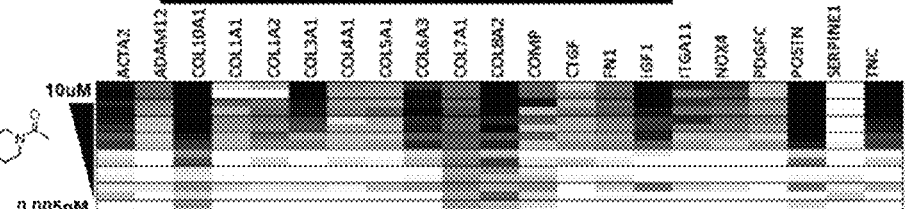
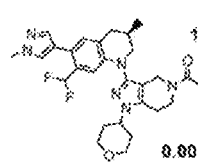
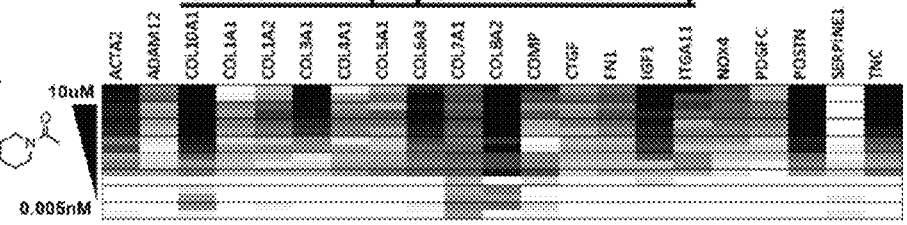
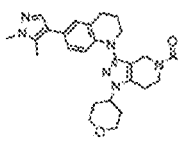
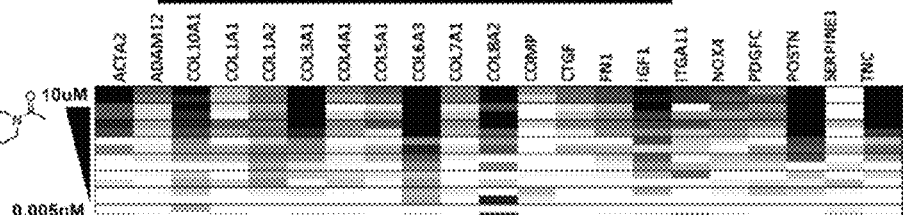
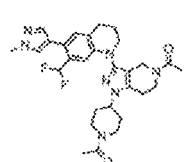

Figure 3A-B.
A
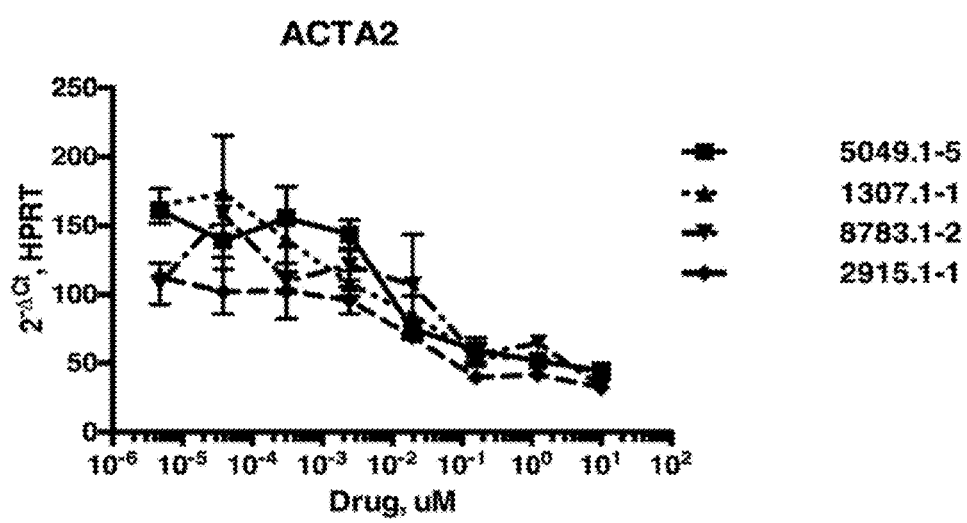
B
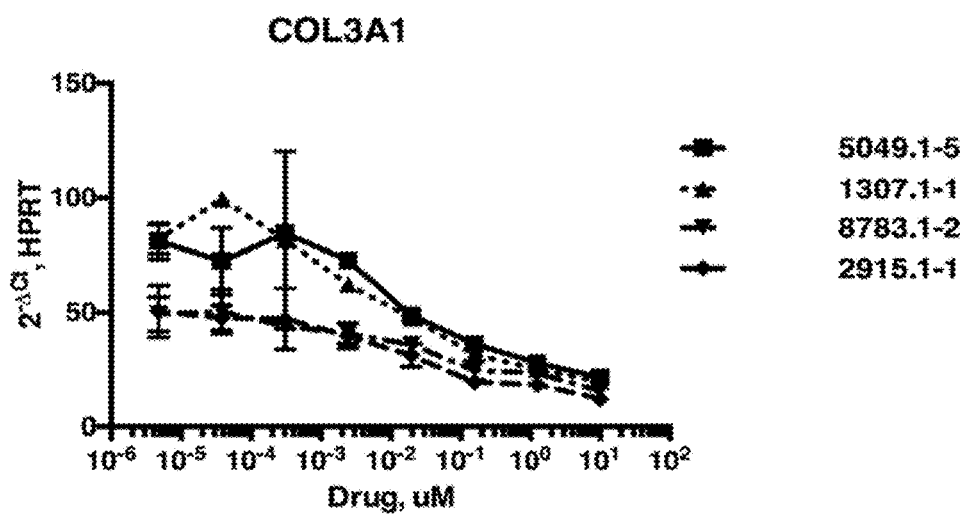

Figure 4A-E.
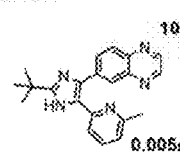
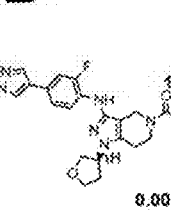
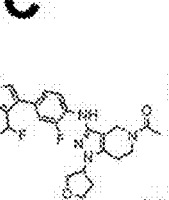
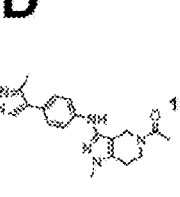
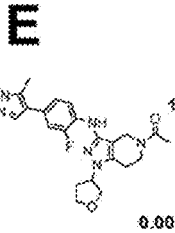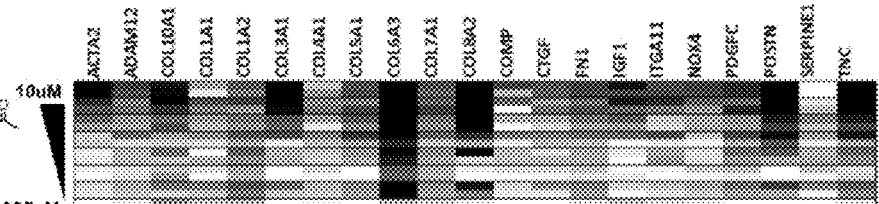

Figure 5A-B.
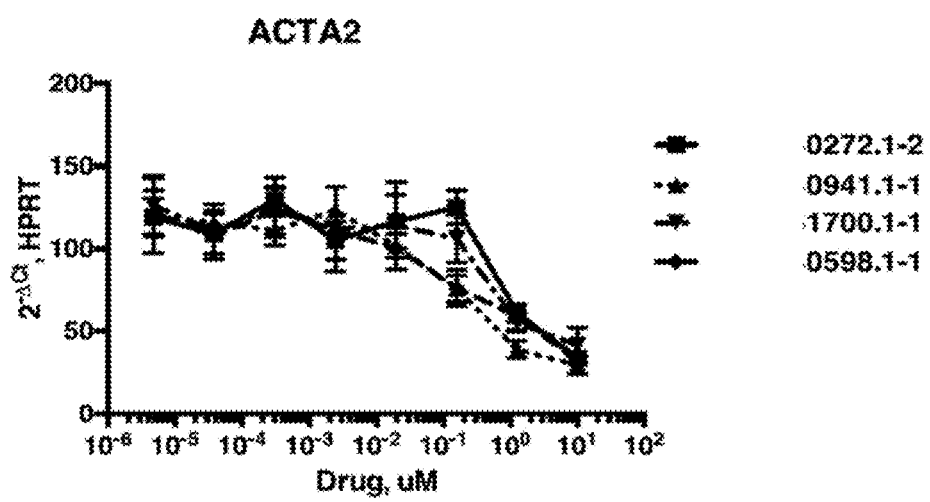
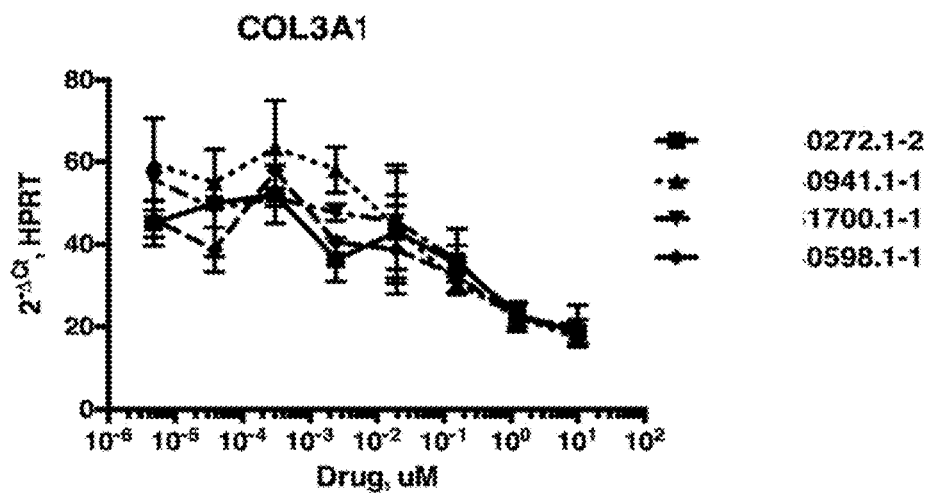

Figure 6A-E.
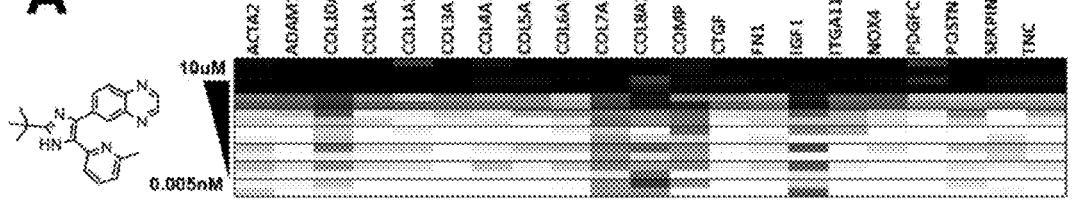
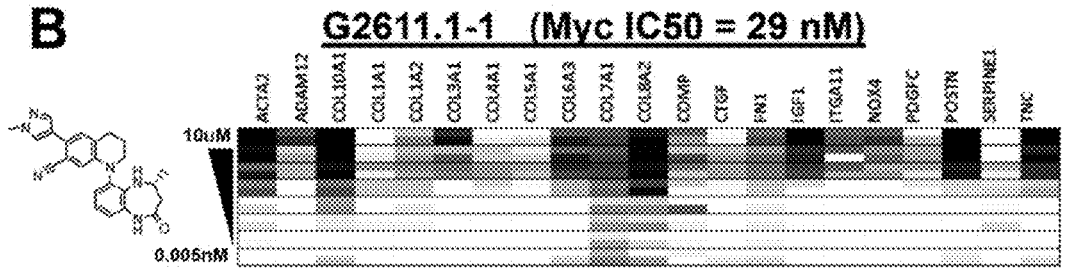
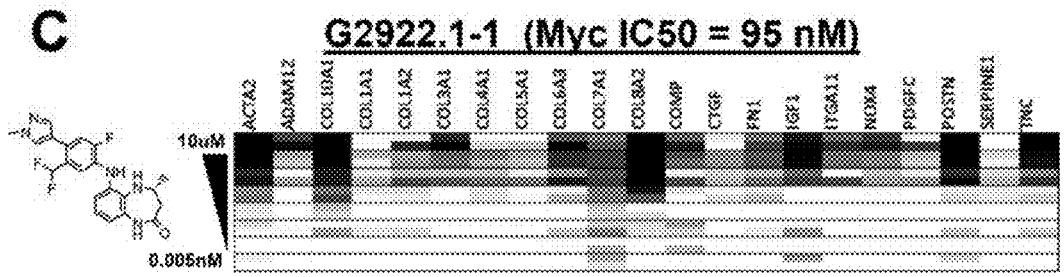
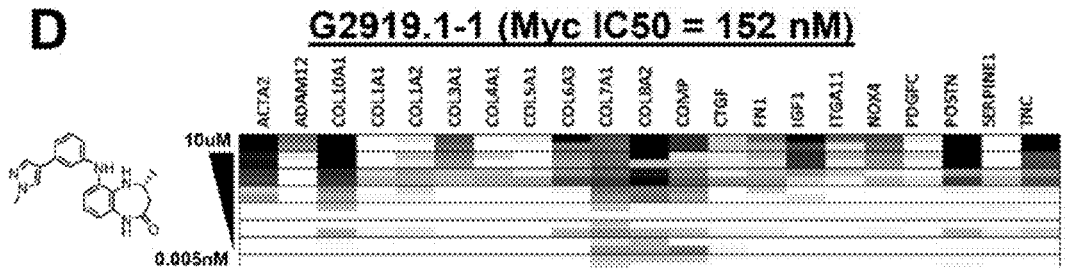
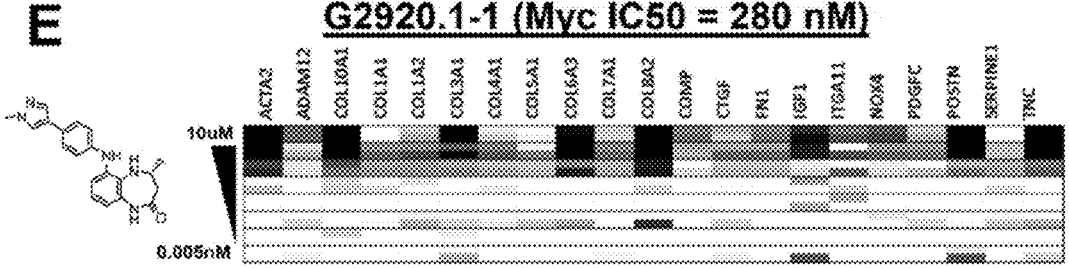

Figure 7A-B.
A
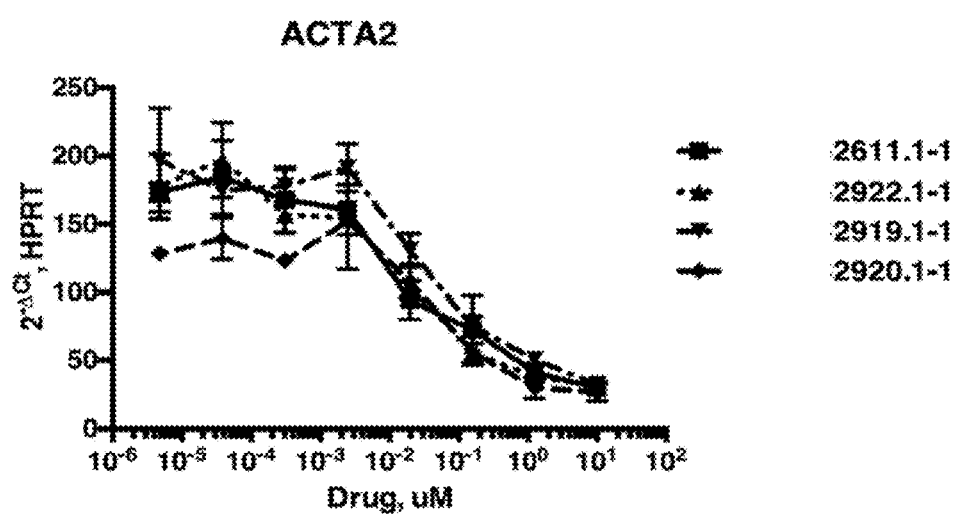
B
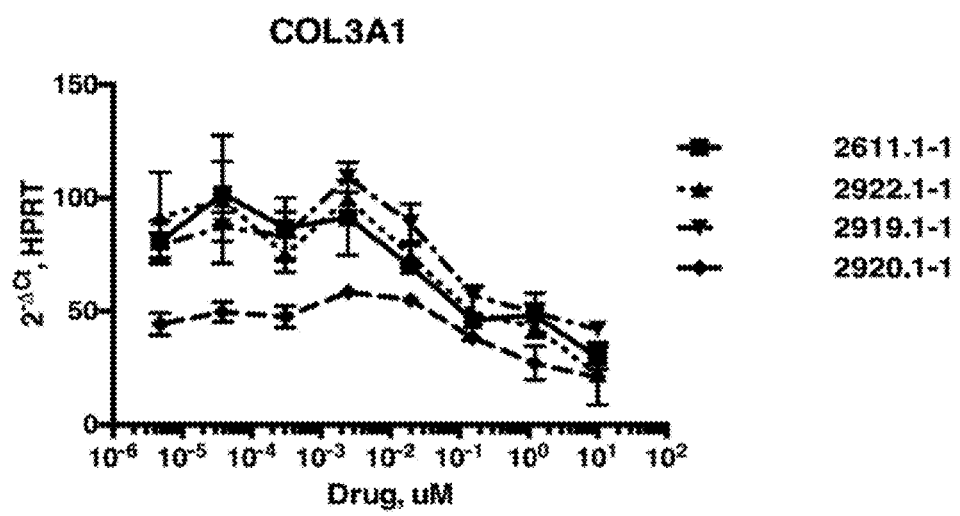

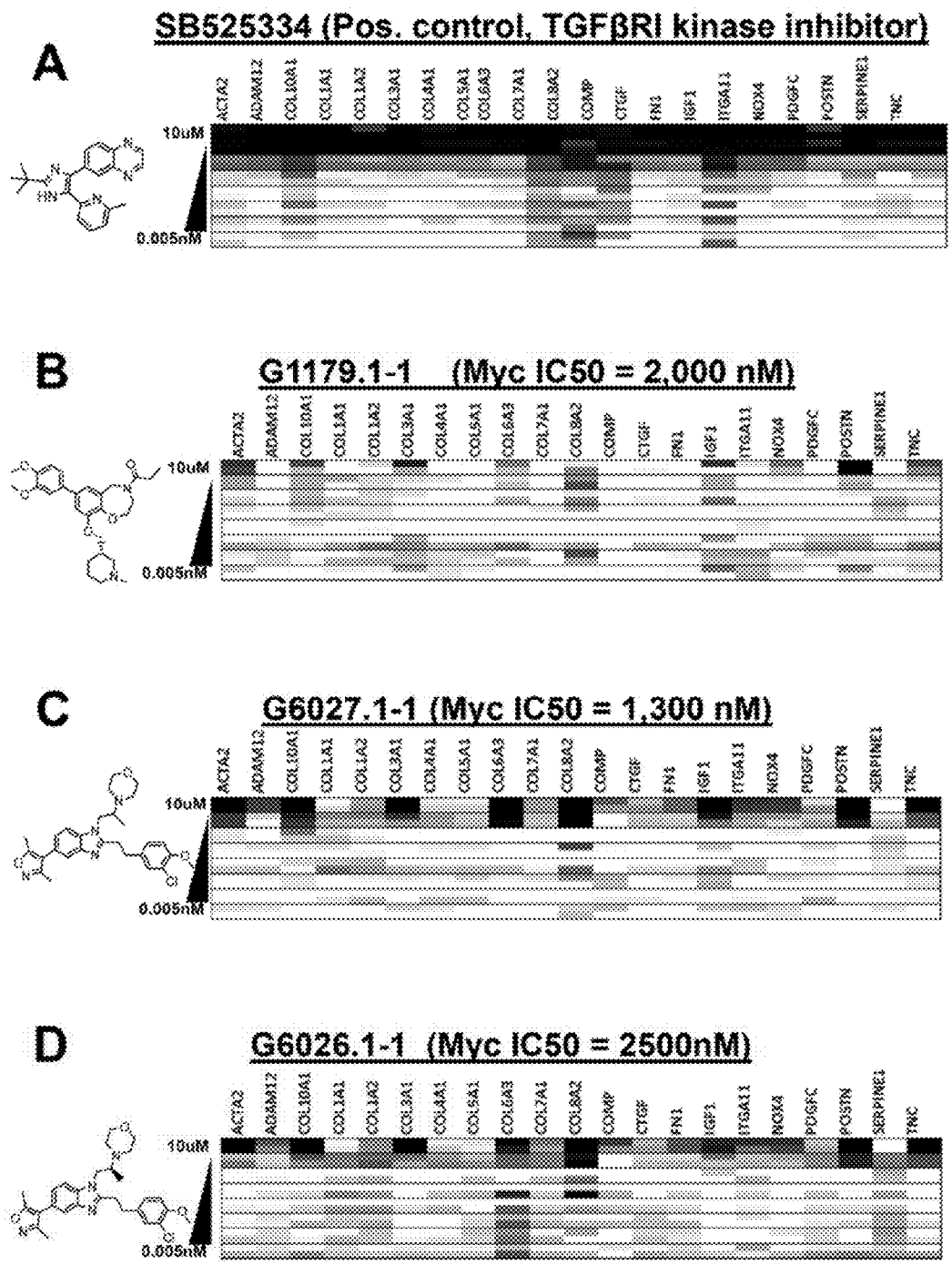
Figure 8A-D.

Figure 9A-B.
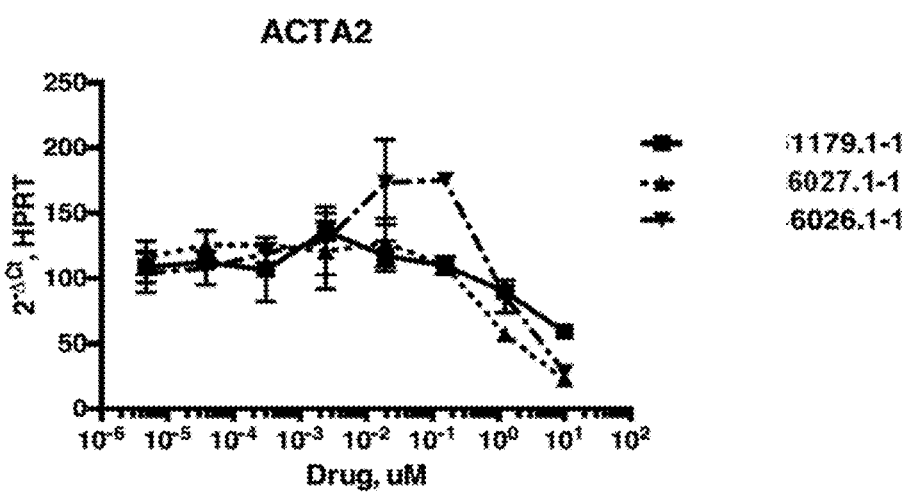
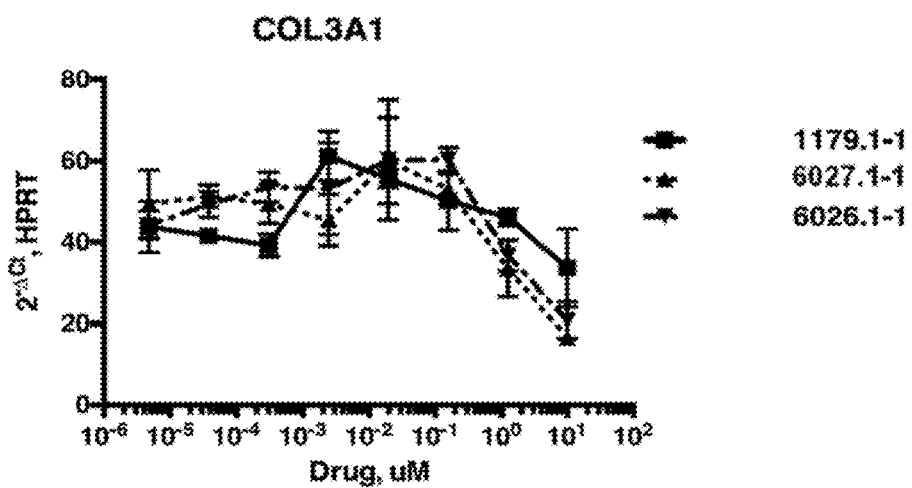

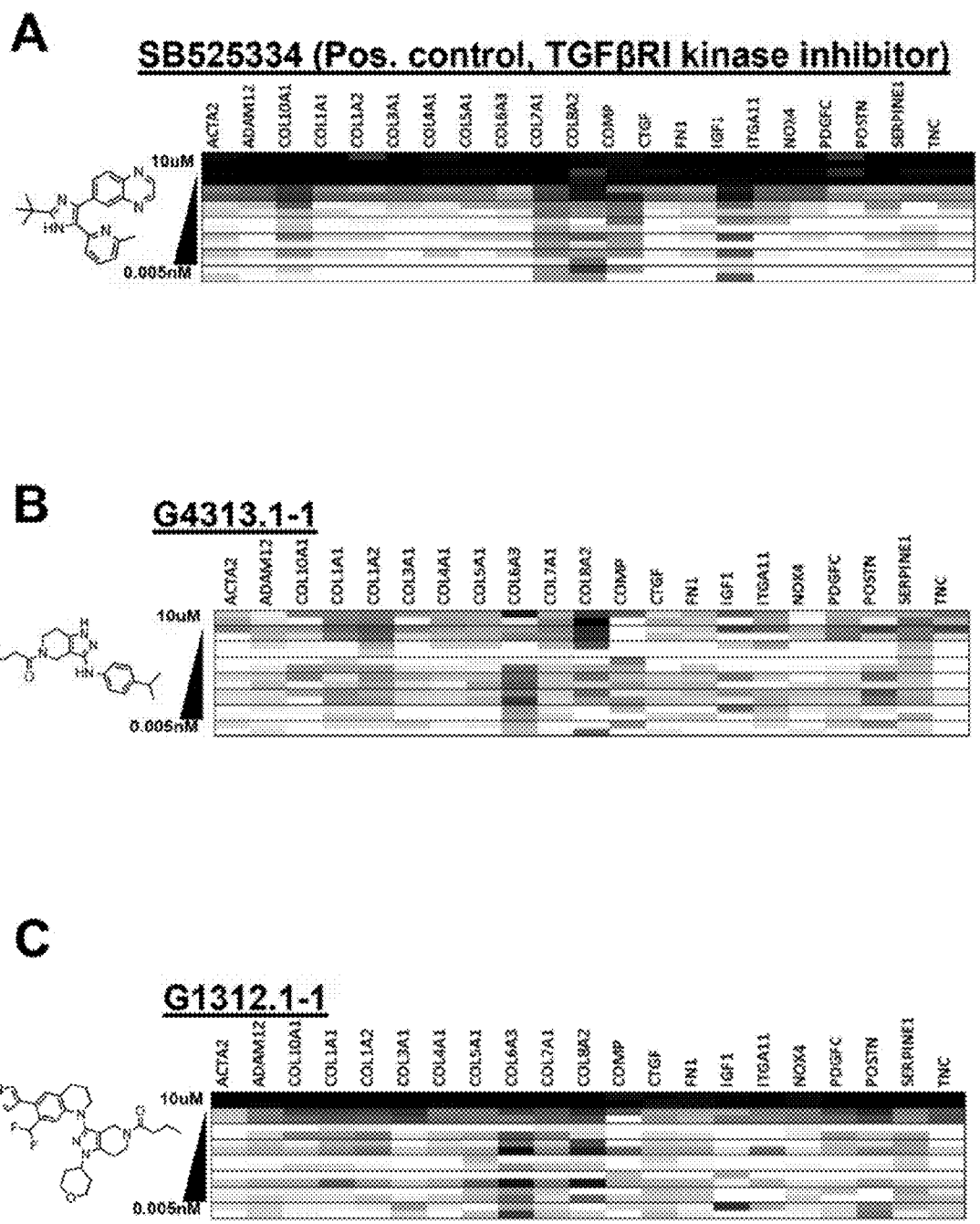
Figure 10A-C.

Figure 11A-B.
A
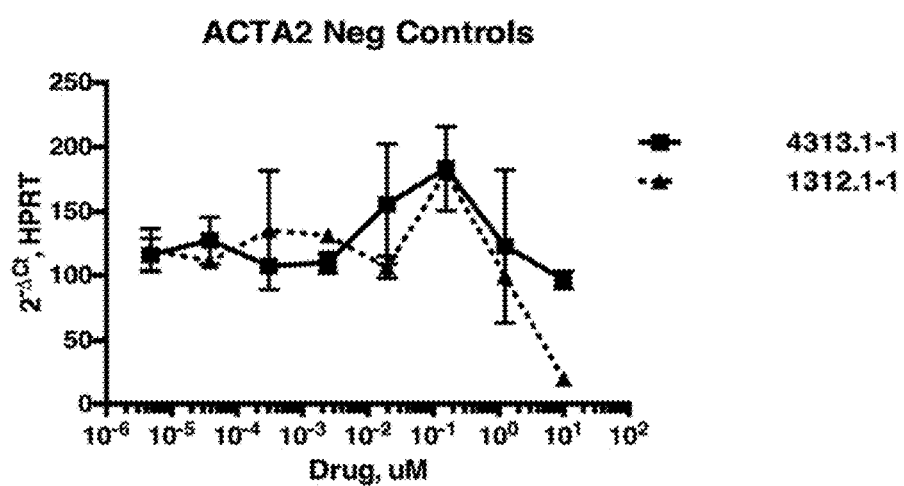
B
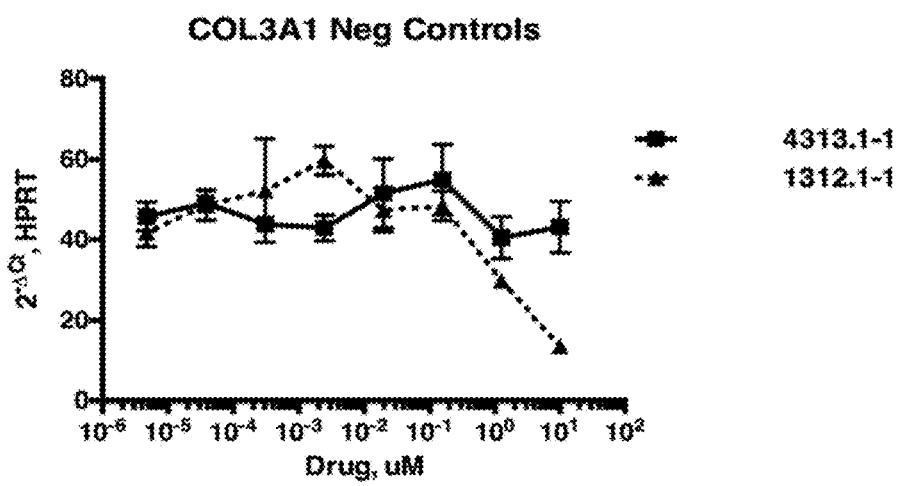

Figure 12A-B.
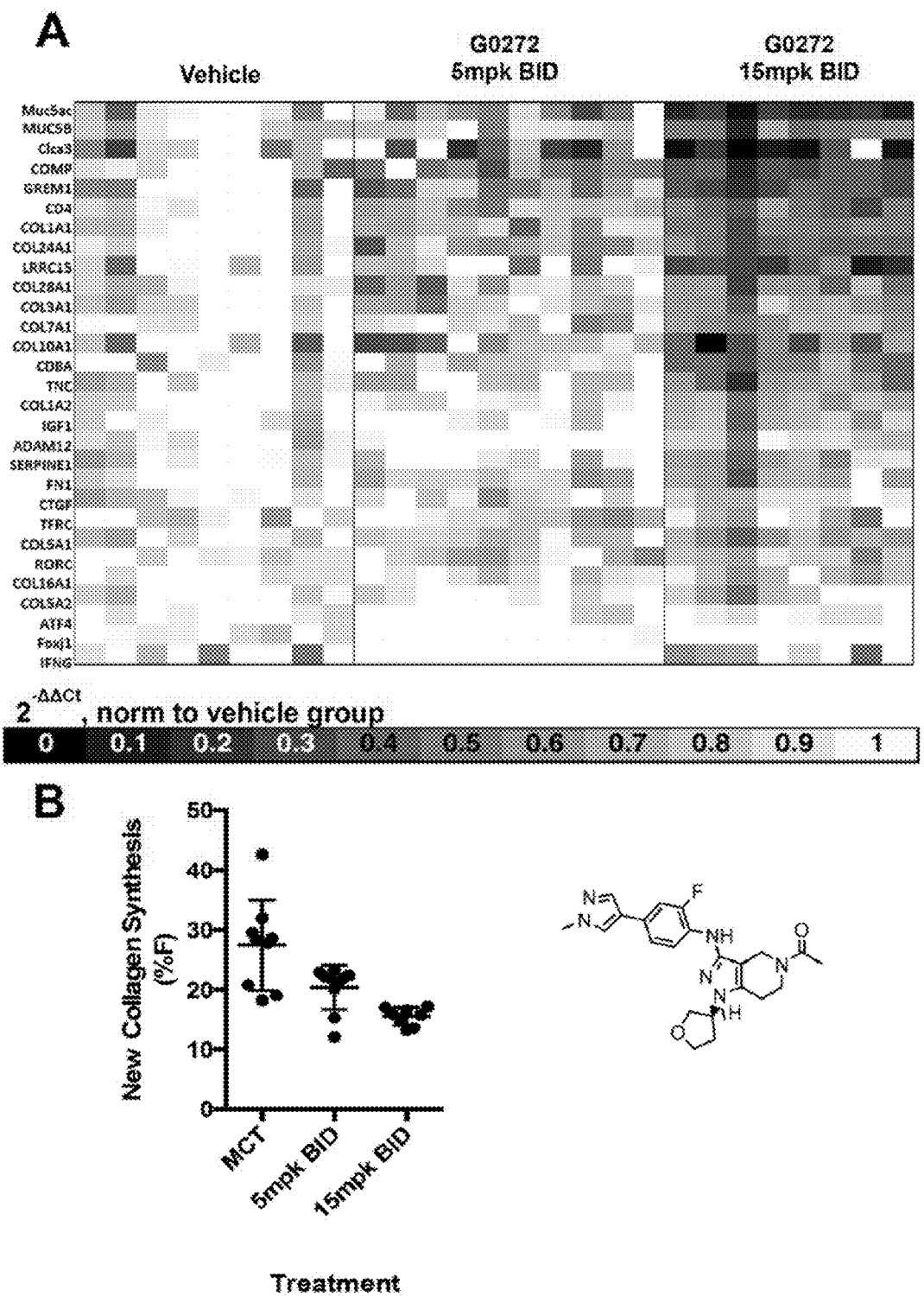

Figure 13A-B.
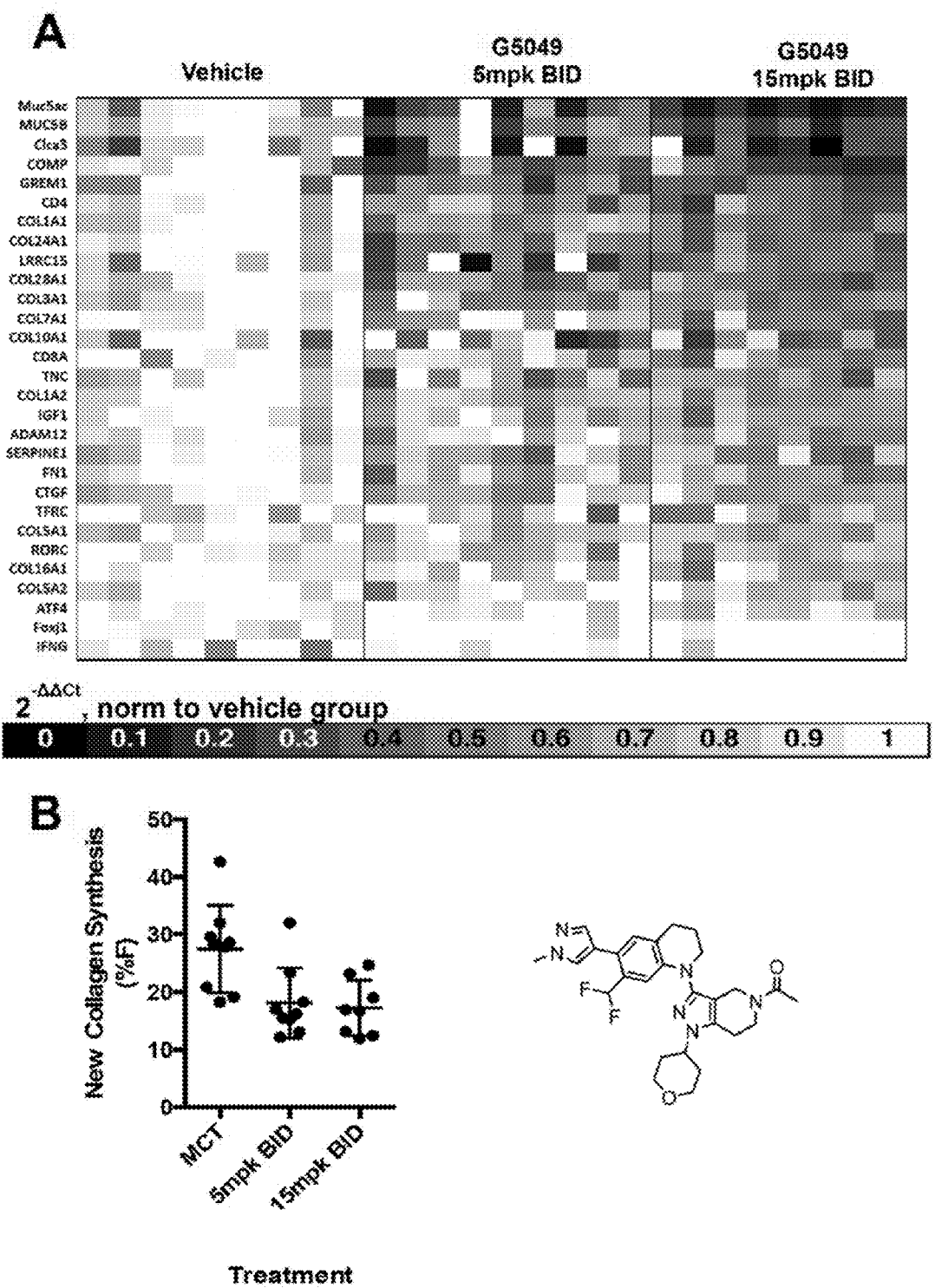

Figure 14A-B.
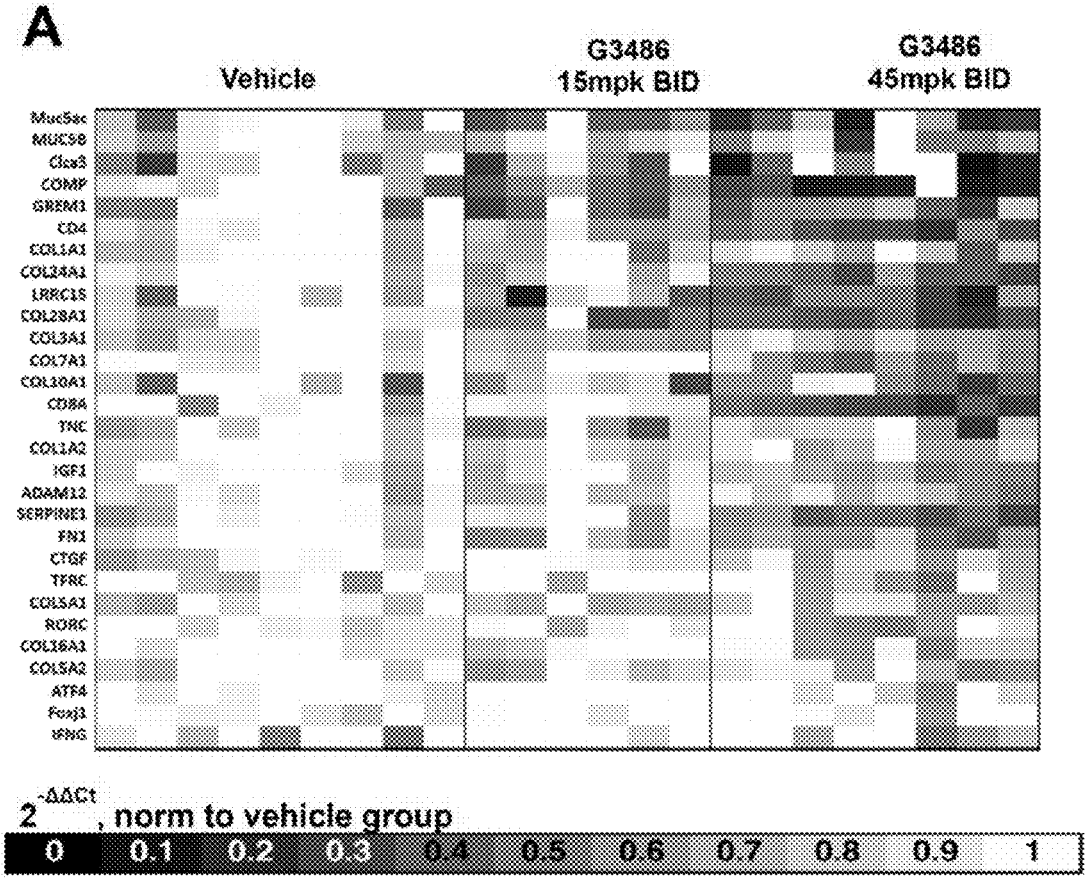
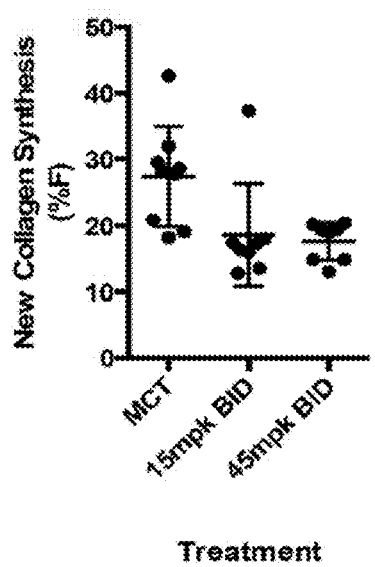
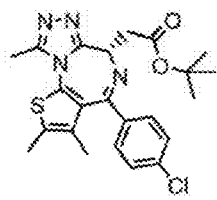

SEQUENCE LISTING

```
<160> NUMBER OF SEQ ID NOS: 3

<210> SEQ ID NO 1
<211> LENGTH: 381
<212> TYPE: PRT
<213> ORGANISM: Homo sapiens

<400> SEQUENCE: 1

Glu Asn Lys Phe Ser Ala Lys Arg Leu Gln Thr Thr Arg Leu Gly Asn
1               5                   10                  15

His Leu Glu Asp Arg Val Asn Lys Phe Leu Arg Arg Gln Asn His Pro
            20                  25                  30

Glu Ala Gly Glu Val Phe Val Arg Val Val Ala Ser Ser Asp Lys Thr
        35                  40                  45

Val Glu Val Lys Pro Gly Met Lys Ser Arg Phe Val Asp Ser Gly Glu
    50                  55                  60

Met Ser Glu Ser Phe Pro Tyr Arg Thr Lys Ala Leu Phe Ala Phe Glu
65                  70                  75                  80

Glu Ile Asp Gly Val Asp Val Cys Phe Phe Gly Met His Val Gln Glu
                85                  90                  95

Tyr Gly Ser Asp Cys Pro Pro Pro Asn Thr Arg Arg Val Tyr Ile Ser
            100                 105                 110
```

```
Tyr Leu Asp Ser Ile His Phe Phe Arg Pro Arg Cys Leu Arg Thr Ala
            115                 120                 125

Val Tyr His Glu Ile Leu Ile Gly Tyr Leu Glu Tyr Val Lys Lys Leu
    130                 135                 140

Gly Tyr Val Thr Gly His Ile Trp Ala Cys Pro Pro Ser Glu Gly Asp
145                 150                 155                 160

Asp Tyr Ile Phe His Cys His Pro Pro Asp Gln Lys Ile Pro Lys Pro
                165                 170                 175

Lys Arg Leu Gln Glu Trp Tyr Lys Lys Met Leu Asp Lys Ala Phe Ala
            180                 185                 190

Glu Arg Ile Ile His Asp Tyr Lys Asp Ile Phe Lys Gln Ala Thr Glu
            195                 200                 205

Asp Arg Leu Thr Ser Ala Lys Glu Leu Pro Tyr Phe Glu Gly Asp Phe
    210                 215                 220

Trp Pro Asn Val Leu Glu Glu Ser Ile Lys Glu Leu Glu Gln Glu Glu
225                 230                 235                 240

Glu Glu Arg Lys Lys Glu Glu Ser Thr Ala Ala Ser Glu Thr Thr Glu
                245                 250                 255

Gly Ser Gln Gly Asp Ser Lys Asn Ala Lys Lys Asn Asn Lys Lys
            260                 265                 270

Thr Asn Lys Asn Lys Ser Ser Ile Ser Arg Ala Asn Lys Lys Pro
            275                 280                 285

Ser Met Pro Asn Val Ser Asn Asp Leu Ser Gln Lys Leu Tyr Ala Thr
    290                 295                 300

Met Glu Lys His Lys Glu Val Phe Phe Val Ile His Leu His Ala Gly
305                 310                 315                 320

Pro Val Ile Asn Thr Leu Pro Pro Ile Val Asp Pro Asp Pro Leu Leu
                325                 330                 335

Ser Cys Asp Leu Met Asp Gly Arg Asp Ala Phe Leu Thr Leu Ala Arg
            340                 345                 350

Asp Lys His Trp Glu Phe Ser Ser Leu Arg Arg Ser Lys Trp Ser Thr
            355                 360                 365

Leu Cys Met Leu Val Glu Leu His Thr Gln Gly Gln Asp
    370                 375                 380

<210> SEQ ID NO 2
<211> LENGTH: 380
<212> TYPE: PRT
<213> ORGANISM: Homo sapiens

<400> SEQUENCE: 2

Glu Asn Lys Phe Ser Ala Lys Arg Leu Pro Ser Thr Arg Leu Gly Thr
1               5                   10                  15

Phe Leu Glu Asn Arg Val Asn Asp Phe Leu Arg Gln Asn His Pro
            20                  25                  30

Glu Ser Gly Glu Val Thr Val Arg Val Val His Ala Ser Asp Lys Thr
            35                  40                  45

Val Glu Val Lys Pro Gly Met Lys Ala Arg Phe Val Asp Ser Gly Glu
    50                  55                  60

Met Ala Glu Ser Phe Pro Tyr Arg Thr Lys Ala Leu Phe Ala Phe Glu
65                  70                  75                  80
```

```
Glu Ile Asp Gly Val Asp Leu Cys Phe Phe Gly Met His Val Gln Glu
                85                  90                  95

Tyr Gly Ser Asp Cys Pro Pro Asn Gln Arg Arg Val Tyr Ile Ser
            100                 105                 110

Tyr Leu Asp Ser Val His Phe Phe Arg Pro Lys Cys Leu Arg Thr Ala
            115                 120                 125

Val Tyr His Glu Ile Leu Ile Gly Tyr Leu Glu Tyr Val Lys Lys Leu
            130                 135                 140

Gly Tyr Thr Thr Gly His Ile Trp Ala Cys Pro Pro Ser Glu Gly Asp
145                 150                 155                 160

Asp Tyr Ile Phe His Cys His Pro Pro Asp Gln Lys Ile Pro Lys Pro
                165                 170                 175

Lys Arg Leu Gln Glu Trp Tyr Lys Lys Met Leu Asp Lys Ala Val Ser
            180                 185                 190

Glu Arg Ile Val His Asp Tyr Lys Asp Ile Phe Lys Gln Ala Thr Glu
            195                 200                 205

Asp Arg Leu Thr Ser Ala Lys Glu Leu Pro Tyr Phe Glu Gly Asp Phe
            210                 215                 220

Trp Pro Asn Val Leu Glu Glu Ser Ile Lys Glu Leu Glu Gln Glu Glu
225                 230                 235                 240

Glu Glu Arg Lys Arg Glu Glu Asn Thr Ser Asn Glu Ser Thr Asp Val
            245                 250                 255

Thr Lys Gly Asp Ser Lys Asn Ala Lys Lys Lys Asn Asn Lys Lys Thr
            260                 265                 270

Ser Lys Asn Lys Ser Ser Leu Ser Arg Gly Asn Lys Lys Lys Pro Gly
            275                 280                 285

Met Pro Asn Val Ser Asn Asp Leu Ser Gln Lys Leu Tyr Ala Thr Met
            290                 295                 300

Glu Lys His Lys Glu Val Phe Phe Val Ile Arg Leu Ile Ala Gly Pro
305                 310                 315                 320

Ala Ala Asn Ser Leu Pro Pro Ile Val Asp Pro Asp Pro Leu Ile Pro
            325                 330                 335

Cys Asp Leu Met Asp Gly Arg Asp Ala Phe Leu Thr Leu Ala Arg Asp
            340                 345                 350

Lys His Leu Glu Phe Ser Ser Leu Arg Arg Ala Gln Trp Ser Thr Met
            355                 360                 365

Cys Met Leu Val Glu Leu His Thr Gln Ser Gln Asp
            370                 375                 380

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5
```

THERAPEUTIC COMPOUNDS AND USES THEREOF

CROSS REFERENCE TO RELATED APPLICATIONS

This application claims the benefit of and priority to PCT/CN2014/092380, filed Nov. 27, 2014, and PCT/CN2015/092965, filed Oct. 27, 2015, both of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Feb. 3, 2016, is named 01076.024US1_SL.txt and is 7,162 bytes in size.

TECHNICAL FIELD OF THE INVENTION

The present invention relates to compounds useful as inhibitors of CBP/EP300 and methods of treating cancer using such inhibitors.

BACKGROUND OF THE INVENTION

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin structure is controlled by a series of post-translational modifications to histone proteins, notably histones H3 and H4, and most commonly within the "histone tails" which extend beyond the core nucleosome structure. Histone tails tend to be free for protein-protein interaction and are also the portion of the histone most prone to post-translational modification. These modifications include acetylation, methylation, phosphorylation, ubiquitinylation, and SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translational modification. Histone modifications are dynamic, as they can be added or removed in response to specific stimuli, and these modifications direct both structural changes to chromatin and alterations in gene transcription. Distinct classes of enzymes, namely histone acetyltransferases (HATs) and histone deacetylases (HDACs), acetylate or de-acetylate specific histone lysine residues (Struhl K., *Genes Dev.*, 1989, 12, 5, 599-606).

Bromodomains, which are approximately 110 amino acids long, are found in a large number of chromatin-associated proteins and have been identified in approximately 70 human proteins, often adjacent to other protein motifs (Jeanmougin F., et al., *Trends Biochem. Sci.*, 1997, 22, 5, 151-153; and Tamkun J. W., et al., *Cell*, 1992, 7, 3, 561-572). Interactions between bromodomains and modified histones may be an important mechanism underlying chromatin structural changes and gene regulation. Bromodomain-containing proteins have been implicated in disease processes including cancer, inflammation and viral replication. See, e.g., Prinjha et al., *Trends Pharm. Sci.*, 33(3):146-153 (2012) and Muller et al., *Expert Rev.*, 13(29):1-20 (September 2011).

Cell-type specificity and proper tissue functionality requires the tight control of distinct transcriptional programs that are intimately influenced by their environment. Alterations to this transcriptional homeostasis are directly associated with numerous disease states, most notably cancer, immuno-inflammation, neurological disorders, and metabolic diseases. Bromodomains reside within key chromatin modifying complexes that serve to control distinctive disease-associated transcriptional pathways. This is highlighted by the observation that mutations in bromodomain-containing proteins are linked to cancer, as well as immune and neurologic dysfunction. Hence, the selective inhibition of bromodomains across a specific family, such as the selective inhibition of a bromodomain of CBP/EP300, creates varied opportunities as novel therapeutic agents in human dysfunction.

There is a need for treatments for cancer, immunological disorders, and other CBP/EP300 bromodomain related diseases.

SUMMARY OF THE INVENTION

Compounds of Formula (I) or Formula (II)
One aspect is a compound of formula (I) or formula (II):

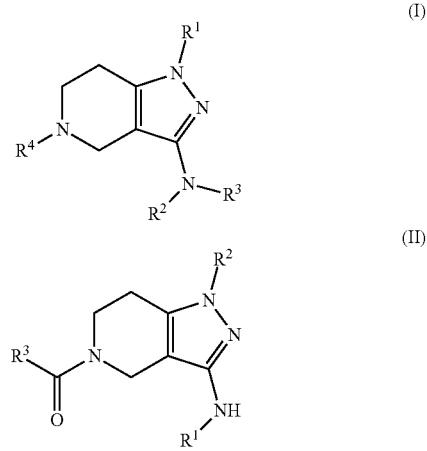

or a salt thereof, wherein:

$R^1$ of Formula (I) is $C_{1-12}$alkyl, $C_{2-12}$alkenyl, $C_{2-12}$alkynyl, 3-12 membered carbocycle, and 3-12 membered heterocycle, wherein each $C_{1-12}$alkyl, $C_{2-12}$alkenyl, $C_{2-12}$alkynyl, 3-12 membered carbocycle, and 3-12 membered heterocycle of $R^1$ is optionally substituted with one or more groups $R^b$;

$R^2$ of Formula (I) is selected from $C_6$-$C_{20}$ aryl, $C_1$-$C_{20}$ heteroaryl, —($C_6$-$C_{20}$ aryl)-($C_1$-$C_{20}$ heteroaryl), —($C_1$-$C_{20}$ heteroaryl)-($C_6$-$C_{20}$ aryl), and —($C_1$-$C_{20}$ heteroaryl)-($C_1$-$C_{20}$ heteroaryl), wherein each $C_6$-$C_{20}$ aryl, $C_1$-$C_{20}$ heteroaryl, —($C_6$-$C_{20}$ aryl)-($C_1$-$C_{20}$ heteroaryl) and —($C_1$-$C_{20}$ heteroaryl)-($C_1$-$C_{20}$ heteroaryl) is independently optionally substituted with one or more substituent groups independently selected from $R^c$, oxo, —F, —Cl, —Br, —I, —NO$_2$, —N(R$^a$)$_2$, —CN, —C(O)—N(R$^a$)$_2$, —S(O)—N(R$^a$)$_2$, —S(O)$_2$—N(R$^a$)$_2$, —O—R$^a$, —S—R$^a$, —O—C(O)—R$^a$, —O—C(O)—O—R$^a$, —C(O)—R$^a$, —C(O)—O—R$^a$, —S(O)—R$^a$, —S(O)$_2$—R$^a$, —O—C(O)—N(R$^a$)$_2$, —N(R$^a$)—C(O)—OR$^a$, —N(R$^a$)—C(O)—N(R$^a$)$_2$, —N(R$^a$)—C(O)—R$^a$, —N(R$^a$)—S(O)—R$^a$, —N(R$^a$)—S(O)$_2$—R$^a$, —N(R$^a$)—S(O)—N(R$^a$)$_2$, and —N(R$^a$)—S(O)$_2$—N(R$^a$)$_2$;

R$^3$ of Formula (I) is C$_{1-12}$alkyl, C$_{2-12}$alkenyl, C$_{2-12}$alkynyl, 3-12 membered carbocycle, and 3-12 membered heterocycle, wherein each C$_{1-12}$alkyl, C$_{2-12}$alkenyl, C$_{2-12}$alkynyl, 3-12 membered carbocycle, and 3-12 membered heterocycle of R$^3$ is optionally substituted with one or more groups R$^e$; or R$^2$ and R$^3$ of Formula (I) taken together with the nitrogen to which they are attached form a 3-12 membered heterocycle that is optionally substituted with one or more groups R$^e$;

R$^4$ of Formula (I) is C$_{1-4}$alkyl, C$_{2-4}$alkenyl, C$_{2-4}$alkynyl, 3-5 membered carbocycle, 3-5 membered heterocycle, —C(O)—N(R$^h$)$_2$, —S(O)—N(R$^h$)$_2$, —S(O)$_2$—N(R$^h$)$_2$, —C(O)—R$^h$, —C(O)—O—R$^h$, —S(O)—R$^h$, or —S(O)$_2$—R$^h$, wherein any C$_{1-4}$alkyl, C$_{2-4}$alkenyl, C$_{2-4}$alkynyl, 3-5 membered carbocycle, and 3-5 membered heterocycle is optionally substituted with one or more substituent groups independently selected from —F, —Cl, —Br, —I, 3-5 membered carbocycle, —C(O)—N(R$^h$)$_2$, —S(O)—N(R$^h$)$_2$, —S(O)$_2$—N(R$^h$)$_2$, —O— R$^h$, —S—R$^h$, —O—C(O)—R$^h$, —O—C(O)—O—R$^h$, —C(O)—R$^h$, —C(O)—O—R$^h$, —S(O)—R$^h$, —S(O)$_2$—R$^h$, —O—C(O)—N(R$^h$)$_2$, —N(R$^h$)—C(O)—OR$^h$, —N(R$^h$)—C(O)—N(R$^h$)$_2$, —N(R$^h$)—C(O)—R$^a$, —N(R$^h$)—S(O)—R$^h$, —N(R$^h$)—S(O)$_2$—R$^h$, —N(R$^h$)—S(O)—N(R$^h$)$_2$, and —N(R$^h$)—S(O)$_2$—N(R$^h$)$_2$;

each R$^a$ of Formula (I) is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, and heterocyclyl is optionally substituted with one or more groups independently selected from oxo, halo, amino, hydroxyl, C$_{1-6}$alkoxy, carbocyclyl, heterocyclyl, and C$_1$-C$_6$ alkyl that is optionally substituted with one or more groups independently selected from oxo and halo; or two R$^a$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^b$ of Formula (I) is independently selected from oxo, C$_{1-6}$alkyl, C$_{2-6}$alkenyl, C$_{2-6}$alkynyl, carbocyclyl, heterocyclyl, aryl, heteroaryl, —F, —Cl, —Br, —I, —NO$_2$, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—R$^c$, —O—C(O)—O—R$^c$, —C(O)—R$^c$, —C(O)—O—R$^c$, —S(O)—R$^c$, —S(O)$_2$—R$^c$, —O—C(O)—N(R$^c$)$_2$, —N(R$^c$)—C(O)—OR$^c$, —N(R$^c$)—C(O)—N(R$^c$)$_2$, —N(R$^c$)—C(O)—R$^c$, —N(R$^c$)—S(O)—R$^c$, —N(R$^c$)—S(O)$_2$—R$^c$, —N(R$^c$)—S(O)—N(R$^c$)$_2$, and —N(R$^c$)—S(O)$_2$—N(R$^c$)$_2$, wherein any C$_{1-6}$alkyl, C$_{2-6}$alkenyl, C$_{2-6}$alkynyl, carbocyclyl, heterocyclyl, aryl, and heteroaryl is optionally substituted with one or more groups independently selected from oxo, halo, —NO$_2$, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—R$^c$, —C(O)—R$^c$, —C(O)—O—R$^c$, —S(O)—R$^c$, —S(O)$_2$—R$^c$, —C(O)—N(R$^c$)$_2$, —N(R$^c$)—C(O)—R$^c$, —N(R$^c$)—S(O)—R$^c$, —N(R$^c$)—S(O)$_2$—R$^c$ and C$_{1-6}$alkyl that is optionally substituted with one or more groups independently selected from oxo and halo;

each R$^c$ of Formula (I) is independently selected from hydrogen, C$_{1-6}$-alkyl, C$_{2-6}$alkenyl, C$_{2-6}$alkynyl, carbocyclyl, and heterocyclyl, wherein any C$_{1-6}$alkyl, C$_{2-6}$alkenyl, C$_{2-6}$alkynyl, carbocyclyl, and heterocyclyl is optionally substituted with one or more groups independently selected from oxo, carbocyclyl, heterocyclyl, halo, —NO$_2$, —N(R$^d$)$_2$, —CN, —C(O)—N(R$^d$)$_2$, —S(O)—N(R$^d$)$_2$, —S(O)$_2$—N(R$^d$)$_2$, —O—R$^d$, —S—R$^d$, —O—C(O)—R$^d$, —C(O)—R$^d$, —C(O)—O—R$^d$, —S(O)—R$^d$, —S(O)$_2$—R$^d$, —C(O)—N(R$^d$)$_2$, —N(R$^d$)—C(O)—R$^d$, —N(R$^d$)—S(O)—R$^d$, N(R$^d$)—S(O)$_2$—R$^d$, and C$_{1-6}$alkyl, which carbocyclyl and C$_{1-6}$alkyl are optionally substituted with one or more groups independently selected from oxo, halo, C$_{1-6}$alkyl, cyano, —N(R$^d$)$_2$, —O—R$^d$, heterocyclyl, and carbocyclyl that is optionally substituted with one or more groups independently selected from halo, and C$_{1-6}$alkyl;

each R$^d$ of Formula (I) is independently selected from hydrogen, C$_{1-6}$alkyl, C$_{2-6}$alkenyl, C$_{2-6}$alkynyl, C$_{1-6}$alkoxy, carbocyclyl, and heterocyclyl, wherein each C$_{1-6}$alkyl, C$_{2-6}$alkenyl, C$_{2-6}$alkynyl, C$_{1-6}$alkoxy, carbocyclyl, and heterocyclyl is optionally substituted with one or more groups independently selected from oxo, halo, amino, hydroxyl, C$_{1-6}$alkoxy, carbocyclyl, heterocyclyl, and C$_1$-C$_6$ alkyl that is optionally substituted with one or more groups independently selected from oxo and halo; or two R$^d$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^e$ of Formula (I) is independently selected from oxo, C$_{1-6}$alkyl, C$_{2-6}$alkenyl, C$_{2-6}$alkynyl, carbocyclyl, heterocyclyl, aryl, heteroaryl, —F, —Cl, —Br, —I, —NO$_2$, —N(R$^f$)$_2$, —CN, —C(O)—N(R$^f$)$_2$, —S(O)—N(R$^f$)$_2$, —S(O)$_2$—N(R$^f$)$_2$, —O—R$^f$, —S—R$^f$, —O—C(O)—R$^f$, —O—C(O)—O—R$^f$, —C(O)—R$^f$, —C(O)—O—R$^f$, —S(O)—R$^f$, —S(O)$_2$—R$^f$, —O—C(O)—N(R$^f$)$_2$, —N(R$^f$)—C(O)—OR$^f$, —N(R$^f$)—C(O)—N(R$^f$)$_2$, —N(R$^f$)—C(O)—R$^f$, —N(R$^f$)—S(O)—R$^f$, —N(R$^f$)—S(O)$_2$—R$^f$, —N(R$^f$)—S(O)—N(R$^f$)$_2$, and —N(R$^f$)—S(O)$_2$—N(R$^f$)$_2$, wherein any C$_{1-6}$alkyl, C$_{2-6}$alkenyl, C$_{2-6}$alkynyl, carbocyclyl, heterocyclyl, aryl, and heteroaryl is optionally substituted with one or more groups independently selected from oxo, halo, —NO$_2$, —N(R$^f$)$_2$, —CN, —C(O)—N(R$^f$)$_2$, —S(O)—N(R$^f$)$_2$, —S(O)$_2$—N(R$^f$)$_2$, —O—R$^f$, —S—R$^f$, —O—C(O)—R$^f$, —C(O)—R$^f$, —C(O)—O—R$^f$, —S(O)—R$^f$, —S(O)$_2$—R$^f$, —C(O)—N(R$^f$)$_2$, —N(R$^f$)—C(O)—R$^f$, —N(R$^f$)—S(O)—R$^f$, —N(R$^f$)—S(O)$_2$—R$^f$, carbocycle, and C$_{1-6}$alkyl that is optionally substituted with one or more groups independently selected from oxo and halo;

each R$^f$ of Formula (I) is independently selected from hydrogen, C$_{1-6}$alkyl, C$_{2-6}$alkenyl, C$_{2-6}$alkynyl, carbocyclyl, and heterocyclyl, wherein any C$_{1-6}$alkyl, C$_{2-6}$alkenyl, C$_{2-6}$alkynyl, carbocyclyl, and heterocyclyl is optionally substituted with one or more groups independently selected from oxo, carbocyclyl, heterocyclyl, halo, —NO$_2$, —N(R$^g$)$_2$, —CN, —C(O)—N(R$^g$)$_2$, —S(O)—N(R$^g$)$_2$, —S(O)$_2$—N(R$^g$)$_2$, —O—R$^g$, —S—R$^g$, —O—C(O)—R$^g$, —C(O)—R$^g$, —C(O)—O—R$^g$, —S(O)—R$^g$, —S(O)$_2$—R$^g$, —C(O)—N(R$^g$)$_2$, —N(R$^g$)—C(O)—R$^g$, —N(R$^g$)—S(O)—R$^g$, N(R$^g$)—S(O)$_2$—R$^g$, and C$_{1-6}$alkyl, which carbocyclyl and C$_{1-6}$alkyl are optionally substituted with one or more groups independently selected from oxo, halo, C$_{1-6}$alkyl, cyano, —N(R$^g$)$_2$, —O—R$^g$, heterocyclyl, and carbocyclyl that is optionally substituted with one or more groups independently selected from halo, and C$_{1-6}$alkyl;

each R$^g$ of Formula (I) is independently selected from hydrogen, C$_{1-6}$alkyl, C$_{2-6}$alkenyl, C$_{2-6}$alkynyl, C$_{1-6}$alkoxy, carbocyclyl, and heterocyclyl, wherein each C$_{1-6}$alkyl, C$_{2-6}$alkenyl, C$_{2-6}$alkynyl, C$_{1-6}$alkoxy, carbocyclyl, and heterocyclyl is optionally substituted with one or more groups independently selected from oxo, halo, amino, hydroxyl, C$_{1-6}$alkoxy, carbocyclyl, heterocyclyl, and C$_1$-C$_6$ alkyl that is optionally substituted with one or more groups independently selected from oxo and halo; or two R$^g$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^h$ of Formula (I) is independently selected from hydrogen, C$_{1-4}$alkyl, C$_{2-4}$alkenyl, C$_{2-4}$alkynyl, and C$_{2-5}$cycloalkyl, wherein each C$_{1-4}$alkyl, C$_{2-4}$alkenyl, C$_{2-4}$alkynyl, and C$_{2-5}$cycloalkyl is optionally substituted with one or more groups independently selected from oxo, halo, amino, hydroxyl, C$_{1-3}$alkoxy, and C$_1$-C$_3$ alkyl that is optionally substituted with one or more groups independently selected from halo; and R$^1$ of Formula (II) is selected from C$_6$-C$_{20}$ aryl, C$_1$-C$_{20}$ heteroaryl, —(C$_6$-C$_{20}$ aryl)-(C$_1$-C$_{20}$ heteroaryl), and —(C$_1$-C$_{20}$ heteroaryl)-(C$_1$-C$_{20}$ heteroaryl), wherein each C$_6$-C$_{20}$ aryl, C$_1$-C$_{20}$ heteroaryl, —(C$_6$-C$_{20}$ aryl)-(C$_1$-C$_{20}$ heteroaryl) and —(C$_1$-C$_{20}$ heteroaryl)-(C$_1$-C$_{20}$ heteroaryl) is independently optionally substituted with one or more substituent groups independently selected from R$^c$, oxo, —F, —Cl, —Br, —I, —NO$_2$, —N(R$^a$)$_2$, —CN, —C(O)—N(R$^a$)$_2$, —S(O)—N(R$^a$)$_2$, —S(O)$_2$—N(R$^a$)$_2$, —O—R$^a$, —S—R$^a$, —O—C(O)—R$^a$, —O—C(O)—O—R$^a$, —C(O)—R$^a$, —C(O)—O—R$^a$, —S(O)—R$^a$, —S(O)$_2$—R$^a$, —O—C(O)—N(R$^a$)$_2$, —N(R$^a$)—C(O)—OR$^a$, —N(R$^a$)—C(O)—N(R$^a$)$_2$, —N(R$^a$)—C(O)—R$^a$, —N(R$^a$)—S(O)—R$^a$, —N(R$^a$)—S(O)$_2$—R$^a$, —N(R$^a$)—S(O)—N(R$^a$)$_2$, and —N(R$^a$)—S(O)$_2$—N(R$^a$)$_2$;

R$^2$ of Formula (II) is C$_{1-12}$alkyl, C$_{2-12}$alkenyl, C$_{2-12}$alkynyl, 3-12 membered carbocycle, and 3-12 membered heterocycle, wherein each C$_{1-12}$alkyl, C$_{2-12}$alkenyl, C$_{2-12}$alkynyl, 3-12 membered carbocycle, and 3-12 membered heterocycle of R$^2$ is optionally substituted with one or more groups R$^b$;

R$^3$ of Formula (II) is C$_{1-4}$alkyl, C$_{2-4}$alkenyl, C$_{2-4}$alkynyl, 3-5 membered carbocycle, 3-5 membered heterocycle, —C(O)—N(R$^e$)$_2$, —S(O)—N(R$^e$)$_2$, —S(O)$_2$—N(R$^e$)$_2$, —C(O)—R$^e$, —C(O)—O—R$^e$, —S(O)—R$^e$, or —S(O)$_2$—R$^e$, wherein any C$_{1-4}$alkyl, C$_{2-4}$alkenyl, C$_{2-4}$alkynyl, 3-5 membered carbocycle, and 3-5 membered heterocycle is optionally substituted with one or more substituent groups independently selected from —F, —Cl, —Br, —I, 3-5 membered carbocycle, —C(O)—N(R$^e$)$_2$, —S(O)—N(R$^e$)$_2$, —S(O)$_2$—N(R$^e$)$_2$, —O—R$^e$, —S—R$^e$, —O—C(O)—R$^e$, —O—C(O)—O—R$^e$, —C(O)—R$^e$, —C(O)—O—R$^e$, —S(O)—R$^e$, —S(O)$_2$—R$^e$, —O—C(O)—N(R$^e$)$_2$, —N(R$^e$)—C(O)—OR$^e$, —N(R$^e$)—C(O)—N(R$^e$)$_2$, —N(R$^e$)—C(O)—R$^e$, —N(R$^e$)—S(O)—R$^e$, —N(R$^e$)—S(O)$_2$—R$^e$, —N(R$^e$)—S(O)—N(R$^e$)$_2$, and —N(R$^e$)—S(O)$_2$—N(R$^e$)$_2$;

each R$^a$ of Formula (II) is independently selected from hydrogen, C$_{1-6}$alkyl, C$_{2-6}$alkenyl, C$_{2-6}$alkynyl, carbocyclyl, and heterocyclyl, wherein each C$_{1-6}$-alkyl, C$_{2-6}$alkenyl, C$_{2-6}$alkynyl, carbocyclyl, and heterocyclyl is optionally substituted with one or more groups independently selected from oxo, halo, amino, hydroxyl, C$_{1-6}$alkoxy, carbocyclyl, heterocyclyl, and C$_1$-C$_6$ alkyl that is optionally substituted with one or more groups independently selected from oxo and halo; or two R$^a$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^b$ of Formula (II) is independently selected from oxo, C$_{1-6}$alkyl, C$_{2-6}$alkenyl, C$_{2-6}$alkynyl, carbocyclyl, heterocyclyl, aryl, heteroaryl, —F, —Cl, —Br, —I, —NO$_2$, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—R$^c$, —O—C(O)—O—R$^c$, —C(O)—R$^c$, —C(O)—O—R$^c$, —S(O)—R$^c$, —S(O)$_2$—R$^c$, —O—C(O)—N(R$^c$)$_2$, —N(R$^c$)—C(O)—OR$^c$, —N(R$^c$)—C(O)—N(R$^c$)$_2$, —N(R$^c$)—C(O)—R$^c$, —N(R$^c$)—S(O)—R$^c$, —N(R$^c$)—S(O)$_2$—R$^c$, —N(R$^c$)—S(O)—N(R$^c$)$_2$, and —N(R$^c$)—S(O)$_2$—N(R$^c$)$_2$, wherein any C$_{1-6}$alkyl, C$_{2-6}$alkenyl, C$_{2-6}$alkynyl, carbocyclyl, heterocyclyl, aryl, and heteroaryl is optionally substituted with one or more groups independently selected from oxo, halo, —NO$_2$, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—R$^c$, —C(O)—R$^c$, —C(O)—O—R$^c$, —S(O)—R$^c$, —S(O)$_2$—R$^c$, —C(O)—N(R$^c$)$_2$, —N(R$^c$)—C(O)—R$^c$, —N(R$^c$)—S(O)—R$^c$, —N(R$^c$)—S(O)$_2$—R$^c$ and C$_{1-6}$alkyl that is optionally substituted with one or more groups independently selected from oxo and halo;

each R$^c$ of Formula (II) is independently selected from hydrogen, C$_{1-6}$alkyl, C$_{2-6}$alkenyl, C$_{2-6}$alkynyl, carbocyclyl, and heterocyclyl, wherein any C$_{1-6}$alkyl, C$_{2-6}$alkenyl, C$_{2-6}$alkynyl, carbocyclyl, and heterocyclyl is optionally substituted with one or more groups independently selected from oxo, carbocyclyl, heterocyclyl, halo, —NO$_2$, —N(R$^d$)$_2$, —CN, —C(O)—N(R$^d$)$_2$, —S(O)—N(R$^d$)$_2$, —S(O)$_2$—N(R$^d$)$_2$, —O—R$^d$, —S—R$^d$, —O—C(O)—R$^d$, —C(O)—R$^d$, —C(O)—O—R$^d$, —S(O)—R$^d$, —S(O)$_2$—R$^d$, —C(O)—N(R$^d$)$_2$, —N(R$^d$)—C(O)—R$^d$, —N(R$^d$)—S(O)—R$^d$, N(R$^d$)—S(O)$_2$—R$^d$, and C$_{1-6}$alkyl, which carbocyclyl and C$_{1-6}$alkyl are optionally substituted with one or more groups independently selected from oxo, halo, C$_{1-6}$alkyl, cyano, —N(R$^d$)$_2$, —O—R$^d$, heterocyclyl, and carbocyclyl that is optionally substituted with one or more groups independently selected from halo, and C$_{1-6}$alkyl;

each R$^d$ of Formula (II) is independently selected from hydrogen, C$_{1-6}$alkyl, C$_{2-6}$alkenyl, C$_{2-6}$alkynyl, C$_{1-6}$alkoxy, carbocyclyl, and heterocyclyl, wherein each C$_{1-6}$alkyl, C$_{2-6}$alkenyl, C$_{2-6}$alkynyl, C$_{1-4}$alkoxy, carbocyclyl, and heterocyclyl is optionally substituted with one or more groups independently selected from oxo, halo, amino, hydroxyl, C$_{1-6}$alkoxy, carbocyclyl, heterocyclyl, and C$_1$-C$_6$ alkyl that is optionally substituted with one or more groups independently selected from oxo and halo; or two R$^d$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo; and each R$^e$ of Formula (II) is independently selected from hydrogen, C$_{1-4}$alkyl, C$_{2-4}$alkenyl, C$_{2-4}$alkynyl, and C$_{2-5}$cycloalkyl, wherein each C$_{1-4}$alkyl, C$_{2-4}$alkenyl, C$_{2-4}$alkynyl, and C$_{2-5}$cycloalkyl is optionally substituted with one or more groups independently selected from oxo, halo, amino, hydroxyl, C$_{1-3}$alkoxy, and C$_1$-C$_3$ alkyl that is optionally substituted with one or more groups independently selected from halo; provided that R¹ is not unsubstituted phenyl, when R² is carboxymethyl or 2-carboxyethyl.

Compounds of Formula (I)

Another aspect includes a compound of formula (I):

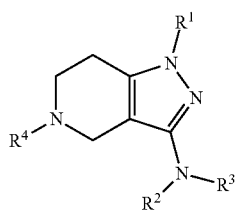

(I)

or a salt thereof, wherein:

R¹ is $C_{1-12}$alkyl, $C_{2-12}$alkenyl, $C_{2-12}$alkynyl, 3-12 membered carbocycle, and 3-12 membered heterocycle, wherein each $C_{1-12}$alkyl, $C_{2-12}$alkenyl, $C_{2-12}$alkynyl, 3-12 membered carbocycle, and 3-12 membered heterocycle of R¹ is optionally substituted with one or more groups $R^b$;

R² is selected from $C_6$-$C_{20}$ aryl, $C_1$-$C_{20}$ heteroaryl, —($C_6$-$C_{20}$ aryl)-($C_1$-$C_{20}$ heteroaryl), —($C_1$-$C_{20}$ heteroaryl)-($C_6$-$C_{20}$ aryl), and —($C_1$-$C_{20}$ heteroaryl)-($C_1$-$C_{20}$ heteroaryl), wherein each $C_6$-$C_{20}$ aryl, $C_1$-$C_{20}$ heteroaryl, —($C_6$-$C_{20}$ aryl)-($C_1$-$C_{20}$ heteroaryl) and —($C_1$-$C_{20}$ heteroaryl)-($C_1$-$C_{20}$ heteroaryl) is independently optionally substituted with one or more substituent groups independently selected from $R^c$, oxo, —F, —Cl, —Br, —I, —NO₂, —N($R^a$)₂, —CN, —C(O)—N($R^a$)₂, —S(O)—N($R^a$)₂, —S(O)₂—N($R^a$)₂, —O—$R^a$, —S—$R^a$, —O—C(O)—$R^a$, —O—C(O)—O—$R^a$, —C(O)—$R^a$, —C(O)—O—$R^a$, —S(O)—$R^a$, —S(O)₂—$R^a$, —O—C(O)—N($R^a$)₂, —N($R^a$)—C(O)—O$R^a$, —N($R^a$)—C(O)—N($R^a$)₂, —N($R^a$)—C(O)—$R^a$, —N($R^a$)—S(O)—$R^a$, —N($R^a$)—S(O)₂—$R^a$, —N($R^a$)—S(O)—N($R^a$)₂, and —N($R^a$)—S(O)₂—N($R^a$)₂;

R³ is $C_{1-12}$alkyl, $C_{2-12}$alkenyl, $C_{2-12}$alkynyl, 3-12 membered carbocycle, and 3-12 membered heterocycle, wherein each $C_{1-12}$alkyl, $C_{2-12}$alkenyl, $C_{2-12}$alkynyl, 3-12 membered carbocycle, and 3-12 membered heterocycle of R³ is optionally substituted with one or more groups $R^e$; or R² and R³ taken together with the nitrogen to which they are attached form a 3-12 membered heterocycle that is optionally substituted with one or more groups $R^e$;

R⁴ is $C_{1-4}$alkyl, $C_{2-4}$alkenyl, $C_{2-4}$alkynyl, 3-5 membered carbocycle, 3-5 membered heterocycle, —C(O)—N($R^h$)₂, —S(O)—N($R^h$)₂, —S(O)₂—N($R^h$)₂, —C(O)—$R^h$, —C(O)—O—$R^h$, —S(O)—$R^h$, or —S(O)₂—$R^h$, wherein any $C_{1-6}$alkyl, $C_{2-6}$alkenyl, $C_{2-6}$alkynyl, 3-5 membered carbocycle, and 3-5 membered heterocycle is optionally substituted with one or more substituent groups independently selected from —F, —Cl, —Br, —I, 3-5 membered carbocycle, —C(O)—N($R^h$)₂, —S(O)—N($R^h$)₂, —S(O)₂—N($R^h$)₂, —O—$R^h$, —S—$R^h$, —O—C(O)—$R^h$, —O—C(O)—O—$R^h$, —C(O)—$R^h$, —C(O)—O—$R^h$, —S(O)—$R^h$, —S(O)₂—$R^h$, —O—C(O)—N($R^h$)₂, —N($R^h$)—C(O)—O$R^h$, —N($R^h$)—C(O)—N($R^h$)₂, —N($R^h$)—C(O)—$R^a$, —N($R^h$)—S(O)—$R^h$, —N($R^h$)—S(O)₂—$R^h$, —N($R^h$)—S(O)—N($R^h$)₂, and —N($R^h$)—S(O)₂—N($R^h$)₂;

each $R^a$ is independently selected from hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from oxo, halo, amino, hydroxyl, $C_{1-6}$alkoxy, carbocyclyl, heterocyclyl, and $C_1$-$C_6$ alkyl that is optionally substituted with one or more groups independently selected from oxo and halo; or two $R^a$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^b$ is independently selected from oxo, $C_{1-6}$alkyl, $C_{2-6}$alkenyl, $C_{2-6}$alkynyl, carbocyclyl, heterocyclyl, aryl, heteroaryl, —F, —Cl, —Br, —I, —NO₂, —N($R^c$)₂, —CN, —C(O)—N($R^c$)₂, —S(O)—N($R^c$)₂, —S(O)₂—N($R^c$)₂, —O—$R^c$, —S—$R^c$, —O—C(O)—$R^c$, —O—C(O)—$R^c$, —C(O)—$R^c$, —C(O)—O—$R^c$, —S(O)—$R^c$, —S(O)₂—$R^c$, —O—C(O)—N($R^c$)₂, —N($R^c$)—C(O)—O$R^c$, —N($R^c$)—C(O)—N($R^c$)₂, —N($R^c$)—C(O)—$R^c$, —N($R^c$)—S(O)—$R^c$, —N($R^c$)—S(O)₂—$R^c$, —N($R^c$)—S(O)—N($R^c$)₂, and —N($R^c$)—S(O)₂—N($R^c$)₂, wherein any $C_{1-6}$alkyl, $C_{2-6}$alkenyl, $C_{2-6}$alkynyl, carbocyclyl, heterocyclyl, aryl, and heteroaryl is optionally substituted with one or more groups independently selected from oxo, halo, —NO₂, —N($R^c$)₂, —CN, —C(O)—N($R^c$)₂, —S(O)—N($R^c$)₂, —S(O)₂—N($R^c$)₂, —O—$R^c$, —S—$R^c$, —O—C(O)—$R^c$, —C(O)—$R^c$, —C(O)—O—$R^c$, —S(O)—$R^c$, —S(O)₂—$R^c$, —C(O)—N($R^c$)₂, —N($R^c$)—C(O)—$R^c$, —N($R^c$)—S(O)—$R^c$, —N($R^c$)—S(O)₂—$R^c$ and $C_{1-6}$alkyl that is optionally substituted with one or more groups independently selected from oxo and halo;

each $R^c$ is independently selected from hydrogen, $C_{1-6}$alkyl, $C_{2-6}$alkenyl, $C_{2-6}$alkynyl, carbocyclyl, and heterocyclyl, wherein any $C_{1-6}$alkyl, $C_{2-6}$alkenyl, $C_{2-6}$alkynyl, carbocyclyl, and heterocyclyl is optionally substituted with one or more groups independently selected from oxo, carbocyclyl, heterocyclyl, halo, —NO₂, —N($R^d$)₂, —CN, —C(O)—N($R^d$)₂, —S(O)—N($R^d$)₂, —S(O)₂—N($R^d$)₂, —O—$R^d$, —S—$R^d$, —O—C(O)—$R^d$, —C(O)—$R^d$, —C(O)—O—$R^d$, —S(O)—$R^d$, —S(O)₂—$R^d$, —C(O)—N($R^d$)₂, —N($R^d$)—C(O)—$R^d$, —N($R^d$)—S(O)—$R^d$, N($R^d$)—S(O)₂—$R^d$, and $C_{1-6}$alkyl, which carbocyclyl and $C_{1-6}$alkyl are optionally substituted with one or more groups independently selected from oxo, halo, $C_{1-6}$alkyl, cyano, —N($R^d$)₂, —O—$R^d$, heterocyclyl, and carbocyclyl that is optionally substituted with one or more groups independently selected from halo, and $C_{1-6}$alkyl;

each $R^d$ is independently selected from hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from oxo, halo, amino, hydroxyl, $C_{1-6}$alkoxy, carbocyclyl, heterocyclyl, and $C_1$-$C_6$ alkyl that is optionally substituted with one or more groups independently selected from oxo and halo; or two $R^d$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^e$ is independently selected from oxo, $C_{1-6}$alkyl, $C_{2-6}$alkenyl, $C_{2-6}$alkynyl, carbocyclyl, heterocyclyl, aryl, heteroaryl, —F, —Cl, —Br, —I, —NO₂, —N($R^f$)₂, —CN, —C(O)—N($R^f$)₂, —S(O)—N($R^f$)₂, —S(O)₂—N($R^f$)₂, —O—$R^f$, —S—$R^f$, —O—C(O)—$R^f$, —O—C(O)—O—$R^f$, —C(O)—$R^f$, —C(O)—O—$R^f$, —S(O)—$R^f$, —S(O)₂—$R^f$, —O—C(O)—N($R^f$)₂, —N($R^f$)—C(O)—O$R^f$, —N($R^f$)—C(O)—N($R^f$)₂, —N($R^f$)—C(O)—$R^f$, —N($R^f$)—S(O)—$R^f$, —N($R^f$)—S(O)₂—$R^f$, —N($R^f$)—S(O)—N($R^f$)₂, and —N(R$^f$)—S(O)$_2$—N(R$^f$)$_2$, wherein any C$_{1-6}$alkyl, C$_{2-6}$alkenyl, C$_{2-6}$alkynyl, carbocyclyl, heterocyclyl, aryl, and heteroaryl is optionally substituted with one or more groups independently selected from oxo, halo, —NO$_2$, —N(R$^f$)$_2$, —CN, —C(O)—N(R$^f$)$_2$, —S(O)—N(R$^f$)$_2$, —S(O)$_2$—N(R$^f$)$_2$, —O—R$^f$, —S—R$^f$, —O—C(O)—R$^f$, —C(O)—R$^f$, —C(O)—O—R$^f$, —S(O)—R$^f$, —S(O)$_2$—R$^f$, —C(O)—N(R$^f$)$_2$, —N(R$^f$)—C(O)—R$^f$, —N(R$^f$)—S(O)—R$^f$, —N(R$^f$)—S(O)$_2$—R$^f$, carbocycle, and C$_{1-6}$alkyl that is optionally substituted with one or more groups independently selected from oxo and halo;

each R$^f$ is independently selected from hydrogen, C$_{1-6}$alkyl, C$_{2-6}$alkenyl, C$_{2-6}$alkynyl, carbocyclyl, and heterocyclyl, wherein any C$_{1-6}$alkyl, C$_{2-6}$alkenyl, C$_{2-6}$alkynyl, carbocyclyl, and heterocyclyl is optionally substituted with one or more groups independently selected from oxo, carbocyclyl, heterocyclyl, halo, —NO$_2$, —N(R$^g$)$_2$, —CN, —C(O)—N(R$^g$)$_2$, —S(O)—N(R$^g$)$_2$, —S(O)$_2$—N(R$^g$)$_2$, —O—R$^g$, —S—R$^g$, —O—C(O)—R$^g$, —C(O)—R$^g$, —C(O)—O—R$^g$, —S(O)—R$^g$, —S(O)$_2$—R$^g$, —C(O)—N(R$^g$)$_2$, —N(R$^g$)—C(O)—R$^g$, —N(R$^g$)—S(O)—R$^g$, N(R$^g$)—S(O)$_2$—R$^g$, and C$_{1-6}$alkyl, which carbocyclyl and C$_{1-6}$alkyl are optionally substituted with one or more groups independently selected from oxo, halo, C$_{1-6}$alkyl, cyano, —N(R$^g$)$_2$, —O—R$^g$, heterocyclyl, and carbocyclyl that is optionally substituted with one or more groups independently selected from halo, and C$_{1-6}$alkyl;

each R$^g$ is independently selected from hydrogen, C$_{1-6}$alkyl, C$_{2-6}$alkenyl, C$_{2-6}$alkynyl, C$_{1-6}$alkoxy, carbocyclyl, and heterocyclyl, wherein each C$_{1-6}$alkyl, C$_{2-6}$alkenyl, C$_{2-6}$alkynyl, C$_{1-6}$alkoxy, carbocyclyl, and heterocyclyl is optionally substituted with one or more groups independently selected from oxo, halo, amino, hydroxyl, C$_{1-6}$alkoxy, carbocyclyl, heterocyclyl, and C$_1$-C$_6$ alkyl that is optionally substituted with one or more groups independently selected from oxo and halo; or two R$^g$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo; and each R$^h$ is independently selected from hydrogen, C$_{1-4}$alkyl, C$_{2-4}$alkenyl, C$_{2-4}$alkynyl, and C$_{2-5}$cycloalkyl, wherein each C$_{1-4}$alkyl, C$_{2-4}$alkenyl, C$_{2-4}$alkynyl, and C$_{2-5}$cycloalkyl is optionally substituted with one or more groups independently selected from oxo, halo, amino, hydroxyl, C$_{1-3}$alkoxy, and C$_1$-C$_3$ alkyl that is optionally substituted with one or more groups independently selected from halo.

Compounds of Formula (II)

Another aspect includes a compound of formula (II):

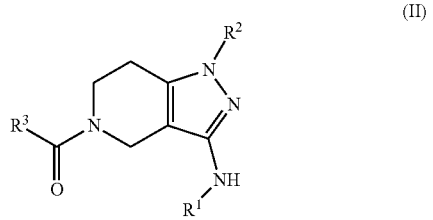

(II)

or a salt thereof, wherein:

R$^1$ is selected from C$_6$-C$_{20}$ aryl, C$_1$-C$_{20}$ heteroaryl, —(C$_6$-C$_{20}$ aryl)-(C$_1$-C$_{20}$ heteroaryl), and —(C$_1$-C$_{20}$ heteroaryl)-(C$_1$-C$_{20}$ heteroaryl), wherein each C$_6$-C$_{20}$ aryl, C$_1$-C$_{20}$ heteroaryl, —(C$_6$-C$_{20}$ aryl)-(C$_1$-C$_{20}$ heteroaryl) and —(C$_1$-C$_{20}$ heteroaryl)-(C$_1$-C$_{20}$ heteroaryl) is optionally substituted with one or more substituent groups independently selected from R$^c$, oxo, —F, —Cl, —Br, —I, —NO$_2$, —N(R$^a$)$_2$, —CN, —C(O)—N(R$^a$)$_2$, —S(O)—N(R$^a$)$_2$, —S(O)$_2$—N(R$^a$)$_2$, —O—R$^a$, —S—R$^a$, —O—C(O)—R$^a$, —O—C(O)—O—R$^a$, —C(O)—R$^a$, —C(O)—O—R$^a$, —S(O)—R$^a$, —S(O)$_2$—R$^a$, —O—C(O)—N(R$^a$)$_2$, —N(R$^a$)—C(O)—OR$^a$, —N(R$^a$)—C(O)—N(R$^a$)$_2$, —N(R$^a$)—C(O)—R$^a$, —N(R$^a$)—S(O)—R$^a$, —N(R$^a$)—S(O)$_2$—R$^a$, —N(R$^a$)—S(O)—N(R$^a$)$_2$, and —N(R$^a$)—S(O)$_2$—N(R$^a$)$_2$;

R$^2$ is C$_{1-12}$alkyl, C$_{2-12}$alkenyl, C$_{2-12}$alkynyl, 3-12 membered carbocycle, and 3-12 membered heterocycle, wherein each C$_{1-12}$alkyl, C$_{2-12}$alkenyl, C$_{2-12}$alkynyl, 3-12 membered carbocycle, and 3-12 membered heterocycle of R$^2$ is optionally substituted with one or more groups R$^b$;

R$^3$ is C$_{1-4}$alkyl, C$_{2-4}$alkenyl, C$_{2-4}$alkynyl, 3-5 membered carbocycle, 3-5 membered heterocycle, —C(O)—N(R$^e$)$_2$, —S(O)—N(R$^e$)$_2$, —S(O)$_2$—N(R$^e$)$_2$, —C(O)—R$^e$, —C(O)—O—R$^e$, —S(O)—R$^e$, or —S(O)$_2$—R$^e$, wherein any C$_{1-4}$alkyl, C$_{2-4}$alkenyl, C$_{2-4}$alkynyl, 3-5 membered carbocycle, and 3-5 membered heterocycle is optionally substituted with one or more substituent groups independently selected from —F, —Cl, —Br, —I, 3-5 membered carbocycle, —C(O)—N(R$^e$)$_2$, —S(O)—N(R$^e$)$_2$, —S(O)$_2$—N(R$^e$)$_2$, —O—R$^e$, —S—R$^e$, —O—C(O)—R$^e$, —O—C(O)—O—R$^e$, —C(O)—R$^e$, —C(O)—O—R$^e$, —S(O)—R$^e$, —S(O)$_2$—R$^e$, —O—C(O)—N(R$^e$)$_2$, —N(R$^e$)—C(O)—OR$^e$, —N(R$^e$)—C(O)—N(R$^e$)$_2$, —N(R$^e$)—C(O)—R$^e$, —N(R$^e$)—S(O)—R$^e$, —N(R$^e$)—S(O)$_2$—R$^e$, —N(R$^e$)—S(O)—N(R$^e$)$_2$, and —N(R$^e$)—S(O)$_2$—N(R$^e$)$_2$;

each R$^a$ is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, and heterocyclyl is optionally substituted with one or more groups independently selected from oxo, halo, amino, hydroxyl, C$_{1-6}$alkoxy, carbocyclyl, heterocyclyl, and C$_1$-C$_6$ alkyl that is optionally substituted with one or more groups independently selected from oxo and halo; or two R$^a$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^b$ is independently selected from oxo, C$_{1-6}$alkyl, C$_{2-6}$alkenyl, C$_{2-6}$alkynyl, carbocyclyl, heterocyclyl, aryl, heteroaryl, —F, —Cl, —Br, —I, —NO$_2$, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—R$^c$, —O—C(O)—O—R$^c$, —C(O)—R$^c$, —C(O)—O—R$^c$, —S(O)—R$^c$, —S(O)$_2$—R$^c$, —O—C(O)—N(R$^c$)$_2$, —N(R$^c$)—C(O)—OR$^c$, —N(R$^c$)—C(O)—N(R$^c$)$_2$, —N(R$^c$)—C(O)—R$^c$, —N(R$^c$)—S(O)—R$^c$, —N(R$^c$)—S(O)$_2$—R$^c$, —N(R$^c$)—S(O)—N(R$^c$)$_2$, and —N(R$^c$)—S(O)$_2$—N(R$^c$)$_2$, wherein any C$_{1-6}$alkyl, C$_{2-6}$alkenyl, C$_{2-6}$alkynyl, carbocyclyl, heterocyclyl, aryl, and heteroaryl is optionally substituted with one or more groups independently selected from oxo, halo, —NO$_2$, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—R$^c$, —C(O)—R$^c$, —C(O)—O—R$^c$, —S(O)—R$^c$, —S(O)$_2$—R$^c$, —C(O)—N(R$^c$)$_2$, —N(R$^c$)—C(O)—R$^c$, —N(R$^c$)—S(O)—R$^c$, —N(R$^c$)—S(O)$_2$—R$^c$ and C$_{1-6}$alkyl that is optionally substituted with one or more groups independently selected from oxo and halo;

each R$^c$ is independently selected from hydrogen, C$_{1-6}$alkyl, C$_{2-6}$alkenyl, C$_{2-6}$alkynyl, carbocyclyl, and heterocyclyl, wherein any C$_{1-6}$alkyl, C$_{2-6}$alkenyl, C$_{2-6}$alkynyl, carbocyclyl, and heterocyclyl is optionally substituted with one or more groups independently selected from oxo, carbocyclyl, heterocyclyl, halo, —NO$_2$, —N(R$^d$)$_2$, —CN, —C(O)—N(R$^d$)$_2$, —S(O)—N(R$^d$)$_2$, —S(O)$_2$—N(R$^d$)$_2$, —O—R$^d$, —S—R$^d$, —O—C(O)—R$^d$, —C(O)—R$^d$, —C(O)—O—R$^d$, —S(O)—R$^d$, —S(O)$_2$—R$^d$, —C(O)—N(R$^d$)$_2$, —N(R$^d$)—C(O)—R$^d$, —N(R$^d$)—S(O)—R$^d$, N(R$^d$)—S(O)$_2$—R$^d$, and C$_{1-6}$alkyl, which carbocyclyl and C$_{1-6}$alkyl are optionally substituted with one or more groups independently selected from oxo, halo, C$_{1-6}$alkyl, cyano, —N(R$^d$)$_2$, —O—R$^d$, heterocyclyl, and carbocyclyl that is optionally substituted with one or more groups independently selected from halo, and C$_{1-6}$alkyl;

each R$^d$ is independently selected from hydrogen, C$_{1-6}$alkyl, C$_{2-6}$alkenyl, C$_{2-6}$alkynyl, C$_{1-6}$alkoxy, carbocyclyl, and heterocyclyl, wherein each C$_{1-6}$alkyl, C$_{2-6}$alkenyl, C$_{2-6}$alkynyl, C$_{1-6}$alkoxy, carbocyclyl, and heterocyclyl is optionally substituted with one or more groups independently selected from oxo, halo, amino, hydroxyl, C$_{1-6}$alkoxy, carbocyclyl, heterocyclyl, and C$_1$-C$_6$ alkyl that is optionally substituted with one or more groups independently selected from oxo and halo; or two R$^d$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo; and each R$^e$ is independently selected from hydrogen, C$_{1-4}$alkyl, C$_{2-4}$alkenyl, C$_{2-4}$alkynyl, and C$_{2-5}$cycloalkyl, wherein each C$_{1-4}$alkyl, C$_{2-4}$alkenyl, C$_{2-4}$alkynyl, and C$_{2-5}$cycloalkyl is optionally substituted with one or more groups independently selected from oxo, halo, amino, hydroxyl, C$_{1-3}$alkoxy, and C$_1$-C$_3$ alkyl that is optionally substituted with one or more groups independently selected from halo.

Another aspect includes a composition comprising a compound of formula (I) or formula (II) or a pharmaceutically acceptable salt thereof, and a pharmaceutically acceptable adjuvant, carrier, or vehicle.

Another aspect includes a method for treating a CBP and/or EP300-mediated disorder in an animal comprising administering a compound of formula (I) or formula (II) or a pharmaceutically acceptable salt thereof to the animal.

Another aspect includes a method for treating a CBP and/or EP300-mediated disorder in an animal, wherein the disorder is cancer, comprising administering a compound of formula (I) or formula (II) or a pharmaceutically acceptable salt thereof to the animal.

Another aspect includes a method for treating a CBP and/or EP300-mediated disorder in an animal, wherein the disorder is a fibrotic disease, comprising administering a compound of formula (I) or formula (II) or a pharmaceutically acceptable salt thereof to the animal.

Another aspect includes a method for treating a CBP and/or EP300-mediated disorder in an animal, wherein the disorder is a fibrotic lung disease, comprising administering a compound of formula (I) or formula (II) or a pharmaceutically acceptable salt thereof to the animal.

Another aspect includes a compound of formula (I) or formula (II) or a pharmaceutically acceptable salt thereof for use in medical therapy.

Another aspect includes a compound of formula (I) or formula (II) or a pharmaceutically acceptable salt thereof for the prophylactic or therapeutic treatment of a CBP and/or EP300-mediated disorder.

Another aspect includes the use of a compound of formula (I) or formula (II) or a pharmaceutically acceptable salt thereof to prepare a medicament for treating a CBP and/or EP300-mediated disorder in an animal (e.g. a mammal such as a human).

Another aspect includes compounds for the study of CBP and/or EP300.

Another aspect includes synthetic intermediates and synthetic processes disclosed herein that are useful for preparing a compound of formula (I) or formula (II) or a salt thereof.

BRIEF DESCRIPTION OF THE FIGURES

FIGS. 2A-E. Gene expression as measured by qPCR in primary human fibroblasts treated with TGFβ and (FIG. 2A) an inhibitor of TGFβ receptor kinase activity or (FIGS. 2B-E) CBP/p300 inhibitors of Formula (I). Heat maps show TGFβ induction of each gene in the presence of CBP/p300 inhibitor after normalization to induction in the absence of inhibitor. Duplicate treatments are represented as two rows for each inhibitor concentration. CBP/p300 inhibitors reduce TGFβ-driven gene expression in a dose-dependent manner. Expression of Serpine1 is unchanged, indicating that TGFβ signaling is intact.

FIGS. 3A-B. Expression as measured by qPCR of (FIG. 3A) ACTA2 or (FIG. 3B) COL3A1 in primary human fibroblasts treated with TGFβ and CBP/p300 inhibitors of Formula (I). CBP/p300 inhibitors reduce TGFβ-driven ACTA2 and COL3A1 expression in a dose-dependent manner.

FIGS. 4A-E. Gene expression as measured by qPCR in primary human fibroblasts treated with TGFβ and (FIG. 4A) an inhibitor of TGFβ receptor kinase activity or (FIGS. 4B-E) CBP/p300 inhibitors of Formula (II). Heat maps show TGFβ induction of each gene in the presence of CBP/p300 inhibitor after normalization to induction in the absence of inhibitor. Duplicate treatments are represented as two rows for each inhibitor concentration. CBP/p300 inhibitors reduce TGFβ-driven gene expression in a dose-dependent manner. Expression of Serpine1 is unchanged, indicating that TGFβ signaling is intact.

FIGS. 5A-B. Expression as measured by qPCR of (FIG. 5A) ACTA2 or (FIG. 5B) COL3A1 in primary human fibroblasts treated with TGFβ and CBP/p300 inhibitors of Formula (II). CBP/p300 inhibitors reduce TGFβ-driven ACTA2 and COL3A1 expression in a dose-dependent manner.

FIGS. 6A-E. Gene expression as measured by qPCR in primary human fibroblasts treated with TGFβ and (FIG. 6A) an inhibitor of TGFβ receptor kinase activity or (FIGS. 6B-E) benzodiazepinone ("BZD") series CBP/p300 inhibitors. Heat maps show TGFβ induction of each gene in the presence of CBP/p300 inhibitor after normalization to induction in the absence of inhibitor. Duplicate treatments are represented as two rows for each inhibitor concentration. CBP/p300 inhibitors reduce TGFβ-driven gene expression in a dose-dependent manner. Expression of Serpine1 is unchanged, indicating that TGFβ signaling is intact.

FIGS. 7A-B. Expression as measured by qPCR of (FIG. 7A) ACTA2 or (FIG. 7B) COL3A1 in primary human fibroblasts treated with TGFβ and BZD series CBP/p300 inhibitors. CBP/p300 inhibitors reduce TGFβ-driven ACTA2 and COL3A1 expression in a dose-dependent manner.

FIGS. 8A-D. Gene expression as measured by qPCR in primary human fibroblasts treated with TGFβ and (FIG. 8A)

Figure 1:
FIG. 1. Outline of protocol for assaying CBP/p300 SMIs for inhibition of profibrotic gene induction by TGFβ.
Figure 1:
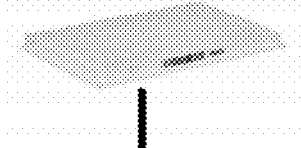
Figure 1:
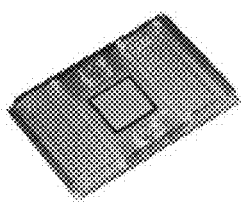

an inhibitor of TGFβ receptor kinase activity or (FIGS. 8B-D) heterocyclic CBP/p300 inhibitors. Heat maps show TGFβ induction of each gene in the presence of CBP/p300 inhibitor after normalization to induction in the absence of inhibitor. Duplicate treatments are represented as two rows for each inhibitor concentration. CBP/p300 inhibitors reduce TGFβ-driven gene expression in a dose-dependent manner. Expression of Serpine1 is unchanged, indicating that TGFβ signaling is intact.

FIGS. 9A-B. Expression as measured by qPCR of (FIG. 9A) ACTA2 or (FIG. 9B) COL3A1 in primary human fibroblasts treated with TGFβ and heterocyclic CBP/p300 inhibitors. CBP/p300 inhibitors reduce TGFβ-driven ACTA2 and COL3A1 expression in a dose-dependent manner.

FIGS. 10A-C. Gene expression as measured by qPCR in primary human fibroblasts treated with TGFβ and (FIG. 10A) an inhibitor of TGFβ receptor kinase activity or (FIGS. 10B-C) modified CBP/p300 inhibitors with decreased activity. Heat maps show TGFβ induction of each gene in the presence of CBP/p300 inhibitor after normalization to induction in the absence of inhibitor. Duplicate treatments are represented as two rows for each inhibitor concentration. After modification of CBP/p300 inhibitors, the effect on TGFβ-driven gene expression is either (B) eliminated or (C) reduced.

FIGS. 11A-B. Expression as measured by qPCR of (FIG. 11A) ACTA2 or (FIG. 11B) COL3A1 in primary human fibroblasts treated with TGFβ and modified CBP/p300 inhibitors with decreased activity. The effect on TGFβ-driven gene expression is reduced or eliminated.

FIGS. 12A-B. (FIG. 12A) Gene expression as measured by qPCR in the lung of mice treated with bleomycin to induce pulmonary fibrosis. Mice were treated with bleomycin plus vehicle or bleomycin plus the indicated dose of CBP/p300 inhibitor G0272 (compound of Formula II). Heat maps show expression of genes assayed, after normalization to GAPDH endogenous control, with each column representing one mouse. G0272 decreased the expression of fibrotic genes in the lung of mice treated with bleomycin to induce pulmonary fibrosis. (FIG. 12B) Collagen synthesis as measured by mass spectrometry of deuterated hydroxyproline in the lung of mice treated with bleomycin to induce pulmonary fibrosis. Mice were treated with bleomycin plus vehicle or indicated dose of CBP/p300 inhibitor G0272. G0272 decreased collagen synthesis in the lung of mice treated with bleomycin to induce pulmonary fibrosis.

FIGS. 13A-B. (FIG. 13A) Gene expression as measured by qPCR in the lung of mice treated with bleomycin to induce pulmonary fibrosis. Mice were treated with bleomycin plus vehicle or indicated dose of CBP/p300 inhibitor G5049 (compound of Formula (I)). Heat maps show expression of genes assayed, after normalization to GAPDH endogenous control, with each column representing one mouse. G5049 decreased the expression of fibrotic genes in mice treated with bleomycin to induce pulmonary fibrosis. (FIG. 13B) Collagen synthesis as measured by mass spectrometry of deuterated hydroxyproline in the lung of mice treated with bleomycin to induce pulmonary fibrosis. Mice were treated with bleomycin plus vehicle or indicated dose of CBP/p300 inhibitor G5049. G5049 decreased collagen synthesis in the lung of mice treated with bleomycin to induce pulmonary fibrosis.

FIGS. 14A-B. (FIG. 14A) Gene expression as measured by qPCR in the lung of mice in decreased collagen synthesis in the lung of mice treated with bleomycin to induce pulmonary fibrosis. Mice were treated with bleomycin plus vehicle or indicated dose of CBP/p300 inhibitor G3486. Heat maps show expression of genes assayed, after normalization to GAPDH endogenous control, with each column representing one mouse. G3486 decreased the expression of fibrotic genes in the lung of mice treated with bleomycin to induce pulmonary fibrosis. (FIG. 14B) Collagen synthesis as measured by mass spectrometry of deuterated hydroxyproline in the lung of mice treated with bleomycin to induce pulmonary fibrosis. Mice were treated with bleomycin plus vehicle or indicated dose of CBP/p300 inhibitor G3486. G3486 decreased collagen synthesis in the lung of mice treated with bleomycin to induce pulmonary fibrosis.

DETAILED DESCRIPTION

Compounds and Definitions

Definitions and terms are described in more detail below. Chemical elements are identified in accordance with the Periodic Table of the Elements, CAS version, *Handbook of Chemistry and Physics*, 75$^{th}$ Ed.

Unless otherwise stated, compounds of formula I or formula II include enantiomeric, diastereomeric and geometric (or conformational) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included. Additionally, unless otherwise stated, structures depicted herein are also meant to include compounds that differ only in the presence of one or more isotopically enriched atoms. For example, compounds of formula I or formula II, wherein the independent replacement or enrichment of one or more hydrogen by deuterium or tritium, carbon by $^{13}$C— or $^{14}$C carbon, nitrogen by a $^{15}$N nitrogen, sulfur by a $^{33}$S, $^{34}$S or $^{36}$S sulfur, oxygen by a $^{17}$O or $^{18}$O oxygen, or fluorine by a $^{18}$F are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically-enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N. Y, 1962); Wilen, S. H. *Tables of Resolving Agents and*

*Optical Resolutions* p. 268 (E. L. Eliel, Ed., Univ. of Notre Dame Press, Notre Dame, Ind. 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "oxo" refers to =O.

The term "unsaturated", as used herein, means that a moiety has one or more units of unsaturation.

The term "carbocyclyl" used alone or as part of a larger moiety, refers to a saturated, partially unsaturated, or aromatic ring system having 3 to 20 carbon atoms. In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In other embodiment, carbocyclyl, as a monocycle, includes $C_3$-$C_8$, $C_3$-$C_6$ or $C_5$-$C_6$. In another embodiment, carbocyclyl, as a bicycle, includes $C_7$-$C_{12}$. In another embodiment, carbocyclyl, as a spiro system, includes $C_5$-$C_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, for example bicyclo[2.2.1]heptane, bicyclo[2.2.2]octane, naphthalene, and bicyclo[3.2.2]nonane; and spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g. saturated or partially unsaturated mono-, bi-, or spiro-carbocycles).

The term "alkyl," as used herein, refers to a saturated linear or branched-chain hydrocarbon radical. In one embodiment, the alkyl radical is one to eighteen carbon atoms ($C_1$-$C_{18}$). In other embodiments, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$ or $C_1$-$C_3$. $C_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), heptyl, octyl, nonyl, decyl, undecyl and dodecyl.

The term "alkenyl," as used herein, denotes a linear or branched-chain hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl.

The term "alkoxy" refers to a linear or branched radical represented by the formula —OR in which R is alkyl, alkenyl, alkynyl or carbocycyl. Alkoxy groups include methoxy, ethoxy, propoxy, isopropoxy, and cyclopropoxy.

The term "haloalkyl," as used herein, refers to an alkyl as defined herein that is substituted with one or more (e.g. 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-20 carbon atoms ($C_6$-$C_{20}$ aryl). In another embodiment, aryl includes groups having 6-10 carbon atoms ($C_6$-$C_{10}$ aryl). Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In another embodiment aryl includes an aryl ring fused to one or more carbocyclic rings, such as indanyl, dihydrophenanthryl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. In some embodiments, the heteroaryl group is a $C_1$-$C_{20}$ heteroaryl group, where the heteroaryl ring contains 1-20 carbon atoms and the remaining ring atoms include one or more nitrogen, sulfur, or oxygen atoms. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, pyrid-2-yl N-oxide, and pyrazolo[4,3-c]pyridinyl. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono-, bi- or tri-cyclic.

As used herein, the term "heterocyclyl" or "heterocycle" refers to a "carbocyclyl" as defined herein, wherein one or more (e.g. 1, 2, 3, or 4) carbon atoms have been replaced with a heteroatom (e.g. O, N, or S). In some embodiments, a heterocyclyl or heterocycle refers to a saturated ring system, such as a 3 to 12 membered saturated heterocyclyl ring system. In some embodiments, a heterocyclyl or heterocycle refers to a heteroaryl ring system, such as a 5 to 14 membered heteroaryl ring system. A heterocyclyl or heterocycle can optionally be substituted with one or more substituents independently selected from those defined herein.

In one example, heterocyclyl or heterocycle includes 3-12 ring atoms and includes monocycles, bicycles, tricycles and spiro ring systems, wherein the ring atoms are carbon, and one to five ring atoms is a heteroatom selected from nitrogen, sulfur or oxygen, which is independently optionally substituted by one or more groups. In one example, heterocyclyl or heterocycle includes 1 to 4 heteroatoms. In another example, heterocyclyl or heterocycle includes 3- to 7-membered monocycles having one or more heteroatoms selected from nitrogen, sulfur or oxygen. In another example, heterocyclyl or heterocycle includes 4- to 6-membered monocycles having one or more heteroatoms selected from nitrogen, sulfur or oxygen. In another example, heterocyclyl or heterocycle includes 3-membered monocycles. In another example, heterocyclyl or heterocycle includes 4-membered monocycles. In another example, heterocyclyl or heterocycle includes 5-6 membered monocycles. In one example, the heterocyclyl or heterocycle group includes 0 to 3 double bonds. Any nitrogen or sulfur heteroatom may optionally be oxidized (e.g. NO, SO, $SO_2$), and any nitrogen heteroatom may optionally be quaternized (e.g. $[NR_4]^+Cl^-$, $[NR_4]^+OH^-$). Example heterocyclyls or heterocycles include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls or heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls or heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls or heterocycles are benzoxazol-2-yl, benzthiazol-2-yl and benzimidazol-2-yl. Example 6-membered heterocyclyls or heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

The term "heterocyclyl" or "heterocycle" also includes groups in which a heterocyclyl is fused to one or more aryl, carbocyclyl, or heterocyclyl rings, where the radical or point of attachment is on the heterocyclyl ring. Nonlimiting examples include tetrahydroquinolinyl and tetrahydroisoquinolinyl.

As used herein, the term "partially unsaturated" refers to a ring moiety that includes at least one double or triple bond between ring atoms but the ring moiety is not aromatic.

As used herein, the term "inhibitor" refers to a compound that binds to and inhibits the bromodomain of CBP and/or EP300 with measurable affinity and activity. In certain embodiments, an inhibitor has an $IC_{50}$ or binding constant of less about 20 µM, less than about 1 µM, less than about 500 nM, less than about 100 nM, or less than about 10 nM.

The terms "measurable affinity" and "measurably inhibit," as used herein, refer to a measurable reduction in activity (e.g., reduction in recognition of lysine acetyl recognition of chromatin) of the bromodomain of CBP and/or EP300 between: (i) a sample comprising a compound of formula I or formula II or composition thereof and such bromodomain, and (ii) an equivalent sample comprising such bromodomain, in the absence of said compound, or composition thereof.

"Pharmaceutically acceptable salts" include both acid and base addition salts. It is to be understood that when a compound or Example herein is shown as a specific salt, the corresponding free-base, as well as other salts of the corresponding free-base (including pharmaceutically acceptable salts of the corresponding free-base) are contemplated.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound of the present invention that (i) treats the particular disease, condition or disorder, (ii) attenuates, ameliorates or eliminates one or more symptoms of the particular disease, condition, or disorder, or (iii) delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound of formula I or formula II is used to delay development of a disease or disorder or to slow the progression of a disease or disorder. Those individuals in need of treatment include those already with the condition or disorder as well as those prone to have the condition or disorder, (for example, through a genetic mutation or abberent expression of a gene or protein).

"CBP/EP300 bromodomain inhibitor" or "CBP and/or EP300 bromodomain inhibitor" refers to a compound that binds to the CBP bromodomain and/or EP300 bromodomain and inhibits and/or reduces a biological activity of CBP and/or EP300. In some embodiments, CBP/EP300 bromodomain inhibitor binds to the CBP and/or EP300 primarily (e.g., solely) through contacts and/or interactions with the CBP bromodomain and/or EP300 bromodomain. In some embodiments, CBP/EP300 bromodomain inhibitor binds to the CBP and/or EP300 through contacts and/or interactions with the CBP bromodomain and/or EP300 bromodomain as well as additional CBP and/or EP300 residues and/or domains. In some embodiments, CBP/EP300 bromodomain inhibitor substantially or completely inhibits the biological activity of the CBP and/or EP300. In some embodiments, the biological activity is binding of the bromodomain of CBP and/or EP300 to chromatin (e.g., histones associated with DNA) and/or another acetylated protein. In certain embodiments, the CBP/EP300 bromodomain inhibitor blocks CBP/EP300 activity so as to restore a functional response by T-cells (e.g., proliferation, cytokine production, target cell killing) from a dysfunctional state to antigen stimulation. In some embodiments, the CBP/EP300 bromodomain inhibitor binds to and inhibits CBP bromodomain. In some embodiments, the CBP/EP300 bromodomain inhibitor binds to and inhibits EP300 bromodomain.

As used herein, "a" or "an" means one or more, unless clearly indicated otherwise. As used herein, "another" means at least a second or more.

Exemplary Values for Compounds of Formula (I)

In certain embodiments of compounds of Formula (I), $R^1$ is $C_{1-12}$alkyl or 3-12 membered heterocycle, wherein each $C_{1-12}$alkyl and 3-12 membered heterocycle of $R^1$ is optionally substituted with one or more groups $R^b$.

In certain embodiments of compounds of Formula (I), $R^1$ is methyl or a 4-6 membered heterocycle, wherein each methyl and 4-6 membered heterocycle of $R^1$ is optionally substituted with one or more groups $R^b$.

In certain embodiments of compounds of Formula (I), $R^1$ is methyl, oxetanyl, tetrahydrofuranyl, tetrahydropyranyl, dioxothiolanyl, piperidyl, or pyrrolidinyl, wherein each methyl, oxetanyl, tetrahydrofuranyl, tetrahydropyranyl, dioxothiolanyl, piperidyl, or pyrrolidinyl of $R^1$ is optionally substituted with one or more groups $R^b$.

In certain embodiments of compounds of Formula (I), $R^1$ is methyl or cyclopropylmethyl.

In certain embodiments of compounds of Formula (I), $R^1$ is oxetanyl, tetrahydrofuranyl, tetrahydropyranyl, dioxothiolanyl, piperidyl, or pyrrolidinyl, and each $R^b$ is independently selected from methyl, acetyl, and oxo.

In certain embodiments of compounds of Formula (I), $R^1$ is cyclohexyl, aryl, oxetanyl, tetrahydrofuranyl, tetrahydropyranyl, dioxothiolanyl, dioxothianyl, piperidyl, pyrrolidinyl, pyridyl, or oxepanyl, and each $R^b$ is independently selected from oxo, $C_{1-6}$alkyl, $-OR^c$, $-C(O)-R^c$, oxetanyl, $-S(O)_2-R^c$, and $-CH_2CN$.

In certain embodiments of compounds of Formula (I), $R^1$ is selected from the group consisting of:

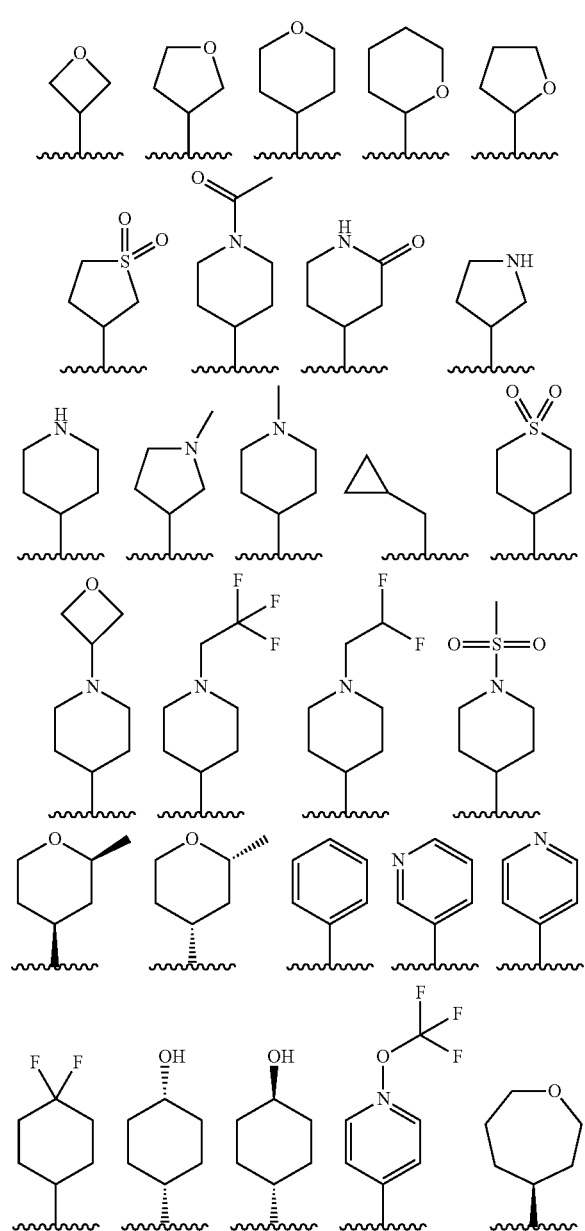

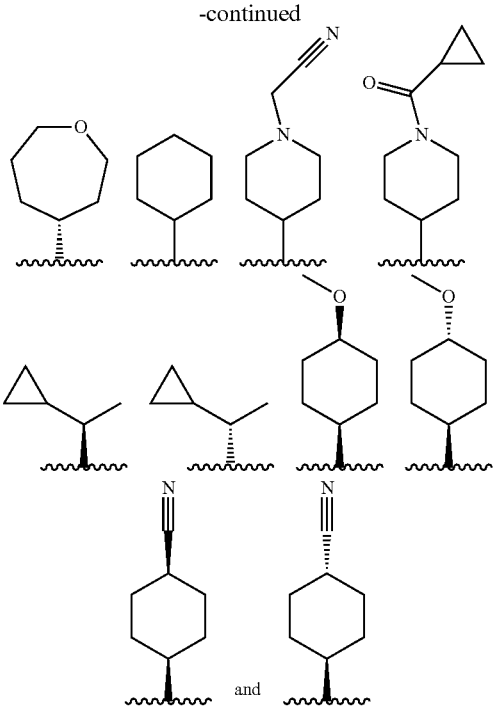

In certain embodiments of compounds of Formula (I), $R^1$ is:

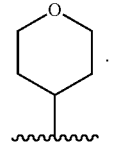

In certain embodiments of compounds of Formula (I), $R^2$ is $C_6$-$C_{20}$ aryl optionally substituted with one or more substituent groups independently selected from $R^c$, and $R^3$ is $C_{1-12}$alkyl or 3-12 membered carbocycle, wherein each $C_{1-12}$alkyl and 3-12 membered carbocycle of $R^3$ is optionally substituted with one or more groups $R^e$.

In certain embodiments of compounds of Formula (I), $R^2$ is phenyl optionally substituted with one or more substituent groups independently selected from $R^c$, and $R^3$ is methyl or phenyl, wherein each methyl and phenyl of $R^3$ is optionally substituted with one or more groups $R^e$.

In certain embodiments of compounds of Formula (I), $R^c$ is a 5-membered heterocyclyl optionally substituted with methyl; and $R^3$ is benzyl, methyl, cyanomethyl, or phenyl.

In certain embodiments of compounds of Formula (I), $R^c$ is pyrazolyl optionally substituted with methyl; and $R^3$ is benzyl, methyl, cyanomethyl, or phenyl.

In certain embodiments of compounds of Formula (I), $R^2$ and $R^3$ taken together with the nitrogen to which they are attached form a 3-12 membered heterocycle that is optionally substituted with one or more groups $R^e$.

In certain embodiments of compounds of Formula (I), $R^2$ and $R^3$ taken together with the nitrogen to which they are attached form a bicyclic heterocycle that is optionally substituted with one or more groups $R^e$.

In certain embodiments of compounds of Formula (I), $R^2$ and $R^3$ taken together with the nitrogen to which they are attached form a 9-12 membered bicyclic heterocycle that is optionally substituted with one or more groups $R^e$.

In certain embodiments of compounds of Formula (I), $R^2$ and $R^3$ taken together with the nitrogen to which they are attached form a 9- or 10-membered bicyclic heterocycle that is optionally substituted with one or more groups $R^e$.

In certain embodiments of compounds of Formula (I), $R^2$ and $R^3$ taken together with the nitrogen to which they are attached form a 9- or 10-membered bicyclic heterocycle that is optionally substituted with one or more groups $R^e$; and wherein the 9- or 10-membered bicyclic heterocycle comprises at least one aromatic ring. In certain embodiments the at least one aromatic ring is a benzo ring.

In certain embodiments of compounds of Formula (I), —NR$^2$R$^3$ taken together is selected from the group consisting of:

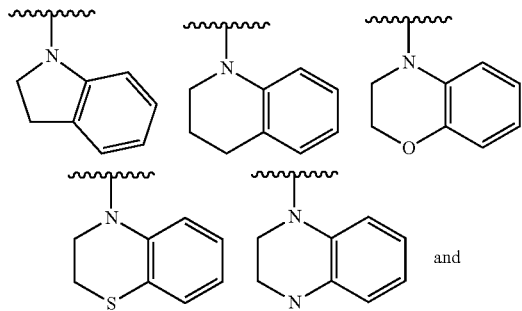

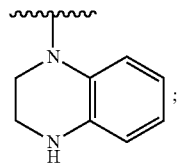

and wherein each —NR$^2$R$^3$ is optionally substituted with one or more groups $R^e$.

In certain embodiments of compounds of Formula (I), —NR$^2$R$^3$ taken together is selected from the group consisting of:

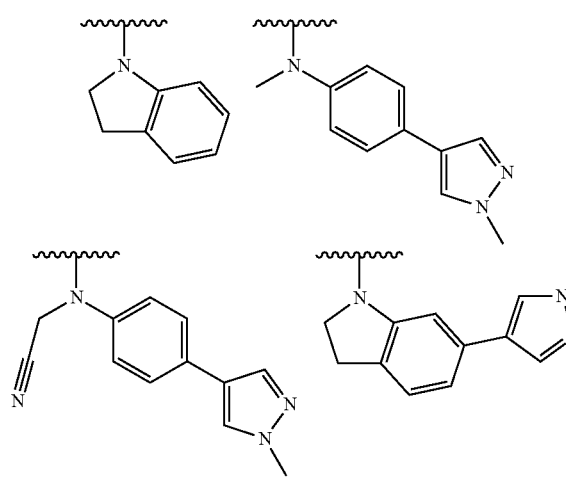

-continued

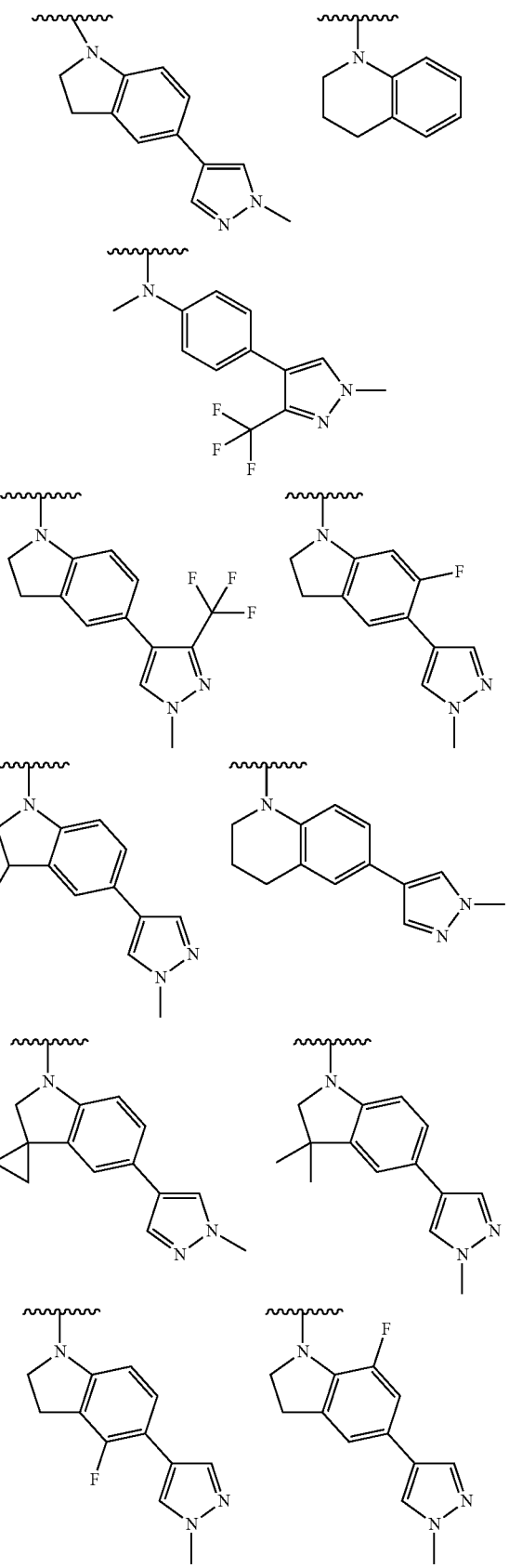

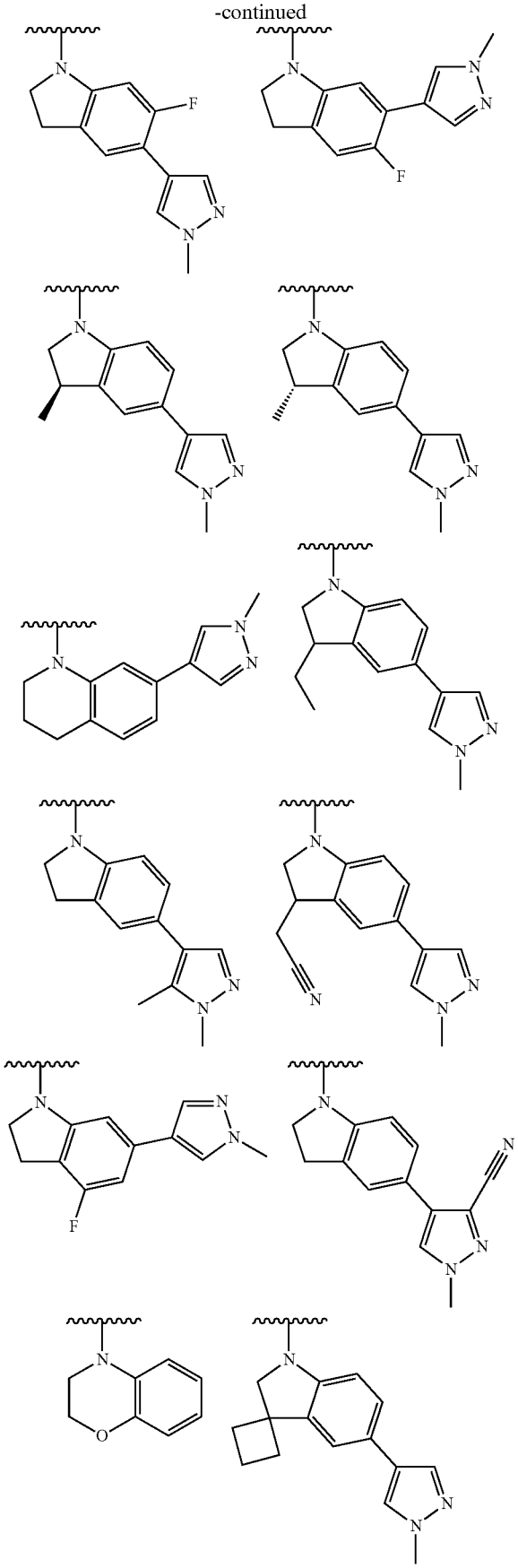
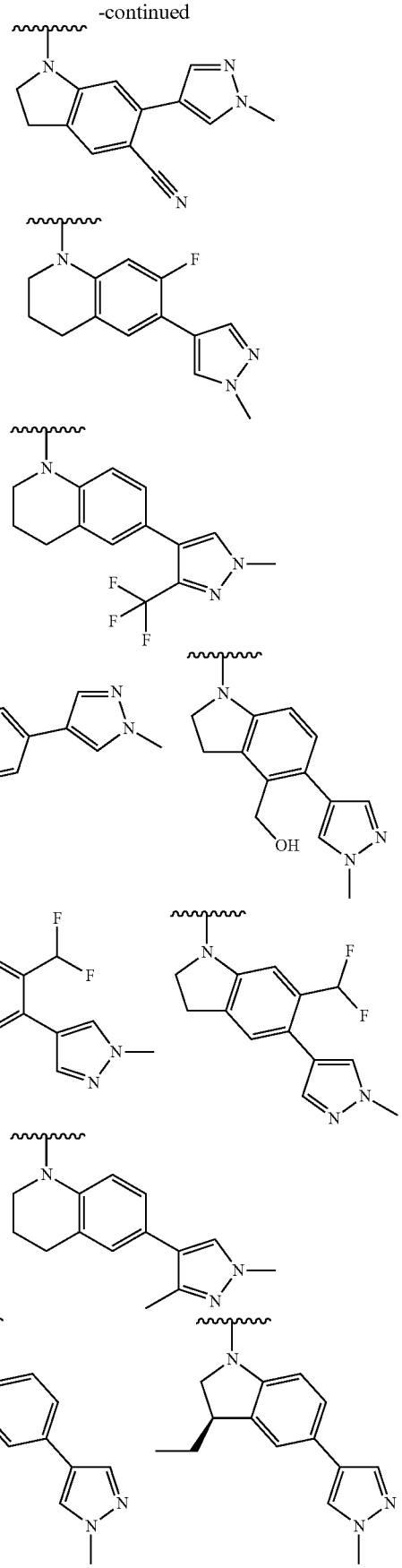

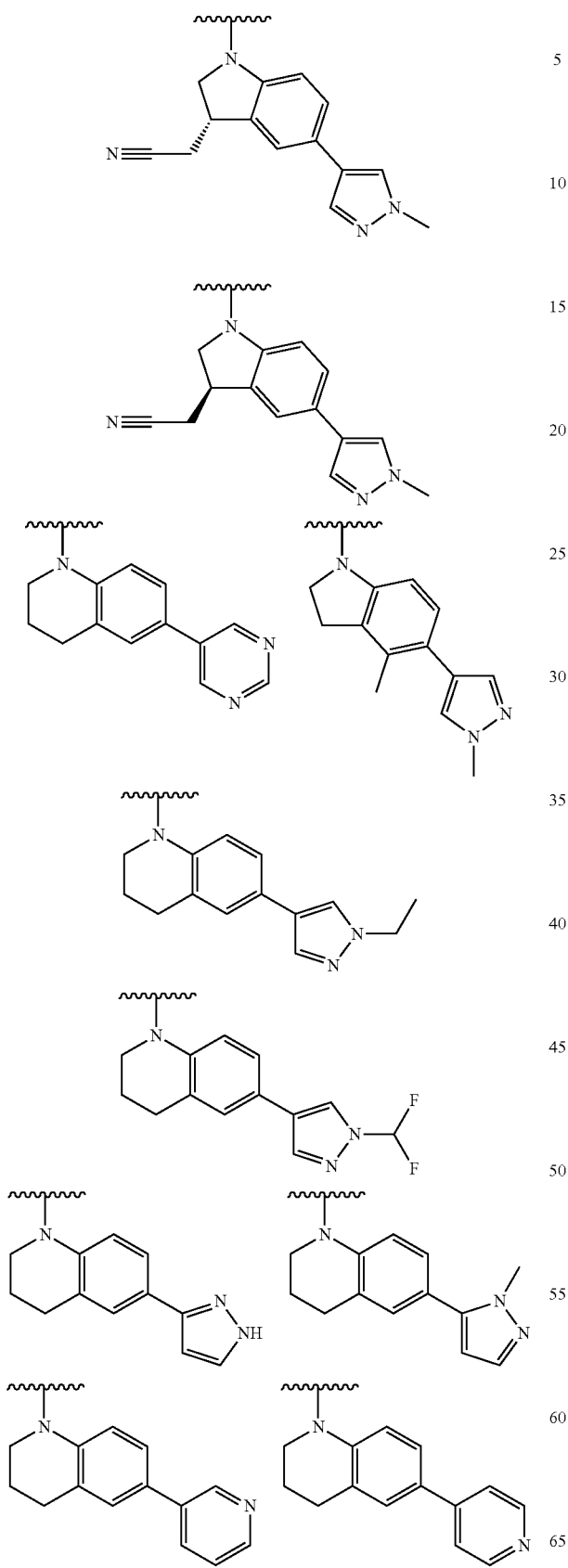
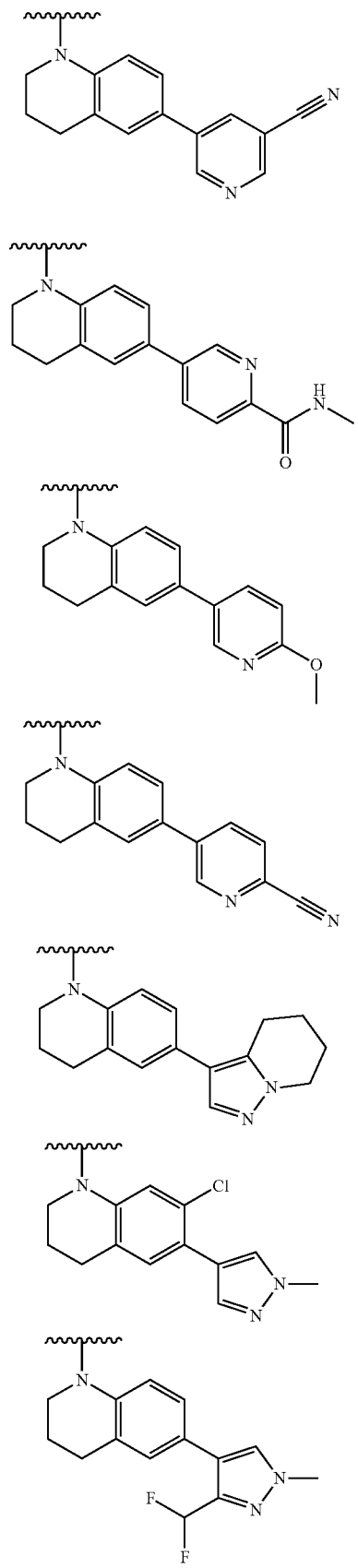

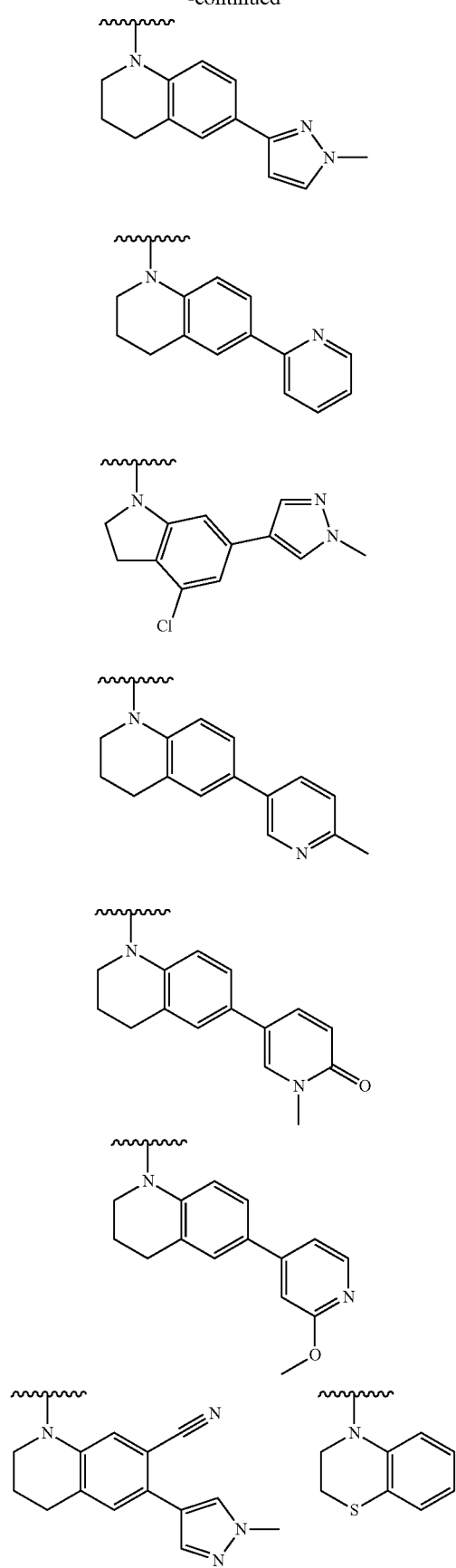
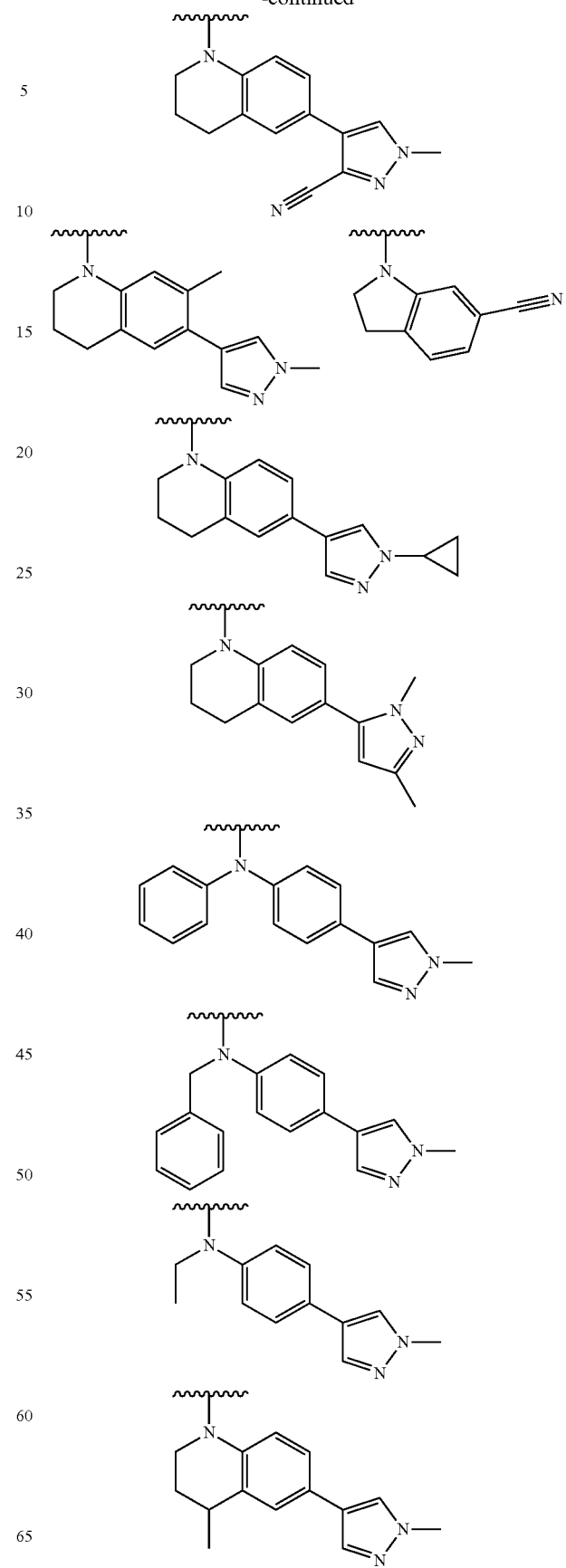

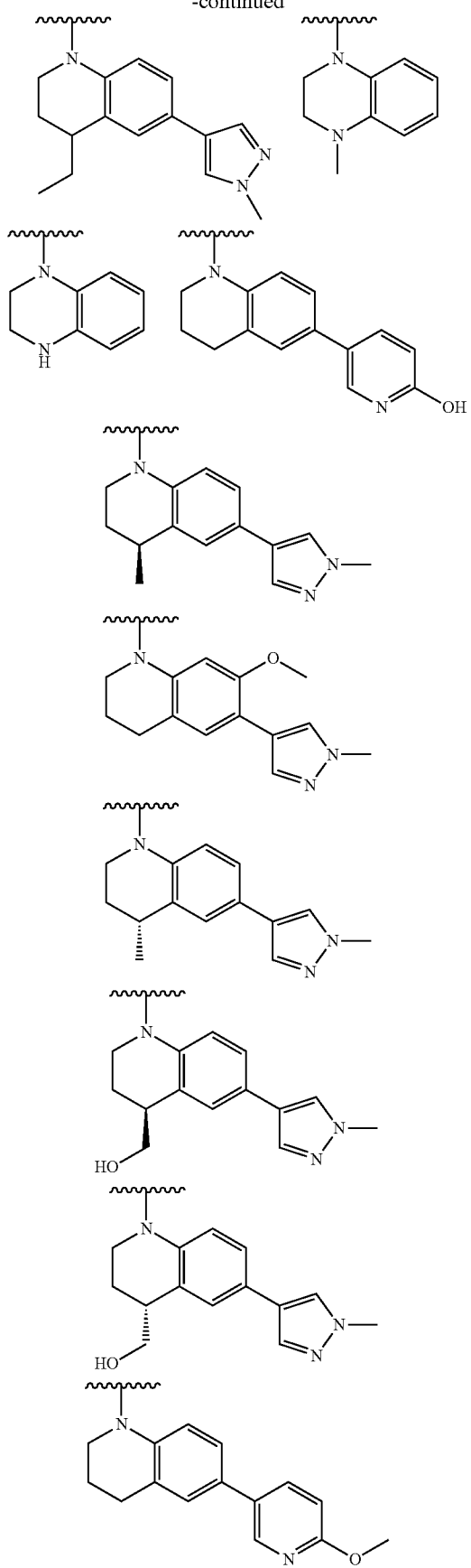
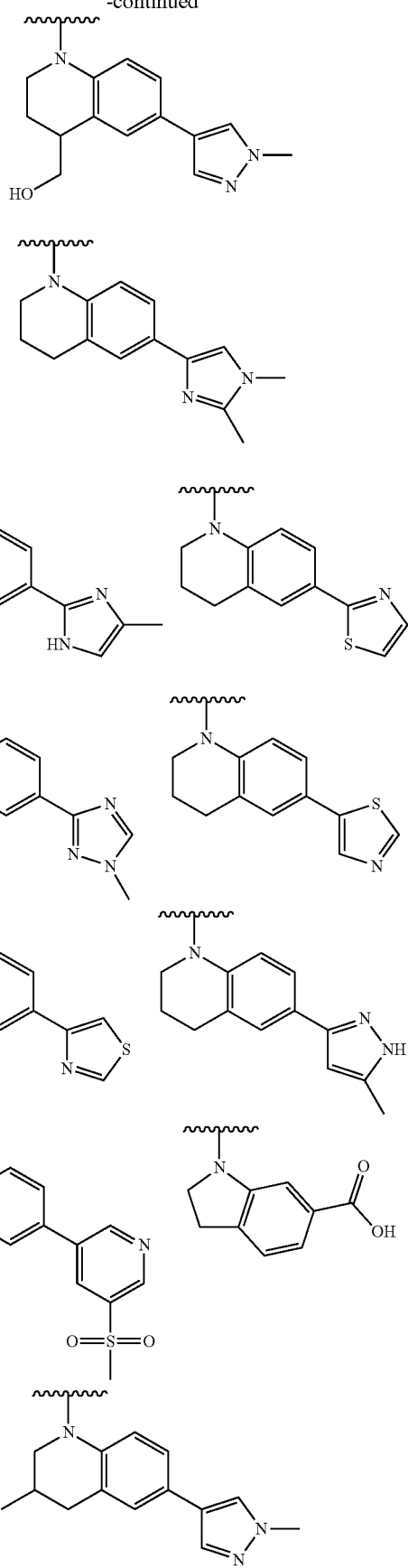

33
-continued
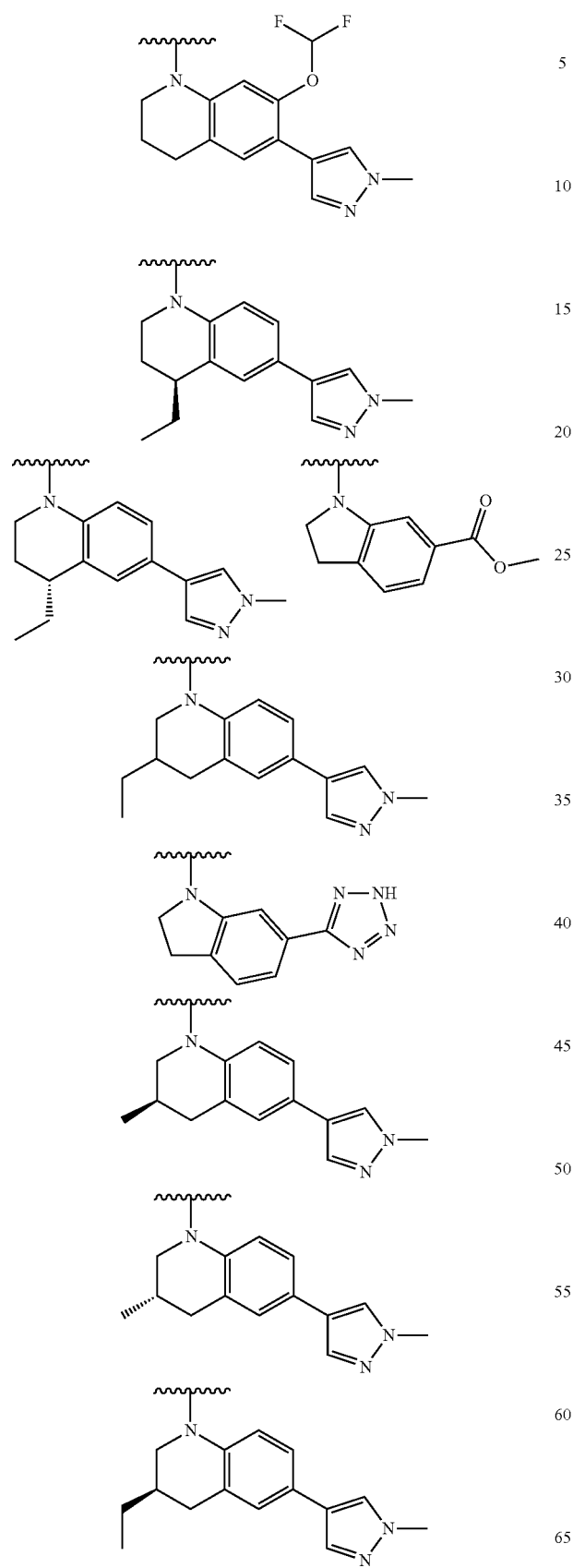
34
-continued
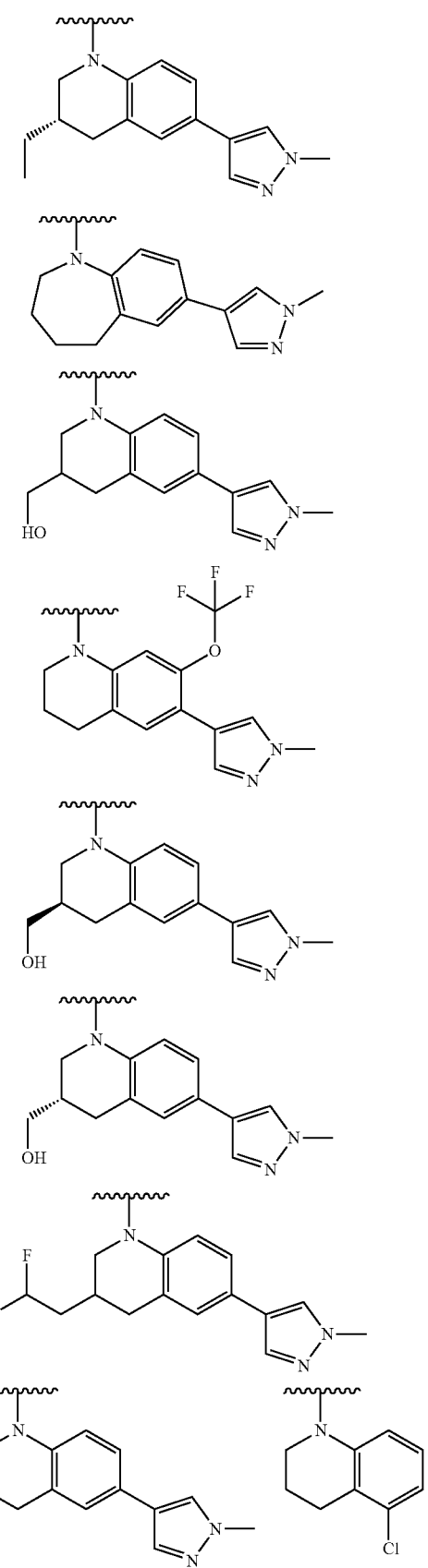

35
-continued
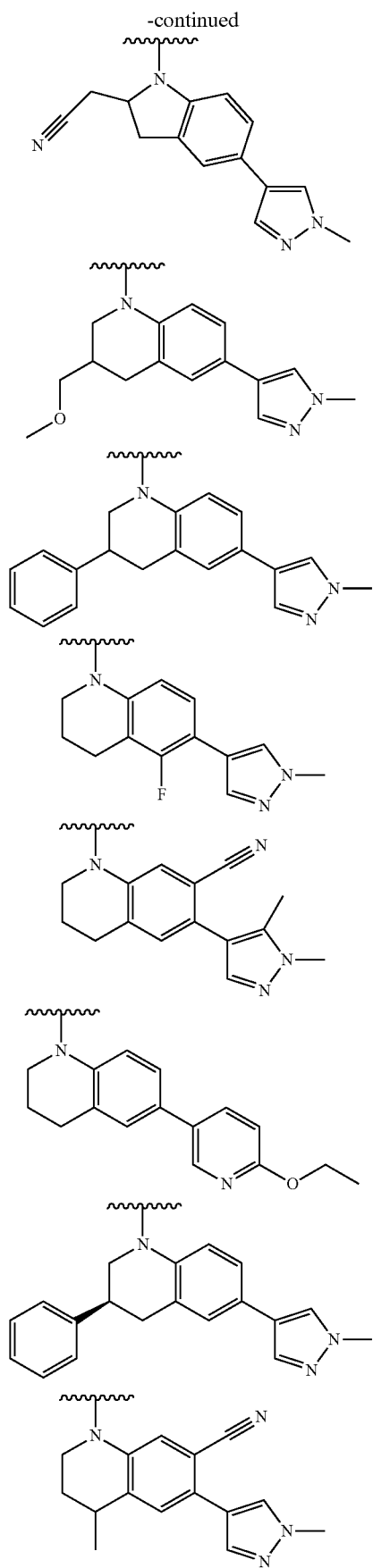
36
-continued
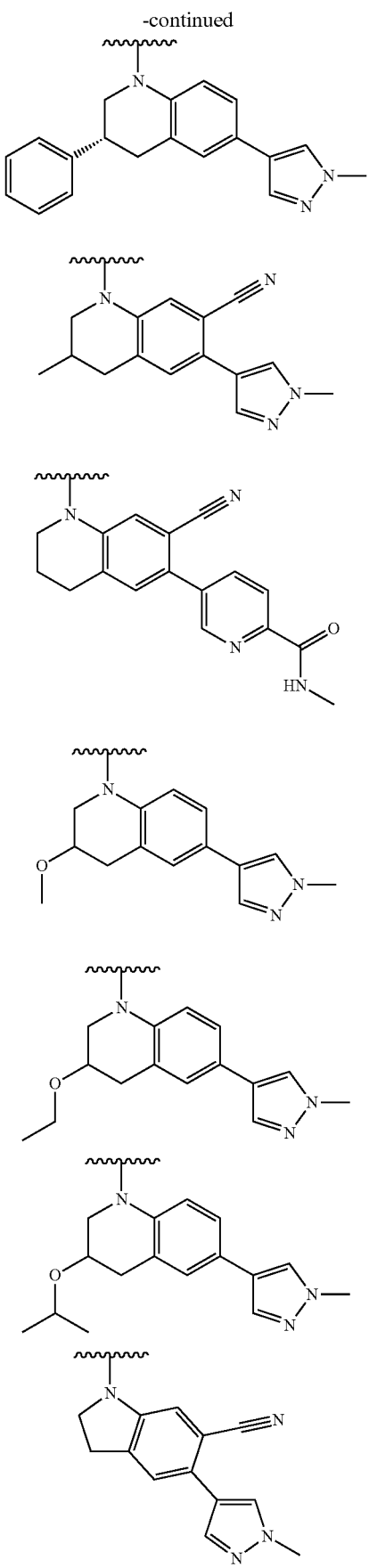

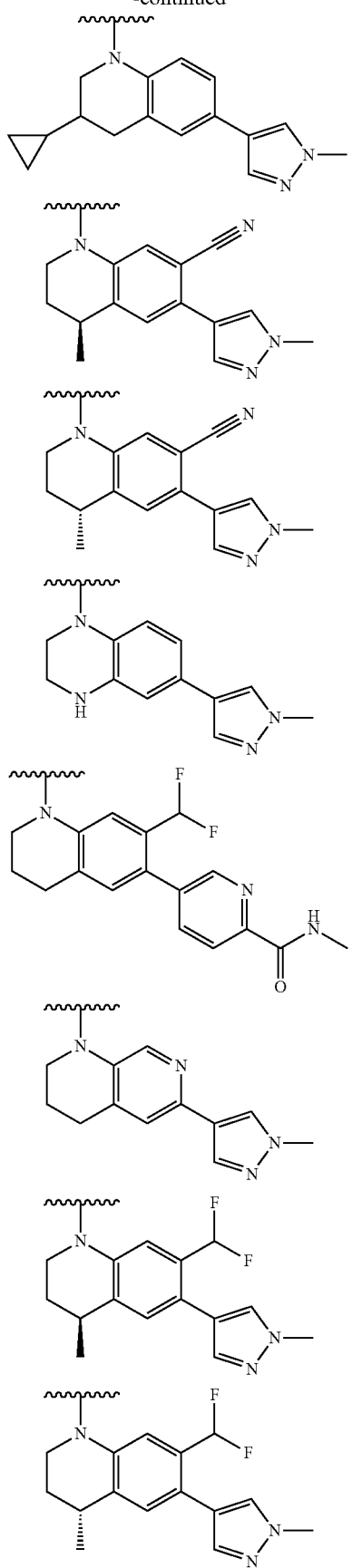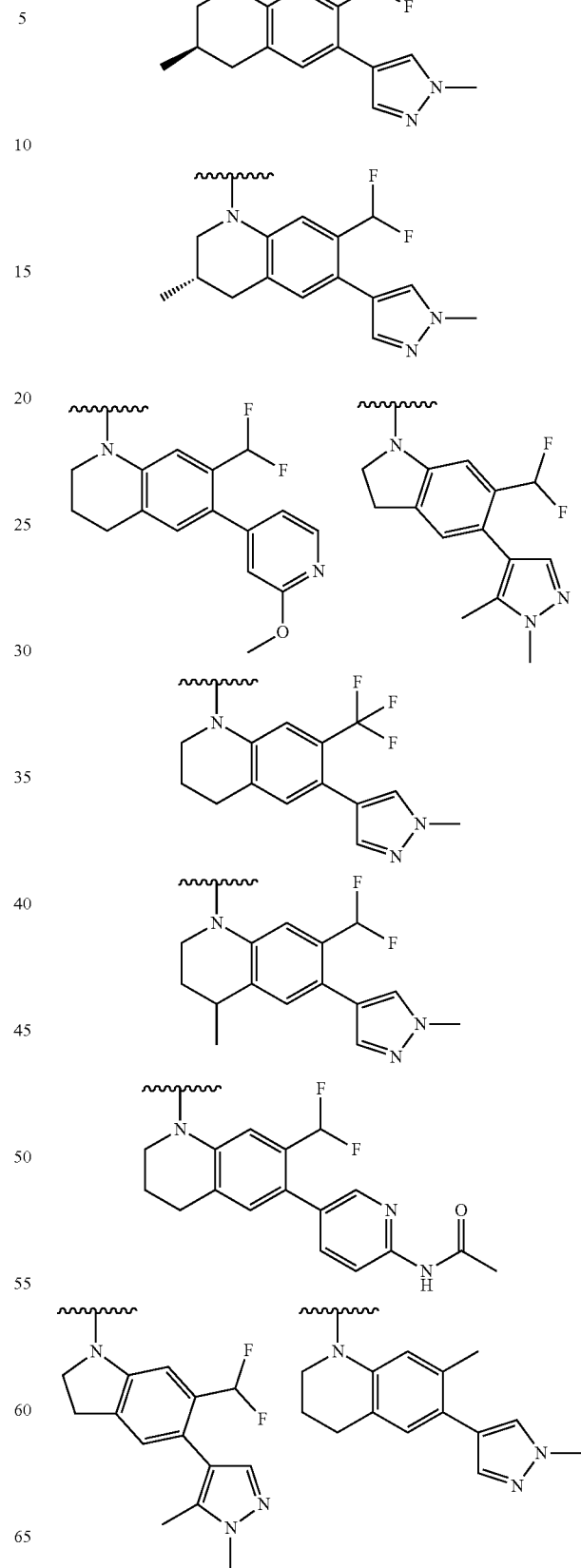

-continued
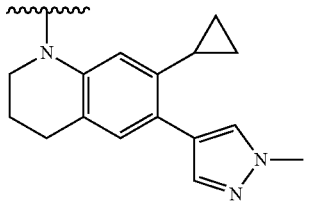
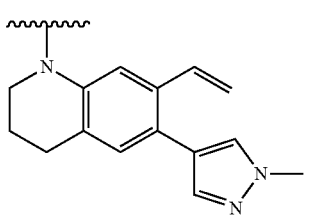
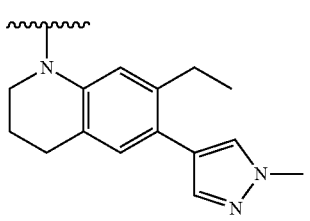
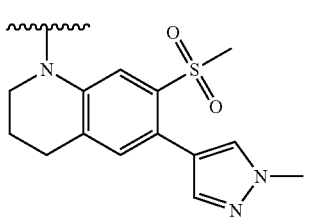
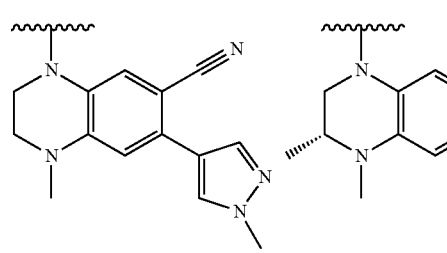
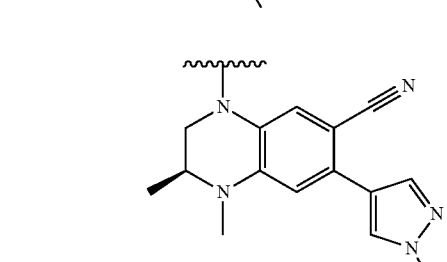
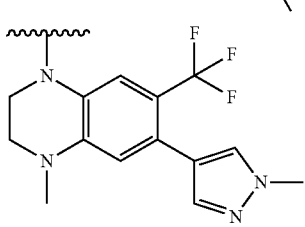
-continued
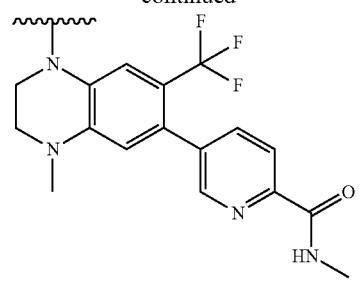
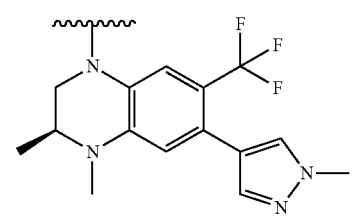
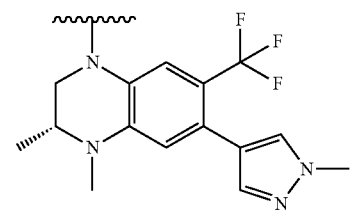
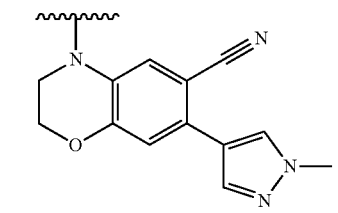
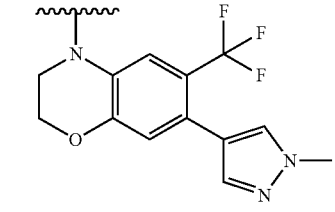
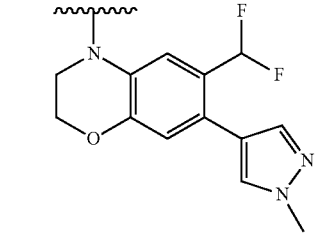
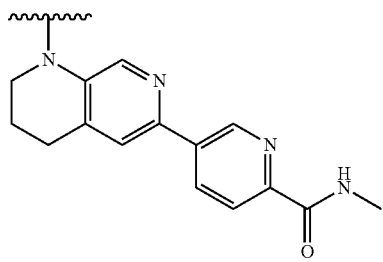

-continued
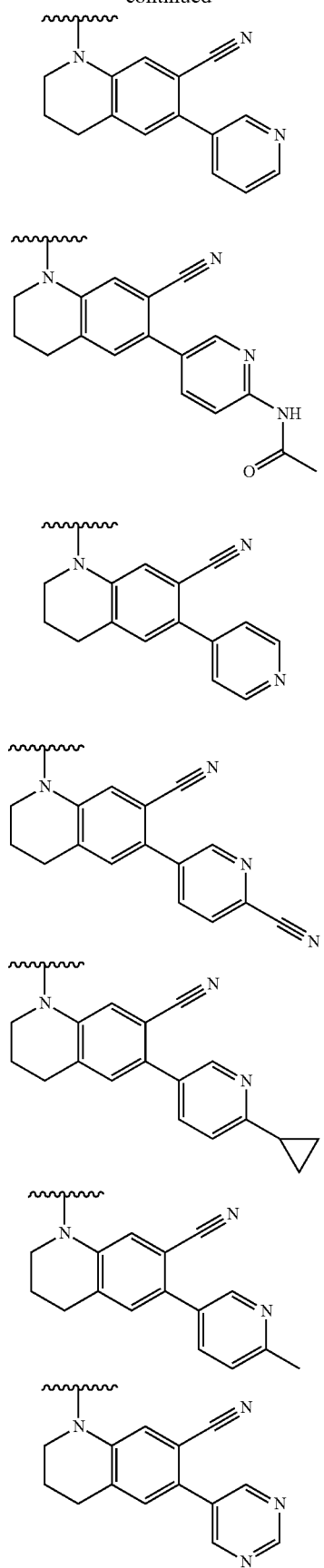
-continued
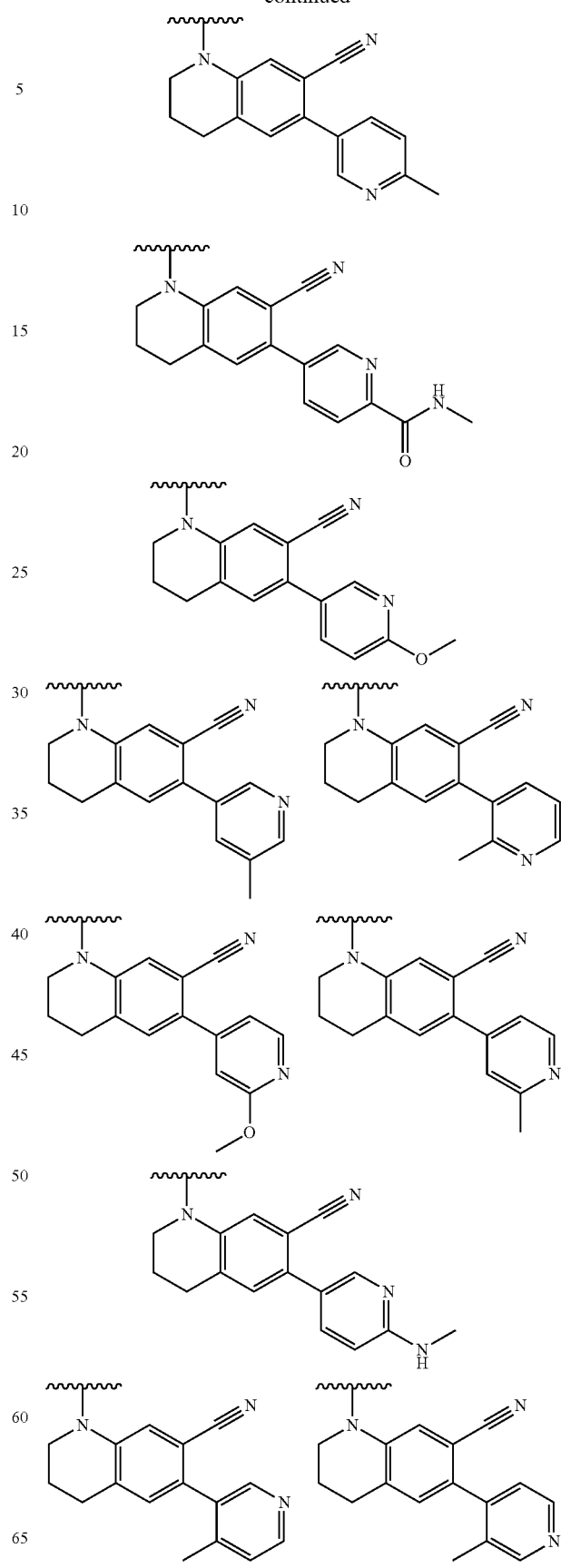

43
-continued
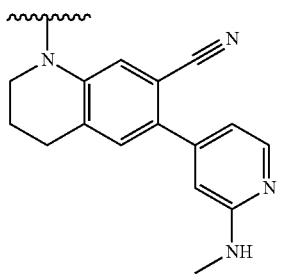
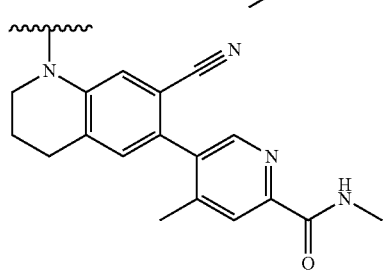
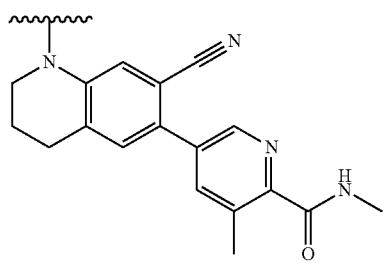
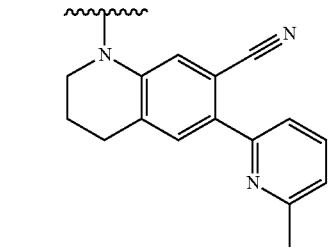
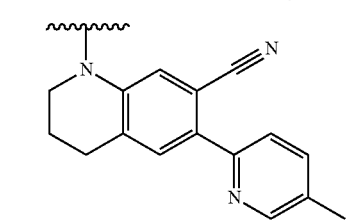
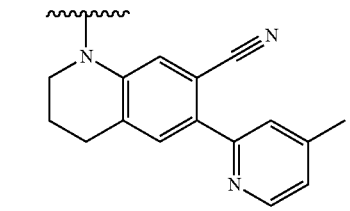
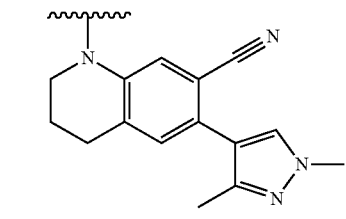
44
-continued
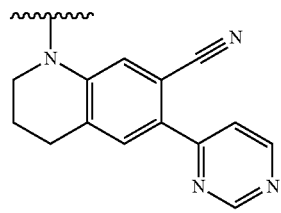
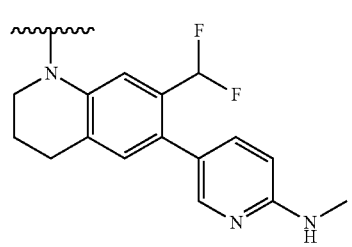
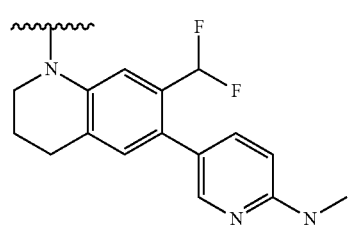
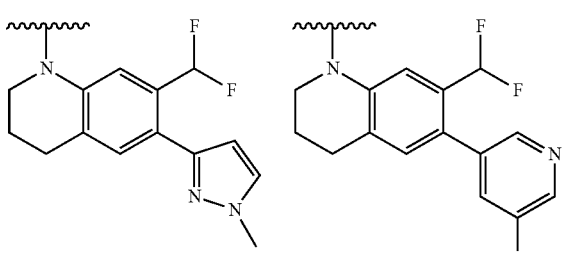
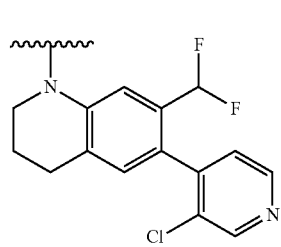
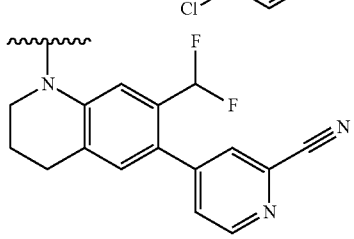
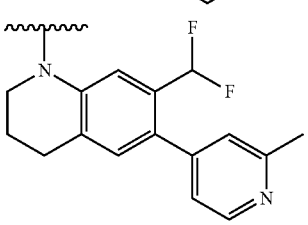

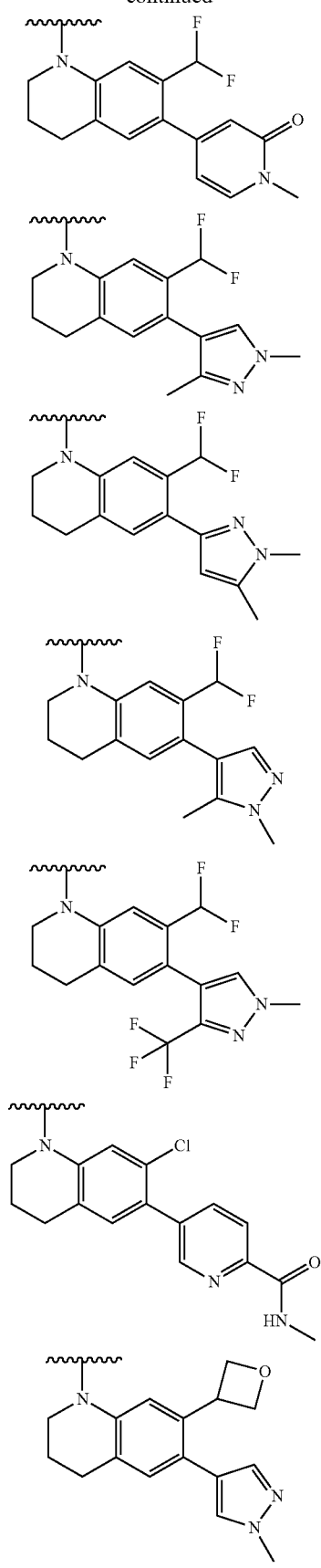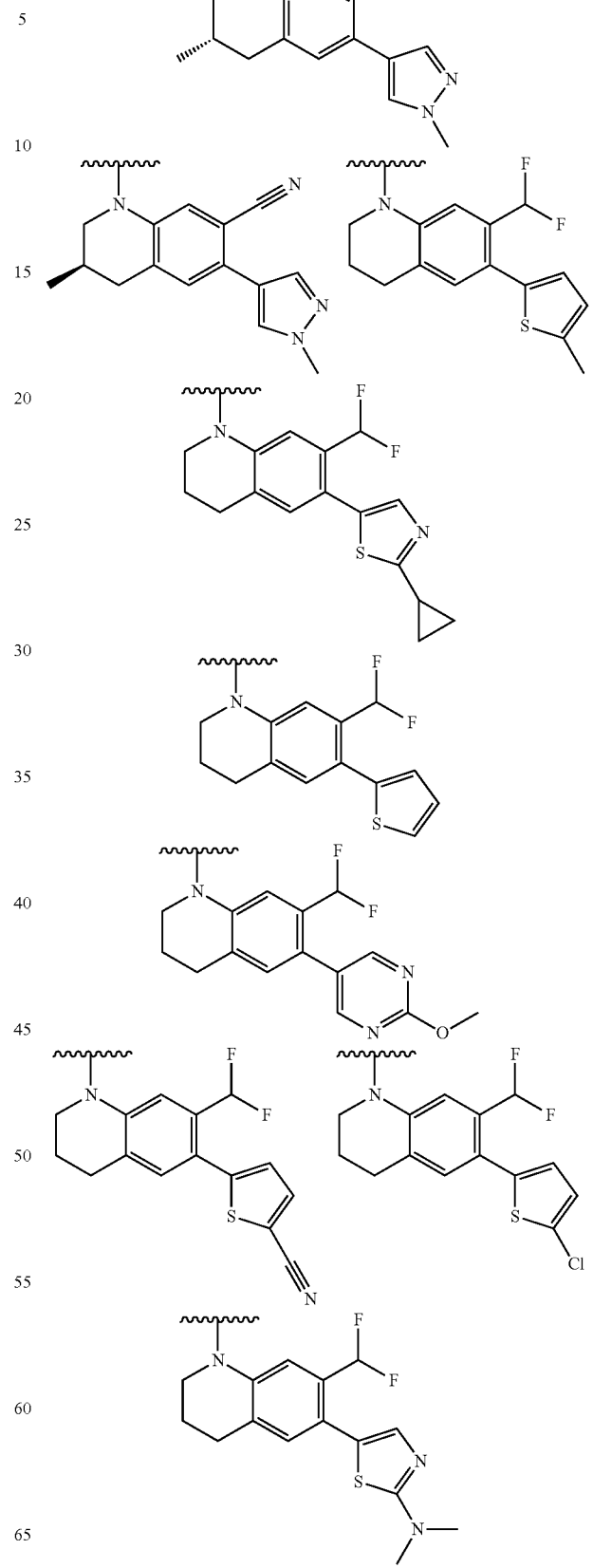

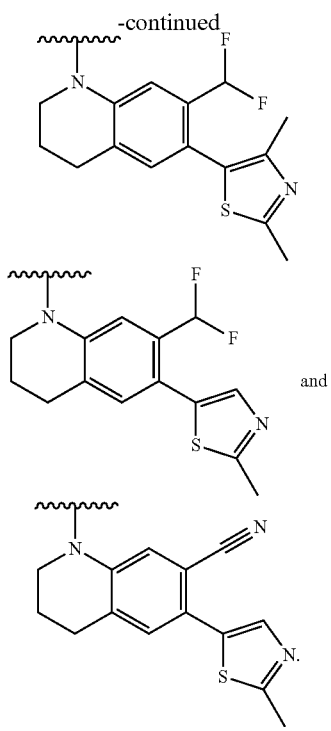

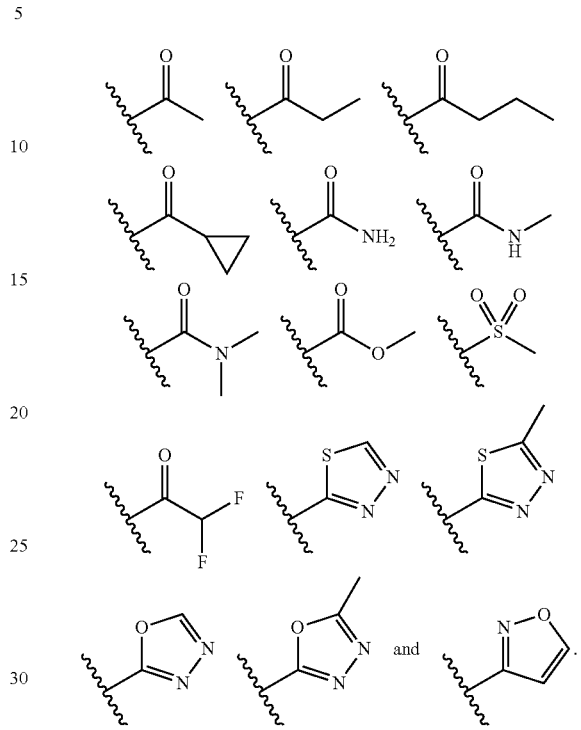

fonyl, difluoroacetyl, thiadiazole, methylthiadiazole, oxadiazole, methyloxadiazole, or isoxazole.

In certain embodiments of compounds of Formula (I), $R^4$ is selected from the group consisting of:

In certain embodiments of compounds of Formula (I), $R^3$ is $C_{1-12}$alkyl or 3-12 membered carbocycle, wherein each $C_{1-12}$alkyl and 3-12 membered carbocycle of $R^3$ is optionally substituted with one or more groups $R^e$.

In certain embodiments of compounds of Formula (I), $R^3$ is methyl or phenyl, wherein each methyl and phenyl of $R^3$ is optionally substituted with one or more groups $R^e$.

In certain embodiments of compounds of Formula (I), $R^3$ is benzyl, methyl, cyanomethyl, or phenyl.

In certain embodiments of compounds of Formula (I), $R^4$ is 3-5 membered heterocycle, —C(O)—N($R^h$)$_2$, —C(O)—$R^h$, —C(O)—O—$R^h$, or —S(O)$_2$—$R^h$, wherein any 3-5 membered heterocycle is optionally substituted with one or more substituent groups independently selected from —F, —Cl, —Br, —I, 3-5 membered carbocycle, —C(O)—N($R^h$)$_2$, —S(O)—N($R^h$)$_2$, —S(O)$_2$—N($R^h$)$_2$, —O—$R^h$, —S—$R^h$, —O—C(O)—$R^h$, —O—C(O)—O—$R^h$, —C(O)—$R^h$, —C(O)—O—$R^h$, —S(O)—$R^h$, —S(O)$_2$—$R^h$, —O—C(O)—N($R^h$)$_2$, —N($R^h$)—C(O)—O$R^h$, —N($R^h$)—C(O)—N($R^h$)$_2$, —N($R^h$)—C(O)—$R^h$, —N($R^h$)—S(O)—$R^h$, —N($R^h$)—S(O)$_2$—$R^h$, —N($R^h$)—S(O)—N($R^h$)$_2$, and —N($R^h$)—S(O)$_2$—N($R^h$)$_2$.

In certain embodiments of compounds of Formula (I), $R^h$ is independently selected from hydrogen, $C_{1-4}$alkyl, and $C_{2-5}$cycloalkyl, wherein each $C_{1-4}$alkyl, and $C_{2-5}$cycloalkyl is optionally substituted with one or more groups independently selected from oxo, halo, amino, hydroxyl, $C_{1-3}$alkoxy, and $C_1$-$C_3$ alkyl that is optionally substituted with one or more groups independently selected from halo.

In certain embodiments of compounds of Formula (I), $R^4$ is acetyl, aminocarbonyl, methylaminocarbonyl, dimethylaminocarbonyl, methoxycarbonyl, propanoyl, cyclopropylcarbonyl, methylsulfonyl, butanoyl, difluoroacetyl, thiadiazole or isoxazole.

In certain embodiments of compounds of Formula (I), $R^4$ is substituted or unsubstituted acetyl, propionyl, butyryl, cyclopropylcarbonyl, aminocarbonyl, methylaminocarbonyl, dimethylaminocarbonyl, methoxycarbonyl, methylsul- In certain embodiments of compounds of Formula (I):
$R^1$ is methyl or a 4-6 membered heterocycle, wherein each methyl and 4-6 membered heterocycle of $R^1$ is optionally substituted with one or more groups $R^b$;
$R^2$ is phenyl optionally substituted with one or more substituent groups independently selected from $R^c$; and
$R^3$ is methyl or phenyl, wherein each methyl and phenyl of $R^3$ is optionally substituted with one or more groups $R^e$.

In certain embodiments of compounds of Formula (I):
$R^1$ is methyl, oxetanyl, tetrahydrofuranyl, tetrahydropyranyl, dioxothiolanyl, piperidyl, or pyrrolidinyl, wherein each methyl, oxetanyl, tetrahydrofuranyl, tetrahydropyranyl, dioxothiolanyl, piperidyl, or pyrrolidinyl of $R^1$ is optionally substituted with one or more groups $R^b$
$R^2$ is phenyl optionally substituted with one or more substituent groups independently selected from $R^c$; and
$R^3$ is methyl or phenyl, wherein each methyl and phenyl of $R^3$ is optionally substituted with one or more groups $R^e$.

In certain embodiments of compounds of Formula (I):
$R^1$ is methyl or a 4-6 membered heterocycle, wherein each methyl and 4-6 membered heterocycle of $R^1$ is optionally substituted with one or more groups $R^b$; and
$R^2$ and $R^3$ taken together with the nitrogen to which they are attached form a 9- or 10-membered bicyclic heterocycle that is optionally substituted with one or more groups $R^e$.

In certain embodiments of compounds of Formula (I):
$R^1$ is tetrahydrofuranyl, tetrahydropyranyl, dioxothiolanyl, piperidyl, or pyrrolidinyl, wherein each tetrahydrofuranyl, tetrahydropyranyl, dioxothiolanyl, piperidyl, or pyrrolidinyl of $R^1$ is optionally substituted with one or more groups $R^b$; and
$R^2$ and $R^3$ taken together with the nitrogen to which they are attached form a 9- or 10-membered bicyclic heterocycle that is optionally substituted with one or more groups $R^e$.

In certain embodiments of compounds of Formula (I), $R^1$ is methyl, oxetanyl, tetrahydrofuranyl, tetrahydropyranyl, dioxothiolanyl, piperidyl, or pyrrolidinyl, wherein each methyl, oxetanyl, tetrahydrofuranyl, tetrahydropyranyl, dioxothiolanyl, piperidyl, or pyrrolidinyl of $R^1$ is optionally substituted with one or more groups $R^b$; and —$NR^2R^3$ taken together is selected from the group consisting of:

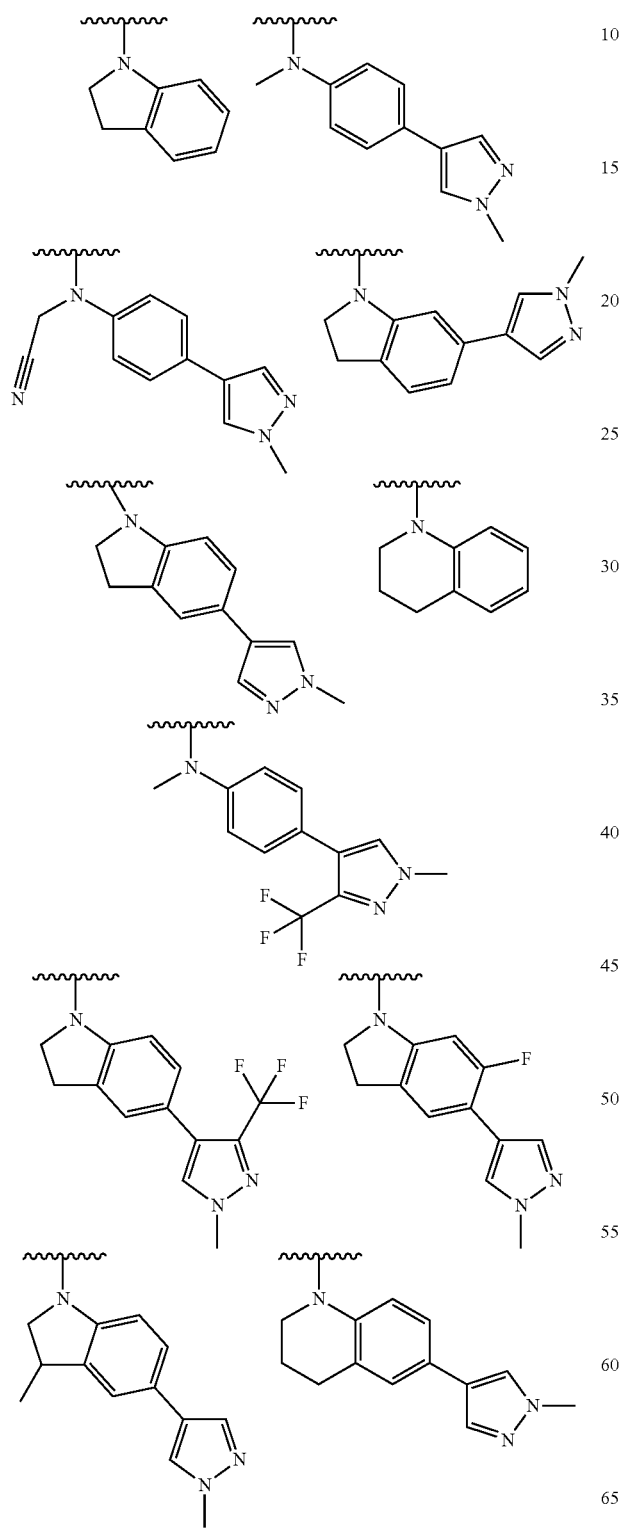
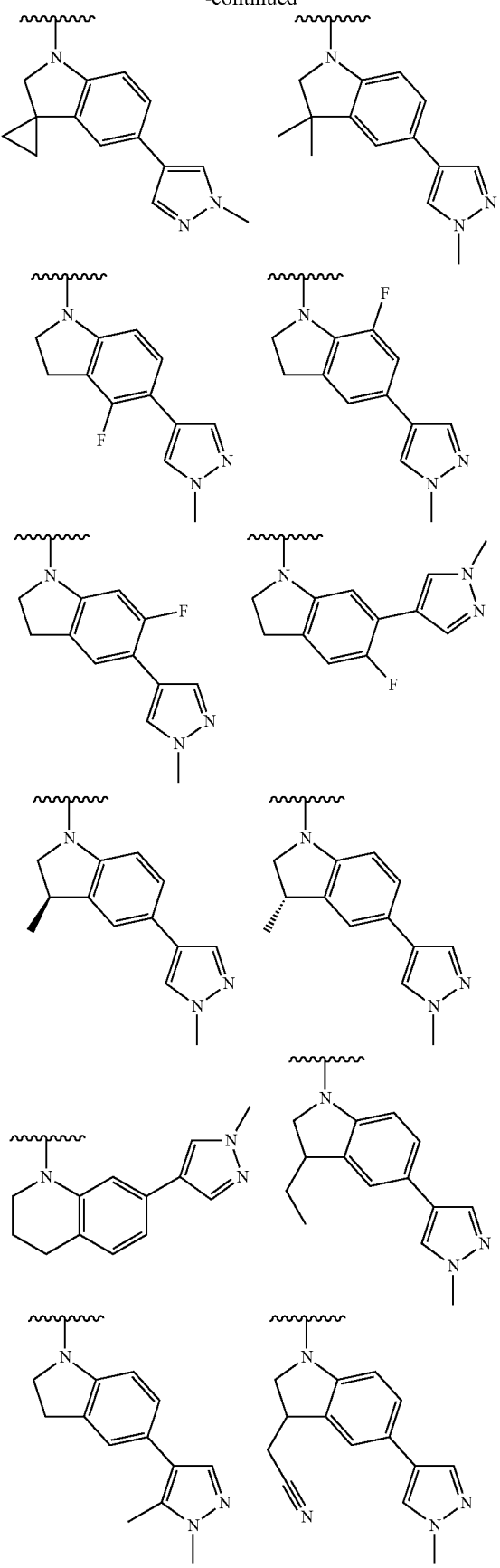

-continued

51
-continued
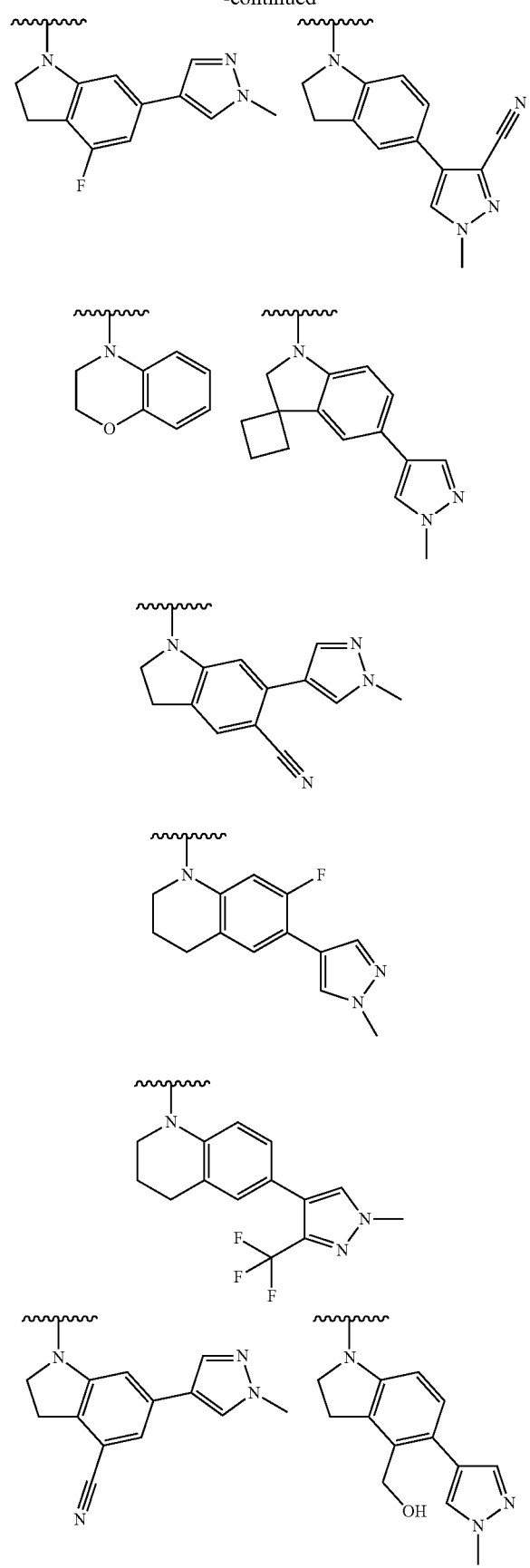
52
-continued
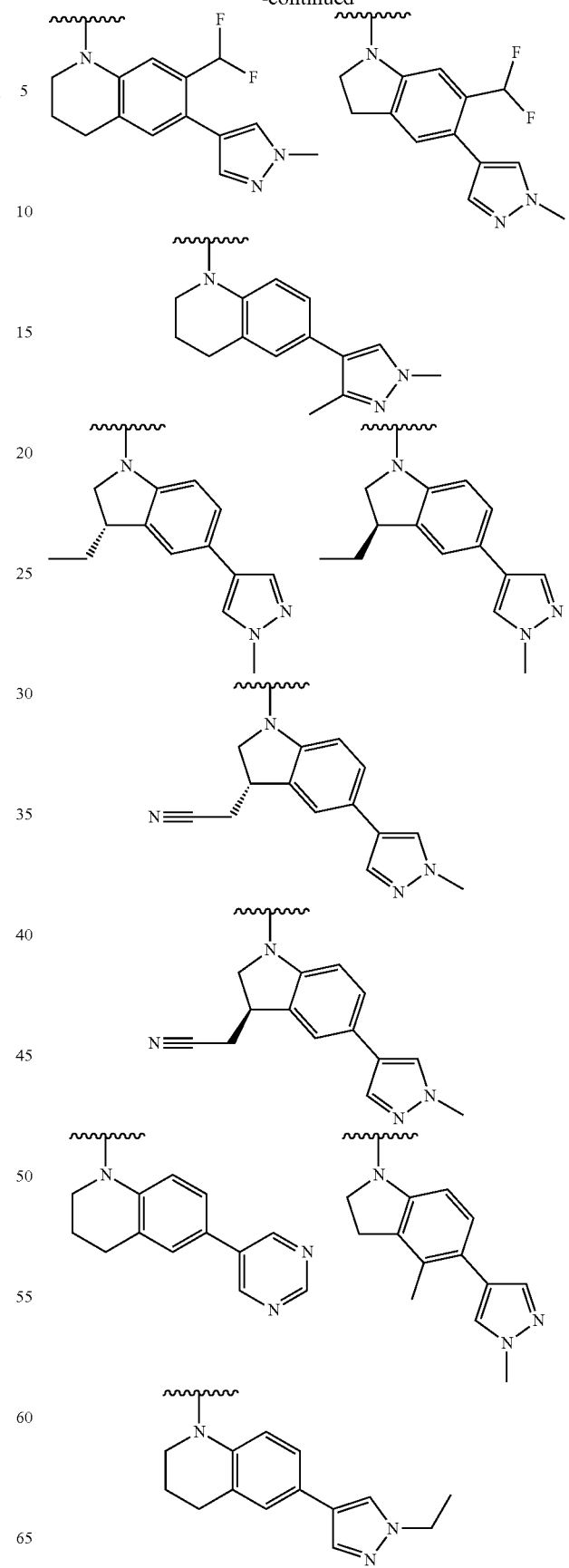

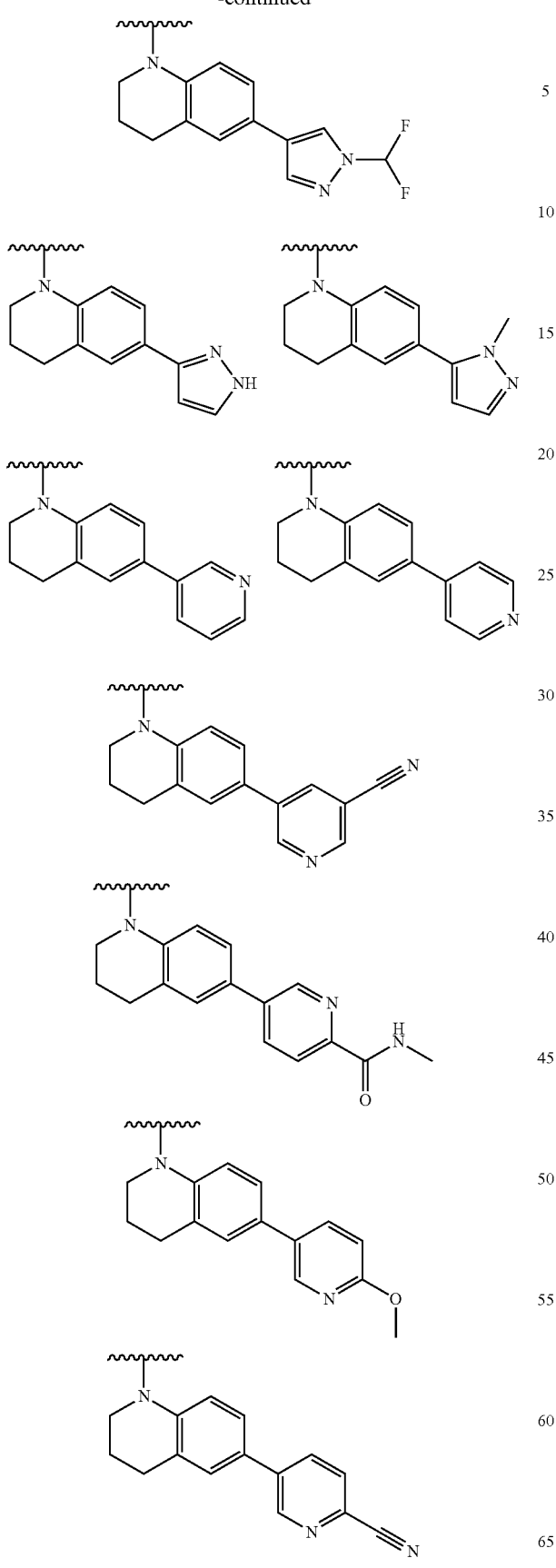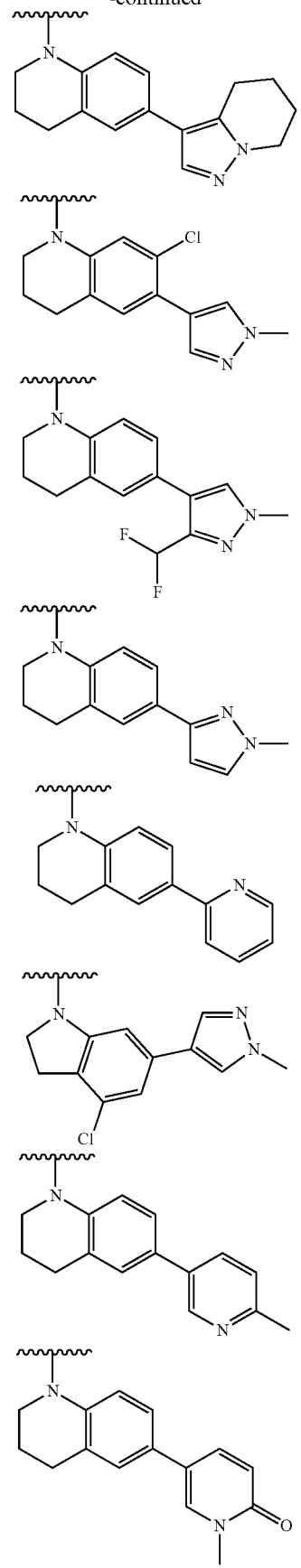

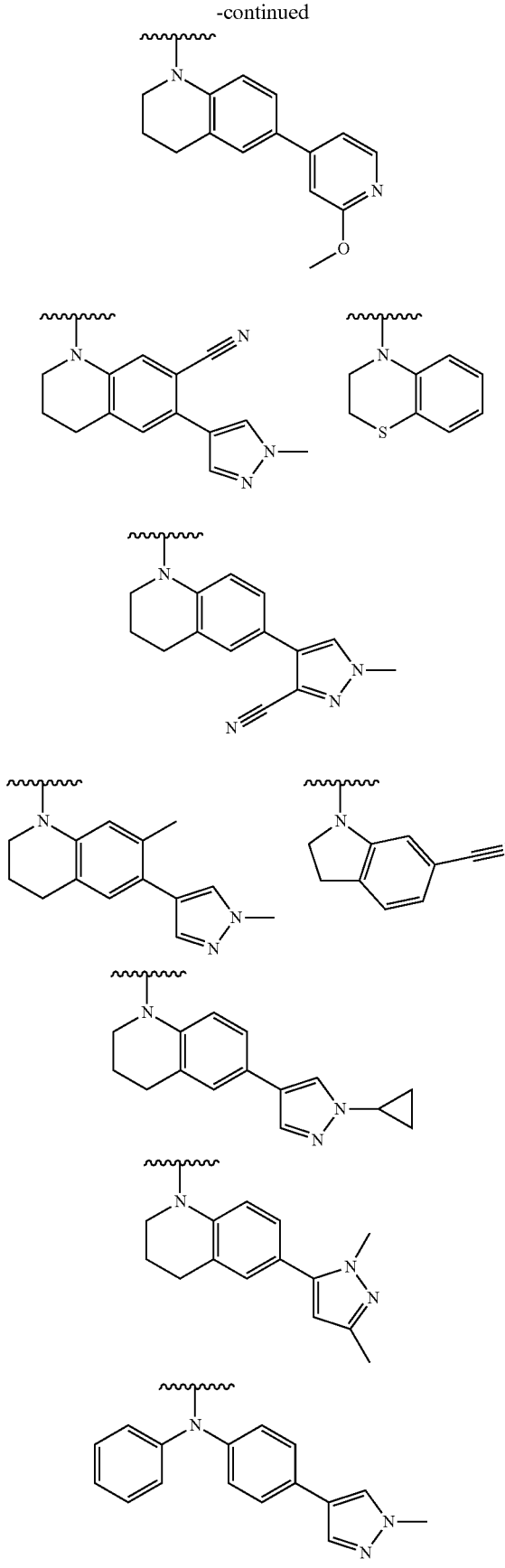
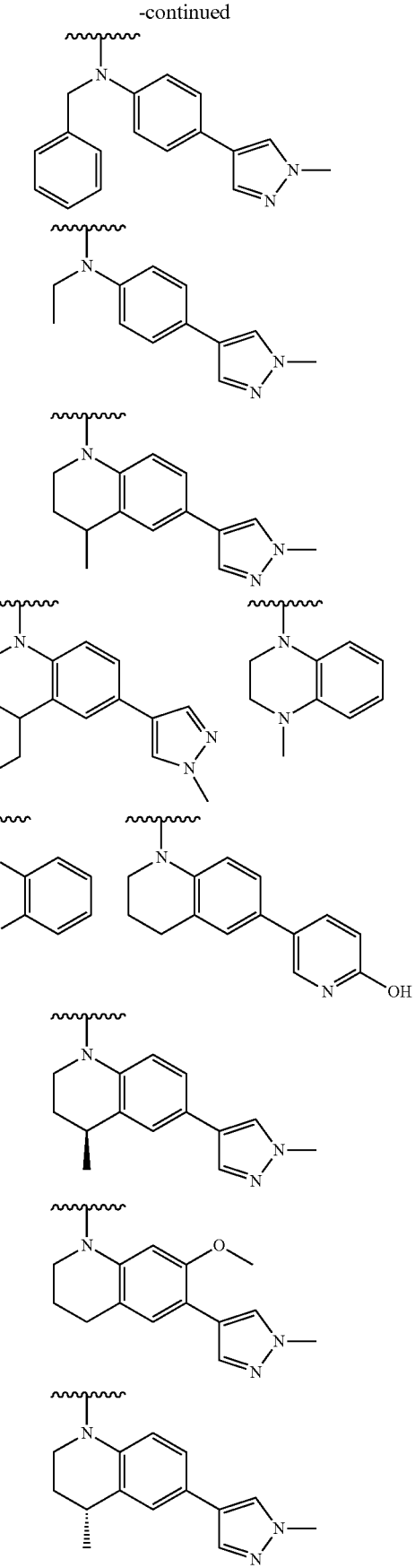

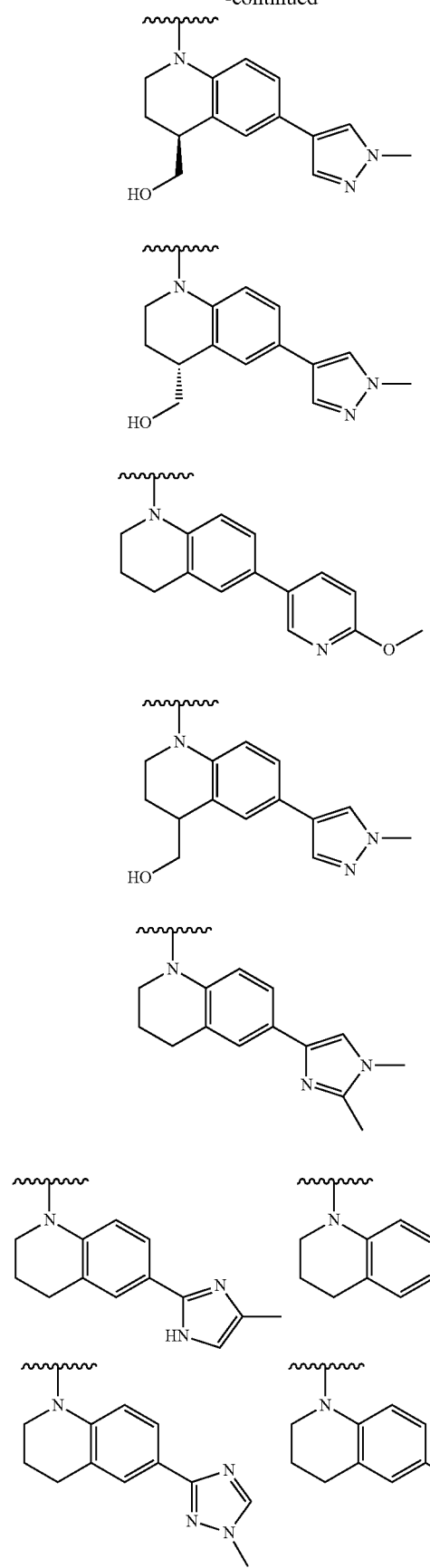
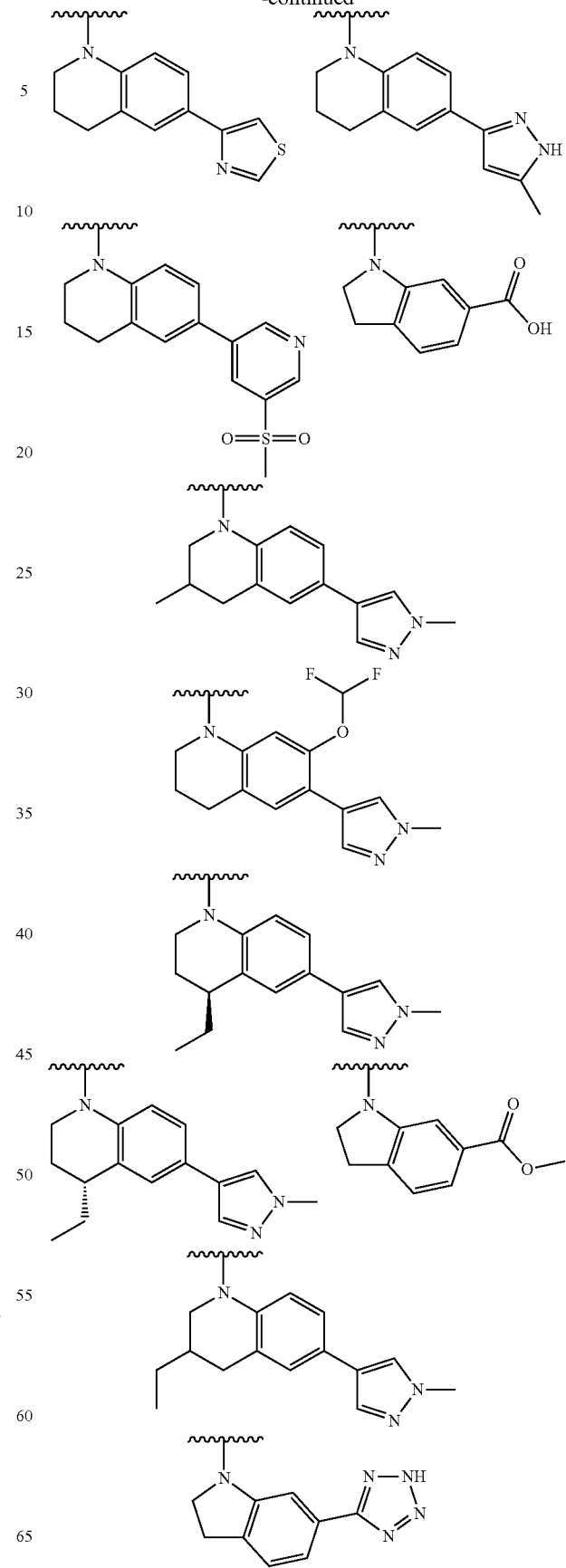

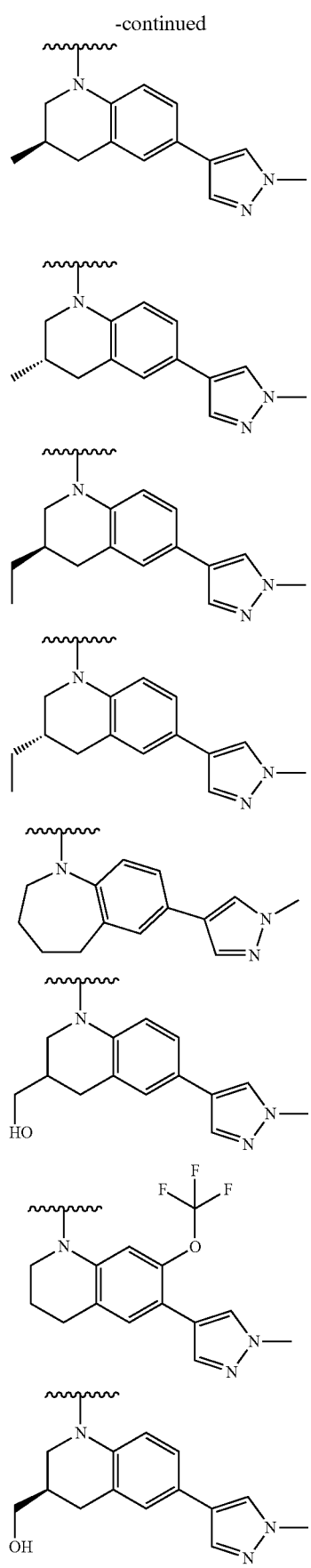
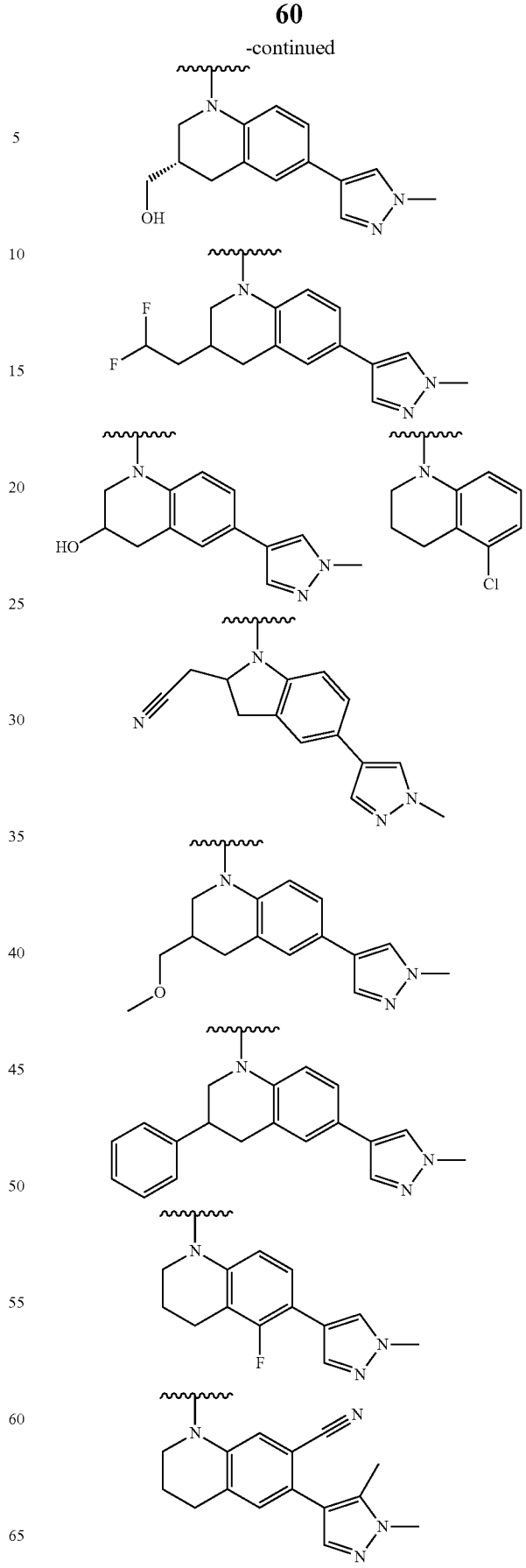

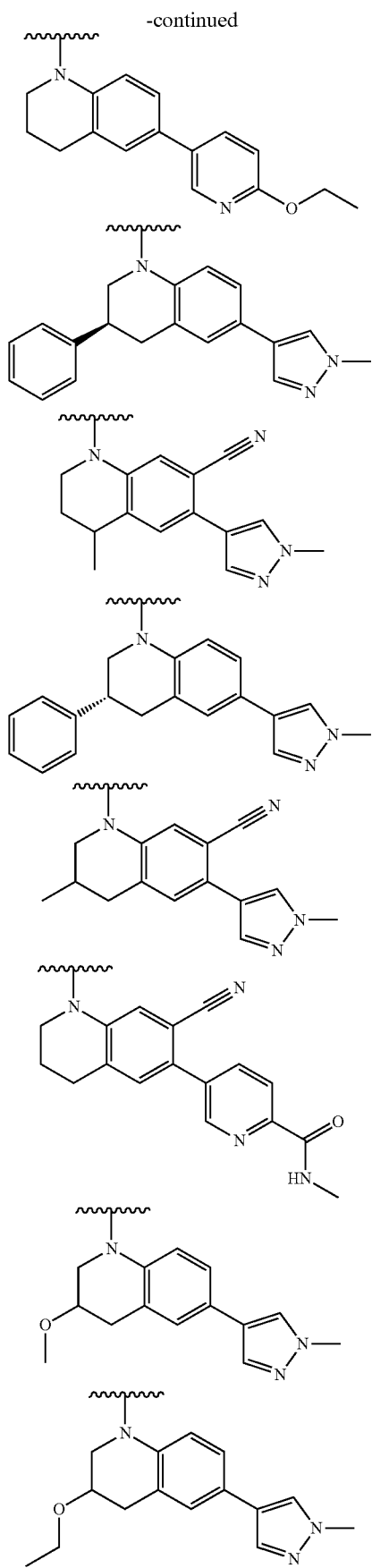
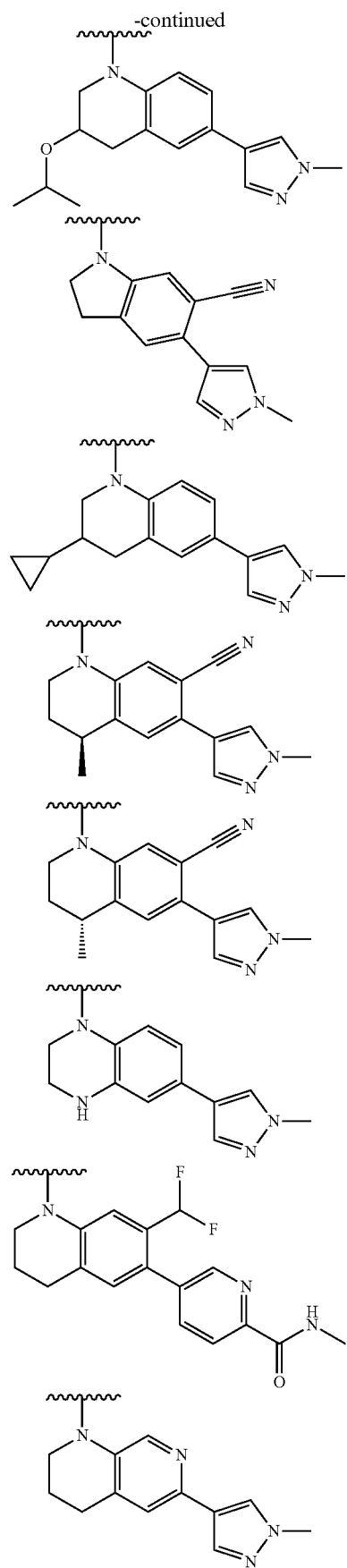

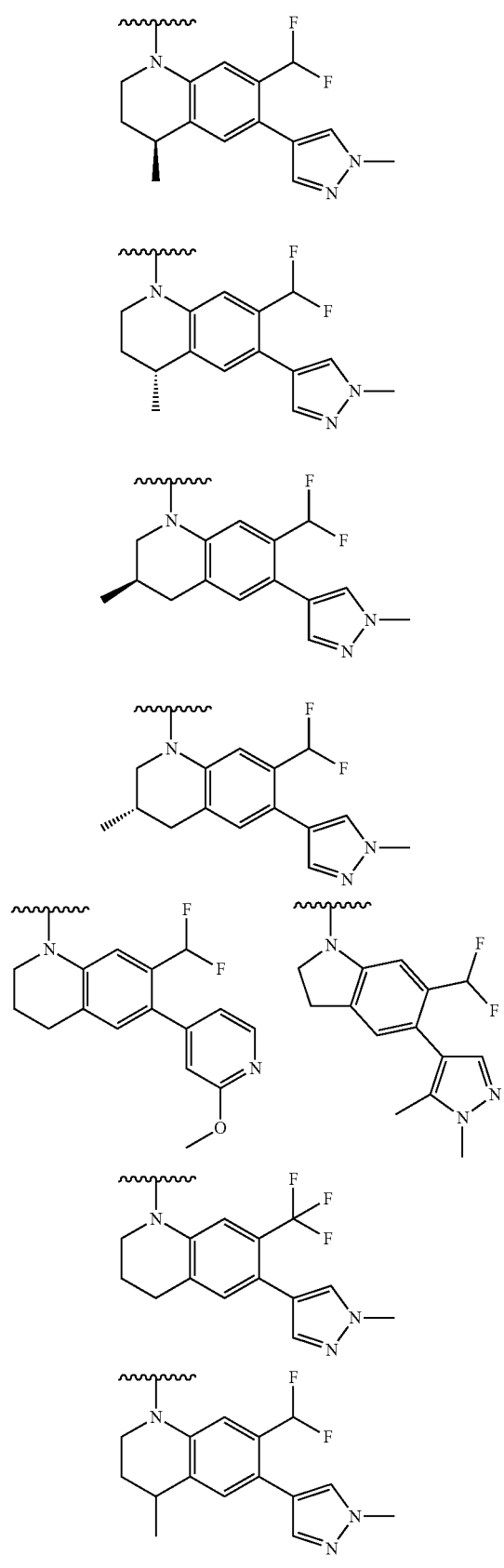
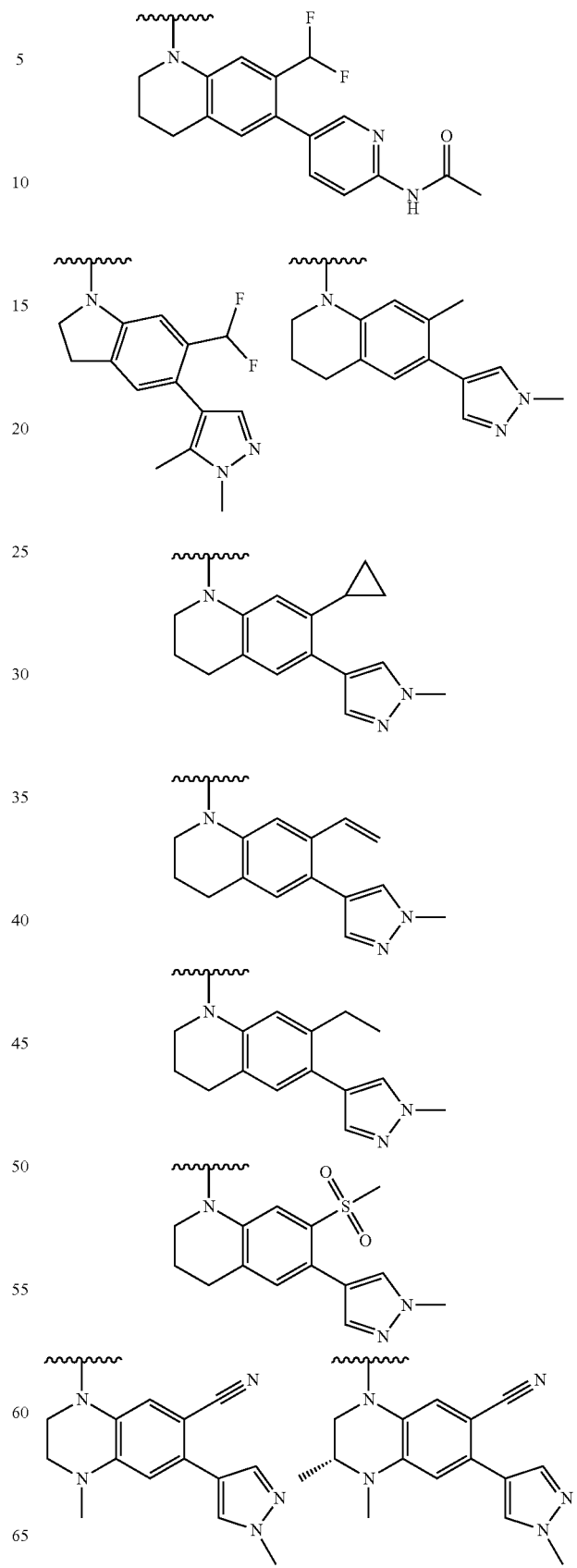

65
-continued
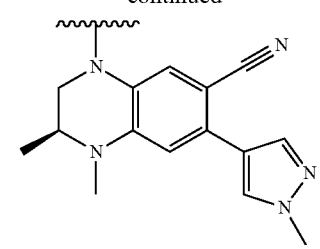
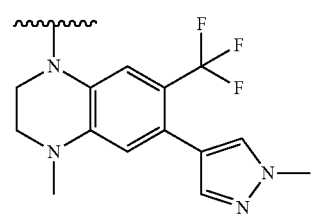
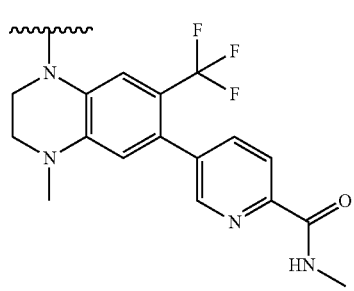
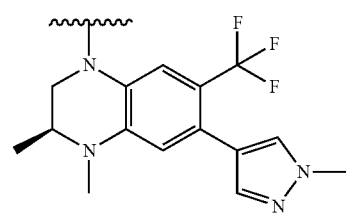
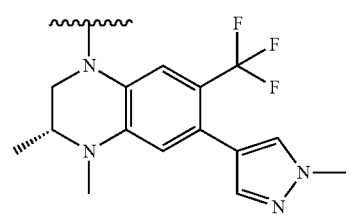
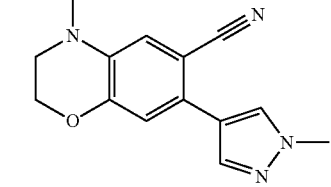
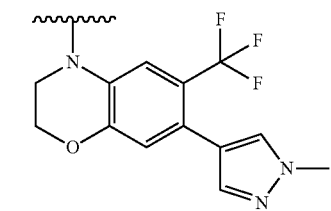
66
-continued
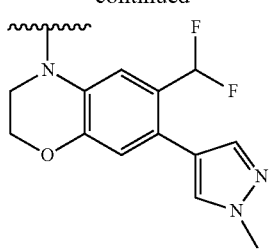
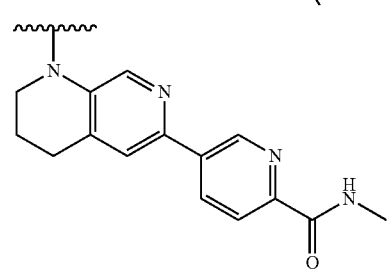
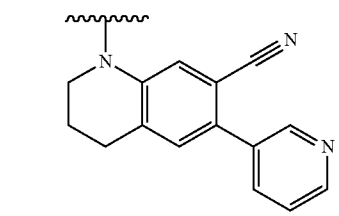
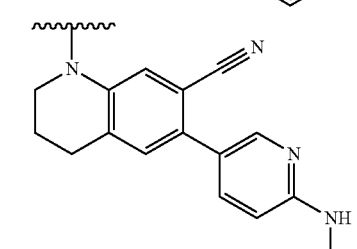
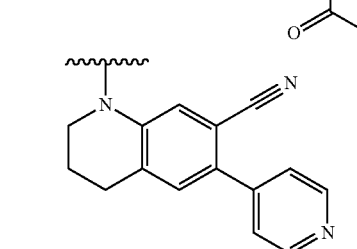
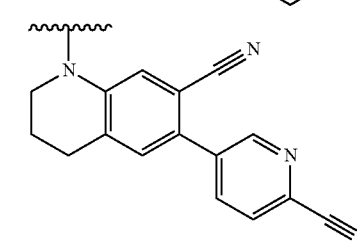
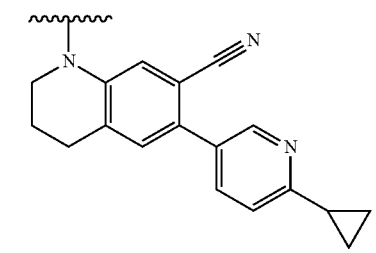

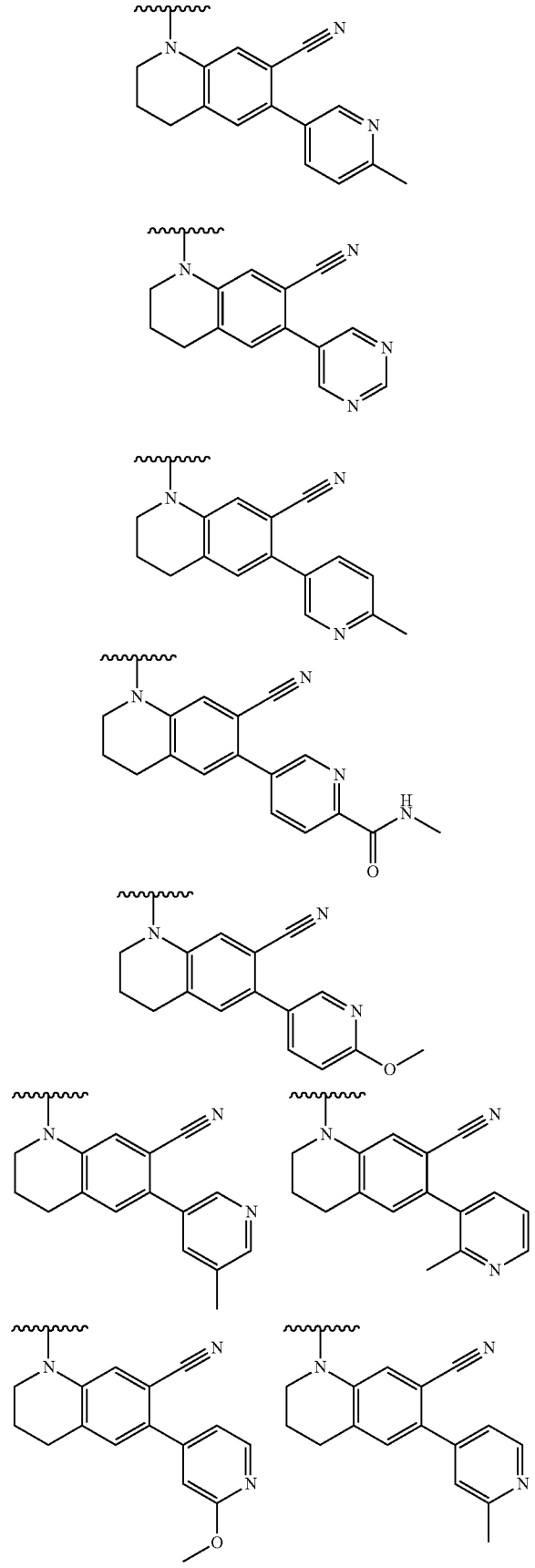
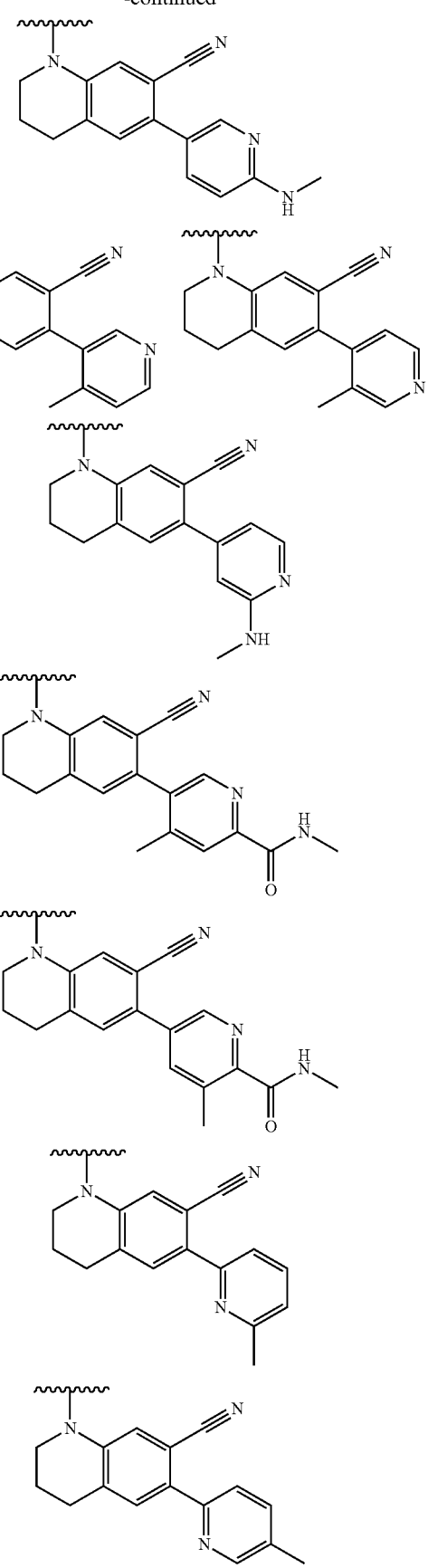

69
-continued
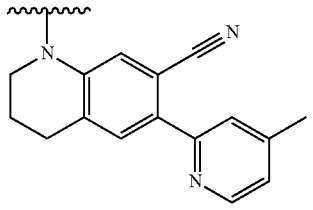
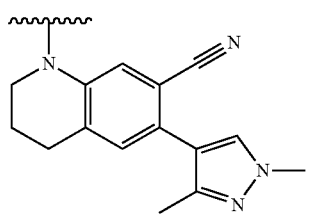
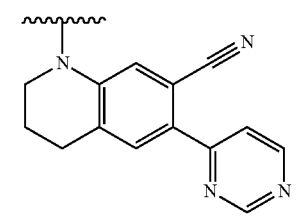
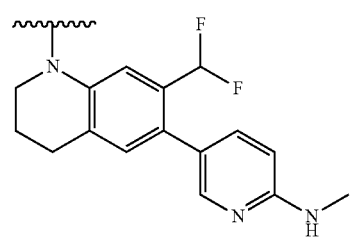
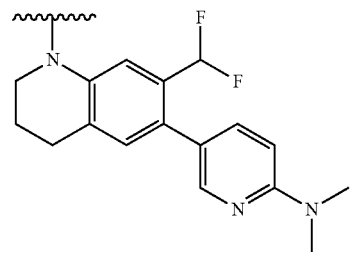
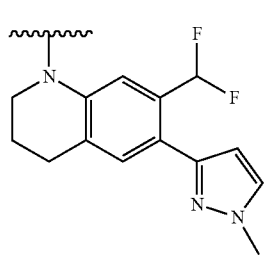 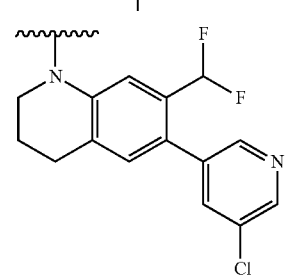
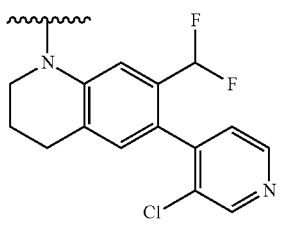
70
-continued
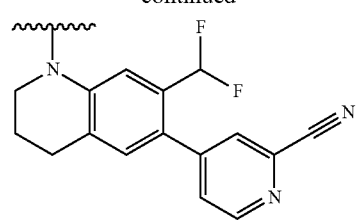
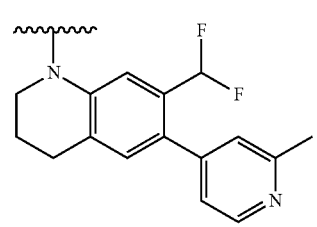
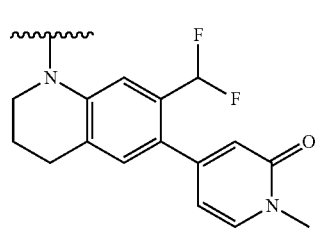
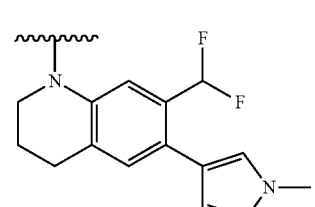
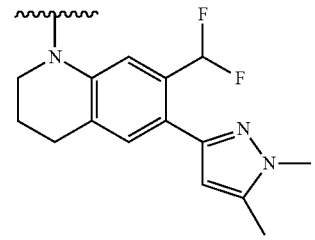
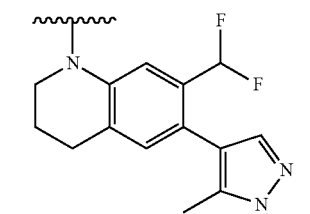
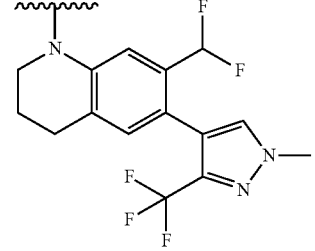

71
-continued

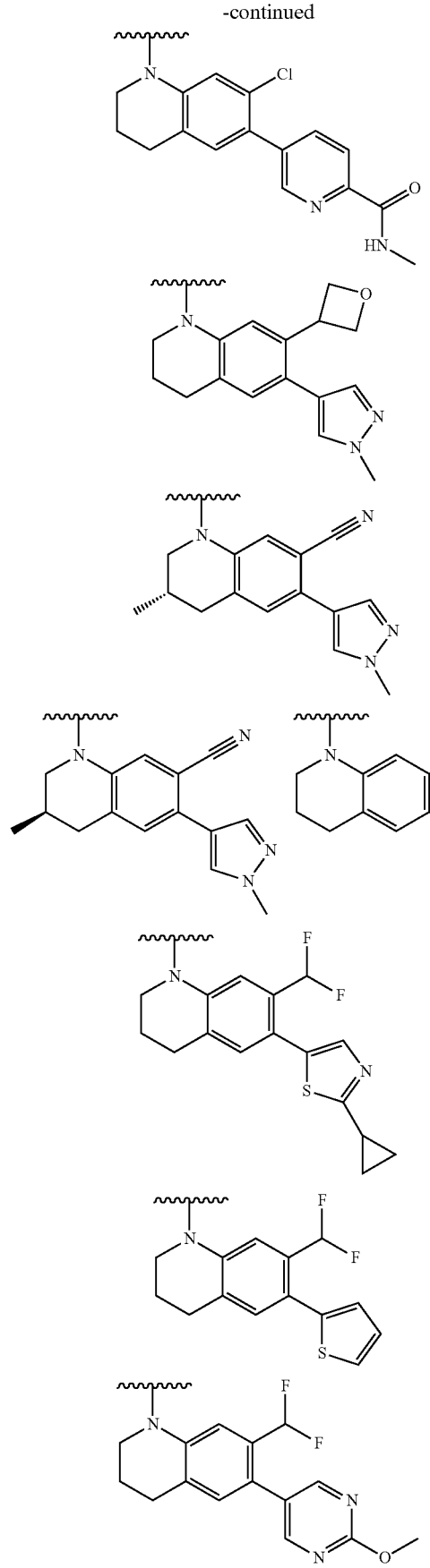

72
-continued

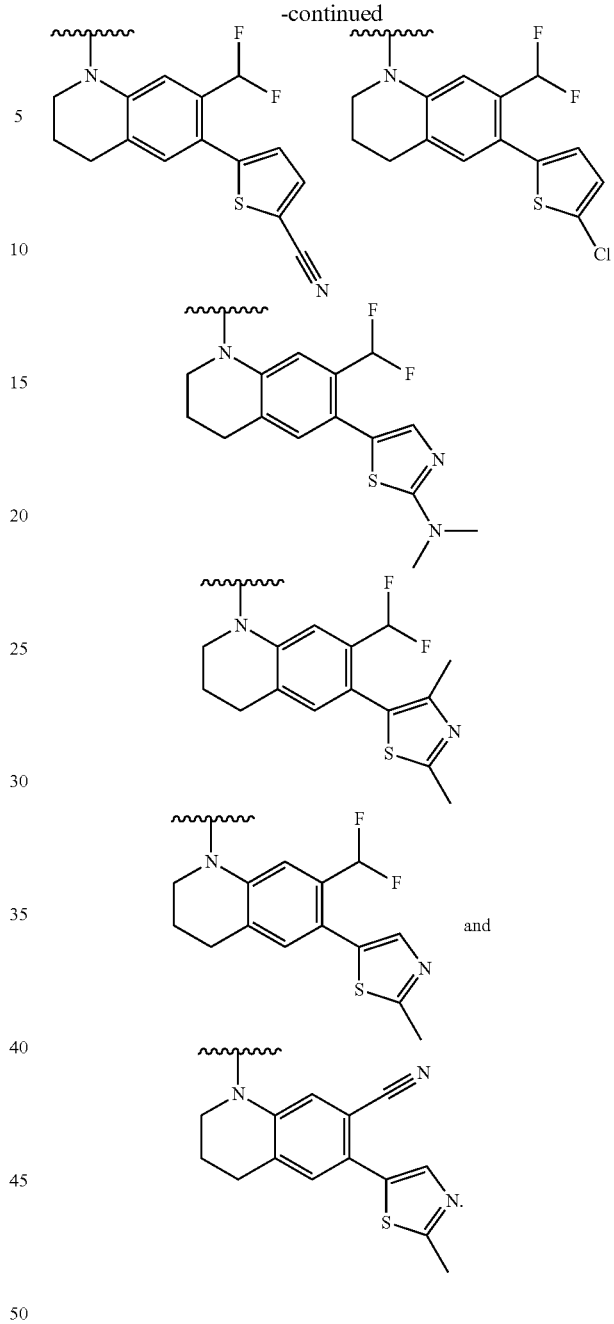

In certain embodiments of compounds of Formula (I):

R$^1$ is methyl, oxetanyl, tetrahydrofuranyl, tetrahydropyranyl, dioxothiolanyl, piperidyl, or pyrrolidinyl, wherein each methyl, oxetanyl, tetrahydrofuranyl, tetrahydropyranyl, dioxothiolanyl, piperidyl, or pyrrolidinyl of R$^1$ is optionally substituted with one or more groups R$^b$ R$^2$ is phenyl optionally substituted with one or more substituent groups independently selected from R$^c$;

R$^3$ is methyl or phenyl, wherein each methyl and phenyl of R$^3$ is optionally substituted with one or more groups R$^e$; and R$^4$ is acetyl, aminocarbonyl, methylaminocarbonyl, dimethylaminocarbonyl, methoxycarbonyl, propanoyl, cyclopropylcarbonyl, methylsulfonyl, butanoyl, difluoroacetyl, thiadiazole or isoxazole.

In certain embodiments of compounds of Formula (I):

$R^1$ is methyl or a 4-6 membered heterocycle, wherein each methyl and 4-6 membered heterocycle of $R^1$ is optionally substituted with one or more groups $R^b$;

$R^2$ and $R^3$ taken together with the nitrogen to which they are attached form a 9- or 10-membered bicyclic heterocycle that is optionally substituted with one or more groups $R^e$; and $R^4$ is acetyl, aminocarbonyl, methylaminocarbonyl, dimethylaminocarbonyl, methoxycarbonyl, propanoyl, cyclopropylcarbonyl, methylsulfonyl, butanoyl, difluoroacetyl, thiadiazole or isoxazole.

In certain embodiments of compounds of Formula (I):

$R^1$ is methyl, oxetanyl, tetrahydrofuranyl, tetrahydropyranyl, dioxothiolanyl, piperidyl, or pyrrolidinyl, wherein each methyl, oxetanyl, tetrahydrofuranyl, tetrahydropyranyl, dioxothiolanyl, piperidyl, or pyrrolidinyl of $R^1$ is optionally substituted with one or more groups $R^b$;

$R^2$ and $R^3$ taken together with the nitrogen to which they are attached form a 9- or 10-membered bicyclic heterocycle that is optionally substituted with one or more groups $R^e$; and $R^4$ is acetyl, aminocarbonyl, methylaminocarbonyl, dimethylaminocarbonyl, methoxycarbonyl, propanoyl, cyclopropylcarbonyl, methylsulfonyl, butanoyl, difluoroacetyl, thiadiazole or isoxazole.

In certain embodiments of compounds of Formula (I):

$R^1$ is methyl, oxetanyl, tetrahydrofuranyl, tetrahydropyranyl, dioxothiolanyl, piperidyl, or pyrrolidinyl, wherein each methyl, oxetanyl, tetrahydrofuranyl, tetrahydropyranyl, dioxothiolanyl, piperidyl, or pyrrolidinyl of $R^1$ is optionally substituted with one or more groups $R^b$;

—$NR^2R^3$ taken together is selected from the group consisting of:

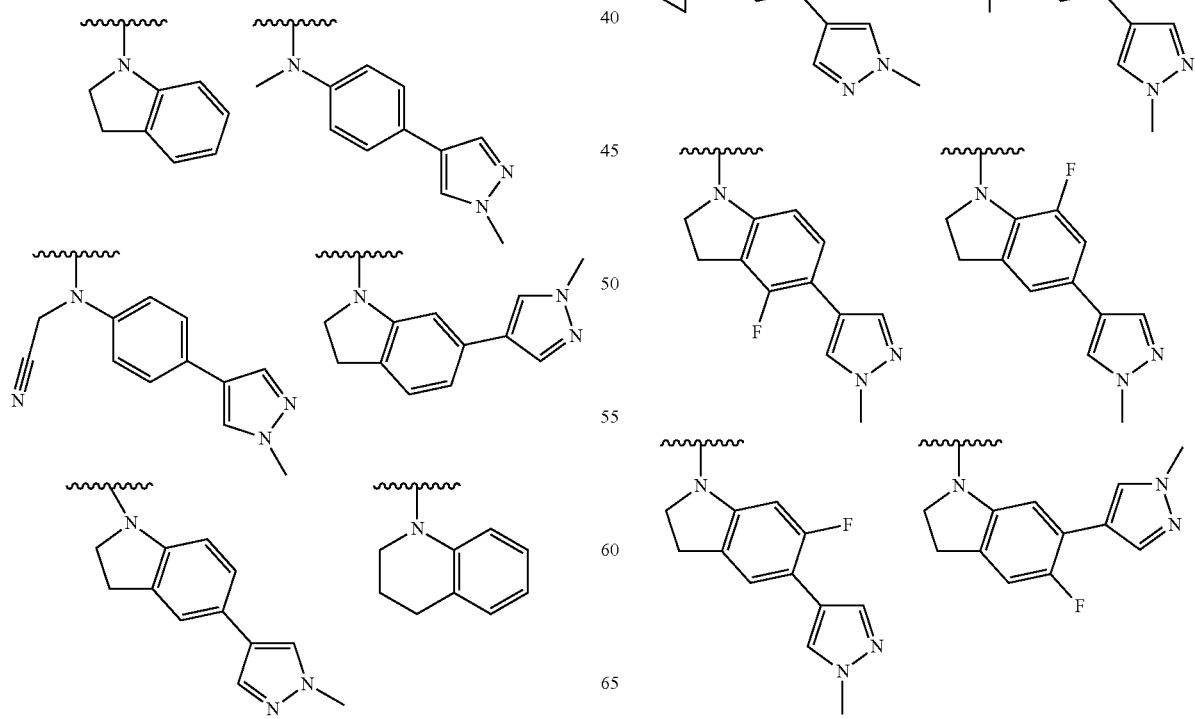

-continued

75
-continued
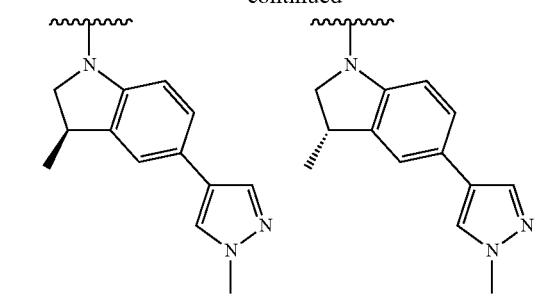
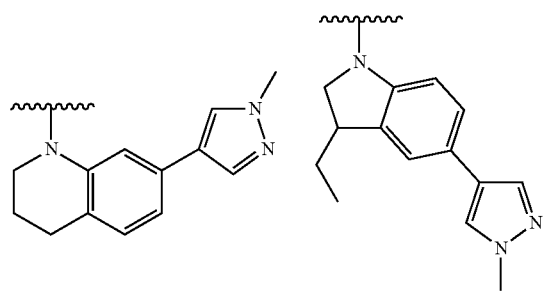
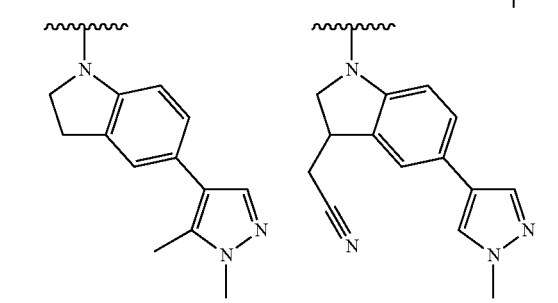
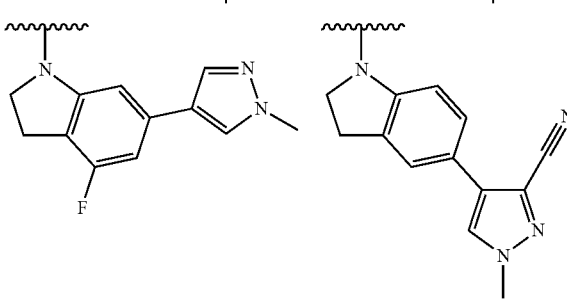
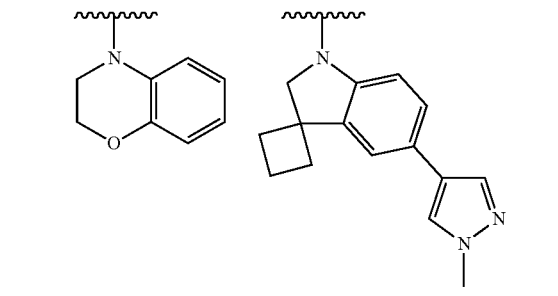
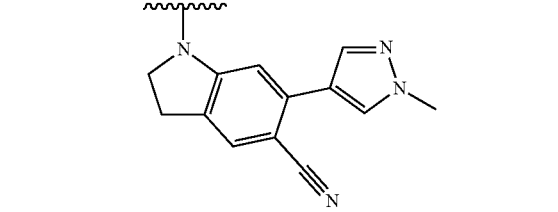
76
-continued
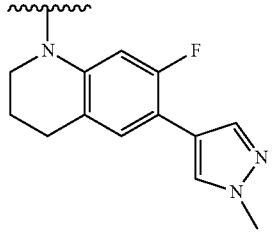
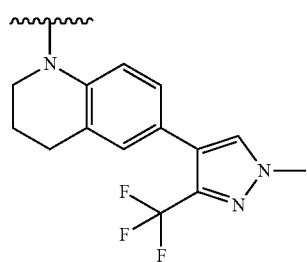
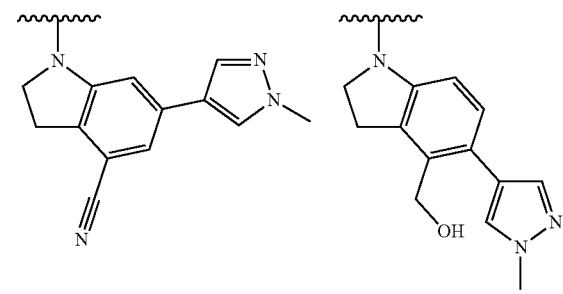
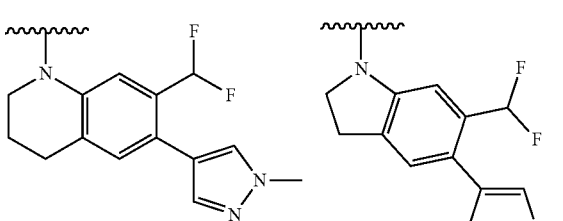
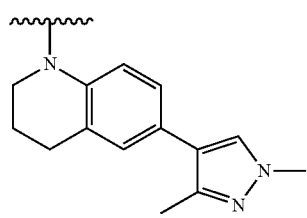
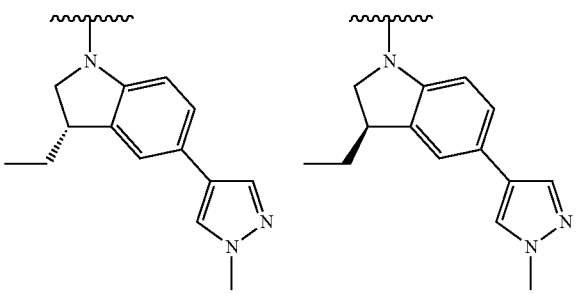

-continued
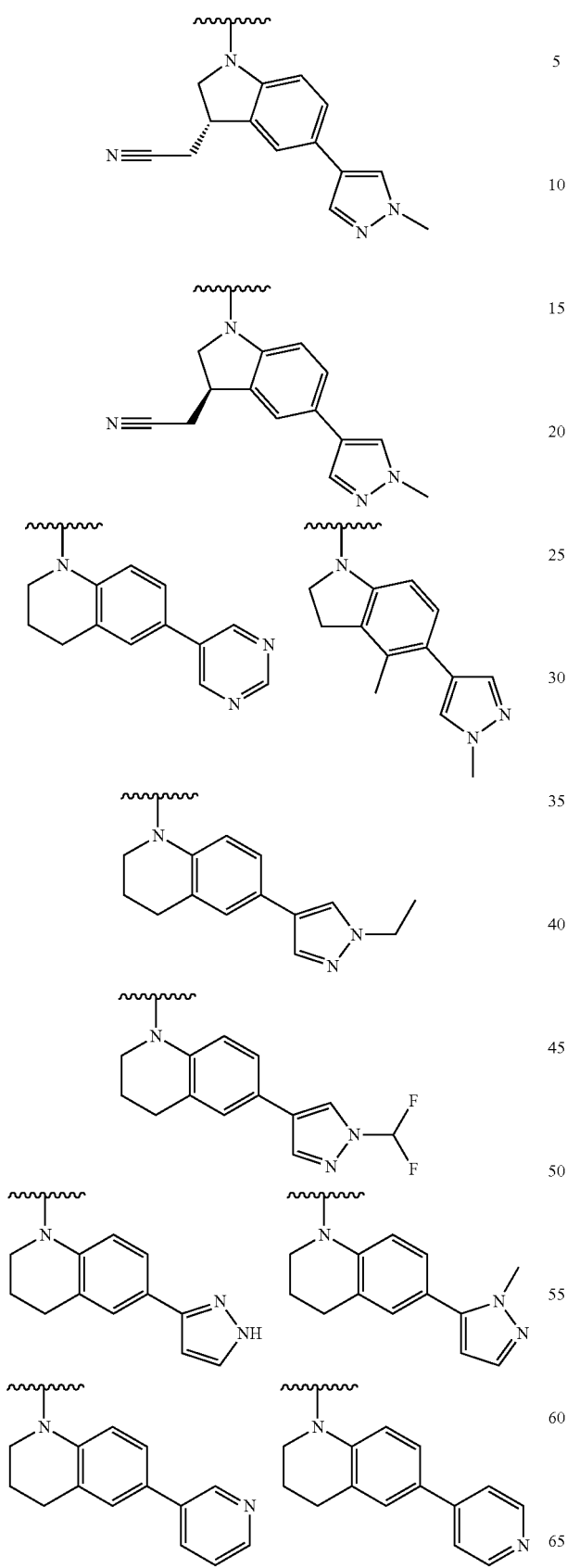
-continued
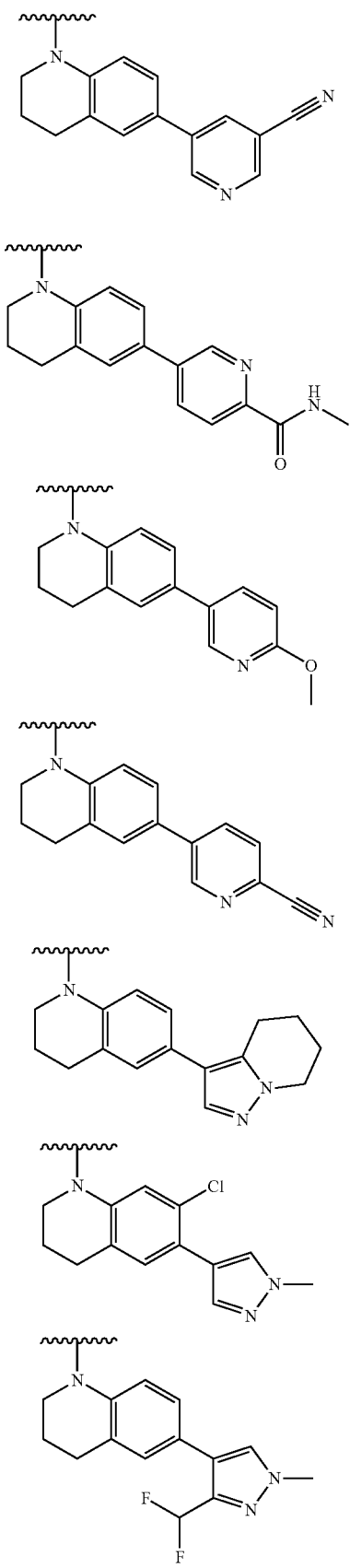

-continued
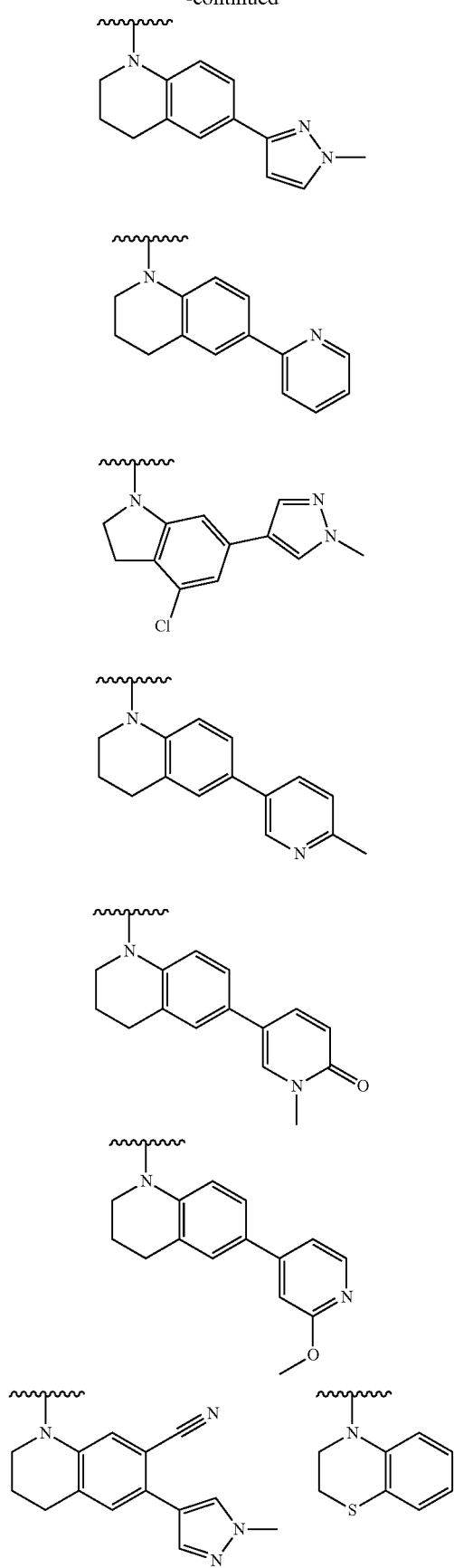
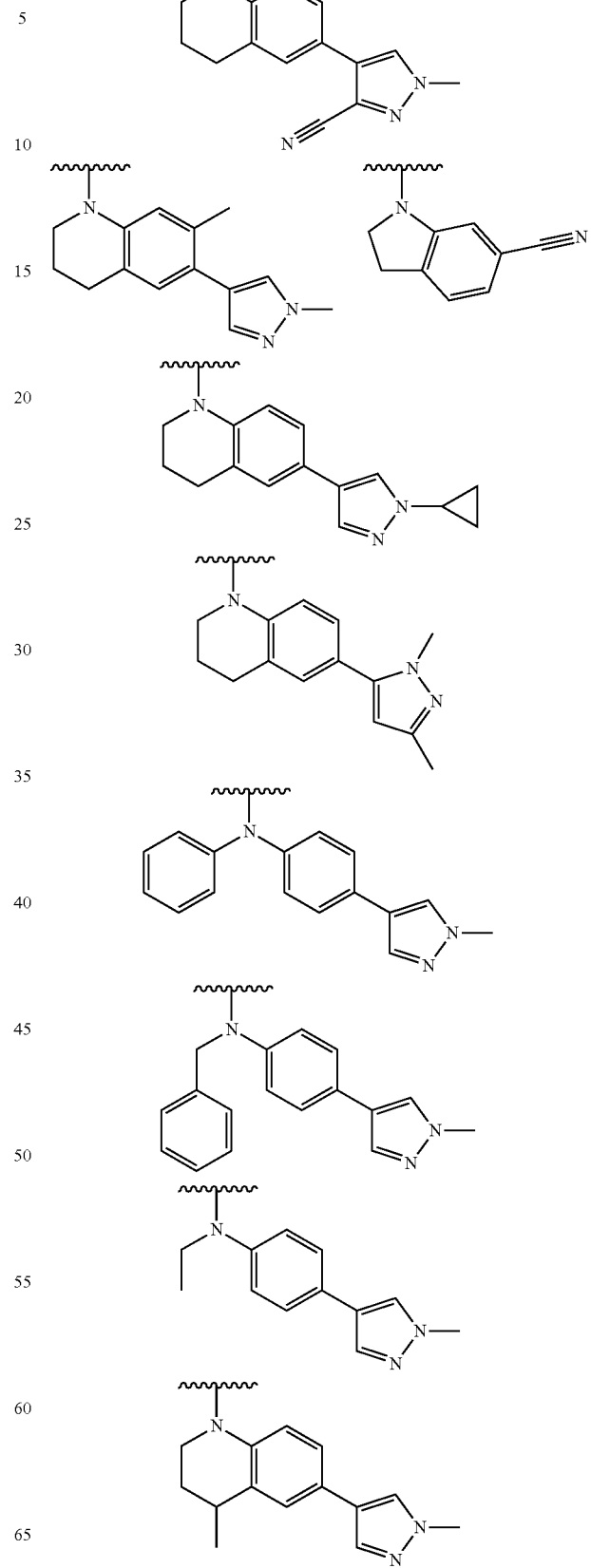

-continued
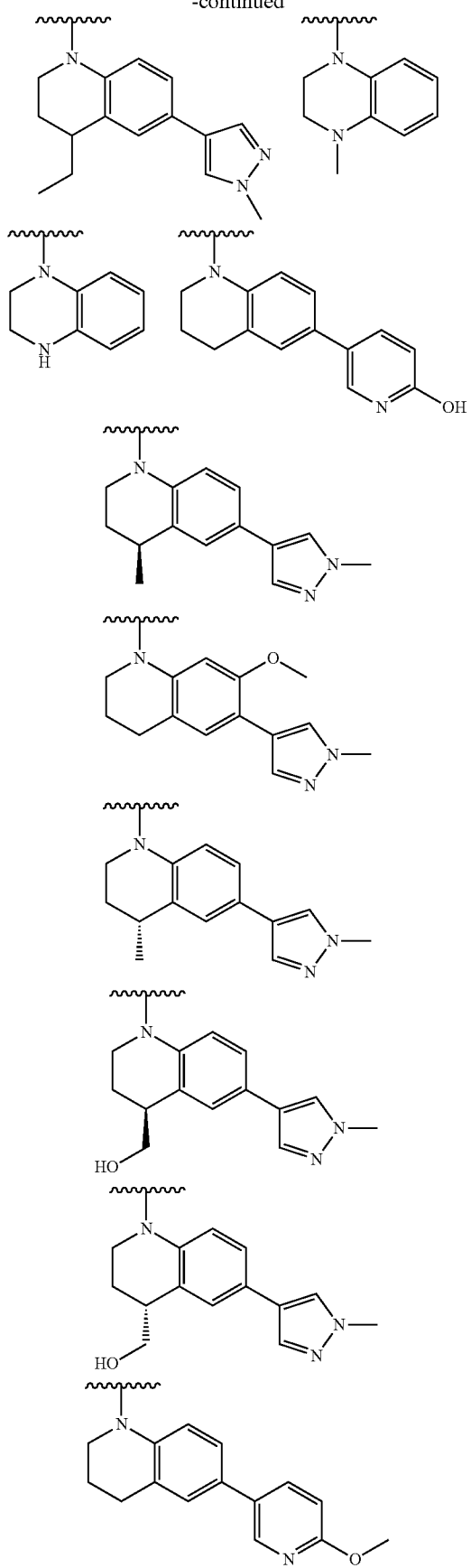
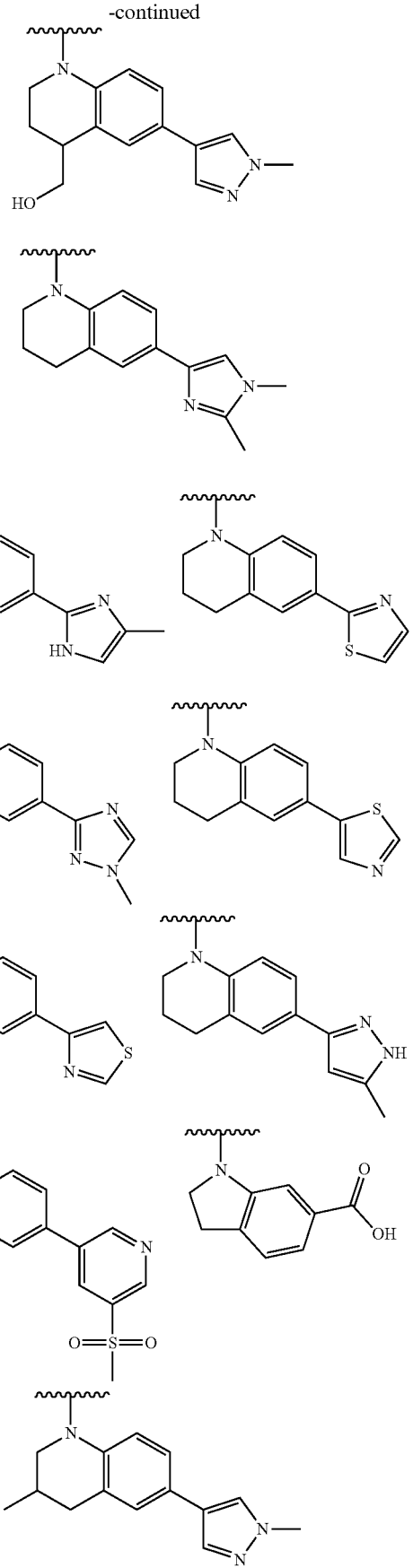

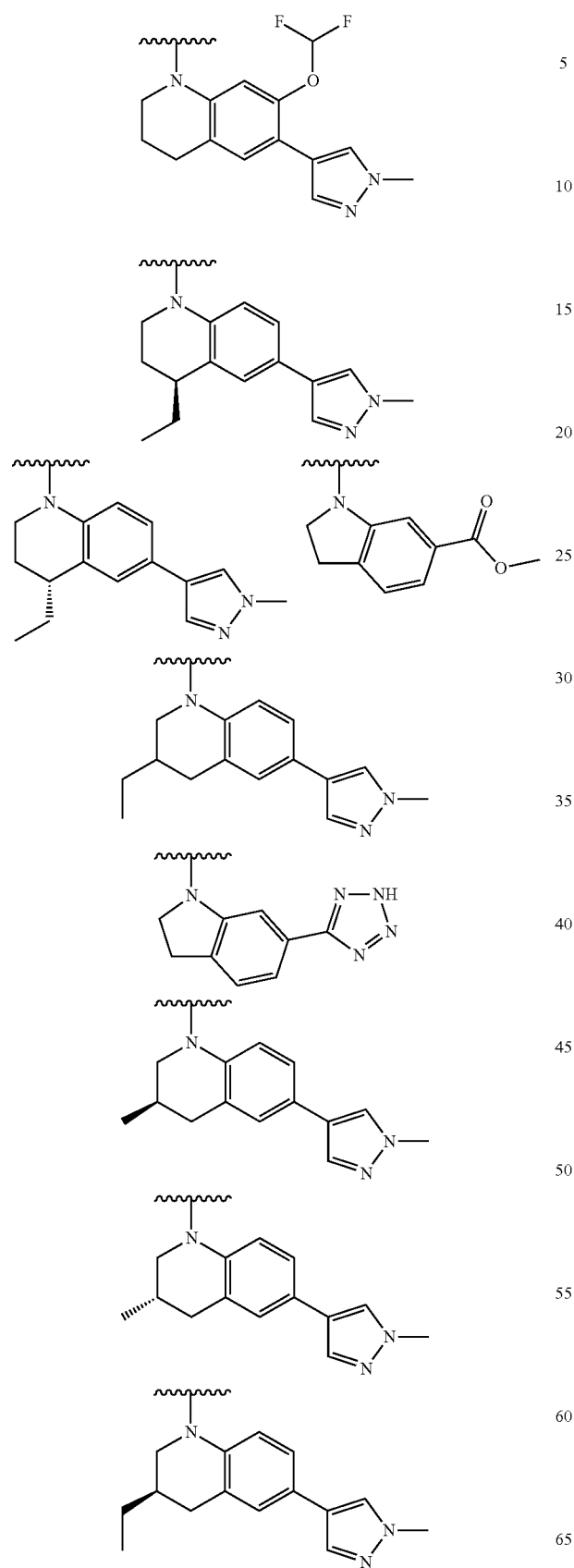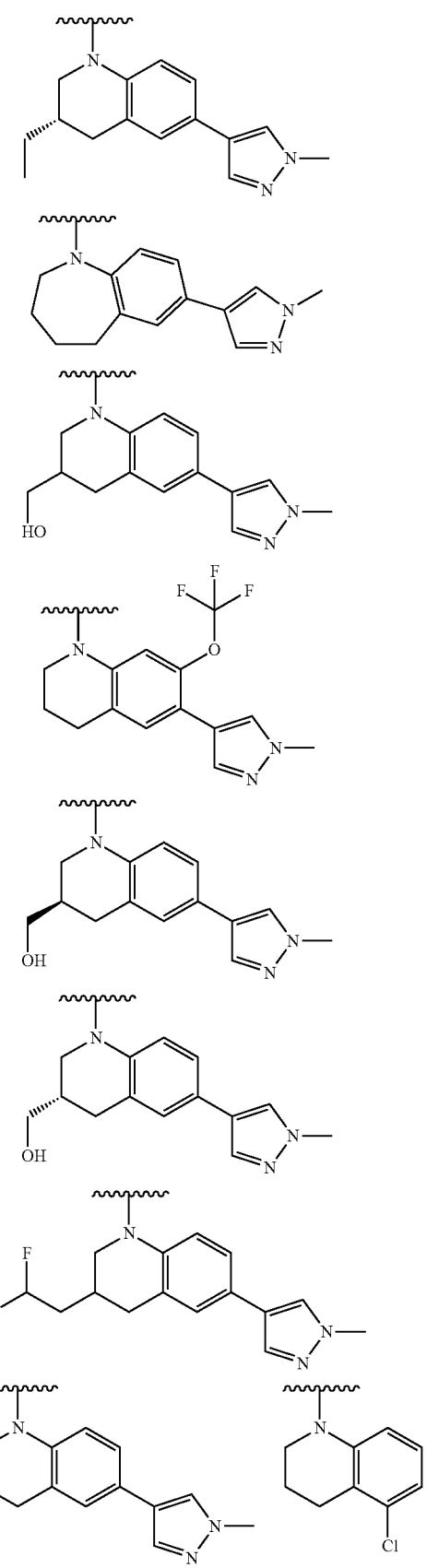


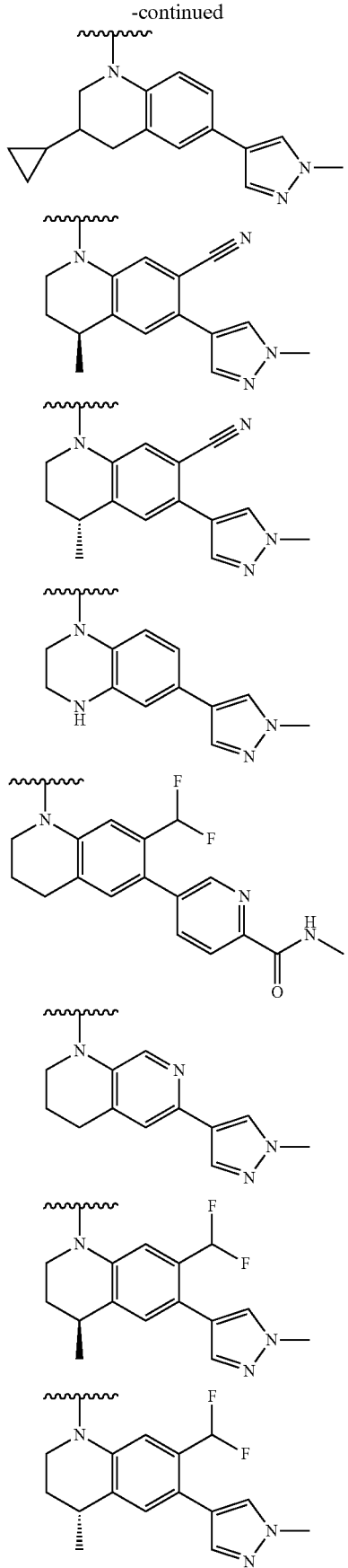
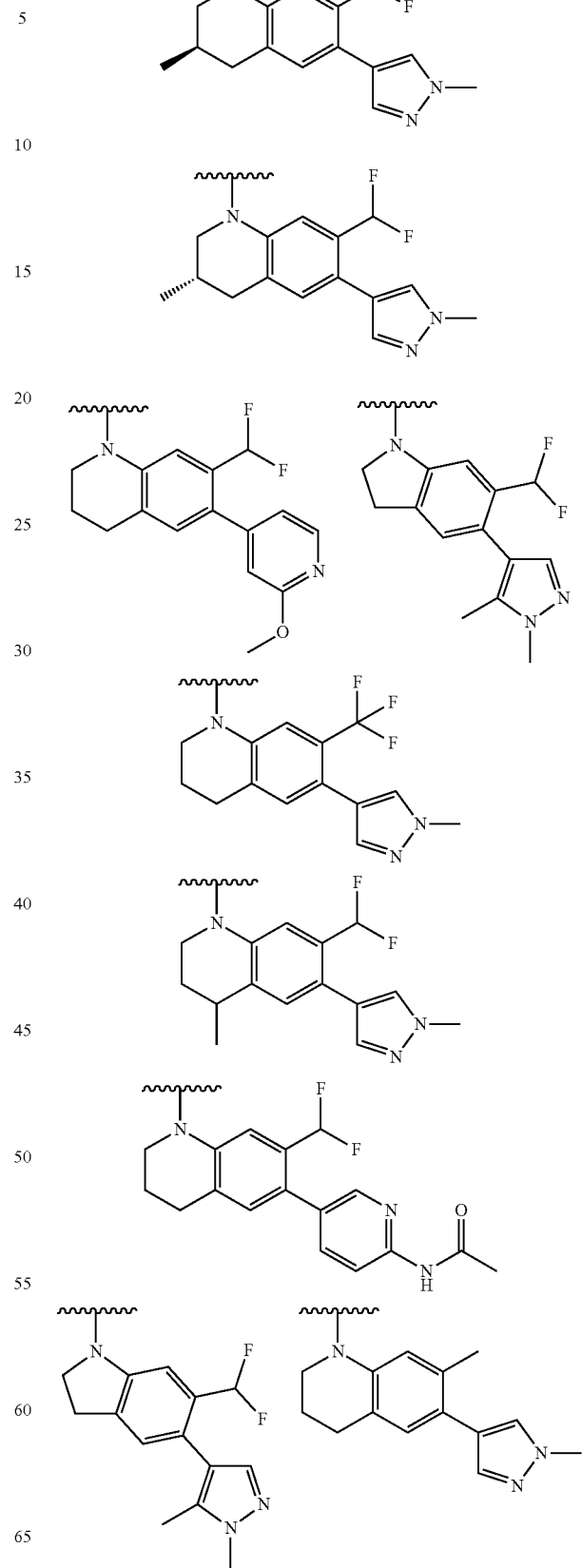

89
-continued
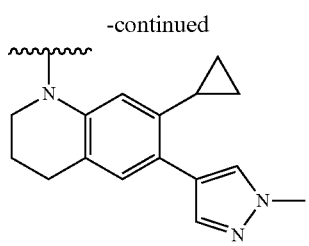
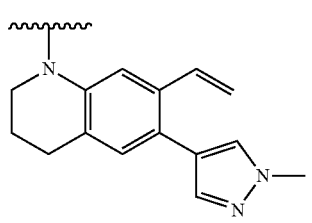
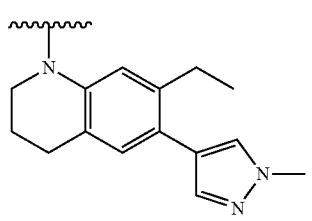
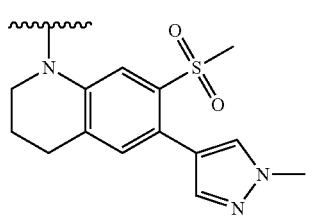
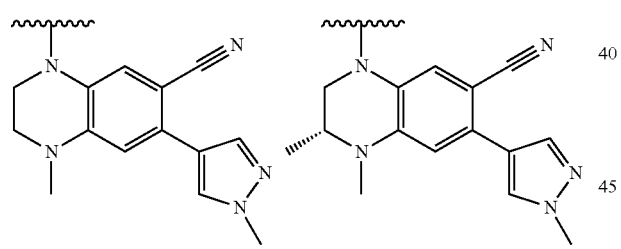
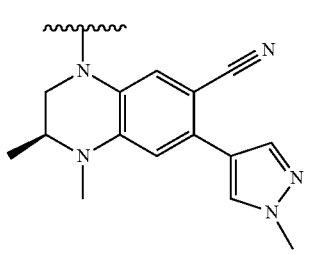
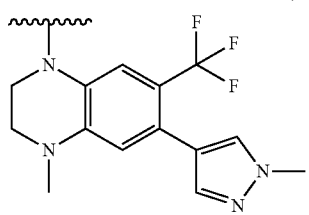
90
-continued
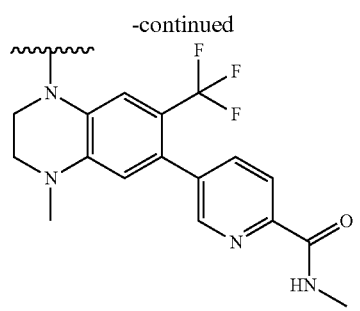
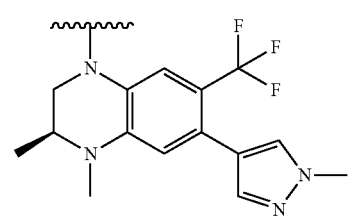
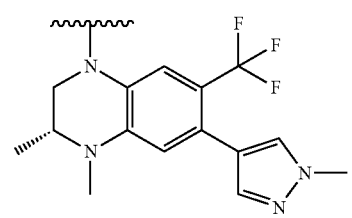
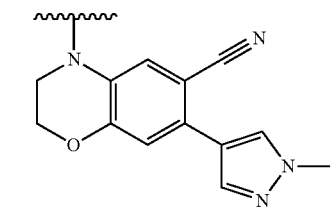
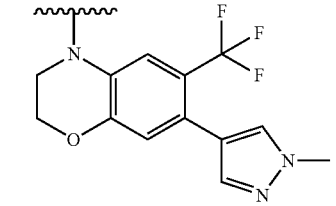
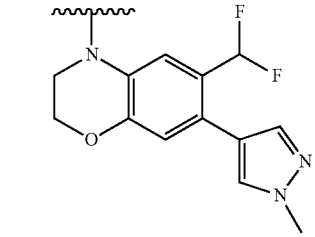
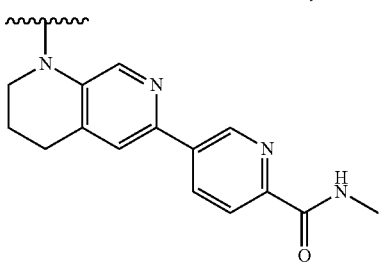

91
-continued
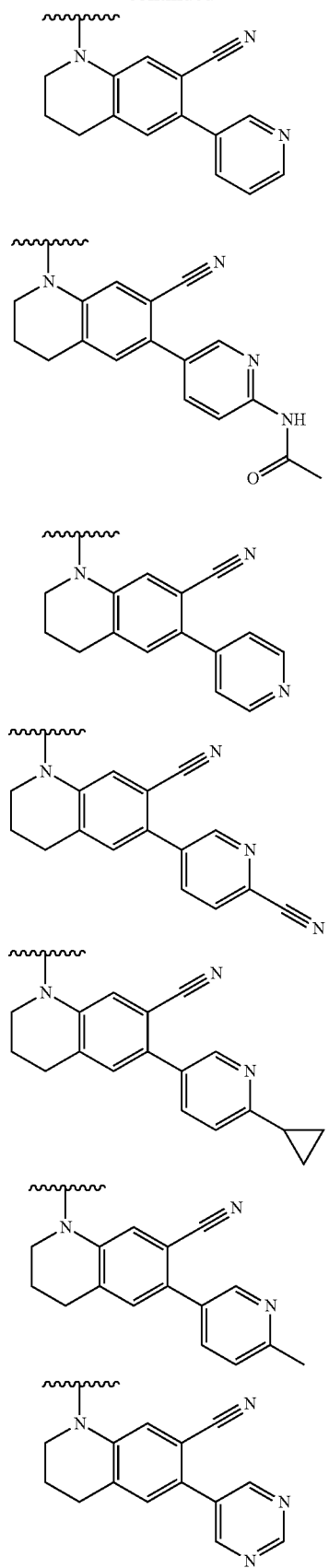
92
-continued
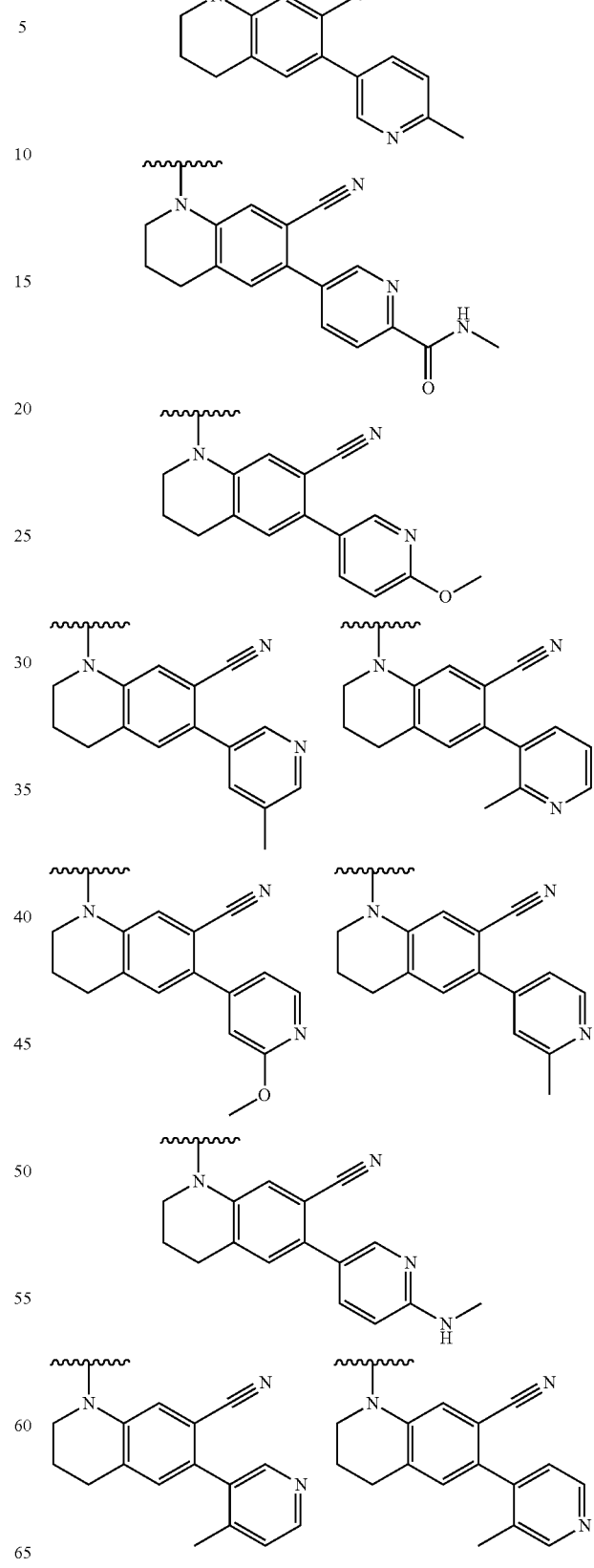

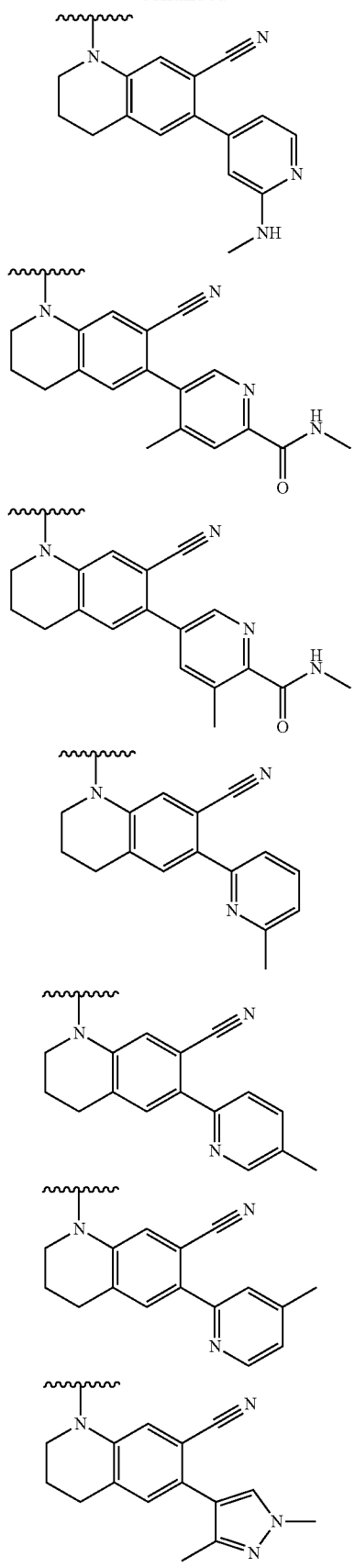
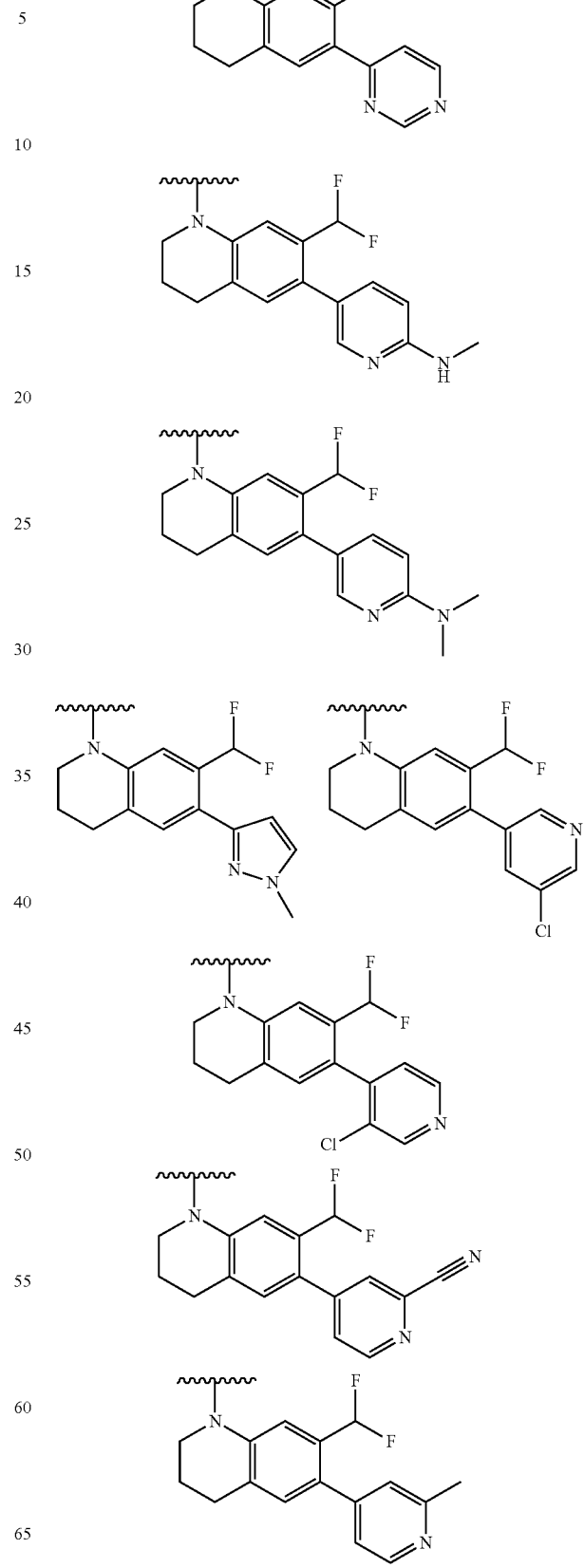

95
-continued
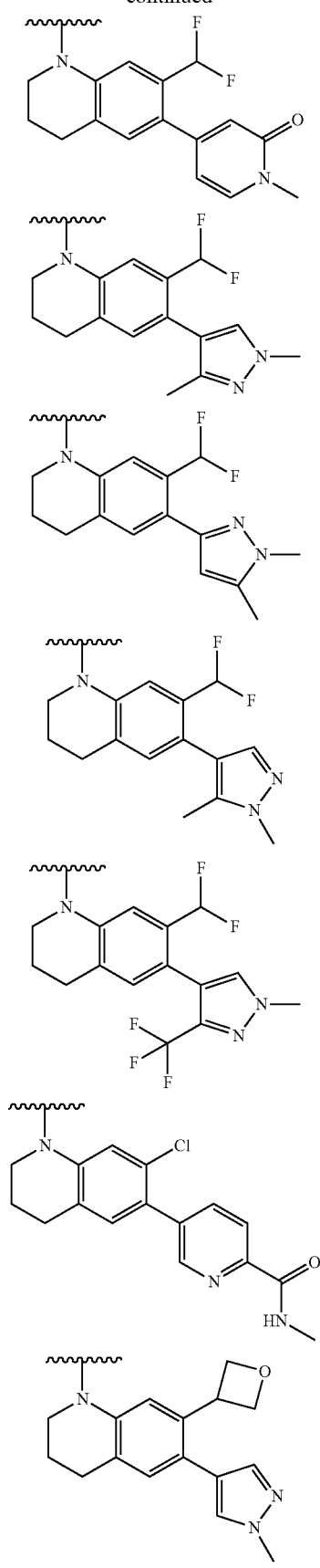
96
-continued
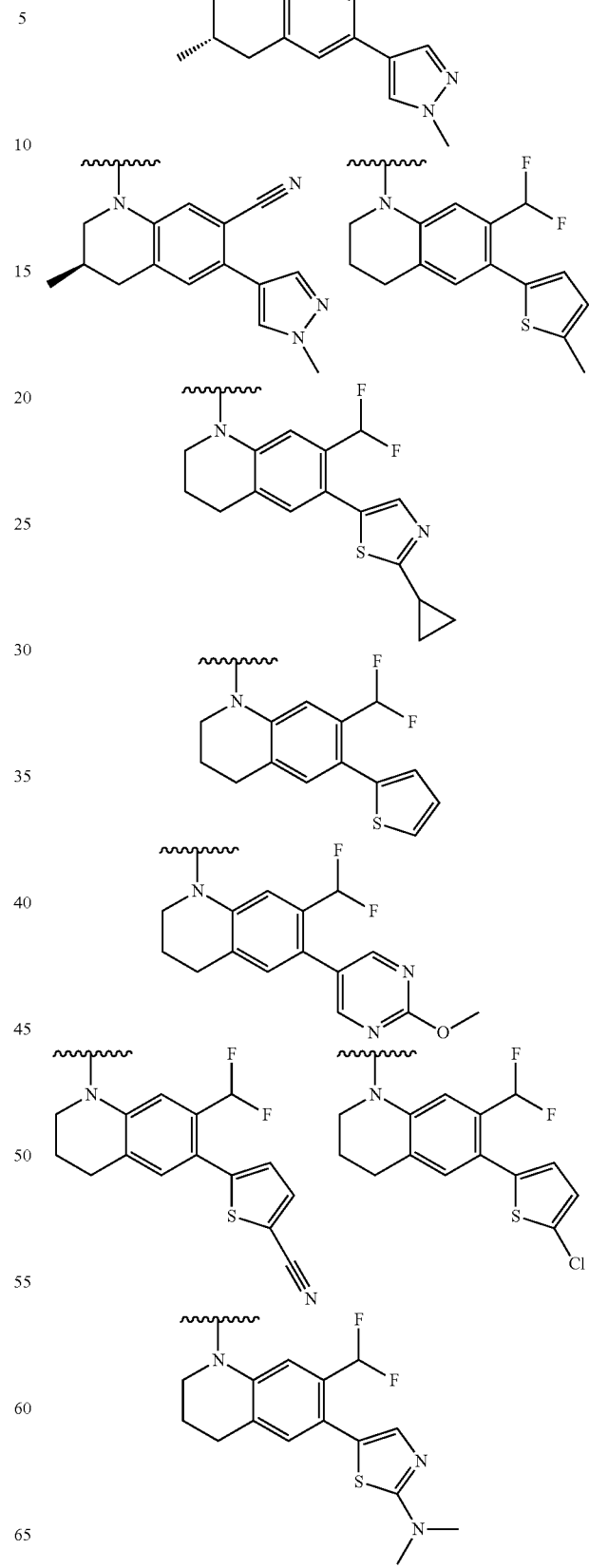

-continued
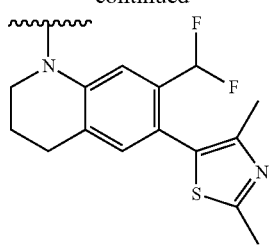
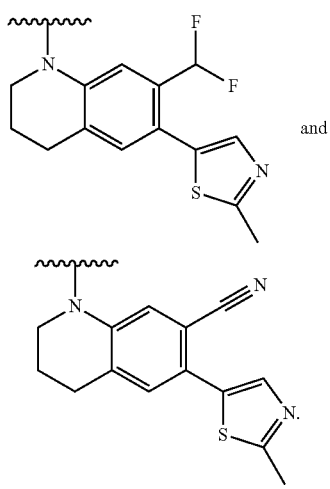
and R⁴ is acetyl, aminocarbonyl, methylaminocarbonyl, dimethylaminocarbonyl, methoxycarbonyl, propanoyl, cyclopropylcarbonyl, methylsulfonyl, butanoyl, difluoroacetyl, thiadiazole or isoxazole.
In certain embodiments the compound of Formula (I) is selected from the group consisting of:
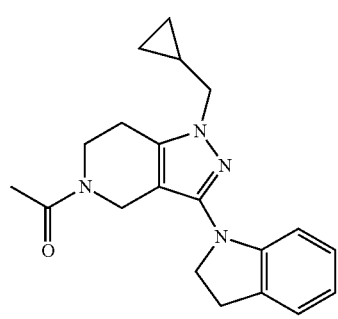
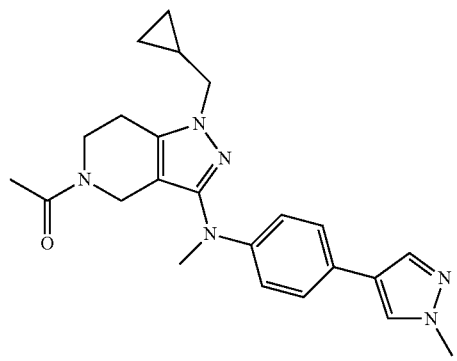
-continued
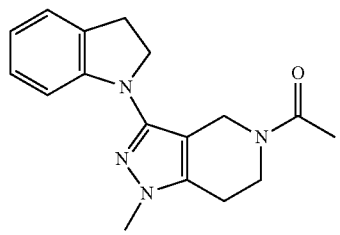
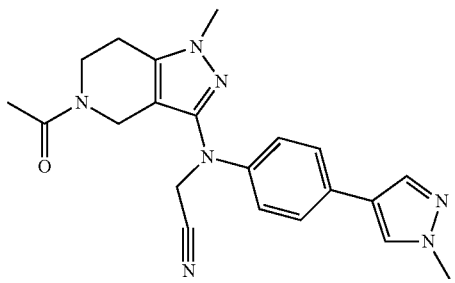
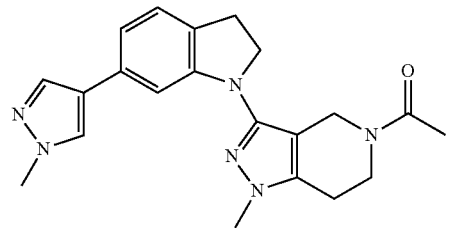
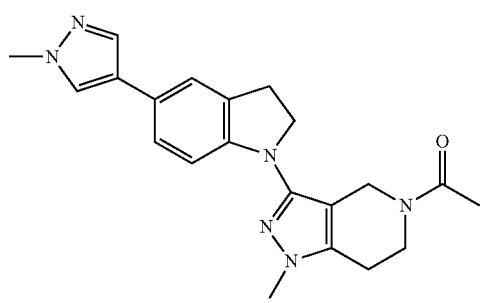
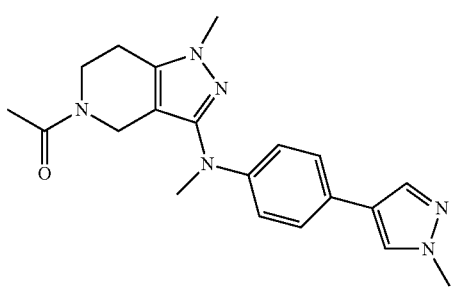
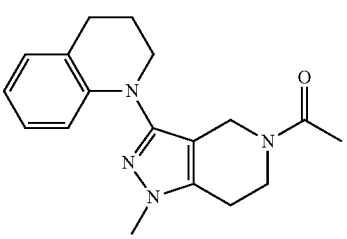

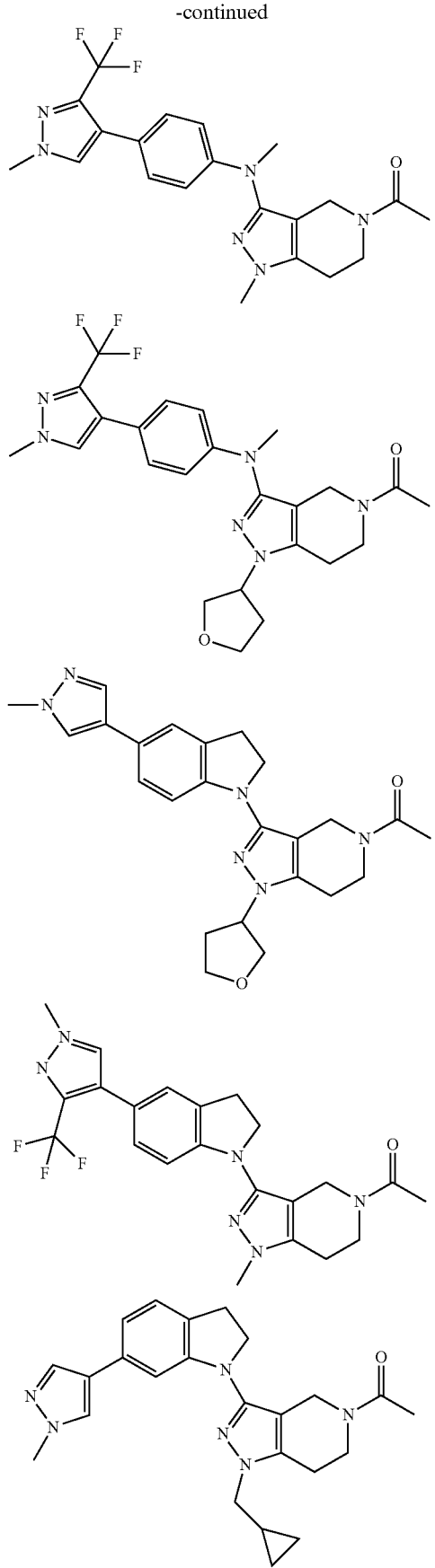
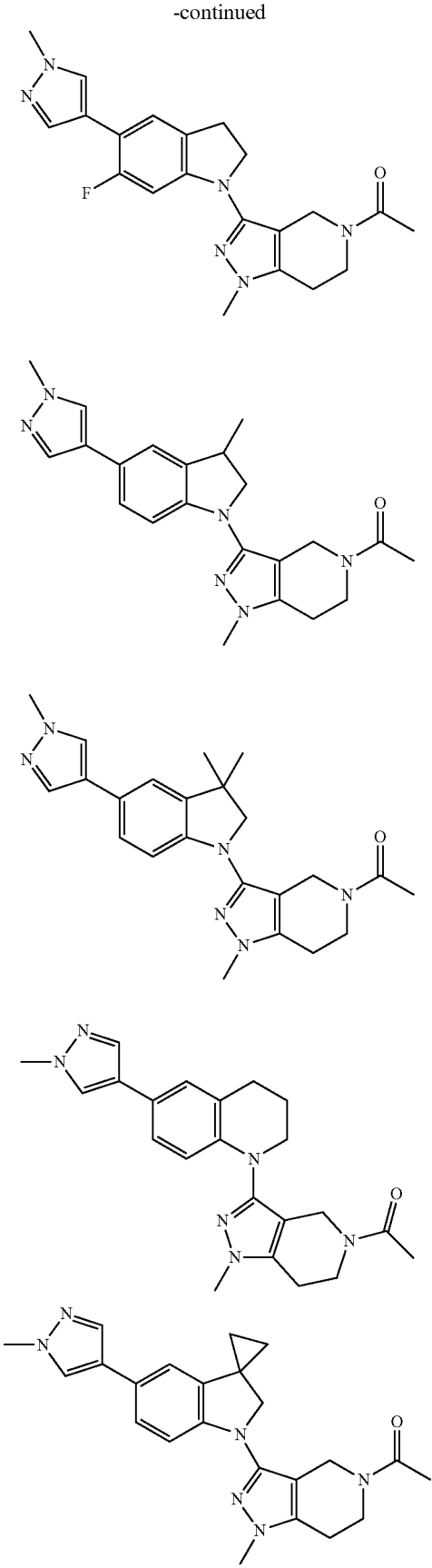

101
-continued
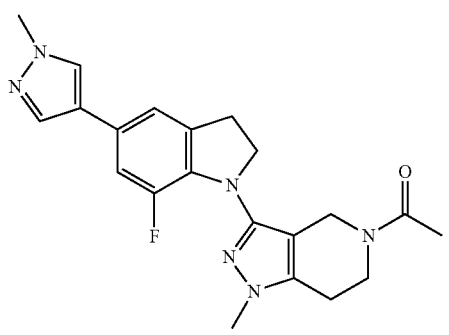
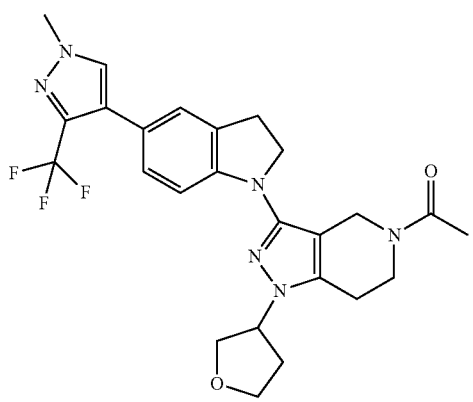
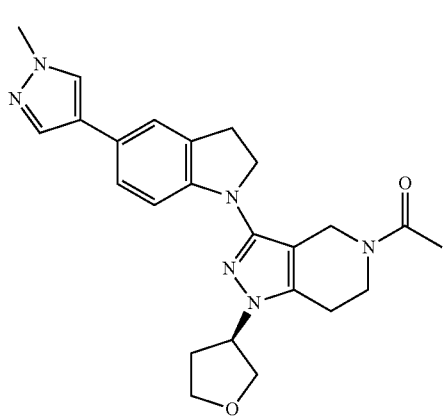
102
-continued
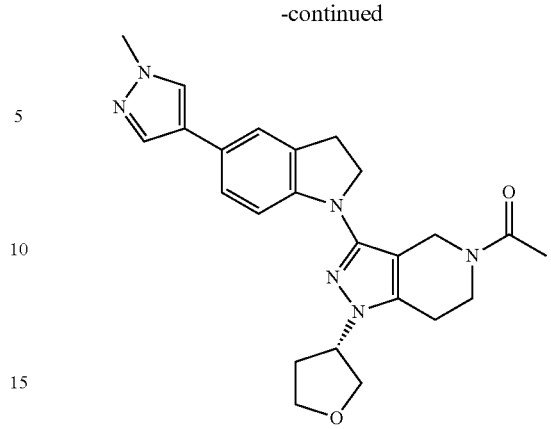
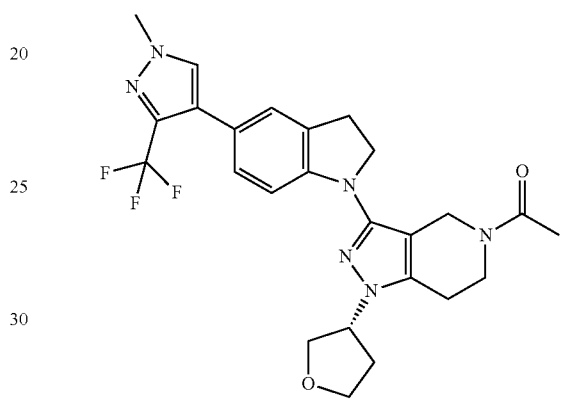
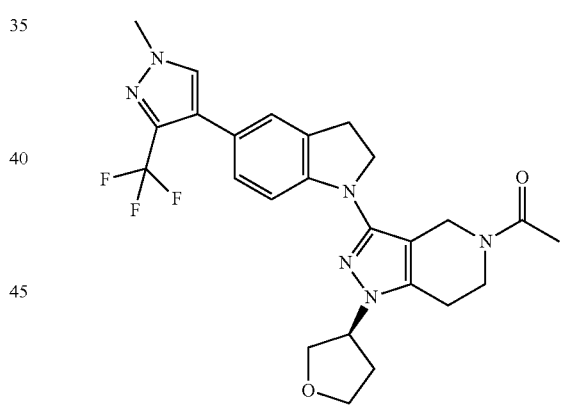
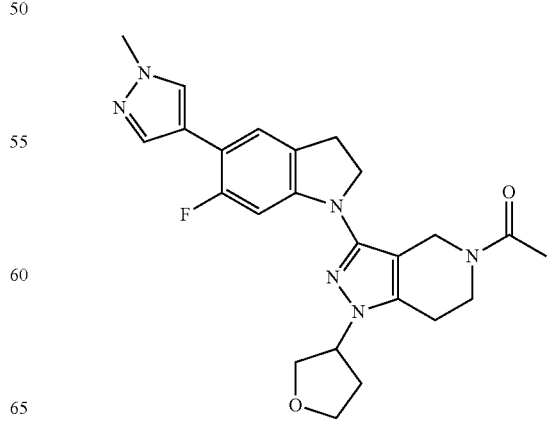

103
-continued
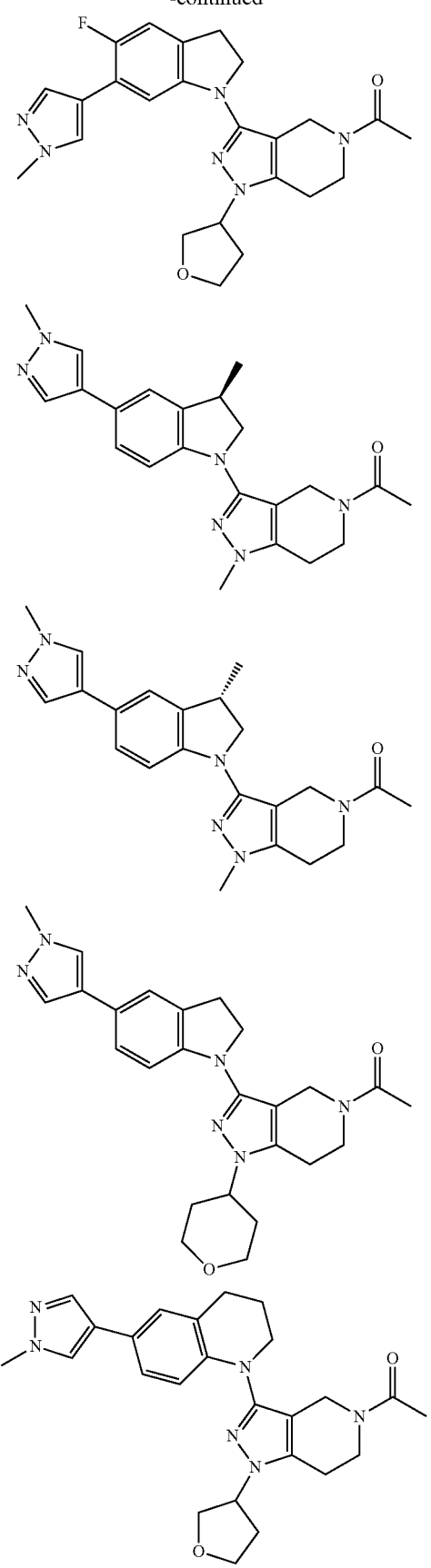
104
-continued
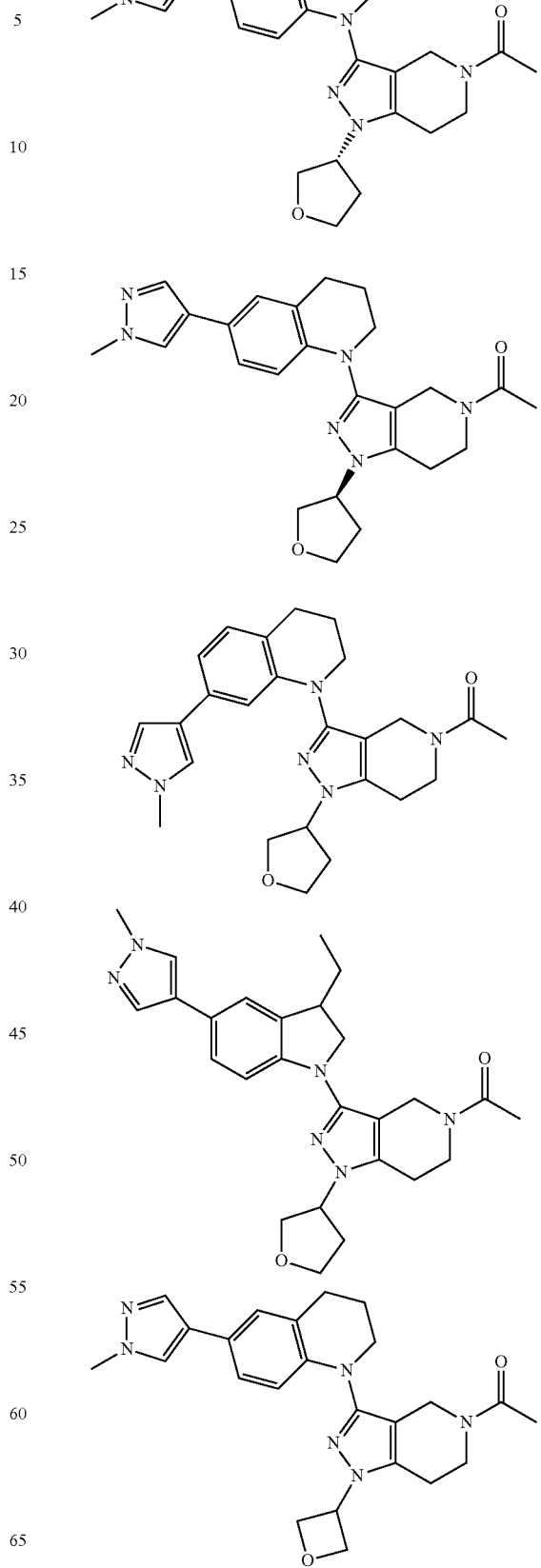

-continued
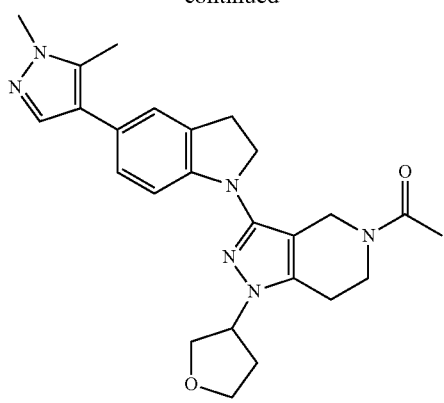
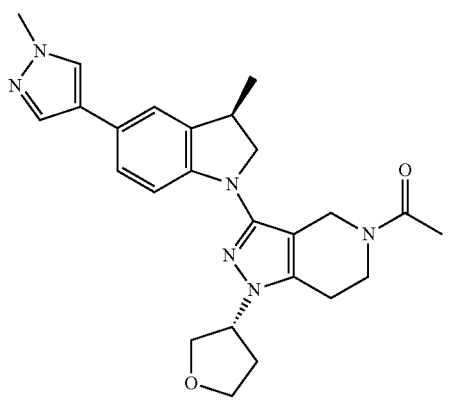
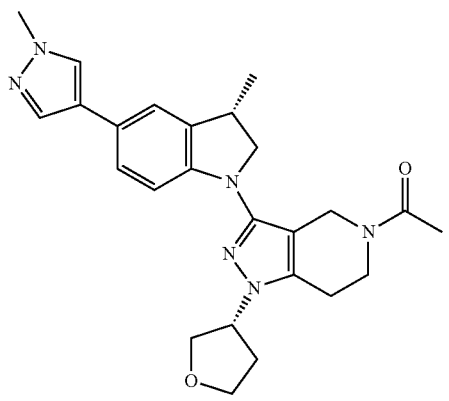
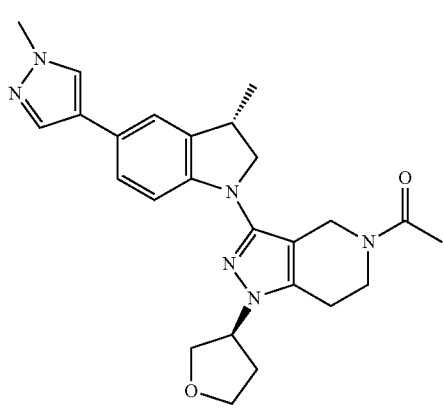
-continued
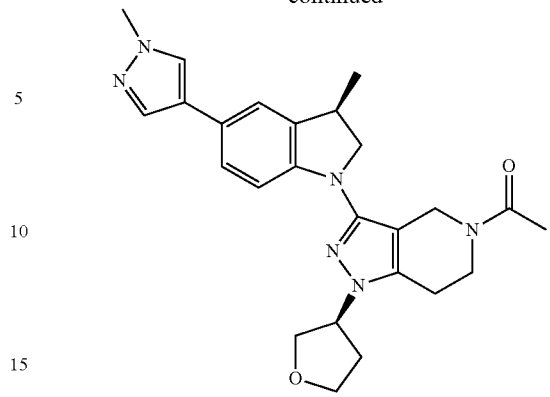
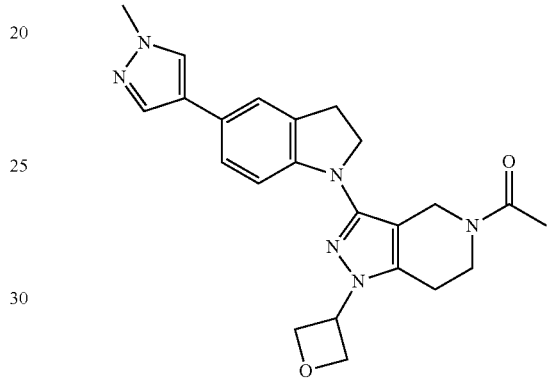
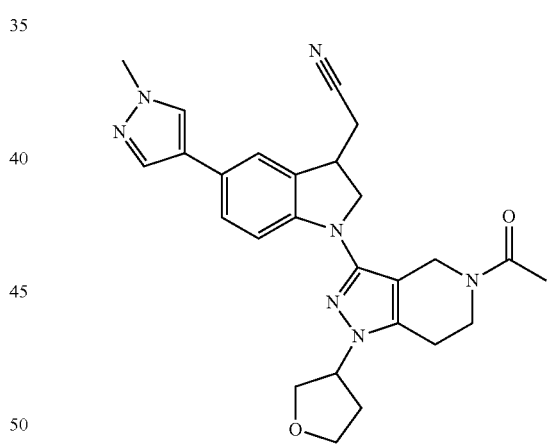
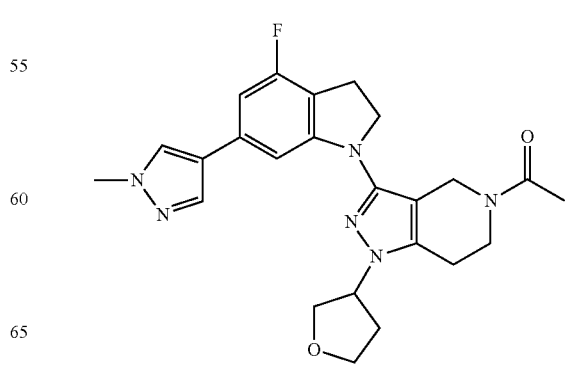

107
-continued
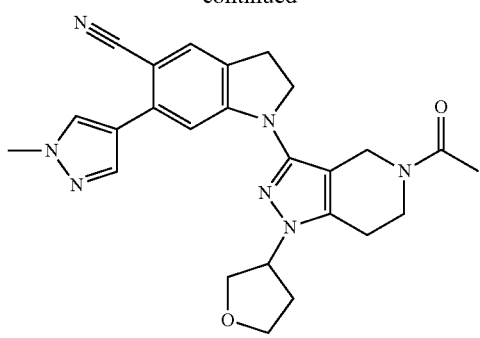
108
-continued
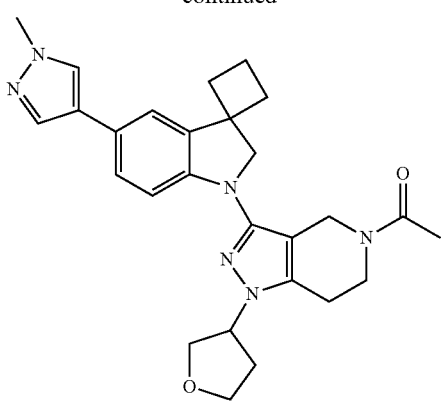
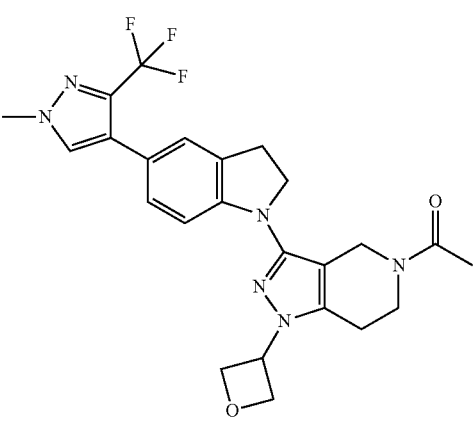
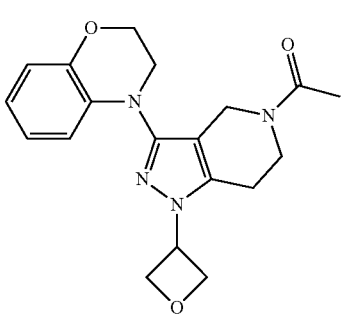
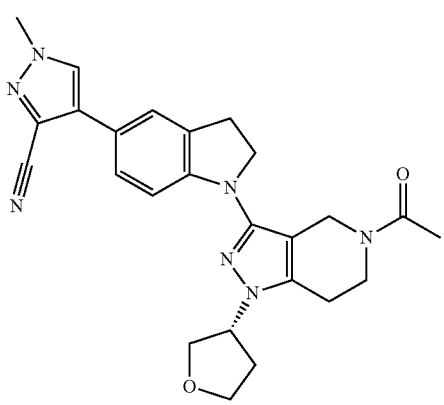

109
-continued
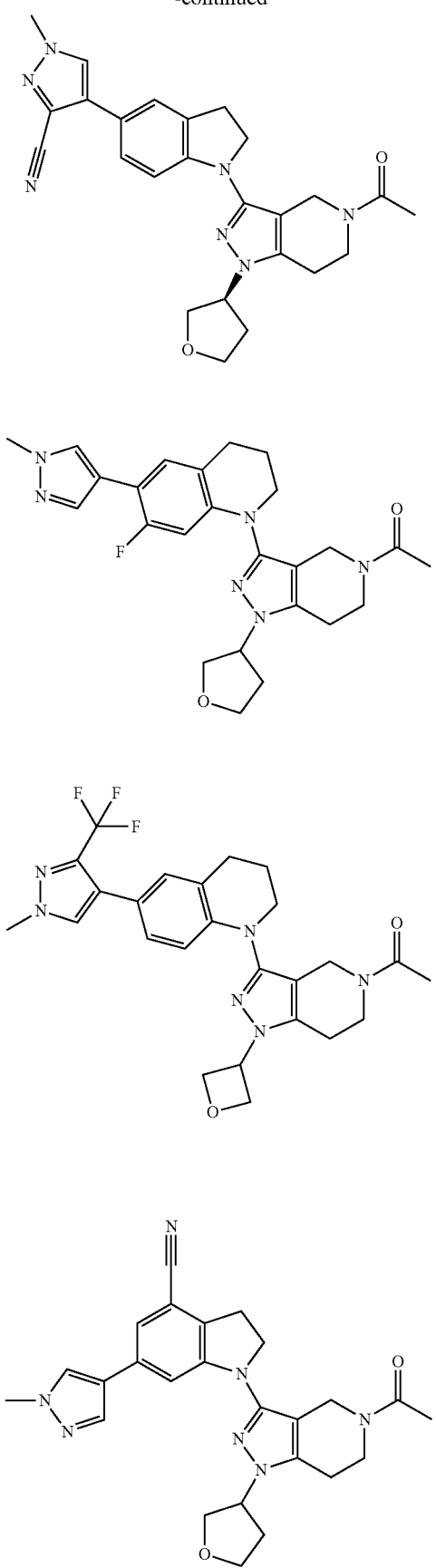
110
-continued
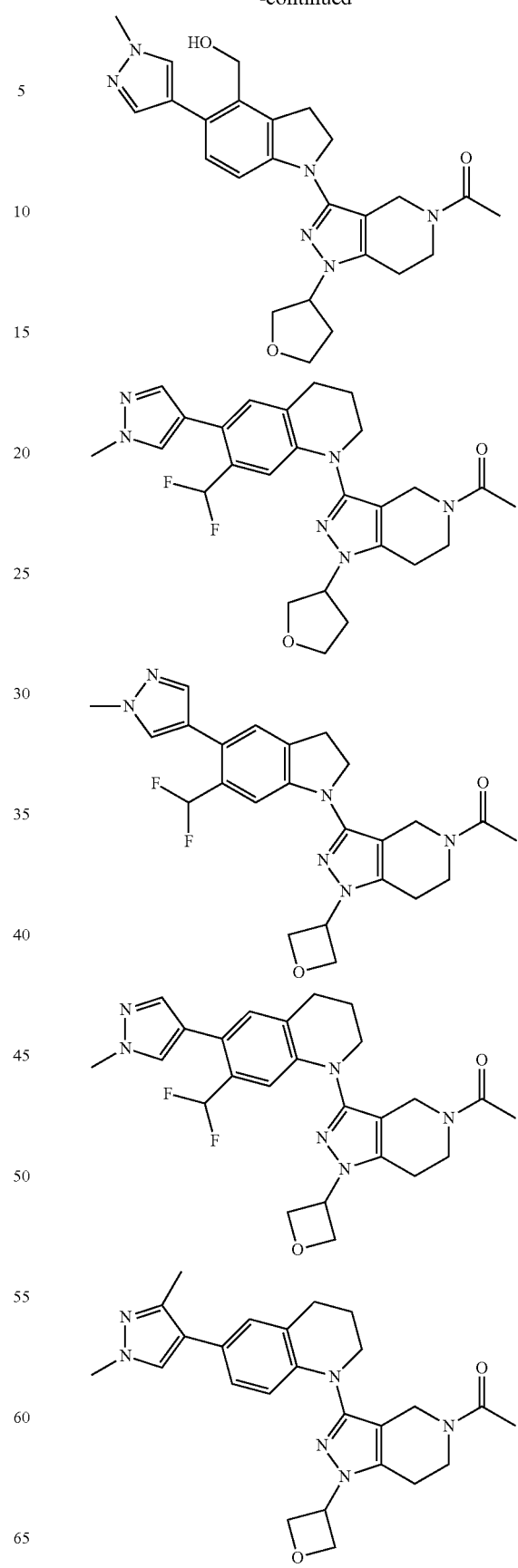

111
-continued
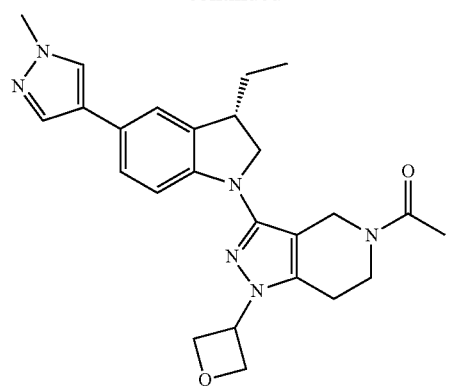
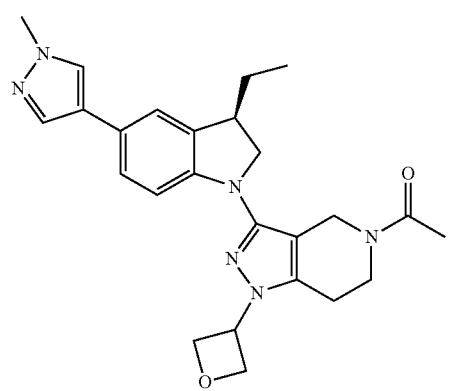
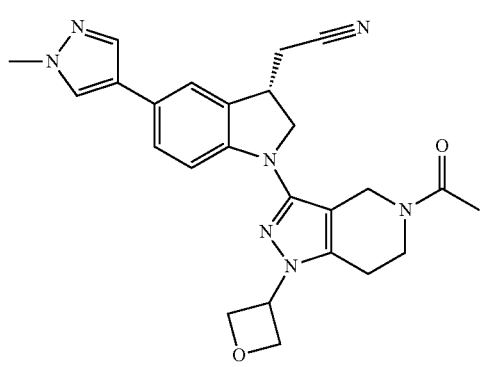
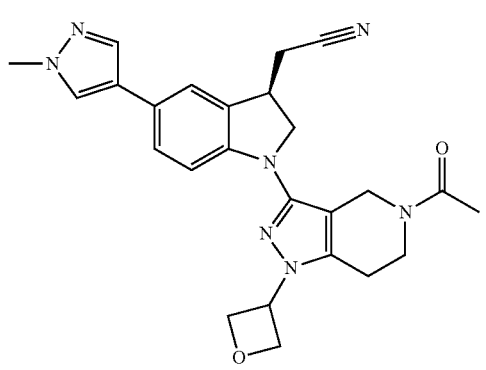
112
-continued
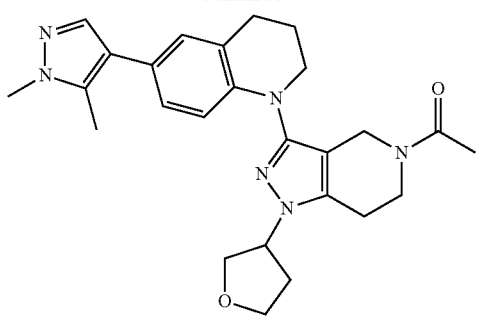
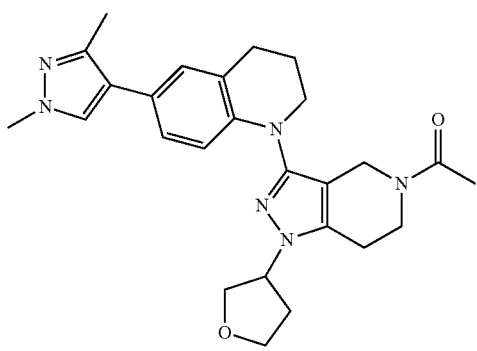
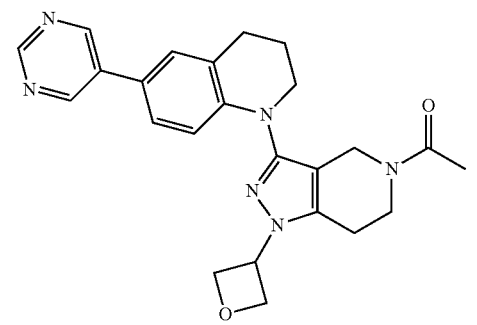
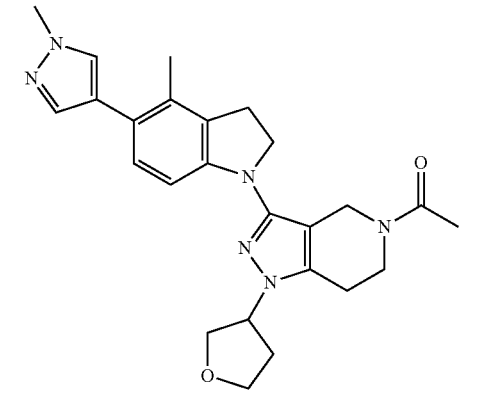
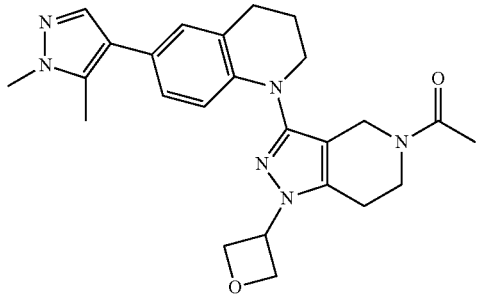

113
-continued
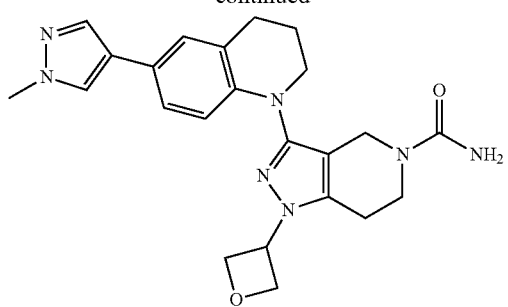
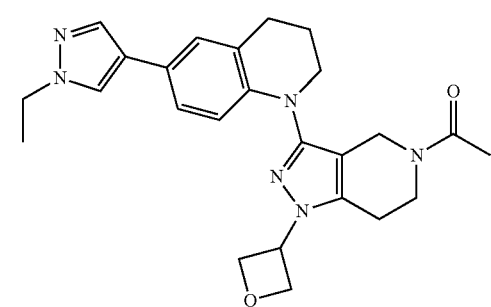
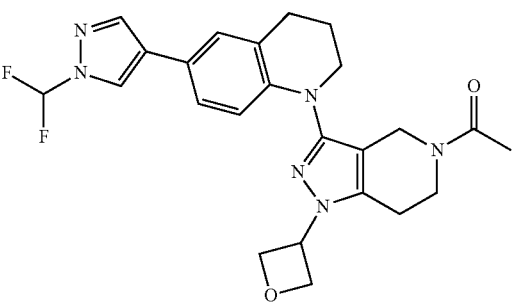
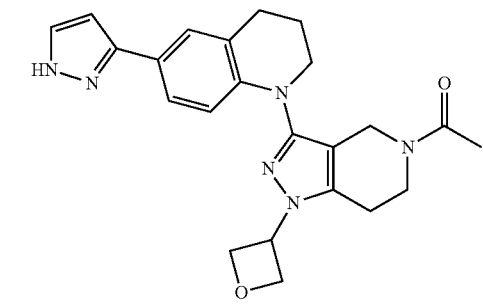
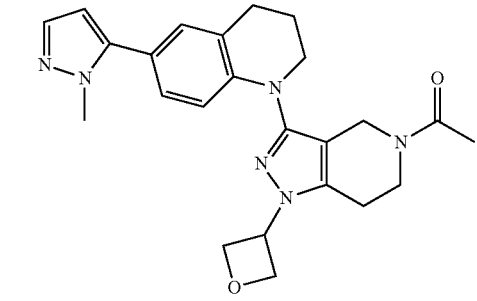
114
-continued
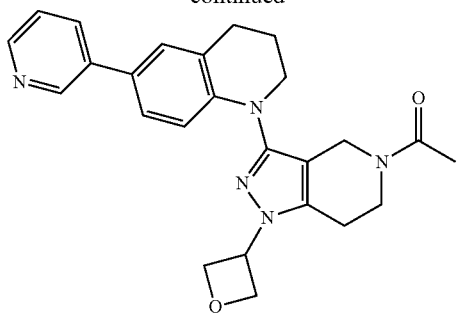
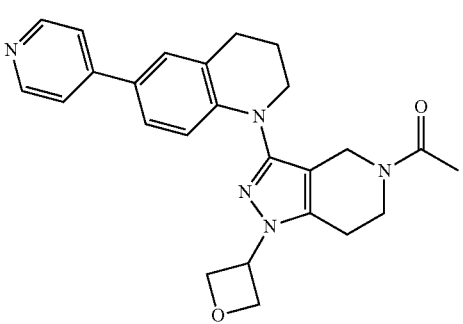
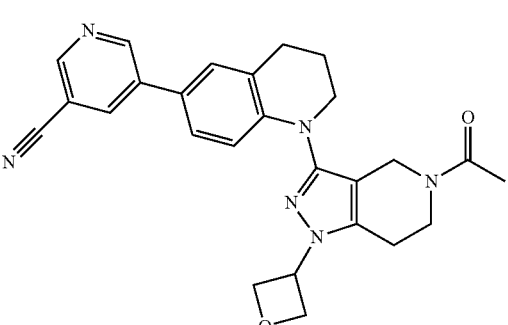
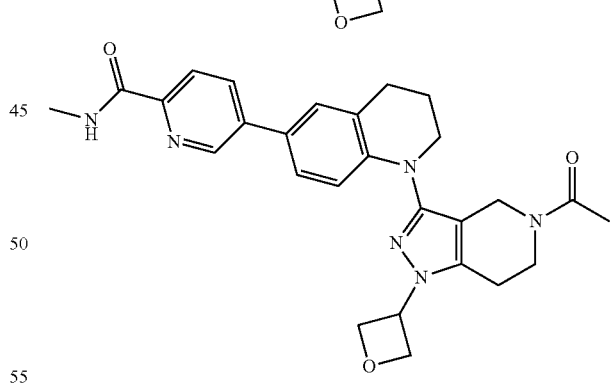
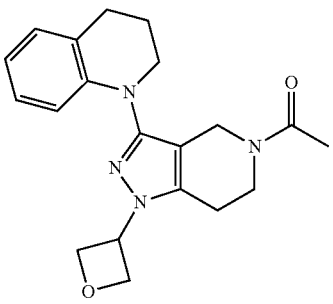

115
-continued
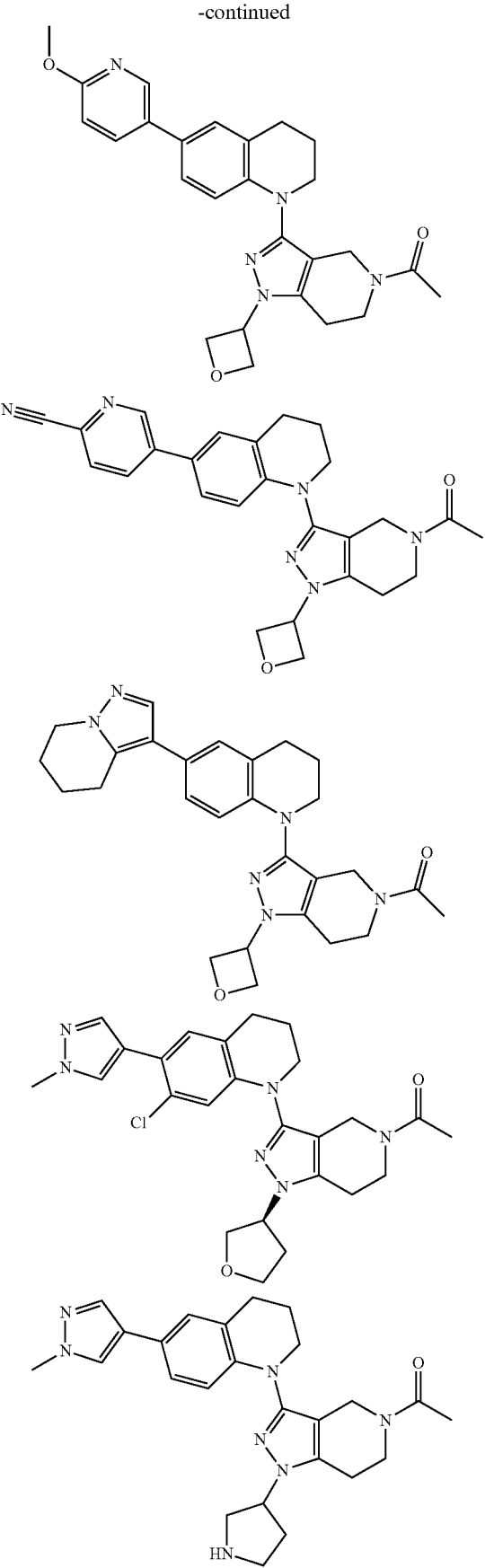
116
-continued
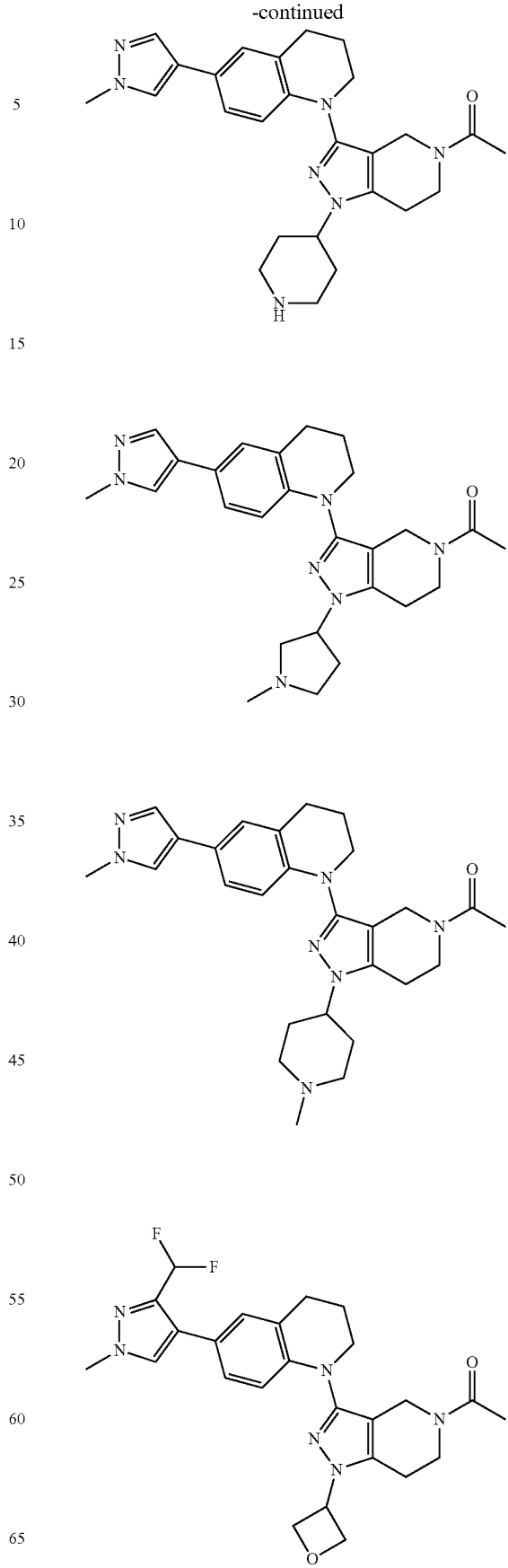

117
-continued
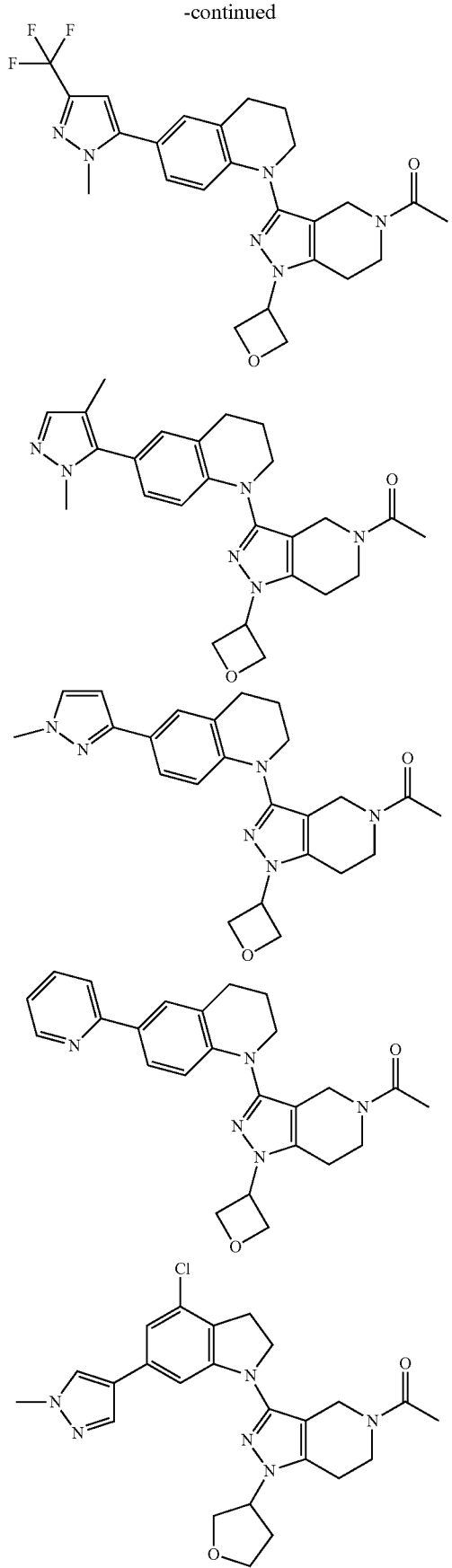
118
-continued
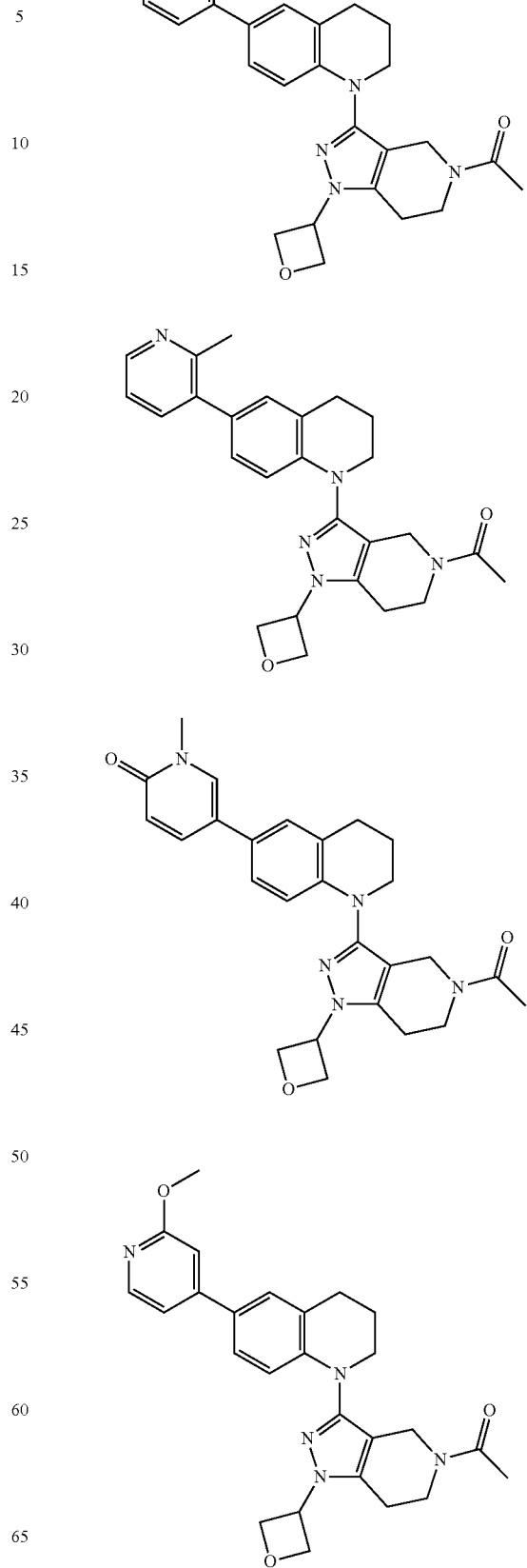

119
-continued
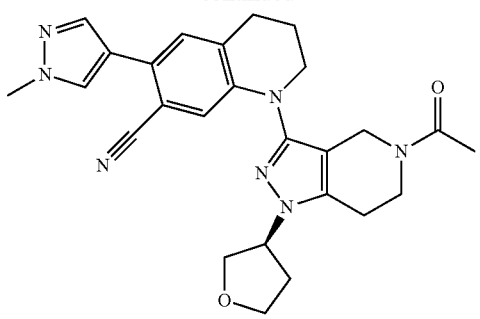
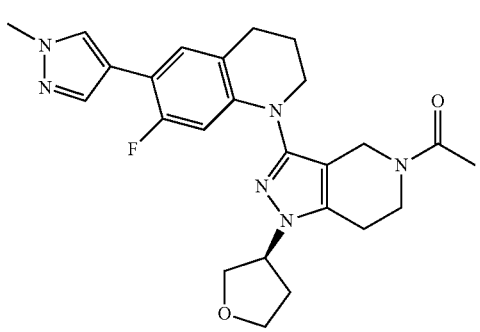
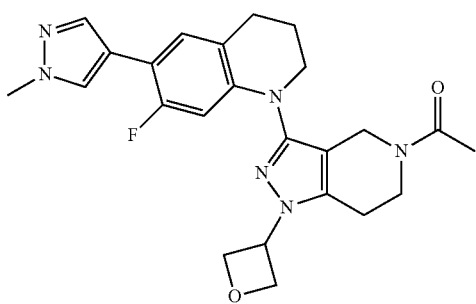
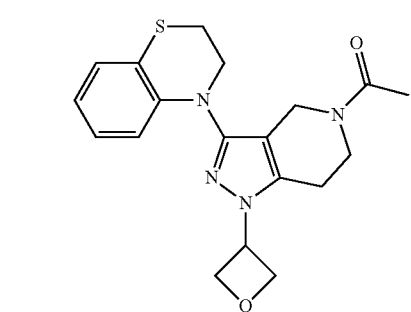
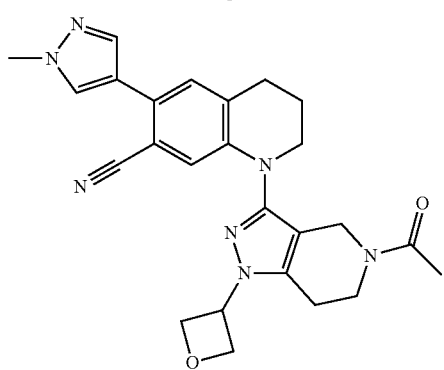
120
-continued
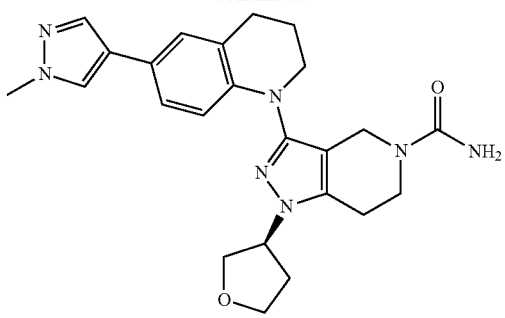
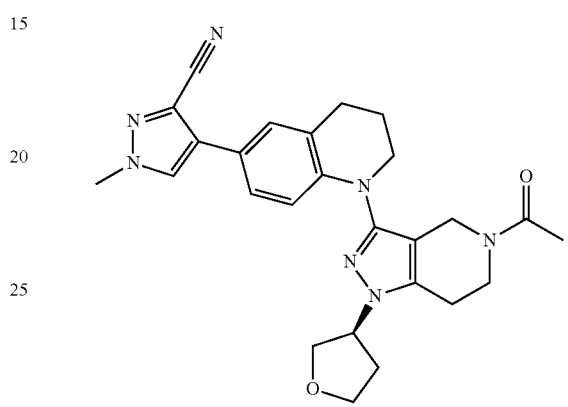
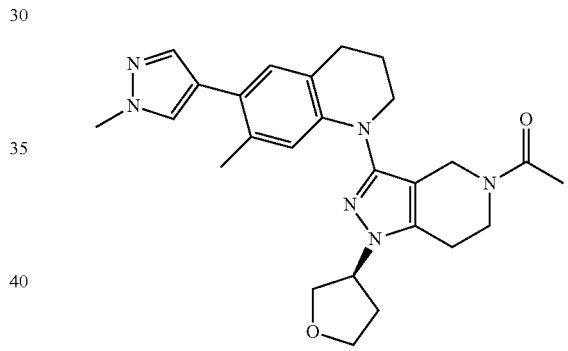
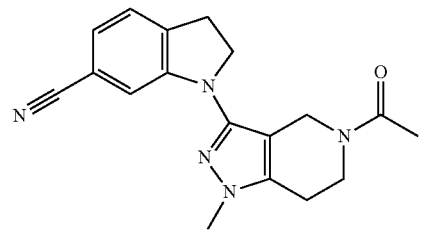
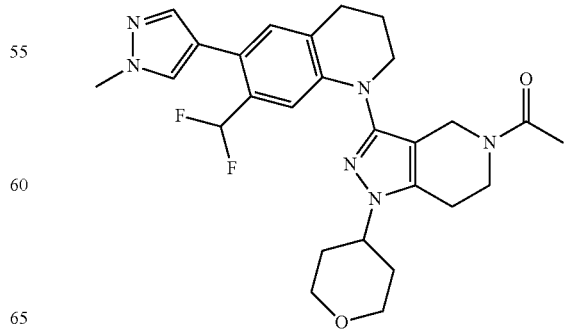

121
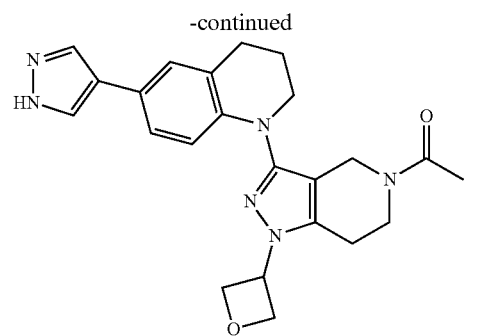
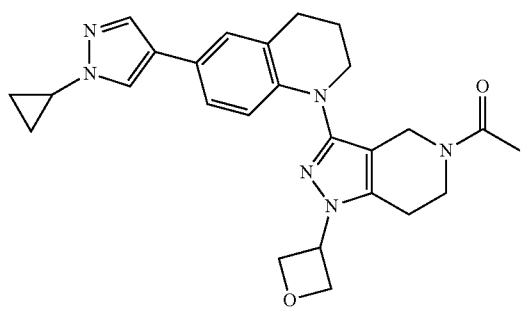
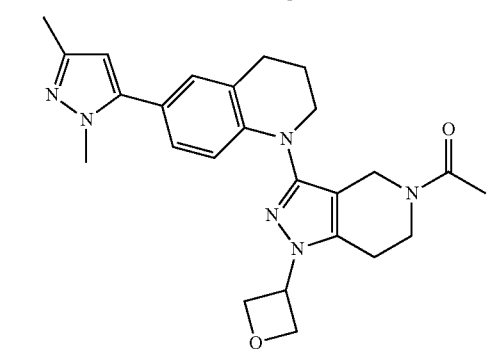
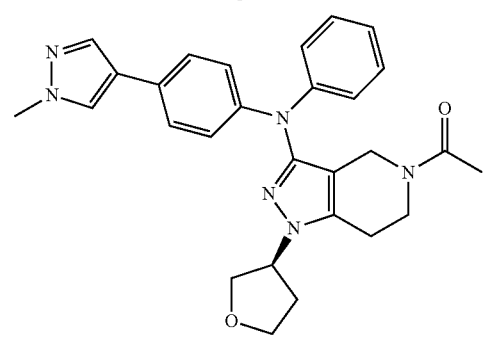
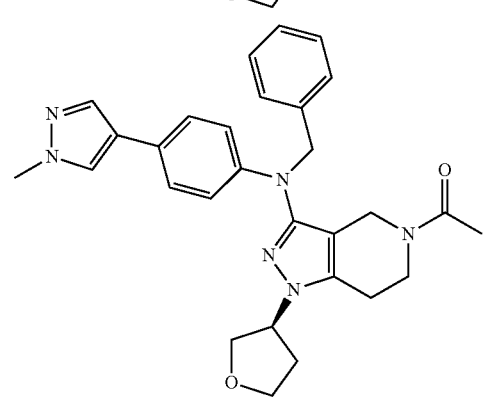
122
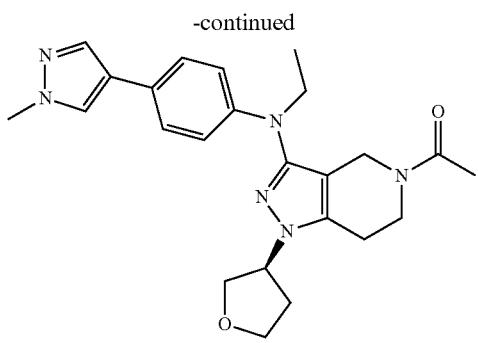
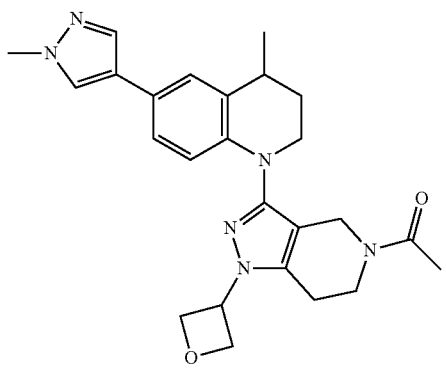
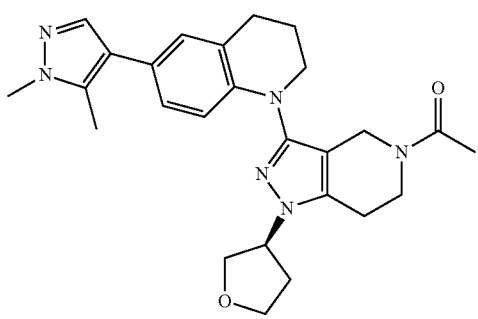
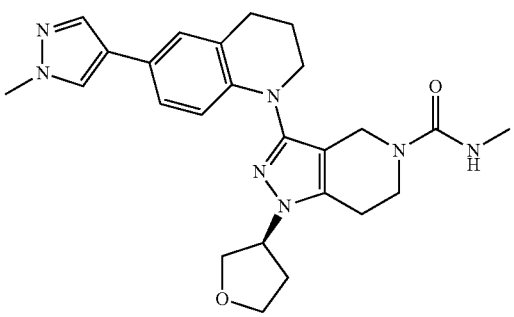
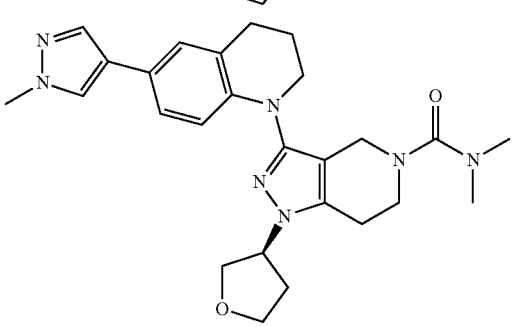

123
-continued
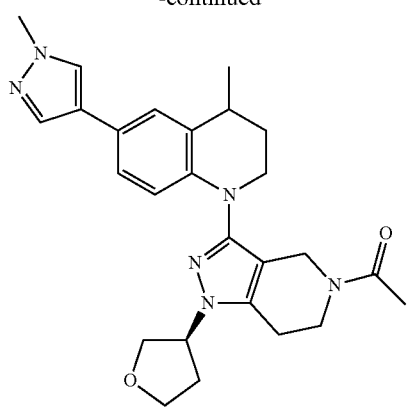
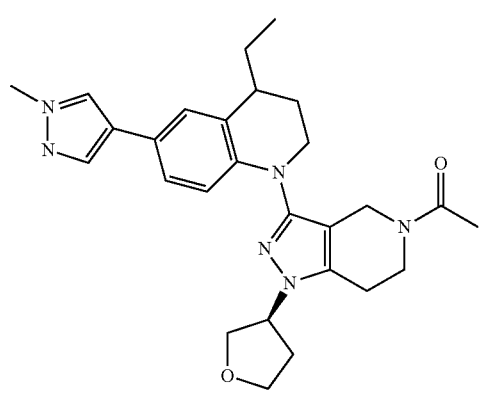
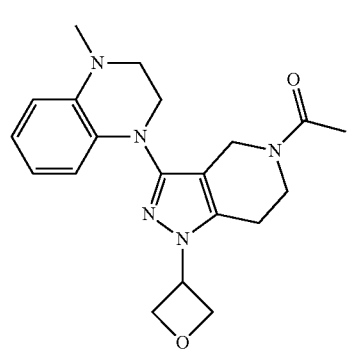
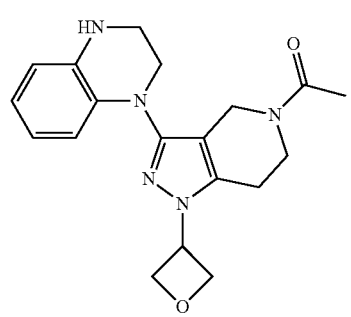
124
-continued
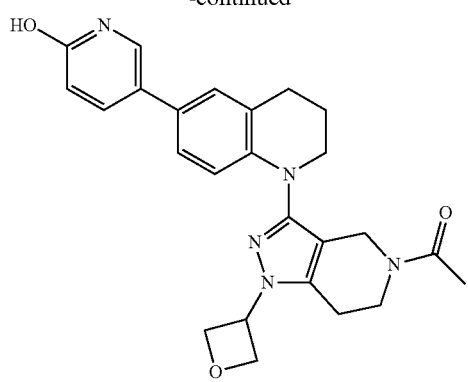
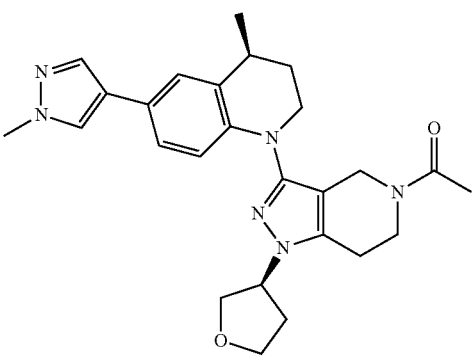
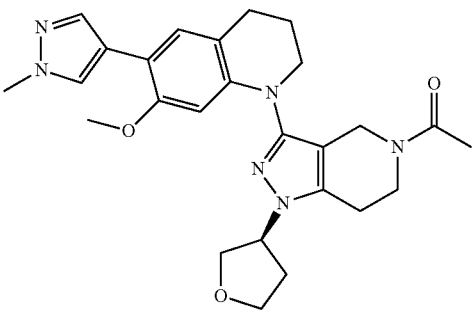
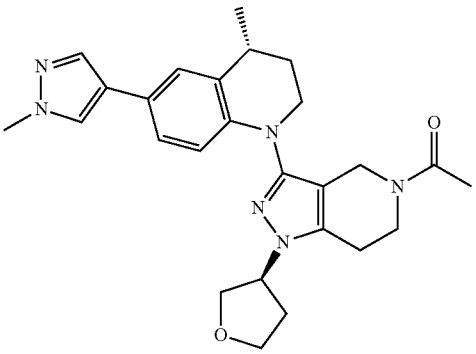

125
-continued
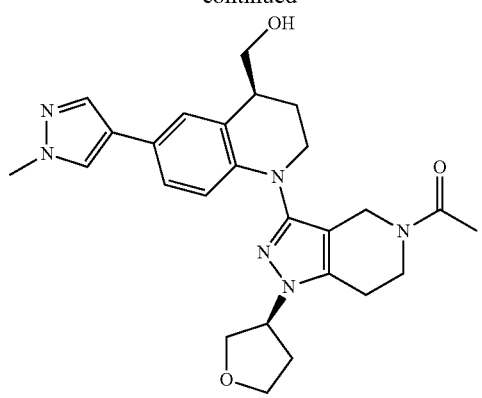
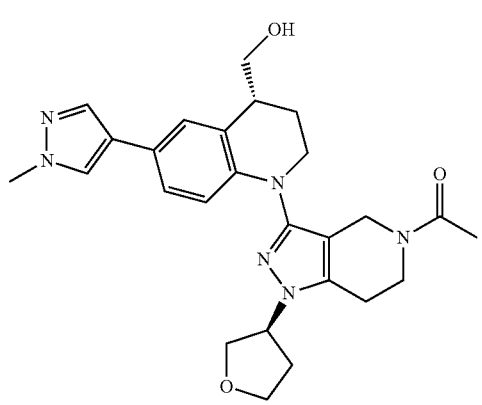
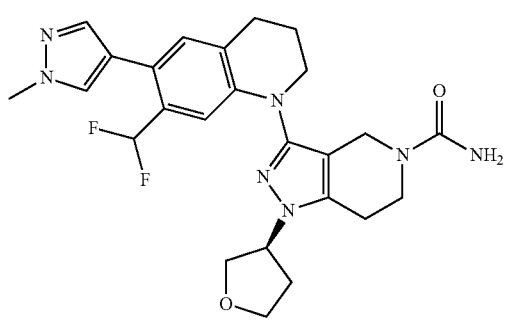
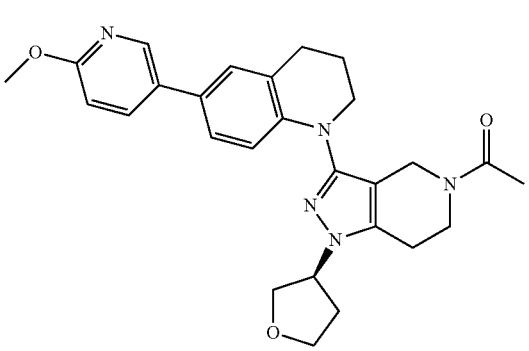
126
-continued
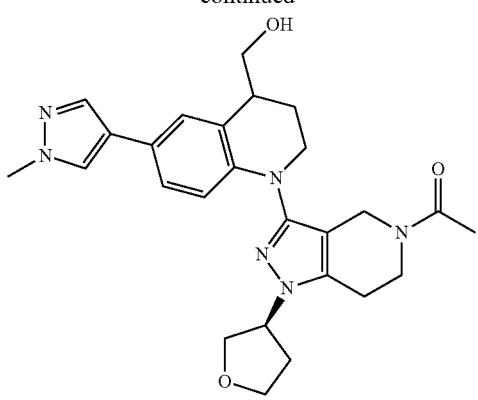
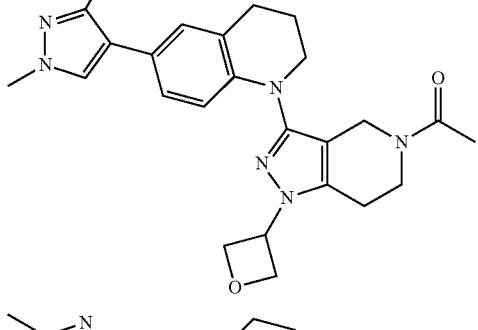
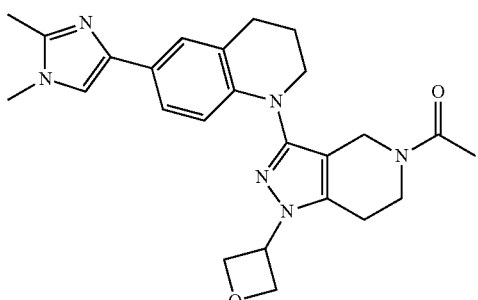
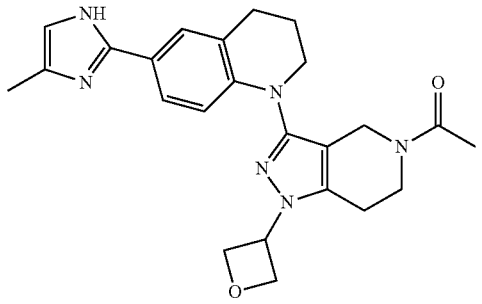
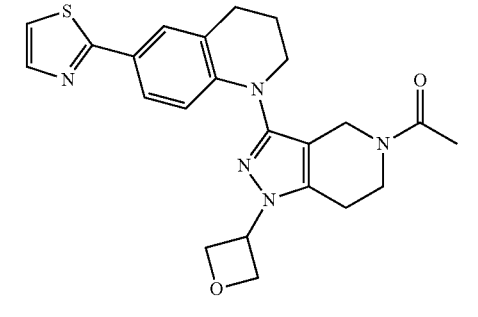

127
-continued
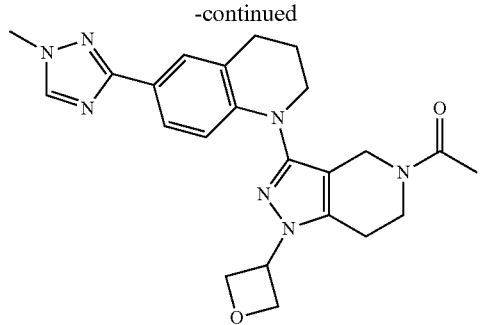
128
-continued
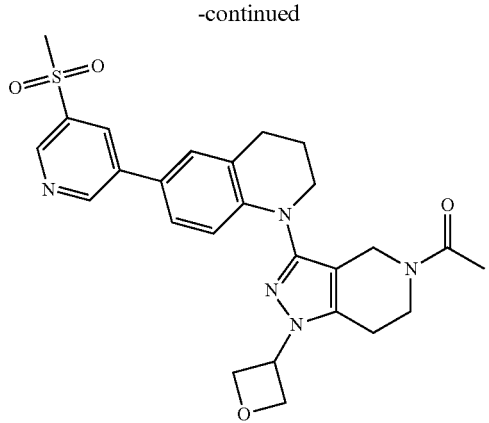
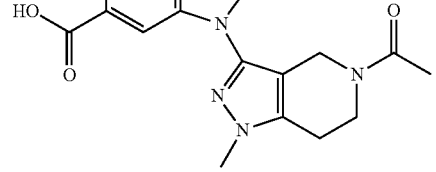
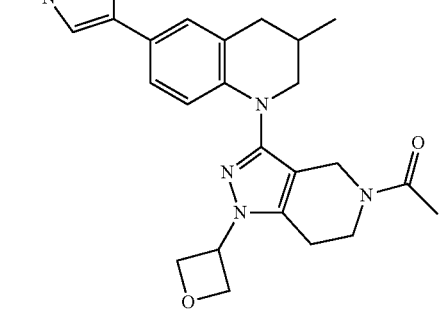
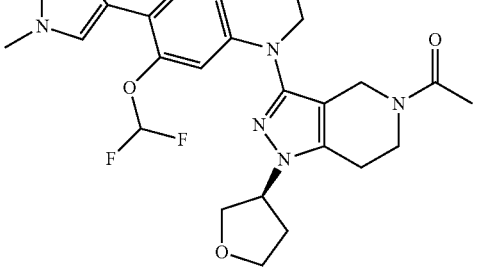
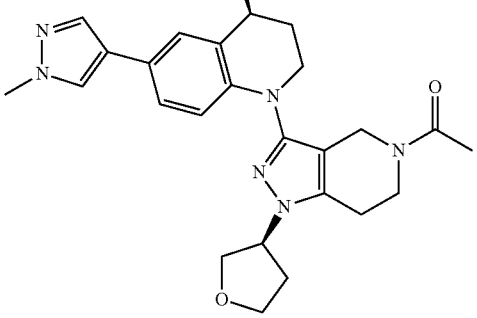

129
-continued
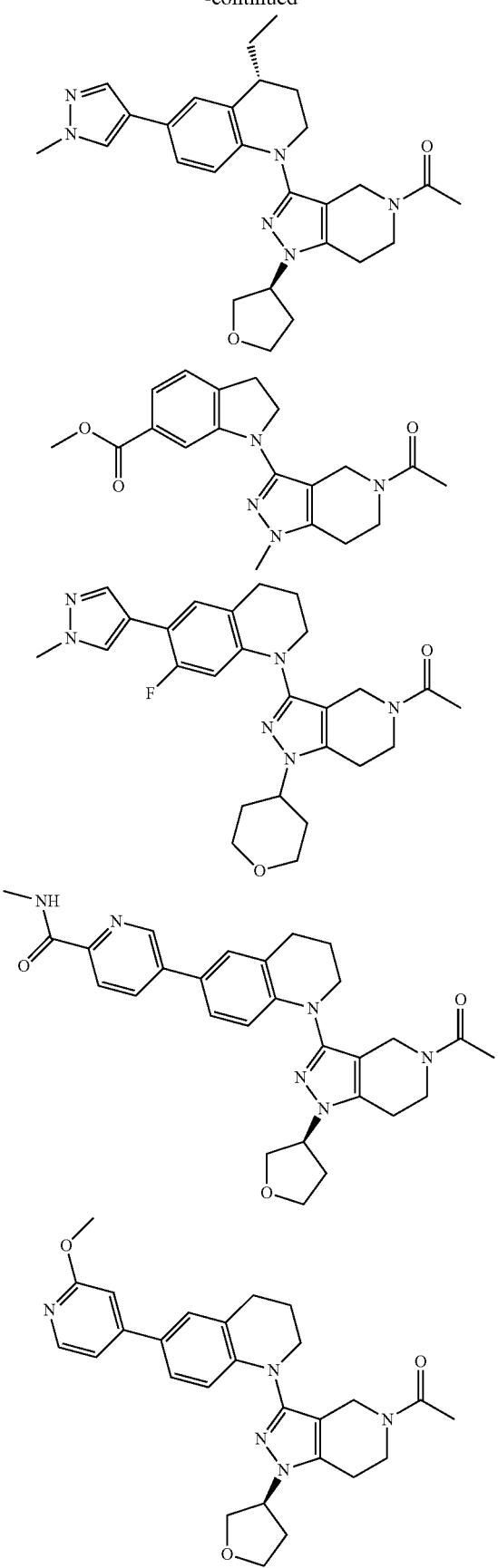
130
-continued
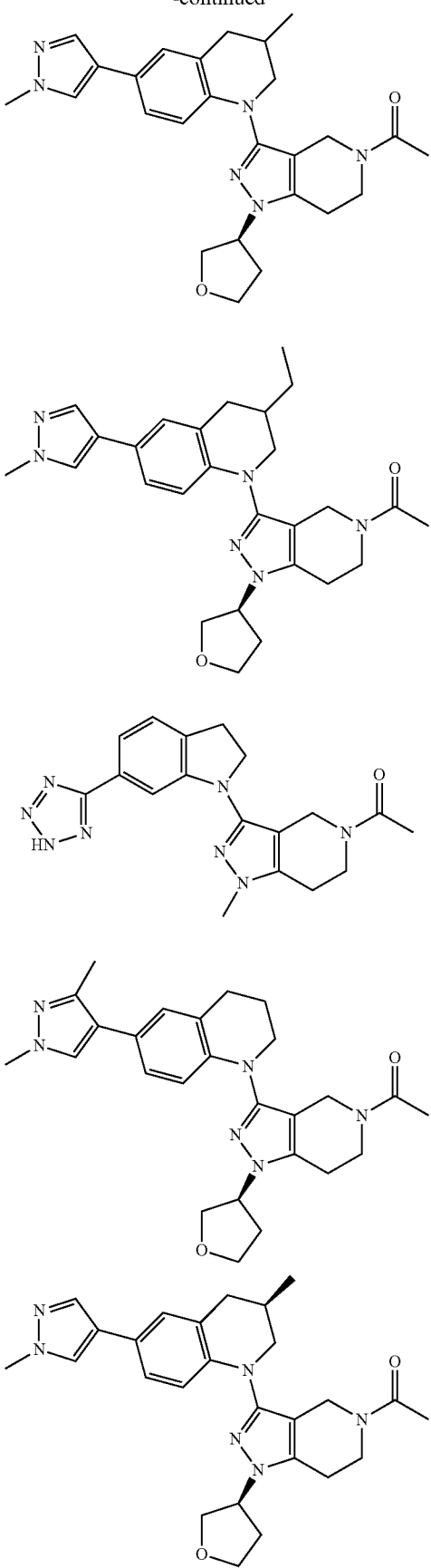

131
-continued
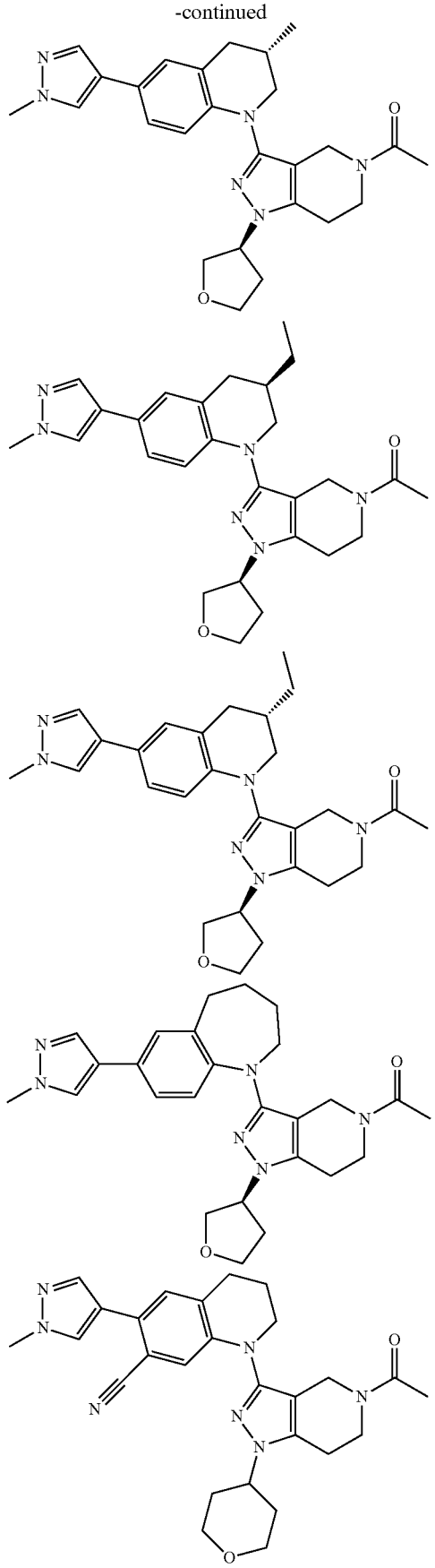
132
-continued
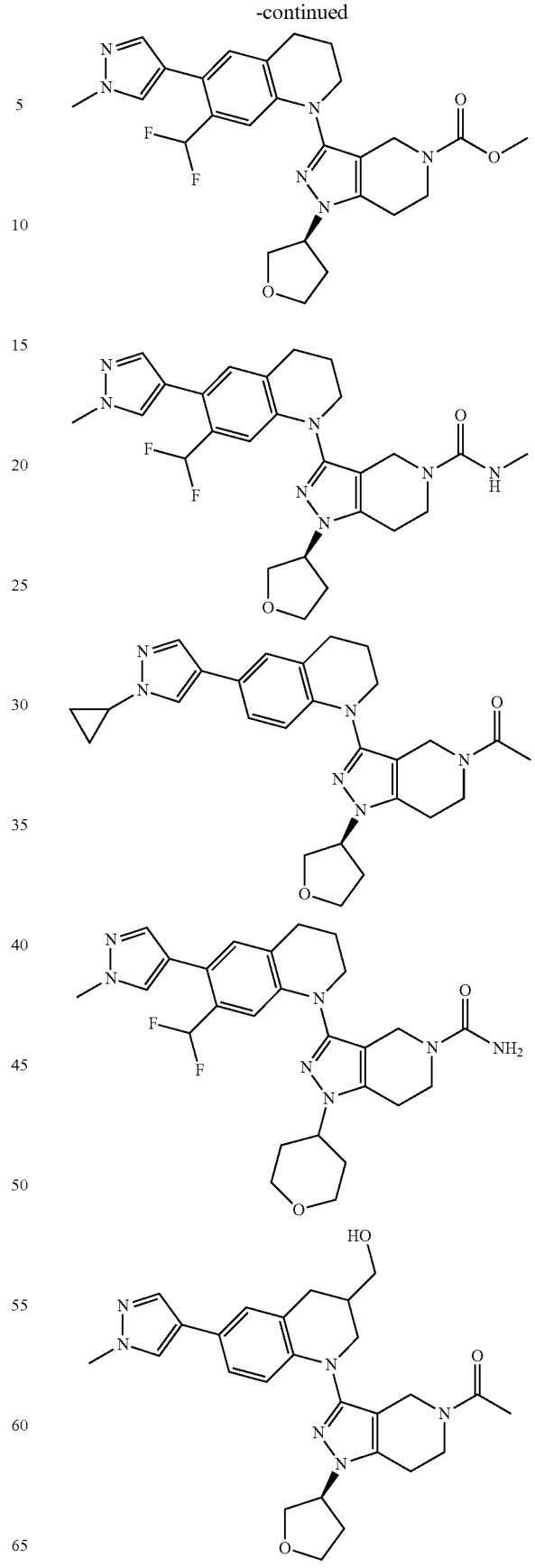

133
-continued
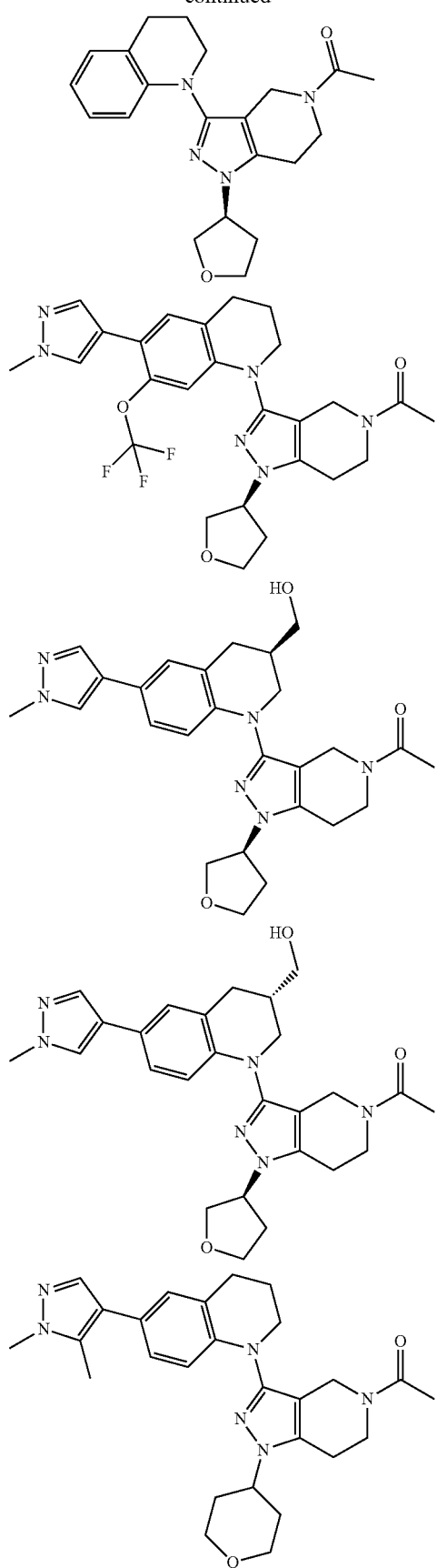
134
-continued
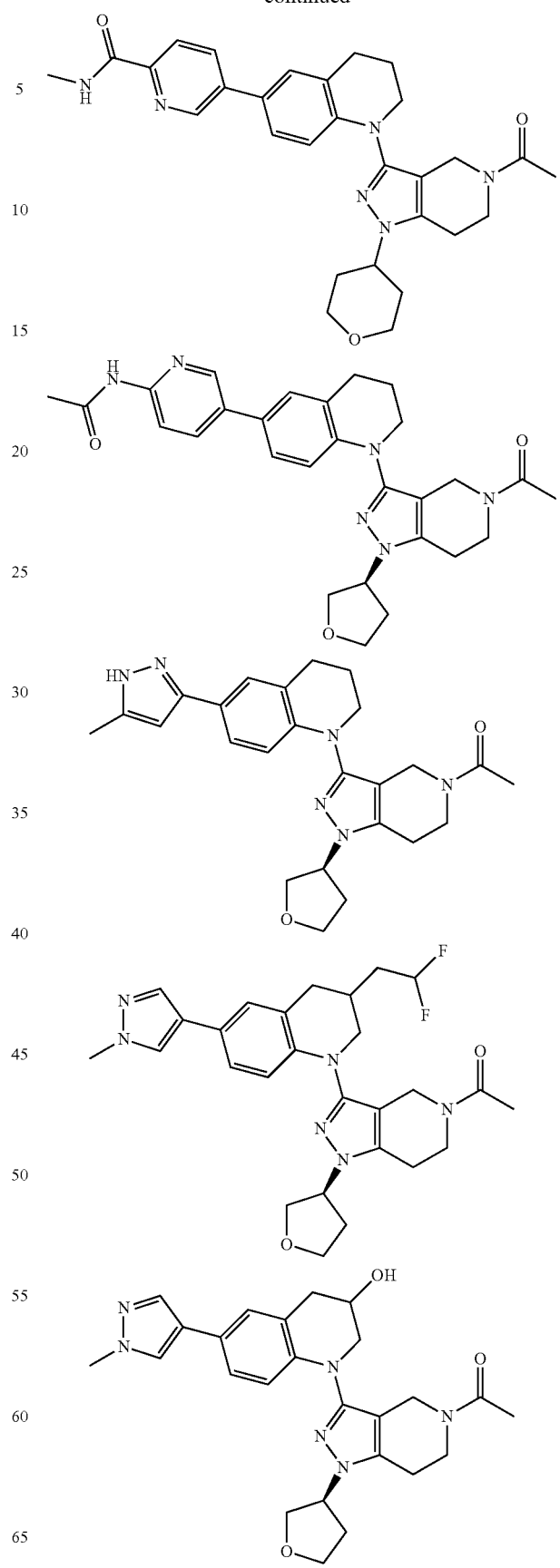

135
-continued
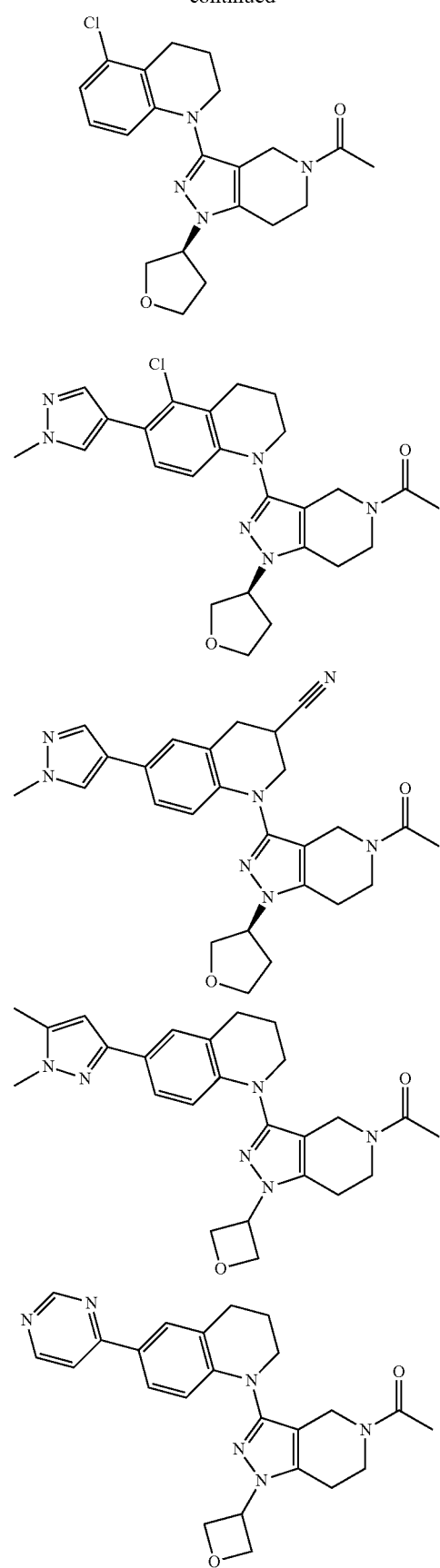
136
-continued
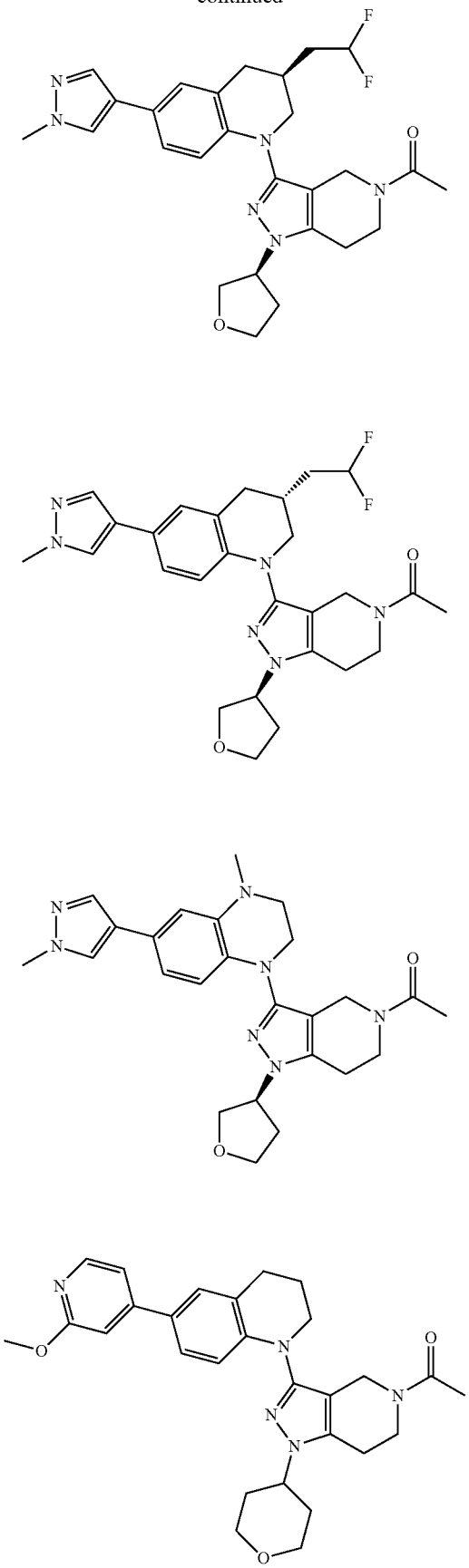

137
-continued
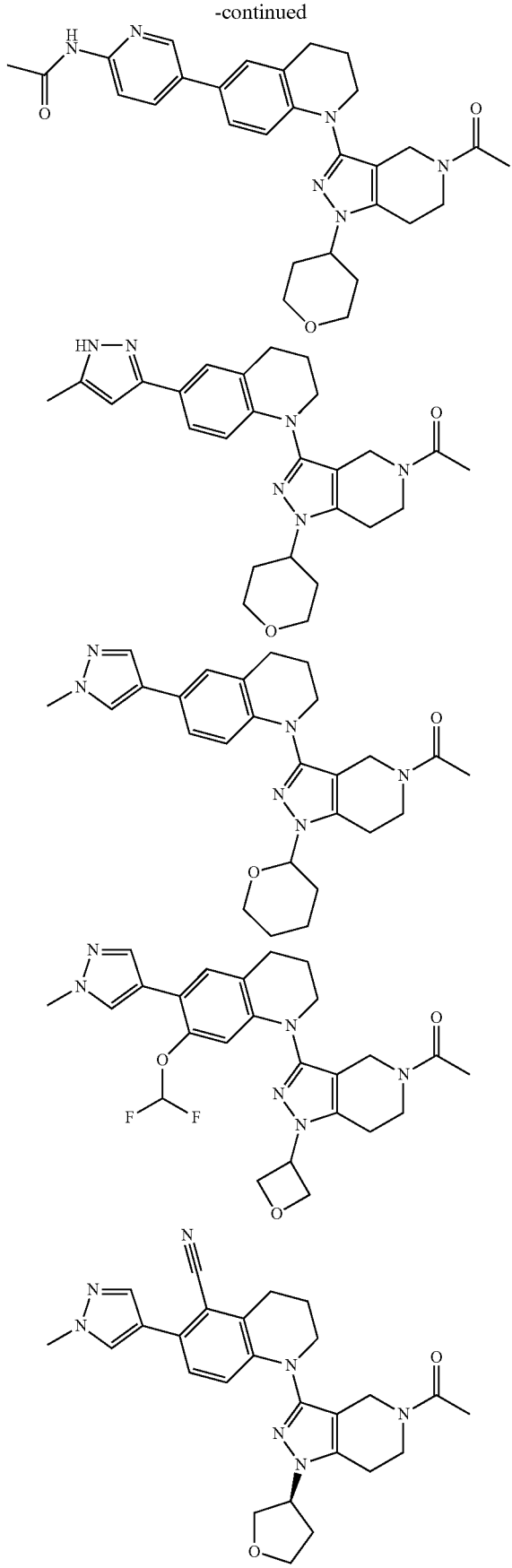
138
-continued
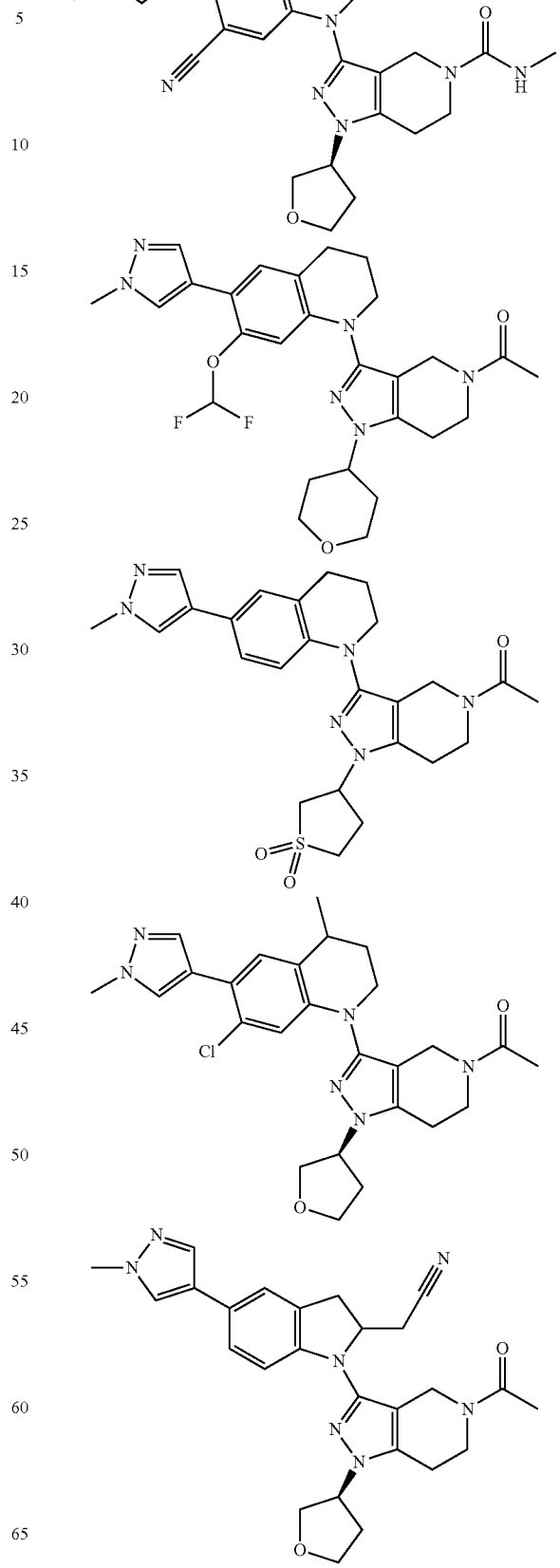

139
-continued
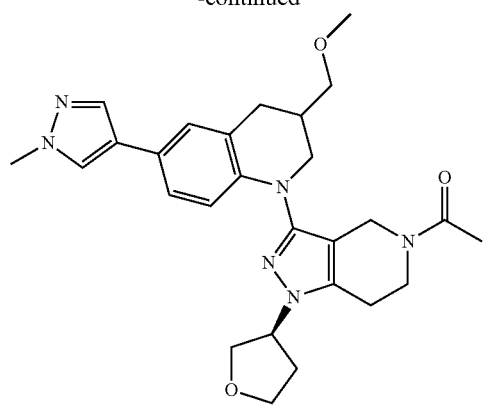
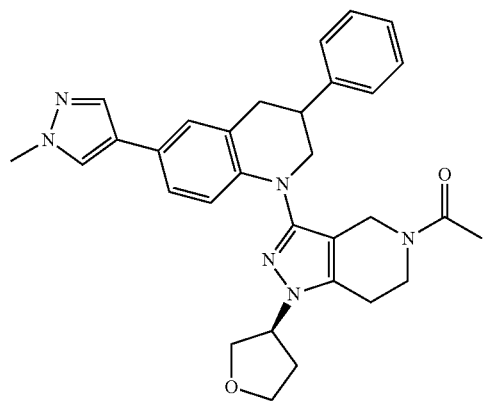
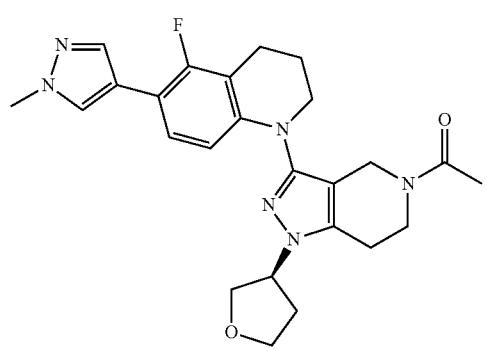
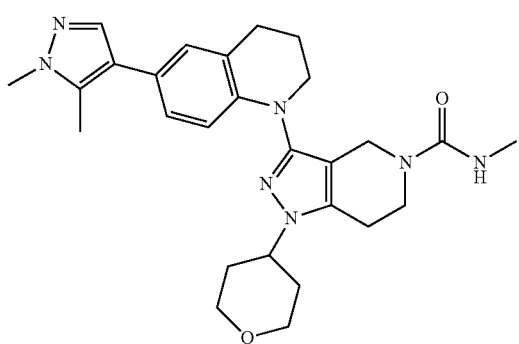
140
-continued
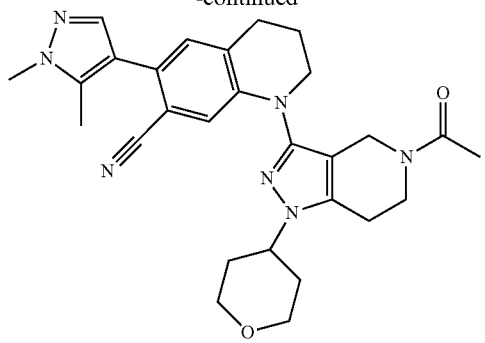
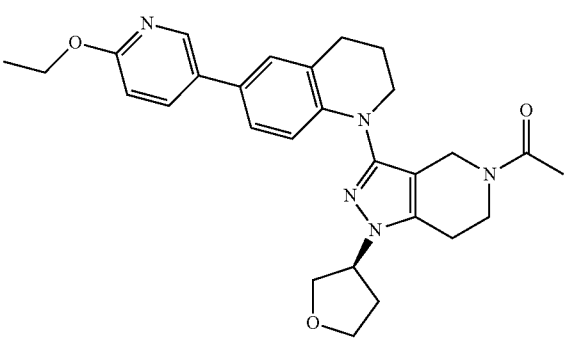
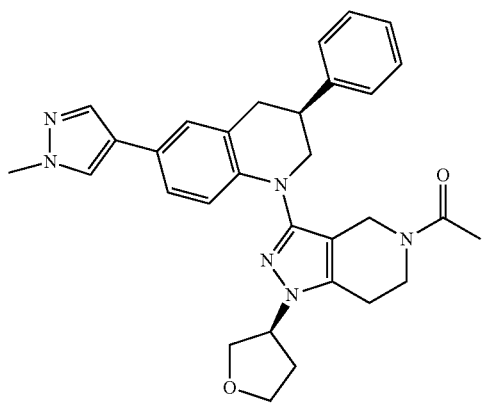
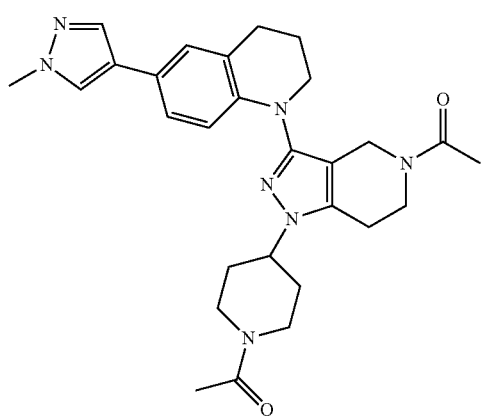

141
-continued
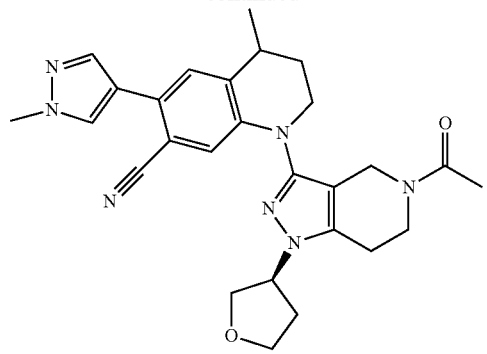
142
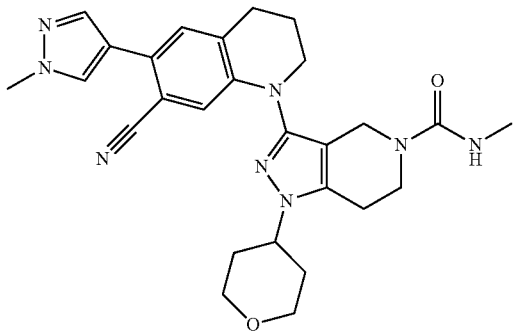
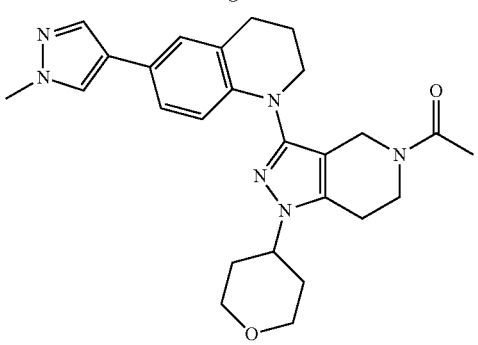
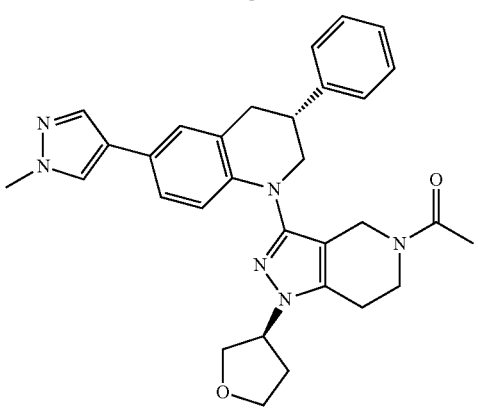
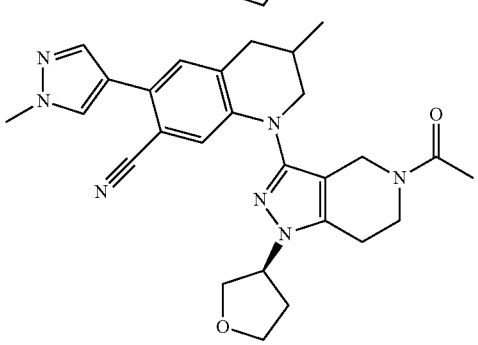
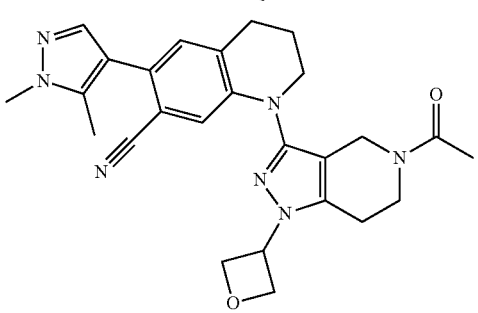

143
-continued
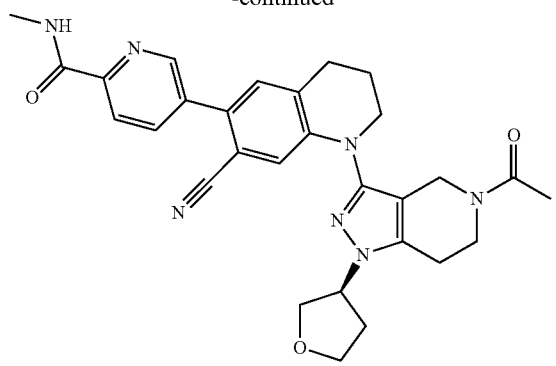
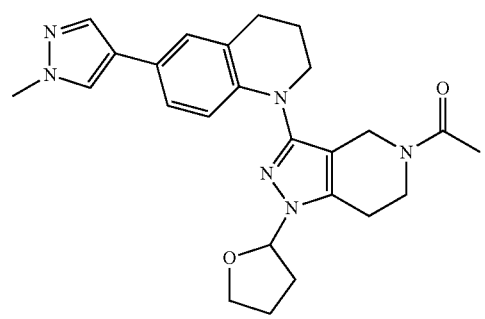
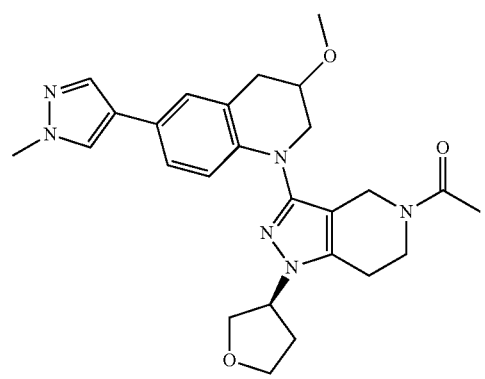
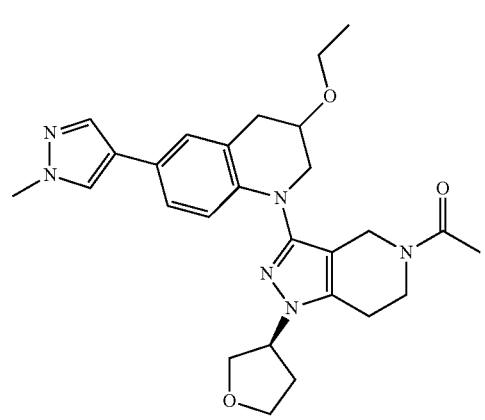
144
-continued
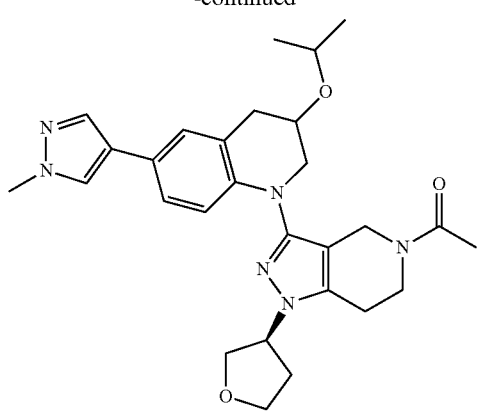
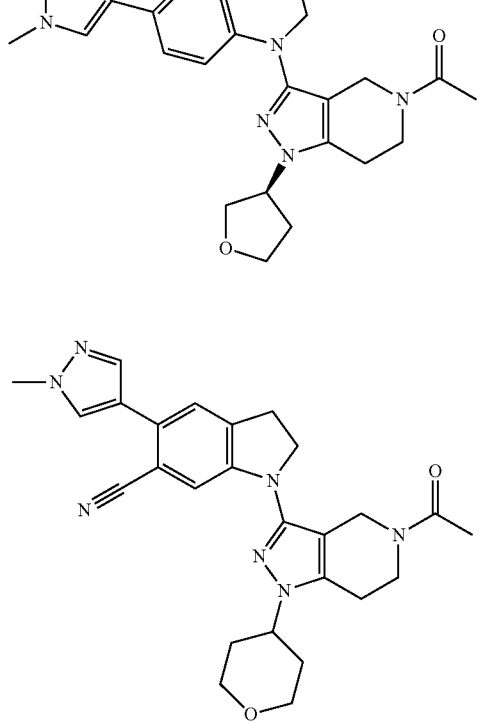
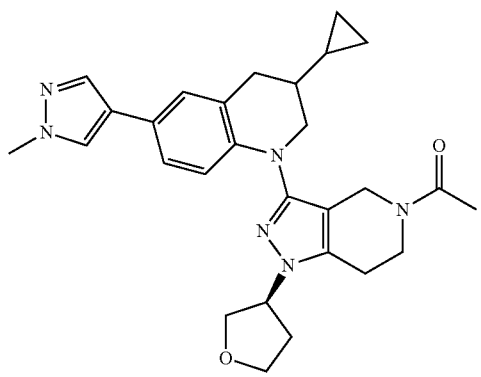
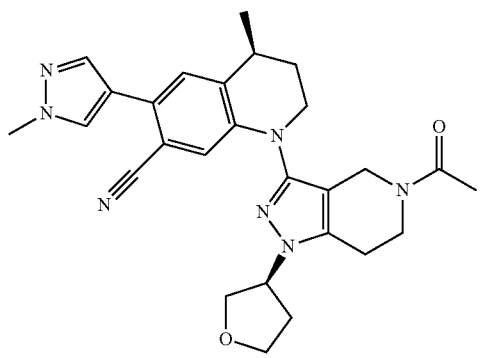

145
-continued
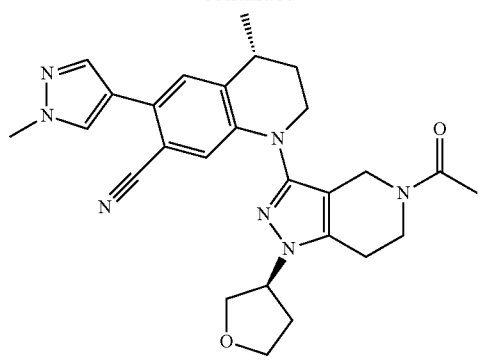
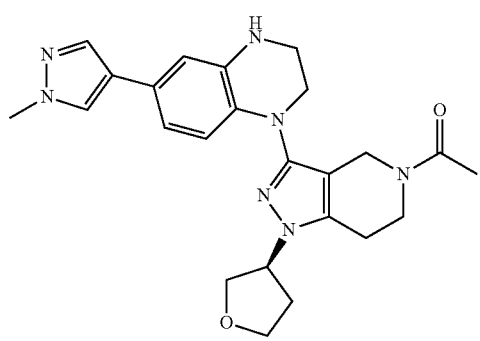
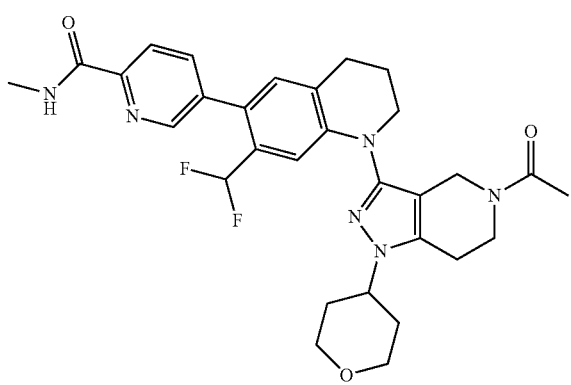
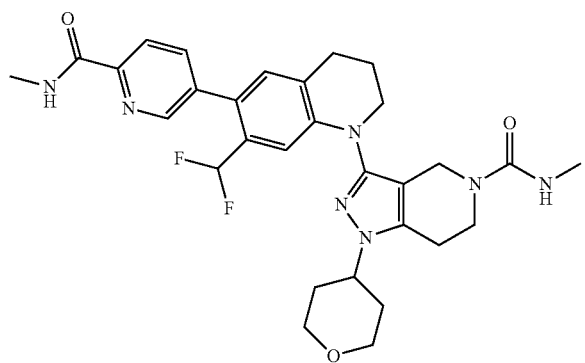
146
-continued
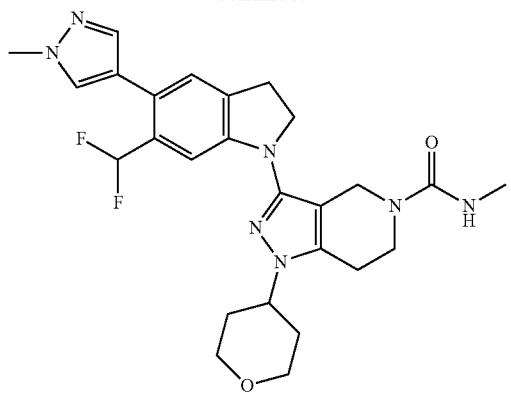
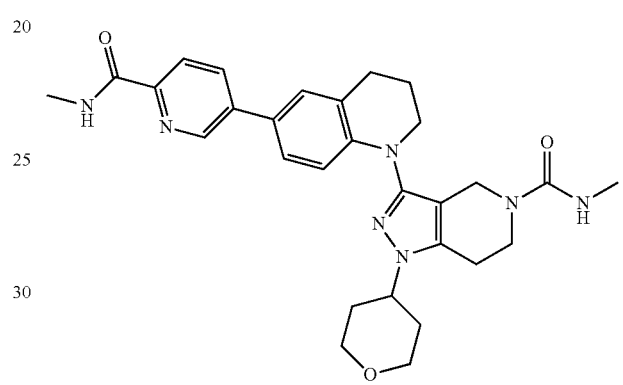
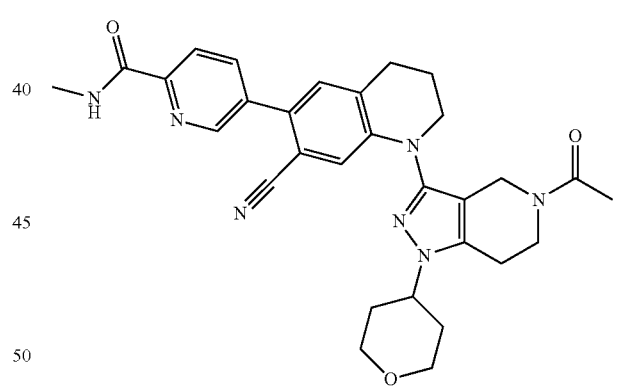
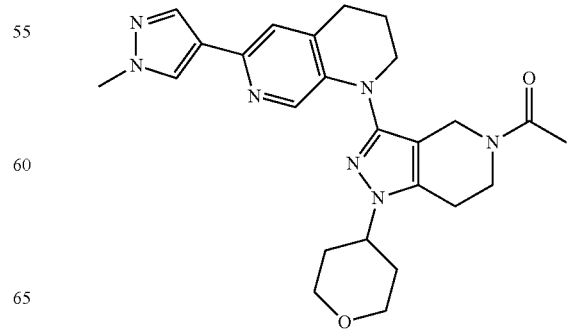

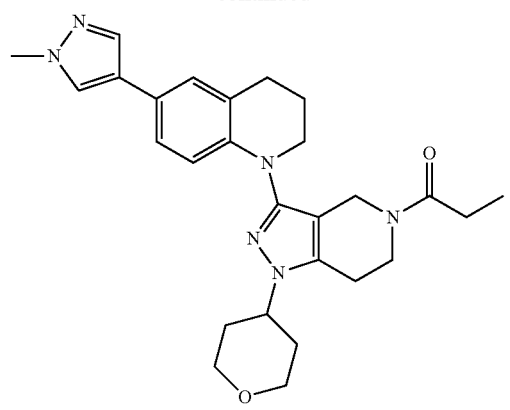
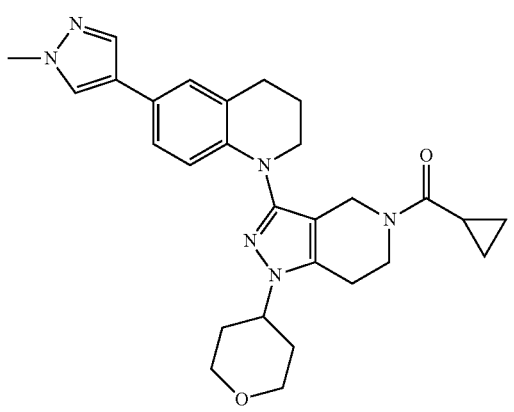
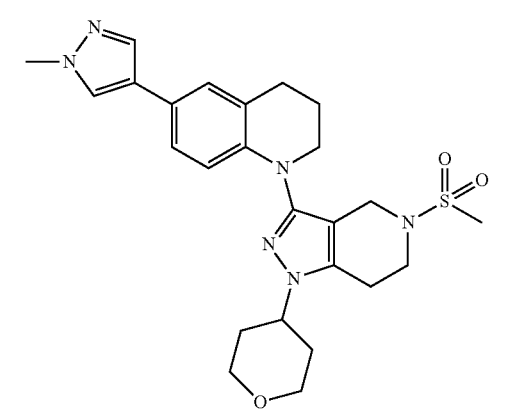
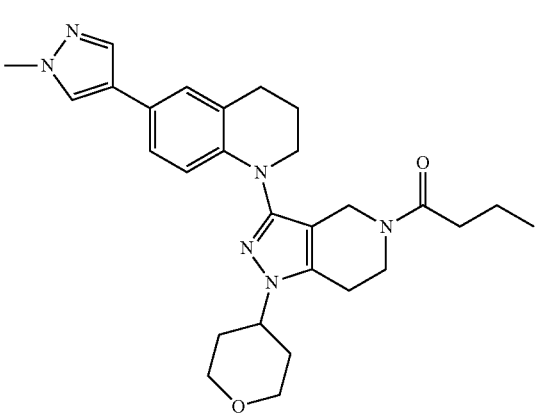
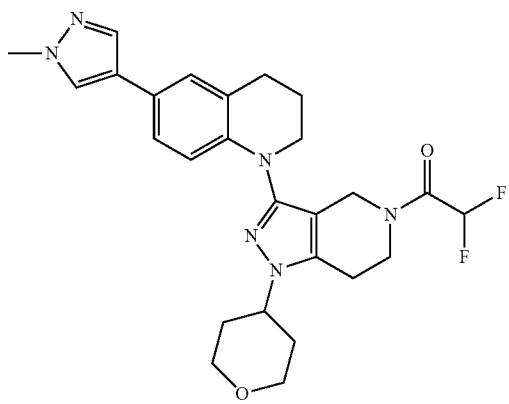
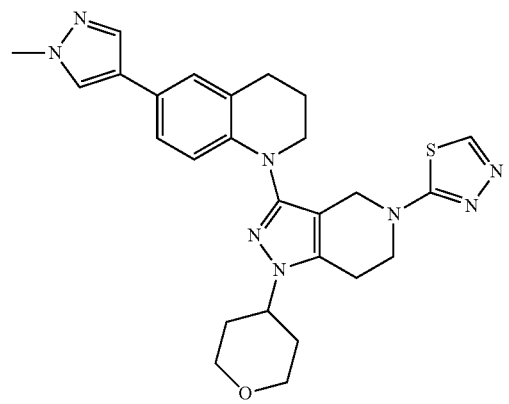
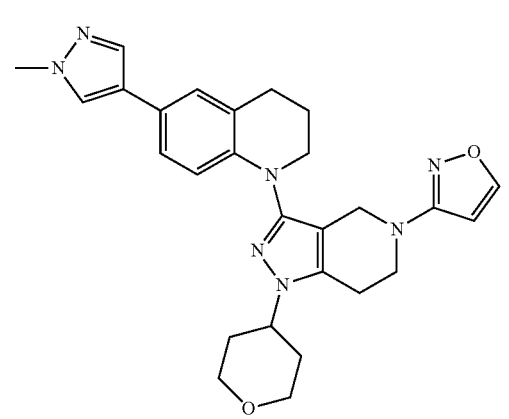
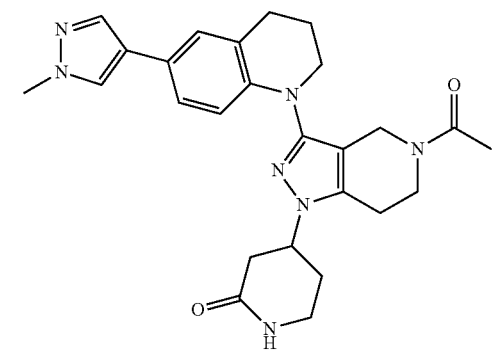

149
-continued
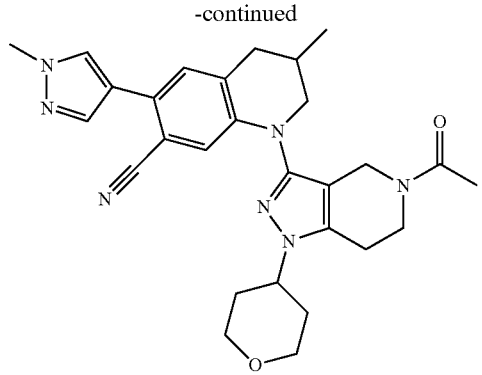
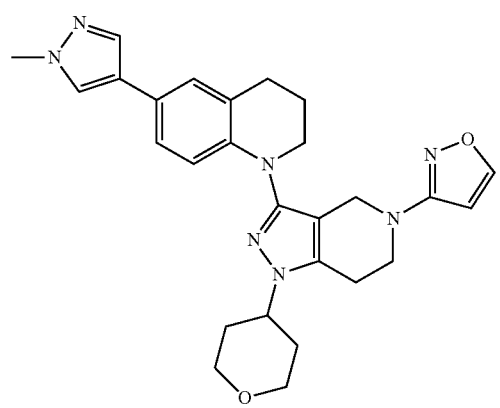
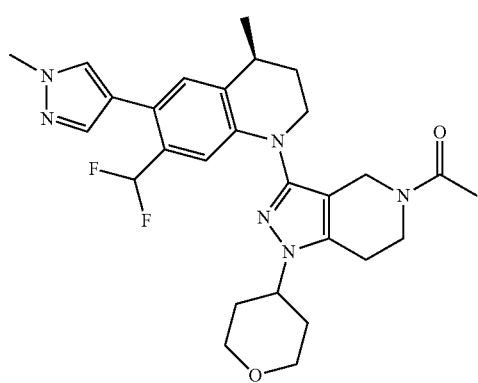
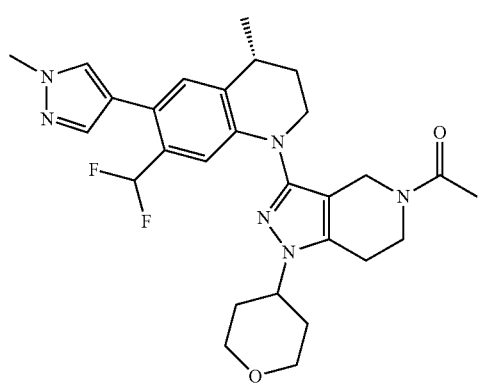
150
-continued
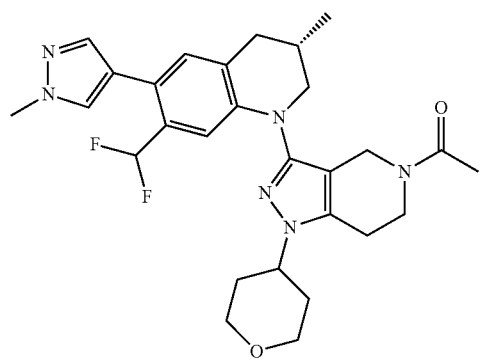
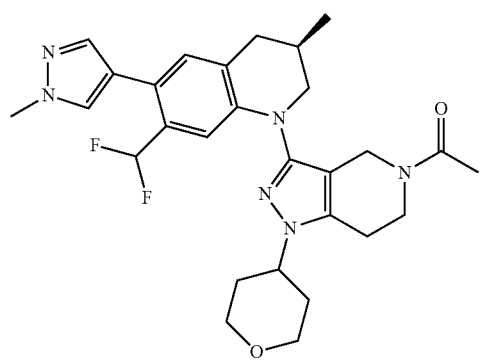
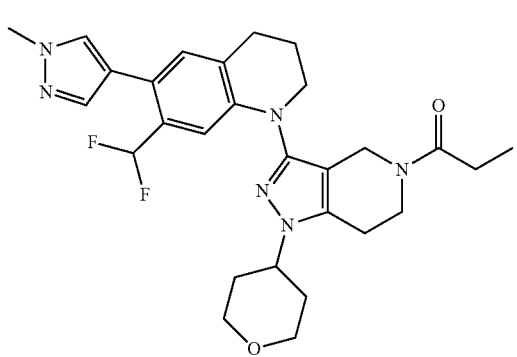
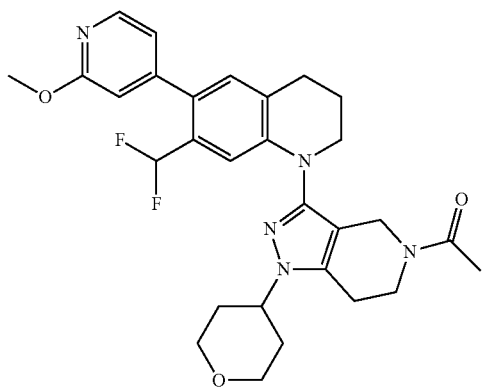

151
-continued
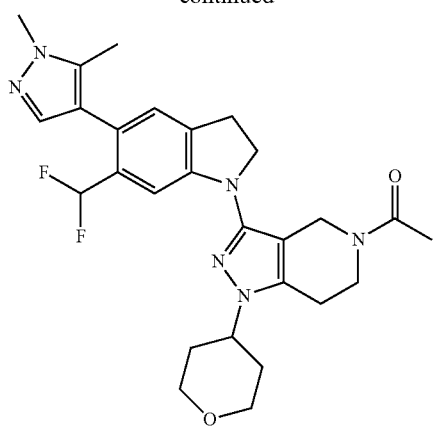
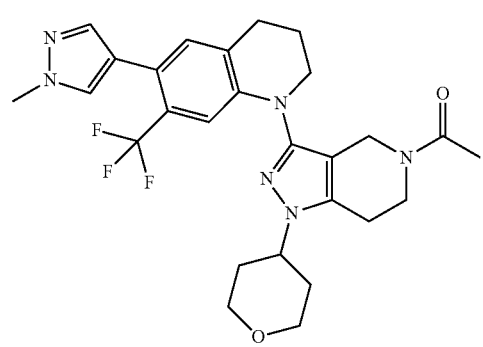
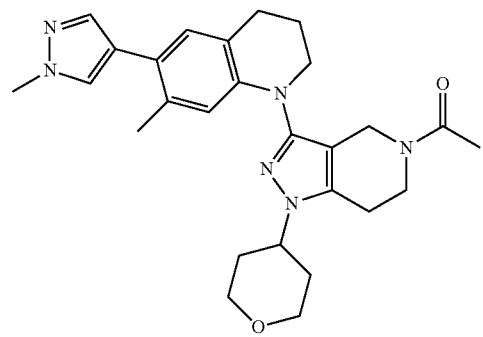
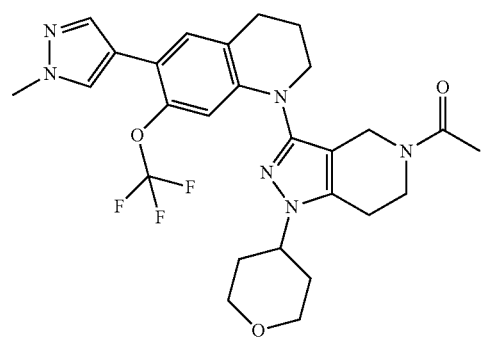
152
-continued
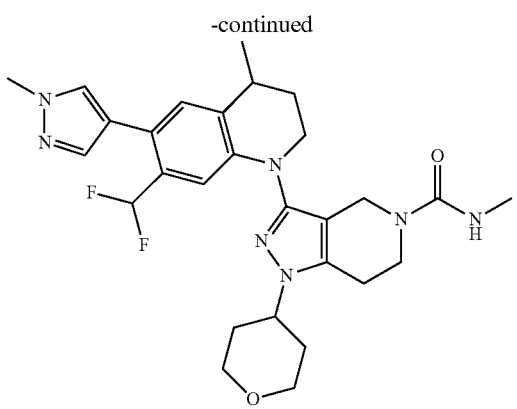
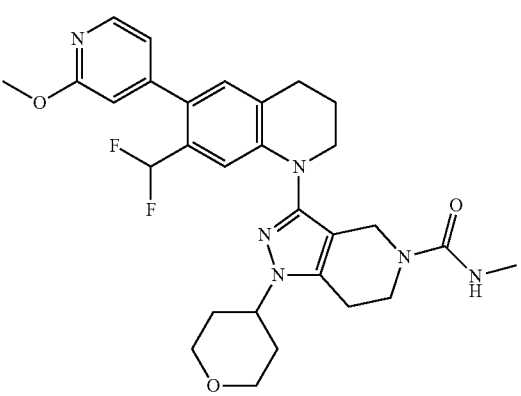
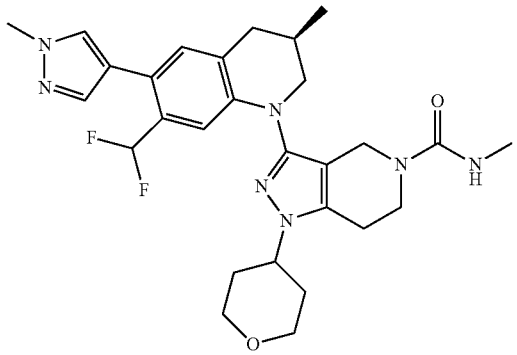
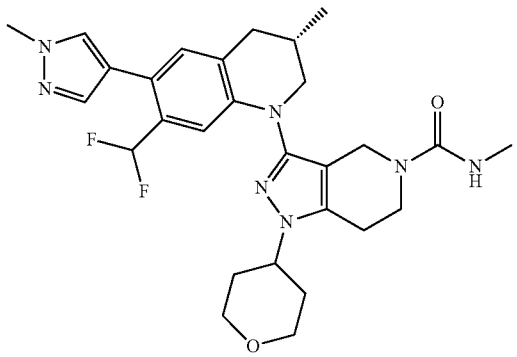

153
-continued
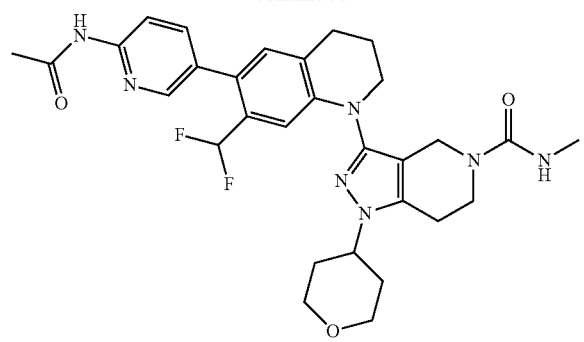
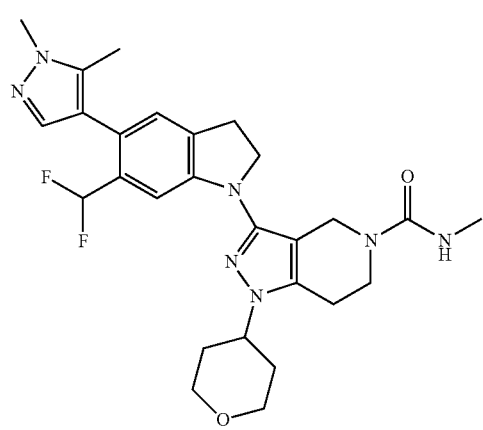
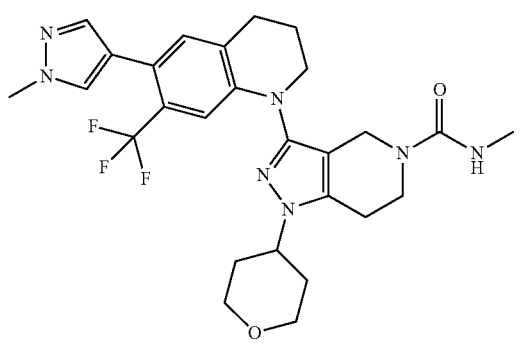
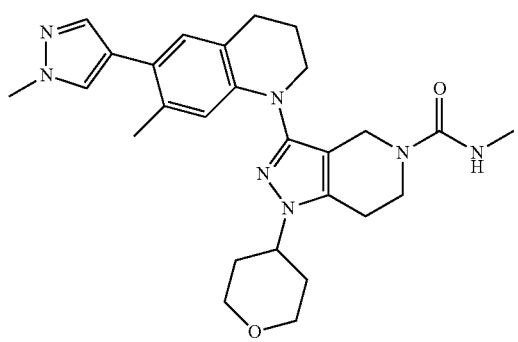
154
-continued
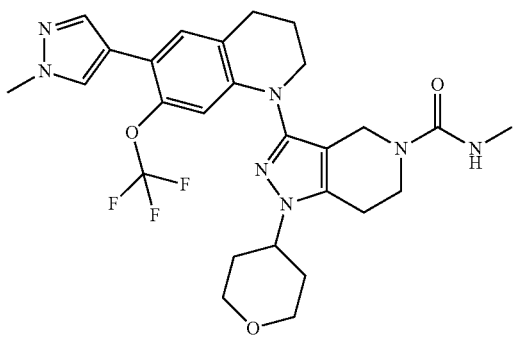
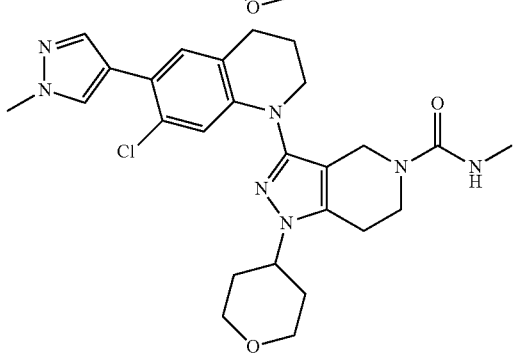
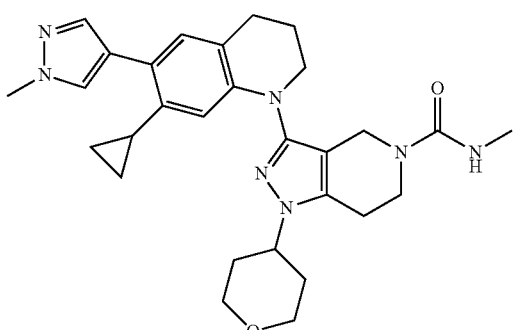
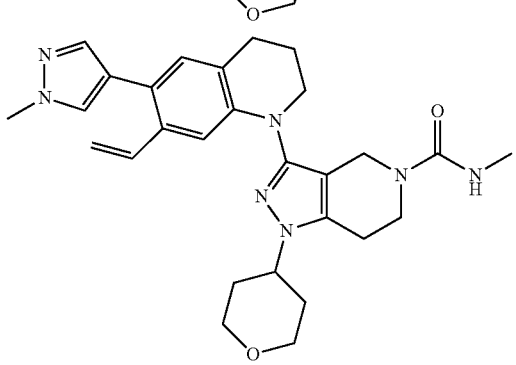
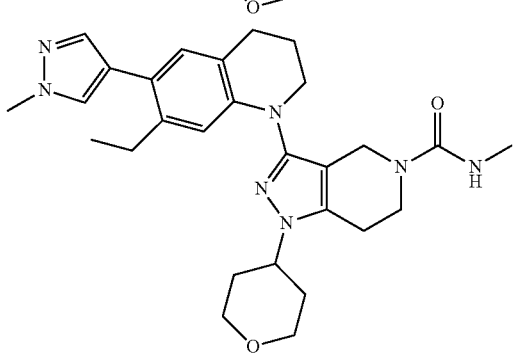

155
-continued
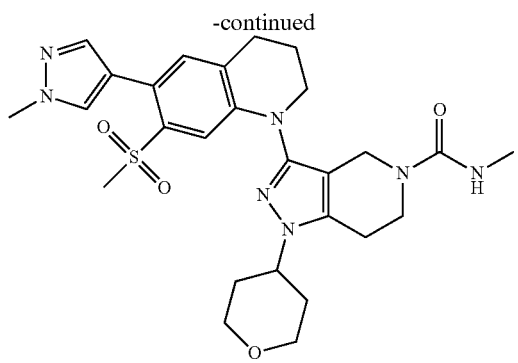
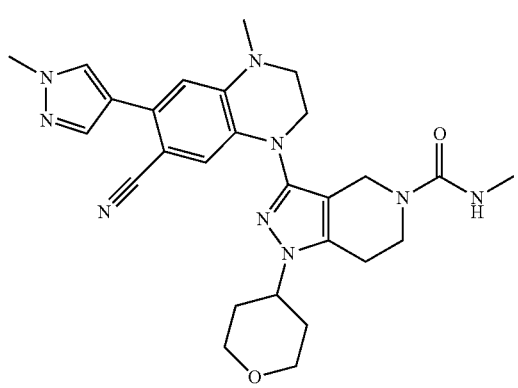
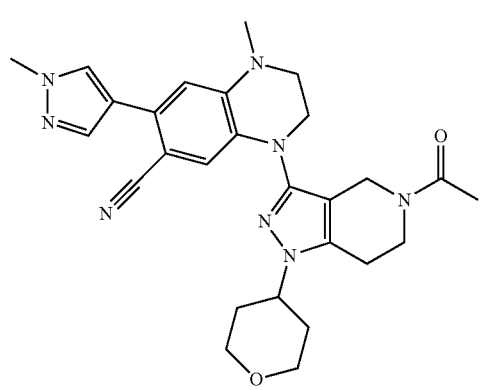
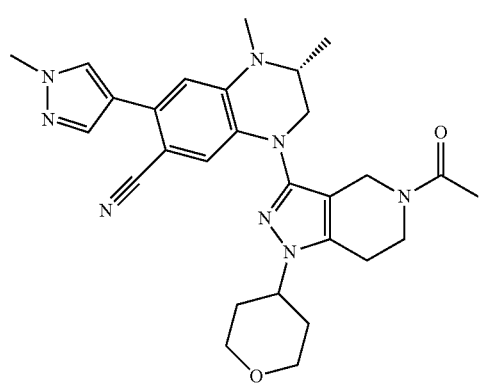
156
-continued
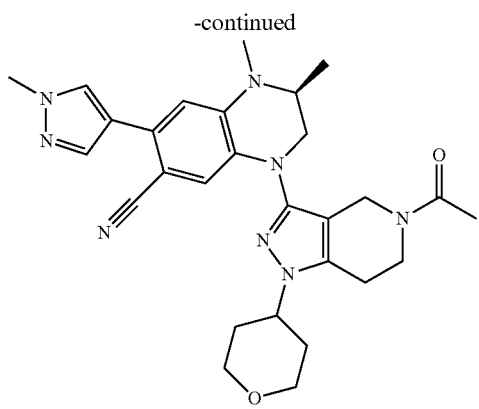
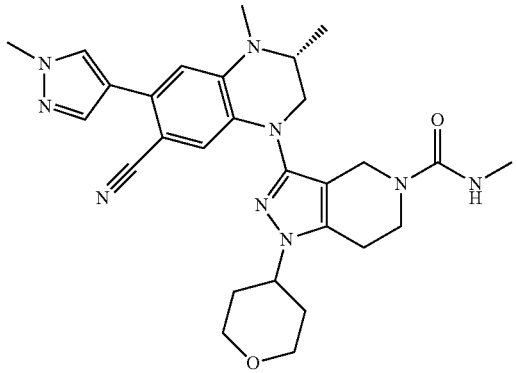
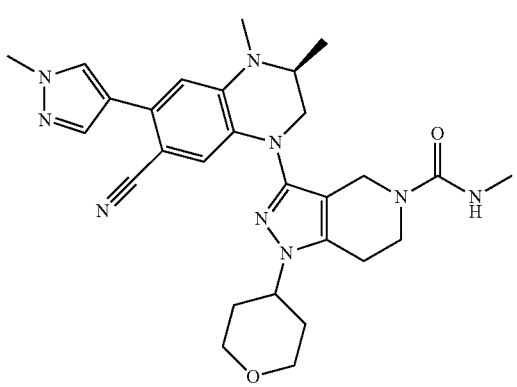
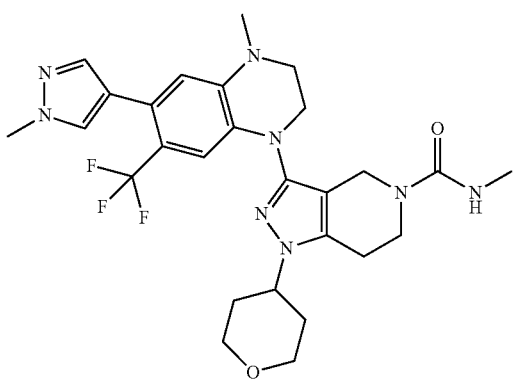

157
-continued
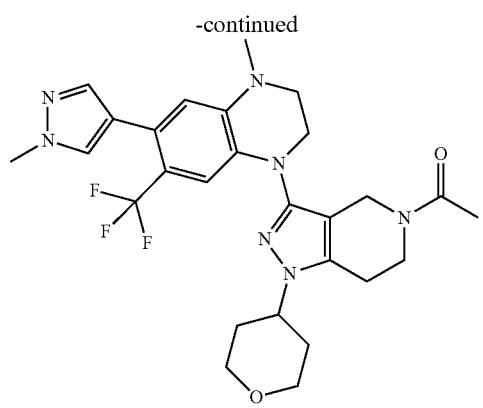
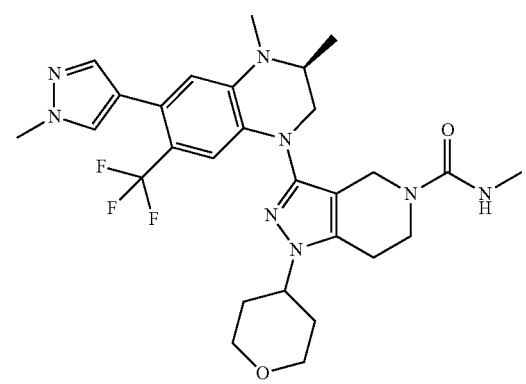
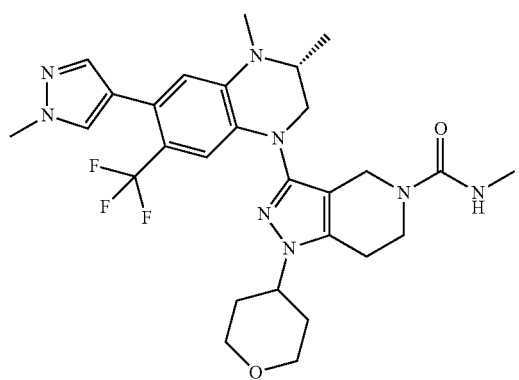
158
-continued
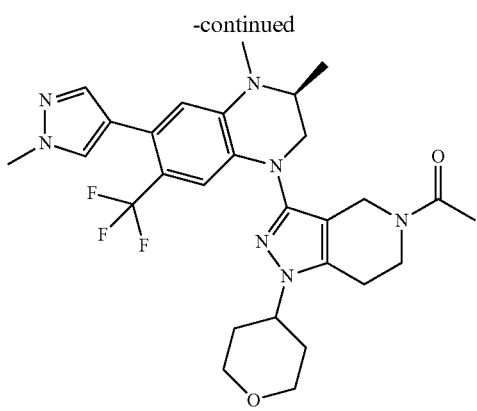
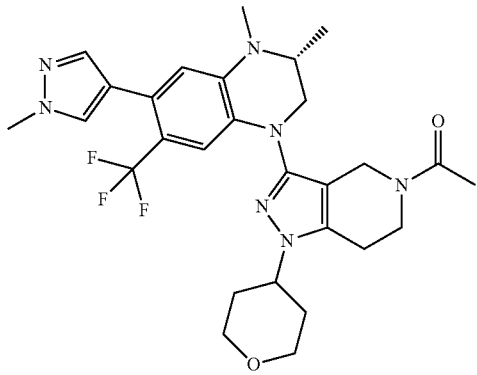
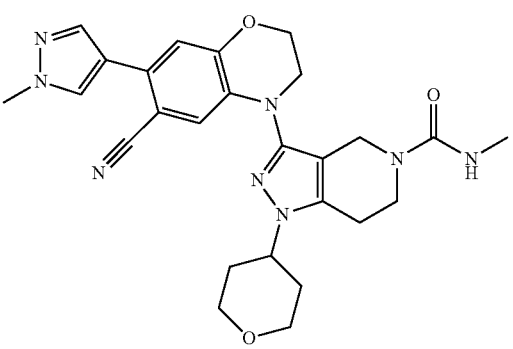
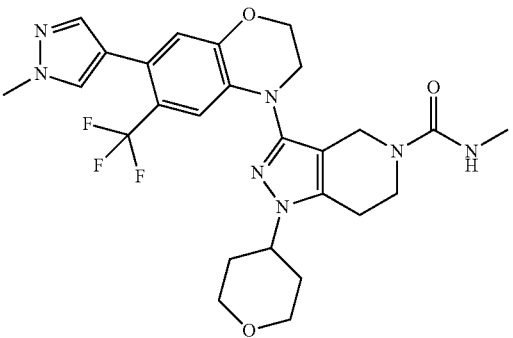

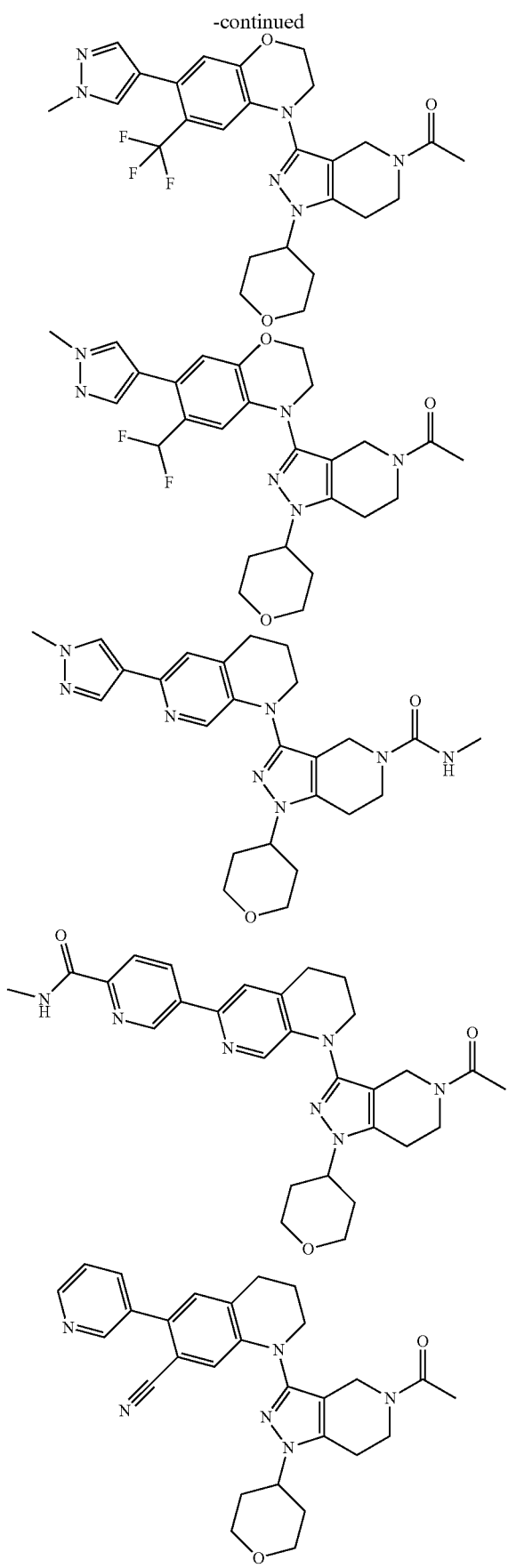
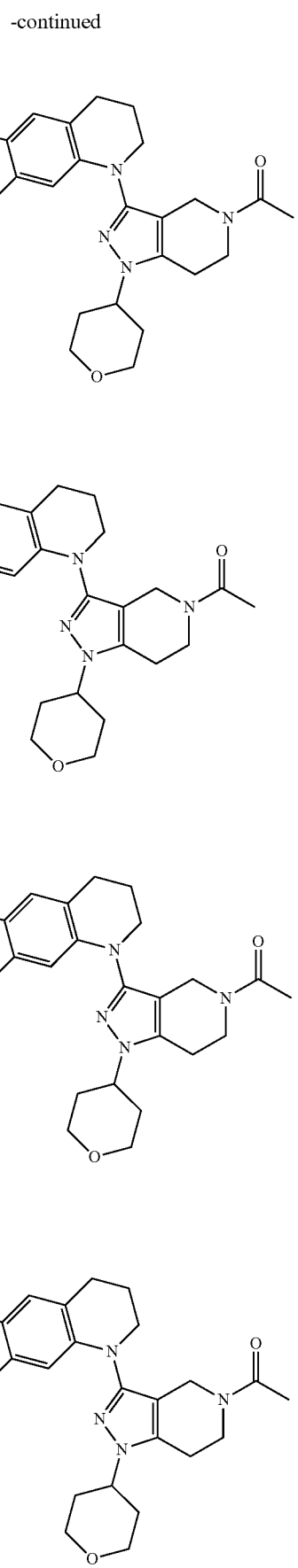

161
-continued
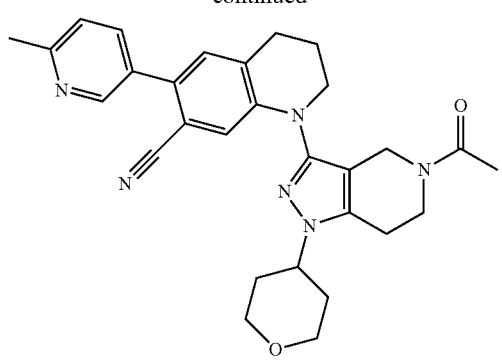
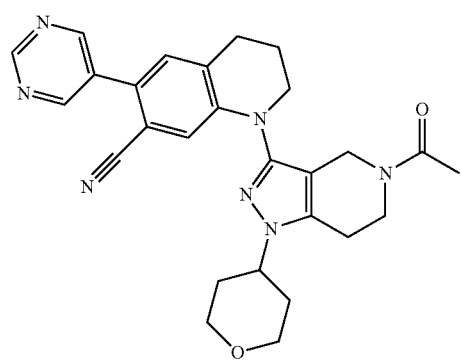
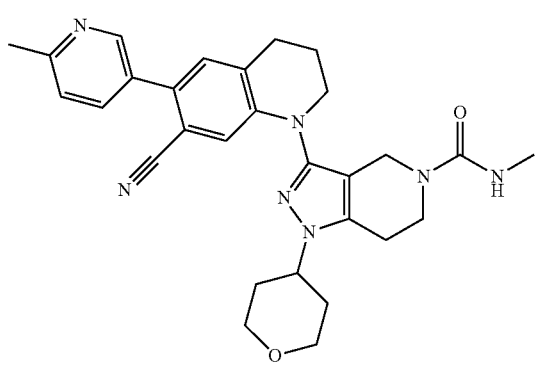
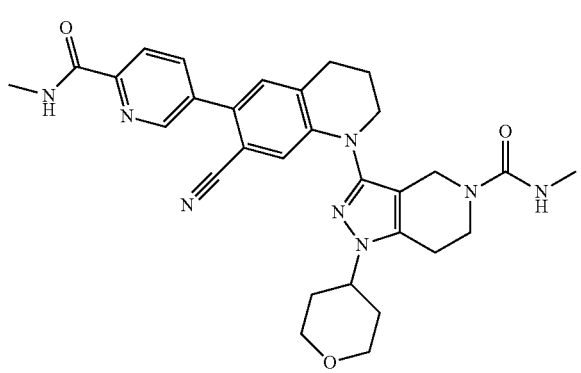
162
-continued
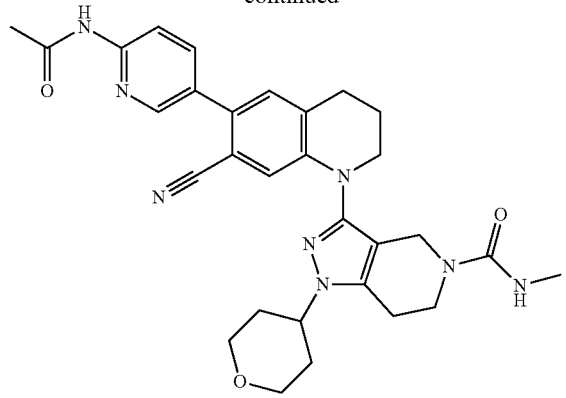
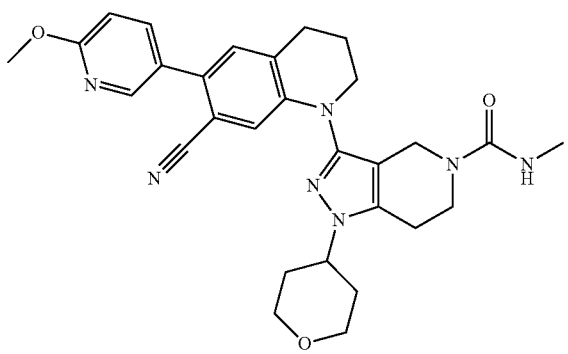
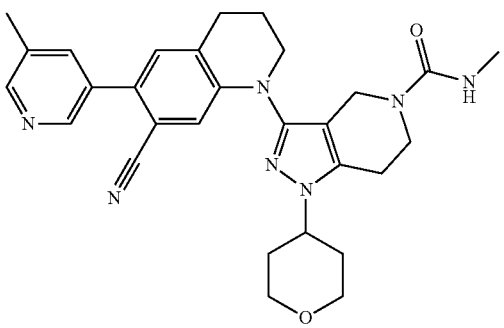
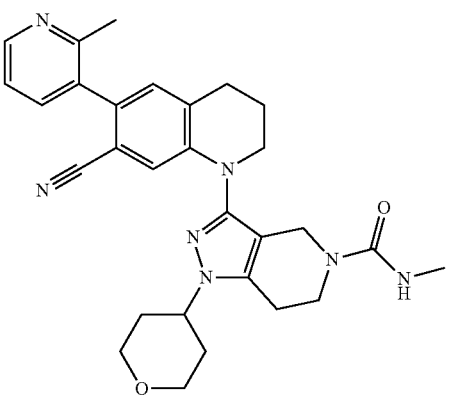

-continued
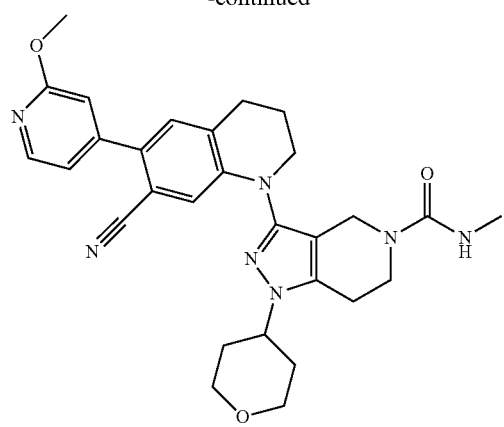
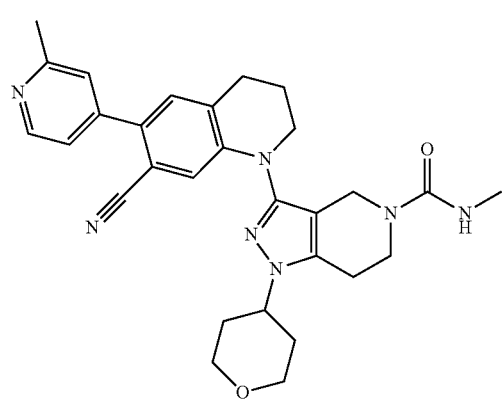
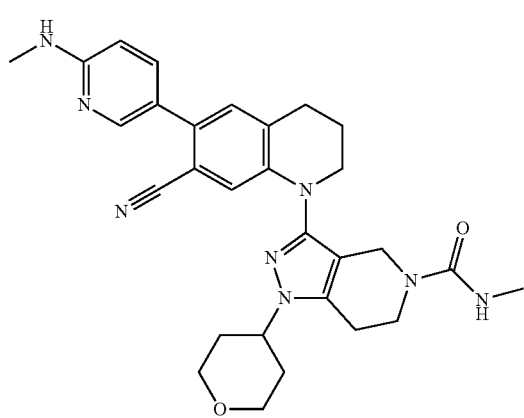
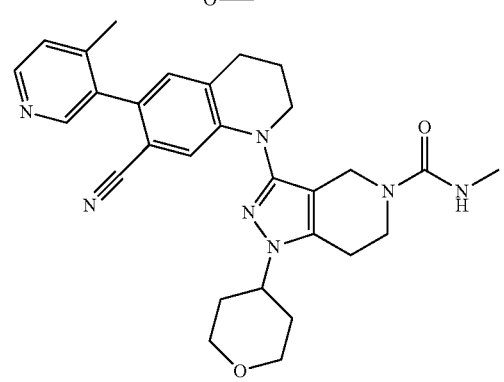
-continued
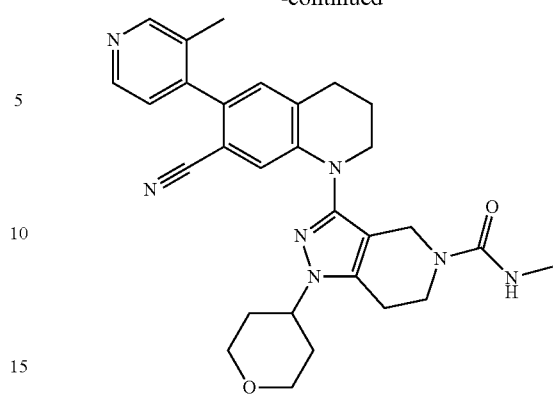
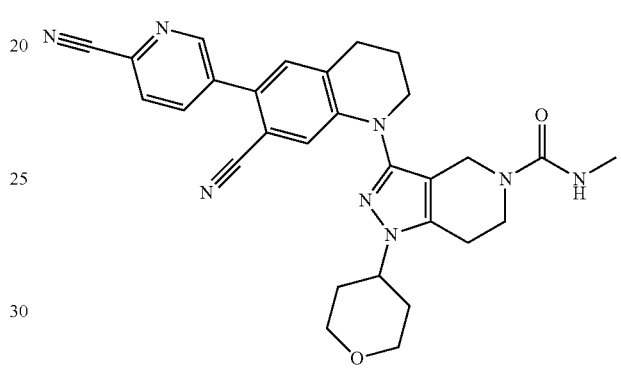
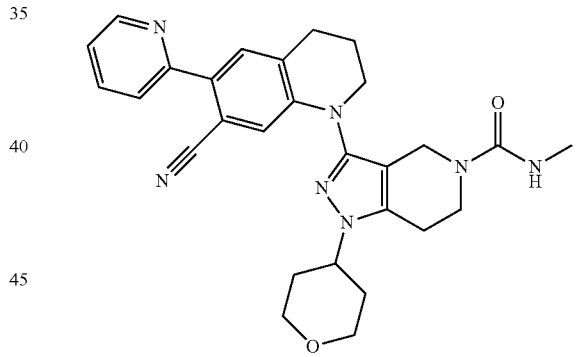
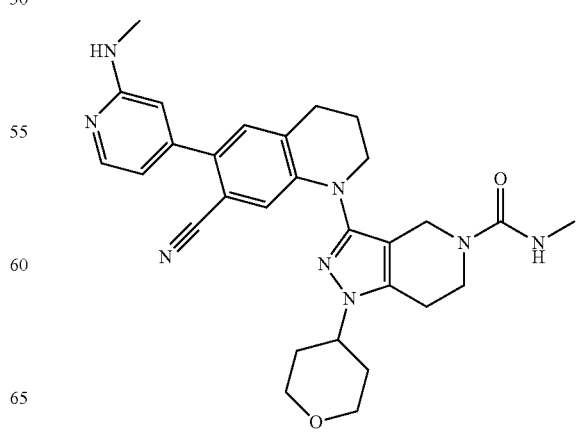

165
-continued
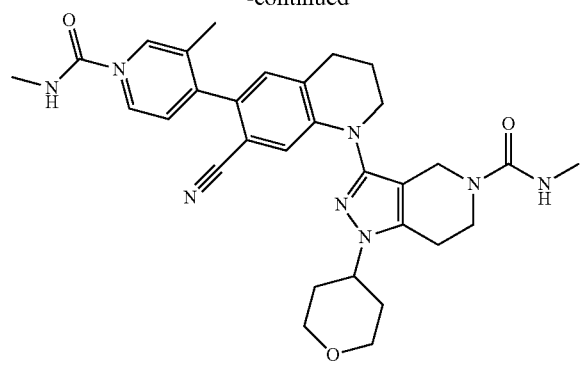
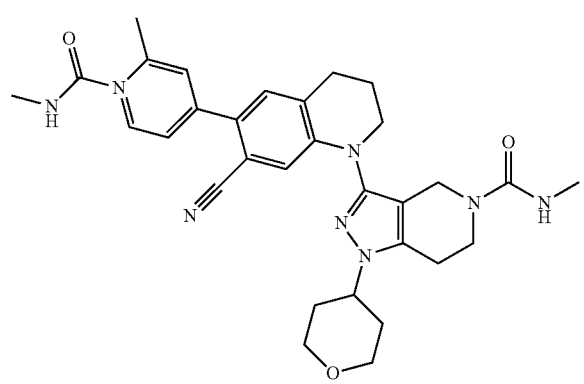
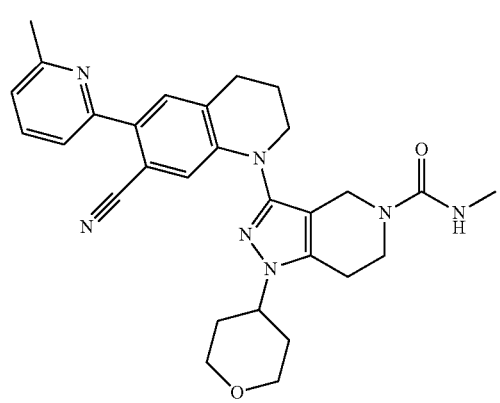
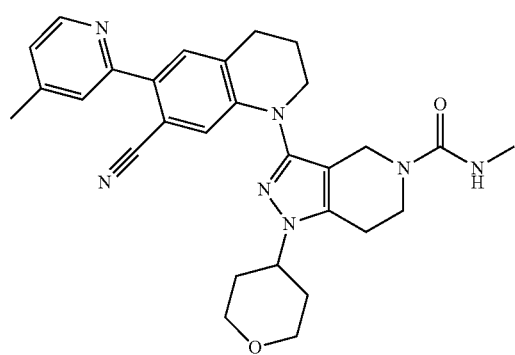
166
-continued
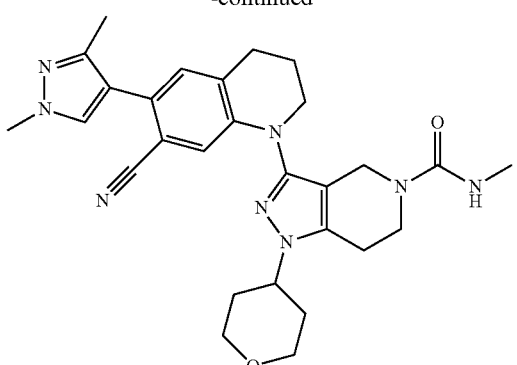
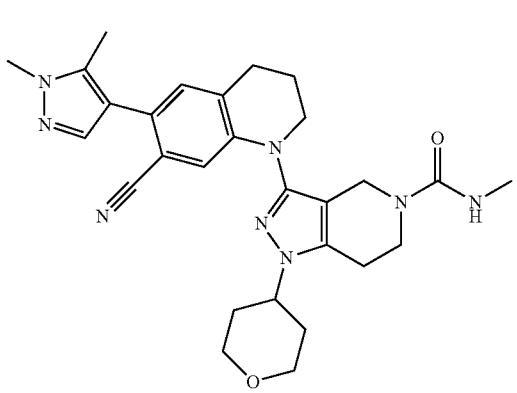
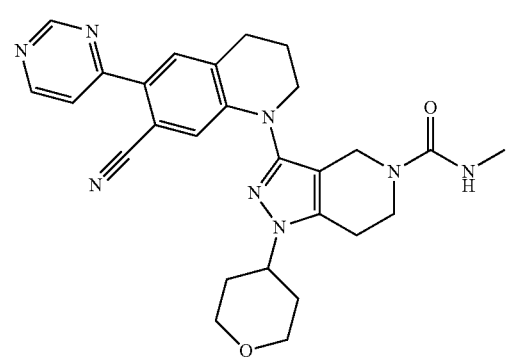
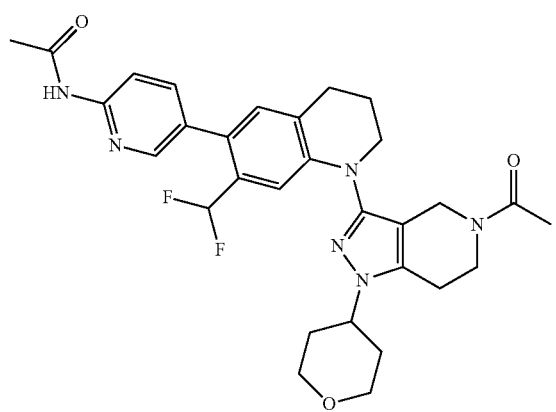

167
-continued
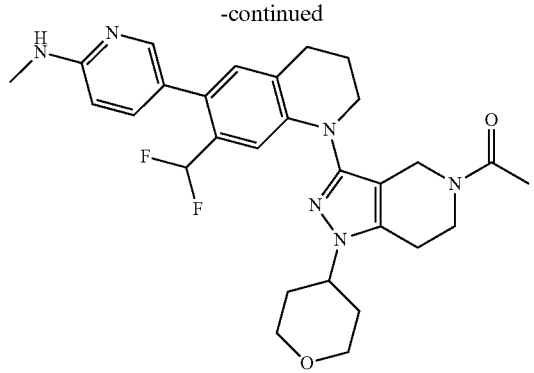
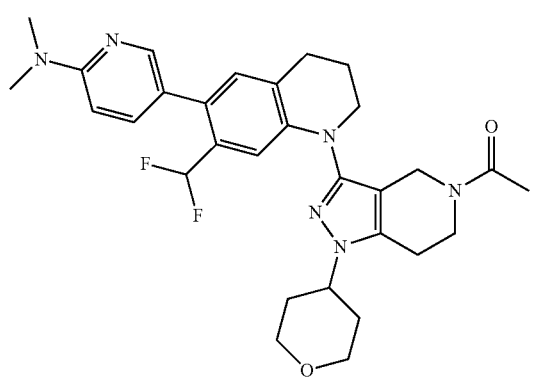
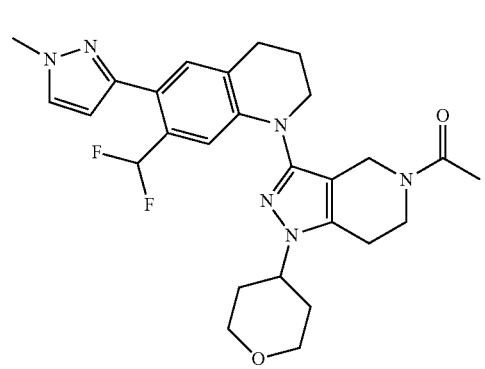
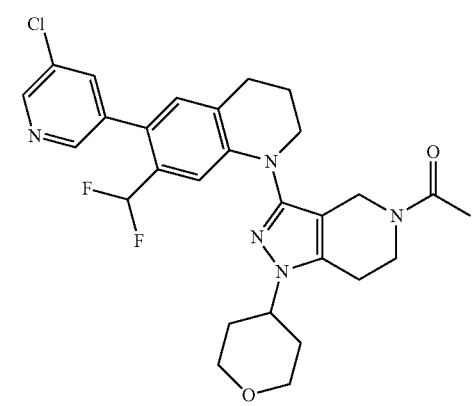
168
-continued
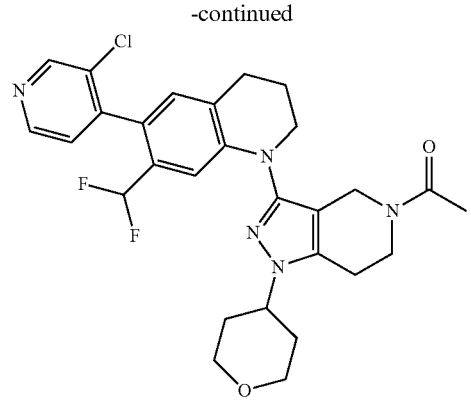
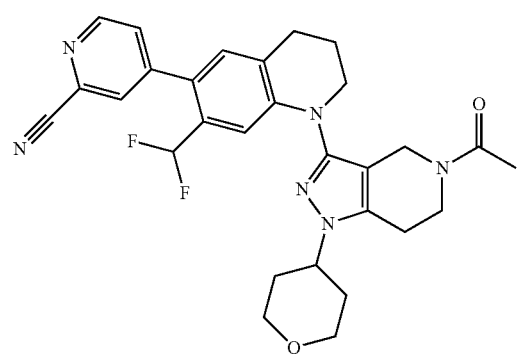
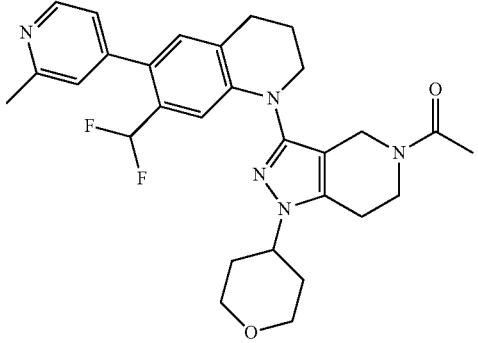
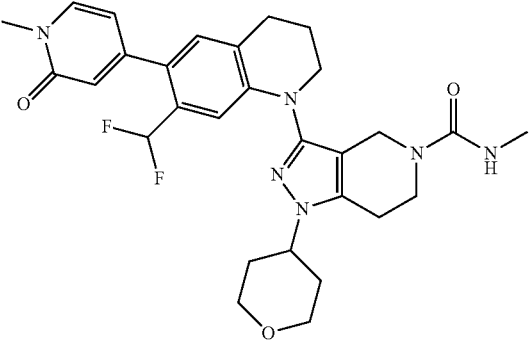

| 169 | 170 |
|---|---|
| -continued | -continued |
| 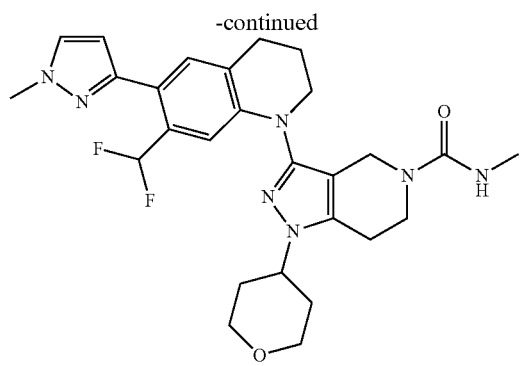 | 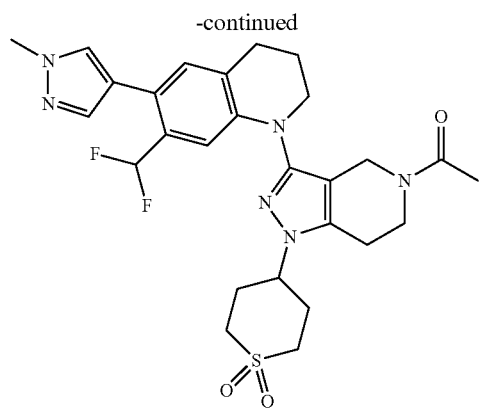 |
| 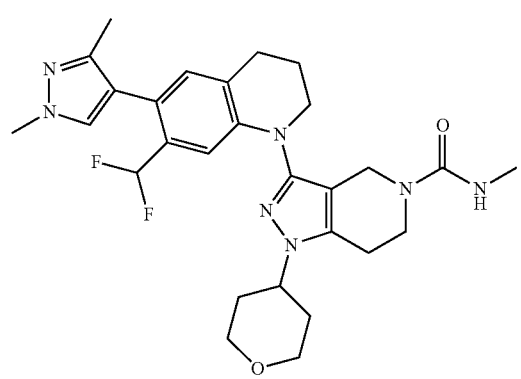 | 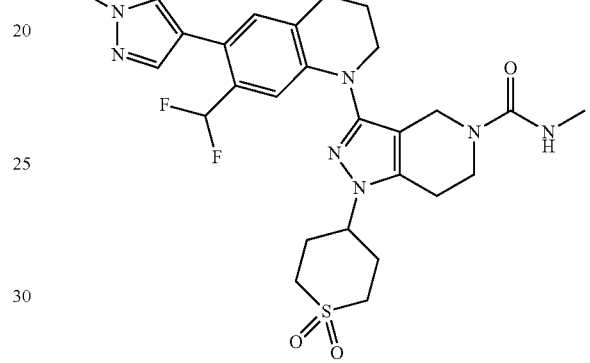 |
| 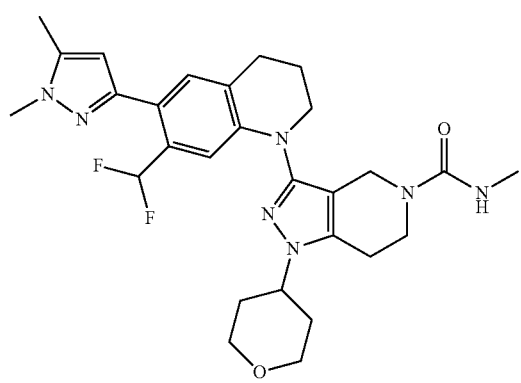 | 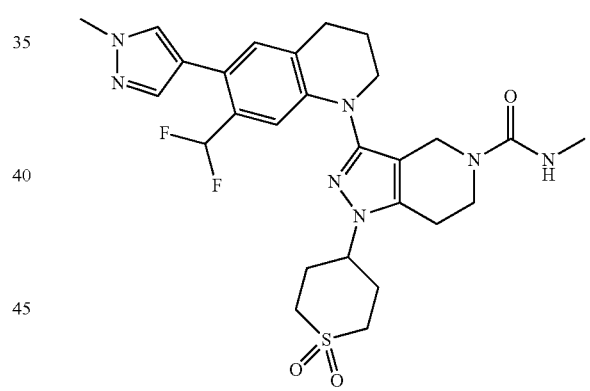 |
| 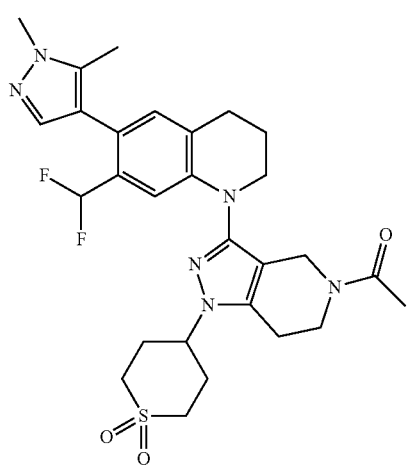 | 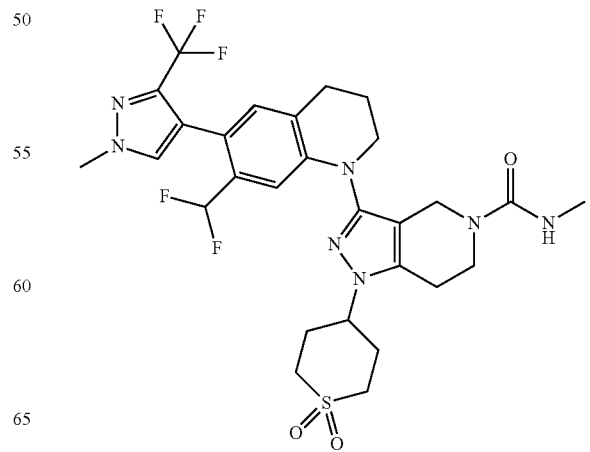 |

171
-continued
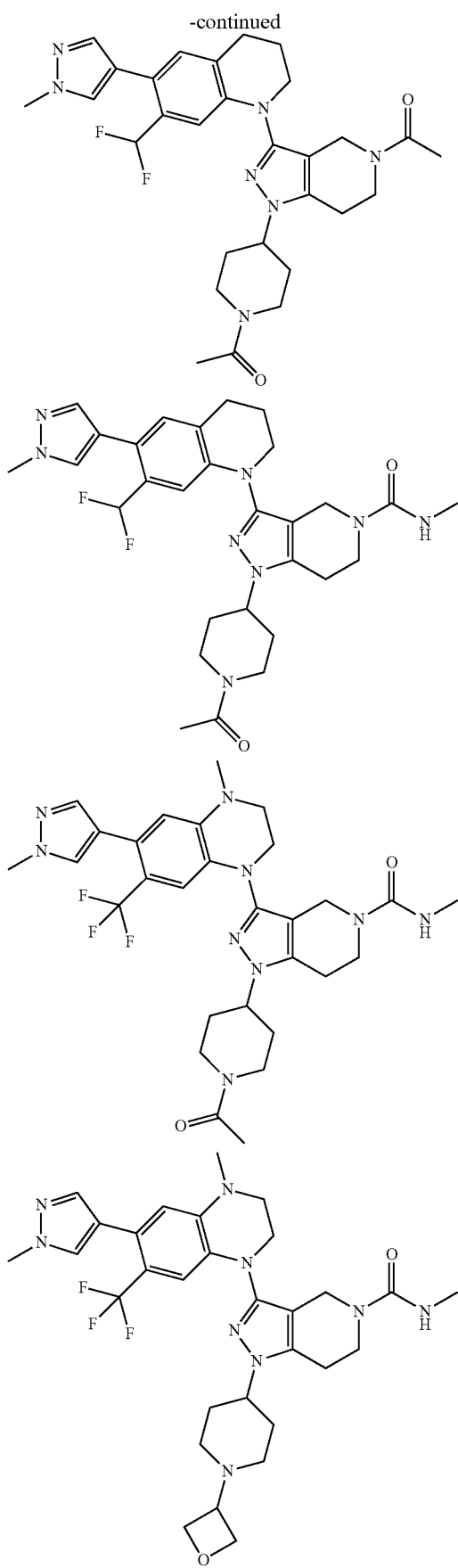
172
-continued
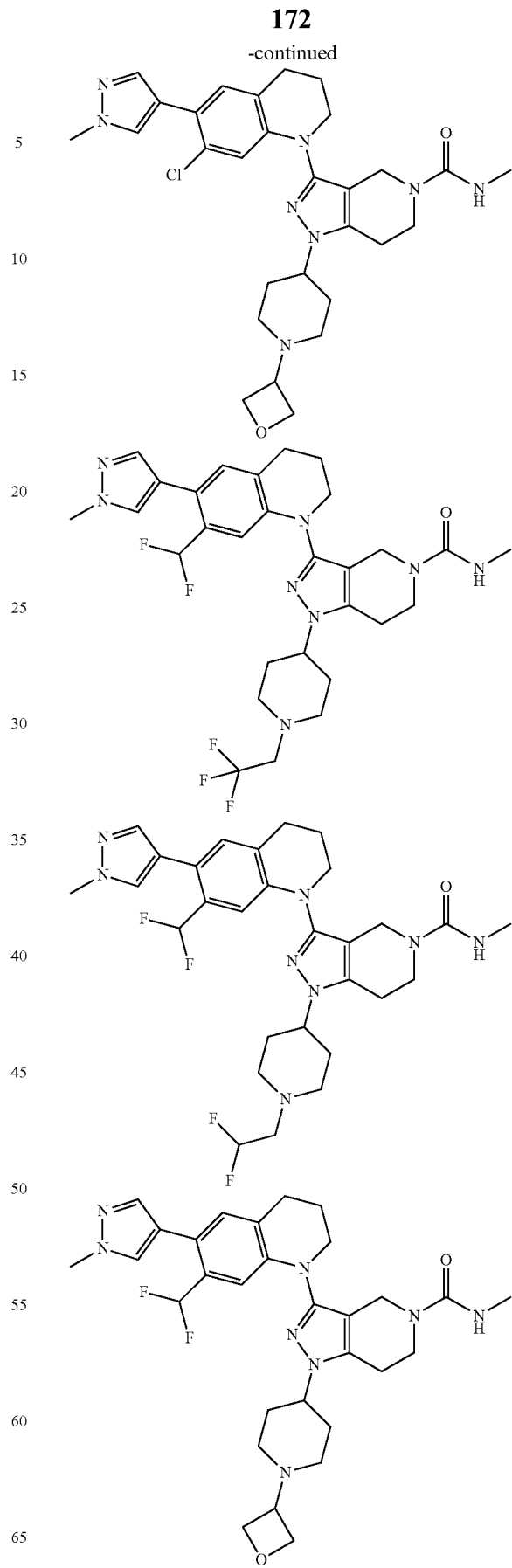

173
-continued
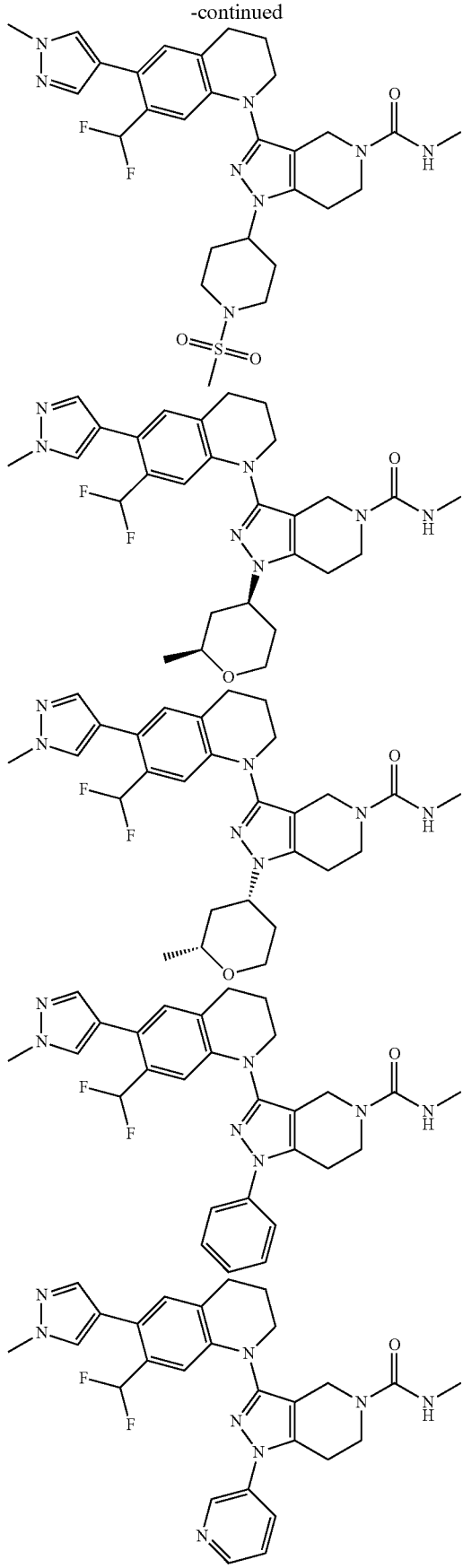
174
-continued
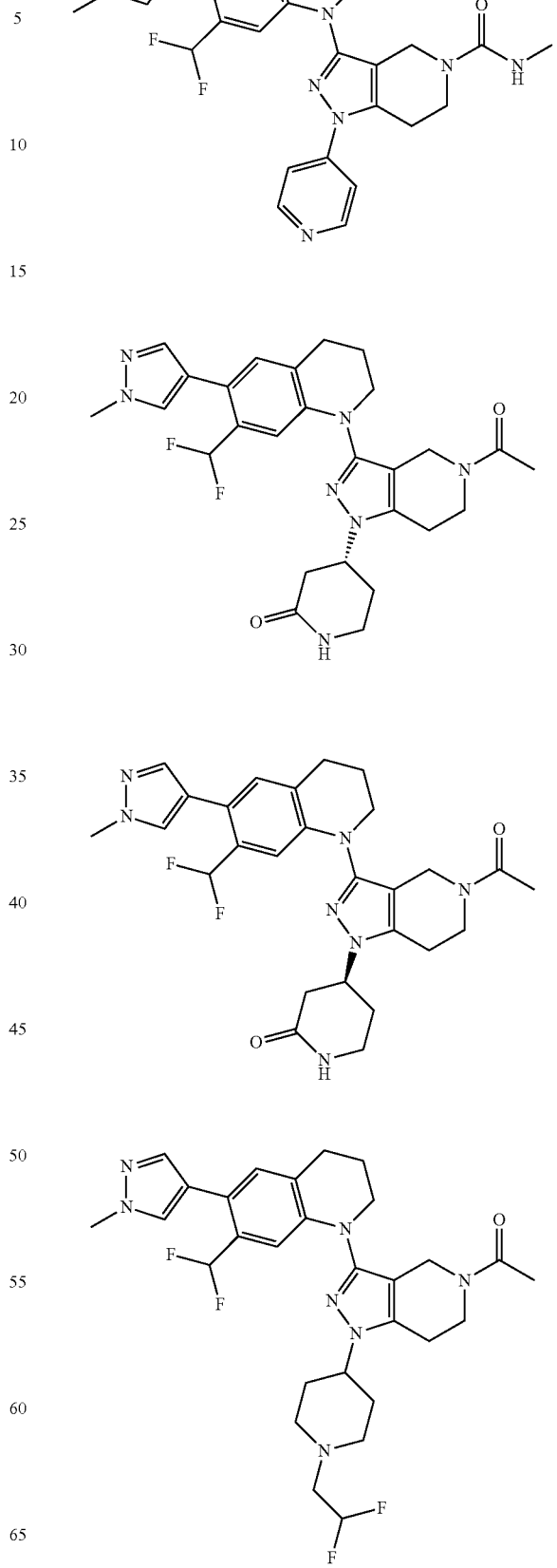

175
-continued
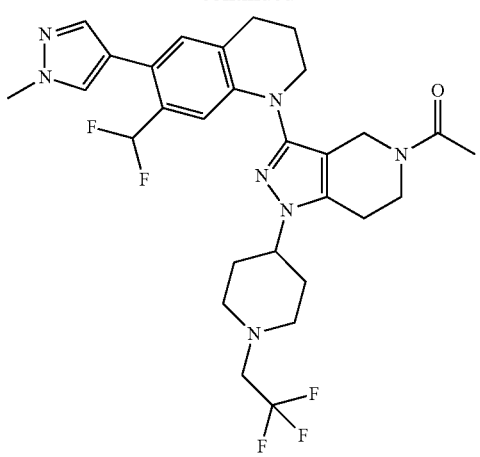
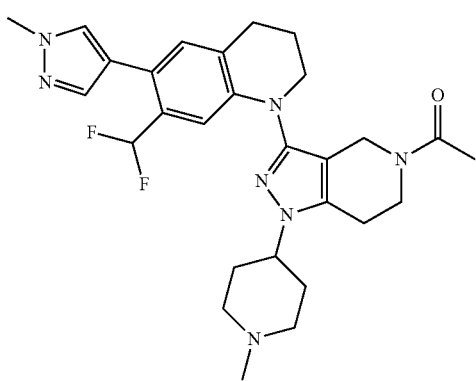
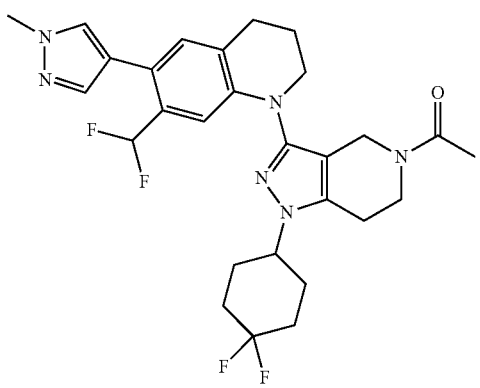
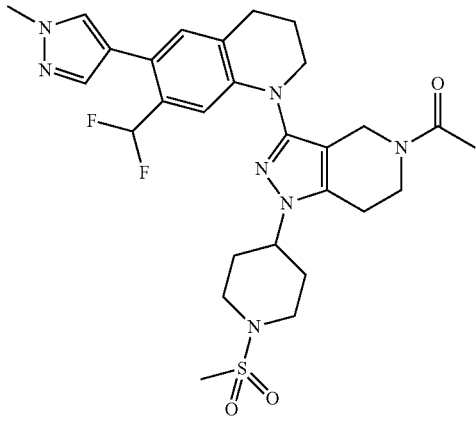
176
-continued
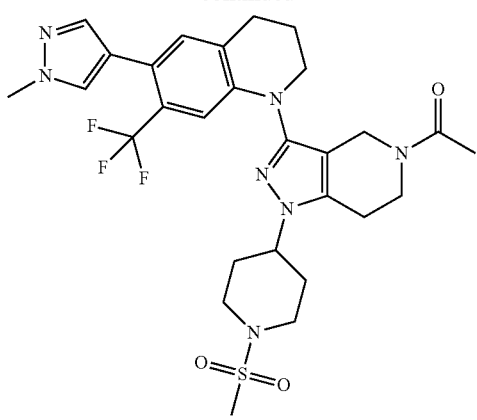
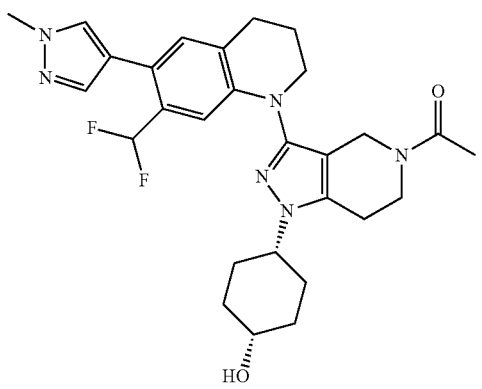
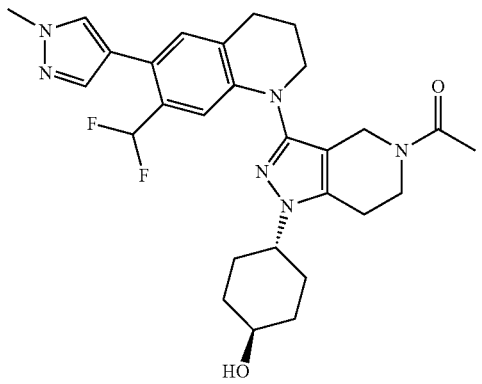
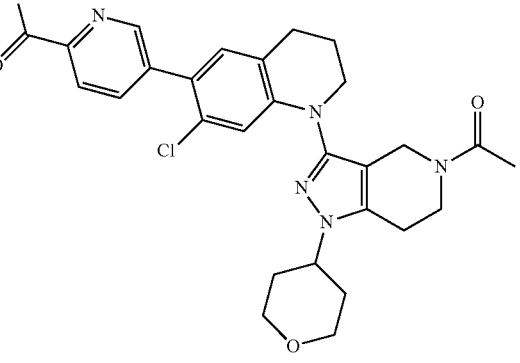

177
-continued
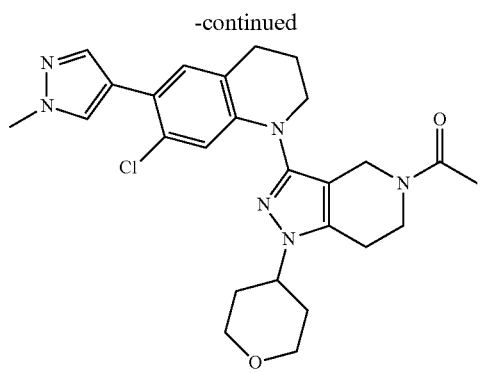
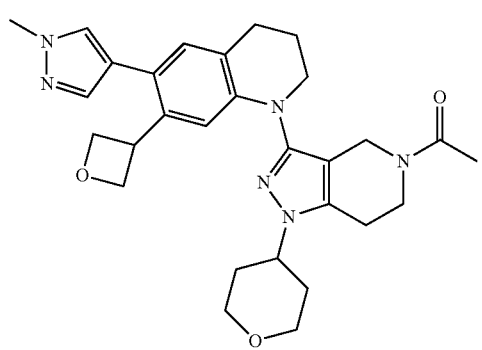
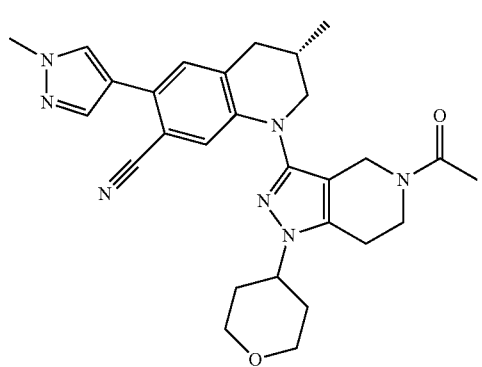
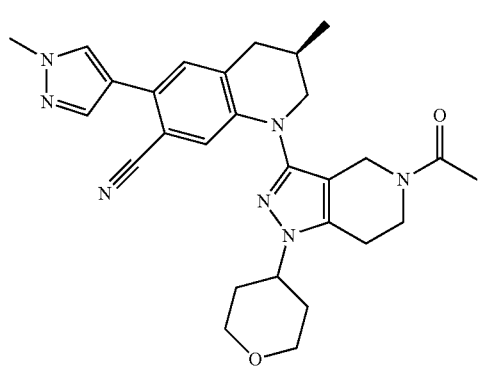
178
-continued
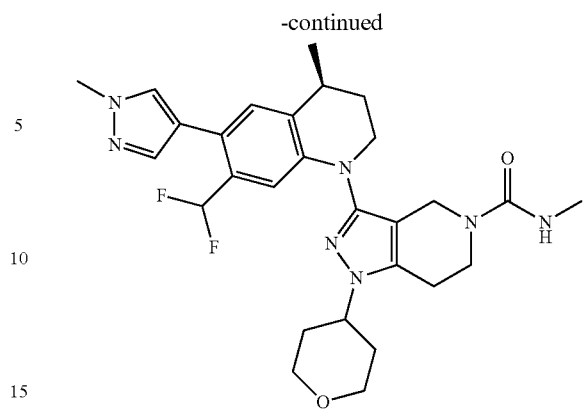
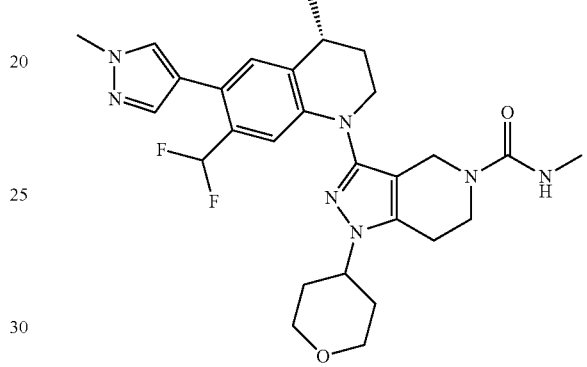
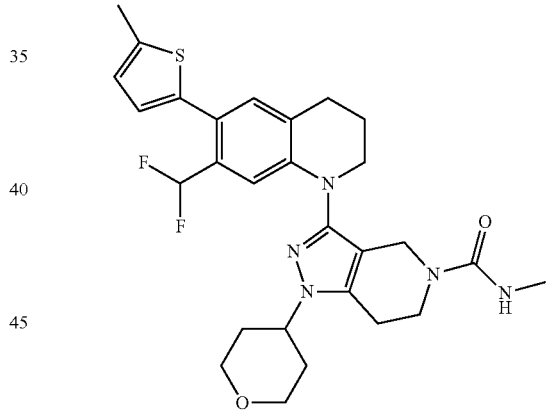
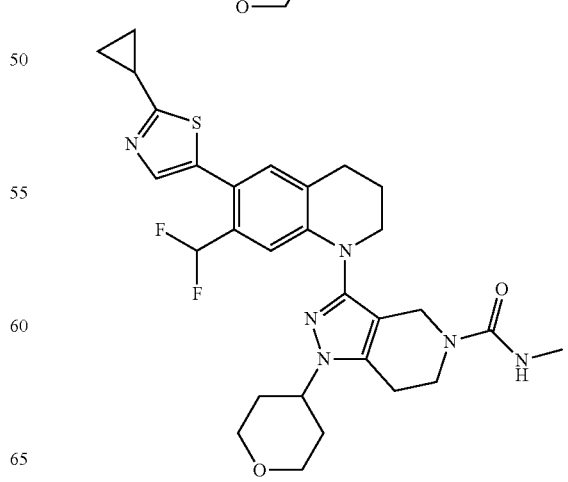

179
-continued
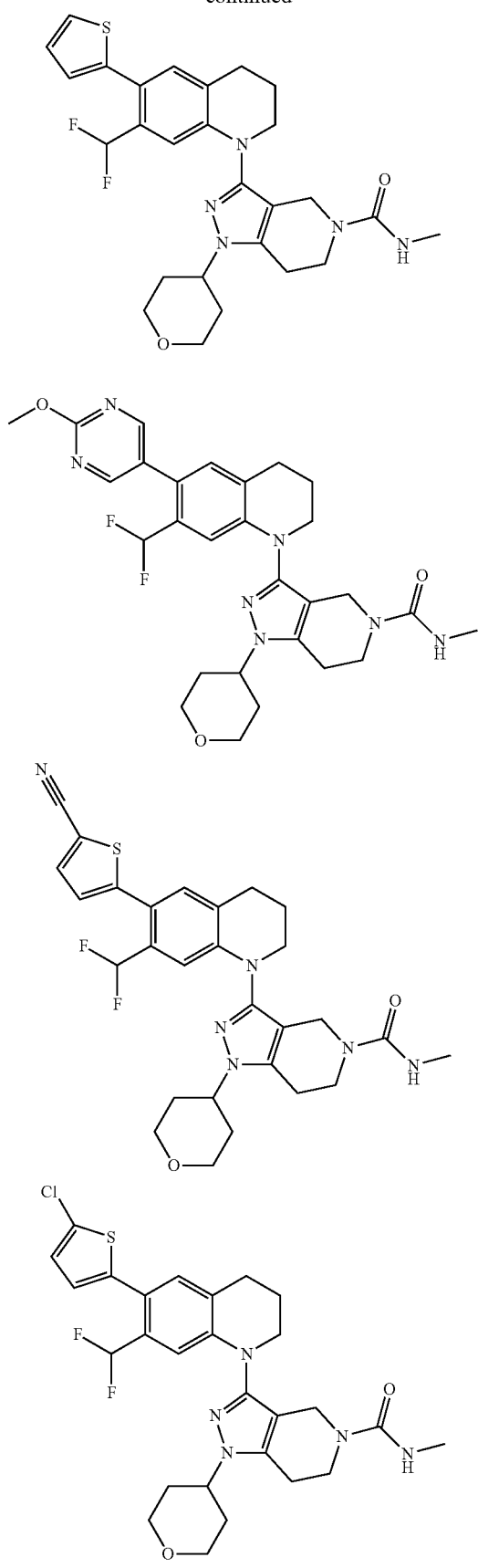
180
-continued
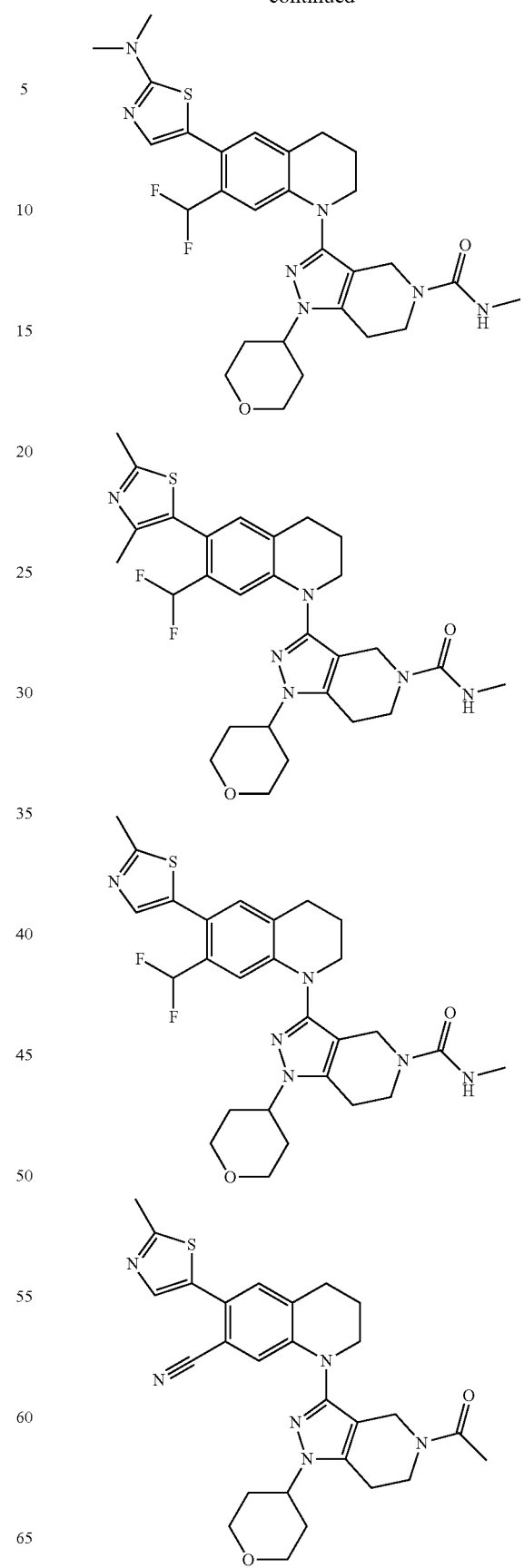

181
-continued
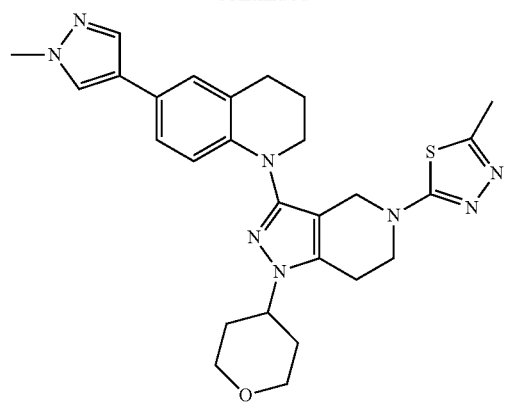
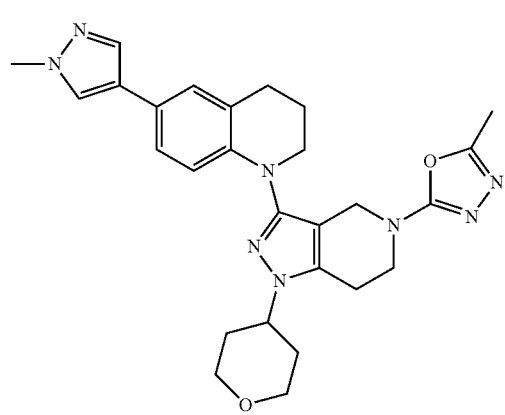
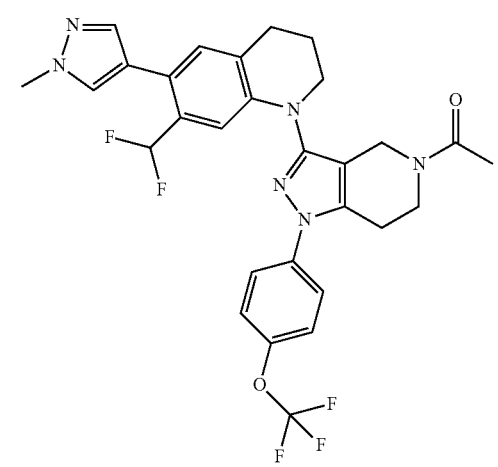
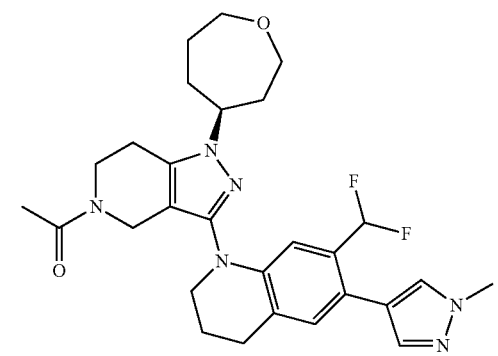
182
-continued
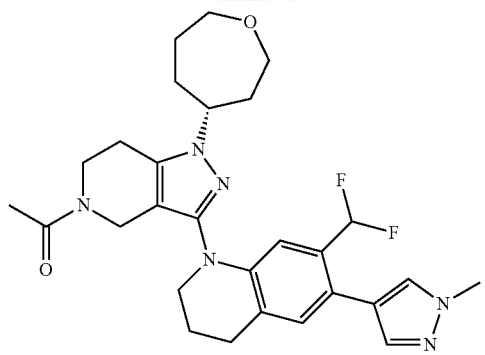
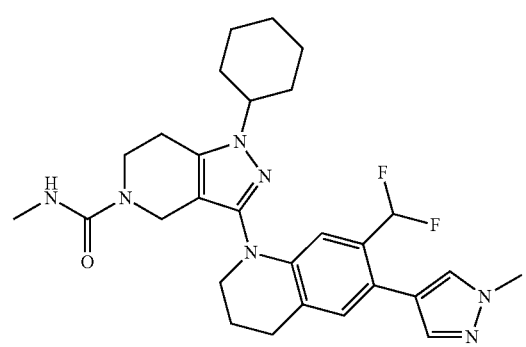
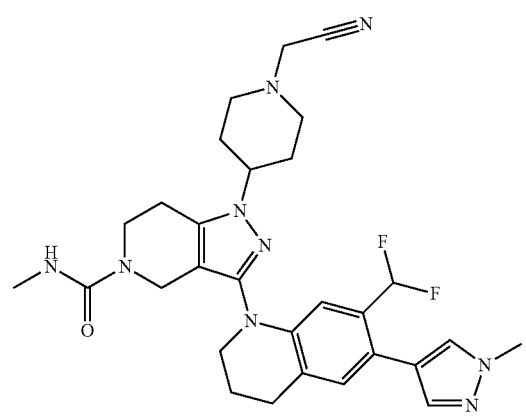
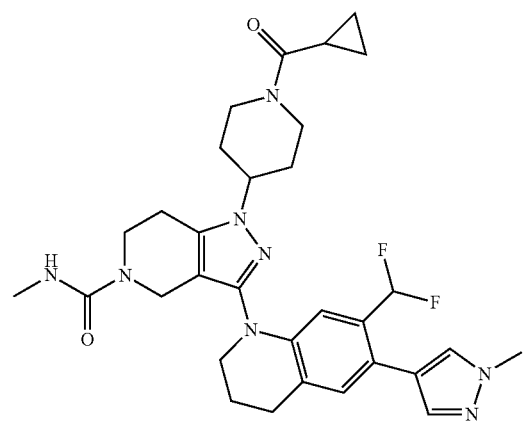

-continued
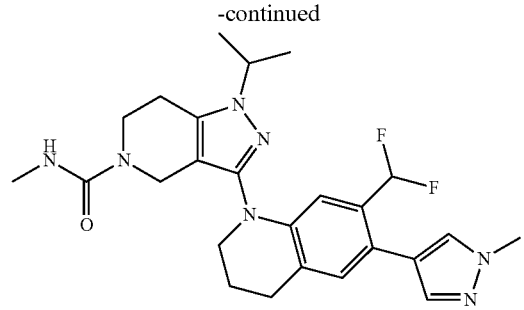
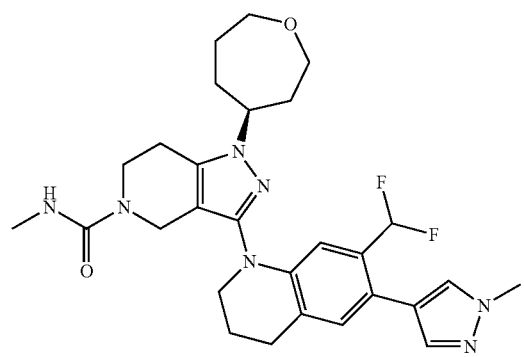
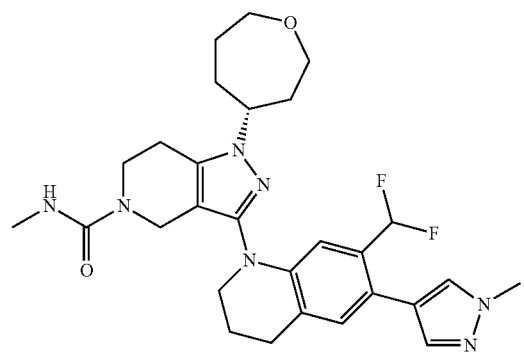
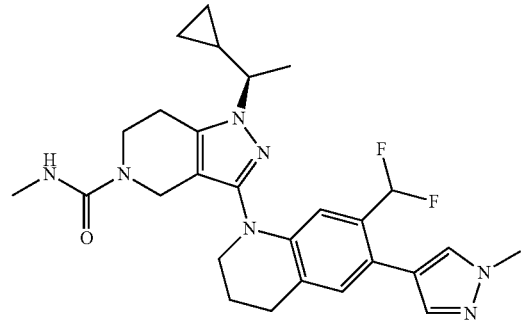
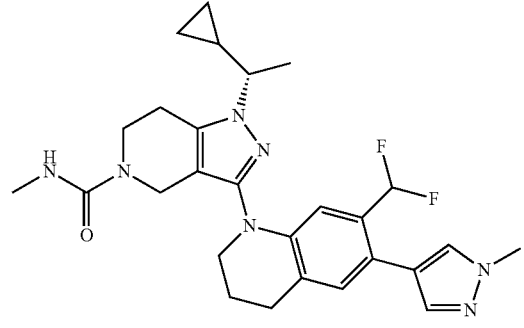
-continued
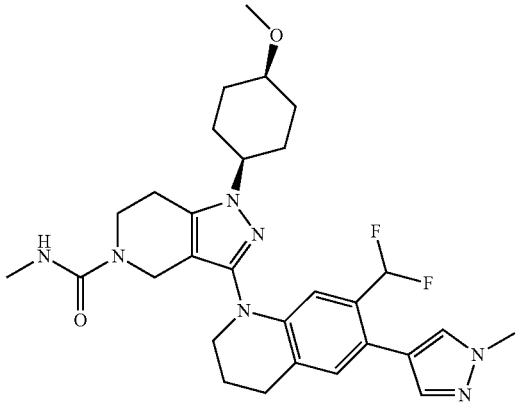
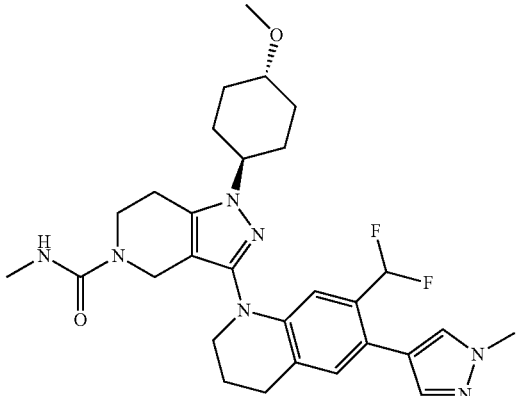
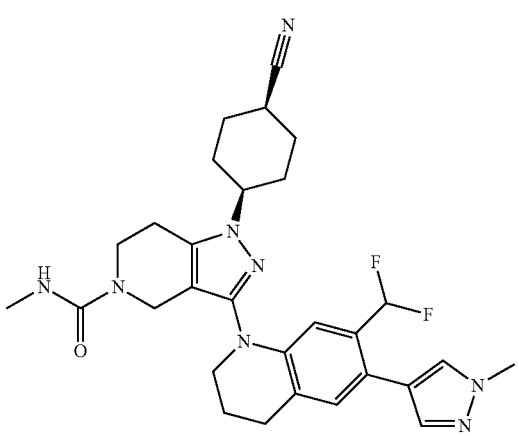
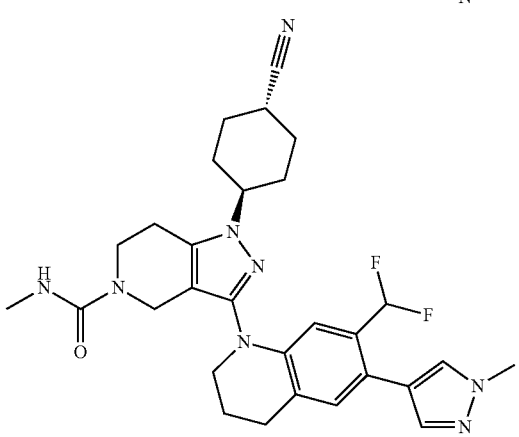

-continued

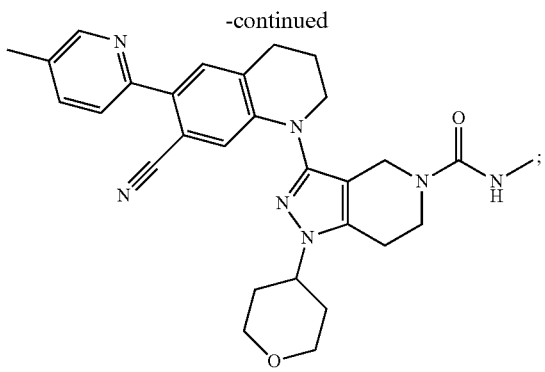

and salts thereof.

In certain embodiments the compound of Formula (I) is a compound as described in the Examples herein, or a freebase or salt thereof.

In certain embodiments any of the embodiments described for the compound of Formula (I) may be combined with any other embodiment described for the compound of Formula (I).

Exemplary Values for Compounds of Formula (I)

In certain embodiments of compounds of Formula (II), $R^1$ is not unsubstituted phenyl, when $R^2$ is carboxymethyl or 2-carboxyethyl.

In certain embodiments of compounds of Formula (II), $R^1$ is selected from $C_6$-$C_{20}$ aryl, $C_1$-$C_{20}$ heteroaryl, —($C_6$-$C_{20}$ aryl)-($C_1$-$C_{20}$ heteroaryl), and —($C_1$-$C_{20}$ heteroaryl)-($C_1$-$C_{20}$ heteroaryl), wherein each $C_6$-$C_{20}$ aryl, $C_1$-$C_{20}$ heteroaryl, —($C_6$-$C_{20}$ aryl)-($C_1$-$C_{20}$ heteroaryl) and —($C_1$-$C_{20}$ heteroaryl)-($C_1$-$C_{20}$ heteroaryl) is optionally substituted with one or more substituent groups independently selected from $R^c$, oxo, —F, —Cl, —Br, —N($R^a$)$_2$, —CN, —C(O)—N($R^a$)$_2$, —O—$R^a$, —C(O)—$R^a$, —N($R^a$)—S(O)—$R^a$, and —S(O)$_2$—$R^a$.

In certain embodiments of compounds of Formula (II), $R^1$ is selected from —($C_6$-$C_{20}$ aryl)-($C_1$-$C_{20}$ heteroaryl) and —($C_1$-$C_{20}$ heteroaryl)-($C_1$-$C_{20}$ heteroaryl), wherein each —($C_6$-$C_{20}$ aryl)-($C_1$-$C_{20}$ heteroaryl) and —($C_1$-$C_{20}$ heteroaryl)-($C_1$-$C_{20}$ heteroaryl) is optionally substituted with one or more substituent groups independently selected from $R^c$, oxo, —F, —Cl, —Br, —N($R^a$)$_2$, —CN, —C(O)—N($R^a$)$_2$, —O—$R^a$, —C(O)—$R^a$, —N($R^a$)—S(O)—$R^a$, and —S(O)$_2$—$R^a$.

In certain embodiments of Compounds of Formula (II), $R^1$ is selected from $C_6$-$C_{20}$ aryl and $C_1$-$C_{20}$ heteroaryl, wherein each $C_6$-$C_{20}$ aryl and $C_1$-$C_{20}$ heteroaryl, is optionally substituted with one or more substituent groups independently selected from $R^c$, oxo, —F, —Cl, —Br, —N($R^a$)$_2$, —CN, —C(O)—N($R^a$)$_2$, —O—$R^a$, —C(O)—$R^a$, —N($R^a$)—S(O)—$R^a$, and —S(O)$_2$—$R^a$.

In certain embodiments of compounds of Formula (II), $R^1$ is selected from —($C_6$-$C_{20}$ aryl)-($C_1$-$C_{20}$ heteroaryl), and —($C_1$-$C_{20}$ heteroaryl)-($C_1$-$C_{20}$ heteroaryl), wherein each —($C_6$-$C_{20}$ aryl)-($C_1$-$C_{20}$ heteroaryl) and —($C_1$-$C_{20}$ heteroaryl)-($C_1$-$C_{20}$ heteroaryl) is optionally substituted with one or more substituent groups independently selected from $R^c$, oxo, —F, —Cl, —Br, —I, —NO$_2$, —N($R^a$)$_2$, —CN, —C(O)—N($R^a$)$_2$, —S(O)—N($R^a$)$_2$, —S(O)$_2$—N($R^a$)$_2$, —O—$R^a$, —S—$R^a$, —O—C(O)—$R^a$, —O—C(O)—O—$R^a$, —C(O)—$R^a$, —C(O)—O—$R^a$, —S(O)—$R^a$, —S(O)$_2$—$R^a$, —O—C(O)—N($R^a$)$_2$, —N($R^a$)—C(O)—O$R^a$, —N($R^a$)—C(O)—N($R^a$)$_2$, —N($R^a$)—C(O)—$R^a$, —N($R^a$)—S(O)—$R^a$, —N($R^a$)—S(O)$_2$—$R^a$, —N($R^a$)—S(O)—N($R^a$)$_2$, and —N($R^a$)—S(O)$_2$—N($R^a$)$_2$.

In certain embodiments of compounds of Formula (II), $R^1$ is —($C_6$-$C_{20}$ aryl)-($C_1$-$C_{20}$ heteroaryl), wherein —($C_6$-$C_{20}$ aryl)-($C_1$-$C_{20}$ heteroaryl) is optionally substituted with one or more substituent groups independently selected from $R^c$, oxo, —F, —Cl, —Br, —I, —NO$_2$, —N($R^a$)$_2$, —CN, —C(O)—N($R^a$)$_2$, —S(O)—N($R^a$)$_2$, —S(O)$_2$—N($R^a$)$_2$, —O—$R^a$, —S—$R^a$, —O—C(O)—$R^a$, —O—C(O)—O—$R^a$, —C(O)—$R^a$, —C(O)—O—$R^a$, —S(O)—$R^a$, —S(O)$_2$—$R^a$, —O—C(O)—N($R^a$)$_2$, —N($R^a$)—C(O)—O$R^a$, —N($R^a$)—C(O)—N($R^a$)$_2$, —N($R^a$)—C(O)—$R^a$, —N($R^a$)—S(O)—$R^a$, —N($R^a$)—S(O)$_2$—$R^a$, —N($R^a$)—S(O)—N($R^a$)$_2$, and —N($R^a$)—S(O)$_2$—N($R^a$)$_2$.

In certain embodiments of compounds of Formula (II), $R^1$ is —($C_1$-$C_{20}$ heteroaryl)-($C_1$-$C_{20}$ heteroaryl), wherein —($C_1$-$C_{20}$ heteroaryl)-($C_1$-$C_{20}$ heteroaryl) is optionally substituted with one or more substituent groups independently selected from $R^c$, oxo, —F, —Cl, —Br, —I, —NO$_2$, —N($R^a$)$_2$, —CN, —C(O)—N($R^a$)$_2$, —S(O)—N($R^a$)$_2$, —S(O)$_2$—N($R^a$)$_2$, —O—$R^a$, —S—$R^a$, —O—C(O)—$R^a$, —O—C(O)—O—$R^a$, —C(O)—$R^a$, —C(O)—O—$R^a$, —S(O)—$R^a$, —S(O)$_2$—$R^a$, —O—C(O)—N($R^a$)$_2$, —N($R^a$)—C(O)—O$R^a$, —N($R^a$)—C(O)—N($R^a$)$_2$, —N($R^a$)—C(O)—$R^a$, —N($R^a$)—S(O)—$R^a$, —N($R^a$)—S(O)$_2$—$R^a$, —N($R^a$)—S(O)—N($R^a$)$_2$, and —N($R^a$)—S(O)$_2$—N($R^a$)$_2$.

In certain embodiments of compounds of Formula (II), each $R^b$ is independently selected from oxo, $C_{1-6}$alkyl, $C_{2-6}$alkenyl, $C_{2-6}$alkynyl, carbocyclyl, heterocyclyl, aryl, heteroaryl, —F, —Cl, —Br, —I, —NO$_2$, —N($R^c$)$_2$, —CN, —C(O)—N($R^c$)$_2$, —S(O)—N($R^c$)$_2$, —S(O)$_2$—N($R^c$)$_2$, —O—$R^c$, —S—$R^c$, —O—C(O)—$R^c$, —O—C(O)—O—$R^c$, —C(O)—$R^c$, —S(O)—$R^c$, —S(O)$_2$—$R^c$, —O—C(O)—N($R^c$)$_2$, —N($R^c$)—C(O)—O$R^c$, —N($R^c$)—C(O)—N($R^c$)$_2$, —N($R^c$)—C(O)—$R^c$, —N($R^c$)—S(O)—$R^c$, —N($R^c$)—S(O)$_2$—$R^c$, —N($R^c$)—S(O)—N($R^c$)$_2$, and —N($R^c$)—S(O)$_2$—N($R^c$)$_2$.

In certain embodiments of compounds of Formula (II), each $R^c$ is independently selected from $C_{1-6}$alkyl, $C_{2-6}$alkenyl, $C_{2-6}$alkynyl, carbocyclyl, and heterocyclyl.

In certain embodiments of compounds of Formula (II), each $R^a$ is independently selected from hydrogen, $C_{1-6}$alkyl, carbocyclyl, and heterocyclyl, wherein each $C_{1-6}$alkyl, carbocyclyl, and heterocyclyl is optionally substituted with one or more groups independently selected from halo, $C_{1-6}$alkoxy, and $C_1$-$C_6$ alkyl that is optionally substituted with one or more groups independently selected from oxo and halo; or two $R^a$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

In certain embodiments of compounds of Formula (II), each $R^b$ is independently selected from $C_{1-6}$alkyl, carbocyclyl, heterocyclyl, —CN, —C(O)—N($R^c$)$_2$, —O—$R^c$, —C(O)—O—$R^c$, and —S(O)$_2$—$R^c$, wherein any $C_{1-6}$alkyl, $C_{2-6}$alkenyl, $C_{2-6}$alkynyl, carbocyclyl, and heterocyclyl, is optionally substituted with one or more groups independently selected from halo and $C_{1-6}$alkyl that is optionally substituted with one or more groups independently selected from oxo and halo.

In certain embodiments of compounds of Formula (II), each $R^c$ is independently selected from hydrogen, $C_{1-6}$alkyl, and carbocyclyl, wherein any $C_{1-6}$alkyl and carbocyclyl is optionally substituted with one or more groups independently selected from halo, —N(R$^d$)$_2$, —CN, —C(O)—N(R$^d$)$_2$, —O—R$^d$, —S(O)$_2$—R$^d$, —N(R$^d$)—C(O)—R$^d$, N(R$^d$)—S(O)$_2$—R$^d$, and C$_{1-6}$alkyl, which carbocyclyl and C$_{1-6}$alkyl are optionally substituted with one or more groups independently selected from halo and —O—R$^d$.

In certain embodiments of compounds of Formula (II), each R$^d$ is independently selected from hydrogen and C$_{1-6}$alkyl, wherein each C$_{1-6}$alkyl is optionally substituted with one or more groups independently selected from halo and C$_{1-6}$alkoxy; or two R$^d$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo.

In certain embodiments of compounds of Formula (II), R$^1$ is selected from aryl that is optionally substituted with one or more substituent groups independently selected from R$^c$, —F, —Cl, —Br, —I, —NO$_2$, —N(R$^a$)$_2$, —CN, —C(O)—N(R$^a$)$_2$, —S(O)—N(R$^a$)$_2$, —S(O)$_2$—N(R$^a$)$_2$, —O—R$^a$, —S—R$^a$, —O—C(O)—R$^a$, —O—C(O)—O—R$^a$, —C(O)—R$^a$, —C(O)—O—R$^a$, —S(O)—R$^a$, —S(O)$_2$—R$^a$, —O—C(O)—N(R$^a$)$_2$, —N(R$^a$)—C(O)—OR$^a$, —N(R$^a$)—C(O)—N(R$^a$)$_2$, —N(R$^a$)—C(O)—R$^a$, —N(R$^a$)—S(O)—R$^a$, —N(R$^a$)—S(O)$_2$—R$^a$, —N(R$^a$)—S(O)—N(R$^a$)$_2$, and —N(R$^a$)—S(O)$_2$—N(R$^a$)$_2$.

In certain embodiments of compounds of Formula (II), R$^1$ is selected from heteroaryl that is optionally substituted with one or more substituent groups independently selected from R$^c$, —F, —Cl, —Br, —I, —NO$_2$, —N(R$^a$)$_2$, —CN, —C(O)—N(R$^a$)$_2$, —S(O)—N(R$^a$)$_2$, —S(O)$_2$—N(R$^a$)$_2$, —O—R$^a$, —S—R$^a$, —O—C(O)—R$^a$, —O—C(O)—O—R$^a$, —C(O)—R$^a$, —C(O)—O—R$^a$, —S(O)—R$^a$, —S(O)$_2$—R$^a$, —O—C(O)—N(R$^a$)$_2$, —N(R$^a$)—C(O)—OR$^a$, —N(R$^a$)—C(O)—N(R$^a$)$_2$, —N(R$^a$)—C(O)—R$^a$, —N(R$^a$)—S(O)—R$^a$, —N(R$^a$)—S(O)$_2$—R$^a$, —N(R$^a$)—S(O)—N(R$^a$)$_2$, and —N(R$^a$)—S(O)$_2$—N(R$^a$)$_2$.

In certain embodiments of compounds of Formula (II), R$^1$ is phenyl that is optionally substituted with one or more substituent groups independently selected from R$^c$, —F, —Cl, —Br, —I, —NO$_2$, —N(R$^a$)$_2$, —CN, —C(O)—N(R$^a$)$_2$, —S(O)—N(R$^a$)$_2$, —S(O)$_2$—N(R$^a$)$_2$, —O—R$^a$, —S—R$^a$, —O—C(O)—R$^a$, —O—C(O)—O—R$^a$, —C(O)—R$^a$, —C(O)—O—R$^a$, —S(O)—R$^a$, —S(O)$_2$—R$^a$, —O—C(O)—N(R$^a$)$_2$, —N(R$^a$)—C(O)—OR$^a$, —N(R$^a$)—C(O)—N(R$^a$)$_2$, —N(R$^a$)—C(O)—R$^a$, —N(R$^a$)—S(O)—R$^a$, —N(R$^a$)—S(O)$_2$—R$^a$, —N(R$^a$)—S(O)—N(R$^a$)$_2$, and —N(R$^a$)—S(O)$_2$—N(R$^a$)$_2$.

In certain embodiments of compounds of Formula (II), R$^1$ is selected from:

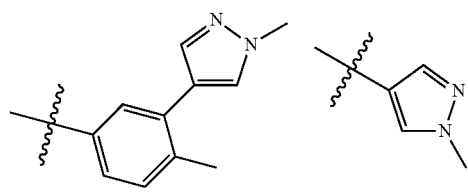

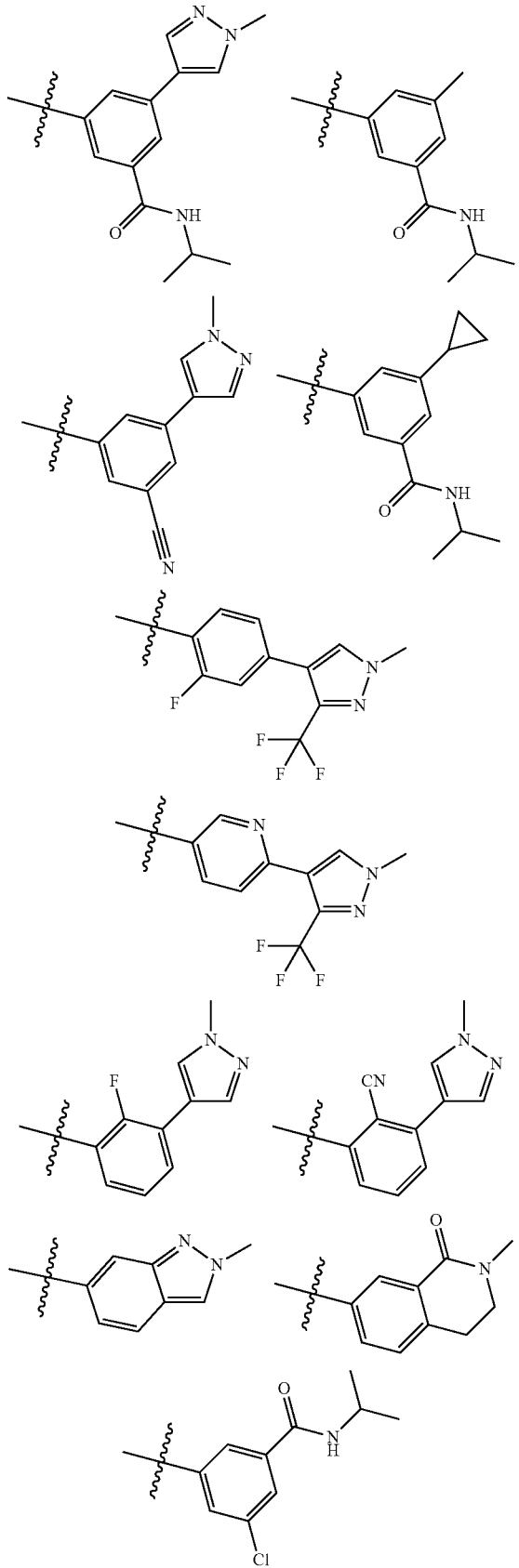

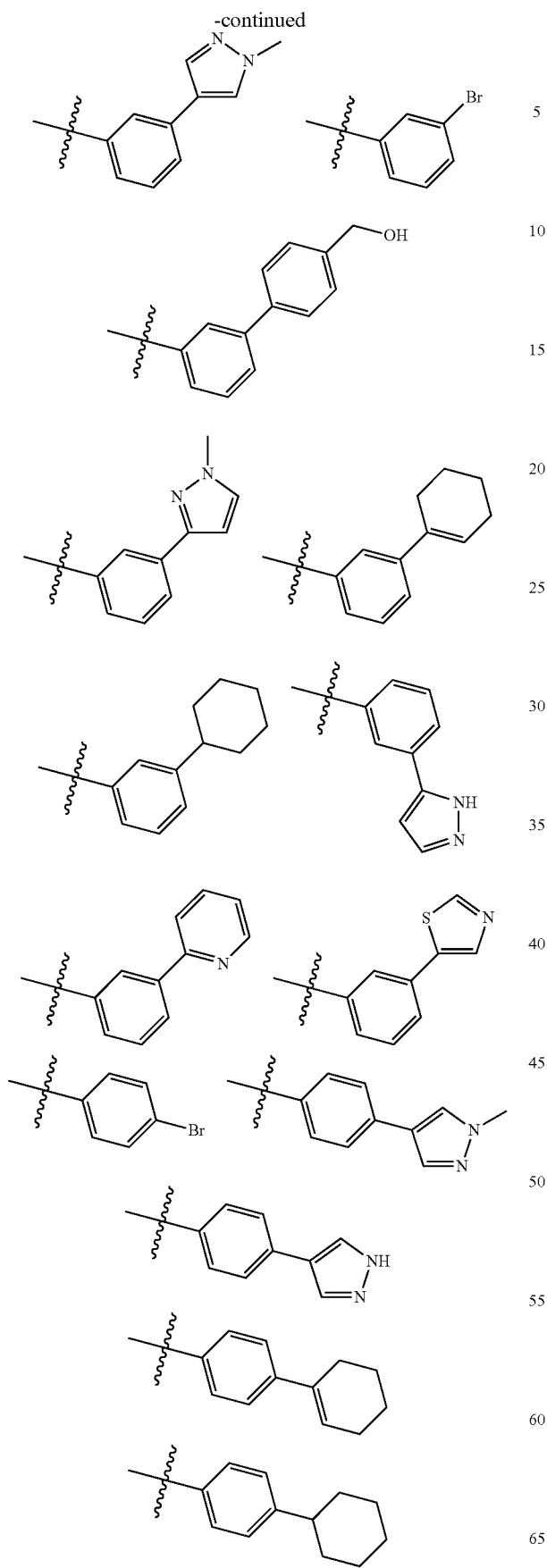
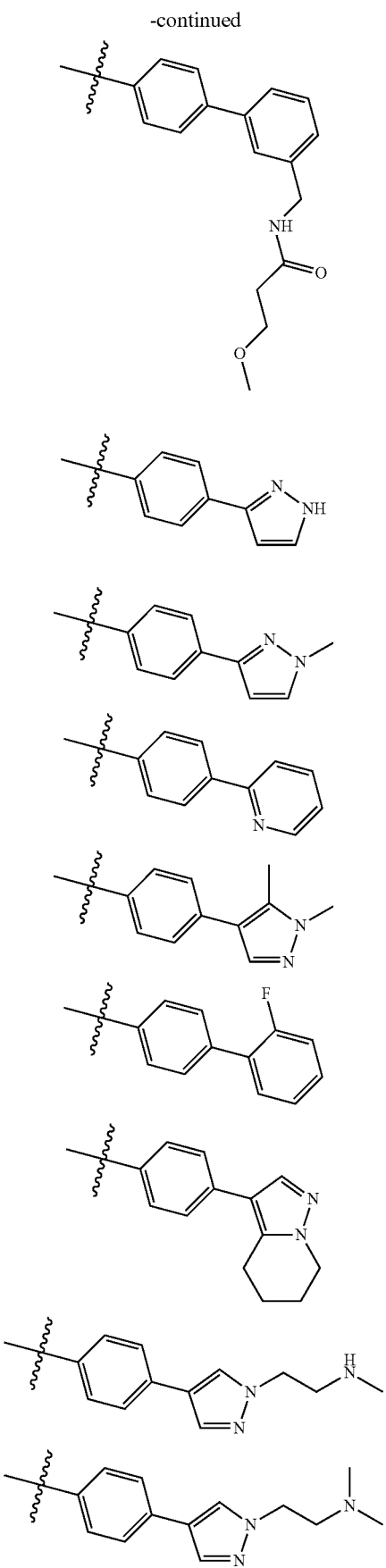

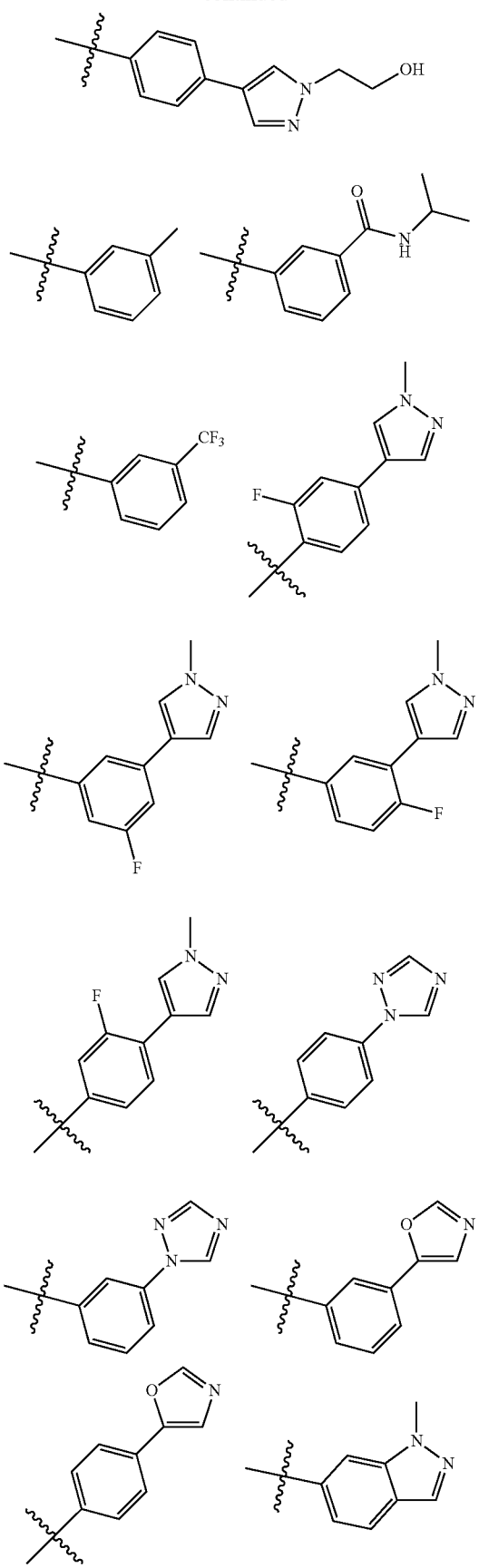
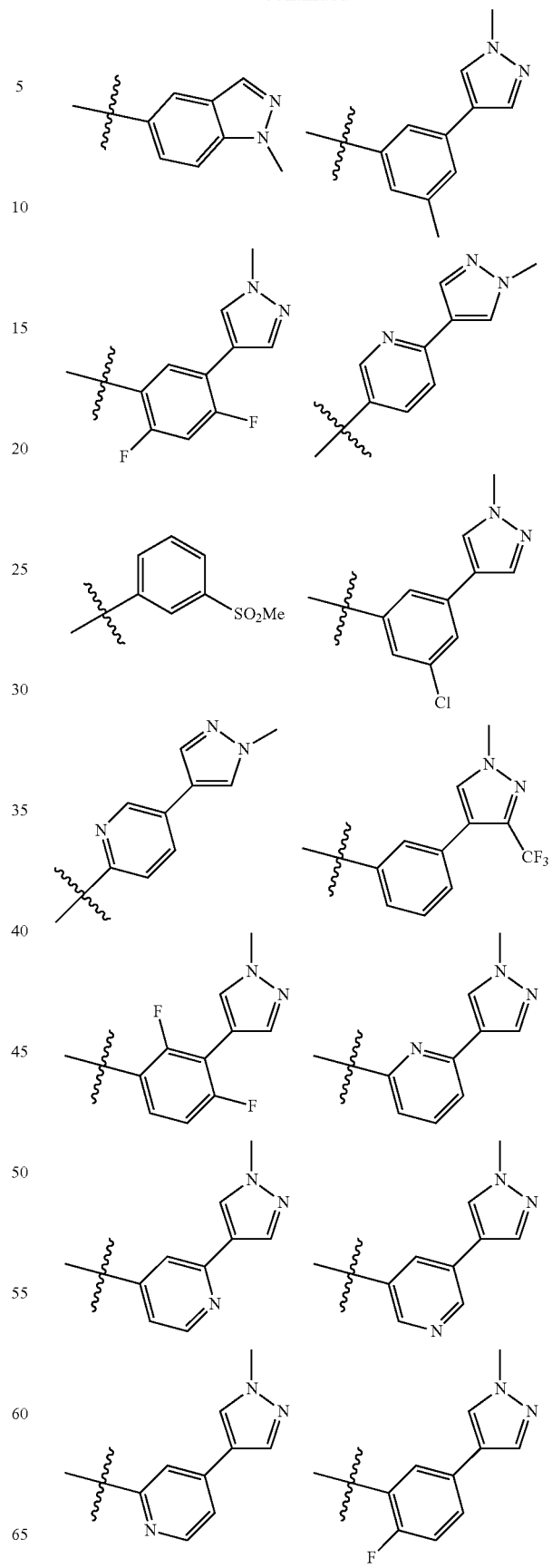

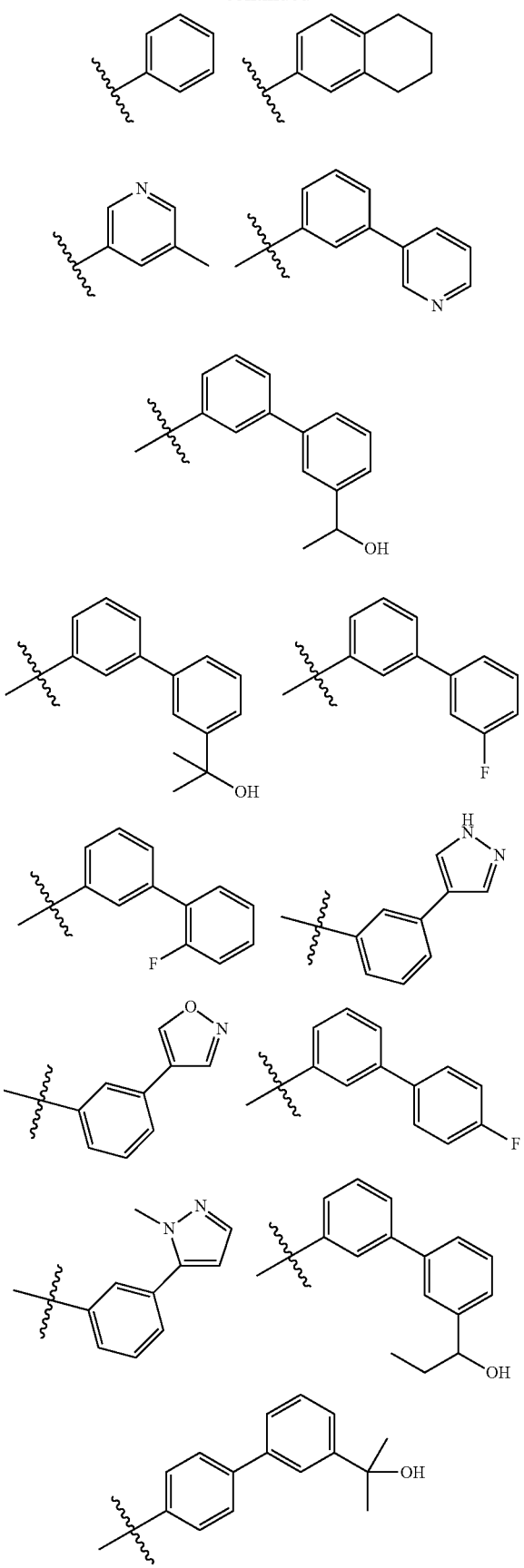
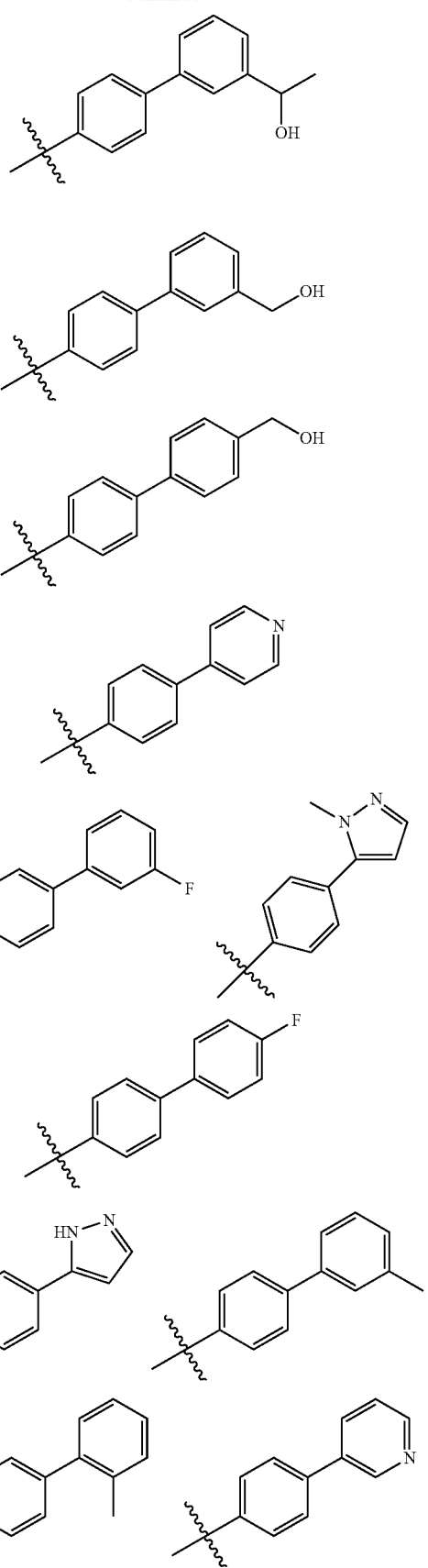

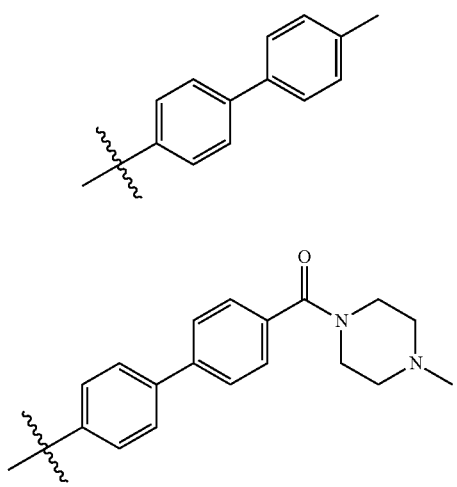
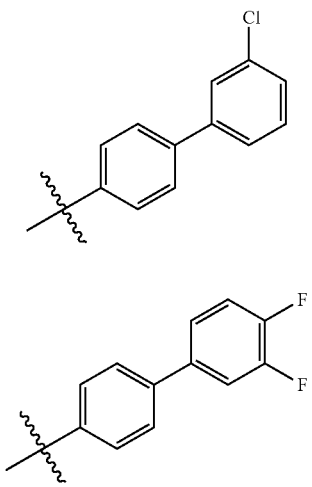

| 197 -continued | 198 -continued |
|---|---|
| 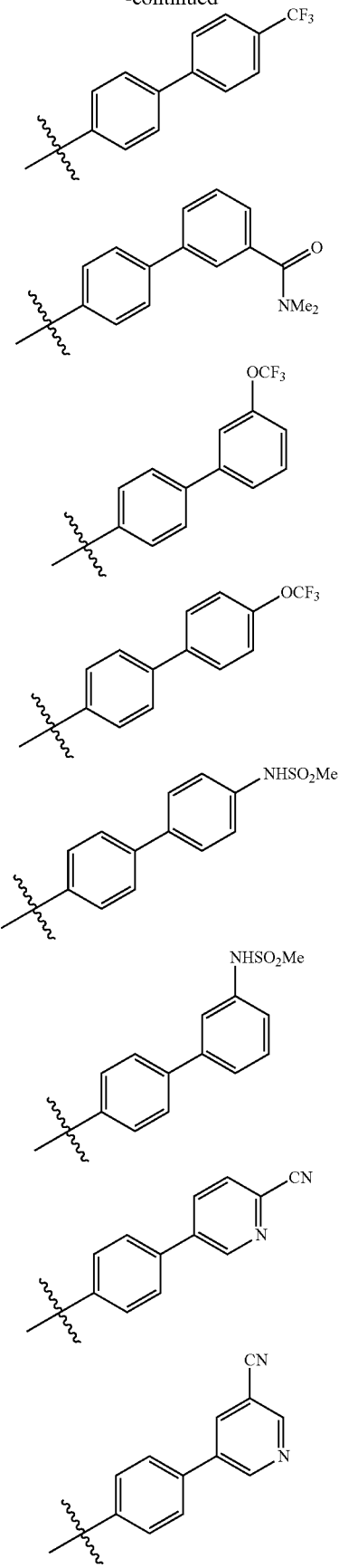 | 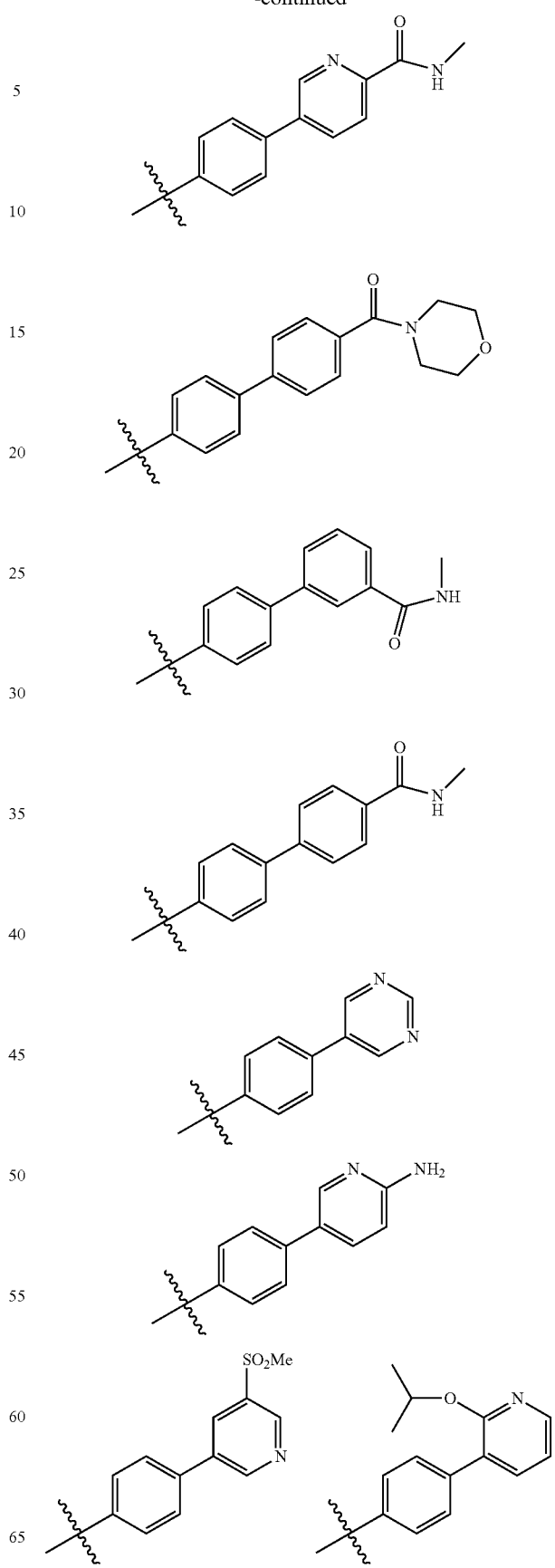 |

199
-continued
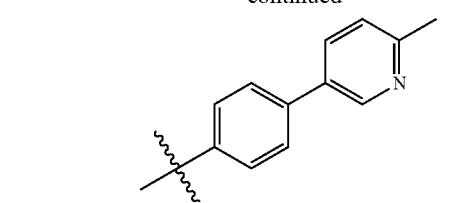
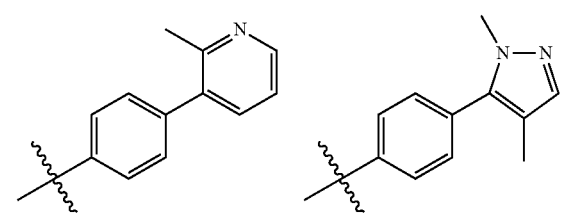
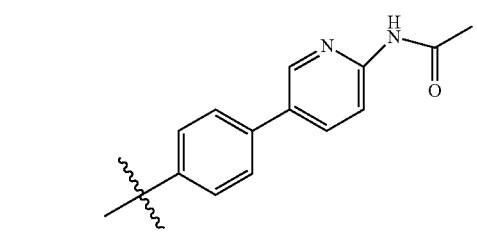
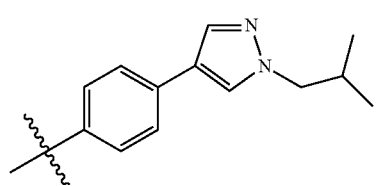
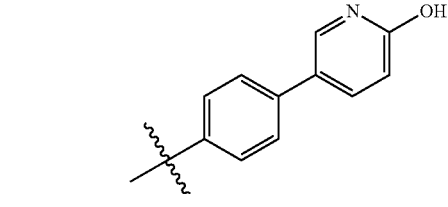
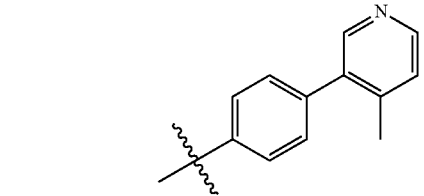
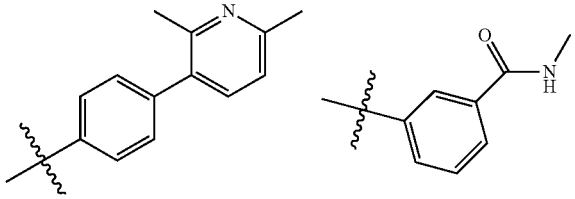
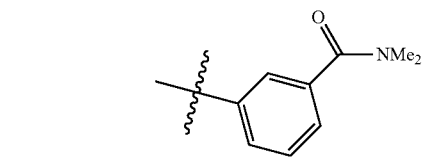
200
-continued
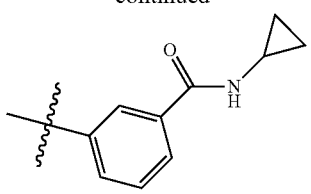
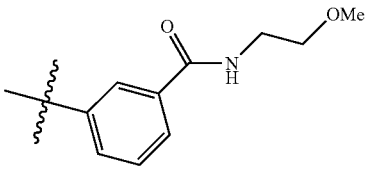
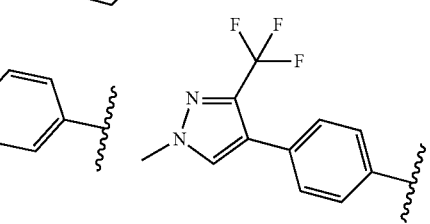
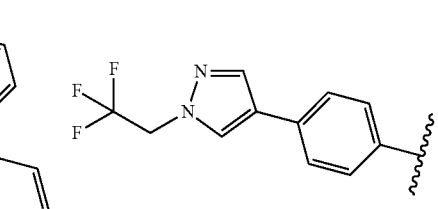
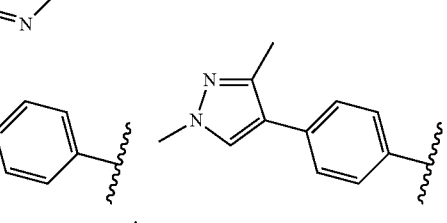
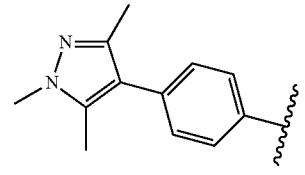
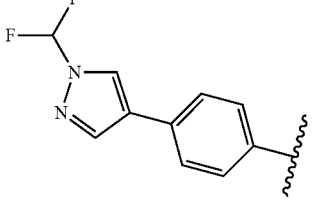
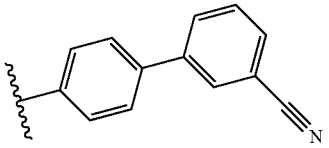
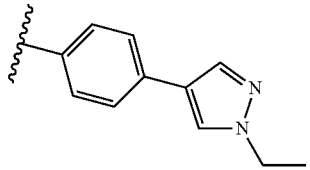

201
-continued
202
-continued
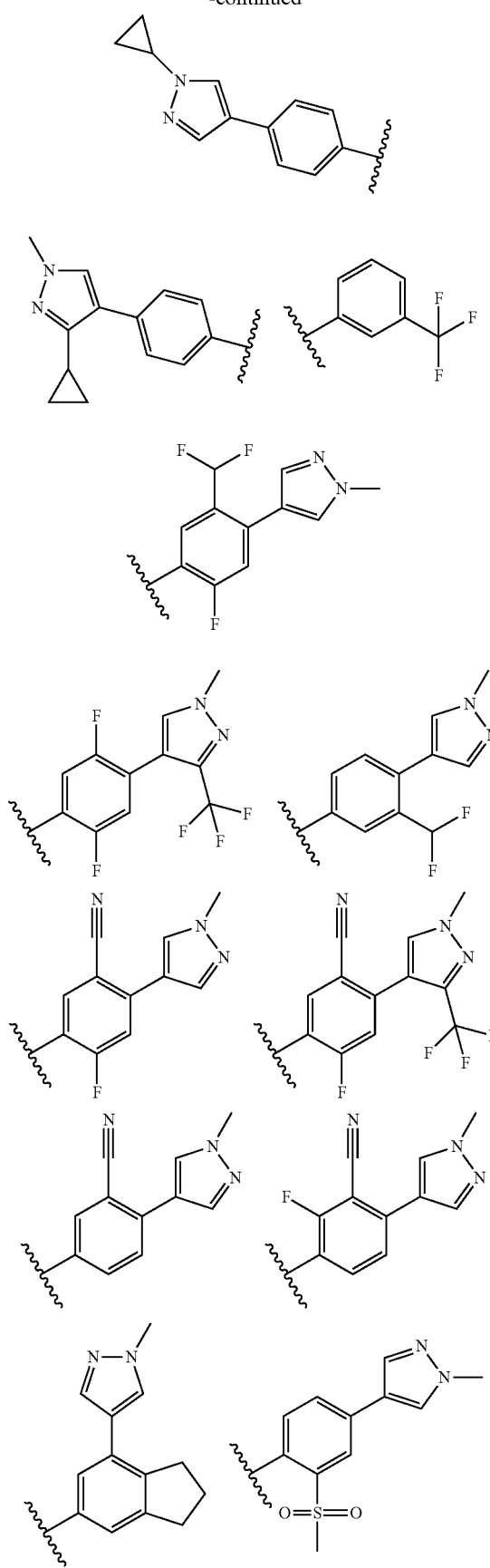
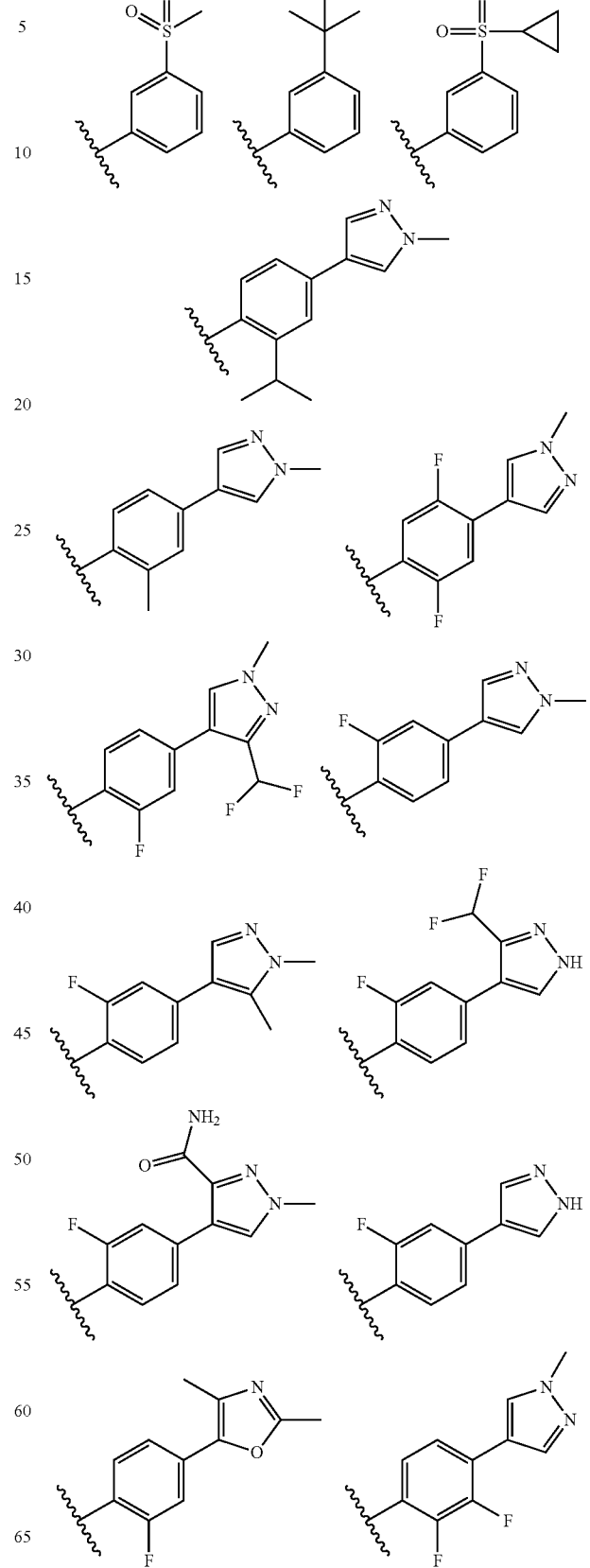

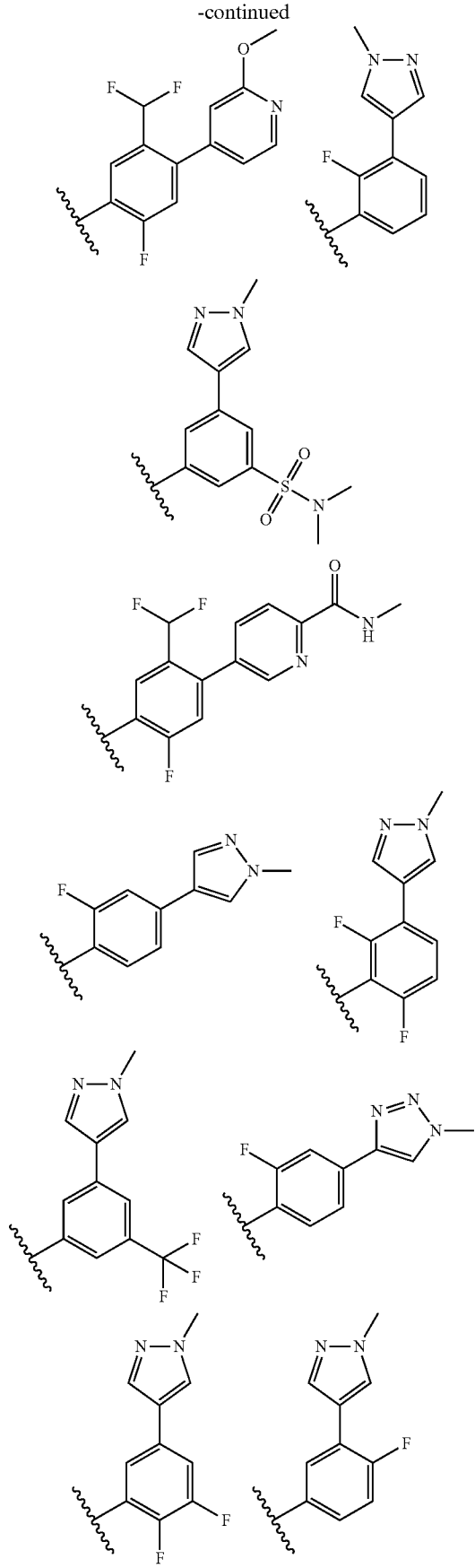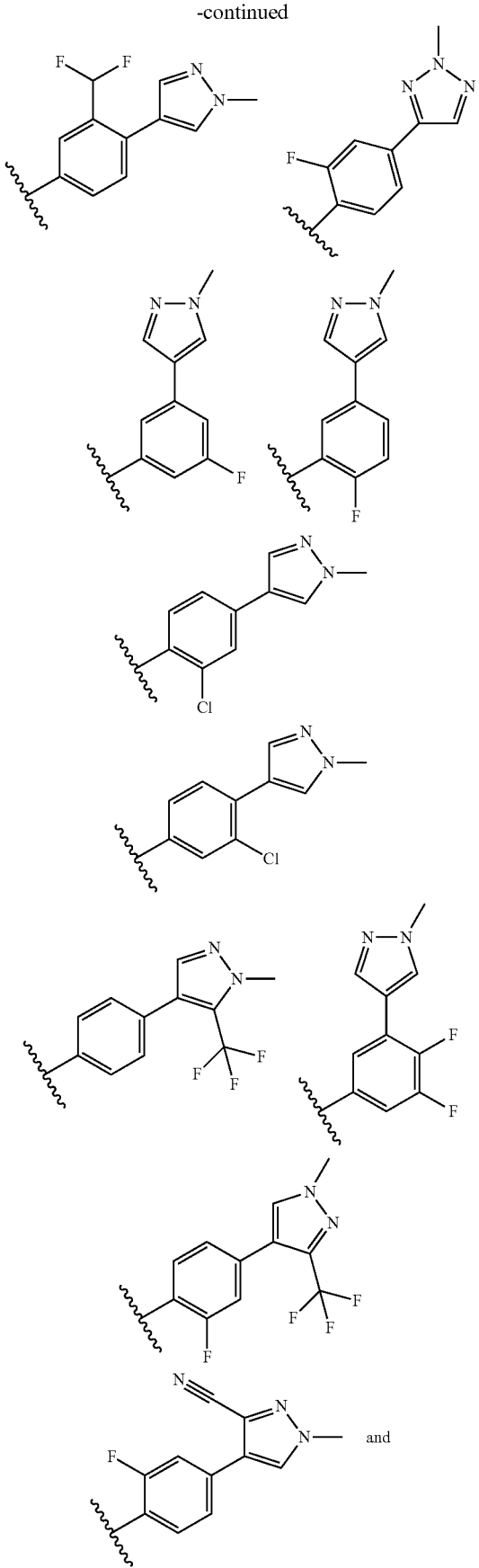

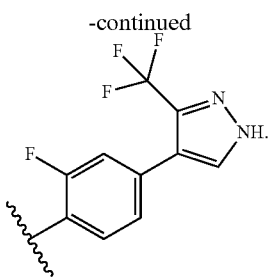

In certain embodiments of compounds of Formula (II), R¹ is phenyl-pyrazolyl, pyrazolyl, phenyl-triazolyl, indazolyl, phenyl-oxazolyl, phenyl, pyridyl-pyrazolyl, tetralinyl, pyridyl, 3,4-dihydroisoquinolin-1-one, phenyl-phenyl, phenyl-pyridyl, phenyl-isoxazolyl, phenyl-cyclohexenyl, phenyl-cyclohexyl, phenyl-thiazolyl, and phenyl-pyrimidinyl, wherein each phenyl, pyrazolyl, triazolyl, indazolyl, oxazolyl, pyridyl, tetralinyl, 3,4-dihydroisoquinolin-1-one, isoxazolyl, cyclohexenyl, cyclohexyl, thiazolyl, and pyrimidinyl is optionally substituted with one or more substituent groups independently selected from $R^c$, oxo, —F, —Cl, —Br, —N($R^a$)$_2$, —CN, —C(O)—N($R^a$)$_2$, —O—$R^a$, —C(O)—$R^a$ and —S(O)$_2$—$R^a$.

In certain embodiments of compounds of Formula (II), R² is $C_{1-12}$alkyl, $C_{2-12}$alkenyl, 3-12 membered carbocycle, or 3-12 membered heterocycle, wherein each $C_{1-12}$alkyl, $C_{2-12}$alkenyl, 3-12 membered carbocycle, and 3-12 membered heterocycle of R² is optionally substituted with one or more groups $R^b$.

In certain embodiments of compounds of Formula (II), R² is $C_{1-6}$alkyl, $C_{2-6}$alkenyl, 3-6 membered carbocycle, or 3-6 membered heterocycle, wherein each $C_{1-6}$alkyl, $C_{2-6}$alkenyl, 3-6 membered carbocycle, and 3-6 membered heterocycle of R² is optionally substituted with one or more groups $R^b$.

In certain embodiments of compounds of Formula (II), R² is methyl, ethyl, isopropyl, cyclopropylmethyl, 2-methoxyethyl, benzyl, N-methylacetamide, 2-pyridylmethyl, 3-pyridylmethyl, N-ethylacetamide, 4-pyridylmethyl, cyclopropyl, 1-phenylethyl, oxazol-5-ylmethyl, (1-methyl-3-piperidyl)methyl, propanamide, 2-hydroxyethyl, 3-hydroxypropyl, 2-hydroxy-1-methyl-ethyl, butanenitrile, propanenitrile, 2,2-difluorocyclopropylmethyl, (E)-pent-3-enyl, ethyl-2-acetate, 2-(3-piperidyl)ethyl, 2-(1-methyl-3-piperidyl)ethyl, 1-(1-methylpyrazol-3-yl)ethyl, 2,2,2-trifluoroethyl, 3,3,3-trifluoropropyl, 2-(methylsulfonyl)ethyl, 2-fluorocyclopropylmethyl, 1-methylcyclopropylmethyl, 2-phenylethyl, 3-propanamide, 2-propenyl, 2-(aminocarbonyl)ethyl, 2-cyanoethyl, N-ethylaminocarbonylmethyl, 2-(pyrid-2-yl)ethyl, 2-(pyrid-4-yl)ethyl, 3-methylphenyl, tetrahydrofuran-3-yl, oxetan-3-yl, oxetan-3-ylmethyl, or tetrahydropyran-4-yl.

In certain embodiments of compounds of Formula (II), R² is methyl, cyclopropylmethyl, 2,2,2-trifluoroethyl, 2,2-difluorocyclopropylmethyl, 2-(aminocarbonyl)ethyl, 3,3,3-trifluoropropyl, 2-(methylsulfonyl)ethyl, 2-fluorocyclopropylmethyl, 1-methylcyclopropylmethyl, 2-cyanoethyl, 2-methoxyethyl, oxazol-5-ylmethyl, N-ethylaminocarbonylmethyl, phenethyl, 2-(pyrid-2-yl)ethyl, 2-(pyrid-4-yl)ethyl, tetrahydrofuran-3-yl, oxetan-3-yl, oxetan-3-ylmethyl, or tetrahydropyran-4-yl.

In certain embodiments of compounds of Formula (II), R² is methyl, cyclopropylmethyl, tetrahydrofuran-3-yl, oxetan-3-yl, oxetan-3-ylmethyl, or tetrahydropyran-4-yl.

In certain embodiments of compounds of Formula (II), R¹ is phenyl-pyrazolyl, pyrazolyl, phenyl-triazolyl, indazolyl, phenyl-oxazolyl, phenyl, pyridyl-pyrazolyl, tetralinyl, pyridyl, 3,4-dihydroisoquinolin-1-one, phenyl-phenyl, phenyl-pyridyl, phenyl-isoxazolyl, phenyl-cyclohexenyl, phenyl-cyclohexyl, phenyl-thiazolyl, and phenyl-pyrimidinyl, wherein each phenyl, pyrazolyl, triazolyl, indazolyl, oxazolyl, pyridyl, tetralinyl, 3,4-dihydroisoquinolin-1-one, isoxazolyl, cyclohexenyl, cyclohexyl, thiazolyl, and pyrimidinyl is optionally substituted with one or more substituent groups independently selected from $R^c$, oxo, —F, —Cl, —Br, —N($R^a$)$_2$, —CN, —C(O)—N($R^a$)$_2$, —O—$R^a$, —C(O)—$R^a$ and —S(O)$_2$—$R^a$ and R² is methyl, ethyl, isopropyl, cyclopropylmethyl, 2-methoxyethyl, benzyl, N-methylacetamide, 2-pyridylmethyl, 3-pyridylmethyl, N-ethylacetamide, 4-pyridylmethyl, cyclopropyl, 1-phenylethyl, oxazol-5-ylmethyl, (1-methyl-3-piperidyl)methyl, propanamide, 2-hydroxyethyl, 3-hydroxypropyl, 2-hydroxy-1-methyl-ethyl, butanenitrile, propanenitrile, 2,2-difluorocyclopropylmethyl, (E)-pent-3-enyl, ethyl-2-acetate, 2-(3-piperidyl)ethyl, 2-(1-methyl-3-piperidyl)ethyl, 1-(1-methylpyrazol-3-yl)ethyl, 2,2,2-trifluoroethyl, 3,3,3-trifluoropropyl, 2-(methylsulfonyl)ethyl, 2-fluorocyclopropylmethyl, 1-methylcyclopropylmethyl, 2-phenylethyl, 3-propanamide, 2-propenyl, 2-(aminocarbonyl)ethyl, 2-cyanoethyl, N-ethylaminocarbonylmethyl, 2-(pyrid-2-yl)ethyl, 2-(pyrid-4-yl)ethyl, 3-methylphenyl, tetrahydrofuran-3-yl, oxetan-3-yl, oxetan-3-ylmethyl, or tetrahydropyran-4-yl.

In certain embodiments of compounds of Formula (II), R¹ is phenyl-pyrazolyl, pyrazolyl, phenyl-triazolyl, indazolyl, phenyl-oxazolyl, phenyl, pyridyl-pyrazolyl, tetralinyl, pyridyl, 3,4-dihydroisoquinolin-1-one, phenyl-phenyl, phenyl-pyridyl, phenyl-isoxazolyl, phenyl-cyclohexenyl, phenyl-cyclohexyl, phenyl-thiazolyl, and phenyl-pyrimidinyl, wherein each phenyl, pyrazolyl, triazolyl, indazolyl, oxazolyl, pyridyl, tetralinyl, 3,4-dihydroisoquinolin-1-one, isoxazolyl, cyclohexenyl, cyclohexyl, thiazolyl, and pyrimidinyl is optionally substituted with one or more substituent groups independently selected from $R^c$, oxo, —F, —Cl, —Br, —N($R^a$)$_2$, —CN, —C(O)—N($R^a$)$_2$, —O—$R^a$, —C(O)—$R^a$ and —S(O)$_2$—$R^a$ and R² is methyl, cyclopropylmethyl, 2,2,2-trifluoroethyl, 2,2-difluorocyclopropylmethyl, 2-(aminocarbonyl)ethyl, 3,3,3-trifluoropropyl, 2-(methylsulfonyl)ethyl, 2-fluorocyclopropylmethyl, 1-methylcyclopropylmethyl, 2-cyanoethyl, 2-methoxyethyl, oxazol-5-ylmethyl, N-ethylaminocarbonylmethyl, phenethyl, 2-(pyrid-2-yl)ethyl, 2-(pyrid-4-yl)ethyl, tetrahydrofuran-3-yl, oxetan-3-yl, oxetan-3-ylmethyl, or tetrahydropyran-4-yl.

In certain embodiments of compounds of Formula (II), R¹ is phenyl-pyrazolyl, pyrazolyl, phenyl-triazolyl, indazolyl, phenyl-oxazolyl, phenyl, pyridyl-pyrazolyl, tetralinyl, pyridyl, 3,4-dihydroisoquinolin-1-one, phenyl-phenyl, phenyl-pyridyl, phenyl-isoxazolyl, phenyl-cyclohexenyl, phenyl-cyclohexyl, phenyl-thiazolyl, and phenyl-pyrimidinyl, wherein each phenyl, pyrazolyl, triazolyl, indazolyl, oxazolyl, pyridyl, tetralinyl, 3,4-dihydroisoquinolin-1-one, isoxazolyl, cyclohexenyl, cyclohexyl, thiazolyl, and pyrimidinyl is optionally substituted with one or more substituent groups independently selected from $R^c$, oxo, —F, —Cl, —Br, —N($R^a$)$_2$, —CN, —C(O)—N($R^a$)$_2$, —O—$R^a$, —C(O)—$R^a$ and —S(O)$_2$—$R^a$ and R¹ is methyl, cyclopropylmethyl, tetrahydrofuran-3-yl, oxetan-3-yl, oxetan-3-ylmethyl, or tetrahydropyran-4-yl.

In certain embodiments of compounds of Formula (II), R² is:

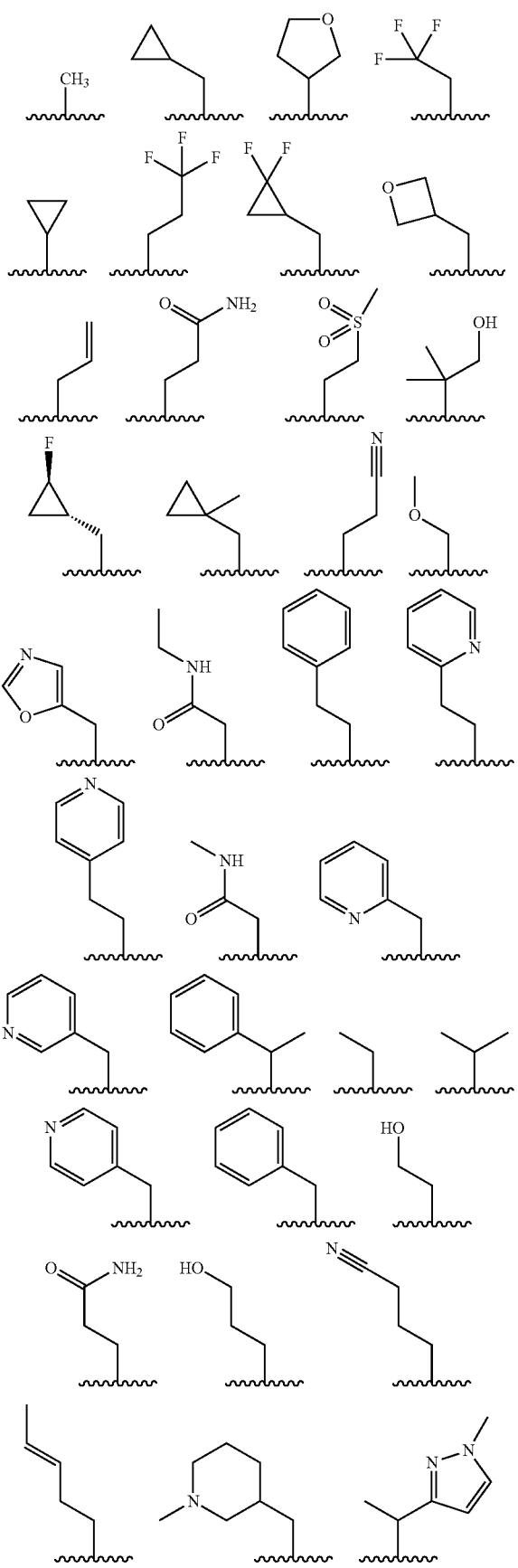

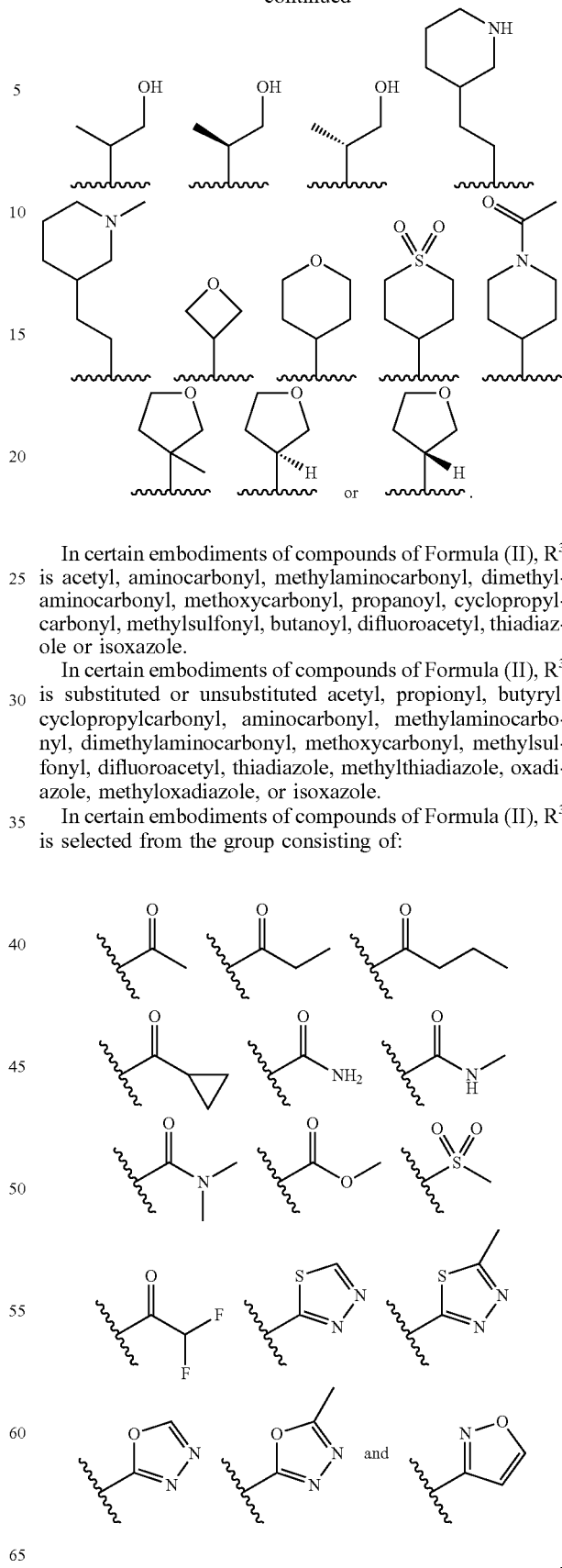

In certain embodiments of compounds of Formula (II), $R^3$ is acetyl, aminocarbonyl, methylaminocarbonyl, dimethylaminocarbonyl, methoxycarbonyl, propanoyl, cyclopropylcarbonyl, methylsulfonyl, butanoyl, difluoroacetyl, thiadiazole or isoxazole.

In certain embodiments of compounds of Formula (II), $R^3$ is substituted or unsubstituted acetyl, propionyl, butyryl, cyclopropylcarbonyl, aminocarbonyl, methylaminocarbonyl, dimethylaminocarbonyl, methoxycarbonyl, methylsulfonyl, difluoroacetyl, thiadiazole, methylthiadiazole, oxadiazole, methyloxadiazole, or isoxazole.

In certain embodiments of compounds of Formula (II), $R^3$ is selected from the group consisting of:

In certain embodiments of compounds of Formula (II), $R^3$ is selected from the group consisting of:

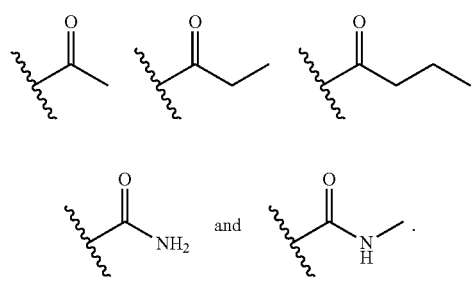
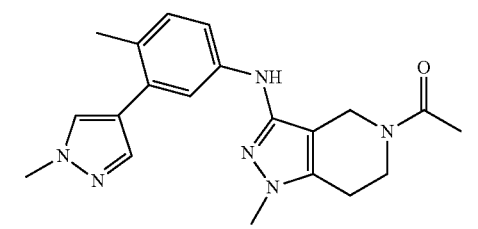
In certain embodiments the compound of Formula (II) is selected from the group consisting of:
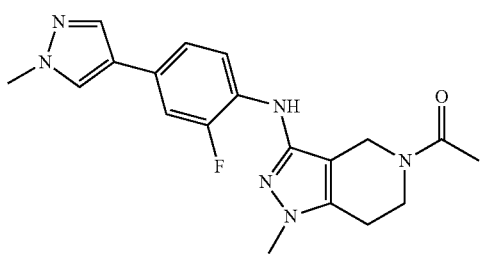
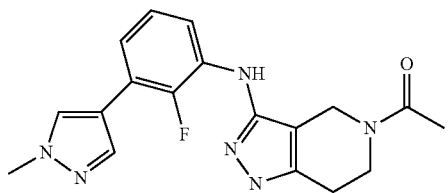
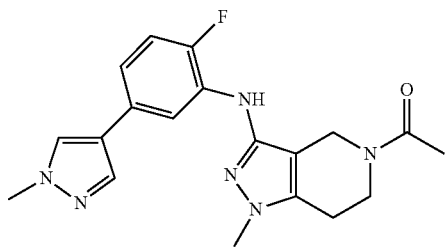
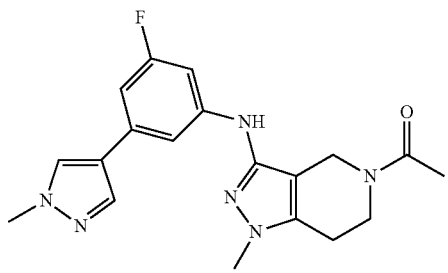
-continued
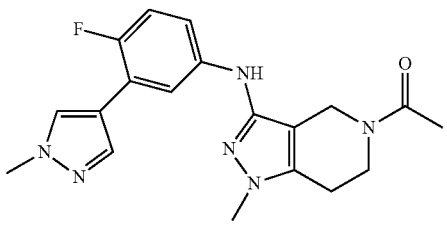
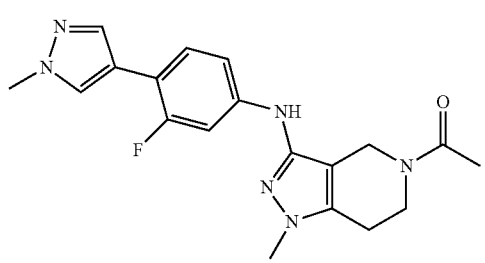
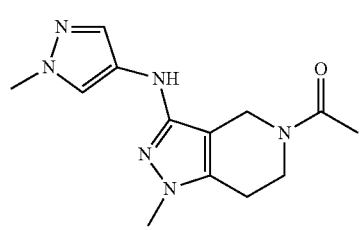
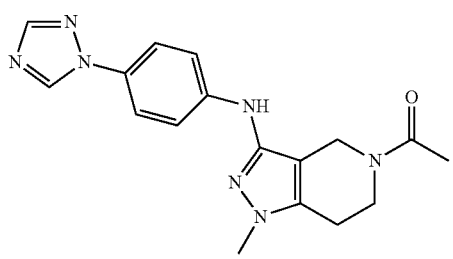
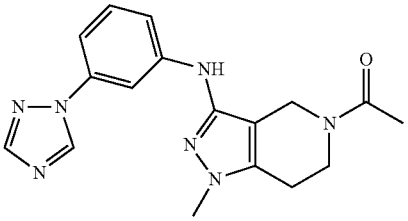
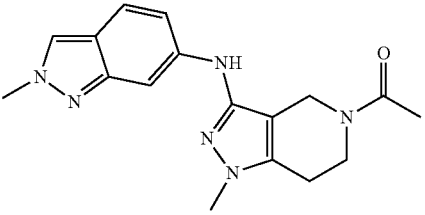
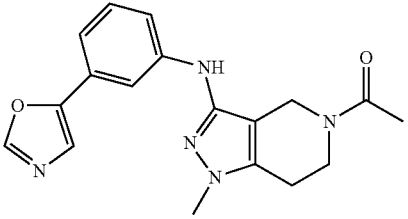

211
-continued
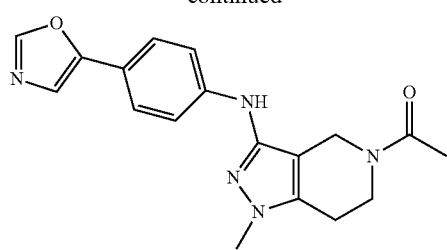
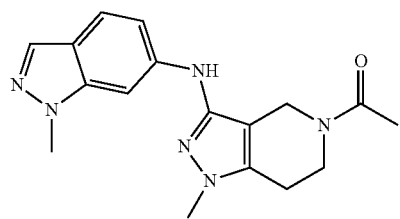
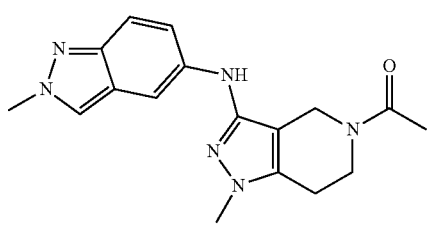
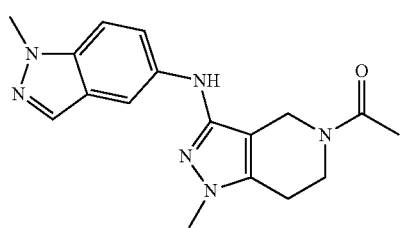
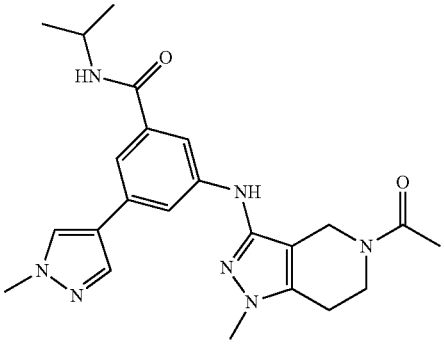
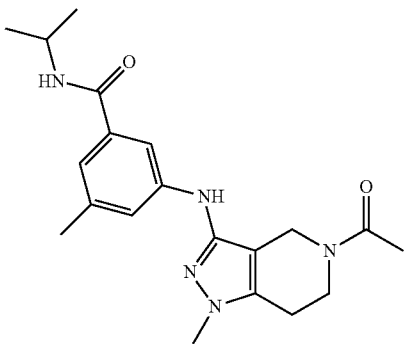
212
-continued
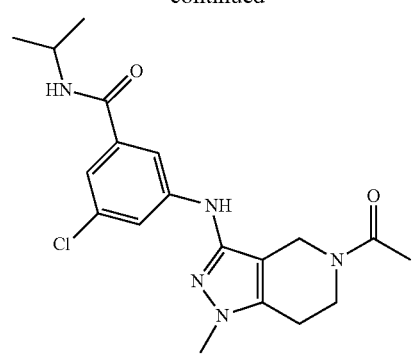
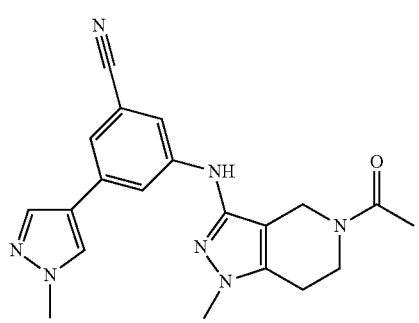
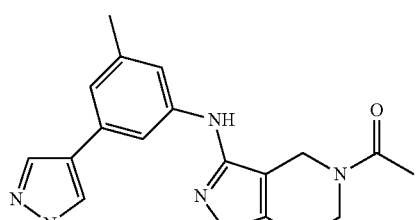
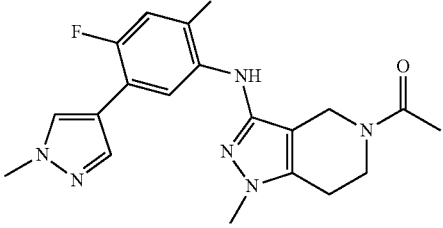
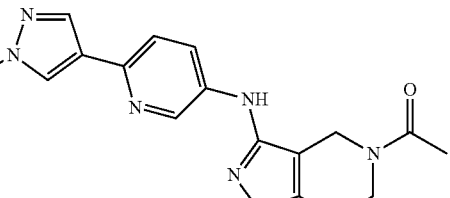
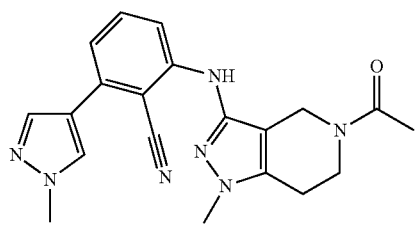

213
-continued
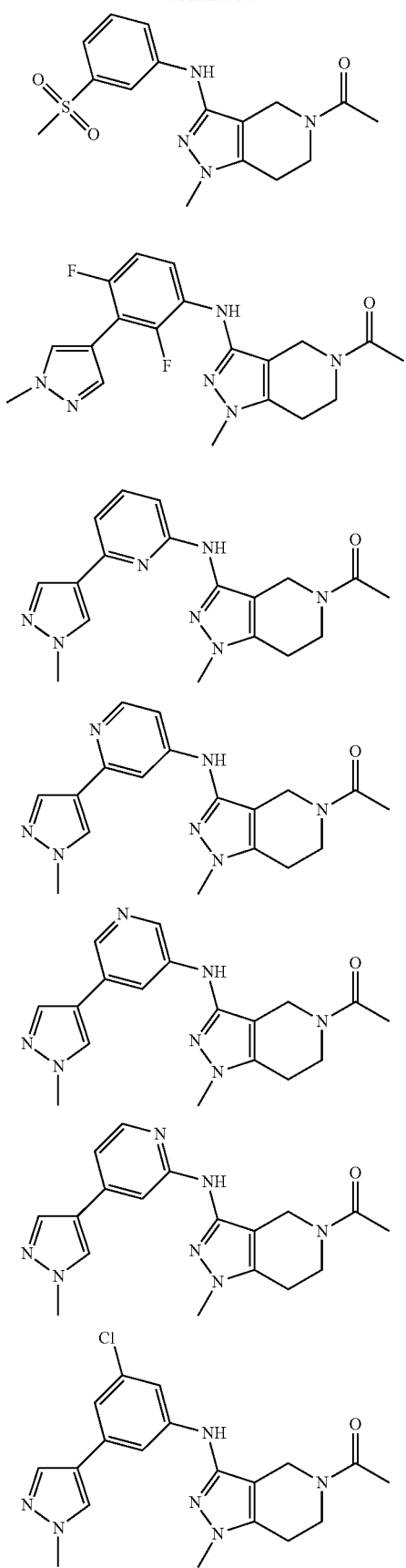
214
-continued
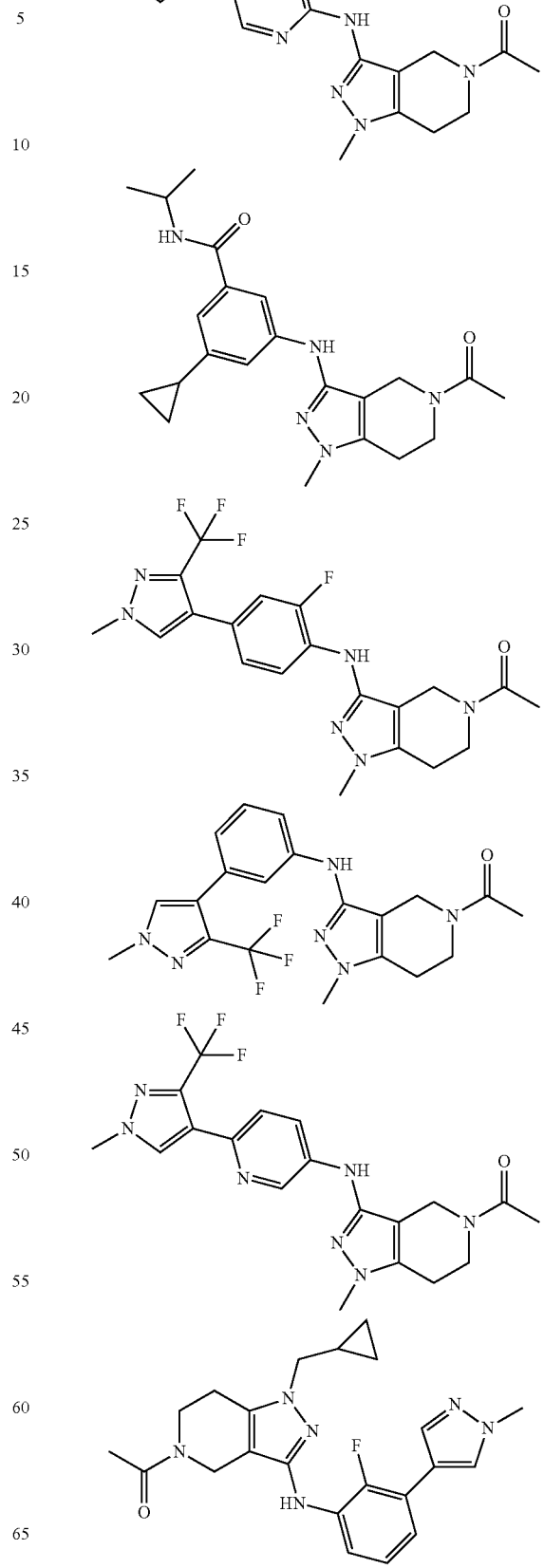

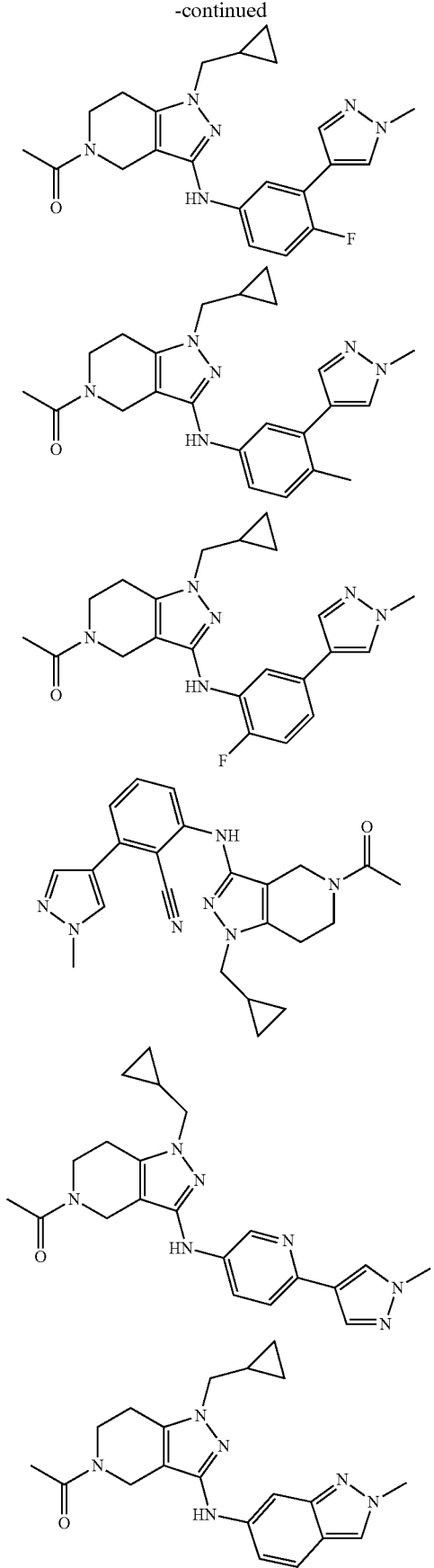
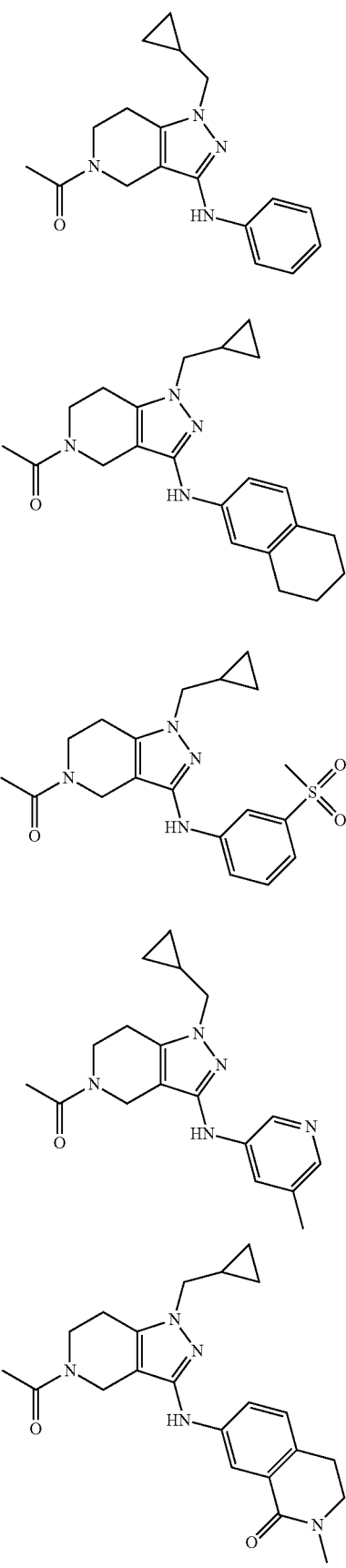

217
-continued
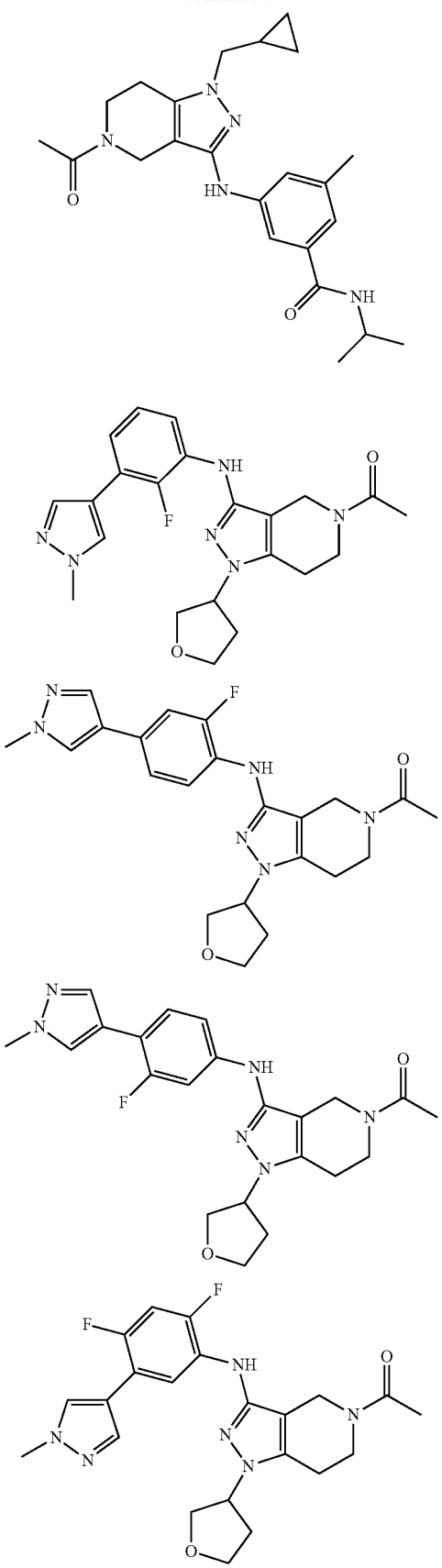
218
-continued
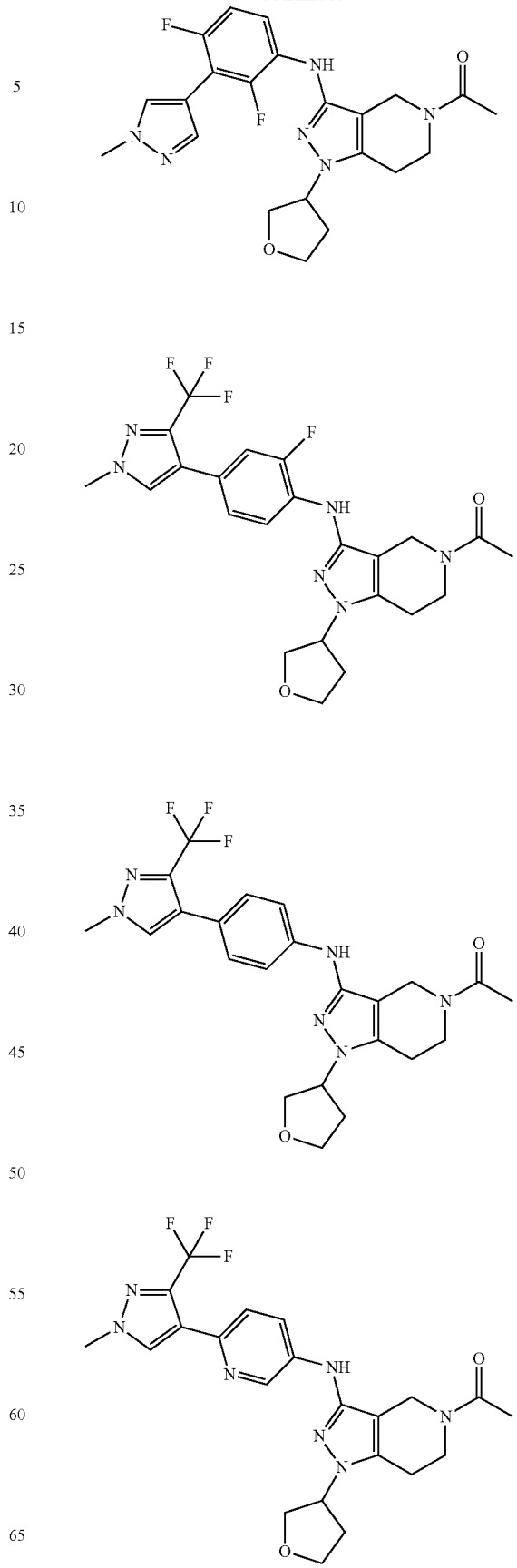

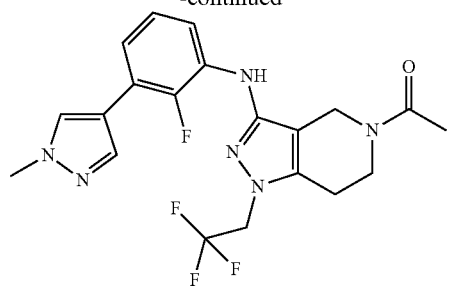
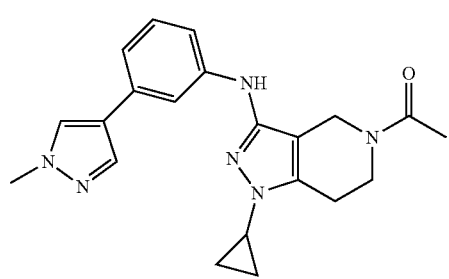
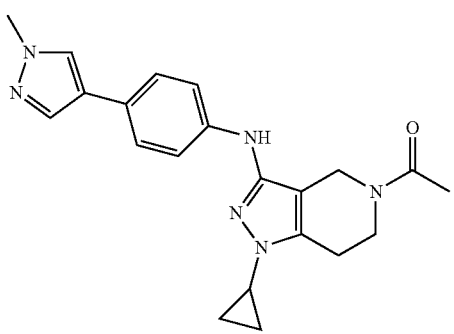

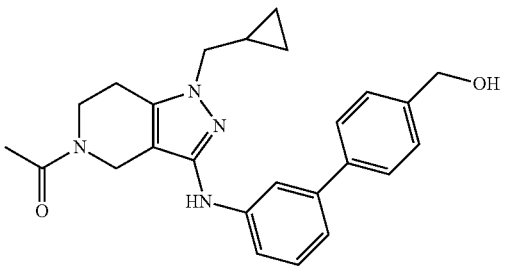
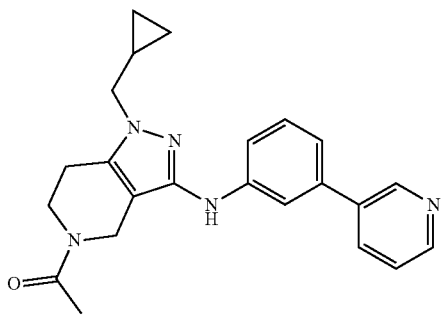
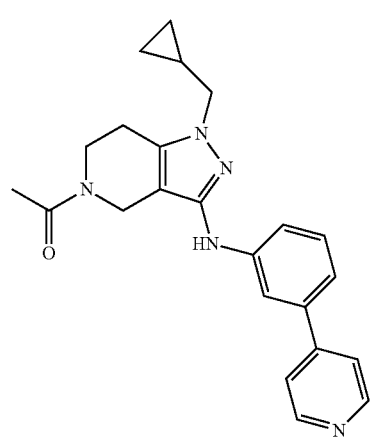
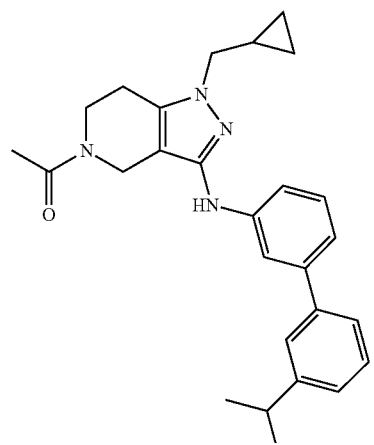
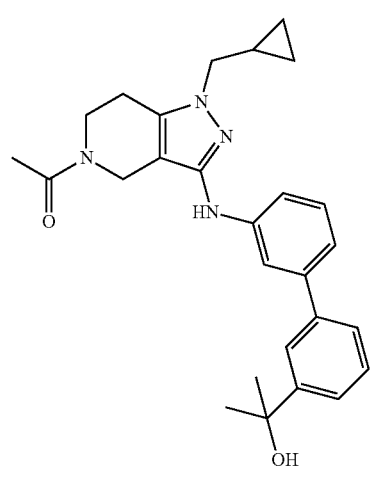

221
-continued
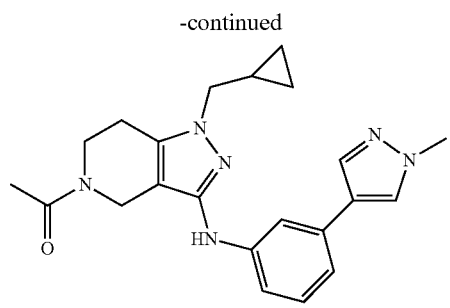
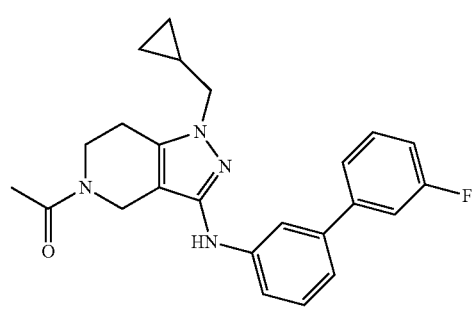
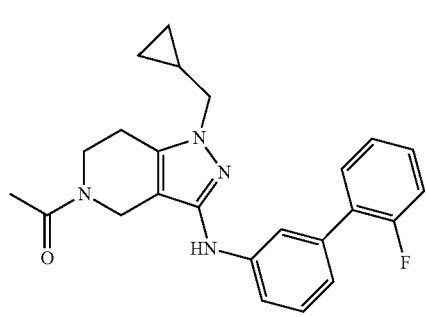
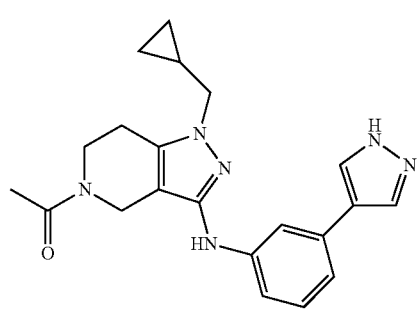
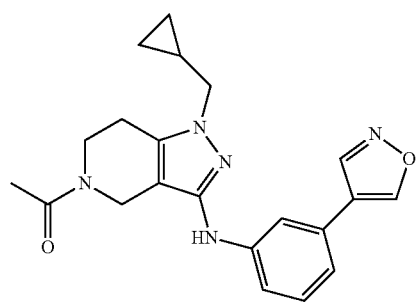
222
-continued
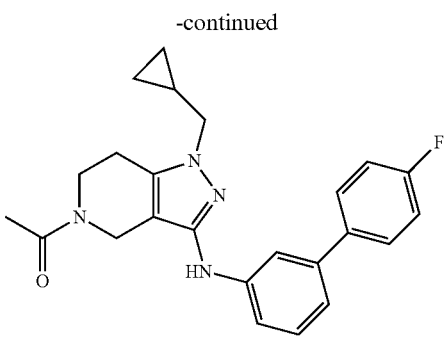
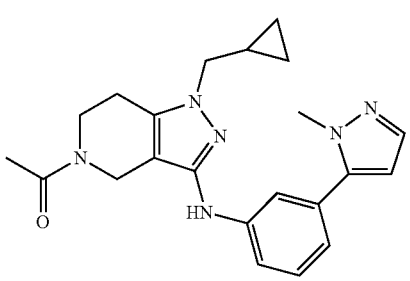
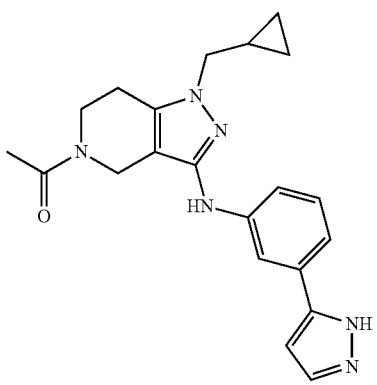
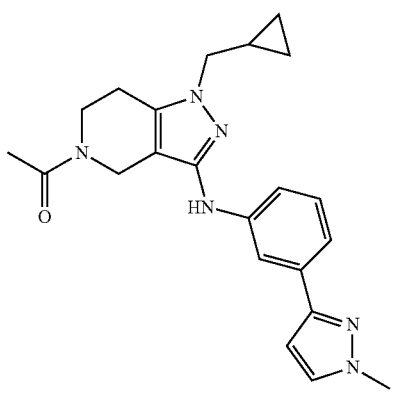

223
-continued
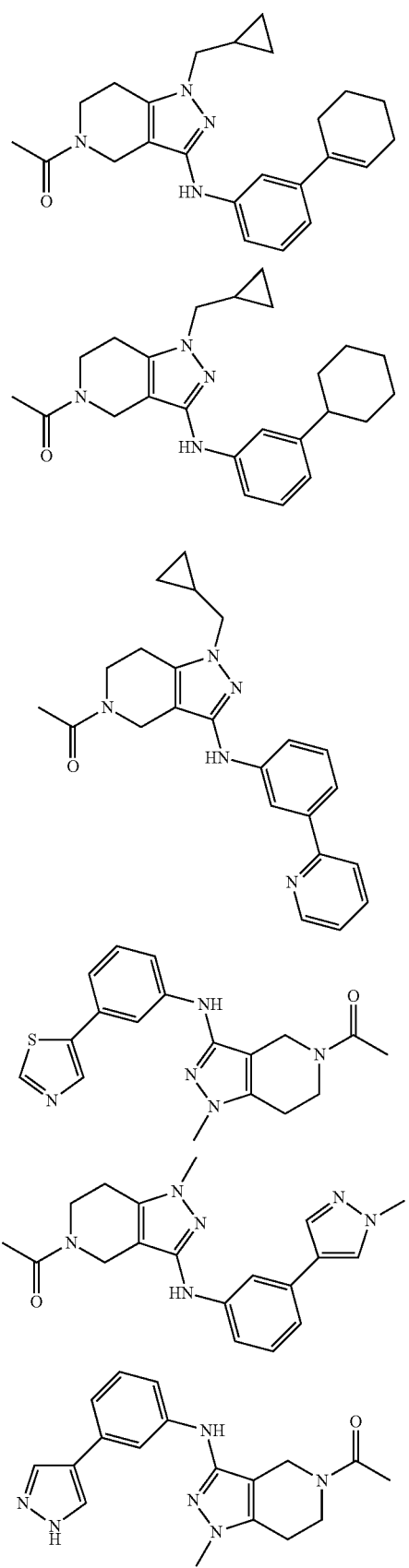
224
-continued
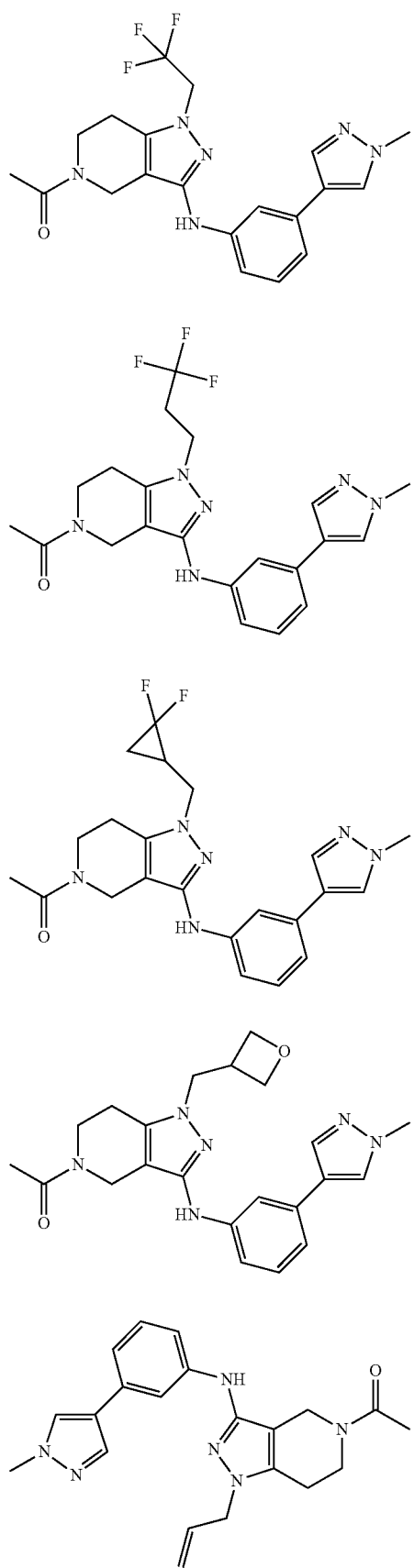

225
-continued
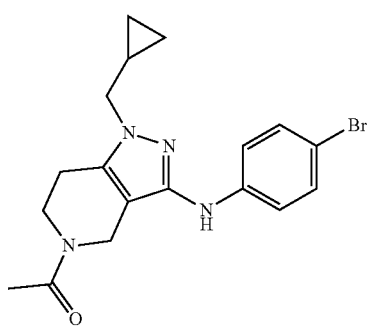
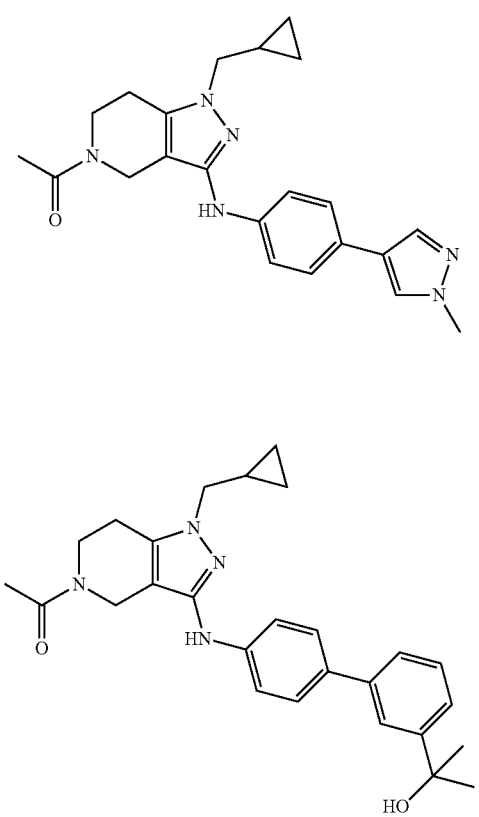
226
-continued
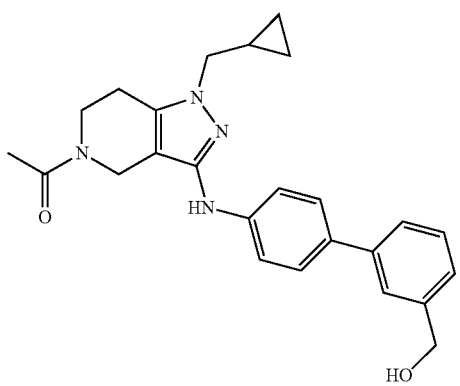
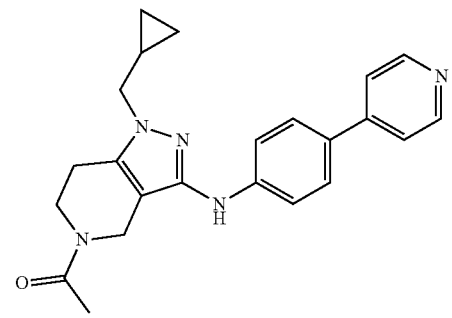
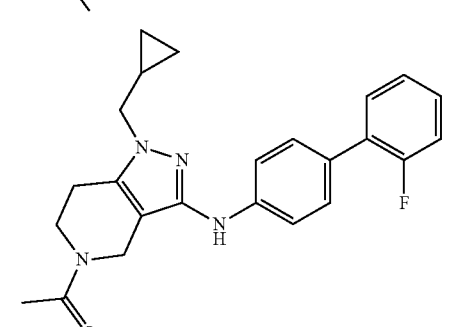
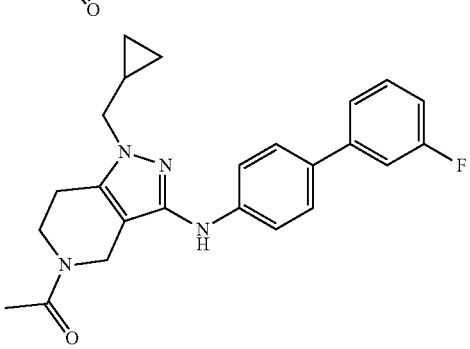
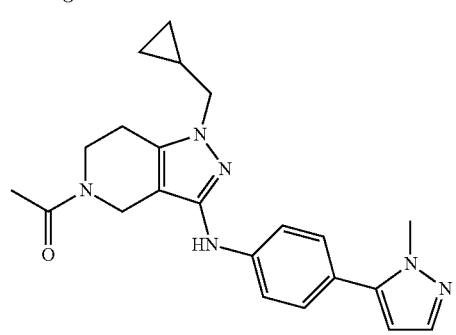

227
-continued
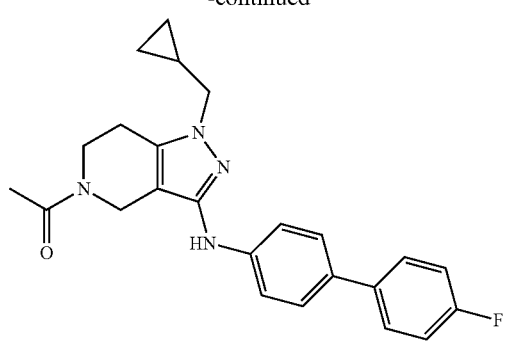
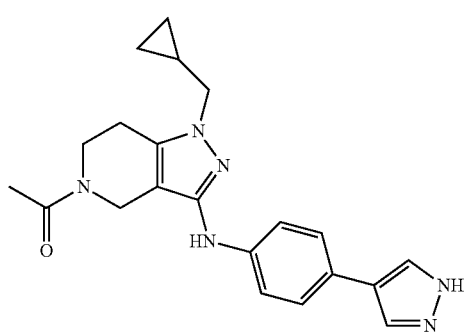
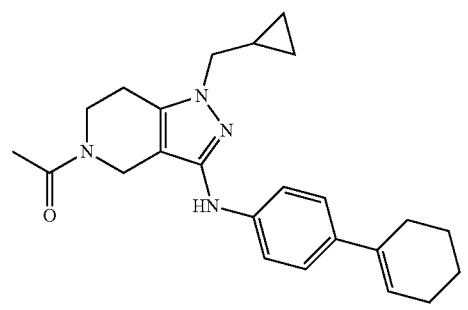
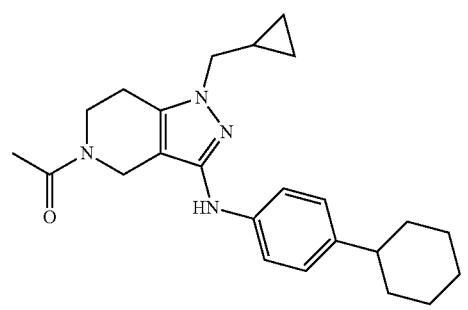
228
-continued
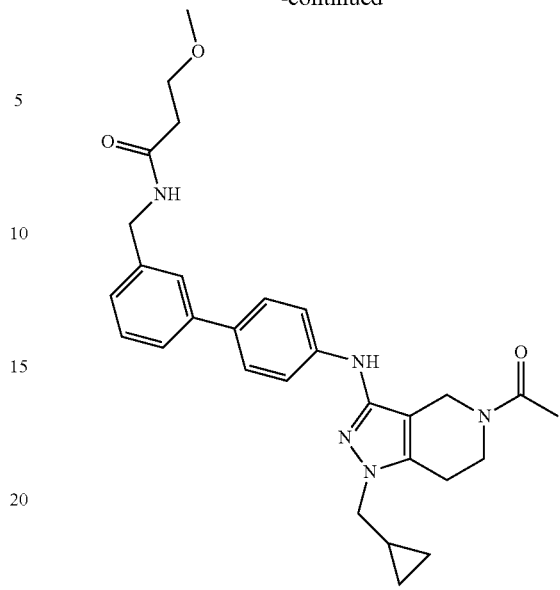
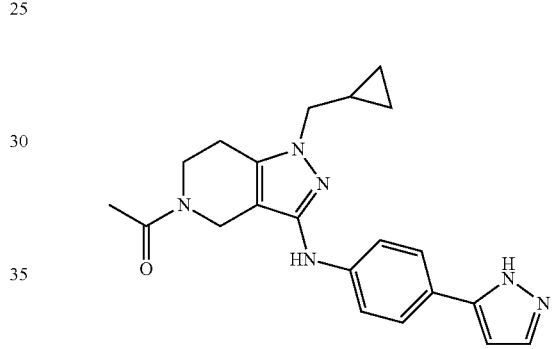
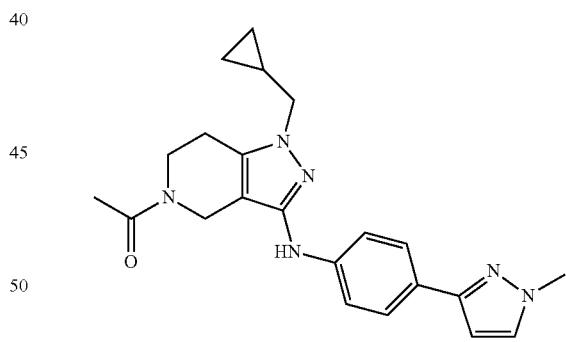
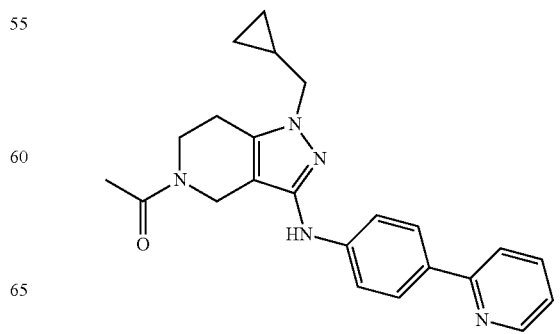

229
-continued
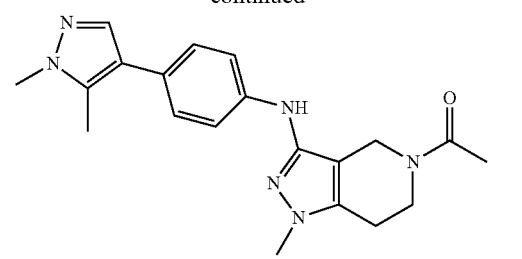
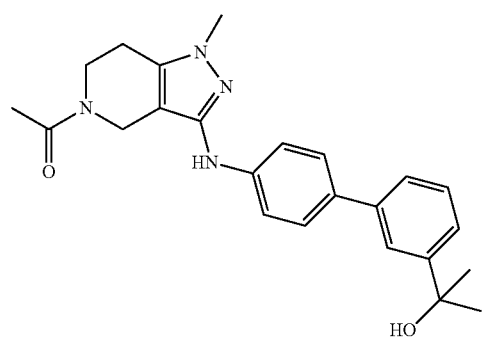
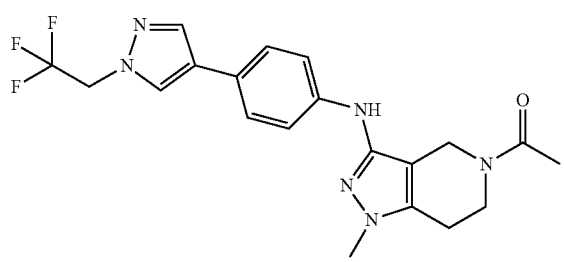
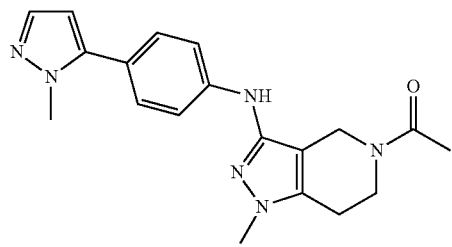
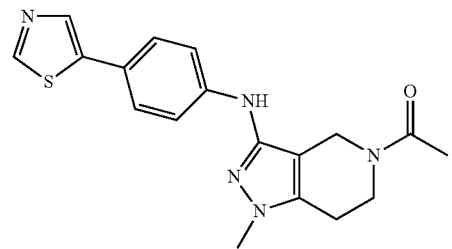
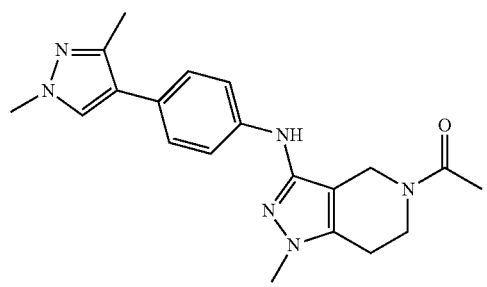
230
-continued
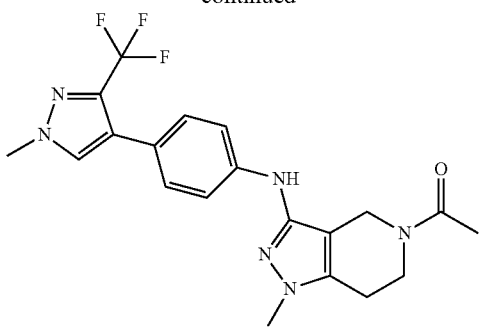
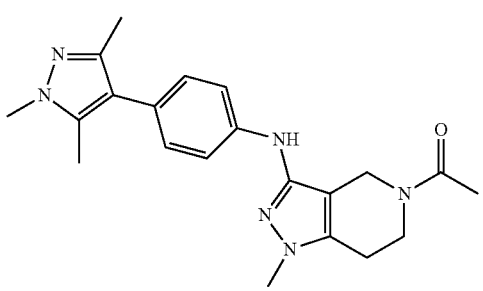
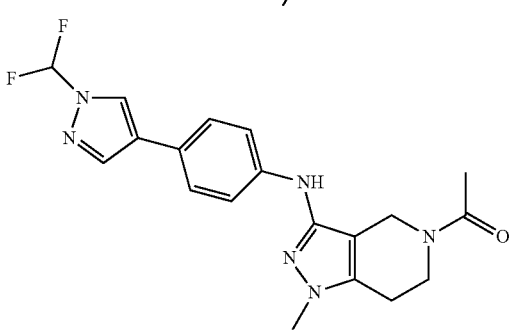
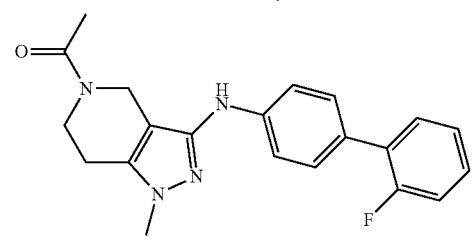
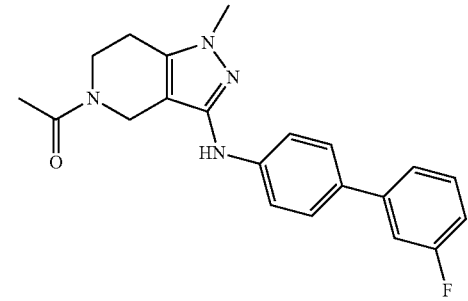
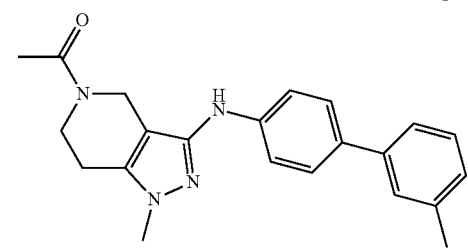

231
-continued
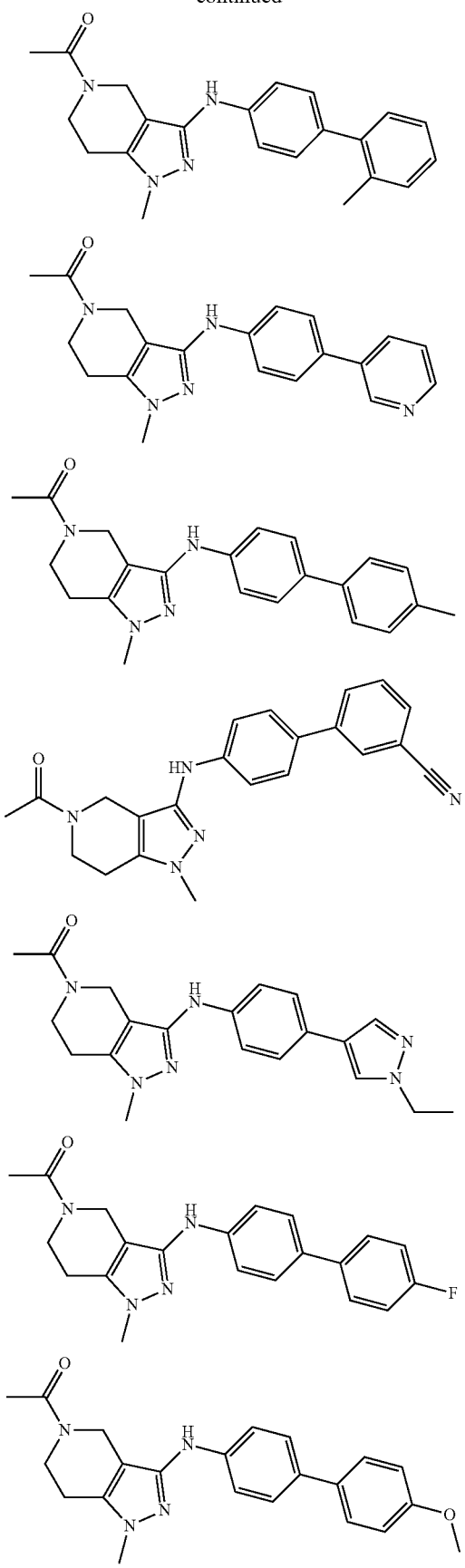
232
-continued
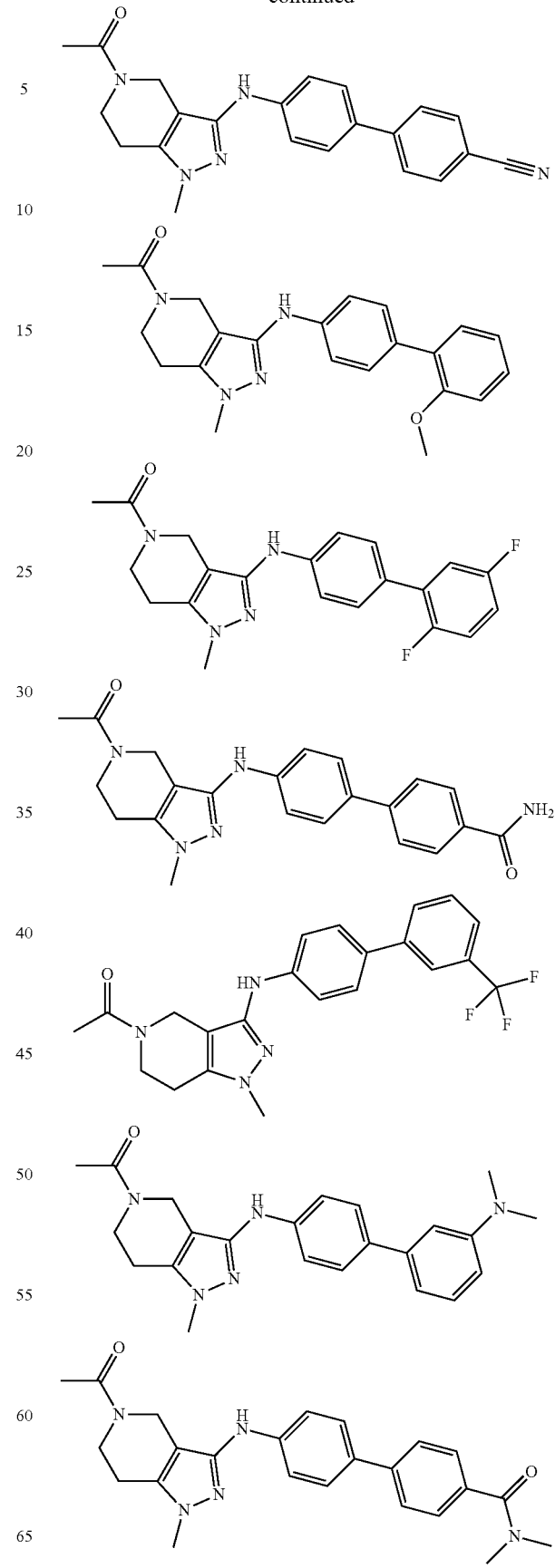

233
-continued
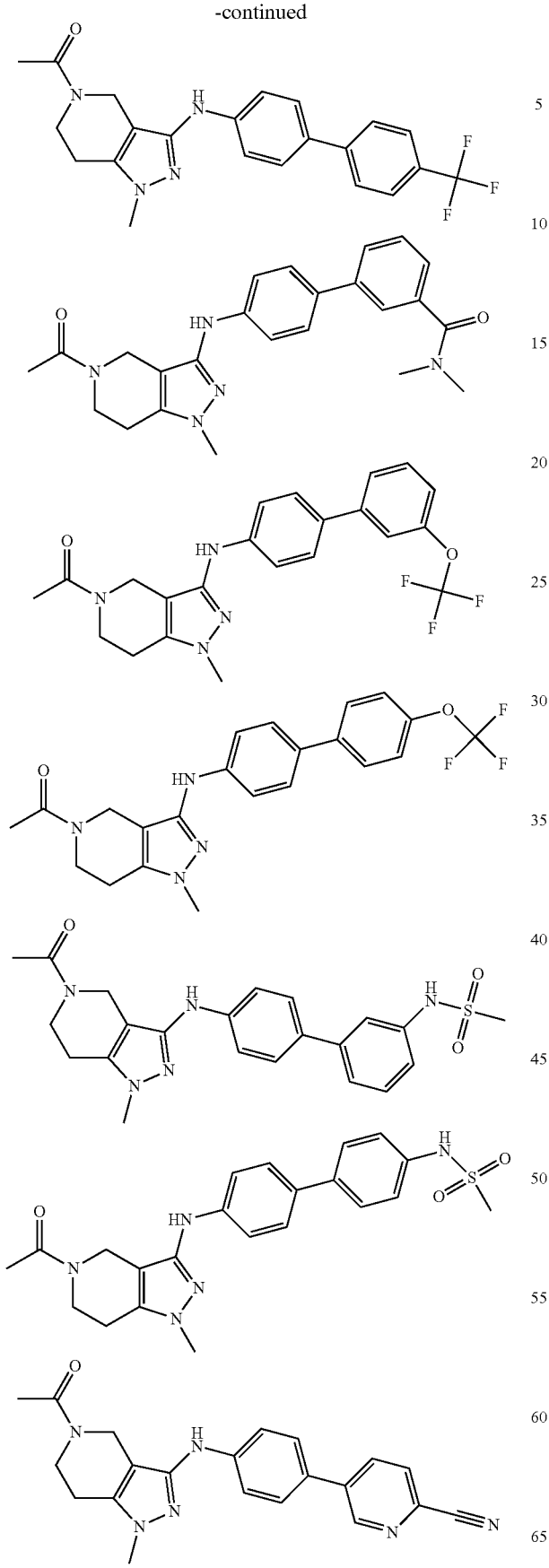
234
-continued
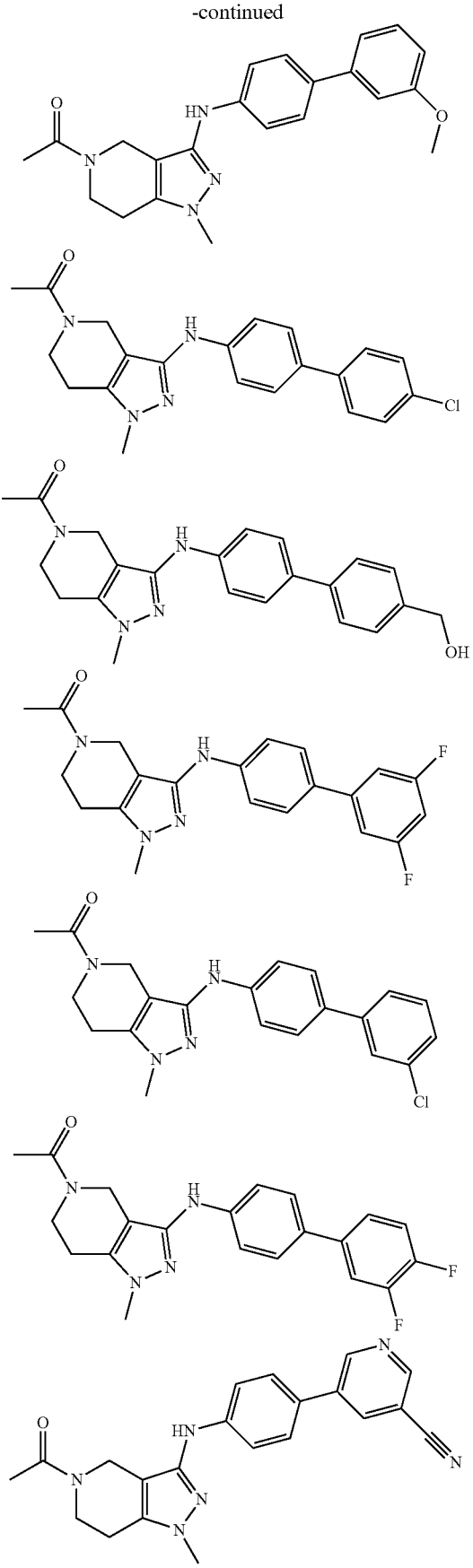

235
-continued
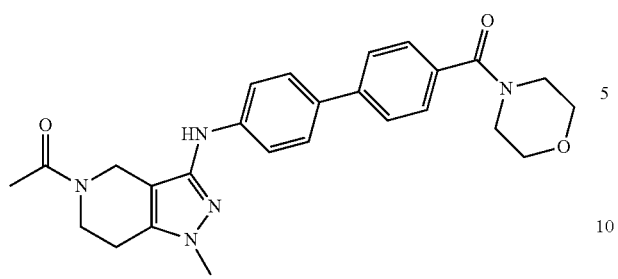

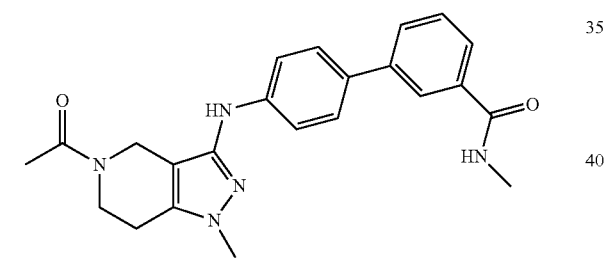
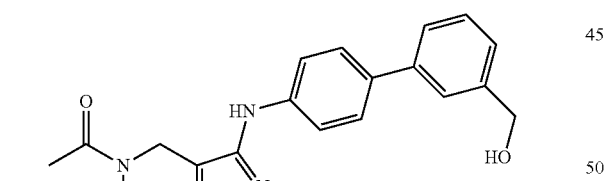
236
-continued
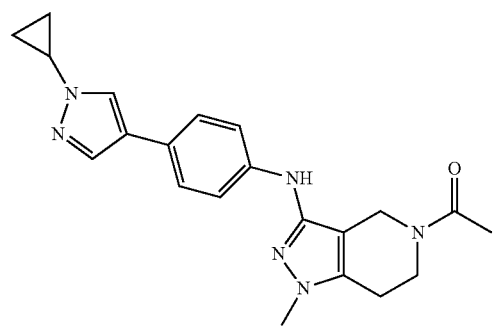
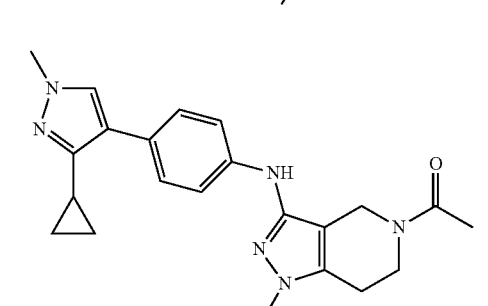
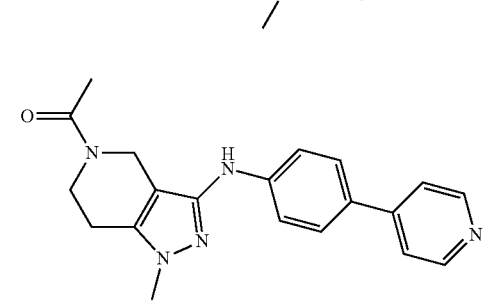
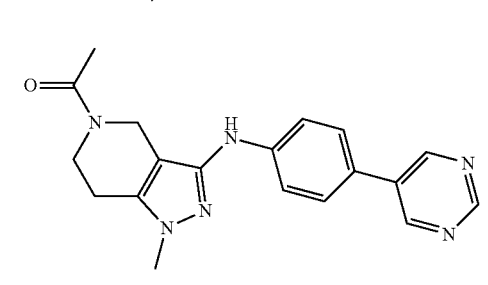

237
-continued
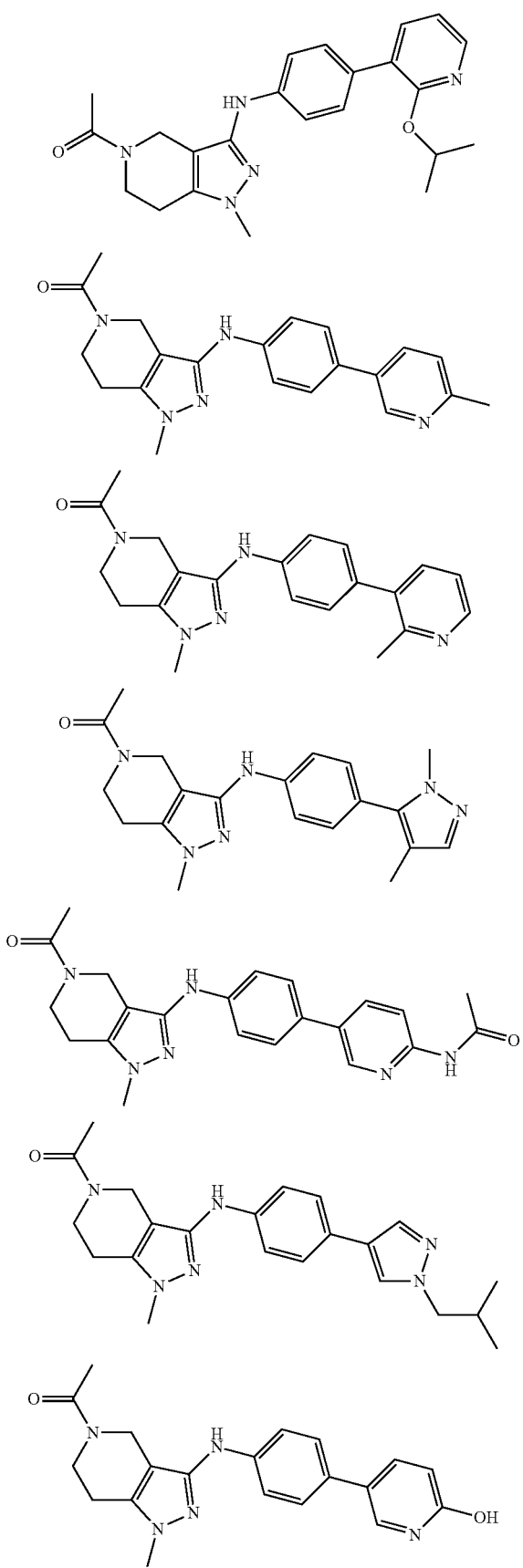
238
-continued
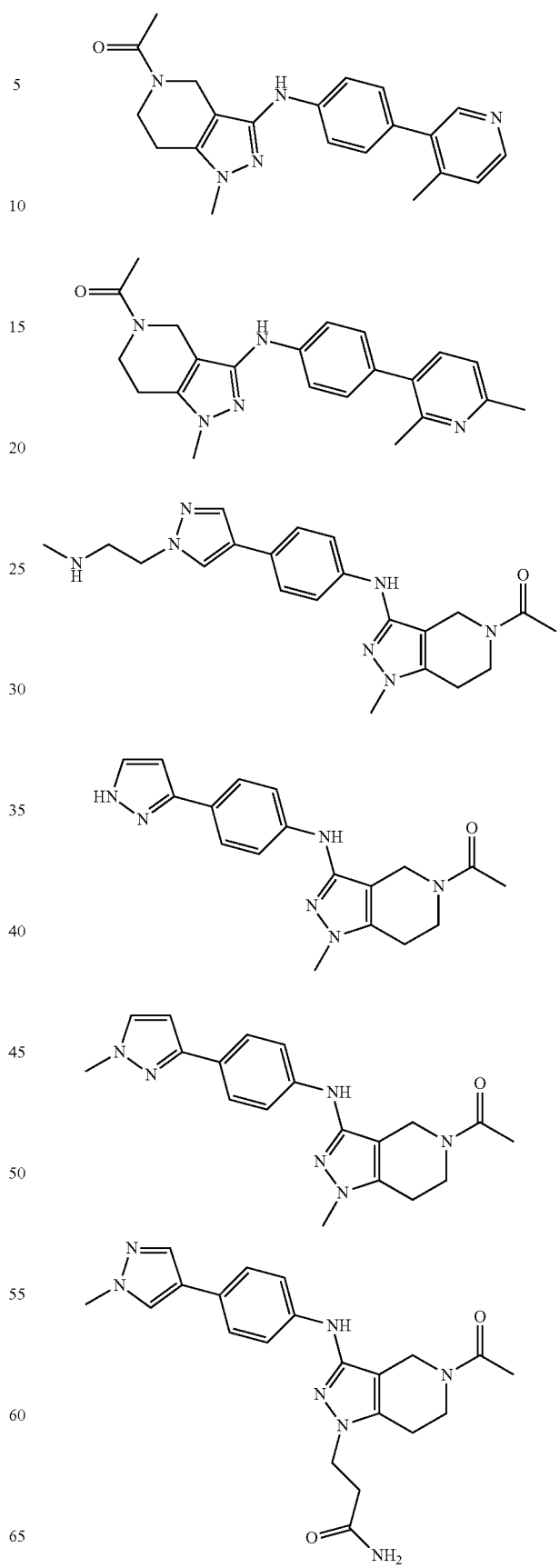

239
-continued
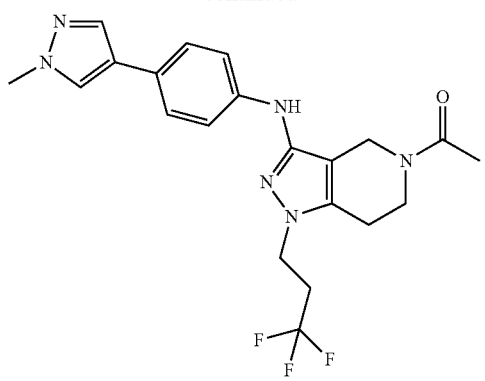
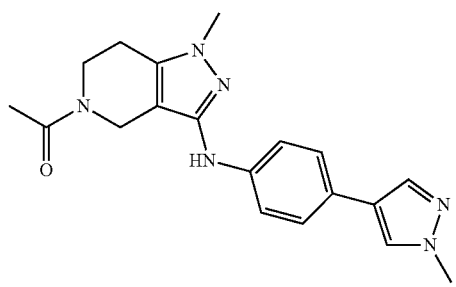
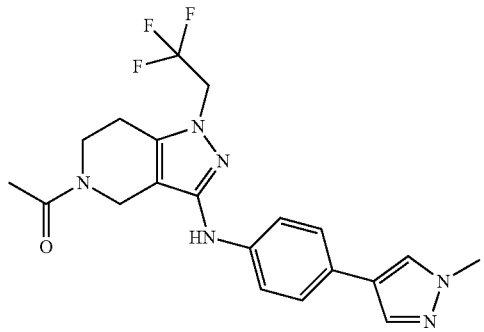
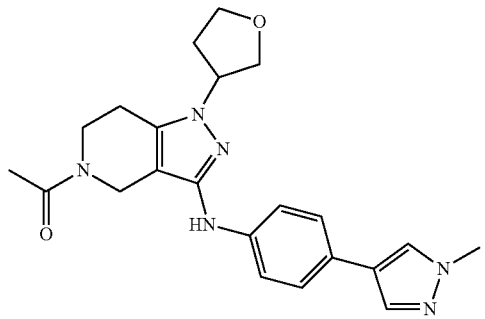
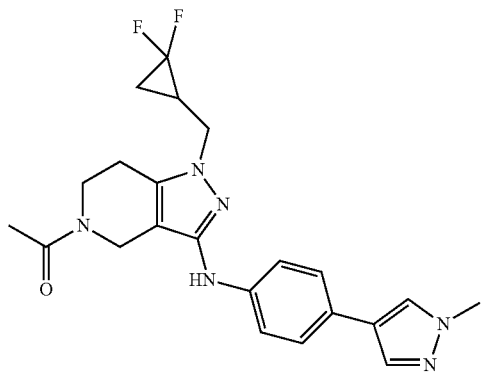
240
-continued
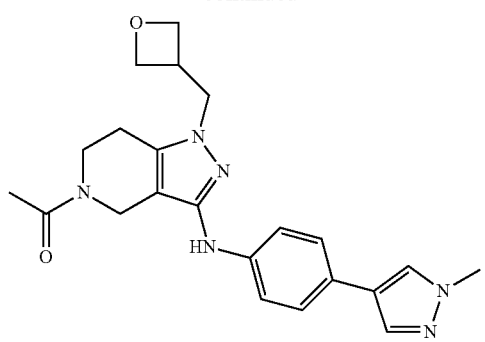
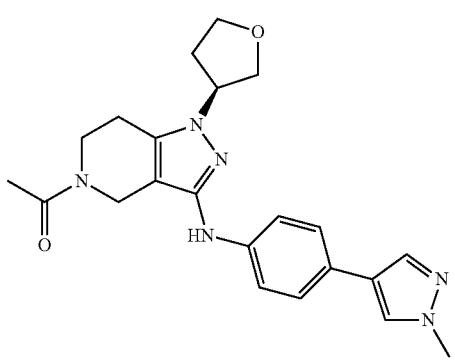
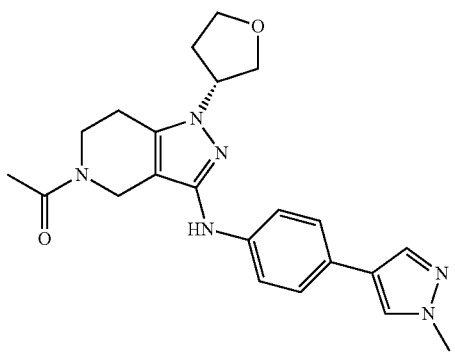
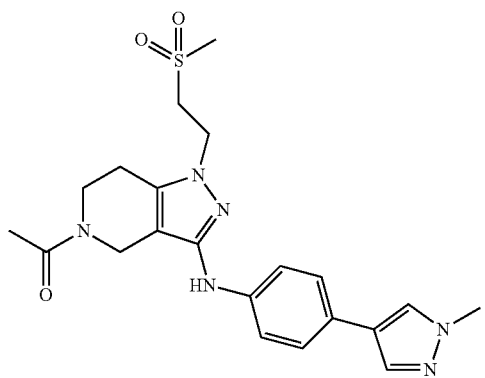

241
-continued
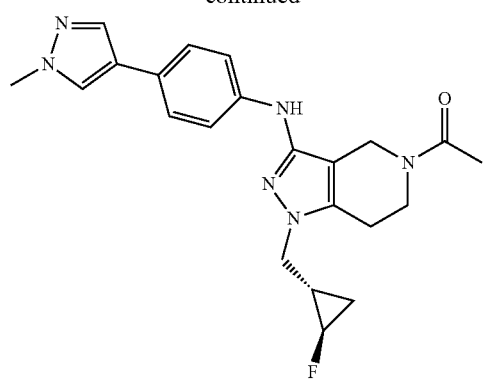
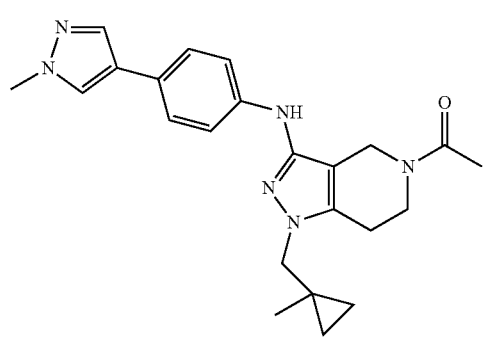
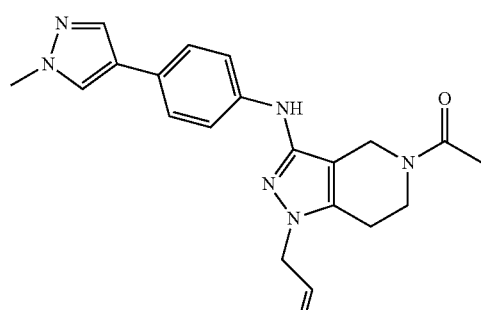
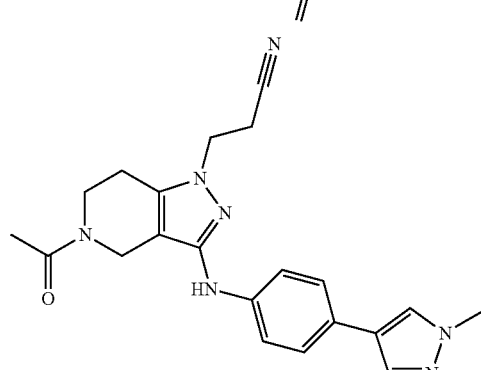
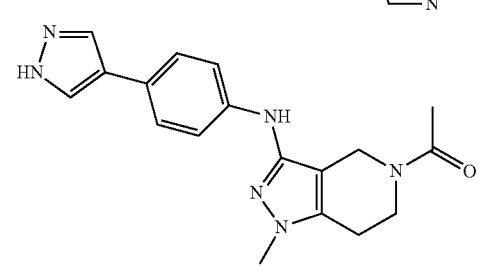
242
-continued
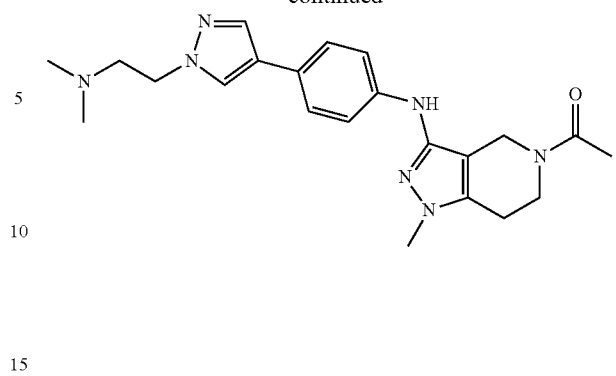
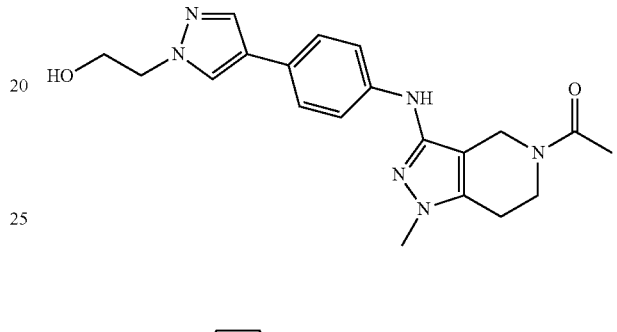
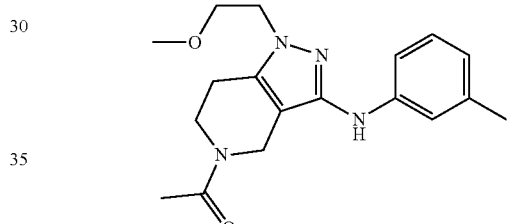
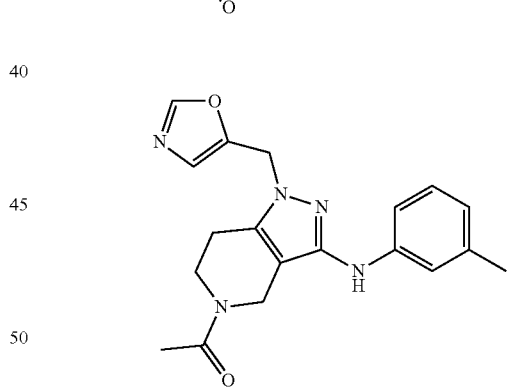
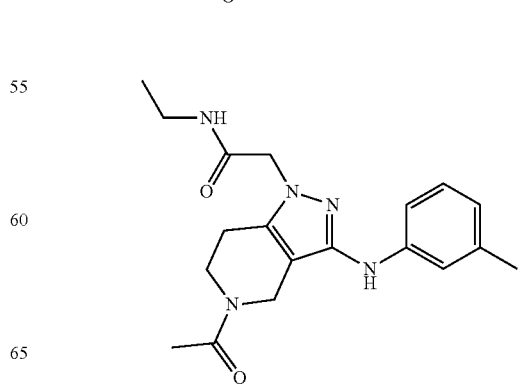

243
-continued
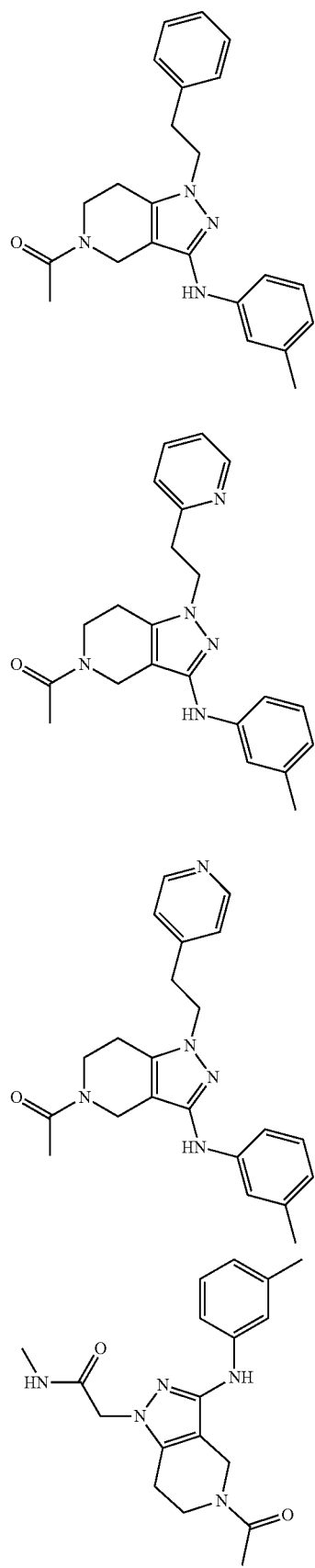
244
-continued
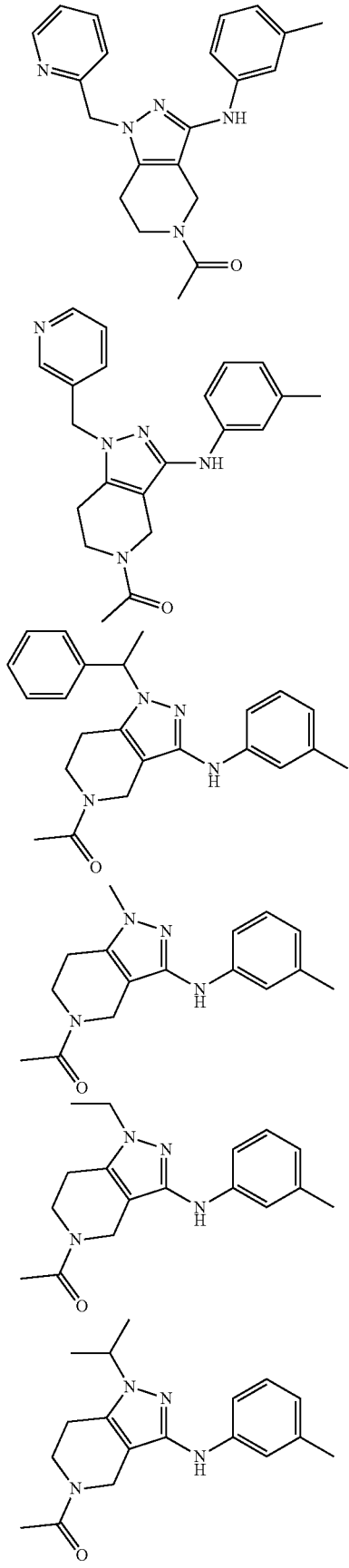

245
-continued
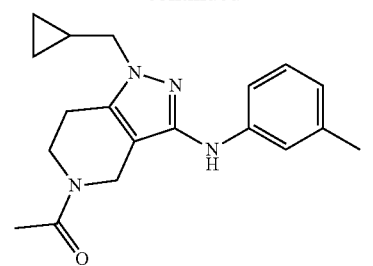
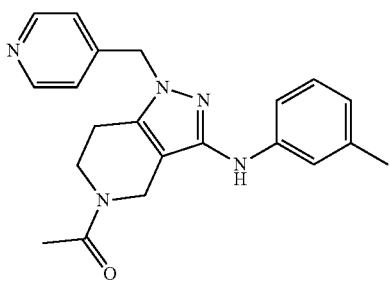
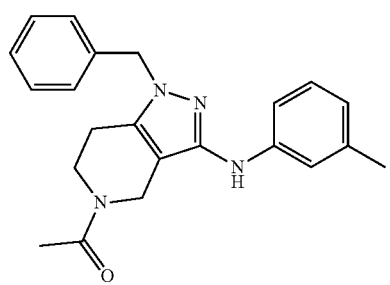
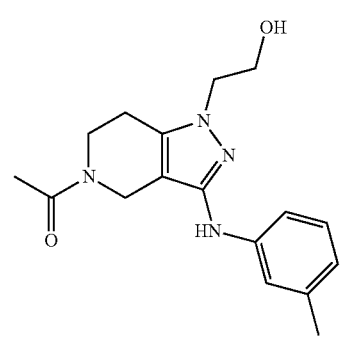
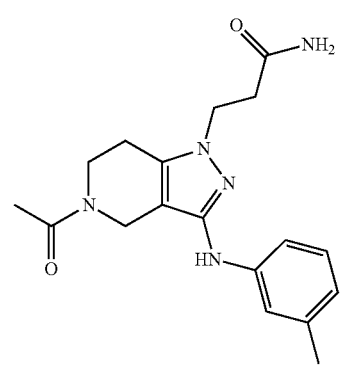
246
-continued
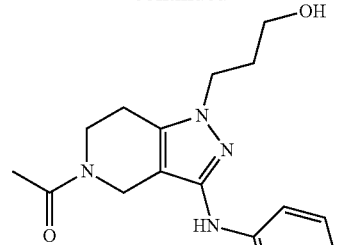
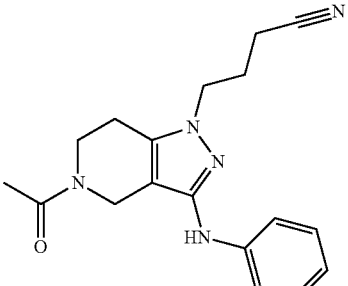
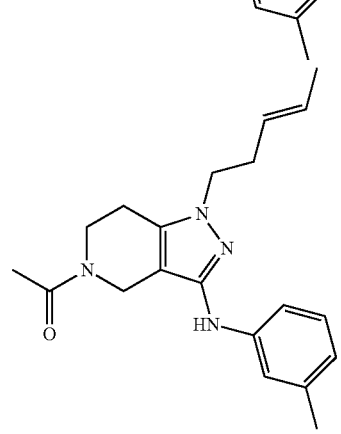
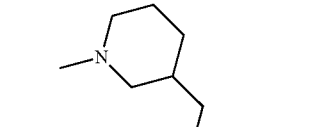
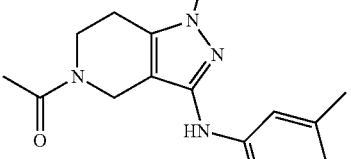
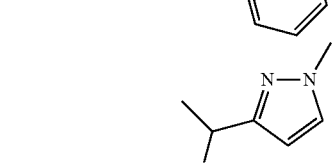

247
-continued
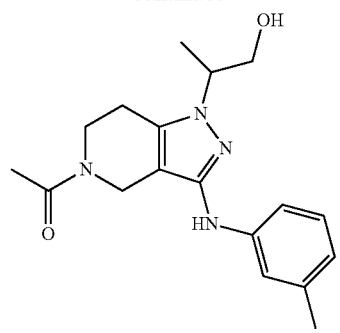
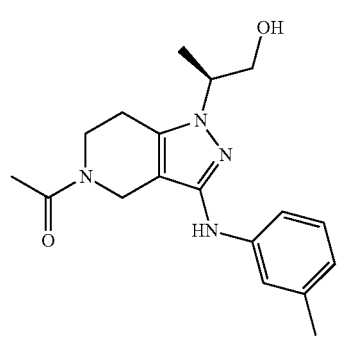
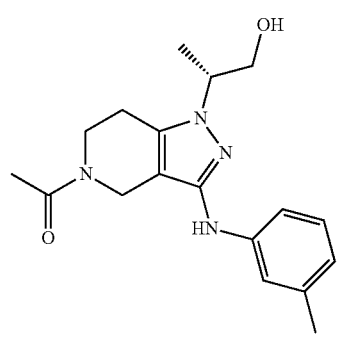
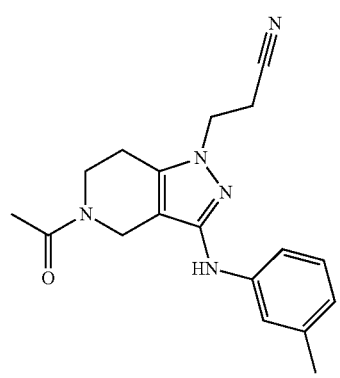
248
-continued
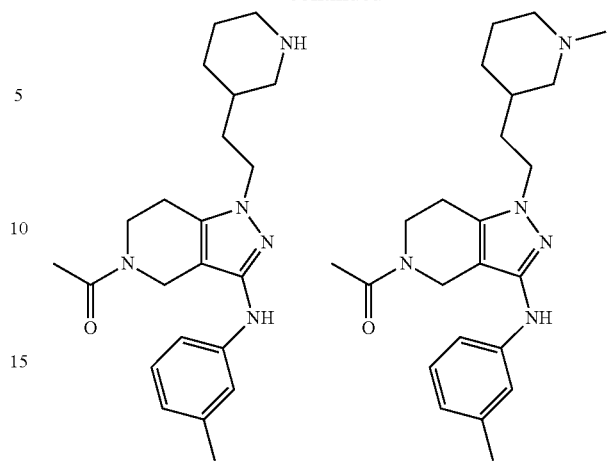
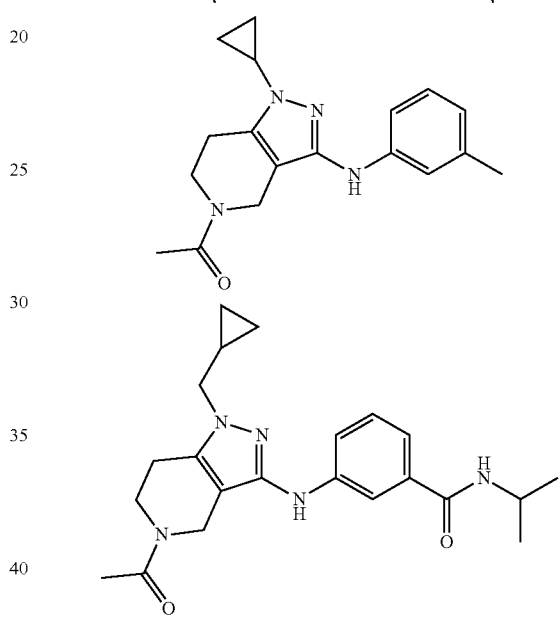
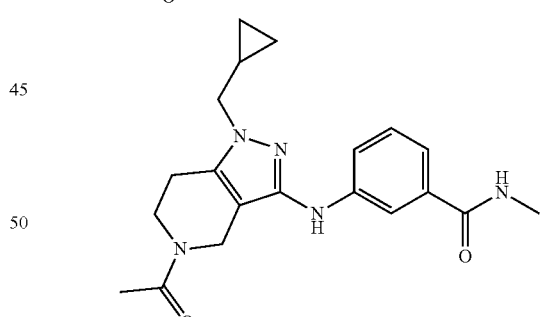
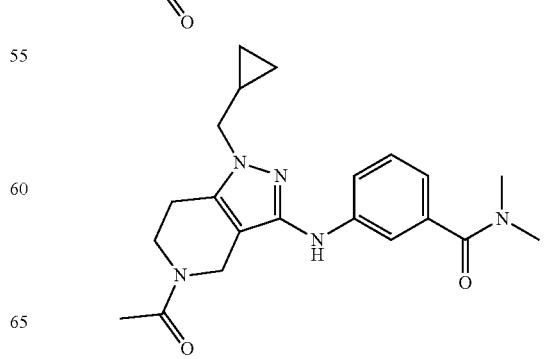

249
-continued
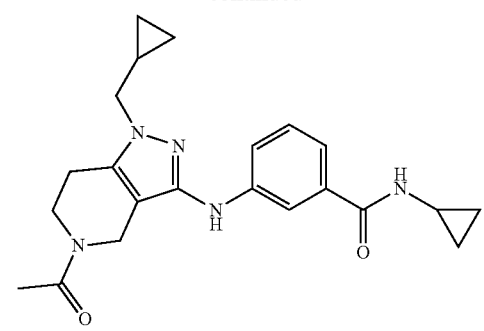
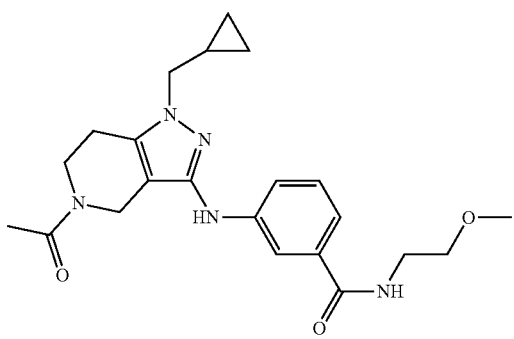
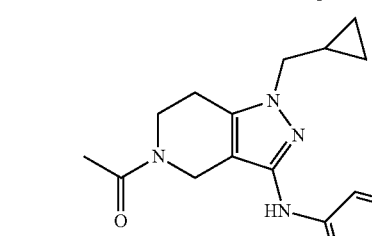
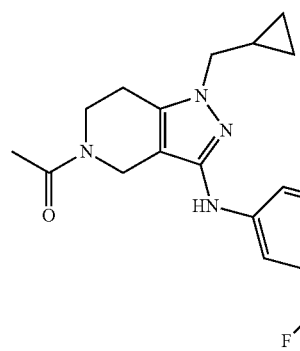
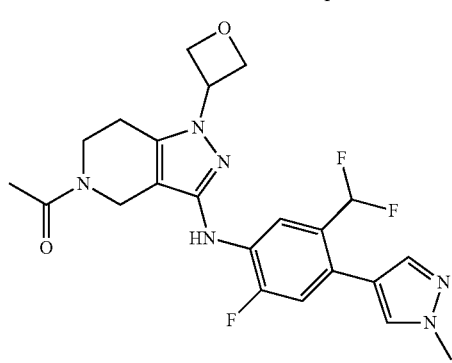
250
-continued
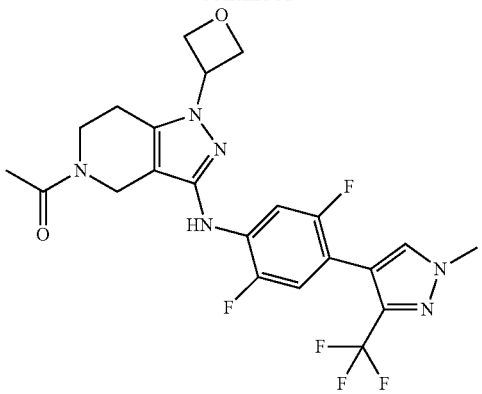
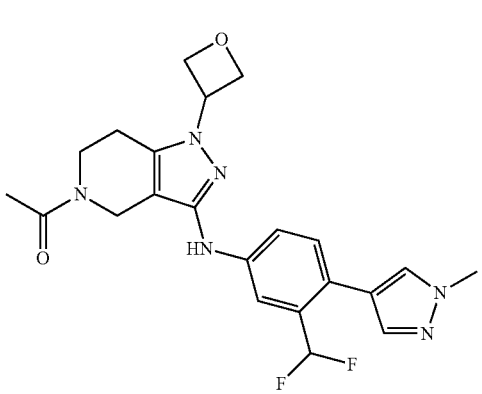
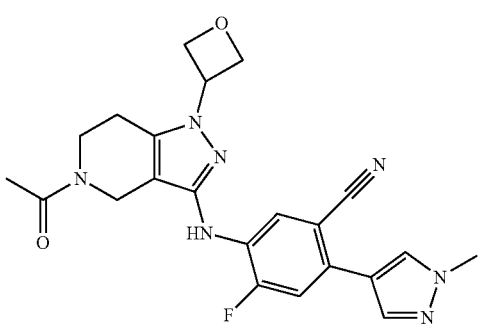
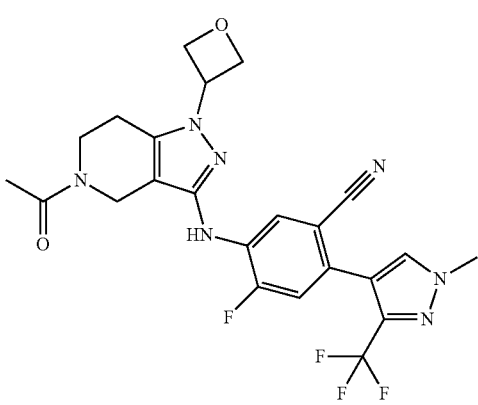

251
-continued
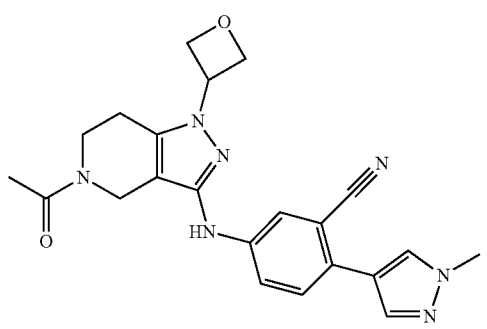
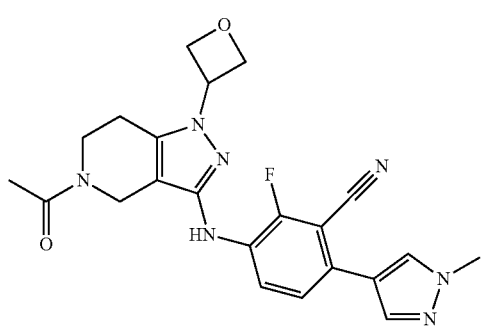
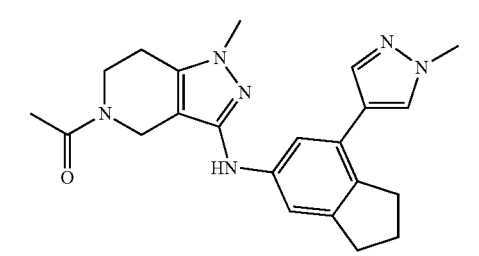
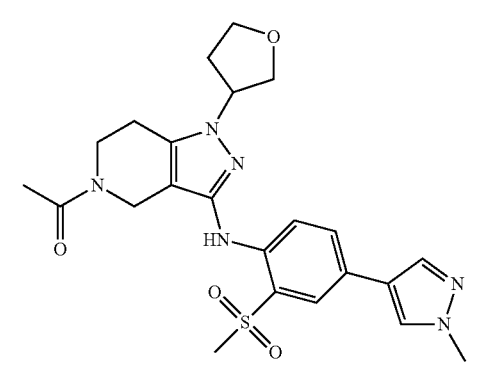
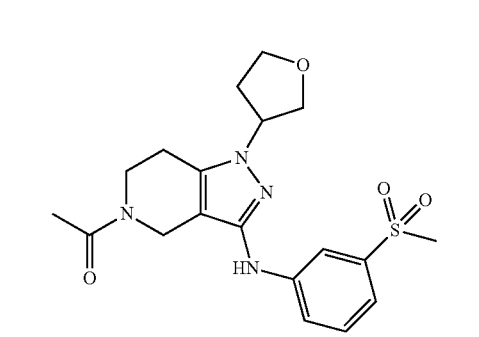
252
-continued
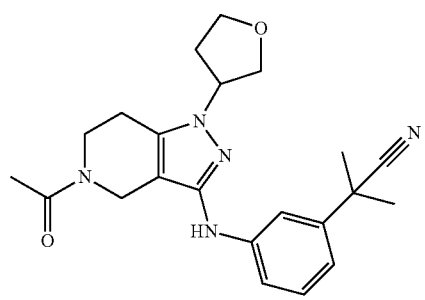
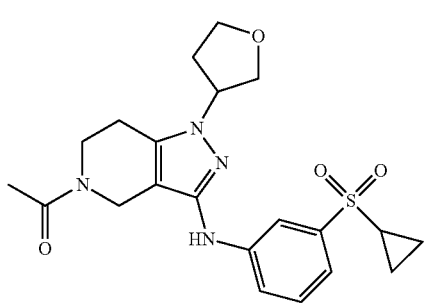
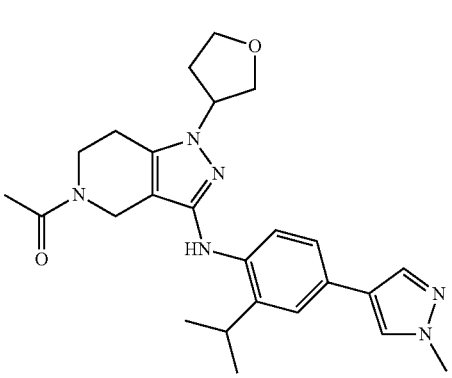
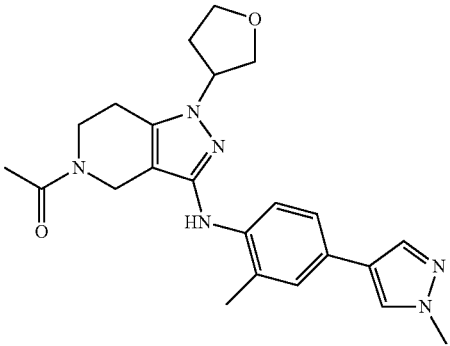
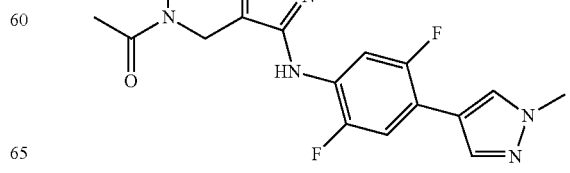

253
-continued
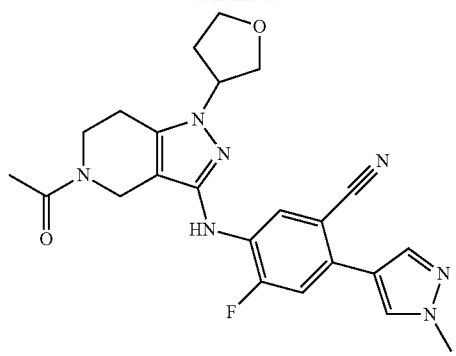
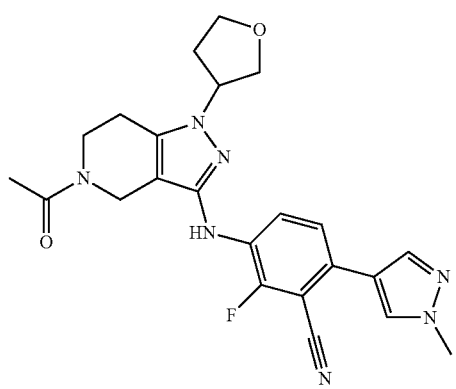
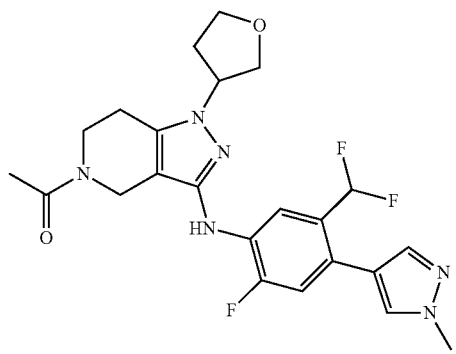
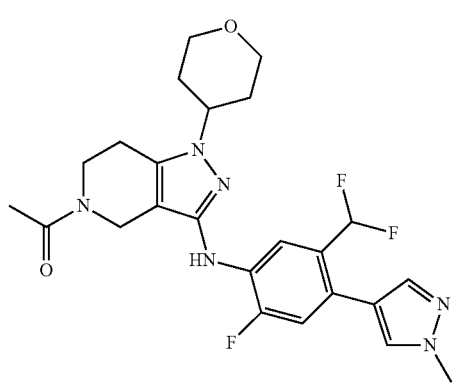
254
-continued
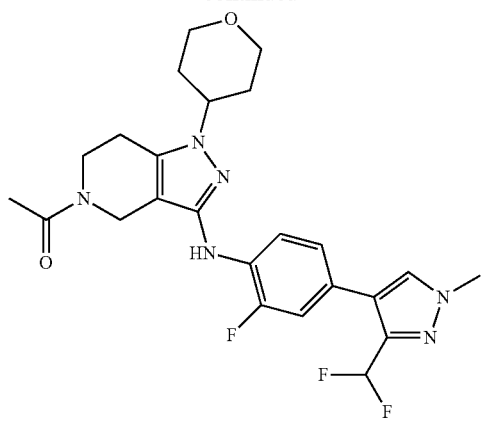
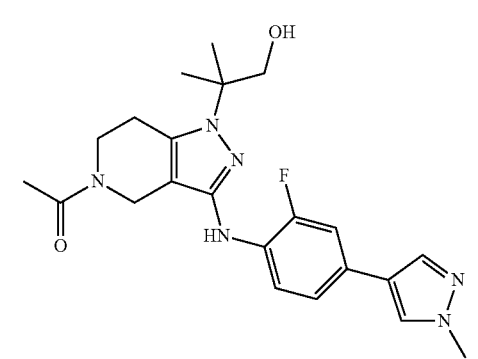
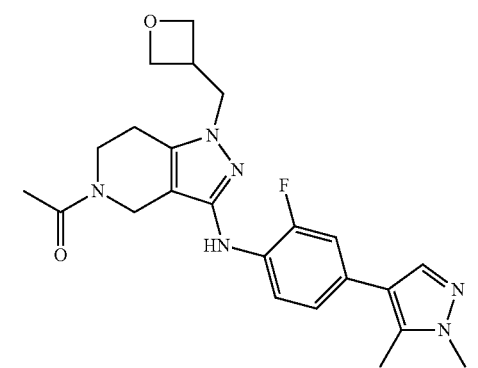
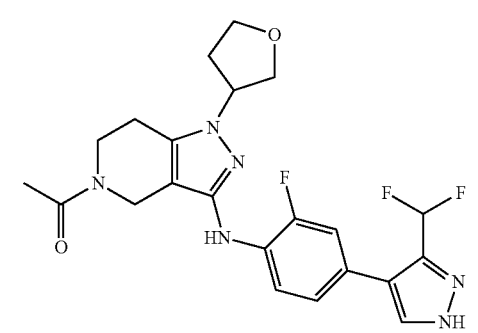

255
-continued
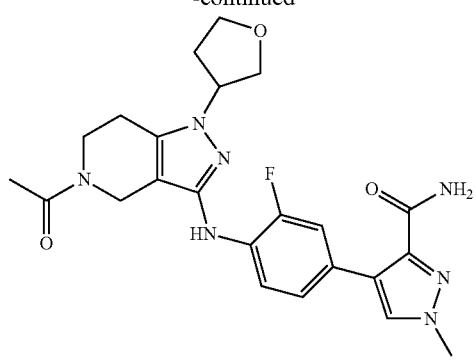
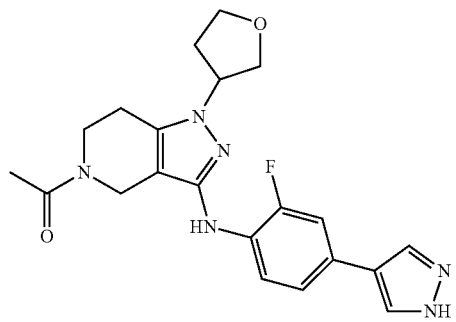
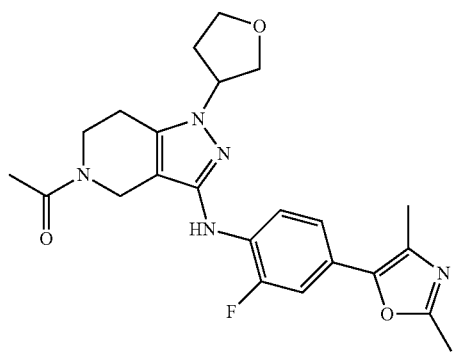
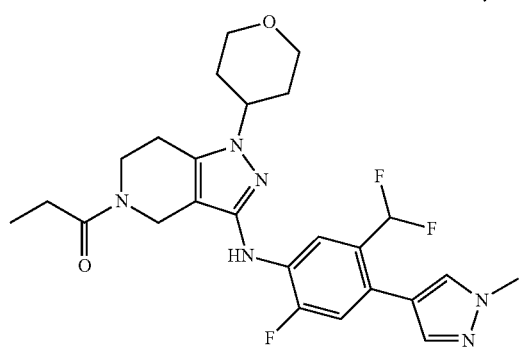
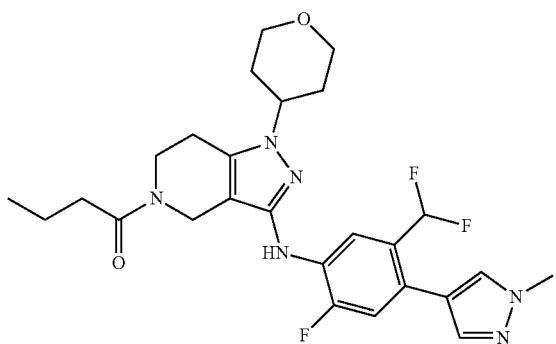
256
-continued
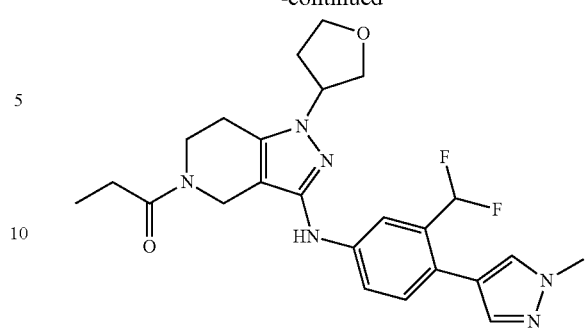
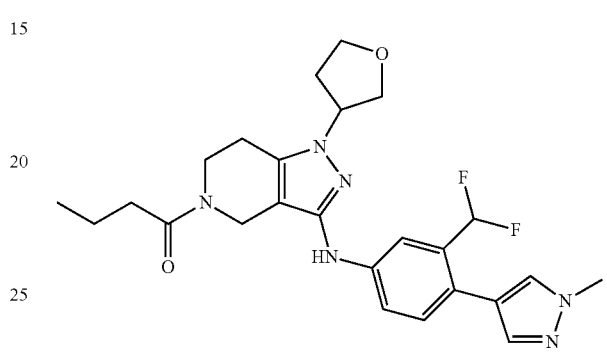
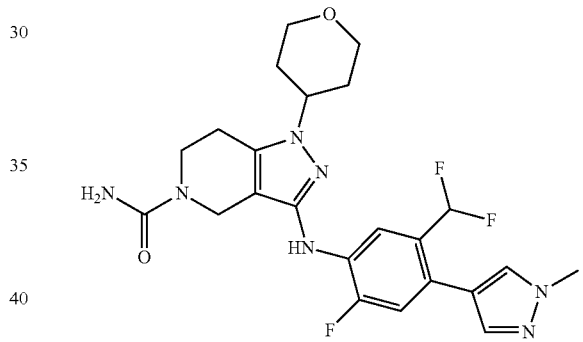
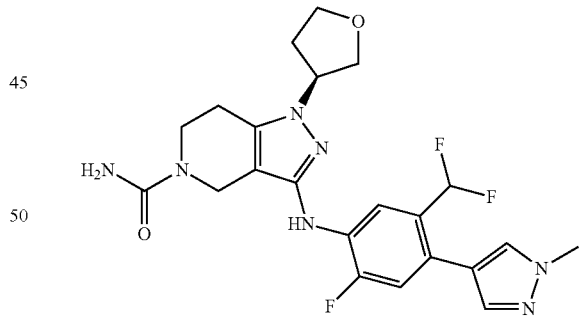
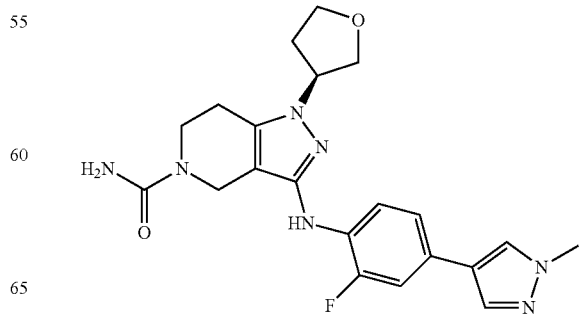

257
-continued
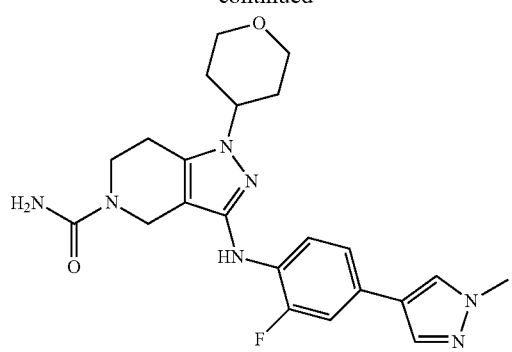
258
-continued
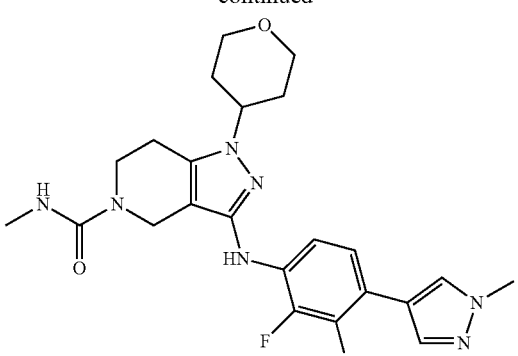
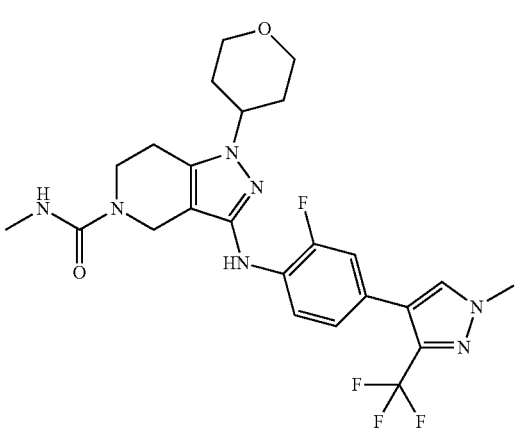
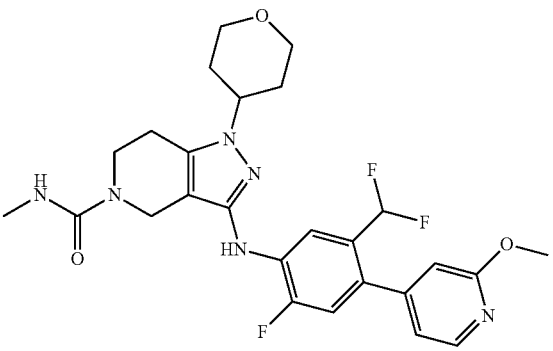
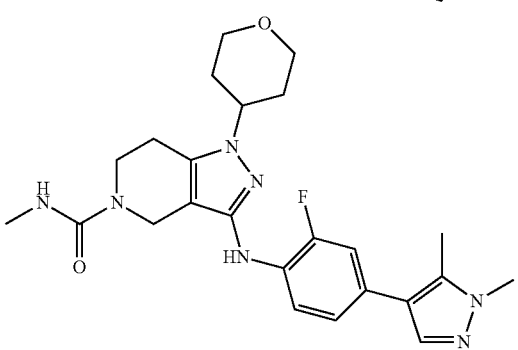

| 259 | 260 |
|---|---|
| -continued | -continued |
| 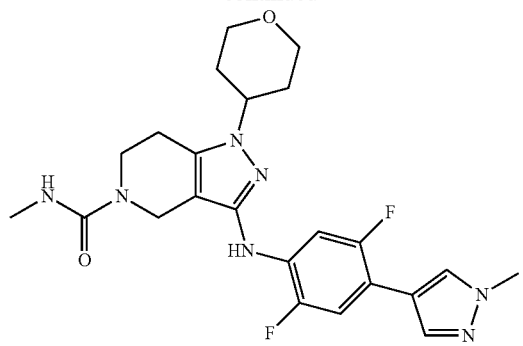 | 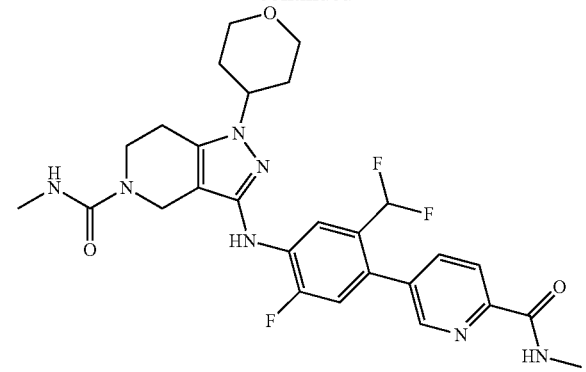 |
| 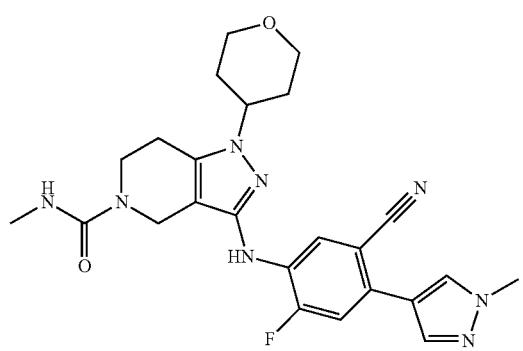 | 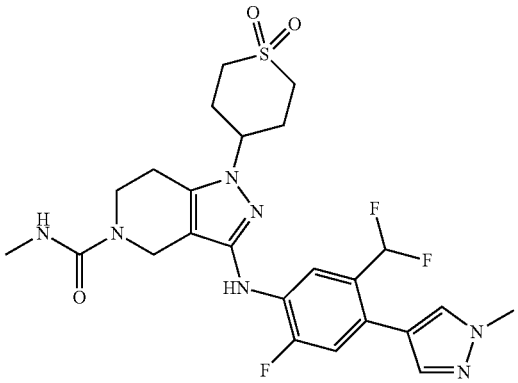 |
| 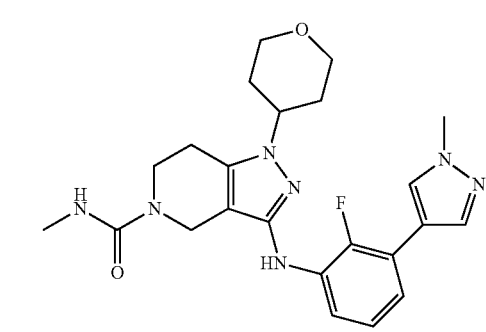 | 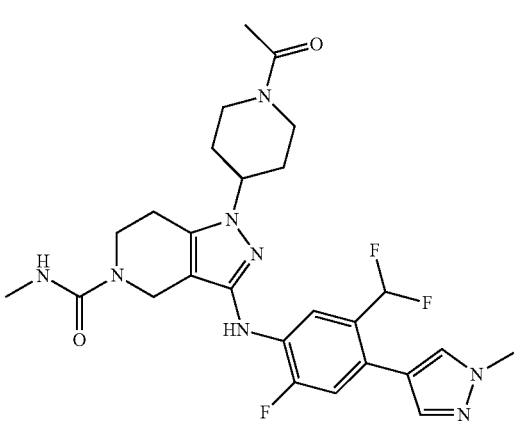 |
| 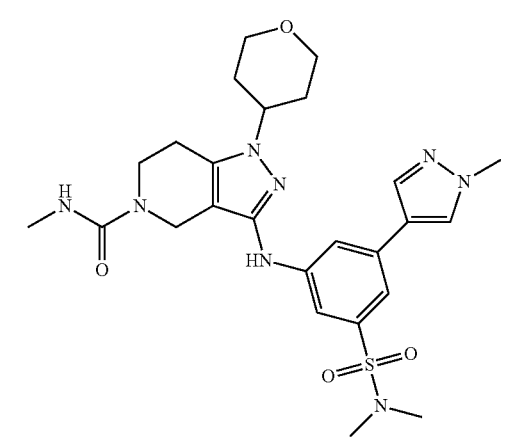 | 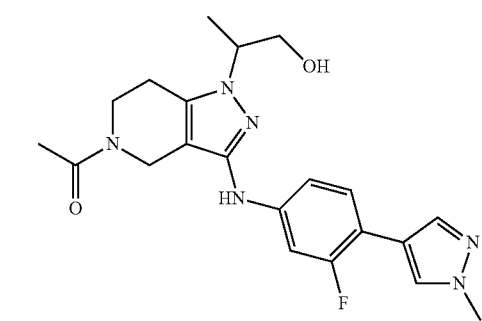 |

261
-continued
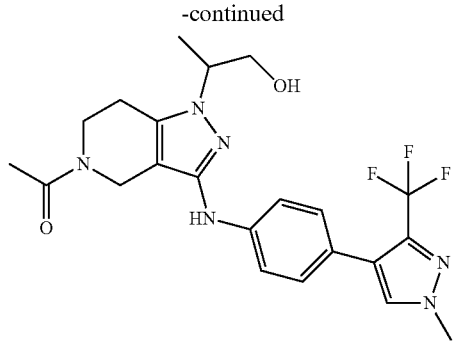
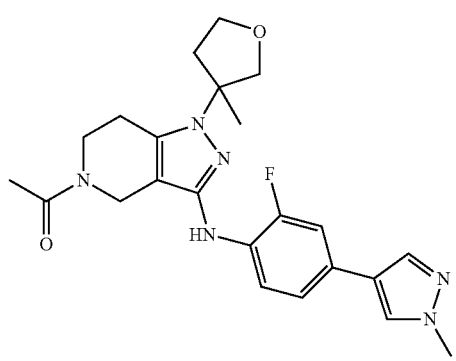
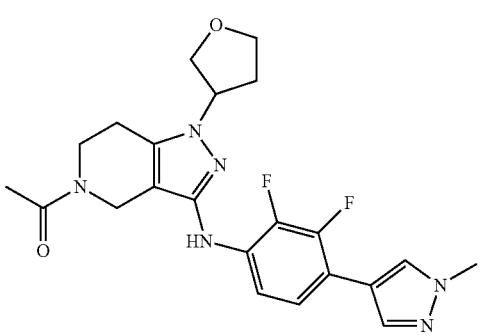
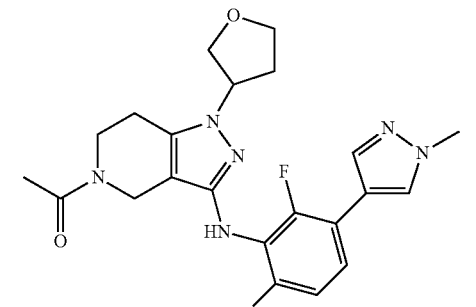
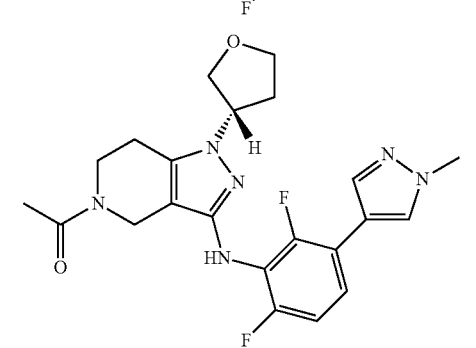
262
-continued
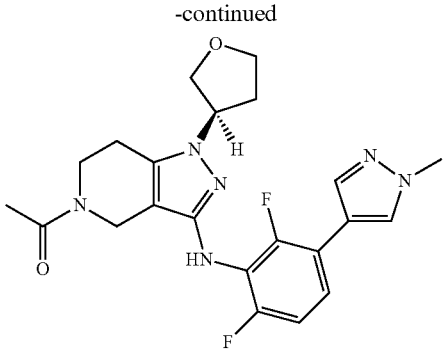
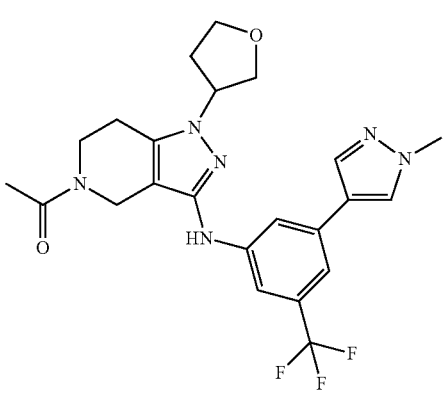
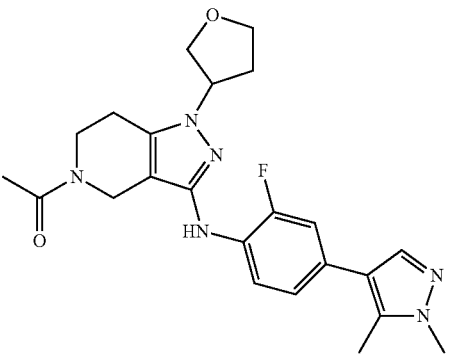
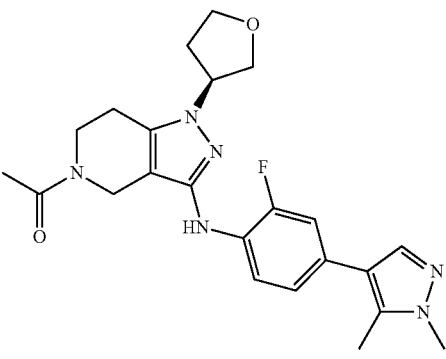

263
-continued
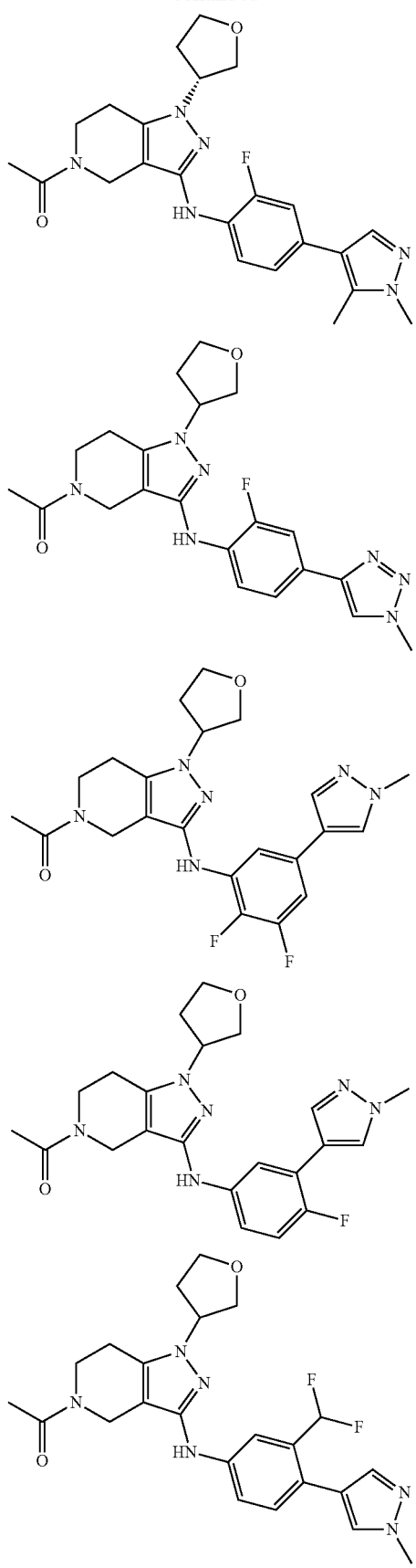
264
-continued
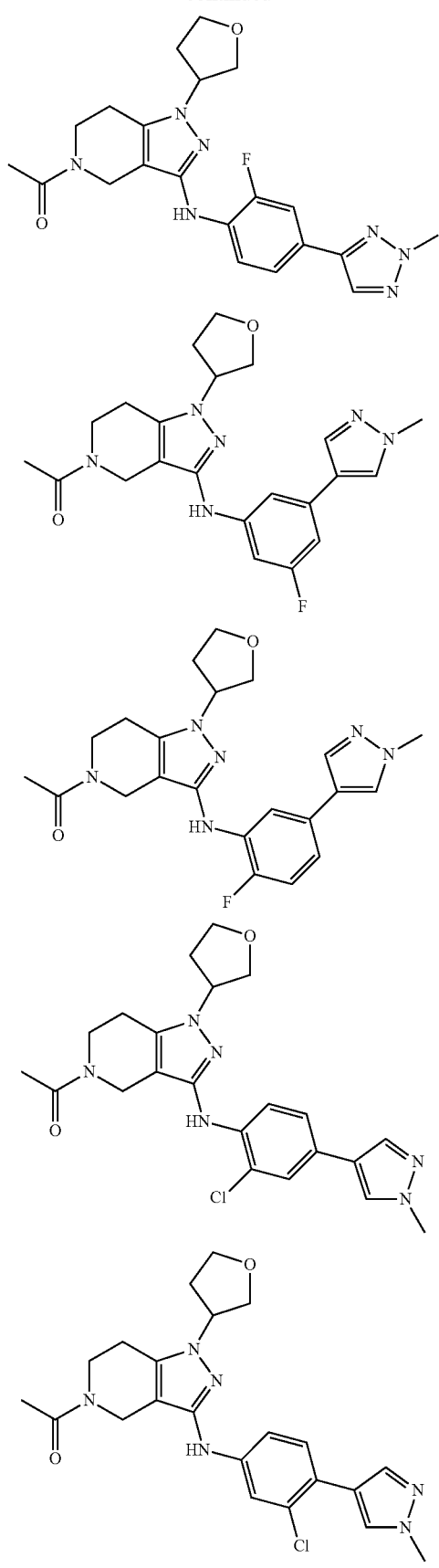

265
-continued
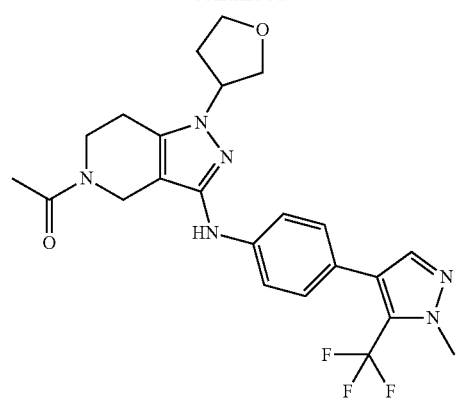
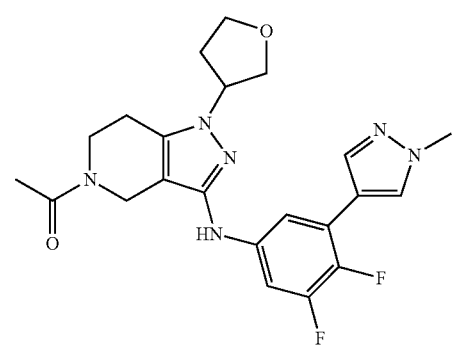
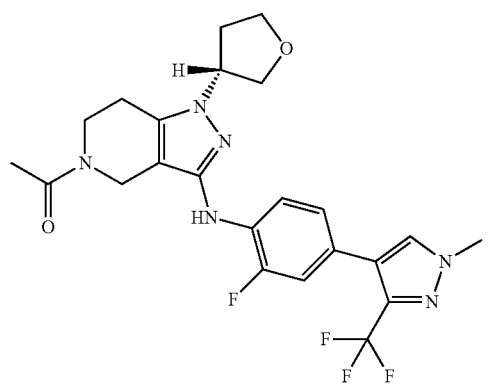
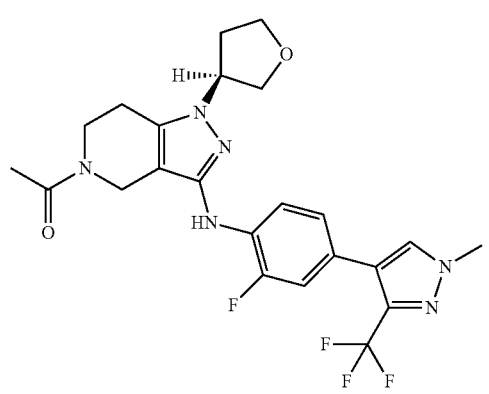
266
-continued
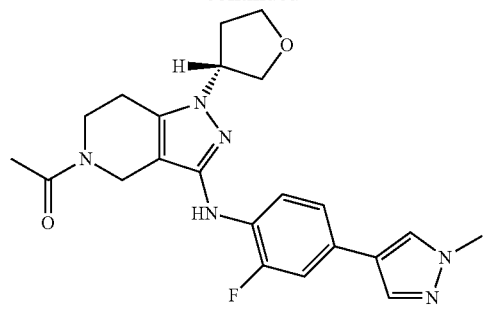
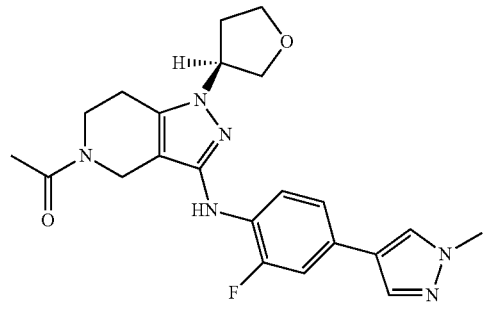
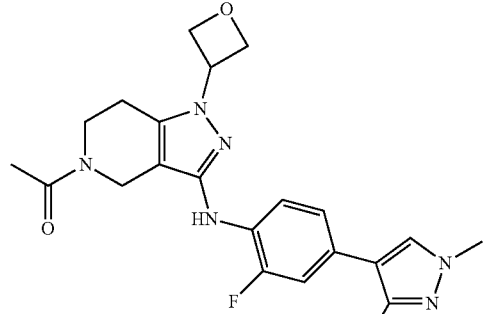
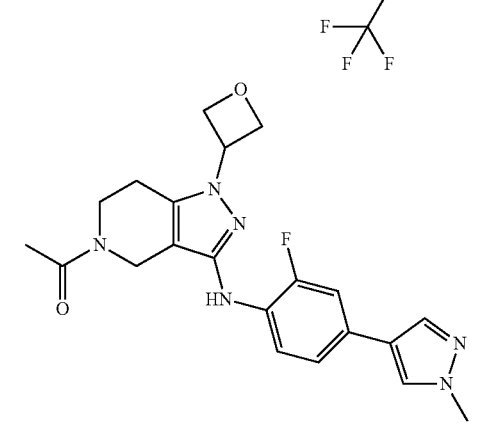
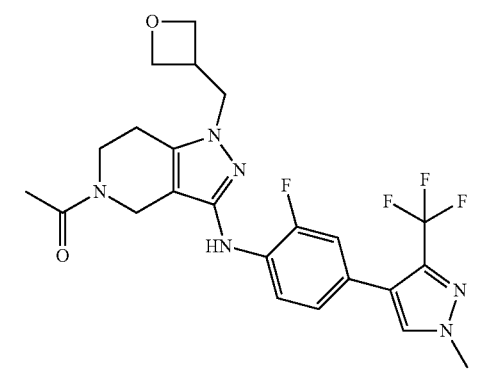

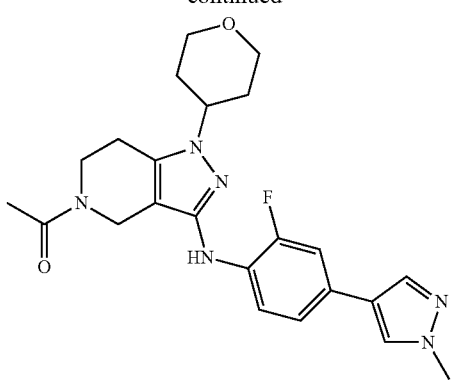

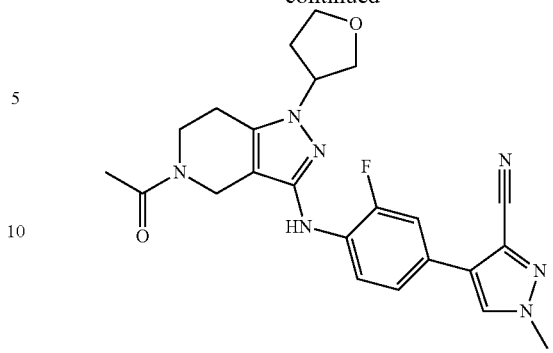

and salts thereof.

In certain embodiments the compound of Formula (II) is a compound as described in the Examples herein, or a freebase or salt thereof.

In certain embodiments any of the embodiments described for the compound of Formula (II) may be combined with any other embodiment described for the compound of Formula (II).

Uses, Formulation and Administration of Compounds of Formula (I) or Formula (II) Pharmaceutically Acceptable Compositions Another aspect includes a pharmaceutical composition comprising a compound of formula (I) or formula (II) or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit a bromodomain of CBP and/or EP300. In certain embodiments, the composition is formulated for administration to a patient in need thereof.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of formula I or formula II or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of formula I or formula II or salt thereof is formulated as a solid dosage form for oral administration. Solid dosage forms for oral administration include capsules, tablets, pills, powders, and granules. In certain embodiments, the solid oral dosage form comprising a compound of formula (I) or formula (II) or a salt thereof further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula I or formula II or salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polyethylene glycols and the like.

In another embodiment, a composition comprises microencapsulated compound of formula (I) or formula (II) or salt thereof, and optionally, further comprises one or more excipients.

In another embodiment, compositions comprise liquid dosage formulations comprising a compound of formula I or formula II or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula (I) or formula (II), it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly (anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula (I) or formula (II) or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula (I) or formula (II).

Example dosage forms for topical or transdermal administration of a compound of formula (I) or formula (II) include ointments, pastes, creams, lotions, gels, powders, solutions, sprays, inhalants or patches. The compound of formula (I) or formula (II) or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound of formula (I) or formula (II) or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula (I) or formula (II) or a salt thereof may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula I or formula II or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or formula (II) or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or formula II or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound of formula (I) or formula (II) or a salt thereof for the inhibition of a bromodomain (in vitro or in vivo) (e.g., in vitro or in vivo inhibition of the bromodomain of CBP/EP300).

Another embodiment includes a method for treating a bromodomain-mediated disorder (e.g., CBP/EP300 bromodomain-mediated disorder) in an animal comprising administering a compound of formula (I) or formula (II), or a pharmaceutically acceptable salt thereof to the animal. CBP/EP300-mediated disorders include, but are not limited to those disorders described herein.

Another embodiment includes a method of increasing efficacy of a cancer treatment comprising a cytotoxic agent in an animal comprising administering to the animal an effective amount of a compound of formula (I) or formula (II) or a pharmaceutically acceptable salt thereof.

Another embodiment includes a method of extending the duration of response to a cancer therapy in an animal, comprising administering to an animal undergoing the cancer therapy a compound of formula (I) or formula (II) or a pharmaceutically acceptable salt thereof, wherein the duration of response to the cancer therapy when the compound of formula (I) or formula (II) or the pharmaceutically acceptable salt thereof is administered is extended over the duration of response to the cancer therapy in the absence of the administration of the compound of formula (I) or formula (II) or the pharmaceutically acceptable salt thereof.

Another embodiment includes a method of treating cancer in an individual comprising administering to the individual (a) a compound of formula (I) or formula (II) or a pharmaceutically acceptable salt thereof, and (b) a cytotoxic agent. In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine or a pharmaceutically acceptable salt thereof (e.g., erlotinib). In one embodiment the cytotoxic agent is a RAF inhibitor. In one embodiment the RAF inhibitor is a BRAF or CRAF inhibitor. In one embodiment the RAF inhibitor is vemurafenib. In one embodiment the cytotoxic agent is a PI3K inhibitor.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the CBP/EP300 bromodomain inhibitor interferes with the associating of CBP and/or EP300 with histones, in particular acetylated lysines in histones. In some embodiments, the CBP/EP300 bromodomain inhibitor inhibits binding of CBP and/or EP300 to chromatin (e.g., histone associated DNA). In some embodiments, the CBP/EP300 bromodomain inhibitor inhibits and/or reduces binding of the CBP bromodomain and/or EP300 bromodomain to chromatin (e.g., histone associated DNA). In some embodiments, the CBP/EP300 bromodomain inhibitor does not affect association of other domains of CBP and/or EP300 to chromatin. In some embodiments, CBP/EP300 bromodomain inhibitor binds to the CBP and/or EP300 primarily (e.g., solely) through contacts and/or interactions with the CBP bromodomain and/or EP300 bromodomain. In some embodiments, CBP/EP300 bromodomain inhibitor binds to the CBP and/or EP300 through contacts and/or interactions with the CBP bromodomain and/or EP300 bromodomain as well as additional CBP and/or EP300 residues and/or domains. Methods of assaying association with chromatin are known in the art and include, but are not limited to, chromatin fractionation, BRET assay (Promega), FRAP assay, Chromatin Immunoprecipitation (ChIP), biophysical binding assay, and/or Histone Association Assay. See, e.g., Das et al., *BioTechniques* 37:961-969 (2004).

In some embodiments, the CBP/EP300 bromodomain inhibitor does not affect effector function in CD8 cells (i.e., effector function is substantially the same in the presence and/or absence of the CBP/EP300 bromodomain inhibitor). In some embodiments, the CBP/EP300 bromodomain inhibitor does not affect expression levels of perforin, granzyme, and/or EOMES (i.e., expression levels of one or more perforin, granzyme, and/or EOMES are substantially the same in the presence and/or absence of the CBP/EP300 bromodomain inhibitor). In some embodiments, the CBP/EP300 bromodomain inhibitor does not affect expression levels of effector cytokines IFN-γ and/or TNFα (i.e., expression levels of effector cytokines IFN-γ and/or TNFα are substantially the same in the presence and/or absence of the CBP/EP300 bromodomain inhibitor). In some embodiments, the CBP/EP300 bromodomain inhibitor enhances naïve T cell responsiveness to CD3/CD28 stimulation in the presence of Treg cells.

In some embodiments, the CBP/EP300 bromodomain inhibitor does not substantially bind to (e.g., does not bind to) the HAT domain of CBP and/or EP300. In some embodiments, the CBP/EP300 bromodomain inhibitor does not substantially bind to (e.g., does not bind to) the HAT domain of CBP and/or EP300 as identified in Delvecchio et al., *Nat. Struct. & Mol. Biol.* 20:1040-1046 (2013), which is incorporated by reference in its entirety. In some embodiments, the CBP/EP300 bromodomain inhibitor does not substantially bind to one or more residues of the amino acid sequence ENKFSAKRLQTTR LGNHLEDRVNKFLR-RQNHPEAGEVFVRVVASSDKTVEVKPGMKSRFVDS-GEMSESF PYRTKALFAFEEIDGVDVCFFGM-HVQEYGSDCPPPNTRRVYISYLDSIHFFRPRCLRT AVYHEILIGYLEYVKKLGYVTGHIWACPPSEGDDYIF-HCHPPDQKIPKPKRLQEWYK KMLDKAFAERIIH-DYKDIFKQATEDRLTSAKELPYFEGDFWPNVLEESI-KELEQEEEE RKKEESTAASETTEGSQGDSKNAKKKNNKK-TNKNKSSISRANKKKPSMPNVSNDLS QKLYATME-KHKEVFFVIHLHAGPVINTLPPIVDPDPLLSCDLM-DGRDAFLTLARDKH WEFSSLRRSKWSTLCMLVELHTQGQD (amino acid residues 1321-1701 of UniProt No. Q92793 (SEQ ID NO:1)). In some embodiments, the CBP/EP300 bromodomain inhibitor does not substantially bind to one or more residues of the amino acid sequence ENKFSAKRLPSTRL-GTFLENRVNDFLRRQNHPESGEVTVRVVHASDKT-VEVKPGMK ARFVDSGEMAESFPYRTKALFAFEE-IDGVDLCFFGMHVQEYGSDCPPPNQRRVYISY LDSVHFFRPKCLRTAVYHEILIGYLEYVKKLGYTT-GHIWACPPSEGDDYIFHCHPPDQ KIPKPKRLQEWYK-KMLDKAVSERIVHDYKDIFKQATEDRLTSAKELPY-FEGDFWPN VLEESIKELEQEEEERKREENTSNESTDVTKGD-SKNAKKKNNKKTSKNKSSLSRGNK KKPGMPN-VSNDLSQKLYATMEKHKEVFFVIRLIAGPAANSLP-PIVDPDPLIPCDLMDG RDAFLTLARDKHLEFSSLRRAQWSTMCM-LVELHTQSQD (amino acid residues 1285-1664 of UniProt No. Q09472 (SEQ ID NO:2)). In some embodiments, the CBP/EP300 bromodomain inhibitor does not inhibit the histone acetyltransferase (HAT) catalytic activity of CBP and/or EP300.

Compounds that are CBP/EP300 bromodomain inhibitors are expected to have improved and/or distinct properties over other compounds, such as "HAT" inhibitor compounds. HAT inhibition is expected to result in a global reduction in protein acetylation (histone and non-histone), likely affecting cell viability in a significant way. In some embodiments, CBP/EP300 bromodomain inhibition preserves the HAT activity of these proteins while resulting in the reduction of transcriptional activity of a relatively small subset of target genes.

In some embodiments, provided are methods of enhancing immune function in an individual having cancer comprising administering an effective amount of any CBP/EP300 bromodomain inhibitors disclosed herein. In some embodiments of any of the methods, the CD8 T cells in the individual have enhanced priming, activation, proliferation, and/or cytolytic activity relative to prior to the administration of the CBP/EP300 bromodomain inhibitor. In some embodiments, the number of CD8 T cells is elevated relative to prior to administration of the CBP/EP300 bromodomain inhibitors. In some embodiments, the CD8 T cells have reduced levels of expression of one or more of the following biomarkers: IFNA17, IGF1, FSCN1, SUMO2, C1orf129, EIF2S2, TDGF1, AIDA, CCR4, CD160, MC4R, KRTAP2-2, MTIJP, OR4N2, KRTAP4-5, MTIL//MTIL,ILI3, LCEID, KIR2DL2, LOC158696, LIF, IL28A, TAS2R13, CTLA4, and/or FOXP3 relative to prior to administration of the CBP/EP300 bromodomain inhibitor. In some embodiments, the CD8 T cells have reduced levels of expression of CD160 and/or KIR2DL2 relative to prior to administration of the CBP/EP300 bromodomain inhibitor.

In some embodiments of the methods of enhancing immune function, the enhanced immune function is characterized by Treg cells in the individual (e.g., at the tumor site(s)) have reduced levels of expression of one or more of the following markers: IL28A, GPR87, ANKRD37, CABLES1, RAPGEF2, TRIM69, MT1L//MT1L, FAM1138, FOXP3, CSF2, OCM2, GLIPR1, FGFBP2, CTLA4, CST7, GOLGA6L1, IFIT3, FAM13A, APOD, AK2, CLDN1, HSD11B1, DNAJC12, PHEX, IL2, FOXD4L3, GNA15, ZBTB32, RDH10, OR52E5, CYP2A6, GZMH, CCL20, ADM, LOC100131541, RNF122, FAM36A, AMY2B, GPR183, MYOF, IL29, AIDA, SPRYI, ENOPH1, IL1RN, SLAMF1, PGM2L1, SSBP3, MMP23B, HIST1H3J, MYO1B, BEND5, SIPR1, CDK6, GPR56, ZC3HIZA, DOK5, DUSPI, CYB5R2, KCNAB2, LAG3, KLF10, GK, SHC4, IL12RB2, CD109, HAVCR2 (TIM-3), LTA, FAM40B, HMGCSI, HSPA1A, ZNF705A, CMAH, KIF3A, CHN1, KBTBD8, TNF, MOP-1, RASGRP4, INSIG1, SLAMF7, OR10H4, LPL, HIST1H2BJ, LIF, IGF1, IL18RAP, OR52N4, OR1D2, CCR4, CXCR5, IL1R1, MICAL2, NRN1, PICALM, B3GNT5, IFI44L, CXCR3, ICOS, IFIT2, NCR3, HSPA1B, CD80, GNG2, C7orf68, GPR171, RPS10P7, IL23A, LOC283174, PLK2, EMP1, FNBP1L, CD226, RBMS3, IL23R, PTGER4, GZMB, F5, and/or HIST1H2BK relative to prior to administration of CBP/EP300 bromodomain inhibitor. In some embodiments, the Treg cell biomarker is one or more of LAG3, CTLA4, and/or FOXP3. In some embodiments of the methods of enhancing immune function, the enhanced immune function is characterized by enhanced naive T cell responsiveness to CD3/CD28 stimulation in the presence of Treg cells. In some embodiments, the CD8 T cell priming is characterized by increased T cell proliferation and/or enhanced cytolytic activity in CD8 T cells. In some embodiments, the CD8 T cell activation is characterized by an elevated frequency of T-IFN$^+$ CD8 T cells. In some embodiments, the CD8 T cell is an antigen-specific T-cell. In some embodiments, the immune evasion is inhibited.

In some embodiments, the methods provided herein are useful in treating conditions where enhanced immunogenicity is desired such as increasing tumor immunogenicity for the treatment of cancer. For example, provided herein are CBP/EP300 bromodomain inhibitors for use to enhance T-cell function to upregulate cell-mediated immune responses and for the treatment of T cell dysfunctional disorders, tumor immunity. In some embodiments, the CBP/EP300 bromodomain inhibitors promote anti-tumor immunity by inhibiting the suppressive function of regulatory T (Treg) cells and/or relieving T cell exhaustion on chronically stimulated CD8$^+$ T cells. CBP/EP300 bromodomain inhibitors are further useful in reducing FOXP3 expression during extra-thymic Treg cell differentiation. Continual FOXP3 expression is essential to maintain suppressive activity in Treg cells. In some embodiments, reduced FOXP3 expression through CBP/EP300 bromodomain inhibition impairs Treg cells suppressive activity and promotes tumor antiimmunity. Treg cells are highly enriched in tumors derived from multiple cancer indications, including melanoma, NSCLC, renal, ovarian, colon, pancreatic, hepatocellular, and breast cancer. In a subset of these indications, increased intratumoral Treg cell densities are associated with poor patient prognosis. These indications include NSCLC, ovarian, pancreatic, hepatocellular, and breast cancer. CBP/EP300 bromodomain inhibitors are predicted to impair intratumoral Treg cell function in these cancer indications to enhance effector T cell activity. In other embodiments, the CBP/EP300 bromodomain inhibitors may be used to treat infectious diseases, where some pathogens may have evolved to manipulate regulatory T (Treg) cells to immunosuppress the host to ensure survival, such as in retroviral infections (e.g., HIV), mycobacterial infections (e.g., tuberculosis), and parasitic infections (e.g., *Leishmania* and malaria).

In some embodiments, the methods provided herein are useful in treating a CBP and/or EP300-mediated disorder involving fibrosis. In some embodiments, the CBP and/or EP300-mediated disorder is a fibrotic disease. Certain fibrotic diseases may include, for example, pulmonary fibrosis, silicosis, cystic fibrosis, renal fibrosis, liver fibrosis, liver cirrhosis, primary sclerosing cholangitis, primary biliary cirrhosis, endomyocardial fibrosis, mediastinal fibrosis, myelofibrosis, retroperitoneal fibrosis, progressive massive fibrosis, nephrogenic systemic fibrosis, Crohn's disease, keloid, myocardial infarction, systemic sclerosis or arthro fibrosis.

In other embodiments, the CBP and/or EP300-mediated disorder is a fibrotic lung disease. Fibrotic lung diseases may include, for example, idiopathic pulmonary fibrosis, fibrotic interstitial lung disease, interstitial pneumonia, fibrotic variant of non-specific interstitial pneumonia, cystic fibrosis, lung fibrosis, chronic obstructive pulmonary lung disease (COPD), or pulmonary arterial hypertension. In certain embodiments, the fibrotic lung disease is idiopathic pulmonary fibrosis.

In some embodiments, any CBP and/or EP300 inhibitor may be used to treat fibrotic disease. In some embodiments, the CBP and/or EP300 inhibitor is a compound of formula (I) or of formula (II), as described herein. In some embodiments, the CBP and/or EP300 inhibitor is a compound of formula (III):

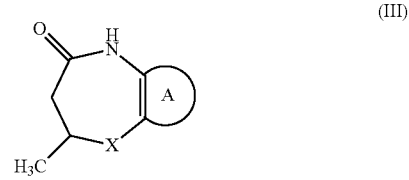

(III)

or a salt thereof, wherein:

X is NH, O, S, or —C(R$^a$)$_2$—;

each R$^a$ is independently selected from the group consisting of H, C$_{1-6}$alkyl, C$_{2-6}$alkenyl, C$_{2-6}$-alkynyl, and C$_{3-6}$carbocyclyl;

ring A is a 6 membered heteroaryl ring or a benzo ring, wherein ring A is optionally substituted with one or more groups R$^b$ that are independently selected from the group consisting of R$^c$, —F, —Cl, —Br, —I, —NO$_2$, —N(R$^d$)$_2$, —CN, —C(O)—N(R$^d$)$_2$, —S(O)—N(R$^d$)$_2$, —S(O)$_2$—N(R$^d$)$_2$, —O—R$^d$, —S—R$^d$, —O—C(O)—R$^d$, —O—C(O)—O—R$^d$, —C(O)—R$^d$, —C(O)—O—R$^d$, —S(O)—R$^d$, —S(O)$_2$—R$^d$, —O—C(O)—N(R$^d$)$_2$, —N(R$^d$)—C(O)—OR$^d$, —N(R$^d$)—C(O)—N(R$^d$)$_2$, —N(R$^d$)—C(O)—R$^d$, —N(R$^d$)—S(O)—R$^d$, —N(R$^d$)—S(O)$_2$—R$^d$, —N(R$^d$)—S(O)—N(R$^d$)$_2$, —CH=C(R$^e$)$_2$, and —N(R$^d$)—S(O)$_2$—N(R$^d$)$_2$, each R$^c$ is independently selected from the group consisting of hydrogen, C$_{1-6}$alkyl, C$_{2-6}$alkenyl, C$_{2-6}$alkynyl, 3-20 membered carbocyclyl, 3-20 membered heterocyclyl, wherein any C$_{1-6}$alkyl, C$_{2-6}$alkenyl, C$_{2-6}$alkynyl, 3-20 membered carbocyclyl, and 3-20 membered heterocyclyl is optionally substituted with one or more groups R$^f$;

each R$^f$ is independently selected from the group consisting of oxo, 3-20 membered carbocyclyl, 3-20 membered heterocyclyl, halo, —NO$_2$, —N(R$^g$)$_2$, —CN, —C(O)—N(R$^g$)$_2$, —S(O)—N(R$^g$)$_2$, —S(O)$_2$—N(R$^g$)$_2$, —O—R$^g$, —S—R$^g$, —O—C(O)—R$^g$, —C(O)—R$^g$, —C(O)—O—R$^g$, —S(O)—R$^g$, —S(O)$_2$—R$^g$, —C(O)—N(R$^g$)$_2$, —N(R$^g$)—C(O)—R$^g$, —Si(R$^h$)$_3$, —N(R$^g$)—C(O)—O—R?, —N(R$^g$)—S(O)—R$^g$, N(R$^g$)—S(O)$_2$—R$^g$, and C$_{1-6}$alkyl, which 3-20 membered carbocyclyl, 3-20 membered heterocyclyl, and C$_{1-6}$alkyl are optionally substituted with one or more groups R$^i$, each $R^g$ is independently selected from the group consisting of hydrogen, $C_{1-6}$alkyl, $C_{2-6}$alkenyl, $C_{2-6}$alkynyl, 3-20 membered carbocyclyl, and 3-20 membered heterocyclyl, wherein each $C_{1-6}$alkyl, $C_{2-6}$alkenyl, $C_{2-6}$alkynyl, $C_{1-6}$alkoxy, 3-20 membered carbocyclyl, and 3-20 membered heterocyclyl is optionally substituted with one or more groups $R^j$, or two $R^g$ are taken together with the nitrogen to which they are attached to form a 3-20 membered heterocyclyl that is optionally substituted with one or more groups independently selected from the group consisting of oxo, halo and $C_{1-3}$alkyl that is optionally substituted with one or more groups independently selected from the group consisting of oxo and halo;

each $R^h$ is independently selected from the group consisting of H, $C_{1-6}$alkyl, $C_{2-6}$alkenyl, $C_{2-6}$alkynyl, and $C_{3-6}$carbocyclyl;

each $R^j$ is independently selected from the group consisting of oxo, halo, amino, hydroxyl, —Si($R^k$)$_3$, 3-20 membered carbocyclyl, 3-20 membered heterocyclyl, and $C_1$-$C_6$ alkyl, wherein any 3-20 membered carbocyclyl, 3-20 membered heterocyclyl, and $C_1$-$C_6$ alkyl is optionally substituted with one or more groups independently selected from the group consisting of oxo, $C_1$-$C_4$alkyl, and halo;

each $R^k$ is independently selected from the group consisting of H, $C_{1-6}$alkyl, $C_{2-6}$alkenyl, $C_{2-6}$alkynyl, and $C_{3-6}$carbocyclyl;

each $R^i$ is independently selected from the group consisting of oxo, halo, $C_{1-6}$alkyl, cyano, —N($R^l$)$_2$, —O—$R^l$, —S(O)—$R^l$, —S(O)$_2$—$R^l$, —S(O)—N($R^l$)$_2$, —S(O)$_2$—N($R^l$)$_2$, —N($R^l$)—S(O)—$R^l$, —N($R^l$)—C(O)—$R^l$, —N($R^l$)—C(O)—O—$R^l$, —N($R^l$)—S(O)$_2$—$R^l$, 3-20 membered heterocyclyl, and 3-20 membered carbocyclyl that is optionally substituted with one or more groups independently selected from the group consisting of halo, and $C_{1-6}$alkyl;

each $R^l$ is independently selected from the group consisting of hydrogen, $C_{1-6}$alkyl, $C_{2-6}$alkenyl, $C_{2-6}$alkynyl, 3-20 membered carbocyclyl, and 3-20 membered heterocyclyl, wherein each $C_{1-6}$alkyl, $C_{2-6}$alkenyl, $C_{2-6}$alkynyl, $C_{1-6}$alkoxy, 3-20 membered carbocyclyl, and 3-20 membered heterocyclyl is optionally substituted with one or more groups $R^m$; or two $R^l$ are taken together with the nitrogen to which they are attached to form a 3-20 membered heterocyclyl that is optionally substituted with one or more groups independently selected from the group consisting of oxo, halo and $C_{1-3}$alkyl that is optionally substituted with one or more groups independently selected from the group consisting of oxo and halo; and each $R^m$ is independently selected from the group consisting of oxo, halo, amino, hydroxyl, —Si($R^n$)$_3$, 3-20 membered carbocyclyl, 3-20 membered heterocyclyl, and $C_1$-$C_6$ alkyl, wherein any 3-20 membered carbocyclyl, 3-20 membered heterocyclyl, and $C_1$-$C_6$ alkyl is optionally substituted with one or more groups independently selected from the group consisting of oxo, $C_1$-$C_4$alkyl, and halo;

each $R^n$ is independently selected from the group consisting of H, $C_{1-6}$alkyl, $C_{2-6}$alkenyl, $C_{2-6}$alkynyl, and $C_3$-6carbocyclyl;

each $R^d$ is independently selected from the group consisting of hydrogen, $C_{1-6}$alkyl, $C_{2-6}$alkenyl, $C_{2-6}$alkynyl, 3-20 membered carbocyclyl, and 3-20 membered heterocyclyl, wherein each $C_{1-6}$alkyl, $C_{2-6}$alkenyl, $C_{2-6}$alkynyl, 3-20 membered carbocyclyl, and 3-20 membered heterocyclyl is optionally substituted with one or more groups $R^o$, or two $R^d$ are taken together with the nitrogen to which they are attached to form a 3-20 membered heterocyclyl that is optionally substituted with one or more groups independently selected from the group consisting of oxo, halo and $C_{1-3}$alkyl that is optionally substituted with one or more groups independently selected from oxo and halo;

each $R^o$ is independently selected from the group consisting of oxo, halo, amino, hydroxyl, cyano, —O—$R^p$, 3-20 membered carbocyclyl, 3-20 membered heterocyclyl, and $C_1$-$C_6$ alkyl, wherein any $C_1$-$C_6$ alkyl, 3-20 membered carbocyclyl and 3-20 membered heterocyclyl is optionally substituted with one or more groups independently selected from the group consisting of oxo, $C_1$-$C_4$ alkyl, —O—$R^q$, and halo;

each $R^p$ is independently selected from the group consisting of hydrogen, $C_{1-6}$alkyl, $C_{2-6}$alkenyl, $C_{2-6}$alkynyl, 3-20 membered carbocyclyl, and 3-20 membered heterocyclyl, wherein each $C_{1-6}$alkyl, $C_{2-6}$alkenyl, $C_{2-6}$alkynyl, $C_{1-6}$alkoxy, 3-20 membered carbocyclyl, and 3-20 membered heterocyclyl is optionally substituted with one or more groups $R^r$, each $R^r$ is independently selected from the group consisting of oxo, halo, amino, hydroxyl, —Si($R^s$)$_3$, 3-20 membered carbocyclyl, 3-20 membered heterocyclyl, and $C_1$-$C_6$ alkyl, wherein any 3-20 membered carbocyclyl, 3-20 membered heterocyclyl, and $C_1$-$C_6$ alkyl is optionally substituted with one or more groups independently selected from the group consisting of oxo, $C_1$-$C_4$alkyl, and halo;

each $R^s$ is independently selected from the group consisting of H, $C_{1-6}$alkyl, $C_{2-6}$alkenyl, $C_{2-6}$alkynyl, and $C_{3-6}$carbocyclyl;

each $R^q$ is independently selected from the group consisting of hydrogen, $C_{1-6}$alkyl, $C_{2-6}$alkenyl, $C_{2-6}$alkynyl, 3-20 membered carbocyclyl, and 3-20 membered heterocyclyl, wherein each $C_{1-6}$alkyl, $C_{2-6}$alkenyl, $C_{2-6}$alkynyl, $C_{1-6}$alkoxy, 3-20 membered carbocyclyl, and 3-20 membered heterocyclyl is optionally substituted with one or more groups $R^t$, each $R^t$ is independently selected from the group consisting of oxo, halo, amino, hydroxyl, —Si($R^u$)$_3$, 3-20 membered carbocyclyl, 3-20 membered heterocyclyl, and $C_1$-$C_6$ alkyl, wherein any 3-20 membered carbocyclyl, 3-20 membered heterocyclyl, and $C_1$-$C_6$ alkyl is optionally substituted with one or more groups independently selected from the group consisting of oxo, $C_1$-$C_4$alkyl, and halo;

each $R^u$ is independently selected from the group consisting of H, $C_{1-6}$alkyl, $C_{2-6}$alkenyl, $C_{2-6}$alkynyl, and $C_{3-6}$carbocyclyl; and two $R^e$ groups taken together with the carbon to which they are attached form a 3-20 membered carbocyclyl;

or a salt thereof.

In some embodiments, the CBP and/or EP300 inhibitor is:

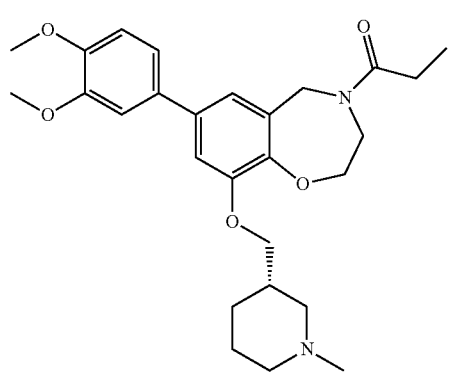

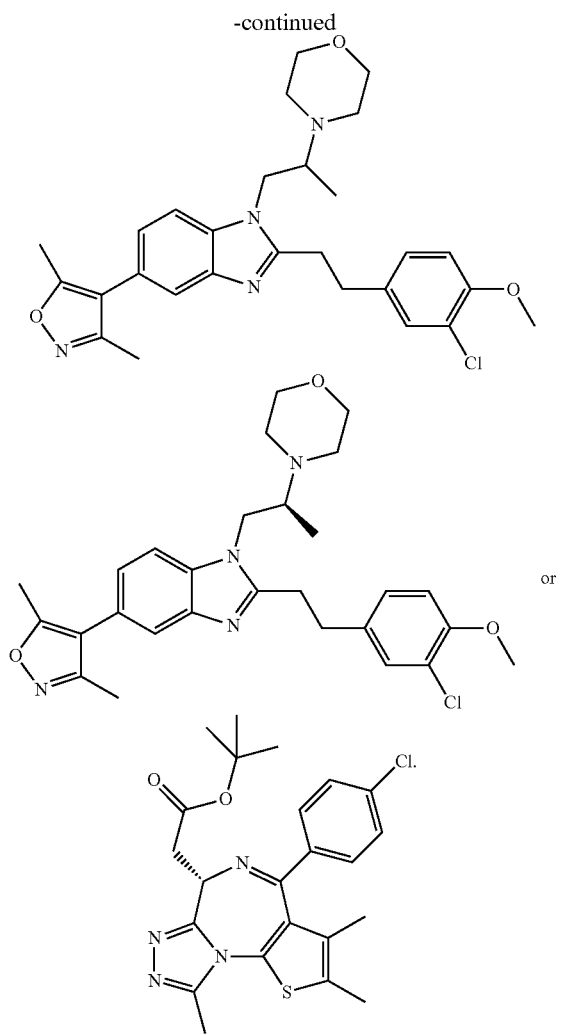

CBP and/or EP300-Mediated Disorders or

A "CBP and/or EP300-mediated disorder" is characterized by the participation of the bromodomains of CBP and/or EP300 in the inception, manifestation of one or more symptoms or disease markers, severity, or progression of a disorder. In one embodiment the bromodomain-mediated disorder is a CBP bromodomain-mediated disorder. In one embodiment the bromodomain-mediated disorder is an EP300 bromodomain-mediated disorder.

CBP and/or EP300 bromodomain-mediated disorders include cancers, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstr6m's macroglobulinemia, testicular tumors, uterine cancer and Wilms' tumor.

In certain embodiments, the cancer is lung cancer, breast cancer, pancreatic cancer, colorectal cancer, and/or melanoma. In certain embodiments, the cancer is lung. In certain embodiments, the lung cancer is NSCLC. In certain embodiments, the cancer is breast cancer.

In certain embodiments, the cancer is melanoma.

CBP and/or EP300-mediated disorders also include inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

CBP and/or EP300-mediated disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radio-contrast agent induced, sepsis induced, pneumonia induced, and drug toxicity induced; obesity; dyslipidemia; hypercholesterolemia; Alzheimer's disease; metabolic syndrome; hepatic steatosis; type II diabetes; insulin resistance; and diabetic retinopathy.

CBP and/or EP300 inhibitors may also be used to provide male contraception.

CBP and/or EP300-mediated disorders also include fibrotic diseases. Certain fibrotic diseases may include, for example, pulmonary fibrosis, silicosis, cystic fibrosis, renal fibrosis, liver fibrosis, liver cirrhosis, primary sclerosing cholangitis, primary biliary cirrhosis, endomyocardial fibrosis, mediastinal fibrosis, myelofibrosis, retroperitoneal fibrosis, progressive massive fibrosis, nephrogenic systemic fibrosis, Crohn's disease, keloid, myocardial infarction, systemic sclerosis or arthro fibrosis.

CBP and/or EP300-mediated disorders also include fibrotic lung diseases. Fibrotic lung diseases may include, for example, idiopathic pulmonary fibrosis, fibrotic interstitial lung disease, interstitial pneumonia, fibrotic variant of non-specific interstitial pneumonia, cystic fibrosis, lung fibrosis, chronic obstructive pulmonary lung disease (COPD), or pulmonary arterial hypertension. In certain embodiments, the fibrotic lung disease is idiopathic pulmonary fibrosis.

Co-Administration of Compounds and Other Agents

The compounds of formula (I) or formula (II) or salts thereof may be employed alone or in combination with other agents for treatment. For example, the second agent of the pharmaceutical combination formulation or dosing regimen may have complementary activities to the compound of formula (I) or formula (II) such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer. The term "co-administering" refers to either simultaneous administration, or any manner of separate sequential administration, of a compound of formula (I) or formula (II) or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I or formula II, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

Typically, any agent that has activity against a disease or condition being treated may be co-administered. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (I) or formula (II) or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG(geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CBI 1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γII and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1\lambda$ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 ($C_{225}$ or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/ Amgen); EMD 55900 (Stragliotto et al. *Eur. J Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenyl-ethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK 165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-Smith-Kline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-MI prime; Secreted homotrimeric LTa3 and membrane bound heterotrimer LTa1/(2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-$OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), *vinca* alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound of the present invention is administered in combination with a biologic agent, such as bevacizumab or panitumumab.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacizumab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

In another embodiment, provided are methods of using CBP/EP300 bromodomain inhibitors to treat and/or delay progression of cancer in combination with a PD-1 axis binding antagonist. Further provided herein are methods of enhancing immune function in an individual having cancer comprising administering to the individual an effective amount of a CBP/EP300 bromodomain inhibitor and an effective amount of a PD-1 axis binding antagonist. A PD-1 axis binding antagonist includes a PD-1 binding antagonist, a PD-L1 binding antagonist and a PD-L2 binding antagonist.

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PDL1, PDL2. In some embodiments, the PD-1 binding antagonist is a molecule that inhibits the binding of PD-1 to its binding partners. In a specific aspect, the PD-1 binding antagonist inhibits the binding of PD-1 to PDL1 and/or PDL2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PDL1 and/or PDL2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is nivolumab described herein (also known as MDX-1106-04, MDX-1106, ONO-4538, BMS-936558, and OPDIVO®). In another specific aspect, a PD-1 binding antagonist is pembrolizumab described herein (also known as MK-3475, Merck 3475, KEYTRUDA®, and SCH-900475). In another specific aspect, a PD-1 binding antagonist is CT-011 described herein (also known as hBAT or hBAT-1). In yet another specific aspect, a PD-1 binding antagonist is AMP-224 (also known as B7-DCIg) described herein.

The term "PDL1 binding antagonists" is a molecule that decreases, blocks, inhibits, abrogates or interferes with signal transduction resulting from the interaction of PDL1 with either one or more of its binding partners, such as PD-1, B7-1. In some embodiments, a PDL1 binding antagonist is a molecule that inhibits the binding of PDL1 to its binding partners. In a specific aspect, the PDL1 binding antagonist inhibits binding of PDL1 to PD-1 and/or B7-1. In some embodiments, the PDL1 binding antagonists include anti-PDL1 antibodies, antigen binding fragments thereof, immunoadhesins, fusion proteins, oligopeptides and other molecules that decrease, block, inhibit, abrogate or interfere with signal transduction resulting from the interaction of PDL1 with one or more of its binding partners, such as PD-1, B7-1. In one embodiment, a PDL1 binding antagonist reduces the negative co-stimulatory signal mediated by or through cell surface proteins expressed on T lymphocytes mediated signaling through PDL1 so as to render a dysfunctional T-cell less dysfunctional (e.g., enhancing effector responses to antigen recognition). In some embodiments, a PDL1 binding antagonist is an anti-PDL1 antibody. In a specific aspect, an anti-PDL1 antibody is YW243.55.S70 described herein. In another specific aspect, an anti-PDL1 antibody is MDX-1105 described herein (also known as BMS-936559). In still another specific aspect, an anti-PDL1 antibody is MPDL3280A described herein. In still another specific aspect, an anti-PDL1 antibody is MEDI4736 described herein.

The term "PDL2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

Alternative names for "PD-1" include CD279 and SLEB2. Alternative names for "PD-L1" include B7-H 1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2. In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide. In some embodiment, the PD-1 binding antagonist is an anti-PD-1 antibody (e.g., a human antibody, a humanized antibody, or a chimeric antibody). In some embodiments, the anti-PD-1 antibody is selected from the group consisting of MDX-1 106, Merck 3475 (also known as: pembrolizumab, lambrolizumab, or MK-3475), nivolumab (BMS-936558), CT-011, and MPDL3280A. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is anti-PD-L1 antibody. In some embodiments, the anti-PD-L1 binding antagonist is selected from the group consisting of YW243.55.S70, MPDL3280A and MDX-1 105. MDX-1 105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634 A1. MDX-1 106, also known as MDX-1 106-04, ONO-4538 or BMS-936558, is an anti-PD-1 antibody described in WO2006/121168. Merck 3745, also known as MK-3475 or SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342. In some embodiments, the anti-PD-1 antibody is MDX-1 106. Alternative names for "MDX-1106" include MDX-1 106-04, ONO-4538, BMS-936558 or Nivolumab. In some embodiments, the anti-PD-1 antibody is Nivolumab (CAS Registry Number: 946414-94-4). In some embodiments, the cancer is melanoma, NSCLC, and renal cell carcinoma.

For treating an inflammatory disease or an autoimmune disease, a compound of formula (I) or formula (II) or a pharmaceutically acceptable salt thereof may be co-administered with methotrexate, tofacitinib, 6-mercaptopurine, azathioprine sulphasalazine, mesalazine, olsalazine chloroquinine/hydroxychloroquinine, penicillamine, aurothiomalate (intramuscular and oral), azathioprine, cochicine, corticosteroids (oral, inhaled, and local injection), a beta-2 adrenoreceptor agonist (salbutamol, terbutaline, salmeteral), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-1RI, siL-1RII, siL-6R), an antiinflammatory cytokine (e.g. IL-4, IL-10, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCi, sulfadiazine, oxycodone HCVacetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL1S, BIRB-796, SCI0-469, VX-702, AMG-548, VX-740, Roflumilast, IC-485, CDC-801, S1P1 agonists (such as FTY720), a PKC family inhibitor (e.g. Ruboxistaurin or AEB-071) or Mesopram. In certain embodiments, a compound of formula (I) or formula (II) or a pharmaceutically acceptable salt thereof may be co-administered with methotrexate or leflunomide. In moderate or severe Rheumatoid arthritis cases, a compound of formula (I) or formula (II) or a pharmaceutically acceptable salt thereof may be co-administered with cyclosporine and anti-TNF antibodies as noted above. A compound of formula (I) or formula (II) or a pharmaceutically acceptable salt thereof may also be co-administered with: budenoside; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-1RI, siL-1RII, siL-6R), and an antiinflammatory cytokine (e.g. IL-4, IL-10, IL-11, IL-13 or TGF).

For treating Crohn's disease, a compound of formula (I) or formula (II) or a pharmaceutically acceptable salt thereof may be co-administered with a TNF antagonist (e.g. an anti-TNF antibody), D2E7 (adalimumab), CA2 (infliximab), CDP 571, a TNFR-Ig construct, (p75TNFRigG (etanercept)), a p55TNFRigG (LENERCEPT™) inhibitor, or a PDE4 inhibitor.

For treating inflammatory bowel disease, a compound of formula (I) or formula (II) or a pharmaceutically acceptable salt thereof may be co-administered with a corticosteroid (e.g. budenoside or dexamethasone); sulfasalazine, 5-aminosalicylic acid; olsalazine; an agent that interferes with synthesis or action of proinflammatory cytokines such as IL-1 (e.g. an IL-1 converting enzyme inhibitor or IL-Ira); a T cell signaling inhibitor (e.g. a tyrosine kinase inhibitor); 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab or interferon-gamma.

For treating multiple sclerosis, a compound of formula (I) or formula (II) or a pharmaceutically acceptable salt thereof may be co-administered with a corticosteroid; prednisolone;

methylprednisolone; azathioprine; cyclophosphamide; cyclosporine; methotrexate; 4-aminopyridine; tizanidine; interferon-1a (AVONEX®; Biogen); interferon-1b (BETA-SERON®; Chiron/Berlex); interferon-n3) (Interferon Sciences/Fujimoto), interferon-(Alfa Wassermann/J&J), interferon IA-IF (Serono/Inhale Therapeutics), Peginterferon 2b (Enzon/Schering-Plough), Copolymer 1 (Cop-1; COPAXONE®; Teva Pharmaceutical Industries, Inc.); hyperbaric oxygen; intravenous immunoglobulin; cladribine; an antibody to or antagonist of other human cytokines or growth factors and their receptors (e.g. TNF, LT, IL-1, IL-2, IL-6, IL-7, IL-8, IL-12, IL-23, IL-15, IL-16, EMAP-II, GM-CSF, FGF, or PDGF).

For treating AIDS a compound of formula (I) or formula (II) or a pharmaceutically acceptable salt therof may be co-administered with antibodies to cell surface molecules such as CD2, CD3, CD4, CD8, CD19, CD20, CD25, CD28, CD30, CD40, CD45, CD69, CD80, CD86, CD90 or their ligands. A compound of formula (I) or formula (II) or a pharmaceutically acceptable salt therof may also be co-administered with methotrexate, cyclosporine, FK506, rapamycin, mycophenolate mofetil, leflunomide, an SIP1 agonist, an NSAID (e.g. ibuprofen), a corticosteroid (e.g. prednisolone), a phosphodiesterase inhibitor, an adensosine agonist, an antithrombotic agent, acomplement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a TACE inhibitor, a T-cell signaling inhibitor (e. g. a kinase inhibitor), a metalloproteinase inhibitor, sulfasalazine, azathioprine, a 6-mercaptopurine, an angiotensin converting enzyme inhibitor, a soluble cytokine receptor (e.g. soluble p55 or p75 TNF receptors, siL-1RI, siL-1RII, or siL-6R), or an antiinflammatory cytokine (e.g. IL-4, IL-10, IL-13 or TGF).

A compound of formula (I) or formula (II) or a pharmaceutically acceptable salt thereof may also be co-administered with agents, such as alemtuzumab, dronabinol, daclizumab, mitoxantrone, xaliproden hydrochloride, fampridine, glatiramer acetate, natalizumab, sinnabidol, immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, an anti-IL-6 receptor antibody, neurovax, pirfenidone allotrap 1258 (RDP-1258), sTNF-RI, talampanel, teriflunomide, TGF-beta2, tiplimotide, a VLA-4 antagonist (e.g. TR-14035, VLA4 Ultrahaler, or Antegran-ELAN/Biogen), an interferon gamma antagonist, or an IL-4 agonist.

For treating ankylosing spondylitis a compound of formula (I) or formula (II) or a pharmaceutically acceptable salt thereof may be co-administered with ibuprofen, diclofenac, misoprostol, naproxen, meloxicam, indomethacin, diclofenac, celecoxib, rofecoxib, sulfasalazine, methotrexate, azathioprine, minocyclin, prednisone, an anti-TNF antibody, D2E7 (HUMIRA®), CA2 (infliximab), CDP 571, a TNFR-Ig construct, (p75TNFRigG (ENBREL®), or p55TNFRigG (LENERCEPT®).

For treating asthma a compound of formula (I) or formula (II) or a pharmaceutically acceptable salt thereof may be co-administered with albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, cromolyn sodium, fexofenadine hydrochloride, flunisolide/menthol, amoxicillin/clavulanate, levofloxacin, guaifenesin, dexamethasone sodium phosphate, moxifloxacin HCl, doxycycline hyclate, guaifenesin/d-methorphan, p-ephedrine/cod/-chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chiorpheniramine/hydrocodone, nedocromil sodium, terbutaline sulfate, epinephrine, methylprednisolone, an anti-IL-13 antibody, or metaproterenol sulfate.

For treating COPD a compound of formula (I) or formula (II) or a pharmaceutically acceptable salt thereof may be co-administered with albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast, or roflumilast.

For treating psoriasis, a compound of formula (I) or formula (II) or a pharmaceutically acceptable salt thereof may be co-administered with calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, he/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 or ustekinamab.

For treating psoriatic arthritis, a compound of formula (I) or formula (II) or a pharmaceutically acceptable salt thereof may be co-administered with methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), or efalizumab.

For treating lupus, a compound of formula (I) or formula (II) or a pharmaceutically acceptable salt thereof may be co-administered with an NSAID (e.g. diclofenac, naproxen, ibuprofen, piroxicam, or indomethacin); a COX2 inhibitor (e.g. celecoxib, rofecoxib, or valdecoxib); an anti-malarial (e.g. hydroxychloroquine); a steroid (e.g. prednisone, prednisolone, budenoside, or dexamethasone); a cytotoxic (e.g. azathioprine, cyclophosphamide, mycophenolate mofetil, or methotrexate); an inhibitor ofPDE4, or a purine synthesis inhibitor (e.g. Cellcept®). For example, acompound of formula (I) or formula (II) or a pharmaceutically acceptable salt thereof may be co-administered with sulfasalazine, 5-aminosalicylic acid, olsalazine, Imuran®, an agent that interferes with the synthesis, production, or action of a proinflammatory cytokine (e.g. IL-1), or a caspase inhibitor (e.g. a IL-1 converting enzyme inhibitor or IL-Ira).

A compound of formula (I) or formula (II) or a pharmaceutically acceptable salt thereof may also be co-administered with a T cell signaling inhibitor (e.g. a tyrosine kinase inhibitor), or a molecule that targets T cell activation (e.g. CTLA-4-IgG, an anti-B7 family antibody, or an anti-PD-1 family antibody).

A compound of formula (I) or formula (II) or a pharmaceutically acceptable salt thereof can also be co-administered with an IL-11 antibody, an anti-cytokine antibody (e.g. fonotolizumab (anti-IFNg antibody)), or an anti-receptor receptor antibodies (e.g. an anti-IL-6 receptor antibody or an antibody to a B-cell surface molecule).

A compound of formula (I) or formula (II) or a pharmaceutically acceptable salt thereof can also be co-administered with LJP 394 (abetimus), an agent that depletes or inactivates B-cells (e.g. Rituximab (anti-CD20 antibody) or lymphostat-B (anti-BlyS antibody)), a TNF antagonist (e.g. an anti-TNF antibody), D2E7 (adalimumab), CA2 (infliximab), CDP 571, a TNFR-Ig construct, (p75TNFRigG (etanercept), or p55TNFRigG (LENERCEPT™).

A compound of formula (I) or formula (II) or a pharmaceutically acceptable salt thereof can also be co-administered with one or more agents used in the prevention or treatment of AIDS: an HIV reverse transcriptase inhibitor, an HIV protease inhibitor, an immunomodulator, or another retroviral drug. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

For treating type II diabetes, hepatic steatosis, insulin resistance, metabolic syndrome or a related disorder, a compound of formula (I) or formula (II) or a pharmaceutically acceptable salt thereof may be co-administered with insulin or insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide or tolbutamide; agents that are glucagon-like peptide agonists such as exanatide, liraglutide or taspoglutide; agents that inhibit dipeptidyl-peptidase IV such as vildagliptin, sitagliptin, saxagliptin, linagliptin, allogliptin or septagliptin; agents that bind to the peroxisome proliferator-activated receptor gamma such as rosiglitazone or pioglitazone; agents that decrease insulin resistance such as metformin; or agents that reduce glucose absorbance in the small intestine such as acarbose, miglitol or voglibose.

For treating acute kidney disorders or a chronic kidney disease, a compound of formula (I) or formula (II) or a pharmaceutically acceptable salt thereof may be co-administered with dopamine, a diuretic (e.g. furosemide), bumetanide, thiazide, mannitol, calcium gluconate, sodium bicarbonate, albuterol, paricalcitol, doxercalciferol, cinacalcet, or bardoxalone methyl.

The amount of both the compound of formula (I) or formula (II) or salt thereof and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound of formula (I) or formula (II) may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 µg/kg body weight/day of the additional therapeutic agent can be administered.

Provided herein are methods of extending the duration of response to a cytotoxic agent in an individual with cancer comprising administering to the individual (a) an effective amount of a compound of formula (I) or formula (II) or a pharmaceutically acceptable salt thereof and (b) an effective amount of the cytotoxic agent.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl)ethylamino)methyl)furan-2-yl)quinazolin-4-amine, di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor.

In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS#878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a *vinca* alkyloid. In certain embodiments, the Exemplification of Compounds of Formula (I)

As depicted in the Examples of Compounds of Formula (I), below, in certain exemplary embodiments, compounds of Formula (I) are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

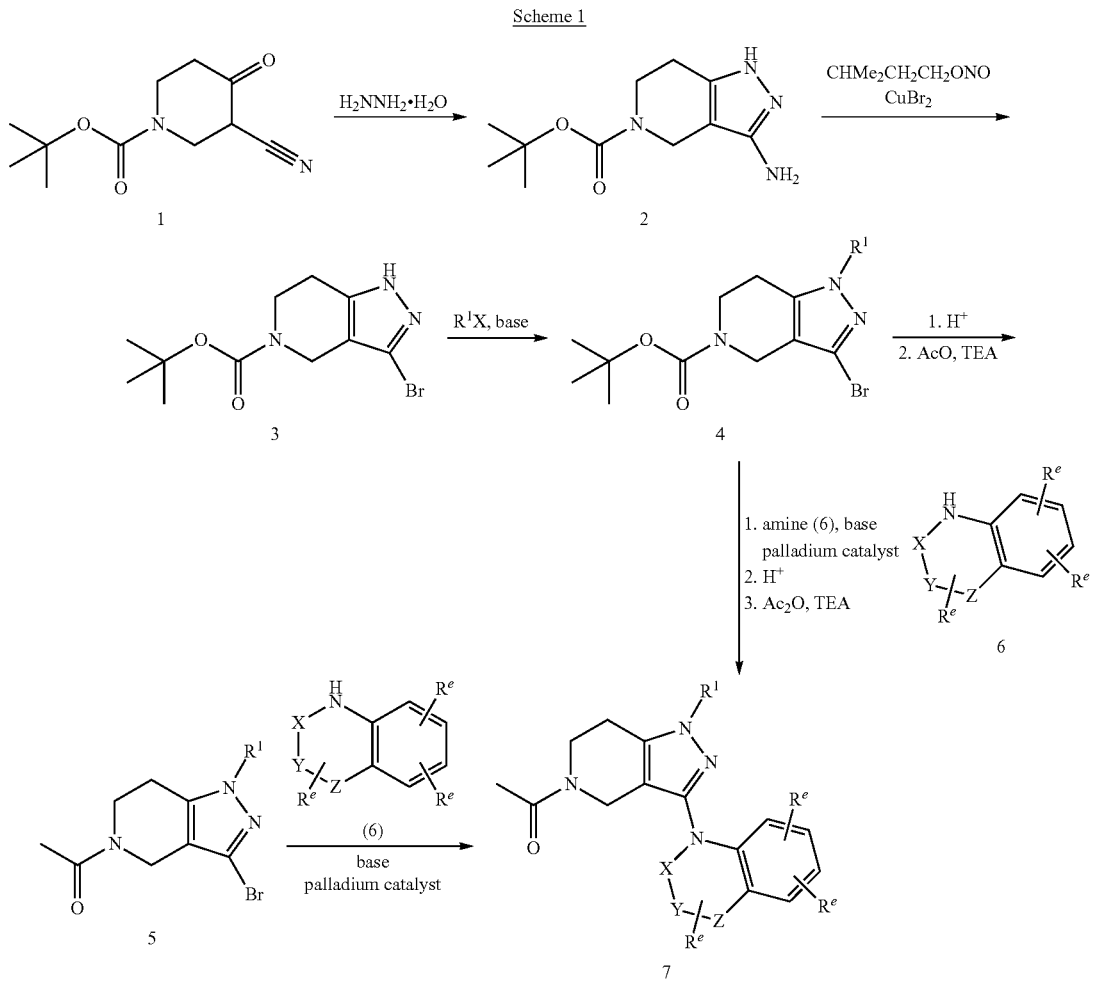

*vinca* alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound of formula (I) or formula (II) or a pharmaceutically acceptable salt thereof is concomitantly administered with the cytotoxic agent (e.g., targeted therapy, chemotherapy, and/or radiotherapy). In certain embodiments, the compound of formula (I) or formula (II) or a pharmaceutically acceptable salt thereof is administered prior to and/or concurrently with the cytotoxic agent (e.g., targeted therapy, chemotherapy, and/or radiotherapy).

Compounds of formula (7) may be prepared by general synthetic methods as shown in Scheme 1.

Reaction between cyano-ketone (1) and hydrazine in a suitable solvent such as ethanol at a temperature ranging from about room temperature to reflux and for a time varying from about 30 minutes to about 2 hours, can readily produce bicycle-pyrazole (2). The bromo pyrazole can be formed by converting the amino pyrazole (2) using a nitrite such as, but not limited to, isoamylnitrite, sodium nitrite, or tert-butyl nitrite and a copper(II) bromide in organic an solvent such as, but not limited to, acetonitrile at a temperature of about 20° C. to about 60° C. for a time of about 5 hours. The alkylation of pyraozle $N^1$ nitrogen of (2) can be carried out using an alkyl iodide/bromide/mesylate/triflate in the presense of an inorganic base such as, but not limited to, sodium hydride or cesium carbonate in a suitable organic solvent such as, but not limited to, N,N-dimethylformamide (DMF) or tetrahydrofuran (THF) at a temperature ranging from about 0° C. to 120° C. and for a time varying from about 30 minutes to about 16 hours to form compounds of formula (4). Deprotection of N-tert-butoxycarbonyl (Boc) group using a protic acid such as, but not limited to, trifluoroacetic acid or hydrochloric acid, and subsequent N-acetylation using acetic anhydride in the presence of a base such as, but not limited to, triethylamine (TEA) can readily afford compounds of formula (5). The bromide (5) can cross-couple with aryl/heteroaryl/cycloalkyl amine (6) under a palladium catalyst system such as, but not limited to, Ruphos pre-catalyst in combination with Brettphos/Ruphos ligand or Pd-(ipent-PEPPSI) in the presence of an inorganic base such as, but not limited to, sodium tert-butoxide or cesium carbonate in 1,4-dioxane at elevated temperature to yield compounds of formula (7). Alternatively, compounds of formula (7) can be prepared from the bromide (5) upon treatment with amine (6) in the presence of an inorganic base under the analogous palladium-catalyzed conditions mentioned above, followed by sequential Boc deprotection and N-acetylation.

halides under the analogous palladium catalyst conditions can also yield compounds of formula (9).

Scheme 3

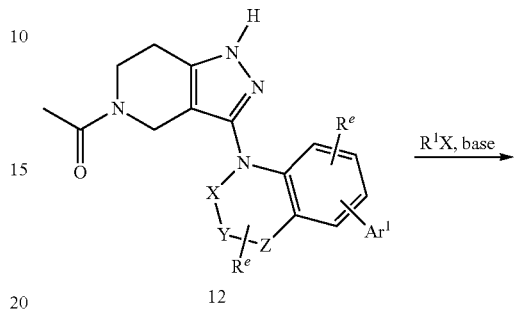

Compounds of formula (9) may be prepared by general synthetic methods as shown in Scheme 2.

Compounds of formula (9) can be prepared from the bromide (8) upon treatment with aryl, heteroaryl or heterocyclic boronic acids or boronate esters under palladium catalyst conditions such as, but not limited to, [1,1'-bis(diphenylphosphino)ferrocene]dichloropalladium(II) in the presence of an inorganic base such as, but not limited to, sodium carbonate in an organic solvent such as, but not limited to, 1,4-dioxane at an elevated temperature. Alternatively, reaction between bromide (8) and 4,4,4',4',5,5,5',5'-octamethyl-2,2'-bi(1,3,2-dioxaborolane) (10) under a palladium catalyst conditions can produce the corresponding boronate ester (11) that upon treatment with aryl, heteroaryl or heterocyclic Scheme 2

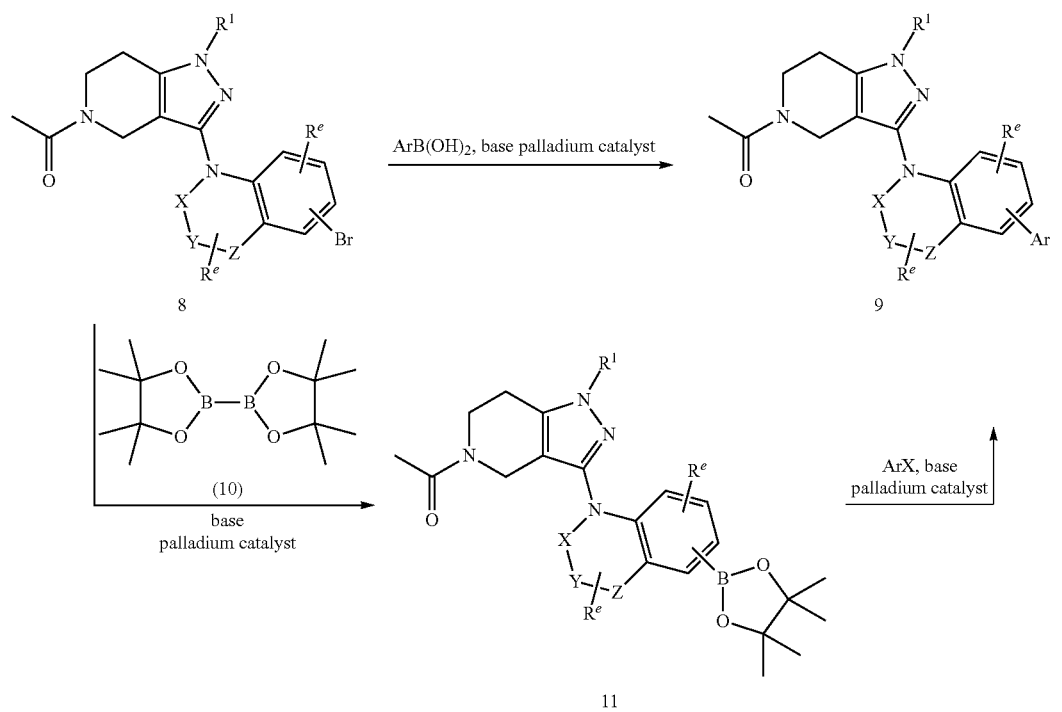

-continued

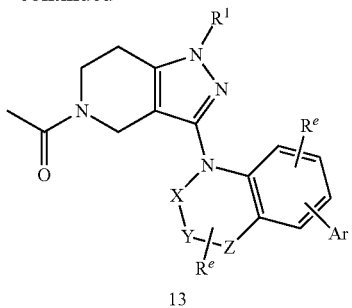

Compounds of formula (13) may be prepared by general synthetic methods as shown in Scheme 3.

Compounds of formula (12) can be alkylated using an alkyl iodide/bromide/mesylate/triflate in the presence of an inorganic base such as, but not limited to, sodium hydride or cesium carbonate in a suitable organic solvent such as, but not limited to, DMF or THF at a temperature ranging from about 0° C. to 120° C. to yield compounds of formula (13).

-continued

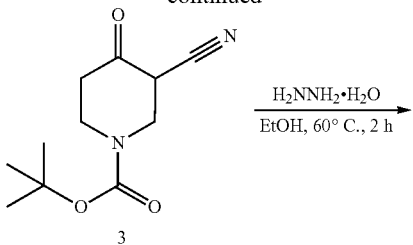

3

Scheme 4

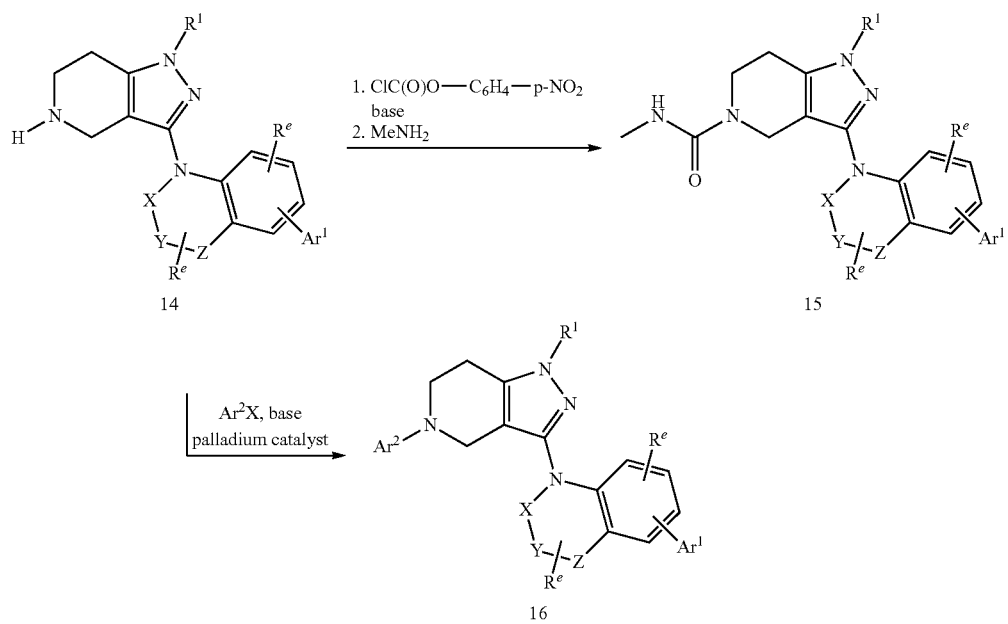

Compounds of formula (14) and (15) may be prepared by general synthetic methods as shown in Scheme 4.
Treatment of piperidine (14) with 4-nitrophenyl chloroformate in the presence of base such as, but not limited to, pyridine followed by addition of methyl amine yields compounds of formula (15). Piperidine (14) can also react with aryl, heteroaryl or heterocyclic halides under palladium catalyst conditions to produce compounds of formula (16).

General Procedure for Intermediates A & B

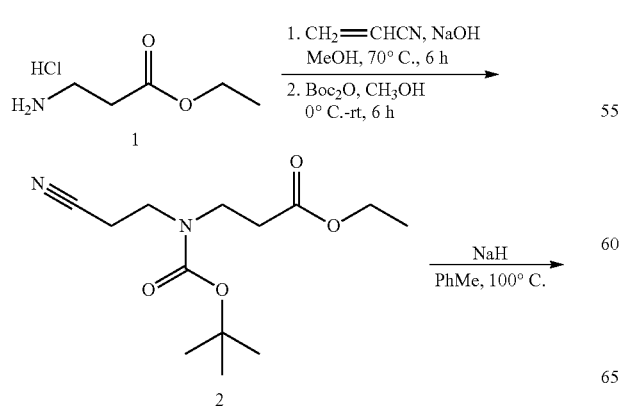

-continued

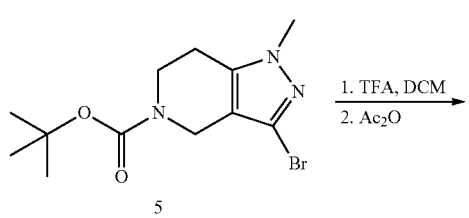

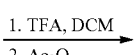

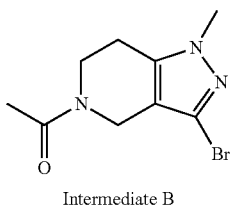

Intermediate B

Step 1 ethyl 3-((tert-butoxycarbonyl)(2-cyanoethyl)amino)propanoate

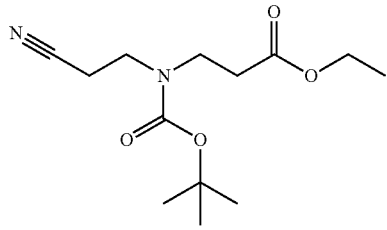 [SMILES: CCOC(=O)CCN(CCC#N)C(=O)OC(C)(C)C]

To a solution of ethyl 3-aminopropanoate hydrochloride (366.5 g, 2.39 mol) in MeOH (1.2 L) at room temperature was added NaOH (95.6 g, 2.39 mol) in portions. The mixture was heated to 70° C., acrylonitrile (158 g, 2.98 mol) was added dropwise and the reaction mixture stirred for 6 h. The solution was cooled to 0° C. before (Boc)$_2$O (521 g, 2.39 mol) was added. The reaction was stirred at room temperature for 6 h, filtered, and washed with MeOH (200 mL). The filtrate was concentrated in vacuo to give a yellow oil residue that was re-dissolved in EtOAc and water (500 mL). The aqueous layer was extracted with EtOAc (800 mL). The combined organic layers were dried over anhydrous Na$_2$SO$_4$, filtered and concentrated in vacuo to give the title compound (638 g) as light yellow oil that required no further purification. $^1$H NMR (400 MHz, CDCl$_3$) δ 4.17 (q, J=7.2 Hz, 2H), 3.68-3.62 (m, 4H), 2.57-2.53 (m, 4H), 1.49 (s, 9H), 1.29 (t, J=7.2 Hz, 3H).

Step 2 tert-butyl 3-cyano-4-oxopiperidine-1-carboxylate

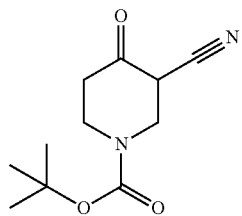 [SMILES: CC(C)(C)OC(=O)N1CCC(=O)C(C#N)C1]

To toluene (2.7 L) at 25° C. was added NaH (80 g, 2.0 mol) portion-wise and the suspension was heated to 80° C. Ethyl 3-((tert-butoxycarbonyl)(2-cyanoethyl)amino)propanoate (270 g, crude) in anhydrous toluene (270 mL) was added dropwise. The mixture was heated to 100° C. and stirred for 5 hours. The mixture was cooled to room temperature, quenched with sat. aq. ammonium chloride (800 mL) and washed with hexanes (800 mL). The aqueous phase was acidified with HCl (2 N) to pH 6 and then extracted with EtOAc (1 L×2). The combined organic layers were dried over anhydrous Na$_2$SO$_4$, filtered and concentrated in vacuo to give the title compound (310 g) as yellow oil that required no further purification. $^1$H NMR (400 MHz, CDCl$_3$) δ 4.17-4.14 (m, 1H), 3.59-3.56 (m, 2H), 3.43-3.41 (m, 2H), 2.70-2.66 (m, 2H), 1.51 (s, 9H).

Step 3 tert-butyl 3-amino-6,7-dihydro-1H-pyrazolo[4,3-c]pyridine-5(4H)-carboxylate

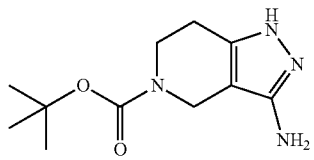 [SMILES: CC(C)(C)OC(=O)N1CCc2[nH]nc(N)c2C1]

A mixture of tert-butyl 3-cyano-4-oxopiperidine-1-carboxylate (310 g, 1.38 mol) and hydrazine mono-hydrate (140 mL, 2.08 mol) in EtOH (1.5 L) was heated to 60° C. for 2 h. The mixture was concentrated in vacuo to give the crude product that was dissolved in EtOAc (1 L) and washed with water (1 L×2). The organic layer was dried over anhydrous Na$_2$SO$_4$, filtered and concentrated in vacuo to afford the title compound (230 g, 70%) as a colorless solid. $^1$H NMR (400 MHz, CD$_3$OD) δ 4.28 (s, 2H), 3.66-3.63 (m, 2H), 2.62-2.59 (m, 2H), 1.49 (s, 9H).

Step 4 tert-butyl 3-bromo-6,7-dihydro-1H-pyrazolo[4,3-c]pyridine-5(4H)-carboxylate

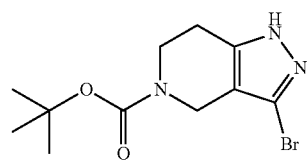 [SMILES: CC(C)(C)OC(=O)N1CCc2[nH]nc(Br)c2C1]

To a stirred mixture of tert-butyl 3-amino-6,7-dihydro-1H-pyrazolo[4,3-c]pyridine-5(4H)-carboxylate (120 g, 503.6 mmol), CuBr$_2$ (112.5 g, 503.6 mmol) and MeCN (1.2 L) at 0° C. was added isopentyl nitrite (76.7 g, 654.7 mmol) and the reaction mixture stirred for 20 min. The temperature was raised to 60° C. and the reaction mixture was stirred for an additional 5 h. After cooling the reaction to room temperature, the reaction mixture was quenched with water (1 L) and the mixture was extracted with EtOAc (1 L×2). The combined organic layers were dried over anhydrous Na$_2$SO$_4$, filtered and concentrated in vacuo. The crude residue was purified by silica gel chromatography (petroleum ether/EtOAc=4:1) to afford the title compound (Intermediate A, 52 g, 34%) as light yellow solid. LCMS M/Z (M+H) 302.

Step 5 tert-butyl 3-bromo-1-methyl-6,7-dihydro-1H-pyrazolo[4,3-c]pyridine-5(4H)-carboxylate

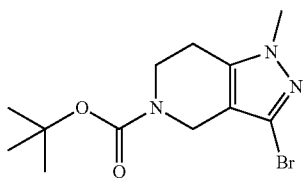 [SMILES: Cn1nc(Br)c2c1CCN(C(=O)OC(C)(C)C)C2]

To a stirred solution of tert-butyl 3-bromo-6,7-dihydro-1H-pyrazolo[4,3-c]pyridine-5(4H)-carboxylate (Intermediate A, 32 g, 105.9 mmol) in THF at 0° C. (350 mL) was added NaH (5.08 g, 127.1 mmol) and the mixture was stirred for 30 min. Methyliodide (18.05 g, 127.1 mmol) was added dropwise and the mixture stirred for an additional 2 h. The mixture was quenched with water and extracted with EtOAc (300 mL×2). The combined organic layers were dried over anhydrous $Na_2SO_4$, filtered and concentrated in vacuo. The crude residue was purified by silica gel chromatography (petroleum ether/EtOAc=8:1) to afford the title compound (16 g, 48%) as a colorless oil. $^1$H NMR (400 MHz, $CD_3OD$) δ 4.24 (s, 2H), 3.70 (s, 3H), 3.69-3.67 (m, 2H), 2.70-2.67 (m, 2H), 1.47 (s, 9H).

Step 6

1-(3-bromo-1-methyl-6,7-dihydro-1H-pyrazolo[4,3-c]pyridin-5(4H)-yl)ethanone

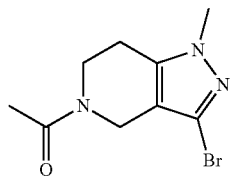

A mixture of tert-butyl 3-bromo-1-methyl-6,7-dihydro-1H-pyrazolo[4,3-c]pyridine-5(4H)-carboxylate (12 g, 38.0 mmol) and trifluoroacetic acid (40 mL) in DCM (80 mL) was stirred at room temperature for 2 h. The mixture was concentrated in vacuo and the residue was re-dissolved in DCM (120 mL). The mixture was cooled to 0° C. before TEA (12.1 g, 120 mmol) and acetic anhydride (5.3 g, 52 mmol) were added dropwise. The mixture stirred at room temperature for an additional 2 h before water (100 mL) was added. The organic layer was dried over anhydrous $Na_2SO_4$, filtered and concentrated in vacuo. The crude residue was purified by silica gel chromatography (DCM/MeOH=20:1) to afford the title compound (Intermediate B, 8.5 g, 87%) as white solid. $^1$H NMR (400 MHz, $CD_3OD$) δ 4.40-4.39 (m, 2H), 3.88-3.78 (m, 2H), 3.72 (s, 3H), 2.83-2.70 (m, 2H), 2.20-2.17 (m, 3H).

General Procedure for Intermediate C

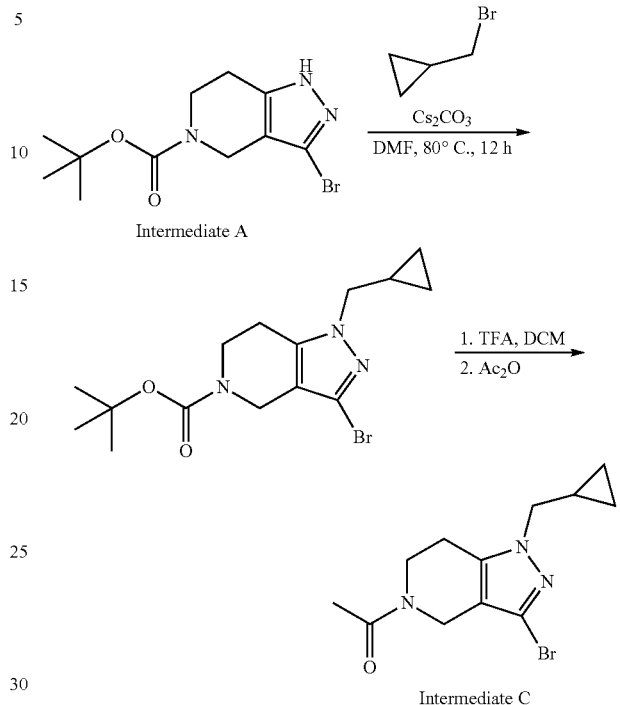

Intermediate A

Intermediate C

Step 1 tert-butyl 3-bromo-1-(cyclopropylmethyl)-6,7-dihydro-1H-pyrazolo[4,3-c]pyridine-5(4H)-carboxylate

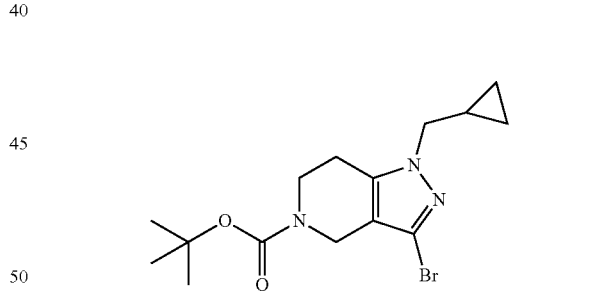

To a stirred solution of tert-butyl 3-bromo-6,7-dihydro-1H-pyrazolo[4,3-c]pyridine-5(4H)-carboxylate (Intermediate A, 6.0 g, 19.8 mmol) in DMF (40 mL) was added $Cs_2CO_3$ (9.70 g, 29.8 mmol) and (bromomethyl)cyclopropane (4.0 g, 29.8 mmole). The reaction mixture was heated to 80° C. for 12 h. The mixture was diluted with EtOAc (200 mL), washed with brine (100 mL×3), dried over $Na_2SO_4$, filtered and concentrated in vacuo. The crude residue was purified by silica gel chromatography (eluent gradient from petroleum ether to petroleum ether/tert-butyl methyl ether/THF=10:1:1) to give the title compound (3.0 g, 42%) as a white solid. $^1$H NMR (400 MHz, $CDCl_3$) δ 4.29 (s, 2H), 3.85 (d, J=3.4 Hz, 2H), 3.71 (t, J=5.2 Hz, 2H), 2.67 (t, J=5.2 Hz, 2H), 1.49 (s, 9H), 1.25-1.18 (m, 1H), 0.61-0.55 (m, 2H), 0.35-0.31 (m, 2H).

Step 2

1-(3-bromo-1-(cyclopropylmethyl)-6,7-dihydro-1H-pyrazolo[4,3-c]pyridin-5(4H)-yl)ethanone

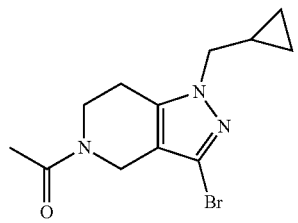 [SMILES: CC(=O)N1CCc2c(c(Br)nn2CC2CC2)C1]

A mixture of tert-butyl 3-bromo-1-(cyclopropylmethyl)-6,7-dihydro-1H-pyrazolo[4,3-c]pyridine-5(4H)-carboxylate (3.0 g, 8.4 mmol) and trifluoroacetic acid (30 mL) in DCM (30 mL) was stirred at room temperature for 2 h. The solvent was concentrated in vacuo and the crude product was re-dissolved in DCM (120 mL). The solution was cooled to 0° C. before TEA (2.49 g, 24.6 mmol) and acetic anhydride (1.26 g, 12.3 mmol) were added dropwise. The reaction mixture was stirred at room temperature for additional 2 h before it was quenched with water. The organic layer was dried over anhydrous $Na_2SO_4$, filtered and concentrated in vacuo. The crude residue was purified by silica gel chromatography (DCM/MeOH=20:1) to afford the title compound (2.40 g, 96%) as a white solid. $^1$H NMR (400 MHz, $CDCl_3$) δ 4.49-4.33 (m, 3H), 3.90-3.70 (m, 4H), 2.77-2.67 (m, 2H), 2.23-2.19 (m, 3H), 1.28-1.18 (m, 1H), 0.63-0.58 (m, 2H), 0.36-0.32 (m, 2H).

General Procedure for Intermediates D & E

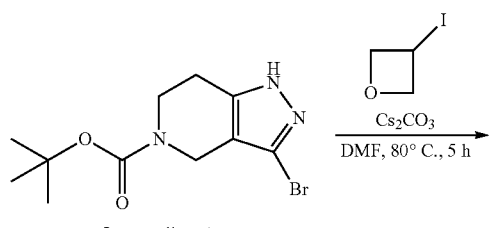

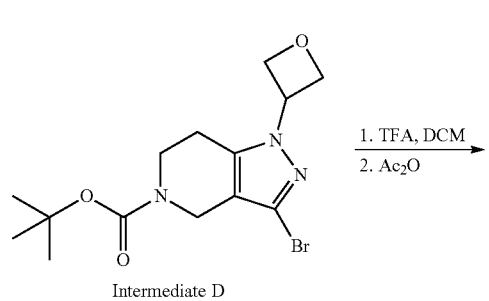

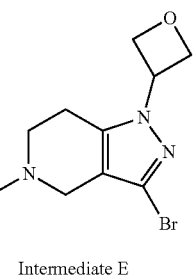

Intermediate E

Step 1 tert-butyl 3-bromo-1-(oxetan-3-yl)-6,7-dihydro-1H-pyrazolo[4,3-c]pyridine-5(4H)-carboxylate

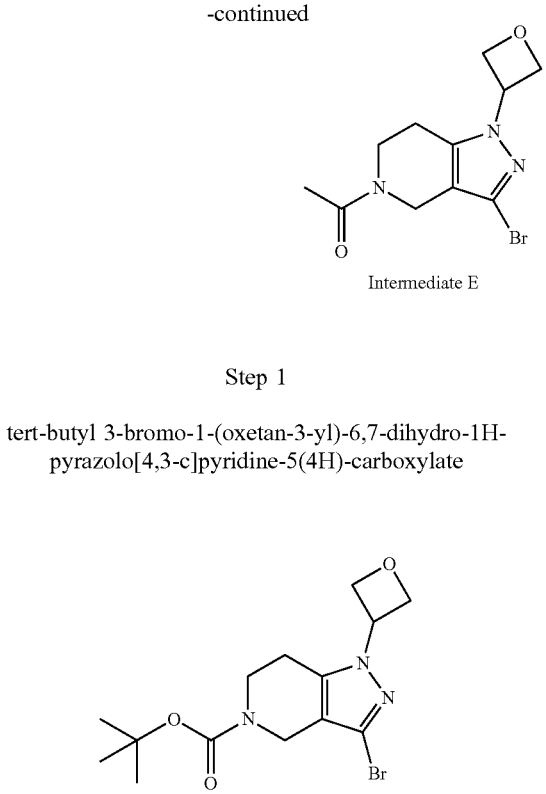

To a solution of tert-butyl 3-bromo-6,7-dihydro-1H-pyrazolo[4,3-c]pyridine-5(4H)-carboxylate (Intermediate A, 40.0 g, 132 mmol) in DMF (500 mL) was added $Cs_2CO_3$ (87 g, 264 mmol) and 3-iodooxetane (27 g, 146 mmol). The mixture was heated to 60° C. for 12 h before 3-iodooxetane (5 g, 27.0 mmol) was added and the mixture was stirred at 60° C. for an additional 6 h. After cooling the reaction to room temperature, the mixture was filtered, washed with EtOAc (500 mL) and concentrated in vacuo. The crude residue was purified by silica gel chromatography (petroleum ether:tert-butyl methyl ether:THF=from 100:1:1 to 5:1:1) to give the title compound (Intermediate D, 30 g, 64%) as a white solid. $^1$H NMR (400 MHz, $CDCl_3$) δ 5.30-5.25 (m 1H), 5.18-5.14 (m, 2H), 4.95-4.91 (m, 2H), 4.28 (s, 2H), 3.73-3.66 (m, 2H), 2.64 (t, J=5.6 Hz, 2H), 1.48 (s, 9H).

Step 2

1-(3-bromo-1-(oxetan-3-yl)-6,7-dihydro-1H-pyrazolo[4,3-c]pyridin-5(4H)-yl)ethanone

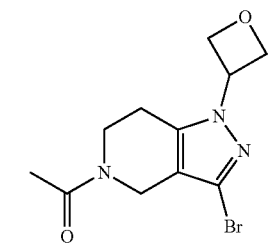 [SMILES: CC(=O)N1CCc2c(c(Br)nn2C2COC2)C1]

To a solution of tert-butyl 3-bromo-1-(oxetan-3-yl)-6,7-dihydro-1H-pyrazolo[4,3-c]pyridine-5(4H)-carboxylate (Intermediate D, 25.0 g, 70.0 mmol) in DCM (50 mL) was added trifluoroacetic acid (50 mL) dropwise at 0° C. The mixture was stirred at room temperature for 2 h. The mixture was concentrated in vacuo and the residue was re-dissolved in DCM (500 mL). The mixture was cooled to 0° C. before triethylamine (36.0 g, 350 mmol) and acetic anhydride (7.2 g, 70.0 mmol) were added dropwise. The mixture was stirred at room temperature for additional 2 h. The reaction was quenched with water. The organic layer was dried over anhydrous $Na_2SO_4$, filtered and concentrated in vacuo. The crude residue was purified by silica gel chromatography (DCM/MeOH=80:1) to give the title compound (Intermediate E, 17.0 g, 81%) as a light yellow solid. $^1$H NMR (400 MHz, $CDCl_3$) δ 5.32-5.27 (m 1H), 5.16-5.13 (m, 2H), 4.95-4.91 (m, 2H), 4.47-4.31 (m, 2H), 3.88-3.70 (m, 2H), 2.75-2.63 (m, 2H), 2.17 (s, 3H).

General Procedure for Intermediates F & G

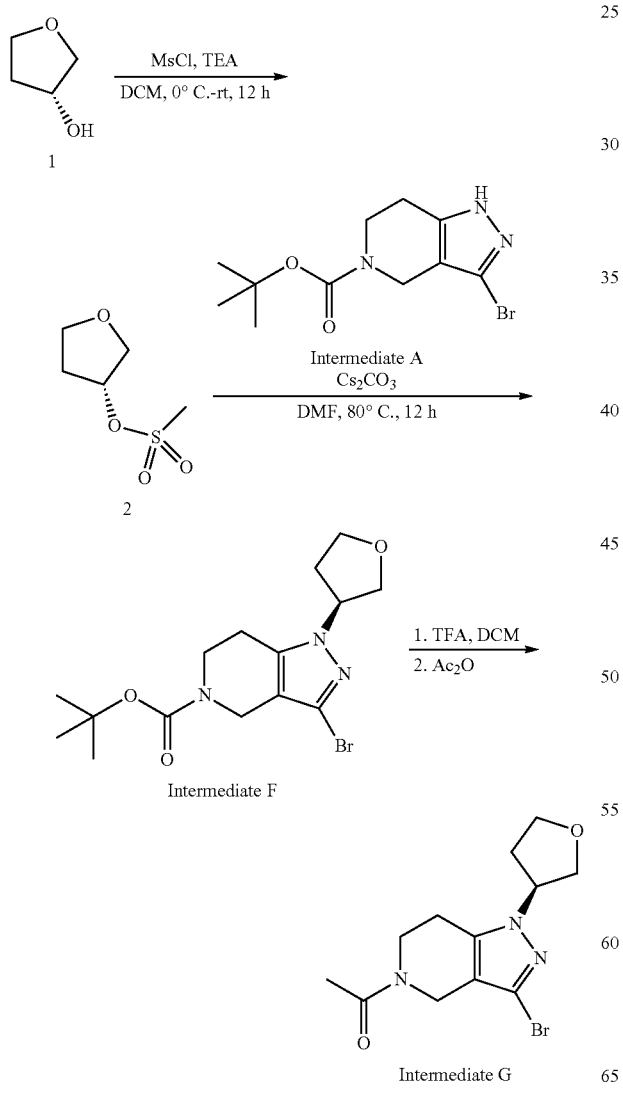

Intermediate F

Intermediate G

Step 1

(R)-tetrahydrofuran-3-yl methanesulfonate

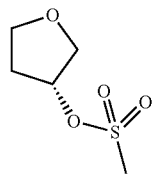

To a solution of (R)-tetrahydrofuran-3-ol (25 g, 253.7 mmol) in DCM (250 mL) at 0° C. was added triethylamine (86 g, 851.2 mmol) and mesyl chloride (39 g, 340.48 mmol) dropwise. The mixture was stirred at room temperature for 12 h. The reaction was quenched with water (100 mL) and extracted with DCM (100 mL×2). The combined organic layers were dried over anhydrous $Na_2SO_4$, filtered and concentrated in vacuo to give the title compound (47 g, 99%) as a brown oil. $^1$H NMR (400 MHz, $CDCl_3$) δ 5.35-5.27 (m, 1H), 4.05-3.83 (m, 4H), 3.04 (s, 3H), 2.28-2.20 (m, 2H).

Step 2

(S)-tert-butyl 3-bromo-1-(tetrahydrofuran-3-yl)-6,7-dihydro-1H-pyrazolo[4,3-c]pyridine-5(4H)-carboxylate

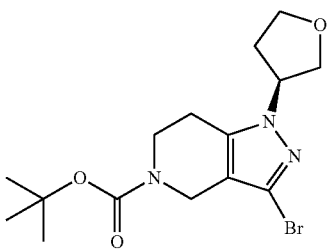 [SMILES: CC(C)(C)OC(=O)N1CCc2c(c(Br)nn2[C@H]2CCOC2)C1]

To a solution of tert-butyl 3-bromo-6,7-dihydro-1H-pyrazolo[4,3-c]pyridine-5(4H)-carboxylate (Intermediate A, 24.8 g, 82 mmol) in DMF (200 mL) was added $Cs_2CO_3$ (79 g, 246 mmol) and (R)-tetrahydrofuran-3-yl methanesulfonate (17.4 g, 98 mmol). The mixture was heated to 80° C. for 12 h. After cooling the reaction to room temperature, the mixture was concentrated in vacuo. The crude residue was purified by silica gel chromatography (petroleum ether/EtOAc=from 10:1 to 3:1) to give the title compound (Intermediate F, 50 g, 71%) as a yellow oil. $^1$H NMR (400 MHz, DMSO-$d_6$) δ 4.97-4.78 (m, 1H), 4.13 (s, 2H), 3.98-3.86 (m, 2H), 3.81-3.67 (m, 2H), 3.56 (t, J=5.6 Hz, 2H), 2.68 (t, J=5.6 Hz, 2H), 2.33-2.08 (m, 2H), 1.38 (s, 9H).

Step 3

(S)-1-(3-bromo-1-(tetrahydrofuran-3-yl)-6,7-dihydro-1H-pyrazolo[4,3-c]pyridin-5(4H)-yl)ethanone

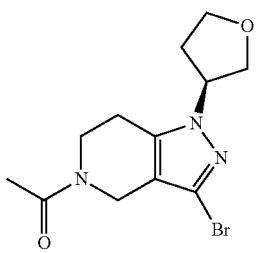 [SMILES: CC(=O)N1CCc2c(c(Br)nn2[C@H]2CCOC2)C1]

To a solution of (S)-tert-butyl 3-bromo-1-(tetrahydrofuran-3-yl)-6,7-dihydro-1H-pyrazolo[4,3-c]pyridine-5(4H)-carboxylate (29 g, 78 mmol) in DCM (300 mL) was added trifluroacetic acid (70 mL) dropwise. The mixture was stirred at room temperature for 2 h. The solvent was concentrated in vacuo and the crude residue was re-dissolved in DMF (100 mL). The mixture was cooled to 0° C. before triethylamine (30 g, 156 mmol) and acetic anhydride (8.7 g, 86 mmol) were added dropwise. The mixture was stirred at room temperature for an additional 2 h. The reaction was quenched with water (200 mL) at 0° C. and extracted with EtOAc (150 mL×3). The combined organic layers were dried over anhydrous $Na_2SO_4$, filtered and concentrated in vacuo. The crude residue was purified by silica gel chromatography (DCM/MeOH=30:1) to give the title compound (Intermediate G, 21.3 g, 87%) as a white solid. $^1$H NMR (400 MHz, CDCl$_3$) δ 4.78-4.67 (m, 1H), 4.45-4.29 (m, 2H), 4.15-4.06 (m, 2H), 3.96-3.92 (m, 2H), 3.88-3.70 (m, 2H), 2.71-2.67 (m, 2H), 2.38-2.34 (m, 2H), 2.16 (s, 3H).

General Procedure for Intermediates H & I

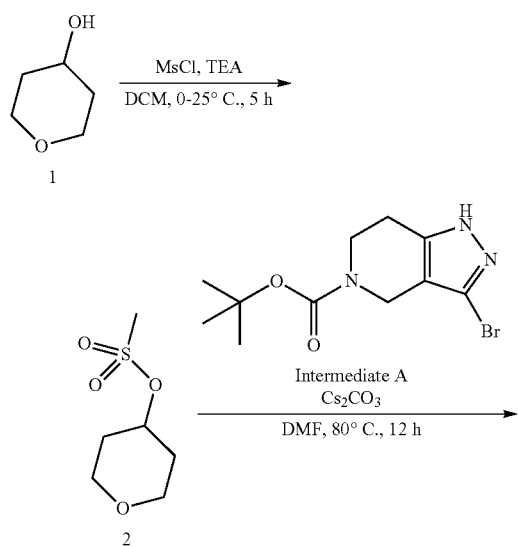

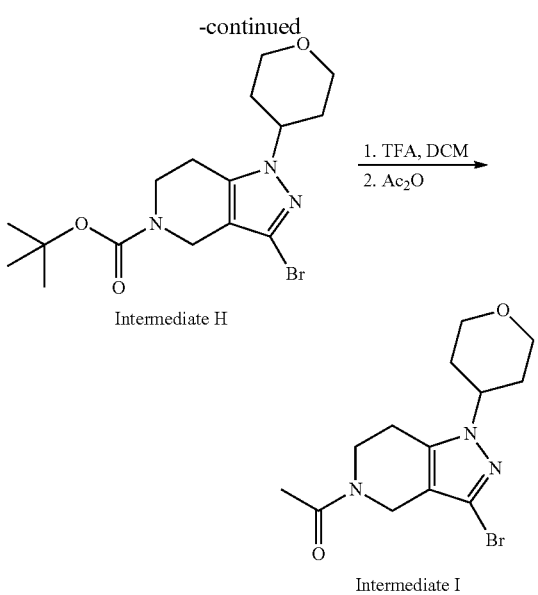

Step 1 tetrahydro-2H-pyran-4-yl methanesulfonate

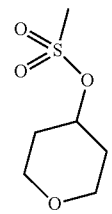

To a solution of tetrahydro-2H-pyran-4-ol (5 g, 49.0 mmol) and triethylamine (5.94 g, 58.7 mmol) in DCM (100 mL) was added mesyl chloride (16.8 g, 146.9 mmol) dropwise at 0° C. under a nitrogen atmosphere. The mixture was stirred at room temperature for 5 h. Water (100 mL) was added and extracted with DCM (100 mL×2). The combined organic layers were dried over anhydrous $Na_2SO_4$, filtered and concentrated in vacuo to give the title compound (4 g, 45%) as a yellow solid. $^1$H NMR (400 MHz, CDCl$_3$) δ 4.85-4.81 (m 1H), 3.90-3.87 (m, 2H), 3.52-3.46 (m, 2H), 2.99 (s, 3H), 2.01-1.97 (m, 2H), 1.83-1.80 (m, 2H).

Step 2 tert-butyl 3-bromo-1-(tetrahydro-2H-pyran-4-yl)-6,7-dihydro-1H-pyrazolo[4,3-c]pyridine-5(4H)-carboxylate

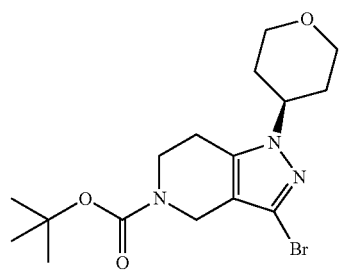

313

To a solution of tert-butyl 3-bromo-6,7-dihydro-1H-pyrazolo[4,3-c]pyridine-5(4H)-carboxylate (Intermediate A, 6 g, 19.8 mmol) in DMF (40 mL) was added $Cs_2CO_3$ (19.5 g, 59.6 mmol) and tetrahydro-2H-pyran-4-yl methanesulfonate (3.9 g, 21.8 mmol). The mixture was heated to 80° C. for 12 h under a nitrogen atmosphere. After cooling the reaction to room temperature, the mixture was filtered. The mixture was diluted with EtOAc (100 mL) and washed with brine (100 mL×2). The organic layer was concentrated in vacuo. The crude residue was purified by silica gel chromatography (petroleum ether:tert-butyl methyl ether:THF=from 10:1:1 to 2:1:1) to give the title compound (Intermediate H, 3.2 g, 47%) as a clear oil. $^1H$ NMR (400 MHz, DMSO-$d_6$) δ 4.35-4.25 (m, 1H), 4.17 (s, 2H), 3.95-3.93 (m, 2H), 3.62-3.57 (m, 2H), 3.42 (t, J=11.2 Hz, 2H), 2.74-2.73 (m, 2H), 1.98-1.89 (m, 2H), 1.80-1.77 (m, 2H), 1.41 (s, 9H).

Step 3

1-(3-bromo-1-(tetrahydro-2H-pyran-4-yl)-6,7-dihydro-1H-pyrazolo[4,3-c]pyridin-5(4H)-yl)ethanone

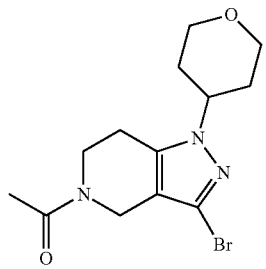 [SMILES: CC(=O)N1CCc2c(c(Br)nn2C2CCOCC2)C1]

To a solution of tert-butyl 3-bromo-1-(tetrahydro-2H-pyran-4-yl)-6,7-dihydro-1H-pyrazolo[4,3-c]pyridine-5(4H)-carboxylate (Intermediate H, 3.2 g, 8.3 mmol) in DCM (20 mL) was added trifluoroacetic acid (20 mL) dropwise at 0° C. The mixture was stirred at room temperature for 2 h. The mixture was concentrated in vacuo and the residue was re-dissolved in DCM (30 mL). The mixture was cooled to 0° C. before triethylamine (2.1 g, 21 mmol) and acetic anhydride (0.93 g, 9.1 mmol) were added dropwise. The mixture was stirred at room temperature for an additional 0.5 h. The reaction was quenched with water (60 mL). The organic layer was dried over anhydrous $Na_2SO_4$, filtered and concentrated in vacuo. The crude residue was purified by silica gel chromatography (DCM/MeOH=50:1) to give the title compound (Intermediate I, 2.1 g, 77%) as a light yellow solid. $^1H$ NMR (400 MHz, DMSO-$d_6$) δ 4.33-4.29 (m, 1H), 4.28 (s 2H), 3.95-3.92 (m, 2H), 3.70-3.67 (m, 2H), 3.43-3.36 (m, 2H), 2.84-2.69 (m, 2H), 2.09-2.08 (m, 3H), 1.96-1.91 (m, 2H), 1.80-1.76 (m, 2H).

General Procedure for Intermediate J

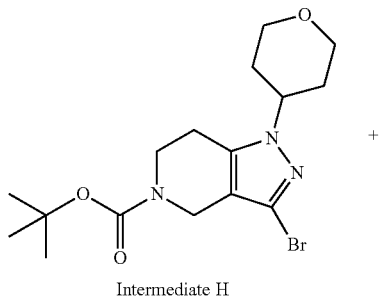

Intermediate H

314

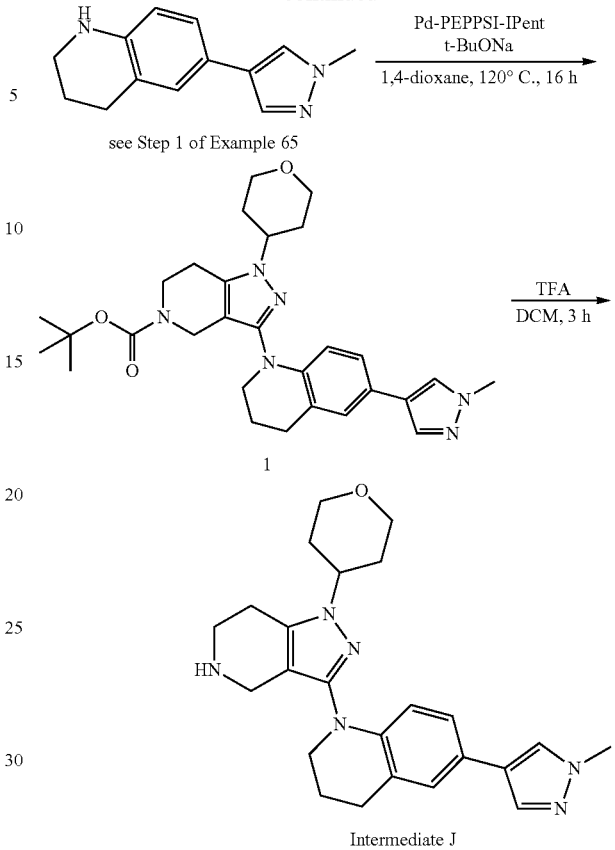

see Step 1 of Example 65

Intermediate J

Step 1 tert-butyl 3-[6-(1-methyl-1H-pyrazol-4-yl)-3,4-dihydroquinolin-1(2H)-yl]-1-(tetrahydro-2H-pyran-4-yl)-6,7-dihydro-1H-pyrazolo[4,3-c]pyridine-5(4H)-carboxylate

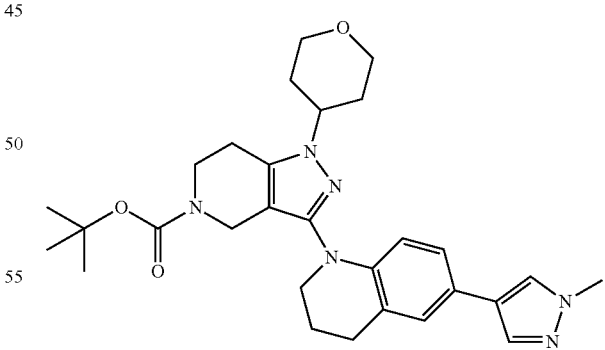

To a vial was added 6-(1-methylpyrazol-4-yl)-1,2,3,4-tetrahydroquinoline (see step 1 of Example 65, 0.300 g, 1.41 mmol), tert-butyl 3-bromo-1-tetrahydropyran-4-yl-6,7-dihydro-4H-pyrazolo[4,3-c]pyridine-5-carboxylate (Intermediate H, 0.625 g, 1.62 mmol), dichloro[1,3-bis(2,6-di-3-pentylphenyl)imidazol-2-ylidene](3-chloropyridyl)palladium(II) (176 mg, 0.221 mmol), t-BuONa (0.270 g, 2.81 mmol) and 1,4-dioxane (4.7 mL). The mixture was sparged with an argon ballon, and then heated to 120° C. for 16 h under an argon atmosphere. After cooling the reaction to room temperature, DCM (5 mL) was added and the reaction was filtered through celite and concentrated in vacuo. The crude residue was purified by silica gel chromatography (100% heptanes to 100% EtOAc gradient) to give the title compound (0.311 g, 43%) as a white solid. $^1$H NMR (400 MHz, DMSO-$d_6$) δ 7.90 (s, 1H), 7.66 (s, 1H), 7.19 (d, J=2.1 Hz, 1H), 7.10 (dd, J=8.5, 2.1 Hz, 1H), 6.41 (d, J=8.4 Hz, 1H), 4.31-4.20 (m, 1H), 4.02-3.91 (m, 4H), 3.82 (s, 3H), 3.61 (t, J=5.8 Hz, 2H), 3.57-3.50 (m, 2H), 3.44 (dd, J=12.7, 10.6 Hz, 2H), 2.79 (t, J=6.4 Hz, 2H), 2.74 (t, J=5.9 Hz, 2H), 2.01-1.89 (m, 4H), 1.80 (d, J=13.0 Hz, 2H), 1.36 (s, 9H). LCMS M/Z (M+H) 520.

Step 2

6-(1-methyl-1H-pyrazol-4-yl)-1-(4,5,6,7-tetrahydro-1H-pyrazolo[4,3-c]pyridin-3-yl)-1,2,3,4-tetrahydroquinoline

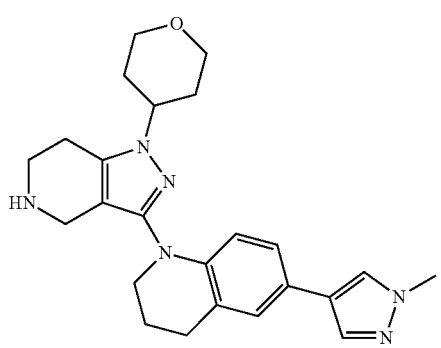 [SMILES: Cn1cc(-c2ccc3c(c2)CCCN3c2nn(C3CCOCC3)c3c2CNCC3)cn1]

To a solution of tert-butyl 3-[6-(1-methylpyrazol-4-yl)-3,4-dihydro-2H-quinolin-1-yl]-1-tetrahydropyran-4-yl-6,7-dihydro-4H-pyrazolo[4,3-c]pyridine-5-carboxylate (311 mg, 0.600 mmol) in DCM (4 mL) was added trifluoroacetic acid (2 mL). The mixture was stirred at room temperature for 3 h and then quenched via the dropwise addition of saturated NaHCO$_3$ and extracted with EtOAc (100 mL×3). The combined organic layers were dried over anhydrous Na$_2$SO$_4$, filtered and concentrated in vacuo to give crude product that was purified by silica gel chromatography (100% DCM to 15% MeOH in DCM gradient) to give the title compound (158 mg, 63%) as a tan solid. $^1$H NMR (400 MHz, CD$_3$OD) δ 7.78 (s, 1H), 7.66 1H), 7.23 (d, J=2.1 Hz, 1H), 7.16 (dd, J=8.5, 2.1 Hz, 1H), 6.48 (d, J=8.4 Hz, 1H), 4.39-4.28 (m, 1H), 4.07 (dd, J=11.7, 4.3 Hz, 2H), 3.89 (s, 3H), 3.83 (s, 2H), 3.66 (t, J=5.8 Hz, 2H), 3.57 (dt, J=12.5, 8.3 Hz, 4H), 3.12 (t, J=6.2 Hz, 2H), 2.86 (t, J=6.4 Hz, 2H), 2.21 (qd, J=12.4, 4.6 Hz, 2H), 2.04 (p, J=6.2 Hz, 2H), 1.87 (dd, J=13.7, 4.0 Hz, 2H). LCMS M/Z (M+H) 419.

General Procedure for Intermediate K

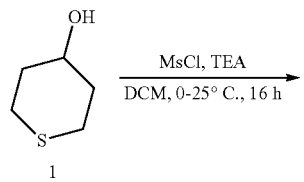

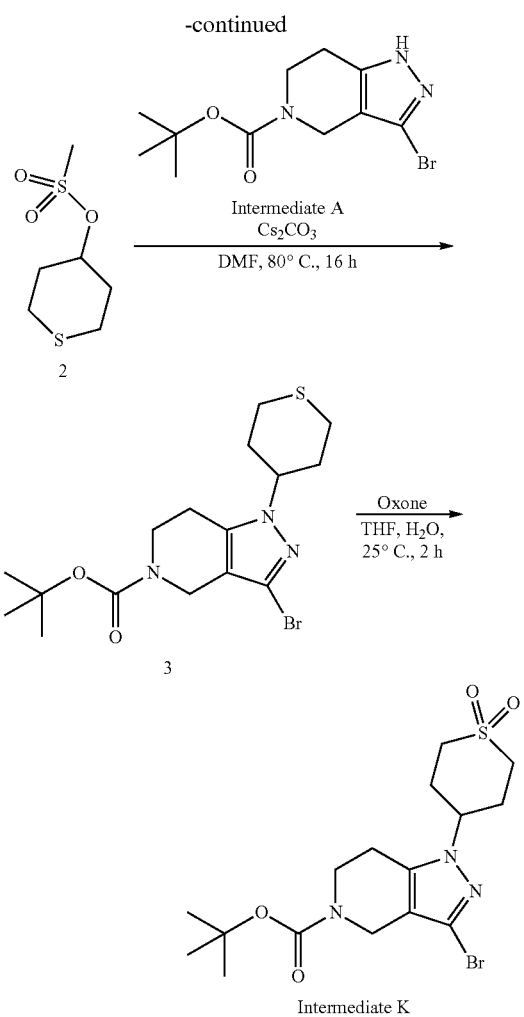

Step 1 tetrahydro-2H-thiopyran-4-yl methanesulfonate

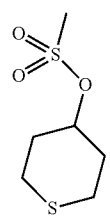

To a solution of tetrahydro-2H-thiopyran-4-ol (10 g, 84.6 mmol) and triethylamine (35.4 mL, 253.8 mmol) in DCM (150 mL) at 0° C. was added methanesulfonyl chloride (10.7 mL, 138.8 mmol) dropwise under a nitrogen atmosphere. The mixture was stirred at 25° C. for 16 h. Water (100 mL) was added and extracted with DCM (100 mL×2). The combined organic layers were dried over anhydrous Na$_2$SO$_4$, filtered and concentrated in vacuo to give the title compound (17 g, crude) as yellow oil that required no further purification. $^1$H NMR (400 MHz, DMSO-$d_6$) δ

4.73-4.69 (m, 1H), 3.19 (s, 3H), 2.76-2.63 (m, 4H), 2.17-2.16 (m, 2H), 1.87-1.84 (m, 2H).

Step 2 tert-butyl 3-bromo-1-(tetrahydro-2H-thiopyran-4-yl)-6,7-dihydro-1H-pyrazolo[4,3-c]pyridine-5(4H)-carboxylate

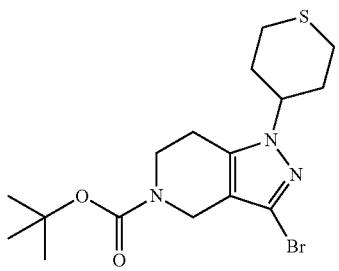 [SMILES: CC(C)(C)OC(=O)N1CCc2c(c(Br)nn2C2CCSCC2)C1]

To a solution of tert-butyl 3-bromo-6,7-dihydro-1H-pyrazolo[4,3-c]pyridine-5(4H)-carboxylate (Intermediate A, 10 g, 33.1 mmol) in DMF (50 mL) was added $Cs_2CO_3$ (27 g, 82.7 mmol) and tetrahydro-2H-thiopyran-4-yl methanesulfonate (8.4 g, 43.0 mmol). The mixture was heated to 80° C. for 16 h under a nitrogen atmosphere. After cooling the reaction to room temperature, the mixture was filtered. The mixture was diluted with EtOAc (100 mL) and washed with brine (100 mL×2). The organic layer was dried over anhydrous $Na_2SO_4$, filtered and concentrated in vacuo. The crude residue was purified by silica gel chromatography (petroleum ether:tert-butyl methyl ether:THF=from 10:1:1 to 3:1:1) to give the title compound (5.9 g, 44%) as a white solid. $^1$H NMR (400 MHz, DMSO-$d_6$) δ 4.17 (s, 2H), 4.09-4.04 (m, 1H), 3.62-3.59 (m, 2H), 2.83-2.77 (m, 2H), 2.71-2.68 (m, 4H), 2.13-2.10 (m, 2H), 2.03-1.93 (m, 2H), 1.44 (s, 9H).

Step 3 tert-butyl 3-bromo-1-(1,1-dioxidotetrahydro-2H-thiopyran-4-yl)-6,7-dihydro-1H-pyrazolo[4,3-c]pyridine-5(4H)-carboxylate

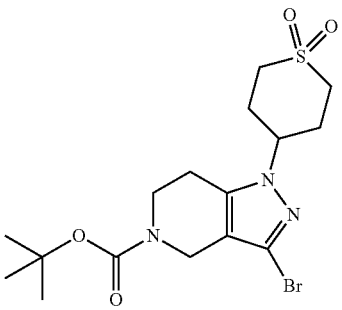 [SMILES: CC(C)(C)OC(=O)N1CCc2c(c(Br)nn2C2CCS(=O)(=O)CC2)C1]

To a solution of tert-butyl 3-bromo-1-(tetrahydro-2H-thiopyran-4-yl)-6,7-dihydro-1H-pyrazolo[4,3-c]pyridine-5(4H)-carboxylate (2.0 g, 5.0 mmol) in THF (10 mL) and water (2 mL) at 0° C. was added Oxone (3.1 g, 5 mmol) portionwise. The mixture was stirred at 25° C. for 2 h. The reaction was quenched by sat. aq. $Na_2SO_3$ and extracted with DCM (20 mL×3). The combined organic layers were dried over anhydrous $Na_2SO_4$, filtered and concentrated in vacuo to give the title compound (Intermediate K, 2.1 g, 98%) as a white solid. LCMS M/Z (M+H) 436.

General Procedure for Intermediate L

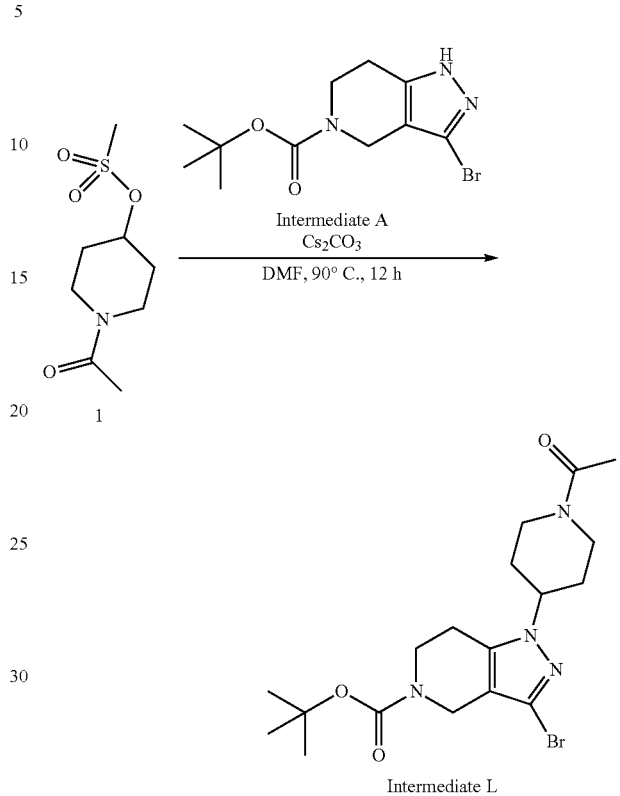

tert-butyl 1-(1-acetylpiperidin-4-yl)-3-bromo-6,7-dihydro-1H-pyrazolo[4,3-c]pyridine-5(4H)-carboxylate

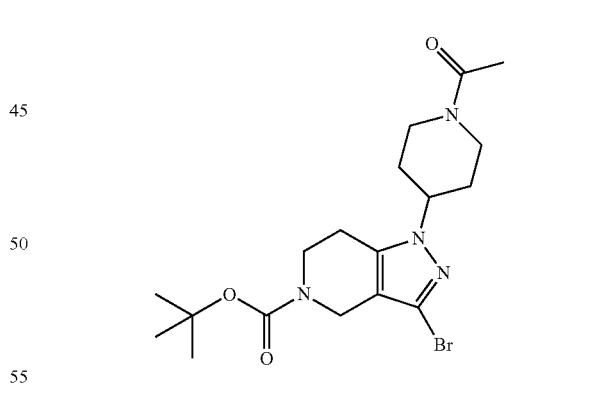

To a solution of tert-butyl 3-bromo-6,7-dihydro-1H-pyrazolo[4,3-c]pyridine-5(4H)-carboxylate (Intermediate A, 5 g, 16.6 mmol) in DMF (40 mL) was added $Cs_2CO_3$ (19.5 g, 59.6 mmol) and 1-acetylpiperidin-4-yl methanesulfonate (see step 1 of Example 75, 5.5 g, 24.8 mmol). The mixture was heated to 90° C. for 12 h under a nitrogen atmosphere. After cooling the reaction to room temperature, the mixture was filtered and concentrated in vacuo. The mixture was diluted with DCM (100 mL) and washed with brine (80 mL×2). The organic layer was dried over anhydrous $Na_2SO_4$, filtered and concentrated in vacuo. The crude residue was purified by silica gel chromatography (petroleum ether:tert-butyl methyl ether:THF=from 10:1:1 to 2:1:1) to give the title compound (Intermediate L, 2 g, 28%) as clear oil. $^1$H NMR (400 MHz, DMSO-d$_6$) δ 4.50-4.41 (m, 1H), 4.38-4.29 (m, 1H), 4.16 (s, 2H), 3.94-3.85 (m, 1H), 3.64-3.57 (m, 2H), 3.21-3.09 (m, 1H), 2.75-2.58 (m, 3H), 2.03 (s, 3H), 1.91-1.80 (m, 3H), 1.73-1.61 (m, 1H), 1.41 (s, 9H).

General Procedure for Intermediate M

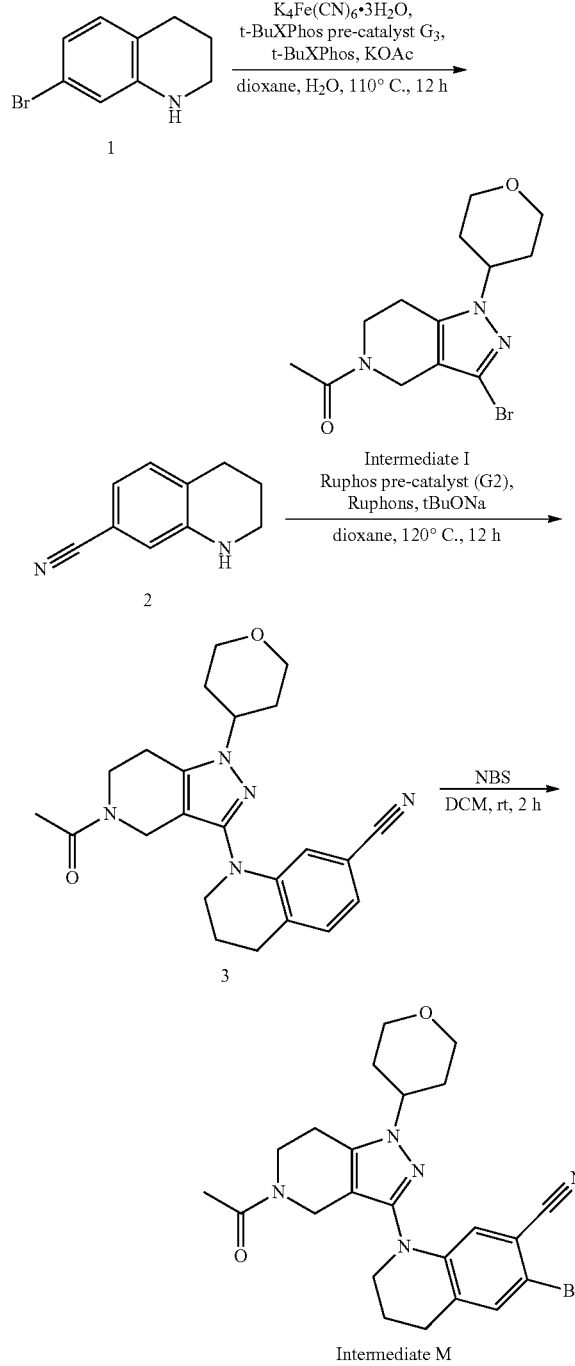

Step 1

1,2,3,4-tetrahydroquinoline-7-carbonitrile

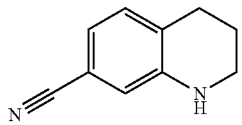 [SMILES: N#Cc1ccc2c(c1)NCCC2]

To a solution of 7-bromo-1,2,3,4-tetrahydroquinoline (8 g, 37 mmol) in 1,4-dioxane (50 mL) and water (50 mL) was added potassium hexacyanoferrate(II) trihydrate (14 g, 37 mmol), KOAc (15 g, 151 mmol), methanesulfonato(2-di-t-butylphosphino-2',4',6'-tri-i-propyl-1,1'-biphenyl)(2'-amino-1,1'-biphenyl-2-yl)palladium(II) (3 g, 3.7 mmol) and 2-di-tert-butylphosphino-2',4',6'-triisopropylbiphenyl (1.6 g, 3.7 mmol). The mixture was heated to 110° C. for 12 h under a nitrogen atmosphere. After cooling the reaction to room temperature, the mixture was filtered and concentrated in vacuo. The crude residue was diluted with EtOAc (100 mL), washed with water (50 mL×2) and brine (50 mL). The organic layer was dried over anhydrous Na$_2$SO$_4$, filtered and concentrated in vacuo. The crude residue was purified by silica gel chromatography (petroleum ether/EtOAc=1:1) to give the title compound (5 g, 84%) as a yellow solid. LCMS M/Z (M+H) 158.

Step 2

1-(5-acetyl-1-(tetrahydro-2H-pyran-4-yl)-4,5,6,7-tetrahydro-1H-pyrazolo[4,3-c]pyridin-3-yl)-1,2,3,4-tetrahydroquinoline-7-carbonitrile

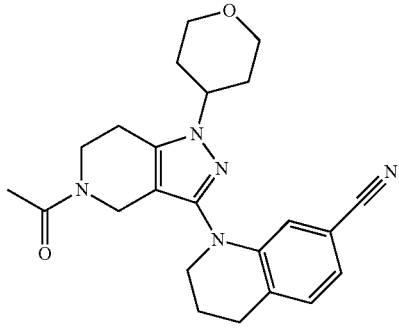 [SMILES: CC(=O)N1CCc2c(c(N3CCCc4ccc(C#N)cc43)nn2C2CCOCC2)C1]

To a solution of 1-(3-bromo-1-tetrahydropyran-4-yl-6,7-dihydro-4H-pyrazolo[4,3-c]pyridin-5-yl)ethanone (Intermediates I, 1.0 g, 3.0 mmol) in 1,4-dioxane (10 mL) was added chloro(2-dicyclohexylphosphino-2',6'-di-i-propoxy-1,1'-biphenyl)(2'-amino-1,1'-biphenyl-2-yl)palladium(II) (240 mg, 0.3 mmol), 2-dicyclohexylphosphino-2',6'-di-i-propoxy-1,1'-biphenyl (142 mg, 0.3 mmol), 1,2,3,4-tetrahydroquinoline-7-carbonitrile (482 mg, 3 mmol) and t-BuONa (0.88 g, 9.1 mmol). The mixture was heated to 120° C. for 12 h under a nitrogen atmosphere. After cooling the reaction to room temperature, the mixture was filtered and concentrated in vacuo. The crude residue was diluted with DCM (100 mL), washed with water (50 mL×3) and brine (50 mL). The organic layer was dried over anhydrous Na$_2$SO$_4$, filtered and concentrated in vacuo. The crude residue was purified by silica gel chromatography (DCM/MeOH=50:1) to give the title compound (900 mg, 73%) as a yellow solid. LCMS M/Z (M+H) 406.

Step 3

1-(5-acetyl-1-(tetrahydro-2H-pyran-4-yl)-4,5,6,7-tetrahydro-1H-pyrazolo[4,3-c]pyridin-3-yl)-6-bromo-1,2,3,4-tetrahydroquinoline-7-carbonitrile

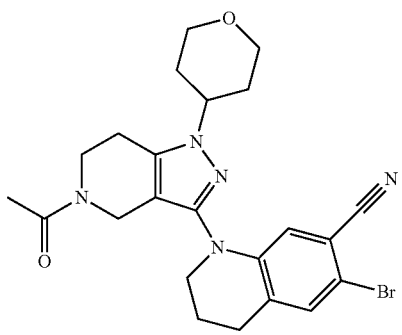 [SMILES: CC(=O)N1CCc2c(c(N3CCCc4cc(Br)c(C#N)cc43)nn2C2CCOCC2)C1]

To a solution of 1-(5-acetyl-1-tetrahydropyran-4-yl-6,7-dihydro-4H-pyrazolo[4,3-c]pyridin-3-yl)-3,4-dihydro-2H-quinoline-7-carbonitrile (900 mg, 2.2 mmol) in DCM (5 mL) at 0° C. was added N-bromosuccinimide (395 mg, 2.2 mmol) by portionwise. The mixture was stirred at room temperature for 1 h. DCM (50 mL) was added, washed with water (30 mL×3) and brine (30 mL). The organic layer was dried over anhydrous Na₂SO₄, filtered and concentrated in vacuo to give the title compound (Intermediate M, 1 g, 93%) as a yellow solid. LCMS M/Z (M+H) 484.

General Procedure for Intermediates N & O

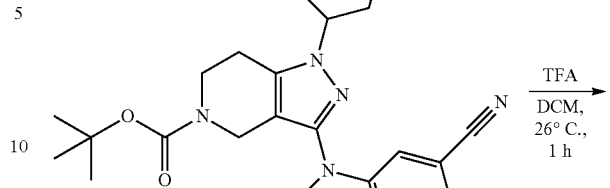

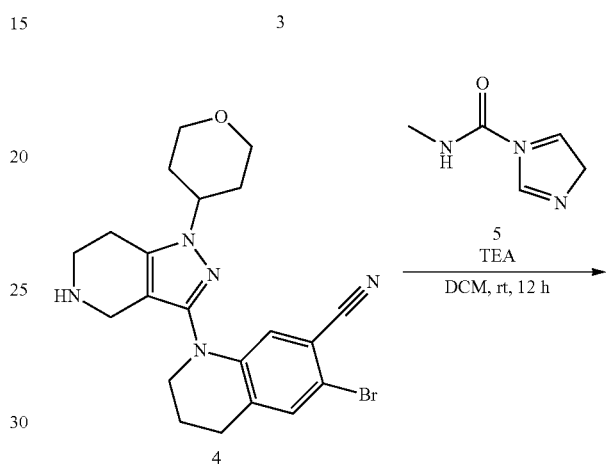

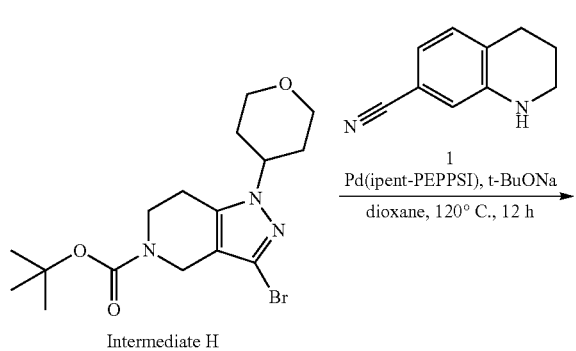

Intermediate H

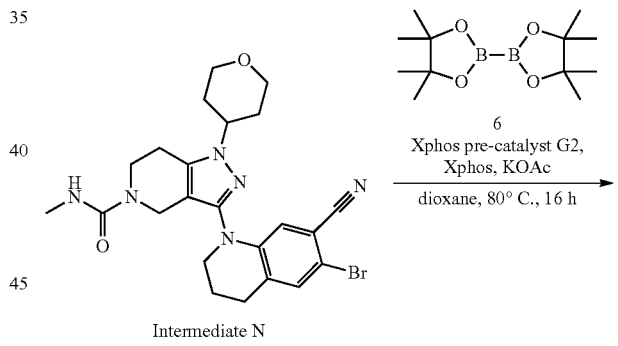

Intermediate N

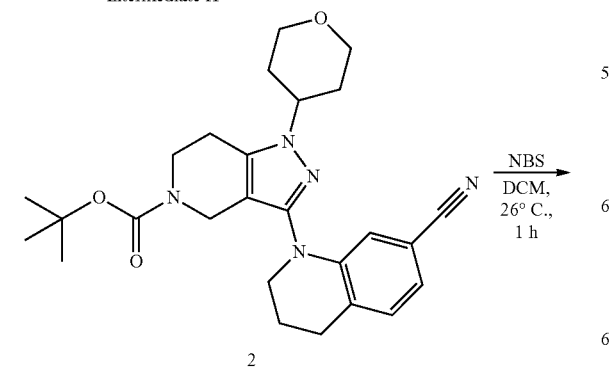

2

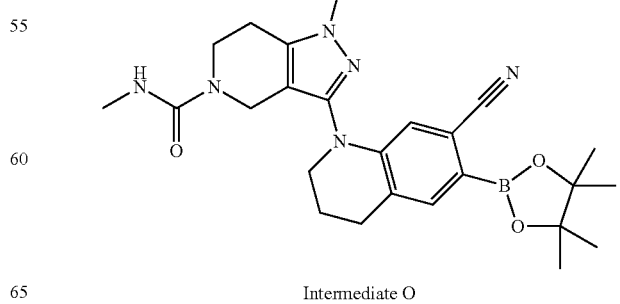

Intermediate O

Step 1 tert-butyl 3-(7-cyano-3,4-dihydroquinolin-1(2H)-yl)-1-(tetrahydro-2H-pyran-4-yl)-6,7-dihydro-1H-pyrazolo[4,3-c]pyridine-5(4H)-carboxylate

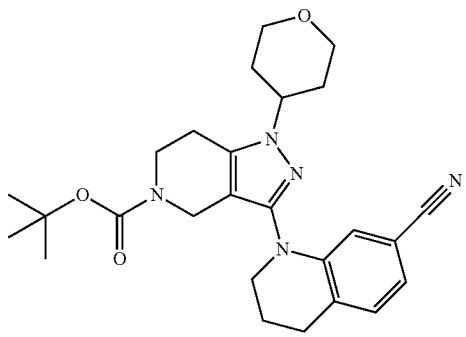 [SMILES: CC(C)(C)OC(=O)N1CCc2c(c(N3CCCc4ccc(C#N)cc43)nn2C2CCOCC2)C1]

To a solution of tert-butyl 3-bromo-1-tetrahydropyran-4-yl-6,7-dihydro-4H-pyrazolo[4,3-c]pyridine-5-carboxylate (Intermediate H, 10 g, 26 mmol) in 1,4-dioxane (80 mL) was added dichloro[1,3-bis(2,6-di-3-pentylphenyl)imidazol-2-ylidene](3-chloropyridyl)palladium(II) (2 g, 2.6 mmol), 1,2,3,4-tetrahydroquinoline-7-carbonitrile (4 g, 26 mmol) and t-BuONa (7.3 g, 76 mmol). The mixture was heated to 120° C. for 12 h under a nitrogen atmosphere. After cooling the reaction to room temperature, the mixture was filtered and concentrated in vacuo. The crude residue was diluted with DCM (100 mL), washed with water (50 mL×2) and brine (50 mL). The organic layer was dried over anhydrous Na$_2$SO$_4$, filtered and concentrated in vacuo. The crude residue was purified by silica gel chromatography (DCM/MeOH=100:1) to give the title compound (8 g, 67%) as a yellow solid. LCMS M/Z (M+H) 464.

Step 2 tert-butyl 3-(6-bromo-7-cyano-3,4-dihydroquinolin-1(2H)-yl)-1-(tetrahydro-2H-pyran-4-yl)-6,7-dihydro-1H-pyrazolo[4,3-c]pyridine-5(4H)-carboxylate

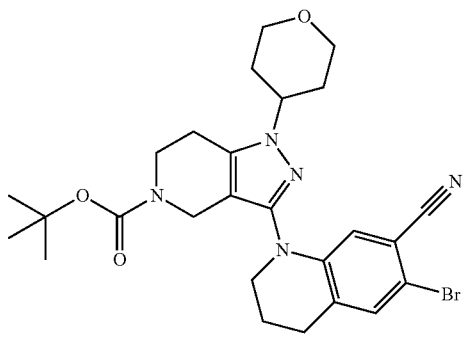 [SMILES: CC(C)(C)OC(=O)N1CCc2c(c(N3CCCc4cc(Br)c(C#N)cc43)nn2C2CCOCC2)C1]

To a solution of tert-butyl 3-(7-cyano-3,4-dihydro-2H-quinolin-1-yl)-1-tetrahydropyran-4-yl-6,7-dihydro-4H-pyrazolo[4,3-c]pyridine-5-carboxylate (8 g, 17 mmol) in DCM (50 mL) at 0° C. was added N-bromosuccinimide (3 g, 17 mmol) by portionwise. The mixture was stirred at 26° C. for 1 h. DCM (80 mL) was added, washed with water (30 mL×3) and brine (30 mL). The organic layer was dried over anhydrous Na$_2$SO$_4$, filtered and concentrated in vacuo to give the title compound (9 g, 96%) as a yellow solid. LCMS M/Z (M+H) 542.

Step 3

6-bromo-1-(1-(tetrahydro-2H-pyran-4-yl)-4,5,6,7-tetrahydro-1H-pyrazolo[4,3-c]pyridin-3-yl)-1,2,3,4-tetrahydroquinoline-7-carbonitrile

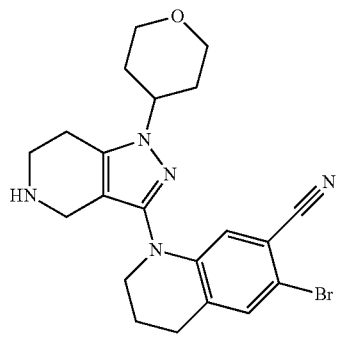 [SMILES: N#Cc1cc2c(cc1Br)CCCN2c1nn(C2CCOCC2)c2c1CNCC2]

To a solution of tert-butyl 3-(6-bromo-7-cyano-3,4-dihydro-2H-quinolin-1-yl)-1-tetrahydropyran-4-yl-6,7-dihydro-4H-pyrazolo[4,3-c]pyridine-5-carboxylate (8 g, 14 mmol) in DCM (20 mL) was added trifluoroacetic acid (10 mL, 174 mmol). The reaction was stirred at 26° C. for 1 h and concentrated in vacuo. The crude residue was diluted with DCM (100 mL), washed with sat. aq. NaHCO$_3$ (50 mL×3) and brine (50 mL). The organic layer was dried over anhydrous Na$_2$SO$_4$, filtered and concentrated in vacuo to give the title compound (6.3 g, 96%) as a yellow solid that required no further purification. LCMS M/Z (M+H) 442.

Step 4

3-(6-bromo-7-cyano-3,4-dihydroquinolin-1(2H)-yl)-N-methyl-1-(tetrahydro-2H-pyran-4-yl)-6,7-dihydro-1H-pyrazolo[4,3-c]pyridine-5(4H)-carboxamide

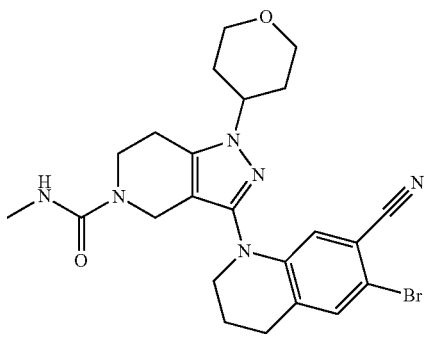 [SMILES: CNC(=O)N1CCc2c(c(N3CCCc4cc(Br)c(C#N)cc43)nn2C2CCOCC2)C1]

To a solution of 6-bromo-1-(1-tetrahydropyran-4-yl-4,5,6,7-tetrahydropyrazolo[4,3-c]pyridin-3-yl)-3,4-dihydro-2H-quinoline-7-carbonitrile (3.3 g, 7.5 mmol) in DCM (20 mL) was added triethylamine (6 mL, 44 mmol) and N-methyl-1 1-imidazole-1-carboxamide (1.8 g, 15 mmol). The reaction was stirred at room temperature for 12 h and concentrated in vacuo. The crude residue was diluted with DCM (100 mL), washed with water (50 mL×3) and brine (50 mL). The organic layer was dried over anhydrous Na$_2$SO$_4$, filtered and concentrated in vacuo. The crude residue was purified by silica gel chromatography (DCM/MeOH=50:1) to give the title compound (Intermediate N, 1.9 g, 51%) as a yellow solid. LCMS M/Z (M+H) 500.

Step 5

3-(7-cyano-6-(4,4,5,5-tetramethyl-1,3,2-dioxaborolan-2-yl)-3,4-dihydroquinolin-1(2H)-yl)-N-methyl-1-(tetrahydro-2H-pyran-4-yl)-6,7-dihydro-1H-pyrazolo[4,3-c]pyridine-5(4H)-carboxamide

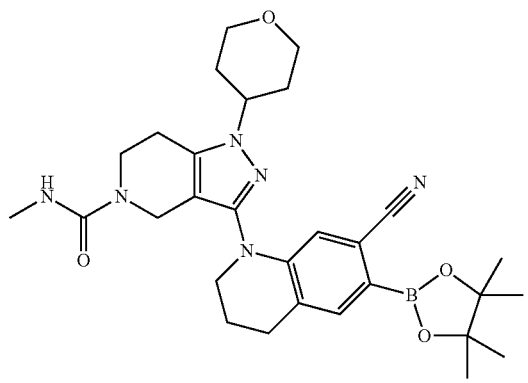

To a solution of 3-(6-bromo-7-cyano-3,4-dihydro-2H-quinolin-1-yl)-N-methyl-1-tetrahydropyran-4-yl-6,7-dihydro-4H-pyrazolo[4,3-c]pyridine-5-carboxamide (Intermediate N, 1.0 g, 2 mmol) in 1,4-dioxane (10 mL) was added chloro(2-dicyclohexylphosphino-2',4',6'-tri-i-propyl-1,1'-biphenyl)(2'-amino-1,1'-biphenyl-2-yl) palladium(II) (157 mg, 0.2 mmol), 2-(dicyclohexylphosphino)-2',4',6'-tri-isopropylbiphenyl (95 mg, 0.2 mmol), 4,4,4',4',5,5,5',5'-octamethyl-2,2'-bi(1,3,2-dioxaborolane) (762 mg, 3 mmol) and KOAc (393 mg, 4 mmol). The mixture was heated to 80° C. for 16 h under a nitrogen atmosphere. After cooling the reaction to room temperature, the mixture was concentrated in vacuo. The crude residue was diluted with DCM (100 mL), washed with water (50 mL×3) and brine (50 mL). The organic layer was dried over anhydrous $Na_2SO_4$, filtered and concentrated in vacuo. The crude residue was purified by silica gel chromatography (DCM/MeOH=50:1) to give the title compound (Intermediate O, 1.2 g, 80%) as a yellow solid. LCMS M/Z (M+H) 547.

General Procedure for Intermediates P & Q

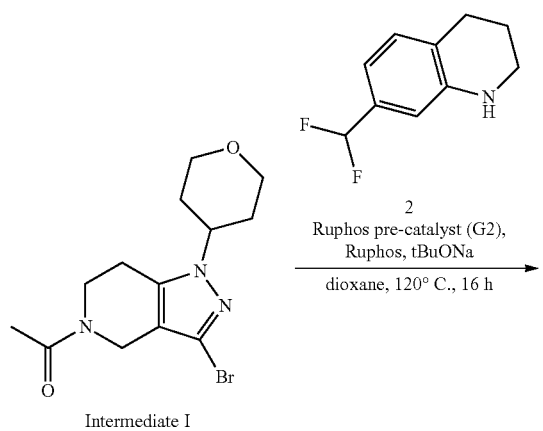

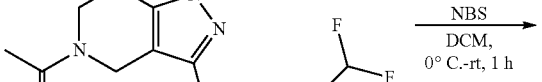

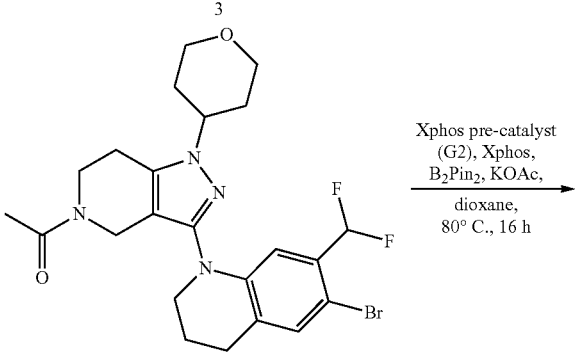

Intermediate P

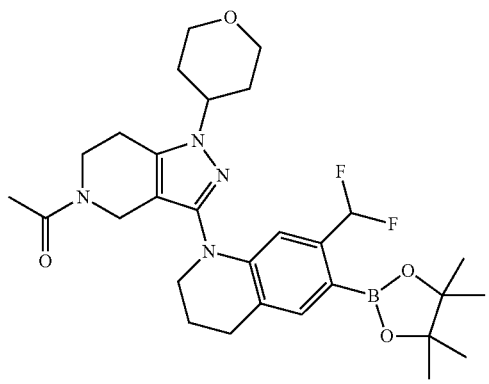

Intermediate Q

Step 1

1-(3-(7-(difluoromethyl)-3,4-dihydroquinolin-1(2H)-yl)-1-(tetrahydro-2H-pyran-4-yl)-6,7-dihydro-1H-pyrazolo[4,3-c]pyridin-5(41H)-yl)ethanone

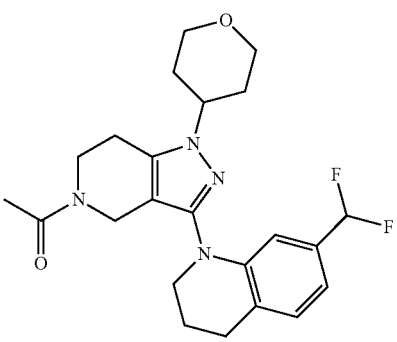 [SMILES: CC(=O)N1CCc2c(c(N3CCCc4ccc(C(F)F)cc43)nn2C2CCOCC2)C1]

To a solution of 1-(3-bromo-1-tetrahydropyran-4-yl-6,7-dihydro-4H-pyrazolo[4,3-c]pyridin-5-yl)ethanone (Intermediate I, 8.0 g, 24.4 mmol) in dioxane (60 mL) was added 7-(difluoromethyl)-1,2,3,4-tetrahydroquinoline (4.5 g, 24.4 mmol), chloro(2-dicyclohexylphosphino-2',6'-di-i-propoxy-1,1'-biphenyl)(2'-amino-1,1'-biphenyl-2-yl)palladium(II) (1.89 g, 2.4 mmol), 2-dicyclohexylphosphino-2',6'-di-i-propoxy-1,1'-biphenyl (1.1 g, 2.4 mmol) and t-BuONa (7.0 g, 73.1 mmol). The mixture was heated to 120° C. for 16 h under a nitrogen atmosphere. After cooling the reaction to room temperature, the mixture was filtered and concentrated in vacuo. The crude residue was purified by silica gel chromatography (DCM/MeOH=100:1) to give the title compound (6 g, 57%) as a light yellow solid. LCMS M/Z (M+H) 431.

Step 2

1-(3-(6-bromo-7-(difluoromethyl)-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone

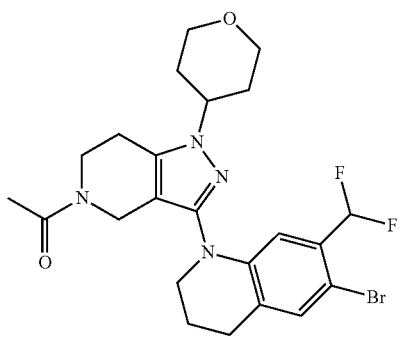 [SMILES: CC(=O)N1CCc2c(c(N3CCCc4cc(Br)c(C(F)F)cc43)nn2C2CCOCC2)C1]

To a solution of 1-(3-(7-(difluoromethyl)-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone (6.0 g, 13.9 mmol) in DCM (50 mL) at 0° C. was added N-bromosuccinimide (1.7 g, 9.8 mmol) portionwise. The mixture was stirred at room temperature for 1 h. The mixture was poured into water (30 mL) and extracted with DCM (30 mL×2). The combined organic layers were dried over anhydrous Na₂SO₄, filtered and concentrated in vacuo. The crude residue was purified by silica gel chromatography (DCM/MeOH=50:1) to give the title compound (Intermediate P, 7.2 g, crude) as a yellow solid that required no further purification. LCMS M/Z (M+H) 509.

Step 3

1-(3-(7-(difluoromethyl)-6-(4,4,5,5-tetramethyl-1,3,2-dioxaborolan-2-yl)-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone

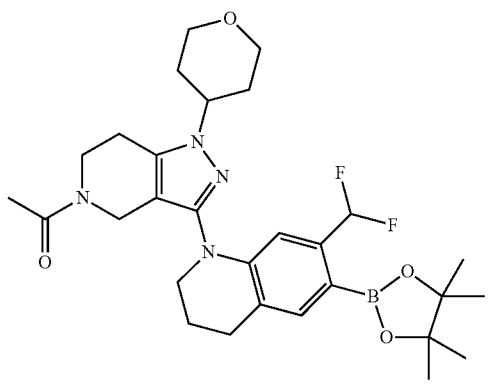 [SMILES: CC(=O)N1CCc2c(c(N3CCCc4cc(B5OC(C)(C)C(C)(C)O5)c(C(F)F)cc43)nn2C2CCOCC2)C1]

To a solution of 1-(3-(6-bromo-7-(difluoromethyl)-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone (Intermediate P, 1.0 g, 1.96 mmol) in 1,4-dioxane (10 mL) was added chloro(2-dicyclohexylphosphino-2',4',6'-tri-i-propyl-1,1'-biphenyl)(2'-amino-1,1'-biphenyl-2-yl) palladium(II) (154 mg, 0.20 mmol), 4,4,4',4',5,5,5',5'-octamethyl-2,2'-bi(1,3,2-dioxaborolane) (748 mg, 2.94 mmol), 2-(dicyclohexylphosphino)-2',4',6'-triisopropylbiphenyl (94 mg, 0.20 mmol) and potassium acetate (385 mg, 3.93 mmol). The mixture was heated to 80° C. for 16 h under a nitrogen atmosphere. After cooling the reaction to room temperature, the mixture was concentrated in vacuo. DCM (100 mL) was added, the mixture was washed with water (100 mL) and brine (100 mL). The organic layer was dried over anhydrous Na₂SO₄, filtered and concentrated in vacuo. The crude residue was purified by silica gel chromatography (DCM/MeOH=10:1) to give the title compound (Intermediate Q, 1.2 g, crude) as black oil that required no further purification.

General Procedure for Intermediates R & S

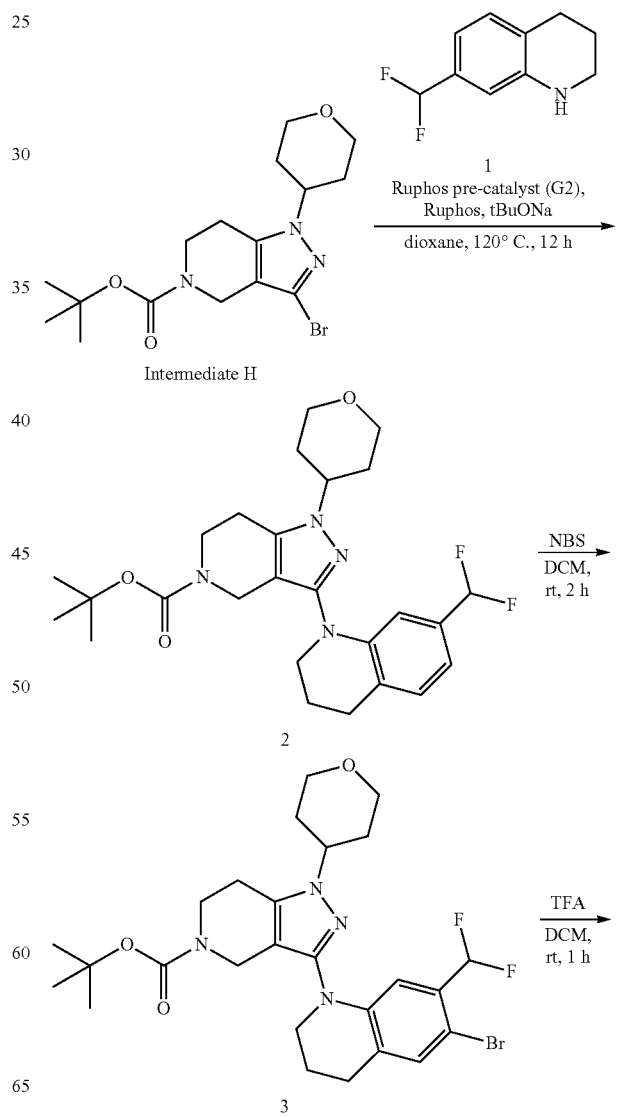

-continued

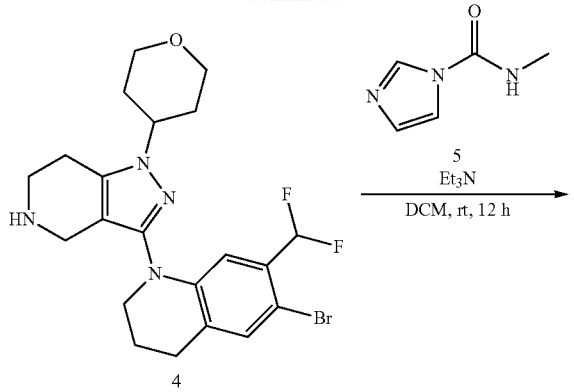

4

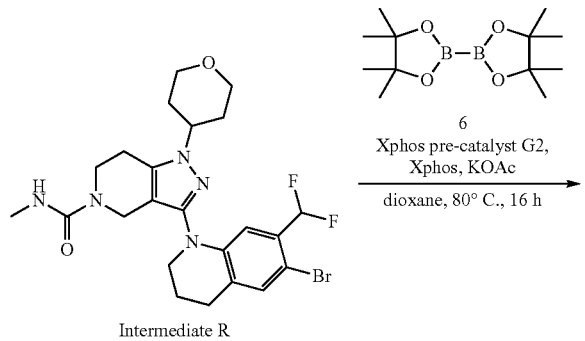

Intermediate R

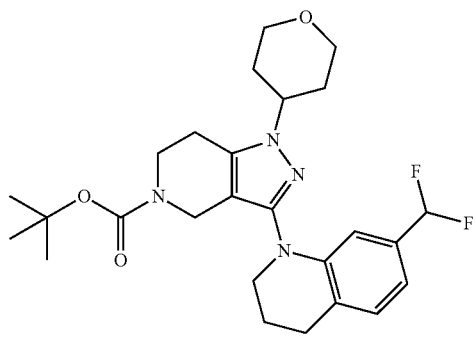 [SMILES: CC(C)(C)OC(=O)N1CCc2c(c(N3CCCc4ccc(C(F)F)cc43)nn2C2CCOCC2)C1]

Intermediate S

Step 1 tert-butyl 3-(7-(difluoromethyl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate To a solution of tert-butyl 3-bromo-1-tetrahydropyran-4-yl-6,7-dihydro-4H-pyrazolo[4,3-c]pyridine-5-carboxylate (Intermediate H, 1.0 g, 2.6 mmol) in 1,4-dioxane (8 mL) was added chloro(2-dicyclohexylphosphino-2',6'-di-i-propoxy-1,1'-biphenyl)(2'-amino-1,1'-biphenyl-2-yl)palladium(II) (201 mg, 0.26 mmol), 2-dicyclohexylphosphino-2',6'-di-i-propoxy-1,1'-biphenyl (121 mg, 0.26 mmol), 7-(difluoromethyl)-1,2,3,4-tetrahydroquinoline (527 mg, 2.6 mmol) and t-BuONa (746 mg, 7.8 mmol). The mixture was heated to 120° C. for 16 h under a nitrogen atmosphere. After cooling the reaction to room temperature, the mixture was concentrated in vacuo. DCM (100 mL) was added, the mixture was washed with water (50 mL×2) and brine (50 mL). The organic layer was dried over anhydrous Na$_2$SO$_4$, filtered and concentrated in vacuo. The crude residue was purified by silica gel chromatography (petroleum ether/EtOAc=1:1) to give the title compound (720 mg, 55%) as a yellow solid. LCMS M/Z (M+H) 489.

Step 2 tert-butyl 3-(6-bromo-7-(difluoromethyl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate

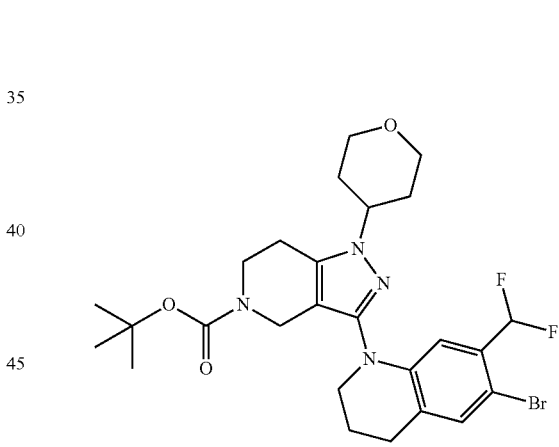

To a solution of tert-butyl 3-(7-(difluoromethyl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate (720 mg, 1.4 mmol) in DCM (10 mL) was added N-bromosuccinimide (250 mg, 1.4 mmol) portionwise. The mixture was stirred at room temperature for 2 h. DCM (30 mL) was added and washed with water (10 mL). The organic layer was dried over anhydrous Na$_2$SO$_4$, filtered and concentrated in vacuo to give the title compound (850 mg, 92%) as a yellow solid that required no further purification. LCMS M/Z (M+H) 567.

Step 3

6-bromo-7-(difluoromethyl)-1-(1-(tetrahydro-2H-pyran-4-yl)-4,5,6,7-tetrahydro-1H-pyrazolo[4,3-c]pyridin-3-yl)-1,2,3,4-tetrahydroquinoline

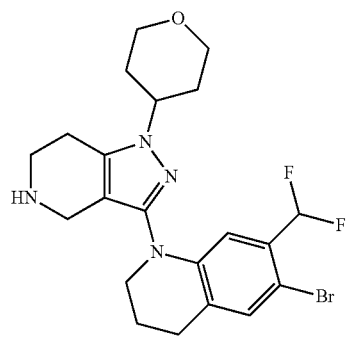 [SMILES: FC(F)c1cc2c(cc1Br)CCCN2c1nn(C2CCOCC2)c2c1CNCC2]

To a solution of tert-butyl 3-(6-bromo-7-(difluoromethyl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate (0.78 g, 1.4 mmol) in DCM (2 mL) was added trifluoroacetic acid (1 mL, 13 mmol) dropwise. The mixture was stirred at room temperature for 1 h and concentrated in vacuo. DCM (30 mL) was added, washed with sat. aq. NaHCO₃ (10 mL) and brine (10 mL). The organic layer was dried over anhydrous Na₂SO₄, filtered and concentrated in vacuo to give the title compound (0.7 g, crude) as yellow oil that required no further purification. LCMS M/Z (M+H) 467.

Step 4

3-(6-bromo-7-(difluoromethyl)-3,4-dihydroquinolin-1(2H)-yl)-N-methyl-1-(tetrahydro-2H-pyran-4-yl)-6,7-dihydro-1H-pyrazolo[4,3-c]pyridine-5(4H)-carboxamide

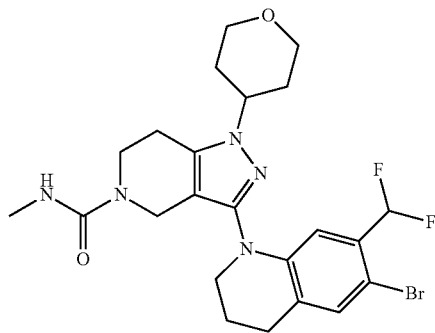 [SMILES: CNC(=O)N1CCc2c(c(N3CCCc4cc(Br)c(C(F)F)cc43)nn2C2CCOCC2)C1]

To a solution of 6-bromo-7-(difluoromethyl)-1-(1-tetrahydropyran-4-yl-4,5,6,7-tetrahydropyrazolo[4,3-c]pyridin-3-yl)-3,4-dihydro-2H-quinoline (0.7 g, 1.3 mmol) in DCM (10 mL) was added triethylamine (0.9 mL, 6.6 mmol) and N-methyl-1H-imidazole-1-carboxamide (330 mg, 2.6 mmol). The mixture was stirred at room temperature for 12 h. DCM (50 mL) was added, washed with water (30 mL×3) and brine (30 mL). The organic layer was dried over anhydrous Na₂SO₄, filtered and concentrated in vacuo. The crude residue was purified by silica gel chromatography (DCM/MeOH=50:1) to give the title compound (Intermediate R, 720 mg, 88%) as light yellow oil. LCMS M/Z (M+H) 524.

Step 5

3-(7-(difluoromethyl)-6-(4,4,5,5-tetramethyl-1,3,2-dioxaborolan-2-yl)-3,4-dihydroquinolin-1(2H)-yl)-N-methyl-1-(tetrahydro-2H-pyran-4-yl)-6,7-dihydro-1H-pyrazolo[4,3-c]pyridine-5(4H)-carboxamide

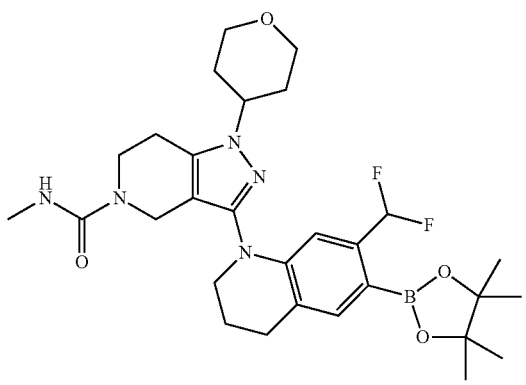

To a solution of 3-(6-bromo-7-(difluoromethyl)-3,4-dihydroquinolin-1 (2H)-yl)-N-methyl-1-(tetrahydro-2H-pyran-4-yl)-6,7-dihydro-1H-pyrazolo[4,3-c]pyridine-5(4H)-carboxamide (Intermediate R, 150 mg, 0.3 mmol) in 1,4-dioxane (5 mL) was added chloro(2-dicyclohexylphosphino-2',4',6'-tri-i-propyl-1,1'-biphenyl)(2'-amino-1,1'-biphenyl-2-yl) palladium(II) (23 mg, 0.03 mmol), 4,4,4',4',5,5,5',5'-octamethyl-2,2'-bi(1,3,2-dioxaborolane) (109 mg, 0.4 mmol), 2-(dicyclohexylphosphino)-2',4',6'-triisopropylbiphenyl (14 mg, 0.03 mmol), potassium acetate (57 mg, 0.6 mmol). The mixture was heated to 80° C. for 16 h under a nitrogen atmosphere. After cooling the reaction to room temperature, the mixture was concentrated in vacuo. DCM (50 mL) was added, the mixture was washed with water (30 mL) and brine (30 mL). The organic layer was dried over anhydrous Na₂SO₄, filtered and concentrated in vacuo. The crude residue was purified by silica gel chromatography (DCM/MeOH=10:1) to give the title compound (Intermediate S, 0.2 g, crude) as a yellow solid. LCMS M/Z (M+H) 572.

General Procedure for Intermediates T & U
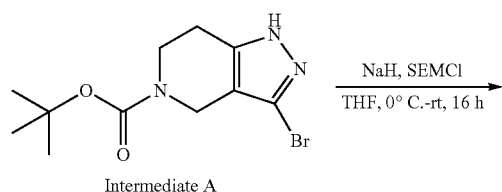
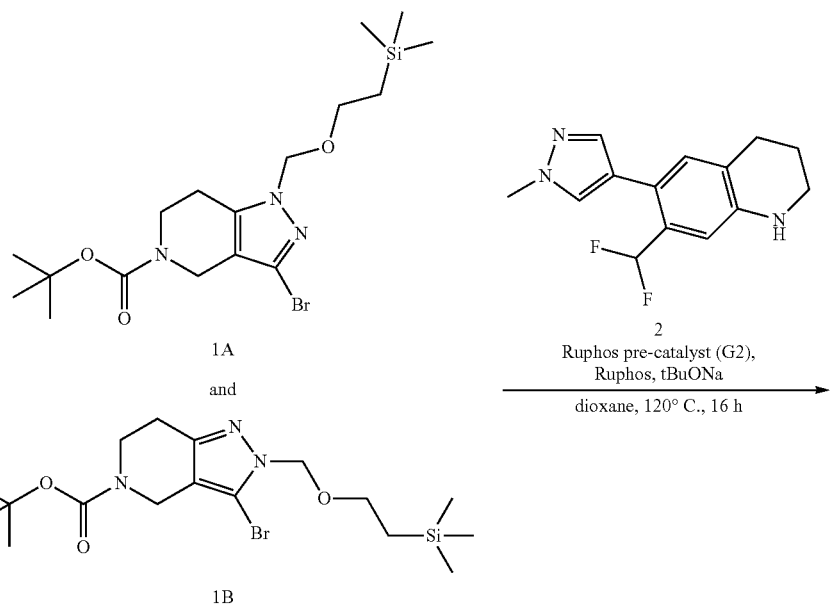
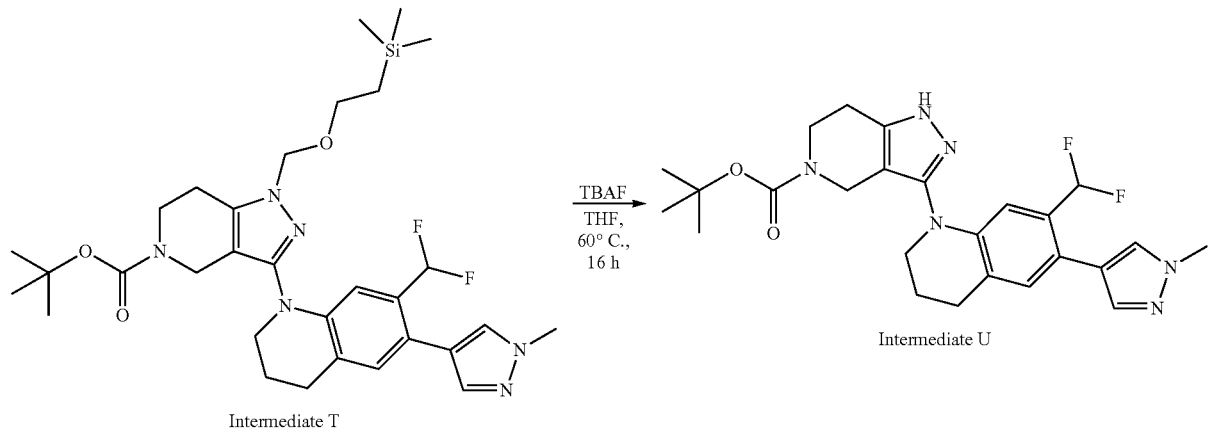

Step 1 tert-butyl 3-bromo-1-((2-(trimethylsilyl)ethoxy)methyl)-6,7-dihydro-1H-pyrazolo[4,3-c]pyridine-5(4H)-carboxylate and tert-butyl 3-bromo-2-((2-(trimethylsilyl)ethoxy)methyl)-6,7-dihydro-2H-pyrazolo[4,3-c]pyridine-5(4H)-carboxylate

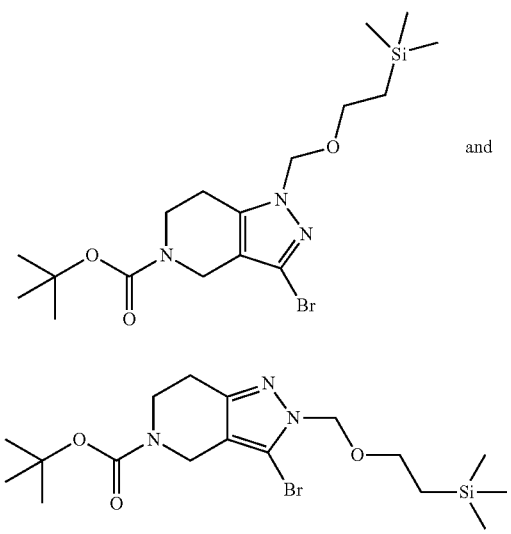

To a solution of tert-butyl 3-bromo-6,7-dihydro-1H-pyrazolo[4,3-c]pyridine-5(4H)-carboxylate (Intermediate A, 80.0 g, 264.8 mmol) in THF (1.5 L) at 0° C. was added sodium hydride (60%, 12.71 g, 317.7 mmol) by portionwise. The mixture was stirred at room temperature for 0.5 h. 2-(Trimethylsilyl)ethoxymethyl chloride (52.97 g, 317.7 mmol) was added dropwise and the mixture stirred at room temperature for an additional 16 h. The mixture was quenched with water (1 L) and extracted with EtOAc (500 mL×3). The combined organic layers were dried over anhydrous $Na_2SO_4$, filtered and concentrated in vacuo. The crude residue was purified by silica gel chromatography (petroleum ether/EtOAc=5:1) to give the mixture of title compounds (95 g, 83%) as yellow oil. LCMS M/Z (M+H) 434.

Step 2 tert-butyl 3-(7-(difluoromethyl)-6-(1-methyl-1H-pyrazol-4-yl)-3,4-dihydroquinolin-1(2H)-yl)-1-((2-(trimethylsilyl)ethoxy)methyl)-6,7-dihydro-1H-pyrazolo[4,3-c]pyridine-5(4H)-carboxylate

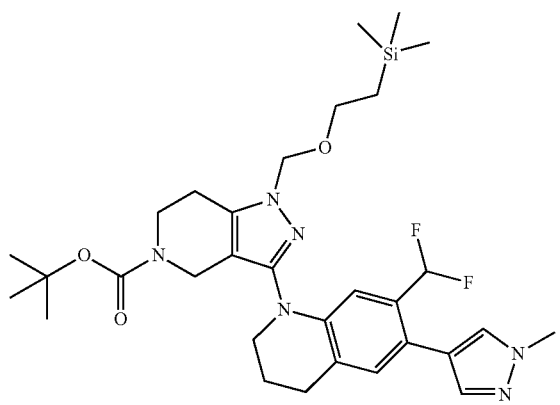 [SMILES: Cn1cc(-c2cc3c(cc2C(F)F)N(c2nn(COCC[Si](C)(C)C)c4c2CN(C(=O)OC(C)(C)C)CC4)CCC3)cn1]

To a solution of tert-butyl 3-bromo-1-((2-(trimethylsilyl)ethoxy)methyl)-6,7-dihydro-1H-pyrazolo[4,3-c]pyridine-5(4H)-carboxylate and tert-butyl 3-bromo-2-((2-(trimethylsilyl)ethoxy)methyl)-6,7-dihydro-2H-pyrazolo[4,3-c]pyridine-5(4H)-carboxylate (65.7 g, 151.9 mmol) in 1,4-dioxane (200 mL) was added chloro(2-dicyclohexylphosphino-2',6'-di-i-propoxy-1,1'-biphenyl)(2'-amino-1,1'-biphenyl-2-yl)palladium(II) (5.9 g, 7.6 mmol), 2-dicyclohexylphosphino-2',6'-di-i-propoxy-1,1'-biphenyl (3.54 g, 7.6 mmol), 7-(difluoromethyl)-6-(1-methyl-1H-pyrazol-4-yl)-1,2,3,4-tetrahydroquinoline (20 g, 75.96 mmol) and t-BuONa (21.9 g, 227.89 mmol). The mixture was heated to 120° C. for 16 h under an argon atmosphere. After cooling the reaction to room temperature, water (800 mL) was added and extracted with EtOAc (500 mL×3). The combined organic layers were washed with brine (500 mL×3), dried over anhydrous $Na_2SO_4$, filtered and concentrated in vacuo. The crude residue was purified by silica gel chromatography (DCM/MeOH=50:1) to give the title compound (Intermediate T, 9.1 g, 20%) as yellow oil. $^1$H NMR (400 MHz, $CDCl_3$) δ 7.54 (s, 1H), 7.41 (s, 1H), 7.03 (s, 1H), 6.88 (s, 1H), 6.52 (t, J=55.6 Hz, 1H), 5.33 (s, 2H), 4.10 (s, 2H), 3.96 (s, 3H), 3.73-3.70 (m, 4H), 3.64 (t, J=8.0 Hz, 1H), 2.87-2.80 (m. 4H), 2.09-2.07 (m, 2H), 1.45 (s, 9H), 0.93 (t, J=8.0 Hz, 1H), 0.00 (s, 9H). LCMS M/Z (M+H) 615.

Step 3 tert-butyl 3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridine-5(4H)-carboxylate

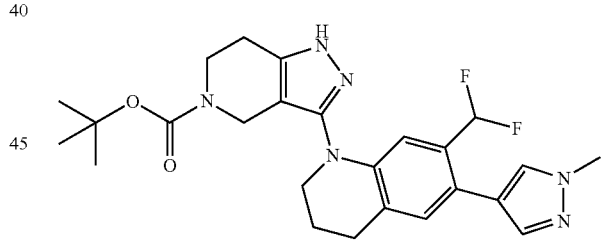

To a solution of tert-butyl 3-(7-(difluoromethyl)-6-(1-methyl-1H-pyrazol-4-yl)-3,4-dihydroquinolin-1(2H)-yl)-1-((2-(trimethylsilyl)ethoxy)methyl)-6,7-dihydro-1H-pyrazolo[4,3-c]pyridine-5(4H)-carboxylate (8.5 g, 13.83 mmol) in THF (50 mL) was added tetrabutylammonium fluoride (1.0 M in THF, 40 mL, 40 mmol). The mixture was heated to 60° C. for 16 h under a nitrogen atmosphere. After cooling the reaction to room temperature, EtOAc (200 mL) was added and washed with brine (100 mL×3). The organic layer was dried over anhydrous $Na_2SO_4$, filtered and concentrated in vacuo. The crude residue was purified by silica gel chromatography (DCM/MeOH=20:1) to give the title compound (Intermediate U, 4.4 g, 66%) as a yellow solid. $^1$H NMR (400 MHz, $CDCl_3$) δ 7.54 (s, 1H), 7.42 (s, 1H), 7.03 (s, 1H), 6.87 (s, 1H), 6.52 (t, J=55.6 Hz, 1H), 4.12 (s, 2H), 3.96 (s, 3H), 3.72-3.69 (m, 4H), 2.86-2.76 (m. 4H), 2.08-2.05 (m, 2H), 1.45 (s, 9H). LCMS M/Z (M+H) 485.

General Procedure for Intermediate V

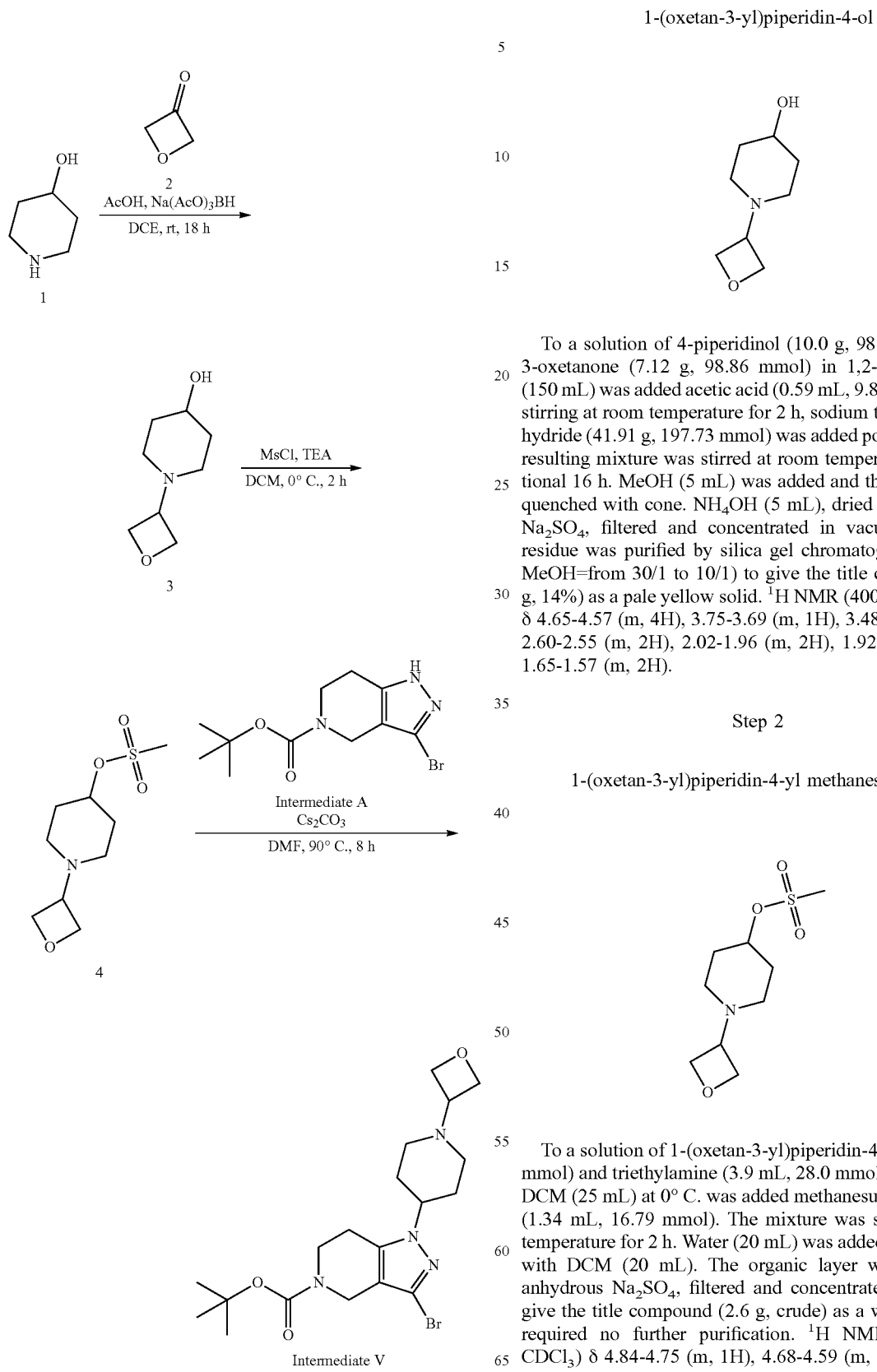

Step 1

1-(oxetan-3-yl)piperidin-4-ol

To a solution of 4-piperidinol (10.0 g, 98.86 mmol) and 3-oxetanone (7.12 g, 98.86 mmol) in 1,2-dichloroethane (150 mL) was added acetic acid (0.59 mL, 9.89 mmol). After stirring at room temperature for 2 h, sodium triacetoxyborohydride (41.91 g, 197.73 mmol) was added portionwise. The resulting mixture was stirred at room temperature for additional 16 h. MeOH (5 mL) was added and the reaction was quenched with conc. $NH_4OH$ (5 mL), dried over anhydrou $Na_2SO_4$, filtered and concentrated in vacuo. The crude residue was purified by silica gel chromatography (DCM/MeOH=from 30/1 to 10/1) to give the title compound (2.2 g, 14%) as a pale yellow solid. $^1H$ NMR (400 MHz, $CDCl_3$) δ 4.65-4.57 (m, 4H), 3.75-3.69 (m, 1H), 3.48-3.41 (m, 1H), 2.60-2.55 (m, 2H), 2.02-1.96 (m, 2H), 1.92-1.82 (m, 2H), 1.65-1.57 (m, 2H).

Step 2

1-(oxetan-3-yl)piperidin-4-yl methanesulfonate

To a solution of 1-(oxetan-3-yl)piperidin-4-ol (2.2 g, 14.0 mmol) and triethylamine (3.9 mL, 28.0 mmol) in anhydrous DCM (25 mL) at 0° C. was added methanesulfonyl chloride (1.34 mL, 16.79 mmol). The mixture was stirred at room temperature for 2 h. Water (20 mL) was added and extracted with DCM (20 mL). The organic layer was dried over anhydrous $Na_2SO_4$, filtered and concentrated in vacuo to give the title compound (2.6 g, crude) as a white solid that required no further purification. $^1H$ NMR (400 MHz, $CDCl_3$) δ 4.84-4.75 (m, 1H), 4.68-4.59 (m, 4H), 3.56-3.49 (m, 1H), 3.03 (s, 3H), 2.60-2.53 (m, 2H), 2.25-2.20 (m, 2H), 2.16-2.04 (m, 2H), 1.98-1.90 (m, 2H).

Step 3 tert-butyl 3-bromo-1-(1-(oxetan-3-yl)piperidin-4-yl)-6,7-dihydro-1H-pyrazolo[4,3-c]pyridine-5(4H)-carboxylate

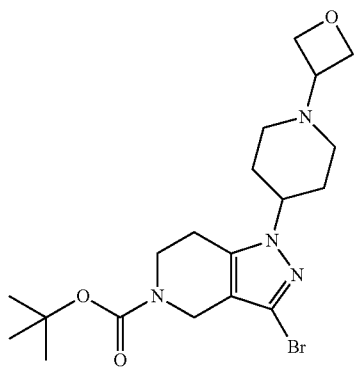 [SMILES: CC(C)(C)OC(=O)N1CCc2c(c(Br)nn2C2CCN(C3COC3)CC2)C1]

To a solution of tert-butyl 3-bromo-6,7-dihydro-1H-pyrazolo[4,3-c]pyridine-5(4H)-carboxylate (Intermediate A, 2.0 g, 6.62 mmol) and 1-(oxetan-3-yl)piperidin-4-yl methanesulfonate (2.6 g, 11.05 mmol) in DMF (30 mL) was added $Cs_2CO_3$ (6.47 g, 19.86 mmol). The mixture was heated to 90° C. for 8 h. After cooling the reaction to room temperature, the mixture was filtered and concentrated in vacuo. The crude residue was purified by silica gel chromatography (petroleum ether:tert-butyl methyl ether:THF=from 5:1:1 to 2:1:1) to give the title compound (Intermediate V, 950 mg, 33%) as a yellow solid. $^1$H NMR (400 MHz, $CDCl_3$) δ 4.67-4.58 (m, 4H), 4.27 (s, 2H), 3.94-3.90 (m, 1H), 3.75-3.70 (m, 2H), 3.54-3.50 (m, 1H), 2.89-2.84 (m, 2H), 2.70-2.66 (m, 2H), 2.27-2.23 (m, 2H), 1.98-1.87 (m, 4H), 1.49 (s, 9H).

Example 1

1-[3-(3,4-dihydro-2H-quinolin-1-yl)-1-(oxetan-3-yl)-6,7-dihydro-4H-pyrazolo[4,3-c]pyridin-5-yl]ethanone

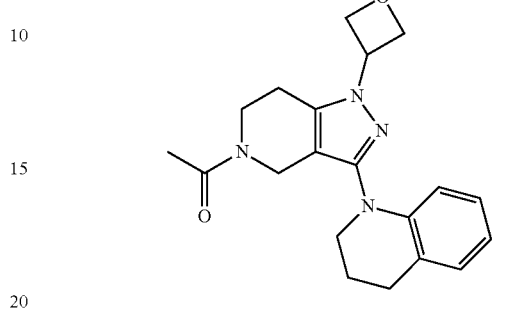

To a solution of 1-[3-bromo-1-(oxetan-3-yl)-6,7-dihydro-4H-pyrazolo[4,3-c]pyridin-5-yl]ethanone (Intermediate E, 8.2 g, 27.32 mmol), 1,2,3,4-tetrahydroquinoline (4.12 mL, 32.78 mmol) and t-BuONa (5.25 g, 54.64 mmol) in toluene (80 mL) was added 4,5-bis(diphenylphosphino)-9,9-dimethylxanthene (1.57 g, 2.73 mmol) and tris(dibenzylideneacetone)dipalladium (1.25 g, 1.37 mmol). The mixture was heated to 110° C. for 16 h under a nitrogen atmosphere. After cooling the reaction to room temperature, water (100 mL) was added and the mixture was extracted with EtOAc (100 mL×3). The combined organic layers were washed with brine (100 mL×3), dried over anhydrous $Na_2SO_4$, filtered and concentrated in vacuo to give crude product that was purified by silica gel chromatography (petroleum ether/EtOAc=1:1) to give the title compound (5.0 g, 44%) as a white solid. $^1$H NMR (400 MHz, DMSO-$d_6$) δ 7.01-6.92 (m, 2H), 6.65-6.61 (m, 1H), 6.49-6.44 (m, 1H), 5.47-5.44 (m, 1H), 4.93-4.90 (m, 2H), 4.86-4.83 (m, 2H), 4.06-4.04 (m, 2H), 3.70-3.58 (m, 4H), 2.80-2.74 (m, 4H), 2.04-1.91 (m, 5H). LCMS M/Z (M+H) 353.

The Following Compounds were Prepared in a Similar Fashion to Example 1

Examples 2-5

| Example | Compound Name | NMR | m/z |
|---|---|---|---|
| Example 2 | 1-[3-(2,3-dihydro-1,4-benzoxazin-4-yl)-1-(oxetan-3-yl)-6,7-dihydro-4H-pyrazolo[4,3-c]pyridin-5-yl]ethanone | $^1$H NMR (400 MHz, DMSO-$d_6$) δ 6.81-6.62 (m, 4H), 5.48-5.45 (m, 1H), 4.93-4.84 (m, 4H), 4.28-4.26 (m, 2H), 4.16-4.15 (m, 2H), 3.72-3.68 (m, 4H), 2.77-2.65 (m, 2H), 2.05-1.95 (m, 3H) | 355 |
| Example 3 | 1-[3-(2,3-dihydro-1,4-benzothiazin-4-yl)-1-(oxetan-3-yl)-6,7-dihydro-4H-pyrazolo[4,3-c]pyridin-5-yl]ethanone | $^1$H NMR (400 MHz, DMSO-$d_6$) δ 7.09-7.07 (m, 1H), 6.93-6.90 (m, 1H), 6.76-6.73 (m, 1H), 6.60-6.54 (m, 1H), 5.46-5.43 (m, 1H), 4.95-4.83 (m, 4H), 3.98-3.93 (m, 4H), 3.69-3.64 (m, 2H), 3.16-3.14 (m, 2H), 2.77-2.64 (m, 2H), 2.04-1.89 (m, 3H) | 371 |
| Example 4 | 1-[3-(3,4-dihydro-2H-quinolin-1-yl)-1-methyl-6,7-dihydro-4H-pyrazolo[4,3-c]pyridin-5-yl]ethanone | $^1$H NMR (400 MHz, DMSO-$d_6$) δ 6.98-6.89 (m, 2H), 6.65-6.62 (m, 1H), 6.44-6.39 (m, 1H), 4.15-4.10 (m, 2H), 3.84-3.76 (m, 2H), 3.68 (s, 3H), 3.59-3.56 (m, 2H), 2.81-2.71 (m, 4H), 2.01-1.97 (m, 5H) | 311 |
| Example 5 | 1-[3-(4-methyl-2,3-dihydroquinoxalin-1-yl)-1-(oxetan-3-yl)- | $^1$H NMR (400 MHz, DMSO-$d_6$) δ 6.70-6.65 (m, 1H), 6.61-6.59 (m, 1H), 6.53-6.47 (m, 1H), 6.43-6.37 (m, 1H), | 368 |

-continued

| Example | Compound Name | NMR | m/z |
|---|---|---|---|
| | 6,7-dihydro-4H-pyrazolo[4,3-c]pyridin-5-yl]ethanone | 5.46-5.39 (m, 1H), 4.94-4.82 (m, 4H), 4.03-4.01 (m, 2H), 3.74-3.65 (m, 4H), 3.34-3.30 (m, 2H), 2.86 (s, 3H), 2.76-2.61 (m, 2H), 2.03-1.90 (m, 3H) | |

Example 6

1-[3-[6-(6-methyl-3-pyridyl)-3,4-dihydro-2H-quinolin-1-yl]-1-(oxetan-3-yl)-6,7-dihydro-4H-pyrazolo[4,3-c]pyridin-5-yl]ethanone

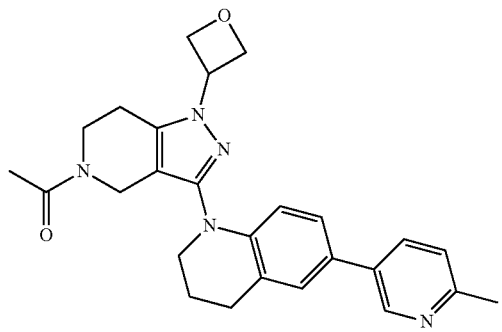 [SMILES: CC(=O)N1CCc2c(c(N3CCCc4cc(-c5ccc(C)nc5)ccc43)nn2C2COC2)C1]

Step 1

1-(3-(6-bromo-3,4-dihydroquinolin-1(2H)-yl)-1-(oxetan-3-yl)-6,7-dihydro-1H-pyrazolo[4,3-c]pyridin-5(4H)-yl)ethanone

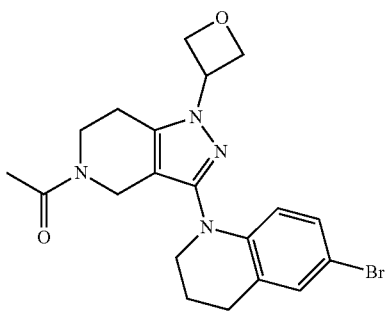 [SMILES: CC(=O)N1CCc2c(c(N3CCCc4cc(Br)ccc43)nn2C2COC2)C1]

To a solution of 1-[3-(3,4-dihydro-2H-quinolin-1-yl)-1-(oxetan-3-yl)-6,7-dihydro-4H-pyrazolo[4,3-c]pyridin-5-yl]ethanone (4.2 g, 11.9 mmol) in DMF (40 mL) was added N-bromosuccinimide (2.55 g, 14.3 mmol). The mixture was stirred at 20° C. for 12 h under a nitrogen atmosphere. The mixture was concentrated in vacuo. The crude residue was purified by silica gel chromatography (DCM/MeOH=20:1) to give the title compound (5.0 g, 78%) as a white solid. LCMS M/Z (M+H) 431.

Step 2

1-[3-[6-(6-methyl-3-pyridyl)-3,4-dihydro-2H-quinolin-1-yl]-1-(oxetan-3-yl)-6,7-dihydro-4H-pyrazolo[4,3-c]pyridin-5-yl]ethanone

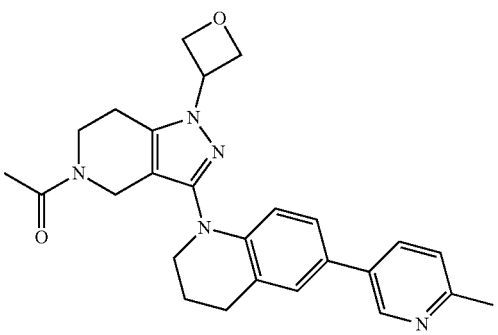 [SMILES: CC(=O)N1CCc2c(c(N3CCCc4cc(-c5ccc(C)nc5)ccc43)nn2C2COC2)C1]

To a solution of 1-[3-(6-bromo-3,4-dihydro-2H-quinolin-1-yl)-1-(oxetan-3-yl)-6,7-dihydro-4H-pyrazolo[4,3-c]pyridin-5-yl]ethanone (100 mg, 0.23 mmol), 2-methyl-5-(4,4,5,5-tetramethyl-1,3,2-dioxaborolan-2-yl)pyridine (60.95 mg, 0.28 mmol) and $Na_2CO_3$ (49.15 mg, 0.46 mmol) in 1,4-dioxane (2 mL) and water (0.5 mL) was added [1,1'-bis(diphenylphosphino)ferrocene]dichloropalladium(II), complex with dichloromethane (16.95 mg, 0.02 mmol). The mixture was stirred at 20° C. for 12 h under a nitrogen atmosphere and then concentrated in vacuo. The crude residue was purified by reverse phase chromatography (acetonitrile 18-48%/0.2% formic acid in water) to give the title compound (38 mg, 36%) as a yellow solid. $^1$H NMR (400 MHz, DMSO-$d_6$) δ 8.66 (s, 1H), 7.86-7.84 (m, 1H), 7.38 (s, 1H), 7.29-7.24 (m, 1H), 6.60-6.54 (m, 1H), 5.49-5.42 (m, 1H), 4.94-4.84 (m, 4H), 4.12-4.10 (m, 2H), 3.69-3.62 (m, 4H), 2.93-2.82 (m, 2H), 2.78-2.62 (m, 2H), 2.46 (s, 3H), 2.05-1.94 (m, 5H). LCMS M/Z (M+H) 444.

The Following Compounds were Prepared in a Similar Fashion to Step 2 of Example 6

Examples 7-26

| Example | Compound Name | NMR | m/z |
|---|---|---|---|
| Example 7 | 1-[3-[6-(1-ethylpyrazol-4-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 7.95 (s, 1H), 7.66 (s, 1H), 7.20 (s, 1H), 7.10-7.08 (m, 1H), 6.48-6.42 (m, 1H), 5.43-5.39 (m, 1H), 4.89-4.81 (m, 4H), 4.08-4.03 (m, 4H), 3.63-3.58 (m, 4H), 2.80-2.73 (m, 4H), 2.01-1.89 (m, 5H), | 447 |

-continued

| Example | Compound Name | NMR | m/z |
|---|---|---|---|
| Example 8 | 1-[1-(oxetan-3-yl)-3-[6-(4-pyridyl)-3,4-dihydro-2H-quinolin-1-yl]-6,7-dihydro-4H-pyrazolo[4,3-c]pyridin-5-yl]ethanone | 1.34 (t, J = 7.2 Hz, 3H)<br>$^1$H NMR (400 MHz, DMSO-d$_6$) δ 8.50 (d, J = 4.4 Hz, 2H), 7.63-7.42 (m, 4H), 6.61-6.55 (m, 1H), 5.50-5.43 (m, 1H), 4.94-4.91 (m, 2H), 4.89-4.86 (m, 2H), 4.13-4.11 (m, 2H), 3.72-3.65 (m, 4H), 2.91-2.88 (m, 2H), 2.79-2.67 (m, 2H), 2.05-1.94 (m, 5H) | 430 |
| Example 9 | 1-[1-(oxetan-3-yl)-3-[6-(1H-pyrazol-4-yl)-3,4-dihydro-2H-quinolin-1-yl]-6,7-dihydro-4H-pyrazolo[4,3-c]pyridin-5-yl]ethanone | $^1$H NMR (400 MHz, DMSO-d$_6$) δ 7.83 (s, 2H), 7.23 (s, 1H), 7.16-7.12 (m, 1H), 6.48-6.43 (m, 1H), 5.42-5.37 (m, 1H), 4.89-4.80 (m, 4H), 4.05-4.03 (m, 2H), 3.63-3.57 (m, 4H), 2.80-2.73 (m, 4H), 2.01-1.93 (m, 5H) | 419 |
| Example 10 | 1-[3-[6-(1-cyclopropylpyrazol-4-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 7.83 (s, 1H), 7.75 (s, 1H), 7.23 (s, 1H), 7.16-7.12 (m, 1H), 7.48-7.43 (m, 1H), 5.42-5.37 (m, 1H), 4.89-4.80 (m, 4H), 4.05-4.03 (m, 2H), 3.63-3.57 (m, 4H), 2.80-2.73 (m, 4H), 2.01-1.89 (m, 3H), 1.01-1.91 (m, 4H) | 459 |
| Example 11 | 1-[3-[6-(2,5-dimethylpyrazol-3-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 7.12 (s, 1H), 7.04-7.02 (m, 1H), 6.57-6.51 (m, 1H), 6.02 (s, 1H), 5.49-5.46 (m, 1H), 4.91-4.85 (m, 4H), 4.14-4.12 (m, 2H), 3.71 (s, 3H), 3.68-3.63 (m, 4H), 2.86-2.77 (m, 4H), 2.12 (s, 3H), 2.05-1.98 (m, 5H) | 447 |
| Example 12 | 1-[3-[6-(6-hydroxy-3-pyridyl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 11.68 (s, 1H), 7.75-7.72 (m, 1H), 7.51 (s, 1H), 7.21 (s, 1H), 7.12-7.10 (m, 1H), 6.51-6.47 (m, 1H), 6.37 (d, J = 9.6 Hz, 1H), 5.48-5.42 (m, 1H), 4.91-4.84 (m, 4H), 4.09-4.07 (m, 2H), 3.66-3.59 (m, 4H), 2.84-2.76 (m, 4H), 2.04-1.93 (m, 5H) | 446 |
| Example 13 | 1-[1-(oxetan-3-yl)-3-[6-(4,5,6,7-tetrahydropyrazolo[1,5-a]pyridin-3-yl)-3,4-dihydro-2H-quinolin-1-yl]-6,7-dihydro-4H-pyrazolo[4,3-c]pyridin-5-yl]ethanone | $^1$H NMR (400 MHz, DMSO-d$_6$) δ 7.55 (s, 1H), 7.09 (s, 1H), 7.03-7.00 (m, 1H), 6.54-6.48 (m, 1H), 5.46-5.43 (m, 1H), 4.94-4.91 (m, 2H), 4.87-4.83 (m, 2H), 4.10-4.05 (m, 4H), 3.69-3.60 (m, 4H), 2.85-2.67 (m, 6H), 2.04-1.93 (m, 7H), 1.80-1.71 (m, 2H) | 473 |
| Example 14 | 1-[3-[6-(2-methylpyrazol-3-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 7.39 (s, 1H), 7.17 (s, 1H), 7.11-7.06 (m, 1H), 6.59-6.53 (m, 1H), 6.25 (s, 1H), 5.50-5.43 (m, 1H), 4.94-4.91 (m, 2H), 4.87-4.84 (m, 2H), 4.15-4.13 (m, 2H), 3.81 (s, 1H), 3.70-3.63 (m, 4H), 2.88-2.50 (m, 4H), 2.05-1.96 (m, 5H) | 433 |
| Example 15 | 5-[1-[5-acetyl-1-(oxetan-3-yl)-6,7-dihydro-4H-pyrazolo[4,3-c]pyridin-3-yl]-3,4-dihydro-2H-quinolin-6-yl]-N-methyl-pyridine-2-carboxamide | $^1$H NMR (400 MHz, DMSO-d$_6$) δ 8.45 (s, 1H), 8.72 (d, J = 4.8 Hz, 1H), 8.15 (d, J = 8.0 Hz, 1H), 8.01 (d, J = 8.0 Hz, 1H), 7.26 (s, 1H), 7.44-7.40 (m, 1H), 6.64-6.58 (m, 1H), 5.49-5.46 (m, 1H), 4.94-4.91 (m, 2H), 4.87-4.84 (m, 2H), 4.15-4.12 (m, 2H), 3.73-3.65 (m, 4H), 2.92-2.79 (m, 7H), 2.06-1.95 (m, 5H) | 487 |
| Example 16 | 1-[3-[6-(2-methyl-3-pyridyl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 8.37 (s, 1H), 7.56-7.53 (m, 1H), 7.25-7.22 (m, 1H), 7.05 (s, 1H), 7.01-6.96 (m, 1H), 6.59-6.53 (m, 1H), 5.49-5.44 (m, 1H), 4.94-4.91 (m, 2H), 4.87-4.84 (m, 2H), 4.15-4.12 (m, 2H), 3.70-3.63 (m, 4H), 2.88-2.70 (m, 4H), 2.45 (s, 3H), 2.06-1.95 (m, 5H) | 444 |
| Example 17 | 1-[3-[6-(2-methoxy-4-pyridyl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 8.12 (d, J = 5.2 Hz, 1H), 7.51 (s, 1H), 7.43-7.39 (m, 1H), 7.22 (d, J = 5.2 Hz, 1H), 6.98 (s, 1H), 6.58-6.52 (m, 1H), 5.48-5.45 (m, 1H), 4.94-4.91 (m, 2H), 4.87-4.84 (m, 2H), 4.13-4.11 (m, 2H), 3.86 (s, 3H), 3.70-3.65 (m, 4H), 2.90-2.66 (m, 4H), 2.05-1.95 (m, 5H) | 460 |
| Example 18 | 1-[1-(oxetan-3-yl)-3-[6-(3-pyridyl)-3,4-dihydro- | $^1$H NMR (400 MHz, DMSO-d$_6$) δ 8.81 (s, 1H), 8.45-8.44 (m, 1H), | 430 |

| Example | Compound Name | NMR | m/z |
|---|---|---|---|
| | 2H-quinolin-1-yl]-6,7-dihydro-4H-pyrazolo[4,3-c]pyridin-5-yl]ethanone | 7.97-7.95 (m, 1H), 7.43-7.31 (m, 3H), 6.61-6.55 (m, 1H), 5.50-5.43 (m, 1H), 4.95-4.85 (m, 4H), 4.14-4.11 (m, 2H), 3.74-3.64 (m, 4H), 2.89 (t, J = 6.4 Hz, 2H), 2.79-2.67 (m, 2H), 2.05-1.95 (m, 5H) | |
| Example 19 | 1-[3-[6-(6-methoxy-3-pyridyl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 8.37 (s, 1H), 7.90 (d, J = 8.4 Hz, 1H), 7.33 (s, 1H), 7.26-7.22 (m, 1H), 6.83 (d, J = 8.0 Hz, 1H), 6.57-6.53 (m, 1H), 5.48-5.44 (m, 1H), 4.93-4.86 (m, 4H), 4.12-4.10 (m, 2H), 3.86 (s, 3H), 3.72-3.64 (m, 4H), 2.87-2.66 (m, 4H), 2.05-1.94 (m, 5H) | 460 |
| Example 20 | 1-[3-[6-(2,4-dimethylpyrazol-3-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 7.23 (s, 1H), 7.01 (s, 1H), 6.95-6.89 (m, 1H), 6.59-6.53 (m, 1H), 5.47-5.40 (s, 1H), 4.91-4.82 (m, 4H), 4.14-4.12 (m, 2H), 3.70-3.60 (m, 7H), 2.85-2.64 (m, 4H), 2.03-1.91 (m, 8H) | 447 |
| Example 21 | 5-[1-[5-acetyl-1-(oxetan-3-yl)-6,7-dihydro-4H-pyrazolo[4,3-c]pyridin-3-yl]-3,4-dihydro-2H-quinolin-6-yl]pyridine-3-carbonitrile | $^1$H NMR (400 MHz, DMSO-$d_6$) δ 9.08 (s, 1 H), 8.83 (s, 1H), 8.49 (s, 1H), 7.53 (s, 1H), 7.46-7.37 (m, 1H), 6.61-6.50 (m, 1H), 5.45-5.42 (m, 1H), 4.94-4.79 (m, 4H), 4.15-4.05 (m, 2H), 3.73-3.58 (m, 4H), 2.86 (t, J = 6.0 Hz, 2H), 2.76-2.60 (m, 2H), 2.06-1.90 (m, 5H) | 455 |
| Example 22 | 1-[3-[6-[2-methyl-5-(trifluoromethyl)pyrazol-3-yl]-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 7.25 (s, 1 H), 7.20-7.10 (m, 1H), 6.74 (s, 1H), 6.64-6.52 (m, 1H), 5.47 (m, 1H), 4.96-4.82 (m, 4H), 4.19-4.10 (m, 2H), 3.89 (s, 3H), 3.76-3.60 (m, 4H), 2.87 (t, J = 5.6 Hz, 2H), 2.81-2.64 (m, 2H), 2.06-1.96 (m, 5H) | 501 |
| Example 23 | 5-[1-[5-acetyl-1-(oxetan-3-yl)-6,7-dihydro-4H-pyrazolo[4,3-c]pyridin-3-yl]-3,4-dihydro-2H-quinolin-6-yl]-1-methyl-pyridin-2-one | $^1$H NMR (400 MHz, DMSO-$d_6$) δ 7.93 (s, 1H), 7.71-7.68 (m, 1H), 7.21 (s, 1H), 7.12-7.96 (m, 1H), 6.55-6.45 (m, 1H), 6.40 (d, J = 9.2 Hz, 1H), 5.42 (m, 1H), 4.94-4.78 (m, 4H), 4.12-3.99 (m, 2H), 3.72-3.56 (m, 4H), 3.45 (s, 3H), 2.81 (t, J = 6.0 Hz, 2H), 2.81-2.63 (m, 2H), 2.10-1.83 (m, 5H) | 460 |
| Example 24 | 1-[1-(oxetan-3-yl)-3-[6-(1H-pyrazol-3-yl)-3,4-dihydro-2H-quinolin-1-yl]-6,7-dihydro-4H-pyrazolo[4,3-c]pyridin-5-yl]ethanone | $^1$H NMR (400 MHz, DMSO-$d_6$) δ 12.75 (s, 1H), 7.58 (s, 1H), 7.45-7.34 (m, 2H), 6.54-6.48 (m, 2H), 5.47-5.43 (m, 1H), 4.92-4.83 (m, 4H), 4.10-4.08 (m, 2H), 3.67-3.62 (m, 4H), 2.82-2.77 (m, 4H), 2.04-1.93 (m, 5H) | 419 |
| Example 25 | 1-[1-(oxetan-3-yl)-3-(6-pyrimidin-5-yl-3,4-dihydro-2H-quinolin-1-yl)-6,7-dihydro-4H-pyrazolo[4,3-c]pyridin-5-yl]ethanone | $^1$H NMR (400 MHz, DMSO-$d_6$) δ 9.03-9.02 (m, 3H), 7.48-7.47 (m, 1H), 7.41-7.36 (m, 1H), 6.67-6.62 (m, 1H), 5.55-5.53 (m, 1H), 5.15-5.12 (m, 2H), 5.04-5.01 (m, 2H), 4.26-4.24 (m, 2H), 3.89-3.76 (m, 4H), 3.00-2.77 (m, 4H), 2.19-2.05 (m, 5H) | 431 |
| Example 26 | 5-[1-[5-acetyl-1-(oxetan-3-yl)-6,7-dihydro-4H-pyrazolo[4,3-c]pyridin-3-yl]-3,4-dihydro-2H-quinolin-6-yl]pyridine-2-carbonitrile | $^1$H NMR (400 MHz, DMSO-$d_6$) δ 9.03 (s, 1H), 8.22 (d, J = 8.4 Hz, 1H), 8.01 (d, J = 8.0 Hz, 1H), 7.59 (s, 1H), 7.49-7.45 (m, 1H), 6.63-6.57 (m, 1H), 5.50-5.46 (m, 1H), 4.95-4.88 (m, 4H), 4.15-4.13 (m, 2H), 3.73-3.68 (m, 4H), 2.92-2.67 (m, 4H), 2.06-1.96 (m, 5H) | 455 |

Example 27

1-[1-(oxetan-3-yl)-3-[6-(2-pyridyl)-3,4-dihydro-2H-quinolin-1-yl]-6,7-dihydro-4H-pyrazolo[4,3-c]pyridin-5-yl]ethanone

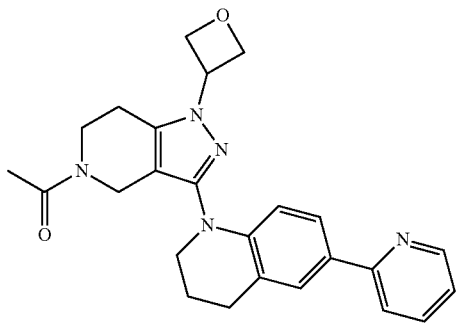 [SMILES: CC(=O)N1CCc2c(c(N3CCCc4cc(-c5ccccn5)ccc43)nn2C2COC2)C1]

To a solution of 1-[3-(6-bromo-3,4-dihydro-2H-quinolin-1-yl)-1-(oxetan-3-yl)-6,7-dihydro-4H-pyrazolo[4,3-c]pyridin-5-yl]ethanone (100 mg, 0.2 mmol) and tributyl(2-pyridyl)stannane (85 mg, 0.2 mmol) in toluene (5 mL) was added tetrakis(triphenylphosphine)palladium(0) (27 mg, 0.02 mmol) under a nitrogen atmosphere. The mixture was heated to 120° C. for 12 h. After cooling the reaction to room temperature, the mixture was concentrated in vacuo. The resultant residue was dissolved in EtOAc (200 mL) and washed with water (200 mL×2) and brine solution (100 mL). The combined organic layers were dried over anhydrous Na$_2$SO$_4$, filtered and concentrated in vacuo. The crude residue was purified by reverse phase chromatography (acetonitrile 10%-40%/0.2% formic acid in water) to give the title compound (9 mg, 8%) as a yellow solid. $^1$H NMR (400 MHz, DMSO-d$_6$) δ 8.55 (d, J=4.4 Hz, 1H), 7.82-7.68 (m, 4H), 7.21-7.18 (m, 1H), 6.59-6.53 (m, 1H), 5.50-5.43 (m, 1H), 4.95-4.85 (m, 4H), 4.13-4.11 (m, 2H), 3.74-3.65 (m, 4H), 2.90 (t, J=6.0 Hz, 2H), 2.80-2.76 (m, 2H), 2.05-1.94 (m, 5H). LCMS M/Z (M+H) 430.

Example 28

1-[3-[6-(1-methylpyrazol-3-yl)-3,4-dihydro-2H-quinolin-1-yl]-1-(oxetan-3-yl)-6,7-dihydro-4H-pyrazolo[4,3-c]pyridin-5-yl]ethanone

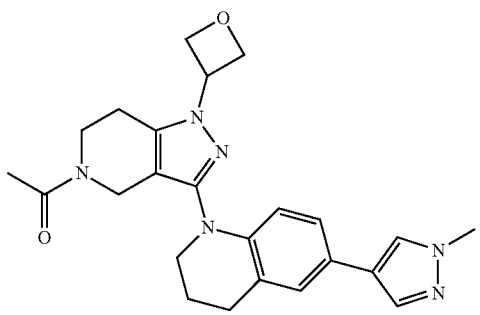 [SMILES: CC(=O)N1CCc2c(c(N3CCCc4cc(-c5cnn(C)c5)ccc43)nn2C2COC2)C1]

Step 1

1-(1-(oxetan-3-yl)-3-(6-(4,4,5,5-tetramethyl-1,3,2-dioxaborolan-2-yl)-3,4-dihydroquinolin-1(2H)-yl)-6,7-dihydro-1H-pyrazolo[4,3-c]pyridin-5(4H)-yl)ethanone

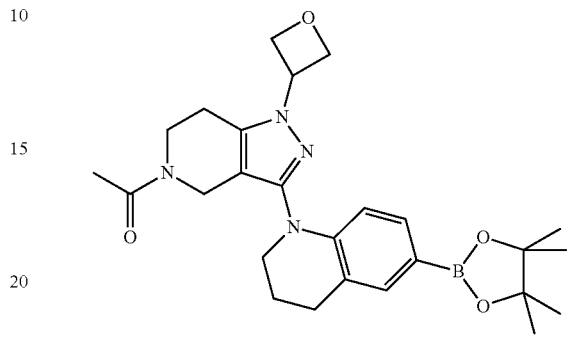

To a mixture of 1-[3-(6-bromo-3,4-dihydro-2H-quinolin-1-yl)-1-(oxetan-3-yl)-6,7-dihydro-4H-pyrazolo[4,3-c]pyridin-5-yl]ethanone (5 g, 11.6 mmol), Na$_2$CO$_3$ (2.46 g, 23.2 mmol) and 4,4,5,5-tetramethyl-2-(4,4,5,5-tetramethyl-1,3,2-dioxaborolan-2-yl)-1,3,2-dioxaborolane (8.83 g, 34.8 mmol) in DMF (50 mL) was added [1,1'-bis(diphenylphosphino)ferrocene]dichloropalladium(II), complex with dichloromethane (847 mg, 1.16 mmol). The mixture was heated to 70° C. for 12 h under a nitrogen atmosphere. After cooling the reaction to room temperature, the mixture was filtered and the filtrate was concentrated in vacuo. The crude residue was purified by silica gel chromatography (DCM/MeOH=50:1) to give the title compound (3.0 g, 27%) as red oil. LCMS M/Z (M+H) 352.

Step 2

1-[3-[6-(1-methylpyrazol-3-yl)-3,4-dihydro-2H-quinolin-1-yl]-1-(oxetan-3-yl)-6,7-dihydro-4H-pyrazolo[4,3-c]pyridin-5-yl]ethanone

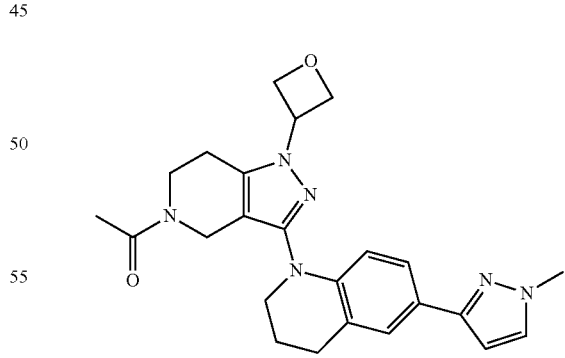

To a mixture of 3-bromo-1-methyl-pyrazole (40 mg, 0.25 mmol), 1-[1-(oxetan-3-yl)-3-[6-(4,4,5,5-tetramethyl-1,3,2-dioxaborolan-2-yl)-3,4-dihydro-2H-quinolin-1-yl]-6,7-dihydro-4H-pyrazolo[4,3-c]pyridin-5-yl]ethanone (100 mg, 0.21 mmol) and Na$_2$CO$_3$ (44 mg, 0.42 mmol) in 1,4-dioxane (1 mL) and water (0.25 mL) was added [1,1'-bis(diphenylphosphino)ferrocene]dichloropalladium(II), complex with dichloromethane (15 mg, 0.02 mmol). The mixture was heated to 100° C. for 12 h under a nitrogen atmosphere. After cooling the reaction to room temperature, the mixture was filtered and the filtrate was concentrated in vacuo. The crude residue was purified by reverse phase chromatography (acetonitrile 22-52%/0.2% formic acid in water) to give the title compound (16 mg, 17%) as a white solid. $^1$H NMR (400 MHz, DMSO-d$_6$) δ 7.60 (s, 1H), 7.41 (s, 1H), 7.35-7.30 (m, 1H), 6.49-6.43 (m, 2H), 5.45-5.40 (m, 1H), 4.91-4.88 (m, 2H), 4.84-4.80 (m, 2H), 4.07-4.04 (m, 2H), 3.79 (s, 3H), 3.64-3.58 (m, 4H), 2.82-2.80 (m, 2H), 2.76-2.61 (m, 2H), 2.01-1.89 (m, 5H). LCMS M/IZ (M+H) 433.

The Following Compounds were Prepared in a Similar Fashion to Step 2 of Example 28

Examples 29-43

| Example | Compound Name | NMR | m/z |
|---|---|---|---|
| Example 29 | 1-[3-[6-(1,3-dimethylpyrazol-4-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 7.69 (s, 1H), 7.06 (s, 1H), 7.02-6.97 (m, 1H), 6.54-6.48 (m, 1H), 5.49-5.41 (m, 1H), 4.96-4.81 (m, 4H), 4.11-4.09 (m, 2H), 3.75 (s, 3H), 3.73-3.59 (m, 4H), 2.87-2.62 (m, 4H), 2.23 (s, 3H), 2.05-1.94 (m, 5H) | 447 |
| Example 30 | 1-[1-(oxetan-3-yl)-3-(6-thiazol-2-yl-3,4-dihydro-2H-quinolin-1-yl)-6,7-dihydro-4H-pyrazolo[4,3-c]pyridin-5-yl]ethanone | $^1$H NMR (400 MHz, DMSO-d$_6$) δ 7.74 (d, J = 3.6 Hz, 1H), 7.58-7.49 (m, 3H), 6.55-6.49 (m, 1H), 5.46-5.43 (m, 1H), 4.92-4.83 (m, 4H), 4.11-4.08 (m, 2H), 3.66-3.62 (m, 4H), 2.87-2.76 (m, 4H), 2.03-1.97 (m, 5H) | 436 |
| Example 31 | 1-[1-(oxetan-3-yl)-3-(6-thiazol-5-yl-3,4-dihydro-2H-quinolin-1-yl)-6,7-dihydro-4H-pyrazolo[4,3-c]pyridin-5-yl]ethanone | $^1$H NMR (400 MHz, DMSO-d$_6$) δ 8.92 (s, 1H), 8.08 (s, 1H), 7.35 (s, 1H), 7.27-7.25 (m, 1H), 6.56-6.50 (m, 1H), 5.47-5.46 (m, 1H), 4.92-4.84 (m, 4H), 4.12-4.09 (m, 2H), 3.69-3.62 (m, 4H), 2.86-2.77 (m, 4H), 2.04-1.94 (m, 5H) | 436 |
| Example 32 | 1-[3-[6-(5-methyl-1H-pyrazol-3-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 7.39 (s, 1H), 7.30-7.28 (m, 1H), 6.51-6.45 (m, 1H), 6.24 (s, 1H), 5.46-5.43 (m, 1H), 4.92-4.83 (m, 4H), 4.09-4.07 (m, 2H), 3.67-3.61 (m, 4H), 2.84-2.76 (m, 4H), 2.19 (s, 3H), 2.04-1.92 (m, 5H) | 433 |
| Example 33 | N-[5-[1-[5-acetyl-1-(oxetan-3-yl)-6,7-dihydro-4H-pyrazolo[4,3-c]pyridin-3-yl]-3,4-dihydro-2H-quinolin-6-yl]-2-pyridyl]acetamide | $^1$H NMR (400 MHz, DMSO-d$_6$) δ 10.45 (s, 1H), 8.50 (s, 1H), 8.06-8.03 (m, 1H), 7.94-7.91 (m, 1H), 7.36 (s, 1H), 7.28-7.26 (m, 1H), 6.56-6.51 (m, 1H), 5.44-5.41 (m, 1H), 4.91-4.81 (m, 4H), 4.09-4.07 (m, 2H), 3.65-3.60 (m, 4H), 2.86-2.75 (m, 4H), 2.06 (s, 3H), 2.02-1.95 (m, 5H) | 487 |
| Example 34 | 4-[1-[5-acetyl-1-(oxetan-3-yl)-6,7-dihydro-4H-pyrazolo[4,3-c]pyridin-3-yl]-3,4-dihydro-2H-quinolin-6-yl]-1-methyl-pyrazole-3-carbonitrile | $^1$H NMR (400 MHz, DMSO-d$_6$) δ 8.21 (s, 1H), 7.30 (s, 1H), 7.24-7.21 (m, 1H), 6.59-6.53 (m, 1H), 5.47-5.44 (m, 1H), 4.92-4.85 (m, 4H), 4.12-4.10 (m, 2H), 3.93 (s, 3H), 3.70-3.62 (m, 4H), 2.85-2.77 (m, 4H), 2.05-1.94 (m, 5H) | 458 |
| Example 35 | 1-[3-[6-(1,5-dimethylpyrazol-3-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 7.39 (s, 1H), 7.34-7.26 (m, 1H), 6.54-6.41 (m, 1H), 6.28 (s, 1H), 5.47-5.42 (m, 1H), 5.02-4.76 (m, 4H), 4.16-4.00 (m, 2H), 3.7 (s, 3H), 3.68-3.61 (m, 4H), 2.88-2.66 (m, 4H), 2.24 (s, 3H), 2.05-1.87 (m, 5H) | 447 |
| Example 36 | 1-[3-[6-(1,5-dimethylpyrazol-4-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 7.42 (s, 1H), 7.03 (s, 1H), 6.98-6.94 (m, 1H), 6.55-6.49 (m, 1H), 5.48-5.43 (m, 1H), 4.94-4.83 (m, 4H), 4.11-4.09 (m, 2H), 3.74 (s, 3H), 3.71-3.61 (m, 4H), 2.84-2.65 (m, 4H), 2.31 (s, 3H), 2.05-1.94 (m, 5H) | 447 |
| Example 37 | 1-[3-[6-[1-(difluoromethyl)pyrazol-4-yl]-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 8.49 (s, 1H), 8.12 (s, 1H), 7.78 (t, J = 59.6 Hz, 1H), 7.37 (s, 1H), 7.28-7.24 (m, 1H), 6.54-6.48 (m, 1H), 5.49-5.42 (m, 1H), 4.94-4.84 (m, 4H), 4.10-4.08 (m, 2H), 3.73-3.61 (m, 4H), 2.85-2.65 (m, 4H), 2.05-1.93 (m, 5H) | 469 |

| Example | Compound Name | NMR | m/z |
|---|---|---|---|
| Example 38 | 1-[3-[6-[3-(difluoromethyl)-1-methyl-pyrazol-4-yl]-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 7.95 (s, 1H), 7.13 (s, 1H), 7.08-7.04 (m, 1H), 7.00 (t, J = 53.6 Hz, 1H), 6.54-6.48 (m, 1H), 5.49-5.42 (m, 1H), 4.94-4.84 (m, 4H), 4.12-4.10 (m, 2H), 3.87 (s, 3H), 3.72-3.61 (m, 4H), 2.84-2.65 (m, 4H), 2.05-1.94 (m, 5H) | 483 |
| Example 39 | 1-[3-[6-(1,2-dimethylimidazol-4-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 7.35 (s, 1H), 7.28-7.26 (m, 2H), 6.48-6.42 (m, 1H), 5.45-5.42 (m, 1H), 4.92-4.83 (m, 4H), 4.08-4.06 (m, 2H), 3.68-4.61 (m, 2H), 3.53 (s, 3H), 2.82-2.67 (m, 4H), 2.28 (s, 3H), 2.04-1.92 (m, 5H) | 447 |
| Example 40 | 1-[3-[6-(4-methyl-1H-imidazol-2-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 7.55 (s, 1H), 7.46-7.44 (m, 1H), 6.53-6.47 (m, 1H), 5.47-5.42 (m, 1H), 4.94-4.84 (m, 4H), 4.10-4.08 (m, 2H), 3.68-4.62 (m, 2H), 2.86-2.67 (m, 4H), 2.28 (s, 3H), 2.10-1.93 (m, 8H) | 433 |
| Example 41 | 1-[3-[6-(1-methyl-1,2,4-triazol-3-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 8.40 (s, 1H), 7.65 (s, 1H), 7.60-7.56 (m, 1H), 6.55-6.49 (m, 1H), 5.47-5.44 (m, 1H), 4.95-4.85 (m, 4H), 4.12-4.10 (m, 2H), 3.86 (s, 3H), 3.68-4.63 (m, 4H), 2.88-2.79 (m, 4H), 2.05-1.94 (m, 5H) | 434 |
| Example 42 | 1-[1-(oxetan-3-yl)-3-(6-thiazol-4-yl-3,4-dihydro-2H-quinolin-1-yl)-6,7-dihydro-4H-pyrazolo[4,3-c]pyridin-5-yl]ethanone | $^1$H NMR (400 MHz, DMSO-$d_6$) δ 9.10 (s, 1H), 7.83 (s, 1H), 7.67 (s, 1H), 7.60-7.56 (m, 1H), 6.57-6.51 (m, 1H), 5.48-5.42 (m, 1H), 4.95-4.85 (m, 4H), 4.12-4.10 (m, 2H), 3.72-4.64 (m, 4H), 2.86-2.79 (m, 4H), 2.05-1.94 (m, 5H) | 436 |
| Example 43 | 1-[3-[6-(5-methylsulfonyl-3-pyridyl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 9.16 (s, 1H), 8.90 (s, 1H), 8.42 (s, 1H), 7.59 (s, 1H), 7.49-7.45 (m, 1H), 6.66-6.60 (m, 1H), 5.49-5.46 (m, 1H), 4.95-4.85 (m, 4H), 4.15-4.12 (m, 2H), 3.69-4.66 (m, 4H), 3.38 (s, 3H), 2.93-2.79 (m, 4H), 2.05-1.94 (m, 5H) | 508 |

Example 44

1-[1-(oxetan-3-yl)-3-(6-pyrimidin-4-yl-3,4-dihydro-2H-quinolin-1-yl)-6,7-dihydro-4-pyrazolo[4,3-c]pyridin-5-yl]ethanone

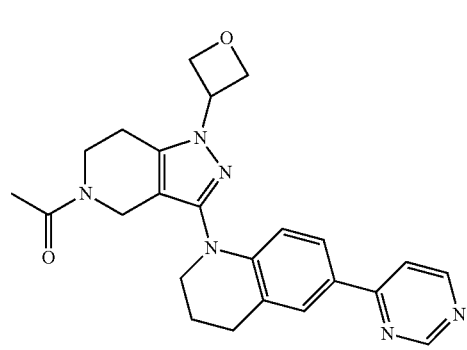 [SMILES: CC(=O)N1CCc2c(c(N3CCCc4cc(-c5ccncn5)ccc43)nn2C2COC2)C1]

Step 1

1-[3-[6-(1-methylpyrazol-3-yl)-3,4-dihydro-2H-quinolin-1-yl]-1-(oxetan-3-yl)-6,7-dihydro-4H-pyrazolo[4,3-c]pyridin-5-yl]ethanone

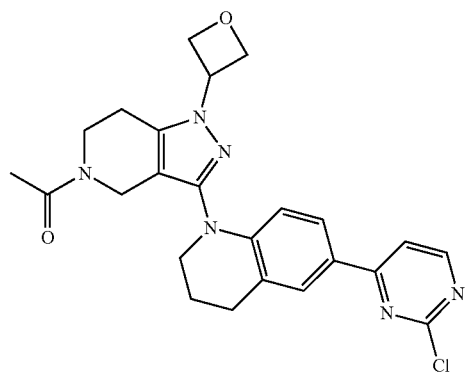 [SMILES: CC(=O)N1CCc2c(c(N3CCCc4cc(-c5ccnc(Cl)n5)ccc43)nn2C2COC2)C1]

To a solution of 1-[1-(oxetan-3-yl)-3-[6-(4,4,5,5-tetramethyl-1,3,2-dioxaborolan-2-yl)-3,4-dihydro-2H-quinolin-1-yl]-6,7-dihydro-4H-pyrazolo[4,3-c]pyridin-5-yl]ethanone (300 mg, 0.44 mmol), 2,4-dichloropyrimidine (78 mg, 0.53 mmol) and Na₂CO₃ (93 mg, 0.88 mmol) in 1,4-dioxane (3.0 mL) and water (1.0 mL) was added [1,1'bis(diphenylphosphino)ferrocene]dichloropalladium(II), complex with dichloromethane (32 mg, 0.04 mmol). The mixture was heated to 100° C. for 2 h under a nitrogen atmosphere. After cooling the reaction to room temperature, the mixture was filtered and the filtrate was concentrated in vacuo. The crude residue was purified by silica gel chromatography (DCM/MeOH=50:1) to give the title compound (150 mg, 62%) as a yellow solid. LCMS M/Z (M+H) 465.

Step 2

1-[1-(oxetan-3-yl)-3-(6-pyrimidin-4-yl-3,4-dihydro-2H-quinolin-1-yl)-6,7-dihydro-4-pyrazolo[4,3-c]pyridin-5-yl]ethanone

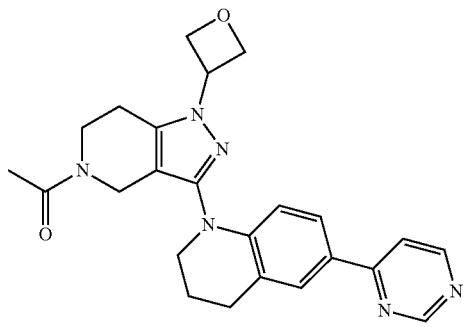 [SMILES: CC(=O)N1CCc2c(c(N3CCCc4cc(-c5ccncn5)ccc43)nn2C2COC2)C1]

To a solution of 1-[3-[6-(2-chloropyrimidin-4-yl)-3,4-dihydro-2H-quinolin-1-yl]-1-(oxetan-3-yl)-6,7-dihydro-4H-pyrazolo[4,3-c]pyridin-5-yl]ethanone (50 mg, 0.09 mmol) in MeOH (2.0 mL) was added 10% Pd/C (10 mg, 0.1 mmol). The mixture was stirred at 25° C. for 12 h under a hydrogen atmosphere (15 Psi). The mixture was filtered and the filtrate was concentrated in vacuo. The crude residue was purified by reverse phase chromatography (acetonitrile 20-16%/0.2% formic acid in water) to give the title compound (8 mg, 19%) as a yellow solid. ¹H NMR (400 MHz, DMSO-d₆) δ 9.06 (s, 1H), 8.67 (d, J=5.6 Hz, 1H), 7.94 (s, 1H), 7.90-7.84 (m, 2H), 6.60-6.54 (m, 1H), 5.50-5.45 (m, 1H), 4.92-4.85 (m, 4H), 4.14-4.12 (m, 2H), 3.69-3.66 (m, 4H), 2.92-2.79 (m, 4H), 2.05-1.94 (m, 5H). LCMS M/Z (M+H) 431.

Example 45

1-[3-(3,4-dihydro-2H-quinolin-1-yl)-1-[(3S)-tetrahydrofuran-3-yl]-6,7-dihydro-4H-pyrazolo[4,3-c]pyridin-5-yl]ethanone

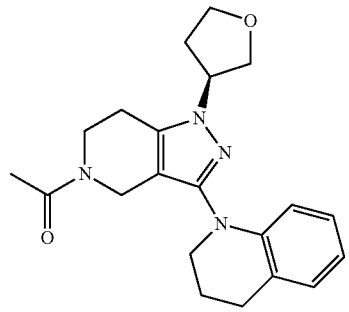 [SMILES: CC(=O)N1CCc2c(c(N3CCCc4ccccc43)nn2[C@H]2CCOC2)C1]

To a solution of (S)-1-(3-bromo-1-(tetrahydrofuran-3-yl)-6,7-dihydro-1H-pyrazolo[4,3-c]pyridin-5(4H)-yl)ethanone (Intermediate G, 200 mg, 0.64 mmol), 1,2,3,4-tetrahydroquinoline (85 mg, 0.64 mmol) and t-BuONa (123 mg, 1.28 mmol) in 1,4-dioxane (2.0 mL) was added chloro(2-dicyclohexylphosphino-2',6'-di-i-propoxy-1,1'-biphenyl)[2-(2-aminoethylphenyl)]palladium(ii), methyl-tert-butylether adduct (52 mg, 0.064 mmol) and 2-dicyclohexylphosphino-2',6'-di-i-propoxy-1,1'-biphenyl (30 mg, 0.064 mmol). The mixture was heated to 120° C. for 12 h under a nitrogen atmosphere. After cooling the reaction to room temperature, the mixture was filtered and the filtrate was concentrated in vacuo. The crude residue was purified by reverse phase chromatography (acetonitrile 38-68%/0.2% formic acid in water) to give the title compound (37 mg, 16%) as a white solid. ¹H NMR (400 MHz, DMSO-d₆) δ 6.99 (d, J=7.2 Hz, 1H), 6.95-6.88 (m, 1H), 6.63-6.60 (m, 1H), 6.44-6.39 (m, 1H), 4.98-4.81 (m, 1H), 4.07-3.94 (m, 4H), 3.82-3.68 (m, 4H), 3.57-3.52 (m, 2H), 2.84-2.70 (m, 4H), 2.33-2.19 (m, 2H), 2.06-1.93 (m, 5H). LCMS M/Z (M+H) 367.

Example 46

5-[1-[5-acetyl-1-[(3S)-tetrahydrofuran-3-yl]-6,7-dihydro-4H-pyrazolo[4,3-c]pyridin-3-yl]-3,4-dihydro-2H-quinolin-6-yl]-N-methyl-pyridine-2-carboxamide

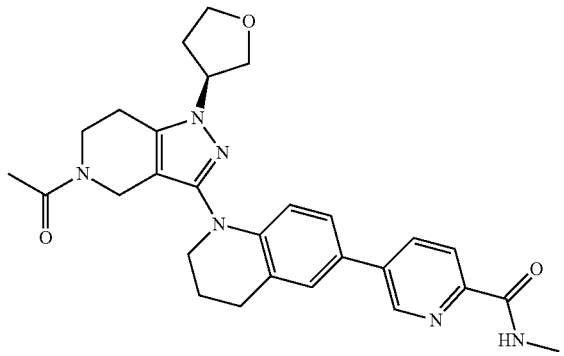 [SMILES: CNC(=O)c1ccc(-c2ccc3c(c2)CCCN3c2nn([C@H]3CCOC3)c3c2CN(C(C)=O)CC3)cn1]

Step 1

(S)-1-(3-(6-bromo-3,4-dihydroquinolin-1(2H)-yl)-1-(tetrahydrofuran-3-yl)-6,7-dihydro-1H-pyrazolo[4,3-c]pyridin-5(4H)-yl)ethanone

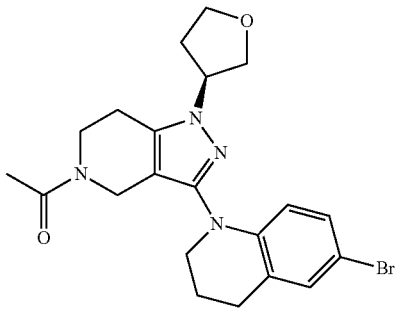 [SMILES: CC(=O)N1CCc2c(c(N3CCCc4cc(Br)ccc43)nn2[C@H]2CCOC2)C1]

To a solution of (S)-1-(3-(3,4-dihydroquinolin-1(2H)-yl)-1-(tetrahydrofuran-3-yl)-6,7-dihydro-1H-pyrazolo[4,3-c]pyridin-5(4H)-yl)ethanone (1.3 g, 3.55 mmol) in DMF (13 mL) was added N-bromosuccinimide (695 mg, 3.9 mmol). The mixture was stirred at 20° C. for 12 h under a nitrogen atmosphere. Water (100 mL) was added and the mixture was extracted with EtOAc (50 mL×3). The combined organic layers were washed with brine (30 mL×3), dried over anhydrous Na$_2$SO$_4$ and concentrated in vacuo. The crude residue was purified by silica gel chromatography (DCM/MeOH=50:1) to give the title compound (1.7 g, 86%) as a yellow oil. LCMS M/Z (M+H) 445.

Step 2

5-[1-[5-acetyl-1-[(3S)-tetrahydrofuran-3-yl]-6,7-dihydro-4H-pyrazolo[4,3-c]pyridin-3-yl]-3,4-dihydro-2H-quinolin-6-yl]-N-methyl-pyridine-2-carboxamide

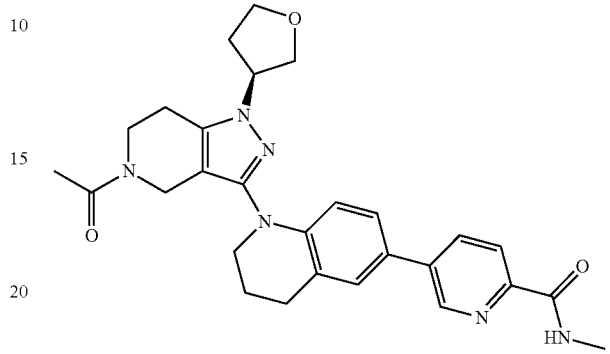

To a solution of N-methyl-5-(4,4,5,5-tetramethyl-1,3,2-dioxaborolan-2-yl)pyridine-2-carboxamide (141 mg, 0.54 mmol) and 1-[3-(6-bromo-3,4-dihydro-2H-quinolin-1-yl)-1-[(3S)-tetrahydrofuran-3-yl]-6,7-dihydro-4H-pyrazolo[4,3-c]pyridin-5-yl]ethanone (200 mg, 0.45 mmol) in 1,4-dioxane (2 mL) and water (0.5 mL) was added [1,1'-bis(diphenylphosphino)ferrocene]dichloropalladium(II), complex with dichloromethane (33 mg, 0.04 mmol). The mixture was heated to 100° C. for 12 h under a nitrogen atmosphere. After cooling the reaction to room temperature, the mixture was filtered and filtrate was concentrated in vacuo. The crude residue was purified by reverse phase chromatography (acetonitrile 22-16%/0.2% formic acid in water) to give the title compound (27 mg, 12%) as a yellow solid. $^1$H NMR (400 MHz, DMSO-d$_6$) δ 8.83 (s, 1H), 8.71-8.69 (m, 1H), 8.14 (d, J=8.0 Hz, 1H), 8.01 (d, J=8.8 Hz, 1H), 7.50 (s, 1H), 7.42-7.38 (m, 1H), 6.57-6.51 (m, 1H), 4.95-4.92 (m, 1H), 4.14-4.12 (m, 2H), 4.02-3.90 (m, 2H), 3.83-3.80 (m, 4H), 3.60-3.59 (m, 2H), 2.90-2.82 (m, 4H), 2.88 (s, 3H), 2.35-2.15 (m, 2H), 2.07-1.96 (m, 5H). LCMS M/Z (M+H) 501.

The Following Compounds were Prepared in a Similar Fashion to Step 2 of Example 46

Examples 47-50

| Example | Compound Name | NMR | m/z |
|---|---|---|---|
| Example 47 | 1-[3-[6-(1,3-dimethylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone | $^1$H NMR (400 MHz, DMSO-d$_6$) δ 7.68 (s, 1H), 7.03 (s, 1H), 6.99-6.94 (m, 1H), 6.49-6.39 (m, 1H), 4.95-4.85 (m, 1H), 4.11-4.09 (m, 2H), 4.05-3.93 (m, 2H), 3.82-3.68 (m, 7H), 3.60-3.50 (m, 2H), 2.89-2.63 (m, 4H), 2.34-2.18 (m, 5H), 2.09-1.90 (m, 5H) | 461 |
| Example 48 | 1-[3-[6-(2-methoxy-4-pyridyl)-3,4-dihydro-2H-quinolin-1-yl]-1-[(3S)-tetrahydrofuran-3-yl]-6,7-dihydro-4H-pyrazolo[4,3-c]pyridin-5-yl]ethanone | $^1$H NMR (400 MHz, DMSO-d$_6$) δ 8.10 (d, J = 5.6 Hz, 1H), 7.48 (s, 1H), 7.39-7.36 (m, 1H), 7.21 (d, J = 5.6 Hz, 1H), 6.97 (s, 1H), 6.51-6.45 (m, 1H), 4.94-4.88 (m, 1H), 4.13-4.11 (m, 2H), 3.91-3.97 (m, 2H), 3.85 (s, 3H), 3.81-3.70 (m, 4H), 3.58-3.57 (m, 2H), 2.87-2.84 (m, 4H), 2.29-2.18 (m, 2H), 2.06-1.95 (m, 5H) | 474 |
| Example 49 | 1-[3-[6-(1-cyclopropylpyrazol-4-yl)-3,4-dihydro-2H-quinolin-1-yl]-1-[(3S)- | $^1$H NMR (400 MHz, DMSO-d$_6$) δ 8.00 (s, 1H), 7.67 (s, 1H), 7.21 (s, 1H), 7.14-7.09 (m, 1H), 6.45-6.39 (m, 1H), 4.91-4.88 (m, 1H), 4.09-4.07 (m, 4H), 3.81-3.67 (m, | 473 |

| Example | Compound Name | NMR | m/z |
|---|---|---|---|
| | tetrahydrofuran-3-yl]-6,7-dihydro-4H-pyrazolo[4,3-c]pyridin-5-yl]ethanone | 5H), 3.55-3.53 (m, 2H), 2.82-2.77 (m, 4H), 2.29-2.15 (m, 2H), 2.07-1.93 (m, 5H), 1.03-0.93 (m, 4H) | |
| Example 50 | 1-[3-[7-(1-methylpyrazol-4-yl)-2,3,4,5-tetrahydro-1-benzazepin-1-yl]-1-[(3S)-tetrahydrofuran-3-yl]-6,7-dihydro-4H-pyrazolo[4,3-c]pyridin-5-yl]ethanone | $^1$H NMR (400 MHz, DMSO-d$_6$) δ 8.06-8.05 (m, 1H), 8.00-7.79 (m, 1H), 7.44-7.42 (m, 1H), 7.31-7.26 (m, 1H), 6.90-6.77 (m, 1H), 4.81-4.78 (m, 1H), 4.03-3.98 (m, 2H), 3.84-3.78 (m, 5H), 3.55-3.43 (m, 6H), 2.77-2.55 (m, 4H), 2.25-2.22 (m, 2H), 1.97-1.62 (m, 7H) | 461 |

Example 51

1-[3-[6-(6-ethoxy-3-pyridyl)-3,4-dihydro-2H-quinolin-1-yl]-1-[(3S)-tetrahydrofuran-3-yl]-6,7-dihydro-4H-pyrazolo[4,3-c]pyridin-5-yl]ethanone

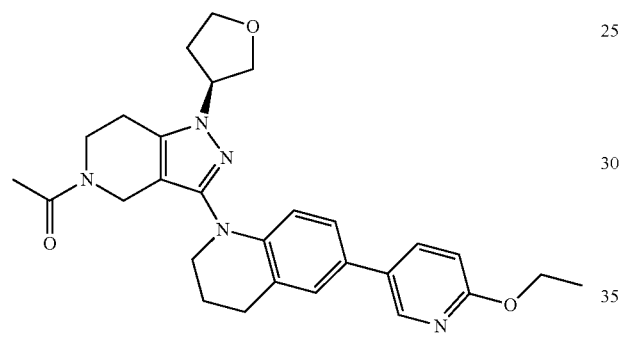

Step 1

(S)-1-(3-(6-(6-fluoropyridin-3-yl)-3,4-dihydroquinolin-1(2H)-yl)-1-(tetrahydrofuran-3-yl)-6,7-dihydro-1H-pyrazolo[4,3-c]pyridin-5(4H)-yl)ethanone

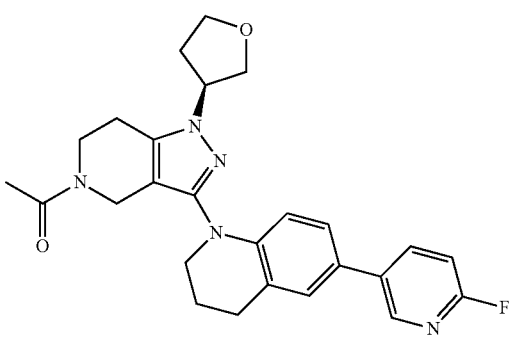 [SMILES: CC(=O)N1CCc2c(c(N3CCCc4cc(-c5ccc(F)nc5)ccc43)nn2[C@H]2CCOC2)C1]

To a solution of (S)-1-(3-(6-bromo-3,4-dihydroquinolin-1(2H)-yl)-1-(tetrahydrofuran-3-yl)-6,7-dihydro-1H-pyrazolo[4,3-c]pyridin-5(4H)-yl)ethanone (762 mg, 1.70 mmol), 2-fluoro-5-(4,4,5,5-tetramethyl-1,3,2-dioxaborolan-2-yl)pyridine (382 mg, 1.70 mmol) and Na$_2$CO$_3$ (363 mg, 3.40 mmol) in 1,4-dioxane (4.0 mL) and water (1 mL) was added [1,1'-bis(diphenylphosphino)ferrocene]dichloropalladium (II) (125 mg, 0.17 mmol). The mixture was heated to 120° C. for 12 h under a nitrogen atmosphere. After cooling the reaction to room temperature, the mixture was concentrated in vacuo. The crude residue was purified by silica gel chromatography (DCM/MeOH=100:1 to 20:1) to give the title compound (0.58 g, 73%) as a yellow oil. LCMS M/Z (M+H) 462.

Step 2

1-[3-[6-(6-ethoxy-3-pyridyl)-3,4-dihydro-2H-quinolin-1-yl]-1-[(3S)-tetrahydrofuran-3-yl]-6,7-dihydro-4H-pyrazolo[4,3-c]pyridin-5-yl]ethanone

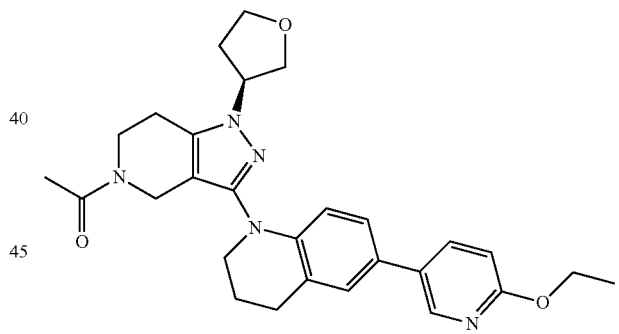

To a solution of(S)-1-(3-(6-(6-fluoropyridin-3-yl)-3,4-dihydroquinolin-1(2H)-yl)-1-(tetrahydrofuran-3-yl)-6,7-dihydro-1H-pyrazolo[4,3-c]pyridin-5 (4H)-yl)ethanone (170 mg, 0.37 mmol) in EtOH (3.0 mL) was added EtONa (1.0 M in EtOH, 0.55 mL, 0.55 mmol). The mixture was heated to 80° C. for 12 h under a nitrogen atmosphere. After cooling the reaction to room temperature, the mixture was filtered and the filtrate concentrated in vacuo. The crude residue was purified by reverse phase chromatography (acetonitrile 30-60%/0.2% formic acid in water) to give the title compound (11 mg, 6%) as a white solid. $^1$H NMR (400 MHz, DMSO-d$_6$) δ 8.34 (s, 1H), 7.87 (d, J=8.0 Hz, 1H), 7.30 (s, 1H), 7.26-7.19 (m, 1H), 6.80 (d, J=8.0 Hz, 1H), 6.52-6.40 (m, 1H), 4.91-4.88 (m, 1H), 4.33-4.28 (m, 2H), 4.17-4.07 (m, 2H), 4.06-3.91 (m, 2H), 3.86-3.65 (m, 4H), 3.63-3.56 (m, 2H), 2.90-2.68 (m, 4H), 2.30-2.25 (m, 2H), 2.09-1.93 (m, 5H), 1.32 (t, J=7.2 Hz, 3H). LCMS M/Z (M+H) 488.

Example 52

4-[1-[5-acetyl-1-[(3S)-tetrahydrofuran-3-yl]-6,7-dihydro-4H-pyrazolo[4,3-c]pyridin-3-yl]-3,4-dihydro-2H-quinolin-6-yl]-1-methyl-pyrazole-3-carbonitrile

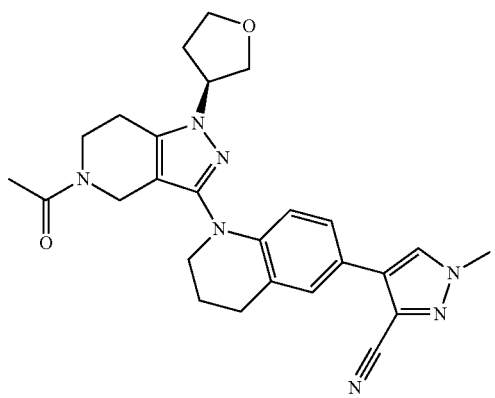 [SMILES: CC(=O)N1CCc2c(c(N3CCCc4cc(-c5cn(C)nc5C#N)ccc43)nn2[C@H]2CCOC2)C1]

Step 1

(S)-1-(1-(tetrahydrofuran-3-yl)-3-(6-(4,4,5,5-tetramethyl-1,3,2-dioxaborolan-2-yl)-3,4-dihydroquinolin-1(2H)-yl)-6,7-dihydro-1H-pyrazolo[4,3-c]pyridin-5(4H)-yl)ethanone

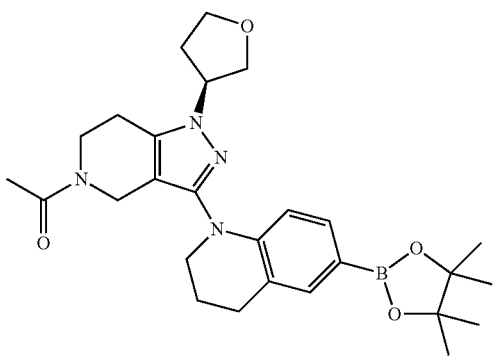 [SMILES: CC(=O)N1CCc2c(c(N3CCCc4cc(B5OC(C)(C)C(C)(C)O5)ccc43)nn2[C@H]2CCOC2)C1]

To a mixture of 1-[3-(6-bromo-3,4-dihydro-2H-quinolin-1-yl)-1-[(3S)-tetrahydrofuran-3-yl]-6,7-dihydro-4H-pyrazolo[4,3-c]pyridin-5-yl]ethanone (1.7 g, 3.82 mmol), 4,4,5,5-tetramethyl-2-(4,4,5,5-tetramethyl-1,3,2-dioxaborolan-2-yl)-1,3,2-dioxaborolane (2.91 g, 11.45 mmol), AcOK (748 mg, 7.63 mmol) in DMF (17 mL) was added [1,1'-bis(diphenylphosphino)ferrocene]dichloropalladium(II), complex with dichloromethane (279 mg, 0.38 mmol). The mixture was heated to 100° C. for 2 h under a nitrogen atmosphere. After cooling the reaction to room temperature, the mixture was filtered and the filtrate concentrated in vacuo. The crude residue was purified by silica gel chromatography (DCM/MeOH=100:1) to give the title compound (0.9 g, 40%) as a yellow solid. LCMS M/Z (M+H) 493.

Step 2

4-[1-[5-acetyl-1-[(3S)-tetrahydrofuran-3-yl]-6,7-dihydro-4H-pyrazolo[4,3-c]pyridin-3-yl]-3,4-dihydro-2H-quinolin-6-yl]-1-methyl-pyrazole-3-carbonitrile

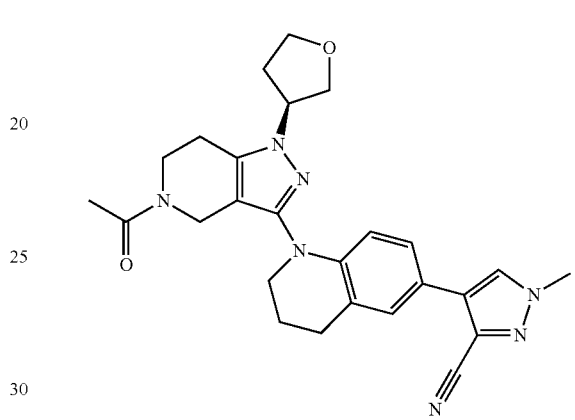

To a suspension of 4-bromo-1-methyl-pyrazole-3-carbonitrile (91 mg, 0.49 mmol), 1-[1-[(3S)-tetrahydrofuran-3-yl]-3-[6-(4,4,5,5-tetramethyl-1,3,2-dioxaborolan-2-yl)-3,4-dihydro-2H-quinolin-1-yl]-6,7-dihydro-4H-pyrazolo[4,3-c]pyridin-5-yl]ethanone (200 mg, 0.41 mmol) and $Na_2CO_3$ (86 mg, 0.81 mmol) in 1,4-dioxane (2 mL) and water (0.5 mL) was added [1,1'-bis(diphenylphosphino)ferrocene]dichloropalladium(II), complex with dichloromethane (30 mg, 0.04 mmol). The mixture was heated to 100° C. for 2 h under a nitrogen atmosphere. After cooling the reaction to room temperature, the mixture was filtered and the filtrate was concentrated in vacuo. The crude residue was purified by reverse phase chromatography (acetonitrile 36-16%/0.2% formic acid in water) to give the title compound (22 mg, 11%) as a white solid. $^1$H NMR (400 MHz, DMSO-$d_6$) δ 8.21 (s, 1H), 7.28 (s, 1H), 7.19 (d, J=6.4 Hz, 1H), 6.53-6.46 (m, 1H), 4.96-4.85 (m, 1H), 4.12-4.11 (m, 2H), 4.00-3.95 (m, 2H), 3.93 (s, 3H), 3.81-3.70 (m, 4H), 3.57-3.56 (m, 2H), 2.83-2.80 (m, 4H), 2.28-2.24 (m, 2H), 2.06-1.95 (m, 5H). LCMS M/Z (M+H) 472.

The Following Compounds were Prepared in a Similar Fashion to Step 2 of Example 52

Examples 53-58

| Example | Compound Name | NMR | m/z |
|---|---|---|---|
| Example 53 | 1-[3-[6-(1,5-dimethylpyrazol-4-yl)-3,4-dihydro-2H-quinolin-1-yl]-1-[(3S)- | $^1$H NMR (400 MHz, DMSO-$d_6$) δ 7.41 (s, 1H), 7.01 (s, 1H), 6.96-6.91 (m, 1H), 6.49-6.43 (m, 1H), 4.92-4.89 (m, 1H), 4.18-4.11 (m, 2H), 4.01-3.85 (m, 2H), | 461 |

| Example | Compound Name | NMR | m/z |
|---|---|---|---|
| | tetrahydrofuran-3-yl]-6,7-dihydro-4H-pyrazolo[4,3-c]pyridin-5-yl]ethanone | 3.82-3.68 (m, 4H), 3.74 (s, 3H), 3.56-3.54 (m, 2H), 2.82-2.79 (m, 4H), 2.30-2.29 (m, 5H), 2.06-1.93 (m, 5H) | |
| Example 54 | 1-[3-[6-(6-methoxy-3-pyridyl)-3,4-dihydro-2H-quinolin-1-yl]-1-[(3S)-tetrahydrofuran-3-yl]-6,7-dihydro-4H-pyrazolo[4,3-c]pyridin-5-yl]ethanone | $^1$H NMR (400 MHz, DMSO-$d_6$) δ 8.32 (s, 1H), 7.87-7.84 (m, 1H), 7.28 (s, 1H), 7.18-7.16 (m, 1H), 6.80 (d, J = 8.4 Hz, 1H), 6.49-6.43 (m, 1H), 4.90-4.85 (m, 1H), 4.09-4.07 (m, 2H), 3.98-3.82 (m, 2H), 3.78 (s, 3H), 3.77-3.67 (m, 4H), 3.63-3.54 (m, 2H), 2.83-2.80 (m, 4H), 2.47-2.27 (m, 2H), 2.03-1.91 (m, 5H) | 474 |
| Example 55 | 1-[3-[6-(1,3-dimethylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone | $^1$H NMR (400 MHz, DMSO-$d_6$) δ 7.68 (s, 1H), 7.03 (s, 1H), 6.99-6.94 (m, 1H), 6.47-6.41 (m, 1H), 4.92-4.86 (m, 1H), 4.11-4.09 (m, 2H), 4.00-3.85 (m, 2H), 3.80-3.69 (m, 4H), 3.73 (s, 3H), 3.55-3.54 (m, 2H), 2.82-2.78 (m, 4H), 2.35-2.29 (m, 2H), 2.22 (s, 3H), 2.21-1.94 (m, 5H) | 461 |
| Example 56 | 1-[3-[6-(1,5-dimethylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone | $^1$H NMR (400 MHz, DMSO-$d_6$) δ 7.41 (s, 1H), 7.01 (s, 1H), 6.96-6.91 (m, 1H), 6.49-6.43 (m, 1H), 4.93-4.86 (m, 1H), 4.11-4.10 (m, 2H), 4.03-3.94 (m, 2H), 3.84-3.78 (m, 2H), 3.74 (s, 3H), 3.71-3.68 (m, 2H), 3.58-3.53 (m, 2H), 2.83-2.71 (m, 4H), 2.30-2.19 (m, 3H), 2.06-1.93 (m, 5H) | 461 |
| Example 57 | N-[5-[1-[5-acetyl-1-[(3S)-tetrahydrofuran-3-yl]-6,7-dihydro-4H-pyrazolo[4,3-c]pyridin-3-yl-]3,4-dihydro-2H-quinolin-6-yl]-2-pyridyl]acetamide | $^1$H NMR (400 MHz, DMSO-$d_6$) δ 10.50 (s., 1H), 8.53 (s., 1H), 8.08 (d, J = 8.4 Hz, 1H), 7.95 (d, J = 8.8 Hz, 1H), 7.38 (s, 1H), 7.33-7.24 (m, 1H), 6.58-6.46 (m, 1H), 4.93-4.88 (m, 1H), 4.17-4.08 (m, 2H), 4.06-3.93 (m, 2H), 3.86-3.66 (m, 4H), 3.64-3.53 (m, 2H), 2.91-2.69 (m, 4H), 2.36-2.20 (m, 2H), 2.10-2.07 (m, 5H), 2.02-1.91 (m, 3H) | 501 |
| Example 58 | 1-[3-[6-(5-methyl-1H-pyrazol-3-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone | $^1$H NMR (400 MHz, DMSO-$d_6$) δ 12.61-12.17 (m, 1H), 7.44-7.19 (m, 2H), 6.49-6.38 (m, 1H), 6.23 (s, 1H), 4.92-4.88 (m., 1H), 4.09 (s., 2H), 4.05-3.92 (m, 2H), 3.86-3.64 (m, 4H), 3.61-3.51 (m, 2H), 2.89-2.66 (m, 4H), 2.35-2.12 (m, 5H), 2.07-1.94 (m, 2H), 1.94 (s, 3H) | 447 |

Example 59

5-[1-(5-acetyl-1-tetrahydropyran-4-yl-6,7-dihydro-4H-pyrazolo[4,3-c]pyridin-3-yl)-3,4-dihydro-2H-quinolin-6-yl]-N-methyl-pyridine-2-carboxamide

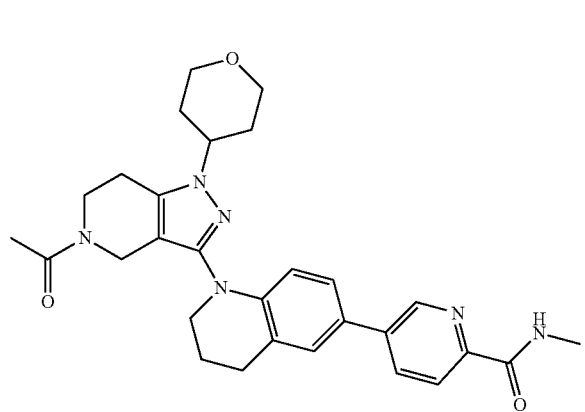 [SMILES: CNC(=O)c1ccc(-c2ccc3c(c2)CCCN3c2nn(C3CCOCC3)c3c2CN(C(C)=O)CC3)cn1]

Step 1

1-(3-(3,4-dihydroquinolin-1(2H)-yl)-1-(tetrahydro-2H-pyran-4-yl)-6,7-dihydro-1H-pyrazolo[4,3-c]pyridin-5(4H)-yl)ethanone

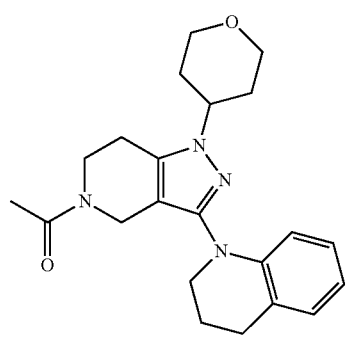 [SMILES: CC(=O)N1CCc2c(c(N3CCCc4ccccc43)nn2C2CCOCC2)C1]

To a solution of 1-(3-bromo-1-tetrahydropyran-4-yl-6,7-dihydro-4H-pyrazolo[4,3-c]pyridin-5-yl)ethanone (Intermediate I, 1.8 g, 5.48 mmol) in 1,4-dioxane (16 mL) was added 1,2,3,4 tetrahydroquinoline (0.7 mL, 5.48 mmol), chloro(2-dicyclohexylphosphino-2',6'-di-i-propoxy-1,1'-biphenyl)(2'-amino-1,1'-biphenyl-2-yl)palladium(II) (426 mg, 0.55 mmol), 2-dicyclohexylphosphino-2',6'-di-i-propoxy-1,1'-biphenyl (256 mg, 0.55 mmol) and t-BuONa (2.1 g, 21.94 mmol). The mixture was heated to 120° C. for 16 h under a nitrogen atmosphere. After cooling the reaction to room temperature, the mixture was concentrated in vacuo. The crude residue was purified by chromatography column (DCM/MeOH=20:1) to give the title compound (1.7 g, 73%) as a yellow solid.

Step 2

1-(3-(6-bromo-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone

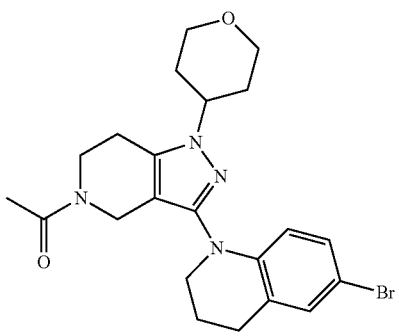 [SMILES: CC(=O)N1CCc2c(c(N3CCCc4cc(Br)ccc43)nn2C2CCOCC2)C1]

To a solution of 1-(3-(6-bromo-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone (1.7 g, 4.02 mmol) in DCM (20 mL) was added N-bromosuccinimide (787 mg, 4.42 mmol) at room temperature portionwise. The mixture was stirred at room temperature for 1 h. The mixture was concentrated in vacuo. The crude residue was purified by silica gel chromatography (DCM/MeOH=20:1) to give the title compound (2 g, 90%) as a yellow solid.

Step 3

5-[1-(5-acetyl-1-tetrahydropyran-4-yl-6,7-dihydro-4H-pyrazolo[4,3-c]pyridin-3-yl)-3,4-dihydro-2H-quinolin-6-yl]-N-methyl-pyridine-2-carboxamide

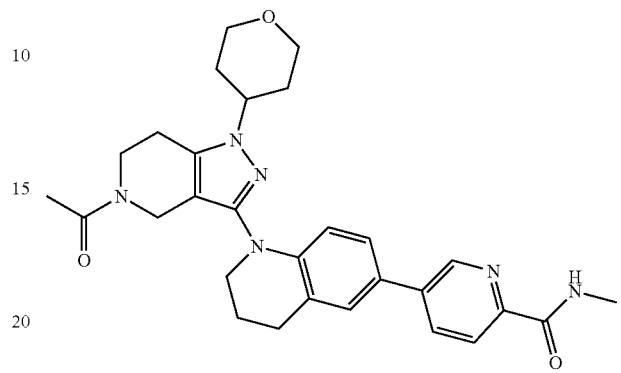

To a solution of 1-(3-(6-bromo-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone (200 mg, 0.36 mmol) in dioxane (10 mL) and water (2 mL) was added N-methyl-5-(4,4,5,5-tetramethyl-1,3,2-dioxaborolan-2-yl)picolinamide (96 mg, 0.36 mmol), $K_2CO_3$ (152 mg, 1.10 mmol) and [1,1'-bis(diphenylphosphino)ferrocene]dichloropalladium(II), complex with dichloromethane (26 mg, 0.036 mmol). The mixture was heated to 110° C. for 12 h under a nitrogen atmosphere. After cooling the reaction to room temperature, the mixture was concentrated in vacuo. The residue was purified by Prep-TLC (DCM/MeOH=15:1) to give the title compound (59 mg, 26%) as a white solid. $^1$H NMR (400 MHz, CDCl$_3$) δ 8.71 (s, 1H), 8.20-8.17 (m, 1H), 8.00-7.94 (m, 2H), 7.33 (s, 1H), 7.24-7.21 (m, 1H), 6.60 (d, J=8.0 Hz, 1H), 4.31-4.12 5H), 3.92 (t, J=6.0 Hz, 1H), 3.76-3.70 (m, 3H), 3.53 (t, J=12 Hz, 1H), 3.06 (t, J=4.8 Hz, 1H), 2.96-2.92 (m, 2H), 2.83-2.75 (m, 2H), 2.33-2.30 (m, 2H), 2.18-2.06 (m, 5H), 1.89-1.85 (m, 2H). LCMS M/Z (M+H) 515.

The Following Compounds were Prepared in a Similar Fashion to Step 3 of Example 59

Examples 60-64

| Example | Compound Name | NMR | m/z |
|---|---|---|---|
| Example 60 | 1-[3-[6-(2-methoxy-4-pyridyl)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, DMSO-d$_6$) δ 8.10 (d, J = 4.0 Hz, 1H), 7.48 (s, 1H), 7.41-7.36 (m, 1H), 7.20 (d, J = 4.0 Hz, 1H), 6.97 (s, 1H), 6.51-6.45 (m, 1H), 4.68-4.44 (m, 1H), 4.14-4.12 (m, 2H), 3.96-3.94 (m, 2H), 3.85 (s, 3H), 3.75-3.70 (m, 2H), 3.61-3.58 (m, 2H), 3.45 (t, J = 11.6 Hz, 2H), 2.86-2.67 (m, 4H), 2.06-1.96 (m, 7H), 1.83-1.80 (m, 2H) | 488 |
| Example 61 | N-[5-[1-(5-acetyl-1-tetrahydropyran-4-yl-6,7-dihydro-4H-pyrazolo[4,3-c]pyridin-3-yl)-3,4-dihydro-2H-quinolin-6-yl]-2-pyridyl]acetamide | $^1$H NMR (400 MHz, DMSO-d$_6$) δ 10.5 (s, 1H), 8.52 (s, 1H), 8.08-8.06 (m, 1H), 7.96-7.93 (m, 1H), 7.37 (s, 1H), 7.29-7.25 (m, 1H), 6.53-6.47 (m, 1H), 4.30-4.24 (m, 1H), 4.13-4.11 (m, 2H), 3.96-3.93 (m, 2H), 3.75-3.68 (m, 2H), 3.60-3.55 (m, 2H), 3.44 (t, J = 12.0 Hz, 2H), 2.85-2.66 (m, 4H), 2.08 (s, 3H), 2.06-1.95 (m, 7H), 1.82-1.79 (m, 2H) | 515 |
| Example 62 | 1-[3-[6-(5-methyl-1H-pyrazol-3-yl)-3,4- | $^1$H NMR (400 MHz, DMSO-d$_6$) δ 12.32 (s, 1H), 7.33 (s, 1H), 7.27-7.22 (m, 1H), | 461 |

| Example | Compound Name | NMR | m/z |
|---|---|---|---|
| | dihydro-2H-quinolin-1-yl]-1-tetrahydropyran-4-yl-6,7-dihydro-4H-pyrazolo[4,3-c]pyridin-5-yl]ethanone | 6.42-6.36 (m, 1H), 6.19 (s, 1H), 4.29-4.23 (m, 1H), 4.11-4.09 (m, 2H), 3.95-3.93 (m, 2H), 3.76-3.68 (m, 2H), 3.58-3.53 (m, 2H), 3.47-3.41 (m, 2H), 2.83-2.66 (m, 4H), 2.18 (s, 3H), 2.05-1.93 (m, 7H), 1.82-1.78 (m, 1H) | |
| Example 63 | 1-[3-[6-(1,5-dimethylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, DMSO-$d_6$) δ 7.41 (s, 1H), 7.01 (s, 1H), 6.96-6.91 (m, 1H), 6.49-6.43 (m, 1H), 4.29-4.24 (m, 1H), 4.13-4.11 (m, 2H), 4.00-3.94 (m, 2H), 3.76-3.69 (m, 5H), 3.58-3.42 (m, 4H), 2.86-2.71 (m, 4H), 2.30 (s, 3H), 2.07-1.94 (m, 7H), 1.82-1.79 (m, 2H) | 475 |
| Example 64 | 1-[3-[6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, DMSO-$d_6$) δ 7.91 (s, 1H), 7.67 (s, 1H), 7.19 (s, 1H), 7.14-7.03 (m, 1H), 6.49-6.36 (m, 1H), 4.35-4.19 (m, 1H), 4.16-4.02 (m, 2H), 3.96-3.94 (m, 2H), 3.82 (s, 3H), 3.77-3.64 (m, 2H), 3.55-3.33 (m, 4H), 2.90-2.69 (m, 4H), 2.06-1.90 (m, 7H), 1.82-1.79 (m, 2H) | 461 |

Example 65

1-[1-methyl-3-[6-(1-methylpyrazol-4-yl)-3,4-dihydro-2H-quinolin-1-yl]-6,7-dihydro-4H-pyrazolo[4,3-c]pyridin-5-yl]ethanone

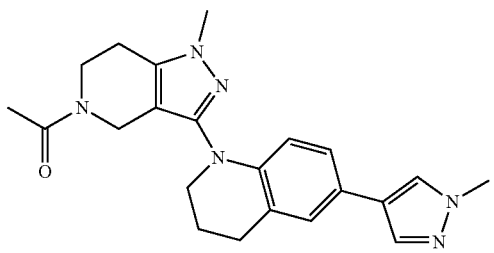 [SMILES: CC(=O)N1CCc2c(c(N3CCCc4cc(-c5cnn(C)c5)ccc43)nn2C)C1]

Step 1

6-(1-methyl-1H-pyrazol-4-yl)-1,2,3,4-tetrahydroquinoline

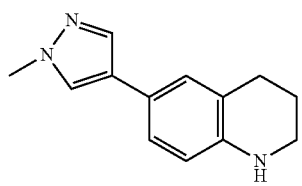 [SMILES: Cn1cc(-c2ccc3c(c2)CCCN3)cn1]

To a solution of 6-bromo-1,2,3,4-tetrahydroquinoline (17.0 g, 80.16 mmol), 1-methyl-4-(4,4,5,5-tetramethyl-1,3,2-dioxaborolan-2-yl)-1H-pyrazole (25.0 g, 120.23 mmol) and K$_2$CO$_3$ (33.2 g, 240.47 mmol) in dioxane/H$_2$O (5:1, 150 mL) was added [1,1'-bis(diphenylphosphino)ferrocene]dichloropalladium(II) (5.8 g, 8.02 mmol). The mixture was heated to 120° C. for 16 h under a nitrogen atmosphere. After cooling the reaction to room temperature, the mixture was filtered and the filtrate was concentrated in vacuo. The crude residue was purified by silica gel chromatography (petroleum ether/EtOAc=1:1) to give the title compound (8.0 g, 47%) as a yellow solid. $^1$H NMR (400 MHz, CD$_3$OD) δ 7.71 (s, 1H), 7.62 (s, 1H), 7.07 (d, J=6.0 Hz, 2H), 6.50 (d, J=8.4 Hz, 1H), 3.87 (s, 3H), 3.23 (t, J=5.2 Hz, 2H), 2.75 (t, J=6.4 Hz, 2H), 1.94-1.88 (m, 2H).

Step 2

1-[1-methyl-3-[6-(1-methylpyrazol-4-yl)-3,4-dihydro-2H-quinolin-1-yl]-6,7-dihydro-4H-pyrazolo[4,3-c]pyridin-5-yl]ethanone

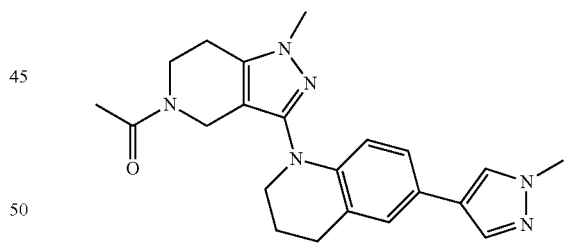

To a solution of 6-(1-methyl-1H-pyrazol-4-yl)-1,2,3,4-tetrahydroquinoline (300 mg, 0.98 mmol), 1-(3-bromo-1-methyl-6,7-dihydro-1H-pyrazolo[4,3-c]pyridin-5(4H)-yl)ethanone (Intermediate B, 280 mg, 1.08 mmol), chloro(2-dicyclohexylphosphino-2',6'-di-i-propoxy-1,1'-biphenyl)[2-(2-aminoethylphenyl)]palladium(II), methyl-tert-butylether adduct (84 mg, 0.10 mmol) and 2-dicyclohexylphosphino-2',6'-di-i-propoxy-1,1'-biphenyl (47 mg, 0.10 mmol) in dioxane (3 mL), was added t-BuONa (284 mg, 2.95 mmol). The mixture was irradiated in a microwave at 120° C. for 30 min. After cooling the reaction to room temperature, the mixture was filtered and the filtrate was concentrated in vacuo. The crude residue was purified by silica gel chromatography (DCM/MeOH=30:1) to give the crude product that was further purified by reverse phase chromatography (acetonitrile 30-60%/0.1% NH₄HCO₃ in water) to give the title compound (30 mg, 8%) as a white solid. ¹H NMR (400 MHz, DMSO-d₆) δ 7.89 (s, 1H), 7.66 (s, 1H), 7.18 (s, 1H), 7.10-7.07 (m, 1H), 6.42-6.37 (m, 1H), 4.06 (s, 2H), 3.80 (s, 3H), 3.72-3.63 (m, 5H), 3.53-3.50 (m, 2H), 2.77 (s, 3H), 2.64-2.49 (m, 1H), 2.04-1.91 (m, 5H). LCMS M/Z (M+H) 391.

The Following Compounds were Prepared in a Similar Fashion to Example 65

Examples 66-69

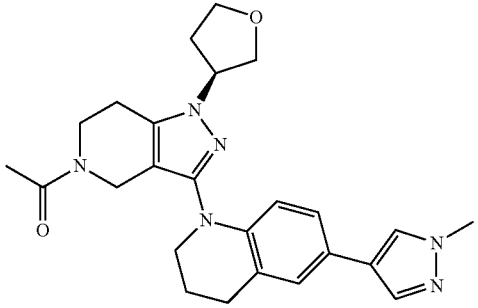

| Example | Compound Name | NMR | m/z |
|---|---|---|---|
| Example 66 | 1-[3-[6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone | ¹H NMR (400 MHz, DMSO-d₆) δ 7.92 (s, 1H), 7.68 (s, 1H), 7.20 (s, 1H), 7.15-7.06 (m, 1H), 6.49-6.37 (m, 1H), 4.93-4.85 (m, 1H), 4.14-4.06 (m, 2H), 4.05-3.92 (m, 2H), 3.87-3.65 (m, 7H), 3.62-3.48 (m, 2H), 2.83-2.78 (m, 4H), 2.37-2.18 (m, 2H), 2.06 (s, 2H), 1.95-1.94 (m, 3H) | 447 |
| Example 67 | 1-[3-[6-(1-methylpyrazol-4-yl)-3,4-dihydro-2H-quinolin-1-yl]-1-(oxetan-3-yl)-6,7-dihydro-4H-pyrazolo[4,3-c]pyridin-5-yl]ethanone | ¹H NMR (400 MHz, DMSO-d₆) δ 7.93 (s, 1H), 7.69 (s, 1H), 7.22 (s, 1H), 7.18-7.08 (m, 1H), 6.54-6.44 (m, 1H), 5.47-5.41 (m, 1H), 4.96-4.82 (m, 4H), 4.11-4.04 (m, 2H), 3.83 (s, 3H), 3.75-3.58 (m, 4H), 2.86-2.61 (m, 4H), 2.05-1.93 (m, 5H) | 433 |
| Example 68 | 1-[3-[7-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone | ¹H NMR (400 MHz, DMSO-d₆) δ 7.88 (s, 1H), 7.57 (s, 1H), 6.97 (d, J = 7.6 Hz, 1H), 6.81 (d, J = 7.6 Hz, 1H), 6.68-6.63 (m, 1H), 4.91-4.88 (m, 1H), 4.09-4.07 (m, 4H), 3.84-3.80 (m, 7H), 3.58-3.57 (m, 2H), 2.84-2.73 (m, 4H), 2.29-2.27 (m, 2H), 2.06-1.85 (m, 5H) | 447 |
| Example 69 | 1-[3-[6-[1-methyl-3-(trifluoromethyl)pyrazol-4-yl]-3,4-dihydro-2H-quinolin-1-yl]-1-(oxetan-3-yl)-6,7-dihydro-4H-pyrazolo[4,3-c]pyridin-5-yl]ethanone | ¹H NMR (400 MHz, DMSO-d₆) δ 8.01 (s, 1H), 7.05 (s, 1H), 7.00-6.96 (m, 1H), 6.56-6.49 (m, 1H), 5.47-5.43 (m, 1H), 4.92-4.85 (m, 4H), 4.10 (s, 2H), 3.92 (s, 3H), 3.72-3.63 (m, 4H), 2.82-2.65 (m, 4H), 2.09-1.94 (m, 5H) | 501 |

Examples 70 & 71

1-[3-[6-(1-methylpyrazol-4-yl)-3,4-dihydro-2H-quinolin-1-yl]-1-[(3R)-tetrahydrofuran-3-yl]-6,7-dihydro-4H-pyrazolo[4,3-c]pyridin-5-yl]ethanone and 1-[3-[6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone

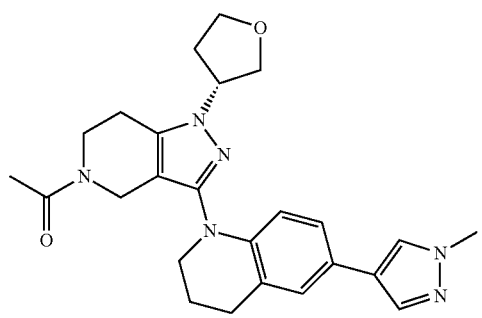

Racemic 1-[3-[6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (Example 66, 75 mg) was separated using chiral SFC (Chiralcel OJ 250×30 mm I.D., 5 um; Supercritical CO₂/EtOH (0.1% NH₃H₂O)=65:35 at 50 mL/min) to give 1-[3-[6-(1-methylpyrazol-4-yl)-3,4-dihydro-2H-quinolin-1-yl]-1-[(3R)-tetrahydrofuran-3-yl]-6,7-dihydro-4H-pyrazolo[4,3-c]pyridin-5-yl]ethanone (23 mg, first peak) and 1-[3-[6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone (30 mg, second peak). Absolute configuration was arbitrarily assigned to each enantiomer. Example 70: ¹H NMR (400 MHz, DMSO-d₆) δ 7.92 (s, 1H), 7.68 (s, 1H), 7.20 (s, 1H), 7.15-7.06 (m, 1H), 6.49-6.37 (m, 1H), 4.93-4.85 (m, 1H), 4.14-4.06 (m, 2H), 4.05-3.92 (m, 2H), 3.87-3.65 (m, 7H), 3.62-3.48 (m, 2H), 2.83-2.78 (m, 4H), 2.37-2.18 (m, 2H), 2.06-1.94 (m, 5H). LCMS M/Z (M+H) 447. Example 71: ¹H NMR (400 MHz, DMSO-d₆) δ 7.92 (s, 1H), 7.68 (s, 1H), 7.20 (s, 1H), 7.15-7.06 (m, 1H), 6.49-6.37 (m, 1H), 4.93-4.85 (m, 1H), 4.14-4.06 (m, 2H), 4.05-3.92 (m, 2H), 3.87-3.65 (m, 7H), 3.62-3.48 (m, 2H), 2.83-2.78 (m, 4H), 2.37-2.18 (m, 2H), 2.06-1.94 (m, 5H). LCMS M/Z (M+H) 447.

Example 72

1-[3-[6-(1-methylpyrazol-4-yl)-3,4-dihydro-2H-quinolin-1-yl]-1-tetrahydropyran-2-yl-6,7-dihydro-4H-pyrazolo[4,3-c]pyridin-5-yl]ethanone

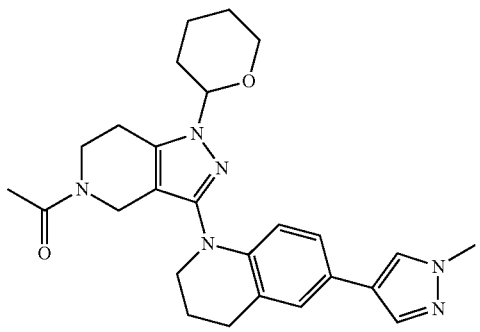 [SMILES: CC(=O)N1CCc2c(c(N3CCCc4cc(-c5cnn(C)c5)ccc43)nn2C2CCCCO2)C1]

Step 1

1-(3-bromo-6,7-dihydro-1H-pyrazolo[4,3-c]pyridin-5(4H)-yl)ethanone

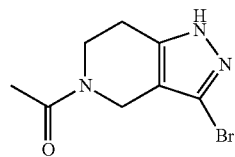

To a solution of tert-butyl 3-bromo-1,4,6,7-tetrahydropyrazolo[4,3-c]pyridine-5-carboxylate (10.0 g, 33.1 mmol) in DCM (80 mL) at 0° C. was added trifluoacetic acid (40 mL, 538.6 mmol) dropwise. The mixture was stirred at room temperature for 2 h. The mixture was concentrated in vacuo to give 3-bromo-4,5,6,7-tetrahydro-1H-pyrazolo[4,3-c]pyridine (5.9 g, 70.6%) that was dissolved in DCM (100 mL). To the mixture at 0° C. was added triethylamine (18.4 mL, 132.4 mmol) and acetic anhydride (2.7 g, 26.5 mmol) dropwise. The mixture was stirred at 0° C. for an additional 1 h. The reaction was quenched with water (100 mL) and extracted with DCM (200 mL×2). The combined organic layers were dried over anhydrous $Na_2SO_4$, filtered and concentrated in vacuo to give the title compound (7.0 g, 87%) as a light green solid.

Step 2

1-(3-bromo-1-(tetrahydro-2H-pyran-2-yl)-6,7-dihydro-1H-pyrazolo[4,3-c]pyridin-5(4H)-yl)ethanone

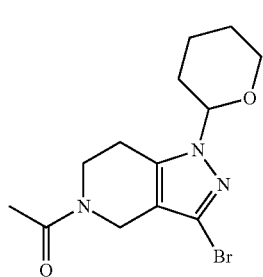 [SMILES: CC(=O)N1CCc2c(c(Br)nn2C2CCCCO2)C1]

To a solution of 1-(3-bromo-1,4,6,7-tetrahydropyrazolo[4,3-c]pyridin-5-yl)ethanone (6.0 g, 20.2 mmol) and p-toluenesulfonic acid (1.7 g, 10.1 mmol) in THF (40 mL) at 25° C. was added 3,4-dihydro-2H-pyran (3.4 g, 40.3 mmol) dropwise. The mixture was heated to 100° C. for 16 h. After cooling the reaction to room temperature, the mixture was filtered and the filtrate was concentrated in vacuo to give the title compound (7.0 g, 64%) as a brown solid. LCMS M/Z (M+H) 328.

Step 3

1-[3-[6-(1-methylpyrazol-4-yl)-3,4-dihydro-2H-quinolin-1-yl]-1-tetrahydropyran-2-yl-6,7-dihydro-4H-pyrazolo[4,3-c]pyridin-5-yl]ethanone

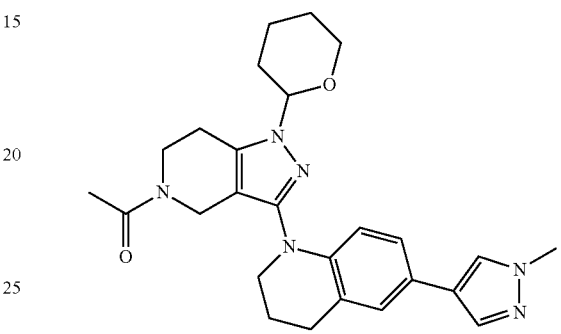

To a solution of 1-(3-bromo-1-tetrahydropyran-2-yl-6,7-dihydro-4H-pyrazolo[4,3-c]pyridin-5-yl)ethanone (7.0 g, 12.6 mmol) in 1,4-dioxane (30 mL) was added t-BuONa (3.6 g, 37.8 mmol), 6-(1-methylpyrazol-4-yl)-1,2,3,4-tetrahydroquinoline (3.2 g, 15.1 mmol), chloro(2-dicyclohexylphosphino-2',6'-di-i-propoxy-1,1'-biphenyl)(2'-amino-1,1'-biphenyl-2-yl)palladium(II) (0.98 g, 1.3 mmol) and 2-dicyclohexylphosphino-2',6'-di-i-propoxy-1,1'-biphenyl (0.59 g, 1.3 mmol). The mixture was heated to 120° C. for 16 h under a nitrogen atmosphere. After cooling the reaction to room temperature, the reaction was filtered and concentrated in vacuo. The crude residue was purified by silica gel chromatography (DCM/MeOH=10:1) to give the title compound (5.8 g, 85%) as a yellow solid. $^1$H NMR (400 MHz, DMSO-$d_6$) δ 7.92 (s, 1H), 7.68 (s, 1H), 7.21 (s, 1H), 7.14-7.10 (m, 1H), 6.45-6.39 (m, 1H), 5.30-5.28 (m, 1H), 4.13-4.09 (m, 1H), 4.01-3.87 (m, 2H), 3.82 (s, 3H), 3.62-3.61 (m, 1H), 3.58-3.53 (m, 3H), 2.87-2.76 (m, 4H), 2.25-2.13 (m, 1H), 2.06 (s, 2H), 1.97-1.93 (m, 3H), 1.86-1.80 (m, 1H), 1.64-1.45 (m, 4H). LCMS M/Z (M+H) 461.

Example 73

1-[3-[6-(1-methylpyrazol-4-yl)-3,4-dihydro-2H-quinolin-1-yl]-1-tetrahydrofuran-2-yl-6,7-dihydro-4H-pyrazolo[4,3-c]pyridin-5-yl]ethanone

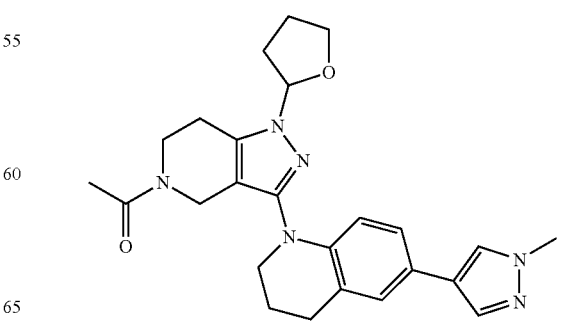

Step 1

1-(3-(6-(1-methyl-1H-pyrazol-4-yl)-3,4-dihydroquinolin-(2H)-yl)-6,7-dihydro-1H-pyrazolo[4,3-c]pyridin-5(4H)-yl)ethanone

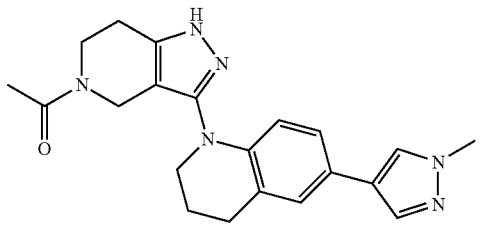 [SMILES: CC(=O)N1CCc2[nH]nc(N3CCCc4cc(-c5cnn(C)c5)ccc43)c2C1]

To a solution of 1-[3-[6-(1-methylpyrazol-4-yl)-3,4-dihydro-2H-quinolin-1-yl]-1-tetrahydropyran-2-yl-6,7-dihydro-4H-pyrazolo[4,3-c]pyridin-5-yl]ethanone (5.8 g, 12.6 mmol) in MeOH (30 mL) at 0° C. was added HCl in MeOH (4M, 10 mL, 40 mmol) dropwise and stirred for 2 h. The mixture was concentrated in vacuo. The crude residue was dissolved in H$_2$O (30 mL) and the pH was adjusted to around 7 with sat. aq. Na$_2$CO$_3$. The mixture was extracted with EtOAc (30 mL×3). The combined organic layers were dried over anhydrous Na$_2$SO$_4$, filtered and concentrated in vacuo to give the title compound (3.7 g, 62%) as a yellow solid. LCMS M/Z (M+H) 377.

Step 2

1-[3-[6-(1-methylpyrazol-4-yl)-3,4-dihydro-2H-quinolin-1-yl]-1-tetrahydrofuran-2-yl-6,7-dihydro-4H-pyrazolo[4,3-c]pyridin-5-yl]ethanone

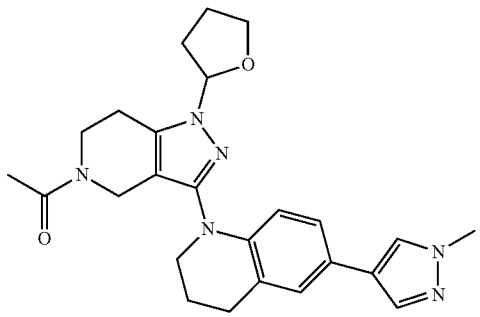 [SMILES: CC(=O)N1CCc2c(c(N3CCCc4cc(-c5cnn(C)c5)ccc43)nn2C2CCCO2)C1]

To a solution of 1-[3-[6-(1-methylpyrazol-4-yl)-3,4-dihydro-2H-quinolin-1-yl]-1,4,6,7-tetrahydropyrazolo[4,3-c]pyridin-5-yl]ethanone (200 mg, 0.53 mmol) and p-toluenesulfonic acid (46 mg, 0.27 mmol) in THF (2 mL) at room temperature was added 2,3-dihydrofuran (74 mg, 1.06 mmol) dropwise. The mixture was heated to 60° C. for 16 h. After cooling the reaction to room temperature, water (10 mL) was added and the mixture was extracted with EtOAc (10 mL×3). The combined organic layers were dried over anhydrous Na$_2$SO$_4$, filtered and concentrated in vacuo. The crude residue was purified by reverse phase chromatography (acetonitrile 32-62%/0.1% NH$_4$OH in water) to give the title compound (22 mg, 9%) as a white solid. $^1$H NMR (400 MHz, DMSO-d$_6$) δ 7.92 (s, 1H), 7.68 (s, 1H), 7.20 (s, 1H), 7.14-7.10 (m, 11H), 6.48-6.42 (m, 1H), 5.95-5.92 (m, 1H), 4.15-4.09 (m, 1H), 4.02-3.95 (m, 1H), 3.88-3.82 (m, 5H), 3.72-3.61 (m, 2H), 3.57-3.54 (m, 2H), 2.81-2.78 (m, 4H), 2.58-2.50 (m, 2H), 2.21-2.18 (m, 2H), 2.06-1.93 (m, 5H). LCMS M/Z (M+H) 447.

Example 74

1-[1-(1,1-dioxothiolan-3-yl)-3-[6-(1-methylpyrazol-4-yl)-3,4-dihydro-2H-quinolin-1-yl]-6,7-dihydro-4H-pyrazolo[4,3-c]pyridin-5-yl]ethanone

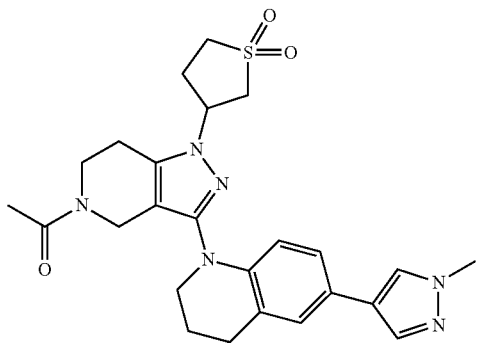 [SMILES: CC(=O)N1CCc2c(c(N3CCCc4cc(-c5cnn(C)c5)ccc43)nn2C2CCS(=O)(=O)C2)C1]

To a solution of 1-[3-[6-(1-methylpyrazol-4-yl)-3,4-dihydro-2H-quinolin-1-yl]-1,4,6,7-tetrahydropyrazolo[4,3-c]pyridin-5-yl]ethanone (Step 1, Example 73, 200 mg, 0.53 mmol) and 1,8-diazabicycloundec-7-ene (149 mg, 1.0 mmol) in MeCN (5 mL) was added 2,3-dihydrothiophene 1,1-dioxide (69 mg, 0.6 mmol). The mixture was heated to 80° C. for 2 h under a nitrogen atmosphere. After cooling the reaction to room temperature, water (20 mL) was added and the mixture was extracted with EtOAc (20 mL×3). The combined organic layers were dried over anhydrous Na$_2$SO$_4$, filtered and concentrated in vacuo. The crude residue was purified by reverse phase chromatography (acetonitrile 16-46%/0.1% NH$_4$OH in water) to give the title compound (60 mg, 25%) as a white solid. $^1$H NMR (400 MHz, DMSO-d$_6$) δ 7.90 (s, 1H), 7.65 (s, 1H), 7.18 (s, 1H), 7.12-7.07 (m, 1H), 6.48-6.42 (m, 1H), 5.14-5.06 (m, 1H), 4.06-4.04 (m, 2H), 3.79 (s, 3H), 3.76-3.68 (m, 3H), 3.60-3.45 (m, 3H), 3.38-3.36 (m, 1H), 2.84-2.73 (m, 4H), 2.58-2.52 (m, 2H), 2.06-1.93 (m, 5H). LCMS M/Z (M+H) 495.

Example 75

1-[4-[5-acetyl-3-[6-(1-methylpyrazol-4-yl)-3,4-dihydro-2H-quinolin-1-yl]-6,7-dihydro-4H-pyrazolo[4,3-c]pyridin-1-yl]-1-piperidyl]ethanone

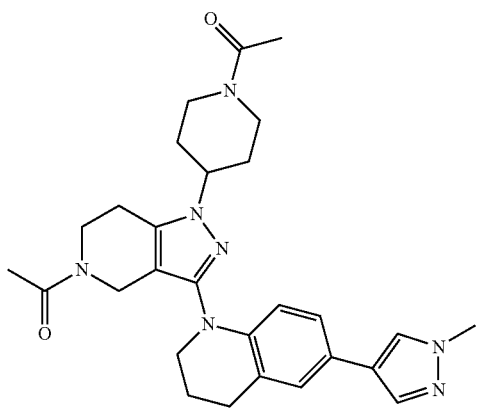 [SMILES: CC(=O)N1CCC(n2nc(N3CCCc4cc(-c5cnn(C)c5)ccc43)c3c2CCN(C(C)=O)C3)CC1]

Step 1

1-acetylpiperidin-4-yl methanesulfonate

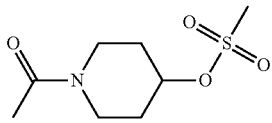

To a solution of 1-(4-hydroxy-1-piperidyl)ethanone (200 mg, 1.4 mmol) in DCM (5 mL) at 0° C. was added triethylamine (212 mg, 2.1 mmol) and methanesulfonyl chloride (480 mg, 4.19 mmol). The mixture was stirred at 25° C. for 2 h. Water (50 mL) was added and the mixture was extracted with DCM (50 mL×3). The combined organic layers were dried over anhydrous $Na_2SO_4$, filtered and concentrated in vacuo to give the title compound (300 mg, crude) as yellow oil that required no further purification. $^1$H NMR (400 MHz, $CDCl_3$) δ 4.98-4.92 (m, 1H), 3.83-3.81 (m, 1H), 3.67-3.65 (m, 1H), 3.58-3.56 (m, 1H), 3.43-3.41 (m, 1H), 3.06 (s, 3H), 2.01 (s, 3H), 2.00-1.88 (m, 4H).

Step 2

1-[4-[5-acetyl-3-[6-(1-methylpyrazol-4-yl)-3,4-di-hydro-2H-quinolin-1-yl]-6,7-dihydro-4H-pyrazolo[4,3-c]pyridin-1-yl]-1-piperidyl]ethanone

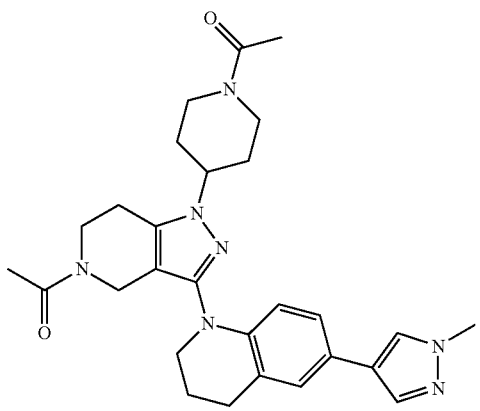 [SMILES: CC(=O)N1CCC(n2nc(N3CCCc4cc(-c5cnn(C)c5)ccc43)c3c2CCN(C(C)=O)C3)CC1]

To a solution of 1-[3-[6-(1-methylpyrazol-4-yl)-3,4-di-hydro-2H-quinolin-1-yl]-1,4,6,7-tetrahydropyrazolo[4,3-c]pyridin-5-yl]ethanone (Step 1, Example 73, 200 mg, 0.53 mmol) in DMF (3 mL) was added (1-acetyl-4-piperidyl) methanesulfonate (309 mg, 1.4 mmol) and $Cs_2CO_3$ (346 mg, 1.06 mmol). The mixture was heated to 60° C. for 16 h. After cooling the reaction to room temperature, the mixture was filtered and the filtrate was concentrated in vacuo. The crude residue was purified by reverse phase chromatography (acetonitrile 30-60%/0.1% $NH_4OH$ in water) to give the title compound (26 mg, 9%) as a light yellow solid. $^1$H NMR (400 MHz, DMSO-$d_6$) δ 7.91 (s, 1H), 7.67 (s, 1H), 7.19 (s, 1H), 7.12-7.08 (m, 1H), 6.44-6.38 (m, 1H), 4.47-4.44 (m, 1H), 4.30-4.28 (m, 1H), 4.11-4.09 (m, 2H), 3.89-3.70 (m, 5H), 3.54-3.51 (m, 2H), 3.32-3.10 (m, 2H), 2.84-2.67 (m, 4H), 2.06-1.73 (m, 7H), 2.03 (s, 3H). LCMS M/Z (M+H) 502.

Example 76

4-(5-acetyl-3-(6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-2-one

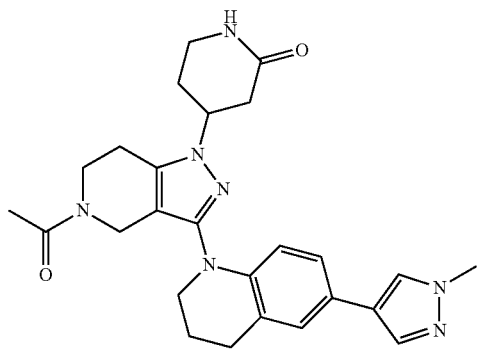 [SMILES: CC(=O)N1CCc2c(c(N3CCCc4cc(-c5cnn(C)c5)ccc43)nn2C2CCNC(=O)C2)C1]

Step 1

4-(5-acetyl-3-(6-(1-methyl-1H-pyrazol-4-yl)-3,4-dihydroquinolin-1(2H)-yl)-4,5,6,7-tetrahydro-1H-pyrazolo[4,3-c]pyridin-1-yl)-1-benzylpiperidin-2-one

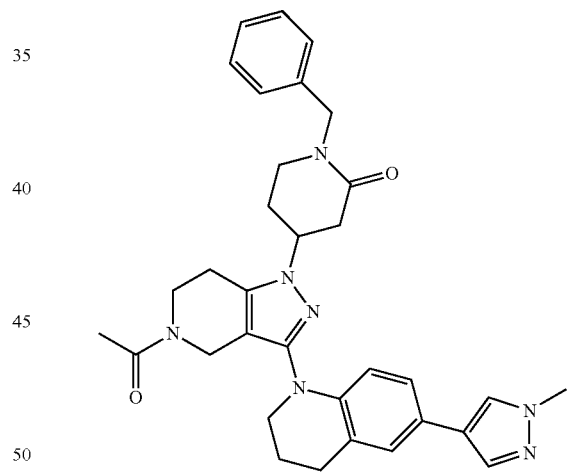

To a solution of 1-[3-[6-(1-methylpyrazol-4-yl)-3,4-di-hydro-2H-quinolin-1-yl]-1,4,6,7-tetrahydropyrazolo[4,3-c]pyridin-5-yl]ethanone (Step 1, Example 73, 300 mg, 0.80 mmol) in MeCN (5 mL) was added 1-benzyl-2,3-dihydropyridin-6-one (298 mg, 1.59 mmol) and 1,8-diazabicyclo[5.4.0]undec-7-ene (243 mg, 1.59 mmol). The mixture was heated to 70° C. for 16 h. After cooling the reaction to room temperature, the mixture was concentrated in vacuo. The crude residue was purified by Prep-TLC (DCM/MeOH=20:1) to give the title compound (200 mg, 45%) as light yellow oil. $^1$H NMR (400 MHz, $CDCl_3$) δ 7.60-7.58 (m, 1H), 7.43-7.41 (m, 1H), 7.22-7.21 (m, 5H), 7.10-7.00 (m, 2H), 6.42-6.38 (m, 1H), 6.11-6.04 (m, 1H), 5.86-5.83 (m, 1H), 4.80-4.76 (m, 1H), 4.44-4.37 (m, 2H), 4.25-4.00 (m, 2H), 3.86-3.85 (m, 3H), 3.58-3.56 m, 1H), 3.60-3.55 (m, 3H), 3.42 (s, 3H), 3.35-3.15 (m, 3H), 2.81-2.62 (m, 4H), 2.27-2.06 (m, 9H). LCMS M/Z (M+H) 564.

Step 2

4-(3-(6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-2-one

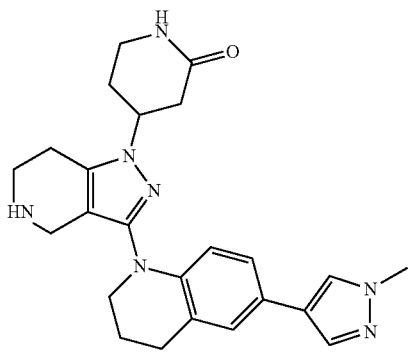 [SMILES: Cn1cc(-c2ccc3c(c2)CCCN3c2nn(C3CCNC(=O)C3)c3c2CNCC3)cn1]

To a solution of sat. NH₃ in THF (10 mL) at −78° C. was added sodium (26 mg, 1.06 mmol). The mixture was stirred at the same temperature for 10 min before a solution of 4-[5-acetyl-3-[6-(1-methylpyrazol-4-yl)-3,4-dihydro-2H-quinolin-1-yl]-6,7-dihydro-4H-pyrazolo[4,3-c]pyridin-1-yl]-1-benzyl-piperidin-2-one (60 mg, 0.11 mmol) in THF (3 mL) was added dropwise. The mixture was stirred at −78° C. for an additional 2 h. The reaction was quenched with solid NH₄Cl (200 mg) and warmed to room temperature. Water (100 mL) was added and the mixture was extracted with DCM (50 mL×2). The combined organic layers were dried over anhydrous Na₂SO₄, filtered and concentrated in vacuo to give the title compound (80 mg, crude) as a white solid that required no further purification. LCMS M/Z (M+H) 432.

Step 3

4-(5-acetyl-3-(6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-2-one

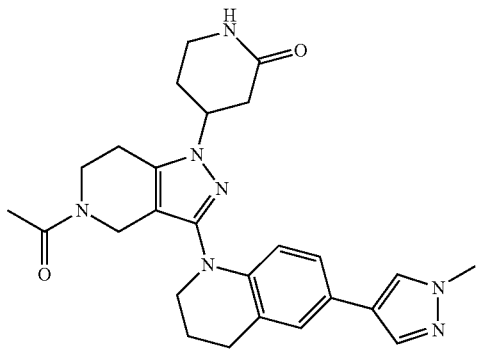 [SMILES: CC(=O)N1CCc2c(c(N3CCCc4cc(-c5cnn(C)c5)ccc43)nn2C2CCNC(=O)C2)C1]

To a solution of 4-[3-[6-(1-methylpyrazol-4-yl)-3,4-dihydro-2H-quinolin-1-yl]-4,5,6,7-tetrahydropyrazolo[4,3-c]pyridin-1-yl]piperidin-2-one (80 mg, 0.19 mmol) in DCM (10 mL) at 0° C. was added triethylamine (0.026 mL, 0.19 mmol) and acetic anhydride (0.018 mL, 0.19 mmol). The mixture stirred for 1 hr before being concentrated in vacuo. The crude residue was purified by reverse phase chromatography (acetonitrile 6-36%/0.2% formic acid in water) to give the title compound (5 mg, 6%) as a white solid. ¹H NMR (400 MHz, CDCl₃) δ 7.67-7.65 (m, 1H), 7.50-7.48 (m, 1H), 7.17-7.05 (m, 2H), 6.53-6.50 (m, 1H), 6.04 (s, 1H), 4.44-4.41 (m, 1H), 4.30-4.15 (m, 1H), 4.10-4.09 (m, 1H), 3.93-3.64 (m, 1H), 3.51-3.30 (m, 2H), 3.03-3.01 (m, 1H), 2.88-2.71 (m, 5H), 2.45-2.25 (m, 1H), 2.17-2.03 (m, 6H). LCMS M/Z (M+H) 474.

Example 77

1-[3-[6-(1-methylpyrazol-4-yl)-3,4-dihydro-2H-quinolin-1-yl]-1-pyrrolidin-3-yl-6,7-dihydro-4H-pyrazolo[4,3-c]pyridin-5-yl]ethanone

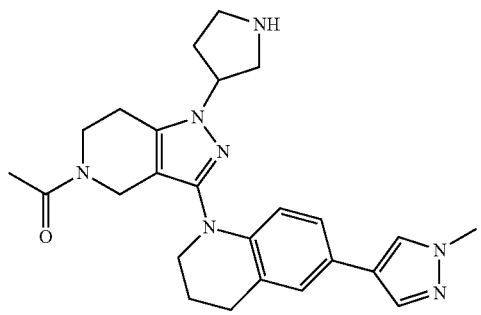 [SMILES: CC(=O)N1CCc2c(c(N3CCCc4cc(-c5cnn(C)c5)ccc43)nn2C2CCNC2)C1]

Step 1 tert-butyl 3-((methylsulfonyl)oxy)pyrrolidine-1-carboxylate

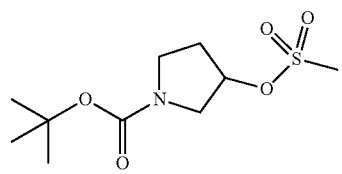 [SMILES: CC(C)(C)OC(=O)N1CCC(OS(C)(=O)=O)C1]

To a solution of tert-butyl 3-hydroxypyrrolidine-1-carboxylate (2 g, 10.68 mmol) and triethylamine (3.24 g, 32.05 mmol) in DCM (10 mL) at 0° C. was added mesyl chloride (1.47 g, 12.82 mmol) dropwise. The mixture was stirred at room temperature for 3 h. The mixture was diluted with DCM (20 mL) and the mixture was washed with brine (10 mL×2). The combined organic layers were dried over anhydrous Na₂SO₄, filtered and concentrated in vacuo to give the title compound (2.1 g, crude) as colorless oil that required no further purification.

Step 2 tert-butyl 3-(5-acetyl-3-bromo-4,5,6,7-tetrahydro-1H-pyrazolo[4,3-c]pyridin-1-yl)pyrrolidine-1-carboxylate

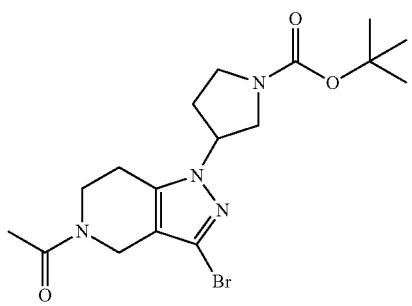 [SMILES: CC(=O)N1CCc2c(c(Br)nn2C2CCN(C(=O)OC(C)(C)C)C2)C1]

To a solution of 1-(3-bromo-6,7-dihydro-1H-pyrazolo[4,3-c]pyridin-5(4H)-yl)ethanone (1.3 g, 5.33 mmol) in DMF (10 mL) was added Cs$_2$CO$_3$ (19.5 g, 59.6 mmol) and tert-butyl 3-((methylsulfonyl)oxy)pyrrolidine-1-carboxylate (2.1 g, 7.99 mmol). The mixture was heated to 80° C. for 12 h. After cooling the reaction to room temperature, the reaction was filtered and concentrated in vacuo. The residue was dissolved in EtOAc (40 mL) and the mixture was washed with brine (20 mL×2). The organic layer was dried over anhydrous Na$_2$SO$_4$, filtered and concentrated in vacuo. The crude residue was purified by silica gel chromatography (petroleum ether/tert-butyl methyl ether/THF=from 10:1:1 to 1:10:10) to give the title compound (680 mg, 31%) as colorless oil. $^1$H NMR (400 MHz, CD$_3$OD) δ 4.41-4.39 (m, 2H), 3.92-3.87 (m, 1H), 3.82-3.70 (m, 2H), 3.66-3.43 (m, 4H), 2.88-2.76 (m, 4H), 2.33-2.31 (m, 2H), 2.20-2.17 (m, 3H), 1.48 (s, 9H).

Step 3 tert-butyl 3-(5-acetyl-3-(6-(1-methyl-1H-pyrazol-4-yl)-3,4-dihydroquinolin-1(2H)-yl)-4,5,6,7-tetrahydro-1H-pyrazolo[4,3-c]pyridin-1-yl)pyrrolidine-1-carboxylate

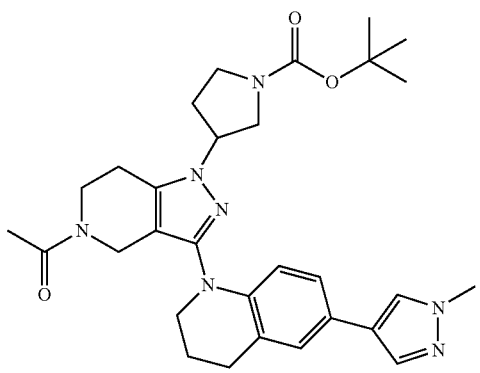 [SMILES: CC(=O)N1CCc2c(c(N3CCCc4cc(-c5cnn(C)c5)ccc43)nn2C2CCN(C(=O)OC(C)(C)C)C2)C1]

To a solution of tert-butyl 3-(5-acetyl-3-bromo-4,5,6,7-tetrahydro-1H-pyrazolo[4,3-c]pyridin-1-yl)pyrrolidine-1-carboxylate (530 mg, 1.28 mmol) in dioxane (8 mL) was added 6-(1-methyl-1H-pyrazol-4-yl)-1,2,3,4-tetrahydroquinoline (328 mg, 1.54 mmol), chloro(2-dicyclohexylphosphino-2',6'-di-i-propoxy-1,1'-biphenyl)[2-(2-aminoethylphenyl)]palladium(II), methyl-tert-butylether adduct (104 mg, 0.13 mmol), 2-dicyclohexylphosphino-2',6'-di-i-propoxy-1,1'-biphenyl (60 mg, 0.13 mmol) and t-BuONa (370 mg, 3.85 mmol). The mixture was heated to 120° C. for 12 h under a nitrogen atmosphere. After cooling the reaction to room temperature, the mixture was concentrated in vacuo. The crude residue was purified by silica gel chromatography (DCM/MeOH=20:1) to give the title compound (420 mg, 60%) as colorless oil. LCMS M/Z (M+H) 546.

Step 4

1-[3-[6-(1-methylpyrazol-4-yl)-3,4-dihydro-2H-quinolin-1-yl]-1-pyrrolidin-3-yl-6,7-dihydro-4H-pyrazolo[4,3-c]pyridin-5-yl]ethanone

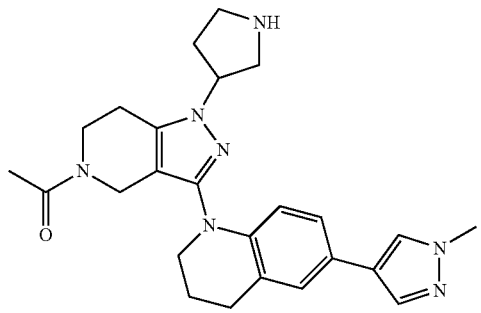 [SMILES: CC(=O)N1CCc2c(c(N3CCCc4cc(-c5cnn(C)c5)ccc43)nn2C2CCNC2)C1]

To a solution of tert-butyl 3-(5-acetyl-3-(6-(1-methyl-1H-pyrazol-4-yl)-3,4-dihydroquinolin-1(2H)-yl)-4,5,6,7-tetrahydro-1H-pyrazolo[4,3-c]pyridin-1-yl)pyrrolidine-1-carboxylate (420 mg, 0.77 mmol) in DCM (10 mL) at 0° C. was added trifluoroacetic acid (2 mL) dropwise. The mixture was stirred at room temperature for 1 h and concentrated in vacuo. Water (20 mL) was added and the mixture was made basic with solid NaHCO$_3$ to pH 8 and then the mixture was extracted with EtOAc (20 mL×3). The combined organic layers were dried over anhydrous Na$_2$SO$_4$, filtered and concentrated in vacuo to give the crude product (220 mg) as a yellow solid. Part of the crude product (100 mg) was purified by reverse phase chromatography (acetonitrile 20-50%/0.1% NH$_4$HCO$_3$ in water) to give the title compound (68 mg) as a white solid. $^1$H NMR (400 MHz, DMSO-d$_6$) δ 7.91 (s, 1H), 7.66 (s, 1H), 7.18 (s, 1H), 7.12-7.07 (m, 1H), 6.43-6.38 (m, 1H), 4.85-4.55 (m, 1H), 4.09-4.06 (m, 2H), 3.81 (s, 3H), 3.75-3.50 (m, 2H), 3.07-3.05 (m, 2H), 2.85-2.75 (m, 5H), 2.70-2.65 (m, 1H), 2.21-2.05 (m, 1H), 1.96-1.91 (m, 6H). LCMS M/Z (M+H) 446.

The Following Compound was Prepared in a Similar Fashion to Example 77

Example 78

| Example | Compound Name | NMR | m/z |
|---|---|---|---|
| Example 78 | 1-[3-[6-(1-methylpyrazol-4-yl)-3,4-dihydro-2H-quinolin-1-yl]-1-(4-piperidyl)-6,7-dihydro-4H-pyrazolo[4,3-c]pyridin-5-yl]ethanone | $^1$H NMR (400 MHz, DMSO-$d_6$) δ 7.90 (s, 1H), 7.66 (s, 1H), 7.19 (s, 1H), 7.11-7.07 (m, 1H), 6.44-6.38 (m, 1H), 4.30-4.25 (m, 2H), 4.24-4.10 (m, 2H), 3.87 (s, 3H), 3.81-3.63 (m, 2H), 3.54-3.51 (m, 2H), 3.24-3.22 (m, 2H), 2.81-2.70 (m, 6H), 2.06-1.93 (m, 9H) | 460 |

$NH_4HCO_3$ in water) to give the title compound (18 mg, 17%) as a white solid. $^1$H NMR (400 MHz, DMSO-$d_6$) δ 7.90 (s, 1H), 7.66 (s, 1H), 7.19 (s, 1H), 7.12-7.08 (m, 1H), 6.43-6.37 (m, 1H), 4.77-4.73 (m, 1H), 4.11-4.10 (m, 2H), 3.81 (s, 3H), 3.75-3.60 (m, 2H), 3.55-3.50 (m, 2H), 3.01-2.90 (m, 1H), 2.81-2.78 (m, 3H), 2.65-2.60 (m, 2H), 2.55-2.50 (m, 2H), 2.30-2.05 (m, 7H), 1.75-1.65 (m, 3H). LCMS M/Z (M+H) 460.

The Following Compound was Prepared in a Similar Fashion to Example 79

Example 80

| Example | Compound Name | NMR | m/z |
|---|---|---|---|
| Example 80 | 1-[1-(1-methyl-4-piperidyl)-3-[6-(1-methylpyrazol-4-yl)-3,4-dihydro-2H-quinolin-1-yl]-6,7-dihydro-4H-pyrazolo[4,3-c]pyridin-5-yl]ethanone | $^1$H NMR (400 MHz, DMSO-$d_6$) δ 8.21 (s, 1H), 7.90 (s, 1H), 7.66 (s, 1H), 7.18 (s, 1H), 7.11-7.07 (m, 1H), 6.43-6.38 (m, 1H), 4.09-4.08 (m, 2H), 4.07-3.99 (m, 1H), 3.81 (s, 3H), 3.73-3.66 (m, 4H), 2.93-2.91 (m, 2H), 2.80-2.77 (m, 4H), 2.25 (s, 3H), 2.14-2.11 (m, 2H), 2.05-1.95 (m, 3H), 2.03-2.00 (m, 4H), 1.93-1.84 (m, 2H) | 474 |

Example 79

1-[3-[6-(1-methylpyrazol-4-yl)-3,4-dihydro-2H-quinolin-1-yl]-1-(1-methylpyrrolidin-3-yl)-6,7-dihydro-4H-pyrazolo[4,3-c]pyridin-5-yl]ethanone

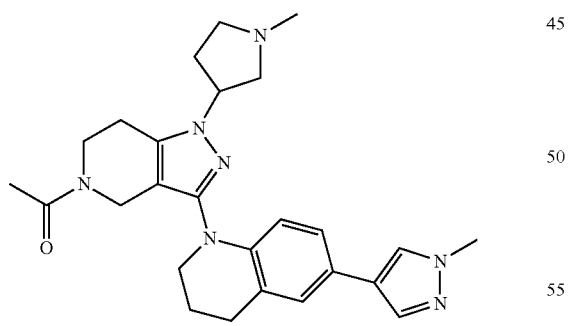

To a solution of 1-[3-[6-(1-methylpyrazol-4-yl)-3,4-dihydro-2H-quinolin-1-yl]-1-pyrrolidin-3-yl-6,7-dihydro-4H-pyrazolo[4,3-c]pyridin-5-yl]ethanone (120 mg, 0.25 mmol) in MeOH (5 mL), was added aqueous formaldehyde (30%, 54 mg, 0.54 mmol), NaBH$_3$CN (34 mg, 0.54 mmol) and AcOH (0.2 mL). The mixture was stirred at room temperature for 1 h. Water (10 mL) was added and the mixture was extracted with EtOAc (20 mL×2). The combined organic layers were dried over anlydrous Na$_2$SO$_4$, filtered and concentrated in vacuo. The crude residue was purified by reverse phase chromatography (acetonitrile 20-50%/0.1%

Example 81

1-(3-(3-(2,2-difluoroethyl)-6-(1-methyl-1H-pyrazol-4-yl)-3,4-dihydroquinolin-1(2H)-yl)-1-((S)-tetrahydrofuran-3-yl)-6,7-dihydro-1H-pyrazolo[4,3-c]pyridin-5(4H)-yl)ethanone

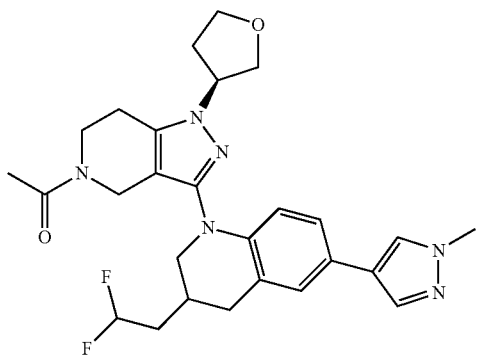 [SMILES: CC(=O)N1CCc2c(c(N3CC(CC(F)F)Cc4cc(-c5cnn(C)c5)ccc43)nn2[C@H]2CCOC2)C1]

Step 1

(E)-3-(2-methoxyvinyl)quinoline

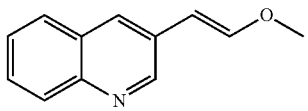

To a solution of (methoxymethyl)triphenylphosphonium chloride (22.9 g, 66.81 mmol) in THF (100 mL) at 0° C. was added n-BuLi (2.5 M in hexanes, 31 mL, 76.35 mmol). The resulting deep-red solution was stirred at 0° C. for 5 min before being quickly added to a solution of quinoline-3-carbaldehyde (10 g, 63.63 mmol) in THF (50 mL) at 0° C. The temperature was slowly raised to 25° C. and stirred for an additional 1 h. The solvent was concentrated in vacuo. The crude residue was purified by silica gel chromatography (petroleum ether/EtOAc=3:1) to give the title compound (5.5 g, 51%) as yellow oil.

Step 2

2-(quinolin-3-yl)acetaldehyde

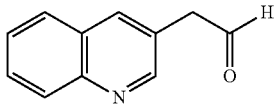 [SMILES: O=CCc1cnc2ccccc2c1]

A mixture of (E)-3-(2-methoxyvinyl)quinoline (5.5 g, 29.69 mmol) in aqueous HCl solution (5.5 M, 115 mL) was heated to 80° C. for 1 h under a nitrogen atmosphere. After cooling the reaction to room temperature, sat. aq. NaHCO$_3$ (100 mL×2) was added dropwise and the mixture was extracted with EtOAc (200 mL×2). The combined organic layers were dried over anhydrous Na$_2$SO$_4$, filtered and concentrated in vacuo to give the title compound (5 g, crude) that required no further purification. $^1$H NMR (400 MHz, CDCl$_3$) δ 9.89 (s, 1H), 8.76 (s, 1H), 8.13-8.10 (m, 1H), 8.03 (s, 1H), 7.83-7.81 (m, 1H), 7.75-7.71 (m, 1H), 7.60-7.58 (m, 1H), 7.24 (s, 1H), 3.94 (s, 2H).

Step 3

3-(2,2-difluoroethyl) quinoline

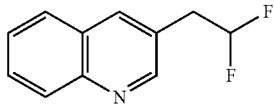 [SMILES: FC(F)Cc1cnc2ccccc2c1]

To a solution of 2-(quinolin-3-yl)acetaldehyde (5 g, 29.21 mmol) in DCM (100 mL) at 0° C. was added diethylaminosulfurtrifluoride (18.83 mg, 116.83 mmol). The mixture was stirred at room temperature for 12 h. The mixture was then added to a sat. aq. NaHCO$_3$ (600 mL) dropwise at 0° C. and extracted with DCM (1 L×2). The combined organic layers were dried over anhydrous Na$_2$SO$_4$, filtered and concentrated in vacuo. The crude residue was purified by silica gel chromatography (petroleum ether/EtOAc=5:1) to give the title compound (900 mg, 16%) as a yellow oil. $^1$H NMR (400 MHz, CDCl$_3$) δ 8.82 (s, 1H), 8.13-8.08 (m, 2H), 7.83-7.81 (m, 1H), 7.73-7.71 (m, 1H), 7.60-7.58 (m, 1H), 6.05 (t, J=60.4 Hz, 1H), 3.40-3.30 (m, 2H).

Step 4

3-(2,2-difluoroethyl)-1,2,3,4-tetrahydroquinoline

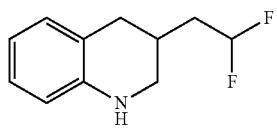 [SMILES: FC(F)CC1CNc2ccccc2C1]

To a solution of 3-(2,2-difluoroethyl)quinoline (900 mg, 4.66 mmol) and NaBH$_3$CN (1.5 g, 23.29 mmol) in MeOH (10 mL) at 0° C. was added boron trifluoride diethyl etherate (1.18 mL, 9.32 mmol) dropwise. The mixture was heated to 70° C. for 12 h under a nitrogen atmosphere. After cooling the reaction to room temperature, water (10 mL) was added and the mixture was extracted with EtOAc (50 mL×2). The combined organic layers were dried over anhydrous Na$_2$SO$_4$, filtered and concentrated in vacuo. The crude residue was purified by silica gel chromatography (petroleum ether/EtOAc=5:1) to give the title compound (230 mg, 25%) as a yellow oil. $^1$H NMR (400 MHz, CDCl$_3$) δ 7.02-6.95 (m, 2H), 6.66-6.62 (m, 1H), 6.51-6.49 (m, 1H), 5.98 (t, J=56.8 Hz, 1H), 3.42-3.39 (m, 1H), 3.08-3.04 (m, 1H), 2.95-2.91 (m, 1H), 2.60-2.54 (m, 1H), 2.33-2.19 (m, 1H), 1.96-1.90 (m, 2H).

Step 5

1-(3-(3-(2,2-difluoroethyl)-3,4-dihydroquinolin-1(2H)-yl)-1-((S)-tetrahydrofuran-3-yl)-6,7-dihydro-1H-pyrazolo[4,3-c]pyridin-5(4H)-yl)ethanone

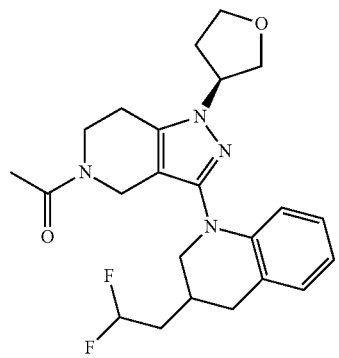 [SMILES: CC(=O)N1CCc2c(c(N3CC(CC(F)F)Cc4ccccc43)nn2[C@H]2CCOC2)C1]

To a solution of 3-(2,2-difluoroethyl)-1,2,3,4-tetrahydroquinoline (260 mg, 1.32 mmol) in 1,4-dioxane (10 mL) was added (S)-1-(3-bromo-1-(tetrahydrofuran-3-yl)-6,7-dihydro-1H-pyrazolo[4,3-c]pyridin-5(4H)-yl)ethanone (Intermediate G, 414 mg, 1.32 mmol), 2-dicyclohexylphosphino-2',6'-di-i-propoxy-1,1'-biphenyl (62 mg, 0.13 mmol), chloro (2-dicyclohexylphosphino-2',6'-di-i-propoxy-1,1'-biphenyl)[2-(2-aminoethylphenyl)]palladium(II), methyl-tert-butylether adduct (96 mg, 0.13 mmol) and t-BuONa (507 mg, 5.27 mmol). The mixture was heated to 120° C. for 16 h under a nitrogen atmosphere. After cooling the reaction to room temperature, the mixture was concentrated in vacuo. The crude residue was purified by silica gel chromatography (DCM/MeOH=20:1) to give the title compound (460 mg, 62%) as a yellow oil. LCMS M/Z (M+H) 431.

Step 6

1-(3-(6-bromo-3-(2,2-difluoroethyl)-3,4-dihydroquinolin-1(2H)-yl)-1-((S)-tetrahydrofuran-3-yl)-6,7-dihydro-1H-pyrazolo[4,3-c]pyridin-5(4H)-yl)ethanone

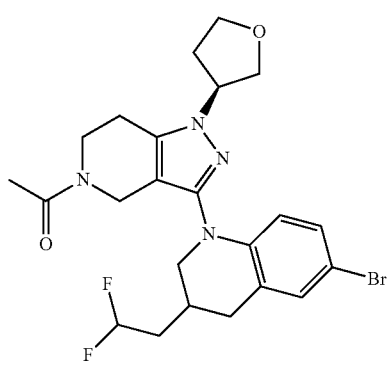 [SMILES: CC(=O)N1CCc2c(c(N3CC(CC(F)F)Cc4cc(Br)ccc43)nn2[C@H]2CCOC2)C1]

To a solution of 1-(3-(3-(2,2-difluoroethyl)-3,4-dihydroquinolin-1(2H)-yl)-1-((S)-tetrahydrofuran-3-yl)-6,7-dihydro-1H-pyrazolo[4,3-c]pyridin-5(4H)-yl)ethanone (460 mg, 0.82 mmol) in DCM (6 mL) was added N-bromosuccinimide (146 mg, 0.82 mmol) at dropwise and the mixture stirred for 1 h. The solvent was concentrated in vacuo and the crude residue was purified by silica gel chromatography (DCM/MeOH=20:1) to give the title compound (400 mg, 76%) as a yellow oil. LCMS M/Z (M+H) 509.

Step 7

1-(3-(3-(2,2-difluoroethyl)-6-(1-methyl-1H-pyrazol-4-yl)-3,4-dihydroquinolin-(2H)-yl)-1-((S)-tetrahydrofuran-3-yl)-6,7-dihydro-1H-pyrazolo[4,3-c]pyridin-5(4H)-yl)ethanone

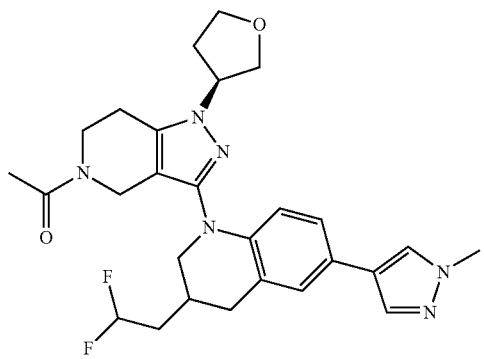 [SMILES: CC(=O)N1CCc2c(c(N3CC(CC(F)F)Cc4cc(-c5cnn(C)c5)ccc43)nn2[C@H]2CCOC2)C1]

To a solution of 1-(3-(6-bromo-3-(2,2-difluoroethyl)-3,4-dihydroquinolin-1(2H)-yl)-1-((S)-tetrahydrofuran-3-yl)-6,7-dihydro-1H-pyrazolo[4,3-c]pyridin-5(4H)-yl)ethanone (400 mg, 0.76 mmol) in 1,4-dioxane (12 mL) and water (3 mL) was added 1-methyl-4-(4,4,5,5-tetramethyl-1,3,2-dioxaborolan-2-yl)-1H-pyrazole (163 mg, 0.76 mmol), [1,1'-bis(diphenylphosphino)ferrocene]dichloropalladium(II) (56 mg, 0.076 mmol) and $K_2CO_3$ (326 mg, 2.36 mmol). The mixture was heated to 110° C. for 12 h under a nitrogen atmosphere. After cooling the reaction to room temperature, water (50 mL) was added and the mixture was extracted with EtOAc (50 mL×2). The combined organic layers were dried over anhydrous $Na_2SO_4$, filtered and concentrated in vacuo. The crude residue was purified by silica gel chromatography (DCM/MeOH=50:1) to give the crude compound that was further purified by reverse phase chromatography (acetonitrile 20-50%/0.1% $NH_4HCO_3$ in water) to give the title compound (80 mg, 27%) as a white solid. $^1$H NMR (400 MHz, $CDCl_3$) δ 7.66-7.64 (m, 1H), 7.50-7.48 (m, 1H), 7.16-7.05 (m, 2H), 6.52-6.49 (m, 1H), 6.15-5.55 (m, 1H), 4.77-4.73 (m, 1H), 4.18-4.10 (m, 4H), 3.97-3.90 (m, 7H), 3.85-3.75 (m, 2H), 3.40-3.35 (m, 1H), 3.10-3.00 (m, 1H), 2.85-2.60 (m, 2H), 2.41-2.39 (m, 2H), 2.16-1.96 (m, 6H). LCMS M/Z (M+H) 511.

Examples 82 & 83

(S,S)-1-[3-[3-(2,2-difluoroethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone and (S,R)-1-[3-[3-(2,2-difluoroethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

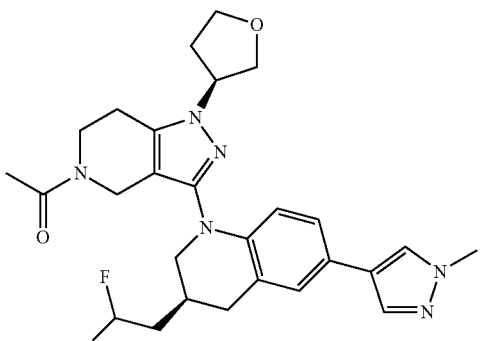

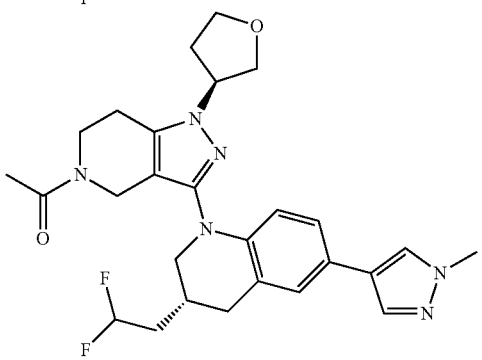

Racemic 1-[3-[3-(2,2-difluoroethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (Example 81, 65 mg) was separated using chiral SFC (MG-II; Chiralpak AD 250×30 mm I.D., 5 um; Supercritical $CO_2$/EtOH (0.1% $NH_3H_2O$)=70:30 at 60 mL/min) to give (S, S)-1-[3-[3-(2,2-difluoroethyl)-6-(1-methylpyrazol-4-yl)-3,4-dihydro-2H-quinolin-1-yl]-1-tetrahydrofuran-3-yl-6,7- dihydro-4H-pyrazolo[4,3-c]pyridin-5-yl]ethanone (19 mg, first peak) and (S,R)-1-[3-[3-(2,2-difluoroethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl] ethanone (21 mg, second peak). Absolute configuration was arbitrarily assigned to each diastereomer. Example 82: $^1$H NMR (400 MHz, CDCl$_3$) δ 7.68-7.66 (m, 1H), 7.52-7.50 (m, 1H), 7.18-7.12 (m, 2H), 6.54-6.50 (m, 1H), 6.01-5.87 (m, 1H), 4.78-4.74 (m, 1H), 4.21-4.04 (m, 4H), 4.02-3.93 (m, 7H), 3.85-3.76 (m, 2H), 3.45-3.35 (m, 1H), 3.10-3.00 (m, 1H), 2.76-2.70 (m, 2H), 2.42-2.39 (m, 2H), 2.18-1.96 (m, 6H). LCMS M/Z (M+H) 511. Example 83: $^1$H NMR (400 MHz, CDCl$_3$) δ 7.65-7.63 (m, 1H), 7.49-7.47 (m, 1H), 7.18-7.06 (m, 2H), 6.51-6.48 (m, 1H), 5.99-5.96 (m, 1H), 4.78-4.74 (m, 1H), 4.27-4.10 (m, 4H), 4.00-3.90 (m, 7H), 3.85-3.75 (m, 2H), 3.45-3.35 (m, 1H), 3.10-3.00 (m, 1H), 2.74-2.66 (m, 2H), 2.40-2.39 (m, 2H), 2.16-1.95 (m, 6H). LCMS M/Z (M+H) 511.

Example 84

1-(5-acetyl-1-((S)-tetrahydrofuran-3-yl)-6,7-dihydro-4H-pyrazolo[4,3-c]pyridin-3-yl)-3-methyl-6-(1-methylpyrazol-4-yl)-3,4-dihydro-2H-quinoline-7-carbonitrile

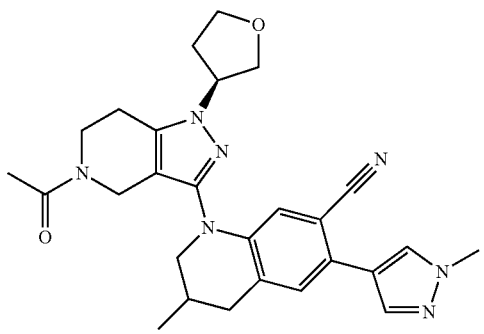 [SMILES: CC(=O)N1CCc2c(c(N3CC(C)Cc4cc(-c5cnn(C)c5)c(C#N)cc43)nn2[C@H]2CCOC2)C1]

Step 1

2-amino-4-bromobenzaldehyde

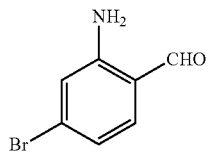

To a solution of 4-bromo-2-nitrobenzaldehyde (10 g, 43.47 mmol) in EtOH (50 mL) and acetic acid (50 mL) was added Fe powder (7.28 g, 130.42 mmol). The mixture was stirred at 0° C. for 40 min under a nitrogen atmosphere. Insoluble solid was filtered off and the filtrate was adjusted to pH=8 by progressively adding solid NaHCO$_3$. The resulting solution was extracted with EtOAc (300 mL×2), washed with saturated NaHCO$_3$ (100 mL) and brine (100 mL), dried over anhydrous Na$_2$SO$_4$, filtered and concentrated in vacuo. The crude residue was purified by silica gel chromatography (petroleum ether/EtOAc=10:1) to give the title compound (6 g, 64%) as a yellow solid. $^1$H NMR (400 MHz, DMSO-d$_6$) δ 9.79 (s, 1H), 7.48 (d, J=8.4 Hz, 1H), 7.27 (s, 2H), 6.99 (s, 1H), 6.78 (d, J=8.0 Hz, 1H).

Step 2

7-bromo-3-methylquinoline

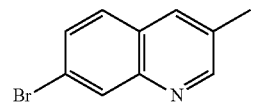

To a solution of 2-amino-4-bromobenzaldehyde (6 g, 28.2 mmol) in toluene (50 mL) was added (E)-1-ethoxyprop-1-ene (6.07 g, 70.49 mmol) and 4-methylbenzenesulfonic acid (0.49 g, 2.82 mmol). The mixture was heated to reflux for 18 h under a nitrogen atmosphere. After cooling the reaction to room temperature, the mixture was concentrated in vacuo. The crude residue was purified by silica gel chromatography (petroleum ether/EtOAc=5:1) to give the title compound (4 g, 57%) as a yellow solid. $^1$H NMR (400 MHz, DMSO-d$_6$) δ 8.80 (s, 1H), 8.19-8.17 (m, 2H), 7.88 (d, J=8.8 Hz, 1H), 7.73-7.70 (m, 1H), 2.47 (s, 3H).

Step 3

7-bromo-3-methyl-1,2,3,4-tetrahydroquinoline

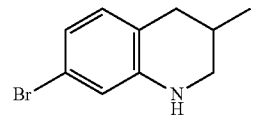

To a solution of 7-bromo-3-methyl-quinoline (2.5 g, 11.26 mmol) in toluene (10 mL) was added diphenyl hydrogen phosphate (28.16 mg, 0.11 mmol) and diethyl 2,6-dimethyl-1,4-dihydropyridine-3,5-dicarboxylate (6.84 g, 27 mmol). The mixture was heated to 60° C. for 12 h under a nitrogen atmosphere. After cooling the reaction to room temperature, the reaction was filtered and the filtrate was concentrated in vacuo. The crude residue was purified by silica gel chromatography (petroleum ether/EtOAc=10:1) to give the title compound (2.1 g, 83%) as a yellow solid. $^1$H NMR (400 MHz, DMSO-d$_6$) δ 6.74 (d, J=8.0 Hz, 1H), 6.58 (s, 1H), 6.51-6.48 (m, 1H), 6.00 (s, 1H), 3.18-3.16 (m, 1H), 2.76-2.71 (m, 1H), 2.65-2.61 (m, 1H), 2.27-2.21 (m, 1H), 1.85-1.83 (m, 1H), 0.95 (d, J=6.8 Hz, 1H).

Step 4

3-methyl-1,2,3,4-tetrahydroquinoline-7-carbonitrile

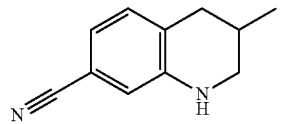

To a solution of 7-bromo-3-methyl-1,2,3,4-tetrahydroquinoline (1.2 g, 5.31 mmol) in 1,4-dioxane (6 mL) and water (6 mL) was added potassium hexacyanoferrate(II) trihydrate (1.57 g, 2.65 mmol), methanesulfonato(2-di-tert-butylphosphino-2',4',6'-tri-i-propyl-1,1'-biphenyl)(2'-amino-1,1'-biphenyl-2-yl)palladium(II) (422 mg, 0.53 mmol), 2-(dicyclohexylphosphino)-2',4',6'-triisopropylbiphenyl (225 mg, 0.53 mmol) and KOAc (65 mg, 0.66 mmol). The mixture was heated to 100° C. for 1 h under a nitrogen atmosphere. After cooling the reaction to room temperature, the reaction was filtered and concentrated in vacuo. The crude residue was purified by silica gel chromatography (petroleum ether/EtOAc=5:1) to give the title compound (780 mg, 85%) as a yellow solid. LCMS M/Z (M+H) 173.

Step 5

1-(5-acetyl-1-((S)-tetrahydrofuran-3-yl)-4,5,6,7-tetrahydro-1H-pyrazolo[4,3-c]pyridin-3-yl)-3-methyl-1,2,3,4-tetrahydroquinoline-7-carbonitrile

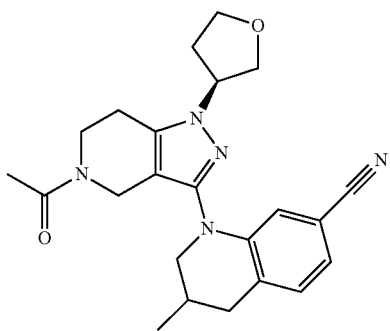 [SMILES: CC(=O)N1CCc2c(c(N3CC(C)Cc4ccc(C#N)cc43)nn2[C@H]2CCOC2)C1]

To a solution of 3-methyl-1,2,3,4-tetrahydroquinoline-7-carbonitrile (430 mg, 2.5 mmol) in 1,4-dioxane (10 mL) was added (S)-1-(3-bromo-1-(tetrahydrofuran-3-yl)-6,7-dihydro-1H-pyrazolo[4,3-c]pyridin-5(4H)-yl)ethanone (Intermediate G, 784 mg, 2.50 mmol), chloro(2-dicyclohexylphosphino-2',6'-di-i-propoxy-1,1'-biphenyl) [2-(2-aminoethylphenyl)]palladium(II), methyl-tert-butylether adduct (182 mg, 0.25 mmol), t-BuONa (720 mg, 7.49 mmol) and 2-dicyclohexylphosphino-2',6'-di-i-propoxy-1,1'-biphenyl (117 mg, 0.25 mmol). The mixture was heated to 120° C. for 12 h under a nitrogen atmosphere. After cooling the reaction to room temperature, the mixture was concentrated in vacuo. The crude residue was purified by silica gel chromatography (DCM/MeOH=20:1) to give the title compound (800 mg, 42%) as a yellow oil. LCMS M/Z (M+H) 406.

Step 6

1-(5-acetyl-1-((S)-tetrahydrofuran-3-yl)-4,5,6,7-tetrahydro-1H-pyrazolo[4,3-c]pyridin-3-yl)-6-bromo-3-methyl-1,2,3,4-tetrahydroquinoline-7-carbonitrile

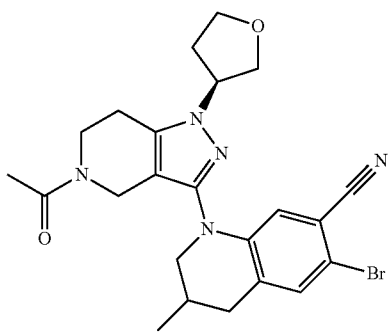 [SMILES: CC(=O)N1CCc2c(c(N3CC(C)Cc4cc(Br)c(C#N)cc43)nn2[C@H]2CCOC2)C1]

To a solution of 1-(5-acetyl-1-((S)-tetrahydrofuran-3-yl)-4,5,6,7-tetrahydro-1H-pyrazolo[4,3-c]pyridin-3-yl)-3-methyl-1,2,3,4-tetrahydroquinoline-7-carbonitrile (800 mg, 1.05 mmol) in MeCN (6 mL) at 0° C. was N-bromosuccinimide (186 mg, 1.05 mmol). The mixture was stirred at 0° C. for 2 h under a nitrogen atmosphere. The mixture was concentrated in vacuo. The crude residue was purified by silica gel chromatography (DCM/MeOH=16:1) to give the title compound (600 mg, 56%) as yellow oil. LCMS M/Z (M+H) 486.

Step 7

1-(5-acetyl-1-((S)-tetrahydrofuran-3-yl)-6,7-dihydro-4H-pyrazolo[4,3-c]pyridin-3-yl)-3-methyl-6-(1-methylpyrazol-4-yl)-3,4-dihydro-2H-quinoline-7-carbonitrile

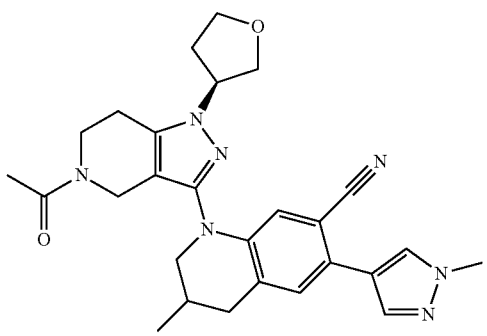 [SMILES: CC(=O)N1CCc2c(c(N3CC(C)Cc4cc(-c5cnn(C)c5)c(C#N)cc43)nn2[C@H]2CCOC2)C1]

To a solution of 1-(5-acetyl-1-((S)-tetrahydrofuran-3-yl)-4,5,6,7-tetrahydro-1H-pyrazolo[4,3-c]pyridin-3-yl)-6-bromo-3-methyl-1,2,3,4-tetrahydroquinoline-7-carbonitrile (600 mg, 0.74 mmol) in THF (5 mL) and water (1 mL) was added 1-methyl-4-(4,4,5,5-tetramethyl-1,3,2-dioxaborolan-2-yl)-1H-pyrazole (309.27 mg, 1.49 mmol), chloro(2-dicyclohexylphosphino-2',4',6'-tri-i-propyl-1,1'-biphenyl)(2'-amino-1,1'-biphenyl-2-yl) palladium(II) (58 mg, 0.07 mmol), Na$_2$CO$_3$ (236 mg, 2.23 mmol) and 2-(dicyclohexylphosphino)-2',4',6'-triisopropylbiphenyl (35 mg, 0.07 mmol). The mixture was heated to 60° C. for 12 h under a nitrogen atmosphere. After cooling the reaction to room temperature, the reaction was filtered and concentrated in vacuo. The crude residue was purified by reverse phase chromatography (acetonitrile 15-45%/0.1% NH$_4$HCO$_3$ in water) to give the title compound (150 mg, 37%) as a white solid. $^1$H NMR (400 MHz, CDCl$_3$) δ 7.88-7.83 (m, 1H), 7.76-7.75 (m, 1H), 7.21-7.16 (m, 1H), 6.73-6.70 (m, 1H), 4.80-4.78 (m, 1H), 4.26-4.11 (m, 4H), 4.05-3.90 (m, 6H), 3.79-3.78 (m, 1H), 3.75-3.60 (m, 1H), 3.30-3.25 (m, 1H), 2.91-2.78 (m, 3H), 2.60-2.50 (m, 1H), 2.42-2.39 (m, 1H), 2.18-2.08 (m, 4H), 1.12-1.08 (m, 3H). LCMS M/Z (M+H) 486.

The Following Compound was Prepared in a Similar Fashion to Example 84

Example 85

| Example | Compound Name | NMR | m/z |
|---|---|---|---|
| Example 85 | 1-(5-acetyl-1-(tetrahydro-2H-pyran-4-yl)-4,5,6,7-tetrahydro-1H-pyrazolo[4,3-c]pyridin-3-yl)-3-methyl-6-(1-methyl-1H-pyrazol-4-yl)-1,2,3,4-tetrahydroquinoline-7-carbonitrile | $^1$H NMR (400 MHz, DMSO-$d_6$) δ 8.05 (s, 1H), 7.79 (s, 1H), 7.34 (s, 1H), 6.72-6.68 (m, 1H), 4.34-4.26 (m, 1H), 4.18-4.16 (m, 2H), 3.96-3.93 (m, 2H), 3.87 (s, 3H), 3.73-3.71 (m, 2H), 3.58-3.48 (m, 2H), 3.35-3.15 (m, 2H), 2.88-2.74 (m, 2H), 2.56-2.54 (m, 2H), 2.08-1.95 (m, 6H), 1.84-1.81 (m, 2H), 1.04-1.02 (m, 3H) | 500 |

Example 86

1-[3-[3-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

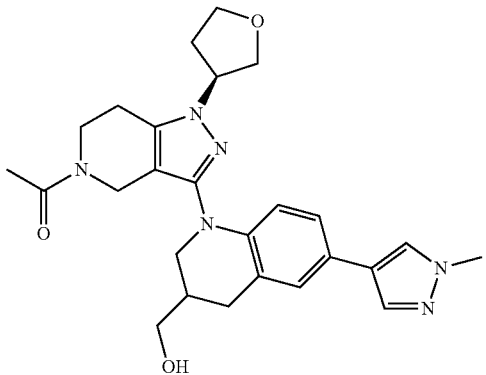 [SMILES: CC(=O)N1CCc2c(c(N3CC(CO)Cc4cc(-c5cnn(C)c5)ccc43)nn2[C@H]2CCOC2)C1]

Step 1 quinolin-3-ylmethanol

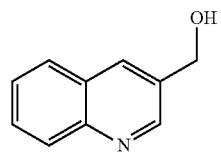 [SMILES: OCc1cnc2ccccc2c1]

To a solution of 3-quinolinecarbaldehyde (6.0 g, 38.2 mmol) in MeOH (60 mL) at 0° C. was added NaBH$_4$ (1.73 g, 45.8 mmol) portionwise. The mixture was stirred at room temperature for 4 h. The reaction was quenched with water (100 mL), concentrated in vacuo and extracted with EtOAc (100 mL×3). The combined organic layers were dried over anhydrous Na$_2$SO$_4$, filtered and concentrated in vacuo to give the title compound (5.6 g, crude) as yellow oil that required no further purification. $^1$H NMR (400 MHz, DMSO-$d_6$) δ 8.88 (s, 1H), 8.23 (s, 1H), 8.03-7.95 (m, 2H), 7.74-7.70 (m, 1H), 7.60-7.57 (m, 1H), 5.53 (s, 1H), 4.73 (d, J=2.8 Hz, 2H).

Step 2

(1,2,3,4-tetrahydroquinolin-3-yl)methanol

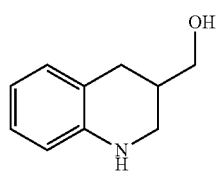 [SMILES: OCC1CNc2ccccc2C1]

To a solution of 3-quinolylmethanol (5.6 g, 35.2 mmol) and NaBH$_3$CN (11.1 g, 175.9 mmol) in MeOH (60 mL) at 0° C. was added boron trifluoride diethyl etherate (28.5 mL, 105.5 mmol) dropwise. The mixture was heated to 70° C. for 12 h under a nitrogen atmosphere. After cooling the reaction to room temperature, the reaction was quenched with sat. aq. NaHCO$_3$ (100 mL), the organic layer was removed and the aqueous layer was extracted with EtOAc (100 mL×3). The combined organic layers were dried over anhydrous Na$_2$SO$_4$, filtered and concentrated in vacuo. The crude residue was purified by silica gel chromatography (petroleum ether/EtOAc=20:1 to 4:1) to give (1,2-dihydroquinolin-3-yl)methanol (2.6 g, 46%). The resulting compound was dissolved in MeOH (25 mL) and 10% Pd/C (1.7 g, 1.61 mmol) was added. The mixture was stirred at 25° C. for 12 h under a hydrogen atmosphere (15 psi). The reaction was filtered and concentrated in vacuo. The crude residue was purified by silica gel chromatography (petroleum ether/EtOAc=9:1 to 2:1) to give the title compound (840 mg, 32%) as a light yellow oil. $^1$H NMR (400 MHz, DMSO-$d_6$) δ 6.83-6.80 (m 2H), 6.42-6.37 (m, 2H), 5.59 (s, 1H), 4.62-4.59 (m, 1H), 3.41-3.40 (m, 1H), 3.33-3.29 (m, 2H), 2.86-2.84 (m, 1H), 2.63-2.62 (m, 1H), 2.39-2.33 (m, 1H), 1.89-1.85 (m, 1H).

Step 3

3-(((tert-butyldimethylsilyl)oxy)methyl)-1,2,3,4-tetrahydroquinoline

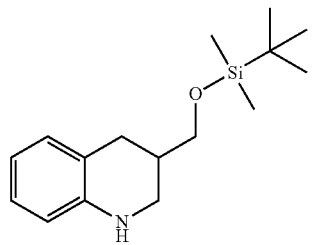 [SMILES: CC(C)(C)[Si](C)(C)OCC1CNc2ccccc2C1]

To a solution of 1,2,3,4-tetrahydroquinolin-3-ylmethanol (840 mg, 5.15 mmol) and imidazole (1.75 g, 25.7 mmol) in THF (40 mL) was added tert-butyl-dimethylsilyl chloride (1.71 g, 11.3 mmol) dropwise. The mixture was stirred at room temperature for 16 h. Brine (40 mL) was added and the mixture was extracted with EtOAc (40 mL×3). The combined organic layers were dried over anhydrous Na₂SO₄, filtered and concentrated in vacuo. The crude residue was purified by silica gel chromatography (petroleum ether/EtOAc=40:1 to 9:1) to give the title compound (1.2 g, 84%) as yellow oil. LCMS M/Z (M+H) 365.

Step 4

1-(3-(3-(((tert-butyldimethylsilyl)oxy)methyl)-3,4-dihydroquinolin-1(2H)-yl)-1-((S)-tetrahydrofuran-3-yl)-6,7-dihydro-1H-pyrazolo[4,3-c]pyridin-5(4H)-yl)ethanone

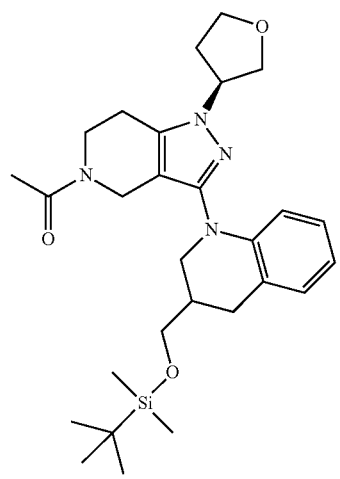 [SMILES: CC(=O)N1CCc2c(c(N3CC(CO[Si](C)(C)C(C)(C)C)Cc4ccccc43)nn2[C@H]2CCOC2)C1]

To a solution of 1-[3-bromo-1-[(3S)-tetrahydrofuran-3-yl]-6,7-dihydro-4H-pyrazolo[4,3-c]pyridin-5-yl]ethanone (Intermediate G, 1.2 g, 3.82 mmol) in 1,4-dioxane (12 mL) was added tert-butoxysodium (532 mg, 5.54 mmol), tert-butyl-dimethyl-(1,2,3,4-tetrahydroquinolin-3-ylmethoxy)silane (615 mg, 2.22 mmol), chloro(2-dicyclohexylphosphino-2',6'-di-i-propoxy-1,1'-biphenyl)[2-(2-aminoethylphenyl)]palladium(II), methyl-tert-butylether adduct (375 mg, 0.46 mmol) and 2-dicyclohexylphosphino-2',6'-di-i-propoxy-1,1'-biphenyl (214 mg, 0.46 mmol). The mixture was heated to 120° C. for 16 h under a nitrogen atmosphere. After cooling the reaction to room temperature, the reaction was filtered and the filtrate was concentrated in vacuo. The crude residue was purified by silica gel chromatography (DCM/MeOH=100:1) to give the title compound (1.2 g, 61%) as yellow oil. LCMS M/Z (M+H) 511.

Step 5

1-(3-(6-bromo-3-(((tert-butyldimethylsilyl)oxy)methyl)-3,4-dihydroquinolin-1(2H)-yl)-1-((S)-tetrahydrofuran-3-yl)-6,7-dihydro-1H-pyrazolo[4,3-c]pyridin-5(4H)-yl)ethanone

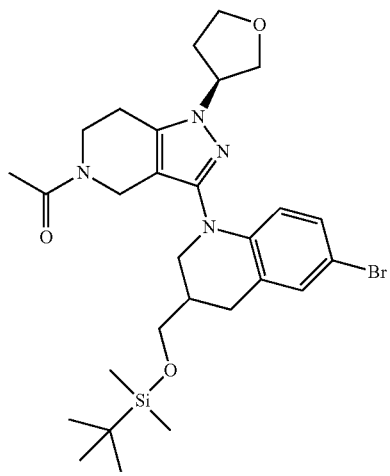 [SMILES: CC(=O)N1CCc2c(c(N3CC(CO[Si](C)(C)C(C)(C)C)Cc4cc(Br)ccc43)nn2[C@H]2CCOC2)C1]

To a solution of 1-[3-[3-[[tert-butyl(dimethyl)silyl]oxymethyl]-3,4-dihydro-2H-quinolin-1-yl]-1-[(3S)-tetrahydrofuran-3-yl]-6,7-dihydro-4H-pyrazolo[4,3-c]pyridin-5-yl]ethanone (1.2 g, 2.35 mmol) in DCM (90 mL) at 0° C. was added N-bromosuccinimide (376 mg, 2.11 mmol) dropwise. The mixture was stirred at 0° C. for 0.5 h, quenched with water (100 mL), and extracted with DCM (100 mL×2). The combined organic layers were dried over anhydrous Na₂SO₄, filtered and concentrated in vacuo. The crude residue was purified by silica gel chromatography (DCM/MeOH=50:1 to 20:1) to give the title compound (1.16 g, 84%) as light yellow oil. LCMS M/Z (M+H) 591.

Step 6

1-(3-(3-(((tert-butyldimethylsilyl)oxy)methyl)-6-(1-methyl-1H-pyrazol-4-yl)-3,4-dihydroquinolin-1(2H)-yl)-1-((S)-tetrahydrofuran-3-yl)-6,7-dihydro-1H-pyrazolo[4,3-c]pyridin-5(4H)-yl)ethanone

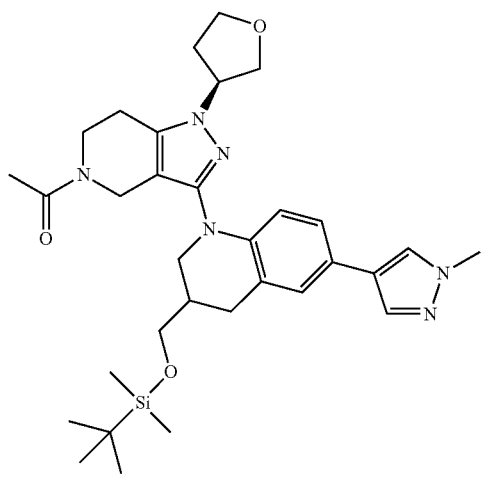 [SMILES: CC(=O)N1CCc2c(c(N3CC(CO[Si](C)(C)C(C)(C)C)Cc4cc(-c5cnn(C)c5)ccc43)nn2[C@H]2CCOC2)C1]

To a solution of 1-[3-[6-bromo-3-[[tert-butyl(dimethyl)silyl]oxymethyl]-3,4-dihydro-2H-quinolin-1-yl]-1-[(3S)-tetrahydrofuran-3-yl]-6,7-dihydro-4H-pyrazolo[4,3-c]pyridin-5-yl]ethanone (0.6 g, 1.02 mmol) in 1,4-dioxane (4 mL) and water (1 mL) was added $Na_2CO_3$ (324 mg, 3.05 mmol), 1-methyl-4-(4,4,5,5-tetramethyl-1,3,2-dioxaborolan-2-yl)pyrazole (254 mg, 1.22 mmol) and [1,1'-bis(diphenylphosphino)ferrocene]dichloropalladium(II) (85 mg, 0.10 mmol). The mixture was heated to 120° C. for 16 h under a nitrogen atmosphere. After cooling the reaction to room temperature, the mixture was filtered and the filtrate was concentrated in vacuo. The crude residue was purified by silica gel chromatography (DCM/MeOH=50:1 to 20:1) to give the title compound (340 mg, 57%) as a yellow oil. LCMS M/Z (M+H) 591.

etonitrile 23-53%/0.1% $NH_4OH$ in water) to give the title compound (102 mg, 37%) as a white solid. $^1$H NMR (400 MHz, DMSO-$d_6$) δ 7.92 (s, 1H), 7.68 (s, 1H), 7.21 (s, 1H), 7.13-7.10 (m, 1H), 6.45-6.39 (m, 1H), 4.95-4.70 (m, 1H), 4.68 (br s, 1H), 4.08-3.96 (m, 4H), 3.82-3.67 (m, 7H), 3.45-3.50 (m, 2H), 3.27-3.25 (m, 2H), 2.83-2.62 (m, 3H), 2.54-2.52 (m, 1H), 2.33-2.25 (m, 2H), 2.06-1.93 (m, 4H). LCMS M/Z (M+H) 477.

The Following Compound was Prepared in a Similar Fashion to Example 86

Example 87

| Example | Compound Name | NMR | m/z |
|---------|---------------|-----|-----|
| Example 87 | 1-[3-[4-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone | $^1$H NMR (400 MHz, DMSO-$d_6$) δ 7.92 (s, 1H), 7.68 (s, 1H), 7.29 (s, 1H), 7.14-7.10 (m, 1H), 6.46-6.39 (m, 1H), 4.90-4.83 (m, 2H), 4.07-3.80 (m, 4H), 3.69-3.60 (m, 7H), 3.55-3.48 (m, 2H), 3.31-3.25 (m, 2H), 2.89-2.83 (m, 2H), 2.73-2.65 (m, 1H), 2.28-2.23 (m, 2H), 2.06-1.93 (m, 5H). | 477 |

Step 7

1-[3-[3-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

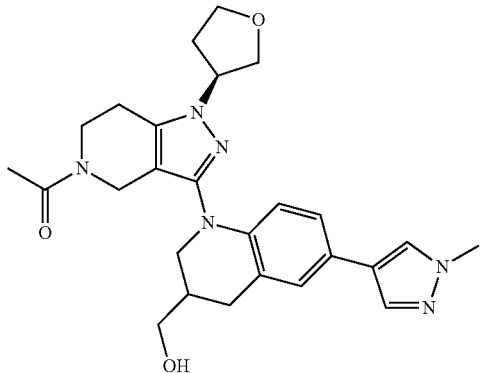 [SMILES: CC(=O)N1CCc2c(c(N3CC(CO)Cc4cc(-c5cnn(C)c5)ccc43)nn2[C@H]2CCOC2)C1]

To a solution of 1-[3-[3-[[tert-butyl(dimethyl)silyl]oxymethyl]-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone (340 mg, 0.58 mmol) in THF (2 mL) was added tetrabutylammonium fluoride (1.0 M in THF, 0.69 mL, 0.69 mmol). The mixture was heated to 80° C. for 16 h under a nitrogen atmosphere. After cooling the reaction to room temperature, water (10 mL) was added and the mixture was extracted with EtOAc (5 mL×3). The combined organic layers were dried over anhydrous $Na_2SO_4$, filtered and concentrated in vacuo. The crude residue was purified by reverse phase chromatography (ac-

Examples 88 & 89

(S, R)-1-[3-[3-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone and (S, S)-1-[3-[3-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

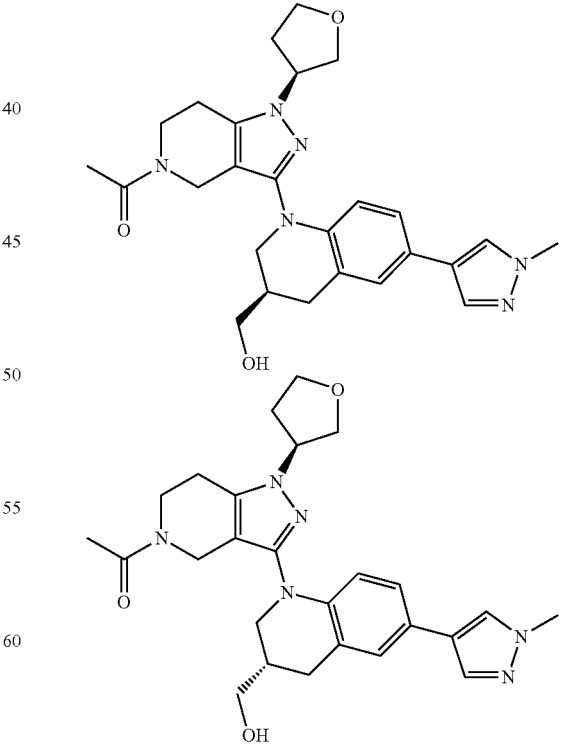

Racemic 1-[3-[3-(hydroxymethyl)-6-(1-methylpyrazol-4-yl)-3,4-dihydro-2H-quinolin-1-yl]-1-tetrahydrofuran-3-yl--

6,7-dihydro-4H-pyrazolo[4,3-c]pyridin-5-yl]ethanone (Example 86, 76 mg) was separated using chiral SFC (SFC80; Chiralpak AD 250×30 mm I.D., 5 um; Supercritical $CO_2$/MeOH+$NH_3$.$H_2O$=55/45; 50 mL/min) to give (S,R)-1-[3-[3-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (24 mg, first peak) and (S,S)-1-[3-[3-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (24 mg, second peak). Absolute configuration was arbitrarily assigned to each diastereomer. Example 88: $^1$H NMR (400 MHz, DMSO-$d_6$) δ 7.91 (s, 1H), 7.67 (s, 1H), 7.21 (s, 1H), 7.13-7.09 (m, 1H), 6.45-6.39 (m, 1H), 4.92-4.88 (m, 1H), 4.68-4.67 (m, 1H), 4.08-3.98 (m, 4H), 3.82-3.69 (m, 7H), 3.67-3.45 (m, 1H), 3.42-3.39 (m, 2H), 3.25-3.20 (m, 1H), 2.83-2.60 (m, 3H), 2.55-2.53 (m, 1H), 2.28-2.25 (m, 2H), 2.06-1.93 (m, 4H). LCMS M/Z (M+H) 477. Example 89: $^1$H NMR (400 MHz, DMSO-$d_6$) δ 7.91 (s, 1H), 7.67 (s, 1H), 7.21 (s, 1H), 7.13-7.09 (m, 1H), 6.45-6.39 (m, 1H), 4.92-4.88 (m, 1H), 4.68-4.67 (m, 1H), 4.08-3.98 (m, 4H), 3.82-3.69 (m, 7H), 3.67-3.45 (m, 1H), 3.42-3.39 (m, 2H), 3.25-3.20 (m, 1H), 2.83-2.60 (m, 3H), 2.55-2.53 (m, 1H), 2.28-2.24 (m, 2H), 2.06-1.93 (m, 4H). LCMS M/Z (M+H) 477.

Examples 90 & 91

(S, S)-1-[3-[4-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone and (S, R)-1-[3-[4-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone Racemic 1-[3-[4-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (Example 87, 100 mg) was separated using chiral SFC (Chiralpak AD 250×30 mm I.D., 5 um; Supercritical $CO_2$/MeOH+$NH_3$.$H_2O$=55/45; 25 mL/min) to give (S,S)-1-[3-[4-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (30 mg, first peak) and (S,R)-1-[3-[4-(hydroxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (34 mg, second peak). Absolute configuration was arbitrarily assigned to each diastereomer. Example 90: $^1$H NMR (400 MHz, DMSO-$d_6$) δ 7.92 (s, 1H), 7.68 (s, 1H), 7.29 (s, 1H), 7.14-7.10 (m, 1H), 6.45-6.39 (m, 1H), 4.90-4.83 (m, 2H), 4.07-3.80 (m, 4H), 3.69 (s, 3H), 3.68-3.60 (m, 8H), 2.89-2.83 (m, 2H), 2.73-2.65 (m, 1H), 2.28-2.24 (m, 2H), 2.06-1.92 (m, 5H). LCMS M/Z (M+H) 477. Example 91: $^1$H NMR (400 MHz, DMSO-$d_6$) δ 7.91 (s, 1H), 7.67 (s, 1H), 7.28 (s, 1H), 7.13-7.09 (m, 1H), 6.42-6.38 (m, 1H), 4.92-4.87 (m, 2H), 3.69 (s, 3H), 3.68-3.60 (m, 8H), 2.89-2.83 (m, 2H), 2.73-2.60 (m, 1H), 2.26-2.21 (m, 2H), 2.05-1.84 (m, 5H). LCMS M/Z (M+H) 477.

Example 92

1-[3-[3-(methoxymethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

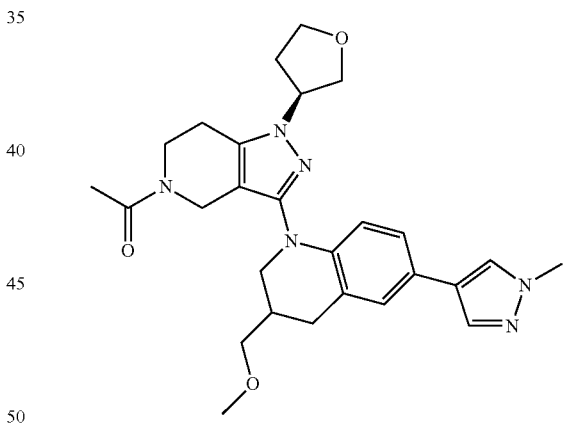

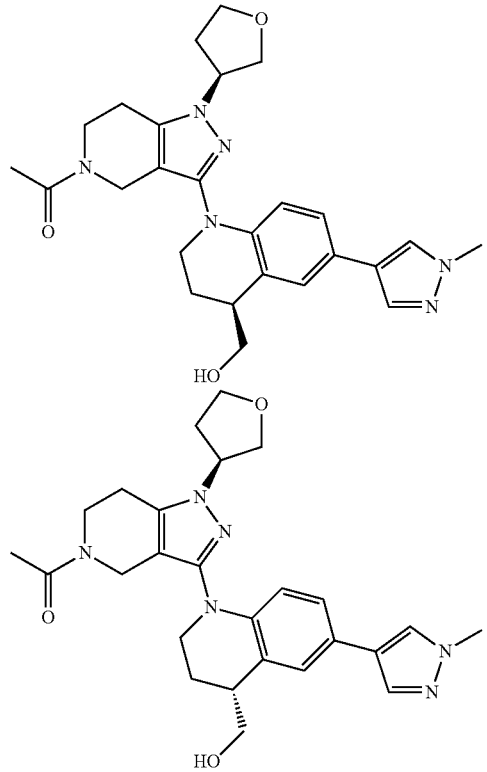

To a solution of 1-[3-[3-(hydroxymethyl)-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone (190 mg, 0.40 mmol) in DMF (1 mL) at 0° C. was added NaH (60%, 19 mg, 0.48 mmol). The mixture was stirred at 0° C. for 1 h under a nitrogen atmosphere. MeI (68 mg, 0.48 mmol) was added dropwise at 0° C. The mixture was stirred at 25° C. for an additional 2 h. The reaction mixture was quenched with water (2 mL) and extracted with EtOAc (2 mL×3). The combined organic layers were dried over anhydrous $Na_2SO_4$, filtered and concentrated in vacuo. The crude residue was purified by reverse phase chromatography (acetonitrile 27-57%/0.1% $NH_4OH$ in water) to give the title compound (24 mg, 14%) as a white solid. $^1$H NMR (400 MHz, DMSO-$d_6$) δ 7.92 (s, 1H), 7.68 (s, 1H), 7.22 (s, 1H), 7.14-7.10 (m, 1H), 6.45-6.39 (m, 1H), 4.93-

4.87 (m, 1H), 4.09-4.08 (m, 2H), 4.01-3.96 (m, 2H), 3.82-3.80 (m, 5H), 3.74-3.62 (m, 2H), 3.37-3.25 (m, 7H), 2.85-2.84 (m, 2H), 2.70-2.55 (m, 2H), 2.29-2.25 (m, 3H), 2.06-1.94 (m, 3H). LCMS M/Z (M+H) 491.

Example 93

1-[3-[6-(1-methylpyrazol-4-yl)-3,4-dihydro-2H-quinoxalin-1-yl]-1-[(3S)-tetrahydrofuran-3-yl]-6,7-dihydro-4H-pyrazolo[4,3-c]pyridin-5-yl]ethanone

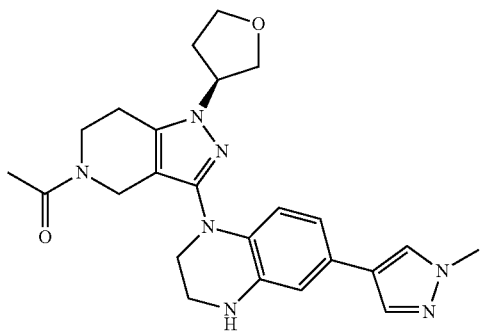 [SMILES: CC(=O)N1CCc2c(c(N3CCNc4cc(-c5cnn(C)c5)ccc43)nn2[C@H]2CCOC2)C1]

Step 1 tert-butyl 3,4-dihydroquinoxaline-1(2H)-carboxylate

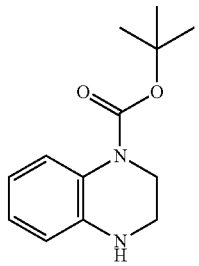 [SMILES: CC(C)(C)OC(=O)N1CCNc2ccccc21]

To a solution of 1,2,3,4-tetrahydroquinoxaline (50 g, 372.6 mmol) in THF (200 mL) and water (50 mL) was added sodium hydroxide (29.8 g, 745.3 mmol) and di-tert-butyl dicarbonate (89.5 g, 409.9 mmol). The mixture was stirred at the room temperature for 16 h. After completion of the reaction, water (20 mL) was added and the mixture was extracted with DCM (200 mL×3). The combined organic layers were dried over anhydrous Na₂SO₄, filtered and concentrated in vacuo. The crude residue was purified by silica gel chromatography (petroleum ether/EtOAc=20:1 to 4:1) to give the title compound (17.0 g, 20%) as a yellow solid.

Step 2 tert-butyl 7-bromo-3,4-dihydroquinoxaline-1(2H)-carboxylate

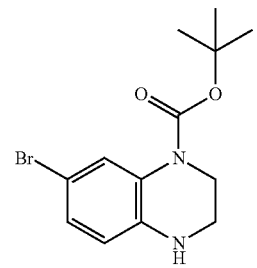 [SMILES: CC(C)(C)OC(=O)N1CCNc2ccc(Br)cc21]

To a solution of tert-butyl 3,4-dihydro-2H-quinoxaline-1-carboxylate (17 g, 72.6 mmol) in MeCN (150 mL) was added N-bromosuccinimide (12.3 g, 68.9 mmol) by portionwise at 0° C. The mixture was stirred at 0° C. for 1 h. The reaction was quenched with water (200 mL), extracted with EtOAc (200 mL×3). The combined organic layers were dried over anhydrous Na₂SO₄, filtered and concentrated in vacuo. The crude residue was purified by silica gel chromatography (petroleum ether/EtOAc=20:1 to 4:1) to give the title compound (14.0 g, 62%) as a light yellow solid. ¹H NMR (400 MHz, DMSO-d₆) δ 7.50 (s, 1H), 6.95-6.92 (m, 1H), 6.52-6.50 (m, 1H), 6.29 (s, 1H), 3.58-3.56 (m, 2H), 3.24-3.23 (m, 2H), 1.45 (s, 9H).

Step 3 tert-butyl 7-(1-methyl-1H-pyrazol-4-yl)-3,4-dihydroquinoxaline-1(2H)-carboxylate

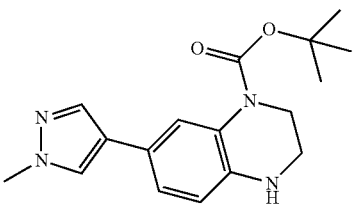 [SMILES: Cn1cc(-c2ccc3c(c2)N(C(=O)OC(C)(C)C)CCN3)cn1]

To a solution of tert-butyl 7-bromo-3,4-dihydro-2H-quinoxaline-1-carboxylate (14 g, 44.7 mmol) in THF (75 mL) and water (15 mL) was added [2-(2-aminophenyl)phenyl]-chloro-palladium-dicyclohexyl-[3-(2,4,6-triisopropylphenyl)phenyl]phosphane (3.5 g, 4.47 mmol), 1-methyl-4-(4,4,5,5-tetramethyl-1,3,2-dioxaborolan-2-yl)-1H-pyrazole (11.2 g, 53.6 mmol), Na₂CO₃ (14.2 g, 134.1 mmol) and dicyclohexyl-[3-(2,4,6-triisopropylphenyl)phenyl]phosphane (2.2 g, 4.5 mmol). The mixture was heated to 60° C. for 16 h. Water (20 mL) was added and the mixture was extracted with DCM (60 mL×3). The combined organic layers were dried over anhydrous Na₂SO₄, filtered and concentrated in vacuo. The crude residue was purified by silica gel chromatography (petroleum ether/EtOAc=20:1 to 3:1) to give the title compound (7.7 g, 55%) as a yellow solid. LCMS M/Z (M+H) 315.

Step 4

(S)-tert-butyl 4-(5-acetyl-1-(tetrahydrofuran-3-yl)-4,5,6,7-tetrahydro-1H-pyrazolo[4,3-c]pyridin-3-yl)-7-(1-methyl-1H-pyrazol-4-yl)-3,4-dihydroquinoxaline-1 (2H)-carboxylate

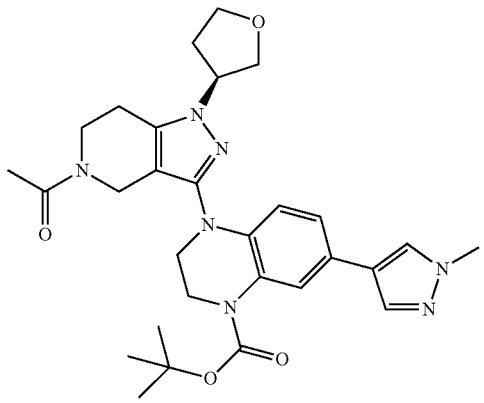 [SMILES: CC(=O)N1CCc2c(c(N3CCN(C(=O)OC(C)(C)C)c4cc(-c5cnn(C)c5)ccc43)nn2[C@H]2CCOC2)C1]

To a solution of 1-[3-bromo-1-[(3S)-tetrahydrofuran-3-yl]-6,7-dihydro-4H-pyrazolo[4,3-c]pyridin-5-yl]ethanone (Intermediate G, 6.5 g, 20.7 mmol) in 1,4-dioxane (40 mL) was added [2-(2-aminoethyl)phenyl]-chloro-palladium, dicyclohexyl-[2-(2,6-diisopropoxyphenyl)phenyl]phosphane (1.5 g, 2.1 mmol), tert-butoxysodium (5.96 g, 62.1 mmol), dicyclohexyl-[2-(2,6-diisopropoxyphenyl)phenyl]phosphane (965 mg, 2.1 mmol) and tert-butyl 7-(1-methylpyrazol-4-yl)-3,4-dihydro-2H-quinoxaline-1-carboxylate (7.2 g, 22.8 mmol). The mixture was heated to 110° C. for 16 h under a nitrogen atmosphere. After cooling the reaction to room temperature, the reaction was filtered and concentrated. The crude residue was purified by silica gel chromatography (DCM/MeOH=20:1) to give the title compound (7 g, 53%) as a yellow solid. LCMS M/Z (M+H) 548.

Step 5

1-[3-[6-(1-methylpyrazol-4-yl)-3,4-dihydro-2H-quinoxalin-1-yl]-1-[(3S)-tetrahydrofuran-3-yl]-6,7-dihydro-4H-pyrazolo[4,3-c]pyridin-5-yl]ethanone

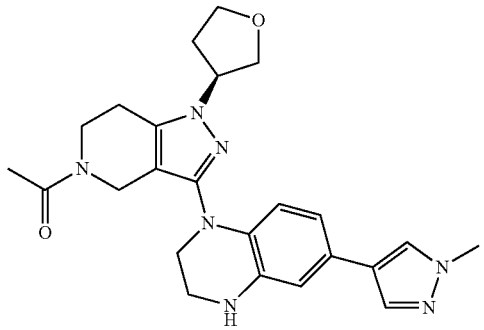 [SMILES: CC(=O)N1CCc2c(c(N3CCNc4cc(-c5cnn(C)c5)ccc43)nn2[C@H]2CCOC2)C1]

To a solution of tert-butyl 4-[5-acetyl-1-[(3S)-tetrahydrofuran-3-yl]-6,7-dihydro-4H-pyrazolo[4,3-c]pyridin-3-yl]-7-(1-methylpyrazol-4-yl)-2,3-dihydroquinoxaline-1-carboxylate (7 g, 12.8 mmol) in MeOH (25 mL) at 0° C. was added HCl in MeOH (4 M, 6.4 mL, 25.6 mmol) dropwise. The mixture was stirred at 0° C. for 2 h and then concentrated in vacuo. Water (30 mL) was added and the mixture was made basic with sat. aq. NaHCO$_3$ to pH 7 and then extracted with EtOAc (30 mL×3). The combined organic layers were dried over anhydrous Na$_2$SO$_4$, filtered and concentrated in vacuo to give crude product (3.9 g) as a brown solid. The crude product (200 mg) was purified by reverse phase chromatography (acetonitrile 18-48%/0.1% NH$_4$HCO$_3$ in water) to give the title compound (103 mg) as a white solid. $^1$H NMR (400 MHz, DMSO-d$_6$) δ 7.82 (s, 1H), 7.58 (s, 1H), 6.66 (s, 1H), 6.58-6.55 (m, 1H), 6.40-6.34 (m, 1H), 5.75 (s, 1H), 4.89-4.84 (m, 1H), 4.08-4.07 (m, 2H), 3.99-3.97 (m, 2H), 3.81-3.79 (m, 5H), 3.70-3.55 (m, 2H), 3.55-3.53 (m, 2H), 3.33-3.31 (m, 2H), 2.81-2.62 (m, 2H), 2.26-2.23 (m, 2H), 2.05-1.92 (m, 3H). LCMS M/Z (M+H) 448.

The Following Compound was Prepared in a Similar Fashion to Example 93

Example 94

| Example | Compound Name | NMR | m/z |
|---|---|---|---|
| Example 94 | 1-[3-(3,4-dihydro-2H-quinoxalin-1-yl)-1-(oxetan-3-yl)-6,7-dihydro-4H-pyrazolo[4,3-c]pyridin-5-yl]ethanone | $^1$H NMR (400 MHz, DMSO-d$_6$) δ 6.73-6.53 (m, 4H), 5.28-5.19 (m, 3H), 4.95-4.92 (m, 2H), 4.23-4.05 (m, 2H), 4.02-3.90 (m, 1H), 3.87-3.78 (m, 4H), 3.51-3.49 (m, 2H), 2.74-2.63 (m, 2H), 2.13-1.99 (m, 3H) | 354 |

Example 95

1-[3-[4-methyl-6-(1-methylpyrazol-4-yl)-2,3-dihydroquinoxalin-1-yl]-1-[(3S)-tetrahydrofuran-3-yl]-6,7-dihydro-4H-pyrazolo[4,3-c]pyridin-5-yl]ethanone

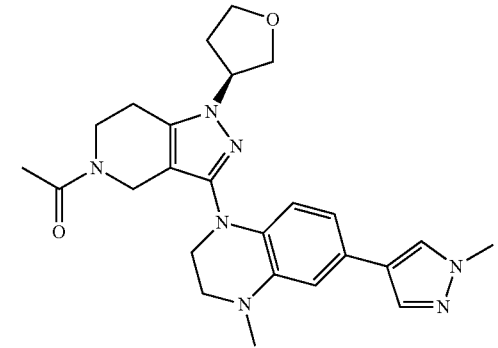 [SMILES: CC(=O)N1CCc2c(c(N3CCN(C)c4cc(-c5cnn(C)c5)ccc43)nn2[C@H]2CCOC2)C1]

To a solution of 1-[3-[6-(1-methylpyrazol-4-yl)-3,4-dihydro-2H-quinoxalin-1-yl]-1-[(3S)-tetrahydrofuran-3-yl]-6,7-dihydro-4H-pyrazolo[4,3-c]pyridin-5-yl]ethanone (Example 93, 220 mg, 0.49 mmol) in DMF (2 mL) at 0° C. was added NaH (60%, 24 mg, 0.59 mmol). The mixture was stirred at 0° C. for 1 h, then MeI (0.04 mL, 0.59 mmol) was added. The mixture was stirred at room temperature for 4 h. The reaction was quenched with water (5 mL) and extracted with EtOAc (5 mL×3). The combined organic layers were dried over anhydrous Na₂SO₄, filtered and concentrated in vacuo. The crude residue was purified by reverse phase chromatography (acetonitrile 50%/0.1% NH₄OH in water) to give the title compound (30 mg, 13%) as a brown solid. ¹H NMR (400 MHz, DMSO-d₆) δ 7.94 (s, 1H), 7.68 (s, 1H), 6.74 (s, 1H), 6.70-6.66 (m, 1H), 6.38-6.32 (m, 1H), 4.90-4.85 (m, 1H), 4.06-4.05 (m, 2H), 3.99-3.98 (m, 2H), 3.82-3.79 (m, 5H), 3.68-3.65 (m, 4H), 3.30-3.29 (m, 2H), 2.91 (s, 3H), 2.81-2.65 (m, 2, 2H), 2.29-2.23 (m, 2H), 2.05-1.92 (m, 3H). LCMS M/Z (M+H) 462.

Example 96

1-[3-(5-chloro-3,4-dihydro-2H-quinolin-1-yl)-1-[(3S)-tetrahydrofuran-3-yl]-6,7-dihydro-4H-pyrazolo[4,3-c]pyridin-5-yl]ethanone

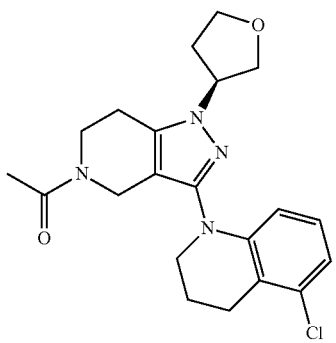 [SMILES: CC(=O)N1CCc2c(c(N3CCCc4c(Cl)cccc43)nn2[C@H]2CCOC2)C1]

Step 1

5-chloroquinoline

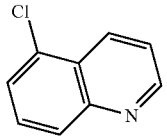

To a solution of 5-quinolinamine (9 g, 62.4 mmol) in water (80 mL) at 0° C. was added concentrated HCl (5.2 mL, 62.4 mmol) and NaNO₂ (6.5 g, 93.6 mmol) portionwise. The mixture was stirred at 0° C. for 1 h, then a solution of CuCl (9.2 g, 93.7 mmol) in concentrated HCl (5.2 mL, 62.4 mmol) was added dropwise at 0° C. After stirring at 0° C. for 2 h, the mixture was made basic with sat. aq. NaHCO₃ to pH 7 and then extracted with EtOAc (100 mL×3). The combined organic layers were dried over anhydrous Na₂SO₄, filtered and concentrated in vacuo. The crude residue was purified by silica gel chromatography (petroleum ether/EtOAc=9:1 to 5:1) to give the title compound (9.2 g, 90%) as clear oil. ¹H NMR (400 MHz, DMSO-d₆) δ 8.99-8.98 (m, 1H), 8.51 (d, J=8.0 Hz, 1H), 8.01 (d, J=8.0 Hz, 1H), 7.77-7.73 (m, 2H), 7.68-7.65 (m, 1H).

Step 2

5-chloro-1,2,3,4-tetrahydroquinoline

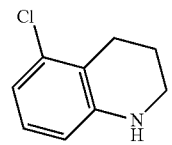 [SMILES: Clc1cccc2c1CCCN2]

To a solution of 5-chloroquinoline (5.0 g, 30.7 mmol), NaBH₃CN (7.7 g, 122.3 mmol) in EtOH (200 mL) at 0° C. was added conc. HCl (10.2 mL, 122.3 mmol) dropwise. The reaction was allowed to stir at room temperature for 15 min, and then heated to 60° C. for 2 h. After cooling the reaction to room temperature, the mixture was basified with NaOH (2 N) to pH 9 and then extracted with EtOAc (200 mL×3). The combined organic layers were dried over anhydrous Na₂SO₄, filtered and concentrated in vacuo. The crude residue was purified by silica gel chromatography (petroleum ether/EtOAc=9:1) to give the title compound (4.88 g, 95%) as a light yellow oil. ¹H NMR (400 MHz, DMSO-d₆) δ 6.85-6.81 (m, 1H), 6.49 (d, J=8.0 Hz, 1H), 6.41 (d, J=8.0 Hz, 1H), 5.98 (s, 1H), 3.15-3.12 (m, 2H), 2.65 (t, J=6.4 Hz, 2H), 1.83-1.79 (m, 2H).

Step 3

1-[3-(5-chloro-3,4-dihydro-2H-quinolin-1-yl)-1-[(3S)-tetrahydrofuran-3-yl]-6,7-dihydro-4H-pyrazolo[4,3-c]pyridin-5-yl]ethanone

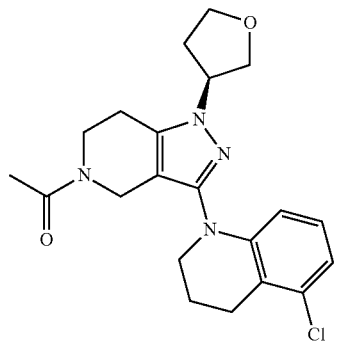 [SMILES: CC(=O)N1CCc2c(c(N3CCCc4c(Cl)cccc43)nn2[C@H]2CCOC2)C1]

To a solution of 1-[3-bromo-1-[(3S)-tetrahydrofuran-3-yl]-6,7-dihydro-4H-pyrazolo[4,3-c]pyridin-5-yl]ethanone (Intermediate G, 1.0 g, 3.2 mmol) in 1,4-dioxane (10 mL) was added 5-chloro-1,2,3,4-tetrahydroquinoline (0.64 g, 3.8 mmol), t-BuONa (0.92 g, 9.6 mmol), tris(dibenzylideneacetone)dipalladium (0.29 g, 0.32 mmol) and (5-diphenylphosphanyl-9,9-dimethyl-xanthen-4-yl)-diphenyl-phosphane (0.37 g, 0.64 mmol). The mixture was heated to 110° C. for 16 h under a nitrogen atmosphere. After cooling the reaction to room temperature, the reaction was filtered and concentrated in vacuo. The crude residue was purified by reverse phase chromatography (acetonitrile 70%-40%/0.1% NH$_4$OH in water) to give the title compound as a yellow solid. $^1$H NMR (400 MHz, DMSO-d$_6$) δ 6.96-6.90 (m, 1H), 6.75 (d, J=8.0 Hz, 1H), 6.41-6.35 (m, 1H), 4.93-4.87 (m, 1H), 4.09-4.08 (m, 2H), 4.02-3.93 (m, 2H), 3.81-3.68 (m, 4H), 3.55-3.50 (m, 2H), 2.83-2.71 (m, 4H), 2.33-2.20 (m, 2H), 2.06-1.94 (m, 5H). LCMS M/Z (M+H) 401.

Example 97

1-[3-[5-chloro-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone

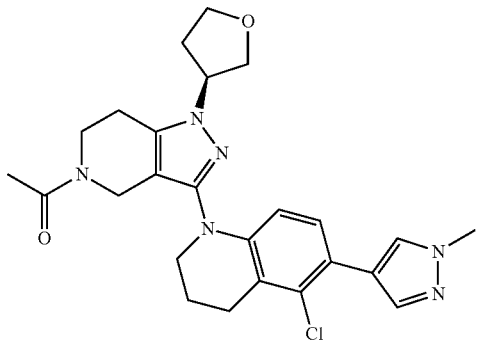 [SMILES: CC(=O)N1CCc2c(c(N3CCCc4c3ccc(-c3cnn(C)c3)c4Cl)nn2[C@H]2CCOC2)C1]

Step 1

(S)-1-(3-(6-bromo-5-chloro-3,4-dihydroquinolin-1(2H)-yl)-1-(tetrahydrofuran-3-yl)-6,7-dihydro-1H-pyrazolo[4,3-c]pyridin-5(4H)-yl)ethanone

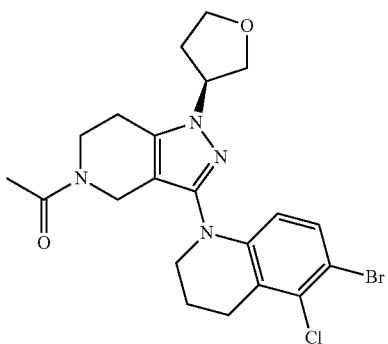 [SMILES: CC(=O)N1CCc2c(c(N3CCCc4c3ccc(Br)c4Cl)nn2[C@H]2CCOC2)C1]

To a solution of 1-[3-(5-chloro-3,4-dihydro-2H-quinolin-1-yl)-1-[(3S)-tetrahydrofuran-3-yl]-6,7-dihydro-4H-pyrazolo[4,3-c]pyridin-5-yl]ethanone (880 mg, 1.67 mmol) in DCM (6 mL) at 0° C. was added N-bromosuccinimide (281 mg, 1.6 mmol) portionwise. The mixture was stirred at 25° C. for 0.5 h and then concentrated in vacuo. The crude residue was purified by silica gel chromatography (DCM/MeOH=50:1 to 20:1) to give the title compound (1 g, 95%) as a yellow solid. LCMS M/Z (M+H) 481.

Step 2

1-[3-[5-chloro-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone

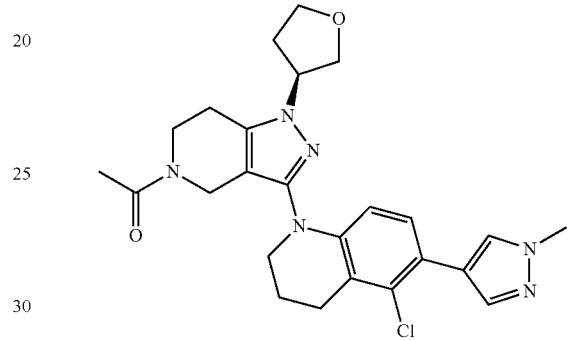

To a solution of 1-[3-(6-bromo-5-chloro-3,4-dihydro-2H-quinolin-1-yl)-1-[(3S)-tetrahydrofuran-3-yl]-6,7-dihydro-4H-pyrazolo[4,3-c]pyridin-5-yl]ethanone (1.0 g, 2.1 mmol) in 1,4-dioxane (8 mL) and water (2 mL) was added Na$_2$CO$_3$ (663 mg, 6.3 mmol), 1-methyl-4-(4,4,5,5-tetramethyl-1,3,2-dioxaborolan-2-yl)pyrazole (477 mg, 2.3 mmol) and [1,1'-bis(diphenylphosphino)ferrocene]dichloropalladium(II) (152 mg, 0.21 mmol). The mixture was heated to 100° C. for 16 h under a nitrogen atmosphere. After cooling the reaction to room temperature, the mixture was filtered and the filtrate was concentrated in vacuo. The crude residue was purified by reverse phase chromatography (acetonitrile 40-70%/0.1% NH$_4$OH in water) to give the title compound (430 mg, 32%) as a white solid. $^1$H NMR (400 MHz, DMSO-d$_6$) δ 7.94 (s, 1H), 7.63 (s, 1H), 7.13-7.08 (m, 1H), 6.47-6.41 (m, 1H), 4.95-4.85 (m, 1H), 4.12-4.10 (m, 2H), 4.01-3.99 (m, 2H), 3.86-3.69 (m, 7H), 3.58-3.48 (m, 2H), 2.87-2.68 (m, 4H), 2.32-2.15 (m, 2H), 2.07-1.96 (m, 5H). LCMS M/Z (M+H) 481.

The Following Compound was Prepared in a Similar Fashion to Example 97

Example 98

| Example | Compound Name | NMR | m/z |
|---|---|---|---|
| Example 98 | 1-[3-[5-fluoro-6-(1-methylpyrazol-4-yl)-3,4-dihydro-2H-quinolin-1-yl]-1-[(3S)-tetrahydrofuran-3-yl]-6,7-dihydro-4H- | $^1$H NMR (400 MHz, DMSO-d$_6$) δ 7.94 (s, 1H), 7.71 (s, 1H), 7.25-7.19 (m, 1H), 6.35-6.24 (m, 1H), 4.96-4.85 (m, 1H), 4.16-4.08 (m, 2H), 4.06-3.91 (m, 2H), 3.89-3.65 (m, 7H), 3.58-3.48 (m, 2H), 2.88-2.66 (m, 4H), 2.35-2.17 (m, 2H), | 465 |

| Example | Compound Name | NMR | m/z |
|---|---|---|---|
| | pyrazolo[4,3-c]pyridin-5-yl]ethanone | 1.96 (s, 2H), 2.07 (s, 3H) | |

Example 99

1-[3-[3-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

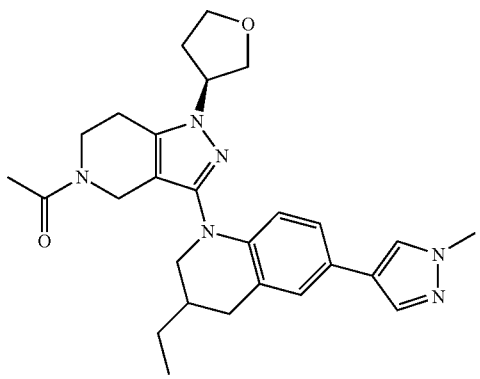 [SMILES: CCC1Cc2cc(-c3cnn(C)c3)ccc2N(c2nn([C@H]3CCOC3)c3c2CN(C(C)=O)CC3)C1]

Step 1

3-ethylquinoline

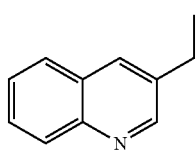

To a solution of 3-bromoquinoline (10.0 g, 48.06 mmol) was added diethyl zinc (1M in THF, 192 mL, 192 mmol) and [1,1'-bis(diphenylphosphino)ferrocene]dichloropalladium (II) (1.8 g, 4.81 mmol) in THF (100 mL). The mixture was heated to 70° C. for 16 h under a nitrogen atmosphere. After cooling the reaction to room temperature, saturated aqueous NH₄Cl (50 mL) was added and the mixture was extracted with EtOAc (50 mL×3). The combined organic layers were washed with brine, dried over anhydrous Na₂SO₄ and concentrated in vacuo. The crude residue was purified by silica gel chromatography (petroleum ether/EtOAc 5=9:1) to give the title compound (5.2 g, 68%) as brown oil. ¹H NMR (400 MHz, DMSO-d₆) δ 8.79 (s, 1H), 8.08 (d, J=8.8 Hz, 1H), 7.91 (s, 1H), 7.75 (d, J=8.0 Hz, 1H), 7.64 (t, J=8.0 Hz, 1H), 7.50 (t, J=7.6 Hz, 1H), 1.36-1.32 (m, 2H), 1.34 (t, J=7.6 Hz, 3H).

Step 2

3-ethyl-1,2,3,4-tetrahydroquinoline

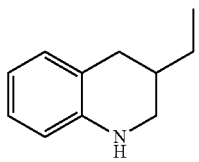

To a solution of 3-ethylquinoline (5.2 g, 32.68 mmol) in MeOH (5.0 mL) was added NaBH₃CN (6.2 g, 98.04 mmol) and boron trifluoride diethyl etherate (9.3 g, 65.36 mmol). The mixture was heated to 80° C. for 16 h. After cooling the reaction to room temperature, sat. aq. NaHCO₃ (100 mL) was added and the mixture was extracted with EtOAc (100 mL×2). The combined organic layers were dried over anhydrous Na₂SO₄, filtered and concentrated in vacuo to give 3-ethyl-1,2-dihydroquinoline (5.0 g, crude) as a brown oil. To a solution of 3-ethyl-1,2-dihydroquinoline (5.0 g, 30.83 mmol) in MeOH (50 mL) was added 10% Pd/C (1.0 g). The mixture was stirred at 30° C. under a hydrogen atmosphere (15 psi) for 16 h. The mixture was filtered and the filtrate was concentrated in vacuo. The crude residue was purified by silica gel chromatography (petroleum ether/EtOAc=100:1) to give the title compound (1.8 g, 33%) as a brown oil.

Step 3

6-bromo-3-ethyl-1,2,3,4-tetrahydroquinoline

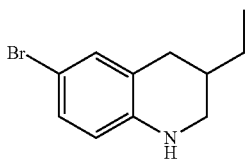

To a solution of 3-ethyl-1,2,3,4-tetrahydroquinoline (2.0 g, 12.30 mmol) in DCM (20 mL), N-bromosuccinimide (2.0 g, 11.10 mmol) was added. The mixture was stirred at 30° C. for 2 h and concentrated in vacuo. The crude residue was purified by silica gel chromatography (petroleum ether/EtOAc=100:1) to give the title compound (2.0 g, 66%) as a brown solid.

Step 4

3-ethyl-6-(1-methyl-1H-pyrazol-4-yl)-1,2,3,4-tetrahydroquinoline

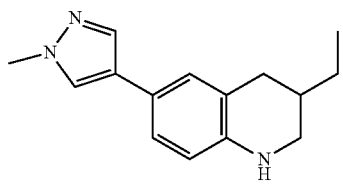 [SMILES: CCC1CNc2ccc(-c3cnn(C)c3)cc2C1]

To a solution of 6-bromo-3-ethyl-1,2,3,4-tetrahydroquinoline (2.0 g, 5.50 mmol), 1-methyl-4-(4,4,5,5-tetramethyl-1,3,2-dioxaborolan-2-yl)-1H-pyrazole (1.4 g, 6.60 mmol) and K₂CO₃ (2.3 g, 16.49 mmol) in dioxane/H₂O (25 mL, 4:1) was added [1,1'-bis(diphenylphosphino)ferrocene]dichloropalladium(II) (403 mg, 0.55 mmol). The mixture was heated to 110° C. for 16 h under a nitrogen atmosphere. After cooling the reaction to room temperature, the mixture was filtered and the filtrate was concentrated in vacuo. The crude residue was purified by silica gel chromatography (petroleum ether/EtOAc=5:1) to give the title compound (600 mg, 46%) as a brown solid.

Step 5

1-[3-[3-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

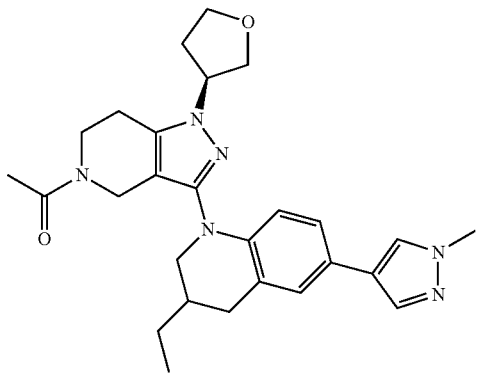 [SMILES: CCC1Cc2cc(-c3cnn(C)c3)ccc2N(c2nn([C@H]3CCOC3)c3c2CN(C(C)=O)CC3)C1]

To a solution of 3-ethyl-6-(1-methyl-1H-pyrazol-4-yl)-1,2,3,4-tetrahydroquinoline (600 mg, 2.49 mmol) and (S)-1-(3-bromo-1-(tetrahydrofuran-3-yl)-6,7-dihydro-1H-pyrazolo[4,3-c]pyridin-5(4H)-yl)ethanone (Intermediate G, 859 mg, 2.74 mmol) in dioxane (10 mL) was added chloro(2-dicyclohexylphosphino-2',6'-di-i-propoxy-1,1'-biphenyl)[2-(2-aminoethylphenyl)]palladium(II), methyl-tert-butylether adduct (203 mg, 0.25 mmol), 2-dicyclohexylphosphino-2',6'-di-i-propoxy-1,1'-biphenyl (116 mg, 0.25 mmol) and t-BuONa (716 mg, 7.46 mmol). The mixture was stirred at 120° C. for 16 h under a nitrogen atmosphere. After cooling the reaction to room temperature, the mixture was filtered and the filtrate was concentrated in vacuo. The crude residue was purified by reverse phase chromatography (acetonitrile 34-64%/0.1% NH₄OH in water) to give the title compound (130 mg, 11%) as a white solid. ¹H NMR (400 MHz, DMSO-d₆) δ 7.91 (s, 1H), 7.68 (s, 1H), 7.21 (s, 1H), 7.14-7.07 (m, 1H), 6.47-6.36 (m, 1H), 4.94-4.85 (m, 1H), 4.09 (s, 2H), 4.04-3.93 (m, 2H), 3.86-3.64 (m, 7H), 3.60 (d, J=11.6 Hz, 1H), 3.27-3.16 (m, 1H), 2.95-2.80 (m, 2H), 2.75-2.65 (m, 1H), 2.46 (s, 1H), 2.35-2.19 (m, 2H), 2.06 (s, 2H), 1.94 (s, 1H), 1.85 (s, 1H), 1.46-1.28 (m, 2H), 1.00-0.87 (m, 3H). LCMS M/Z (M+H) 475.

Examples 100 & 101

(S, R)-1-[3-[3-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone and (S, S)-1-[3-[3-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

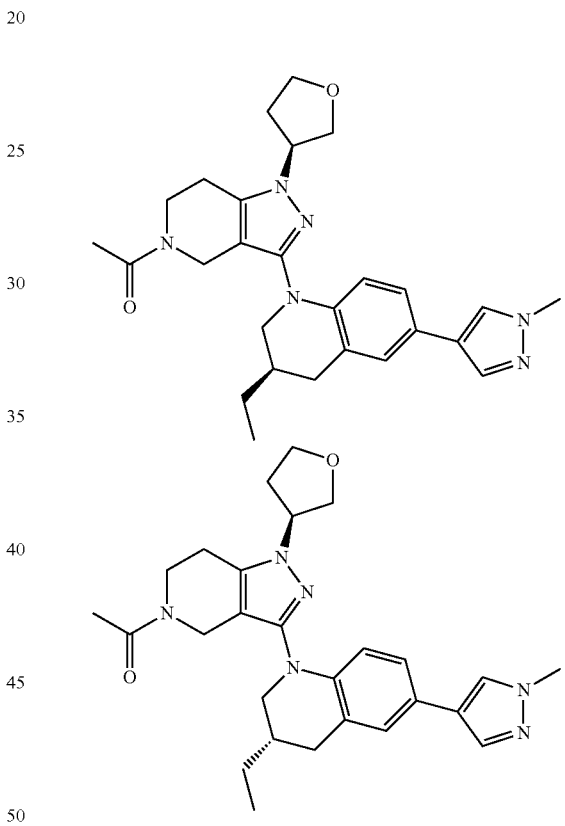

Racemic 1-[3-[3-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (Example 99, 104 mg) was separated using chiral SFC (SFC80; Chiralpak AD 250×30 mm I.D., 5 um; Supercritical CO₂/MeOH+NH₃.H₂O=55/45; 50 mL/min) to give (S, R)-1-[3-[3-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (26 mg, first peak) and (S, S)-1-[3-[3-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (26 mg, second peak). Absolute configuration was arbitrarily assigned to each diastereomer. Example 100: ¹H NMR (400 MHz, DMSO-d₆) δ 7.91 (s, 1H), 7.68 (s, 1H), 7.21 (s, 1H), 7.14-7.07 (m, 1H), 6.47-6.36 (m, 1H), 4.94-4.85 (m, 1H), 4.09 (s, 2H), 4.04-3.93 (m, 2H), 3.86-3.64 (m, 7H), 3.60 (d, J=11.6 Hz, 1H), 3.27-3.16 (m, 1H), 2.95-2.80 (m, 2H), 2.75-2.65 (m, 1H), 2.46 (s, 1H), 2.35-2.19 (m, 2H), 2.06 (s, 2H), 1.94 (s, 1H), 1.85 (s, 1H), 1.46-1.28 (m, 2H), 1.00-0.87 (m, 3H). LCMS M/Z (M+H) 475. Example 101: $^1$H NMR (400 MHz, DMSO-$d_6$) δ 7.91 (s, 1H), 7.68 (s, 1H), 7.21 (s, 1H), 7.14-7.07 (m, 1H), 6.47-6.36 (m, 1H), 4.94-4.85 (m, 1H), 4.09 (s, 2H), 4.04-3.93 (m, 2H), 3.86-3.64 (m, 7H), 3.60 (d, J=11.6 Hz, 1H), 3.27-3.16 (m, 1H), 2.95-2.80 (m, 2H), 2.75-2.65 (m, 1H), 2.46 (s, 1H), 2.35-2.19 (m, 2H), 2.06 (s, 2H), 1.94 (s, 1H), 1.85 (s, 1H), 1.46-1.28 (m, 2H), 1.00-0.87 (m, 3H). LCMS M/Z (M+H) 475.

Example 102

1-[3-[7-chloro-4-methyl-6-(1-methylpyrazol-4-yl)-3,4-dihydro-2H-quinolin-1-yl]-1-((S)-tetrahydrofuran-3-yl]-6,7-dihydro-4H-pyrazolo[4,3-c]pyridin-5-yl]ethanone

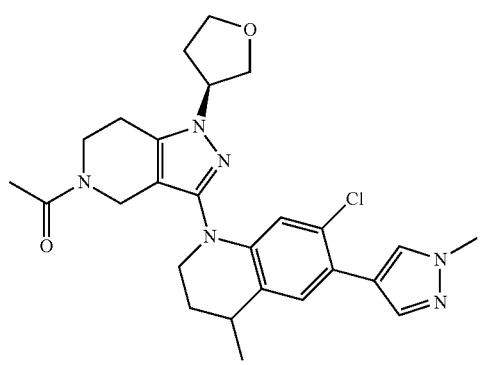 [SMILES: CC(=O)N1CCc2c(c(N3CCC(C)c4cc(-c5cnn(C)c5)c(Cl)cc43)nn2[C@H]2CCOC2)C1]

Step 1

7-chloro-4-methyl-1,2,3,4-tetrahydroquinoline

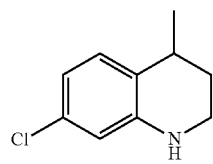

To a solution of 7-chloro-4-methyl-quinoline (5 g, 28.15 mmol) and sodium cyanoborohydride (5.31 g, 84.45 mmol) in MeOH (60 mL) was added boron trifluoride diethyl etherate (3.41 mL, 56.3 mmol) dropwise. The mixture was heated to 70° C. for 16 h under a nitrogen atmosphere. After cooling the reaction to room temperature, the mixture was concentrated in vacuo. EtOAc (100 mL) was added and the mixture was washed with water (100 mL×2) and brine (100 mL), dried over anhydrous Na$_2$SO$_4$, filtered and concentrated in vacuo. The crude residue was purified by silica gel chromatography (petroleum ether/EtOAc=20:1) to give the title compound (3 g, 53%) as brown solid.

Step 2

1-(3-(7-chloro-4-methyl-3,4-dihydroquinolin-1(2H)-yl)-1-((S)-tetrahydrofuran-3-yl)-6,7-dihydro-1H-pyrazolo[4,3-c]pyridin-5(4H)-yl)ethanone

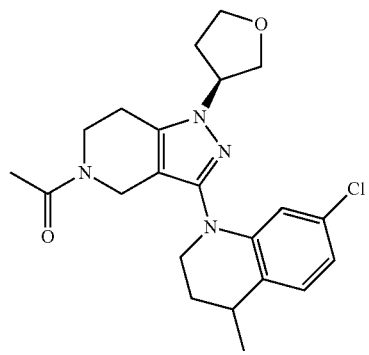 [SMILES: CC(=O)N1CCc2c(c(N3CCC(C)c4ccc(Cl)cc43)nn2[C@H]2CCOC2)C1]

To a solution of 1-[3-bromo-1-[(3S)-tetrahydrofuran-3-yl]-6,7-dihydro-4H-pyrazolo[4,3-c]pyridin-5-yl]ethanone (Intermediate G, 5.19 g, 16.51 mmol) in 1,4-dioxane (40 mL) was added 4,5-bis(diphenylphosphino)-9,9-dimethylxanthene (1.91 g, 3.3 mmol), cesium carbonate (16.14 g, 49.54 mmol), 7-chloro-4-methyl-1,2,3,4-tetrahydroquinoline (3.33 g, 16.51 mmol) and tris(dibenzylideneacetone)dipalladium(0) (1.51 g, 1.65 mmol). The mixture was heated to 120° C. for 16 h under a nitrogen atmosphere. After cooling the reaction to room temperature, the mixture was filtered and the filtrate was concentrated in vacuo. The crude residue was purified by silica gel chromatography (DCM/MeOH=50:1) to give the title compound (3.1 g, 27%) as a brown solid.

Step 3

1-(3-(6-bromo-7-chloro-4-methyl-3,4-dihydroquinolin-(2H)-yl)-1-((S)-tetrahydrofuran-3-yl)-6,7-dihydro-1H-pyrazolo[4,3-c]pyridin-5(4H)-yl)ethanone

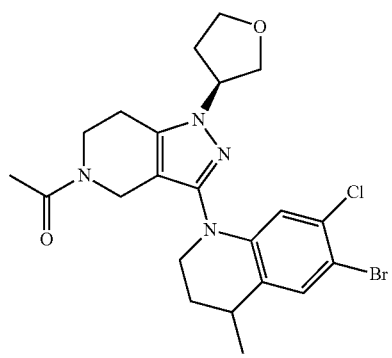 [SMILES: CC(=O)N1CCc2c(c(N3CCC(C)c4cc(Br)c(Cl)cc43)nn2[C@H]2CCOC2)C1]

To a solution of 1-[3-(7-chloro-4-methyl-3,4-dihydro-2H-quinolin-1-yl)-1-[(3S)-tetrahydrofuran-3-yl]-6,7-dihydro-4H-pyrazolo[4,3-c]pyridin-5-yl]ethanone (3.4 g, 4.92 mmol) in DCM (30 mL) at 0° C. was added N-bromosuccinimide (788 mg, 4.42 mmol). The mixture was stirred at 26° C. for 16 h and then stirred at 30° C. for 0.5 h. The mixture was concentrated in vacuo. The crude residue was purified by silica gel chromatography (DCM/MeOH=20:1) to give the title compound (2.7 g, 89%) as a brown solid.

Step 4

1-[3-[7-chloro-4-methyl-6-(1-methylpyrazol-4-yl)-3,4-dihydro-2H-quinolin-1-yl]-1-((S)-tetrahydrofuran-3-yl]-6,7-dihydro-4H-pyrazolo[4,3-c]pyridin-5-yl]ethanone

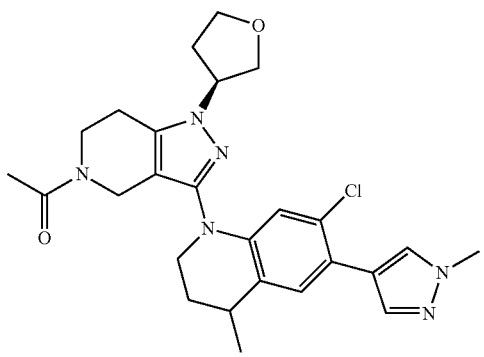 [SMILES: CC(=O)N1CCc2c(c(N3CCC(C)c4cc(-c5cnn(C)c5)c(Cl)cc43)nn2[C@H]2CCOC2)C1]

To a solution of 1-[3-(6-bromo-7-chloro-4-methyl-3,4-dihydro-2H-quinolin-1-yl)-1-[(3S)-tetrahydrofuran-3-yl]-6,7-dihydro-4H-pyrazolo[4,3-c]pyridin-5-yl]ethanone (1.5 g, 3.04 mmol) and 1-methyl-4-(4,4,5,5-tetramethyl-1,3,2-dioxaborolan-2-yl)-1H-pyrazole (758 mg, 3.65 mmol) in 1,4-dioxane (15 mL) and water (3 mL) was added potassium carbonate (1.26 9.11 mmol) and [1,1'-bis(diphenylphosphino)ferrocene]dichloropalladium(II) (222 mg, 0.300 mmol). The mixture was heated to 120° C. for 16 h under a nitrogen atmosphere. After cooling the reaction to room temperature, the mixture was concentrated in vacuo. The crude residue was purified by silica gel chromatography (DCM/MeOH=20:1) to give the crude product (900 mg) as a brown solid. The crude product (50 mg) was purified by Prep-TLC (DCM/MeOH=20:1) to give the title compound (18 mg) as a white solid. $^1$H NMR (400 MHz, DMSO-d$_6$) δ 7.97 (s, 1H), 7.70 (s, 1H), 7.26 (s, 1H), 6.56-6.45 (m, 1H), 4.92 (s, 1H), 4.21-4.10 (m, 2H), 4.07-3.96 (m, 2H), 3.89-3.66 (m, 7H), 3.62-3.50 (m, 2H), 3.00-2.70 (m, 3H), 2.30-2.17 (m, 2H), 2.12-1.93 (m, 4H), 1.70 (d, J=6.0 Hz, 1H), 1.34-1.20 (m, 3H). LCMS M/Z (M+H) 495.

Example 103

1-(5-acetyl-1-tetrahydrofuran-3-yl-6,7-dihydro-4H-pyrazolo[4,3-c]pyridin-3-yl)-4-methyl-6-(1-methylpyrazol-4-yl)-3,4-dihydro-2H-quinoline-7-carbonitrile

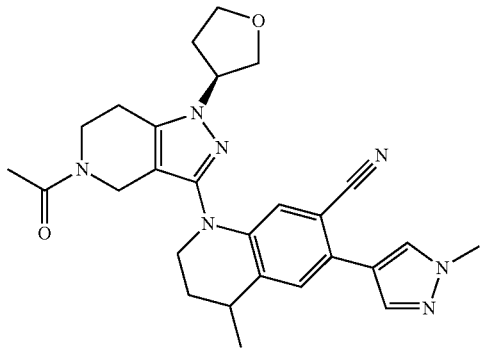 [SMILES: CC(=O)N1CCc2c(c(N3CCC(C)c4cc(-c5cnn(C)c5)c(C#N)cc43)nn2[C@H]2CCOC2)C1]

To a solution of 1-[3-[7-chloro-4-methyl-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone (200 mg, 0.36 mmol) in 1,4-dioxane (2 mL) and water (2 mL) was added KOAc (4.46 mg, 0.05 mmol), potassium hexacyanoferrate(II) trihydrate (72 mg, 0.22 mmol), methanesulfonato(2-di-tert-butylphosphino-2',4',6'-tri-i-propyl-1,1'-biphenyl)(2'-amino-1,1'-biphenyl-2-yl)palladium(II) (32 mg, 0.04 mmol) and 2-di-tert-butylphosphino-2',4',6'-triisopropylbiphenyl (28 mg, 0.04 mmol). The mixture was heated to 110° C. for 1 h under a nitrogen atmosphere. After cooling the reaction to room temperature, the mixture was concentrated in vacuo. The crude residue was purified by Prep-TLC (DCM/MeOH=20:1) to give the title compound (110 mg, 62%) as a white solid. $^1$H NMR (400 MHz, DMSO-d$_6$) δ 8.09 (s, 1H), 7.82 (s, 1H), 7.42 (s, 1H), 6.80-6.71 (m, 1H), 4.94 (s, 1H), 4.16 (d, J=11.6 Hz, 2H), 4.05-3.93 (m, 2H), 3.89 (s, 3H), 3.85-3.70 (m, 4H), 3.64-3.53 (m, 2H), 3.07-2.98 (m, 1H), 2.89-2.72 (m, 2H), 2.34-2.22 (m, 2H), 2.11-1.97 (m, 4H), 1.80-1.70 (m, 1H), 1.37-1.28 (m, 3H). LCMS M/Z (M+H) 486.

Examples 104 & 105

(S, S)-1-(5-acetyl-1-tetrahydrofuran-3-yl-6,7-dihydro-4H-pyrazolo[4,3-c]pyridin-3-yl)-4-methyl-6-(1-methylpyrazol-4-yl)-3,4-dihydro-2H-quinoline-7-carbonitrile and (S, R)-1-(5-acetyl-1-tetrahydrofuran-3-yl-6,7-dihydro-4H-pyrazolo[4,3-c]pyridin-3-yl)-4-methyl-6-(1-methylpyrazol-4-yl)-3,4-dihydro-2H-quinoline-7-carbonitrile

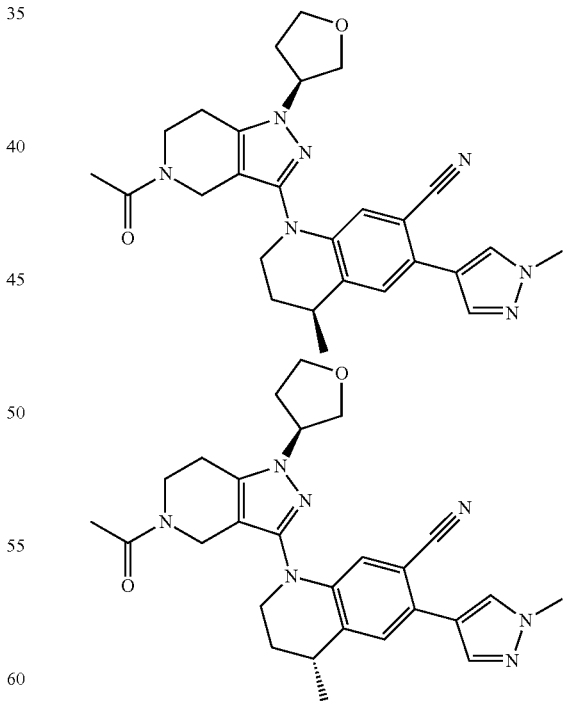

Racemic 1-(5-acetyl-1-tetrahydrofuran-3-yl-6,7-dihydro-4H-pyrazolo[4,3-c]pyridin-3-yl)-4-methyl-6-(1-methylpyrazol-4-yl)-3,4-dihydro-2H-quinoline-7-carbonitrile (Example 103, 150 mg) was separated using chiral SFC (Chiralpak AD 250 mm×30 mm I.D., 5 um; Supercritical CO$_2$/MEOH+NH$_4$OH=75/25; 60 mL/min) to give (S, S)-1-(5-acetyl-1-tetrahydrofuran-3-yl-6,7-dihydro-4H-pyrazolo[4,3-c]pyridin-3-yl)-4-methyl-6-(1-methylpyrazol-4-yl)-3,4-dihydro-2H-quinoline-7-carbonitrile (32 mg, first peak) and (S, R)-1-(5-acetyl-1-tetrahydrofuran-3-yl-6,7-dihydro-4H-pyrazolo[4,3-c]pyridin-3-yl)-4-methyl-6-(1-methyl-pyrazol-4-yl)-3,4-dihydro-2H-quinoline-7-carbonitrile (27 mg, second peak). Absolute configuration was arbitrarily assigned to each diastereomer. Example 104: $^1$H NMR (400 MHz, DMSO-d$_6$) δ 8.09 (s, 1H), 7.82 (s, 1H), 7.42 (s, 1H), 6.80-6.71 (m, 1H), 4.94 (s, 1H), 4.16 (d, J=11.6 Hz, 2H), 4.05-3.93 (m, 2H), 3.89 (s, 3H), 3.85-3.70 (m, 4H), 3.64-3.53 (m, 2H), 3.07-2.98 (m, 1H), 2.89-2.72 (m, 2H), 2.34-2.22 (m, 2H), 2.11-1.97 (m, 4H), 1.80-1.70 (m, 1H), 1.37-1.28 (m, 3H). LCMS M/Z (M+H) 486. Example 105: $^1$H NMR (400 MHz, DMSO-d$_6$) δ 8.09 (s, 1H), 7.82 (s, 1H), 7.42 (s, 1H), 6.80-6.71 (m, 1H), 4.94 (s, 1H), 4.16 (d, J=11.6 Hz, 2H), 4.05-3.93 (m, 2H), 3.89 (s, 3H), 3.85-3.70 (m, 4H), 3.64-3.53 (m, 2H), 3.07-2.98 (m, 1H), 2.89-2.72 (m, 2H), 2.34-2.22 (m, 2H), 2.11-1.97 (m, 4H), 1.80-1.70 (m, 1H), 1.37-1.28 (m, 3H). LCMS M/Z (M+H) 486.

Example 106

1-[3-[4-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

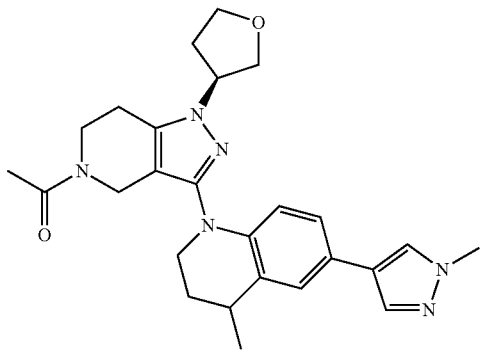

Step 1

4-methyl-1,2,3,4-tetrahydroquinoline

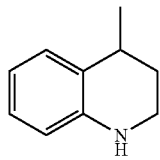

To a solution of 4-methylquinoline (5.0 g, 34.9 mmol) and NaBH$_3$CN (8.78 g, 139.7 mmol) in MeOH (30 mL) was added boron trifluoride diethyl etherate (37 mL, 70 mmol) dropwise. The mixture was heated to 70° C. for 16 h under a nitrogen atmosphere. After cooling the reaction to room temperature, the reaction was quenched with sat. aq. NaHCO$_3$ (10 mL) and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by silica gel chromatography (petroleum ether/EtOAc=10:1) to give the title compound (4.0 g, 78%) as colorless oil. LCMS M/Z (M+H) 148.

Step 2

6-bromo-4-methyl-1,2,3,4-tetrahydroquinoline

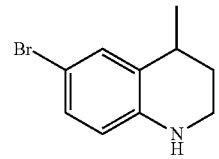

To a solution of 4-methyl-1,2,3,4-tetrahydroquinoline (2.0 g, 13.6 mmol) in DCM (20.0 mL) was added N-bromosuccinimide (2.42 g, 13.6 mmol) in portionwise. The mixture was stirred at 30° C. for 3 h under a nitrogen atmosphere. After cooling the reaction to room temperature, the reaction was quenched with sat. aq. NaHCO$_3$ (10 mL) and extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by silica gel chromatography (petroleum ether/EtOAc=20:1) to give the title compound (1.0 g, 33%) as a brown oil.

Step 3

4-methyl-6-(1-methyl-1H-pyrazol-4-yl)-1,2,3,4-tetrahydroquinoline

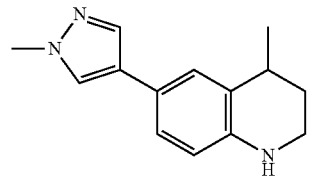 [SMILES: CC1CCNc2ccc(-c3cnn(C)c3)cc21]

To a stirred solution of 6-bromo-4-methyl-1,2,3,4-tetrahydroquinoline (750 mg, 3.32 mmol), 1-methyl-4-(4,4,5,5-tetramethyl-1,3,2-dioxaborolan-2-yl)-1H-pyrazole (830 mg, 3.98 mmol), K$_2$CO$_3$ (1.38 g, 10 mmol) in dioxane/H$_2$O (8 mL, 3:1) was added [1,1'-bis(diphenylphosphino)ferrocene]dichloropalladium(II) (121 mg, 0.166 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by silica gel chromatography (petroleum ether/EtOAc=5:1) to give the title compound (700 mg, 93%) as a light yellow solid. $^1$H NMR (400 MHz, CDCl$_3$) δ 7.63 (s, 1H), 7.46 (s, 1H), 7.14 (s, 1H), 7.08-7.05 (m, 1H), 6.48 (d, J=8.4 Hz, 1H), 3.90 (s, 3H), 3.33-3.26 (m, 2H), 3.93-3.90 (m, 1H), 2.00-1.97 (m, 1H), 1.70-1.66 (m, 1H), 1.31 (d, J=7.2 Hz, 3H).

Step 4

1-[3-[4-methyl-6-(1-methylpyrazol-4-yl)-3,4-di-hydro-2H-quinolin-1-yl]-1-tetrahydrofuran-3-yl-6,7-dihydro-4H-pyrazolo[4,3-c]pyridin-5-yl]ethanone

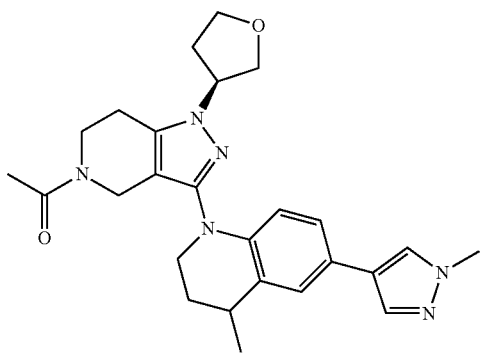

To a solution of 4-methyl-6-(1-methyl-1H-pyrazol-4-yl)-1,2,3,4-tetrahydroquinoline (400 mg, 1.76 mmol), (S)-1-(3-bromo-1-(tetrahydrofuran-3-yl)-6,7-dihydro-1H-pyrazolo[4,3-c]pyridin-5(4H)-yl)ethanone (634 mg, 2.11 mmol) and t-BuONa (507 mg, 5.28 mmol) in dioxane (5 mL) was added chloro(2-dicyclohexylphosphino-2',6'-di-i-propoxy-1,1'-biphenyl)[2-(2-aminoethylphenyl)]palladium(II), methyl-tert-butylether adduct (72 mg, 0.088 mmol) and 2-dicyclohexylphosphino-2',6'-di-i-propoxy-1,1'-biphenyl (39 mg, 0.088 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by reverse phase chromatography (acetonitrile 25-55%/0.1% NH$_4$HCO$_3$ in water) to give the title compound (200 mg, 25%) as a white solid. $^1$H NMR (400 MHz, CDCl$_3$) δ 7.68-7.65 (m, 1H), 7.51-7.49 (m, 1H), 7.23-7.19 (m, 1H), 7.10-7.05 (m, 1H), 6.54-6.50 (m, 1H), 4.78-4.74 (m, 1H), 4.27-3.89 (m, 10H), 3.71-3.55 (m, 2H), 2.30-2.72 (m, 3H), 2.45-2.35 (m, 2H), 2.15-1.77 (m, 4H), 1.79-1.77 (m, 1H), 1.38-1.36 (m, 3H). LCMS M/Z (M+H) 461.

The Following Compounds were Prepared in a Similar Fashion to Example 106

Examples 107-110

| Example | Compound Name | NMR | m/z |
|---|---|---|---|
| Example 107 | 1-[3-[4-methyl-6-(1-methylpyrazol-4-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 7.93 (s, 1H), 7.68 (s, 1H), 7.28 (s, 1H), 7.13-7.09 (m, 1H), 6.49-6.42 (m, 1H), 5.46-5.40 (m, 1 H), 4.92-4.87 (m, 2H), 4.85-4.81 (m, 2H), 4.01-3.80 (m, 2H), 3.80 (s, 3H), 3.39-3.57 (m, 4H), 2.96-2.91 (m, 1H), 2.75-2.62 (m, 2H), 2.02-1.89 (m, 4H), 1.71-1.66 (m, 1H), 1.31 (d, J = 6.8 Hz, 3H) | 447 |
| Example 108 | 1-[3-[4-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone | $^1$H NMR (400 MHz, CDCl$_3$) δ 7.66-7.64 (m, 1H), 7.50-7.47 (m, 1H), 7.18-7.04 (m, 2H), 6.54-6.49 (m, 1H), 4.75-4.73 (m, 1H), 4.17-4.10 (m, 3H), 4.00-3.90 (m, 7H), 3.71-3.64 (m, 3H), 2.72-2.70 (m, 3H), 2.43-2.34 (m, 2H), 2.14-1.94 (m, 5H), 1.81-1.78 (m, 1H), 1.61-1.59 (m, 1H), 1.03 (t, J = 7.2 Hz, 3H) | 475 |
| Example 109 | 1-[3-[3-methyl-6-(1-methylpyrazol-4-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 7.93 (s, 1H), 7.69 (s, 1H), 7.22 (s, 1H), 7.15-7.11 (m, 1H), 6.51-6.45 (m, 1H), 5.48-5.43 (m, 1H), 4.94-4.84 (m, 4H), 4.08-4.07 (m, 2H), 3.83 (s, 3H), 3.73-3.64 (m, 4H), 3.26-3.20 (m, 1H), 2.91-2.67 (m, 4H), 2.05-1.92 (m, 3H), 1.07-1.04 (m, 3H) | 447 |
| Example 110 | 1-[3-[3-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone | $^1$H NMR (400 MHz, DMSO-d$_6$) δ 7.91 (s, 1H), 7.67 (s, 1H), 7.19 (s, 1H), 7.13-7.08 (m, 1H), 6.44-6.39 (m, 1H), 4.92-4.86 (m, 1H), 4.08 (s, 2H), 4.00-3.95 (m, 2H), 3.82 (s, 3H), 3.75-3.54 (m, 4H), 3.42-3.38 (m, 2H), 3.18-3.13 (m, 1H), 2.87-2.67 (m, 4H), 2.33-2.22 (m, 2H), 2.06-1.93 (m, 3H), 1.06-1.01 (m, 3H) | 461 |

Examples 111 & 112

(S, S)-1-[3-[4-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone and (S, R)-1-[3-[4-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

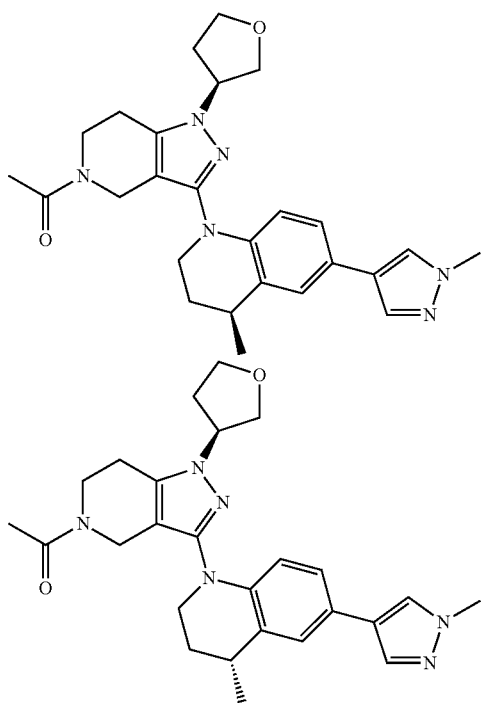

Racemic 1-[3-[4-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (Example 106, 190 mg) was separated using chiral SFC (Chiralpak AD-3 50*4.6 mm I.D., 3 um; Mobile phase: ethanol (0.05% diethyl amine) in $CO_2$ from 5% to 40%; Flow rate: 60 mL/min) to give (S, S)-1-[3-[4-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (92 mg, first peak) and (S, R)-1-[3-[4-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (76 mg, second peak). Absolute configuration was arbitrarily assigned to each diastereomer. Example 111: $^1$H NMR (400 MHz, CDCl$_3$) δ 7.68-7.65 (m, 1H), 7.51-7.49 (m, 1H), 7.23-7.19 (m, 1H), 7.10-7.05 (m, 1H), 6.54-6.50 (m, 1H), 4.78-4.74 (m, 1H), 4.27-3.89 (m, 10 OH), 3.71-3.55 (m, 2H), 3.00-2.72 (m, 3H), 2.45-2.35 (m, 2H), 2.15-1.77 (m, 4H), 1.79-1.77 (m, 1H), 1.38-1.36 (m, 3H). LCMS M/Z (M+H) 461. Example 112: $^1$H NMR (400 MHz, CDCl$_3$) δ 7.68-7.65 (m, 1H), 7.51-7.49 (m, 1H), 7.23-7.19 (m, 1H), 7.10-7.05 (m, 1H), 6.54-6.50 (m, 1H), 4.78-4.74 (m, 1H), 4.27-3.89 (m, 10H), 3.71-3.55 (m, 2H), 3.00-2.72 (m, 3H), 2.45-2.35 (m, 2H), 2.15-1.77 (m, 4H), 1.79-1.77 (m, 1H), 1.38-1.36 (m, 3H). LCMS M/Z (M+H) 461.

Examples 113 & 114

(S, R)-1-[3-[3-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone and (S, S)-1-[3-[3-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

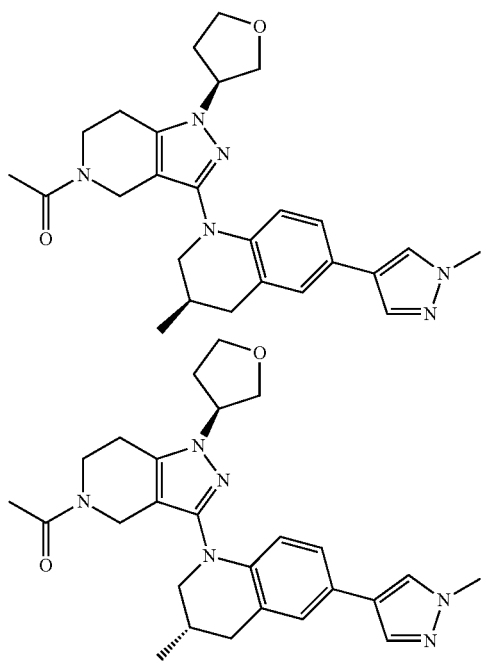

Racemic 1-[3-[3-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (Example 110, 85 mg) was separated using chiral SFC (Chiralpak AD 250×30 mm I.D., 5 um; Supercritical $CO_2$/EtOH+ NH$_3$.H$_2$O=45/55; 45 ml/min) to give (S,R)-1-[3-[3-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (18 mg, first peak) and (S,S)-1-[3-[3-methyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (21 mg, second peak). Absolute configuration was arbitrarily assigned to each diastereomer. Example 113: $^1$H NMR (400 MHz, DMSO-d$_6$) δ 7.89 (s, 1H), 7.65 (s, 1H), 7.16 (s, 1H), 7.11-7.06 (m, 1H), 6.42-6.37 (m, 1H), 4.87-4.84 (m, 1H), 4.06 (s, 2H), 4.00-3.93 (m, 2H), 3.79 (s, 3H), 3.76-3.52 (m, 4H), 3.28-3.26 (m, 2H), 3.16-3.11 (m, 1H), 2.85-2.65 (m, 4H), 2.30-2.20 (m, 2H), 2.04-1.91 (m, 3H), 1.02-0.99 (m, 3H). LCMS M/Z (M+H) 461. Example 114: $^1$H NMR (400 MHz, DMSO-d$_6$) δ 7.89 (s, 1H), 7.65 (s, 1H), 7.16 (s, 1H), 7.11-7.06 (m, 1H), 6.43-6.37 (m, 1H), 4.88-4.84 (m, 1H), 4.06 (s, 2H), 4.01-3.92 (m, 2H), 3.79 (s, 3H), 3.77-3.52 (m, 4H), 3.28-3.26 (m, 2H), 3.19-3.11 (m, 1H), 2.85-2.65 (m, 4H), 2.30-2.19 (m, 2H), 2.04-1.91 (m, 3H), 1.01-0.99 (m, 3H). LCMS M/Z (M+H) 461.

Examples 115 & 116

(S, S)-1-[3-[4-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone and (S, R)-1-[3-[4-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

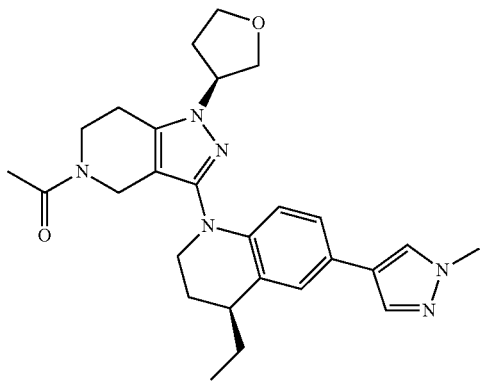

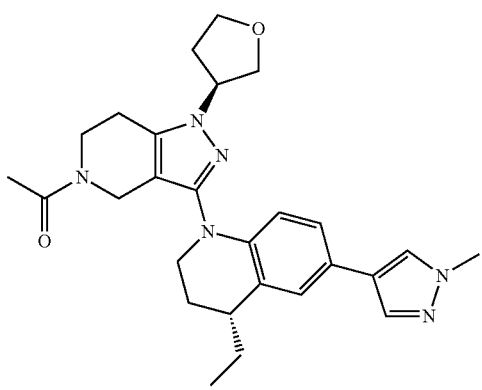

Racemic 1-[3-[4-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (Example 108, 100 mg) was separated using chiral SFC (Chiralpak AD-H 250×4.6 mm I.D., 5 um Mobile phase: 40% ethanol (0.05% diethylamine) in CO₂ Flow rate: 60 mL/min) to give (S,S)-1-[3-[4-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (33 mg, first peak) and (S,R)-1-[3-[4-ethyl-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (22 mg, second peak). Absolute configuration was arbitrarily assigned to each diastereomer. Example 115: ¹H NMR (400 MHz, CDCl₃) δ 7.66-7.64 (m, 1H), 7.50-7.47 (m, 1H), 7.18-7.04 (m, 2H), 6.54-6.49 (m, 1H), 4.75-4.73 (m, 1H), 4.17-4.10 (m, 3H), 4.00-3.90 (m, 7H), 3.71-3.64 (m, 3H), 2.72-2.70 (m, 3H), 2.43-2.34 (m, 2H), 2.14-1.94 (m, 5H), 1.81-1.78 (m, 1H), 1.61-1.59 (m, 1H), 1.03 (t, J=7.2 Hz, 3H). LCMS M/Z (M+H) 475. Example 116: ¹H NMR (400 MHz, CDCl₃) δ 7.66-7.64 (m, 1H), 7.50-7.47 (m, 1H), 7.18-7.04 (m, 2H), 6.54-6.49 (m, 1H), 4.75-4.73 (m, 1H), 4.17-4.10 (m, 3H), 4.00-3.90 (m, 7H), 3.71-3.64 (m, 3H), 2.72-2.70 (m, 3H), 2.43-2.34 (m, 2H), 2.14-1.94 (m, 5H), 1.81-1.78 (m, 1H), 1.61-1.59 (m, 1H), 1.03 (t, J=7.2 Hz, 3H). LCMS M/Z (M+H) 475.

Example 117

1-[3-[3-cyclopropyl-6-(1-methylpyrazol-4-yl)-3,4-dihydro-2H-quinolin-1-yl]-1-((S)-tetrahydrofuran-3-yl)-6,7-dihydro-4H-pyrazolo[4,3-c]pyridin-5-yl]ethanone

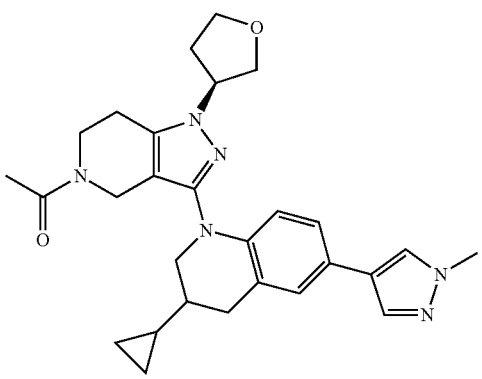 [SMILES: CC(=O)N1CCc2c(c(N3CC(C4CC4)Cc4cc(-c5cnn(C)c5)ccc43)nn2[C@H]2CCOC2)C1]

Step 1

3-cyclopropylquinoline

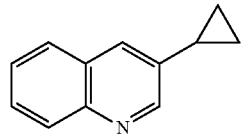 [SMILES: c1ccc2ncc(C3CC3)cc2c1]

To a solution of 3-bromoquinoline (3.0 g, 14.4 mmol) in toluene/H₂O (22 mL, 10:1) was added cyclopropylboronic acid (6.2 g, 7.21 mmol), palladium(II) acetate (162 mg, 0.72 mmol), tricyclohexylphosphine (404 mg, 1.44 mmol) and K₃PO₄ (10.7 g, 50.5 mmol). The mixture was heated to 100° C. for 16 h under a nitrogen atmosphere. After cooling the reaction to room temperature, EtOAc (40 mL) was added and washed with H₂O (50 mL×2). The organic layer was dried over anhydrous Na₂SO₄, filtered and concentrated in vacuo. The crude residue was purified by silica gel chromatography (petroleum ether/EtOAc=3:1) to give the title compound (2.4 g, 98%) as yellow oil. ¹H NMR (400 MHz, DMSO-d₆) δ 8.75 (d, J=2.0 Hz, 1H), 7.97 (s, 1H), 7.95-7.93 (m, 1H), 7.87-7.85 (m, 1H), 7.65-7.63 (m, 1H), 7.56-7.54 (m, 1H), 2.16-2.11 (m, 1H), 1.08-1.06 (m, 2H), 0.89-0.86 (m, 2H).

Step 2

3-cyclopropyl-1,2,3,4-tetrahydroquinoline

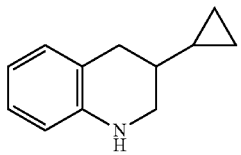 [SMILES: c1ccc2c(c1)CC(C1CC1)CN2]

To a solution of 3-cyclopropylquinoline (2.3 g, 13.6 mmol) in dry toluene (45 mL) was added diethyl 2,6-dimethyl-1,4-dihydropyridine-3,5-dicarboxylate (8.3 g, 32.6 mmol) and diphenyl hydrogen phosphate (34 mg, 0.14 mmol). The mixture was heated to 60° C. for 12 h under a nitrogen atmosphere. After cooling the reaction to room temperature, the mixture was concentrated in vacuo. The crude residue was purified by silica gel chromatography (petroleum ether/EtOAc=30:1) to give the title compound (2.3 g, 98%) as a white solid; $^1$H NMR (400 MHz, DMSO-$d_6$) δ 6.83-6.79 (m, 2H), 6.41-6.36 (m, 2H), 5.63 (s, 1H), 3.25-3.22 (m, 1H), 2.97-2.92 (m, 1H), 2.75-2.70 (m, 1H), 2.53-2.48 (m, 1H), 1.08-0.98 (m, 1H), 0.64-0.55 (m, 1H), 0.46-0.38 (m, 2H), 0.22-0.15 (m, 2H).

Step 3

1-(3-(3-cyclopropyl-3,4-dihydroquinolin-1(2H)-yl)-1-((S)-tetrahydrofuran-3-yl)-6,7-dihydro-1H-pyrazolo[4,3-c]pyridin-5(4H)-yl)ethanone

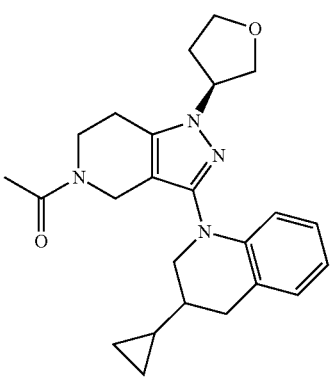 [SMILES: CC(=O)N1CCc2c(c(N3CC(C4CC4)Cc4ccccc43)nn2[C@H]2CCOC2)C1]

To a solution of (S)-1-(3-bromo-1-(tetrahydrofuran-3-yl)-6,7-dihydro-1H-pyrazolo[4,3-c]pyridin-5(4H)-yl)ethanone (Intermediate G, 200 mg, 0.64 mmol) in dioxane (8 mL) was added 3-cyclopropyl-1,2,3,4-tetrahydroquinoline (132 mg, 0.76 mmol), 2-dicyclohexylphosphino-2',6'-di-i-propoxy-1,1'-biphenyl (30 mg, 0.06 mmol), chloro(2-dicyclohexylphosphino-2',6'-di-i-propoxy-1,1'-biphenyl) [2-(2-aminoethylphenyl)]palladium(II), methyl-tert-butylether adduct (52 mg, 0.06 mmol) and t-BuONa (214 mg, 2.23 mmol). The mixture was heated to 120° C. for 16 h under a nitrogen atmosphere. After cooling the reaction to room temperature, EtOAc (30 mL) was added the mixture was washed with H$_2$O (30 mL×2). The organic layer was dried over anhydrous Na$_2$SO$_4$, filtered and the filtrate was concentrated in vacuo. The crude residue was purified by silica gel chromatography (DCM/MeOH=3:1) to give the title compound (150 mg, crude) as yellow oil that required no further purification. LCMS M/Z (M+H) 407.

Step 4

1-(3-(6-bromo-3-cyclopropyl-3,4-dihydroquinolin-1(2H)-yl)-1-((S)-tetrahydrofuran-3-yl)-6,7-dihydro-1H-pyrazolo[4,3-c]pyridin-5(4H)-yl)ethanone

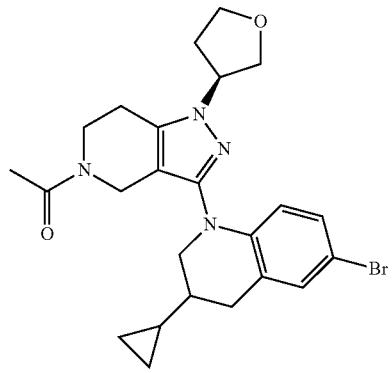 [SMILES: CC(=O)N1CCc2c(c(N3CC(C4CC4)Cc4cc(Br)ccc43)nn2[C@H]2CCOC2)C1]

To a solution of 1-(1-cyclopentyl-3-(3-cyclopropyl-3,4-dihydroquinolin-1(2H)-yl)-6,7-dihydro-1H-pyrazolo[4,3-c]pyridin-5(4H)-yl)ethanone (150 mg, crude) in DCM (4 mL) at 0° C. was added N-bromosuccinimide (41 mg, 0.23 mmol). The mixture was stirred at 0° C. and gradually raised to room temperature for 1 h under a nitrogen atmosphere. DCM (30 mL) was added and the mixture was washed with H$_2$O (30 mL) and sat. aq. NaHCO$_3$ (30 mL×2). The organic layer was dried over anhydrous Na$_2$SO$_4$, filtered and the filtrate was concentrated in vacuo to give the title compound (130 mg, crude) as brown oil that required no further purification.

Step 5

1-[3-[3-cyclopropyl-6-(1-methylpyrazol-4-yl)-3,4-dihydro-2H-quinolin-1-yl]-1-((S)-tetrahydrofuran-3-yl)-6,7-dihydro-4H-pyrazolo[4,3-c]pyridin-5-yl]ethanone

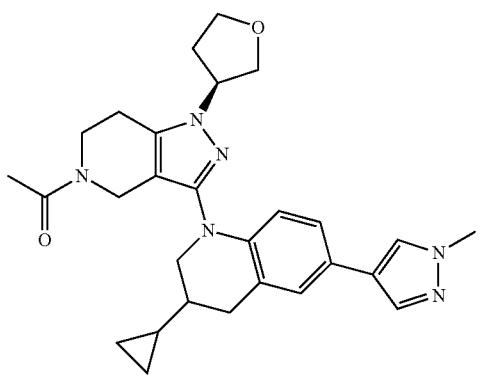 [SMILES: CC(=O)N1CCc2c(c(N3CC(C4CC4)Cc4cc(-c5cnn(C)c5)ccc43)nn2[C@H]2CCOC2)C1]

To a solution of 1-(3-(6-bromo-3-cyclopropyl-3,4-dihydroquinolin-1(2H)-yl)-1-((S)-tetrahydrofuran-3-yl)-6,7-dihydro-1H-pyrazolo[4,3-c]pyridin-5(4H)-yl)ethanone (630 mg, 1.3 mmol) in THF/H₂O (6 mL, 5:1) was added 1-methyl-4-(4,4,5,5-tetramethyl-1,3,2-dioxaborolan-2-yl)-1H-pyrazole (405 mg, 2.0 mmol), 2-(dicyclohexylphosphino)-2',4',6'-triisopropylbiphenyl (62 mg, 0.13 mmol), chloro(2-dicyclohexylphosphino-2',4',6'-tri-i-propyl-1,1'-biphenyl)(2'-amino-1,1'-biphenyl-2-yl) palladium(II) (102 mg, 0.13 mmol) and K₂CO₃ (448 mg, 3.24 mmol). The mixture was heated to 60° C. for 16 h under a nitrogen atmosphere. After cooling the reaction to room temperature, EtOAc (100 mL) was added and reverse phase chromatography (acetonitrile 32-62%/0.225% formic acid in water) to give the title compound (240 mg, 27%) as a white solid. ¹H NMR (400 MHz, DMSO-d₆) δ 7.91 (s, 1H), 7.67 (s, 1H), 7.22 (s, 1H), 7.12-7.08 (m, 1H), 6.45-6.39 (m, 1H), 4.93-4.85 (m, 1H), 4.08 (s, 2H), 4.03-3.95 (m, 2H), 3.82 (s, 3H), 3.77-3.63 (m, 4H), 3.41-3.33 (m, 2H), 2.93-2.83 (m, 2H), 2.72-2.63 (m, 2H), 2.32-2.25 (m, 2H), 2.06, 1.96 (2s, 3H), 1.30-1.19 (m, 1H), 0.74-0.63 (m, 1H), 0.50-0.40 (m, 2H), 0.29-0.17 (m, 2H). LCMS M/Z (M+H) 487.

The Following Compound was Prepared in a Similar Fashion to Example 117

Example 118

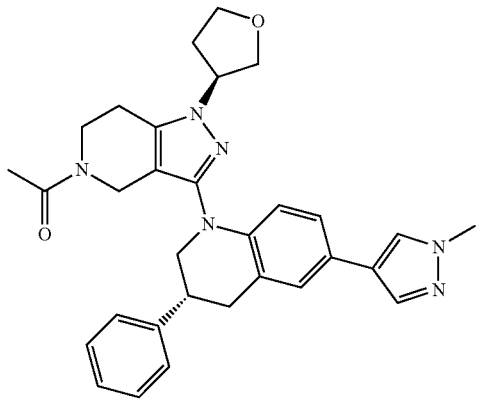

Racemic 1-[3-[6-(1-methylpyrazol-4-yl)-3-phenyl-3,4-dihydro-2H-quinolin-1-yl]-1-tetrahydrofuran-3-yl-6,7-dihydro-4H-pyrazolo[4,3-c]pyridin-5-yl]ethanone (Example

| Example | Compound Name | NMR | m/z |
|---|---|---|---|
| Example 118 | 1-[3-[6-(1-methylpyrazol-4-yl)-3-phenyl-3,4-dihydro-2H-quinolin-1-yl]-1-tetrahydrofuran-3-yl-6,7-dihydro-4H-pyrazolo[4,3-c]pyridin-5-yl]ethanone | ¹H NMR (400 MHz, DMSO-d₆) δ 7.93 (s, 1H), 7.70 (s, 1H), 7.40-7.27 (m, 5H), 7.27-7.21 (m, 1H), 7.20-7.13 (m, 1H), 6.53-6.47 (m, 1H), 4.88 (br s, 1H), 4.18-3.91 (m, 4H), 3.84-3.59 (m, 9H), 3.28-3.16 (m, 1H), 3.14-2.96 (m, 2H), 2.86-2.65 (m, 2H), 2.31-2.16 (m, 2H), 2.10-1.88 (m, 3H) | 523 |

Examples 119 & 120

(S, S)-1-[3-[6-(1-methylpyrazol-4-yl)-3-phenyl-3,4-dihydro-2H-quinolin-1-yl]-1-tetrahydrofuran-3-yl-6,7-dihydro-4H-pyrazolo[4,3-c]pyridin-5-yl]ethanone and (S, R)-1-[3-[6-(1-methylpyrazol-4-yl)-3-phenyl-3,4-dihydro-2H-quinolin-1-yl]-1-tetrahydrofuran-3-yl-6,7-dihydro-4H-pyrazolo[4,3-c]pyridin-5-yl]ethanone

118, 150 mg) was separated using chiral SFC (Chiralpak AD 250 mm×30 mm I.D., 5 um; Supercritical CO₂/MeOH+ NH₄OH=55/45; 50 mL/min) to give (S, 5)-1-[3-[6-(1-methylpyrazol-4-yl)-3-phenyl-3,4-dihydro-2H-quinolin-1-yl]-1-tetrahydrofuran-3-yl-6,7-dihydro-4H-pyrazolo[4,3-c]pyridin-5-yl]ethanone (52 mg, first peak) and (S,R)-1-[3-[6-(1-methylpyrazol-4-yl)-3-phenyl-3,4-dihydro-2H-quinolin-1-yl]-1-tetrahydrofuran-3-yl-6,7-dihydro-4H-pyrazolo[4,3-c]pyridin-5-yl]ethanone (64 mg, second peak). Absolute configuration was arbitrarily assigned to each diastereomer. Example 119: ¹H NMR (400 MHz, DMSO-d₆) 7.93 (s, 1H), 7.70 (s, 1H), 7.40-7.27 (m, 5H), 7.27-7.21 (m, 1H), 7.20-7.13 (m, 1H), 6.53-6.47 (m, 1H), 4.90-4.87 (m, 1H), 4.18-3.91 (m, 4H), 3.84-3.59 (m, 9H), 3.28-3.16 (m, 1H), 3.14-2.96 (m, 2H), 2.86-2.65 (m, 2H), 2.31-2.16 (m, 2H), 2.10-1.88 (m, 3H). LCMS M/Z (M+H) 523. Example 120: ¹H NMR (400 MHz, DMSO-d₆) δ 7.93 (s, 1H), 7.70 (s, 1H), 7.40-7.27 (m, 5H), 7.27-7.21 (m, 1H), 7.20-7.13 (m, 1H), 6.53-6.47 (m, 1H), 4.90-4.87 (m, 1H), 4.18-3.91 (m, 4H), 3.84-3.59 (m, 9H), 3.28-3.16 (m, 1H), 3.14-2.96 (m, 2H), 2.86-2.65 (m, 2H), 2.31-2.16 (m, 2), 2.10-1.88 (m, 3H). LCMS M/Z (M+H) 523.

Example 121

1-[3-[7-(difluoromethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

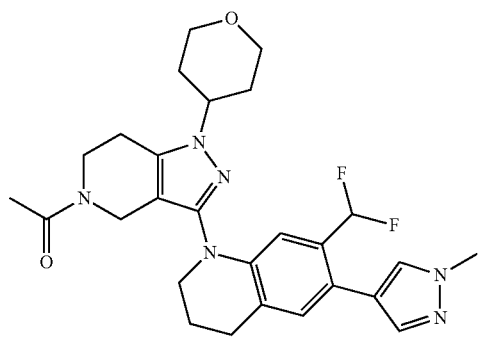 [SMILES: CC(=O)N1CCc2c(c(N3CCCc4cc(-c5cnn(C)c5)c(C(F)F)cc43)nn2C2CCOCC2)C1]

Step 1 quinoline-7-carbaldehyde

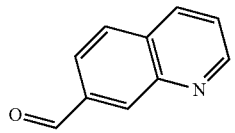 [SMILES: O=Cc1ccc2cccnc2c1]

To a solution of 7-methylquinoline (27.0 g, 189 mmol) at 160° C. was added SeO$_2$ (21.0 g, 189 mmol) portionwise over 5 min. The mixture was stirred at 160° C. for 8 h. After cooling the reaction to room temperature, DCM (400 mL) was added and the mixture was filtered though celite. The organic layer was concentrated in vacuo. The crude residue was purified by silica gel chromatography (petroleum ether/EtOAc=10:1) to give the title compound (14.0 g, 47%) as yellow oil. $^1$H NMR (400 MHz, CDCl$_3$) δ 10.23 (s, 1H), 9.03 (d, J=2.8 Hz, 1H), 8.56 (s, 1H), 8.22 (d, J=8.4 Hz, 1H), 8.04 (d, J=8.4 Hz, 1H), 7.93 (d, J=8.4 Hz, 1H), 7.55-7.52 (m, 1H).

Step 2

7-(difluoromethyl)quinoline

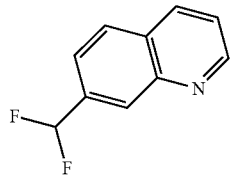 [SMILES: FC(F)c1ccc2cccnc2c1]

To a solution of 7-(difluoromethyl)quinoline (14.0 g, 89.2 mmol) in DCM (150 mL) 0° C. was added diethylaminosulfurtrifluoride (65.0 g, 446 mmol) dropwise over 20 min. The mixture was stirred at room temperature for 16 h. The mixture was poured into sat. aq. NaHCO$_3$ (1 L) at 0° C. and extracted with DCM (200 mL×2). The combined organic layers were dried over anhydrous Na$_2$SO$_4$, filtered and concentrated in vacuo. The crude residue was purified by silica gel chromatography (petroleum ether/EtOAc=5:1) to give the title compound (13.0 g, 81%) as yellow oil. $^1$H NMR (400 MHz, CDCl$_3$) δ 8.92 (d, J=2.8 Hz, 1H), 8.15 (d, J=8.4 Hz, 2H), 7.86 (d, J=8.4 Hz, 1H), 7.63 (d, J=8.8 Hz, 1H), 7.44-7.41 (m, 1H), 6.78 (t, J=56.0 Hz, 1H).

Step 3

7-(difluoromethyl)-1,2,3,4-tetrahydroquinoline

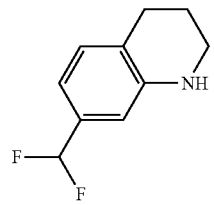 [SMILES: FC(F)c1ccc2c(c1)NCCC2]

To a solution of 7-(difluoromethyl)quinoline (13.0 g, 72.6 mmol) and NaBH$_3$CN (23.0 g, 363 mmol) in MeOH (150 mL) at 0° C. was added boron trifluoride diethyl etherate (17.9 mL, 145 mmol) dropwise over 20 min. The mixture was heated to 90° C. for 24 h. After cooling the reaction to room temperature, the mixture was poured into sat. aq. NaHCO$_3$ (1 L) at 0° C. and extracted with DCM (200 mL×2). The combined organic layers were dried over Na$_2$SO$_4$, filtered and concentrated in vacuo. The crude residue was purified by silica gel chromatography (petroleum ether/EtOAc=20:1) to give the title compound (8.0 g, 56%) as brown oil. $^1$H NMR (400 MHz, CDCl$_3$) δ 7.00 (d, J=7.2 Hz, 1H), 6.71 (d, J=8.0 Hz, 1H), 6.59 (s, 1H), 6.50 (t, J=56.8 Hz, 1H), 3.33 (t, J=5.6 Hz, 2H), 2.79 (t, J=6.4 Hz, 2H), 1.98-1.92 (m, 2H).

Step 4

6-bromo-7-(difluoromethyl)-1,2,3,4-tetrahydroquinoline

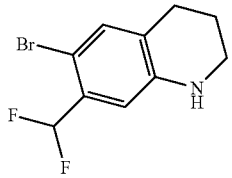 [SMILES: FC(F)c1cc2c(cc1Br)CCCN2]

To a solution of 7-(difluoromethyl)-1,2,3,4-tetrahydroquinoline (7.0 g, 38.3 mmol) in DCM (100 mL) at 0° C. was added N-bromosuccinimide (6.9 g, 38.3 mmol) portionwise over 20 min. The mixture was stirred at room temperature for 16 h. The mixture was poured into water (100 mL) and extracted with DCM (200 mL×2). The combined organic layers were dried over $Na_2SO_4$, filtered and concentrated in vacuo. The crude residue was purified by silica gel chromatography (petroleum ether/EtOAc=300:1) to give the title compound (6.0 g, 60%) as light yellow oil. $^1$H NMR (400 MHz, $CDCl_3$) δ 7.13 (s, 1H), 6.78 (t, J=55.2 Hz, 1H), 6.72 (s, 1H), 3.31 (t, J=5.2 Hz, 2H), 2.74 (t, J=6.0 Hz, 2H), 1.95-1.87 (m, 2H).

Step 5

7-(difluoromethyl)-6-(1-methyl-1H-pyrazol-4-yl)-1,2,3,4-tetrahydroquinoline

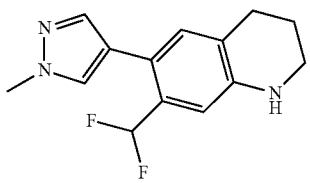 [SMILES: Cn1cc(-c2cc3c(cc2C(F)F)NCCC3)cn1]

le;2qTo a solution of 6-bromo-7-(difluoromethyl)-1,2,3,4-tetrahydroquinoline (600 mg, 2.3 mmol) in dioxane (8 mL) and $H_2O$ (2 mL) was added $K_2CO_3$ (635 mg, 4.6 mmol), [1,1'-bis(diphenylphosphino)ferrocene]dichloropalladium(II) (169 mg, 0.23 mmol) and 1-methyl-4-(4,4,5,5-tetramethyl-1,3,2-dioxaborolan-2-yl)-1H-pyrazole (478 mg, 2.3 mmol). The mixture was heated to 110° C. for 18 h under a nitrogen atmosphere. After cooling the reaction to room temperature, the mixture was concentrated in vacuo. The crude residue was purified by silica gel chromatography (petroleum ether/EtOAc=40:1) to give the title compound (520 mg, 86%) as yellow oil. LCMS M/Z (M+H) 264.

Step 6

1-[3-[7-(difluoromethyl)-6-(l-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

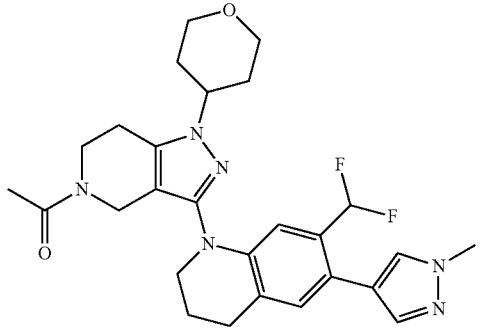 [SMILES: CC(=O)N1CCc2c(c(N3CCCc4cc(-c5cnn(C)c5)c(C(F)F)cc43)nn2C2CCOCC2)C1]

To a solution of 7-(difluoromethyl)-6-(1-methyl-1H-pyrazol-4-yl)-1,2,3,4-tetrahydroquinoline (263 mg, 1.0 mmol) in dioxane (10 mL) was added 1-(3-bromo-1-(tetrahydro-2H-pyran-4-yl)-6,7-dihydro-1H-pyrazolo[4,3-c]pyridin-5(4H)-yl)ethanone (Intermediate I, 327 mg, 1.0 mmol), chloro(2-dicyclohexylphosphino-2',6'-di-i-propoxy-1,1'-biphenyl)[2-(2-aminoethylphenyl)]palladium(II), methyl-tert-butylether adduct (82 mg, 0.10 mmol), 2-dicyclohexylphosphino-2',6'-di-i-propoxy-1,1'-biphenyl (47 mg, 0.10 mmol) and t-BuONa (288 mg, 3.0 mmol). The mixture was heated to 120° C. for 16 h under a nitrogen atmosphere. After cooling the reaction to room temperature, the mixture was concentrated in vacuo. The crude residue was purified by prep-TLC (DCM/MeOH=20:1) to give the title compound (26 mg, 6%) as a white solid. $^1$H NMR (400 MHz, DMSO-$d_6$) δ 7.75 (s, 1H), 7.50 (s, 1H), 7.10 (s, 1H), 6.96-6.63 (m, 2H), 4.33-4.25 (m, 1H), 4.20-4.09 (m, 2H), 3.99-3.90 (m, 2H), 3.86 (s, 3H), 3.78-3.66 (m, 2H), 3.63-3.55 (m, 2H), 3.49-3.41 (m, 2H), 2.89-2.66 (m, 4H), 2.11-1.90 (m, 7H), 1.85-1.80 (m, 2H). LCMS M/Z (M+H) 511.

The Following Compounds were Prepared in a Similar Fashion to Example 121

Examples 122-124

| Example | Compound Name | NMR | m/z |
|---|---|---|---|
| Example 122 | 1-[3-[7-(difluoromethyl)-6-(1-methylpyrazol-4-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 7.77 (s, 1H), 7.51 (s, 1H), 7.14 (s, 1H), 6.96-6.67 (m, 2H), 5.48-5.45 (m, 1H), 4.93-4.84 (m, 4H), 4.15-4.10 (m, 2H), 3.87 (s, 3H), 3.71-3.66 (m, 4H), 2.86-2.68 (m, 4H), 2.06-1.95 (m, 5H) | 483 |
| Example 123 | 1-[3-[7-(difluoromethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone | $^1$H NMR (400 MHz, DMSO-$d_6$) δ 7.76 (s, 1H), 7.50 (s, 1H), 7.11 (s, 1H), 6.94-6.65 (m, 2H), 4.94-4.88 (m, 1H), 4.16-4.12 (m, 2H), 4.03-3.90 (m, 2H), 3.86 (s, 3H), 3.82-3.79 (m, 4H), 3.70-3.56 (m, 2H), 2.86-2.74 (m, 4H), 2.29-2.22 (m, 2H), 2.07-1.96 (m, 5H) | 497 |
| Example 124 | 5-(1-(5-acetyl-1-(tetrahydro-2H-pyran-4-yl)-4,5,6,7-tetrahydro-1H- | $^1$H NMR (400 MHz, DMSO-$d_6$) δ 8.84-8.82 (m, 1H), 8.55 (d, J = 4.0 Hz, 1H), 8.06 (d, J = 8.0 Hz, 1H), 7.92-7.90 (m, 1H), 7.14 (s, 1H), 6.89 (s, 1H), 6.74 (t, J = 54.8 | 565 |

| Example | Compound Name | NMR | m/z |
|---|---|---|---|
| | pyrazolo[4,3-c]pyridin-3-yl)-7-(difluoromethyl)-1,2,3,4-tetrahydroquinolin-6-yl)-N-methylpicolinamide | Hz, 1H), 4.37-4.26 (m, 1H), 4.22-4.18 (m, 2H), 3.98-3.94 (m, 2H), 3.80-3.68 (m, 2H), 3.67-3.58 (m, 2H), 3.46 (t, J = 12.0 Hz, 2H), 2.93-2.74 (m, 7H), 2.09-1.91 (m, 7H), 1.87-1.80 (m, 2H) | |

Example 125

1-[3-[7-chloro-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone

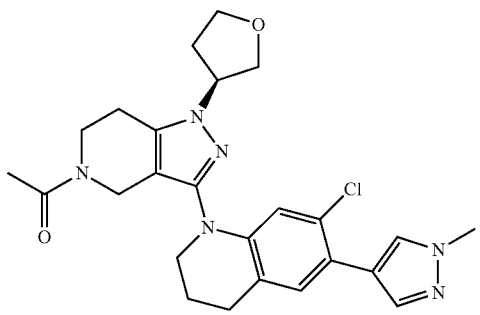 [SMILES: CC(=O)N1CCc2c(c(N3CCCc4cc(-c5cnn(C)c5)c(Cl)cc43)nn2[C@H]2CCOC2)C1]

Step 1

6-bromo-7-chloro-1,2,3,4-tetrahydroquinoline

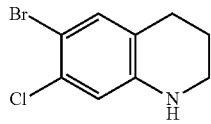

To a solution of 7-chloro-1,2,3,4-tetrahydroquinoline (14 g, 80 mmol) in DCM (100 mL) at 0° C. was added N-bromosuccinimide (14.8 g, 80 mmol). The mixture was stirred at room temperature for 1 h. Water (100 mL) was added and the mixture was extracted with DCM (100 mL×2). The combined organic layers were dried over anhydrous $Na_2SO_4$, filtered and concentrated in vacuo. The crude residue was purified by silica gel chromatography (petroleum ether/EtOAc=100:1) to give the title compound (7.1 g, 36%) as a light yellow solid. LCMS M/Z (M+H) 246.

Step 2

7-chloro-6-(1-methyl-1H-pyrazol-4-yl)-1,2,3,4-tetrahydroquinoline

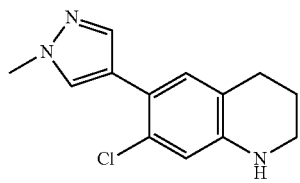 [SMILES: Cn1cc(-c2cc3c(cc2Cl)NCCC3)cn1]

To a solution of 6-bromo-7-chloro-1,2,3,4-tetrahydroquinoline (2.1 g, 8.5 mmol) in dioxane/$H_2O$ (60 mL, 5:1) was added 1-methyl-4-(4,4,5,5-tetramethyl-1,3,2-dioxaborolan-2-yl)-1H-pyrazole (1.9 g, 9.4 mmol), $Na_2CO_3$ (1.8 g, 17 mmol) and [1,1'-bis(diphenylphosphino)ferrocene]dichloropalladium(II) (622 mg, 0.9 mmol). The mixture was heated to 100° C. for 12 h under a nitrogen atmosphere. After cooling the reaction to room temperature, the mixture was concentrated in vacuo. The crude residue was purified by silica gel chromatography (petroleum ether/EtOAc=4:1) to give the title compound (2.0 g, 95%) as yellow solid. $^1$H NMR (400 MHz, DMSO-$d_6$) δ 7.88-7.85 (m, 1H), 7.61 (s, 1H), 7.01 (s, 1H), 6.53 (s, 1H), 5.95 (s, 1H), 3.86-3.84 (m, 3H), 3.38-3.16 (m, 2H), 2.65-2.62 (m, 2H), 1.80-1.74 (m, 2H).

Step 3

1-[3-[7-chloro-6-(1-methylpyrazol-4-yl)-3,4-dihydro-2H-quinolin-1-yl]-1-1[(3S)-tetrahydrofuran-3-yl]-6,7-dihydro-4H-pyrazolo[4,3-c]pyridin-5-yl]ethanone

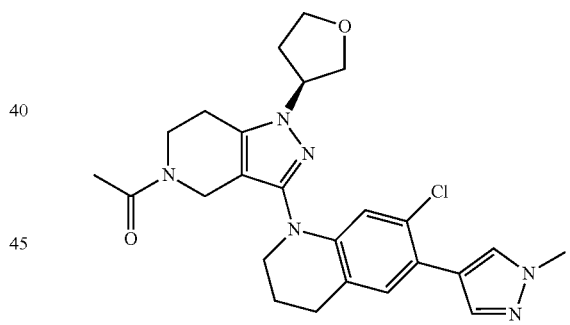

To a solution of 7-chloro-6-(1-methyl-1H-pyrazol-4-yl)-1,2,3,4-tetrahydroquinoline (247 mg, 1.0 mmol) in dioxane (3 mL) and toluene (3 mL) was added t-BuONa (288 mg, 3.0 mmol), tris(dibenzylideneacetone)dipalladium (46 mg, 0.05 mmol), 4,5-bis(diphenylphosphino)-9,9-dimethylxanthene (59 mg, 0.1 mmol) and (S)-1-(3-bromo-1-(tetrahydrofuran-3-yl)-6,7-dihydro-1H-pyrazolo[4,3-c]pyridin-5(4H)-yl)ethanone (Intermediate G, 313 mg, 1.0 mmol). The mixture was heated to 90° C. for 16 h under a nitrogen atmosphere. After cooling the reaction to room temperature, the mixture was concentrated in vacuo. The crude residue was purified by Prep-TLC (DCM/MeOH=20:1) to give the title compound (240 mg, 50%) as a light yellow solid. $^1$H NMR (400 MHz, DMSO-$d_6$) δ 7.97 (s, 1H), 7.68 (s, 1H), 7.21-7.20 (m, 1H), 6.54-6.50 (m, 1H), 4.95-4.89 (m, 1H), 4.18-4.15 (m, 2H), 4.03-3.98 (m, 2H), 3.85-3.71 (m, 7H), 3.54-3.50 (m, 2H), 2.86-2.77 (m, 4H), 2.33-2.27 (m, 2H), 2.08-1.94 (m, 5H). LCMS M/Z (M+H) 481.

Example 126

1-[5-acetyl-1-[(3S)-tetrahydrofuran-3-yl]-6,7-dihydro-4H-pyrazolo[4,3-c]pyridin-3-yl]-6-(1-methyl-pyrazol-4-yl)-3,4-dihydro-2H-quinoline-7-carbonitrile

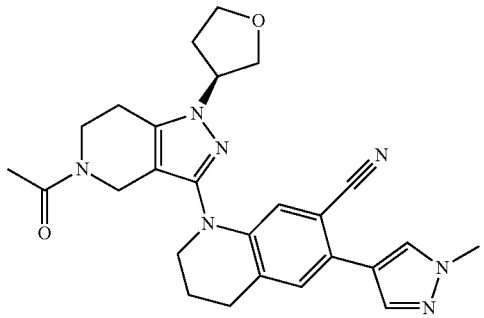 [SMILES: CC(=O)N1CCc2c(c(N3CCCc4cc(-c5cnn(C)c5)c(C#N)cc43)nn2[C@H]2CCOC2)C1]

To a solution of 1-(3-(7-chloro-6-(1-methyl-1H-pyrazol-4-yl)-3,4-dihydroquinolin-1(2H)-yl)-1-(oxetan-3-yl)-6,7-dihydro-1H-pyrazolo[4,3-c]pyridin-5(4H)-yl)ethanone (200 mg, 0.429 mmol) in dioxane (5 mL) and $H_2O$ (3 mL) was added KOAc (170 mg, 1.72 mmol), tris(dibenzylideneacetone)dipalladium (40 mg, 0.0429 mmol), 2-di-tert-butylphosphino-2',4',6'-triisopropylbiphenyl (69 mg, 0.0858 mmol) and potassium hexacyanoferrate(II) trihydrate (1.0 g, 2.57 mmol). The mixture was heated to 120° C. for 36 h under a nitrogen atmosphere. After cooling the reaction to room temperature, the mixture was concentrated in vacuo. The crude residue was purified by reverse phase chromatography (acetonitrile 37-67%/0.1% $NH_4OH$ in water) to give the title compound (50 mg, 25%) as a white solid. $^1$H NMR (400 MHz, DMSO-$d_6$) δ 8.07 (s, 1H), 7.80 (s, 1H), 7.36 (s, 1H), 6.79-6.74 (m, 1H), 4.94-4.91 (m, 1H), 4.19-4.17 (m, 2H), 4.03-3.96 (m, 2H), 3.83-3.72 (m, 7H), 3.58-3.54 (m, 2H), 2.89-2.75 (m, 411), 2.32-2.25 (m, 2H), 2.09-1.95 (m, 511H). LCMS M/Z (M+H) 472.

The Following Compounds were Prepared in a Similar Fashion to Example 126

Examples 127-133

| Example | Compound Name | NMR | m/z |
| --- | --- | --- | --- |
| Example 127 | 1-[5-acetyl-1-(oxetan-3-yl)-6,7-dihydro-4H-pyrazolo[4,3-c]pyridin-3-yl]-6-(1-methylpyrazol-4-yl)-3,4-dihydro-2H-quinoline-7-carbonitrile | $^1$H NMR (400 MHz, DMSO-$d_6$) δ 8.07 (s, 1H), 7.80 (s, 1H), 7.38 (s, 1H), 6.83-6.77 (m, 1H), 5.51-5.44 (m, 1H), 4.93-4.87 (m, 4H), 4.18-4.15 (m, 2H), 3.88 (s, 3H), 3.73-3.61 (m, 4H), 2.91-2.67 (m, 4H), 2.07-1.98 (m, 5H) | 458 |
| Example 128 | 1-(5-acetyl-1-tetrahydropyran-4-yl-6,7-dihydro-4H-pyrazolo[4,3-c]pyridin-3-yl)-6-(1-methylpyrazol-4-yl)-3,4-dihydro-2H-quinoline-7-carbonitrile | $^1$H NMR (400 MHz, DMSO-$d_6$) δ 8.06 (s, 1H), 7.80 (s, 1H), 7.35 (s, 1H), 6.75-6.70 (m, 1H), 4.36-4.31 (m, 1H), 4.20-4.17 (m, 2H), 3.97-3.94 (m, 2H), 3.88 (s, 3H), 3.77-3.72 (m, 2H), 3.59-3.51 (m, 4H), 2.89-2.67 (m, 4H), 2.08-1.99 (m, 3H), 1.96-1.81 (m, 6H) | 486 |
| Example 129 | 1-(5-acetyl-1-tetrahydropyran-4-yl-6,7-dihydro-4H-pyrazolo[4,3-c]pyridin-3-yl)-6-(1,5-dimethylpyrazol-4-yl)-3,4-dihydro-2H-quinoline-7-carbonitrile | $^1$H NMR (400 MHz, DMSO-$d_6$) δ 7.44 (s, 1H), 7.08 (s, 1H), 6.79-6.74 (m, 1H), 4.33-4.28 (m, 1H), 4.21-4.18 (m, 2H), 3.96-3.94 (m, 2H), 3.78 (s, 3H), 3.73-3.71 (m, 2H), 3.60-3.55 (m, 2H), 3.48-3.42 (m, 2H), 2.89-2.75 (m, 4H), 2.23 (s, 3H), 2.08-2.00 (m, 3H), 2.06-1.96 (m, 4H), 1.85-1.82 (m, 2H) | 500 |
| Example 130 | 1-[5-acetyl-1-(oxetan-3-yl)-6,7-dihydro-4H-pyrazolo[4,3-c]pyridin-3-yl]-6-(1,5-dimethylpyrazol-4-yl)-3,4-dihydro-2H-quinoline-7-carbonitrile | $^1$H NMR (400 MHz, DMSO-$d_6$) δ 7.45 (s, 1H), 7.11 (s, 1H), 6.91-6.72 (m, 1H), 5.51-5.45 (m, 1H), 5.08-4.73 (m, 4H), 4.30-4.08 (m, 2H), 3.78 (s, 3H), 3.76-3.68 (m, 2H), 3.67-3.61 (m, 2H), 2.90-2.68 (m, 4H), 2.24 (s, 3H), 2.07-1.99 (m, 5H) | 472 |
| Example 131 | 5-[1-[5-acetyl-1-[(3S)-tetrahydrofuran-3-yl]-6,7-dihydro-4H-pyrazolo[4,3-c]pyridin-3-yl]-7-cyano-3,4-dihydro-2H-quinolin-6-yl]-N-methyl-pyridine-2-carboxamide | $^1$H NMR (400 MHz, DMSO-$d_6$) δ 8.86 (d, J = 4.4 Hz, 1H), 8.77 (s, 1H), 8.13-8.08 (m, 2H), 7.43 (s, 1H), 6.90-6.87 (m, 1H), 5.05-4.85 (m, 1H), 4.23-4.20 (m, 2H), 4.02-4.00 (m, 2H), 3.84-3.80 (m, 4 H), 3.61-3.59 (m, 2H), 2.93-2.84 (m, 5H), 2.66-2.50 (m, 2H), 2.35-2.20 (m, 2H), 2.09-1.99 (m, 5H) | 526 |
| Example 132 | 1-[5-acetyl-1-[(3S)-tetrahydrofuran-3-yl]-6,7-dihydro-4H-pyrazolo[4,3-c]pyridin-3-yl]-6-(1-methylpyrazol-4-yl)-3,4-dihydro-2H-quinoline-5-carbonitrile | $^1$H NMR (400 MHz, DMSO-$d_6$) δ 8.05 (s, 1H), 7.77 (s, 1H), 7.24-7.20 (m, 1H), 6.78-6.71 (m, 1H), 4.93-4.90 (m, 1H), 4.14-4.12 (m, 2H), 4.01-3.94 (m, 4H), 3.88 (s, 3H), 3.83-3.79 (m, 2H), 2.99-2.96 (m, 2H), 2.84-2.60 (m, 2H), 2.30-2.20 (m, 2H), 2.07-1.96 (m, 5H) | 472 |

-continued

| Example | Compound Name | NMR | m/z |
|---|---|---|---|
| Example 133 | 5-(1-(5-acetyl-1-(tetrahydro-2H-pyran-4-yl)-4,5,6,7-tetrahydro-1H-pyrazolo[4,3-c]pyridin-3-yl)-7-cyano-1,2,3,4-tetrahydroquinolin-6-yl)-N-methylpicolinamide | $^1$H NMR (400 MHz, DMSO-$d_6$) δ 8.86-8.85 (m, 1H), 8.78 (s, 1H), 8.14-8.09 (m, 2H), 7.43 (s, 1 H), 6.91-6.84 (m, 1H), 4.35-4.27 (m, 1H), 4.25-4.22 (m, 2H), 3.98-3.95 (m, 2H), 3.76-3.74 (m, 2H), 3.63-3.61(m, 2H), 3.50-3.44 (m, 2H), 2.96-2.83 (m, 7H), 2.10-1.97 (m, 7H), 1.87-1.82 (m, 2H) | 540 |

Example 134

1-[3-[7-methyl-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone

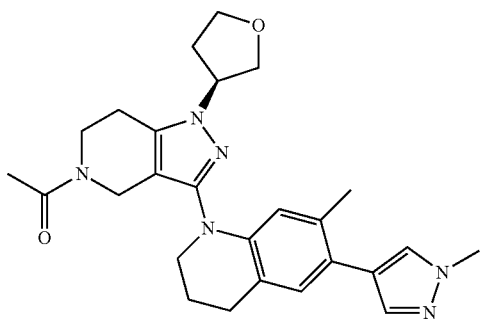 [SMILES: CC(=O)N1CCc2c(c(N3CCCc4cc(-c5cnn(C)c5)c(C)cc43)nn2[C@H]2CCOC2)C1]

To a solution of 1-[3-[7-chloro-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone (150 mg, 0.313 mmol) in toluene (3 mL) and H$_2$O (1 mL), was added MeBF$_3$K (116 mg, 0.939 mmol), palladium(II) acetate (7 mg, 0.0313 mmol), Cs$_2$CO$_3$ (612 mg, 0.626 mmol) and di(adamantan-1-yl)(butyl)phosphine (23 mg, 0.0616 mmol). The mixture was heated to 100° C. for 18 h under a nitrogen atmosphere. After cooling the reaction to room temperature, the mixture was concentrated in vacuo. The crude residue was purified by Prep-TLC (DCM/MeOH=20:1) to give the title compound (21 mg, 15%) as a white solid. $^1$H NMR (400 MHz, DMSO-$d_6$) δ 7.76 (s, 1H), 7.52 (s, 1H), 6.99-6.98 (m, 1H), 6.36-6.34 (m, 1H), 4.90-4.85 (m, 1H), 4.14-4.05 (m, 2H), 4.04-3.93 (m, 2H), 3.87-3.66 (m, 7H), 3.58-3.52 (m, 2H), 2.84-2.67 (m, 4H), 2.34-2.21 (m, 2H), 2.15 (s, 3H), 2.09-1.81 (m, 5H). LCMS M/Z (M+H) 461.

Example 135

1-[3-[7-(difluoromethyl)-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

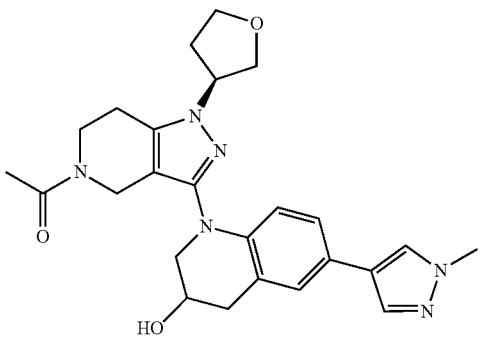 [SMILES: CC(=O)N1CCc2c(c(N3CC(O)Cc4cc(-c5cnn(C)c5)ccc43)nn2[C@H]2CCOC2)C1]

Step 1

1,2,3,4-tetrahydroquinolin-3-ol

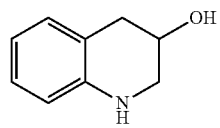 [SMILES: OC1CNc2ccccc2C1]

To a solution of sodium (41.2 g, 1.8 mol) in EtOH (1200 mL) was added quinolin-3-ol (20 g, 137.8 mmol) at 80° C. The mixture was heated to 80° C. for 2 h. After cooling the reaction to room temperature, ice water (100 mL) was added and the mixture was extracted with EtOAc (300 mL×3). The combined organic layers were concentrated in vacuo. The crude residue was purified by silica gel chromatography (petroleum ether/EtOAc=10:1) to give the title compound (10 g, 48%) as a yellow oil, LCMS M/Z (M+H) 150.

Step 2

3-((tert-butyldimethylsilyl)oxy)-1,2,3,4-tetrahydroquinoline

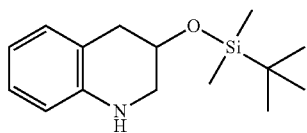 [SMILES: CC(C)(C)[Si](C)(C)OC1CNc2ccccc2C1]

To a solution of 1,2,3,4-tetrahydroquinolin-3-ol (5.0 g, 33.5 mmol) and imidazole (11.4 g, 167.6 mmol) in THF (50 mL) was added tert-butyl-dimethylsilyl chloride (12.6 g, 83.8 mmol). The mixture was heated to 80° C. for 12 h. After cooling the reaction to room temperature, the mixture was concentrated in vacuo. EtOAc (100 mL) was added and the mixture was washed with water (100 mL×3) and brine (100 mL). The organic layer was dried over anhydrous Na$_2$SO$_4$, filtered and concentrated in vacuo. The crude residue was purified by silica gel chromatography (petroleum ether/EtOAc=10:1) to give the title compound (3.5 g, 38%) as yellow oil, $^1$H NMR (400 MHz, DMSO-d$_6$) δ 6.86-6.82 (m, 2H), 6.47-6.40 (m, 2H), 5.64 (s, 1H), 4.09-4.05 (m, 1H), 3.22-3.19 (m, 1H), 2.93-2.80 (m, 2H), 2.63-2.57 (m, 1H), 0.87 (s, 9H), 0.09-0.01 (m, 6H).

Step 3

1-(3-(3-((tert-butyldimethylsilyl)oxy)-3,4-dihydro-quinolin-1(2H)-yl)-1-((S)-tetrahydrofuran-3-yl)-6,7-dihydro-1H-pyrazolo[4,3-c]pyridin-5(4H)-yl)ethanone

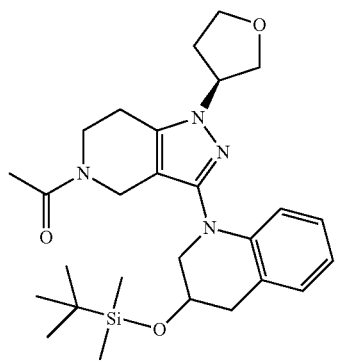 [SMILES: CC(=O)N1CCc2c(c(N3CC(O[Si](C)(C)C(C)(C)C)Cc4ccccc43)nn2[C@H]2CCOC2)C1]

To a solution of tert-butyl-dimethyl-(1,2,3,4-tetrahydro-quinolin-3-yloxy)silane (260.79 mg, 0.99 mmol) in 1,4-dioxane (3 mL) was added 1-[3-bromo-1-[(3S)-tetrahydrofuran-3-yl]-6,7-dihydro-4H-pyrazolo[4,3-c]pyridin-5-yl]ethanone (Intermediate G, 313 mg, 0.99 mmol), dicyclohexyl-[2-(2,6-diisopropoxyphenyl)phenyl]phosphane (46.19 mg, 0.10 mmol) and dichloro[1,3-bis(2,6-di-3-pentylphenyl)imidazol-2-ylidene](3-chloropyridyl)palladium(II) (76.89 mg, 0.10 mmol). The mixture was heated to 120° C. for 16 h under a nitrogen atmosphere. After cooling the reaction to room temperature, the mixture was concentrated in vacuo. The crude residue was purified by silica gel chromatography (DCM/MeOH=80:1) to give the title compound (200 mg, 41%) as a light yellow solid. LCMS M/Z (M+H) 497.

Step 4

1-(3-(6-bromo-3-((tert-butyldimethylsilyl)oxy)-3,4-dihydroquinolin-1(2H)-yl)-1-((S)-tetrahydrofuran-3-yl)-6,7-dihydro-1H-pyrazolo[4,3-c]pyridin-5(4H)-yl)ethanone

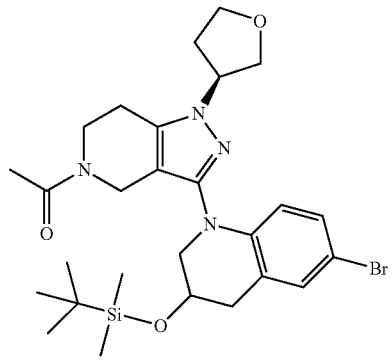 [SMILES: CC(=O)N1CCc2c(c(N3CC(O[Si](C)(C)C(C)(C)C)Cc4cc(Br)ccc43)nn2[C@H]2CCOC2)C1]

To a solution of 1-[3-[3-[tert-butyl(dimethyl)silyl]oxy-3,4-dihydro-2H-quinolin-1-yl]-1-[(3S)-tetrahydrofuran-3-yl]-6,7-dihydro-4H-pyrazolo[4,3-c]pyridin-5-yl]ethanone (200 mg, 0.40 mmol) in DCM (2 mL) was added N-bromosuccinimide (71.66 mg, 0.40 mmol) portionwise. The mixture was stirred at room temperature for 2 h. Water (20 mL) was added and the mixture was extracted with DCM (20 mL×2). The combined organic layers were dried over anhydrous Na$_2$SO$_4$, filtered and concentrated in vacuo to give the title compound (280 mg, crude) as yellow oil that required no further purification. LCMS M/Z (M+H) 575.

Step 5

1-(3-(3-((tert-butyldimethylsilyl)oxy)-6-(1-methyl-1H-pyrazol-4-yl)-3,4-dihydroquinolin-1(2H)-yl)-1-((S)-tetrahydrofuran-3-yl)-6,7-dihydro-1H-pyrazolo[4,3-c]pyridin-5(4H)-yl)ethanone

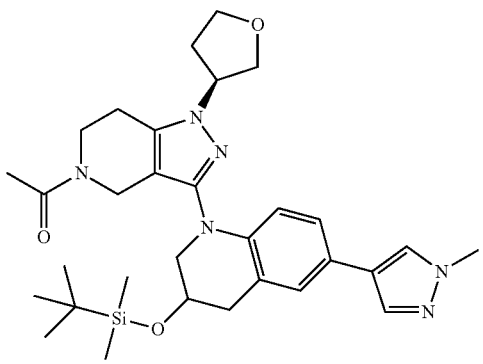 [SMILES: CC(=O)N1CCc2c(c(N3CC(O[Si](C)(C)C(C)(C)C)Cc4cc(-c5cnn(C)c5)ccc43)nn2[C@H]2CCOC2)C1]

A solution of 1-methyl-4-(4,4,5,5-tetramethyl-1,3,2-dioxaborolan-2-yl)pyrazole (97.17 mg, 0.47 mmol), 1-[3-[6-bromo-3-[tert-butyl(dimethyl)silyl]oxy-3,4-dihydro-2H-quinolin-1-yl]-1-[(3S)-tetrahydrofuran-3-yl]-6,7-dihydro-4H-pyrazolo[4,3-c]pyridin-5-yl]ethanone (Intermediate G, 280 mg, 0.39 mmol), [1,1'-bis(diphenylphosphino)ferrocene]dichloropalladium(II) (28.47 mg, 0.04 mmol) and Na₂CO₃ (82.49 mg, 0.78 mmol) in 1,4-dioxane (2 mL) and water (0.5 mL) was heated to 110° C. for 12 h under a nitrogen atmosphere. After cooling the reaction to room temperature, the mixture was concentrated in vacuo. The crude residue was purified by Prep-TLC (DCM/MeOH=20: 1) to give the title compound (200 mg, 62%) as a light yellow solid. LCMS M/Z (M+H) 577.

Step 6

(S)-1-[3-[3-hydroxy-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

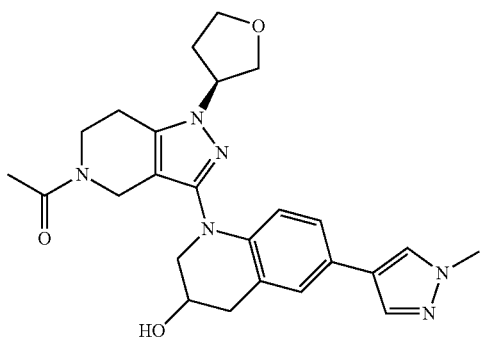 [SMILES: CC(=O)N1CCc2c(c(N3CC(O)Cc4cc(-c5cnn(C)c5)ccc43)nn2[C@H]2CCOC2)C1]

To a solution of 1-[3-[3-[tert-butyl(dimethyl)silyl]oxy-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone (200 mg, 0.24 mmol) in THF (2 mL) was added tetrabutylammonium fluoride (253.8 mg, 0.97 mmol). The mixture was heated to 80° C. for 16 h under a nitrogen atmosphere. After cooling the reaction to room temperature, water (20 mL) was added and the mixture was extracted with DCM (20 mL×2). The combined organic layers were dried over anhydrous Na₂SO₄, filtered and concentrated in vacuo. The crude residue was purified by reverse phase chromatography (acetonitrile 8-28%/0.1% NH₄HCO₃ in water) to give the title compound (8 mg, 7%) as a white solid. ¹H NMR (400 MHz, DMSO-d₆) δ 7.67-7.65 (m, 1H), 7.51-7.49 (m, 1H), 7.20-7.09 (m, 2H), 6.57-6.53 (m, 1H), 4.78-4.73 (m, 1H), 4.29-4.25 (m, 2H), 4.17-4.12 (m, 3H), 3.99-3.64 (m, 9H), 3.17-3.14 (m, 1H), 2.92-2.73 (m, 3H), 2.42-2.31 (m, 2H), 2.17-2.03 (m, 3H). LCMS M/Z (M+H) 463.

Example 136

(S)-1-[3-[3-methoxy-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone

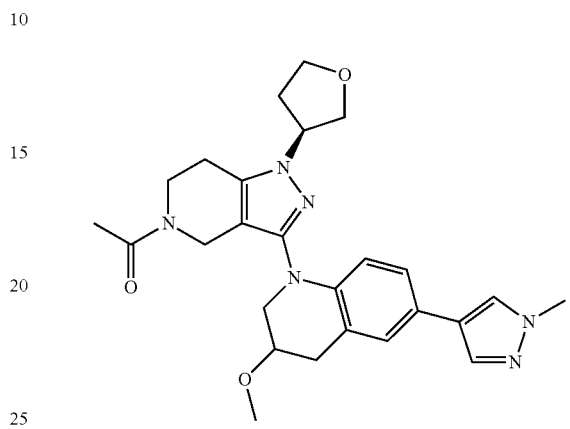

To a solution of(S)-1-[3-[3-hydroxy-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone (Example 135, 150 mg, 0.32 mmol) in THF (3 mL) at 0° C. was added NaH (60%, 38.92 mg, 0.97 mmol). The mixture was stirred at 0° C. for 30 min. Iodomethane (0.1 mL, 1.6 mmol) was added at 0° C. The mixture was stirred at 25° C. for an additional 16 h, quenched with MeOH (1 mL) and concentrated in vacuo. The crude residue was purified by reverse phase chromatography (acetonitrile 36-66%/0.1% NH₄HCO₃ in water) to give the title compound (62 mg, 40%) as a white solid. ¹H NMR (400 MHz, DMSO-d₆) δ 7.92 (s, 1H), 7.68 (s, 1H), 7.22 (s, 1H), 7.15-7.11 (m, 1H), 6.45-6.38 (m, 1H), 4.90-4.86 (m, 1H), 4.06-3.96 (m, 4H), 3.83-3.80 (m, 6H), 3.69-3.64 (m, 3H), 3.54-3.45 (m, 1H), 3.41 (s, 3H), 3.05-3.00 (m, 1H), 2.82-2.67 (m, 3H), 2.28-2.24 (m, 2H), 2.05-1.90 (m, 3H). LCMS M/Z (M+H) 477.

The Following Compounds were Prepared in a Similar Fashion to Example 136

Examples 137 and 138

| Example | Compound Name | NMR | m/z |
| --- | --- | --- | --- |
| Example 137 | (S)-1-[3-[3-ethoxy-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone | ¹H NMR (400 MHz, DMSO-d₆) δ 7.92 (s, 1H), 7.68 (s, 1H), 7.22 (s, 1H), 7.15-7.11 (m, 1H), 6.46-6.39 (m, 1H), 4.90-4.86 (m, 1H), 4.12-3.98 (m, 4H), 3.85-3.80 (m, 6H), 3.70-3.65 (m, 2H), 3.50-3.41 (m, 4H), 3.04-3.00 (m, 1H), 2.82-2.67 (m, 3H), 2.28-2.23 (m, 2H), 2.05-1.90 (m, 3H), 1.07 (t, J = 6.8 Hz, 3H) | 491 |
| Example 138 | (S)-1-[3-[3-isopropoxy-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone | ¹H NMR (400 MHz, DMSO-d₆) δ 7.92 (s, 1H), 7.68 (s, 1H), 7.22 (s, 1H), 7.15-7.10 (m, 1H), 6.47-6.40 (m, 1H), 4.92-4.87 (m, 1H), 4.06-3.95 (m, 5H), 3.83-3.63 (m, 9H), 3.44-3.35 (m, 1H), 3.03-3.00 (m, 1H), 2.83-2.71 (m, 3H), 2.28-2.24 (m, 2H), 2.05-1.91 (m, 3H), 1.09-1.03 (m, 6H) | 505 |

Examples 139 & 140

(S)-1-(5-acetyl-1-tetrahydrofuran-3-yl-6,7-dihydro-4H-pyrazolo[4,3-c]pyridin-3-yl)-6-(1-methylpyrazol-4-yl)-3,4-dihydro-2H-quinoline-3-carbonitrile & (S)-2-[1-(5-acetyl-1-tetrahydrofuran-3-yl-6,7-dihydro-4H-pyrazolo[4,3-c]pyridin-3-yl)-5-(1-methylpyrazol-4-yl)indolin-2-yl]acetonitrile

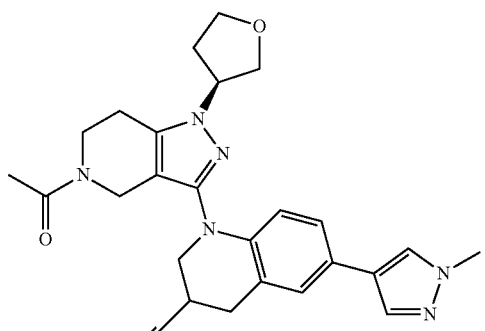

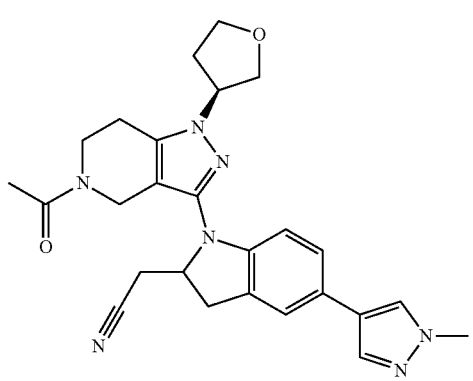

Step 1

1-(5-acetyl-1-((S)-tetrahydrofuran-3-yl)-4,5,6,7-tetrahydro-1H-pyrazolo[4,3-c]pyridin-3-yl)-6-(1-methyl-1H-pyrazol-4-yl)-1,2,3,4-tetrahydroquinolin-3-ylmethanesulfonate

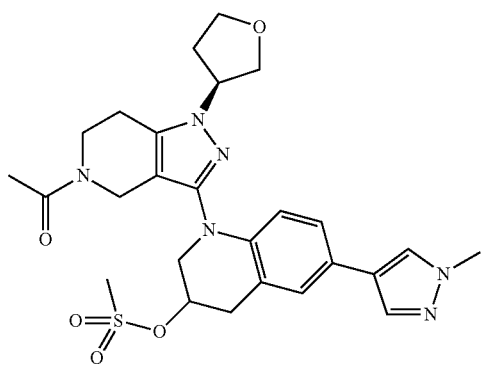 [SMILES: CC(=O)N1CCc2c(c(N3CC(OS(C)(=O)=O)Cc4cc(-c5cnn(C)c5)ccc43)nn2[C@H]2CCOC2)C1]

To a solution of 1-[3-[3-hydroxy-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone (200 mg, 0.43 mmol) in DCM (2 mL) at 0° C. was added methanesulfonyl chloride (0.07 mL, 0.86 mmol) and triethylamine (0.18 mL, 1.3 mmol). The mixture was stirred at 25° C. for 2 h. Water (10 mL) was added and the mixture was extracted with DCM (10 mL×2). The combined organic layers were dried over anhydrous $Na_2SO_4$ and concentrated in vacuo to give the title compound (400 mg, crude) as a yellow oil that required no further purification. LCMS M/Z (M+H)=541.

Step 2

(S)-1-(5-acetyl-1-tetrahydrofuran-3-yl-6,7-dihydro-4H-pyrazolo[4,3-c]pyridin-3-yl)-6-(1-methylpyrazol-4-yl)-3,4-dihydro-2H-quinoline-3-carbonitrile & (S)-2-[1-(5-acetyl-1-tetrahydrofuran-3-yl-6,7-dihydro-4H-pyrazolo[4,3-c]pyridin-3-yl)-5-(1-methylpyrazol-4-yl)indolin-2-yl]acetonitrile

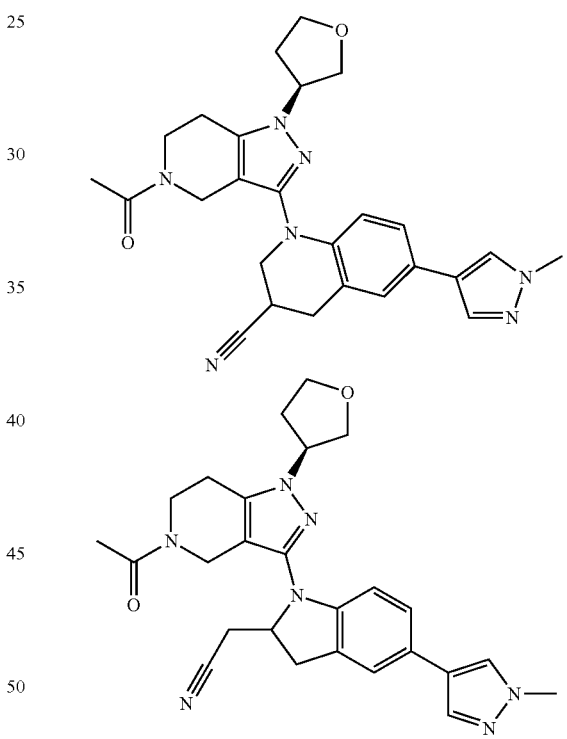

To a solution of potassium cyanide (48 mg, 0.74 mmol) in DMSO (2 mL) was added [1-[5-acetyl-1-[(3S)-tetrahydrofuran-3-yl]-6,7-dihydro-4H-pyrazolo[4,3-c]pyridin-3-yl]-6-(1-methylpyrazol-4-yl)-3,4-dihydro-2H-quinolin-3-yl]methanesulfonate (400 mg, 0.74 mmol). The mixture was stirred at room temperature for 16 h. Water (20 mL) was added and the mixture was extracted with DCM (20 mL×2). The combined organic layers were dried over anhydrous $Na_2SO_4$, filtered and concentrated in vacuo. The crude residue was purified by reverse phase chromatography (acetonitrile 15-45%/0.1% $NH_4HCO_3$ in water) to give (S)-1-(5-acetyl-1-tetrahydrofuran-3-yl-6,7-dihydro-4H-pyrazolo[4,3-c]pyridin-3-yl)-6-(1-methylpyrazol-4-yl)-3,4-dihydro-2H-quinoline-3-carbonitrile (17.5 mg, 5%) as a white solid and (S)-2-[1-(5-acetyl-1-tetrahydrofuran-3-yl-6,7-dihydro-4H-pyrazolo[4,3-c]pyridin-3-yl)-5-(1-methylpyrazol-4-yl)indolin-2-yl]acetonitrile (10 mg, 3%) as a light yellow solid. Example 139: $^1$H NMR (400 MHz, DMSO-$d_6$) δ 7.95 (s, 1H), 7.71 (s, 1H), 7.30 (s, 1H), 7.22-7.17 (m, 1H), 6.50-6.43 (m, 1H), 4.95-4.90 (m, 1H), 4.15-4.11 (m, 1H), 4.02-3.93 (m, 3H), 3.83-3.75 (m, 6H), 3.74-3.70 (m, 1H), 3.55-3.52 (m, 1H), 3.26-3.22 (m, 1H), 3.12-3.09 (m, 1H), 2.87-2.84 (m, 1H), 2.65-2.60 (m, 2H), 2.33-2.30 (m, 3H), 2.07-1.89 (m, 3H). LCMS M/Z (M+H) 472. Example 140: $^1$H NMR (400 MHz, DMSO-$d_6$) δ 7.96 (s, 1H), 7.72 (s, 1H), 7.37 (s, 1H), 7.23-7.21 (m, 1H), 6.66-6.60 (m, 1H), 4.93-4.89 (m, 1H), 4.58-4.47 (m, 1H), 4.35-4.33 (m, 2H), 4.01-3.97 (m, 3H), 3.86-3.79 (m, 6H), 3.42-3.34 (m, 2H), 2.98-2.85 (m, 4H), 2.68-2.65 (m, 1H), 2.33-2.25 (m, 2H), 2.09-2.00 (m, 3H). LCMS M/Z (M+H) 472.

Example 141

1-[3-[7-fluoro-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone

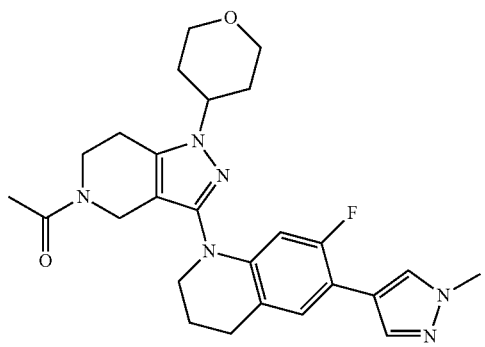 [SMILES: CC(=O)N1CCc2c(c(N3CCCc4cc(-c5cnn(C)c5)c(F)cc43)nn2C2CCOCC2)C1]

Step 1

3-chloro-N-(3-fluorophenyl)propanamide

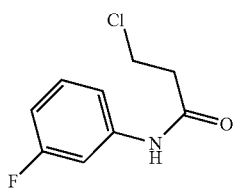

To a solution of 3-fluoroaniline (5.0 g, 45 mmol) and pyridine (7.2 g, 90 mmol) in acetone (120 mL), was added 3-chloropropanoyl chloride (6.3 g, 49.5 mmol). The mixture was heated to 50° C. for 12 h under nitrogen. After cooling the reaction to room temperature, the mixture was concentrated in vacuo. Water (200 mL) was added and the mixture was acidified with HCl (1 N) to pH 7 and then extracted with EtOAc (200 mL×3). The combined organic layers were washed with brine (100 mL×3), dried over anhydrous Na$_2$SO$_4$ and concentrated in vacuo to give the title compound (9 g, 99%) as a brown solid.

Step 2

7-fluoro-3,4-dihydroquinolin-2(1H)-one

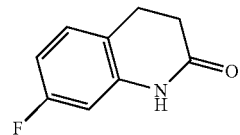 [SMILES: O=C1CCc2ccc(F)cc2N1]

To a solution of 3-chloro-N-(3-fluorophenyl)propanamide (2.0 g, 9.9 mmol) was added AlCl$_3$ (5.0 g, 37.9 mmol). The mixture was heated to 120° C. for 5 h under a nitrogen atmosphere. After cooling the reaction to room temperature, ice (20 g) and conc. HCl (15 mL) were added. The resulting precipitate was filtered, washed with H$_2$O (20 mL) and recrystallized from EtOH. The precipitate was collected and dried to give the title compound (1.0 g, 62%) as a white solid. $^1$H NMR (400 MHz, CDCl$_3$) δ 8.42 (s, 1H), 7.13-7.10 (m, 1H), 6.72-6.67 (m, 1H), 6.56-6.53 (m, 1H), 2.95 (t, J=7.2 Hz, 2H), 2.65 (t, J=7.6 Hz, 2H).

Step 3

7-fluoro-1,2,3,4-tetrahydroquinoline

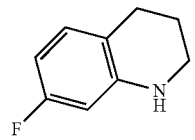 [SMILES: Fc1ccc2c(c1)NCCC2]

To a solution of 7-fluoro-3,4-dihydroquinolin-2(1H)-one (1.0 g, 6.0 mmol) in THF (20 mL) was added BH$_3$-THF (18 mL, 18 mmol). The mixture was heated to 70° C. for 12 h under a nitrogen atmosphere. After cooling the reaction to room temperature, MeOH (10 mL) and conc. HCl (4 mL) were added. The mixture was concentrated in vacuo. The crude residue was dissolved in EtOAc (50 mL), washed with sat. aq. NaHCO$_3$ (20 mL×2) and brine (20 mL×2), dried over anhydrous Na$_2$SO$_4$ and concentrated in vacuo. The crude residue was purified by silica gel chromatography (petroleum ether/EtOAc=10:1) to give the title compound (730 mg, 80%) as a colorless oil. LCMS M/Z (M+H) 151.

Step 4 tert-butyl 7-fluoro-3,4-dihydroquinoline-1(2H)-carboxylate

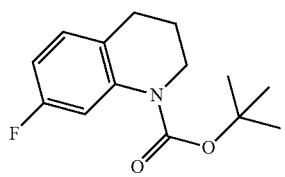 [SMILES: CC(C)(C)OC(=O)N1CCCc2ccc(F)cc21]

To a solution of 7-fluoro-1,2,3,4-tetrahydroquinoline (3.0 g, 20 mmol) and triethylamine (6.1 g, 60 mmol) in DCM (100 mL) was added DMAP (cat.) and di-tert-butyl dicarbonate (6.5 g, 30 mmol). The mixture was stirred at 20° C. for 12 h under a nitrogen atmosphere. The mixture was concentrated in vacuo. The crude residue was purified by silica gel chromatography (petroleum ether/EtOAc=20:1) to give the title compound (600 mg, 12%) as a brown oil.

Step 5 tert-butyl 6-bromo-7-fluoro-3,4-dihydroquinoline-1 (2H)-carboxylate

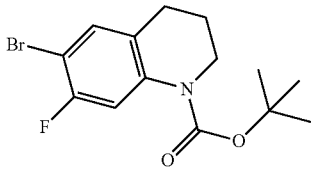 [SMILES: CC(C)(C)OC(=O)N1CCCc2cc(Br)c(F)cc21]

To a solution of tert-butyl 7-fluoro-3,4-dihydroquinoline-1(2H)-carboxylate (600 mg, 2.4 mmol) in DCM (20 mL) was added N-bromosuccinimide (420 mg, 2.4 mmol). The mixture was stirred at 15° C. for 2 h under a nitrogen atmosphere. Water (30 mL) was added and the mixture was extracted with DCM (20 mL×2). The combined organic layers were dried over anhydrous $Na_2SO_4$, filtered and concentrated in vacuo. The crude residue was purified by silica gel chromatography (petroleum ether/EtOAc=10:1) to give the title compound (500 mg, 63%) as a brown oil.

Step 6 tert-butyl 7-fluoro-6-(1-methyl-1H-pyrazol-4-yl)-3,4-dihydroquinoline-1(2H)-carboxylate

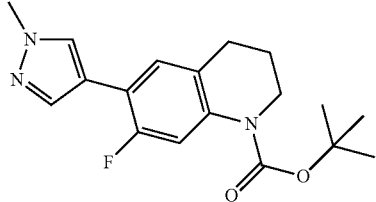 [SMILES: Cn1cc(-c2cc3c(cc2F)N(C(=O)OC(C)(C)C)CCC3)cn1]

To a solution of tert-butyl 6-bromo-7-fluoro-3,4-dihydroquinoline-1(2H)-carboxylate (500 mg, 1.5 mmol), 1-methyl-4-(4,4,5,5-tetramethyl-1,3,2-dioxaborolan-2-yl)-1H-pyrazole (320 mg, 1.5 mmol) and $K_2CO_3$ (520 mg, 3.8 mmol) in dioxane (20 mL) and $H_2O$ (2 mL) was added [1,1'-bis(diphenylphosphino)ferrocene]dichloropalladium(II) (70 mg, 0.1 mmol). The mixture was heated to 90° C. for 12 h under a nitrogen atmosphere. After cooling the reaction to room temperature, the mixture was concentrated in vacuo. The crude residue was purified by silica gel chromatography (petroleum ether/EtOAc=3:1) to give the title compound (300 mg, 61%) as a brown oil. LCMS M/Z (M+H) 332.

Step 7

7-fluoro-6-(1-methyl-1H-pyrazol-4-yl)-1,2,3,4-tetrahydroquinoline

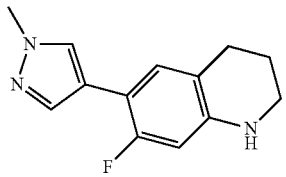 [SMILES: Cn1cc(-c2cc3c(cc2F)NCCC3)cn1]

To a solution of tert-butyl 7-fluoro-6-(1-methyl-1H-pyrazol-4-yl)-3,4-dihydroquinoline-1(2H)-carboxylate (300 mg, 0.9 mmol) in DCM (10 mL) was added trifluoroacetic acid (5 mL). The mixture was stirred at 18° C. for 2 h under a nitrogen atmosphere. The mixture was concentrated in vacuo to give the crude residue that was dissolved in EtOAc (50 mL), washed with sat. aq. $NaHCO_3$ (50 mL×2) and brine (50 mL×2), dried over anhydrous $Na_2SO_4$, filtered and concentrated in vacuo. The crude residue was was purified by silica gel chromatography (petroleum ether/EtOAc=3:1) to give the title compound (130 mg, 65%) as a brown solid. $^1$H NMR (400 MHz, $CDCl_3$) δ 7.72 (s, 1H), 7.62 (s, 1H), 7.08 (d, J=8.8 1H), 6.23 (d, J=12.4 Hz, 1H), 3.93 (s, 3H), 3.31 (t, J=5.2 Hz, 2H), 2.75 (t, J=6.4 Hz, 2H), 1.97-1.91 (m, 2H).

Step 8

1-[3-[7-fluoro-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone

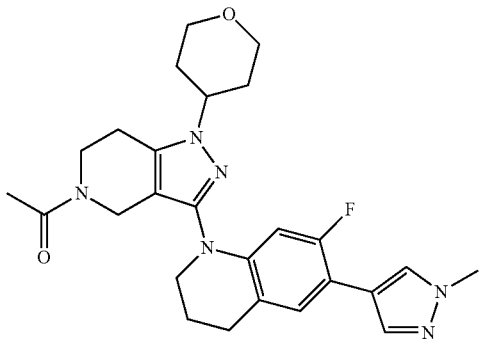

To a solution of 7-fluoro-6-(1-methyl-1H-pyrazol-4-yl)-1,2,3,4-tetrahydroquinoline (200 mg, 0.86 mmol) in dioxane (10 mL) was added 1-(3-bromo-1-(tetrahydro-2H-pyran-4-yl)-6,7-dihydro-1H-pyrazolo[4,3-c]pyridin-5(4H)-yl)ethanone (Intermediate I, 312 mg, 0.95 mmol), chloro(2-dicyclohexylphosphino-2',6'-di-i-propoxy-1,1'-biphenyl)(2'-amino-1,1'-biphenyl-2-yl)palladium(II) (67 mg, 0.09 mmol), 2-dicyclohexylphosphino-2',6'-di-i-propoxy-1,1'-biphenyl (40 mg, 0.09 mmol) and t-BuONa (333 mg, 3.46 mmol). The mixture was heated to 120° C. for 16 h under a nitrogen atmosphere. After cooling the reaction to room temperature, the mixture was concentrated in vacuo. The crude residue was purified by reverse phase chromatography (acetonitrile 30-60%/0.1% $NH_4HCO_3$ in water) to give the title compound (75 mg, 18%) as a white solid. $^1$H NMR (400 MHz, $CDCl_3$) δ 7.75-7.73 (m, 1H), 7.64-7.60 (m, 1H), 7.19-7.11 (m, 1H), 6.28-6.24 (m, 1H), 4.31-4.11 (m, 5H), 3.92-3.90 (m, 4H), 3.76-3.65 (m, 3H), 3.55-3.55 (m, 2H), 2.85-2.75 (m, 4H), 2.32-2.29 (m, 2H), 2.11-2.05 (m, 5H), 1.88-1.60 (m, 2H). LCMS M/Z (M+H) 479.

The Following Compounds were Prepared in a Similar Fashion to Example 141

Examples 142-144

| Example | Compound Name | NMR | m/z |
|---|---|---|---|
| Example 142 | 1-[3-[7-fluoro-6-(1-methylpyrazol-4-yl)-3,4-dihydro-2H-quinolin-1-yl]-1-tetrahydrofuran-3-yl-6,7-dihydro-4H-pyrazolo[4,3-c]pyridin-5-yl]ethanone | $^1$H NMR (400 MHz, DMSO-$d_6$) δ 7.91 (s, 1H), 7.71 (s, 1H), 7.30 (d, J = 8.8 Hz, 1H), 6.29-6.20 (m, 1H), 4.94-4.88 (m, 1H), 4.18-4.15 (m, 2H), 4.03-3.94 (m, 2H), 3.84 (s, 3H), 3.82-3.69 (m, 2H), 3.53-3.51 (m, 2H), 3.48-3.41 (m, 2H), 2.86-2.66 (m, 4H), 2.33-2.21 (m, 2H), 2.07-1.90 (m, 5H) | 465 |
| Example 143 | 1-[3-[7-fluoro-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone | $^1$H NMR (400 MHz, DMSO-$d_6$) δ 7.91 (s, 1H), 7.71 (s, 1H), 7.30 (d, J = 8.8 Hz, 1H), 6.29-6.20 (m, 1H), 4.94-4.88 (m, 1H), 4.18-4.15 (m, 2H), 4.03-3.94 (m, 2H), 3.84 (s, 3H), 3.82-3.69 (m, 2H), 3.53-3.51 (m, 2H), 3.48-3.41 (m, 2H), 2.86-2.66 (m, 4H), 2.33-2.21 (m, 2H), 2.07-1.94 (m, 5H) | 465 |
| Example 144 | 1-[3-[7-fluoro-6-(1-methylpyrazol-4-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 7.89 (s, 1H), 7.70 (s, 1H), 7.31 (d, J = 8.8 Hz, 1H), 6.31-6.23 (m, 1H), 5.45-5.42 (m, 1H), 4.89-4.83 (m, 4H), 4.14-4.12 (m, 2H), 3.82 (s, 3H), 3.70-3.66 (m, 2H), 3.58-3.57 (m, 2H), 2.77-2.63 (m, 4H), 2.03-1.93 (m, 5H) | 451 |

Example 145

1-[3-[7-methoxy-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone

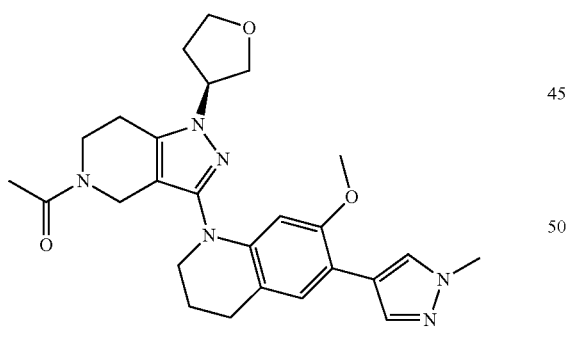

Step 1

7-methoxyquinoline

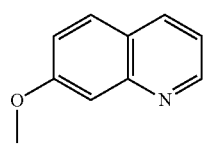

To a solution of quinolin-7-ol (5 g, 34.44 mmol) and Cs$_2$CO$_3$ (22.46 g, 68.89 mmol) in DMF (50 mL) was added iodomethane (2.1 mL, 34.44 mmol). The mixture was stirred at 20° C. for 12 h under a nitrogen atmosphere. Water (100 mL) was added and the mixture was extracted with EtOAc (50 mL×3). The combined organic layers were washed with brine (100 mL×3), dried over anhydrous Na$_2$SO$_4$ and concentrated in vacuo. The crude residue was purified by silica gel chromatography (petroleum ether/EtOAc=10:1) to give the title compound (2.0 g, 25%) as a yellow oil.

Step 2

7-methoxy-1,2,3,4-tetrahydroquinoline

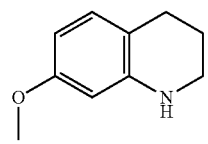

To a solution of 7-methoxyquinoline (800 mg, 5.03 mmol) in MeOH (8 mL) was added PtO$_2$ (137 mg, 0.6 mmol). The mixture was heated to 76° C. for 12 h under a hydrogen atmosphere (15 psi). After cooling the reaction to room temperature, the mixture was concentrated in vacuo. The crude residue was purified by silica gel chromatography (petroleum ether/EtOAc=10:1) to give the title compound (350 mg, 38%) as a yellow solid.

Step 2

(S)-1-(3-(7-methoxy-3,4-dihydroquinolin-1(2H)-yl)-1-(tetrahydrofuran-3-yl)-6,7-dihydro-1H-pyrazolo[4,3-c]pyridin-5(4H)-yl)ethanone

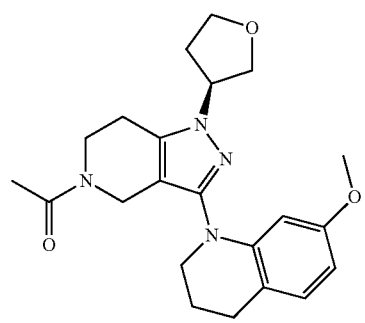 [SMILES: COc1ccc2c(c1)N(c1nn([C@H]3CCOC3)c3c1CN(C(C)=O)CC3)CCC2]

To a solution of 1-[3-bromo-1-[(3S)-tetrahydrofuran-3-yl]-6,7-dihydro-4H-pyrazolo[4,3-c]pyridin-5-yl]ethanone (Intermediate G, 566 mg, 1.8 mmol), 7-methoxy-1,2,3,4-tetrahydroquinoline (353 mg, 2.16 mmol) and t-BuONa (346 mg, 3.6 mmol) in toluene (5 mL) was added chloro(2-dicyclohexylphosphino-2',6'-di-i-propoxy-1,1'-biphenyl)[2-(2-aminoethylphenyl)]palladium(II), methyl-tert-butylether adduct (146.91 mg, 0.18 mmol) and 2-dicyclohexylphosphino-2',6'-di-i-propoxy-1,1'-biphenyl (84 mg, 0.18 mmol). The mixture was heated to 120° C. for 12 h under a nitrogen atmosphere. After cooling the reaction to room temperature, the mixture was concentrated in vacuo. The crude residue was purified by silica gel chromatography (DCM/MeOH=100:1) to give the title compound (240 mg, 26%) as a red oil. LCMS M/Z (M+H) 397.

Step 4

(S)-1-(3-(6-bromo-7-methoxy-3,4-dihydroquinolin-1(2H)-yl)-1-(tetrahydrofuran-3-yl)-6,7-dihydro-1H-pyrazolo[4,3-c]pyridin-5(4H)-yl)ethanone

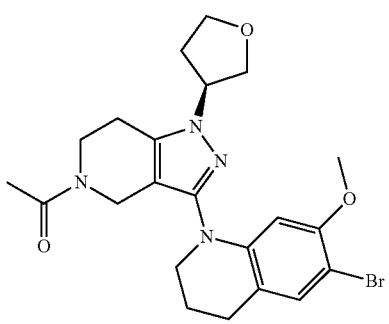 [SMILES: COc1cc2c(cc1Br)CCCN2c1nn([C@H]2CCOC2)c2c1CN(C(C)=O)CC2]

To a solution of 1-[3-(7-methoxy-3,4-dihydro-2H-quinolin-1-yl)-1-[(3S)-tetrahydrofuran-3-yl]-6,7-dihydro-4H-pyrazolo[4,3-c]pyridin-5-yl]ethanone (442 mg, 1.11 mmol) in DCM (5 mL) was added N-bromosuccinimide (198 mg, 1.11 mmol). The mixture was stirred at 20° C. for 1 h under a nitrogen atmosphere. Water (50 mL) was added and the mixture was extracted with EtOAc (50 mL×3). The combined organic layers were washed with brine (30 mL×3), dried over anhydrous $Na_2SO_4$ and concentrated in vacuo to give the title compound (320 mg, crude) as a yellow oil that required no further purification. LCMS M/Z (M+H) 475.

Step 5

1-[3-[7-methoxy-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone

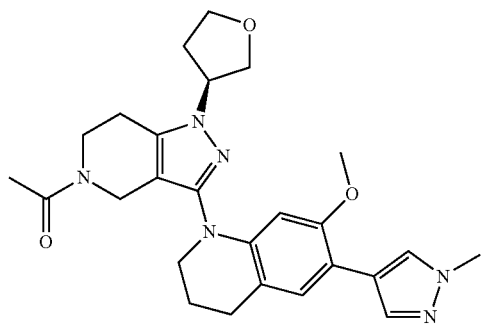 [SMILES: COc1cc2c(cc1-c1cnn(C)c1)CCCN2c1nn([C@H]2CCOC2)c2c1CN(C(C)=O)CC2]

To a solution of 1-[3-(6-bromo-7-methoxy-3,4-dihydro-2H-quinolin-1-yl)-1-[(3S)-tetrahydrofuran-3-yl]-6,7-dihydro-4H-pyrazolo[4,3-c]pyridin-5-yl]ethanone (320 mg, 0.67 mmol) in dioxane (3 mL) and water (1 mL) was added [1,1'-bis(diphenylphosphino)ferrocene]dichloropalladium (II) (49 mg, 0.07 mmol), 1-methyl-4-(4,4,5,5-tetramethyl-1,3,2-dioxaborolan-2-yl)pyrazole (168 mg, 0.81 mmol) and $Na_2CO_3$ (143 mg, 1.35 mmol). The mixture was heated to 110° C. for 12 h under a nitrogen atmosphere. After cooling the reaction to room temperature, the mixture was concentrated in vacuo. The crude residue was purified by reverse phase chromatography (acetonitrile 30-16%/0.2% formic acid in water) to give the title compound (85 mg, 24%) as a white solid. $^1$H NMR (400 MHz, DMSO-$d_6$) δ 7.90 (s, 1H), 7.72 (s, 1H), 7.19 (s, 1H), 6.29 (s, 1H), 4.95-4.86 (m, 1H), 4.19-4.22 (m, 2H), 4.00-3.92 (m, 2H), 3.82-3.55 (m, 6H), 3.80 (s, 3H), 3.61 (s, 3H), 2.83-2.72 (m, 4H), 2.38-2.12 (m, 2H), 2.07-1.91 (m, 5H). LCMS M/Z (M+H) 477.

Example 146

1-[3-[7-(difluoromethoxy)-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone

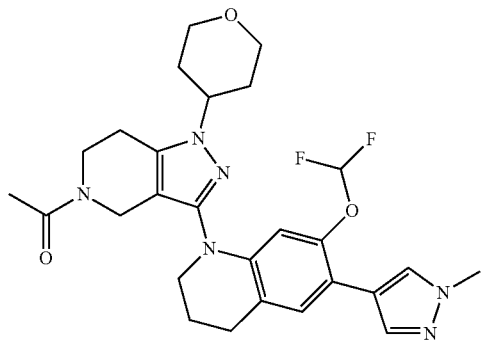 [SMILES: CC(=O)N1CCc2c(c(N3CCCc4cc(-c5cnn(C)c5)c(OC(F)F)cc43)nn2C2CCOCC2)C1]

449

Step 1

7-(difluoromethoxy)quinoline

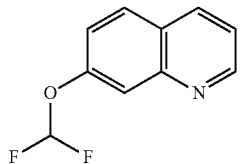 [SMILES: FC(F)Oc1ccc2cccnc2c1]

To a solution of quinolin-7-ol (1 g, 6.89 mmol) and (2-chloro-2,2-difluoro-acetyl)oxysodium (10.5 g, 68.89 mmol) in DMF (10 mL) and water (10 mL) was added $K_2CO_3$ (9.51 g, 68.89 mmol). The mixture was heated to 100° C. for 12 h under a nitrogen atmosphere. After cooling the reaction to room temperature, the mixture was concentrated in vacuo. The crude residue was purified by silica gel chromatography (petroleum ether/EtOAc=20:1) to give the title compound (240 mg, 16%) as a yellow solid.

Step 2

7-(difluoromethoxy)-1,2,3,4-tetrahydroquinoline

To a solution of 7-(difluoromethoxy)quinoline (230 mg, 1.18 mmol) and $NaBH_3CN$ (371 mg, 5.89 mmol) in MeOH (5 mL) was added boron trifluoride diethyl etherate (0.29 mL, 2.36 mmol). The mixture was heated to 80° C. for 12 h under a nitrogen atmosphere. Water (20 mL) was added and the mixture was extracted with EtOAc (50 mL×3). The combined organic layers were washed with brine (30 mL×3), dried over anhydrous $Na_2SO_4$ and concentrated in vacuo. The crude residue was purified by silica gel chromatography (petroleum ether/EtOAc=100:1) to give the title compound (120 mg, 44%) as a white solid. $^1H$ NMR ($CDCl_3$) δ 6.89 (d, J=8.0 Hz, 1H), 6.43 (t, J=74.8 Hz, 1H), 6.34-6.32 (m, 1H), 6.22 (s, 1H), 3.30 (t, J=5.2 Hz, 2H), 2.72 (t, J=6.8 Hz, 2H), 1.95-1.89 (m, 2H).

Step 3

1-(3-(7-(difluoromethoxy)-3,4-dihydroquinolin-1 (2H)-yl)-1-(tetrahydro-2H-pyran-4-yl)-6,7-dihydro-1H-pyrazolo[4,3-c]pyridin-5(4H)-yl)ethanone

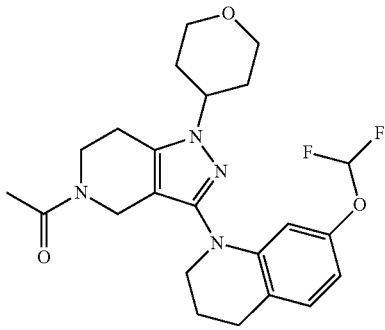 [SMILES: CC(=O)N1CCc2c(c(N3CCCc4ccc(OC(F)F)cc43)nn2C2CCOCC2)C1]

450

To a solution of 1-(3-bromo-1-tetrahydropyran-4-yl-6,7-dihydro-4H-pyrazolo[4,3-c]pyridin-5-yl)ethanone (Intermediate I, 500 mg, 1.4 mmol), t-BuONa (269 mg, 2.8 mmol) and 7-(difluoromethoxy)-1,2,3,4-tetrahydroquinoline (335 mg, 1.68 mmol) in dioxane (5 mL) was added 2-dicyclohexylphosphino-2',6'-di-i-propoxy-1,1'-biphenyl (65 mg, 0.14 mmol) and chloro(2-dicyclohexylphosphino-2',6'-di-i-propoxy-1,1'-biphenyl)(2'-amino-1,1'-biphenyl-2-yl)palladium(II) (109 mg, 0.14 mmol). The mixture was heated to 120° C. for 12 h under a nitrogen atmosphere. After cooling the reaction to room temperature, the mixture was concentrated in vacuo. The crude residue was purified by silica gel chromatography (DCM/MeOH=100:1) to give the title compound (340 mg, 43%) as a yellow oil. LCMS M/Z (M+H) 447.

Step 4

1-(3-(6-bromo-7-(difluoromethoxy)-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone

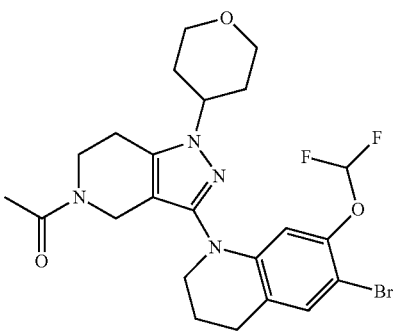 [SMILES: CC(=O)N1CCc2c(c(N3CCCc4cc(Br)c(OC(F)F)cc43)nn2C2CCOCC2)C1]

To a solution of 1-[3-[7-(difluoromethoxy)-3,4-dihydro-2H-quinolin-1-yl]-1-tetrahydropyran-4-yl-6,7-dihydro-4H-pyrazolo[4,3-c]pyridin-5-yl]ethanone (340 mg, 0.61 mmol) in DCM (3 mL) was added N-bromosuccinimide (0.12 g, 0.67 mmol). The mixture was stirred at 30° C. for 1 h. Water (50 mL) was added and the mixture was extracted with EtOAc (50 mL×3). The combined organic layers were dried over anhydrous $Na_2SO_4$, filtered and concentrated in vacuo to give the title compound (250 mg, crude) as yellow oil that required no further purification. LCMS M/Z (M+H) 525.

Step 5

1-[3-[7-(difluoromethoxy)-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone

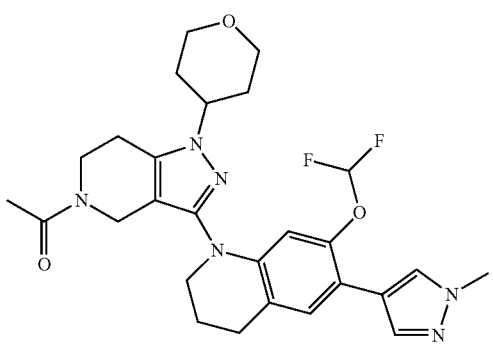 [SMILES: CC(=O)N1CCc2c(c(N3CCCc4cc(-c5cnn(C)c5)c(OC(F)F)cc43)nn2C2CCOCC2)C1]

To a solution of 1-[3-[6-bromo-7-(difluoromethoxy)-3,4-dihydro-2H-quinolin-1-yl]-1-tetrahydropyran-4-yl-6,7-dihydro-4H-pyrazolo[4,3-c]pyridin-5-yl]ethanone (300 mg, 0.46 mmol) in dioxane (3 mL) and water (1 mL) was added [1,1'-bis(diphenylphosphino)ferrocene]dichloropalladium (II) (41 mg, 0.05 mmol), 1-methyl-4-(4,4,5,5-tetramethyl-1,3,2-dioxaborolan-2-yl)-1H-pyrazole (114 mg, 0.55 mmol) and Na$_2$CO$_3$ (99 mg, 0.91 mmol). The mixture was heated to 100° C. for 12 h under a nitrogen atmosphere. After cooling the reaction to room temperature, the mixture was concentrated in vacuo. The crude residue was purified by reverse phase chromatography (acetonitrile 1-28%/0.2% formic acid in water) to give the title compound (38 mg, 15%) as a white solid. $^1$H NMR (400 MHz, DMSO-d$_6$) δ 7.87 (s, 1H), 7.71 (s, 1H), 7.29 (s, 1H), 6.93 (t, J=74.4 Hz, 1H), 6.46-6.43 (m, 1H), 4.31-4.24 (m, 1H), 4.20-4.18 (m, 2H), 3.95-3.93 (m, 2H), 3.84 (s, 3H), 3.75-3.67 (m, 2H), 3.55-3.53 (m, 2H), 3.47-3.44 (m, 2H), 2.85-2.73 (m, 4H), 2.08-1.94 (m, 7H), 1.87-1.81 (m, 2H). LCMS M/Z (M+H) 527.

The Following Compounds were Prepared in a Similar Fashion to Example 146

Examples 147 and 148

| Example | Compound Name | NMR | m/z |
|---|---|---|---|
| Example 147 | 1-[3-[7-(difluoromethoxy)-6-(1-methylpyrazol-4-yl)-3,4-dihydro-2H-quinolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 7.86 (s, 1H), 7.69 (s, 1H), 7.30 (s, 1H), 6.94 (t, J = 74.4 Hz, 1H), 6.47-6.43 (m, 1H), 5.46-5.43 (m, 1H), 4.90-4.80 (m, 4H), 4.15-4.12 (m, 2H), 3.81 (s, 3H), 3.65-3.57 (m, 4H), 2.79-2.75 (m, 4H), 2.47-1.91(m, 5H) | 499 |
| Example 148 | 1-[3-[7-(difluoromethoxy)-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridin-5-yl]ethanone | $^1$H NMR (400 MHz, DMSO-d$_6$) δ 7.88 (s, 1H), 7.71 (s, 1H), 7.30 (s, 1H), 6.94 (t, J = 74.4 Hz, 1H), 6.46-6.43 (m, 1H), 4.85-4.94 (m, 1H), 4.19-4.17 (m, 2H), 4.01-3.92 (m, 2H), 3.84 (s, 3H), 3.80-3.69 (m, 4H), 3.56-3.54 (m, 2H), 3.84-3.77 (m, 4H), 2.15-2.35 (m, 2H), 2.08-1.98 (m, 5H) | 513 |

Example 149

1-[3-[6-(1-methylpyrazol-4-yl)-7-(trifluoromethoxy)-3,4-dihydro-2H-quinolin-1-yl]-1-[(3S)-tetrahydrofuran-3-yl]-6,7-dihydro-4H-pyrazolo[4,3-c]pyridin-5-yl]ethanone

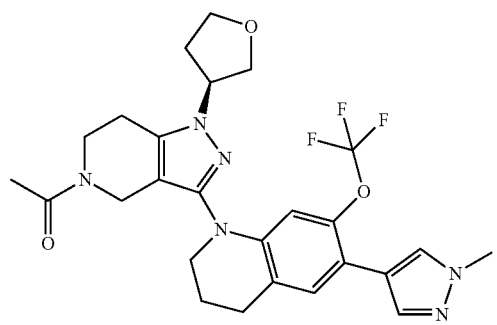 [SMILES: CC(=O)N1CCc2c(c(N3CCCc4cc(-c5cnn(C)c5)c(OC(F)(F)F)cc43)nn2[C@H]2CCOC2)C1]

Step 1

(E)-ethyl 3-(2-amino-4-(trifluoromethoxy)phenyl) acrylate

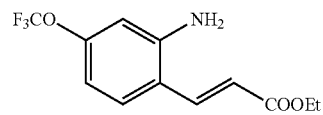 [SMILES: CCOC(=O)/C=C/c1ccc(OC(F)(F)F)cc1N]

To a solution of 2-bromo-5-(trifluoromethoxy)aniline (7 g, 27.34 mmol), ethyl acrylate (4.4 mL, 40.95 mmol) and triethylamine (7.6 mL, 54.68 mmol) in MeCN (70 mL) was added palladium(II) acetate (614 mg, 2.73 mmol) and tris(2-methylphenyl)phosphine (2.24 g, 8.2 mmol). The mixture was heated to 120° C. for 12 h under a nitrogen atmosphere. After cooling the reaction to room temperature, the mixture was concentrated in vacuo. The crude residue was purified by silica gel chromatography (petroleum ether/EtOAc=100:1 to 50:1 to 20:1) to give the title compound (2.8 g, 29%) as a yellow oil.

Step 2

Ethyl 3-(2-amino-4-(trifluoromethoxy)phenyl)propanoate

To a solution of ethyl (E)-3-[2-amino-4-(trifluoromethoxy)phenyl]prop-2-enoate (500 mg, 1.82 mmol) in MeOH (5 mL) was added 10% Pd/C (50 mg, 1.82 mmol). The mixture was stirred at 20° C. for 12 h under a hydrogen atmosphere (15 Psi). The mixture was concentrated in vacuo to give the title compound (410 mg, crude) as yellow oil that required no further purification. LCMS M/Z (M+H) 278.

Step 3

7-(trifluoromethoxy)-3,4-dihydroquinolin-2(1H)-one

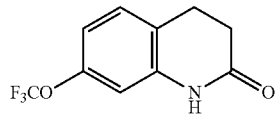

To a solution of ethyl 3-[2-amino-4-(trifluoromethoxy) phenyl]propanoate (2.7 g, 7.79 mmol) in AcOH (27 mL) was added conc. HCl (0.65 mL, 7.79 mmol). The mixture was heated to 90° C. for 1 h under a nitrogen atmosphere. After cooling the reaction to room temperature, ice water (20 mL) was added and the mixture was made basic with NaOH (2 N) to pH 9 and then extracted with EtOAc (100 mL×3). The combined organic layers were washed with brine (100 mL×3), dried over anhydrous $Na_2SO_4$ and concentrated in vacuo to give the title compound (1.8 g, crude) as a yellow solid that required no further purification. LCMS M/Z (M+H) 232.

Step 4

7-(trifluoromethoxy)-1,2,3,4-tetrahydroquinoline

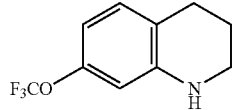 [SMILES: FC(F)(F)Oc1ccc2c(c1)NCCC2]

To a solution of 7-(trifluoromethoxy)-3,4-dihydro-1H-quinolin-2-one (500 mg, 1.73 mmol) in THF (5 mL) was added lithium aluminium hydride (85 mg, 2.25 mmol). The mixture was stirred at 20° C. for 12 h under a nitrogen atmosphere. Water (1 mL) was added and the mixture was filtered and concentrated in vacuo to give the title compound (0.35 g, crude) as yellow oil that required no further purification. LCMS M/Z (M+H) 218.

Step 5

(S)-1-(1-(tetrahydrofuran-3-yl)-3-(7-(trifluoromethoxy)-3,4-dihydroquinolin-1(2H)-yl)-6,7-dihydro-1H-pyrazolo[4,3-c]pyridin-5(4H)-yl)ethanone

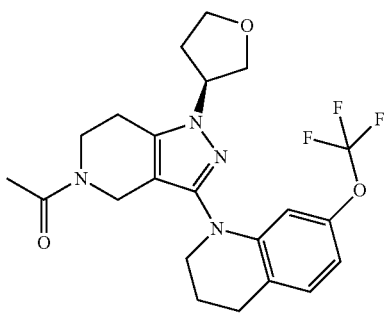 [SMILES: CC(=O)N1CCc2c(c(N3CCCc4ccc(OC(F)(F)F)cc43)nn2[C@H]2CCOC2)C1]

To a solution of 1-[3-bromo-1-[(3S)-tetrahydrofuran-3-yl]-6,7-dihydro-4H-pyrazolo[4,3-c]pyridin-5-yl]ethanone (Intermediate G, 400 mg, 1.21 mmol), 7-(trifluoromethoxy)-1,2,3,4-tetrahydroquinoline (371 mg, 1.45 mmol) and t-BuONa (256 mg, 2.42 mmol) in dioxane (4 mL), was added chloro(2-dicyclohexylphosphino-2',6'-di-i-propoxy-1,1'-biphenyl)[2-(2-aminoethylphenyl)]palladium(II), methyl-tert-butylether adduct (99 mg, 0.12 mmol) and 2-dicyclohexylphosphino-2',6'-di-i-propoxy-1,1'-biphenyl (57 mg, 0.12 mmol). The mixture was heated to 120° C. for 12 h under a nitrogen atmosphere. After cooling the reaction to room temperature, the mixture was concentrated in vacuo. The crude residue was purified by silica gel chromatography (DCM/MeOH=100:1) to give the title compound (200 mg, 29%) as yellow oil. LCMS M/Z (M+H) 451.

Step 6

(S)-1-(3-(6-bromo-7-(trifluoromethoxy)-3,4-dihydroquinolin-1(2H)-yl)-1-(tetrahydrofuran-3-yl)-6,7-dihydro-1H-pyrazolo[4,3-c]pyridin-5(4H)-yl)ethanone

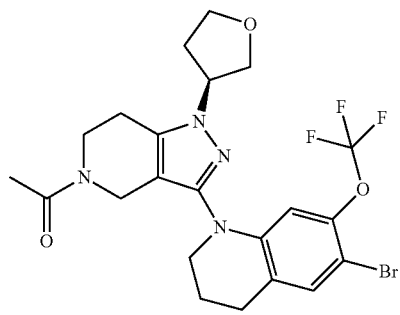 [SMILES: CC(=O)N1CCc2c(c(N3CCCc4cc(Br)c(OC(F)(F)F)cc43)nn2[C@H]2CCOC2)C1]

To a solution of 1-[1-[(3S)-tetrahydrofuran-3-yl]-3-[7-(trifluoromethoxy)-3,4-dihydro-2H-quinolin-1-yl]-6,7-dihydro-4H-pyrazolo[4,3-c]pyridin-5-yl]ethanone (300 mg, 0.53 mmol) in DCM (2 mL) was added N-bromosuccinimide (95 mg, 0.53 mmol). The mixture was stirred at 26° C. for 1 h. Water (50 mL) was added and the mixture was extracted with EtOAc (50 mL×3). The combined organic layers were washed with brine (30 mL×3), dried over anhydrous $Na_2SO_4$ and concentrated in vacuo to give the title compound (310 mg, crude) as yellow oil that required no further purification. LCMS M/Z (M+H) 531.

Step 7

1-[3-[6-(1-methylpyrazo-4-yl)-7-(trifluoromethoxy)-3,4-dihydro-2H-quinolin-1-yl]-1-[(3S)-tetrahydrofuran-3-yl]-6,7-dihydro-4H-pyrazolo[4,3-c]pyridin-5-yl]ethanone

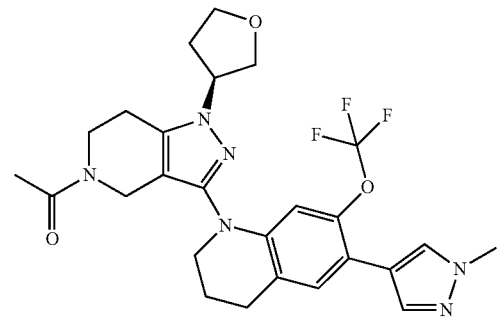 [SMILES: CC(=O)N1CCc2c(c(N3CCCc4cc(-c5cnn(C)c5)c(OC(F)(F)F)cc43)nn2[C@H]2CCOC2)C1]

To a solution of 1-[3-[6-bromo-7-(trifluoromethoxy)-3,4-dihydro-2H-quinolin-1-yl]-1-[(3S)-tetrahydrofuran-3-yl]-6,7-dihydro-4H-pyrazolo[4,3-c]pyridin-5-yl]ethanone (310 mg, 0.47 mmol) in dioxane (3 mL) and water (1 mL) was added Na₂CO₃ (99 mg, 0.94 mmol), 1-methyl-4-(4,4,5,5-tetramethyl-1,3,2-dioxaborolan-2-yl)pyrazole (117 mg, 0.56 mmol) and [1,1'-bis(diphenylphosphino)ferrocene]dichloropalladium(II) (34 mg, 0.05 mmol). The mixture was heated to 120° C. for 12 h under a nitrogen atmosphere. After cooling the reaction to room temperature, the mixture was concentrated in vacuo. The crude residue was purified by reverse phase chromatography (acetonitrile 35-16%/0.2% formic acid in water) to give the title compound (13 mg, 5%) as a white solid. ¹H NMR (400 MHz, DMSO-d₆) δ 7.88 (s, 1H), 7.67 (s, 1H), 7.33 (s, 1H), 6.60-6.56 (m, 1H), 4.93-4.89 (m, 1H), 4.21-4.15 (m, 2H), 4.23-4.02 (m, 2H), 3.85 (s, 3H), 3.73-3.68 (m, 4H), 3.55-3.53 (m, 2H), 2.85-2.80 (m, 4H), 2.08-1.96 (m, 5H). LCMS M/Z (M+H) 531.

Example 150

3-[6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridine-5-carboxamide

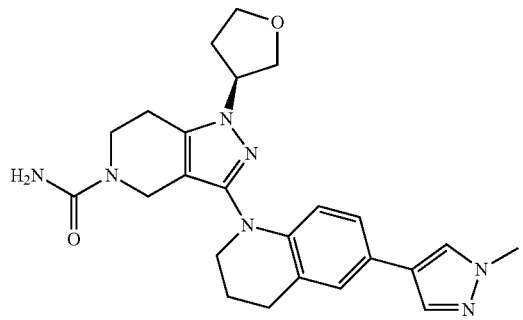 [SMILES: Cn1cc(-c2ccc3c(c2)CCCN3c2nn([C@H]3CCOC3)c3c2CN(C(N)=O)CC3)cn1]

Step 1

(S)-tert-butyl 3-(6-(1-methyl-1H-pyrazol-4-yl)-3,4-dihydroquinolin-1(2H)-yl)-1-(tetrahydrofuran-3-yl)-6,7-dihydro-1H-pyrazolo[4,3-c]pyridine-5(4H)-carboxylate

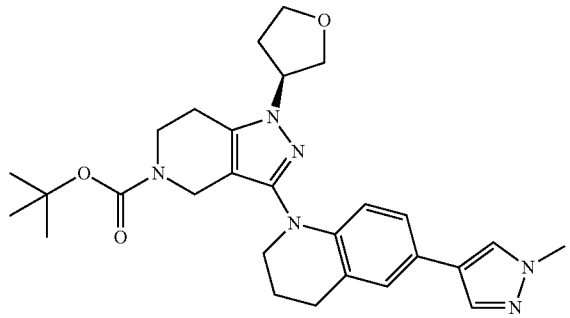 [SMILES: Cn1cc(-c2ccc3c(c2)CCCN3c2nn([C@H]3CCOC3)c3c2CN(C(=O)OC(C)(C)C)CC3)cn1]

To a solution of 6-(1-methyl-1H-pyrazol-4-yl)-1,2,3,4-tetrahydroquinoline (Step 1 of Example 65, 3.0 g, 14.1 mmol) in dioxane (30 mL) was added (S)-tert-butyl 3-bromo-1-(tetrahydrofuran-3-yl)-6,7-dihydro-1H-pyrazolo[4,3-c]pyridine-5(4H)-carboxylate (Intermediate F, 6.3 g, 16.9 mmol), Cs₂CO₃ (9.2 g, 28.1 mmol), 4,5-bis(diphenylphosphino)-9,9-dimethylxanthene (814 mg, 1.41 mmol) and tris(dibenzylideneacetone)dipalladium (644 mg, 0.70 mmol). The mixture was heated to 110° C. for 16 h under a nitrogen atmosphere. After cooling the reaction to room temperature, the mixture was filtered and the filtrate was concentrated in vacuo. The crude residue was purified by silica gel chromatography (DCM/MeOH=30:1) to give the title compound (4.0 g, 56%) as a brown solid.

Step 2

(S)-6-(1-methyl-1H-pyrazol-4-yl)-1-(1-(tetrahydrofuran-3-yl)-4,5,6,7-tetrahydro-1H-pyrazolo[4,3-c]pyridin-3-yl)-1,2,3,4-tetrahydroquinoline

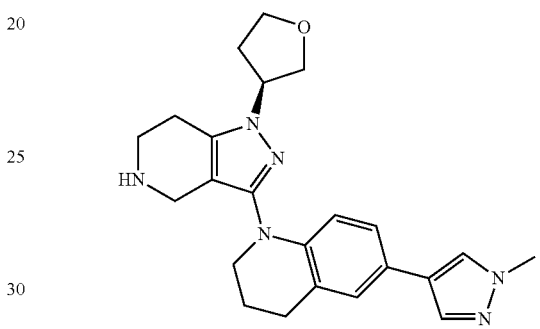

To a solution of (S)-tert-butyl 3-(6-(1-methyl-1H-pyrazol-4-yl)-3,4-dihydroquinolin-1(2H)-yl)-1-(tetrahydrofuran-3-yl)-6,7-dihydro-1H-pyrazolo[4,3-c]pyridine-5(4H)-carboxylate (4.0 g, 7.93 mmol) in DCM (40 mL) was added trifluoroacetic acid (10 mL). The mixture was stirred at 30° C. for 3 h, added sat. aq. NaHCO₃ (200 mL) and the mixture was extracted with DCM (100 mL×2). The combined organic layers were washed with brine (100 mL×3), dried over anhydrous Na₂SO₄ and concentrated in vacuo. The crude residue was purified by silica gel chromatography (DCM/MeOH=20:1) to give the title compound (1.9 g, 59%) as a brown solid.

Step 3

3-[6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridine-5-carboxamide

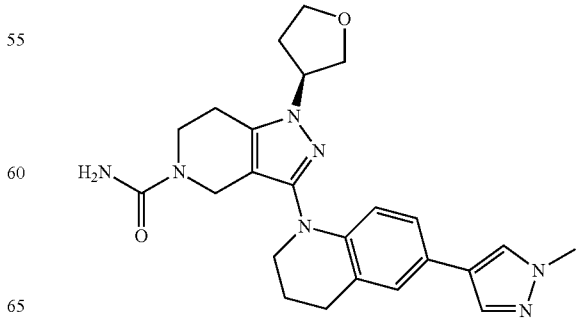

To a solution of (S)-6-(1-methyl-1H-pyrazol-4-yl)-1-(1-(tetrahydrofuran-3-yl)-4,5,6,7-tetrahydro-1H-pyrazolo[4,3-c]pyridin-3-yl)-1,2,3,4-tetrahydroquinoline (200 mg, 0.49 mmol) in DCM (5 mL) was added trimethylsilyl isocyanate (114 mg, 0.99 mmol). The mixture was stirred at 30° C. for 3 h and concentrated in vacuo. The crude residue was purified by reverse phase chromatography (acetonitrile 27-57%/0.1% NH$_4$OH in water) to give the title compound (125 mg, 57%) as a white solid. $^1$H NMR (400 MHz, DMSO-d$_6$) δ 7.91 (s, 1H), 7.67 (s, 1H), 7.18 (s, 1H), 7.09 (d, J=8.0 Hz, 1H), 6.41 (d, J=8.4 Hz, 1H), 6.05 (s, 2H), 4.93-4.84 (m, 1H), 4.05-3.91 (m, 4H), 3.85-3.74 (m, 5H), 3.56 (m, 4H), 2.80 (t, J=6.0 Hz, 2H), 2.70 (s, 2H), 2.32-2.16 (m, 2H), 2.01-1.89 (m, 2H). LCMS M/Z (M+H) 448.

The Following Compounds were Prepared in a Similar Fashion to Example 150

Examples 151-155

Example 156

N-methyl-3-[6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridine-5-carboxamide

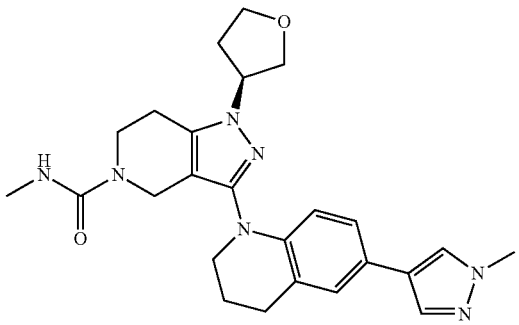

To a solution of (S)-6-(1-methyl-1H-pyrazol-4-yl)-1-(1-(tetrahydrofuran-3-yl)-4,5,6,7-tetrahydro-1H-pyrazolo[4,3-c]pyridin-3-yl)-1,2,3,4-tetrahydroquinoline (200 mg, 0.49 mmol) in DMF (3 mL) was added 4-nitrophenyl carbonochloridate (150 mg, 0.74 mmol) and pyridine (117 mg, 1.48 mmol). The mixture was stirred at 30° C. for 4 h before a

| Example | Compound Name | NMR | m/z |
|---|---|---|---|
| Example 151 | 3-[6-(1-methylpyrazol-4-yl)-3,4-dihydro-2H-quinolin-1-yl]-1-(oxetan-3-yl)-6,7-dihydro-4H-pyrazolo[4,3-c]pyridine-5-carboxamide | $^1$H NMR (400 MHz, DMSO-d$_6$) δ 7.89 (s, 1H), 7.65 (s, 1H), 7.18 (s, 1H), 7.09 (d, J = 8.4 Hz, 1H), 6.46 (d, J = 8.4 Hz, 1H), 6.01 (s, 2H), 5.45-5.38 (m, 1H), 4.90 (t, J = 8.4 Hz, 2H), 4.83 (t, J = 8.4 Hz, 2H), 3.94 (s, 2H), 3.88 (s, 3H), 3.59-3.51 (m, 4H), 2.80 (t, J = 6.0 Hz, 2H), 2.62-2.60 (m, 3H), 1.97-1.91 (m, 2H) | 434 |
| Example 152 | 3-[7-(difluoromethoxy)-6-(1-methylpyrazol-4-yl)-3,4-dihydro-2H-quinolin-1-yl]-1-tetrahydropyran-4-yl-6,7-dihydro-4H-pyrazolo[4,3-c]pyridine-5-carboxamide | $^1$H NMR (400 MHz, DMSO-d$_6$) δ 7.87 (s, 1H), 7.71 (s, 1H), 7.29 (s, 1H), 6.95 (t, J = 74.4 Hz, 1H), 6.45 (s, 1H), 6.10 (s, 2H), 4.31-4.24 (m, 1H), 4.08 (s, 2H), 3.94-3.92 (m, 2H), 3.84 (s, 3H), 3.60-3.53 (m, 4H), 3.48-3.42 (m, 2H), 2.81-2.71(m, 4H), 2.07-1.94 (m, 4H), 1.81-1.78 (m, 2H) | 528 |
| Example 153 | 3-[7-cyano-6-(1-methylpyrazol-4-yl)-3,4-dihydro-2H-quinolin-1-yl]-1-tetrahydropyran-4-yl-6,7-dihydro-4H-pyrazolo[4,3-c]pyridine-5-carboxamide | $^1$H NMR (400 MHz, DMSO-d$_6$) δ 8.06 (s, 1H), 7.79 (s, 1H), 7.34 (s, 1H), 6.72 (s, 1H), 4.32-4.30 (m, 1H), 4.07 (s, 2H), 3.96-3.93 (m, 2H), 3.87 (s, 3H), 3.64-3.61 (m, 2H), 3.57-3.54 (m, 2H), 3.46-3.42 (m, 2H), 2.88-2.85 (m, 2H), 2.76-2.75 (m, 2H), 1.98-1.92 (m, 4H), 1.84-1.81 (m, 2H) | 487 |
| Example 154 | 3-[7-(difluoromethyl)-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridine-5-carboxamide | $^1$H NMR (400 MHz, DMSO-d$_6$) δ 7.75 (s, 1H), 7.49 (s, 1H), 7.09 (s, 1H), 6.84 (s, 1H), 6.78 (t, J = 55.2 Hz, 1H), 6.07 (s, 2H), 4.94-4.89 (m, 1H), 4.03-3.86 (m, 4H), 3.82 (s, 3H), 3.80-3.78 (m, 2H), 3.59-3.57 (m, 4H), 2.83-2.74 (m, 4H), 2.29-2.21 (m, 2H), 1.98-1.96 (m, 2H) | 498 |
| Example 155 | 3-[7-(difluoromethyl)-6-(1-methylpyrazol-4-yl)-3,4-dihydro-2H-quinolin-1-yl]-1-tetrahydropyran-4-yl-6,7-dihydro-4H-pyrazolo[4,3-c]pyridine-5-carboxamide | $^1$H NMR (400 MHz, DMSO-d$_6$) δ 7.75 (s, 1H), 7.50 (s, 1H), 7.09 (s, 1H), 6.83 (s, 1H), 6.78 (t, J = 55.2 Hz, 1H), 6.08 (s, 2H), 4.31-4.26 (m, 1H), 4.02 (s, 2H), 3.97-3.94 (m, 2H), 3.86 (s, 3H), 3.60-3.55 (m, 4H), 3.48-3.42 (m, 2H), 2.84-2.67 (m, 4H), 2.00-1.94 (m, 4H), 1.83-1.80 (m, 2H) | 512 | solution of methanamine in THF (1M, 2.5 mL, 2.50 mmol) was added. The mixture was heated to 70° C. for 16 h. After cooling the reaction to room temperature, the mixture was concentrated in vacuo. The crude residue was purified by Prep-TLC (DCM/MeOH=20:1) to give the title compound (26 mg, 23%) as a yellow solid. $^1$H NMR (400 MHz, DMSO-d$_6$) δ 7.90 (s, 1H), 7.67 (s, 1H), 7.18 (s, 11H), 7.09 (d, J=8.4 Hz, 1H), 6.54 (d, J=4.0 Hz, 1H), 6.40 (d, J=8.0 Hz, 1H), 4.90-4.86 (m, 1H), 4.06-3.90 (m, 5H), 3.87-3.70 (m, 7H), 3.61-3.52 (m, 4H), 2.81-2.70 (m, 4H), 2.32-2.16 (m, 2H), 1.98-1.93 (m, 2H). LCMS M/Z (M+H) 462.

The Following Compounds were Prepared in a Similar Fashion to Example 156

Examples 157-165

| Example | Compound Name | NMR | m/z |
|---|---|---|---|
| Example 157 | 3-[7-(difluoromethoxy)-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 7.87 (s, 1H), 7.71 (s, 1H), 7.29 (s, 1H), 6.93 (t, J = 74.4 Hz, 1H), 6.55 (d, J = 4.4 Hz, 1H), 6.43 (s, 1H), 4.29-4.26 (m, 1H), 4.07 (s, 2H), 3.95-3.92 (m, 2H), 3.84 (s, 3H), 3.60-3.52 (m, 4H), 3.44 (t, J = 11.6 Hz, 2H), 2.81-2.70 (m, 4H), 2.54 (d, J = 4.4 Hz, 3H), 2.07-1.93 (m, 4H), 1.80-1.77 (m, 2H) | 542 |
| Example 158 | 3-[7-cyano-6-(1-methylpyrazol-4-yl)-3,4-dihydro-2H-quinolin-1-yl]-N-methyl-1-[(3S)-tetrahydrofuran-3-yl]-6,7-dihydro-4H-pyrazolo[4,3-c]pyridine-5-carboxamide | $^1$H NMR (400 MHz, DMSO-d$_6$) δ 8.06 (s, 1H), 7.79 (s, 1H), 7.35 (s, 1H), 6.74 (s, 1H), 6.57-6.56 (m, 1H), 4.95-4.89 (m, 1H), 4.04-3.95 (m, 4H), 3.88 (s, 3H), 3.82-3.80 (m, 2H), 3.61-3.55 (m, 4H), 2.89-2.85 (m, 2H), 2.73-2.70 (m, 2H), 2.55 (d, J = 4.8 Hz, 3H), 2.30-2.20 (m, 2H), 1.99-1.96 (m, 2H) | 487 |
| Example 159 | 3-[7-cyano-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 8.06 (s, 1H), 7.79 (s, 1H), 7.35 (s, 1H), 6.70 (s, 1H), 6.57-6.56 (m, 1H), 4.33-4.28 (m, 1H), 4.05 (s, 2H), 3.99-3.94 (m, 2H), 3.88 (s, 3H), 3.62-3.56 (m, 4H), 3.48-3.40 (m, 3H), 2.87-2.74 (m, 4H), 2.55-2.54 (m, 3H), 1.98-1.81 (m, 6H) | 501 |
| Example 160 | 3-[6-(1,5-dimethylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 7.41 (s, 1H), 7.00 (s, 1H), 6.92 (d, J = 8.0 Hz, 1H), 6.54 (s, 1H), 6.45 (d, J = 8.0 Hz, 1H), 4.18-4.08 (m, 1H), 4.07-3.88 (m, 4H), 3.74 (s, 3H), 3.65-3.50 (m, 4H), 3.48-3.41 (m, 2H), 2.81-2.70 (m, 4H), 2.52 (s, 3H), 2.03-1.87 (m, 4H), 1.85-1.71 (m, 2H) | 490 |
| Example 161 | 3-[7-(difluoromethyl)-6-(1-methylpyrazol-4-yl)-3,4-dihydro-2H-quinolin-1-yl]-N-methyl-1-[(3S)-tetrahydrofuran-3-yl]-6,7-dihydro-4H-pyrazolo[4,3-c]pyridine-5-carboxamide | $^1$H NMR (400 MHz, DMSO-d$_6$) δ 7.75 (s, 1H), 7.50 (s, 1H), 7.10 (s, 1H), 6.83 (s, 1H), 6.79 (t, J = 55.2 Hz, 1H), 6.56-6.55 (m, 1H), 4.93-4.89 (m, 1H), 4.04-3.96 (m, 4H), 3.87 (s, 3H), 3.86-3.71 (m, 2H), 3.60-3.55 (m, 4H), 2.84-2.60 (m, 4H), 2.55-2.53 (m, 3H), 2.28-2.22 (m, 2H), 1.98-1.95 (m, 2H) | 534 |
| Example 162 | 3-[7-(difluoromethyl)-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 7.76-7.75 (m, 1H), 7.49 (s, 1H), 7.10 (s, 1H), 6.83 (s, 1H), 6.92-6.78 (t, J = 55.2 Hz, 1H), 6.65-6.53 (m, 1H), 4.31-4.28 (m, 1H), 4.13-3.93 (m, 4H), 3.86 (s, 3H), 3.69-3.58 (m, 4H), 3.48-3.42 (m, 2H), 2.84-2.74 (m, 4H), 2.54-2.53 (m, 3H), 1.97-1.80 (m, 6H) | 526 |
| Example 163 | 3-(7-(difluoromethyl)-6-(6-(methylcarbamoyl)pyridin-3-yl)-3,4-dihydroquinolin-1(2H)-yl)-N-methyl-1-(tetrahydro-2H-pyran-4-yl)-6,7-dihydro-1H-pyrazolo[4,3-c]pyridine-5(4H)-carboxamide | $^1$H NMR (400 MHz, DMSO-d$_6$) δ 8.84-8.82 (m, 1H), 8.55 (s, 1H), 8.07 (d, J = 8.0 Hz, 1H), 7.92-7.90 (m, 1H), 7.13 (s, 1H), 6.89 (s, 1H), 6.75 (t, J = 54.8 Hz, 1H), 6.57 (d, J = 4.0 Hz, 1H), 4.37-4.24 (m, 1H), 4.07 (s, 2H), 3.95 (d, J = 8.0 Hz, 2H), 3.64-3.60 (m, 4H), 3.46 (t, J = 11.6 Hz, 2H), 2.94-2.70 (m, 7H), 2.55 (d, J = 4.0 Hz, 3H), 2.06-1.91 (m, 4H), 1.82-1.76 (m, 1H) | 580 |
| Example 164 | 3-(6-(difluoromethyl)-5-(1-methyl-1H-pyrazol-4-yl)indolin-1-yl)-N-methyl-1-(tetrahydro-2H-pyran-4-yl)-6,7-dihydro-1H-pyrazolo[4,3-c]pyridine-5(4H)-carboxamide | $^1$H NMR (400 MHz, DMSO-d$_6$) δ 7.80 (s, 1H), 7.77 (s, 1H), 7.52 (s, 1H), 7.19 (s, 1H), 6.83 (t, J = 55.6 Hz, 1H), 6.62-6.61 (m, 1H), 4.41 (s, 2H), 4.27-4.21 (m, 1H), 4.06 (t, J = 10.0 Hz, 2H), 3.98-3.95 (m, 2H), 3.88 (s, 3H), 3.60 (t, J = 6.0 Hz, 2H), 3.49-3.43 (m, 2H), 3.18 (t, J = 8.0 Hz, 2H), 2.70-2.65 (m, 2H), 2.59 (d, J = 4.0 Hz, 3H), 2.05-1.98 (m, 2H), 1.80-1.77 (m, 2H) | 512 |

-continued

| Example | Compound Name | NMR | m/z |
|---|---|---|---|
| Example 165 | N-methyl-3-(6-(6-(methylcarbamoyl)pyridin-3-yl)-3,4-dihydroquinolin-1(2H)-yl)-1-(tetrahydro-2H-pyran-4-yl)-6,7-dihydro-1H-pyrazolo[4,3-c]pyridine-5(4H)-carboxamide | $^1$H NMR (400 MHz, DMSO-$d_6$) δ 8.83 (d, J = 1.6 Hz, 1H), 8.71 (d, J = 5.2 Hz, 1H), 8.15-8.12 (m, 1H), 8.00 (d, J = 8.8 Hz, 1H), 7.49 (s, 1H), 7.40-7.38 (m, 1H), 6.55-6.51 (m, 2H), 4.31-4.26 (m, 1H), 4.02 (s, 2H), 3.96-3.94 (m, 2H), 3.61-3.57 (m, 4H), 3.48-3.45 (m, 2H), 2.89 (t, J = 6.8 Hz, 2H), 2.82 (d, J = 5.2 Hz, 3H), 2.75-2.70 (m, 2H), 2.53 (d, J = 4.8 Hz, 3H), 2.02-1.93 (m, 4H), 1.82-1.80 (m, 2H) | 530 |

Example 166

N,N-dimethyl-3-[6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridine-5-carboxamide

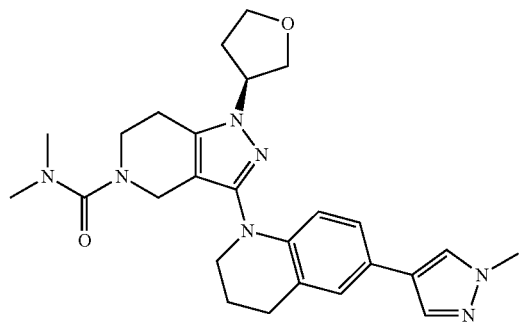

To a solution of (S)-6-(1-methyl-1H-pyrazol-4-yl)-1-(1-(tetrahydrofuran-3-yl)-4,5,6,7-tetrahydro-1H-pyrazolo[4,3-c]pyridin-3-yl)-1,2,3,4-tetrahydroquinoline (200 mg, 0.49 mmol) in DMF (3 mL) was added dimethylcarbamic chloride (106 mg, 0.99 mmol) and triethylamine (149 mg, 1.47 mmol). The mixture was stirred at 30° C. for 16 h. The mixture was filtered and the filtrate was concentrated in vacuo. The crude residue was purified by reverse phase chromatography (acetonitrile 31-61%/0.1% NH$_4$OH in water) to give the title compound (108 mg, 46%) as a white solid. $^1$H NMR (400 MHz, DMSO-$d_6$) δ 7.91 (s, 1H), 7.68 (s, 1H), 7.19 (s, 1H), 7.12-7.08 (m, 1H), 6.40 (d, J=8.4 Hz, 1H), 4.93-4.84 (m, 1H), 4.06-3.93 (m, 2H), 3.86-3.71 (m, 7H), 3.55-3.50 (m, 2H), 3.40-3.36 (m, 2H), 2.84-2.75 (m, 4H), 2.69 (s, 6H), 2.35-2.17 (m, 2H), 1.98-1.88 (m, 2H). LCMS M/Z (M+H) 476.

The Following Compound was Prepared in a Similar Fashion to Example 166

Example 167

| Example | Compound Name | NMR | m/z |
|---|---|---|---|
| Example 167 | methyl 3-[7-(difluoromethyl)-6-(1-methylpyrazol-4-yl)-3,4-dihydro-2H-quinolin-1-yl]-1-[(3S)-tetrahydrofuran-3-yl]-6,7-dihydro-4H-pyrazolo[4,3-c]pyridine-5-carboxylate | $^1$H NMR (400 MHz, DMSO-$d_6$) δ 7.76 (s, 1H), 7.51 (s, 1H), 7.10 (s, 1H), 6.81 (s, 1H), 6.79 (t, J = 55.2 Hz, 1H), 4.93-4.89 (m, 1H), 4.09 (s, 2H), 4.06-3.81 (m, 2H), 3.80 (s, 3H), 3.77-3.71 (m, 2H), 3.67-3.57 (m, 7H), 2.88-2.65 (m, 4H), 2.28-2.22 (m, 2H), 1.97-1.94 (m, 2H) | 513 |

Example 168

1-[1-methyl-3-[6-(1-methylpyrazol-4-yl)indolin-1-yl]-6,7-dihydro-4H-pyrazolo[4,3-c]pyridin-5-yl]ethanone

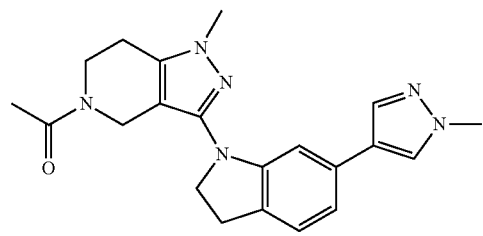 [SMILES: CC(=O)N1CCc2c(c(N3CCc4ccc(-c5cnn(C)c5)cc43)nn2C)C1]

Step 1

6-(1-methyl-1H-pyrazol-4-yl)indoline

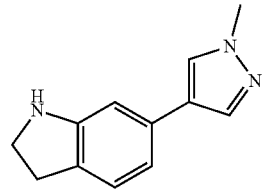

To a solution of 6-bromoindoline (5 g, 25.1 mmol) and 1-methyl-4-(4,4,5,5-tetramethyl-1,3,2-dioxaborolan-2-yl)-1H-pyrazole (6.3 g, 30.3 mmol) in dioxane (80 mL) and water (20 mL) was added Na$_2$CO$_3$ (8.03 g, 75.7 mmol) and [1,1'-bis(diphenylphosphino)ferrocene]dichloropalladium (II) (1.83 g, 2.51 mmol). The mixture was heated to 100° C. for 12 h under a nitrogen atmosphere. After cooling the reaction to room temperature, water (200 mL) was added and the mixture was extracted with EtOAc (200 mL×2). The combined organic layers were dried over anhydrous Na$_2$SO$_4$, filtered and concentrated in vacuo. The crude residue was purified by silica gel chromatography (petroleum ether/EtOAc=1:1) to give the title compound (1.8 g, 36%) as a yellow solid. $^1$H NMR (400 MHz, CDCl$_3$) δ 7.70 (s, 1H), 7.54 (s, 1H), 7.10 (d, J=8.0 Hz, 1H), 6.83 (d, J=8.0 Hz, 1H), 6.77 (s, 1H), 3.93 (s, 3H), 3.59 (t, J=8.4 Hz, 2H), 3.04 (t, J=8.4 Hz, 2H).

Step 2

1-[1-methyl-3-[6-(1-methylpyrazol-4-yl)indolin-1-yl]-6,7-dihydro-4H-pyrazolo[4,3-c]pyridin-5-yl]ethanone

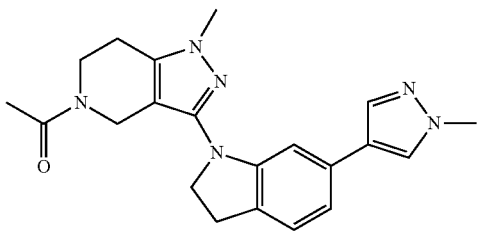 [SMILES: CC(=O)N1CCc2c(c(N3CCc4ccc(-c5cnn(C)c5)cc43)nn2C)C1]

A mixture of 1-(3-bromo-1-methyl-6,7-dihydro-4H-pyrazolo[4,3-c]pyridin-5-yl)ethanone (Intermediated B, 200 mg, 0.77 mol), 6-(1-methylpyrazol-4-yl)indoline (154 mg, 0.77 mmol), 2-dicyclohexylphosphino-2',6'-di-i-propoxy-1,1'-biphenyl (36 mg, 0.08 mmol), chloro(2-dicyclohexylphosphino-2',6'-di-i-propoxy-1,1'-biphenyl) [2-(2-aminoethylphenyl)]palladium(II), methyl-tert-butylether adduct (63 mg, 0.08 mmol), t-BuONa (223 mg, 2.32 mmol) in 1,4-dioxane (4 mL) was heated to 120° C. for 12 h. After cooling the reaction to room temperature, the mixture was diluted with water (20 mL), extracted with DCM (20 mL×2). The combined organic layers were dried over anhydrous Na$_2$SO$_4$, filtered and concentrated in vacuo. The crude residue was purified by reverse phase chromatography (acetonitrile 8-38%/0.2% formic acid in water) to give the title compound (39 mg, 13%) as a white solid. $^1$H NMR (400 MHz, CD$_3$OD) δ 7.86 (d, J=4.8 Hz, 1H), 7.71 (s, 1H), 7.13-7.11 (m, 1H), 7.00-6.90 (m, 2H), 4.53-4.47 (m, 2H), 3.97-3.85 (m, 4H), 3.90 (s, 3H), 3.71 (s, 3H), 3.19-3.11 (m, 2H), 2.86-2.75 (m, 2H), 2.22-2.08 (m, 3H). LCMS M/Z (M+H) 377.

The Following Compounds were Prepared in a Similar Fashion to Example 168

Examples 169-176

| Example | Compound Name | NMR | m/z |
| --- | --- | --- | --- |
| Example 169 | 1-[1-methyl-3-[5-(1-methylpyrazol-4-yl)indolin-1-yl]-6,7-dihydro-4H-pyrazolo[4,3-c]pyridin-5-yl]ethanone | $^1$H NMR (400 MHz, CD$_3$OD) δ 7.79 (s, 1H), 7.69 (s, 1H), 7.32 (d, J = 4.8 Hz, 1H), 7.24-7.21 (m, 1H), 6.91-6.87 (m, 1H), 4.52-4.48 (m, 2H), 3.97-3.83 (m, 4H), 3.89 (s, 3H), 3.68 (s, 3H), 3.17-3.13 (m, 2H), 2.84-2.73 (m, 2H), 2.20-2.12 (m, 3H) | 377 |
| Example 170 | 1-[1-(cyclopropylmethyl)-3-[6-(1-methylpyrazol-4-yl)indolin-1-yl]-6,7-dihydro-4H-pyrazolo[4,3-c]pyridin-5-yl]ethanone | $^1$H NMR (400 MHz, CD$_3$OD) δ 7.85 (s, 1H), 7.71 (s, 1H), 7.14-7.04 (m, 2H), 6.94-6.90 (m, 1H), 4.55-4.50 (m, 2H), 3.99-3.85 (m, 6H), 3.90 (s, 3H), 3.15-3.13 (m, 2H), 2.90-2.78 (m, 2H), 2.22-2.10 (m, 3H), 1.26-1.25 (m, 1H), 0.63-0.57 (m, 2H), 0.43-0.41 (m, 2H) | 417 |
| Example 171 | 1-[3-[5-(1-methylpyrazol-4-yl)indolin-1-yl]-1-tetrahydrofuran-3-yl-6,7-dihydro-4H-pyrazolo[4,3-c]pyridin-5-yl]ethanone | $^1$H NMR (400 MHz, CDCl$_3$) δ 7.69 (s, 1H), 7.51 (s, 1H), 7.41-7.13 (m, 3H), 4.74-4.71 (m, 1H), 4.68-4.48 (m, 2H), 4.12-4.06 (m, 2H), 4.04-4.01 (m, 4H), 3.99 (s, 3H), 3.93-3.75 (m, 2H), 3.21-3.17 (m, 2H), 2.73-2.70 (m, 2H), 2.45-2.32 (m, 2H), 2.20-2.15 (m, 3) | 433 |
| Example 172 | 1-[1-(cyclopropylmethyl)-3-indolin-1-yl-6,7-dihydro-4H-pyrazolo[4,3-c]pyridin-5-yl]ethanone | $^1$H NMR (400 MHz, CD$_3$OD) δ 7.16-7.13 (m, 1H), 7.05-7.04 (m, 1H), 6.90-6.87 (m, 1H), 6.73-6.72 (m, 1H), 4.52-4.49 (m, 2H), 3.96-3.86 (m, 6H), 3.16-3.14 (m, 2H), 2.88-2.78 (m, 2H), 2.22-2.15 (m, 3H), 1.29-1.27 (m, 1H), 0.61-0.58 (m, 2H), 0.42-0.38 (m, 2H) | 337 |
| Example 173 | 1-(3-indolin-1-yl-1-methyl-6,7-dihydro-4H-pyrazolo[4,3-c]pyridin-5-yl)ethanone | $^1$H NMR (400 MHz, CD$_3$OD) δ 7.12-7.08 (m, 1H), 7.01-6.97 (m, 1H), 6.83-6.79 (m, 1H), 6.69-6.68 (m, 1H), 4.47-4.43 (m, 2H), 3.92-3.80 (m, 4H), 3.66 (s, 3H), 3.11-3.09 (m, 2H), 2.81-2.71 (m, 2H), 2.18-2.09 (m, 3H) | 297 |
| Example 174 | 1-[3-[5-(1-methylpyrazol-4-yl)indolin-1-yl]-1-tetrahydropyran-4-yl-6,7-dihydro-4H-pyrazolo[4,3-c]pyridin-5-yl]ethanone | $^1$H NMR (400 MHz, DMSO-d$_6$) δ 7.94 (s, 1H), 7.71 (s, 1H), 7.44-7.24 (m, 3H), 4.55-4.53 (m, 2H), 4.27-4.19 (m, 1H), 4.04-3.96 (m, 4H), 3.83 (s, 3H), 3.74-3.70 (m, 2H), 3.48-3.42 (m, 2H), 3.14-3.10 (m, 2H), 2.80-2.68 (m, 2H), 2.10-1.99 (m, 5H), 1.79-1.77 (m, 2H) | 446 |

| Example | Compound Name | NMR | m/z |
|---|---|---|---|
| Example 175 | 1-[3-[5-(1-methylpyrazol-4-yl)indolin-1-yl]-1-(oxetan-3-yl)-6,7-dihydro-4H-pyrazolo[4,3-c]pyridin-5-yl]ethanone | $^1$H NMR (400 MHz, DMSO-$d_6$) δ 7.95 (s, 1H), 7.73 (s, 1H), 7.56-7.47 (m, 1H), 5.44-4.41 (m, 1H), 5.50-4.96 (m, 2H), 4.86-4.84 (m, 2H), 4.55-4.54 (m, 2H), 4.08-4.01 (m, 2H), 3.83 (s, 3H), 3.71-3.68 (m, 2H), 3.17-3.15 (m, 2H), 2.74-2.61 (m, 2H), 2.50-2.09 (m, 3) | 419 |
| Example 176 | 1-[1-methyl-3-[5'-(1-methylpyrazol-4-yl)spiro[cyclopropane-1,3'-indoline]-1'-yl]-6,7-dihydro-4H-pyrazolo[4,3-c]pyridin-5-yl]ethanone | $^1$H NMR (400 MHz, CD$_3$OD) δ 7.76-7.77 (m, 1H), 7.66 (s, 1H), 7.17-7.21 (m, 1H), 6.91-6.97 (m, 1H), 6.81-6.82 (m, 1H), 4.47-4.51 (m, 2H), 3.97 (s, 2H), 3.79-3.89 (m, 5H), 3.66-3.67 (m, 3H), 2.70-2.82 (m, 2H), 2.11-2.18 (m, 3H), 1.04-1.11 (m, 4H) | 403 |

Examples 177 & 178

(R)-1-[3-[5-(1-methylpyrazol-4-yl)indolin-1-yl]-1-tetrahydrofuran-3-yl-6,7-dihydro-4H-pyrazolo[4,3-c]pyridin-5-yl]ethanone and (S)-1-[3-[5-(1-methylpyrazol-4-yl)indolin-1-yl]-1-tetrahydrofuran-3-yl-6,7-dihydro-4H-pyrazolo[4,3-c]pyridin-5-yl]ethanone

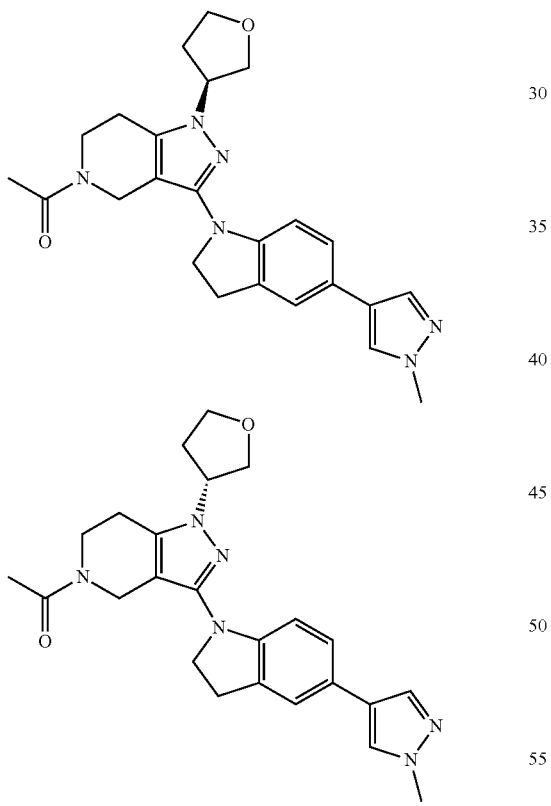

Racemic 1-[3-[5-(1-methylpyrazol-4-yl)indolin-1-yl]-1-tetrahydrofuran-3-yl-6,7-dihydro-4H-pyrazolo[4,3-c]pyridin-5-yl]ethanone (Example 71, 50 mg) was separated by using chiral SFC (Chiralcel OJ 250×30 mm I.D., 10 um; Supercritical CO$_2$/MeOH (0.1% NH$_3$H$_2$O)=50/50 at 70 mL/min) to give (R)-1-[3-[5-(1-methylpyrazol-4-yl)indolin-1-yl]-1-tetrahydrofuran-3-yl-6,7-dihydro-4H-pyrazolo[4,3-c]pyridin-5-yl]ethanone (5 mg, first peak) and (S)-1-[3-[5-(1-methylpyrazol-4-yl)indolin-1-yl]-1-tetrahydrofuran-3-yl-6,7-dihydro-4H-pyrazolo[4,3-c]pyridin-5-yl]ethanone (27 mg, second peak). Absolute configuration was arbitrarily assigned to each enantiomer. Example 177: $^1$H NMR (400 MHz, DMSO-$d_6$) δ 7.94 (s, 1H), 7.72 (s, 1H), 7.42-7.32 (m, 2H), 7.26-7.23 (m, 1H), 4.89-4.83 (m, 1H), 4.55-4.53 (m, 2H), 4.05-3.97 (m, 4H), 3.86-3.70 (m, 7H), 3.14-3.10 (m, 2H), 2.80-2.67 (m, 2H), 2.26-2.23 (m, 2H), 2.10-2.28 (m, 3H). LCMS M/Z (M+H) 433. Example 178: $^1$H NMR (400 MHz, DMSO-$d_6$) δ 7.94 (s, 1H), 7.72 (s, 1H), 7.42-7.32 (m, 2H), 7.26-7.23 (m, 1H), 4.88-4.86 (m, 1H), 4.55-4.53 (m, 2H), 4.03-3.96 (m, 4H), 3.86-3.70 (m, 7H), 3.14-3.10 (m, 2H), 2.80-2.67 (m, 2H), 2.26-2.24 (m, 2H), 2.10-2.28 (m, 3H). LCMS M/Z (M+H) 433.

Example 179

1-[3-[5-[1-methyl-3-(trifluoromethyl)pyrazol-4-yl]indolin-1-yl]-1-tetrahydrofuran-3-yl-6,7-dihydro-4H-pyrazolo[4,3-c]pyridin-5-yl]ethanone

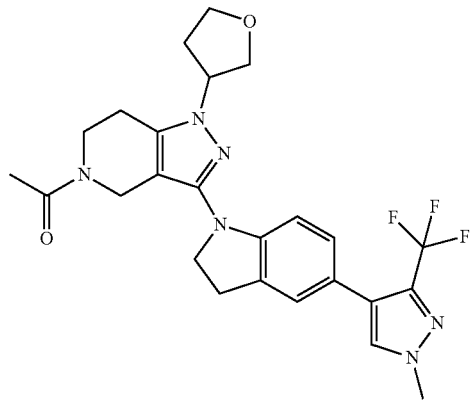 [SMILES: CC(=O)N1CCc2c(c(N3CCc4cc(-c5cn(C)nc5C(F)(F)F)ccc43)nn2C2CCOC2)C1]

Step 1 tert-butyl 5-bromoindoline-1-carboxylate

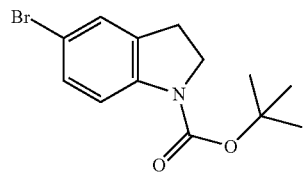 [SMILES: CC(C)(C)OC(=O)N1CCc2cc(Br)ccc21]

To a solution of 5-bromoindoline (3.3 g, 16.7 mmol) in DCM (33 mL) at room temperature was added 4-dimethylaminopyridine (0.21 g, 1.7 mmol), di-iso-propylethyl amine (4.3 g, 33.4 mmol) and di-tert-butyldicarbonate (5.8 g, 26.7 mmol). The resulting mixture was stirred at room temperature for 16 h and then concentrated in vacuo. The crude residue was purified by silica gel chromatography (petroleum ether/EtOAc=9:1) to give the title compound (3.63 g, 73%) as a white solid.

Step 2 tert-butyl 5-(4,4,5,5-tetramethyl-1,3,2-dioxaborolan-2-yl)indoline-1-carboxylate

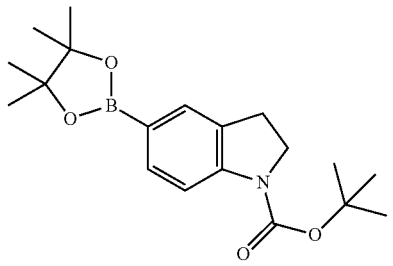 [SMILES: CC(C)(C)OC(=O)N1CCc2cc(B3OC(C)(C)C(C)(C)O3)ccc21]

To a solution of tert-butyl 5-bromoindoline-1-carboxylate (6 g, 20.12 mmol) in dioxane (100 mL) was added [1,1'-bis(diphenylphosphino)ferrocene]dichloropalladium(II) (1.5 g, 2.01 mmol), KOAc (6 g, 60.37 mmol) and 4,4,4',4',5,5,5',5'-Octamethyl-2,2'-bi(1,3,2-dioxaborolane) (6.1 g, 24.15 mmol). The mixture was heated to 80° C. for 12 h under a nitrogen atmosphere. After cooling the reaction to room temperature, the mixture was concentrated in vacuo. The crude residue was purified by silica gel chromatography (petroleum ether/EtOAc=10:1) to give the title compound (5.5 g, 80%) as a yellow solid.

Step 3 tert-butyl 5-(1-methyl-3-(trifluoromethyl)-1H-pyrazol-4-yl)indoline-1-carboxylate

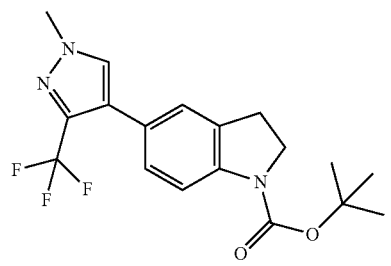 [SMILES: Cn1cc(-c2ccc3c(c2)CCN3C(=O)OC(C)(C)C)c(C(F)(F)F)n1]

To a solution of tert-butyl 5-(4,4,5,5-tetramethyl-1,3,2-dioxaborolan-2-yl)indoline-1-carboxylate (2.5 g, 7.24 mmol) in dioxane (20 mL) and H₂O (4 mL) was added Na₂CO₃ (1.5 g, 14.48 mmol), [1,1'-bis(diphenylphosphino)ferrocene]dichloropalladium(II) (500 mg, 0.7 mmol) and 4-bromo-1-methyl-3-(trifluoromethyl)-1H-pyrazole (1.7 g, 7.24 mmol). The mixture was heated to 120° C. for 12 h under a nitrogen atmosphere. After cooling the reaction to room temperature, the mixture was concentrated in vacuo.

The crude residue was purified by silica gel chromatography (petroleum ether/EtOAc=1:1) to give the title compound (2.3 g, 86%) as a yellow solid. LCMS M/Z (M+H) 368.

Step 4

5-(1-methyl-3-(trifluoromethyl)-1H-pyrazol-4-yl)indoline

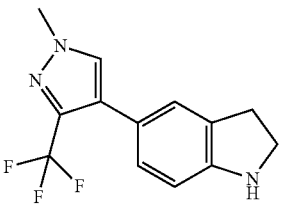 [SMILES: Cn1cc(-c2ccc3c(c2)CCN3)c(C(F)(F)F)n1]

To a solution of tert-butyl 5-(1-methyl-3-(trifluoromethyl)-1H-pyrazol-4-yl)indoline-1-carboxylate (2.3 g, 6.26 mmol) in EtOAc (10 mL) was added HCl/EtOAc (4 M, 10 mL) at 0° C. The mixture was stirred at room temperature for 1 h and concentrated in vacuo. Water (20 mL) was added and the mixture was made basic with solid NaHCO₃ to pH 8 and then the mixture extracted with EtOAc (50 mL×2). The combined organic layers were dried over anhydrous Na₂SO₄, filtered and concentrated in vacuo to give the title compound (1.6 g, 95%) as a yellow solid. LCMS M/Z (M+H) 268.

Step 5

1-[3-[5-[1-methyl-3-(trifluoromethyl)pyrazol-4-yl]indolin-1-yl]-1-tetrahydrofuran-3-yl-6,7-dihydro-4H-pyrazolo[4,3-c]pyridin-5-yl]ethanone

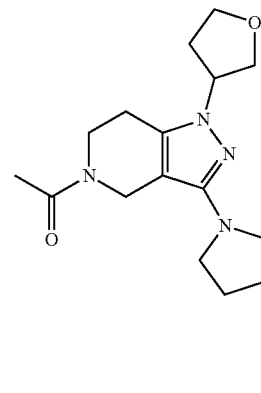

To a solution of 5-(1-methyl-3-(trifluoromethyl)-1H-pyrazol-4-yl)indoline (600 mg, 2.25 mmol) in dioxane (10 mL) was added 1-(3-bromo-1-(tetrahydrofuran-3-yl)-6,7-dihydro-1H-pyrazolo[4,3-c]pyridin-5(4H)-yl)ethanone (705 mg, 2.25 mmol), chloro(2-dicyclohexylphosphino-2',6'-di-i-propoxy-1,1'-biphenyl)[2-(2-aminoethylphenyl)]palladium(II), methyl-tert-butylether adduct (167 mg, 0.23 mmol), 2-dicyclohexylphosphino-2',6'-di-i-propoxy-1,1'-biphenyl (107 mg, 0.23 mmol) and t-BuONa (863 mg, 8.98 mmol). The mixture was heated to 120° C. for 12 h under a nitrogen atmosphere. After cooling the reaction to room temperature, the mixture was concentrated in vacuo. The crude residue was purified by reverse phase chromatography (acetonitrile 15-45%/0.1% NH$_4$HCO$_3$ in water) to give the title compound (150 mg, 13%) as a white solid. $^1$H NMR (400 MHz, DMSO-d$_6$) δ 8.01 (s, 1H), 7.42-7.33 (m, 1H), 7.13 (s, 1H), 7.07-7.05 (m, 1H), 4.90-4.86 (m, 1H), 4.55-4.54 (m, 2H), 4.05-4.00 (m, 4H), 3.99 (s, 3H), 3.99-3.86 (m, 2H), 3.85-3.70 (m, 2H), 3.14 (t, J=8.0 Hz, 2H), 2.80-2.67 (m, 2H), 2.26-2.24 (m, 2H), 2.10-2.08 (m, 3H). LCMS M/Z (M+H) 501.

The Following Compounds were Prepared in a Similar Fashion to Example 179

Examples 180 and 181

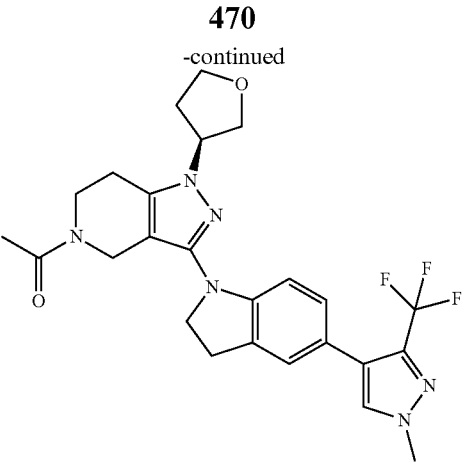

| Example | Compound Name | NMR | m/z |
|---|---|---|---|
| Example 180 | 1-[1-methyl-3-[5-[1-methyl-3-(trifluoromethyl)pyrazol-4-yl]indolin-1-yl]-6,7-dihydro-4H-pyrazolo[4,3-c]pyridin-5-yl]ethanone | $^1$H NMR (400 MHz, CD$_3$OD) δ 7.74 (s, 1H), 7.17 (s, 1H), 7.11-7.08 (m, 1H), 6.94-6.91 (m, 1H), 4.53-4.49 (m, 2H), 3.99-3.97 (m, 2H), 3.94 (s, 3H), 3.88-3.81 (m, 2H), 3.68 (s, 3H), 3.14 (t, J = 8.0 Hz, 2H), 2.82-2.72 (m, 2H), 2.22-2.13 (m, 3H) | 445 |
| Example 181 | 1-[3-[5-[1-methyl-3-(trifluoromethyl)pyrazol-4-yl]indolin-1-yl]-1-(oxetan-3-yl)-6,7-dihydro-4H-pyrazolo[4,3-c]pyridin-5-yl]ethanone | $^1$H NMR (400 MHz, DMSO-d$_6$) δ 8.02 (s, 1H), 7.58-7.47 (m, 1H), 7.15 (s, 1H), 7.13-7.09 (m, 1H), 5.47-5.43 (m, 1H), 4.98-4.95 (m, 2H), 4.87-4.82 (m, 2H), 4.56-4.54 (m, 2H), 4.09-4.00 (m, 2H), 3.93 (s, 3H), 3.71-3.67 (m, 2H), 3.19-3.15 (m, 2H), 2.74-2.61 (m, 2H), 2.09-2.07 (m, 3H) | 487 |

Examples 182 & 183

(R)-1-[3-[5-[1-methyl-3-(trifluoromethyl)pyrazol-4-yl]indolin-1-yl]-1-tetrahydrofuran-3-yl-6,7-dihydro-4H-pyrazolo[4,3-c]pyridin-5-yl]ethanone and (S)-1-[3-[5-[1-methyl-3-(trifluoromethyl)pyrazol-4-yl]indolin-1-yl]-1-tetrahydrofuran-3-yl-6,7-dihydro-4H-pyrazolo[4,3-c]pyridin-5-yl]ethanone

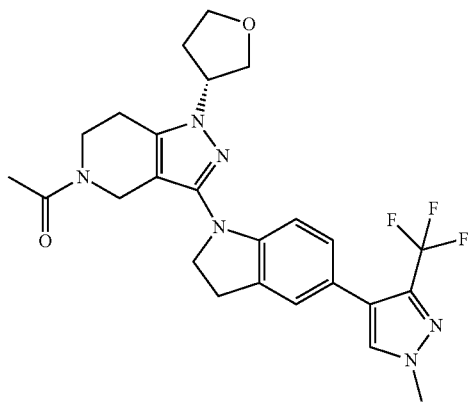 [SMILES: CC(=O)N1CCc2c(c(N3CCc4cc(-c5cn(C)nc5C(F)(F)F)ccc43)nn2C2CCOC2)C1]

Racemic 1-[3-[5-[1-methyl-3-(trifluoromethyl)pyrazol-4-yl]indolin-1-yl]-1-tetrahydrofuran-3-yl-6,7-dihydro-4H-pyrazolo[4,3-c]pyridin-5-yl]ethanone (Example 179, 120 mg) was separated by using chiral SFC (Chiralcel OJ 250×30 mm I.D., 5 um; Supercritical CO$_2$/MeOH(0.1% NH$_3$H$_2$O)=65/35 at 50 mL/min) to give (R)-1-[3-[5-[1-methyl-3-(trifluoromethyl)pyrazol-4-yl]indolin-1-yl]-1-tetrahydrofuran-3-yl-6,7-dihydro-4H-pyrazolo[4,3-c]pyridin-5-yl]ethanone (47 mg, first peak) and (S)-1-[3-[5-[1-methyl-3-(trifluoromethyl)pyrazol-4-yl]indolin-1-yl]-1-tetrahydrofuran-3-yl-6,7-dihydro-4H-pyrazolo[4,3-c]pyridin-5-yl]ethanone (32 mg, second peak). Absolute configuration was arbitrarily assigned to each enantiomer. Example 182: $^1$H NMR (400 MHz, DMSO-d$_6$) δ 8.01 (s, 1H), 7.42-7.33 (m, 1H), 7.13 (s, 1H), 7.07-7.05 (m, 1H), 4.90-4.89 (m, 1H), 4.55-4.54 (m, 2H), 4.05-4.00 (m, 4H), 3.99 (s, 3H), 3.99-3.86 (m, 2H), 3.85-3.70 (m, 2H), 3.15 (t, J=8.0 Hz, 2H), 2.80-2.67 (m, 2H), 2.26-2.24 (m, 2H), 2.10-2.08 (m, 3H). LCMS M/Z (M+H) 501. Example 183: $^1$H NMR (400 MHz, DMSO-d$_6$) δ 8.01 (s, 1H), 7.42-7.33 (m, 1H), 7.12 (s, 1H), 7.06-7.04 (m, 1H), 4.89-4.86 (m, 1H), 4.54-4.53 (m, 2H), 4.04-4.00 (m, 4H), 3.99 (s, 3H), 3.98-3.85 (m, 2H), 3.83-3.69 (m, 2H), 3.14 (t, J=8.0 Hz, 2H), 2.80-2.67 (m, 2H), 2.25-2.24 (m, 2H), 2.09-2.07 (m, 3H). LCMS M/Z (M+H) 501.

Example 184

1-[3-[5-(1,5-dimethylpyrazol-4-yl)indolin-1-yl]-1-tetrahydrofuran-3-yl-6,7-dihydro-4H-pyrazolo[4,3-c]pyridin-5-yl]ethanone

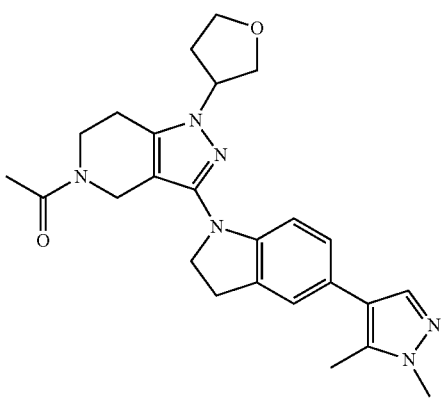 [SMILES: CC(=O)N1CCc2c(c(N3CCc4cc(-c5cnn(C)c5C)ccc43)nn2C2CCOC2)C1]

Step 1 tert-butyl 5-(1,5-dimethyl-1H-pyrazol-4-yl)indoline-1-carboxylate

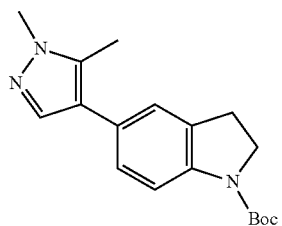 [SMILES: Cc1c(-c2ccc3c(c2)CCN3C(=O)OC(C)(C)C)cnn1C]

To a solution of tert-butyl 5-(4,4,5,5-tetramethyl-1,3,2-dioxaborolan-2-yl)indoline-1-carboxylate (1.5 g, 4.34 mmol) in dioxane (15 mL) and H₂O (3 mL) was added K₂CO₃ (1.2 g, 8.69 mmol), [1,1'-bis(diphenylphosphino)ferrocene]dichloropalladium(II) (290 mg, 0.4 mmol) and 4-bromo-1,5-dimethyl-1H-pyrazole (912 mg, 5.21 mmol). The mixture was heated to 120° C. for 12 h under a nitrogen atmosphere. After cooling the reaction to room temperature, the mixture was concentrated in vacuo. The crude residue was purified by silica gel chromatography (petroleum ether/EtOAc=1:1) to give the title compound (1.2 g, 88%) as a yellow solid. LCMS M/Z (M+H) 314.

Step 2

5-(1,5-dimethyl-1H-pyrazol-4-yl)indoline

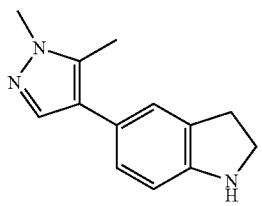 [SMILES: Cc1c(-c2ccc3c(c2)CCN3)cnn1C]

To a solution of tert-butyl 5-(1,5-dimethyl-1H-pyrazol-4-yl)indoline-1-carboxylate (1.2 g, 3.83 mmol) in EtOAc (10 mL) was added HCl in EtOAc (4 M, 10 mL). The resulting mixture was stirred at room temperature for 1 h and concentrated in vacuo. Water (20 mL) was added and the mixture was mad basic with solid NaHCO₃ to pH 8 and then extracted with EtOAc (50 mL×2). The combined organic layers were dried over anhydrous Na₂SO₄, filtered and concentrated in vacuo to give the title compound (700 mg, 74%) as a yellow solid.

Step 3

1-[3-[5-(1,5-dimethylpyrazol-4-yl)indolin-1-yl]-1-tetrahydrofuran-3-yl-6,7-dihydro-4H-pyrazolo[4,3-c]pyridin-5-yl]ethanone

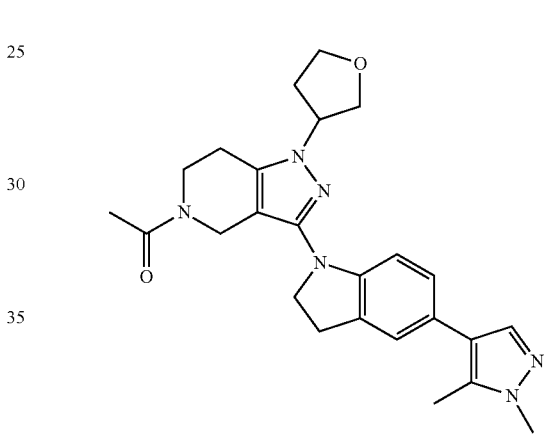

To a solution of 5-(1,5-dimethyl-1H-pyrazol-4-yl)indoline (400 mg, 1.88 mmol) in dioxane (10 mL) was added 1-(3-bromo-1-(tetrahydrofuran-3-yl)-6,7-dihydro-1H-pyrazolo[4,3-c]pyridin-5(4H)-yl)ethanone (590 mg, 1.88 mmol), chloro(2-dicyclohexylphosphino-2',6'-di-i-propoxy-1,1'-biphenyl) [2-(2-aminoethylphenyl)]palladium(II), methyl-tert-butylether adduct (136 mg, 0.19 mmol), 2-dicyclohexylphosphino-2',6'-di-i-propoxy-1,1'-biphenyl (88 mg, 0.19 mmol) and tBuONa (721 mg, 7.5 mmol). The mixture was heated to 120° C. for 12 h under a nitrogen atmosphere. After cooling the reaction to room temperature, the mixture was concentrated in vacuo. The crude residue was purified by silica gel chromatography (DCM/MeOH=20:1) to give the title compound (200 mg, 24%) as a white solid. ¹H NMR (400 MHz, DMSO-d₆) δ 7.45-7.35 (m, 2H), 7.14 (s, 1H), 7.06-7.03 (m, 1H), 4.90-4.83 (m, 1H), 4.56-4.54 (m, 2H), 4.05-3.95 (m, 4H), 3.88-3.82 (m, 4H), 3.75 (s, 3H), 3.14 (t, J=8.8 Hz, 2H), 2.80-2.67 (m, 2H), 2.33 (s, 3H), 2.26-2.24 (m, 2H), 2.10-2.08 (m, 3H). LCMS M/Z (M+H) 447.

Examples 185 & 186

(R)-1-[3-[5-(1,5-dimethylpyrazol-4-yl)indolin-1-yl]-1-tetrahydrofuran-3-yl-6,7-dihydro-4H-pyrazolo[4,3-c]pyridin-5-yl]ethanone and (S)-1-[3-[5-(1,5-dimethylpyrazol-4-yl)indolin-1-yl]-1-tetrahydrofuran-3-yl-6,7-dihydro-4H-pyrazolo[4,3-c]pyridin-5-yl]ethanone

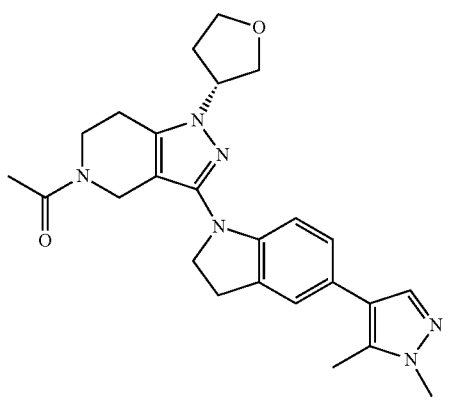 [SMILES: CC(=O)N1CCc2c(c(N3CCc4cc(-c5cnn(C)c5C)ccc43)nn2C2CCOC2)C1]

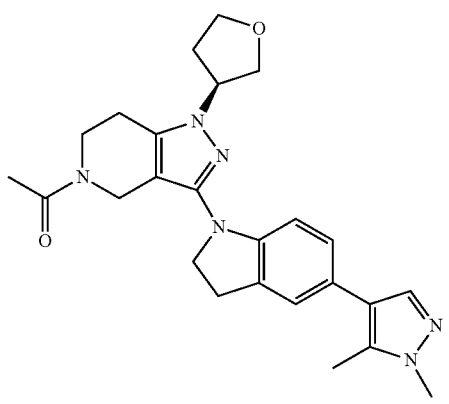

Racemic 1-[3-[5-(1,5-dimethylpyrazol-4-yl)indolin-1-yl]-1-tetrahydrofuran-3-yl-6,7-dihydro-4H-pyrazolo[4,3-c]pyridin-5-yl]ethanone (Example 184, 167 mg) was separated by using chiral SFC (Chiralcel OJ 250×30 mm I.D., 5 um; Supercritical $CO_2$/MeOH (0.1% $NH_3H_2O$)=65/35 at 50 mL/min) to give (R)-1-[3-[5-(1,5-dimethylpyrazol-4-yl)indolin-1-yl]-1-tetrahydrofuran-3-yl-6,7-dihydro-4H-pyrazolo[4,3-c]pyridin-5-yl]ethanone (76 mg, first peak) and (S)-1-[3-[5-(1,5-dimethylpyrazol-4-yl)indolin-1-yl]-1-tetrahydrofuran-3-yl-6,7-dihydro-4H-pyrazolo[4,3-c]pyridin-5-yl]ethanone (68 mg, second peak). Absolute configuration was arbitrarily assigned to each enantiomer. Example 185: $^1$H NMR (400 MHz, DMSO-$d_6$) δ 7.45-7.43 (m, 2H), 7.14 (s, 1H), 7.06-7.03 (m, 1H), 4.89-4.83 (m, 1H), 4.55-4.54 (m, 2H), 4.03-3.97 (m, 4H), 3.85-3.70 (m, 4H), 3.75 (s, 3H), 3.14 (t, J=8.8 Hz, 2H), 2.80-2.67 (m, 2H), 2.32 (s, 3H), 2.25-2.24 (m, 2H), 2.10-2.08 (m, 3H). LCMS M/Z (M+H) 447. Example 186: $^1$H NMR (400 MHz, DMSO-$d_6$) δ 7.45-7.43 (m, 2H), 7.14 (s, 1H), 7.06-7.03 (m, 1H), 4.90- 4.83 (m, 1H), 4.56-4.54 (m, 2H), 4.03-3.97 (m, 4H), 3.86-3.70 (m, 4H), 3.83 (s, 3H), 3.14 (t, J=8.8 Hz, 2H), 2.80-2.67 (m, 2H), 2.33 (s, 3H), 2.26-2.24 (m, 2H), 2.10-2.08 (m, 3H). LCMS M/Z (M+H) 447.

Example 187

4-[1-(5-acetyl-1-tetrahydrofuran-3-yl-6,7-dihydro-4H-pyrazolo[4,3-c]pyridin-3-yl)indolin-5-yl]-1-methyl-pyrazole-3-carbonitrile

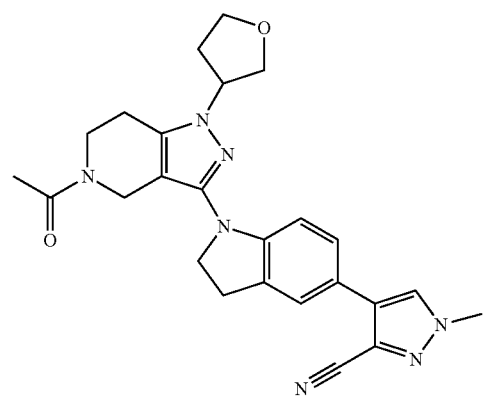 [SMILES: CC(=O)N1CCc2c(c(N3CCc4cc(-c5cn(C)nc5C#N)ccc43)nn2C2CCOC2)C1]

Step 1 tert-butyl 5-(3-cyano-1-methyl-1H-pyrazol-4-yl)indoline-1-carboxylate

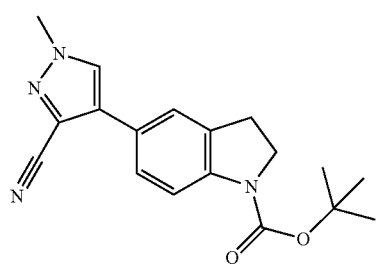 [SMILES: Cn1cc(-c2ccc3c(c2)CCN3C(=O)OC(C)(C)C)c(C#N)n1]

To a solution of tert-butyl 5-(4,4,5,5-tetramethyl-1,3,2-dioxaborolan-2-yl)indoline-1-carboxylate (1.8 g, 5.32 mmol) in dioxane (20 mL) and $H_2O$ (4 mL) was added $K_2CO_3$ (2 g, 14.52 mmol), [1,1'-bis(diphenylphosphino)ferrocene]dichloropalladium(II) (350 mg, 0.5 mmol) and 4-bromo-1-methyl-1H-pyrazole-3-carbonitrile (0.9 g, 4.84 mmol). The mixture was heated to 120° C. for 12 h under a nitrogen atmosphere. After cooling the reaction to room temperature, the mixture was concentrated in vacuo. The crude residue was purified by silica gel chromatography (petroleum ether/EtOAc=1:1) to give the title compound (1.13 g, 70%) as yellow solid. LCMS M/Z (M+H-t-Bu) 269.

Step 2

4-(indolin-5-yl)-1-methyl-1H-pyrazole-3-carbonitrile

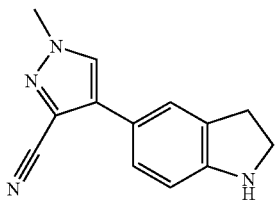 [SMILES: Cn1cc(-c2ccc3c(c2)CCN3)c(C#N)n1]

To a solution of tert-butyl 5-(3-cyano-1-methyl-1H-pyrazol-4-yl)indoline-1-carboxylate (1.13 g, 3.50 mmol) in EtOAc (10 mL) was added HCl/EtOAc (4 M, 4 mL). The mixture was stirred at room temperature for 1 h and concentrated in vacuo. Water (20 mL) was added and the mixture was made basic with solid NaHCO₃ to pH 8 and then extracted with EtOAc (50 mL×2). The combined organic layers were dried over anhydrous Na₂SO₄, filtered and concentrated in vacuo to give the title compound (0.79 g, 90%) as yellow solid.

Step 3

4-[1-(5-acetyl-1-tetrahydrofuran-3-yl-6,7-dihydro-4H-pyrazolo[4,3-c]pyridin-3-yl)indolin-5-yl]-1-methyl-pyrazole-3-carbonitrile

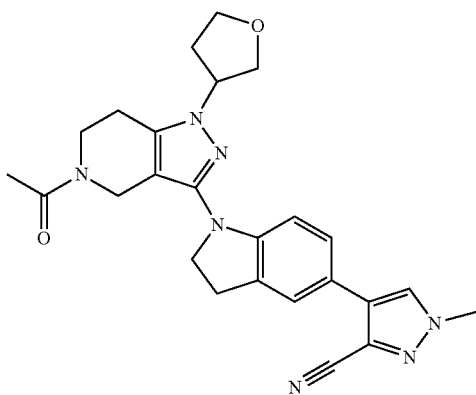 [SMILES: CC(=O)N1CCc2c(c(N3CCc4cc(-c5cn(C)nc5C#N)ccc43)nn2C2CCOC2)C1]

To a solution of 4-(indolin-5-yl)-1-methyl-1H-pyrazole-3-carbonitrile (500 mg, 2.23 mmol) in dioxane (10 mL) was added 1-(3-bromo-1-(tetrahydrofuran-3-yl)-6,7-dihydro-1H-pyrazolo[4,3-c]pyridin-5(4H)-yl)ethanone (770 mg, 2.45 mmol), chloro(2-dicyclohexylphosphino-2',6'-di-i-propoxy-1,1'-biphenyl)[2-(2-aminoethylphenyl)]palladium (II), methyl-tert-butylether adduct (160 mg, 0.22 mmol), 2-dicyclohexylphosphino-2',6'-di-i-propoxy-1,1'-biphenyl (100 mg, 0.22 mmol) and t-BuONa (856 mg, 8.91 mmol). The mixture was heated to 120° C. for 12 h. After cooling the reaction to room temperature, the mixture was concentrated in vacuo. The crude residue was purified by silica gel chromatography (DCM/MeOH=20:1) to give the title compound (250 mg, 24%) as a white solid. $^1$H NMR (400 MHz, DMSO-d₆) δ 8.24 (s, 1H), 7.49-7.32 (m, 3H), 4.90-4.84 (m, 1H), 4.56-4.54 (m, 2H), 4.10-3.99 (m, 4H), 3.95 (s, 3H), 3.86-3.70 (m, 4H), 3.17 (t, J=8.0 Hz, 2H), 2.80-2.68 (m, 2H), 2.26-2.25 (m, 2H), 2.10-2.08 (m, 3H). LCMS M/Z (M+H) 458.

Examples 188 & 189

(R)-4-[1-(5-acetyl-1-tetrahydrofuran-3-yl-6,7-dihydro-4H-pyrazolo[4,3-c]pyridin-3-yl)indolin-5-yl]-1-methyl-pyrazole-3-carbonitrile and (S)-4-[1-(5-acetyl-1-tetrahydrofuran-3-yl-6,7-dihydro-4H-pyrazolo[4,3-c]pyridin-3-yl)indolin-5-yl]-1-methyl-pyrazole-3-carbonitrile

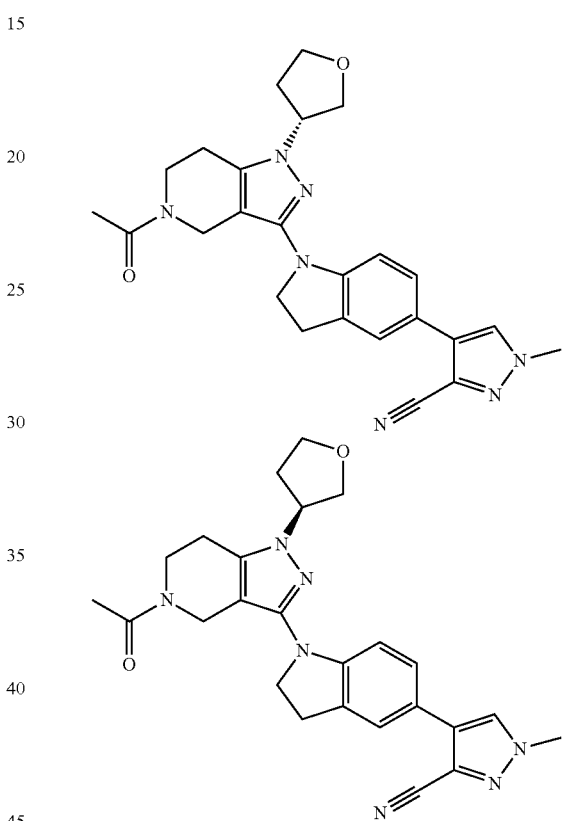

Racemic 4-(1-(5-acetyl-1-(tetrahydrofuran-3-yl)-4,5,6,7-tetrahydro-1H-pyrazolo[4,3-c]pyridin-3-yl)indolin-5-yl)-1-methyl-1H-pyrazole-3-carbonitrile (Example 187, 200 mg) was separated by using chiral SFC (Chiralcel OJ 250×30 mm I.D., 5 um; Supercritical CO₂/MeOH (0.1% NH₃H₂O) =60/40 at 80 mL/min) to give (R)-4-(1-(5-acetyl-1-(tetrahydrofuran-3-yl)-4,5,6,7-tetrahydro-1H-pyrazolo[4,3-c]pyridin-3-yl)indolin-5-yl)-1-methyl-1H-pyrazole-3-carbonitrile (62 mg, first peak) and (S)-4-(1-(5-acetyl-1-(tetrahydrofuran-3-yl)-4,5,6,7-tetrahydro-1H-pyrazolo[4,3-c]pyridin-3-yl)indolin-5-yl)-1-methyl-1H-pyrazole-3-carbonitrile (65 mg, second peak). Absolute configuration was arbitrarily assigned to each enantiomer. Example 188: $^1$H NMR (400 MHz, DMSO-d₆) δ 8.25 (s, 1H), 7.49-7.35 (m, 3H), 4.89-4.87 (m, 1H), 4.56-4.54 (m, 2H), 4.07-3.99 (m, 4H), 3.95 (s, 3H), 3.86-3.70 (m, 4H), 3.17 (t, J=8.0 Hz, 2H), 2.81-2.68 (m, 2H), 2.27-2.25 (m, 2H), 2.10-2.08 (m, 3H). LCMS M/Z (M+H) 458. Example 189: $^1$H NMR (400 MHz, DMSO-d₆) δ 8.25 (s, 1H), 7.49-7.33 (m, 3H), 4.89-4.85 (m, 1H), 4.56-4.54 (m, 2H), 4.10-3.99 (m, 4H), 3.95 (s, 3H), 3.86-

3.70 (m, 4H), 3.17 (t, J=8.0 Hz, 2H), 2.81-2.68 (m, 2H), 2.27-2.23 (m, 2H), 2.10-2.08 (s, 3H). LCMS M/Z (M+H) 458.

Example 190

1-[3-[6-fluoro-5-(1-methylpyrazol-4-yl)indolin-1-yl]-1-tetrahydrofuran-3-yl-6,7-dihydro-4H-pyrazolo[4,3-c]pyridin-5-yl]ethanone

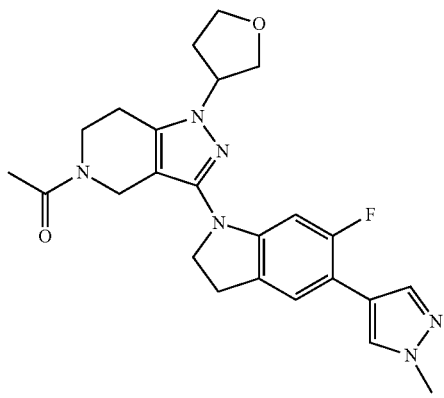 [SMILES: CC(=O)N1CCc2c(c(N3CCc4cc(-c5cnn(C)c5)c(F)cc43)nn2C2CCOC2)C1]

Step 1 tert-butyl 6-fluoroindoline-1-carboxylate

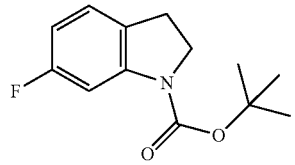 [SMILES: CC(C)(C)OC(=O)N1CCc2ccc(F)cc21]

To a solution of 6-fluoroindoline (5 g, 36.46 mmol) in DCM (100 mL) was added DMAP (445 mg, 3.65 mmol), triethylamine (15 mL, 109 mmol) and di-tert-butyl dicarbonate (9.5 g, 43.75 mmol). The resulting mixture was stirred at room temperature for 16 h. The mixture was concentrated in vacuo. The crude residue was purified by silica gel chromatography (petroleum ether/EtOAc=50:1) to give the title compound (6.8 g, 78%) as a white solid.

Step 2 tert-butyl 5-bromo-6-fluoroindoline-1-carboxylate

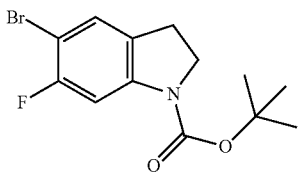 [SMILES: CC(C)(C)OC(=O)N1CCc2cc(Br)c(F)cc21]

To a solution of tert-butyl 6-fluoroindoline-1-carboxylate (3 g, 12.64 mmol) in DCM (50 mL), was added N-bromosuccinimide (2.7 g, 15.17 mmol). The mixture was stirred at room temperature for 2 h. The mixture was concentrated in vacuo. The crude residue was purified by silica gel chromatography (petroleum ether/EtOAc=20:1) to give the title compound (3.6 g, 90%) as a yellow solid.

Step 3 tert-butyl 6-fluoro-5-(1-methyl-1H-pyrazol-4-yl)indoline-1-carboxylate

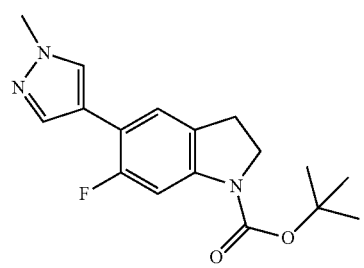 [SMILES: Cn1cc(-c2cc3c(cc2F)N(C(=O)OC(C)(C)C)CC3)cn1]

To a solution of tert-butyl 5-bromo-6-fluoroindoline-1-carboxylate (1.5 g, 4.74 mmol) in dioxane/H$_2$O (12 mL, 5/1) was added 1-methyl-4-(4,4,5,5-tetramethyl-1,3,2-dioxaborolan-2-yl)-1H-pyrazole (1.09 g, 5.22 mmol), K$_2$CO$_3$ (1.3 g, 9.5 mmol) and [1,1'-bis(diphenylphosphino)ferrocene]dichloropalladium(II) (340 mg, 0.47 mmol). The mixture was irradiated in a microwave at 120° C. for 0.5 h. After cooling the reaction to room temperature, the mixture was concentrated in vacuo. The crude residue was purified by silica gel chromatography (DCM/MeOH=20:1) to give the title compound (900 mg, 60%) as a yellow solid. LCMS M/Z (M+H) 318.

Step 4

6-fluoro-5-(1-methyl-1H-pyrazol-4-yl)indoline

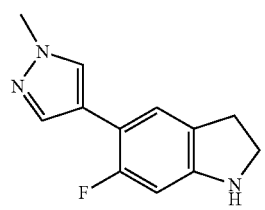 [SMILES: Cn1cc(-c2cc3c(cc2F)NCC3)cn1]

To a solution of tert-butyl 6-fluoro-5-(1-methyl-1H-pyrazol-4-yl)indoline-1-carboxylate (900 mg, 2.84 mmol) in EtOAc (10 mL) was added HCl in EtOAc (4 M, 2 mL). The resulting mixture was stirred at room temperature for 1 h and then concentrated in vacuo. Water (20 mL) was added and the mixture was made basic with solid NaHCO$_3$ to pH 8 and then extracted with EtOAc (50 mL×2). The combined organic layers were dried over anhydrous Na$_2$SO$_4$, filtered and concentrated in vacuo to give the title compound (400 mg, crude) as a light yellow solid that required no further purification.

479

Step 5

1-[3-[6-fluoro-5-(1-methylpyrazol-4-yl)indolin-1-yl]-1-tetrahydrofuran-3-yl-6,7-dihydro-4H-pyrazolo[4,3-c]pyridin-5-yl]ethanone

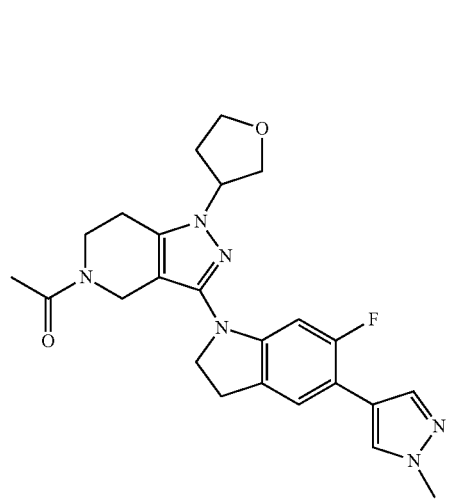 [SMILES: CC(=O)N1CCc2c(c(N3CCc4cc(-c5cnn(C)c5)c(F)cc43)nn2C2CCOC2)C1]

To a solution of 6-fluoro-5-(1-methyl-1H-pyrazol-4-yl)indoline (200 mg, 0.9 mmol) in dioxane (5 mL) was added 1-(3-bromo-1-(tetrahydrofuran-3-yl)-6,7-dihydro-1H-pyrazolo[4,3-c]pyridin-5(4H)-yl)ethanone (318 mg, 1.01 mmol), chloro(2-dicyclohexylphosphino-2',6'-di-i-propoxy-1,1'-biphenyl) [2-(2-aminoethylphenyl)]palladium(II), methyl-tert-butylether adduct (70 mg, 0.09 mmol), 2-dicyclohexylphosphino-2',6'-di-i-propoxy-1,1'-biphenyl (40 mg, 0.09 mmol) and tBuONa (306 mg, 3.18 mmol). The mixture was irradiated in a microwave at 120° C. for 0.5 h. After cooling the reaction to room temperature, the mixture was concentrated in vacuo. The crude residue was purified by silica gel chromatography (DCM/MeOH=10:1) to give the title compound (60 mg, 15%) as a white solid. $^1$H NMR (400 MHz, DMSO-$d_6$) δ 7.94 (s, 1H), 7.75 (s, 1H), 7.40-7.25 (m, 2H), 4.59-4.56 (m, 1H), 4.58-4.57 (m, 2H), 4.13-4.00 (m, 4H), 3.86-3.82 (m, 5H), 3.73-3.69 (m, 2H), 3.17-3.10, (m, 2H), 2.80-2.67 (m, 2H), 2.32-2.24 (m, 2H), 2.10-2.09 (m, 3H). LCMS M/Z (M+H) 451.

The Following Compound was Prepared in a Similar Fashion to Example 190

Example 191

| Example | Compound Name | NMR | m/z |
|---|---|---|---|
| Example 191 | 1-[3-[6-fluoro-5-(1-methylpyrazol-4-yl)indolin-1-yl]-1-methyl-6,7-dihydro-4H-pyrazolo[4,3-c]pyridin-5-yl]ethanone | $^1$H NMR (400 MHz, DMSO-$d_6$) δ 7.91 (s, 1H), 7.71 (s, 1H), 7.37-7.35 (m, 1H), 7.27-7.16 (m, 1H), 4.53-4.51 (m, 2H), 4.07-3.97 (m, 2H), 3.93 (s, 3H), 3.70-3.65 (m, 2 H), 3.61 (s, 3H), 3.11-3.06 (m, 2H), 2.74-2.60 (m, 2H), 2.07-2.05 (m, 3H) | 395 |

480

Example 192

1-[1-methyl-3-[3-methyl-5-(1-methylpyrazol-4-yl)indolin-1-yl]-6,7-dihydro-4H-pyrazol[4,3-c]pyridin-5-yl]ethanone

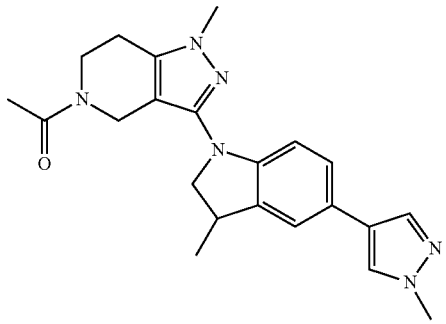 [SMILES: CC(=O)N1CCc2c(c(N3CC(C)c4cc(-c5cnn(C)c5)ccc43)nn2C)C1]

Step 1

5-bromo-3-methylindoline

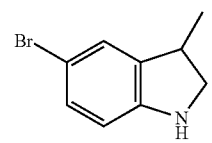

To a stirred solution of 5-bromo-3-methyl-1H-indole (1.0 g, 4.76 mmol) in AcOH (10 mL) was added NaBH$_3$CN (898 mg, 14.28 mmol) portionwise. The mixture was stirred at room temperature for 4 h under a nitrogen atmosphere. The mixture was concentrated in vacuo. The crude residue was purified by silica gel chromatography (petroleum ether/EtOAc=20:1) to give the title compound (400 mg, 40%) as a colorless oil.

Step 2

3-methyl-5-(1-methyl-1H-pyrazol-4-yl)indoline

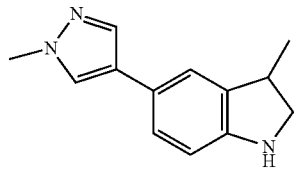 [SMILES: CC1CNc2ccc(-c3cnn(C)c3)cc21]

To a stirred solution of 5-bromo-3-methylindoline (200 mg, 0.94 mmol), 1-methyl-4-(4,4,5,5-tetramethyl-1,3,2-dioxaborolan-2-yl)-1H-pyrazole (216 mg, 1.04 mmol) and K₂CO₃ (391 mg, 2.83 mmol) in dioxane/H₂O (3.0 mL, 3:1) was added [1,1'-bis(diphenylphosphino)ferrocene]dichloropalladium(II) (70 mg, 0.094 mmol). The mixture was irradiated in a microwave at 120° C. for 0.5 h. After cooling the reaction to room temperature, water (10 mL) was added and the mixture was extracted with EtOAc (10 mL×3). The combined organic layers were washed with sat. aq. NaHCO₃ (10 mL×3), dried over anhydrous Na₂SO₄, filtered and concentrated in vacuo. The crude residue was purified by silica gel chromatography (petroleum ether/EtOAc=3:1) to give the title compound (120 mg, 60%) as a light yellow oil.

Step 3

1-[1-methyl-3-[3-methyl-5-(1-methylpyrazol-4-yl)indolin-1-yl]-6,7-dihydro-4H-pyrazolo[4,3-c]pyridin-5-yl]ethanone

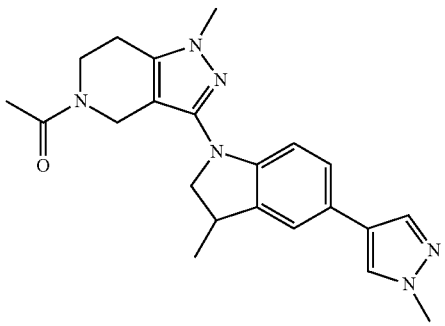 [SMILES: CC(=O)N1CCc2c(c(N3CC(C)c4cc(-c5cnn(C)c5)ccc43)nn2C)C1]

To a solution of 3-methyl-5-(1-methyl-1H-pyrazol-4-yl)indoline (110 mg, 0.52 mmol), 1-(3-bromo-1-methyl-6,7-dihydro-1H-pyrazolo[4,3-c]pyridin-5 (4H)-yl)ethanone (Intermediate B, 160 mg, 0.62 mmol) and t-BuONa (149 mg, 1.53 mmol) in dioxane (2.0 mL) was added chloro(2-dicyclohexylphosphino-2',6'-di-i-propoxy-1,1'-biphenyl)[2-(2-aminoethylphenyl)]palladium(II), methyl-tert-butylether adduct (42 mg, 0.052 mmol), 2-dicyclohexylphosphino-2',6'-di-i-propoxy-1,1'-biphenyl (24 mg, 0.052 mmol). The mixture was irradiated in a microwave at 120° C. for 45 min. After cooling the reaction to room temperature, water (10 mL) was added and the mixture was extracted with EtOAc (10 mL×3). The combined organic layers were washed with sat. aq. NaHCO₃ (10 mL×3), dried over anhydrous Na₂SO₄, filtered and concentrated in vacuo. The crude residue was purified by reverse phase chromatography (acetonitrile 25-55%/0.1% NH₄HCO₃ in water) to give the title compound (50 mg, 25%) as a white solid. ¹H NMR (400 MHz, DMSO-d₆) δ 7.93 (s, 1H), 7.70 (s, 1H), 7.29 (s, 1H), 7.23-7.15 (m, 2H), 4.48-4.46 (m, 2H), 4.14-4.06 (m, 1H), 3.80 (s, 3H), 3.68-3.65 (m, 2H), 3.59 (s, 3H), 3.47-3.41 (m, 2H), 2.74-2.58 (m, 2H), 2.07-2.04 (m, 3H), 1.31 (d, J=4.4 Hz, 3H). LCMS M/Z (M+H) 391.

Examples 193 & 194

(R)-1-[1-methyl-3-[3-methyl-5-(1-methylpyrazol-4-yl)indolin-1-yl]-6,7-dihydro-4H-pyrazolo[4,3-c]pyridin-5-yl]ethanone and (S)-1-[1-methyl-3-[3-methyl-5-(1-methylpyrazol-4-yl)indolin-1-yl]-6,7-dihydro-4H-pyrazolo[4,3-c]pyridin-5-yl]ethanone

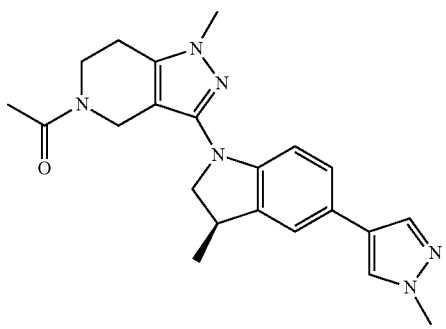

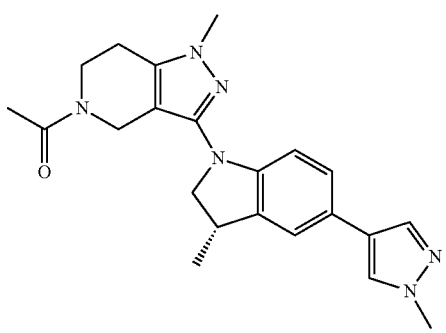

Racemic 1-[1-methyl-3-[3-methyl-5-(1-methylpyrazol-4-yl)indolin-1-yl]-6,7-dihydro-4H-pyrazolo[4,3-c]pyridin-5-yl]ethanone (Example 192, 160 mg) was separated by using chiral SFC (Chiralpak AS-H 150*4.6 mm I.D., 5 um Mobile phase: ethanol (0.05% diethylamine) in CO₂ from 5% to 40% Flow rate: 60 mL/min) to give (R)-1-[1-methyl-3-[3-methyl-5-(1-methylpyrazol-4-yl)indolin-1-yl]-6,7-dihydro-4H-pyrazolo[4,3-c]pyridin-5-yl]ethanone (38 mg, first peak) and (S)-1-[1-methyl-3-[3-methyl-5-(1-methylpyrazol-4-yl)indolin-1-yl]-6,7-dihydro-4H-pyrazolo[4,3-c]pyridin-5-yl]ethanone (42 mg, second peak). Absolute configuration was arbitrarily assigned to each enantiomer. Example 193: ¹H NMR (400 MHz, DMSO-d₆) δ 7.93 (s, 1H), 7.70 (s, 1H), 7.29 (s, 1H), 7.23-7.15 (m, 2H), 4.48-4.47 (m, 2H), 4.14-4.06 (m, 1H), 3.80 (s, 3H), 3.68-3.65 (m, 2H), 3.59 (s, 3H), 3.47-3.41 (m, 2H), 2.74-2.58 (m, 2H), 2.07-2.04 (m, 3H), 1.31 (d, J=4.4 Hz, 3H). LCMS M/Z (M+H) 391. Example 194: ¹H NMR (400 MHz, DMSO-d₆) δ 7.93 (s, 1H), 7.70 (s, 1H), 7.29 (s, 1H), 7.23-7.15 (m, 2H), 4.48-4.47 (m, 2H), 4.14-4.06 (m, 1H), 3.80 (s, 3H), 3.68-3.65 (m, 2H), 3.59 (s, 3H), 3.47-3.41 (m, 2H), 2.74-2.58 (m, 2H), 2.07-2.04 (m 3H), 1.31 (d, J=4.4 Hz, 3H). LCMS M/Z (M+H) 391.

Examples 195 & 196

(R,R)-1-[3-[3-methyl-5-(1-methylpyrazol-4-yl)indolin-1-yl]-1-tetrahydrofuran-3-yl-6,7-dihydro-4H-pyrazolo[4,3-c]pyridin-5-yl]ethanone and (R,S)-1-[3-[3-methyl-5-(1-methylpyrazol-4-yl)indolin-1-yl]-1-tetrahydrofuran-3-yl-6,7-dihydro-4H-pyrazolo[4,3-c]pyridin-5-yl]ethanone

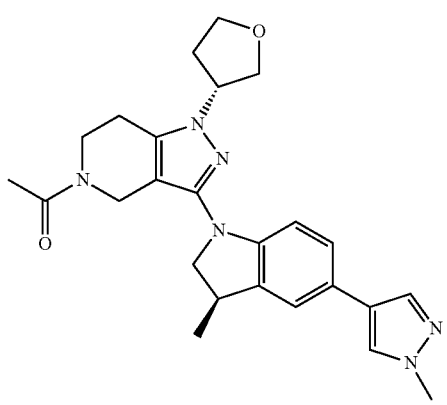

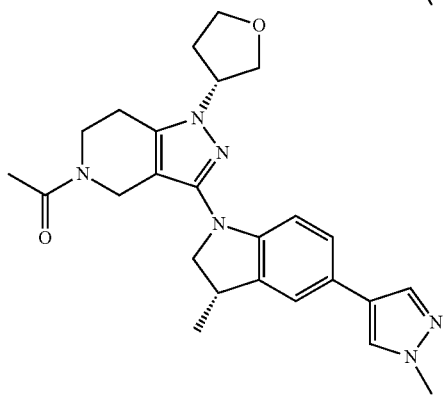

To a solution of 3-methyl-5-(1-methyl-1H-pyrazol-4-yl)indoline (185 mg, 0.87 mmol), (R)-1-(3-bromo-1-(tetrahydrofuran-3-yl)-6,7-dihydro-1H-pyrazolo[4,3-c]pyridin-5(4H)-yl)ethanone (300 mg, 0.95 mmol) and t-BuONa (25 mg, 2.6 mmol) in dioxane (5 mL), was added chloro(2-dicyclohexylphosphino-2',6'-di-i-propoxy-1,1'-biphenyl)[2-(2-aminoethylphenyl)]palladium(ii), methyl-tert-butylether adduct (74 mg, 0.088 mmol), 2-dicyclohexylphosphino-2',6'-di-i-propoxy-1,1'-biphenyl (41 mg, 0.088 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO₃ (10 mL×3), dried over anhydrous Na₂SO₄ and concentrated in vacuo. The crude residue was purified by reverse phase chromatography (acetonitrile 25-55%/0.1% NH₄HCO₃ in water) to give racemic (R)-1-[1-methyl-3-[3-methyl-5-(1-methylpyrazol-4-yl)indolin-1-yl]-6,7-dihydro-4H-pyrazolo[4,3-c]pyridin-5-yl]ethanone (120 mg, 31%) as a white solid which was separated by using chiral SFC (Chiralcel OJ-3 50*4.6 mm I.D., 3 um Mobile phase: ethanol (0.05% diethylamine) in CO₂ from 5% to 40% Flow rate: 80 mL/min) to give (R,R)-1-[3-[3-methyl-5-(1-methylpyrazol-4-yl)indolin-1-yl]-1-tetrahydrofuran-3-yl-6,7-dihydro-4H-pyrazolo[4,3-c]pyridin-5-yl]ethanone (32 mg, first peak) and (R,S)-1-[3-[3-methyl-5-(1-methylpyrazol-4-yl)indolin-1-yl]-1-tetrahydrofuran-3-yl-6,7-dihydro-4H-pyrazolo[4,3-c]pyridin-5-yl]ethanone (24 mg, second peak). Absolute configuration was arbitrarily assigned to each diastereomer. Example 195: ¹H NMR (400 MHz, DMSO-d₆) δ 7.95 (s, 1H), 7.72 (s, 1H), 7.40-7.23 (m, 3H), 4.88-4.83 (m, 1H), 4.54-4.53 (m, 2H), 4.16-4.02 (m, 1H), 4.00-3.98 (m, 2H), 3.85-3.77 (m, 7H), 3.68-3.44 (m, 2H), 2.78-2.66 (m, 2H), 2.24-2.21 (m, 2H), 2.09-2.07 (m, 3H), 1.34 (d, J=6.4 Hz, 3H). LCMS M/Z (M+H) 447. Example 196: ¹H NMR (400 MHz, DMSO-d₆) δ 7.95 (s, 1H), 7.72 (s, 1H), 7.40-7.23 (m, 3H), 4.88-4.83 (m, 1H), 4.54-4.53 (m, 2H), 4.16-4.02 (m, 1H), 4.00-3.98 (m, 2H), 3.85-3.77 (m, 7H), 3.68-3.44 (m, 2H), 2.78-2.66 (m, 2H), 2.24-2.21 (m, 2H), 2.09-2.07 (m, 3H), 1.34 (d, J=6.4 Hz, 3H). LCMS M/Z (M+H) 447.

Examples 197 & 198

(S,S)-1-[3-[3-methyl-5-(1-methylpyrazol-4-yl)indolin-1-yl]-1-tetrahydrofuran-3-yl-6,7-dihydro-4H-pyrazolo[4,3-c]pyridin-5-yl]ethanone and (S,R)-1-[3-[3-methyl-5-(1-methylpyrazol-4-yl)indolin-1-yl]-1-tetrahydrofuran-3-yl-6,7-dihydro-4H-pyrazolo[4,3-c]pyridin-5-yl]ethanone

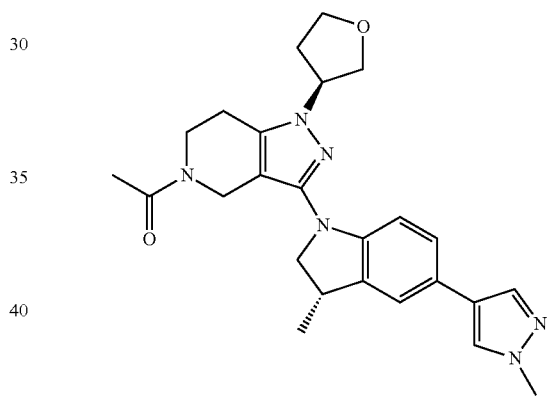

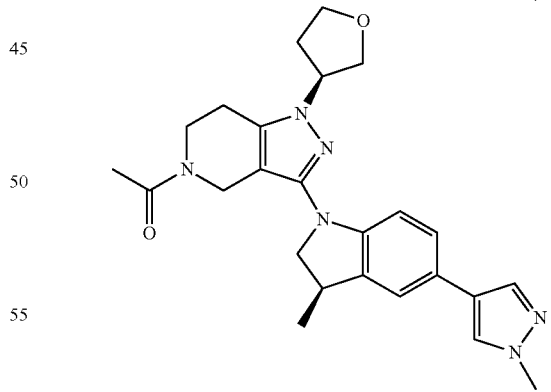

To a solution of 3-methyl-5-(1-methyl-1H-pyrazol-4-yl)indoline (185 mg, 0.87 mmol), (S) 1-(3-bromo-1-(tetrahydrofuran-3-yl)-6,7-dihydro-1H-pyrazolo[4,3-c]pyridin-5(4H)-yl)ethanone (Intermediate G, 300 mg, 0.95 mmol) and t-BuONa (25 mg, 2.6 mmol) in dioxane (5 mL), was added chloro(2-dicyclohexylphosphino-2',6'-di-i-propoxy-1,1'-biphenyl)[2-(2-aminoethylphenyl)]palladium(II), methyl-tert-butylether adduct (74 mg, 0.088 mmol) and 2-dicyclohexylphosphino-2',6'-di-i-propoxy-1,1'-biphenyl (41 mg, 0.088 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO₃ (10 mL×3), dried over anhydrous Na₂SO₄ and concentrated in vacuo. The crude residue was purified by reverse phase chromatography (acetonitrile 25-55%/0.1% NH₄HCO₃ in water) to give racemic 1-(3-(3-methyl-5-(1-methyl-1H-pyrazol-4-yl)indolin-1-yl)-1-((S)-tetrahydrofuran-3-yl)-6,7-dihydro-1H-pyrazolo[4,3-c]pyridin-5(4H)-yl)ethanone (130 mg, 34%) as a white solid that was separated by chiral SFC (Chiralpak AD-3 150×4.6 mm I.D., 3 um Mobile phase: 40% of ethanol (0.05% diethylamine) in CO₂ Flow rate: 50 mL/min) to give (S,S)-1-[3-[3-methyl-5-(1-methylpyrazol-4-yl)indolin-1-yl]-1-tetrahydrofuran-3-yl-6,7-dihydro-4H-pyrazolo[4,3-c]pyridin-5-yl]ethanone (36 mg, first peak) and (R,S)-1-[3-[3-methyl-5-(1-methylpyrazol-4-yl)indolin-1-yl]-1-tetrahydrofuran-3-yl-6,7-dihydro-4H-pyrazolo[4,3-c]pyridin-5-yl]ethanone (43 mg, second peak). Absolute configuration was arbitrarily assigned to each diastereomer. Example 197: ¹H NMR (400 MHz, DMSO-d₆) δ 7.95 (s, 1H), 7.72 (s, 1H), 7.40-7.23 (m, 3H), 4.88-4.83 (m, 1H), 4.54-4.53 (m, 2H), 4.16-4.02 (m, 1H), 4.00-3.98 (m, 2H), 3.85-3.77 (m, 7H), 3.68-3.44 (m, 2H), 2.78-2.66 (m, 2H), 2.24-2.21 (m, 2H), 2.09-2.07 (m, 3H), 1.34 (d, J=6.4 Hz, 3H). LCMS M/Z (M+H) 447. Example 198: ¹H NMR (400 MHz, DMSO-d₆) δ 7.95 (s, 1H), 7.72 (s, 1H), 7.40-7.23 (m, 3H), 4.88-4.83 (m, 1H), 4.54-4.53 (m, 2H), 4.16-4.02 (m, 1H), 4.00-3.98 (m, 2H), 3.85-3.77 (m, 7H), 3.68-3.44 (m, 2H), 2.78-2.66 (m, 2H), 2.24-2.21 (m, 2H), 2.09-2.07 (m, 3H), 1.34 (d, J=6.4 Hz, 3H). LCMS M/Z (M+H) 447.

Example 199

1-[3-[3,3-dimethyl-5-(1-methylpyrazol-4-yl)indolin-1-yl]-1-methyl-6,7-dihydro-4H-pyrazolo[4,3-c]pyridin-5-yl]ethanone

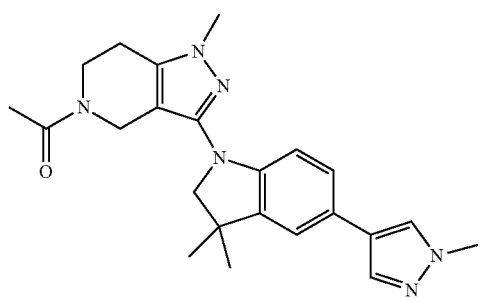 [SMILES: CC(=O)N1CCc2c(c(N3CC(C)(C)c4cc(-c5cnn(C)c5)ccc43)nn2C)C1]

Step 1

5-bromo-3,3-dimethylindoline

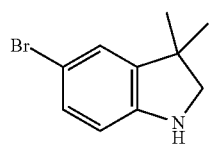

To a solution of (4-bromophenyl)hydrazine (6.0 g, 26.8 mmol) in AcOH (60 mL) was added isobutyraldehyde (1.94 g, 26.8 mmol) dropwise. The mixture was heated to 60° C. for 3 h under a nitrogen atmosphere. After cooling the reaction to room temperature, NaBH(OAc)₃ (5.69 g, 26.8 mmol) was added in portionwise at 0° C. The mixture was stirred at room temperature for an additional 1 h. The mixture was concentrated in vacuo. The crude residue was purified by silica gel chromatography (petroleum ether/EtOAc=10:1) to give the title compound (600 mg, 10%) as a yellow oil.

Step 2

3,3-dimethyl-5-(1-methyl-1H-pyrazol-4-yl)indoline

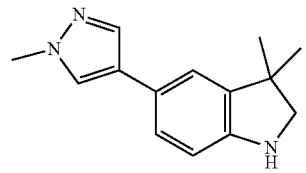

To a solution of 5-bromo-3,3-dimethylindoline (360 mg, 1.59 mmol), 1-methyl-4-(4,4,5,5-tetramethyl-1,3,2-dioxaborolan-2-yl)-1H-pyrazole (364 mg, 1.75 mmol), K₂CO₃ (660 mg, 4.78 mmol) in dioxane/H₂O (3.0 mL, 3:1) was added [1,1'-bis(diphenylphosphino)ferrocene]dichloropalladium(II) (117 mg, 0.160 mmol). The mixture was heated to 120° C. for 0.5 h under microwave conditions. After cooling the reaction to room temperature, water (10 mL) was added and the mixture was extracted with EtOAc (10 mL×3). The combined organic layers were washed with sat. aq. NaHCO₃ (10 mL×3), dried over anhydrous Na₂SO₄ and concentrated in vacuo. The crude residue was purified by silica gel chromatography (petroleum ether/EtOAc=3:1) to give the title compound (140 mg, 39%) as a light yellow oil.

Step 3

1-[3-[3,3-dimethyl-5-(1-methylpyrazol-4-yl)indolin-1-yl]-1-methyl-6,7-dihydro-4H-pyrazolo[4,3-c]pyridin-5-yl]ethanone

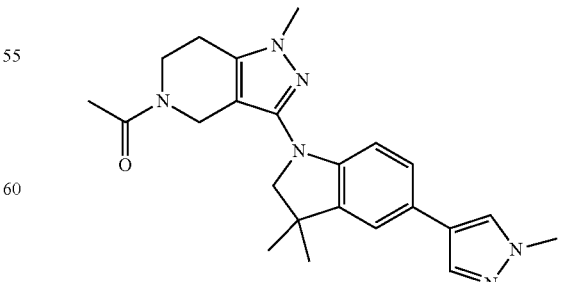

To a solution of 3,3-dimethyl-5-(1-methyl-1H-pyrazol-4-yl)indoline (200 mg, 0.88 mmol), 1-(3-bromo-1-methyl-6, 7-dihydro-1H-pyrazolo[4,3-c]pyridin-5(4H)-yl)ethanone (Intermediate B, 272 mg, 1.06 mmol) and t-BuONa (254 mg, 2.64 mmol) in dioxane (5 mL) was added chloro(2-dicyclohexylphosphino-2',6'-di-i-propoxy-1,1'-biphenyl)[2-(2-aminoethylphenyl)]palladium(II), methyl-tert-butylether adduct (74 mg, 0.088 mmol) and 2-dicyclohexylphosphino-2',6'-di-i-propoxy-1,1'-biphenyl (41 mg, 0.088 mmol). The mixture was irradiated in a microwave at 120° C. for 45 min. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by reverse phase chromatography (acetonitrile 25-55%/ 0.1% NH$_4$HCO$_3$ in water) to give the title compound (65 mg, 18%) as a white solid. $^1$H NMR (400 MHz, CDCl$_3$) δ 7.68 (s, 1H), 7.52-7.51 (m, 1H), 7.29 (s, 1H), 7.21-6.88 (m, 3H), 4.62 (s, 1H), 4.40 (s, 1H), 3.92-3.91 (m, 4H), 3.76-3.72 (m, 3H), 3.68 (s, 3H), 2.75-2.67 (m, 2H), 2.19-2.12 (m, 3H), 1.40-1.37 (m, 3H). LCMS M/Z (M+H) 405.

Example 200

1-[3-[3-ethyl-5-(1-methylpyrazol-4-yl)indolin-1-yl]-1-tetrahydrofuran-3-yl-6,7-dihydro-4H-pyrazolo[4,3-c]pyridin-5-yl]ethanone

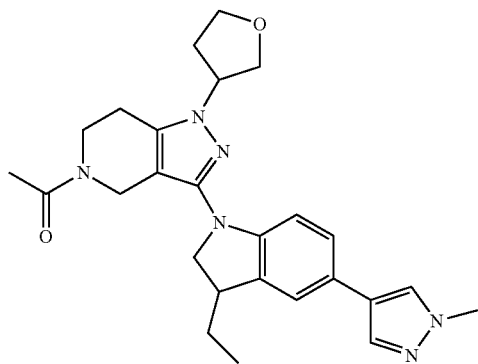 [SMILES: CCC1CN(c2nn(C3CCOC3)c3c2CN(C(C)=O)CC3)c2ccc(-c3cnn(C)c3)cc21]

Step 1

5-bromo-3-ethyl-1H-indole

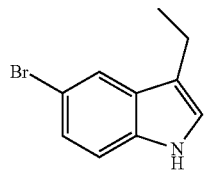

To a solution of (4-bromophenyl)hydrazine hydrochloride (5.0 g, 22.4 mmol) in AcOH (20 mL) was added butyraldehyde (1.61 g, 22.4 mmol) dropwise. The mixture was heated to 60° C. for 3 h under a nitrogen atmosphere. After cooling the reaction to room temperature, the mixture was concentrated in vacuo. The crude residue was purified by silica gel chromatography (petroleum ether/EtOAc=10:1) to give the title compound (800 mg, 16%) as a yellow oil.

Step 2

3-ethyl-5-(1-methyl-1H-pyrazol-4-yl)-1H-indole

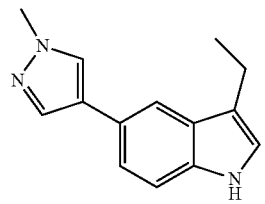 [SMILES: CCc1c[nH]c2ccc(-c3cnn(C)c3)cc12]

To a solution of 5-bromo-3-ethyl-1H-indole (800 mg, 3.57 mmol), 1-methyl-4-(4,4,5,5-tetramethyl-1,3,2-dioxaborolan-2-yl)-1H-pyrazole (891 mg, 4.28 mmol) and K$_2$CO$_3$ (1.48 g, 10.7 mmol) in dioxane/H$_2$O (10 mL, 4:1) was added [1,1'-bis(diphenylphosphino)ferrocene]dichloropalladium (II) (250 mg, 0.36 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$, filtered and concentrated in vacuo. The crude residue was purified by silica gel chromatography (petroleum ether/EtOAc=3:1) to give the title compound (500 mg, 62%) as a yellow solid.

Step 3

3-ethyl-5-(1-methyl-1H-pyrazol-4-yl)indoline

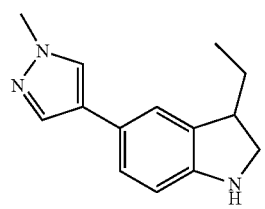 [SMILES: CCC1CNc2ccc(-c3cnn(C)c3)cc21]

To a stirred solution of 3-ethyl-5-(1-methyl-1H-pyrazol-4-yl)-1H-indole (0.5 g, 2.22 mmol) in AcOH (6 mL) was added NaBH$_3$CN (418 mg, 6.66 mmol) portionwise. The mixture was stirred at room temperature for 3 h under a nitrogen atmosphere. The mixture was concentrated in vacuo. The crude residue was purified by silica gel chromatography (petroleum ether/EtOAc=3:1) to give the title compound (280 mg, 56%) as a yellow oil.

Step 4

1-[3-[3-ethyl-5-(1-methylpyrazol-4-yl)indolin-1-yl]-1-tetrahydrofuran-3-yl-6,7-dihydro-4H-pyrazolo[4,3-c]pyridin-5-yl]ethanone

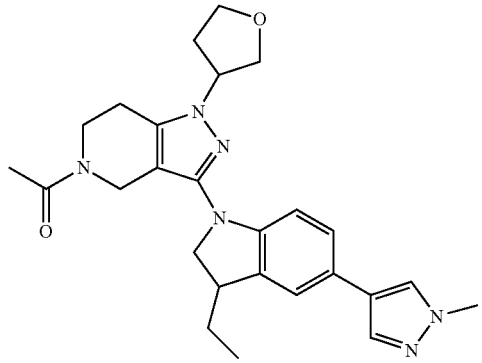 [SMILES: CCC1CN(c2nn(C3CCOC3)c3c2CN(C(C)=O)CC3)c2ccc(-c3cnn(C)c3)cc21]

To a solution of 3-ethyl-5-(1-methyl-1H-pyrazol-4-yl)indoline (150 mg, 0.66 mmol), 1-(3-bromo-1-(tetrahydrofuran-3-yl)-6,7-dihydro-1H-pyrazolo[4,3-c]pyridin-5 (4H)-yl)ethanone (249 mg, 0.79 mmol) and t-BuONa (190 mg, 1.98 mmol) in dioxane (3 mL) was added chloro(2-dicyclohexylphosphino-2',6'-di-i-propoxy-1,1'-biphenyl)[2-(2-aminoethylphenyl)]palladium(II), methyl-tert-butylether adduct (56 mg, 0.068 mmol) and 2-dicyclohexylphosphino-2',6'-di-i-propoxy-1,1'-biphenyl (32 mg, 0.068 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by reverse phase chromatography (acetonitrile 25-55%/0.1% NH$_4$HCO$_3$ in water) to give the title compound (33 mg, 11%) as a white solid. $^1$H NMR (400 MHz, CDCl$_3$) δ 7.95 (s, 1H), 7.71 (s, 1H), 7.38-7.25 (m, 3H), 4.86-4.85 (m, 1H), 4.57-4.52 (m, 2H), 4.09-3.97 (m, 3H), 3.85-3.62 (m, 9H), 2.78-2.66 (m, 2H), 2.24-2.23 (m, 2H), 2.09-2.07 (m, 3H), 1.88-1.83 (m, 1H), 1.60-1.55 (m, 1H), 0.96 (t, J=3.2 Hz, 3H). LCMS M/Z (M+H) 461.

Examples 201 & 202

(S)-1-[3-[3-ethyl-5-(1-methylpyrazol-4-yl)indolin-1-yl]-1-(oxetan-3-yl)-6,7-dihydro-4H-pyrazolo[4,3-c]pyridin-5-yl]ethanone and (R)-1-[3-[3-ethyl-5-(1-methylpyrazol-4-yl)indolin-1-yl]-1-(oxetan-3-yl)-6,7-dihydro-4H-pyrazolo[4,3-c]pyridin-5-yl]ethanone

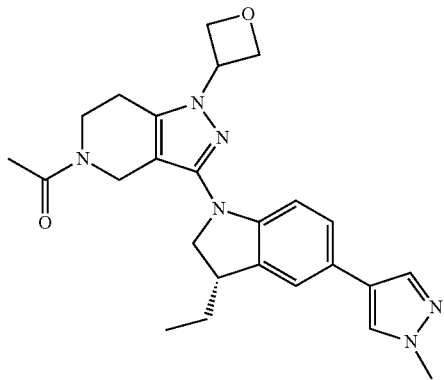

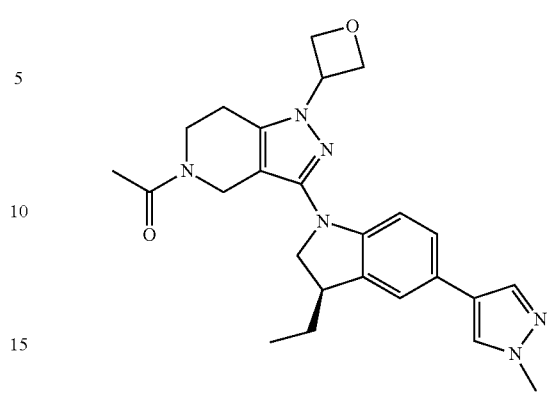

To a solution of 3-ethyl-5-(1-methyl-1H-pyrazol-4-yl)indoline (320 mg, 1.41 mmol), 1-(3-bromo-1-(oxetan-3-yl)-6,7-dihydro-1H-pyrazolo[4,3-c]pyridin-5(4H)-yl)ethanone (423 mg, 1.41 mmol) and t-BuONa (406 mg, 4.22 mmol) in dioxane (3 mL) was added chloro(2-dicyclohexylphosphino-2',6'-di-i-propoxy-1,1'-biphenyl)[2-(2-aminoethylphenyl)]palladium(II), methyl-tert-butylether adduct (114 mg, 0.14 mmol) and 2-dicyclohexylphosphino-2',6'-di-i-propoxy-1,1'-biphenyl (63 mg, 0.14 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by reverse phase chromatography (acetonitrile 25-55%/0.1% NH$_4$HCO$_3$ in water) to give racemic 1-[3-[3-ethyl-5-(1-methylpyrazol-4-yl)indolin-1-yl]-1-(oxetan-3-yl)-6,7-dihydro-4H-pyrazolo[4,3-c]pyridin-5-yl]ethanone (175 mg, 28%) as a white solid that was separated by chiral SFC (Chiralpak AD-3 50*4.6 mm I.D., 3 um; Mobile phase: ethanol (0.05% diethylamine) in CO$_2$ from 5% to 40%; Flow rate: 80 mL/min) to give (S)-1-[3-[3-ethyl-5-(1-methylpyrazol-4-yl)indolin-1-yl]-1-(oxetan-3-yl)-6,7-dihydro-4H-pyrazolo[4,3-c]pyridin-5-yl]ethanone (30 mg, first peak) and (R)-1-[3-[3-ethyl-5-(1-methylpyrazol-4-yl)indolin-1-yl]-1-(oxetan-3-yl)-6,7-dihydro-4H-pyrazolo[4,3-c]pyridin-5-yl]ethanone (30 mg, second peak). Absolute configuration was arbitrarily assigned to each enantiomer. Example 201: $^1$H NMR (400 MHz, DMSO-d$_6$) δ 7.97 (s, 1H), 7.73 (s, 1H), 7.51-7.41 (m, 1H), 7.34-7.28 (m, 2H), 5.43-5.38 (m, 1H), 4.97-4.94 (m, 2H), 4.85-4.81 (m, 2H), 4.55-4.22 (m, 2H), 4.20-4.12 (m, 1H), 3.83 (s, 3H), 3.71-3.63 (m, 3H), 2.74-2.60 (m, 2H), 2.08-2.07 (m, 3H), 1.90-1.84 (m, 1H), 1.61-1.55 (m, 1H), 0.99-0.95 (m, 3H). LCMS M/Z (M+H) 447. Example 202: $^1$H NMR (400 MHz, DMSO-d$_6$) δ 7.97 (s, 1H), 7.73 (s, 1H), 7.51-7.41 (m, 1H), 7.34-7.28 (m, 2H), 5.43-5.38 (m, 1H), 4.97-4.94 (m, 2H), 4.85-4.81 (m, 2H), 4.55-4.22 (m, 2H), 4.20-4.12 (m, 1H), 3.83 (s, 3H), 3.71-3.63 (m, 3H), 2.74-2.60 (m, 2H), 2.08-2.07 (m, 3H), 1.90-1.84 (m, 1H), 1.61-1.55 (m, 1H), 0.99-0.95 (m, 3H). LCMS M/Z (M+H) 447.

Example 203

1-(5-acetyl-1-methyl-6,7-dihydro-4H-pyrazolo[4,3-c]pyridin-3-yl)indoline-6-carbonitrile

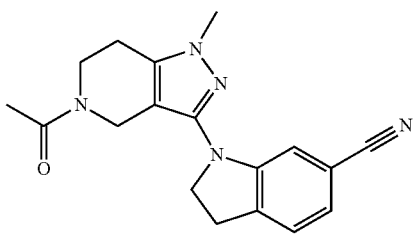 [SMILES: CC(=O)N1CCc2c(c(N3CCc4ccc(C#N)cc43)nn2C)C1]

Step 1 indoline-6-carbonitrile

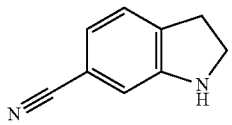 [SMILES: N#Cc1ccc2c(c1)NCC2]

To a stirred solution of 1H-indole-6-carbonitrile (3.0 g, 21.1 mmol) in AcOH (10 mL) was added NaBH₃CN (3.98 g, 63.3 mmol) portionwise. The mixture was stirred at room temperature for 16 h under a nitrogen atmosphere. The mixture was concentrated in vacuo. The crude residue was purified by silica gel chromatography (petroleum ether/EtOAc=5:1) to give the title compound (800 mg, 26%) as a white solid.

Step 2

1-(5-acetyl-1-methyl-6,7-dihydro-4H-pyrazolo[4,3-c]pyridin-3-yl)indoline-6-carbonitrile

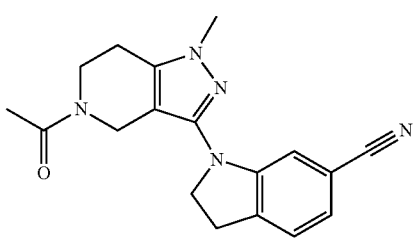 [SMILES: CC(=O)N1CCc2c(c(N3CCc4ccc(C#N)cc43)nn2C)C1]

To a solution of indoline-6-carbonitrile (120 mg, 0.83 mmol), 1-(3-bromo-1-methyl-6,7-dihydro-1H-pyrazolo[4,3-c]pyridin-5(4H)-yl)ethanone (Intermediate B, 258 mg, 1.0 mmol) and t-BuONa (200 mg, 2.08 mmol) in dioxane (5 mL) was added chloro(2-dicyclohexylphosphino-2',6'-di-i-propoxy-1,1'-biphenyl)[2-(2-aminoethylphenyl)]palladium (II), methyl-tert-butylether adduct (68 mg, 0.083 mmol) and 2-dicyclohexylphosphino-2',6'-di-i-propoxy-1,1'-biphenyl (37 mg, 0.083 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO₃ (10 mL×3), dried over anhydrous Na₂SO₄ and concentrated in vacuo. The crude residue was purified by reverse phase chromatography (acetonitrile 25-55%/0.1% NH₄HCO₃ in water) to give the title compound (150 mg, 56%) as colorless oil. $^1$H NMR (400 MHz, CDCl₃) δ 7.54-7.34 (m, 1H), 7.18-7.13 (m, 1H), 7.05-7.01 (m, 1H), 4.62-4.44 (m, 2H), 4.06-4.02 (m, 2H), 3.92-3.91 (m, 1H), 3.77-3.71 (m, 4H), 3.24-3.18 (m, 2H), 3.78-3.70 (m, 2H), 2.20-2.16 (m, 3H). LCMS M/Z (M+H) 322.

Example 204

1-(3-(6-(2H-tetrazol-5-yl)indolin-1-yl)-1-methyl-6,7-dihydro-1H-pyrazolo[4,3-c]pyridin-5(4H)-yl)etha-none

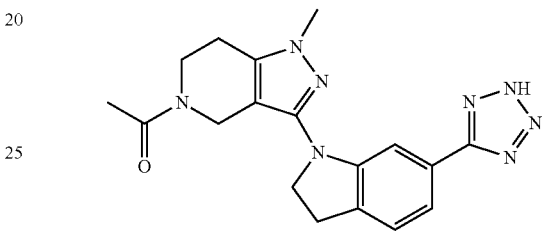

To a stirred solution of 1-(5-acetyl-1-methyl-4,5,6,7-tetrahydro-1H-pyrazolo[4,3-c]pyridin-3-yl)indoline-6-carbonitrile (Example 203, 190 mg, 0.59 mmol) in DMF (3.0 mL) was added tri-n-butuytin azide (390 mg, 1.18 mmol) in portions. The mixture was heated to 120° C. for 24 h under a nitrogen atmosphere. The mixture was concentrated in vacuo. The crude residue was purified by reverse phase chromatography (acetonitrile 25-55%/0.1% NH₄HCO₃ in water) to give the title compound (8 mg, 4%) as a white solid. $^1$H NMR (400 MHz, CDCl₃) δ 7.58-7.57 (m, 1H), 7.22-7.20 (m, 1H), 6.93 (s, 1H), 4.57 (s, 2H), 4.01 (t, J=8.0 Hz, 2H), 3.86-3.83 (m, 2H), 3.63 (s, 3H), 3.12 (m, J=8.0 Hz, 2H), 2.80-2.77 (m, 2H), 2.26 (s, 3H). LCMS M/Z (M+H) 365.

Example 205

1-[3-[5'-(1-methylpyrazol-4-yl)spiro[cyclobutane-1,3'-indoline]-1'-yl]-1-tetrahydrofuran-3-yl-6,7-dihydro-4H-pyrazolo[4,3-c]pyridin-5-yl]ethanone

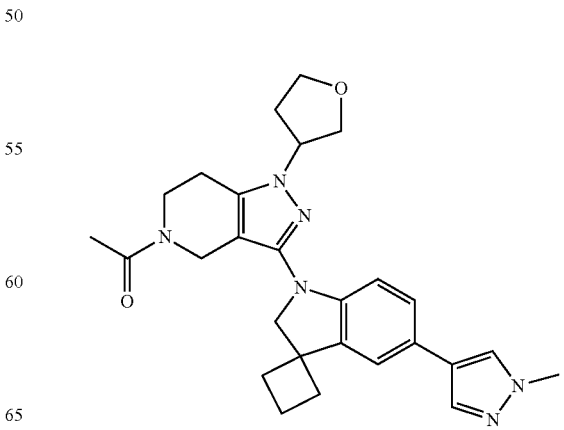

Step 1

5'-bromospiro[cyclobutane-1,3'-indole]

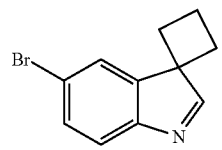 [SMILES: Brc1ccc2c(c1)C1(C=N2)CCC1]

To a solution of (4-bromophenyl)hydrazine hydrochloride (5.0 g, 22.4 mmol) in AcOH (20 mL) was added cyclobutanecarbaldehyde (1.61 g, 22.4 mmol) dropwise. The mixture was heated to 60° C. for 3 h under under a nitrogen atmosphere. The mixture was concentrated in vacuo. The crude residue was purified by column chromatography (petroleum ether/EtOAc=10:1) to give the title compound (2.5 g, 47%) as a yellow oil.

Step 2

5'-(1-methyl-1H-pyrazol-4-yl)spiro[cyclobutane-1,3'-indole]

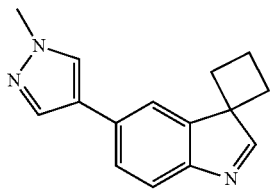 [SMILES: Cn1cc(-c2ccc3c(c2)C2(C=N3)CCC2)cn1]

To a stirred solution of 5'-bromospiro[cyclobutane-1,3'-indole](1.2 g, 5.08 mmol), 1-methyl-4-(4,4,5,5-tetramethyl-1,3,2-dioxaborolan-2-yl)-1H-pyrazole (1.27 g, 6.10 mmol) and K$_2$CO$_3$ (2.11 g, 15.25 mmol) in dioxane/H$_2$O (10 mL, 4:1) was added [1,1'-bis(diphenylphosphino)ferrocene]dichloropalladium(II) (450 mg, 0.5 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by silica gel chromatography (petroleum ether/EtOAc=3:1) to give the title compound (0.65 g, 54%) as a yellow solid. LCMS M/Z (M+H) 238.

Step 1

5'-(1-methyl-1H-pyrazol-4-yl)spiro[cyclobutane-1,3'-indoline]

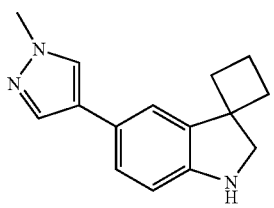 [SMILES: Cn1cc(-c2ccc3c(c2)C2(CCC2)CN3)cn1]

To a solution of 5'-(1-methyl-1H-pyrazol-4-yl)spiro[cyclobutane-1,3'-indole](0.65 g, 2.74 mmol) in AcOH (5.0 mL) was added NaBH$_3$CN (0.52 g, 8.22 mmol) portionwise. The mixture was stirred at room temperature for 3 h under a nitrogen atmosphere. The mixture was concentrated in vacuo. The crude residue was purified by silica gel chromatography (petroleum ether/EtOAc=3:1) to give the title compound (160 mg, 40%) as a colorless oil.

Step 4

1-[3-[5'-(1-methylpyrazol-4-yl)spiro[cyclobutane-1,3'-indoline]-1'-yl]-1-tetrahydrofuran-3-yl-6,7-dihydro-4H-pyrazolo[4,3-c]pyridin-5-yl]ethanone

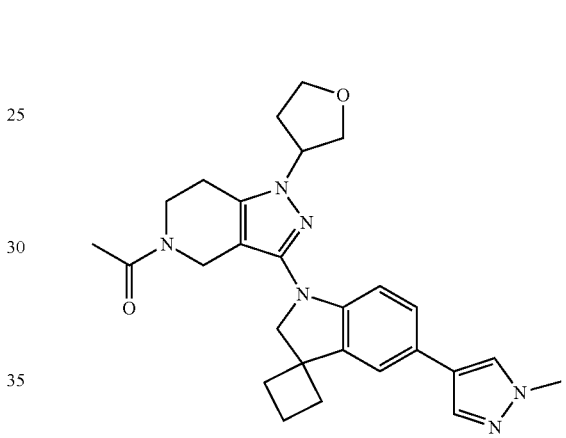

To a solution of 5'-(1-methyl-1H-pyrazol-4-yl)spiro[cyclobutane-1,3'-indoline](160 mg, 0.67 mmol), 1-(3-bromo-1-(tetrahydrofuran-3-yl)-6,7-dihydro-1H-pyrazolo[4,3-c]pyridin-5(4H)-yl)ethanone (252 mg, 0.80 mmol) and t-BuONa (193 mg, 2.00 mmol) in dioxane (3 mL) was added chloro(2-dicyclohexylphosphino-2',6'-di-i-propoxy-1,1'-biphenyl)[2-(2-aminoethylphenyl)]palladium(II), methyl-tert-butylether adduct (56 mg, 0.067 mmol) and 2-dicyclohexylphosphino-2',6'-di-i-propoxy-1,1'-biphenyl (32 mg, 0.067 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by reverse phase chromatography (acetonitrile 25-55%/0.1% NH$_4$HCO$_3$ in water) to give the title compound (20 mg, 6%) as a white solid. $^1$H NMR (400 MHz, DMSO-d$_6$) δ 7.95 (s, 1H), 7.72 (s, 1H), 7.35-7.20 (m, 3H), 4.88-4.71 (m, 2H), 4.54-4.48 (m, 2H), 4.04-4.00 (m, 2H), 3.89-3.69 (m, 8H), 2.82-2.68 (m, 2H), 2.30-2.25 (m, 2H), 2.10-2.08 (m, 3H), 1.85-1.62 (m, 5H), 1.30-1.24 (m, 1H). LCMS M/Z (M+H) 473.

Example 206

1-(5-acetyl-1-tetrahydrofuran-3-yl-6,7-dihydro-4H-pyrazolo[4,3-c]pyridin-3-yl)-6-(1-methylpyrazol-4-yl)indoline-5-carbonitrile

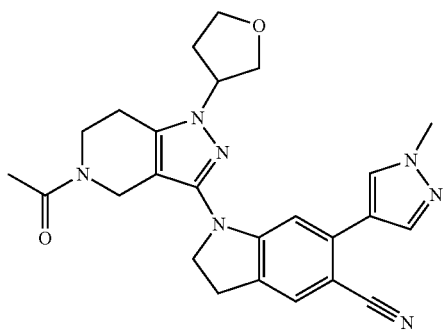 [SMILES: CC(=O)N1CCc2c(c(N3CCc4cc(C#N)c(-c5cnn(C)c5)cc43)nn2C2CCOC2)C1]

Step 1

5-chloro-6-(1-methyl-1H-pyrazol-4-yl)-1H-indole

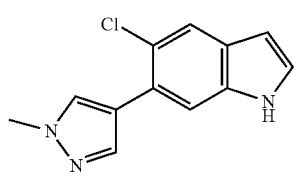 [SMILES: Cn1cc(-c2cc3[nH]ccc3cc2Cl)cn1]

To a solution of 6-bromo-5-chloro-1H-indole (500 mg, 2.17 mmol), 1-methyl-4-(4,4,5,5-tetramethyl-1,3,2-dioxaborolan-2-yl)-1H-pyrazole (0.54 g, 2.60 mmol) and $Na_2CO_3$ (0.69 g, 6.51 mmol) in $DME/H_2O$ (10 mL, 4:1) was added bis(triphenylphosphine)palladium(II) dichloride (140 mg, 0.22 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. $NaHCO_3$ (10 mL×3), dried over anhydrous $Na_2SO_4$ and concentrated in vacuo. The crude residue was purified by silica gel chromatography (petroleum ether/EtOAc=3:1) to give the title compound (0.38 g, 76%) as a light yellow solid.

Step 2

5-chloro-6-(1-methyl-1H-pyrazol-4-yl)indoline

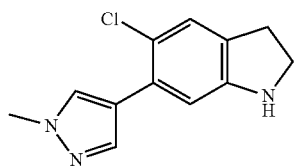 [SMILES: Cn1cc(-c2cc3c(cc2Cl)CCN3)cn1]

To a solution of 5-chloro-6-(1-methyl-1H-pyrazol-4-yl)-1H-indole (0.32 g, 1.38 mmol) in AcOH (4.0 mL) was added $NaBH_3CN$ (0.26 g, 4.14 mmol) portionwise. The mixture was stirred at room temperature for 3 h under a nitrogen atmosphere. The mixture was concentrated in vacuo. The crude residue was purified by silica gel chromatography (petroleum ether/EtOAc=3:1) to give the title compound (150 mg, 46%) as a white solid.

Step 3

1-(3-(5-chloro-6-(1-methyl-1H-pyrazol-4-yl)indolin-1-yl)-1-(tetrahydrofuran-3-yl)-6,7-dihydro-1H-pyrazolo[4,3-c]pyridin-5(4H)-yl)ethanone

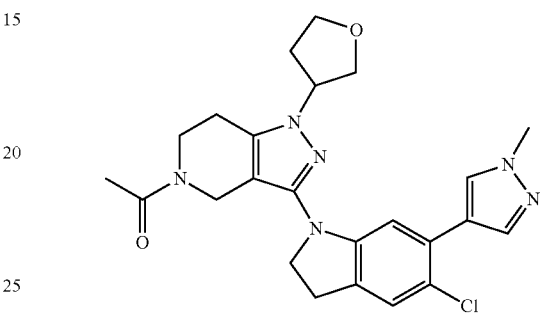

To a solution of 5-chloro-6-(1-methyl-1H-pyrazol-4-yl) indoline (150 mg, 0.64 mmol), 1-(3-bromo-1-(tetrahydrofuran-3-yl)-6,7-dihydro-1H-pyrazolo[4,3-c]pyridin-5(4H)-yl)ethanone (262 mg, 0.83 mmol) and t-BuONa (185 mg, 1.93 mmol) in dioxane (5 mL) was added chloro(2-dicyclohexylphosphino-2',6'-di-i-propoxy-1,1'-biphenyl)[2-(2-aminoethylphenyl)]palladium(II), methyl-tert-butylether adduct (52 mg, 0.064 mmol) and 2-dicyclohexylphosphino-2',6'-di-i-propoxy-1,1'-biphenyl (28 mg, 0.064 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. $NaHCO_3$ (10 mL×3), dried over anhydrous $Na_2SO_4$ and concentrated in vacuo. The crude residue was purified by Prep-TLC (DCM/MeOH=20:1) to give the title compound (110 mg, 37%) as a yellow oil. LCMS M/Z (M+H) 467.

Step 4

1-(5-acetyl-t-tetrahydrofuran-3-yl-6,7-dihydro-4H-pyrazolo[4,3-c]pyridin-3-yl)-6-(1-methylpyrazol-4-yl)indoline-5-carbonitrile

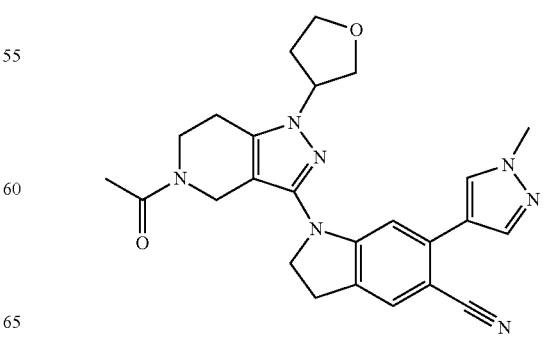

To a solution of 1-(3-(5-chloro-6-(1-methyl-1H-pyrazol-4-yl)indolin-1-yl)-1-(tetrahydrofuran-3-yl)-6,7-dihydro-1H-pyrazolo[4,3-c]pyridin-5(4H)-yl)ethanone (100 mg, 0.21 mmol), potassium hexacyanoferrate(II) trihydrate (248 mg, 0.63 mmol), 2-di-tert-butylphosphino-2',4',6'-triisopropylbiphenyl (18 mg, 0.021 mmol) and KOAc (84 mg, 0.86 mmol) in dioxane/H$_2$O (5 mL, 4:1) was added tris(dibenzylideneacetone)dipalladium (10 mg, 0.011 mmol). The mixture was heated to 120° C. for 36 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by reverse phase chromatography (acetonitrile 25-55%/0.1% NH$_4$HCO$_3$ in water) to give the title compound (10 mg, 11%) as a white solid. $^1$H NMR (400 MHz, DMSO-d$_6$) δ 8.13 (d, J=5.6 Hz, 1H), 7.79-7.57 (m, 2H), 7.46 (s, 1H), 4.92-4.89 (m, 2H), 4.57-4.54 (m, 2H), 4.09-3.98 (m, 4H), 3.89-3.84 (m, 5H), 3.71-3.70 (m, 2H), 3.17 (t, J=8.8 Hz, 2H), 2.83-2.69 (m, 2H), 2.32-2.21 (m, 2H), 2.10-2.07 (m, 3H). LCMS M/Z (M+H) 458.

Example 207

1-[3-[4-chloro-6-(1-methylpyrazol-4-yl)indolin-1-yl]-1-tetrahydrofuran-3-yl-6,7-dihydro-4H-pyrazolo[4,3-c]pyridin-5-yl]ethanone

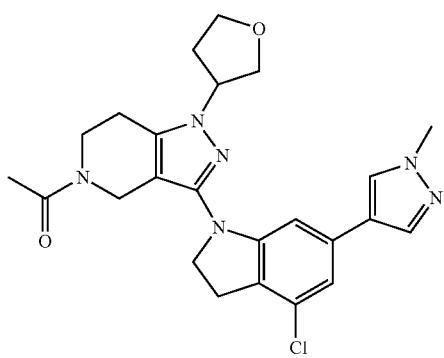 [SMILES: CC(=O)N1CCc2c(c(N3CCc4c(Cl)cc(-c5cnn(C)c5)cc43)nn2C2CCOC2)C1]

Step 1

4-chloro-6-(1-methyl-1H-pyrazol-4-yl)-1H-indole

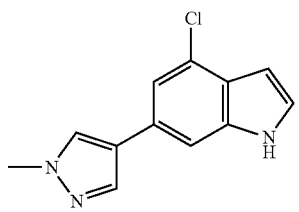 [SMILES: Cn1cc(-c2cc(Cl)c3cc[nH]c3c2)cn1]

To a solution of 6-bromo-4-chloro-1H-indole (500 mg, 2.17 mmol), 1-methyl-4-(4,4,5,5-tetramethyl-1,3,2-dioxaborolan-2-yl)-1H-pyrazole (0.54 g, 2.60 mmol) and Na$_2$CO$_3$ (0.69 g, 6.51 mmol) in DME/H$_2$O (10 mL, 4:1) was added bis(triphenylphosphine)palladium(II) dichloride (140 mg, 0.22 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by silica gel chromatography (petroleum ether/EtOAc=3:1) to give the title compound (0.38 g, 76%) as a light yellow solid.

Step 2

4-chloro-6-(1-methyl-1H-pyrazol-4-yl)indoline

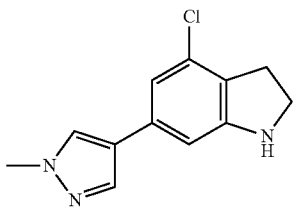 [SMILES: Cn1cc(-c2cc(Cl)c3c(c2)NCC3)cn1]

To a solution of 4-chloro-6-(1-methyl-1H-pyrazol-4-yl)-1H-indole (0.33 g, 1.53 mmol) in AcOH (3 mL) was added NaBH$_3$CN (0.27 g, 4.27 mmol) in portions. The mixture was stirred at room temperature for 3 h under a nitrogen atmosphere. The mixture was concentrated in vacuo. The crude residue was purified by silica gel chromatography (petroleum ether/EtOAc=3:1) to give the title compound (200 mg, 60%) as a light yellow solid. LCMS M/Z (M+H) 234.

Step 3

1-[3-[4-chloro-6-(1-methylpyrazol-4-yl)indolin-1-yl]-1-tetrahydrofuran-3-yl-6,7-dihydro-4H-pyrazolo[4,3-c]pyridin-5-yl]ethanone

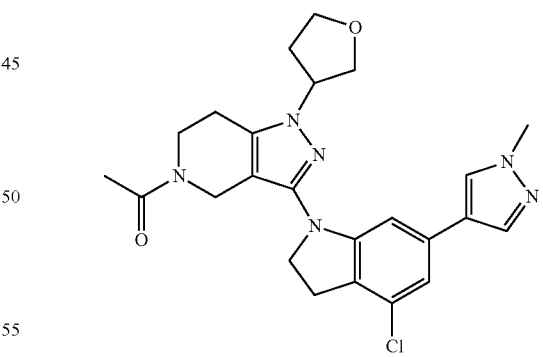

To a solution of 4-chloro-6-(1-methyl-1H-pyrazol-4-yl)indoline (180 mg, 0.77 mmol), 1-(3-bromo-1-(tetrahydrofuran-3-yl)-6,7-dihydro-1H-pyrazolo[4,3-c]pyridin-5(4H)-yl)ethanone (314 mg, 1.00 mmol) and t-BuONa (222 mg, 2.31 mmol) in dioxane (4 mL) was added chloro(2-dicyclohexylphosphino-2',6'-di-i-propoxy-1,1'-biphenyl)[2-(2-aminoethylphenyl)]palladium(II), methyl-tert-butylether adduct (63 mg, 0.077 mmol) and 2-dicyclohexylphosphino-2',6'-di-i-propoxy-1,1'-biphenyl (34 mg, 0.077 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by Prep-TLC (DCM/MeOH=20:1) to give the title compound (130 mg, 36%) as a white solid. $^1$H NMR (400 MHz, DMSO-d$_6$) δ 8.06-8.05 (m, 1H), 7.76-7.75 (m, 1H), 7.46 (s, 1H), 7.62-7.48 (m, 1H), 6.94 (s, 1H), 4.90 (s, 1H), 4.54-4.53 (m, 2H), 4.10-4.02 (m, 24H), 3.88-3.84 (m, 5H), 3.74-3.71 (m, 2H), 3.13 (t, J=8.4 Hz, 2H), 2.81-2.68 (m, 2H), 2.30-2.22 (m, 2H), 2.10-2.07 (m, 3H). LCMS M/Z (M+H) 467.

Example 208

1-(5-acetyl-1-tetrahydrofuran-3-yl-6,7-dihydro-4H-pyrazolo[4,3-c]pyridin-3-yl)-6-(1-methylpyrazol-4-yl)indoline-4-carbonitrile

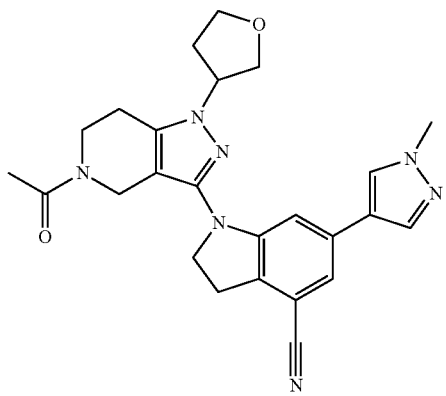 [SMILES: CC(=O)N1CCc2c(c(N3CCc4c(C#N)cc(-c5cnn(C)c5)cc43)nn2C2CCOC2)C1]

To a solution of 1-(3-(4-chloro-6-(1-methyl-1H-pyrazol-4-yl)indolin-1-yl)-1-(tetrahydrofuran-3-yl)-6,7-dihydro-1H-pyrazolo[4,3-c]pyridin-5(4H)-yl)ethanone (130 mg, 0.28 mmol), potassium hexacyanoferrate(II) trihydrate (323 mg, 0.84 mmol) and 2-di-tert-butylphosphino-2',4',6'-triisopropylbiphenyl (45 mg, 0.056 mmol), KOAc (109 mg, 1.11 mmol) in dioxane/H$_2$O (5 mL, 4:1) was added tris(dibenzylideneacetone)dipalladium (30 mg, 0.028 mmol). The mixture was heated to 120° C. for 36 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$ and concentrated in vacuo. The crude residue was purified by reverse phase chromatography (acetonitrile 25-55%/0.1% NH$_4$HCO$_3$ in water) to give the title compound (16 mg, 13%) as a white solid. $^1$H NMR (400 MHz, DMSO-d$_6$) δ 8.11 (d, J=4.4 Hz, 1H), 7.97-7.85 (m, 2H), 7.29 (s, 1H), 4.92-4.89 (m, 1H), 4.57-4.56 (m, 2H), 4.10-4.02 (m, 4H), 3.90-3.85 (m, 5H), 3.73-3.72 (m, 2H), 3.29-3.26 (m, 2H), 2.83-2.70 (m, 2H), 2.34-2.29 (m, 2H), 2.11-2.08 (m, 3H). LCMS M/Z (M+H) 458.

Example 209

1-[3-[4-fluoro-6-(1-methylpyrazol-4-yl)indolin-1-yl]-1-tetrahydrofuran-3-yl-6,7-dihydro-4H-pyrazolo[4,3-c]pyridin-5-yl]ethanone

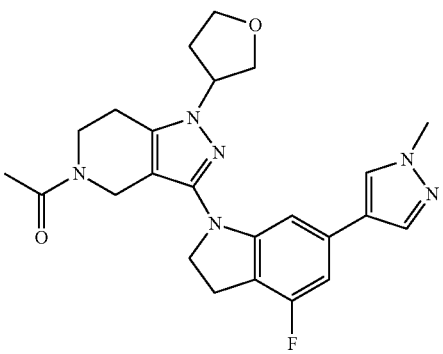 [SMILES: CC(=O)N1CCc2c(c(N3CCc4c(F)cc(-c5cnn(C)c5)cc43)nn2C2CCOC2)C1]

Step 1

4-fluoro-6-(1-methyl-1H-pyrazol-4-yl)-1H-indole

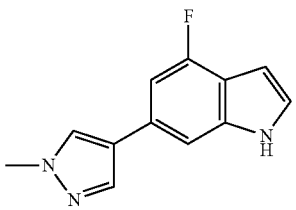 [SMILES: Cn1cc(-c2cc(F)c3cc[nH]c3c2)cn1]

To a solution of 6-bromo-4-fluoro-1H-indole (500 mg, 2.34 mmol), 1-methyl-4-(4,4,5,5-tetramethyl-1,3,2-dioxaborolan-2-yl)-1H-pyrazole (0.63 g, 3.04 mmol) and K$_2$CO$_3$ (0.97 g, 7.01 mmol) in dioxane/H$_2$O (10.0 mL, 4:1) was added [1,1'-bis(diphenylphosphino)ferrocene]dichloropalladium(II) (171 mg, 0.24 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$, filtered and concentrated in vacuo. The crude residue was purified by silica gel chromatography (petroleum ether/EtOAc=3:1) to give the title compound (0.33 g, 66%) as a light yellow solid.

Step 2

4-fluoro-6-(1-methyl-1H-pyrazol-4-yl)indoline

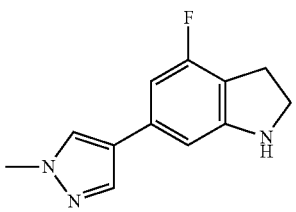 [SMILES: Cn1cc(-c2cc(F)c3c(c2)NCC3)cn1]

501

To a solution of 4-fluoro-6-(1-methyl-1H-pyrazol-4-yl)-1H-indole (0.33 g, 1.53 mmol) in AcOH (3 mL) was added NaBH$_3$CN (0.29 g, 4.6 mmol) in portions. The mixture was stirred at room temperature for 3 h under a nitrogen atmosphere. The crude mixture was concentrated in vacuo. The crude residue was purified by silica gel chromatography (petroleum ether/EtOAc=3:1) to give the title compound (210 mg, 63%) as a light yellow solid. LCMS M/Z (M+H) 218.

Step 3

1-[3-[4-fluoro-6-(1-methylpyrazol-4-yl)indolin-1-yl]-1-tetrahydrofuran-3-yl-6,7-dihydro-4H-pyrazolo[4,3-c]pyridin-5-yl]ethanone

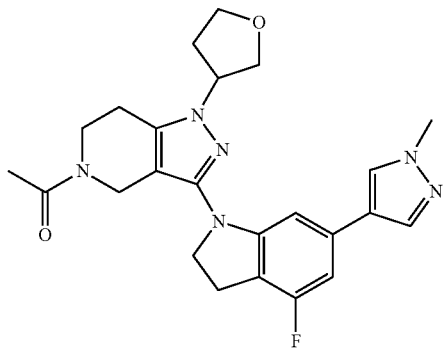 [SMILES: CC(=O)N1CCc2c(c(N3CCc4c(F)cc(-c5cnn(C)c5)cc43)nn2C2CCOC2)C1]

To a solution of 4-fluoro-6-(1-methyl-1H-pyrazol-4-yl)indoline (150 mg, 0.69 mmol), 1-(3-bromo-1-(tetrahydrofuran-3-yl)-6,7-dihydro-1H-pyrazolo[4,3-c]pyridin-5(4H)-yl)ethanone (282 mg, 0.90 mmol) and t-BuONa (200 mg, 2.07 mmol) in dioxane (3 mL) was added chloro(2-dicyclohexylphosphino-2',6'-di-i-propoxy-1,1'-biphenyl) [2-(2-aminoethylphenyl)]palladium(II), methyl-tert-butylether adduct (56 mg, 0.069 mmol) and 2-dicyclohexylphosphino-2',6'-di-i-propoxy-1,1'-biphenyl (31 mg, 0.069 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO$_3$ (10 mL×3), dried over anhydrous Na$_2$SO$_4$, filtered and concentrated in vacuo. The crude residue was purified by reverse phase chromatography (acetonitrile 25-55%/0.1% NH$_4$HCO$_3$ in water) to give the title compound (60 mg, 19%) as a white solid. $^1$H NMR (400 MHz, DMSO-d$_6$) δ 8.04 (s, 1H), 7.75 (s, 1H), 7.33 (s, 1H), 6.76 (s, 1H), 4.92-4.89 (m, 1H), 4.55-4.53 (m, 2H), 4.06-4.02 (m, 4H), 3.88-3.84 (m, 5H), 3.75-3.72 (m, 2H), 3.14 (t, J=8.4 Hz, 2H), 2.84-2.69 (m, 2H), 2.30-2.28 (m, 2H), 2.11-2.07 (m, 3H). LCMS M/Z (M+H) 451.

502

Example 210

1-[3-[5-fluoro-6-(1-methylpyrazol-4-yl)indolin-1-yl]-1-tetrahydrofuran-3-yl-6,7-dihydro-4H-pyrazolo[4,3-c]pyridin-5-yl]ethanone

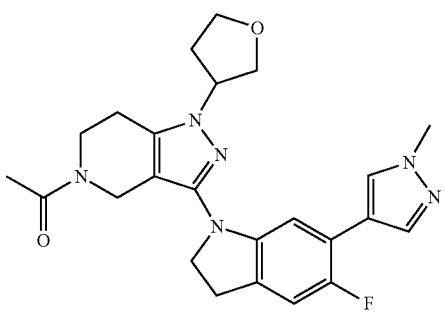

Step 1

6-bromo-5-fluoroindoline

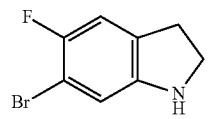

To a solution of 5-fluoroindoline hydrochloride (1.6 g, 9.2 mmol) in H$_2$SO$_4$ (10 mL) at 0° C. was added Ag$_2$SO$_4$ (1.72 g, 5.5 mmol) portionwise. The mixture was stirred at that temperature for 0.5 h before bromine (2.2 g, 13.8 mmol) was added dropwise. The crude mixture was stirred at room temperature for an additional 2 h. Water (20 mL) was added and the mixture was neutralized with sat. aq. NaHCO$_3$ to pH 7 and then extracted with EtOAc (20 mL×3). The combined organic layers were washed with sat. aq. NaHCO$_3$ (20 mL×3), dried over anhydrous Na$_2$SO$_4$, filtered and concentrated in vacuo. The crude residue was purified by silica gel chromatography (petroleum ether/EtOAc=3:1) to give the title compound (560 mg, 28%) as a brown oil. $^1$H NMR (400 MHz, DMSO-d$_6$) δ 7.03 (d, J=8.8 Hz, 1H), 6.62 (d, J=5.6 Hz, 1H), 5.85 (s, 1H), 3.43 (t, J=8.8 Hz, 2H), 3.43 (t, J=8.8 Hz, 2H).

Step 2 tert-butyl 6-bromo-5-fluoroindoline-1-carboxylate

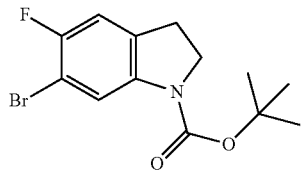 [SMILES: CC(C)(C)OC(=O)N1CCc2cc(F)c(Br)cc21]

To a solution of 6-bromo-5-fluoroindoline (560 mg, 2.59 mmol) in DCM (10.0 mL) was added di-tert-butyl dicarbonate (848 mg, 3.89 mmol) and diisopropylethylamine (580 mg, 4.51 mmol). The mixture was stirred at room temperature for 12 h under a nitrogen atmosphere. The mixture was concentrated in vacuo. The crude residue was purified by silica gel chromatography (petroleum ether/EtOAc=20:1) to give the title compound (520 mg, 63%) as a brown oil.

Step 3 tert-butyl 5-fluoro-6-(1-methyl-1H-pyrazol-4-yl)indoline-1-carboxylate

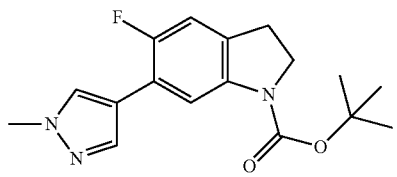 [SMILES: Cn1cc(-c2cc3c(cc2F)CCN3C(=O)OC(C)(C)C)cn1]

To a solution of tert-butyl 6-bromo-5-fluoroindoline-1-carboxylate (520 mg, 1.64 mmol), 1-methyl-4-(4,4,5,5-tetramethyl-1,3,2-dioxaborolan-2-yl)-1H-pyrazole (410 mg, 1.97 mmol) and K₂CO₃ (682 mg, 4.93 mmol) in dioxane/H₂O (4 mL, 3:1) was added [1,1'-bis(diphenylphosphino)ferrocene]dichloropalladium(II) (120 mg, 0.165 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO₃ (10 mL×3), dried over anhydrous Na₂SO₄ and concentrated in vacuo. The crude residue was purified by silica gel chromatography (petroleum ether/EtOAc=5:1) to give the title compound (380 mg, 78%) as a colorless oil.

Step 4

5-fluoro-6-(1-methyl-1H-pyrazol-4-yl)indoline

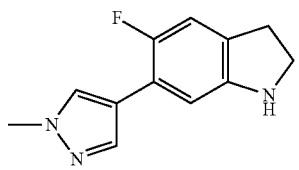 [SMILES: Cn1cc(-c2cc3c(cc2F)CCN3)cn1]

To a stirred solution of tert-butyl 5-fluoro-6-(1-methyl-1H-pyrazol-4-yl)indoline-1-carboxylate (460 mg, 1.45 mmol) in EtOAc (3 mL) was added HCl in EtOAc (4 M, 10 mL). The mixture was stirred at room temperature for 4 h under a nitrogen atmosphere. The mixture was concentrated in vacuo. Water (20 mL) was added and the mixture was neutralized with sat. aq. NaHCO₃ to pH 7 and then extracted with EtOAc (20 mL×3). The combined organic layers were washed with sat. aq. NaHCO₃ (20 mL×3), dried over anhydrous Na₂SO₄, filtered and concentrated in vacuo to give the title compound (260 mg, 83%) as a colorless oil.

Step 5

1-[3-[5-fluoro-6-(1-methylpyrazol-4-yl)indolin-1-yl]-1-tetrahydrofuran-3-yl-6,7-dihydro-4H-pyrazolo[4,3-c]pyridin-5-yl]ethanone

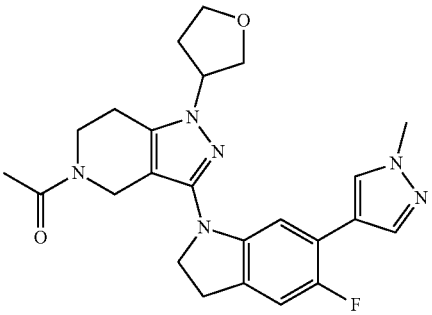 [SMILES: CC(=O)N1CCc2c(c(N3CCc4cc(F)c(-c5cnn(C)c5)cc43)nn2C2CCOC2)C1]

To a solution of 5-fluoro-6-(1-methyl-1H-pyrazol-4-yl)indoline (150 mg, 0.69 mmol), 1-(3-bromo-1-(tetrahydrofuran-3-yl)-6,7-dihydro-1H-pyrazolo[4,3-c]pyridin-5(4H)-yl)ethanone (260 mg, 0.83 mmol) and t-BuONa (299 mg, 2.07 mmol) in dioxane (3 mL) was added chloro(2-dicyclohexylphosphino-2',6'-di-i-propoxy-1,1'-biphenyl)[2-(2-aminoethylphenyl)]palladium(II), methyl-tert-butylether adduct (56 mg, 0.069 mmol) and 2-dicyclohexylphosphino-2',6'-di-i-propoxy-1,1'-biphenyl (32 mg, 0.069 mmol). The mixture was heated to 120° C. for 12 h under a nitrogen atmosphere. After cooling the reaction to room temperature, water (10 mL) was added and the mixture was extracted with EtOAc (10 mL×3). The combined organic layers were washed with sat. aq. NaHCO₃ (10 mL×3), dried over anhydrous Na₂SO₄, filtered and concentrated in vacuo. The crude residue was purified by reverse phase chromatography (acetonitrile 25-55%/0.1% NH₄HCO₃ in water) to give the title compound (49 mg, 16%) as a light yellow solid. ¹H NMR (400 MHz, DMSO-d₆) δ 7.97 (s, 1H), 7.83-7.67 (m, 2H), 7.04 (d, J=10.4 Hz, 1H), 4.89-4.87 (m, 1H), 4.56-4.54 (m, 2H), 4.05-3.98 (m, 4H), 3.88 (s, 3H), 3.88-3.86 (m, 2H), 3.72-3.69 (m, 2H), 3.11-3.07 (m, 2H), 2.81-2.66 (m, 2H), 2.27-2.19 (m, 2H), 2.09-2.06 (m, 3H). LCMS M/Z (M+H) 451.

Example 211

1-(5-acetyl-1-methyl-4,5,6,7-tetrahydro-1H-pyrazolo[4,3-c]pyridin-3-yl)indoline-6-carboxylic Acid

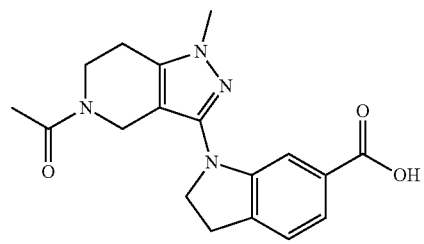 [SMILES: CC(=O)N1CCc2c(c(N3CCc4ccc(C(=O)O)cc43)nn2C)C1]

Step 1 methyl indoline-6-carboxylate

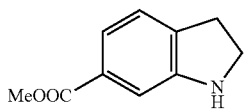 [SMILES: COC(=O)c1ccc2c(c1)NCC2]

To a solution of methyl 1H-indole-6-carboxylate (5.0 g, 28.54 mmol) in AcOH (30 mL) was added NaBH$_3$CN (5.4 g, 85.62 mmol). The mixture was stirred at 30° C. for 16 h. The reaction was quenched with sat. aq. NaHCO$_3$ (300 mL) and extracted with EtOAc (100 mL×3). The combined organic layers were washed with brine, dried over anhydrous Na$_2$SO$_4$, filtered and concentrated in vacuo. The crude residue was purified by silica gel chromatography (petroleum ether/EtOAc=50:1 to 3:1) to give the title compound (1.2 g, 24%) as a white solid. $^1$H NMR (400 MHz, DMSO-d$_6$) δ 7.16 (d, J=7.6 Hz, 1H), 7.14 (d, J=7.6 Hz, 1H), 5.75 (s, 1H), 3.78 (s, 3H), 3.52 (t, J=8.4 Hz, 2H), 2.95 (t, J=8.4 Hz, 2H).

Step 2

1-(5-acetyl-1-methyl-4,5,6,7-tetrahydro-1H-pyrazolo[4,3-c]pyridin-3-yl)indoline-6-carboxylic Acid

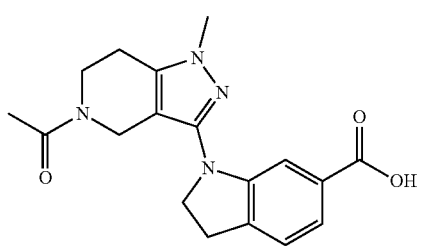 [SMILES: CC(=O)N1CCc2c(c(N3CCc4ccc(C(=O)O)cc43)nn2C)C1]

To a solution of methyl indoline-6-carboxylate (600 mg, 3.40 mmol), 1-(3-bromo-1-methyl-6,7-dihydro-1H-pyrazolo[4,3-c]pyridin-5(4H)-yl)ethanone (Intermediate B, 960 mg, 3.74 mmol), 2-dicyclohexylphosphino-2',6'-di-i-propoxy-1,1'-biphenyl (158 mg, 0.34 mmol) and chloro(2-dicyclohexylphosphino-2',6'-di-i-propoxy-1,1'-biphenyl)[2-(2-aminoethylphenyl)]palladium(II), methyl-tert-butylether adduct (277 mg, 0.34 mmol) in dioxane (10 mL) was added t-BuONa (976 mg, 10.20 mmol). The mixture was heated to 120° C. for 16 h under a nitrogen atmosphere. After cooling the reaction to room temperature, water (20 mL) was added and the mixture was extracted with EtOAc (20 mL×2). 1 M HCl (2 mL) was added to aqueous phase and then extracted with EtOAc (20 mL×2). The combined organic layers were washed with brine, dried over anhydrous Na$_2$SO$_4$, filtered and concentrated in vacuo. The crude residue was purified by reverse phase chromatography (acetonitrile 5-35%/0.1% NH$_4$HCO$_3$ in water) to give the title compound (120 mg, 10%) as a brown solid. $^1$H NMR (400 MHz, DMSO-d$_6$) δ 7.58 (s, 1H), 7.28 (d, J=7.2 Hz, 1H), 7.10 (d, J=7.6 Hz, 1H), 4.45 (s, 2H), 3.96-3.90 (m, 2H), 3.76-3.69 (m, 5H), 3.16-3.05 (m, 2H), 2.77-2.65 (m, 2H), 2.08-2.06 (m, 3H). LCMS M/Z (M+H) 341.

Example 212 methyl 1-(5-acetyl-1-methyl-6,7-dihydro-4H-pyrazolo[4,3-c]pyridin-3-yl)indoline-6-carboxylate

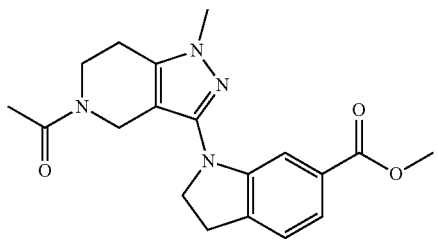 [SMILES: COC(=O)c1ccc2c(c1)N(c1nn(C)c3c1CN(C(C)=O)CC3)CC2]

To a solution of 1-(5-acetyl-1-methyl-4,5,6,7-tetrahydro-1H-pyrazolo[4,3-c]pyridin-3-yl)indoline-6-carboxylic acid (90 mg, 0.26 mmol) in MeOH (5 mL) was added SOCl$_2$ (60 mg, 0.5 mmol). The mixture was heated to 70° C. for 2 h under a nitrogen atmosphere. After cooling the reaction to room temperature, the mixture was concentrated in vacuo. The crude residue was purified by silica gel chromatography (DCM/MeOH=20:1) to give the title compound (30 mg, 32%) as a brown solid. $^1$H NMR (400 MHz, DMSO-d$_6$) δ 7.78 (d, J=10.8 Hz, 1H), 7.34 (d, J=7.6 Hz, 1H), 7.23 (d, J=7.6 Hz, 1H), 4.50 (d, J=4.0 Hz, 2H), 4.09-3.95 (m, 2H), 3.80 (s, 3H), 3.76-3.68 (m, 2H), 3.65 (s, 3H), 3.17 (t, J=8.4 Hz, 2H), 2.77-2.66 (m, 2H), 2.10-2.07 (m, 3H). LCMS M/Z (M+H) 355.

Example 213

2-[1-(5-acetyl-1-tetrahydrofuran-3-yl-6,7-dihydro-4H-pyrazolo[4,3-c]pyridin-3-yl)-5-(1-methylpyrazol-4-yl)indolin-3-yl]acetonitrile

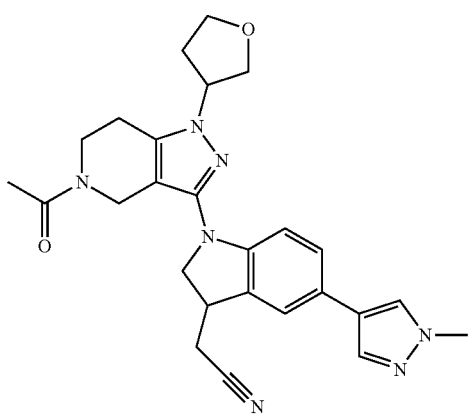 [SMILES: CC(=O)N1CCc2c(c(N3CC(CC#N)c4cc(-c5cnn(C)c5)ccc43)nn2C2CCOC2)C1]

Step 1

2-(5-bromo-1H-indol-3-yl)acetonitrile

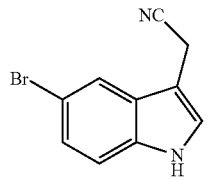 [SMILES: N#CCc1c[nH]c2ccc(Br)cc12]

To a solution of 5-bromo-1H-indole (4.0 g, 20.4 mmol) in MeCN/AcOH (80 mL, 19:1) was added N-methyl-N-methylenemethanaminium iodide (4.5 g, 24.3 mmol). After stirring at 20° C. for 3 h, additional N-methyl-N-methylenemethanaminium iodide (0.4 g, 2.2 mmol) was added. The mixture was stirred at 20° C. for additional 1 h. Water (50 mL) was added and the mixture was was made basic with 10% aq. KOH (45 mL) to pH>9 and then extracted with EtOAc (300 mL×3). The combined organic layers were dried over anhydrous $Na_2SO_4$, filtered and concentrated in vacuo. The residue was dissolved in EtOH (40 mL) before MeI (5.7 g, 40 mmol) was added and the mixture stirred at 20° C. for 16 h. The mixture was concentrated in vacuo to give the ammonium salt as a yellow solid (7.9 g, crude). To this crude salt (7.9 g) in DMF (50 mL) was added a solution of NaCN (5.0 g, 0.10 mmol) in water (10 mL). The mixture was heated to 70° C. for 4 h. After cooling the reaction to room temperature, EtOAc (350 mL) was added and the mixture was washed with water (50 mL×5). The organic layer was dried over anhydrous $Na_2SO_4$, filtered and concentrated in vacuo. The crude residue was purified by silica gel chromatography (petroleum ether/EtOAc=1:1) to give the title compound (2.6 g, 54%) as a yellow solid.

Step 2

2-(5-(1-methyl-1H-pyrazol-4-yl)-1H-indol-3-yl)acetonitrile

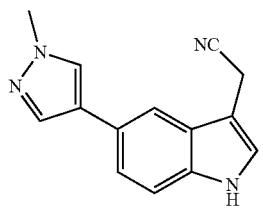 [SMILES: Cn1cc(-c2ccc3[nH]cc(CC#N)c3c2)cn1]

To a solution of 2-(5-bromo-1H-indol-3-yl)acetonitrile (1.3 g, 5.53 mmol), 1-methyl-4-(4,4,5,5-tetramethyl-1,3,2-dioxaborolan-2-yl)-1H-pyrazole (1.4 g, 6.64 mmol) and $K_2CO_3$ (2.3 g, 16.59 mmol) in dioxane/$H_2O$ (13 mL, 3:1) was added [1,1'-bis(diphenylphosphino)ferrocene]dichloropalladium(II) (405 mg, 0.55 mmol). The mixture was heated to 120° C. for 16 h under a nitrogen atmosphere. After cooling the reaction to room temperature, the mixture was concentrated in vacuo. The crude residue was purified by silica gel chromatography (DCM/MeOH=30:1) to give the title compound (1.1 g, 83%) as a brown solid.

Step 3

2-(5-(1-methyl-1H-pyrazol-4-yl)indolin-3-yl)acetonitrile

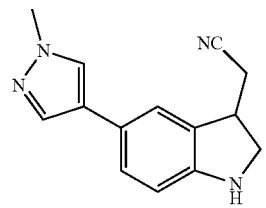 [SMILES: Cn1cc(-c2ccc3c(c2)C(CC#N)CN3)cn1]

To a solution of 2-(5-(1-methyl-1H-pyrazol-4-yl)-1H-indol-3-yl)acetonitrile (1.1 g, 4.66 mmol) in trifluoroacetic acid (10 mL) was added triethylsilane (1.6 g, 13.97 mmol) at 0° C. The mixture was stirred at 20° C. for 24 h. Water (20 mL) was added and the mixture was extracted with EtOAc (10 mL×3). The combined organic layers were washed with brine, dried over anhydrous $Na_2SO_4$ and concentrated in vacuo. The crude residue was purified by silica gel chromatography (DCM/MeOH=30:1) to give the title compound (1.0 g, 91%) as brown solid.

Step 4

2-[1-(5-acetyl-1-tetrahydrofuran-3-yl-6,7-dihydro-4H-pyrazolo[4,3-c]pyridin-3-yl)-5-(1-methylpyrazol-4-yl)indolin-3-yl]acetonitrile

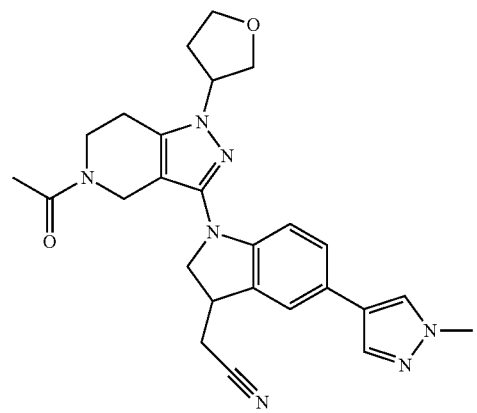 [SMILES: CC(=O)N1CCc2c(c(N3CC(CC#N)c4cc(-c5cnn(C)c5)ccc43)nn2C2CCOC2)C1]

To a solution of 2-(5-(1-methyl-1H-pyrazol-4-yl)indolin-3-yl)acetonitrile (230 mg, 1.0 mmol), 1-(3-bromo-1-(tetrahydrofuran-3-yl)-6,7-dihydro-1H-pyrazolo[4,3-c]pyridin-5(4H)-yl)ethanone (334 mg, 1.1 mmol), chloro(2-dicyclohexylphosphino-2',6'-di-i-propoxy-1,1'-biphenyl)[2-(2-aminoethylphenyl)]palladium(II), methyl-tert-1-butylether adduct (81 mg, 0.1 mmol) and 2-dicyclohexylphosphino-2',6'-di-i-propoxy-1,1'-biphenyl (45 mg, 0.1 mmol) was added t-BuONa (278 mg, 3.0 mmol). The mixture was heated to 120° C. for 12 h under a nitrogen atmosphere. After cooling the reaction to room temperature, the mixture was concentrated in vacuo. The crude residue was purified by reverse phase chromatography (acetonitrile 27-57%/0.1% $NH_4OH$ in water) to give the title compound (32 mg, 7%) as a white solid. $^1$H NMR (400 MHz, DMSO-d$_6$) δ 8.02 (s, 1H), 7.74 (s, 1H), 7.60-7.48 (m, 1H), 7.24 (d, J=7.2 Hz, 1H), 6.96 (d, J=7.6 Hz, 1H), 4.97-4.86 (m, 1H), 4.61-4.49 (m, 2H), 4.30-4.13 (m, 1H), 4.11-3.99 (m, 2H), 3.89 (d, J=5.0 Hz, 2H), 3.85 (s, 3H), 3.80-3.62 (m, 4H), 3.06-2.90 (m, 2H), 2.83-2.51 (m, 2H), 2.37-2.19 (m, 2H), 2.12-2.06 (m, 3H). LCMS M/Z (M+H) 472.

Examples 214 & 215

(S)-2-[1-[5-acetyl-1-(oxetan-3-yl)-6,7-dihydro-4H-pyrazolo[4,3-c]pyridin-3-yl]-5-(1-methylpyrazol-4-yl)indolin-3-yl]acetonitrile and (R)-2-[1-[5-acetyl-1-(oxetan-3-yl)-6,7-dihydro-4H-pyrazolo[4,3-c]pyridin-3-yl]-5-(1-methylpyrazol-4-yl)indolin-3-yl]acetonitrile

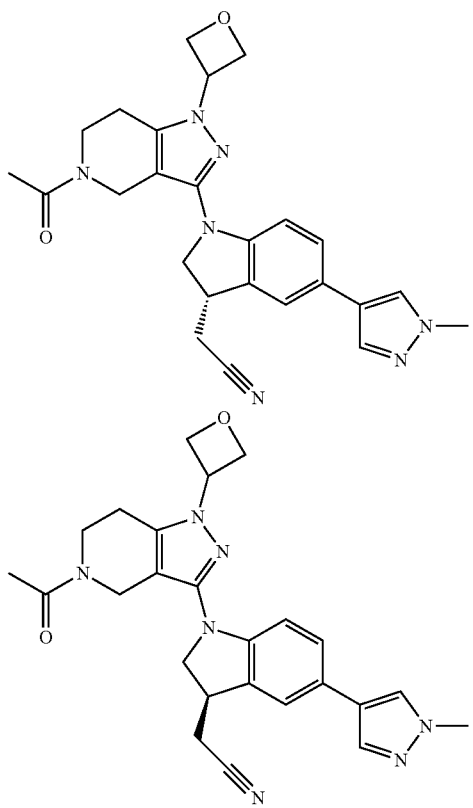

To a solution of 2-(5-(1-methyl-1H-pyrazol-4-yl)indolin-3-yl)acetonitrile (600 mg, 2.52 mmol), 1-(3-bromo-1-(oxetan-3-yl)-6,7-dihydro-1H-pyrazolo[4,3-c]pyridin-5(4H)-yl)ethanone (Intermediate E, 831 mg, 2.77 mmol), chloro(2-dicyclohexylphosphino-2',6'-di-i-propoxy-1,1'-biphenyl)[2-(2-aminoethylphenyl)]palladium(II), methyl-tert-butylether adduct (211 mg, 0.25 mmol) and 2-dicyclohexylphosphino-2',6'-di-i-propoxy-1,1'-biphenyl (118 mg, 0.25 mmol) in dioxane (6 mL) was added t-BuONa (726 mg, 7.55 mmol). The mixture was heated to 120° C. for 16 h under a nitrogen atmosphere. After cooling the reaction to room temperature, the mixture was concentrated in vacuo. The crude residue was purified by reverse phase chromatography (acetonitrile 26-56%/0.1% NH$_4$OH in water) to give racemic 2-[1-[5-acetyl-1-(oxetan-3-yl)-6,7-dihydro-4H-pyrazolo[4,3-c]pyridin-3-yl]-5-(1-methylpyrazol-4-yl)indolin-3-yl]acetonitrile (150 mg, 13%) as a white solid which was separated by chiral SFC (Chiralpak AD 250×30 mm I.D., 5 um; Supercritical CO$_2$/MeOH+NH$_3$.H$_2$O=55/45; 80 ml/min) to give (S)-2-[1-[5-acetyl-1-(oxetan-3-yl)-6,7-dihydro-4H-pyrazolo[4,3-c]pyridin-3-yl]-5-(1-methylpyrazol-4-yl)indolin-3-yl]acetonitrile (65 mg, first peak) and (R)-2-[1-[5-acetyl-1-(oxetan-3-yl)-6,7-dihydro-4H-pyrazolo[4,3-c]pyridin-3-yl]-5-(1-methylpyrazol-4-yl)indolin-3-yl]acetonitrile (62 mg, second peak). Absolute configuration was arbitrarily assigned to each enantiomer. Example 214: $^1$H NMR (400 MHz, DMSO-d$_6$) δ 8.01 (s, 1H), 7.72 (s, 1H), 7.52-7.43 (m, 1H), 7.24 (d, J=7.6 Hz, 1H), 6.95 (d, J=7.6 Hz, 1H), 5.42 (m, 1H), 4.97-4.93 (m, 2H), 4.89-4.80 (m, 2H), 4.53-4.41 (m, 2H), 4.29-4.14 (m, 1H), 3.81 (s, 3H), 3.80-3.59 (m, 4H), 3.02-2.93 (m, 2H), 2.74-2.62 (m, 2H), 2.07-2.00 (m, 3H). LCMS M/Z (M+H) 458. Example 215: $^1$H NMR (400 MHz, DMSO-d$_6$) δ 8.01 (s, 1H), 7.72 (s, 1H), 7.52-7.43 (m, 1H), 7.24 (d, J=7.6 Hz, 1H), 6.95 (d, J=7.6 Hz, 1H), 5.42 (m, 1H), 4.97-4.93 (m, 2H), 4.89-4.80 (m, 2H), 4.53-4.41 (m, 2H), 4.29-4.14 (m, 1H), 3.81 (s, 3H), 3.80-3.59 (m, 4H), 3.02-2.93 (m, 2H), 2.74-2.62 (m, 2H), 2.07-2.00 (m, 3H). LCMS M/Z (M+H) 458.

Example 216

1-[3-[4-fluoro-5-(1-methylpyrazol-4-yl)indolin-1-yl]-1-methyl-6,7-dihydro-4H-pyrazolo[4,3-c]pyridin-5-yl]ethanone

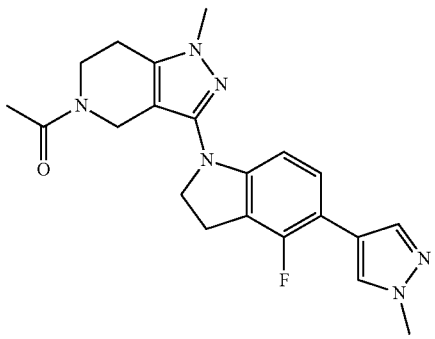 [SMILES: CC(=O)N1CCc2c(c(N3CCc4c3ccc(-c3cnn(C)c3)c4F)nn2C)C1]

Step 1

4-fluoroindoline

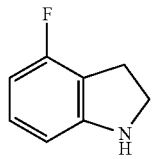

To a solution of 4-fluoro-1H-indole (5.0 g, 37.0 mmol) in AcOH (50 mL), NaBH$_3$CN (4.7 g, 74.0 mmol) was added. The mixture was stirred at 20° C. for 30 min. Water (50 mL) was added and the mixture was extracted with EtOAc (50 mL×2). The combined organic layers were washed with brine, dried over anhydrous Na$_2$SO$_4$ and concentrated in vacuo to give the title compound (4.5 g, 90%) as a brown oil.

511 tert-butyl 4-fluoroindoline-1-carboxylate

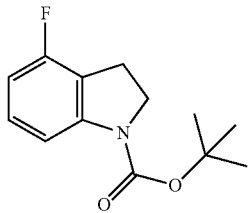 [SMILES: CC(C)(C)OC(=O)N1CCc2c(F)cccc21]

To a solution of 4-fluoroindoline (2.5 g, 18.23 mmol), di-tert-butyl dicarbonate (6.0 g, 27.34 mmol) and di-isopropyl-ethylamine (5.5 g, 54.68 mmol) in DCM (25 mL) was added DMAP (222 mg, 1.82 mmol). The mixture was stirred at 20° C. for 12 h. The mixture was concentrated in vacuo. The crude residue was purified by silica gel chromatography (petroleum ether/EtOAc=50:1) to give the title compound (4 g, 93%) as a brown oil.

Step 3 tert-butyl 5-bromo-4-fluoroindoline-1-carboxylate

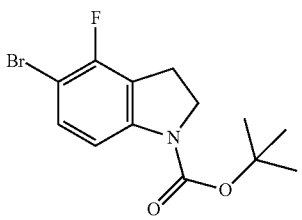 [SMILES: CC(C)(C)OC(=O)N1CCc2c1ccc(Br)c2F]

To a solution of tert-butyl 4-fluoroindoline-1-carboxylate (3.0 g, 12.64 mmol) in DCM (30 mL) was added N-bromosuccinimide (3.4 g, 12.64 mmol). The mixture was stirred at 20° C. for 2 h. The mixture was concentrated in vacuo. The crude residue was purified by silica gel chromatography (petroleum ether/EtOAc=9:1) to give the title compound (3.0 g, 75%) as a brown oil.

Step 4 tert-butyl 4-fluoro-5-(1-methyl-1H-pyrazol-4-yl)indoline-1-carboxylate

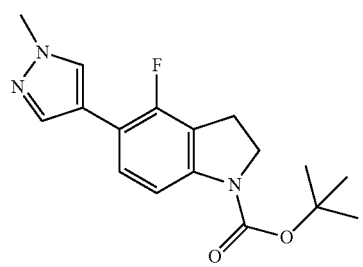 [SMILES: Cn1cc(-c2ccc3c(c2F)CCN3C(=O)OC(C)(C)C)cn1]

To a solution of tert-butyl 5-bromo-4-fluoroindoline-1-carboxylate (2.0 g, 6.33 mmol), 1-methyl-4-(4,4,5,5-tetramethyl-1,3,2-dioxaborolan-2-yl)-1H-pyrazole (2.0 g, 9.49 mmol) and Na$_2$CO$_3$ (2.0 g, 18.98 mmol) in dioxane/H$_2$O (27 mL, 3:1) was added [1,1'-bis(diphenylphosphino)ferrocene]dichloropalladium(II) (461 mg, 0.63 mmol). The mixture was heated to 120° C. for 12 h under a nitrogen atmosphere. After cooling the reaction to room temperature, the mixture was concentrated in vacuo. The crude residue was purified by silica gel chromatography (petroleum ether/EtOAc=1:1) to give the title compound (1.5 g, 75%) as a brown solid.

Step 5

4-fluoro-5-(1-methyl-1H-pyrazol-4-yl)indoline

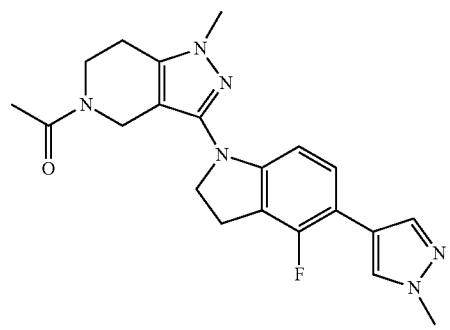 [SMILES: CC(=O)N1CCc2c(c(N3CCc4c3ccc(-c3cnn(C)c3)c4F)nn2C)C1]

A solution of tert-butyl 4-fluoro-5-(1-methyl-1H-pyrazol-4-yl)indoline-1-carboxylate (1.0 g, 3.15 mmol) in HCl/EtOAc (4 M, 10 mL) was stirred at 20° C. for 12 h. The mixture was concentrated in vacuo to give the title compound (500 mg, 73%) as a brown solid.

Step 6

1-[3-[4-fluoro-5-(1-methylpyrazol-4-yl)indolin-1-yl]-1-methyl-6,7-dihydro-4H-pyrazolo[4,3-c]pyridin-5-yl]ethanone To a solution of 4-fluoro-5-(1-methyl-1H-pyrazol-4-yl)indoline (300 mg, 1.38 mmol), 1-(3-bromo-1-methyl-6,7-dihydro-1H-pyrazolo[4,3-c]pyridin-5(4H)-yl)ethanone (Intermediate 392 mg, 1.52 mmol), chloro(2-dicyclohexylphosphino-2',6'-di-i-propoxy-1,1'-biphenyl)[2-(2-aminoethylphenyl)]palladium(II), methyl-tert-butylether adduct (117 mg, 0.14 mmol) and 2-dicyclohexylphosphino-2',6'-di-i-propoxy-1,1'-biphenyl (65 mg, 0.14 mmol) in dioxane (3 mL) was added t-BuONa (398 mg, 4.14 mmol). The mixture was irradiated in a microwave at 120° C. for 45 min. After cooling the reaction to room temperature, the mixture was concentrated in vacuo. The crude residue was purified by reverse phase chromatography (acetonitrile 20-50%/0.1% NH$_4$HCO$_3$ in water) to give the title compound (17 mg, 3%) as a green solid. $^1$H NMR (400 MHz, DMSO-d$_6$)

δ 7.94 (s, 2H), 7.72 (s, 1H), 7.34-7.31 (m, 1H), 7.15-7.03 (m, 1H), 4.50-4.48 (m, 2H), 4.09-3.99 (m, 2H), 3.86 (s, 3H), 3.73-3.62 (m, 2H), 3.41 (s, 3H), 3.17 (t, J=8.4 Hz, 1H), 2.75-2.62 (m, 2H), 2.09-2.06 (m, 3H). LCMS M/Z (M+H) 395.

Example 217

1-[3-[7-fluoro-5-(1-methylpyrazol-4-yl)indolin-1-yl]-1-methyl-6,7-dihydro-4H-pyrazolo[4,3-c]pyridin-5-yl]ethanone

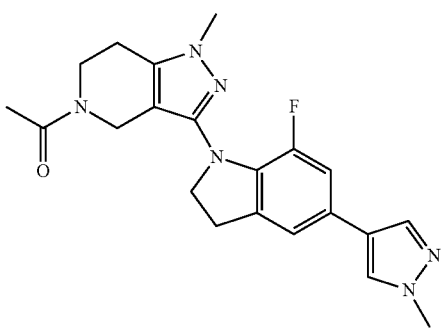 [SMILES: CC(=O)N1CCc2c(c(N3CCc4cc(-c5cnn(C)c5)cc(F)c43)nn2C)C1]

Step 1

7-fluoroindoline

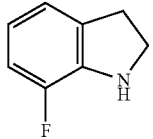

To a solution of 7-fluoro-1H-indole (5.0 g, 37 mmol) in AcOH (30 mL) at 0° C. was added NaCNBH₃ (9.3 g, 148 mmol). The mixture was stirred at room temperature for 2 h. Water (50 mL) was added and the mixture was extracted with EtOAc (50 mL×3). The combined organic layers were dried over anhydrous Na₂SO₄, filtered and concentrated in vacuo to give the title compound (4.6 g, 90%) as a white solid. ¹H NMR (400 MHz, DMSO-d₆) δ 9.82 (s, 1H), 7.37-7.32 (m, 1H), 7.23-7.15 (m, 2H), 3.75-3.65 (m, 1H), 3.52-3.44 (m, 1H), 3.36-3.27 (m, 1H), 3.15-3.09 (m, 1H).

Step 2

5-bromo-7-fluoroindoline

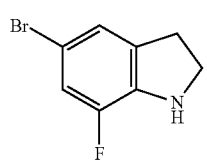

To a solution of 7-fluoroindoline (4.5 g, 32.8 mmol) in DCM (10 mL) was added N-bromosuccinimide (5.8 g, 32.8 mmol). The mixture was stirred at room temperature for 2 h. The mixture was concentrated in vacuo. The crude residue was purified by silica gel chromatography (petroleum ether/EtOAc=20:1) to give the title compound (4.0 g, 56%) as a yellow solid. LCMS M/Z (M+H) 216.

Step 3

7-fluoro-5-(1-methyl-1H-pyrazol-4-yl)indoline

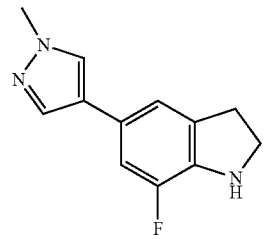 [SMILES: Cn1cc(-c2cc(F)c3c(c2)CCN3)cn1]

To a solution of 5-bromo-7-fluoroindoline (1.0 g, 4.6 mmol) and 1-methyl-4-(4,4,5,5-tetramethyl-1,3,2-dioxaborolan-2-yl)-1H-pyrazole (963 mg, 4.6 mmol) in dioxane (12 mL) and H₂O (3 mL) was added [1,1'-bis(diphenylphosphino)ferrocene]dichloropalladium(II) (336 mg, 0.46 mmol) and Na₂CO₃ (980 mg, 9.3 mmol). The mixture was heated to 110° C. for 12 h under a nitrogen atmosphere. After cooling the reaction to room temperature, the mixture was concentrated in vacuo. The crude residue was purified by silica gel chromatography (petroleum ether/EtOAc=2:1) to give the title compound (560 mg, 55%) as a yellow solid. LCMS M/Z (M+H) 218.

Step 4

1-[3-[7-fluoro-5-(1-methylpyrazol-4-yl)indolin-1-yl]-1-methyl-6,7-dihydro-4H-pyrazolo[4,3-c]pyridin-5-yl]ethanone

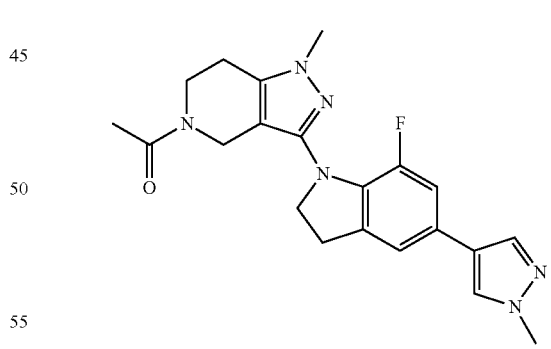

To a solution of 7-fluoro-5-(1-methyl-1H-pyrazol-4-yl)indoline (200 mg, 0.92 mmol) and 1-(3-bromo-1-methyl-6,7-dihydro-1H-pyrazolo[4,3-c]pyridin-5(4H)-yl)ethanone (Intermediate B, 238 mg, 0.92 mmol) in dioxane (5 mL) was added chloro(2-dicyclohexylphosphino-2',6'-di-i-propoxy-1,1'-biphenyl)[2-(2-aminoethylphenyl)]palladium(II), methyl-tert-butylether adduct (82 mg, 0.10 mmol), dicyclohexyl(2',6'-diisopropoxy-[1,1'-biphenyl]-2-yl)phosphine (54 mg, 0.10 mmol) and t-BuONa (177 mg, 1.8 mmol). The mixture was heated to 120° C. for 12 h under a nitrogen atmosphere. After cooling the reaction to room temperature, the mixture was concentrated in vacuo. The crude residue was purified by reverse phase chromatography (acetonitrile 20-55%/0.1% NH$_4$HCO$_3$ in water) to give the title compound (25 mg, 7%) as a white solid. $^1$H NMR (400 MHz, DMSO-d$_6$) δ 8.03 (s, 1H), 7.78 (s, 1H), 7.21 (s, 1H), 7.13-7.08 (m, 1H), 4.29-4.27 (m, 2H), 3.83 (s, 3H), 3.80-3.75 (m, 2H), 3.71-3.63 (m, 2H), 3.56 (s, 3H), 3.11 (t, J=8.6 Hz, 2H), 2.73-2.60 (m, 2H), 2.05-1.99 (m, 3H). LCMS M/Z (M+H) 395.

Example 218

1-[3-[6-(difluoromethyl)-5-(1-methylpyrazol-4-yl)indolin-1-yl]-1-(oxetan-3-yl)-6,7-dihydro-4H-pyrazolo[4,3-c]pyridin-5-yl]ethanone

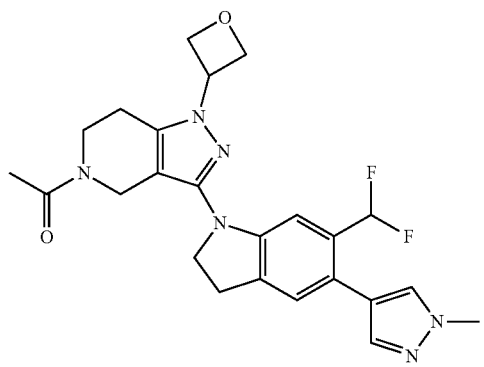 [SMILES: CC(=O)N1CCc2c(c(N3CCc4cc(-c5cnn(C)c5)c(C(F)F)cc43)nn2C2COC2)C1]

Step 1 tert-butyl 6-formyl-1H-indole-1-carboxylate

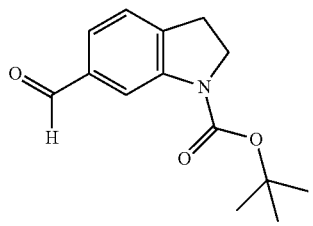 [SMILES: CC(C)(C)OC(=O)N1CCc2ccc(C=O)cc21]

To a solution of 1H-indole-6-carbaldehyde (19.0 g, 131 mmol) and triethylamine (40.0 g, 390 mmol) in DCM (100 mL) was added 4-dimethylaminopyridine (catalytic) and di-tert-butyl dicarbonate (42.8 g, 196 mmol). The mixture was stirred at 15° C. for 16 h under a nitrogen atmosphere. The mixture was concentrated in vacuo. The crude residue was purified by silica gel chromatography (petroleum ether/EtOAc=20:1) to give the title compound (23.0 g, 72%) as a brown solid. LCMS M/Z (M+H) 246.

Step 2 tert-butyl 6-(difluoromethyl)-1H-indole-1-carboxylate

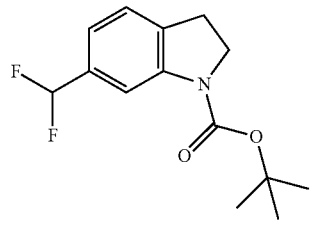 [SMILES: CC(C)(C)OC(=O)N1CCc2ccc(C(F)F)cc21]

To a solution of tert-butyl 6-formyl-1H-indole-1-carboxylate (1.0 g, 4.1 mmol) in DCM (15 mL) was added (diethylamino)sulfur trifluoride (3.0 g, 18.6 mmol) under a nitrogen atmosphere. The mixture was stirred at 20° C. for 16 h. The mixture was quenched with sat. aq. NaHCO$_3$ (30 mL) and then extracted with DCM (50 mL×2). The combined organic layers were washed with brine (50 mL×2), dried over anhydrous Na$_2$SO$_4$, filtered and concentrated in vacuo. The crude residue was purified by silica gel chromatography (petroleum ether/EtOAc=20:1) to give the title compound (450 mg, 45%) as a white solid. $^1$H NMR (400 MHz, CDCl$_3$) δ 8.36 (s, 1H), 7.69 (d, J=3.6 Hz, 1H), 7.64 (d, J=8.4 Hz, 1H), 7.40 (d, J=8.4 Hz, 1H), 6.77 (t, J=56.8 Hz, 1H), 6.62 (d, J=3.6 Hz, 1H), 1.70 (s, 9H).

Step 3 tert-butyl 6-(difluoromethyl)indoline-1-carboxylate

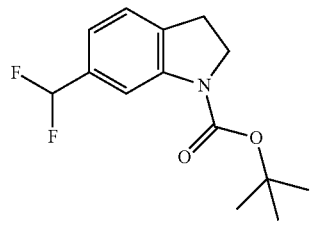 [SMILES: CC(C)(C)OC(=O)N1CCc2ccc(C(F)F)cc21]

To a solution of tert-butyl 6-(difluoromethyl)-1H-indole-1-carboxylate (450 mg, 1.7 mmol) in MeOH (20 mL) was added Pd/C (70 mg, 10% by weight). The mixture was stirred at room temperature for 12 h under hydrogen atmosphere (15 psi). The mixture was concentrated in vacuo. The crude residue was purified by silica gel chromatography (petroleum ether/EtOAc=20:1) to give the title compound (310 mg, 69%) as a white solid.

Step 4 tert-butyl 5-bromo-6-(difluoromethyl)indoline-1-carboxylate

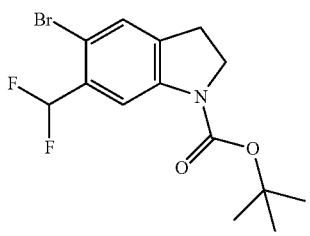 [SMILES: CC(C)(C)OC(=O)N1CCc2cc(Br)c(C(F)F)cc21]

To a solution of tert-butyl 6-(difluoromethyl)indoline-1-carboxylate (310 mg, 1.2 mmol) in DMF (5 mL) was added N-bromosuccinimide (210 mg, 1.2 mmol). The mixture was stirred at 15° C. for 12 h under a nitrogen atmosphere. EtOAc (30 mL) was added and the mixture was washed with brine (20 mL×2), dried over anhydrous $Na_2SO_4$, filtered and concentrated in vacuo. The crude residue was purified by silica gel chromatography (petroleum ether/EtOAc=20:1) to give the title compound (300 mg, 75%) as a white solid. $^1$H NMR (400 MHz, $CDCl_3$) δ 8.15-7.79 (m, 1H), 7.34 (s, 1H), 6.87 (t, J=55.2 Hz, 1H), 4.02 (t, J=8.0 Hz, 2H), 3.12 (t, J=8.4 Hz, 2H), 1.58-1.57 (m, 9H).

Step 5 tert-butyl 6-(difluoromethyl)-5-(1-methyl-1H-pyrazol-4-yl)indoline-1-carboxylate

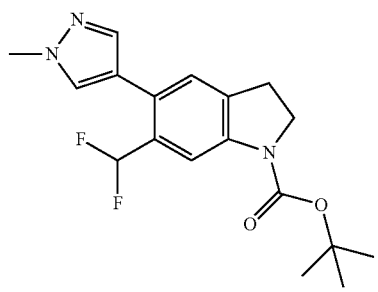 [SMILES: Cn1cc(-c2cc3c(cc2C(F)F)N(C(=O)OC(C)(C)C)CC3)cn1]

To a solution of tert-butyl 5-bromo-6-(difluoromethyl)indoline-1-carboxylate (300 mg, 0.86 mmol), 1-methyl-4-(4,4,5,5-tetramethyl-1,3,2-dioxaborolan-2-yl)-1H-pyrazole (220 mg, 1.0 mmol) and $K_2CO_3$ (520 mg, 3.8 mmol) in dioxane (20 mL) and $H_2O$ (2 mL) was added [1,1'-bis(diphenylphosphino)ferrocene]dichloropalladium(II) (70 mg, 0.1 mmol). The mixture was heated to 90° C. for 12 h under a nitrogen atmosphere. After cooling the reaction to room temperature, the mixture was concentrated in vacuo. The crude residue was purified by silica gel chromatography (petroleum ether/EtOAc=3:1) to give the title compound (280 mg, 93%) as a brown oil. LCMS M/Z (M+H) 350.

Step 6

6-(difluoromethyl)-5-(1-methyl-1H-pyrazol-4-yl)indoline

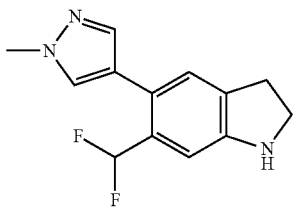 [SMILES: Cn1cc(-c2cc3c(cc2C(F)F)NCC3)cn1]

To a solution of tert-butyl 6-(difluoromethyl)-5-(1-methyl-1H-pyrazol-4-yl)indoline-1-carboxylate (280 mg, 0.8 mmol) in DCM (10 mL) was added trifluoroacetic acid (5 mL). The mixture was stirred at 18° C. for 2 h under a nitrogen atmosphere. The mixture was concentrated in vacuo. EtOAc (50 mL) was added and the mixture was washed with sat. aq. $NaHCO_3$ (50 mL) and brine (50 mL×2), filtered and concentrated in vacuo. The crude residue was purified by silica gel chromatography (petroleum ether/EtOAc=5:1 to 3:1) to give the title compound (190 mg, 95%) as a brown solid. $^1$H NMR (400 MHz, $CDCl_3$) δ 7.53 (s, 1H), 7.41 (s, 1H), 7.11 (s, 1H), 6.97 (s, 1H), 6.56 (t, J=55.6 Hz, 1H), 3.96 (s, 3H), 3.63 (t, J=8.4 Hz, 2H), 3.08 (t, J=8.4 Hz, 2H).

Step 7

1-[3-[6-(difluoromethyl)-5-(1-methylpyrazol-4-yl)indolin-1-yl]-1-(oxetan-3-yl)-6,7-dihydro-4H-pyrazolo[4,3-c]pyridin-5-yl]ethanone

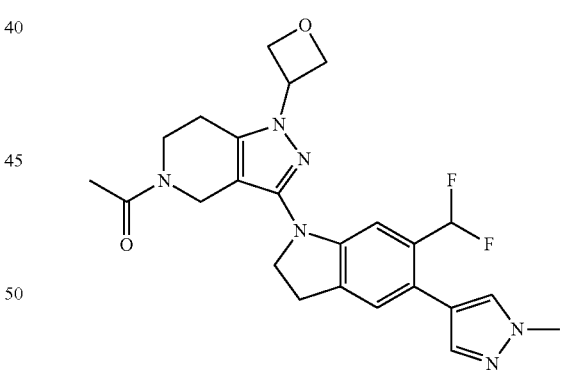

To a solution of 6-(difluoromethyl)-5-(1-methylpyrazol-4-yl)indoline (90 mg, 0.36 mmol), tert-butoxysodium (69 mg, 0.72 mmol) and 1-[3-bromo-1-(oxetan-3-yl)-6,7-dihydro-4H-pyrazolo[4,3-c]pyridin-5-yl]ethanone (Intermediate E, 108 mg, 0.36 mmol) in 1,4-dioxane (5 mL) was added chloro(2-dicyclohexylphosphino-2',6'-di-i-propoxy-1,1'-biphenyl)[2-(2-aminoethylphenyl)]palladium(II), methyl-tert-butylether adduct (30 mg, 0.04 mmol) and 2-dicyclohexylphosphino-2',6'-di-i-propoxy-1,1'-biphenyl (16 mg, 0.04 mmol). The mixture was heated to 120° C. for 12 h under a nitrogen atmosphere. After cooling the reaction to room temperature, the mixture was concentrated in vacuo. EtOAc (100 ml) was added and the mixture was washed with water (100 mL×2) and brine (50 mL), dried over anhydrous Na₂SO₄ and concentrated in vacuo. The crude residue was purified by reverse phase chromatography (acetonitrile 6-36%/0.2% formic acid in water) to give the title compound (48 mg, 28%) as a white solid. $^1$H NMR (400 MHz, DMSO-$d_6$) δ 7.88-7.78 (m, 2H), 7.53 (s, 1H), 7.22 (s, 1H), 7.00-6.71 (m, 1H), 5.47-5.41 (m, 1H), 4.98-4.83 (m, 2H), 4.86-4.83 (m, 2H), 4.57-4.55 (m, 2H), 4.15-4.05 (m, 2H), 3.88 (s, 3H), 3.72-3.67 (m, 2H), 3.23-3.19 (m, 2H), 2.76-2.61 (m, 2H), 2.09-2.08 (m, 3H). LCMS M/Z (M+H) 469.

Example 219

1-(5-acetyl-1-tetrahydropyran-4-yl-6,7-dihydro-4H-pyrazolo[4,3-c]pyridin-3-yl)-5-(1-methylpyrazol-4-yl)indoline-6-carbonitrile

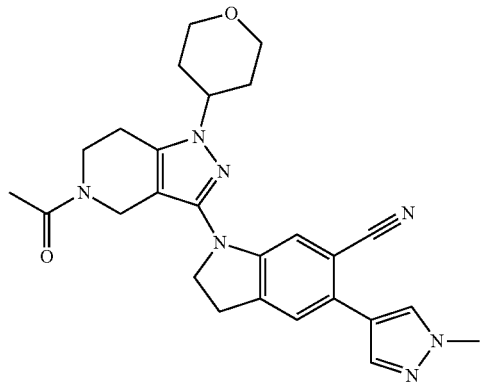 [SMILES: CC(=O)N1CCc2c(c(N3CCc4cc(-c5cnn(C)c5)c(C#N)cc43)nn2C2CCOCC2)C1]

Step 1

6-chloro-5-(1-methyl-1H-pyrazol-4-yl)-1H-indole

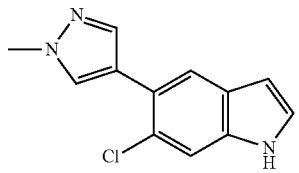 [SMILES: Cn1cc(-c2cc3cc[nH]c3cc2Cl)cn1]

To a solution of 5-bromo-6-chloro-H-indole (10.0 g, 43.4 mmol) in THF (20 mL) and water (4 mL) was added 1-methyl-4-(4,4,5,5-tetramethyl-1,3,2-dioxaborolan-2-yl)-1H-pyrazole (9.0 g, 43.4 mmol), chloro(2-dicyclohexylphosphino-2',4',6'-tri-i-propyl-1,1'-biphenyl)(2'-amino-1,1'-biphenyl-2-yl) palladium(II) (1.7 g, 2.2 mmol), 2-(dicyclohexylphosphino)-2',4',6'-triisopropylbiphenyl (2.1 g, 4.34 mmol) and Na₂CO₃ (9.2 g, 86.8 mmol). The mixture was heated to 60° C. for 16 h under a nitrogen atmosphere. The solution was concentrated in vacuo. The crude residue was purified by silica gel chromatography (DCM/MeOH=20:1) to give the title compound (9.6 g, 74%) as a yellow solid. LCMS M/Z (M+H) 232.

Step 2

6-chloro-5-(1-methyl-1H-pyrazol-4-yl)indoline

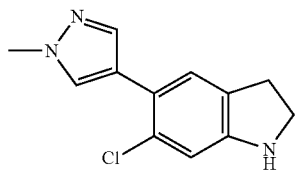 [SMILES: Cn1cc(-c2cc3c(cc2Cl)NCC3)cn1]

To a solution of 6-chloro-5-(1-methylpyrazol-4-yl)-1H-indole (2.0 g, 6.7 mmol) in AcOH (10 mL) was added sodium cyanoborohydride (410 mg, 6.7 mmol). The mixture was stirred at 26° C. for 2 h. The mixture was concentrated in vacuo. EtOAc (200 mL) was added and the mixture was washed with water (200 mL×2) and brine (100 mL), dried over Na₂SO₄, filtered and concentrated in vacuo. The crude residue was purified by silica gel chromatography (petroleum ether/EtOAc=3:1) to give the title compound (1.4 g, 57%) as a yellow solid. LCMS M/Z (M+H) 234.

Step 3

5-(1-methyl-1H-pyrazol-4-yl)indoline-6-carbonitrile

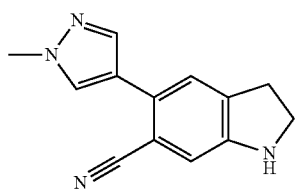 [SMILES: Cn1cc(-c2cc3c(cc2C#N)NCC3)cn1]

To a solution of 6-chloro-5-(1-methylpyrazol-4-yl)indoline (0.7 g, 2.6 mmol), potassium acetate (1.0 g, 10.3 mmol) and potassium hexacyanoferrate(II) trihydrate (5.9 g, 15.4 mmol) in 1,4-dioxane (30 mL) and water (30 mL) was added [2-(2-aminophenyl)phenyl]-methylsulfonyloxy-palladium di-tert-butyl-[2-(2,4,6-triisopropylphenyl)phenyl]phosphane (204 mg, 0.3 mmol) and di-tert-butyl(2',4',6'-triisopropyl-[1,1'-biphenyl]-2-yl)phosphine (218 mg, 0.5 mmol). The mixture was heated to 120° C. for 2 h under a nitrogen atmosphere. After cooling the reaction to room temperature, the mixture was concentrated in vacuo. EtOAc (500 mL) was added and the mixture was washed with water (200 mL×2) and brine (100 mL), dried over Na₂SO₄, filtered and concentrated in vacuo. The crude residue was purified by silica gel chromatography (petroleum ether/EtOAc=3:1) to give the title compound (540 mg, 67%) as a yellow solid. LCMS M/Z (M+H) 225.

Step 4

1-(5-acetyl-1-tetrahydropyran-4-yl-6,7-dihydro-4H-pyrazolo[4,3-c]pyridin-3-yl)-5-(1-methylpyrazol-4-yl)indoline-6-carbonitrile

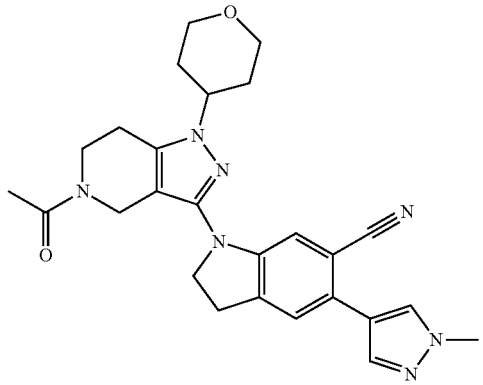 [SMILES: CC(=O)N1CCc2c(c(N3CCc4cc(-c5cnn(C)c5)c(C#N)cc43)nn2C2CCOCC2)C1]

To a solution of 1-(3-bromo-1-tetrahydropyran-4-yl-6,7-dihydro-4H-pyrazolo[4,3-c]pyridin-5-yl)ethanone (Intermediate I, 300 mg, 0.9 mmol), 5-(1-methylpyrazol-4-yl)indoline-6-carbonitrile (246 mg, 1.1 mmol) and tert-butoxysodium (176 mg, 1.8 mmol) in 1,4-dioxane (5 mL) was added chloro(2-dicyclohexylphosphino-2',6'-di-i-propoxy-1,1'-biphenyl)(2'-amino-1,1'-biphenyl-2-yl)palladium(II) (71 mg, 0.09 mmol), dicyclohexyl(2',6'-diisopropoxy-[1,1'-biphenyl]-2-yl)phosphine (43 mg, 0.09 mmol). The mixture was heated to 120° C. for 12 h under a nitrogen atmosphere. After cooling the reaction to room temperature, the mixture was concentrated in vacuo. EtOAc (300 mL) was added and the mixture was washed with water (300 mL×2) and brine (100 mL), dried over anhydrous Na$_2$SO$_4$, filtered and concentrated in vacuo. The crude residue was recrystallized from MeOH (5 mL) to give the title compound (155 mg, 36%) as a white solid. $^1$H NMR (400 MHz, DMSO-d$_6$) δ 8.11 (s, 1H), 7.83 (s, 1H), 7.78-7.71 (m, 1H), 7.44 (s, 1H), 4.60-4.58 (m, 2H), 4.29-4.24 (m, 1H), 4.16-4.06 (m, 2H), 4.00-3.98 (m, 2H), 3.90 (s, 3H), 3.75-3.69 (m, 2H), 3.50-3.44 (m, 2H), 3.26-3.21 (m, 2H), 2.84-2.68 (m, 2H), 2.11-2.10 (m, 3H), 2.05-1.98 (m, 2H), 1.82-1.79 (m, 2H). LCMS M/Z (M+H) 472.

Example 220

1-[3-[4-(hydroxymethyl)-5-(1-methylpyrazol-4-yl)indolin-1-yl]-1-tetrahydrofuran-3-yl-6,7-dihydro-4H-pyrazolo[4,3-c]pyridin-5-yl]ethanone

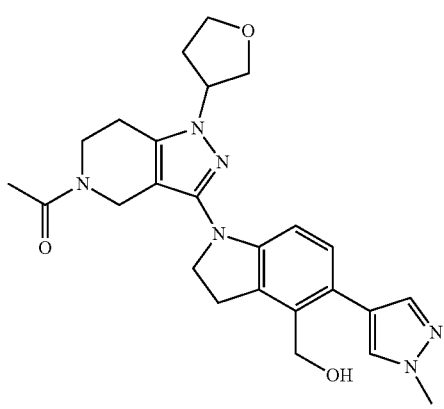 [SMILES: CC(=O)N1CCc2c(c(N3CCc4c3ccc(-c3cnn(C)c3)c4CO)nn2C2CCOC2)C1]

Step 1

(1H-indol-4-yl)methanol

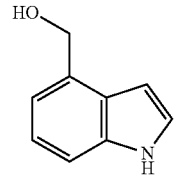 [SMILES: OCc1cccc2[nH]ccc12]

To a solution of 1H-indole-4-carbaldehyde (10 g, 68.89 mmol) in MeOH (200 mL) at 0° C. was added NaBH$_4$ (3.1 g, 82.67 mmol). The resulting mixture was stirred at 0° C. for 0.5 h. Water (100 mL) was added slowly and the mixture was extracted with EtOAc (300 mL×3). The combined organic layers were dried over anhydrous Na$_2$SO$_4$, filtered and concentrated to give the title compound (10 g, crude) as a colorless oil that required no further purification.

Step 2 indolin-4-ylmethanol

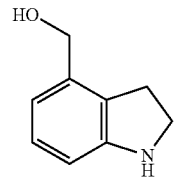 [SMILES: OCc1cccc2c1CCN2]

To a solution of (1H-indol-4-yl)methanol (10 g, 67.95 mmol) in AcOH (100 mL) was added NaBH$_3$CN (12.8 g, 203.84 mmol) portionwise. The resulting mixture was stirred at room temperature for 2 h. Water (200 mL) was added and the mixture was made basic with solid NaHCO$_3$ to pH 8 and then extracted with EtOAc (600 mL×3). The combined organic layers were dried over anhydrous Na$_2$SO$_4$, filtered and concentrated in vacuo. The crude residue was purified by silica gel chromatography (petroleum ether/EtOAc=10:1) to give the title compound (6 g, 60%) as a white solid.

Step 3

4-(((tert-butyldimethylsilyl)oxy)methyl)indoline

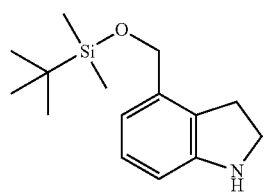 [SMILES: CC(C)(C)[Si](C)(C)OCc1cccc2c1CCN2]

To a solution of indolin-4-ylmethanol (6 g, 40.22 mmol) in THF (200 mL) was added 1H-Imidazole (11 g, 160.87 mmol) and tert-butyl-dimethylsilyl chloride (13.3 g, 88.48 mmol). The mixture was stirred at room temperature for 12 h and the resulting precipitate was removed by filtration. The filtrate was concentrated in vacuo. EtOAc (200 mL) was added and the mixture was washed with water (200 mL×2). The organic layer was dried over anhydrous $Na_2SO_4$, filtered and concentrated in vacuo. The crude residue was purified by silica gel chromatography (petroleum ether/EtOAc=10:1) to give the title compound (8 g, 75%) as a white solid. $^1$H NMR (400 MHz, DMSO-$d_6$) δ 6.89-6.86 (m, 1H), 6.52 (d, J=7.6 Hz, 1H), 6.40 (d, J=7.6 Hz, 1H), 5.43 (s, 1H), 4.57 (s, 2H), 3.40 (t, J=8.4 Hz, 2H), 2.85 (t, J=8.4 Hz, 2H), 0.89 (s, 9H), 0.06 (s, 6H).

Step 4 tert-butyl 4-(((tert-butyldimethylsilyl)oxy)methyl) indoline-1-carboxylate

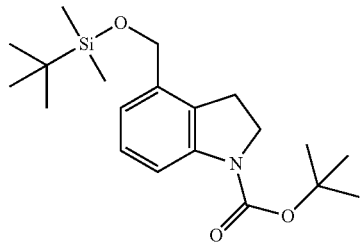 [SMILES: CC(C)(C)OC(=O)N1CCc2c(CO[Si](C)(C)C(C)(C)C)cccc21]

To a solution of 4-(((tert-butyldimethylsilyl)oxy)methyl) indoline (8 g, 30.37 mmol) in DCM (200 mL) was added DMAP (371 mg, 3.04 mmol), triethylamine (9.2 g, 91.1 mmol) and di-tert-butyl dicarbonate (8 g, 36.44 mmol). The resulting mixture was stirred at room temperature for 16 h. The mixture was concentrated in vacuo. Water (100 mL) was added and the mixture was extracted with EtOAc (200 mL×2). The combined organic layers were dried over anhydrous $Na_2SO_4$, filtered and concentrated in vacuo. The crude residue was purified by silica gel chromatography (petroleum ether/EtOAc=50:1) to give the title compound (9 g, 81%) as a white solid.

Step 5 tert-butyl 5-bromo-4-(((tert-butyldimethylsilyl)oxy) methyl)indoline-1-carboxylate

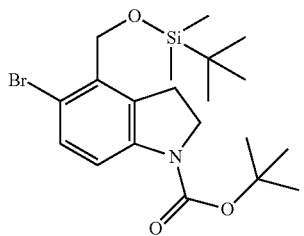 [SMILES: CC(C)(C)OC(=O)N1CCc2c1ccc(Br)c2CO[Si](C)(C)C(C)(C)C]

To a solution of tert-butyl 4-(((tert-butyldimethylsilyl) oxy)methyl)indoline-1-carboxylate (9 g, 24.75 mmol) in DCM (200 mL) was added N-bromosuccinimide (4.9 g, 27.23 mmol). The resulting mixture was stirred at room temperature for 2 h. The mixture was concentrated in vacuo. The crude residue was purified by silica gel chromatography (petroleum ether/EtOAc=50:1) to give the title compound (9.5 g, 86%) as a white solid. $^1$H NMR (400 MHz, DMSO-$d_6$) δ 7.58-7.50 (m, 1H), 7.37 (d, J=8.4 Hz, 1H), 4.70 (s, 2H), 3.93 (t, J=8.4 Hz, 2H), 3.15 (t, J=8.4 Hz, 2H), 1.49 (s, 9H), 0.87 (s, 9H), 0.08 (s, 6H).

Step 6 tert-butyl 4-(((tert-butyldimethylsilyl)oxy)methyl)-5-(1-methyl-1H-pyrazol-4-yl)indoline-1-carboxylate

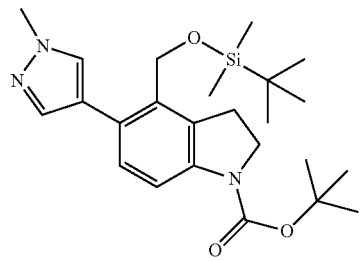 [SMILES: Cn1cc(-c2ccc3c(c2CO[Si](C)(C)C(C)(C)C)CCN3C(=O)OC(C)(C)C)cn1]

To a solution of tert-butyl 5-bromo-4-(((tert-butyldimethylsilyl)oxy)methyl)indoline-1-carboxylate (9.5 g, 21.47 mmol) in dioxane (100 mL) and $H_2O$ (10 mL) was added $K_2CO_3$ (6.8 g, 64.41 mmol), [1,1'-bis(diphenylphosphino) ferrocene]dichloropalladium(II) (1 g, 2.2 mmol) and 1-methyl-4-(4,4,5,5-tetramethyl-1,3,2-dioxaborolan-2-yl)-1H-pyrazole (4.5 g, 21.47 mmol). The mixture was heated to 120° C. for 12 h under a nitrogen atmosphere. After cooling the reaction to room temperature, the mixture was concentrated in vacuo. The crude residue was purified by silica gel chromatography (petroleum ether/EtOAc=3:1) to give the title compound (4.9 g, 51%) as a yellow solid.

Step 7

4-(((tert-butyldimethylsilyl)oxy)methyl)-5-(1-methyl-1H-pyrazol-4-yl)indoline

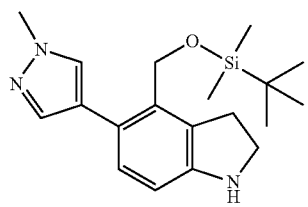 [SMILES: Cn1cc(-c2ccc3c(c2CO[Si](C)(C)C(C)(C)C)CCN3)cn1]

To a solution of tert-butyl4-(((tert-butyldimethylsilyl) oxy)methyl)-5-(1-methyl-1H-pyrazol-4-yl)indoline-1-carboxylate (1 g, 2.25 mmol) in DCM (60 mL) was added trifluoroacetic acid (10 mL). The mixture was stirred at room temperature for 1 h. Water (60 mL) was added and the mixture was made basic with solid $NaHCO_3$ to pH 8 and then extracted with DCM (60 mL×2). The combined organic layers were dried over anhydrous $Na_2SO_4$, filtered and concentrated in vacuo to give the title compound (600 mg, crude) as a yellow solid that required no further purification. $^1$H NMR (400 MHz, DMSO-$d_6$) δ 7.69 (s, 1H), 7.48 (s, 1H), 6.92 (d, J=8.4 Hz, 1H), 6.49 (d, J=8.4 Hz, 1H), 5.76 (s, 1H), 4.50 (s, 2H), 3.84 (s, 3H), 3.44 (t, J=8.4 Hz, 2H), 2.99 (t, J=8.4 Hz, 2H), 0.88 (s, 9H), 0.06 (s, 6H).

Step 8

1-(3-(4-(((tert-butyldimethylsilyl)oxy)methyl)-5-(1-methyl-1H-pyrazol-4-yl)indolin-1-yl)-1-(tetrahydrofuran-3-yl)-6,7-dihydro-1H-pyrazolo[4,3-c]pyridin-5(4H)-yl)ethanone

To a solution of 4-(((tert-butyldimethylsilyl)oxy)methyl)-5-(1-methyl-1H-pyrazol-4-yl)indoline (300 mg, 0.87 mmol) in dioxane (10 mL) was added 1-(3-bromo-1-(tetrahydrofuran-3-yl)-6,7-dihydro-1H-pyrazolo[4,3-c]pyridin-5(4H)-yl)ethanone (302 mg, 0.96 mmol), chloro(2-dicyclohexylphosphino-2',6'-di-i-propoxy-1,1'-biphenyl)[2-(2-aminoethylphenyl)]palladium(II), methyl-tert-butylether adduct (65 mg, 0.08 mmol), 2-dicyclohexylphosphino-2',6'-di-i-propoxy-1,1'-biphenyl (35 mg, 0.08 mmol) and t-BuONa (336 mg, 3.49 mmol). The mixture was heated to 120° C. for 12 h under a nitrogen atmosphere. After cooling the reaction to room temperature, the mixture was concentrated in vacuo. The crude residue was purified by silica gel chromatography (DCM/MeOH=20:1) to give the title compound (150 mg, 30%) as a yellow solid. LCMS M/Z (M+H) 577.

Step 9

1-[3-[4-(hydroxymethyl)-5-(1-methylpyrazol-4-yl)indolin-1-yl]-1-tetrahydrofuran-3-yl-6,7-dihydro-4H-pyrazolo[4,3-c]pyridin-5-yl]ethanone

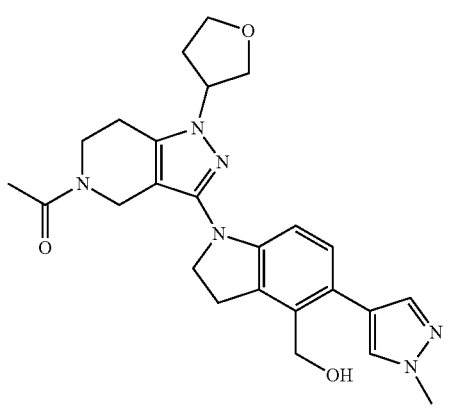 [SMILES: CC(=O)N1CCc2c(c(N3CCc4c3ccc(-c3cnn(C)c3)c4CO)nn2C2CCOC2)C1]

To a solution of 1-(3-(4-(((tert-butyldimethylsilyl)oxy)methyl)-5-(1-methyl-1H-pyrazol-4-yl)indolin-1-yl)-1-(tetrahydrofuran-3-yl)-6,7-dihydro-1H-pyrazolo[4,3-c]pyridin-5(4H)-yl)ethanone (150 mg, 0.26 mmol) in THF (10 mL) was added tetrabutylammonium fluoride (82 mg, 0.31 mmol). The mixture was stirred at room temperature for 3 h. The resulting mixture was concentrated in vacuo. Water (10 mL) was added and the mixture was extracted with EtOAc (20 mL×2). The combined organic layers were dried over anhydrous Na$_2$SO$_4$, filtered and concentrated in vacuo. The crude residue was purified by reverse phase chromatography (acetonitrile 20-50%/0.1% NH$_4$HCO$_3$ in water) to give the title compound (33 mg, 24%) as a yellow solid. $^1$H NMR (400 MHz, DMSO-d$_6$) δ 7.87 (s, 1H), 7.78 (s, 1H), 7.69-7.65 (m, 1H), 7.56 (s, 1H), 7.48 (s, 1H), 7.24 (d, J=8.0 Hz, 2H), 7.07 (d, J=8.0 Hz, 1H), 6.90-6.89 (m, 1H), 5.01-4.90 (m, 1H), 4.85-4.78 (m, 4H), 4.77 (s, 1H), 4.53 (s, 2H), 4.49 (s, 2H), 4.43-4.42 (m, 2H), 4.07-4.01 (m, 8H), 3.90-3.84 (m, 10H), 3.82 (s, 2H), 3.26 (t, J=8.6 Hz, 2H), 2.95-2.70 (m, 2H), 2.69-2.60 (m, 2H), 2.30-2.27 (m, 2H), 2.25-2.09 (m, 2H), 2.05 (s, 6H). LCMS M/Z (M+H) 463.

Example 221

1-[3-[4-methyl-5-(1-methylpyrazol-4-yl)indolin-1-yl]-1-tetrahydrofuran-3-yl-6,7-dihydro-4H-pyrazolo[4,3-c]pyridin-5-yl]ethanone

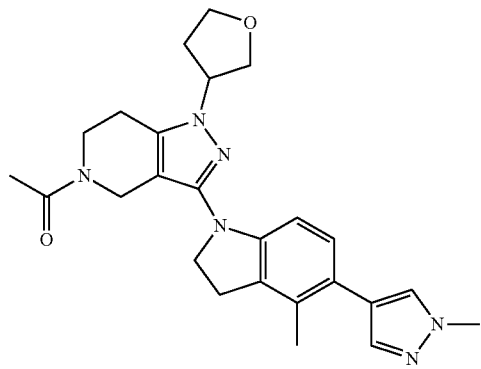 [SMILES: CC(=O)N1CCc2c(c(N3CCc4c3ccc(-c3cnn(C)c3)c4C)nn2C2CCOC2)C1]

Step 1 tert-butyl 4-(hydroxymethyl)-5-(1-methyl-1H-pyrazol-4-yl)indoline-1-carboxylate

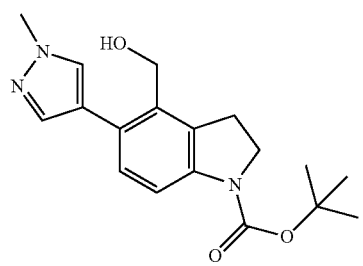 [SMILES: Cn1cc(-c2ccc3c(c2CO)CCN3C(=O)OC(C)(C)C)cn1]

To a solution of tert-butyl 4-(((tert-butyldimethylsilyl)oxy)methyl)-5-(1-methyl-1H-pyrazol-4-yl)indoline-1-carboxylate (1 g, 2.26 mmol) in DCM (40 mL) was added HCl in EtOAc (10 mL). The mixture was stirred at room temperature for 30 min. Water (20 mL) was added and the mixture was made basic with solid NaHCO₃ to pH 8 and then extracted with EtOAc (100 mL×2). The combined organic layers were dried over anhydrous Na₂SO₄, filtered and concentrated in vacuo to give the title compound (700 mg, crude) as a white solid that required no further purification. LCMS M/Z (M+H) 330.

Step 2 tert-butyl 4-methyl-5-(1-methyl-1H-pyrazol-4-yl)indoline-1-carboxylate

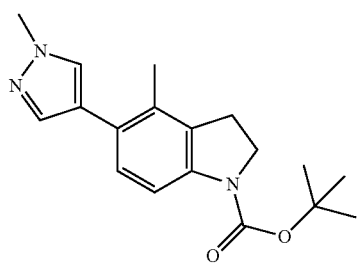 [SMILES: Cc1c(-c2cnn(C)c2)ccc2c1CCN2C(=O)OC(C)(C)C]

To a solution of tert-butyl 4-(hydroxymethyl)-5-(1-methyl-1H-pyrazol-4-yl)indoline-1-carboxylate (700 mg, 2.13 mmol) in MeOH (10 mL) was added Pd/C (1 g, 10% wt.). The mixture was stirred at room temperature for 12 h under hydrogen atmosphere (15 psi). The reaction was filtered and the filtrate was concentrated in vacuo. The crude residue was purified by silica gel chromatography (petroleum ether/EtOAc=1:1) to give the title compound (120 mg, 18%) as a yellow solid. LCMS M/Z (M+H) 314.

Step 3

4-methyl-5-(1-methyl-1H-pyrazol-4-yl)indoline

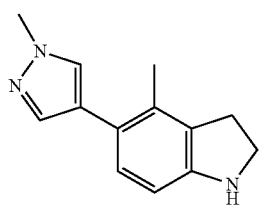 [SMILES: Cc1c(-c2cnn(C)c2)ccc2c1CCN2]

To a solution of tert-butyl 4-methyl-5-(1-methyl-1H-pyrazol-4-yl)indoline-1-carboxylate (120 mg, 0.38 mmol) in EtOAc (2 mL) was added HCl in EtOAc (4M, 2 mL). The mixture was stirred at room temperature for 1 h. The resulting mixture was concentrated in vacuo. Water (10 mL) was added and the mixture was made basic with solid NaHCO₃ to pH 8 and then extracted with EtOAc (30 mL×2). The combined organic layers were dried over anhydrous Na₂SO₄, filtered and concentrated in vacuo to give the title compound (80 mg, crude) as a yellow solid that required no further purification.

Step 4

1-[3-[4-methyl-5-(1-methylpyrazol-4-yl)indolin-1-yl]-1-tetrahydrofuran-3-yl-6,7-dihydro-4H-pyrazolo[4,3-c]pyridin-5-yl]ethanone

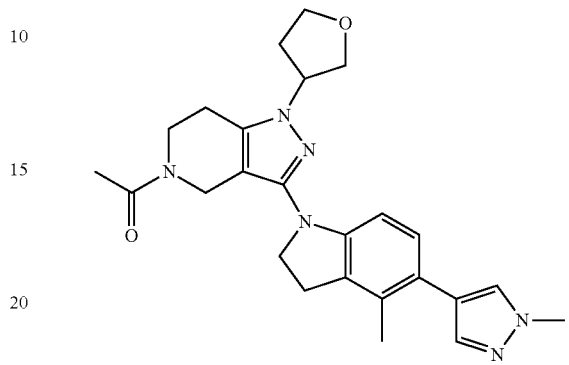

To a solution of 4-methyl-5-(1-methyl-1H-pyrazol-4-yl)indoline (80 mg, 0.38 mmol) in dioxane (5 mL) was added 1-(3-bromo-1-(tetrahydrofuran-3-yl)-6,7-dihydro-1H-pyrazolo[4,3-c]pyridine-5(4H)-yl)ethanone (142 mg, 0.45 mmol), chloro(2-dicyclohexylphosphino-2',6'-di-i-propoxy-1,1'-biphenyl) [2-(2-aminoethylphenyl)]palladium(II), methyl-tert-butylether adduct (180 mg, 0.04 mmol), 2-dicyclohexylphosphino-2',6'-di-i-propoxy-1,1'-biphenyl (25 mg, 0.04 mmol) and t-BuONa (144 mg, 1.5 mmol). The mixture was heated to 100° C. for 12 h under a nitrogen atmosphere. After cooling the reaction to room temperature, the mixture was concentrated in vacuo. The crude residue was purified by reverse phase chromatography (acetonitrile 20-50%/0.1% NH₄HCO₃ in water) to give the title compound (45 mg, 20%) as a white solid. ¹H NMR (400 MHz, DMSO-d₆) δ 7.76 (s, 1H), 7.50 (s, 1H), 7.23-7.17 (m, 1H), 7.03-7.00 (m, 1H), 4.88-4.82 (m, 1H), 4.54-4.52 (m, 2H), 4.03-3.98 (m, 3H), 3.85 (s, 3H), 3.83-3.69 (m, 2H), 3.31 (s, 3H), 3.08 (t, J=8.4 Hz, 2H), 2.79-2.66 (m, 2H), 2.25-2.08 (m, 7H). LCMS M/Z (M+H) 447.

Example 222

1-[3-[N-ethyl-4-(1-methylpyrazol-4-yl)anilino]-1-[(3S)-tetrahydrofuran-3-yl]-6,7-dihydro-4H-pyrazolo[4,3-c]pyridin-5-yl]ethanone

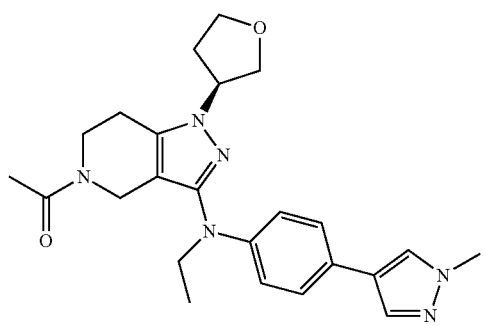 [SMILES: CCN(c1ccc(-c2cnn(C)c2)cc1)c1nn([C@H]2CCOC2)c2c1CN(C(C)=O)CC2]

Step 1

4-(1-methyl-1H-pyrazol-4-yl)aniline

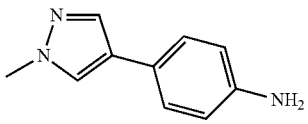

To a solution of 4-bromoaniline (3.0 g, 17.4 mmol), 1-methyl-4-(4,4,5,5-tetramethyl-1,3,2-dioxaborolan-2-yl) pyrazole (4.4 g, 20.9 mmol) and K$_2$CO$_3$ (4.9 g, 34.9 mmol) in 1,4-dioxane (20 mL) and water (5 mL) was added [1,1'-bis(diphenylphosphino)ferrocene]dichloropalladium (II) (1.2 g, 1.7 mmol). The mixture was heated to 120° C. for 12 h. After cooling the reaction to room temperature, the mixture was filtered and the filtrate was concentrated in vacuo. Water (100 mL) was added and the mixture was extracted with EtOAc (300 mL×3). The combined organic layers were washed with brine (100 mL×3), dried over anhydrous Na$_2$SO$_4$ and concentrated in vacuo. The crude residue was purified by silica gel chromatography (petroleum ether/EtOAc=1:1) to give the title compound (2.7 g, 72%) as a yellow solid. $^1$H NMR (400 MHz, DMSO-d$_6$) δ 7.85 (s, 1H), 7.63 (s, 1H), 7.19 (d, J=8.8 Hz, 2H), 6.54 (d, J=8.4 Hz, 2H), 5.00 (s, 2H), 3.81 (s, 3H).

Step 2

(S)-1-(3-((4-(1-methyl-1H-pyrazol-4-yl)phenyl)amino)-1-(tetrahydrofuran-3-yl)-6,7-dihydro-1H-pyrazolo[4,3-c]pyridin-5(4H)-yl)ethanone

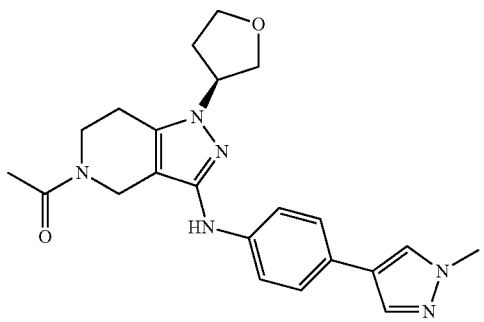 [SMILES: CC(=O)N1CCc2c(c(Nc3ccc(-c4cnn(C)c4)cc3)nn2[C@H]2CCOC2)C1]

To a solution of 1-[3-bromo-1-[(3S)-tetrahydrofuran-3-yl]-6,7-dihydro-4H-pyrazolo[4,3-c]pyridin-5-yl]ethanone (Intermediate G, 1.0 g, 3.2 mmol), t-BuONa (0.6 g, 6.4 mmol) and 4-(1-methylpyrazol-4-yl)aniline (661.6 mg, 3.8 mmol) in 1,4-dioxane (10 mL) was added chloro(2-dicyclohexylphosphino-2',6'-di-i-propoxy-1,1'-biphenyl)[2-(2-aminoethylphenyl)]palladium(II), methyl-tert-butylether adduct (260.0 mg, 0.3 mmol) and 2-(dicyclohexylphosphino)3,6-dimethoxy-2',4',6'-triisopropyl-1,1'-biphenyl (170.6 mg, 0.3 mmol). The mixture was heated to 120° C. for 12 h. After cooling the reaction to room temperature, the mixture was filtered and the filtrate was concentrated in vacuo. Water (100 mL) was added and the mixture was extracted with EtOAc (100 mL×3). The combined organic layers were washed with brine (100 mL×3), dried over anhydrous Na$_2$SO$_4$ and concentrated in vacuo. The crude residue was purified by silica gel chromatography (DCM/MeOH=20:1) to give the title compound (920 mg, 59%) as a yellow solid. LCMS M/Z (M+H) 407.

Step 3

1-[3-[N-ethyl-4-(1-methylpyrazol-4-yl)anilino]-1-[(3S)-tetrahydrofuran-3-yl]-6,7-dihydro-4H-pyrazolo[4,3-c]pyridin-5-yl]j ethanone

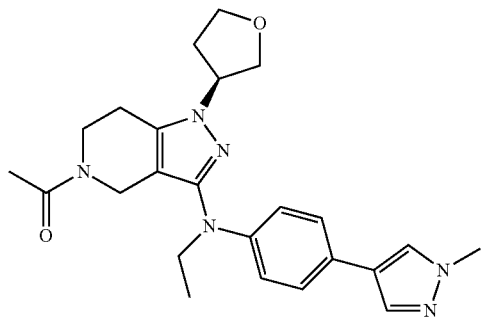 [SMILES: CCN(c1ccc(-c2cnn(C)c2)cc1)c1nn([C@H]2CCOC2)c2c1CN(C(C)=O)CC2]

To a solution of 1-[3-[4-(1-methylpyrazol-4-yl)anilino]-1-[(3S)-tetrahydrofuran-3-yl]-6,7-dihydro-4H-pyrazolo[4,3-c]pyridin-5-yl]ethanone (100 mg, 0.25 mmol) in DMF (2 mL) was added NaH (60%, 20 mg, 0.49 mmol). The mixture was stirred at 25° C. for 0.5 h before iodoethane (46 mg, 0.3 mmol) was added dropwise. The mixture was stirred at 25° C. for another 2 h. Water (5 mL) was added and the mixture was extracted with EtOAc (5 mL×3). The combined organic layers were dried over anhydrous Na$_2$SO$_4$ and concentrated in vacuo. The crude residue was purified by reverse phase chromatography (acetonitrile 29-59%/0.1% NH$_4$OH in water) to give the title compound (45 mg, 42%) as a light yellow solid. $^1$H NMR (400 MHz, DMSO-d$_6$) 7.97 (s, 1H), 7.72 (s, 1H), 7.40-7.36 (m, 2H), 6.78-6.74 (m, 2H), 4.91-4.84 (m, 1H), 4.01-3.99 (m, 2H), 3.90 (s, 2H), 3.83-3.79 (m, 5H), 3.72-3.65 (m, 4H), 2.82-2.67 (m, 2H), 2.27-2.22 (m, 2H), 2.03-1.85 (m, 3H), 1.16-1.12 (m, 3H). LCMS M/Z (M+H) 435.

The Following Compounds were Prepared in a Similar Fashion to Example 222

Examples 223-226

| Example | Compound Name | NMR | m/z |
|---|---|---|---|
| Example 223 | 1-[3-[N-benzyl-4-(1-methylpyrazol-4-yl)anilino]-1-[(3S)-tetrahydrofuran-3-yl]-6,7-dihydro-4H-pyrazolo[4,3-c]pyridin- | $^1$H NMR (400 MHz, DMSO-d$_6$) δ 7.94 (s, 1H), 7.69 (s, 1H), 7.39-7.19 (m, 7H), 6.78-6.73 (m, 2H), 4.96 (s, 2H), 4.89-4.85 (m, 1H), 4.00-3.94 (m, 4H), 3.81 (s, 3H), 3.80-3.66 (m, 4H), 2.81-2.67 (m, 2H), 2.28-2.22 (m, 2H), 2.04-1.85 (m, 3H) | 495 |

| Example | Compound Name | NMR | m/z |
|---|---|---|---|
| Example 224 | 5-yl]ethanone<br>1-[1-methyl-3-[N-methyl-4-[1-methyl-3-(trifluoromethyl)pyrazol-4-yl]anilino]-6,7-dihydro-4H-pyrazolo[4,3-c]pyridin-5-yl]ethanone | ¹H NMR (400 MHz, DMSO-d₆) δ 8.05 (d, J = 4.0 Hz, 1H), 7.26-7.23 (m, 2H), 6.88-6.84 (m, 2H), 3.98-3.92 (m, 5H), 3.72-3.66 (m, 5H), 3.27 (s, 3H), 2.78-2.63 (m, 2H), 2.05-1.88 (m, 5H) | 433 |
| Example 225 | 1-[1-(cyclopropylmethyl)-3-[N-methyl-4-(1-methylpyrazol-4-yl)anilino]-6,7-dihydro-4H-pyrazolo[4,3-c]pyridin-5-yl]ethanone | ¹H NMR (400 MHz, DMSO-d₆) δ 7.97 (s, 1H), 7.72 (s, 1H), 7.41-7.38 (m, 2H), 6.82-6.77 (m, 2H), 3.99-3.97 (m, 2H), 3.83-3.81 (m, 5H), 3.71-3.65 (m, 2H), 3.25 (s, 3H), 2.80-2.67 (m, 2H), 2.05-1.89 (m, 3H), 1.19-1.17 (m, 1H), 0.53-0.49 (m, 2H), 0.34-0.33 (m, 2H) | 405 |
| Example 226 | 1-[3-[N-methyl-4-[1-methyl-3-(trifluoromethyl)pyrazol-4-yl]anilino]-1-tetrahydrofuran-3-yl-6,7-dihydro-4H-pyrazolo[4,3-c]pyridin-5-yl]ethanone | ¹H NMR (400 MHz, DMSO-d₆) δ 8.04-8.03 (m, 1H), 7.25-7.22 (m, 2H), 6.85-6.80 (m, 2H), 4.93-4.87 (m, 1H), 4.03-3.93 (m, 4H), 3.82 (s, 3H), 3.80-3.71 (m, 4H), 3.36 (s, 3H), 2.84-2.70 (m, 2H), 2.28-2.24 (m, 2H), 2.07-1.90 (m, 3H) | 489 |
| Example 227 | 2-[N-(5-acetyl-1-methyl-6,7-dihydro-4H-pyrazolo[4,3-c]pyridin-3-yl)-4-(1-methylpyrazol-4-yl)anilino]acetonitrile | Not Determined | 390 |
| Example 228 | 1-[1-methyl-3-[N-methyl-4-(1-methylpyrazol-4-yl)anilino]-6,7-dihydro-4H-pyrazolo[4,3-c]pyridin-5-yl]ethanone | ¹H NMR (400 MHz, DMSO-d₆) δ 8.00-7.67 (m, 2H), 7.45-7.33 (m, 2H), 6.86-6.73 (m, 2H), 3.95 (d, J = 1.7 Hz, 2H), 3.83 (s, 3H), 3.74-3.58 (m, 5H), 3.24 (d, J = 1.4 Hz, 3H), 2.81-2.58 (m, 2H), 2.04 (s, 2H), 1.87 (s, 1H) | 365 |

Example 229

1-[3-(N-[4-(1-methylpyrazol-4-yl)phenyl]anilino)-1-[(3S)-tetrahydrofuran-3-yl]-6,7-dihydro-4H-pyrazolo[4,3-c]pyridin-5-yl]ethanone

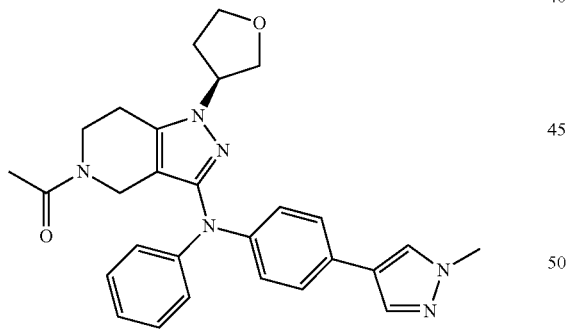

To a solution of 1-[3-[4-(1-methylpyrazol-4-yl)anilino]-1-[(3S)-tetrahydrofuran-3-yl]-6,7-dihydro-4H-pyrazolo[4,3-c]pyridin-5-yl]ethanone (Step 2 of Example 222, 100 mg, 0.3 mmol), iodobenzene (0.04 mL, 0.4 mmol) and t-BuOK (55.2 mg, 0.5 mmol) in toluene (5 mL) was added 2-(dicyclohexylphosphino)-2',4',6'-triisopropylbiphenyl (21 mg, 0.05 mmol) and tris(dibenzylideneacetone)dipalladium (23 mg, 0.02 mmol). The mixture was heated to 130° C. for 12 h under a nitrogen atmosphere. After cooling the reaction to room temperature, the mixture was concentrated in vacuo. Water (50 mL) was added and the mixture was extracted with EtOAc (100 mL×3). The combined organic layers were washed with brine (50 mL), dried over anhydrous Na₂SO₄ and concentrated in vacuo. The crude residue was purified by reverse phase chromatography (acetonitrile 15-45%/0.1% NH₄HCO₃ in water) to give the title compound (13 mg, 10%) as a white solid. ¹H NMR (400 MHz, DMSO-d₆) δ 8.03 (s, 1H), 7.77 (s, 1H), 7.48-7.42 (m, 2H), 7.32-7.18 (m, 2H), 6.98-6.91 (m, 5H), 4.92-4.88 (m, 1H), 4.01-3.97 (m, 1H), 3.84 (s, 3H), 3.81-3.73 (m, 4H), 3.69-3.61 (m, 2H), 2.84-2.69 (m, 2H), 2.29-2.14 (m, 2H), 2.03-1.73 (m, 3H). LCMS M/Z (M+H) 483.

Example 230

1-(3-(6-(1-methyl-1H-pyrazol-4-yl)-3,4-dihydro-1,7-naphthyridin-1(2H)-yl)-1-(tetrahydro-2H-pyran-4-yl)-6,7-dihydro-1H-pyrazolo[4,3-c]pyridin-5(4H)-yl)ethanone

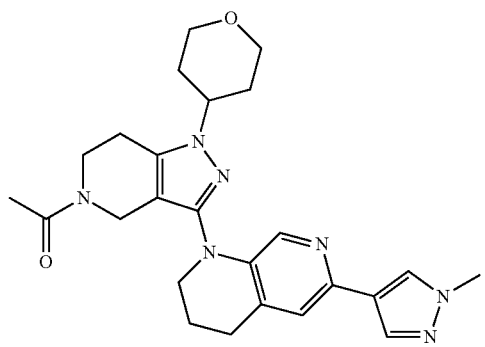 [SMILES: CC(=O)N1CCc2c(c(N3CCCc4cc(-c5cnn(C)c5)ncc43)nn2C2CCOCC2)C1]

Step 1

6-(1-methyl-1H-pyrazol-4-yl)-1,2,3,4-tetrahydro-1,7-naphthyridine

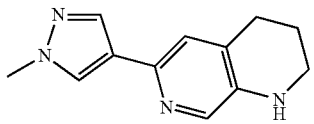 [SMILES: Cn1cc(-c2cc3c(cn2)NCCC3)cn1]

To a solution of 6-chloro-1,2,3,4-tetrahydro-1,7-naphthyridine (200 mg, 1.19 mmol), 1-methyl-4-(4,4,5,5-tetramethyl-1,3,2-dioxaborolan-2-yl)-1H-pyrazole (296 mg, 1.42 mmol) and $Na_2CO_3$ (377 mg, 3.56 mmol) in 1,4-dioxane (5 mL) and $H_2O$ (1 mL) was added chloro(2-dicyclohexylphosphino-2',4',6'-tri-i-propyl-1,1'-biphenyl)(2'-amino-1,1'-biphenyl-2-yl) palladium(II) (93 mg, 0.12 mmol) and 2-(dicyclohexylphosphino)-2',4',6'-triisopropylbiphenyl (57 mg, 0.12 mmol). The resulting mixture was heated to 100° C. for 16 h under a nitrogen atmosphere. After cooling to room temperature, the mixture was filtered and concentrated in vacuo. The crude residue was purified by Prep-TLC (DCM/MeOH=10:1) to give the the title compound (200 mg, 79%) as a pale yellow solid. $^1$H NMR (400 MHz, $CDCl_3$) δ 7.89 (s, 1H), 7.86 (s, 1H), 7.81 (s, 1H), 7.09 (s, 1H), 4.24 (s, 1H), 3.93 (s, 3H), 3.36 (t, J=6.4 Hz, 2H), 2.78 (t, J=6.4 Hz, 2H), 1.99-1.93 (m, 2H).

Step 2

1-(3-(6-(1-methyl-1H-pyrazol-4-yl)-3,4-dihydro-1,7-naphthyridin-1 (2H)-yl)-1-(tetrahydro-2H-pyran-4-yl)-6,7-dihydro-1H-pyrazolo[4,3-c]pyridin-5(4H)-yl)ethanone

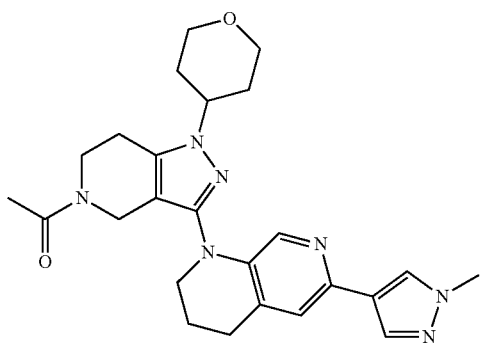 [SMILES: CC(=O)N1CCc2c(c(N3CCCc4cc(-c5cnn(C)c5)ncc43)nn2C2CCOCC2)C1]

To a solution of 6-(1-methylpyrazol-4-yl)-1,2,3,4-tetrahydro-1,7-naphthyridine (100 mg, 0.47 mmol) and 1-(3-bromo-1-tetrahydropyran-4-yl-6,7-dihydro-4H-pyrazolo[4,3-c]pyridin-5-yl)ethanone (Intermediate I, 184 mg, 0.56 mmol) in 1,4-dioxane (1.5 mL) was added t-BuONa (90 mg, 0.93 mmol) and dichloro[1,3-bis(2,6-di-3-pentylphenyl)imidazol-2-ylidene](3-chloropyridyl)palladium(II) (56 mg, 0.07 mmol). The reaction mixture was heated 10 to 120° C. for 16 h under a nitrogen atmosphere. After cooling to room temperature, the mixture was filtered and concentrated in vacuo. The crude residue was purified by reverse phase chromatography (acetonitrile 15-45%/0.05 $NH_4OH$ in water) to give the title compound (23 mg, 11%) as a white solid. $^1$H NMR (400 MHz, DMSO-$d_6$) δ 8.03 (s, 1H), 7.80 (s, 1H), 7.76-7.69 (m, 1H), 7.29 (s, 1H), 4.33-4.22 (m, 1H), 4.21-4.12 (m, 2H), 3.99-3.90 (m, 2H), 3.83 (s, 3H), 3.79-3.68 (m, 2H), 3.59-3.48 (m, 4H), 2.88-2.65 (m, 4H), 2.09-1.91 (m, 7H), 1.85-1.75 (m, 2H). LCMS M/Z (M+H) 462.

Example 231

1-(3-(6-(1-methyl-1H-pyrazol-4-yl)-3,4-dihydroquinolin-1(2H)-yl)-1-(tetrahydro-2H-pyran-4-yl)-6,7-dihydro-1H-pyrazolo[4,3-c]pyridin-5(4H)-yl)propan-1-one

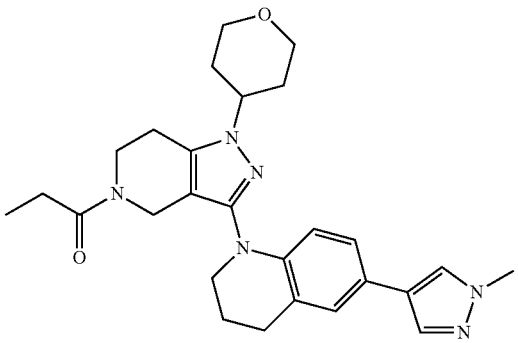 [SMILES: CCC(=O)N1CCc2c(c(N3CCCc4cc(-c5cnn(C)c5)ccc43)nn2C2CCOCC2)C1]

To a solution of 6-(1-methylpyrazol-4-yl)-1-(1-tetrahydropyran-4-yl-4,5,6,7-tetrahydropyrazolo[4,3-c]pyridin-3-yl)-3,4-dihydro-2H-quinoline (Intermediate J, 17.4 mg, 0.0416 mmol) in DCM (0.21 mL) was added TEA (9.3 μL, 0.067 mmol) and propionyl chloride (5.1 μL, 0.058 mmol). The mixture was stirred at room temperature for 1.5 h, water (1 mL) was added and the resulting biphasic mixture was extracted with DCM (1 mL×3). The combined organic layers were dried over anhydrous $Na_2SO_4$, filtered and concentrated in vacuo to give the crude product that was purified by reverse phase chromatography (acetonitrile 5-50%/0.1% formic acid in water) to give the title compound (8.7 mg, 42% yield) as a white solid. $^1$H NMR (400 MHz, DMSO-$d_6$) δ 7.91 (s, 1H), 7.67 (d, J=0.9 Hz, 1H), 7.19 (d, J=2.1 Hz, 1H), 7.09 (d, J=8.5 Hz, 1H), 6.42 (t, J=7.9 Hz, 1H), 4.26 (s, 1H), 4.10 (s, 2H), 3.95 (dd, J=12.1, 3.7 Hz, 2H), 3.82 (s, 3H), 3.79-3.68 (m, 2H), 3.56-3.54 (m, 2H), 3.47-3.42 (m, 2H), 2.88-2.77 (m, 4H), 2.42-2.08 (m, 2H), 2.08-1.89 (m, 4H), 1.81 (d, J=11.8 Hz, 2H), 1.00-0.89 (m, 3H). LCMS M/Z (M+H) 475.

The Following Compounds were Prepared in a Similar Fashion to Example 231

Examples 232-234

| Example | Compound Name | NMR | m/z |
| --- | --- | --- | --- |
| Example 232 | cyclopropyl(3-(6-(1-methyl-1H-pyrazol-4-yl)-3,4- | $^1$H NMR (400 MHz, DMSO-$d_6$) δ 7.90 (d, J = 0.8 Hz, 1H), 7.66 (d, J = 0.8 Hz, 1H), 7.23-7.14 (m, 1H), 7.09 (d, J = 8.3 Hz, | 487 |

-continued

| Example | Compound Name | NMR | m/z |
|---|---|---|---|
|  | dihydroquinolin-1(2H)-yl)-1-(tetrahydro-2H-pyran-4-yl)-6,7-dihydro-1H-pyrazolo[4,3-c]pyridin-5(4H)-yl)methanone | 1H), 6.42 (d, J = 9.2 Hz, 1H), 4.36 (s, 1H), 4.32-4.22 (m, 1H), 4.10 (s, 2H), 3.99-3.92 (m, 3H), 3.82 (s, 4H), 3.59-3.51 (m, 2H), 3.49-3.41 (m, 2H), 2.91-2.70 (m, 4H), 2.04-1.92 (m, 4H), 1.81 (d, J = 12.6 Hz, 2H), 0.71 (d, J = 5.9 Hz, 4H) |  |
| Example 233 | 6-(1-methyl-1H-pyrazol-4-yl)-1-(5-(methylsulfonyl)-1-(tetrahydro-2H-pyran-4-yl)-4,5,6,7-tetrahydro-1H-pyrazolo[4,3-c]pyridin-3-yl)-1,2,3,4-tetrahydroquinoline | $^1$H NMR (400 MHz, DMSO-d$_6$) δ 7.91 (d, J = 0.8 Hz, 1H), 7.67 (d, J = 0.8 Hz, 1H), 7.22-7.16 (m, 1H), 7.10 (dd, J = 8.4, 2.2 Hz, 1H), 6.39 (d, J = 8.4 Hz, 1H), 4.33-4.22 (m, 1H), 3.96 (dd, J = 11.2, 4.3 Hz, 2H), 3.89 (s, 2H), 3.82 (s, 3H), 3.57-3.52 (m, 2H), 3.51-3.42 (m, 4H), 2.92-2.87 (m, 5H), 2.83-2.77 (m, 2H), 2.04-1.93 (m, 4H), 1.82 (d, J = 13.3 Hz, 2H) | 497 |
| Example 234 | 1-(3-(6-(1-methyl-1H-pyrazol-4-yl)-3,4-dihydroquinolin-1(2H)-yl)-1-(tetrahydro-2H-pyran-4-yl)-6,7-dihydro-1H-pyrazolo[4,3-c]pyridin-5(4H)-yl)butan-1-one | 1H NMR (400 MHz, DMSO-d$_6$) δ 7.90 (d, J = 3.0 Hz, 1H), 7.70-7.64 (m, 1H), 7.19 (s, 1H), 7.14-7.06 (m, 1H), 6.44-6.40 (m, 1H), 4.29-4.21 (m, 1H), 4.10 (s, 2H), 3.95 (d, J = 11.9 Hz, 2H), 3.82 (s, 3H), 3.77-3.70 (m, 2H), 3.59-3.52 (m, 2H), 3.48-3.41 (m, 2H), 2.85-2.70 (m, 4H), 2.38-2.17 (m, 2H), 2.00-2.17 (m, 4H), 1.80 (d, J = 12.4 Hz, 2H), 1.53-1.40 (m, 2H), 0.90-0.77 (m, 3H) | 489 |

Example 235

2,2-difluoro-1-(3-(6-(1-methyl-1H-pyrazol-4-yl)-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone

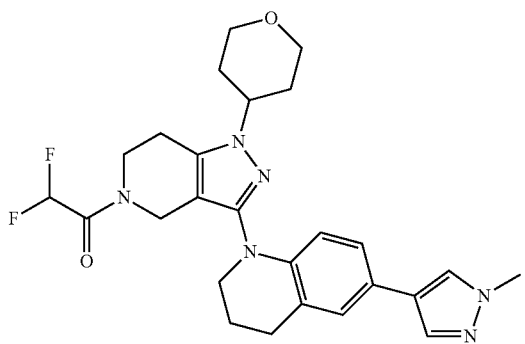 [SMILES: Cn1cc(-c2ccc3c(c2)CCCN3c2nn(C3CCOCC3)c3c2CN(C(=O)C(F)F)CC3)cn1]

To a solution of 6-(1-methylpyrazol-4-yl)-1-(1-tetrahydropyran-4-yl-4,5,6,7-tetrahydropyrazolo[4,3-c]pyridin-3-yl)-3,4-dihydro-2H-quinoline (Intermediate J, 35.5 mg, 0.0848 mmol) in MeCN (0.4 mL) was added O-benzotriazol-1-yl-N,N,N',N'-tetramethyluronium tetrafluoroborate (32.0 mg, 0.0976 mmol), TEA (35.5 µL, 0.254 mmol) and 2,2-difluoroacetic acid (10.7 µL, 0.170 mmol). The mixture was stirred at room temperature for 1.5 h, then concentrated in vacuo to give crude product that was purified by reverse phase chromatography (acetonitrile 5-50%/0.1% formic acid in water) to give the title compound (7.2 mg, 15%) as a white solid. $^1$H NMR (400 MHz, DMSO-d$_6$) δ 7.92-7.91 (m, 1H), 7.68-7.67 (m, 1H), 7.21-7.19 (m, 11H), 7.14-7.07 (m, 1H), 6.82-6.61 (m, 1H), 6.45-6.41 (m, 1H), 4.28 (s, 1H), 4.21-4.17 (m, 2H), 4.00-3.91 (m, 2H), 3.88-3.75 (m, 5H), 3.59-3.52 (m, 2H), 3.51-3.41 (m, 2H), 2.92-2.77 (m, 4H), 2.02-1.89 (m, 4H), 1.81 (d, J=12.8 Hz, 2H). LCMS M/Z (M+H) 497.

Example 236

2-(3-(6-(1-methyl-1H-pyrazol-4-yl)-3,4-dihydroquinolin-1(2H)-yl)-1-(tetrahydro-2H-pyran-4-yl)-6,7-dihydro-1H-pyrazolo[4,3-c]pyridin-5(4H)-yl)-1,3,4-thiadiazole

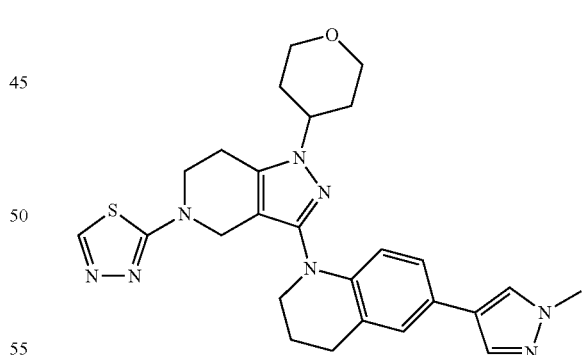

To a vial was added 6-(1-methylpyrazol-4-yl)-1-(1-tetrahydropyran-4-yl-4,5,6,7-tetrahydropyrazolo[4,3-c]pyridin-3-yl)-3,4-dihydro-2H-quinoline (Intermediate J, 18.8 mg, 0.0449 mmol), 2-bromo-1,3,4-thiadiazole (15.0 mg, 0.0898 mmol), dichloro[1,3-bis(2,6-di-3-pentylphenyl)imidazol-2-ylidene](3-chloropyridyl)palladium(II) (7.5 mg, 0.0090 mmol), t-BuONa (8.6 mg, 0.090 mmol) and 1,4-dioxane (0.4 mL). The mixture was sparged with an argon ballon, and then heated to 120° C. for 16 h under an argon atmosphere.

After cooling the reaction to room temperature, DCM (1 mL) was added and the reaction was filtered through celite and concentrated in vacuo to give the crude product that was purified by reverse phase chromatography (acetonitrile 5-85%/0.1% NH₄OH in water) to give the title compound (2.5 mg, 10%) as a white solid. ¹H NMR (400 MHz, DMSO-d₆) δ 8.78 (s, 1H), 7.91 (d, J=0.8 Hz, 1H), 7.68 (d, J=0.8 Hz, 1H), 7.21 (d, J=2.1 Hz, 1H), 7.12 (dd, J=8.4, 2.2 Hz, 1H), 6.45 (d, J=8.4 Hz, 1H), 4.37-4.25 (m, 1H), 4.18 (s, 2H), 4.00-3.90 (m, 2H), 3.85 (t, J=5.8 Hz, 2H), 3.82 (s, 3H), 3.62-3.53 (m, 2H), 3.45 (t, J=11.5 Hz, 2H), 2.94 (t, J=5.7 Hz, 2H), 2.82 (t, J=6.4 Hz, 2H), 2.05-1.92 (m, 4H), 1.81 (d, J=10.9 Hz, 2H). LCMS M/Z (M+H) 503.

Example 237

3-(3-(6-(1-methyl-1H-pyrazol-4-yl)-3,4-dihydroquinolin-1(2H)-yl)-1-(tetrahydro-2H-pyran-4-yl)-6,7-dihydro-1H-pyrazolo[4,3-c]pyridin-5(4H)-yl)isoxazole

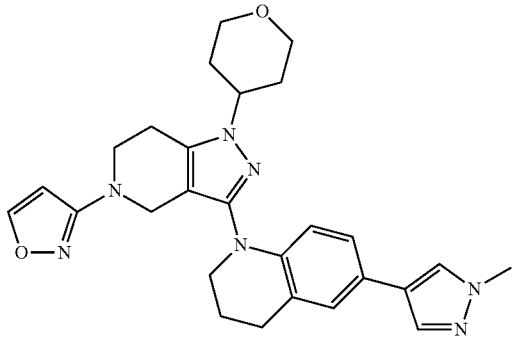 [SMILES: Cn1cc(-c2ccc3c(c2)CCCN3c2nn(C3CCOCC3)c3c2CN(c2ccon2)CC3)cn1]

To a vial was added 6-(1-methylpyrazol-4-yl)-1-(1-tetrahydropyran-4-yl-4,5,6,7-tetrahydropyrazolo[4,3-c]pyridin-3-yl)-3,4-dihydro-2H-quinoline (Intermediate J, 20.0 mg, 0.048 mmol), dichloro[1,3-bis(2,6-di-3-pentylphenyl)imidazol-2-ylidene](3-chloropyridyl)palladium(II) (8.0 mg, 0.0096 mmol), t-BuONa (9.2 mg, 0.096 mmol), 1,4-dioxane (0.2 mL) and 3-bromoisoxazole (10.8 mg, 0.717 mmol). The mixture was sparged with an argon ballon, and then heated to 120° C. for 16 h under an argon atmosphere. After cooling the reaction to room temperature, DCM (1 mL) was added and the reaction was filtered through celite and concentrated in vacuo to give the crude product that was purified by reverse phase chromatography (acetonitrile 5-50%/0.1% formic acid in water) to give the title compound (4.6 mg, 20%) as a white solid. ¹H NMR (400 MHz, DMSO-d₆) δ 7.91-7.90 (m, 1H), 7.67-7.66 (m, 1H), 7.24-7.16 (m, 1H), 7.12-7.05 (m, 1H), 6.54-6.39 (m, 1H), 4.30-4.24 (m, 1H), 4.12 (s, 2H), 4.06 (d, J=8.2 Hz, 2H), 3.95 (d, J=11.4 Hz, 2H), 3.82 (s, 3H), 3.67-3.51 (m, 4H), 3.50-3.42 (m, 2H), 2.90-2.76 (m, 4H), 2.01-1.90 (m, 4H), 1.79 (d, J=12.9 Hz, 2H). LCMS M/Z (M+H) 486.

Example 238 & 239

(S)-1-[3-[7-(difluoromethyl)-4-methyl-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone and (R)-1-[3-[7-(difluoromethyl)-4-methyl-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone

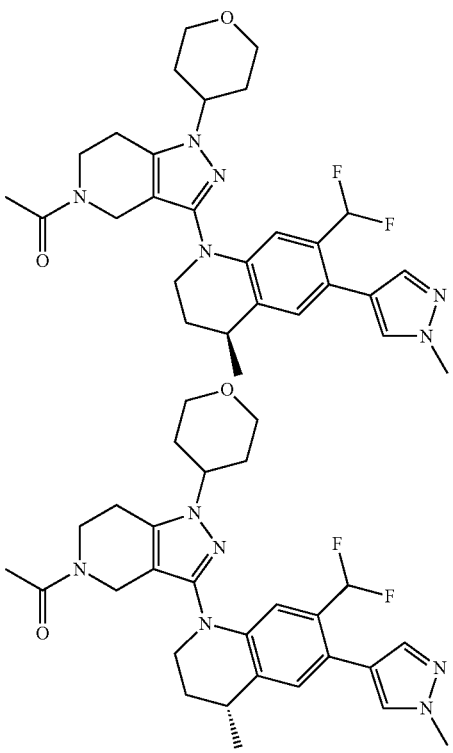

Step 1

2,2-difluoro-2-(4-methylquinolin-7-yl)-1-phenylethanone

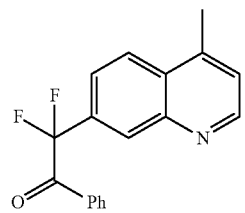

To a solution of 7-chloro-4-methyl-quinoline (5.0 g, 28.15 mmol) in toluene (100 mL) was added 2,2-difluoro-1-phenyl-ethanone (8.79 g, 56.3 mmol), chloro[(tricyclohexylphosphine)-2-(2'-aminobiphenyl)]palladium(II) (1.66 g, 2.81 mmol) and K₃PO₄ (23.9 g, 112.59 mmol). The reaction mixture was heated to 120° C. for 16 h under a nitrogen atmosphere. After cooling the reaction to room temperature, water (100 mL) was added and the mixture was extracted with DCM (100 mL×2). The combined organic layers were dried over anhydrous Na$_2$SO$_4$, filtered and concentrated in vacuo to give the title compound (5 g, crude) as brown oil that required no further purification. LCMS M/Z (M+H) 298.

Step 2

7-(difluoromethyl)-4-methylquinoline

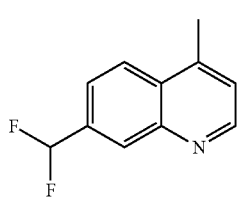

To a solution of 2,2-difluoro-2-(4-methyl-7-quinolyl)-1-phenyl-ethanone (5.0 g, 16.82 mmol) in toluene (100 mL) and water (6 mL) was added KOH (5.66 g, 100.91 mmol). The reaction mixture was heated to 100° C. for 16 h. After cooling the reaction to room temperature, water (100 mL) was added and the mixture was extracted with DCM (100 mL×2). The combined organic layers were dried over anhydrous Na$_2$SO$_4$, filtered and concentrated in vacuo. The crude residue was purified by silica gel chromatography (petroleum ether/EtOAc=10/1) to give the title compound (3.7 g, 80%) as yellow oil. LCMS M/Z (M+H) 194.

Step 3

7-(difluoromethyl)-4-methyl-1,2,3,4-tetrahydroquinoline

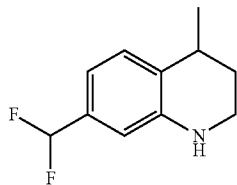

To a solution of 7-(difluoromethyl)-4-methyl-quinoline (3.7 g, 19.15 mmol) and sodium cyanoborohydride (6.02 g, 95.76 mmol) in MeOH (200 mL) at 0° C. was added boron trifluoride diethyl etherate (20.67 mL, 38.30 mmol) dropwise. The reaction mixture was heated to 100° C. for 36 h under a nitrogen atmosphere. After cooling the reaction to room temperature, sat. aq. NaHCO$_3$ (100 mL) was added and the mixture was extracted with DCM (100 mL×2). The combined organic layers were dried over anhydrous Na$_2$SO$_4$, filtered and concentrated in vacuo. The crude residue was purified by silica gel chromatography (petroleum ether/EtOAc=50/1) to give the mixture of 7-(difluoromethyl)-4-methyl-1,2,3,4-tetrahydroquinoline and 7-(difluoromethyl)-4-methyl-1,2-dihydroquinoline (2.5 g, ratio=7:2) as a brown oil. The resulting mixture was dissolved in MeOH (50 mL) and 10% Pd/C (403 mg, 0.19 mmol) was added. The mixture was stirred at 25° C. for 1 h under a hydrogen atmosphere (15 psi). The reaction was filtered and concentrated in vacuo. The crude residue was purified by silica gel chromatography (petroleum ether/EtOAc=100/1) to give the title compound (1.9 g, 50%) as a light yellow oil. LCMS M/Z (M+H) 198.

Step 4 tert-butyl 3-(7-(difluoromethyl)-4-methyl-3,4-dihydroquinolin-1(2H)-yl)-1-(tetrahydro-2H-pyran-4-yl)-6,7-dihydro-1H-pyrazolo[4,3-c]pyridine-5(4H)-carboxylate

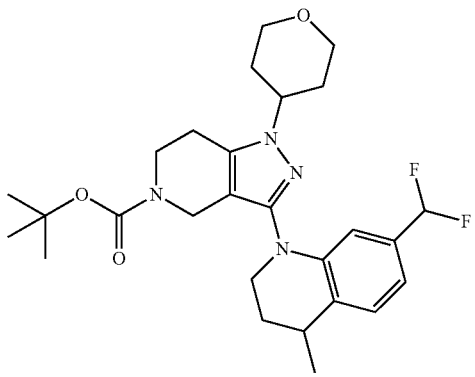 [SMILES: CC1CCN(c2nn(C3CCOCC3)c3c2CN(C(=O)OC(C)(C)C)CC3)c2cc(C(F)F)ccc21]

To a solution of 7-(difluoromethyl)-4-methyl-1,2,3,4-tetrahydroquinoline (899 mg, 4.56 mmol), tert-butyl 3-bromo-1-(tetrahydro-2H-pyran-4-yl)-6,7-dihydro-1H-pyrazolo[4,3-c]pyridine-5(4H)-carboxylate (Intermediate H, 1.6 g, 4.14 mmol) and t-BuONa (1.19 g, 12.43 mmol) in 1,4-dioxane (20 mL) was added chloro(2-dicyclohexylphosphino-2',6'-di-i-propoxy-1,1'-biphenyl)(2'-amino-1,1'-biphenyl-2-yl) palladium(II) (322 mg, 0.41 mmol), 2-dicyclohexylphosphino-2',6'-di-i-propoxy-1,1'-biphenyl (193 mg, 0.41 mmol). The mixture was heated to 120° C. for 16 h under a nitrogen atmosphere. After cooling the reaction to room temperature, the mixture was filtered and concentrated in vacuo. The crude residue was purified by silica gel chromatography (petroleum ether/EtOAc=3/1) to give the title compound (1.15 g, 44%) as a yellow oil. LCMS M/Z (M+H) 503.

Step 5 tert-butyl 3-(6-bromo-7-(difluoromethyl)-4-methyl-3,4-dihydroquinolin-1(2H)-yl)-1-(tetrahydro-2H-pyran-4-yl)-6,7-dihydro-1H-pyrazolo[4,3-c]pyridine-5(4H)-carboxylate

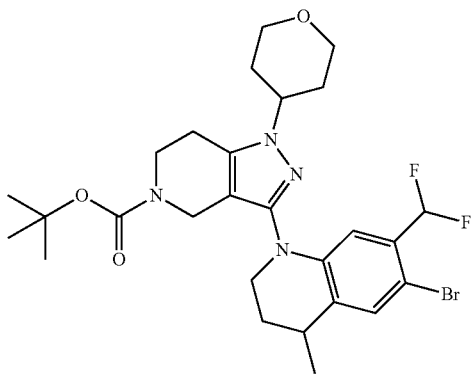 [SMILES: CC1CCN(c2nn(C3CCOCC3)c3c2CN(C(=O)OC(C)(C)C)CC3)c2cc(C(F)F)c(Br)cc21]

To a solution of tert-butyl 3-(7-(difluoromethyl)-4-methyl-3,4-dihydroquinolin-1(2H)-yl)-1-(tetrahydro-2H-pyran-4-yl)-6,7-dihydro-1H-pyrazolo[4,3-c]pyridine-5(4H)-carboxylate (1.15 g, 1.81 mmol) in DCM (12 mL) at 0° C. was added N-bromosuccinimide (322 mg, 1.81 in DCM (8 mL) dropwise. The mixture was stirred at room temperature for 2 h. Water (20 mL) was added and the mixture was extracted with DCM (20 mL×2). The combined organic layers were washed with brine (20 mL×3), dried over anhydrous $Na_2SO_4$, filtered and concentrated in vacuo to give the title compound (1 g, crude) as yellow oil that required no further purification. LCMS M/Z (M+H) 581.

Step 6 tert-butyl 3-(7-(difluoromethyl)-4-methyl-6-(1-methyl-1H-pyrazol-4-yl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate

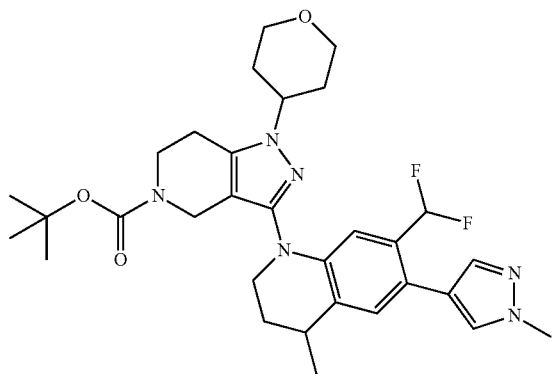 [SMILES: CC1CCN(c2nn(C3CCOCC3)c3c2CN(C(=O)OC(C)(C)C)CC3)c2cc(C(F)F)c(-c3cnn(C)c3)cc21]

To a solution of tert-butyl 3-(6-bromo-7-(difluoromethyl)-4-methyl-3,4-dihydroquinolin-1(2H)-yl)-1-(tetrahydro-2H-pyran-4-yl)-6,7-dihydro-1H-pyrazolo[4,3-c]pyridine-5(4H)-carboxylate (800 mg, 1.38 mmol), 1-methyl-4-(4,4,5,5-tetramethyl-1,3,2-dioxaborolan-2-yl)pyrazole (344 mg, 1.65 mmol) and $Na_2CO_3$ (292 mg, 2.75 mmol) in THF (15 mL) and water (3 mL) was added chloro(2-dicyclohexylphosphino-2',4',6'-tri-i-propyl-1,1'-biphenyl)(2'-amino-1,1'-biphenyl-2-yl) palladium(II) (108 mg, 0.14 mmol) and 2-(dicyclohexylphosphino)-2',4',6'-triisopropylbiphenyl (66 mg, 0.14 mmol). The mixture was heated to 60° C. for 12 h under a nitrogen atmosphere. After cooling the reaction to room temperature, the mixture was filtered and concentrated in vacuo. The crude residue was purified by silica gel chromatography (petroleum ether/EtOAc=1/1) to give the title compound (560 mg, 70%) as yellow oil. LCMS M/Z (M+H) 583.

Step 7

7-(difluoromethyl)-4-methyl-6-(1-methyl-1H-pyrazol-4-yl)-1-(1-(tetrahydro-2H-pyran-4-yl)-4,5,6,7-tetrahydro-1H-pyrazolo[4,3-c]pyridin-3-yl)-1,2,3,4-tetrahydroquinoline

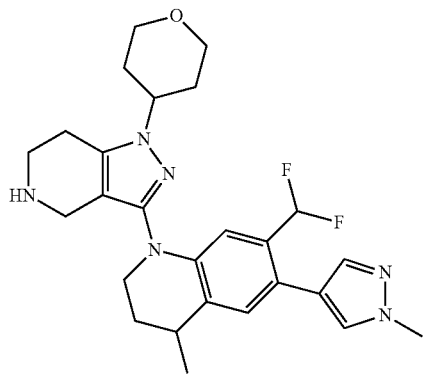 [SMILES: CC1CCN(c2nn(C3CCOCC3)c3c2CNCC3)c2cc(C(F)F)c(-c3cnn(C)c3)cc21]

To a solution of tert-butyl 3-(7-(difluoromethyl)-4-methyl-6-(1-methyl-1H-pyrazol-4-yl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate (200 mg, 0.34 mmol) in DCM (1 mL) at 0° C. was added trifluoroacetic acid (0.2 mL, 0.34 mmol). The mixture was stirred at room temperature for 1 h and concentrated in vacuo to give the title compound (200 mg, crude) as yellow oil that required no further purification. LCMS M/Z (M+H) 483.

Step 8

(S)-1-[3-[7-(difluoromethyl)-4-methyl-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone and (R)-1-[3-[7-(difluoromethyl)-4-methyl-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone

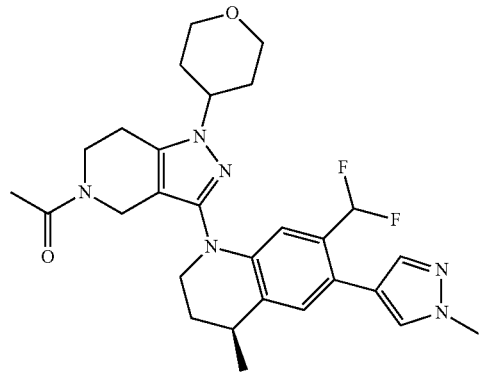

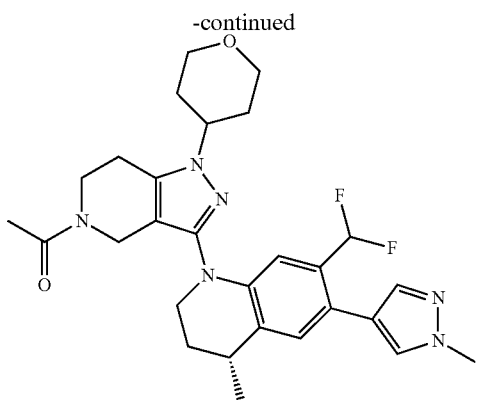

To a solution of 7-(difluoromethyl)-4-methyl-6-(1-methyl-1H-pyrazol-4-yl)-1-(1-(tetrahydro-2H-pyran-4-yl)-4,5,6,7-tetrahydro-1H-pyrazolo[4,3-c]pyridin-3-yl)-1,2,3,4-tetrahydroquinoline (166 mg, 0.34 mmol) in DCM (2 mL) at 0° C. was added triethylamine (0.15 mL, 1.03 mmol) and acetic anhydride (0.065 mL, 0.69 mmol). The mixture was stirred at 0° C. for 1 h and concentrated in vacuo. DCM (10 mL) was added, washed with water (10 mL×3) and brine (10 mL). The organic layer was dried over anhydrous $Na_2SO_4$, filtered and concentrated in vacuo. The crude residue was purified by Prep-TLC (DCM/MeOH=10/1) to give the title compound (60 mg, 31%) as a white solid that was separated by using chiral SFC (SFC80; Chiralpak OJ 250×30 mm, 5 um; Supercritical $CO_2$/MeOH+base=75/25, 60 mL/min) to give (S)-1-[3-[7-(difluoromethyl)-4-methyl-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone (23 mg, first peak) and (R)-1-[3-[7-(difluoromethyl)-4-methyl-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone (14 mg, second peak). Absolute configuration was arbitrarily assigned to each enantiomer. Example 238: $^1$H NMR (400 MHz, DMSO-$d_6$) δ 7.77 (s, 1H), 7.51 (s, 1H), 7.17 (s, 1H), 6.94-6.65 (m, 2H), 4.29-4.23 (m, 1H), 4.15-4.08 (m, 2H), 3.99-3.93 (m, 2H), 3.87 (s, 3H), 3.74-3.50 (m, 6H), 2.92-2.70 (m, 3H), 2.07-1.92 (m, 6H), 1.84-1.72 (m, 3H), 1.32-1.28 (m, 3H). LCMS M/Z (M+H) 525. Example 239: $^1$H NMR (400 MHz, DMSO-$d_6$) δ 7.77 (s, 1H), 7.51 (s, 1H), 7.17 (s, 1H), 6.94-6.65 (m, 2H), 4.29-4.23 (m, 1H), 4.15-4.08 (m, 2H), 3.99-3.93 (m, 2H), 3.87 (s, 3H), 3.74-3.50 (m, 6H), 2.92-2.70 (m, 3H), 2.07-1.92 (m, 6H), 1.84-1.72 (m, 3H), 1.32-1.28 (m, 3H). LCMS M/Z (M+H) 525.

The Following Compounds were Prepared in a Similar Fashion to Example 238

Examples 240-248

| Example | Compound Name | NMR | m/z |
|---|---|---|---|
| Example 240 | (S)-1-[3-[7-(difluoromethyl)-3-methyl-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, DMSO-$d_6$) δ 7.75 (s, 1H), 7.50 (s, 1H), 7.10 (s, 1H), 6.94-6.64 (m, 2H), 4.33-4.24 (m, 1H), 4.16-4.11 (m, 2H), 3.97-3.93 (m, 2H), 3.86 (s, 3H), 3.70-3.57 (m, 2H), 3.48-3.44 (m, 2H), 3.26-3.18 (m, 2H), 2.91-2.66 (m, 4H), 2.13-1.89 (m, 6H), 1.84-1.80 (m, 2H), 1.05-1.03 (m, 3H) | 525 |
| Example 241 | (R)-1-[3-[7-(difluoromethyl)-3-methyl-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, DMSO-$d_6$) δ 7.75 (s, 1H), 7.50 (s, 1H), 7.10 (s, 1H), 6.94-6.64 (m, 2H), 4.34-4.24 (m, 1H), 4.18-4.09 (m, 2H), 3.96-3.93 (m, 2H), 3.86 (s, 3H), 3.73-3.56 (m, 2H), 3.50-3.43 (m, 2H), 3.29-3.17 (m, 2H), 2.98-2.57 (m, 4H), 2.11-1.93 (m, 6H), 1.84-1.80 (m, 2H), 1.07-1.00 (m, 3H) | 525 |
| Example 242 | 1-[3-[7-(difluoromethyl)-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]propan-1-one | $^1$H NMR (400 MHz, DMSO-$d_6$) δ 7.75 (s, 1H), 7.50 (s, 1H), 7.10 (s, 1H), 6.82 (s, 1H), 6.79 (t, J = 55.2 Hz, 1H), 4.30-4.20 (m, 1H), 4.19-4.10 (m, 2H), 3.96-3.93 (m, 2H), 3.86 (s, 3H), 3.79-3.68 (m, 2H), 3.60-3.57 (m, 2H), 3.45 (t, J = 12.0 Hz, 2H), 2.89-2.74 (m, 4H), 2.42-2.26 (m, 2H), 2.00-1.76 (m, 6H), 1.02-0.87 (m, 3H) | 525 |
| Example 243 | 1-[3-[7-(difluoromethyl)-6-(2-methoxy-4-pyridyl)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, DMSO-$d_6$) δ 8.18 (d, J = 5.2 Hz, 1H), 7.09 (s, 1H), 6.95-6.84 (m, 2H), 6.80-6.59 (m, 2H), 4.30-4.25 (m, 1H), 4.23-4.12 (m, 2H), 3.96-3.93 (m, 2H), 3.87 (s, 3H), 3.79-3.67 (m, 2H), 3.63-3.60 (m, 2H), 3.53-3.44 (m, 2H), 2.93-2.72 (m, 4H), 2.10-1.93 (m, 7H), 1.88-1.79 (m, 2H) | 538 |
| Example 244 | 1-[3-[6-(difluoromethyl)-5-(1,5-dimethylpyrazol-4-yl)indolin-1-yl]-1-tetrahydropyran-4-yl-6,7-dihydro-4H-pyrazolo[4,3-c]pyridin-5-yl]ethanone | $^1$H NMR (400 MHz, DMSO-$d_6$) δ 7.81-7.73 (m, 1H), 7.26 (s, 1H), 6.99 (s, 1H), 6.59 (t, J = 54.8 Hz, 1H), 4.59-4.55 (m, 2H), 4.30-4.20 (m, 1H), 4.15-3.90 (m, 4H), 3.83-3.64 (m, 5H), 3.47 (t, J = 12.0 Hz, 2H), 3.19 (t, J = 8.0 Hz, 2H), 2.87-2.67 (m, 2H), 2.23-1.93 (m, 8H), 1.82-1.78 (m, 2H) | 511 |

-continued

| Example | Compound Name | NMR | m/z |
|---|---|---|---|
| Example 245 | 1-[3-[6-(1-methylpyrazol-4-yl)-7-(trifluoromethyl)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, DMSO-$d_6$) δ 7.72 (s, 1H), 7.42 (s, 1H), 7.10 (s, 1H), 6.99-6.95 (m, 1H), 4.32-4.24 (m, 1H), 4.22-4.17 (m, 2H), 3.95-3.91 (m, 2H), 3.84 (s, 3H), 3.70-3.68 (m, 2H), 3.58-3.56 (m, 2H), 3.44 (t, J = 12.0 Hz, 2H), 2.84-2.74 (m, 4H), 2.07-1.94 (m, 7H), 1.82-1.78 (m, 2H) | 529 |
| Example 246 | 1-[3-[7-methyl-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, DMSO-$d_6$) δ 7.76 (s, 1H), 7.52 (s, 1H), 7.01-6.93 (m, 1H), 6.36-6.29 (m, 1H), 4.32-4.20 (m, 1H), 4.14-4.04 (m, 2H), 3.97-3.92 (m, 2H), 3.84 (s, 3H), 3.78-3.65 (m, 2H), 3.58-3.50 (m, 2H), 3.45 (t, J = 11.6 Hz, 2H), 2.90-2.69 (m, 4H), 2.16 (s, 3H), 2.09-1.87 (m, 7H), 1.85-1.80 (m 2H) | 475 |
| Example 247 | 1-[3-[6-(1-methylpyrazol-4-yl)-7-(trifluoromethoxy)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, DMSO-$d_6$) δ 7.88 (s, 1H), 7.67 (s, 1H), 7.33 (s, 1H), 6.65-6.53 (m, 1H), 4.34-4.15 (m, 3H), 3.96-3.93 (m, 2H), 3.86 (s, 3H), 3.78-3.65 (m, 2H), 3.57-3.52 (m, 2H), 3.45 (t, J = 11.6 Hz, 2H), 2.89-2.72 (m, 4H), 2.08-1.85 (m, 7H), 1.83-1.78 (m, 2H) | 545 |

Example 248

3-[7-(difluoromethyl)-4-methyl-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide

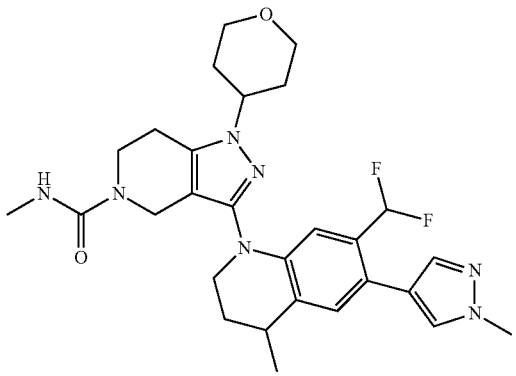

To a solution of 7-(difluoromethyl)-4-methyl-6-(1-methyl-1H-pyrazol-4-yl)-1-(1-(tetrahydro-2H-pyran-4-yl)-4,5,6,7-tetrahydro-1H-pyrazolo[4,3-c]pyridin-3-yl)-1,2,3,4-tetrahydroquinoline (Step 7 of Example 238 & 239, 180 mg, 0.4 mmol) in DMF (2 mL) was added 4-nitrophenyl carbonochloridate (752 mg, 3.7 mmol) and pyridine (3 mL, 3.7 mmol). The mixture was stirred at 26° C. for 12 h before a solution of methanamine in THF (M, 6 mL, 6 mmol) was added. The mixture was heated to 60° C. for 12 h. After cooling the reaction to room temperature, the mixture was concentrated in vacuo. The crude residue was purified by reverse phase chromatography (acetonitrile 30-60%/0.05% NH$_4$OH in water) to give the title compound (106 mg, 31%) as a yellow solid. $^1$H NMR (400 MHz, DMSO-$d_6$) δ 7.77 (s, 1H), 7.51 (s, 1H), 7.17 (s, 1H), 6.82 (s, 1H), 6.79 (t, J=55.6 Hz, 1H), 6.56-6.53 (m, 1H), 4.34-4.28 (m, 1H), 4.03-3.90 (m, 4H), 3.87 (s, 3H), 3.71-3.51 (m, 4H), 3.48-3.42 (m, 2H), 3.00-2.95 (m, 1H), 2.75-2.72 (m, 2H), 2.53 (d, J=4.0 Hz, 3H), 2.10-1.90 (m, 3H), 1.88-1.68 (m, 3H), 1.32 (d, J=6.8 Hz, 3H). LCMS M/Z (M+H) 540.

The Following Compounds were Prepared in a Similar Fashion to Example 248

Examples 249-256

| Example | Compound Name | NMR | m/z |
|---|---|---|---|
| Example 249 | 3-[7-(difluoromethyl)-6-(2-methoxy-4-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.18 (d, J = 5.2 Hz, 1H), 7.09 (s, 1H), 6.97-6.82 (m, 2H), 6.80-6.60 (m, 2H), 6.57 (d, J = 4.4 Hz, 1H), 4.32-4.25 (m, 1H), 4.05 (s, 2H), 3.96-3.93 (m, 2H), 3.88 (s, 3H), 3.62-3.59 (m, 4H), 3.49-3.42 (m, 2H), 2.89-2.85 (m, 2H), 2.77-2.74 (m, 2H), 2.54 (d, J = 4.0 Hz, 3H), 2.09-1.92 (m, 4H), 1.83-1.78 (m, 2H) | 553 |
| Example 250 | (R)-3-[7-(difluoromethyl)-3-methyl-6-(1-methylpyrazol-4-yl)-3,4-dihydro-2H-quinolin-1-yl]-N-methyl-1- | $^1$H NMR (400 MHz, DMSO-$d_6$) δ 7.75 (s, 1H), 7.50 (s, 1H), 7.09 (s, 1H), 6.80 (s, 1H), 6.79 (t, J = 56.0 Hz, 1H), 6.57-6.56 (m, 1H), 4.32-4.25 (m, 1H), 4.01 (s, 2H), 3.95-3.93 (m, 2H), 3.86 (s, 3H), 3.65-3.53 (m, 4H), 3.48-3.42 (m, 2H), | 540 |

| Example | Compound Name | NMR | m/z |
|---|---|---|---|
| | tetrahydropyran-4-yl-6,7-dihydro-4H-pyrazolo[4,3-c]pyridine-5-carboxamide | 3.25-3.19 (m, 1H), 2.91-2.88 (m, 1H), 2.75-2.72 (m, 2H), 2.53 (d, J = 4.0 Hz, 3H), 2.11-2.08 (m, 1H), 2.01-1.94 (m, 2H), 1.82-1.79 (m, 2H), 1.05 (d, J = 6.8 Hz, 3H) | |
| Example 251 | (S)-3-[7-(difluoromethyl)-3-methyl-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 7.75 (s, 1H), 7.50 (s, 1H), 7.09 (s, 1H), 6.78 (s, 1H), 6.77 (t, J = 55.2 Hz, 1H), 6.53-6.52 (m, 1H), 4.32-4.25 (m, 1H), 4.01 (s, 2H), 3.95-3.93 (m, 2H), 3.86 (s, 3H), 3.65-3.53 (m, 4H), 3.48-3.42 (m, 2H), 3.25-3.19 (m, 1H), 2.91-2.88 (m, 1H), 2.77-2.70 (m, 2H), 2.53 (d, J = 4.0 Hz, 3H), 2.11-2.08 (m, 1H), 2.03-1.93 (m, 2H), 1.82-1.79 (m, 2H), 1.05 (d, J = 6.8 Hz, 3H) | 540 |
| Example 252 | 3-[6-(6-acetamido-3-pyridyl)-7-(difluoromethyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, CDCl$_3$) δ 8.26-8.23 (m, 2H), 8.00 (s, 1H), 7.69-7.67 (m, 1H), 6.98 (s, 1H), 6.89 (s, 1H), 6.40 (t, J = 55.2 Hz, 1H), 6.40 (s, 1H), 4.42-4.38 (m, 1H), 4.15-4.12 (m, 2H), 4.01 (s, 2H), 3.80-3.74 (m, 4H), 3.55-3.51 (m, 2H), 2.91-2.88 (m, 2H), 2.81-2.78 (m, 5H), 2.38-2.26 (m, 2H), 2.25 (s, 3H), 2.11-2.08 (m, 2H), 1.89-1.86 (m, 2H) | 580 |
| Example 253 | 3-[6-(difluoromethyl)-5-(1,5-dimethylpyrazol-4-yl)indolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 7.77 (s, 1H), 7.26 (s, 1H), 6.99 (s, 1H), 6.74-6.42 (m, 2H), 4.41 (s, 2H), 4.30-4.17 (m, 1H), 4.06 (t, J = 8.4 Hz, 2H), 3.99-3.94 (m, 2H), 3.78 (s, 3H), 3.62-3.58 (m, 2H), 3.46 (t, J = 11.6 Hz, 2H), 3.22-3.18 (m, 2H), 2.69-2.66 (m, 2H), 2.59 (d, J = 4.4 Hz, 3H), 2.15 (s, 3H), 2.08-1.93 (m, 2H), 1.80-1.77 (m, 2H) | 526 |
| Example 254 | N-methyl-3-[6-(1-methylpyrazol-4-yl)-7-(trifluoromethyl)-3,4-dihydro-2H-quinolin-1-yl]-1-tetrahydropyran-4-yl-6,7-dihydro-4H-pyrazolo[4,3-c]pyridine-5-carboxamide | $^1$H NMR (400 MHz, DMSO-d$_6$) δ 7.71 (s, 1H), 7.42 (s, 1H), 7.09 (s, 1H), 6.96 (s, 1H), 6.55-6.54 (m, 1H), 4.35-4.22 (m, 1H), 4.05 (s, 2H), 3.94-3.92 (m, 2H), 3.84 (s, 3H), 3.60-3.55 (s, 4H), 3.46-3.40 (m, 2H), 2.85-2.82 (m, 2H), 2.73-2.71 (m, 2H), 2.53 (d, J = 4.0 Hz, 3H), 1.99-1.87 (m, 4H), 1.85-1.75 (m, 2H) | 544 |
| Example 255 | N-methyl-3-[7-methyl-6-(1-methylpyrazol-4-yl)-3,4-dihydro-2H-quinolin-1-yl]-1-tetrahydropyran-4-yl-6,7-dihydro-4H-pyrazolo[4,3-c]pyridine-5-carboxamide | $^1$H NMR (400 MHz, DMSO-d$_6$) δ 7.75 (s, 1H), 7.51 (s, 1H), 6.97 (s, 1H), 6.58-6.48 (m, 1H), 6.32 (s, 1H), 4.31-4.19 (m, 1H), 4.03-3.90 (m, 4H), 3.84 (s, 3H), 3.60-3.55 (m, 2H), 3.56-3.50 (m, 2H), 3.45 (t, J = 11.2 Hz, 2H), 2.79-2.68 (m, 4H), 2.54 (d, J = 4.8 Hz, 3H), 2.15 (s, 3H), 2.04-1.89 (m, 4H), 1.82-1.78 (m, 2H) | 490 |
| Example 256 | N-methyl-3-[6-(1-methylpyrazol-4-yl)-7-(trifluoromethoxy)-3,4-dihydro-2H-quinolin-1-yl]-1-tetrahydropyran-4-yl-6,7-dihydro-4H-pyrazolo[4,3-c]pyridine-5-carboxamide | $^1$H NMR (400 MHz, DMSO-d$_6$) δ 7.87 (s, 1H), 7.67 (s, 1H), 7.33 (s, 1H), 6.59 (s, 1H), 6.58-6.50 (m, 1H), 4.35-4.20 (m, 1H), 4.08 (s, 2H), 3.96-3.92 (m, 2H), 3.85 (s, 3H), 3.63-3.57 (m, 2H), 3.57-3.51 (m, 2H), 3.45 (t, J = 11.6 Hz, 2H), 2.82 (t, J = 6.0 Hz, 2H), 2.75-2.65 (m, 2H), 2.55 (d, J = 4.0 Hz, 1.81 3H), 2.04-1.89 (m, 4H), 1.77 (m, 2H) | 560 |

Example 257

3-[7-chloro-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide

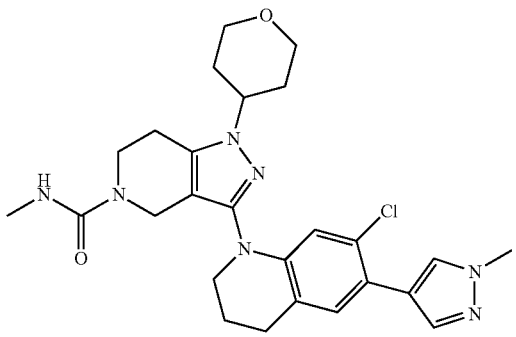

Step 1 tert-butyl 3-(7-chloro-6-(1-methyl-1H-pyrazol-4-yl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate

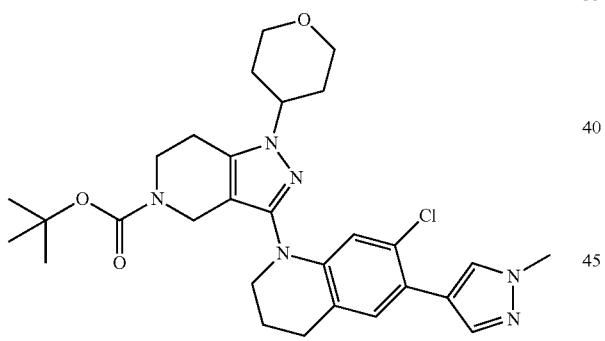

To a solution of tert-butyl 3-bromo-1-(tetrahydro-2H-pyran-4-yl)-6,7-dihydro-1H-pyrazolo[4,3-c]pyridine-5(4H)-carboxylate (Intermediate H, 0.5 g, 1.3 mmol) in 1,4-dioxane (10 mL) was added 7-chloro-6-(1-methyl-1H-pyrazol-4-yl)-1,2,3,4-tetrahydroquinoline (320 mg, 1.3 mmol), chloro(2-dicyclohexylphosphino-2',6'-di-i-propoxy-1,1'-biphenyl)(2'-amino-1,1'-biphenyl-2-yl)palladium(II) (100 mg, 0.13 mmol), 2-dicyclohexylphosphino-2',6'-di-i-propoxy-1,1'-biphenyl (60 mg, 0.13 mmol) and t-BuONa (373 mg, 3.9 mmol). The mixture was heated to 120° C. for 12 h under a nitrogen atmosphere. After cooling the reaction to room temperature, the mixture was filtered and concentrated in vacuo. The crude residue was purified by silica gel chromatography (DCM/MeOH=50:1) to give the title compound (1.1 g, 42% purity) as a yellow solid that required no further purification. LCMS M/Z (M+H) 553.

Step 2

7-chloro-6-(1-methyl-1H-pyrazol-4-yl)-1-(1-(tetrahydro-2H-pyran-4-yl)-4,5,6,7-tetrahydro-1H-pyrazolo[4,3-c]pyridin-3-yl)-1,2,3,4-tetrahydroquinoline

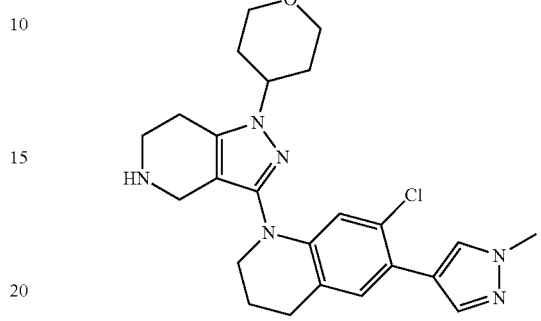

To a solution of tert-butyl 3-(7-chloro-6-(1-methyl-1H-pyrazol-4-yl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate (1.1 g, 2.0 mmol) in DCM (3 mL) was added trifluoroacetic acid (1.5 mL, 20 mmol). The mixture was stirred at 26° C. for 1 h and concentrated in vacuo. DCM (30 mL) was added, washed with sat. aq. NaHCO$_3$ (10 mL×3) and brine (10 mL). The organic layer was dried over anhydrous Na$_2$SO$_4$, filtered and concentrated in vacuo to give the title compound (450 mg, crude) as a yellow oil that required no further purification. LCMS M/Z (M+H) 453.

Step 3

3-[7-chloro-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide

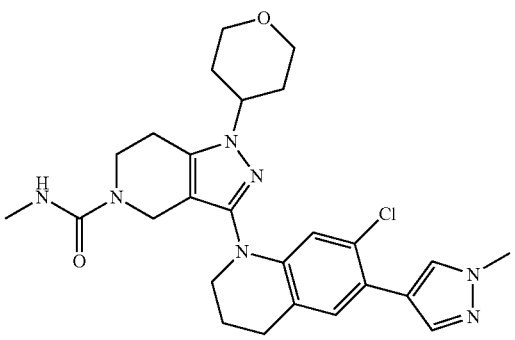

To a solution of 7-chloro-6-(1-methyl-1H-pyrazol-4-yl)-1-(1-(tetrahydro-2H-pyran-4-yl)-4,5,6,7-tetrahydro-1H-pyrazolo[4,3-c]pyridin-3-yl)-1,2,3,4-tetrahydroquinoline (200 mg, 0.36 mmol) in DCM (5 mL) was added triethylamine (2.5 mL, 1.8 mmol) and N-methyl-1H-imidazole-1-carboxamide (135 mg, 1.1 mmol). The mixture was stirred at 20° C. for 1 h and concentrated in vacuo. DCM (50 mL) was added, washed with water (30 mL×3) and brine (30 mL). The organic layer was dried over anhydrous Na$_2$SO$_4$, filtered and concentrated in vacuo. The crude residue was purified by reverse phase chromatography (acetonitrile 30-60%/0.05% NH$_4$OH in water) to give the title compound (23 mg, 12%) as a white solid. $^1$H NMR (400 MHz, DMSO-d$_6$) δ 7.96 (s, 1H), 7.67 (s, 1H), 7.19 (s, 1H), 6.56-6.55 (m, 1H), 6.49 (s, 1H), 4.35-4.24 (m, 1H), 4.04 (s, 2H), 3.96-3.94 (m, 2H), 3.85 (s, 3H), 3.63-3.51 (m, 4H), 3.48-3.42 (m, 2H), 2.82-2.70 (m, 4H), 2.54 (d, J=4.0 Hz, 3H), 1.99-1.90 (m, 4H), 1.83-1.80 (m, 2H). LCMS M/Z (M+H) 510.

Example 258

3-[7-cyclopropyl-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide

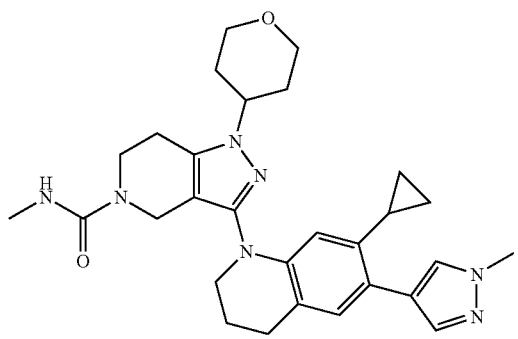

To a solution of 3-[7-chloro-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide (Example 257, 50 mg, 0.1 mmol) in 1,4-dioxane (2 mL) and water (0.5 mL) was added palladium(II) acetate (4 mg, 0.02 mmol), cyclopropylboronic acid (17 mg, 0.2 mmol), tricyclohexylphosphine (6 mg, 0.02 mmol) and Cs$_2$CO$_3$ (96 mg, 0.3 mmol). The mixture was irradiated in a microwave at 80° C. for 0.5 h. After cooling the reaction to room temperature, the mixture was filtered and concentrated in vacuo. The crude residue was purified by reverse phase chromatography (acetonitrile 25-55%/0.05% NH$_4$OH in water) to give the title compound (15 mg, 71% purity) which was further separated by using chiral SFC (SFC80; Chiralpak AD 250×30 mm I.D., 5 um; Supercritical CO$_2$/IPA+ NH$_3$.H$_2$O=65/35; 80 mL/min) to give the title compound (5 mg, 10%) as a white solid. $^1$H NMR (400 MHz, DMSO-d$_6$) δ 7.83 (s, 1H), 7.59 (s, 1H), 6.97 (s, 1H), 6.53-6.52 (m, 1H), 6.21 (s, 1H), 4.29-4.24 (m, 1H), 4.02-3.91 (m, 4H), 3.85 (s, 3H), 3.62-3.49 (m, 4H), 3.48-3.42 (m, 2H), 2.79-2.69 (m, 4H), 2.54 (d, J=4.0 Hz, 3H), 2.05-1.86 (m, 5H), 1.82-1.79 (m, 2H), 0.80-0.78 (m, 2H), 0.35-0.34 (m, 2H). LCMS M/Z (M+H) 516.

Example 259

N-methyl-3-[6-(1-methylpyrazol-4-yl)-7-vinyl-3,4-dihydro-2H-quinolin-1-yl]-1-tetrahydropyran-4-yl-6,7-dihydro-4H-pyrazolo[4,3-c]pyridine-5-carboxamide

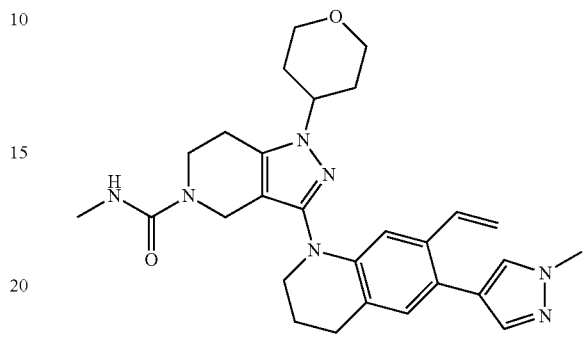

To a solution of 3-[7-chloro-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide (Example 257, 50 mg, 0.1 mmol) in 1,4-dioxane (2 mL) and water (0.5 mL) was added palladium(II) acetate (4 mg, 0.02 mmol), 4,4,5,5-tetramethyl-2-vinyl-1,3,2-dioxaborolane (30 mg, 0.2 mmol), K$_3$PO$_4$ (42 mg, 0.2 mmol) and 2-dicyclohexyl phosphino-2',6'-dimethoxybiphenyl (4 mg, 0.01 mmol). The mixture was irradiated in a microwave at 80° C. for 0.5 h. After cooling the reaction to room temperature, the mixture was filtered and concentrated in vacuo. The crude residue was purified by reverse phase chromatography (acetonitrile 22-52%/0.05% NH$_4$OH in water) to give the title compound (15 mg, 31%) as a white solid. $^1$H NMR (400 MHz, DMSO-d$_6$) δ 7.68 (s, 1H), 7.43 (s, 1H), 6.98 (s, 1H), 6.81-6.74 (m, 1H), 6.70 (s, 1H), 6.56-6.51 (m, 1H), 5.32 (d, J=18.8 Hz, 1H), 5.09 (d, J=12.0 Hz, 1H), 4.32-4.20 (m, 1H), 4.03 (s, 2H), 3.97-3.91 (m, 2H), 3.85 (s, 3H), 3.61-3.54 (m, 4H), 3.48-3.42 (m, 2H), 2.81-2.72 (m, 4H), 2.53 (d, J=4.4 Hz, 3H), 2.01-1.93 (m, 4H), 1.82-1.81 (m, 2H). LCMS M/Z (M+H) 502.

Example 260

3-[7-ethyl-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide

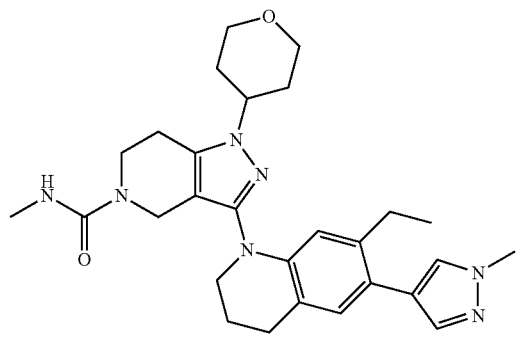

To a solution of N-methyl-3-[6-(1-methylpyrazol-4-yl)-7-vinyl-3,4-dihydro-2H-quinolin-1-yl]-1-tetrahydropyran-4-yl-6,7-dihydro-4H-pyrazolo[4,3-c]pyridine-5-carboxamide (Example 259, 80 mg, 0.16 mmol) in MeOH (5 mL) was added 10% Pd/C (13 mg). The mixture was stirred at 25° C. for 12 h under a hydrogen atmosphere (15 psi). The mixture was filtered and concentrated in vacuo. The crude residue was separated by using chiral SFC (SFC80; Chiralpak AD 250×30 mm I.D., 5 um; Supercritical $CO_2$/MEOH+$NH_3.H_2O$=70/30; 80 mL/min) to give the title compound (6 mg, 2%) as a white solid. $^1$H NMR (400 MHz, DMSO-$d_6$) 7.70 (s, 1H), 7.44 (s, 1H), 6.90 (s, 1H), 6.54-6.53 (m, 1H), 6.37 (s, 1H), 4.32-4.19 (m, 1H), 4.00 (s, 2H), 3.96-3.94 (m, 2H), 3.85 (s, 3H), 3.62-3.51 (m, 4H), 3.48-3.42 (m, 2H), 2.79-2.69 (m, 4H), 2.53 (d, J=4.4 Hz, 3H), 2.46-2.44 (m, 2H), 2.04-1.90 (m, 4H), 1.81-1.79 (m, 2H), 0.98 (t, J=8.0 Hz, 3H). LCMS M/Z (M+H) 504.

Example 261

N-methyl-3-[6-(1-methylpyrazol-4-yl)-7-methylsulfonyl-3,4-dihydro-2H-quinolin-1-yl]-1-tetrahydropyran-4-yl-6,7-dihydro-4H-pyrazolo[4,3-c]pyridine-5-carboxamide

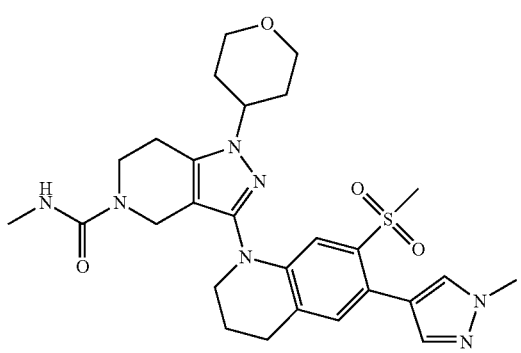

Step 1

7-(methylsulfonyl)quinoline

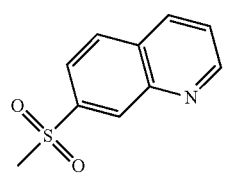

To a solution of 7-bromoquinoline (2.0 g, 9.6 mmol), $N^1$, $N^2$-dimethylethane-1,2-diamine (339 mg, 3.9 mmol) and copper(I) trifluoromethanesulfonate (409 mg, 1.9 mmol) in DMSO (20 mL) was added sodium methanesulfinate (5 g, 48.1 mmol). The mixture was heated to 120° C. for 2 h under a nitrogen atmosphere. After cooling the reaction to room temperature, the mixture was filtered and concentrated in vacuo. The crude residue was purified by silica gel chromatography (petroleum ether/EtOAc=1:1) to give the title compound (1.2 g, 60%) as a light yellow solid. $^1$H NMR (400 MHz, DMSO-$d_6$) δ 9.09-9.08 (m, 1H), 8.55-8.53 (m, 2H), 8.27 (d, J=8.0 Hz, 3H), 8.07-8.05 (m, 1H), 7.75-7.72 (m, 1H), 3.34 (s, 1H).

Step 2

7-(methylsulfonyl)-1,2,3,4-tetrahydroquinoline

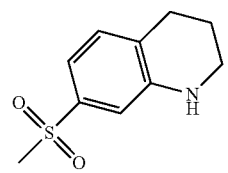

To a solution of 7-(methylsulfonyl)quinoline (1.6 g, 7.9 mmol) in toluene (20 mL) was added diethyl-1,4-dihydro-2,6-dimethyl-3,5-pyridinedicarboxylate (6.0 g, 23.6 mmol) and diphenylphosphate (98 mg, 0.39 mmol). The mixture was heated to 60° C. for 16 h. After cooling the reaction to room temperature, the mixture was filtered and concentrated in vacuo. The crude residue was purified by silica gel chromatography (petroleum ether/EtOAc=2:1) to give the title compound (1.2 g, 72%) as a white solid. $^1$H NMR (400 MHz, DMSO-$d_6$) δ 7.03 (d, J=7.2 Hz, 1H), 6.91-6.90 (m, 1H), 6.86-6.84 (m, 1H), 6.25 (s, 1H), 3.21-3.17 (m, 2H), 3.04 (s, 3H), 2.71-2.68 (m, 2H), 1.80-1.74 (m, 2H).

Step 3 tert-butyl 3-(7-(methylsulfonyl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate

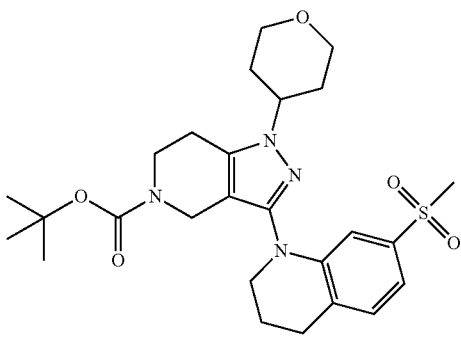 [SMILES: CC(C)(C)OC(=O)N1CCc2c(c(N3CCCc4ccc(S(C)(=O)=O)cc43)nn2C2CCOCC2)C1]

To a solution of tert-butyl 3-bromo-1-(tetrahydro-2H-pyran-4-yl)-6,7-dihydro-1H-pyrazolo[4,3-c]pyridine-5(4H)-carboxylate (Intermediate H, 1.2 g, 3.1 mmol) in 1,4-dioxane (10 mL) was added 7-(methylsulfonyl)-1,2,3,4-tetrahydroquinoline (644 mg, 3.1 mmol), chloro(2-dicyclohexylphosphino-2',6'-di-i-propoxy-1,1'-biphenyl)(2'-amino-1,1'-biphenyl-2-yl)palladium(II) (249 mg, 0.3 mmol), 2-dicyclohexylphosphino-2',6'-di-i-propoxy-1,1'-biphenyl (142 mg, 0.3 mmol) and t-BuONa (878 mg, 9.1 mmol). The mixture was heated to 110° C. for 16 h under a nitrogen atmosphere. After cooling the reaction to room temperature, the mixture was filtered and concentrated in vacuo. The crude residue was purified by silica gel chromatography (DCM/MeOH=50:1) to give the title compound (970 mg, 62%) as a light yellow solid. LCMS M/Z (M+H) 517.

tert-butyl 3-(6-bromo-7-(methylsulfonyl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate

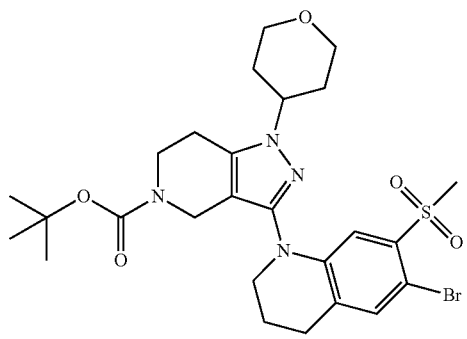 [SMILES: CC(C)(C)OC(=O)N1CCc2c(c(N3CCCc4cc(Br)c(S(C)(=O)=O)cc43)nn2C2CCOCC2)C1]

To a solution of tert-butyl 3-(7-(methylsulfonyl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate (970 mg, 1.9 mmol) in DCM (8 mL) at 0° C. was added N-bromosuccinimide (318 mg, 1.8 mmol). The mixture was stirred at room temperature for 2 h. Water (20 mL) was added and the mixture was extracted with DCM (20 mL×3). The combined organic layers were washed with brine (20 mL×3), dried over anhydrous Na₂SO₄, filtered and concentrated in vacuo to give the title compound (1.1 g, crude) as a yellow solid that required no further purification. LCMS M/Z (M+H) 597.

Step 5 tert-butyl 3-(6-(1-methyl-1H-pyrazol-4-yl)-7-(methylsulfonyl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate

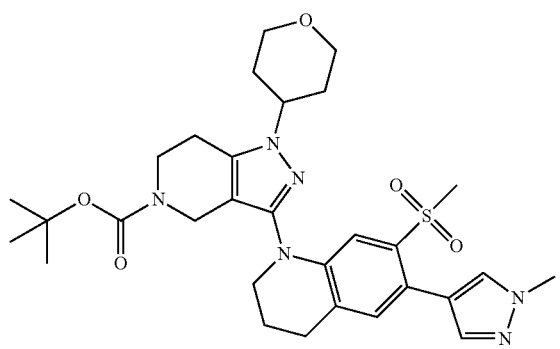 [SMILES: Cn1cc(-c2cc3c(cc2S(C)(=O)=O)N(c2nn(C4CCOCC4)c4c2CN(C(=O)OC(C)(C)C)CC4)CCC3)cn1]

To a solution of tert-butyl 3-(6-bromo-7-(methylsulfonyl)-3,4-dihydroquinolin-1(2H)-yl)-1-(tetrahydro-2H-pyran-4-yl)-6,7-dihydro-1H-pyrazolo[4,3-c]pyridine-5(4H)-carboxylate (300 mg, 0.5 mmol) in THF (5 mL) and water (1 mL) was added 1-methyl-4-(4,4,5,5-tetramethyl-1,3,2-dioxaborolan-2-yl)-1H-pyrazole (126 mg, 0.6 mmol), chloro(2-dicyclohexylphosphino-2',4',6'-tri-i-propyl-1,1'-biphenyl)(2'-amino-1,1'-biphenyl-2-yl) palladium(II) (40 mg, 0.05 mmol), 2-(dicyclohexylphosphino)-2',4',6'-triisopropylbiphenyl (24 mg, 0.05 mmol) and Na₂CO₃ (160 mg, 1.5 mmol). The mixture was heated to 60° C. for 16 h under a nitrogen atmosphere. After cooling the reaction to room temperature, the mixture was filtered and concentrated in vacuo. The crude residue was purified by silica gel chromatography (DCM/MeOH=50:1) to give the title compound (200 mg, 67%) as a yellow solid. LCMS M/Z (M+H) 597.

Step 6

6-(1-methyl-1H-pyrazol-4-yl)-7-(methylsulfonyl)-1-(1-(tetrahydro-2H-pyran-4-yl)-4,5,6,7-tetrahydro-1H-pyrazolo[4,3-c]pyridin-3-yl)-1,2,3,4-tetrahydroquinoline

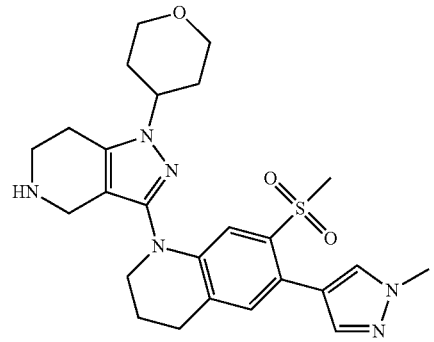 [SMILES: Cn1cc(-c2cc3c(cc2S(C)(=O)=O)N(c2nn(C4CCOCC4)c4c2CNCC4)CCC3)cn1]

To a solution of tert-butyl 3-(6-(1-methyl-1H-pyrazol-4-yl)-7-(methylsulfonyl)-3,4-dihydroquinolin-1 (2H)-yl)-1-(tetrahydro-2H-pyran-4-yl)-6,7-dihydro-1H-pyrazolo[4,3-c]pyridine-5(4H)-carboxylate (100 mg, 0.17 mmol) in DCM (2 mL) at 0° C. was added trifluoroacetic acid (0.12 mL, 1.7 mmol). The mixture was stirred at room temperature for 1 h and concentrated in vacuo to give the title compound (131 mg, crude) as a yellow oil that required no further purification. LCMS M/Z (M+H) 497.

Step 7

N-methyl-3-[6-(1-methylpyrazol-4-yl)-7-methylsulfonyl-3,4-dihydro-2H-quinolin-1-yl]-1-tetrahydropyran-4-yl-6,7-dihydro-4H-pyrazolo[4,3-c]pyridine-5-carboxamide

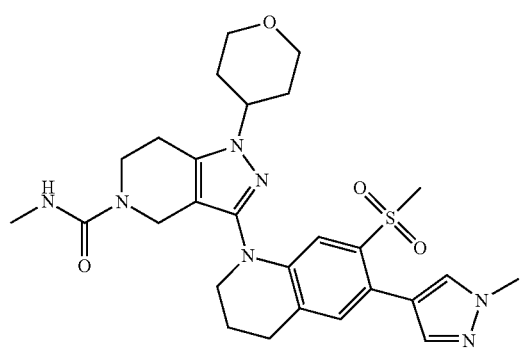

To a solution of 6-(1-methyl-1H-pyrazol-4-yl)-7-(methylsulfonyl)-1-(1-(tetrahydro-2H-pyran-4-yl)-4,5,6,7-tetrahydro-1H-pyrazolo[4,3-c]pyridin-3-yl)-1,2,3,4-tetrahydroquinoline (131 mg, 0.26 mmol) in DCM (2 mL) was added triethylamine (0.18 mL, 1.3 mmol) and N-methyl-1H-imidazole-1-carboxamide (50 mg, 0.4 mmol). The mixture was stirred at room temperature for 16 h and concentrated in vacuo. DCM (10 mL) was added, washed with water (10 mL×3) and brine (10 mL). The organic layer was dried over anhydrous Na₂SO₄, filtered and concentrated in vacuo. The crude residue was purified by reverse phase chromatography (acetonitrile 18-48%/0.05% NH₄OH in water) to give the title compound (28 mg, 19%) as a white solid. ¹H NMR (400 MHz, DMSO-d₆) δ 7.85 (s, 1H), 7.57 (s, 1H), 7.32 (s, 1H), 7.10 (s, 1H), 6.56-6.47 (m, 1H), 4.28-4.27 (m, 1H), 4.03 (s, 2H), 3.92-3.91 (m, 2H), 3.86 (s, 3H), 3.61-3.56 (m, 4H), 3.47-3.40 (m, 2H), 2.86-2.83 (m, 2H), 2.74-2.72 (m, 5H), 2.52 (d, J=4.4 Hz, 3H), 2.00-1.94 (m, 4H), 1.80-1.79 (m, 2H). LCMS M/Z (M+H) 554.

Example 262

3-[7-cyano-4-methyl-6-(1-methylpyrazol-4-yl)-2,3-dihydroquinoxalin-1-yl]-N-methyl-1-tetrahydropyran-4-yl-6,7-dihydro-4H-pyrazolo[4,3-c]pyridine-5-carboxamide

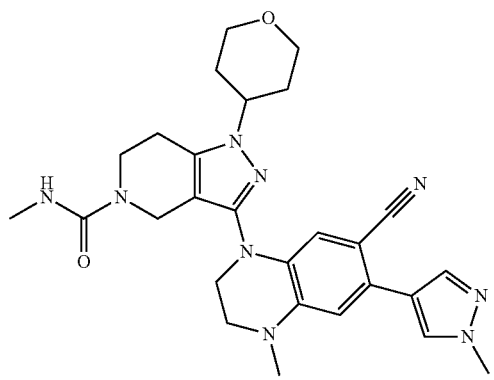

Step 1

2-((5-bromo-4-(difluoromethyl)-2-nitrophenyl)(methyl)amino)ethanol

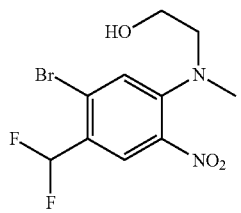 [SMILES: CN(CCO)c1cc(Br)c(C(F)F)cc1[N+](=O)[O-]]

To a solution of 2-(methylamino)ethanol (1.67 g, 22.2 mmol) and 1-bromo-2-(difluoromethyl)-5-fluoro-4-nitrobenzene (5.0 g, 18.5 mmol) in DMF (50 mL) was added N,N-diisopropylethylamine (6.65 mL, 37.0 mmol). The mixture was heated to 80° C. for 16 h. After cooling the reaction to room temperature, water (50 mL) was added and the mixture was extracted with EtOAc (50 mL×3). The combined organic layers were washed with brine (50 mL×3), dried over anhydrous Na₂SO₄, filtered and concentrated in vacuo. The crude residue was purified by silica gel chromatography (petroleum ether/EtOAc=3:1) to give the title compound (5.5 g, 91%) as a red oil. ¹H NMR (400 MHz, CDCl₃) 8.03 (s, 1H), 7.41 (s, 1H), 6.80 (t, J=55.2 Hz, 1H), 3.86 (t, J=5.2 Hz, 2H), 3.49 (t, J=5.2 Hz, 2H), 2.91 (s, 3H).

Step 2

5-bromo-N-(2-chloroethyl)-4-(difluoromethyl)-N-methyl-2-nitroaniline

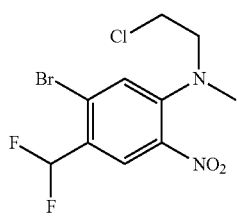 [SMILES: CN(CCCl)c1cc(Br)c(C(F)F)cc1[N+](=O)[O-]]

To a solution of 2-((5-bromo-4-(difluoromethyl)-2-nitrophenyl)(methyl)amino)ethanol (2.0 g, 6.15 mmol) and pyridine (0.5 mL, 6.15 mmol) in DCM (20 mL) at 0° C. was added thionylchloride (0.89 mL, 12.3 mmol) dropwise. The mixture was stirred at room temperature for 16 h. DCM (50 mL) was added, washed with sat. aq. NaHCO₃ (50 mL×3), brine (50 mL×2), dried over anhydrous Na₂SO₄, filtered and concentrated in vacuo to give the title compound (2.2 g, crude) as a red oil that required no further purification. LCMS M/Z (M+H) 345.

Step 3

5-bromo-N¹-(2-chloroethyl)-4-(difluoromethyl)-N¹-methylbenzene-1,2-diamine

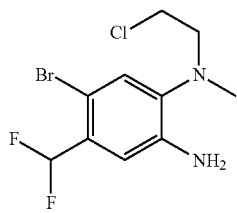 [SMILES: CN(CCCl)c1cc(Br)c(C(F)F)cc1N]

To a solution of 5-bromo-N-(2-chloroethyl)-4-(difluoromethyl)-N-methyl-2-nitro-aniline (2.0 g, 5.82 mmol) in AcOH (20 mL) was added Fe powder (1.63 g, 29.1 mmol). The mixture was stirred at 20° C. for 1 h. Insoluble solid was filtered off, the filtrate was adjusted to pH 8 by addition of sat. aq. NaHCO₃ and the mixture was extracted with EtOAc (50 mL×3). The combined organic layers were washed with brine (50 mL×3), dried over anhydrous Na₂SO₄, filtered and concentrated in vacuo to give the title compound (2 g, crude) as a red oil that required no further purification. LCMS M/Z (M+H) 315.

Step 4

7-bromo-6-(difluoromethyl)-1-methyl-1,2,3,4-tetrahydroquinoxaline

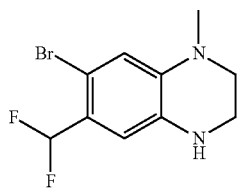

To a solution of 5-bromo-N¹-(2-chloroethyl)-4-(difluoromethyl)-N¹-methylbenzene-1,2-diamine (2.0 g, 6.38 mmol) in DMF (50 mL) was added potassium iodide (2.12 g, 12.8 mmol) and potassium carbonate (2.64 g, 19.1 mmol). The mixture was heated to 80° C. for 3 h. After cooling the reaction to room temperature, water (100 mL) was added and extracted with EtOAc (100 mL×3). The combined organic layers were washed with brine (100 mL×2), dried over anhydrous Na₂SO₄, filtered and concentrated in vacuo to give the title compound (1.7 g, crude) as brown oil that required no further purification. LCMS M/Z 277.

Step 5

1-methyl-7-(1-methyl-1H-pyrazol-4-yl)-1,2,3,4-tetrahydroquinoxaline-6-carbaldehyde

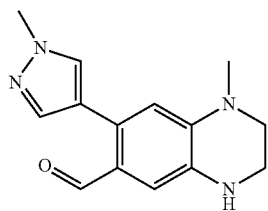 [SMILES: CN1CCNc2cc(C=O)c(-c3cnn(C)c3)cc21]

To a solution of 7-bromo-6-(difluoromethyl)-1-methyl-1,2,3,4-tetrahydroquinoxaline (1.7 g, 6.13 mmol), 1-methyl-4-(4,4,5,5-tetramethyl-1,3,2-dioxaborolan-2-yl)-1H-pyrazole (1.53 g, 7.36 mmol) and sodium carbonate (1.95 g, 18.4 mmol) in THF (20 mL) and water (4 mL) was added chloro(2-dicyclohexylphosphino-2',4',6'-tri-i-propyl-1,1'-biphenyl)(2'-amino-1,1'-biphenyl-2-yl) palladium(II) (483 mg, 0.61 mmol) and 2-(dicyclohexylphosphino)-2',4',6'-triisopropylbiphenyl (292 mg, 0.61 mmol). The mixture was heated to 60° C. for 16 h under a nitrogen atmosphere. After cooling the reaction to room temperature, the mixture was filtered and concentrated in vacuo. The crude residue was purified by silica gel chromatography (petroleum ether/EtOAc=1:3) to give the title compound (500 mg, 32%) as a dark green solid. ¹HNMR (400 MHz, CDCl₃) δ 9.87 (s, 1H), 7.55 (s, 1H), 7.41 (s, 1H), 7.11 (s, 1H), 6.34 (s, 1H), 3.96 (s, 3H), 3.95-3.91 (m, 1H), 3.47-3.43 (m, 4H), 2.99 (s, 3H).

Step 6 tert-butyl 3-(7-formyl-4-methyl-6-(1-methyl-1H-pyrazol-4-yl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate

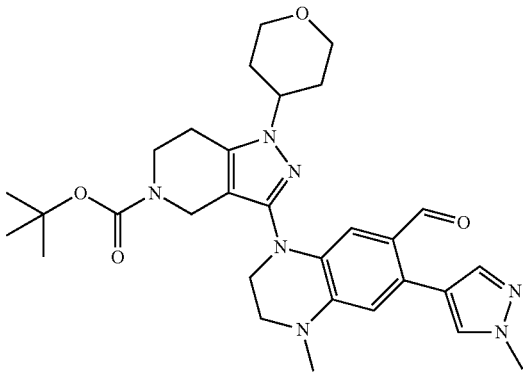 [SMILES: CN1CCN(c2nn(C3CCOCC3)c3c2CN(C(=O)OC(C)(C)C)CC3)c2cc(C=O)c(-c3cnn(C)c3)cc21]

To a solution of 1-methyl-7-(1-methyl-1H-pyrazol-4-yl)-1,2,3,4-tetrahydroquinoxaline-6-carbaldehyde (500 mg, 1.95 mmol), tert-butyl 3-bromo-1-(tetrahydro-2H-pyran-4-yl)-6,7-dihydro-1H-pyrazolo[4,3-c]pyridine-5(4H)-carboxylate (Intermediate H, 904 mg, 2.34 mmol) and t-BuONa (562 mg, 5.85 mmol) in 1,4-dioxane (15 mL) was added dichloro[1,3-bis(2,6-di-3-pentylphenyl)imidazol-2-ylidene](3-chloropyridyl)palladium(II) (155 mg, 0.20 mmol). The mixture was heated to 120° C. for 16 h under a nitrogen atmosphere. After cooling the reaction to room temperature, the mixture was filtered and concentrated in vacuo. The crude residue was purified by silica gel chromatography (DCM/MeOH=50/1) to give the title compound (600 mg, 55%) as a yellow solid. ¹H NMR (400 MHz, CDCl₃) δ 9.87 (s, 1H), 7.57 (s, 1H), 7.44 (s, 1H), 7.10 (s, 1H), 6.41 (s, 1H), 4.20-4.01 (m, 5H), 3.98 (s, 3H), 3.85-3.68 (m, 4H), 3.62-3.43 (m, 4H), 3.07 (s, 3H), 2.74-2.70 (m, 2H), 2.33-2.26 (m, 2H), 1.88-1.82 (m, 2H), 1.43 (s, 9H).

Step 7

(E)-tert-butyl 3-(7-((hydroxyimino)methyl)-4-methyl-6-(1-methyl-1H-pyrazol-4-yl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate

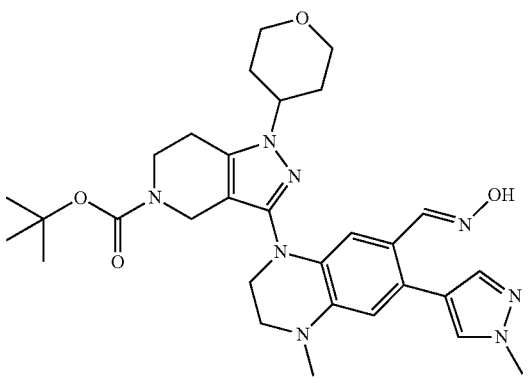 [SMILES: CN1CCN(c2nn(C3CCOCC3)c3c2CN(C(=O)OC(C)(C)C)CC3)c2cc(/C=N/O)c(-c3cnn(C)c3)cc21]

To a solution of tert-butyl 3-(7-formyl-4-methyl-6-(1-methyl-1H-pyrazol-4-yl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate (300 mg, 0.53 mmol) in EtOH (2 mL) was added sodium acetate (66 mg, 0.80 mmol) in water (1 mL) and hydroxylamine hydrochloride (56 mg, 0.80 mmol) in water (1 mL). The mixture was stirred at 20° C. for 16 h. DCM (20 mL) was added and the mixture was washed with water (10 mL×3), dried over anhydrous Na$_2$SO$_4$, filtered and concentrated in vacuo to give the title compound (300 mg, crude) as a brown solid that required no further purification. LCMS M/Z (M+H) 519.

Step 8 tert-butyl 3-(7-cyano-4-methyl-6-(1-methyl-1H-pyrazol-4-yl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate

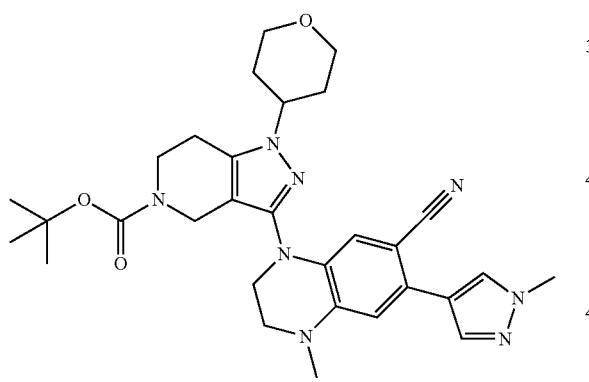

To a solution of (E)-tert-butyl 3-(7-((hydroxyimino)methyl)-4-methyl-6-(1-methyl-1H-pyrazol-4-yl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate (150 mg, 0.26 mmol) in THF (3 mL) was added 2,4,6-tripropyl-1,3,5,2,4,6-trioxatriphosphinane 2,4,6-trioxide (414 mg, 1.3 mmol) and triethylamine (0.55 mL, 3.9 mmol). The mixture was heated to 60° C. for 16 h. After cooling the reaction to room temperature, DCM (20 mL) was added and the mixture was washed with water (10 mL×3), dried over anhydrous Na$_2$SO$_4$, filtered and concentrated in vacuo to give the title compound (150 mg, crude) as a brown solid. LCMS M/Z (M+H) 559.

Step 9

1-methyl-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-1,2,3,4-tetrahydroquinoxaline-6-carbonitrile

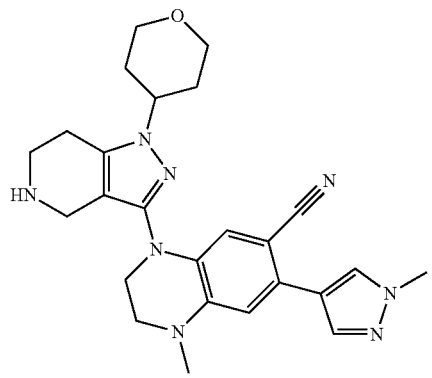 [SMILES: CN1CCN(c2nn(C3CCOCC3)c3c2CNCC3)c2cc(C#N)c(-c3cnn(C)c3)cc21]

To a solution of tert-butyl 3-(7-cyano-4-methyl-6-(1-methyl-1H-pyrazol-4-yl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate (300 mg, 0.54 mmol) in DCM (3 mL) at 0° C. was added trifluoroacetic acid (1.0 mL, 13.5 mmol). The mixture was stirred at room temperature for 2 h.

DCM (20 mL) was added and washed with sat. aq. NaHCO$_3$ (10 mL×3), dried over anhydrous Na$_2$SO$_4$, filtered and concentrated in vacuo to give the title compound (130 mg, crude) as a brown oil that required no further purification. LCMS M/Z (M+H) 459.

Step 10

3-[7-cyano-4-methyl-6-(1-methylpyrazol-4-yl)-2,3-dihydroquinoxalin-1-yl]-N-methyl-1-tetrahydropyran-4-yl-6,7-dihydro-4H-pyrazolo[4,3-c]pyridine-5-carboxamide

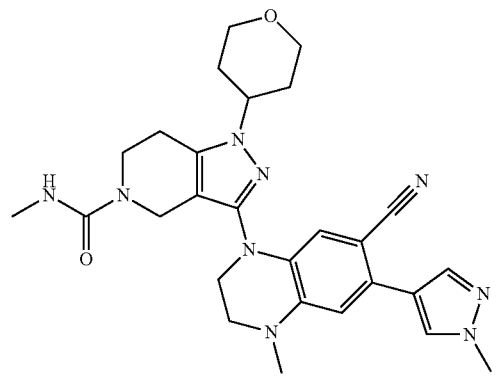

To a solution of 1-methyl-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-1,2,3,4-tetrahydroquinoxaline-6-carbonitrile (130 mg, 0.28 mmol) in DCM (2 mL) was added triethylamine (0.12 mL, 0.85 mmol) and N-methyl- 1H-imidazole-1-carboxamide (71 mg, 0.57 mmol). The mixture was stirred at room temperature for 16 h and concentrated in vacuo. DCM (10 mL) was added, washed with water (10 mL×3) and brine (10 mL). The organic layer was dried over anhydrous Na$_2$SO$_4$, filtered and concentrated in vacuo. The crude residue was purified by reverse phase chromatography (acetonitrile 30-60%/0.05% NH$_4$OH in water) to give the title compound (58 mg, 40%) as a white solid. $^1$H NMR (400 MHz, DMSO-d$_6$) 8.10 (s, 1H), 7.83 (s, 1H), 6.68 (s, 1H), 6.57-6.52 (m, 1H), 6.50 (s, 1H), 4.33-4.28 (m, 1H), 4.02-4.00 (m, 2H), 3.95-3.92 (m, 2H), 3.88 (s, 3H), 3.65-3.60 (m, 4H), 3.52-3.45 (m, 4H), 3.03 (s, 1H), 2.75-2.70 (m, 2H), 2.54 (d, J=4.8 Hz, 3H), 2.01-1.95 (m, 2H), 1.82-1.77 (m, 2H). LCMS M/Z (M+H) 516.

Example 263

4-(5-acetyl-1-tetrahydropyran-4-yl-6,7-dihydro-4H-pyrazolo[4,3-c]pyridin-3-yl)-1-methyl-7-(1-methyl-pyrazol-4-yl)-2,3-dihydroquinoxaline-6-carbonitrile

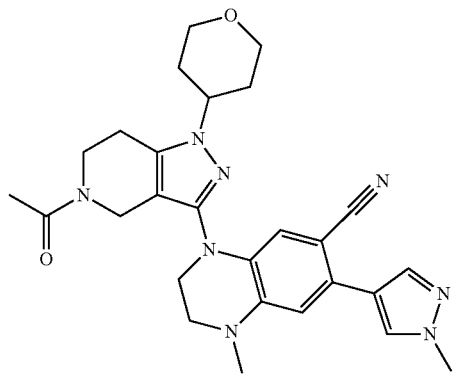 [SMILES: CC(=O)N1CCc2c(c(N3CCN(C)c4cc(-c5cnn(C)c5)c(C#N)cc43)nn2C2CCOCC2)C1]

To a solution of 1-methyl-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-1,2,3,4-tetrahydroquinoxaline-6-carbonitrile (233 mg, 0.51 mmol) in DCM (2 mL) at 0° C. was added triethylamine (0.35 mL, 2.5 mmol) and acetic anhydride (0.05 mL, 0.51 mmol). The mixture was stirred at room temperature for 0.5 h. The reaction solution was diluted with DCM (10 mL), washed with water (10 mL×2), dried over anhydrous Na$_2$SO$_4$, filtered and concentrated in vacuo. The crude residue was purified by reverse phase chromatography (acetonitrile 35-65%/0.05% NH$_4$OH in water) to give the title compound (36 mg, 14%) as a light brown solid. $^1$H NMR (400 MHz, DMSO-d$_6$) δ 8.08 (s, 1H), 7.82 (s, 1H), 6.67 (s, 1H), 6.54-6.49 (m, 1H), 4.30-4.20 (m, 1H), 4.14-4.08 (m, 2H), 3.95-3.92 (m, 2H), 3.86 (s, 3H), 3.70-3.65 (m, 2H), 3.64-3.62 (m, 2H), 3.48-3.44 (m, 4H), 3.02 (s, 3H), 2.85-2.73 (m, 2H), 2.06-1.95 (m, 5H), 1.82-1.79 (m, 2H). LCMS M/Z (M+H) 501.

Examples 264 & 265

(R)-4-(5-acetyl-1-tetrahydropyran-4-yl-6,7-dihydro-4H-pyrazolo[4,3-c]pyridin-3-yl)-1,2-dimethyl-7-(1-methylpyrazol-4-yl)-2,3-dihydroquinoxaline-6-carbonitrile and (S)-4-(5-acetyl-1-tetrahydropyran-4-yl-6,7-dihydro-4H-pyrazolo[4,3-c]pyridin-3-yl)-1,2-dimethyl-7-(1-methylpyrazol-4-yl)-2,3-dihydroquinoxaline-6-carbonitrile

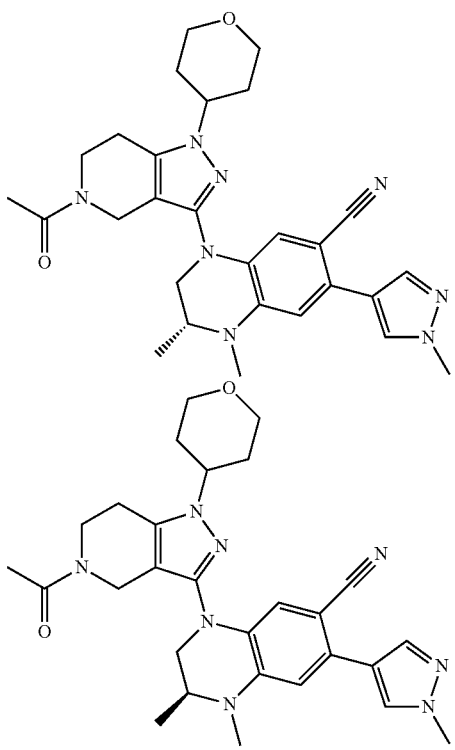

Step 1

2-(methylamino)propan-1-ol

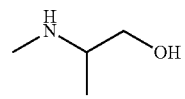

To a solution of 2-(methylamino)propanoic acid (10.0 g, 96.97 mmol) in THF (200 mL) was added LiAlH$_4$ (5.52 g, 145.46 mmol) portionwise. The mixture was heated to 70° C. for 16 h. After cooling the reaction to room temperature, water (10 mL) was added. The mixture was filtered and concentrated in vacuo. The crude residue was washed with HCl/EtOAc (2 M, 50 mL) to give the title compound (5.3 g, 61%) as a brown oil that required no further purification. $^1$H NMR (400 MHz, CD$_3$OD) δ 3.81-3.78 (m, 1H), 3.56-3.51 (m, 1H), 3.26-3.22 (m, 1H), 2.68 (s, 3H), 1.28 (d, J=7.2 Hz, 3H).

Step 2

2-bromo-4-((1-hydroxypropan-2-yl)(methyl)amino)-5-nitrobenzonitrile

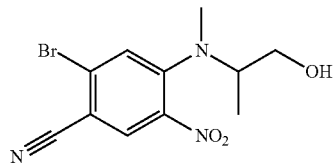 [SMILES: CC(CO)N(C)c1cc(Br)c(C#N)cc1[N+](=O)[O-]]

To a solution of 2-bromo-4-fluoro-5-nitro-benzonitrile (0.5 g, 2.04 mmol) in DMF (10 mL) was added N,N-diisopropylethylamine (0.53 g, 4.08 mmol) and 2-(methylamino)propan-1-ol (0.6 g, 6.73 mmol). The mixture was heated to 80° C. for 12 h. After cooling the reaction to room temperature, water (50 mL) was added and extracted with EtOAc (30 mL×3). The combined organic layers were washed with brine (30 mL×3), dried over anhydrous $Na_2SO_4$, filtered and concentrated in vacuo. The crude residue was purified by silica gel chromatography (petroleum ether/EtOAc=1:1) to give the title compound (440 mg, 69%) as a yellow solid. $^1$H NMR (400 MHz, $CDCl_3$) δ 8.04 (s, 1H), 7.46 (s, 1H), 3.95-3.92 (m, 1H), 3.76-3.73 (m, 1H), 3.65-3.62 (m, 1H), 2.73 (s, 3H), 1.28 (d, J=7.2 Hz, 3H).

Step 3

2-bromo-4-((1-chloropropan-2-yl)(methyl)amino)-5-nitrobenzonitrile

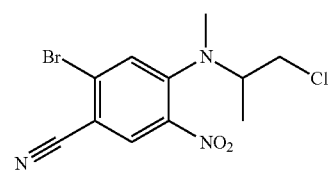

To a solution of 2-bromo-4-((1-hydroxypropan-2-yl)(methyl)amino)-5-nitrobenzonitrile (220 mg, 0.7 mmol) and pyridine (0.056 mL, 0.7 mmol) in DCM (10 mL) at 0° C. was added thionylchloride (0.1 mL, 1.4 mmol) dropwise. The mixture was stirred at 20° C. for 16 h. DCM (70 mL) was added and the mixture was washed with sat. aq. $NaHCO_3$ (40 mL×3), washed with brine (40 mL×2), dried over anhydrous $Na_2SO_4$, filtered and concentrated in vacuo to give the title compound (200 mg, crude) as a brown oil that required no further purification.

Step 4

5-amino-2-bromo-4-((1-chloropropan-2-yl)(methyl)amino)benzonitrile

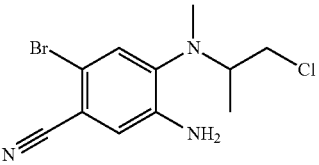 [SMILES: CC(CCl)N(C)c1cc(Br)c(C#N)cc1[N+](=O)[O-]]

To a solution of 2-bromo-4-((1-chloropropan-2-yl)(methyl)amino)-5-nitrobenzonitrile (200 mg, 0.6 mmol) in AcOH (20 mL) was added Fe powder (168 mg, 3 mmol). The mixture was stirred at 20° C. for 2 h. Insoluble solid was filtered off, the filtrate was adjusted to pH=8 by adding sat. aq. $NaHCO_3$ and extracted with EtOAc (50 mL×3). The combined organic layers were washed with brine (50 mL×3), dried over anhydrous $Na_2SO_4$, filtered and concentrated in vacuo to give the title compound (150 mg, crude) as a red oil that required no further purification. LCMS M/Z (M+H) 302.

Step 5

7-bromo-1,2-dimethyl-1,2,3,4-tetrahydroquinoxaline-6-carbonitrile

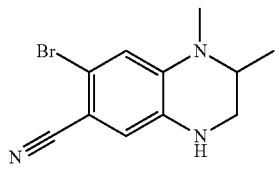

To a solution of 5-amino-2-bromo-4-((1-chloropropan-2-yl)(methyl)amino)benzonitrile (2.63 g, 8.69 mmol) in DMF (50 mL) was added potassium iodide (2.89 g, 17.38 mmol) and potassium carbonate (3.6 g, 26.07 mmol). The mixture was heated to 80° C. for 5 h. After cooling the reaction to room temperature, water (150 mL) was added and the mixture was extracted with EtOAc (100 mL×3). The combined organic layers were washed with brine (100 mL×2), dried over anhydrous $Na_2SO_4$, filtered and concentrated in vacuo. The crude residue was purified by silica gel chromatography (petroleum ether/EtOAc=3:1) to give the title compound (1.1 g, 48%) as a yellow solid. LCMS M/Z (M+H) 266.

Step 6

1,2-dimethyl-7-(1-methyl-1H-pyrazol-4-yl)-1,2,3,4-tetrahydroquinoxaline-6-carbonitrile

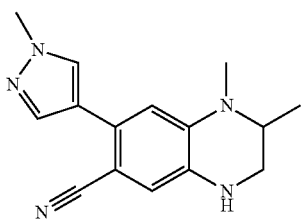 [SMILES: CC1CNc2cc(C#N)c(-c3cnn(C)c3)cc2N1C]

To a solution of 7-bromo-1,2-dimethyl-1,2,3,4-tetrahydroquinoxaline-6-carbonitrile (900 mg, 3.38 mmol), 1-methyl-4-(4,4,5,5-tetramethyl-1,3,2-dioxaborolan-2-yl)-1H-pyrazole (844 mg, 4.06 mmol) and sodium carbonate (1.1 g, 10.15 mmol) in THF (50 mL) and water (10 mL) was added chloro(2-dicyclohexylphosphino-2',4',6'-tri-i-propyl-1,1'-biphenyl)(2'-amino-1,1'-biphenyl-2-yl) palladium(II) (266 mg, 0.34 mmol) and 2-(dicyclohexylphosphino)-2',4',6'-triisopropylbiphenyl (161 mg, 0.34 mmol). The mixture was heated to 60° C. for 12 h under a nitrogen atmosphere. After cooling the reaction to room temperature, the mixture was filtered and concentrated in vacuo. The crude residue was purified by silica gel chromatography (DCM/MeOH=20/1) to give the title compound (0.81 g, 90%) as a brown solid. LCMS M/Z (M+H) 268.

Step 7 tert-butyl 3-(7-cyano-3,4-dimethyl-6-(1-methyl-1H-pyrazol-4-yl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate

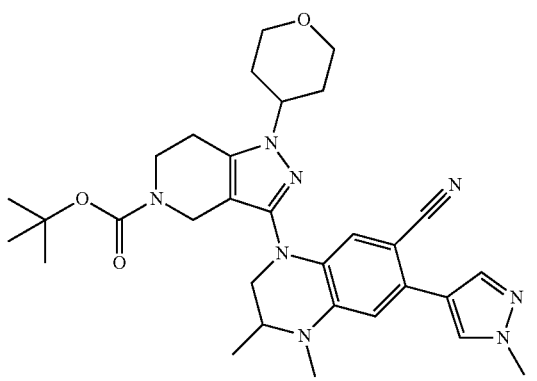 [SMILES: CC1CN(c2nn(C3CCOCC3)c3c2CN(C(=O)OC(C)(C)C)CC3)c2cc(C#N)c(-c3cnn(C)c3)cc2N1C]

To a solution of 1,2-dimethyl-7-(1-methyl-1H-pyrazol-4-yl)-1,2,3,4-tetrahydroquinoxaline-6-carbonitrile (800 mg, 2.99 mmol), tert-butyl 3-bromo-1-(tetrahydro-2H-pyran-4-yl)-6,7-dihydro-1H-pyrazolo[4,3-c]pyridine-5(4H)-carboxylate (Intermediate H, 1.6 g, 4.14 mmol) and t-BuONa (863 mg, 8.98 mmol) in 1,4-dioxane (20 mL) was added chloro(2-dicyclohexylphosphino-2',6'-di-i-propoxy-1,1'-biphenyl)(2'-amino-1,1'-biphenyl-2-yl)palladium(II) (232 mg, 0.30 mmol), 2-dicyclohexylphosphino-2',6'-di-i-propoxy-1,1'-biphenyl (139 mg, 0.30 mmol). The mixture was heated to 120° C. for 16 h under a nitrogen atmosphere. After cooling the reaction to room temperature, the mixture was filtered and concentrated in vacuo. The crude residue was purified by silica gel chromatography (DCM/MeOH=20/1) to give the title compound (1 g, 58%) as a brown solid. LCMS M/Z (M+H) 573.

Step 8

1,2-dimethyl-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-1,2,3,4-tetrahydroquinoxaline-6-carbonitrile

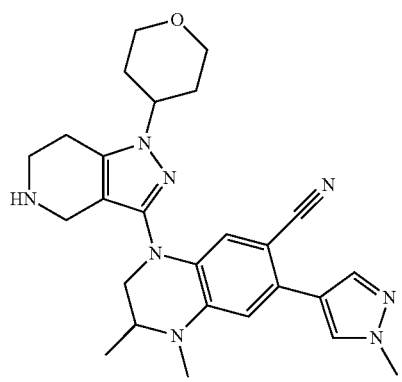 [SMILES: CC1CN(c2nn(C3CCOCC3)c3c2CNCC3)c2cc(C#N)c(-c3cnn(C)c3)cc2N1C]

To a solution of tert-butyl 3-(7-cyano-3,4-dimethyl-6-(1-methyl-1H-pyrazol-4-yl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate (1 g, 1.75 mmol) in DCM (15 mL) at 0° C. was added trifluoroacetic acid (1.53 mL, 17.46 mmol). The mixture was stirred at room temperature for 2 h and concentrated in vacuo to give the title compound (800 mg, crude) as a brown oil that required no further purification. LCMS M/Z (M+H) 473.

Step 9

(R)-4-(5-acetyl-1-tetrahydropyran-4-yl-6,7-dihydro-4H-pyrazol[4,3-c]pyridin-3-yl)-1,2-dimethyl-7-(1-methylpyrazol-4-yl)-2,3-dihydroquinoxaline-6-carbonitrile and (S)-4-(5-acetyl-1-tetrahydropyran-4-yl-6,7-dihydro-4H-pyrazolo[4,3-c]pyridin-3-yl)-1,2-dimethyl-7-(1-methylpyrazol-4-yl)-2,3-dihydroquinoxaline-6-carbonitrile

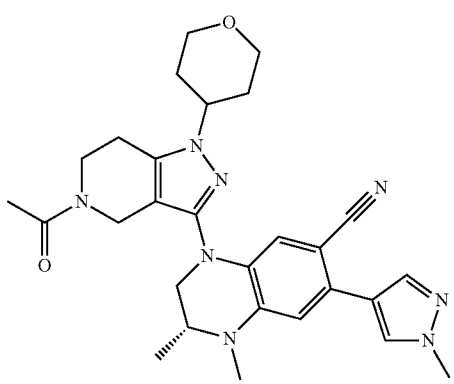

-continued

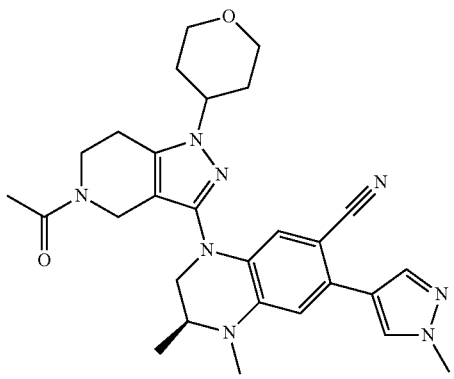

To a solution of 1,2-dimethyl-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-1,2,3,4-tetrahydroquinoxaline-6-carbonitrile (400 mg, 0.85 mmol) in DCM (15 mL) at 0° C. was added triethylamine (0.35 mL, 2.54 mmol) and acetic anhydride (0.16 mL, 1.69 mmol). The mixture was stirred at 17° C. for 1 h and concentrated in vacuo. The crude residue was purified by reverse phase chromatography (acetonitrile 38-68%/0.225% formic acid in water) to give racemic 4-(5-acetyl-1-tetrahydropyran-4-yl-6,7-dihydro-4H-pyrazolo[4,3-c]pyridin-3-yl)-1,2-dimethyl-7-(1-methylpyrazol-4-yl)-2,3-dihydroquinoxaline-6-carbonitrile (230 mg, 51%) as a white solid that was separated using chiral SFC (Chiralcel OJ 250 mm×30 mm, 10 um, I.D., 3 um Mobile phase: ethanol (0.05% diethylamine) in CO₂ from 5% to 40% Flow rate: 80 mL/min) to give (R)-4-(5-acetyl-1-tetrahydropyran-4-yl-6,7-dihydro-4H-pyrazolo[4,3-c]pyridin-3-yl)-1,2-dimethyl-7-(1-methylpyrazol-4-yl)-2,3-dihydroquinoxaline-6-carbonitrile (55 mg, first peak) and (S)-4-(5-acetyl-1-tetrahydropyran-4-yl-6,7-dihydro-4H-pyrazolo[4,3-c]pyridin-3-yl)-1,2-dimethyl-7-(1-methylpyrazol-4-yl)-2,3-dihydroquinoxaline-6-carbonitrile (62 mg, second peak). Absolute configuration was arbitrarily assigned to each enantiomer. Example 264: ¹H NMR (400 MHz, CDCl₃) $\delta$ 7.90-7.84 (m, 1H), 7.77-7.76 (m, 1H), 6.65-6.61 (m, 1H), 6.58-6.52 (m, 1H), 4.57-4.10 (m, 5H), 4.06-3.95 (m, 4H), 3.80-3.60 (m, 3H), 3.55-3.50 (m, 3H), 3.06-3.03 (m. 3H), 2.83-2.76 (m, 2H), 2.32-2.27 (m, 2H), 2.17-2.08 (m, 3H), 1.91-1.82 (m, 2H), 1.28 (d, J=6.4 Hz, 3H). LCMS M/Z (M+H) 515. Example 265: ¹H NMR (400 MHz, CDCl₃) $\delta$ 7.90-7.84 (m, 1H), 7.77-7.76 (m, 1H), 6.65-6.61 (m, 1H), 6.58-6.52 (m, 1H), 4.57-4.10 (m, 5H), 4.06-3.95 (m, 4H), 3.80-3.60 (m, 3H), 3.55-3.50 (m, 3H), 3.06-3.03 (m. 3H), 2.83-2.76 (m, 2H), 2.32-2.27 (m, 2H), 2.17-2.08 (m, 3H), 1.91-1.82 (m, 2H), 1.28 (d, J=6.4 Hz, 3H). LCMS M/Z (M+H) 515.

Examples 266 & 267

(R)-3-[7-cyano-3,4-dimethyl-6-(1-methylpyrazol-4-yl]-2,3-dihydroquinoxalin-1-yl]-N-methyl-1-tetrahydropyran-4-yl-6,7-dihydro-4H-pyrazolo[4,3-c]pyridine-5-carboxamide and (S)-3-[7-cyano-3,4-dimethyl-6-(1-methylpyrazol-4-yl)-2,3-dihydroquinoxalin-1-yl]-N-methyl-1-tetrahydropyran-4-yl-6,7-dihydro-4H-pyrazolo[4,3-c]pyridine-5-carboxamide

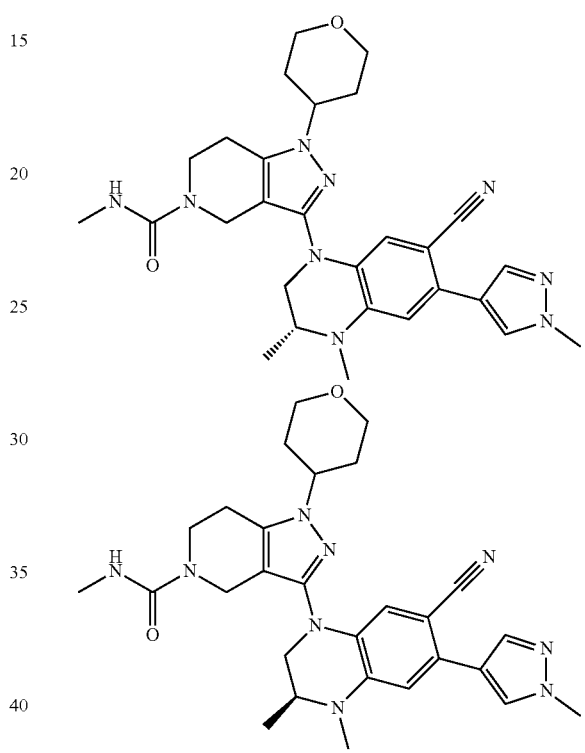

To a solution of 1,2-dimethyl-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-1,2,3,4-tetrahydroquinoxaline-6-carbonitrile (400 mg, 0.85 mmol) in DCM (15 mL) was added triethylamine (0.35 mL, 2.54 mmol) and N-methyl-1H-imidazole-1-carboxamide (213 mg, 1.69 mmol). The mixture was stirred at 20° C. for 16 h and concentrated in vacuo. DCM (100 mL) was added, washed with water (50 mL×3) and brine (50 mL). The organic layer was dried over anhydrous Na₂SO₄, filtered and concentrated in vacuo. The crude residue was purified by reverse phase chromatography (acetonitrile 24-54%/0.05% NH₄OH in water) to give racemic 3-[7-cyano-3,4-dimethyl-6-(1-methylpyrazol-4-yl)-2,3-dihydroquinoxalin-1-yl]-N-methyl-1-tetrahydropyran-4-yl-6,7-dihydro-4H-pyrazolo[4,3-c]pyridine-5-carboxamide (220 mg, 49%) as a white solid which was separated by using chiral SFC (AD 250 mm×30 mm, 5 um, I.D., 3 um Mobile phase: ethanol (0.05% diethylamine) in CO₂ from 5% to 40% Flow rate: 80 mL/min) to give (R)-3-[7-cyano-3,4-dimethyl-6-(1-methylpyrazol-4-yl)-2,3-dihydroquinoxalin-1-yl]-N-methyl-1-tetrahydropyran-4-yl-6,7-dihydro-4H-pyrazolo[4,3-c]pyridine-5-carboxamide (51 mg, first peak) and (S)-3-[7-cyano-3,4-dimethyl-6-(1-methylpyrazol-4-yl)-2,3-dihydroquinoxalin-1-yl]-N-methyl-1-tetrahydropyran-4-yl-6,7-dihydro-4H-pyrazolo[4,3-c]pyridine-5-carboxamide (72 mg, second peak). Absolute configuration was arbitrarily assigned to each diastereomer. Example 266: $^1$H NMR (400 MHz, CDCl$_3$) δ 7.89 (s, 1H), 7.77 (s, 1H), 6.63 (s, 1H), 6.56 (s, 1H), 4.44-4.40 (m, 1H), 4.15-4.10 (m, 3H), 4.00-3.85 (m, 6H), 3.74-3.60 (m, 3H), 3.55-3.50 (m. 3H), 3.05 (s, 3H), 2.81-2.77 (m, 5H), 2.29-2.26 (m, 2H), 1.91-1.82 (m, 2H), 1.28 (d, J=6.0 Hz, 3H). LCMS M/Z (M+H) 530. Example 267: $^1$H NMR (400 MHz, CDCl$_3$) δ 7.89 (s, 1H), 7.77 (s, 1H), 6.63 (s, 1H), 6.56 (s, 1H), 4.43-4.39 (m, 1H), 4.15-4.10 (m, 3H), 4.00-3.85 (m, 6H), 3.74-3.60 (m, 3H), 3.56-3.50 (m. 3H), 3.05 (s, 3H), 2.81-2.77 (m, 5H), 2.32-2.26 (m, 2H), 1.91-1.82 (m, 2H), 1.28 (d, J=6.0 Hz, 3H). LCMS M/Z (M+H) 530.

Example 268

N-methyl-3-[4-methyl-6-(1-methylpyrazol-4-yl)-7-(trifluoromethyl)-2,3-dihydroquinoxalin-1-yl]-1-tetrahydropyran-4-yl-6,7-dihydro-4H-pyrazolo[4,3-c]pyridine-5-carboxamide

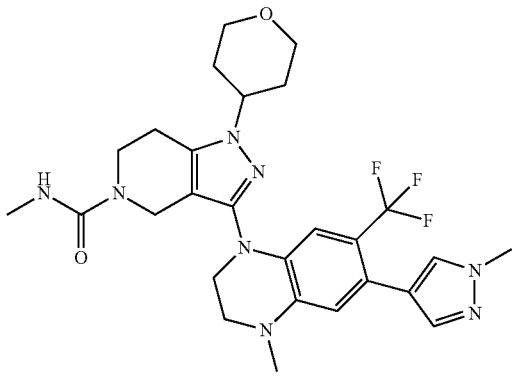

Step 1

2-((5-bromo-2-nitro-4-(trifluoromethyl)phenyl)(methyl)amino)ethanol

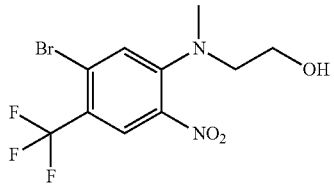 [SMILES: CN(CCO)c1cc(Br)c(C(F)(F)F)cc1[N+](=O)[O-]]

To a solution of 1-bromo-5-fluoro-4-nitro-2-(trifluoromethyl)benzene (7.0 g, 24.3 mmol) in DMF (50 mL) was added N,N-diisopropylethylamine (12.9 mL, 72.9 mmol) and 2-(methylamino)ethanol (2.2 g, 29.2 mmol). The mixture was heated to 80° C. for 16 h. After cooling the reaction to room temperature, water (50 mL) was added and extracted with EtOAc (50 mL×3). The combined organic layers were washed with brine (50 mL×3), dried over anhydrous Na$_2$SO$_4$, filtered and concentrated in vacuo. The crude residue was purified by silica gel chromatography (petroleum ether/EtOAc=3:1) to give the title compound (7.5 g, 90%) as a yellow solid.

Step 2

5-bromo-N-(2-chloroethyl)-N-methyl-2-nitro-4-(trifluoromethyl)aniline

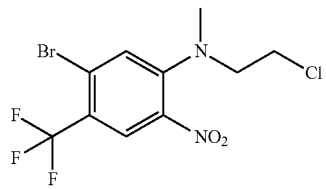 [SMILES: CN(CCCl)c1cc(Br)c(C(F)(F)F)cc1[N+](=O)[O-]]

To a solution of 2-((5-bromo-2-nitro-4-(trifluoromethyl)phenyl)(methyl)amino)ethanol (4 g, 11.7 mmol) and pyridine (0.94 mL, 11.7 mmol) in DCM (40 mL) at 0° C. was added thionylchloride (1.7 mL, 23.3 mmol) dropwise. The mixture was stirred at room temperature for 16 h. DCM (50 mL) was added and the mixture was washed with sat. aq. NaHCO$_3$ (50 mL×3) and brine (50 mL×2). The organic layer was dried over anhydrous Na$_2$SO$_4$, filtered and concentrated in vacuo. The crude residue was purified by silica gel chromatography (petroleum ether/EtOAc=3:1) to give the title compound (2.7 g, 64%) as a yellow oil.

Step 3

5-bromo-N$^1$-(2-chloroethyl)-N$^1$-methyl-4-(trifluoromethyl)benzene-1,2-diamine

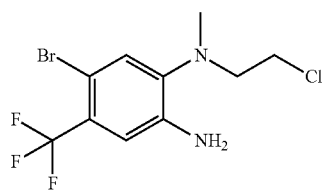 [SMILES: CN(CCCl)c1cc(Br)c(C(F)(F)F)cc1N]

To a solution of 5-bromo-N-(2-chloroethyl)-N-methyl-2-nitro-4-(trifluoromethyl)aniline (2.7 g, 7.5 mmol) in AcOH (20 mL) was added Fe powder (2.1 g, 37.3 mmol). The mixture was stirred at room temperature for 1 h. Insoluble solid was filtered off, the filtrate was adjusted to pH 8 by addition of sat. aq. NaHCO$_3$ and the mixture was extracted with EtOAc (50 mL×3). The combined organic layers were washed with brine (50 mL×3), dried over anhydrous Na$_2$SO$_4$, filtered and concentrated in vacuo to give the title compound (2.2 g, crude) as a brown solid that required no further purification. LCMS M/Z (M+H) 333.

Step 4

7-bromo-1-methyl-6-(trifluoromethyl)-1,2,3,4-tetrahydroquinoxaline

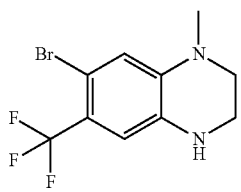 [SMILES: CN1CCNc2cc(C(F)(F)F)c(Br)cc21]

To a solution of 5-bromo-N¹-(2-chloroethyl)-N¹-methyl-4-(trifluoromethyl)benzene-1,2-diamine (2.0 g, 6.0 mmol) in DMF (20 mL) was added potassium iodide (2.0 g, 12.1 mmol) and potassium carbonate (2.5 g, 18.1 mmol). The mixture was heated to 80° C. for 3 h. After cooling the reaction to room temperature, water (50 mL) was added and the mixture was extracted with EtOAc (50 mL×3). The combined organic layers were washed with brine (100 mL×2), dried over anhydrous Na$_2$SO$_4$, filtered and concentrated in vacuo. The crude residue was purified by silica gel chromatography (petroleum ether/EtOAc=3:1) to give the title compound (830 mg, 47%) as a light yellow solid. $^1$H NMR (400 MHz, DMSO-d$_6$) δ 6.72 (s, 1H), 6.63 (s 1H), 6.07 (s, 1H), 3.29-3.26 (m, 2H), 3.24-3.21 (m, 2H), 2.83 (s, 3H).

Step 5

1-methyl-7-(1-methyl-1H-pyrazol-4-yl)-6-(trifluoromethyl)-1,2,3,4-tetrahydroquinoxaline

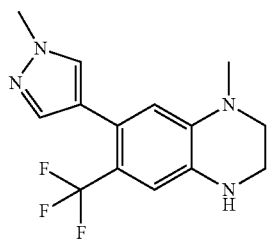 [SMILES: CN1CCNc2cc(C(F)(F)F)c(-c3cnn(C)c3)cc21]

To a solution of 7-bromo-1-methyl-6-(trifluoromethyl)-1,2,3,4-tetrahydroquinoxaline (830 mg, 2.8 mmol), 1-methyl-4-(4,4,5,5-tetramethyl-1,3,2-dioxaborolan-2-yl)-1H-pyrazole (702 mg, 3.4 mmol) and sodium carbonate (894 mg, 8.4 mmol) in THF (10 mL) and water (2 mL) was added chloro(2-dicyclohexylphosphino-2',4',6'-tri-i-propyl-1,1'-biphenyl)(2'-amino-1,1'-biphenyl-2-yl) palladium(II) (221 mg, 0.28 mmol) and 2-(dicyclohexylphosphino)-2',4',6'-tri-isopropylbiphenyl (134 mg, 0.28 mmol). The mixture was heated to 60° C. for 16 h under a nitrogen atmosphere. After cooling the reaction to room temperature, the mixture was filtered and concentrated in vacuo. The crude residue was purified by silica gel chromatography (petroleum ether/EtOAc=1:1) to give the title compound (383 mg, 46%) as a brown solid. LCMS M/Z (M+H) 297.

Step 6 tert-butyl 3-(4-methyl-6-(1-methyl-1H-pyrazol-4-yl)-7-(trifluoromethyl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate

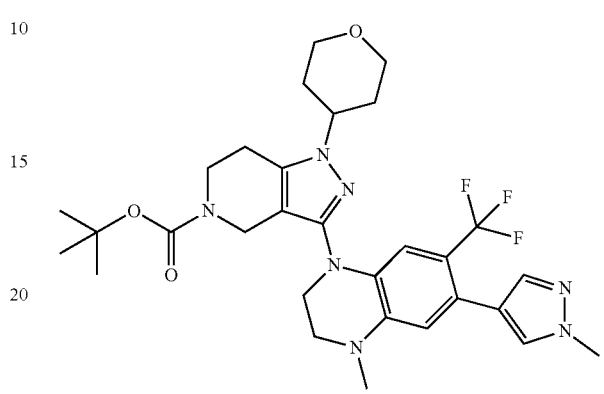

To a solution of 1-methyl-7-(1-methyl-1H-pyrazol-4-yl)-6-(trifluoromethyl)-1,2,3,4-tetrahydroquinoxaline (384 mg, 1.3 mmol), tert-butyl 3-bromo-1-(tetrahydro-2H-pyran-4-yl)-6,7-dihydro-1H-pyrazolo[4,3-c]pyridine-5(4H)-carboxylate (Intermediate H, 0.5 g, 1.3 mmol) and t-BuONa (373 mg, 3.9 mmol) in 1,4-dioxane (5 mL) was added chloro(2-dicyclohexylphosphino-2',6'-di-i-propoxy-1,1'-biphenyl)(2'-amino-1,1'-biphenyl-2-yl)palladium(II) (101 mg, 0.13 mmol) and 2-dicyclohexylphosphino-2',6'-di-i-propoxy-1,1'-biphenyl (373 mg, 3.9 mmol). The mixture was heated to 120° C. for 16 h under a nitrogen atmosphere. After cooling the reaction to room temperature, the mixture was filtered and concentrated in vacuo. The crude residue was purified by silica gel chromatography (DCM/MeOH=20/1) to give the title compound (0.66 g, 85%) as a yellow solid. LCMS M/Z (M+H) 601.

Step 7

1-methyl-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-6-(trifluoromethyl)-1,2,3,4-tetrahydroquinoxaline

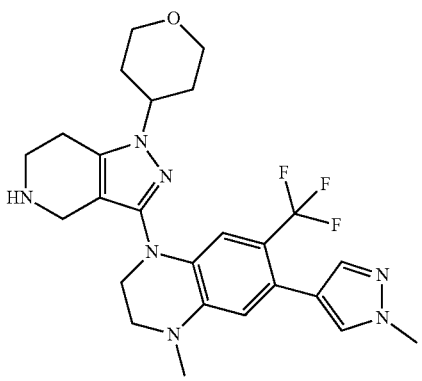

To a solution of tert-butyl 3-(4-methyl-6-(1-methyl-1H-pyrazol-4-yl)-7-(trifluoromethyl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate (240 mg, 0.4 mmol) in DCM (4 mL) at 0° C. was added trifluoroacetic acid (1 mL, 13.3 mmol). The mixture was stirred at room temperature for 1 h and concentrated in vacuo to give the title compound (320 mg, crude) as a brown oil that required no further purification. LCMS M/Z (M+H) 502.

Step 8

N-methyl-3-[4-methyl-6-(1-methylpyrazol-4-yl)-7-(trifluoromethyl)-2,3-dihydroquinoxalin-1-yl]-1-tetrahydropyran-4-yl-6,7-dihydro-4H-pyrazolo[4,3-c]pyridine-5-carboxamide

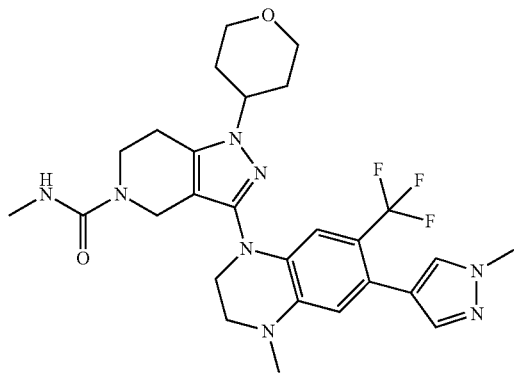

To a solution of 1-methyl-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-6-(trifluoromethyl)-1,2,3,4-tetrahydroquinoxaline (270 mg, 0.54 mmol) in DCM (2 mL) was added triethylamine (0.37 mL, 2.7 mmol) and N-methyl-1H-imidazole-1-carboxamide (135 mg, 1.1 mmol). The mixture was stirred at room temperature for 16 h and concentrated in vacuo. DCM (10 mL) was added, washed with water (10 mL×3) and brine (10 mL). The organic layer was dried over anhydrous Na$_2$SO$_4$, filtered and concentrated in vacuo. The crude residue was purified by reverse phase chromatography (acetonitrile 30-60%/0.225% formic acid in water) to give the title compound (40 mg, 13%) as a white solid. $^1$H NMR (400 MHz, DMSO-d$_6$) δ 7.75 (s, 1H), 7.46 (s, 1H), 6.79 (s, 1H), 6.55-6.51 (m, 2H), 4.28-4.25 (m, 1H), 4.01 (s, 2H), 3.96-3.93 (m, 2H), 3.86 (s, 3H), 3.71-3.67 (m, 2H), 3.60-3.56 (m, 2H), 3.48-3.42 (m, 4H), 2.96 (s, 3H), 2.74-2.71 (m, 2H), 2.54-2.52 (m, 3H), 2.01-1.95 (m, 2H), 1.81-1.76 (m, 2H). LCMS M/Z (M+H) 559.

Example 269

1-[3-[4-methyl-6-(1-methylpyrazol-4-yl)-7-(trifluoromethyl)-2,3-dihydroquinoxalin-1-yl]-1-tetrahydropyran-4-yl-6,7-dihydro-4H-pyrazolo[4,3-c]pyridin-5-yl]ethanone

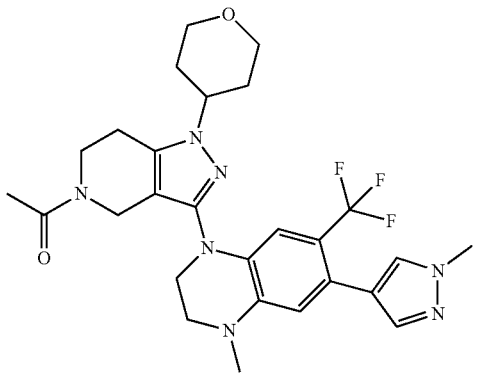 [SMILES: CC(=O)N1CCc2c(c(N3CCN(C)c4cc(-c5cnn(C)c5)c(C(F)(F)F)cc43)nn2C2CCOCC2)C1]

To a solution of 1-methyl-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-6-(trifluoromethyl)-1,2,3,4-tetrahydroquinoxaline (Step 7 of Example 268, 270 mg, 0.54 mmol) in DCM (2 mL) was added triethylamine (0.37 mL, 2.7 mmol) and acetic anhydride (0.05 mL, 0.54 mmol). The mixture was stirred at room temperature for 0.5 h and concentrated in vacuo. The crude residue was purified by reverse phase chromatography (acetonitrile 30-60%/0.05% NH$_4$HCO$_3$ in water) to give the title compound (77 mg, 26%) as a white solid. $^1$H NMR (400 MHz, DMSO-d$_6$) δ 7.77 (s, 1H), 7.47 (s, 1H), 6.82-6.78 (m, 1H), 6.52 (s, 1H), 4.29-4.24 (m, 1H), 4.17-4.10 (m, 2H), 3.96-3.92 (m, 2H), 3.86 (s, 3H), 3.70-3.62 (m, 4H), 3.48-3.42 (m, 4H), 2.96 (s, 3H), 2.88-2.74 (m, 2H), 2.07-1.95 (m, 5H), 1.83-1.78 (m, 2H). LCMS M/Z (M+H) 544.

Example 270

5-[1-(5-acetyl-1-tetrahydropyran-4-yl-6,7-dihydro-4H-pyrazolo[4,3-c]pyridin-3-yl)-4-methyl-7-(trifluoromethyl)-2,3-dihydroquinoxalin-6-yl]-N-methyl-pyridine-2-carboxamide

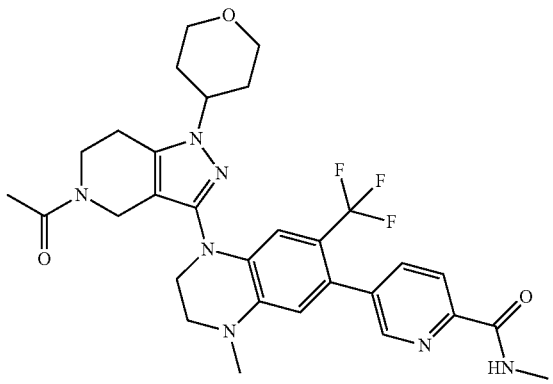 [SMILES: CNC(=O)c1ccc(-c2cc3c(cc2C(F)(F)F)N(c2nn(C4CCOCC4)c4c2CN(C(C)=O)CC4)CCN3C)cn1]

Step 1 tert-butyl 5-(4-methyl-7-(trifluoromethyl)-1,2,3,4-tetrahydroquinoxalin-6-yl)picolinate

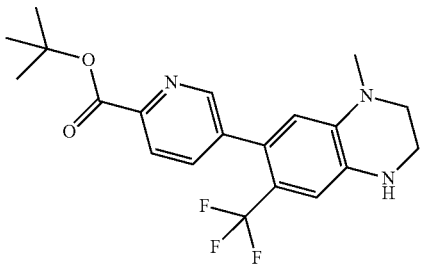 [SMILES: CN1CCNc2cc(C(F)(F)F)c(-c3ccc(C(=O)OC(C)(C)C)nc3)cc21]

To a solution of 7-bromo-1-methyl-6-(trifluoromethyl)-1,2,3,4-tetrahydroquinoxaline (1.0 g, 3.4 mmol), tert-butyl 5-(4,4,5,5-tetramethyl-1,3,2-dioxaborolan-2-yl)picolinate (1.2 g, 4.1 mmol) and $K_3PO_4$ (1.8 g, 8.5 mmol) in dioxane (20 mL) and water (4 mL) was added [1,1'-bis(diphenylphosphino)ferrocene]dichloropalladium(II) (248 mg, 0.34 mmol). The mixture was heated to 90° C. for 2 h under a nitrogen atmosphere. After cooling the reaction to room temperature, the mixture was filtered and concentrated in vacuo. The crude residue was purified by silica gel chromatography (petroleum ether/EtOAc=2:1) to give the title compound (1.27 g, 95%) as a yellow solid. LCMS M/Z (M+H) 394.

Step 2

5-(1-(5-acetyl-1-(tetrahydro-2H-pyran-4-yl)-4,5,6,7-tetrahydro-1H-pyrazolo[4,3-c]pyridin-3-yl)-4-methyl-7-(trifluoromethyl)-1,2,3,4-tetrahydroquinoxalin-6-yl)picolinic acid

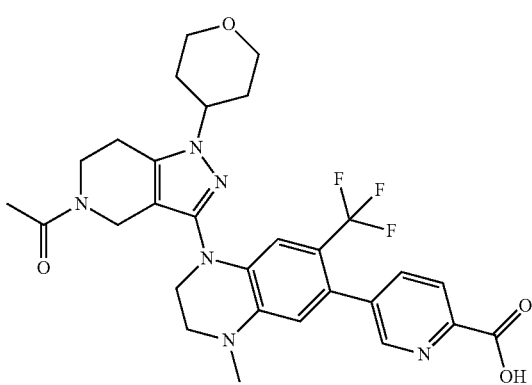 [SMILES: CC(=O)N1CCc2c(c(N3CCN(C)c4cc(-c5ccc(C(=O)O)nc5)c(C(F)(F)F)cc43)nn2C2CCOCC2)C1]

To a solution of tert-butyl 5-(4-methyl-7-(trifluoromethyl)-1,2,3,4-tetrahydroquinoxalin-6-yl)picolinate (599 mg, 1.5 mmol), 1-(3-bromo-1-tetrahydropyran-4-yl-6,7-dihydro-4H-pyrazolo[4,3-c]pyridin-5-yl)ethanone (Intermediate I, 0.5 g, 1.5 mmol) and $K_3PO_4$ (970 mg, 4.6 mmol) in t-AmOH (10 mL) was added methanesulfonato(2-dicyclohexylphosphino-2',4',6'-tri-i-propyl-1,1'-biphenyl)(2'-amino-1,1'-biphenyl-2-yl)palladium(II) (129 mg, 0.15 mmol). The mixture was heated to 105° C. for 16 h under an argon atmosphere. After cooling the reaction to room temperature, the mixture was filtered and concentrated in vacuo. The crude residue was purified by reverse phase chromatography (acetonitrile 14-44%/0.225% formic acid in water) to give the title compound (63 mg, 7%) as a yellow oil. LCMS M/Z (M+H) 585.

Step 3

5-[1-(5-acetyl-1-tetrahydropyran-4-yl-6,7-dihydro-4H-pyrazolo[4,3-c]pyridin-3-yl)-4-methyl-7-(trifluoromethyl)-2,3-dihydroquinoxalin-6-yl]-N-methyl-pyridine-2-carboxamide To a solution of 5-(1-(5-acetyl-1-(tetrahydro-2H-pyran-4-yl)-4,5,6,7-tetrahydro-1H-pyrazolo[4,3-c]pyridin-3-yl)-4-methyl-7-(trifluoromethyl)-1,2,3,4-tetrahydroquinoxalin-6-yl)picolinic acid (63 mg, 0.11 mmol), methanamine hydrochloride (9 mg, 0.13 mmol) and N,N-diisopropylethylamine (0.08 mL, 0.43 mmol) in DCM (2 mL) was added HATU (53 mg, 0.14 mmol). The mixture was stirred at room temperature for 2 h. Water (5 mL) was added and the mixture was extracted with DCM (5 mL×3). The combined organic layers were dried over anhydrous $Na_2SO_4$, filtered and concentrated in vacuo. The crude residue was purified by reverse phase chromatography (acetonitrile 35-65%/0.05% $NH_4HCO_3$ in water) to give the title compound (17 mg, 26%) as a yellow solid. $^1$H NMR (400 MHz, DMSO-$d_6$) δ 8.81-8.78 (m, 1H), 8.53-8.51 (m, 1H), 8.04-8.02 (m, 1H), 7.91-7.88 (m, 1H), 6.88-6.82 (m, 1H), 6.51 (s, 1H), 4.31-4.27 (m, 1H), 4.22-4.14 (m, 2H), 3.95-3.91 (m, 2H), 3.73-3.69 (m, 4H), 3.47-3.42 (m, 4H), 2.95 (s, 3H), 2.88-2.74 (m, 5H), 2.07-1.93 (m, 5H), 1.82-1.78 (m, 2H). LCMS M/Z (M+H) 598.

Examples 271 & 272

(S)-3-[3,4-dimethyl-6-(1-methylpyrazol-4-yl)-7-(trifluoromethyl)-2,3-dihydroquinoxalin-1-yl]-N-methyl-1-tetrahydropyran-4-yl-6,7-dihydro-4H-pyrazolo[4,3-c]pyridine-5-carboxamide and (R)-3-[3,4-dimethyl-6-(1-methylpyrazol-4-yl)-7-(trifluoromethyl)-2,3-dihydroquinoxalin-1-yl]-N-methyl-1-tetrahydropyran-4-yl-6,7-dihydro-4H-pyrazolo[4,3-c]pyridine-5-carboxamide

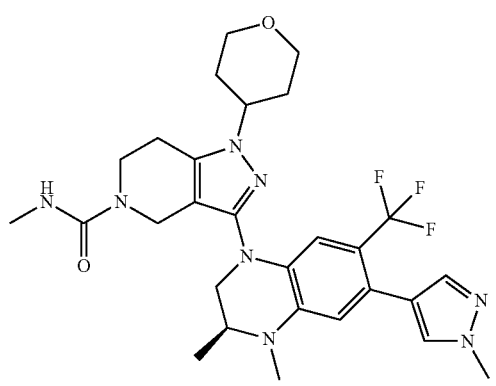

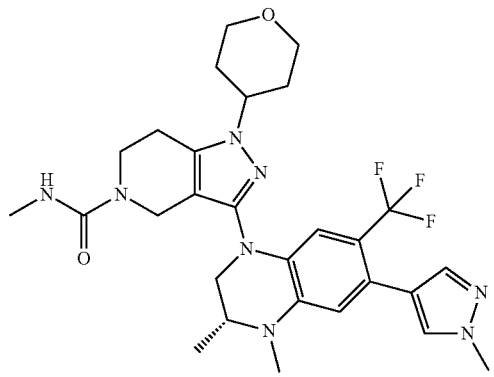

Step 1

2-((5-bromo-2-nitro-4-(trifluoromethyl)phenyl)(methyl)amino)propan-1-ol

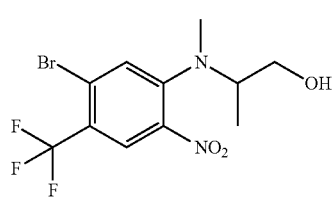 [SMILES: CC(CO)N(C)c1cc(Br)c(C(F)(F)F)cc1[N+](=O)[O-]]

To a solution of 1-bromo-5-fluoro-4-nitro-2-(trifluoromethyl)benzene (5.0 g, 17.36 mmol) in DMF (50 mL) was added N,N-diisopropylethylamine (6.2 mL, 17.36 mmol) and 2-(methylamino)propan-1-ol (3.0 g, 33.66 mmol). The mixture was heated to 80° C. for 12 h. After cooling the reaction to room temperature, water (150 mL) was added and extracted with EtOAc (100 mL×3). The combined organic layers were washed with brine (100 mL×3), dried over anhydrous $Na_2SO_4$, filtered and concentrated in vacuo. The crude residue was purified by silica gel chromatography (petroleum ether/EtOAc=1:1) to give the title compound (5 g, 80%) as a brown oil. LCMS M/Z (M+H) 357.

Step 2

5-bromo-N-(1-chloropropan-2-yl)-N-methyl-2-nitro-4-(trifluoromethyl)aniline

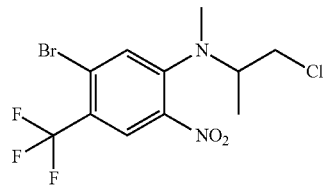 [SMILES: CC(CCl)N(C)c1cc(Br)c(C(F)(F)F)cc1[N+](=O)[O-]]

To a solution of 2-((5-bromo-2-nitro-4-(trifluoromethyl)phenyl)(methyl)amino)propan-1-ol (5.0 g, 14 mmol) and pyridine (1.1 mL, 14 mmol) in DCM (30 mL) at 0° C. was added thionylchloride (2.0 mL, 28 mmol) dropwise. The mixture was stirred at room temperature for 16 h. DCM (200 mL) was added and the mixture was washed with sat. aq. $NaHCO_3$ (150 mL×3) and brine (150 mL×2). The organic layer was dried over anhydrous $Na_2SO_4$, filtered and concentrated in vacuo to give the title compound (5 g, crude) as a brown oil that required no further purification. LCMS M/Z (M+H) 375.

Step 3

5-bromo-$N^1$-(1-chloropropan-2-yl)-$N^1$-methyl-4-(trifluoromethyl)benzene-1,2-diamine

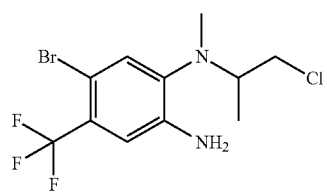 [SMILES: CC(CCl)N(C)c1cc(Br)c(C(F)(F)F)cc1N]

To a solution of 5-bromo-N-(1-chloropropan-2-yl)-N-methyl-2-nitro-4-(trifluoromethyl)aniline (5 g, 13.3 mmol) in AcOH (20 mL) was added Fe powder (3.7 g, 66.6 mmol). The mixture was stirred at room temperature for 2 h. Insoluble solid was filtered off, the filtrate was adjusted to pH 8 by the addition of sat. aq. $NaHCO_3$ and the mixture was extracted with EtOAc (100 mL×3). The combined organic layers were washed with brine (100 mL×3), dried over anhydrous $Na_2SO_4$, filtered and concentrated in vacuo to give the title compound (3.8 g, crude) as a brown oil that required no further purification. LCMS M/Z (M+H) 345.

Step 4

7-bromo-1,2-dimethyl-6-(trifluoromethyl)-1,2,3,4-tetrahydroquinoxaline

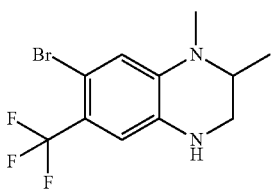 [SMILES: CC1CNc2cc(C(F)(F)F)c(Br)cc2N1C]

To a solution of 5-bromo-N$^1$-(1-chloropropan-2-yl)-N$^1$-methyl-4-(trifluoromethyl)benzene-1,2-diamine (3.8 g, 11 mmol) in DMF (50 mL) was added potassium iodide (3.7 g, 22 mmol) and potassium carbonate (4.6 g, 33 mmol). The mixture was heated to 80° C. for 5 h. After cooling the reaction to room temperature, EtOAc (200 mL) was added and washed with brine (100 mL×3). The organic layer was dried over anhydrous Na$_2$SO$_4$, filtered and concentrated in vacuo. The crude residue was purified by silica gel chromatography (petroleum ether/EtOAc=3:1) to give the title compound (1.6 g, 47%) as a brown oil. LCMS M/Z (M+H) 309.

Step 5

1,2-dimethyl-7-(1-methyl-1H-pyrazol-4-yl)-6-(trifluoromethyl)-1,2,3,4-tetrahydroquinoxaline

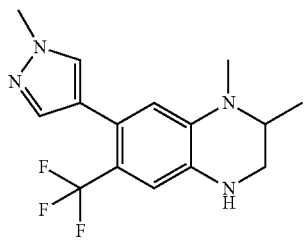 [SMILES: CC1CNc2cc(C(F)(F)F)c(-c3cnn(C)c3)cc2N1C]

To a solution of 7-bromo-1,2-dimethyl-6-(trifluoromethyl)-1,2,3,4-tetrahydroquinoxaline (800 mg, 2.59 mmol), 1-methyl-4-(4,4,5,5-tetramethyl-1,3,2-dioxaborolan-2-yl)-1H-pyrazole (646 mg, 3.11 mmol) and sodium carbonate (823 mg, 7.76 mmol) in THF (10 mL) and water (2 mL) was added chloro(2-dicyclohexylphosphino-2',4',6'-tri-i-propyl-1,1'-biphenyl)(2'-amino-1,1'-biphenyl-2-yl) palladium(II) (203 mg, 0.26 mmol) and 2-(dicyclohexylphosphino)-2',4',6'-triisopropylbiphenyl (123 mg, 0.26 mmol). The mixture was heated to 60° C. for 16 h under a nitrogen atmosphere. After cooling the reaction to room temperature, water (100 mL) was added and the mixture was extracted with EtOAc (50 mL×3). The combined organic layers were washed with brine (50 mL×2), dried over anhydrous Na$_2$SO$_4$, filtered and concentrated in vacuo. The crude residue was purified by silica gel chromatography (petroleum ether/EtOAc=1:1) to give the title compound (0.5 g, 62%) as yellow oil. LCMS M/Z (M+H) 311.

Step 6 tert-butyl 3-(3,4-dimethyl-6-(1-methyl-1H-pyrazol-4-yl)-7-(trifluoromethyl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate

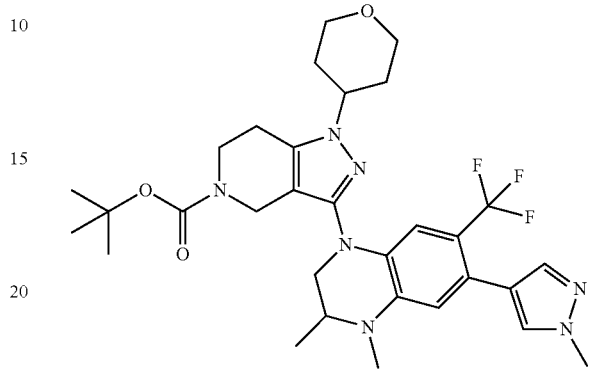

To a solution of 1,2-dimethyl-7-(1-methyl-1H-pyrazol-4-yl)-6-(trifluoromethyl)-1,2,3,4-tetrahydroquinoxaline (200 mg, 0.64 mmol), tert-butyl 3-bromo-1-(tetrahydro-2H-pyran-4-yl)-6,7-dihydro-1H-pyrazolo[4,3-c]pyridine-5(4H)-carboxylate (Intermediate H, 373 mg, 0.97 mmol) and t-BuONa (185 mg, 1.93 mmol) in 1,4-dioxane (5 mL) was added chloro(2-dicyclohexylphosphino-2',6'-di-i-propoxy-1,1'-biphenyl)(2'-amino-1,1'-biphenyl-2-yl)palladium(II) (50 mg, 0.06 mmol) and 2-dicyclohexylphosphino-2',6'-di-i-propoxy-1,1'-biphenyl (30 mg, 0.06 mmol). The mixture was heated to 120° C. for 16 h under a nitrogen atmosphere. After cooling the reaction to room temperature, water (50 mL) was added and the mixture was extracted with EtOAc (30 mL×3). The combined organic layers were washed with brine (30 mL×2), dried over anhydrous Na$_2$SO$_4$, filtered and concentrated in vacuo. The crude residue was purified by silica gel chromatography (DCM/MeOH=20/1) to give the title compound (0.2 g, 50%) as a yellow oil. LCMS M/Z (M+H) 616.

Step 7

1,2-dimethyl-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-6-(trifluoromethyl)-1,2,3,4-tetrahydroquinoxaline

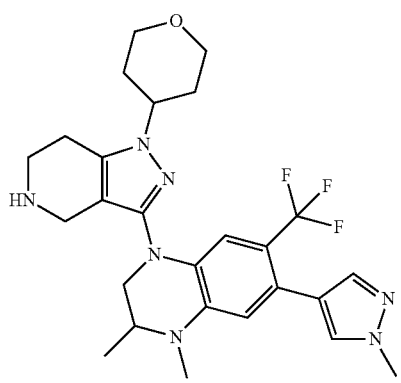 [SMILES: CC1CN(c2nn(C3CCOCC3)c3c2CNCC3)c2cc(C(F)(F)F)c(-c3cnn(C)c3)cc2N1C]

To a solution of tert-butyl 3-(3,4-dimethyl-6-(1-methyl-1H-pyrazol-4-yl)-7-(trifluoromethyl)-3,4-dihydroquinoxalin-1(2H)-yl)-1-(tetrahydro-2H-pyran-4-yl)-6,7-dihydro-1H-pyrazolo[4,3-c]pyridine-5(4H)-carboxylate (0.2 g, 0.32 mmol) in DCM (5 mL) at 0° C. was added trifluoroacetic acid (0.28 mL, 3.25 mmol). The mixture was stirred at 0° C. for 2 h and concentrated in vacuo to give the title compound (0.1 g, crude) as a brown oil that required no further purification. LCMS M/Z (M+H) 516.

Step 8

(S)-3-[3,4-dimethyl-6-(1-methylpyrazol-4-yl)-7-(trifluoromethyl)-2,3-dihydroquinoxalin-1-yl]-N-methyl-1-tetrahydropyran-4-yl-6,7-dihydro-4H-pyrazolo[4,3-c]pyridine-5-carboxamide and (R)-3-[3,4-dimethyl-6-(1-methylpyrazol-4-yl)-7-(trifluoromethyl)-2,3-dihydroquinoxalin-1-yl]-N-methyl-1-tetrahydropyran-4-yl-6,7-dihydro-4H-pyrazolo[4,3-c]pyridine-5-carboxamide

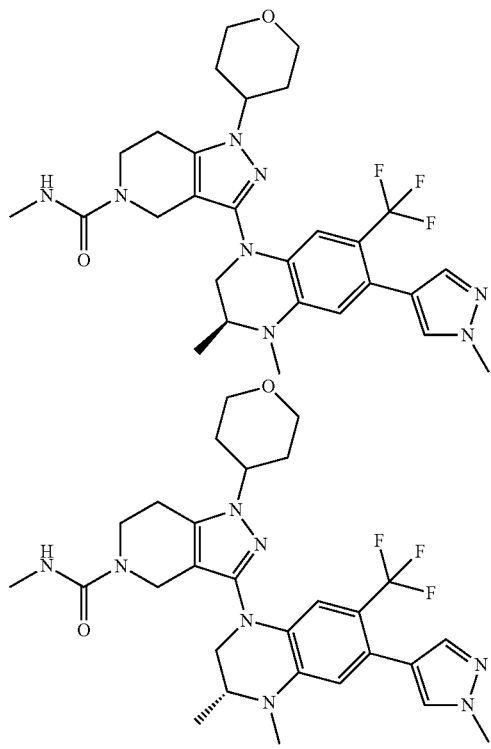

To a solution of 1,2-dimethyl-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-6-(trifluoromethyl)-1,2,3,4-tetrahydroquinoxaline (150 mg, 0.29 mmol) in DCM (5 mL) was added triethylamine (0.12 mL, 0.87 mmol) and N-methyl-1H-imidazole-1-carboxamide (73 mg, 0.58 mmol). The mixture was stirred at room temperature for 16 h and concentrated in vacuo. The crude residue was purified by reverse phase chromatography (acetonitrile 35-65%/0.225% formic acid in water) to give racemic 3-[3,4-dimethyl-6-(1-methylpyrazol-4-yl)-7-(trifluoromethyl)-2,3-dihydroquinoxalin-1-yl]-N-methyl-1-tetrahydropyran-4-yl-6,7-dihydro-4H-pyrazolo[4,3-c]pyridine-5-carboxamide (70 mg, 42%) as a white solid that was separated by chiral SFC (AD 250 mm×30 mm, 5 um, I.D., 3 um Mobile phase: ethanol (0.05% diethylamine) in $CO_2$ from 5% to 40% Flow rate: 80 mL/min) to give (S)-3-[3,4-dimethyl-6-(1-methylpyrazol-4-yl)-7-(trifluoromethyl)-2,3-dihydroquinoxalin-1-yl]-N-methyl-1-tetrahydropyran-4-yl-6,7-dihydro-4H-pyrazolo[4,3-c]pyridine-5-carboxamide (18 mg, first peak) and (R)-3-[3,4-dimethyl-6-(1-methylpyrazol-4-yl)-7-(trifluoromethyl)-2,3-dihydroquinoxalin-1-yl]-N-methyl-1-tetrahydropyran-4-yl-6,7-dihydro-4H-pyrazolo[4,3-c]pyridine-5-carboxamide (24 mg, second peak). Absolute configuration was arbitrarily assigned to each enantiomer. Example 271: $^1$H NMR (400 MHz, $CDCl_3$) δ 7.57 (s, 1H), 7.45 (s, 1H), 6.79 (s, 1H), 6.48 (s, 1H), 4.40-4.36 (m, 1H), 4.14-4.08 (m, 3H), 3.95-3.80 (m, 6H), 3.78-3.70 (m, 2H), 3.62-3.50 (m, 4H), 2.98 (s, 3H), 2.80-2.75 (m, 5H), 2.31-2.26 (m, 2H), 1.92-1.85 (m, 2H), 1.26-1.22 (m, 3H). LCMS M/Z (M+H) 573. Example 272: $^1$H NMR (400 MHz, $CDCl_3$) δ 7.57 (s, 1H), 7.45 (s, 1H), 6.79 (s, 1H), 6.48 (s, 1H), 4.40-4.36 (m, 1H), 4.14-4.08 (m, 3H), 3.96-3.80 (m, 6H), 3.78-3.70 (m, 2H), 3.62-3.50 (m, 4H), 2.98 (s, 3H), 2.80-2.75 (m, 5H), 2.31-2.26 (m, 2H), 1.92-1.85 (m, 2H), 1.26-1.22 (m, 3H). LCMS M/Z (M+H) 573.

Examples 273 & 274

(S)-1-[3-[3,4-dimethyl-6-(1-methylpyrazol-4-yl)-7-(trifluoromethyl)-2,3-dihydroquinoxalin-1-yl]-1-tetrahydropyran-4-yl-6,7-dihydro-4H-pyrazolo[4,3-c]pyridin-5-yl]ethanone and (R)-1-[3-[3,4-dimethyl-6-(1-methylpyrazol-4-yl)-7-(trifluoromethyl)-2,3-dihydroquinoxalin-1-yl]-1-tetrahydropyran-4-yl-6,7-dihydro-4H-pyrazolo[4,3-c]pyridin-5-yl]ethanone

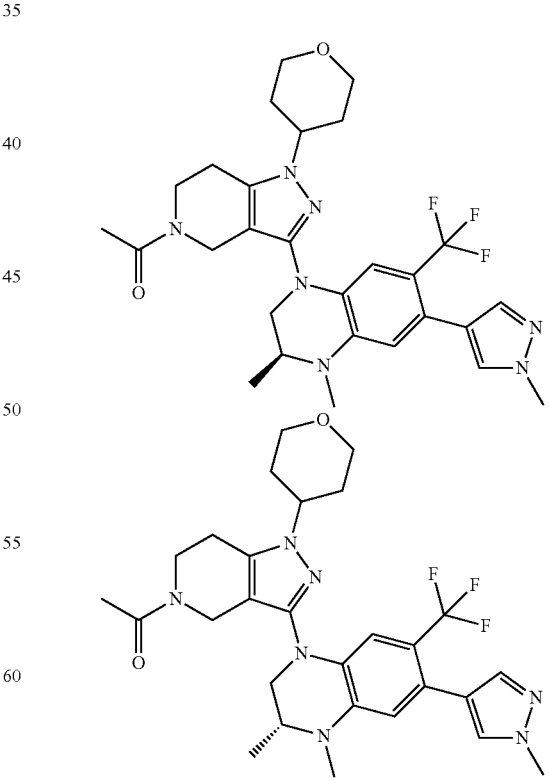

To a solution of 1,2-dimethyl-7-(1-methyl-1H-pyrazol-4-yl)-4-(1-(tetrahydro-2H-pyran-4-yl)-4,5,6,7-tetrahydro-1H- pyrazolo[4,3-c]pyridin-3-yl)-6-(trifluoromethyl)-1,2,3,4-tetrahydroquinoxaline (100 mg, 0.19 mmol) in DCM (5 mL) at 0° C. was added triethylamine (0.054 mL, 0.39 mmol) and acetic anhydride (0.037 mL, 0.39 mmol). The mixture was stirred at room temperature for 1 h and concentrated in vacuo. The crude residue was purified by reverse phase chromatography (acetonitrile 45-75%/0.225% formic acid in water) to give racemic 1-[3-[3,4-dimethyl-6-(1-methylpyrazol-4-yl)-7-(trifluoromethyl)-2,3-dihydroquinoxalin-1-yl]-1-tetrahydropyran-4-yl-6,7-dihydro-4H-pyrazolo[4,3-c]pyridin-5-yl]ethanone (60 mg, 55%) as a white solid that was separated by chiral SFC (OJ 250 mm×30 mm, 5 um, I.D, 3 um Mobile phase: ethanol (0.05% diethylamine) in $CO_2$ from 5% to 40% Flow rate: 80 mL/min) to give (S)-1-[3-[3,4-dimethyl-6-(1-methylpyrazol-4-yl)-7-(trifluoromethyl)-2,3-dihydroquinoxalin-1-yl]-1-tetrahydropyran-4-yl-6,7-dihydro-4H-pyrazolo[4,3-c]pyridin-5-yl]ethanone (23 mg, first peak) and (R)-1-[3-[3,4-dimethyl-6-(1-methylpyrazol-4-yl)-7-(trifluoromethyl)-2,3-dihydroquinoxalin-1-yl]-1-tetrahydropyran-4-yl-6,7-dihydro-4H-pyrazolo[4,3-c]pyridin-5-yl]ethanone (25 mg, second peak). Absolute configuration was arbitrarily assigned to each enantiomer. Example 273: $^1$H NMR (400 MHz, CDCl$_3$) δ 7.57-7.55 (m, 1H), 7.45-7.43 (m, 1H), 6.79 (s, 1H), 6.49-6.44 (m, 1H), 4.16-4.05 (m, 4H), 4.02-3.91 (m, 5H), 3.88-3.75 (m, 2H), 3.61-3.50 (m, 4H), 2.99-2.95 (m, 3H), 2.82-2.75 (m, 2H), 2.32-2.25 (m, 2H), 2.17-2.04 (m, 3H), 1.92-1.86 (m, 2H), 1.26-1.23 (m, 3H). Example 274: $^1$H NMR (400 MHz, CDCl$_3$) δ 7.57-7.55 (m, 1H), 7.45-7.43 (m, 1H), 6.79 (s, 1H), 6.49-6.44 (m, 1H), 4.16-4.05 (m, 4H), 4.02-3.91 (m, 5H), 3.88-3.75 (m, 2H), 3.61-3.50 (m, 4H), 2.99-2.95 (m, 3H), 2.82-2.75 (m, 2H), 2.32-2.25 (m, 2H), 2.17-2.04 (m, 3H), 1.92-1.86 (m, 2H), 1.26-1.23 (m, 3H). LCMS M/Z (M+H) 558.

Example 275

3-[6-cyano-7-(1-methylpyrazol-4-yl)-2,3-dihydro-1,4-benzoxazin-4-yl]-N-methyl-1-tetrahydropyran-4-yl-6,7-dihydro-4H-pyrazolo[4,3-c]pyridine-5-carboxamide

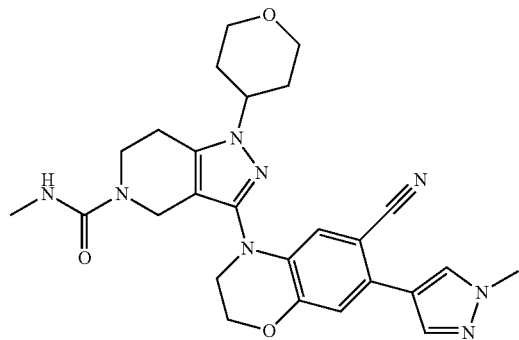

Step 1

2-bromo-4-(2-chloroethoxy)-5-nitrobenzonitrile

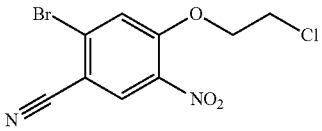

To a solution of 2-chloroethanol (1.25 mL, 18.6 mmol) in THF (18 mL) at 0° C. was added lithium diisopropylamide (2 M, 9.31 mL, 18.62 mmol) dropwise. After stirring at room temperature for 15 min, 2-bromo-4-fluoro-5-nitro-benzonitrile (3.8 g, 15.51 mmol) in THF (7 mL) was added dropwise. The mixture was stirred at room temperature for additional 16 h. Water (30 mL) was added and the mixture was extracted with EtOAc (30 mL×3). The combined organic layers were dried over anhydrous Na$_2$SO$_4$, filtered and concentrated in vacuo. The crude residue was purified by silica gel chromatography (petroleum ether/EtOAc=2:1) to give the title compound (4 g, 84%) as a yellow solid.

Step 2

5-amino-2-bromo-4-(2-chloroethoxy)benzonitrile

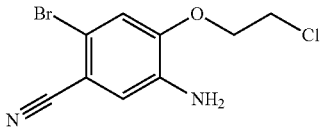 [SMILES: N#Cc1cc(N)c(OCCCl)cc1Br]

To a solution of 2-bromo-4-(2-chloroethoxy)-5-nitrobenzonitrile (4.8 g, 15.8 mmol) in AcOH (50 mL) was added Fe powder (4.4 g, 78.8 mmol). The mixture was stirred at room temperature for 1 h. Insoluble solid was filtered off, the filtrate was adjusted to pH 8 by the addition of sat. aq. NaHCO$_3$ and the mixture was extracted with EtOAc (50 mL×3). The combined organic layers were washed with brine (50 mL×3), dried over anhydrous Na$_2$SO$_4$, filtered and concentrated in vacuo. The crude residue was purified by silica gel chromatography (petroleum ether/EtOAc=2:1) to give the title compound (3.6 g, 83%) as a yellow oil. LCMS M/Z (M+H) 275.

Step 3

7-bromo-3,4-dihydro-2H-benzo[b][1,4]oxazine-6-carbonitrile

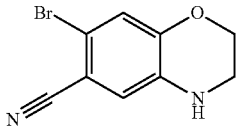 [SMILES: N#Cc1cc2c(cc1Br)OCCN2]

To a solution of 5-amino-2-bromo-4-(2-chloroethoxy)benzonitrile (3.1 g, 11.3 mmol) in DMF (20 mL) was added potassium iodide (3.7 g, 22.5 mmol) and potassium carbonate (4.7 g, 33.8 mmol). The mixture was heated to 80° C. for 7 h. After cooling the reaction to room temperature, water (50 mL) was added and extracted with EtOAc (150 mL×3). The combined organic layers were washed with brine (100 mL×2), dried over anhydrous Na₂SO₄, filtered and concentrated in vacuo to give the title compound (2.68 g, crude) as a brown solid that required no further purification. LCMS M/Z (M+H) 239.

Step 4

7-(1-methyl-1H-pyrazol-4-yl)-3,4-dihydro-2H-benzo[b][1,4]oxazine-6-carbonitrile

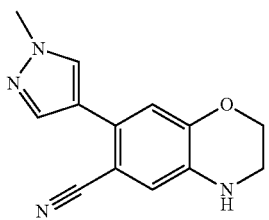 [SMILES: Cn1cc(-c2cc3c(cc2C#N)NCCO3)cn1]

To a solution of 7-bromo-3,4-dihydro-2H-benzo[b][1,4]oxazine-6-carbonitrile (0.6 g, 2.5 mmol), 1-methyl-4-(4,4,5,5-tetramethyl-1,3,2-dioxaborolan-2-yl)-1H-pyrazole (0.63 g, 3.0 mmol) and sodium carbonate (0.8 g, 7.5 mmol) in THF (10 mL) and water (2 mL) was added chloro(2-dicyclohexylphosphino-2',4',6'-tri-i-propyl-1,1'-biphenyl)(2'-amino-1,1'-biphenyl-2-yl) palladium(II) (0.2 g, 0.25 mmol) and 2-(dicyclohexylphosphino)-2',4',6'-triisopropyl-biphenyl (120 mg, 0.25 mmol). The mixture was heated to 60° C. for 16 h under a nitrogen atmosphere. After cooling the reaction to room temperature, the mixture was filtered and concentrated in vacuo. The crude residue was purified by silica gel chromatography (petroleum ether/EtOAc=1:2) to give the title compound (0.47 g, 78%) as a brown solid. LCMS M/Z (M+H) 241.

Step 5 tert-butyl 3-(6-cyano-7-(1-methyl-1H-pyrazol-4-yl)-2H-benzo[b][1,4]oxazin-4(3H)-yl)-1-(tetrahydro-2H-pyran-4-yl)-6,7-dihydro-1H-pyrazolo[4,3-c]pyridine-5(4H)-carboxylate

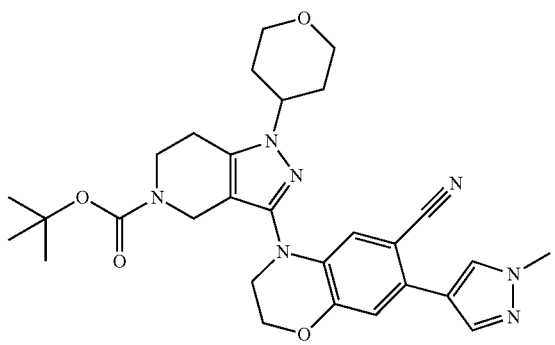 [SMILES: Cn1cc(-c2cc3c(cc2C#N)N(c2nn(C4CCOCC4)c4c2CN(C(=O)OC(C)(C)C)CC4)CCO3)cn1]

To a solution of 7-(1-methyl-1H-pyrazol-4-yl)-3,4-dihydro-2H-benzo[b][1,4]oxazine-6-carbonitrile (230 mg, 0.96 mmol), tert-butyl 3-bromo-1-(tetrahydro-2H-pyran-4-yl)-6,7-dihydro-1H-pyrazolo[4,3-c]pyridine-5(4H)-carboxylate (Intermediate H, 0.37 g, 0.96 mmol) and t-BuONa (276 mg, 2.87 mmol) in 1,4-dioxane (5 mL) was added chloro(2-dicyclohexylphosphino-2',6'-di-i-propoxy-1,1'-biphenyl)(2'-amino-1,1'-biphenyl-2-yl)palladium(II) (74 mg, 0.1 mmol), 2-dicyclohexylphosphino-2',6'-di-i-propoxy-1,1'-biphenyl (45 mg, 0.1 mmol). The mixture was heated to 120° C. for 16 h under an argon atmosphere. After cooling the reaction to room temperature, the mixture was filtered and concentrated in vacuo. The crude residue was purified by silica gel chromatography (petroleum ether/EtOAc=1:2) to give the title compound (0.44 g, 84%) as a yellow solid. LCMS M/Z (M+H) 546.

Step 6

7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-3,4-dihydro-2H-benzo[b][1,4]oxazine-6-carbonitrile

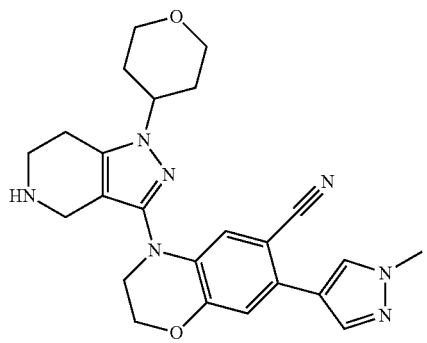 [SMILES: Cn1cc(-c2cc3c(cc2C#N)N(c2nn(C4CCOCC4)c4c2CNCC4)CCO3)cn1]

To a solution of tert-butyl 3-(6-cyano-7-(1-methyl-1H-pyrazol-4-yl)-2H-benzo[b][1,4]oxazin-4(3H)-yl)-1-(tetrahydro-2H-pyran-4-yl)-6,7-dihydro-1H-pyrazolo[4,3-c]pyridine-5(4H)-carboxylate (200 mg, 0.37 mmol) in DCM (2 mL) at 0° C. was added trifluoroacetic acid (0.27 mL, 3.7 mmol). The mixture was stirred at room temperature for 1 h and concentrated in vacuo to give the title compound (163 mg, crude) as a yellow oil that required no further purification. LCMS M/Z (M+H) 446.

Step 7

3-[6-cyano-7-(1-methylpyrazol-4-yl)-2,3-dihydro-1,4-benzoxazin-4-yl]-N-methyl-1-tetrahydropyran-4-yl-6,7-dihydro-4H-pyrazolo[4,3-c]pyridine-5-carboxamide

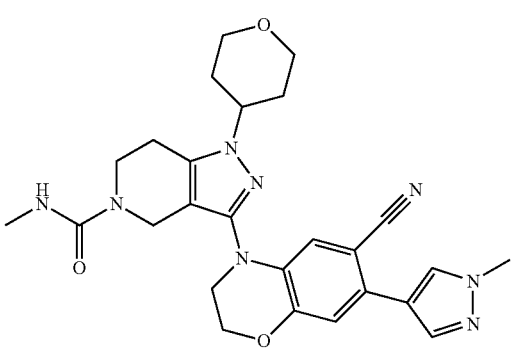

To a solution of 7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-3,4-dihydro-2H-benzo[b][1,4]oxazine-6-carbonitrile (163 mg, 0.37 mmol) in DCM (4 mL) was added triethylamine (0.15 mL, 1.1 mmol) and N-methyl-1H-imidazole-1-carboxamide (92 mg, 0.73 mmol). The mixture was stirred at room temperature for 16 h and concentrated in vacuo. The crude residue was purified by reverse phase chromatography (acetonitrile 20-50%/0.225% formic acid in water) to give the title compound (62 mg, 33%) as a white solid. $^1$H NMR (400 MHz, DMSO) δ 8.11 (s, 1H), 7.83 (s, 1H), 7.11 (s, 1H), 6.98 (s, 1H), 6.56-6.52 (m, 1H), 4.42-4.30 (m, 3H), 4.12 (s, 2H), 3.95-3.90 (m, 2H), 3.88 (s, 3H), 3.70-3.65 (m, 2H), 3.64-3.60 (m, 2H), 3.48-3.44 (m, 2H), 2.74-2.62 (m, 2H), 2.56 (d, J=4.0 Hz, 3H), 1.99-1.90 (m, 2H), 1.85-1.80 (m, 2H). LCMS M/Z (M+H) 503.

Example 276

N-methyl-3-[7-(1-methylpyrazol-4-yl)-6-(trifluoromethyl)-2,3-dihydro-1,4-benzoxazin-4-yl]-1-tetrahydropyran-4-yl-6,7-dihydro-4H-pyrazolo[4,3-c]pyridine-5-carboxamide

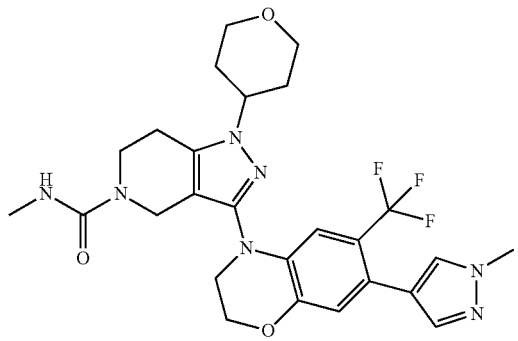

Step 1

1-bromo-5-(2-chloroethoxy)-4-nitro-2-(trifluoromethyl)benzene

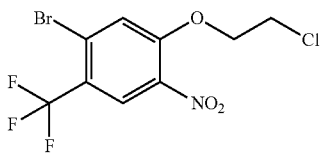

To a solution of 2-chloroethanol (1.7 mL, 25 mmol) in THF (25 mL) at 0° C. was added lithium diisopropylamide (2 M, 12.5 mL, 25 mmol) dropwise. After stirring at room temperature for 15 min, 1-bromo-5-fluoro-4-nitro-2-(trifluoromethyl)benzene (6.0 g, 20.8 mmol) in THF (10 mL) was added dropwise. The mixture was stirred at room temperature for additional 16 h. Water (30 mL) was added and extracted with EtOAc (30 mL×3). The combined organic layers were dried over anhydrous Na$_2$SO$_4$, filtered and concentrated in vacuo. The crude residue was purified by silica gel chromatography (petroleum ether/EtOAc=4:1) to give the title compound (6.8 g, 94%) as a yellow oil.

Step 2

4-bromo-2-(2-chloroethoxy)-5-(trifluoromethyl)aniline

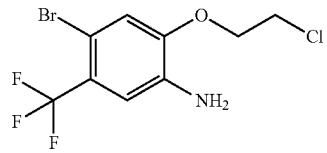 [SMILES: Nc1cc(C(F)(F)F)c(Br)cc1OCCCl]

To a solution of 1-bromo-5-(2-chloroethoxy)-4-nitro-2-(trifluoromethyl)benzene (6.8 g, 19.5 mmol) in AcOH (20 mL) was added Fe powder (5.45 g, 97.6 mmol). The mixture was stirred at room temperature for 1 h. Insoluble solid was filtered off, the filtrate was adjusted to pH 8 by the addition of sat. aq. NaHCO$_3$ and extracted with EtOAc (50 mL×3). The combined organic layers were washed with brine (50 mL×3), dried over anhydrous Na$_2$SO$_4$, filtered and concentrated in vacuo. The crude residue was purified by silica gel chromatography (petroleum ether/EtOAc=3:1) to give the title compound (6 g, 97%) as a brown oil. LCMS M/Z (M+H) 318.

Step 3

7-bromo-6-(trifluoromethyl)-3,4-dihydro-2H-benzo[b][1,4]oxazine

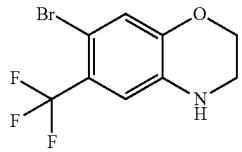 [SMILES: FC(F)(F)c1cc2c(cc1Br)OCCN2]

To a solution of 4-bromo-2-(2-chloroethoxy)-5-(trifluoromethyl)aniline (6.0 g, 18.8 mmol) in DMF (20 mL) was added potassium iodide (6.25 g, 37.7 mmol) and potassium carbonate (7.8 g, 56.5 mmol). The mixture was heated to 80° C. for 7 h. After cooling the reaction to room temperature, water (50 mL) was added and the mixture was extracted with EtOAc (150 mL×3). The combined organic layers were washed with brine (100 mL×2), dried over anhydrous Na$_2$SO$_4$, filtered and concentrated in vacuo. The crude residue was purified by silica gel chromatography (petroleum ether/EtOAc=3:1) to give the title compound (5.3 g, 99%) as a brown oil. LCMS M/Z (M+H) 282.

Step 4

7-(1-methyl-1H-pyrazol-4-yl)-6-(trifluoromethyl)-3,4-dihydro-2H-benzo[b][1,4]oxazine

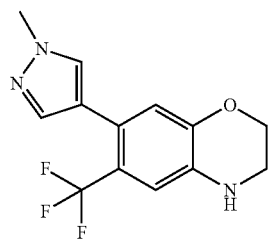 [SMILES: Cn1cc(-c2cc3c(cc2C(F)(F)F)NCCO3)cn1]

To a solution of 7-bromo-6-(trifluoromethyl)-3,4-dihydro-2H-benzo[b][1,4]oxazine (1.0 g, 3.55 mmol), 1-methyl-4-(4,4,5,5-tetramethyl-1,3,2-dioxaborolan-2-yl)-1H-pyrazole (0.89 g, 4.25 mmol) and sodium carbonate (1.13 g, 10.6 mmol) in THF (20 mL) and water (4 mL) was added chloro(2-dicyclohexylphosphino-2',4',6'-tri-i-propyl-1,1'-biphenyl)(2'-amino-1,1'-biphenyl-2-yl) palladium(II) (279 mg, 0.35 mmol) and 2-(dicyclohexylphosphino)-2',4',6'-triisopropylbiphenyl (169 mg, 0.35 mmol). The mixture was heated to 60° C. for 16 h under a nitrogen atmosphere. After cooling the reaction to room temperature, the mixture was filtered and concentrated in vacuo. The crude residue was purified by silica gel chromatography (petroleum ether/EtOAc=1:1) to give the title compound (0.95 g, 95%) as a brown oil. LCMS M/Z (M+H) 284.

Step 5 tert-butyl 3-(7-(1-methyl-1H-pyrazol-4-yl)-6-(trifluoromethyl)-2H-benzo[b][1,4]oxazin-4(3H)-yl)-1-(tetrahydro-2H-pyran-4-yl)-6, 7-dihydro-1H-pyrazolo[4,3-c]pyridine-5(4H)-carboxylate

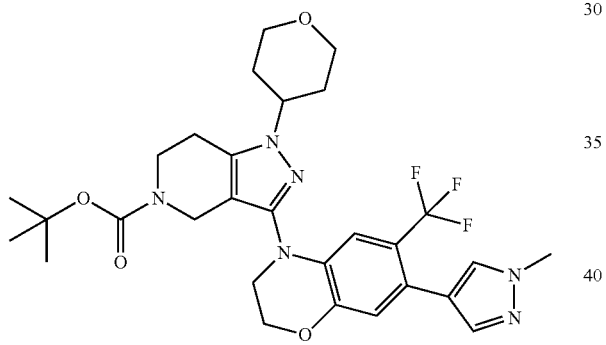

To a solution of 7-(1-methyl-1H-pyrazol-4-yl)-6-(trifluoromethyl)-3,4-dihydro-2H-benzo[b][1,4]oxazine (450 mg, 1.59 mmol), tert-butyl 3-bromo-1-(tetrahydro-2H-pyran-4-yl)-6,7-dihydro-1H-pyrazolo[4,3-c]pyridine-5(4H)-carboxylate (Intermediate H, 0.61 g, 1.59 mmol) and t-BuONa (458 mg, 4.77 mmol) in 1,4-dioxane (15 mL) was added chloro(2-dicyclohexylphosphino-2',6'-di-i-propoxy-1,1'-biphenyl)(2'-amino-1,1'-biphenyl-2-yl)palladium(II) (123 mg, 0.16 mmol) and 2-dicyclohexylphosphino-2',6'-di-i-propoxy-1,1'-biphenyl (74 mg, 0.16 mmol). The mixture was heated to 120° C. for 16 h under an argon atmosphere. After cooling the reaction to room temperature, the mixture was filtered and concentrated in vacuo. The crude residue was purified by silica gel chromatography (petroleum ether/EtOAc=1:2) to give the title compound (670 mg, 72%) as a yellow solid. LCMS M/Z (M+H) 589.

Step 6

7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-6-(trifluoromethyl)-3,4-dihydro-2H-benzo[b][1,4]oxazine

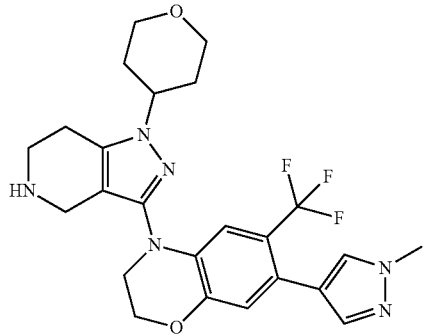 [SMILES: Cn1cc(-c2cc3c(cc2C(F)(F)F)N(c2nn(C4CCOCC4)c4c2CNCC4)CCO3)cn1]

To a solution of tert-butyl 3-(7-(1-methyl-1H-pyrazol-4-yl)-6-(trifluoromethyl)-2H-benzo[b][1,4]oxazin-4(3H)-yl)-1-(tetrahydro-2H-pyran-4-yl)-6,7-dihydro-1H-pyrazolo[4,3-c]pyridine-5(4H)-carboxylate (340 mg, 0.58 mmol) in DCM (4 mL) at 0° C. was added trifluoroacetic acid (1.72 mL, 23.1 mmol). The mixture was stirred at room temperature for 2 h and concentrated in vacuo to give the title compound (282 mg, crude) as a brown oil that required no further purification. LCMS M/Z (M+H) 489.

Step 7

N-methyl-3-[7-(1-methylpyrazol-4-yl)-6-(trifluoromethyl)-2,3-dihydro-1,4-benzoxazin-4-yl]-1-tetrahydropyran-4-yl-6,7-dihydro-4H-pyrazolo[4,3-c]pyridine-5-carboxamide

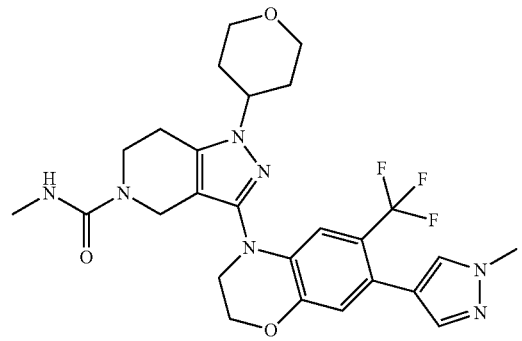

To a solution of 7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-6-(trifluoromethyl)-3,4-dihydro-2H-benzo[b][1,4]oxazine (141 mg, 0.29 mmol) in DCM (4 mL) was added triethylamine (0.12 mL, 0.87 mmol) and N-methyl-1H-imidazole-1-carboxamide (144 mg, 1.15 mmol). The mixture was stirred at room temperature for 18 h and concentrated in vacuo. The crude residue was purified by reverse phase chromatography (acetonitrile 18-48%/0.225% formic acid in water) to give the title compound (40 mg, 25%) as a white solid. $^1$H NMR (400 MHz, CDCl$_3$) δ

7.55 (s, 1H), 7.44 (s, 1H), 7.00 (s, 1H), 6.89 (s, 1H), 4.42-4.38 (m, 3H), 4.16-4.10 (m, 3H), 4.05 (s, 2H), 3.95 (s, 3H), 3.85-3.80 (m, 4H), 3.55-3.50 (m, 2H), 2.81-2.75 (m, 5H), 2.31-2.25 (m, 2H), 1.87-1.85 (m, 2H). LCMS M/Z (M+H) 546.

Example 277

1-[3-[7-(1-methylpyrazol-4-yl)-6-(trifluoromethyl)-2,3-dihydro-1,4-benzoxazin-4-yl]-1-tetrahydropyran-4-yl-6,7-dihydro-4H-pyrazolo[4,3-c]pyridin-5-yl]ethanone

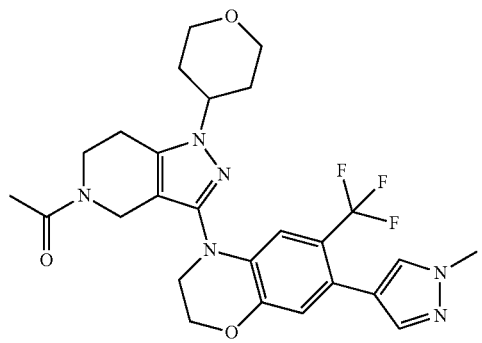 [SMILES: CC(=O)N1CCc2c(c(N3CCOc4cc(-c5cnn(C)c5)c(C(F)(F)F)cc43)nn2C2CCOCC2)C1]

To a solution of 7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)-6-(trifluoromethyl)-3,4-dihydro-2H-benzo[b][1,4]oxazine (141 mg, 0.29 mmol) in DCM (2 mL) was added triethylamine (0.12 mL, 0.87 mmol) and acetic anhydride (0.11 mL, 1.15 mmol). The mixture was stirred at room temperature for 18 h and concentrated in vacuo. The crude residue was purified by reverse phase chromatography (acetonitrile 18-48%/0.225% formic acid in water) to give the title compound (52 mg, 33%) as a white solid. $^1$H NMR (400 MHz, CDCl$_3$) δ 7.55 (s, 1H), 7.45-7.42 (m, 1H), 7.05-6.99 (m, 1H), 6.90-6.86 (m, 1H), 4.43-4.35 (m, 3H), 4.20-4.13 (m, 4H), 3.95-3.90 (m, 4H), 3.83-3.75 (m, 3H), 3.56-3.53 (m, 2H), 2.85-2.75 (m, 2H), 2.32-2.26 (m, 2H), 2.19-2.08 (m, 3H), 1.88-1.85 (m, 2H). LCMS M/Z (M+H) 531.

Example 278

1-[3-[6-(difluoromethyl)-7-(1-methylpyrazol-4-yl)-2,3-dihydro-1,4-benzoxazin-4-yl]-1-tetrahydropyran-4-yl-6,7-dihydro-4H-pyrazolo[4,3-c]pyridin-5-yl]ethanone

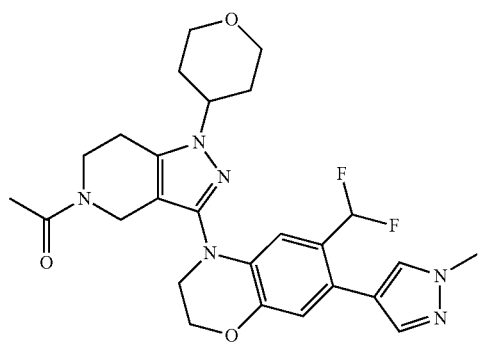 [SMILES: CC(=O)N1CCc2c(c(N3CCOc4cc(-c5cnn(C)c5)c(C(F)F)cc43)nn2C2CCOCC2)C1]

Step 1

1-bromo-5-(2-chloroethoxy)-2-(difluoromethyl)-4-nitrobenzene

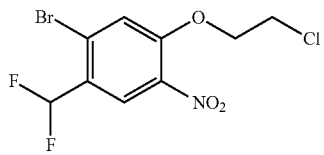 [SMILES: O=[N+]([O-])c1cc(C(F)F)c(Br)cc1OCCCl]

To a solution of 2-chloroethanol (0.3 mL, 4.44 mmol) in THF (5 mL) at 0° C. was added lithium diisopropylamide (2 M, 2.22 mL, 4.44 mmol) dropwise. After stirring at room temperature for 15 min, 1-bromo-2-(difluoromethyl)-5-fluoro-4-nitro-benzene (1.0 g, 3.7 mmol) in THF (5 mL) was added dropwise. The mixture was stirred at room temperature for an additional 16 h. Water (30 mL) was added and the mixture was extracted with EtOAc (30 mL×3). The combined organic layers were dried over anhydrous Na$_2$SO$_4$, filtered and concentrated in vacuo. The crude residue was purified by silica gel chromatography (petroleum ether/EtOAc=9:1) to give the title compound (1 g, 82%) as a yellow oil. $^1$H NMR (400 MHz, CDCl$_3$) δ 8.18 (s, 1H), 7.35 (s, 1H), 6.85 (t, J=54.8 Hz, 1H), 4.41 (t, J=6.0 Hz, 2H), 3.89 (t, J=6.0 Hz, 2H).

Step 2

4-bromo-2-(2-chloroethoxy)-5-(difluoromethyl)aniline

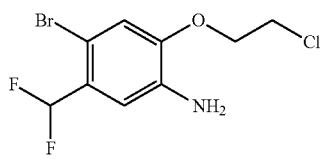 [SMILES: Nc1cc(C(F)F)c(Br)cc1OCCCl]

To a solution of 1-bromo-5-(2-chloroethoxy)-2-(difluoromethyl)-4-nitro-benzene (1.0 g, 3.03 mmol) in AcOH (10 mL) was added Fe powder (0.84 g, 15.1 mmol). The mixture was stirred at room temperature for 2 h. Insoluble solid was filtered off, the filtrate was adjusted to pH 8 by the addition of sat. aq. NaHCO$_3$ and the mixture was extracted with EtOAc (100 mL×3). The combined organic layers were washed with brine (100 mL×3), dried over anhydrous Na$_2$SO$_4$, filtered and concentrated in vacuo to give the title compound (700 mg, 77%) as a red oil that required no further purification. $^1$H NMR (400 MHz, CDCl$_3$) δ 7.00 (s, 1H), 6.93 (s, 1H), 6.81 (t, J=55.2 Hz, 1H), 4.28 (t, J=5.6 Hz, 2H), 3.86 (t, J=5.6 Hz, 2H).

Step 3

7-bromo-6-(difluoromethyl)-3,4-dihydro-2H-benzo[b][1,4]oxazine

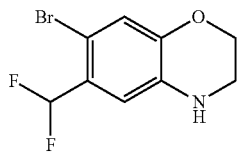 [SMILES: FC(F)c1cc2c(cc1Br)OCCN2]

To a solution of 4-bromo-2-(2-chloroethoxy)-5-(difluoromethyl)aniline (700 mg, 2.33 mmol) in DMF (14 mL) was added potassium iodide (773 mg, 4.66 mmol) and potassium carbonate (966 mg, 6.99 mmol). The mixture was heated to 80° C. for 24 h. After cooling the reaction to room temperature, water (100 mL) was added and the mixture was extracted with EtOAc (100 mL×3). The combined organic layers were washed with brine (100 mL×2), dried over anhydrous $Na_2SO_4$, filtered and concentrated in vacuo to give the title compound (700 mg, crude) as a brown oil. LCMS M/Z (M+H) 264.

Step 4

6-(difluoromethyl)-7-(1-methyl-1H-pyrazol-4-yl)-3,4-dihydro-2H-benzo[b][1,4]oxazine

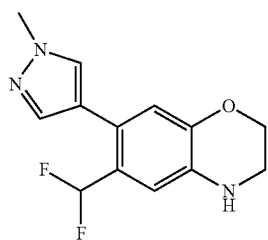 [SMILES: Cn1cc(-c2cc3c(cc2C(F)F)NCCO3)cn1]

To a solution of 7-bromo-6-(difluoromethyl)-3,4-dihydro-2H-benzo[b][1,4]oxazine (700 mg, 2.65 mmol), 1-methyl-4-(4,4,5,5-tetramethyl-1,3,2-dioxaborolan-2-yl)-1H-pyrazole (662 mg, 3.18 mmol) and sodium carbonate (843 mg, 7.95 mmol) in THF (10 mL) in water (2 mL) was added chloro(2-dicyclohexylphosphino-2',4',6'-tri-i-propyl-1,1'-biphenyl)(2'-amino-1,1'-biphenyl-2-yl) palladium(II) (209 mg, 0.27 mmol) and 2-(dicyclohexylphosphino)-2',4',6'-tri-isopropylbiphenyl (130 mg, 0.27 mmol). The mixture was heated to 60° C. for 16 h under a nitrogen atmosphere. After cooling the reaction to room temperature, the mixture was filtered and concentrated in vacuo. The crude residue was purified by silica gel chromatography (petroleum ether/EtOAc=1:1) to give the title compound (300 mg, 43%) as a brown solid. $^1$H NMR (400 MHz, CDCl$_3$) δ 7.51 (s, 1H), 7.39 (s, 1H), 6.93 (s, 1H), 6.76 (s, 1H), 6.52 (t, J=55.6 Hz, 1H), 4.28 (t, J=4.4 Hz, 2H), 3.93 (s, 3H), 3.44 (t, J=4.4 Hz, 2H).

Step 5

1-[3-[6-(difluoromethyl)-7-(1-methylpyrazol-4-yl)-2,3-dihydro-1,4-benzoxazin-4-yl]-1-tetrahydropyran-4-yl-6,7-dihydro-4H-pyrazolo[4,3-c]pyridin-5-yl]ethanone

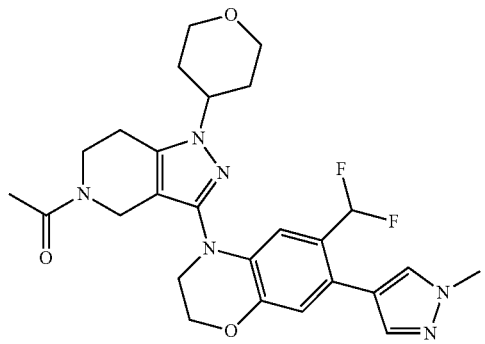 [SMILES: CC(=O)N1CCc2c(c(N3CCOc4cc(-c5cnn(C)c5)c(C(F)F)cc43)nn2C2CCOCC2)C1]

To a solution of 6-(difluoromethyl)-7-(1-methyl-1H-pyrazol-4-yl)-3,4-dihydro-2H-benzo[b][1,4]oxazine (100 mg, 0.38 mmol), 1-(3-bromo-1-(tetrahydro-2H-pyran-4-yl)-6,7-dihydro-1H-pyrazolo[4,3-c]pyridin-5(4H)-yl)ethanone (Intermediate I, 136 mg, 0.41 mmol) and t-BuONa (109 mg, 1.13 mmol) in 1,4-dioxane (3 mL) was added chloro(2-dicyclohexylphosphino-2',6'-di-i-propoxy-1,1'-biphenyl)(2'-amino-1,1'-biphenyl-2-yl)palladium(II) (29 mg, 0.04 mmol), 2-dicyclohexylphosphino-2',6'-di-i-propoxy-1,1'-biphenyl (18 mg, 0.04 mmol). The mixture was heated to 120° C. for 16 h under an argon atmosphere. After cooling the reaction to room temperature, the mixture was filtered and concentrated in vacuo. The crude residue was purified by reverse phase chromatography (acetonitrile 25-55%/0.05% NH$_4$OH in water) to give the title compound (38 mg, 20%) as a pale yellow solid. $^1$H NMR (400 MHz, DMSO-d$_6$) δ 7.79 (s, 1H), 7.53 (s, 1H), 7.08-7.04 (m, 1H), 6.97-6.64 (m, 2H), 4.38-4.18 (m, 5H), 3.97-3.93 (m, 2H), 3.87 (s, 3H), 3.79-3.63 (m, 4H), 3.46 (t, J=11.6 Hz, 2H), 2.92-2.71 (m, 2H), 2.13-1.91 (m, 5H), 1.83-1.80 (m, 2H). LCMS M/Z (M+H) 513.

Example 279

N-methyl-3-[6-(1-methylpyrazol-4-dihydro-2H-1,7-naphthyridin-1-yl]-1-tetrahydropyran-4-yl-6,7-dihydro-4H-pyrazolo[4,3-c]pyridine-5-carboxamide

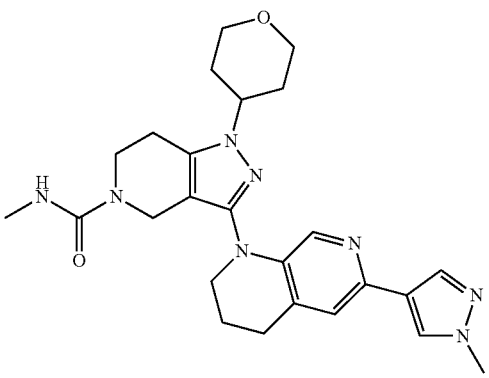

Step 1 tert-butyl 3-(6-(1-methyl-1H-pyrazol-4-yl)-3,4-dihydro-1,7-naphthyridin-1(2H)-yl)-1-(tetrahydro-2H-pyran-4-yl)-6,7-dihydro-1H-pyrazolo[4,3-c]pyridine-5(4H)-carboxylate

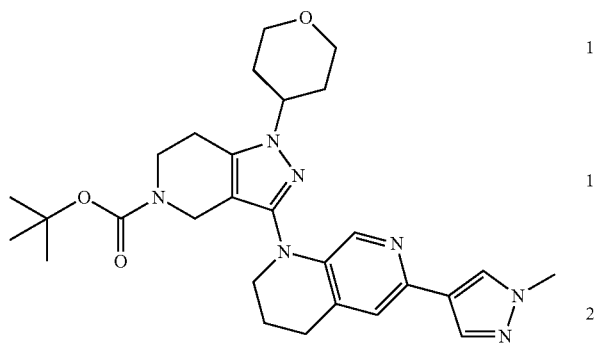

To a solution of 6-(1-methylpyrazol-4-yl)-1,2,3,4-tetrahydro-1,7-naphthyridine (180 mg, 0.84 mmol) and tert-butyl 3-bromo-1-(tetrahydro-2H-pyran-4-yl)-6,7-dihydro-1H-pyrazolo[4,3-c]pyridine-5(4H)-carboxylate (Intermediate H, 389 mg, 1.01 mmol) and t-BuONa (161 mg, 1.68 mmol) in 1,4-dioxane (2 mL) was added dichloro[1,3-bis(2,6-di-3-pentylphenyl)imidazol-2-ylidene](3-chloropyridyl)palladium(II) (100 mg, 0.13 mmol). The mixture was heated to 120° C. for 16 h under an argon atmosphere. After cooling the reaction to room temperature, the mixture was filtered and concentrated in vacuo. The crude residue was purified by Prep-TLC (DCM/MeOH=10:1) to give the title compound (80 mg, 18%) as a yellow oil. LCMS M/Z (M+H) 520.

Step 2

6-(1-methyl-1H-pyrazol-4-yl)-1-(1-(tetrahydro-2H-pyran-4-yl)-4,5,6,7-tetrahydro-1H-pyrazolo[4,3-c]pyridin-3-yl)-1,2,3,4-tetrahydro-1,7-naphthyridine

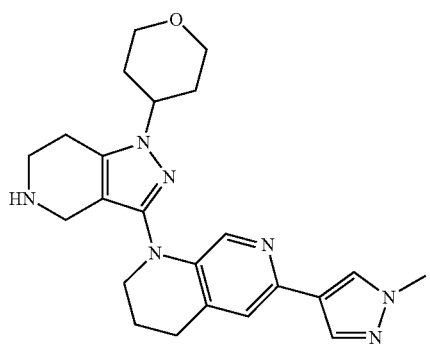 [SMILES: Cn1cc(-c2cc3c(cn2)N(c2nn(C4CCOCC4)c4c2CNCC4)CCC3)cn1]

To a solution of tert-butyl 3-(6-(1-methyl-1H-pyrazol-4-yl)-3,4-dihydro-1,7-naphthyridin-1(2H)-yl)-1-(tetrahydro-2H-pyran-4-yl)-6,7-dihydro-1H-pyrazolo[4,3-c]pyridine-5(4H)-carboxylate (80 mg, 0.15 mmol) in DCM (1.5 mL) at 0° C. was added trifluoroacetic acid (0.3 mL, 4.04 mmol). The mixture was stirred at room temperature for 1 h and concentrated in vacuo. DCM (10 mL) was added and washed with sat. aq. NaHCO$_3$ (5 mL). The organic layer was dried over anhydrous Na$_2$SO$_4$, filtered and concentrated in vacuo to give the title compound (60 mg, 93%) as a brown oil that required no further purification. LCMS M/Z (M+H) 420.

Step 3

N-methyl-3-[6-(1-methylpyrazol-4-yl)-3,4-dihydro-2H-1,7-naphthyridin-1-yl]-1-tetrahydropyran-4-yl-6,7-dihydro-4H-pyrazolo[4,3-c]pyridine-5-carboxamide

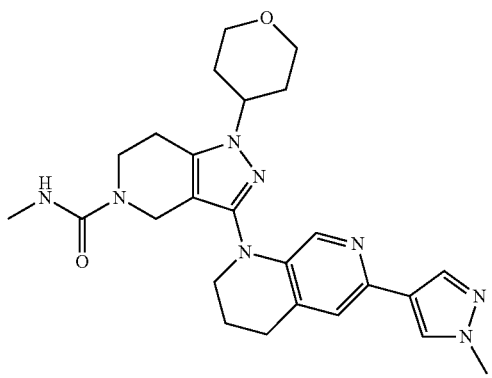

To a solution of 6-(1-methyl-1H-pyrazol-4-yl)-1-(1-(tetrahydro-2H-pyran-4-yl)-4,5,6,7-tetrahydro-1H-pyrazolo[4,3-c]pyridin-3-yl)-1,2,3,4-tetrahydro-1,7-naphthyridine (60 mg, 0.14 mmol) in DCM (2 mL) was added triethylamine (0.06 mL, 0.43 mmol) and N-methyl-1H-imidazole-1-carboxamide (27 mg, 0.21 mmol). The mixture was stirred at room temperature for 16 h and concentrated in vacuo. The crude residue was purified by reverse phase chromatography (acetonitrile 15-45%/0.05% NH$_4$OH in water) to give the title compound (24 mg, 35%) as a white solid. $^1$H NMR (400 MHz, DMSO-d$_6$) δ 8.15 (s, 1H), 7.89 (s, 1H), 7.81 (s, 1H), 7.49 (s, 1H), 6.59-6.55 (m, 1H), 4.32-4.28 (m, 1H), 4.11 (s, 2H), 3.98-3.93 (m, 2H), 3.86 (s, 3H), 3.62-3.57 (m, 4H), 3.46 (t, J=11.6 Hz, 2H), 2.89-2.70 (m, 4H), 2.55 (d, J=4.0 Hz, 3H), 1.99-1.91 (m, 4H), 1.83-1.77 (m, 2H). LCMS M/Z (M+H) 477.

Example 280

5-[1-(5-acetyl-1-tetrahydropyran-4-yl-6,7-dihydro-4H-pyrazolo[4,3-c]pyridin-3-yl)-3,4-dihydro-2H-1,7-naphthyridin-6-yl]-N-methyl-pyridine-2-carboxamide

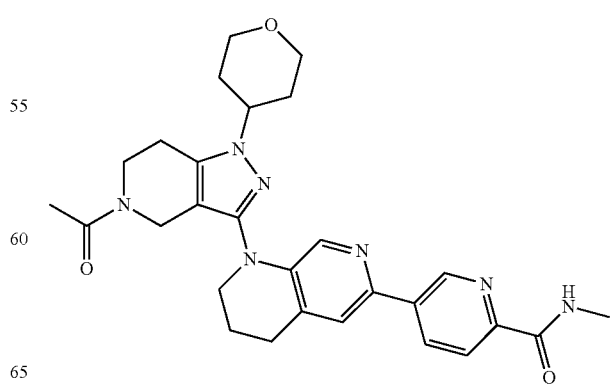

Step 1

1-(3-(6-methoxy-3,4-dihydro-1,7-naphthyridin-1 (2H)-yl)-1-(tetrahydro-2H-pyran-4-yl)-6,7-dihydro-1H-pyrazolo[4,3-c]pyridin-5(4H)-yl)ethanone

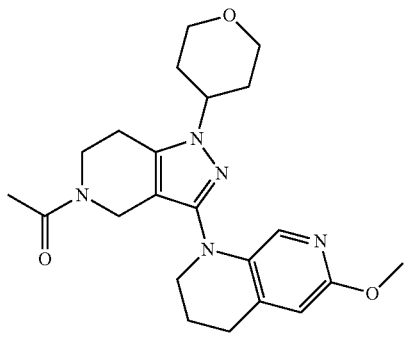 [SMILES: COc1cc2c(cn1)N(c1nn(C3CCOCC3)c3c1CN(C(C)=O)CC3)CCC2]

To a solution of 6-methoxy-1,2,3,4-tetrahydro-1,7-naphthyridine (1.2 g, 7.31 mmol), 1-(3-bromo-1-(tetrahydro-2H-pyran-4-yl)-6,7-dihydro-1H-pyrazolo[4,3-c]pyridin-5(4H)-yl)ethanone (Intermediate I, 2.0 g, 6.09 mmol) and t-BuONa (1.7 g, 18.3 mmol) in 1,4-dioxane (20 mL) was added dichloro[1,3-bis(2,6-di-3-pentylphenyl)imidazol-2-ylidene](3-chloropyridyl)palladium(II) (484 mg, 0.6 mmol). The mixture was heated to 120° C. for 16 h under an argon atmosphere. After cooling the reaction to room temperature, the mixture was filtered and concentrated in vacuo. The crude residue was purified by silica gel chromatography (DCM/MeOH=10/1) to give the title compound (1.7 g, 68%) as a brown solid. $^1$H NMR (400 MHz, DMSO-$d_6$) δ 7.39 (s, 1H), 6.50 (s, 1H), 4.46-4.13 (m, 3H), 4.01-3.92 (m, 2H), 3.77-3.72 (m, 4H), 3.57-3.41 (m, 4H), 3.08 (s, 3H), 2.81-2.78 (m, 3H), 2.09-2.00 (m, 4H), 1.98-1.90 (m, 2H), 1.87-1.75 (m, 2H). LCMS M/Z (M+H) 412.

Step 2

1-(3-(6-hydroxy-3,4-dihydro-1,7-naphthyridin-1 (2H)-yl)-1-(tetrahydro-2H-pyran-4-yl)-6,7-dihydro-1H-pyrazolo[4,3-c]pyridin-5(4H)-yl)ethanone

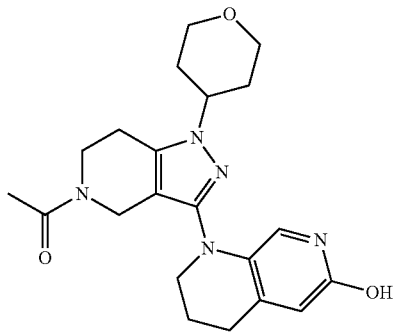 [SMILES: CC(=O)N1CCc2c(c(N3CCCc4cc(O)ncc43)nn2C2CCOCC2)C1]

A mixture of 1-(3-(6-methoxy-3,4-dihydro-1,7-naphthyridin-1 (2H)-yl)-1-(tetrahydro-2H-pyran-4-yl)-6,7-dihydro-1H-pyrazolo[4,3-c]pyridin-5(4H)-yl)ethanone (1.3 g, 3.16 mmol) and pyridine hydrochloride (3.0 g, 26.2 mmol) was heated to 150° C. for 0.5 h. After cooling the reaction to room temperature, DCM (30 mL) was added and the mixture was made basic with triethylamine to pH 8 before being concentrated in vacuo. The crude residue was purified by silica gel chromatography (DCM/MeOH=10/1) to give the title compound (400 mg, 32%) as a brown oil. $^1$H NMR (400 MHz, DMSO-$d_6$) δ 10.65 (s, 1H), 6.76-6.71 1H), 6.16 (s, 1H), 4.29-4.18 (m, 1H), 4.17-4.09 (m, 2H), 3.98-3.94 (m, 2H), 3.76-3.64 (m, 2H), 3.51-3.39 (m, 4H), 2.86-2.65 (m, 4H), 2.11-1.92 (m, 5H), 1.91-1.71 (m, 4H). LCMS M/Z (M+H) 398.

Step 3

1-(5-acetyl-1-(tetrahydro-2H-pyran-4-yl)-4,5,6,7-tetrahydro-1H-pyrazolo[4,3-c]pyridin-3-yl)-1,2,3,4-tetrahydro-1,7-naphthyridin-6-yl trifluoromethanesulfonate

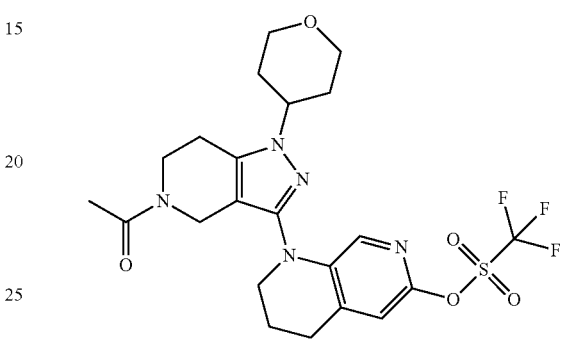

To a solution of 1-(3-(6-hydroxy-3,4-dihydro-1,7-naphthyridin-1(2H)-yl)-1-(tetrahydro-2H-pyran-4-yl)-6,7-dihydro-1H-pyrazolo[4,3-c]pyridin-5(4H)-yl)ethanone (200 mg, 0.5 mmol) in DCM (5 mL) at 0° C. was added triethylamine (0.21 mL, 1.51 mmol) and 1,1,1-trifluoro-N-phenyl-N-((trifluoromethyl)sulfonyl)methanesulfonamide (270 mg, 0.75 mmol). The mixture was stirred at room temperature for 16 h. DCM (50 mL) was added and washed with water (40 mL×2). The organic layer was dried over anhydrous $Na_2SO_4$, filtered and concentrated in vacuo to give the title compound (200 mg, crude) as a brown oil that required no further purification.

Step 4

5-[1-(5-acetyl-1-tetrahydropyran-4-yl-6,7-dihydro-4H-pyrazolo[4,3-c]pyridin-3-yl)-3,4-dihydro-2H-1,7-naphthyridin-6-yl]-N-methyl-pyridine-2-carboxamide

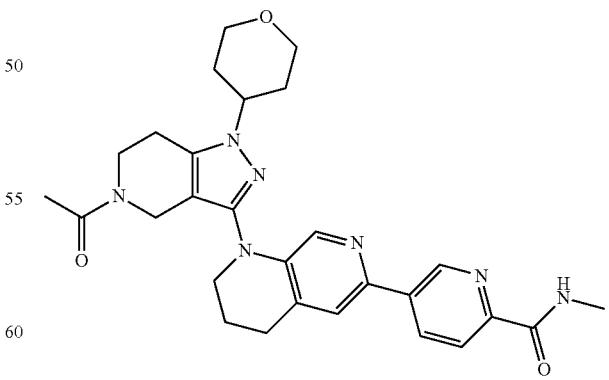

To a solution of 1-(5-acetyl-1-(tetrahydro-2H-pyran-4-yl)-4,5,6,7-tetrahydro-1H-pyrazolo[4,3-c]pyridin-3-yl)-1,2,3,4-tetrahydro-1,7-naphthyridin-6-yl trifluoromethanesulfonate (100 mg, 0.19 mmol), N-methyl-5-(4,4,5,5-tetramethyl-1,3,2-dioxaborolan-2-yl)picolinamide (59 mg, 0.23 mmol) and sodium carbonate (60 mg, 0.6 mmol) in THF (5 mL) and water (1 mL) was added chloro(2-dicyclohexylphosphino-2',4',6'-tri-i-propyl-1,1'-biphenyl)(2'-amino-1,1'-biphenyl-2-yl) palladium(II) (16 mg, 0.02 mmol) and 2-(dicyclohexylphosphino)-2',4',6'-triisopropylbiphenyl (8 mg, 0.02 mmol). The mixture was irradiated in a microwave at 60° C. for 0.5 h. After cooling the reaction to room temperature, DCM (50 mL) was added and washed with water (40 mL×2). The organic layer was dried over anhydrous $Na_2SO_4$, filtered and concentrated in vacuo. The crude residue was purified by Prep-TLC (DCM/MeOH=20/1) to give the title compound (40 mg, 38%) as a yellow solid. $^1$H NMR (400 MHz, DMSO-$d_6$) δ 9.17 (s, 1H), 8.79-8.72 (m, 1H), 8.47-8.45 (m, 1H), 8.04 (d, J=8.4 Hz, 1H), 7.96-7.87 (m, 1H), 7.83 (s, 1H), 4.35-4.29 (m, 1H), 4.26-4.18 (m, 2H), 4.00-3.92 (m, 2H), 3.81-3.71 (m, 2H), 3.66-3.58 (m, 2H), 3.50-3.44 (m, 2H), 2.93-2.86 (m, 3H), 2.83 (d, J=4.8 Hz, 3H), 2.78-2.71 (m, 1H), 2.11-1.94 (m, 7H), 1.86-1.83 (m, 2H). LCMS M/Z (M+H) 516.

Example 281

1-(5-acetyl-1-tetrahydropyran-4-yl-6,7-dihydro-4H-pyrazolo[4,3-c]pyridin-3-yl)-6-(3-pyridyl)-3,4-dihydro-2H-quinoline-7-carbonitrile

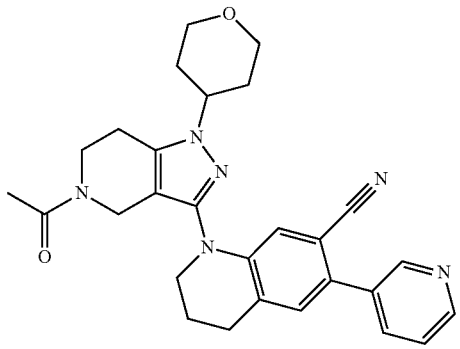 [SMILES: CC(=O)N1CCc2c(c(N3CCCc4cc(-c5cccnc5)c(C#N)cc43)nn2C2CCOCC2)C1]

To a solution of 1-(5-acetyl-1-tetrahydropyran-4-yl-6,7-dihydro-4H-pyrazolo[4,3-c]pyridin-3-yl)-6-bromo-3,4-dihydro-2H-quinoline-7-carbonitrile (Intermediate M, 150 mg, 0.3 mmol) in THF (5 mL) and water (1 mL) was added chloro(2-dicyclohexylphosphino-2',4',6'-tri-i-propyl-1,1'-biphenyl)(2'-amino-1,1'-biphenyl-2-yl) palladium(II) (24 mg, 0.03 mmol), 2-(dicyclohexylphosphino)-2',4',6'-triisopropylbiphenyl (15 mg, 0.03 mmol) and pyridin-3-ylboronic acid (46 mg, 0.37 mmol), $Na_2CO_3$ (65 mg, 0.6 mmol). The mixture was heated to 60° C. for 16 h under a nitrogen atmosphere. After cooling the reaction to room temperature, the mixture was filtered and concentrated in vacuo. DCM (50 mL) was added and the mixture was washed with water (30 mL×3) and brine (30 mL). The organic layer was dried over anhydrous $Na_2SO_4$, filtered and concentrated in vacuo. The crude residue was purified by reverse phase chromatography (acetonitrile 24-54%/0.05% $NH_4OH$ in water) to give the title compound (30 mg, 20%) as a yellow solid. $^1$H NMR (400 MHz, DMSO-$d_6$) δ 8.71 (s, 1H), 8.60-8.59 (m, 1H), 7.94 (d, J=8.0 Hz, 1H), 7.52-7.48 (m, 1H), 7.36 (s, 1H), 6.89-6.82 (m, 1H), 4.35-4.30 (m, 1H), 4.25-4.20 (m, 2H), 3.98-3.95 (m, 2H), 3.81-3.71 (m, 2H), 3.66-3.57 (m, 2H), 3.49-3.43 (m, 2H), 2.96-2.74 (m, 4H), 2.16-1.94 (m, 7H), 1.87-1.83 (m, 2H). LCMS M/Z (M+H) 483.

The Following Compounds were Prepared in a Similar Fashion to Example 281

Examples 282-287

| Example | Compound Name | NMR | m/z |
|---|---|---|---|
| Example 282 | N-[5-[1-(5-acetyl-1-tetrahydropyran-4-yl-6,7-dihydro-4H-pyrazolo[4,3-c]pyridin-3-yl)-7-cyano-3,4-dihydro-2H-quinolin-6-yl]-2-pyridyl]acetamide | $^1$H NMR (400 MHz, DMSO-$d_6$) δ 10.63 (s, 1H), 8.44-8.43 (m, 1H), 8.15-8.12 (m, 1H), 7.93-7.90 (m, 1H), 7.33 (s, 1H), 6.86-6.75 (m, 1H), 4.38-4.27 (m, 1H), 4.25-4.18 (m, 2H), 3.97-3.95 (m, 2H), 3.81-3.70 (m, 2H), 3.64-3.57 (m, 2H), 3.48-3.46 (m, 2H), 2.94-2.74 (m, 4H), 2.11 (s, 3H), 2.10-1.92 (m, 7H), 1.88-1.81 (m, 2H) | 540 |
| Example 283 | 1-(5-acetyl-1-tetrahydropyran-4-yl-6,7-dihydro-4H-pyrazolo[4,3-c]pyridin-3-yl)-6-(4-pyridyl)-3,4-dihydro-2H-quinoline-7-carbonitrile | $^1$H NMR (400 MHz, DMSO-$d_6$) δ 8.73-8.57 (m, 2H), 7.60-7.48 (m, 2H), 7.39 (s, 1H), 6.91-6.79 (m, 1H), 4.37-4.29 (m, 1H), 4.27-4.19 (m, 2H), 3.98-3.95 (m, 2H), 3.79-3.72 (m, 2H), 3.66-3.57 (m, 2H), 3.49-3.43 (m, 2H), 2.96-2.74 (m, 4H), 2.12-1.93 (m, 7H), 1.90-1.80 (m, 2H) | 483 |
| Example 284 | 1-(5-acetyl-1-tetrahydropyran-4-yl-6,7-dihydro-4H-pyrazolo[4,3-c]pyridin-3-yl)-6-(6-cyano-3-pyridyl)-3,4-dihydro-2H-quinoline-7-carbonitrile | $^1$H NMR (400 MHz, DMSO-$d_6$) δ 8.92 (s, 1H), 8.23 (d, J = 8.0 Hz, 1H), 8.16 (d, J = 8.0 Hz, 1H), 7.46 (s, 1H), 6.93-6.82 (m, 1H), 4.39-4.28 (m, 1H), 4.27-4.18 (m, 2H), 3.97-3.93 (m, 2H), 3.82-3.69 (m, 2H), 3.67-3.57 (m, 2H), 3.46 (t, J = 12.0 Hz, 2H), 2.98-2.73 (m, 4H), 2.13-1.91 (m, 7H), 1.90-1.80 (m, 2H) | 508 |
| Example 285 | 1-(5-acetyl-1-tetrahydropyran-4-yl-6,7-dihydro-4H-pyrazolo[4,3-c]pyridin-3-yl)-6-(6-cyclopropyl-3-pyridyl)-3,4-dihydro-2H-quinoline-7-carbonitrile | $^1$H NMR (400 MHz, DMSO-$d_6$) δ 8.51 (s, 1H), 7.79-7.76 (m, 1H), 7.39 (d, J = 8.0 Hz, 1H), 7.30 (s, 1H), 6.85-6.79 (m, 1H), 4.38-4.27 (m, 1H), 4.24-4.17 (m, 2H), 3.97-3.94 (m, 2H), 3.80-3.70 (m, 2H), 3.64-3.56 (m, 2H), 3.49-3.43 (m, 2H), 2.94-2.75 (m, 4H), 2.18-2.11 (m, 1H), | 523 |

| Example | Compound Name | NMR | m/z |
|---|---|---|---|
| | carbonitrile | 2.10-1.96 (m, 7H), 1.86-1.83 (m, 2H), 0.99-0.94 (m, 4H) | |
| Example 286 | 1-(5-acetyl-1-tetrahydropyran-4-yl-6,7-dihydro-4H-pyrazolo[4,3-c]pyridin-3-yl)-6-(6-methyl-3-pyridyl)-3,4-dihydro-2H-quinoline-7-carbonitrile | $^1$H NMR (400 MHz, DMSO-$d_6$) δ 8.57 (s, 1H), 7.83-7.80 (m, 1H), 7.38-7.29 (m, 2H), 6.88-6.76 (m, 1H), 4.39-4.27 (m, 1H), 4.26-4.15 (m, 2H), 3.97-3.93 (m, 2H), 3.82-3.68 (m, 2H), 3.65-3.54 (m, 2H), 3.46 (t, J = 11.6 Hz, 2H), 2.97-2.72 (m, 4H), 2.52 (s, 3H), 2.14-1.90 (m, 7H), 1.89-1.78 (m, 2H) | 497 |
| Example 287 | 1-(5-acetyl-1-tetrahydropyran-4-yl-6,7-dihydro-4H-pyrazolo[4,3-c]pyridin-3-yl)-6-pyrimidin-5-yl-3,4-dihydro-2H-quinoline-7-carbonitrile | $^1$H NMR (400 MHz, DMSO-$d_6$) δ 9.21 (s, 1H), 8.99 (s, 2H), 7.45 (s, 1H), 6.93-6.82 (m, 1H), 4.39-4.28 (m, 1H), 4.27-4.18 (m, 2H), 3.97-3.95 (m, 2H), 3.83-3.70 (m, 2H), 3.65-3.57 (m, 2H), 3.49-3.43 (m, 2H), 2.96-2.74 (m, 4H), 2.10-1.96 (m, 7H), 1.90-1.81 (m, 2H) | 484 |

Example 288

3-[7-cyano-6-(6-methyl-3-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide

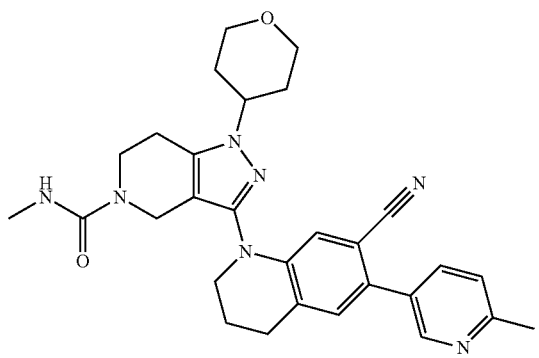

To a solution of 3-(6-bromo-7-cyano-3,4-dihydro-2H-quinolin-1-yl)-N-methyl-1-tetrahydropyran-4-yl-6,7-dihydro-4H-pyrazolo[4,3-c]pyridine-5-carboxamide (Intermediate N, 100 mg, 0.2 mmol) in THF (2.5 mL) and water (0.5 mL) was added chloro(2-dicyclohexylphosphino-2',4',6'-tri-i-propyl-1,1'-biphenyl)(2'-amino-1,1'-biphenyl-2-yl)palladium(II) (16 mg, 0.02 mmol), 2-(dicyclohexylphosphino)-2',4',6'-triisopropylbiphenyl (10 mg, 0.02 mmol), 6-methylpyridine-3-boronicacid (41 mg, 0.3 mmol) and Na$_2$CO$_3$ (42 mg, 0.4 mmol). The mixture was heated to 60° C. for 16 h under a nitrogen atmosphere. After cooling the reaction to room temperature, the mixture was filtered and concentrated in vacuo. DCM (50 mL) was added and the mixture was washed with water (30 mL×3) and brine (30 mL). The organic layer was dried over anhydrous Na$_2$SO$_4$, filtered and concentrated in vacuo. The crude residue was purified by reverse phase chromatography (acetonitrile 22-52%/0.05% NH$_4$OH in water) to give the title compound (37 mg, 36%) as a white solid. $^1$H NMR (400 MHz, DMSO-$d_6$) δ 8.55-8.54 (m, 1H), 7.81-7.79 (m, 1H), 7.35-7.33 (m, 1H), 7.30 (s, 1H), 6.78 (s, 1H), 6.56-6.55 (m, 1H), 4.38-4.25 (m, 1H), 4.06 (s, 2H), 3.97-3.94 (m, 2H), 3.64-3.58 (m, 4H), 3.49-3.43 (m, 2H), 2.93-2.90 (m, 2H), 2.78-2.72 (m, 2H), 2.55 (d, J=4.0 Hz, 3H), 2.52 (s, 3H), 2.02-1.92 (m, 4H), 1.85-1.82 (m, 2H). LCMS M/Z (M+H) 512.

The Following Compounds were Prepared in a Similar Fashion to Example 288

Examples 289-299

| Example | Compound Name | NMR | m/z |
|---|---|---|---|
| Example 289 | 3-[7-cyano-6-[6-(methylcarbamoyl)-3-pyridyl]-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, CDCl$_3$) δ 8.68 (s, 1H), 8.25 (d, J = 8.0 Hz, 1H), 8.03-7.96 (m, 2H), 7.15 (s, 1H), 6.82 (s, 1H), 4.46-4.44 (m, 1H), 4.15-4.09 (m, 5H), 3.78-3.76 (m, 2H), 3.72-3.69 (m, 2H), 3.53 (t, J = 8.0 Hz, 2H), 3.06 (d, J = 4.8 Hz, 3H), 2.97-2.91 (m, 2H), 2.83-2.80 (m, 5H), 2.30-2.26 (m, 2H), 2.13-2.10 (m, 2H), 1.90-1.88 (m, 2H). | 555 |
| Example 290 | 3-[6-(6-acetamido-3-pyridyl)-7-cyano-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, CDCl$_3$) δ 8.39 (d, J = 2.4 Hz, 1H), 8.28 (d, J = 8.4 Hz, 1H), 8.11 (s, 1H), 7.89-7.84 (m, 1H), 7.11 (s, 1H), 6.79 (s, 1H), 4.46-4.39 (m, 1H), 4.21-4.10 (m, 3H), 4.07 (s, 2H), 3.79 (t, J = 5.6 Hz, 2H), 3.70 (t, J = 5.6 Hz, 2H), 3.53 (t, J = 11.2 Hz, 2H), 2.93 (t, J = 6.0 Hz, 2H), 2.87-2.77 (m, 5H), 2.36-2.26 (m, 2H), 2.24 (s, 3H), 2.15-2.07 (m, 2H), 1.93-1.84 (m, 2H) | 555 |

| Example | Compound Name | NMR | m/z |
|---|---|---|---|
| Example 291 | 3-[7-cyano-6-(6-methoxy-3-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.30-8.29 (m, 1H), 7.87-7.84 (m, 1H), 7.29 (s, 1H), 6.93 (d, J = 9.2 Hz, 1H), 6.79 (s, 1H), 6.59-6.51 (m, 1H), 4.33-4.32 (m, 1H), 4.08 (s, 2H), 3.95-3.94 (m, 2H), 3.90 (s, 3H), 3.63-3.58 (m, 4H), 3.46-3.43 (m, 2H), 2.93-2.90 (m, 2H), 2.76-2.74 (m, 2H), 2.56 (d, J = 4.4 Hz, 3H), 2.06-1.91 (m, 4H), 1.87-1.78 (m, 2H). | 528 |
| Example 292 | 3-[7-cyano-6-(5-methyl-3-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.54-8.51 (m, 1H), 8.44 (s, 1H), 7.75 (s, 1H), 7.34 (s, 1H), 6.81 (s, 1H), 6.60-6.52 (m, 1H), 4.35-4.29 (m, 1H), 4.09 (s, 2H), 3.97-3.95 (m, 2H), 3.63-3.59 (m, 4H), 3.49-3.43 (m, 2H), 2.94-2.91 (m, 2H), 2.75-2.76 (m, 2H), 2.56 (d, J = 4.0 Hz, 3H), 2.36 (s, 3H), 2.05-1.90 (m, 4H), 1.86-1.78 (m, 2H) | 512 |
| Example 293 | 3-[7-cyano-6-(2-methyl-3-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, CDCl$_3$) δ 8.55-8.48 (m, 1H), 7.51 (d, J = 8.0 Hz, 1H), 7.23-7.16 (m, 1H), 6.98 (s, 1H), 6.78 (s, 1H), 4.51-4.45 (m, 1H), 4.23-4.08 (m, 5H), 3.78 (t, J = 5.6 Hz, 2H), 3.70 (t, J = 5.6 Hz, 2H), 3.53 (t, J = 12.0 Hz, 3H), 2.91 (t, J = 6.0 Hz, 2H), 2.84-2.79 (m, 5H), 2.46 (s, 3H), 2.36-2.23 (m, 2H), 2.16-2.08 (m, 2H), 1.93-1.83 (m, 2H) | 512 |
| Example 294 | 3-[7-cyano-6-(2-methoxy-4-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz DMSO-$d_6$) δ 8.24 (d, J = 5.2 Hz, 1H), 7.37 (s, 1H), 7.13-7.11 (m, 1H), 6.93 (s, 1H), 6.79 (s, 1H), 6.57-6.49 (m, 1H), 4.41-4.24 (m, 1H), 4.08 (s, 2H), 3.99-3.91 (m, 2H), 3.87 (s, 3H), 3.67-3.55 (m, 4H), 3.46 (t, J = 11.2 Hz, 2H), 2.90 (t, J = 6.0 Hz, 2H), 2.75-2.72 (m, 2H), 2.54 (d, J = 4.4 Hz, 3H), 2.05-1.91 (m, 4H), 1.85-1.80 (m, 2H) | 528 |
| Example 295 | 3-[7-cyano-6-(2-methyl-4-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz DMSO-$d_6$) δ 8.51 (d, J = 4.8 Hz, 1H), 8.12 (s, 1H), 7.39 (s, 1H), 7.38-7.32 (m, 2H), 6.80 (s, 1H), 6.58-6.50 (m, 1H), 4.42-4.26 (m, 1H), 4.08 (s, 2H), 3.95-3.90 (m, 2H), 3.70-3.54 (m, 4H), 3.44 (t, J = 12.0 Hz, 2H), 2.92 (t, J = 6.0 Hz, 2H), 2.80-2.71 (m, 2H), 2.56 (d, J = 4.4 Hz, 3H), 2.50 (s, 3H), 2.06-1.90 (m, 4H), 1.88-1.78 (m, 2H) | 512 |
| Example 296 | 3-[7-cyano-6-[6-(methylamino)-3-pyridyl]-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.11 (d, J = 2.4 Hz, 1H), 7.55-7.50 (m, 1H), 7.20 (s, 1H), 6.74 (s, 1H), 6.71-6.65 (m, 1H), 6.58-6.53 (m, 1H), 6.51 (d, J = 9.2 Hz, 1H), 4.37-4.24 (m, 1H), 4.06 (s, 2H), 3.99-3.92 (m, 2H), 3.64-3.60 (s, 2H), 3.58-3.54 (m, 2H), 3.45 (t, J = 12.0 Hz, 2H), 2.91-2.88 (m, 2H), 2.80 (d, J = 4.8 Hz, 3H), 2.77-2.72 (m, 2H), 2.55 (d, J = 4.4 Hz, 3H), 2.04-1.92 (m, 4H), 1.87-1.81 (m, 2H) | 527 |
| Example 297 | 3-[7-cyano-6-(4-methyl-3-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 Hz, DMSO-$d_6$) δ 8.46 (d, J = 4.8 Hz, 1H), 8.34 (s, 1H), 7.37 (d, J = 4.8 Hz, 1H), 7.18 (s, 1H), 6.84 (s, 1H), 6.61-6.53 (m, 1H), 4.38-4.24 (m, 1H), 4.12 (s, 2H), 3.98-3.94 (m, 2H), 3.67-3.54 (m, 4H), 3.46 (t, J = 11.2 Hz, 2H), 2.93-2.89 (m, 2H), 2.78-2.74 (m., 2H), 2.56 (d, J = 4.0 Hz, 3H), 2.20 (s, 3H), 2.06-1.90 (m, 4H), 1.86-1.80 (m, 2H). | 512 |
| Example 298 | 3-[7-cyano-6-(3-methyl-4-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.54 (s, 1H), 8.46 (d, J = 4.8 Hz, 1H), 7.22 (d, J = 4.8 Hz, 1H), 7.17 (s, 1H), 6.83 (s, 1H), 6.58-6.51 (m, 1H), 4.35-4.27 (m, 1H), 4.11 (s, 2H), 3.99-3.91 (m, 2H), 3.65-3.58 (m, 4H), 3.52-3.41 (m, 2H), 2.92-2.88 (m, 2H), 2.78-2.72 (m, 2H), 2.56 (d, J = 4.4 Hz, 3H), 2.18 (s, 3H), 2.04-1.94 (m, 4H), 1.88-1.80 (m, 2H) | 512 |
| Example 299 | 3-[7-cyano-6-(6-cyano-3-pyridyl)-3,4-dihydro-2H-quinolin-1-yl]-N- | $^1$H NMR (400 MHz, DMSO-$d_6$) δ 8.91 (s, 1H), 8.23-8.20 (m, 1H), 8.15 (d, J = 8.8 Hz, 1H), 7.44 (s, 1H), 6.84 (s, 1H), | 523 |

| Example | Compound Name | NMR | m/z |
|---|---|---|---|
| | methyl-1-tetrahydropyran-4-yl-6,7-dihydro-4H-pyrazolo[4,3-c]pyridine-5-carboxamide | 6.79 (s, 1H), 6.60-6.51 (m, 1H), 4.34-4.30 (m, 1H), 4.07 (s, 2H), 3.95-3.91 (m, 2H), 3.61-3.58 (m, 4H), 3.47-3.41 (m, 2H), 2.95-2.87 (m, 2H), 2.78-2.72 (m, 2H), 2.54 (d, J = 4.4 Hz, 3H), 2.02-1.91 (m, 4H), 1.84-1.81 (m, 2H). | |

Example 300

3-[7-cyano-6-(2-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide

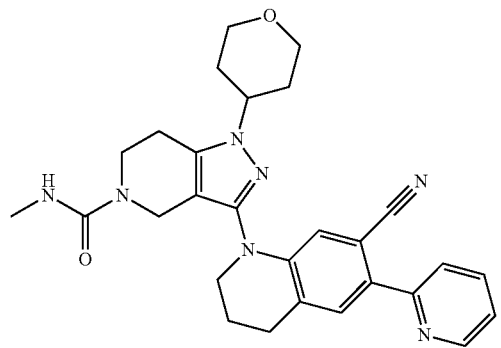 [SMILES: CNC(=O)N1CCc2c(c(N3CCCc4cc(-c5ccccn5)c(C#N)cc43)nn2C2CCOCC2)C1]

To a solution of 3-(7-cyano-6-(4,4,5,5-tetramethyl-1,3,2-dioxaborolan-2-yl)-3,4-dihydroquinolin-1 (2H)-yl)-N-methyl-1-(tetrahydro-2H-pyran-4-yl)-6,7-dihydro-1H-pyrazolo[4,3-c]pyridine-5(4H)-carboxamide (Intermediate O, 100 mg, 0.2 mmol) in THF (2.5 mL) and water (0.5 mL) was added chloro(2-dicyclohexylphosphino-2',4',6'-tri-i-propyl-1,1'-biphenyl)(2'-amino-1,1-biphenyl-2-yl) palladium(II) (16 mg, 0.02 mmol), 2-(dicyclohexylphosphino)-2',4',6'-tri-isopropylbiphenyl (10 mg, 0.02 mmol), 2-bromopyridine (48 mg, 0.3 mmol) and $Na_2CO_3$ (66 mg, 0.6 mmol). The mixture was heated to 60° C. for 16 h under a nitrogen atmosphere. After cooling the reaction to room temperature, the mixture was filtered and concentrated in vacuo. DCM (50 mL) was added and the mixture was washed with water (30 mL×3) and brine (30 mL). The organic layer was dried over anhydrous $Na_2SO_4$, filtered and concentrated in vacuo. The crude residue was purified by Prep-TLC (DCM/MeOH=20:1) to give the title compound (21 mg, 20%) as a white solid. $^1$H NMR (400 MHz, DMSO-$d_6$) δ 8.66-8.63 (m, 1H), 7.93-7.86 (m, 1H), 7.76 (d, J=7.6 Hz, 1H), 7.59 (s, 1H), 7.39-7.35 (m, 1H), 6.80 (s, 1H), 6.60-6.52 (m, 1H), 4.37-4.27 (m, 1H), 4.08 (s, 2H), 3.99-3.93 (m, 2H), 3.65-3.59 (m, 4H), 3.49-3.43 (m, 2H), 2.95-2.92 (m, 2H), 2.77-2.75 (m, 2H), 2.55 (d, J=4.0 Hz, 3H), 2.03-1.93 (m, 4H), 1.89-1.82 (m, 2H). LCMS M/Z (M+H) 498.

The Following Compounds were Prepared in a Similar Fashion to Example 300

Examples 301-308

| Example | Compound Name | NMR | m/z |
|---|---|---|---|
| Example 301 | 3-[7-cyano-6-[2-(methylamino)-4-pyridyl]-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.01 (d, J = 5.6 Hz, 1H), 7.26 (s, 1H), 6.76 (s, 1H), 6.59-6.52 (m, 3H), 4.34-4.27 (m, 1H), 4.06 (s, 2H), 3.95-3.93 (m, 2H), 3.61-3.56 (m, 4H), 3.47-3.41 (m, 2H), 2.92-2.88 (m, 2H), 2.78-2.73 (m, 5H), 2.55 (d, J = 4.4 Hz, 3H), 1.99-1.83 (m, 4H), 1.82-1.78 (m, 2H). | 527 |
| Example 302 | 3-[7-cyano-6-[4-methyl-6-(methylcarbamoyl)-3-pyridyl]-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.88-8.80 (m, 1H), 8.41 (s, 1H), 8.01 (s, 1H), 7.24 (s, 1H), 6.85 (s, 1H), 6.60-6.52 (m, 1H), 4.35-4.25 (m, 1H), 4.12 (s, 2H), 3.96-3.93 (m, 2H), 3.69-3.54 (m, 4H), 3.46 (t, J = 11.2 Hz, 2H), 2.93-2.91 (m, 2H), 2.83 (d, J = 4.8 Hz, 3H), 2.75-2.70 (m, 2H), 2.56 (d, J = 4.4 Hz, 3H), 2.29 (s, 3H), 2.06-1.90 (m, 4H), 1.88-1.78 (m, 2H) | 569 |
| Example 303 | 3-[7-cyano-6-[5-methyl-6-(methylcarbamoyl)-3-pyridyl]-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.67-8.64 (m, 1H), 8.58 (s, 1H), 7.89 (d, J = 1.6 Hz, 1H), 7.40 (s, 1H), 6.83 (s, 1H), 6.60-6.52 (m, 1H), 4.33-4.30 (m, 1H), 4.09 (s, 2H), 3.95-3.90 (m, 2H), 3.63-3.59 (m, 4H), 3.46 (t, J = 11.2 Hz, 2H), 2.93-2.90 (m, 2H), 2.80-2.75 (m, 5H), 2.60 (s, 3H), 2.56 (d, J = 4.0 Hz, 3H), 2.06-1.91 (m, 4H), 1.88-1.79 (m, 2H) | 569 |
| Example 304 | 3-[7-cyano-6-(6-methyl-2-pyridyl)-3,4-dihydro-2H-quinolin-1-yl]-N- | $^1$H NMR (400 MHz, DMSO-$d_6$) δ 7.81-7.74 (m, 1H), 7.58 (s, 1H), 7.56-7.55 (m, 1H), 7.23-7.22 (m, 1H), 6.78 (s, 1H), | 512 |

| Example | Compound Name | NMR | m/z |
|---|---|---|---|
| | methyl-1-tetrahydropyran-4-yl-6,7-dihydro-4H-pyrazolo[4,3-c]pyridine-5-carboxamide | 6.57-6.56 (m, 1H), 4.37-4.27 (m, 1H), 4.07 (s, 2H), 3.97-3.95 (m, 2H), 3.64-3.59 (m, 4H), 3.49-3.43 (m, 2H), 2.93 (t, J = 6.0 Hz, 2H), 2.81-2.72 (m, 2H), 2.55 (d, J = 4.0 Hz, 3H), 2.45 (s, 3H), 2.05-1.92 (m, 4H), 1.88-1.81 (m, 2H) | |
| Example 305 | 3-[7-cyano-6-(5-methyl-2-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 8.47 (s, 1H), 7.70-7.63 (m, 2H), 7.54 (s, 1H), 6.76 (s, 1H), 6.57-6.51 (m, 1H), 4.33-4.27 (m, 1H), 4.06 (s, 2H), 3.95-3.93 (m, 2H), 3.61-3.57 (m, 4H), 3.47-3.44 (m, 2H), 2.93-2.90 (m, 2H), 2.74-2.73 (m, 2H), 2.53 (d, J = 4.0 Hz, 3H), 2.32 (s, 3H), 2.00-1.95 (m, 4H), 1.84-1.81 (m, 2H) | 512 |
| Example 306 | 3-[7-cyano-6-(4-methyl-2-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 8.49 (d, J = 4.4 Hz, 1H), 7.62-7.54 (m, 2H), 7.20 (d, J = 4.4 Hz, 1H), 6.79 (s, 1H), 6.61-6.53 (m, 1H), 4.35-4.25 (m, 1H), 4.08 (s, 2H), 3.97-3.94 (m, 2H), 3.70-3.60 (m, 4H), 3.46 (t, J = 11.2 Hz, 2H), 2.93 (t, J = 6.0 Hz, 2H), 2.77-2.73 (m, 2H), 2.55 (d, J = 4.0 Hz, 3H), 2.38 (s, 3H), 2.05-1.93 (m, 4H), 1.91-1.85 (m, 2H) | 512 |
| Example 307 | 3-[7-cyano-6-(1,3-dimethylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 7.74 (s, 1H), 7.11 (s, 1H), 6.73 (s, 1H), 6.57-6.56 (m, 1H), 4.33-4.27 (m, 1H), 4.07 (s, 2H), 3.96-3.94 (m, 2H), 3.79 (s, 3H), 3.65-3.53 (m, 4H), 3.48-3.43 (m, 2H), 2.87 (t, J = 6.0 Hz, 2H), 2.78-2.72 (m, 2H), 2.55 (d, J = 4.0 Hz, 3H), 2.14 (s, 3H), 2.02-1.90 (m, 4H), 1.84-1.81 (m, 2H) | 515 |
| Example 308 | 3-[7-cyano-6-(1,5-dimethylpyrazol-4-yl)-3,4-dihydro-2H-quinolin-1-yl]N-methyl-1-tetrahydropyran-4-yl-6,7-dihydro-4H-pyrazolo[4,3-c]pyridine-5-carboxamide | $^1$H NMR (400 MHz, DMSO-d$_6$) δ 7.44 (s, 1H), 7.09 (s, 1H), 6.75 (s, IH), 6.59-6.55 (m, 1H), 4.34-4.31 (m, 1H), 4.07 (s, 2H), 3.95-3.94 (m, 2H), 3.79 (s, 3H), 3.64-3.57 (m, 4H), 3.54-3.42 (m, 2H), 2.79-2.86 (m, 2H), 2.76-2.73 (m, 2H), 2.56 (d, J = 4.0 Hz, 3H), 2.24 (s, 3H), 2.04-1.91 (m, 4H), 1.87-1.78 (m, 2H). | 515 |

Example 309

3-(7-cyano-6-pyrimidin-4-yl-3,4-dihydro-2H-quinolin-1-yl)-N-methyl-1-tetrahydropyran-4-yl-6,7-dihydro-4H-pyrazolo[4,3-c]pyridine-5-carboxamide

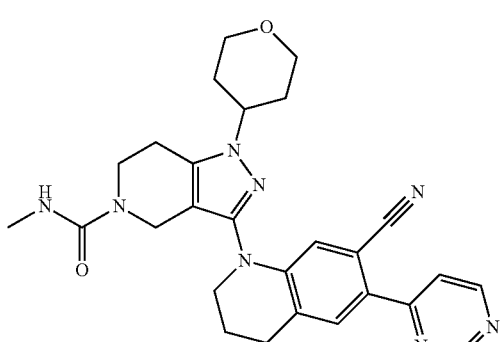

Step 1

3-(6-(2-chloropyrimidin-4-yl)-7-cyano-3,4-dihydro-quinolin-1(2H)-yl)-N-methyl-1-(tetrahydro-2H-pyran-4-yl)-6,7-dihydro-1H-pyrazolo[4,3-c]pyridine-5(4H)-carboxamide

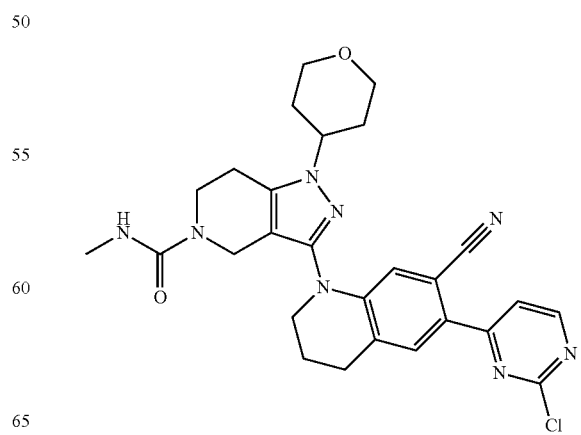

To a solution of 3-(7-cyano-6-(4,4,5,5-tetramethyl-1,3,2-dioxaborolan-2-yl)-3,4-dihydroquinolin-1(2H)-yl)-N-methyl-1-(tetrahydro-2H-pyran-4-yl)-6,7-dihydro-1H-pyrazolo[4,3-c]pyridine-5(4H)-carboxamide (Intermediate O, 200 mg, 0.37 mmol) in THF (2.5 mL) and water (0.5 mL) was added chloro(2-dicyclohexylphosphino-2',4',6'-tri-i-propyl-1,1'-biphenyl)(2'-amino-1,1'-biphenyl-2-yl) palladium(II) (29 mg, 0.04 mmol), 2-(dicyclohexylphosphino)-2',4',6'-triisopropylbiphenyl (17 mg, 0.04 mmol), 2,4-dichloropyrimidine (81 mg, 0.55 mmol) and Na₂CO₃ (78 mg, 0.73 mmol). The mixture was heated to 60° C. for 16 h under a nitrogen atmosphere. After cooling the reaction to room temperature, the mixture was filtered and concentrated in vacuo. DCM (50 mL) was added and the mixture was washed with water (30 mL×3) and brine (30 mL). The organic layer was dried over anhydrous Na₂SO₄, filtered and concentrated in vacuo. The crude residue was purified by silica gel chromatography (DCM/MeOH=50:1) to give the title compound (180 mg, 92%) as a yellow solid. LCMS M/Z (M+H) 533.

Step 2

3-(7-cyano-6-pyrimidin-4-yl-3,4-dihydro-2H-quinolin-1-yl)-N-methyl-1-tetrahydropyran-4-yl-6,7-dihydro-4H-pyrazolo[4,3-c]pyridine-5-carboxamide

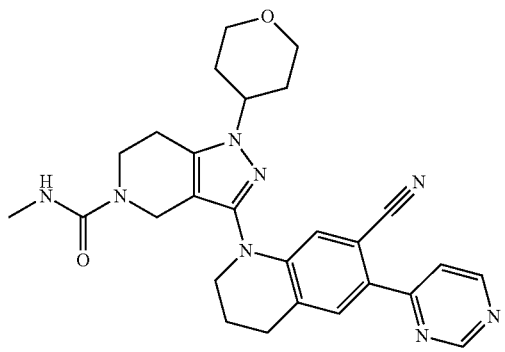 [SMILES: CNC(=O)N1CCc2c(c(N3CCCc4cc(-c5ccncn5)c(C#N)cc43)nn2C2CCOCC2)C1]

To a solution of 3-(6-(2-chloropyrimidin-4-yl)-7-cyano-3,4-dihydroquinolin-1(2H)-yl)-N-methyl-1-(tetrahydro-2H-pyran-4-yl)-6,7-dihydro-1H-pyrazolo[4,3-c]pyridine-5(4H)-carboxamide (130 mg, 0.24 mmol) in MeOH (2 mL) was added 10% Pd/C (13 mg). The reaction mixture was stirred at 25° C. for 12 h under hydrogen atmosphere (15 psi). The mixture was filtered and concentrated in vacuo. The crude residue was purified by reverse phase chromatography (acetonitrile 22-55%/0.05% NH₄OH in water) to give the title compound (14 mg, 12%) as a yellow solid. ¹H NMR (400 MHz, DMSO-d₆) δ 9.23 (s, 1H), 8.87 (d, J=5.6 Hz, 1H), 7.94-7.93 (m, 1H), 7.79 (s, 1H), 6.85 (s, 1H), 6.58-6.57 (m, 1H), 4.39-4.28 (m, 1H), 4.09 (s, 2H), 4.03-3.91 (m, 2H), 3.68-3.59 (m, 4H), 3.51-3.43 (m, 2H), 2.98-2.94 (m, 2H), 2.78-2.76 (m, 2H), 2.56 (d, J=4.0 Hz, 3H), 2.07-1.93 (m, 4H), 1.87-1.81 (m, 2H). LCMS M/Z (M+H) 499.

Example 310

N-[5-[1-(5-acetyl-1-tetrahydropyran-4-yl-6,7-dihydro-4H-pyrazolo[4,3-c]pyridin-3-yl)-7-(difluoromethyl)-3,4-dihydro-2H-quinolin-6-yl]-2-pyridyl]acetamide

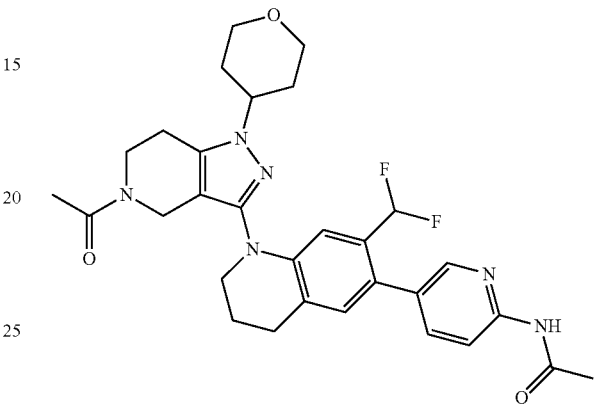

To a solution of 1-(3-(6-bromo-7-(difluoromethyl)-3,4-dihydroquinolin-(2H)-yl)-1-(tetrahydro-2H-pyran-4-yl)-6,7-dihydro-1H-pyrazolo[4,3-c]pyridin-5(4H)-yl)ethanone (Intermediate P, 210 mg, 0.41 mmol) in THF (5 mL) and water (1 mL) was added N-(5-(4,4,5,5-tetramethyl-1,3,2-dioxaborolan-2-yl)pyridin-2-yl)acetamide (130 mg, 0.49 mmol), chloro(2-dicyclohexylphosphino-2',4',6'-tri-i-propyl-1,1'-biphenyl)(2'-amino-1,1'-biphenyl-2-yl) palladium (II) (32 mg, 0.04 mmol), 2-(dicyclohexylphosphino)-2',4',6'-triisopropylbiphenyl (20 mg, 0.04 mmol) and Na₂CO₃ (130 mg, 1.23 mmol). The mixture was heated to 60° C. for 16 h under a nitrogen atmosphere. After cooling the reaction to room temperature, the mixture was concentrated in vacuo. The crude residue was purified by reverse phase chromatography (acetonitrile 30-60%/0.05% NH₄OH in water) to give the title compound (131 mg, 56%) as a white solid. ¹H NMR (400 MHz, DMSO-d₆) δ 8.29-8.19 (m, 2H), 8.05-8.03 (m, 1H), 7.69-7.66 (m, 1H), 6.99-6.95 (m, 1H), 6.90 (s, 1H), 6.53-6.23 (m, 1H), 4.28 (s, 1H), 4.16-4.13 (m, 4H), 3.93-3.91 (m, 1H), 3.77-3.72 (m, 3H), 3.56-3.50 (m, 2H), 2.92-2.88 (m, 3H), 2.84-2.77 (m, 1H), 2.33-2.30 (m, 5H), 2.18-2.07 (m, 4H), 1.90-1.87 (m, 2H). LCMS M/Z (M+H) 565.

The Following Compounds were Prepared in a Similar Fashion to Example 310

Examples 311-312

| Example | Compound Name | NMR | m/z |
|---|---|---|---|
| Example 311 | 1-[3-[7-(difluoromethyl)-6-[6-(methylamino)-3-pyridyl]-3,4-dihydro-2H-quinolin-1-yl]-1-tetrahydropyran-4-yl-6,7-dihydro-4H-pyrazolo[4,3-c]pyridin-5-yl]ethanone | ¹H NMR (400 MHz, CDCl₃) δ 8.06 (s, 1H), 7.43-7.41 (m, 1H), 6.98-6.93 (m, 1H), 6.88 (s, 1H), 6.60-6.28 (m, 2H), 4.66-4.57 (m, 1H), 4.29-4.07 (m, 5H), 3.95-3.90 (m, 1H), 3.78-3.69 (m, 3H), 3.58-3.48 (m, 2H), 2.98 (d, J = 4.8 Hz, 3H), 2.91-2.76 (m, 4H), 2.39-2.25 (m, 2H), 2.30-2.17 (m, 5H), 1.92-1.85 (m, 2H) | 537 |

-continued

| Example | Compound Name | NMR | m/z |
|---|---|---|---|
| Example 312 | 1-[3-[7-(difluoromethyl)-6-[6-(dimethylamino)-3-pyridyl]-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, CDCl$_3$) δ 8.13 (d, J = 2.0 Hz, 1H), 7.46-7.40 (m, 1H), 6.97-6.93 (m, 1H), 6.89 (s, 1H), 6.61-6.29 (m, 2H), 4.30-4.09 (m, 5H), 3.95-3.89 (m, 1H), 3.79-3.74 (m, 3H), 3.58-3.49 (m, 2H), 3.13 (s, 6H), 2.93-2.74 (m, 4H), 2.38-2.26 (m, 2H), 2.19-2.01 (m, 5H), 1.92-1.84 (m, 2H) | 551 |

Example 313

1-[3-[7-(difluoromethyl)-6-(1-methylpyrazol-3-yl)-3,4-dihydro-2H-quinolin-1-yl]-1-tetrahydropyran-4-yl-6,7-dihydro-4H-pyrazolo[4,3-c]pyridin-5-yl]ethanone

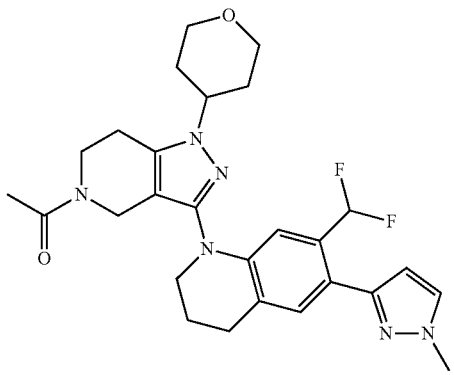 [SMILES: CC(=O)N1CCc2c(c(N3CCCc4cc(-c5ccn(C)n5)c(C(F)F)cc43)nn2C2CCOCC2)C1]

To a solution of 1-(3-(7-(difluoromethyl)-6-(4,4,5,5-tetramethyl-1,3,2-dioxaborolan-2-yl)-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone (Intermediate Q, 200 mg, 0.36 mmol) in THF (5 mL) and water (1 mL) was added 3-bromo-1-methyl-pyrazole (58 mg, 0.36 mmol), chloro(2-dicyclohexylphosphino-2',4',6'-tri-i-propyl-1,1'-biphenyl)(2'-amino-1,1'-biphenyl-2-yl) palladium (II) (28 mg, 0.04 mmol), Na$_2$CO$_3$ (76 mg, 0.72 mmol) and 2-(dicyclohexylphosphino)-2',4',6'-triisopropylbiphenyl (17 mg, 0.04 mmol). The mixture was heated to 60° C. for 16 h under a nitrogen atmosphere. After cooling the reaction to room temperature, the mixture was concentrated in vacuo. The crude residue was purified by reverse phase chromatography (acetonitrile 40-70%/0.225% formic acid in water) to give the title compound (13 mg, 7%) as a white solid. $^1$H NMR (400 MHz, DMSO-d$_6$) δ 7.73 (s, 1H), 7.62-7.29 (m, 2H), 6.86 (s, 1H), 6.47 (s, 1H), 4.40-4.24 (m, 1H), 4.22-4.11 (m, 2H), 3.97-3.94 (m, 2H), 3.86 (s, 3H), 3.78-3.67 (m, 2H), 3.63-3.58 (m, 2H), 3.51-3.44 (m, 2H), 2.93-2.75 (m, 4H), 2.07-1.90 (m, 7H), 1.84-1.74 (m, 2H). LCMS M/Z (M+H) 511.

The Following Compounds were Prepared in a Similar Fashion to Example 313

Examples 314-317

| Example | Compound Name | NMR | m/z |
|---|---|---|---|
| Example 314 | 1-[3-[6-(5-chloro-3-pyridyl)-7-(difluoromethyl)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, DMSO-d$_6$) δ 8.62 (d, J = 2.4 Hz, 1H), 8.46 (s, 1H), 7.91-7.84 (m, 1H), 7.12 (s, 1H), 6.95-6.62 (m, 2H), 4.36-4.26 (m, 1H), 4.23-4.14 (m, 2H), 3.97-3.94 (m, 2H), 3.79-3.68 (m, 2H), 3.66-3.59 (m, 2H), 3.46 (t, J = 12 Hz, 2H), 2.94-2.73 (m, 4H), 2.08-1.92 (m, 7H), 1.85-1.78 (m, 2H) | 542 |
| Example 315 | 1-[3-[6-(3-chloro-4-pyridyl)-7-(difluoromethyl)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, DMSO-d$_6$) δ 8.71 (s, 1H), 8.54 (d, J = 4.4 Hz, 1H), 7.39-7.32 (m, 1H), 6.96 (s, 1H), 6.90-6.83 (m, 1H), 6.70-6.39 (m, 1H), 4.40-4.28 (m, 1H), 4.23-4.17 (m, 2H), 3.97-3.93 (m, 2H), 3.79-3.69 (m, 2H), 3.65-3.60 (m, 2H), 3.50-3.45 (m, 2H), 2.89-2.75 (m, 4H), 2.09-1.92 (m, 7H), 1.85-1.78 (m, 2H) | 542 |
| Example 316 | 4-[1-(5-acetyl-1-tetrahydropyran-4-yl-6,7-dihydro-4H-pyrazolo[4,3-c]pyridin-3-yl)-7-(difluoromethyl)-3,4-dihydro-2H-quinolin-6-yl]pyridine-2-carbonitrile | $^1$H NMR (400 MHz, DMSO-d$_6$) δ 8.75 (d, J = 4.4 Hz, 1H), 8.00 (s, 1H), 7.70-7.58 (m, 1H), 7.18 (s, 1H), 7.05-6.72 (m, 2H), 4.40-4.31 (m, 1H), 4.25-4.12 (m, 2H), 3.97-3.93 (m, 2H), 3.80-3.68 (m, 2H), 3.65-3.62 (m, 2H), 3.46-3.42 (m, 2H), 2.94-2.74 (m, 4H), 2.09-1.92 (m, 7H), 1.85-1.72 (m, 2H) | 533 |

| Example | Compound Name | NMR | m/z |
|---|---|---|---|
| Example 317 | 1-[3-[7-(difluoromethyl)-6-(2-methyl-4-pyridyl)-3,4-dihydro-2H-quinolin-1-yl]-1-tetrahydropyran-4-yl-6,7-dihydro-4H-pyrazolo[4,3-c]pyridin-5-yl]ethanone | $^1$H NMR (400 MHz, CDCl$_3$) δ 8.55-8.49 (m, 1H), 7.13 (s, 1H), 7.08-7.06 (m, 1H), 7.02-6.97 (m, 1H), 6.90 (s, 1H), 6.60-6.26 (m, 1H), 4.32-4.08 (m, 5H), 3.97-3.89 (m, 1H), 3.81-3.69 (m, 3H), 3.54 (t, J = 12.0 Hz, 2H), 2.96-2.74 (m, 4H), 2.61 (s, 3H), 2.37-2.25 (m, 2H), 2.23-2.07 (m, 5H), 1.94-1.83 (m, 2H) | 522 |

Example 318

3-[7-(difluoromethyl)-6-(1-methyl-2-oxo-4-pyridyl)-3,4-dihydro-2H-quinolin-1-yl]-N-methyl-1-tetrahydropyran-4-yl-6,7-dihydro-4H-pyrazolo[4,3-c]pyridine-5-carboxamide

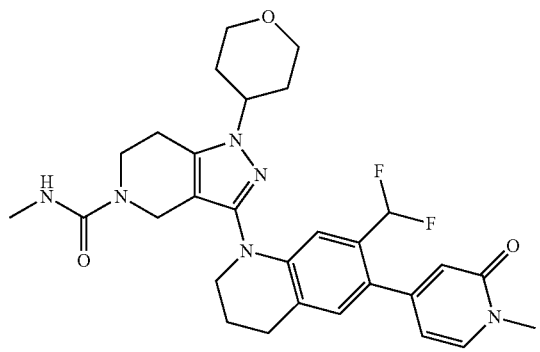

To a solution of 3-(6-bromo-7-(difluoromethyl)-3,4-dihydroquinolin-1(2H)-yl)-N-methyl-1-(tetrahydro-2H-pyran-4-yl)-6,7-dihydro-1H-pyrazolo[4,3-c]pyridine-5 (4H)-carboxamide (Intermediate R, 100 mg, 0.2 mmol) in THF (2.5 mL) and water (0.5 mL) was added chloro(2-dicyclohexylphosphino-2',4',6'-tri-i-propyl-1,1'-biphenyl)(2'-amino-1,1'-biphenyl-2-yl) palladium(II) (16 mg, 0.02 mmol), 2-(dicyclohexylphosphino)-2',4',6'-triisopropylbiphenyl (9 mg, 0.02 mmol), 1-methyl-4-(4,4,5,5-tetramethyl-1,3,2-dioxaborolan-2-yl)pyridin-2-one (70 mg, 0.3 mmol) and Na$_2$CO$_3$ (42 mg, 0.4 mmol). The mixture was heated to 60° C. for 16 h under a nitrogen atmosphere. After cooling the reaction to room temperature, the mixture was concentrated in vacuo. DCM (50 mL) was added and the mixture was washed with water (30 mL×3) and brine (30 mL). The organic layer was dried over anhydrous Na$_2$SO$_4$, filtered and concentrated in vacuo. The crude residue was purified by reverse phase chromatography (acetonitrile 20-50%/0.05% NH$_4$OH in water) to give the title compound (43 mg, 20%) as a white solid. $^1$H NMR (400 MHz, DMSO-d$_6$) δ 7.73-7.71 (m, 1H), 7.07 (s, 1H), 6.86 (s, 1H), 6.81 (t, J=54.8 Hz, 1H), 6.56-6.55 (m, 1H), 6.24 (s, 1H), 6.20-6.18 (m, 1H), 4.35-4.25 (m, 1H), 4.05 (s, 2H), 3.98-3.91 (m, 2H), 3.61-3.60 (m, 4H), 3.50-3.40 (m, 5H), 2.92-2.72 (m, 4H), 2.55 (d, J=4.0 Hz, 3H), 2.06-1.90 (m, 4H), 1.83-1.81 (m, 2H). LCMS M/Z (M+H) 553.

Example 319

3-[7-(difluoromethyl)-6-(1-methylpyrazol-3-yl)-3,4-dihydro-2H-quinolin-1-yl]-N-methyl-1-tetrahydropyran-4-yl-6,7-dihydro-4H-pyrazolo[4,3-c]pyridine-5-carboxamide

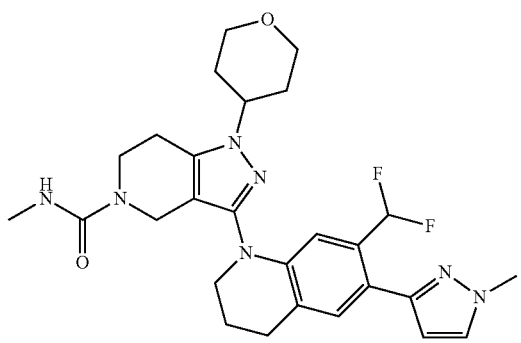

To a solution of 3-(7-(difluoromethyl)-6-(4,4,5,5-tetramethyl-1,3,2-dioxaborolan-2-yl)-3,4-dihydroquinolin-1(2H)-yl)-N-methyl-1-(tetrahydro-2H-pyran-4-yl)-6,7-dihydro-1H-pyrazolo[4,3-c]pyridine-5(4H)-carboxamide (Intermediate S, 100 mg, 0.2 mmol) in THF (2.5 mL) and water (0.5 mL) was added chloro(2-dicyclohexylphosphino-2',4',6'-tri-i-propyl-1,1'-biphenyl)(2'-amino-1,1'-biphenyl-2-yl) palladium (II) (16 mg, 0.02 mmol), 2-(dicyclohexylphosphino)-2',4',6'-triisopropylbiphenyl (9 mg, 0.02 mmol), 3-bromo-1-methyl-pyrazole (48 mg, 0.3 mmol) and Na$_2$CO$_3$ (42 mg, 0.4 mmol). The reaction was heated to 60° C. for 16 h under a nitrogen atmosphere. After cooling the reaction to room temperature, the mixture was concentrated in vacuo. DCM (50 mL) was added and the mixture was washed with water (30 mL×3) and brine (30 mL). The organic layer was dried over anhydrous Na$_2$SO$_4$, filtered and concentrated in vacuo. The crude residue was purified by reverse phase chromatography (acetonitrile 40-70%/0.05% NH$_4$OH in water) to give the title compound (11 mg, 11%) as a white solid. $^1$H NMR (400 MHz, DMSO-d$_6$) δ 7.73 (d, J=2.0 Hz, 1H), 7.44 (t, J=55.6 Hz, 1H), 7.32 (s, 1H), 6.86 (s, 1H), 6.55 (d, J=4.0 Hz, 1H), 6.46 (s, 1H), 4.33-4.23 (m, 1H), 4.02 (s, 2H), 3.95-3.93 (m, 2H), 3.86 (s, 3H), 3.61-3.58 (m, 4H), 3.48-3.42 (m, 2H), 2.89-2.71 (m, 4H), 2.53 (d, J=4.4 Hz, 3H), 2.01-1.93 (m, 4H), 1.82-1.80 (m, 2H). LCMS M/Z (M+H) 526.

The Following Compounds were Prepared in a
Similar Fashion to Example 319

Examples 320-321

| Example | Compound Name | NMR | m/z |
|---|---|---|---|
| Example 320 | 3-[7-(difluoromethyl)-6-(1,3-dimethylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 7.50 (s, 1H), 6.92 (s, 1H), 6.83 (s, 1H), 6.56-6.39 (m, 2H), 4.34-4.23 (m, 1H), 4.05 (s, 2H), 3.95-3.93 (m, 2H), 3.77 (s, 3H), 3.64-3.54 (m, 4H), 3.49-3.40 (m, 2H), 2.87-2.71 (m, 4H), 2.54 (d, J = 4.0 Hz, 3H), 2.05 (s, 3H), 2.01-1.91 (m, 4H), 1.82-1.79 (m, 2H) | 540 |
| Example 321 | 3-[7-(difluoromethyl)-6-(1,5-dimethylpyrazol-3-yl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 7.44 (t, J = 56.0 Hz, 1H), 7.27 (s, 1H), 6.84 (s, 1H), 6.53 (d, J = 4.4 Hz, 1H), 6.26 (s, 1H), 4.31-4.25 (m, 1H), 4.02 (s, 2H), 3.98-3.91 (m, 2H), 3.74 (s, 3H), 3.63-3.55 (m, 4H), 3.48-3.42 (m, 2H), 2.87-2.72 (m, 4H), 2.53 (d, J = 4.0 Hz, 3H), 2.27 (s, 3H), 2.02-1.92 (m, 4H), 1.82-1.80 (m, 2H) | 540 |

Example 322

1-[3-[7-(difluoromethyl)-6-(1,5-dimethylpyrazol-4-yl)-3,4-dihydro-2H-quinolin-1-yl]-1-(1,1-dioxothian-4-yl)-6,7-dihydro-4H-pyrazolo[4,3-c]pyridin-5-yl]ethanone

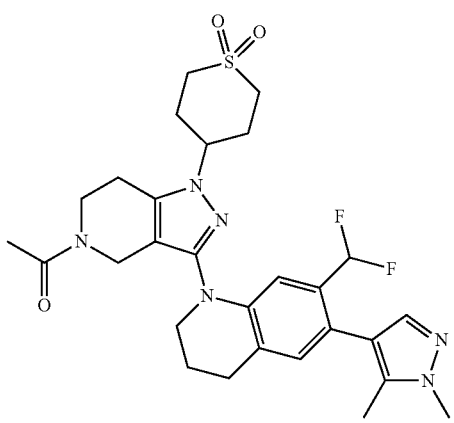 [SMILES: CC(=O)N1CCc2c(c(N3CCCc4cc(-c5cnn(C)c5C)c(C(F)F)cc43)nn2C2CCS(=O)(=O)CC2)C1]

Step 1 tert-butyl 3-(7-(difluoromethyl)-3,4-dihydroquinolin-1(2H)-yl)-1-(1,1-dioxidotetrahydro-2H-thiopyran-4-yl)-6,7-dihydro-1H-pyrazolo[4,3-c]pyridine-5(4H)-carboxylate

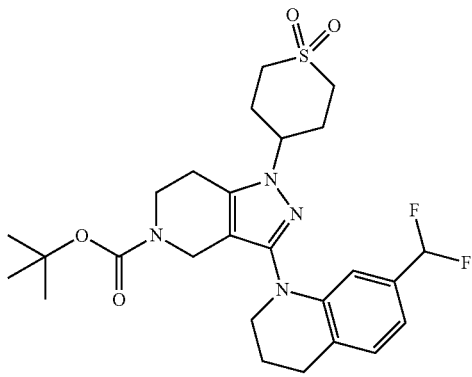 [SMILES: CC(C)(C)OC(=O)N1CCc2c(c(N3CCCc4ccc(C(F)F)cc43)nn2C2CCS(=O)(=O)CC2)C1]

To a solution of 7-(difluoromethyl)-1,2,3,4-tetrahydroquinoline (422 mg, 2.3 mmol) in dioxane (20 mL) was added tert-butyl 3-bromo-1-(1,1-dioxidotetrahydro-2H-thiopyran-4-yl)-6,7-dihydro-1H-pyrazolo[4,3-c]pyridine-5(4H)-carboxylate (Intermediate K, 1.0 g, 2.3 mmol), chloro(2-dicyclohexylphosphino-2',6'-di-i-propoxy-1,1'-biphenyl)(2'-amino-1,1'-biphenyl-2-yl)palladium(II) (179 mg, 0.23 mmol), 2-dicyclohexylphosphino-2',6'-di-i-propoxy-1,1'-biphenyl (107 mg, 0.23 mmol) and t-BuONa (664 mg, 6.9 mmol). The mixture was heated to 120° C. for 16 h under a nitrogen atmosphere. After cooling the reaction to room temperature, the mixture was filtered and concentrated in vacuo. The crude residue was purified by silica gel chromatography (DCM/MeOH=100:1) to give the title compound (1.1 g, 89%) as a light yellow solid. LCMS M/Z (M+H) 537.

Step 2 tert-butyl 3-(6-bromo-7-(difluoromethyl)-3,4-dihydroquinolin-1(2H)-yl)-1-(1,1-dioxidotetrahydro-2H-thiopyran-4-yl)-6,7-dihydro-1H-pyrazolo[4,3-c]pyridine-5(4H)-carboxylate

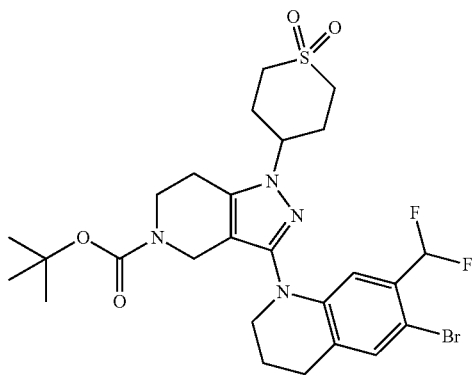 [SMILES: CC(C)(C)OC(=O)N1CCc2c(c(N3CCCc4cc(Br)c(C(F)F)cc43)nn2C2CCS(=O)(=O)CC2)C1]

To a solution of tert-butyl 3-(7-(difluoromethyl)-3,4-dihydroquinolin-1(2H)-yl)-1-(1,1-dioxidotetrahydro-2H-thiopyran-4-yl)-6,7-dihydro-1H-pyrazolo[4,3-c]pyridine-5(4H)-carboxylate (1.1 g, 1.6 mmol) in DCM (10 mL) at 0° C. was added N-bromosuccinimide (281 mg, 1.6 mmol) portionwise. The mixture was stirred at room temperature for 2 h. The mixture was poured into water (20 mL) and extracted with DCM (20 mL×2). The combined organic layers were dried over anhydrous Na₂SO₄, filtered and concentrated in vacuo to give the title compound (1.32 g, crude) as a brown solid that required no further purification. LCMS M/Z (M+H) 617.

Step 3 tert-butyl 3-(7-(difluoromethyl)-6-(1,5-dimethyl-1H-pyrazol-4-yl)-3,4-dihydroquinolin-1(2H)-yl)-1-(1,1-dioxidotetrahydro-2H-thiopyran-4-yl)-6,7-dihydro-1H-pyrazolo[4,3-c]pyridine-5(4H)-carboxylate

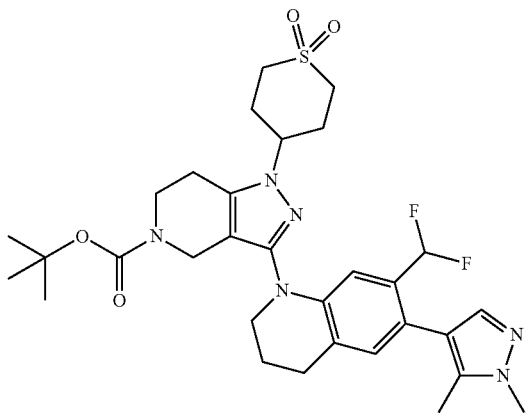 [SMILES: Cc1c(-c2cc3c(cc2C(F)F)N(c2nn(C4CCS(=O)(=O)CC4)c4c2CN(C(=O)OC(C)(C)C)CC4)CCC3)cnn1C]

To a solution of tert-butyl 3-(6-bromo-7-(difluoromethyl)-3,4-dihydroquinolin-1(2H)-yl)-1-(1,1-dioxidotetrahydro-2H-thiopyran-4-yl)-6,7-dihydro-1H-pyrazolo[4,3-c]pyridine-5(4H)-carboxylate (400 mg, 0.65 mmol) in THF (2 mL) and water (0.4 mL) was added Na₂CO₃ (207 mg, 1.9 mmol), chloro(2-dicyclohexylphosphino-2',4',6'-tri-i-propyl-1,1'-biphenyl)(2'-amino-1,1'-biphenyl-2-yl) palladium (II) (51 mg, 0.06 mmol), 2-(dicyclohexylphosphino)-2',4', 6'-triisopropylbiphenyl (32 mg, 0.06 mmol) and 1,5-dimethyl-4-(4,4,5,5-tetramethyl-1,3,2-dioxaborolan-2-yl)-1H-pyrazole (173 mg, 0.78 mmol). The mixture was heated to 60° C. for 16 h under a nitrogen atmosphere. After cooling the reaction to room temperature, the mixture was concentrated in vacuo. The crude residue was purified by silica gel chromatography (DCM/MeOH=100:3) to give the title compound (240 mg, 59%) as a yellow solid. LCMS M/Z (M+H) 631.

Step 4

4-(3-(7-(difluoromethyl)-6-(1,5-dimethyl-1H-pyrazol-4-yl)-3,4-dihydroquinolin-1(2H)-yl)-4,5,6,7-tetrahydro-1H-pyrazolo[4,3-c]pyridin-1-yl)tetrahydro-2H-thiopyran 1,1-dioxide

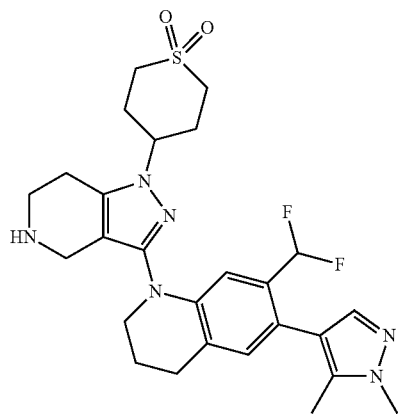 [SMILES: Cc1c(-c2cc3c(cc2C(F)F)N(c2nn(C4CCS(=O)(=O)CC4)c4c2CNCC4)CCC3)cnn1C]

To a solution of tert-butyl 3-(7-(difluoromethyl)-6-(1,5-dimethyl-1H-pyrazol-4-yl)-3,4-dihydroquinolin-1(2H)-yl)-1-(1,1-dioxidotetrahydro-2H-thiopyran-4-yl)-6,7-dihydro-1H-pyrazolo[4,3-c]pyridine-5(4H)-carboxylate (242 mg, 0.38 mmol) in DCM (2 mL) at 0° C. was added trifluoroacetic acid (0.5 mL, 6.8 mmol) dropwise. The mixture was stirred at 25° C. for 1 h and concentrated in vacuo to give the title compound (212 mg, crude) as a brown oil that required no further purification. LCMS M/Z (M+H) 531.

621
Step 5
1-[3-[7-(difluoromethyl)-6-(1,5-dimethylpyrazol-4-yl)-3,4-dihydro-2H-quinolin-1-yl]-1-(1,1-dioxothian-4-yl)-6,7-dihydro-4H-pyrazolo[4,3-c]pyridin-5-yl]ethanone

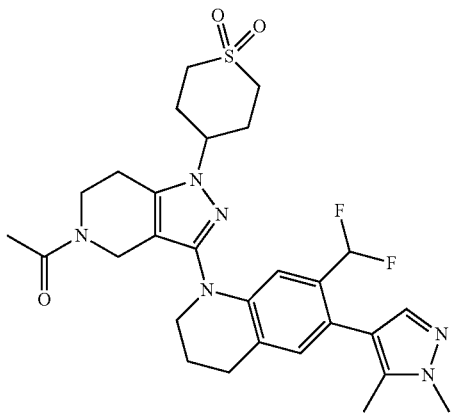 [SMILES: CC(=O)N1CCc2c(c(N3CCCc4cc(-c5cnn(C)c5C)c(C(F)F)cc43)nn2C2CCS(=O)(=O)CC2)C1]

To a solution of 4-(3-(7-(difluoromethyl)-6-(1,5-dimethyl-1H-pyrazol-4-yl)-3,4-dihydroquinolin-1(2H)-yl)-4,5,6,7-tetrahydro-1H-pyrazolo[4,3-c]pyridin-1-yl)tetrahydro-2H-thiopyran 1,1-dioxide (106 mg, 0.2 mmol) in DCM (2 mL) at 0° C. was added triethylamine (0.14 mL, 1.0 mmol) and acetic anhydride (0.02 mL, 0.2 mmol). The mixture was stirred at room temperature for 0.5 h. Water (5 mL) was added and the mixture was extracted with DCM (5 mL×2). The combined organic layers were dried over anhydrous Na$_2$SO$_4$, filtered and concentrated in vacuo. The crude residue was purified by reverse phase chromatography (acetonitrile 28-58%/0.05% NH$_4$OH in water) to give the title compound (16 mg, 14%) as a white solid. $^1$H NMR (400 MHz, CDCl$_3$) δ 7.37 (s, 1H), 6.91-6.87 (m, 1H), 6.85 (s, 1H), 6.57-6.27 (m, 1H), 4.34-4.30 (m, 1H), 4.27-4.14 (m, 2H), 3.92-3.91 (m, 1H), 3.86-3.85 (m, 3H), 3.77-3.72 (m, 5H), 3.06-3.03 (m, 2H), 2.89-2.85 (m, 2H), 2.79-2.73 (m, 2H), 2.56-2.51 (m, 4H), 2.20-2.17 (m, 3H), 2.15-2.07 (m, 5H). LCMS M/Z (M+H) 573.

The Following Compound was Prepared in a Similar Fashion to Example 322

Examples 323

622
Example 324
3-[7-(difluoromethyl)-6-(1,5-dimethylpyrazol-4-yl)-3,4-dihydro-2H-quinolin-1-yl]-1-(1,1-dioxothian-4-yl)-N-methyl-6,7-dihydro-4H-pyrazolo[4,3-c]pyridine-5-carboxamide

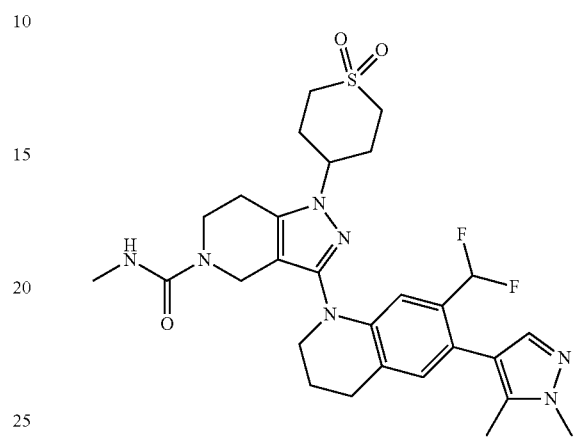

To a solution of 4-(3-(7-(difluoromethyl)-6-(1,5-dimethyl-1H-pyrazol-4-yl)-3,4-dihydroquinolin-1(2H)-yl)-4,5,6,7-tetrahydro-1H-pyrazolo[4,3-c]pyridin-1-yl)tetrahydro-2H-thiopyran 1,1-dioxide (106 mg, 0.2 mmol) in DCM (2 mL) at 0° C. was added triethylamine (0.14 mL, 1.0 mmol) and N-methyl-1H-imidazole-1-carboxamide (50 mg, 0.4 mmol). The mixture was stirred at room temperature for 16 h. Water (5 mL) was added and the mixture was extracted with DCM (5 mL×2). The combined organic layers were dried over anhydrous Na$_2$SO$_4$, filtered and concentrated in vacuo. The crude residue was purified by reverse phase chromatography (acetonitrile 29-59%/0.05% NH$_4$OH in water) to give the title compound (8 mg, 7%) as a white solid. $^1$H NMR (400 MHz, CDCl$_3$) δ 7.37 (s, 1H), 6.91 (s, 1H), 6.85 (s, 1H), 6.44 (t, J=56.0 Hz, 1H), 4.43-4.42 (m, 1H), 4.33-4.32 (m, 1H), 4.00 (s, 2H), 3.86 (s, 3H), 3.81-3.72 (m, 6H), 3.08-3.05 (m, 2H), 2.87-2.86 (m, 2H), 2.79 (d, J=4.4 Hz, 3H), 2.74-2.72 (m, 2H), 2.56-2.54 (m, 4H), 2.21 (s, 3H), 2.10-2.05 (m, 2H). LCMS M/Z (M+H) 588.

| Example | Compound Name | NMR | m/z |
| --- | --- | --- | --- |
| Example 323 | 1-[3-[7-(difluoromethyl)-6-(1-methylpyrazol-4-yl)-3,4-dihydro-2H-quinolin-1-yl]-1-(1,1-dioxothian-4-yl)-6,7-dihydro-4H-pyrazolo[4,3-c]pyridin-5-yl]ethanone | $^1$H NMR (400 MHz, DMSO-d$_6$) δ 7.76 (s, 1H), 7.50 (s, 1H), 7.11 (s, 1H), 6.94-6.65 (m, 2H), 4.52-4.48 (m, 1H), 4.16-4.11 (m, 2H), 3.86 (s, 3H), 3.75-3.69 (m, 2H), 3.60-3.58 (m, 2H), 3.35-3.30 (m, 2H), 3.25-3.22 (m, 2H), 2.84-2.73 (m, 4H), 2.43-2.41 (m, 2H), 2.23-2.20 (m, 2H), 2.07-1.96 (m, 5H) | 559 |

The Following Compounds were Prepared in a
Similar Fashion to Example 324

Examples 325-326

| Example | Compound Name | NMR | m/z |
|---------|---------------|-----|-----|
| Example 325 | 3-[7-(difluoromethyl)-6-(1-methylpyrazol-4-yl)-3,4-dihydro-2H-quinolin-1-yl]-1-(1,1-dioxothian-4-yl)-N-methyl-6,7-dihydro-4H-pyrazolo[4,3-c]pyridine-5-carboxamide | $^1$H NMR (400 MHz, CDCl$_3$) δ 7.55 (s, 1H), 7.43 (s, 1H), 7.08 (s, 1H), 6.85 (s, 1H), 6.57 (t, J = 55.6 Hz, 1H), 4.47-4.38, (m, 1H), 4.35-4.30 (m, 1H), 3.97-3.94 (m, 5H), 3.83-3.62 (m, 6H), 3.10-3.00 (m, 2H), 2.88-2.84 (m, 2H), 2.79 (d, J = 4.4 Hz, 3H), 2.74-2.68 (m, 2H), 2.57-2.53 (m, 4H), 2.11-2.06 (m, 2H) | 574 |
| Example 326 | 3-[7-(difluoromethyl)-6-[1-methyl-3-(trifluoromethyl)pyrazol-4-yl]-3,4-dihydro-2H-quinolin-1-yl]-1-(1,1-dioxothian-4-yl)-N-methyl-6,7-dihydro-4H-pyrazolo[4,3-c]pyridine-5-carboxamide | $^1$H NMR (400 MHz, CDCl$_3$) δ 7.39 (s, 1H), 6.99 (s, 1H), 6.82 (s, 1H), 6.35 (t, J = 55.2 Hz, 1H), 4.38-4.33 (m, 2H), 4.01 (s, 3H), 3.95 (s, 2H), 3.81-3.72 (m, 6H), 3.07-3.03 (m, 2H), 2.88-2.84 (m, 2H), 2.79 (d, J = 4.0 Hz, 3H), 2.74-2.72 (m, 2H), 2.57-2.50 (m, 4H), 2.10-2.06 (m, 2H) | 642 |

Example 327

1-[4-[5-acetyl-3-[7-(difluoromethyl)-6-(1-methyl-pyrazol-4-yl)-3,4-dihydro-2H-quinolin-1-yl]-6,7-dihydro-4H-pyrazolo[4,3-c]pyridin-1-yl]-1-piperidyl]ethanone Step 1 tert-butyl 1-(1-acetylpiperidin-4-yl)-3-(7-(difluoromethyl)-6-(1-methyl-1H-pyrazol-4-yl)-3,4-dihydroquinolin-1 (2H)-yl)-6,7-dihydro-1H-pyrazolo[4,3-c]pyridine-5(4H)-carboxylate

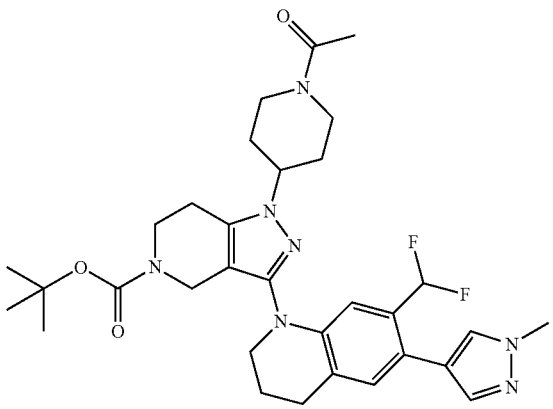 [SMILES: CC(=O)N1CCC(n2nc(N3CCCc4cc(-c5cnn(C)c5)c(C(F)F)cc43)c3c2CCN(C(=O)OC(C)(C)C)C3)CC1]

To a solution of 7-(difluoromethyl)-6-(1-methyl-1H-pyrazol-4-yl)-1,2,3,4-tetrahydroquinoline (370 mg, 1.4 mmol) in dioxane (10 mL) was added tert-butyl 1-(1-acetyl-4-piperidyl)-3-bromo-6,7-dihydro-4H-pyrazolo[4,3-c]pyridine-5-carboxylate (Intermediate L, 500 mg, 1.2 mmol), dichloro[1,3-bis(2,6-di-3-pentylphenyl)imidazol-2-ylidene](3-chloropyridyl)palladium(II) (93 mg, 0.12 mmol) and t-BuONa (562 mg, 5.9 mmol). The mixture was heated to 120° C. for 12 h under a nitrogen atmosphere. After cooling the reaction to room temperature, the mixture was concentrated in vacuo. The crude residue was purified by silica gel chromatography (DCM/MeOH=20:1) to give the title compound (300 mg, 42%) as a yellow solid. ¹H NMR (400 MHz, DMSO-d₆) δ 7.75 (s, 1H), 7.49 (s, 1H), 7.10 (s, 1H), 6.92-6.65 (m, 2H), 4.48-4.41 (m, 1H), 4.31 (s, 2H), 4.02 (s, 2H), 3.94-3.90 (m, 1H), 3.86 (s, 3H), 3.61-3.56 (m, 2H), 3.24-3.09 (m, 1H), 2.84-2.74 (m, 4H), 2.73-2.63 (m, 2H), 2.02 (s, 3H), 1.98-1.85 (m, 6H), 1.41-1.37 (m, 9H).

Step 2

1-(4-(3-(7-(difluoromethyl)-6-(1-methyl-pyrazol-H-pyrazol-4-yl)-3,4-dihydroquinolin-1(2H)-yl)-4,5,6,7-tetrahydro-1H-pyrazolo[4,3-c]pyridin-1-yl)piperidin-1-yl)ethanone

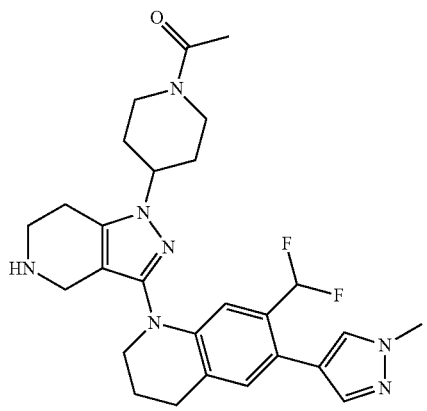 [SMILES: CC(=O)N1CCC(n2nc(N3CCCc4cc(-c5cnn(C)c5)c(C(F)F)cc43)c3c2CCNC3)CC1]

To a solution of tert-butyl 1-(1-acetylpiperidin-4-yl)-3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridine-5(4H)-carboxylate (300 mg, 0.5 mmol) in DCM (2 mL) at 0° C. was added trifluoroacetic acid (0.4 mL, 4.9 mmol) dropwise. The mixture was stirred at room temperature for 1 h. The mixture was concentrated in vacuo. The crude residue was diluted with DCM (50 mL) and washed with sat. aq. NaHCO₃ (30 mL). The organic layer was dried over anhydrous Na₂SO₄, filtered and concentrated in vacuo to give the title compound (200 mg, 70%) as a white solid that required no further purification. LCMS M/Z (M+H) 510.

Step 3

1-[4-[5-acetyl-3-[7-(difluoromethyl)-6-(1-methyl-pyrazol-4-yl)-3,4-dihydro-2H-quinolin-1-yl]-6,7-dihydro-4H-pyrazolo[4,3-c]pyridin-1-yl]-1-piperidyl]ethanone

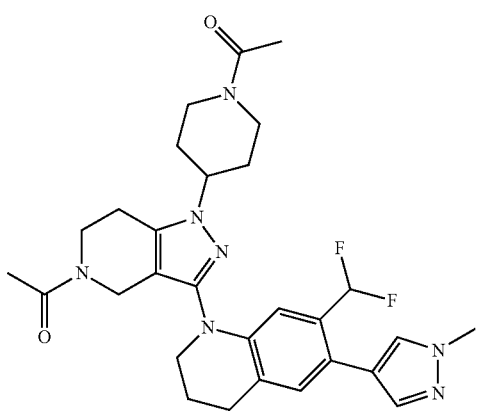 [SMILES: CC(=O)N1CCC(n2nc(N3CCCc4cc(-c5cnn(C)c5)c(C(F)F)cc43)c3c2CCN(C(C)=O)C3)CC1]

To a solution of 1-(4-(3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)ethanone (100 mg, 0.17 mmol) in DCM (2 mL) at 0° C. was added triethylamine (0.07 mL, 0.52 mmol) and acetic anhydride (0.021 mL, 0.21 mmol). The mixture was stirred at room temperature for 1 h. The mixture was diluted with DCM (50 mL), and washed with water (40 mL) and brine (40 mL). The organic layer was dried over anhydrous Na₂SO₄, filtered and concentrated in vacuo. The crude residue was purified by Prep-TLC (DCM/MeOH=20:1) to give the title compound (53 mg, 52%) as a white solid. ¹H NMR (400 MHz, DMSO-d₆) δ 7.75 (s, 1H), 7.50 (s, 1H), 7.10 (s, 1H), 6.94-6.64 (m, 2H), 4.46-4.42 (m, 1H), 4.39-4.26 (m, 1H), 4.21-4.08 (m, 2H), 3.93-3.89 (m, 1H), 3.86 (s, 3H), 3.79-3.65 (m, 2H), 3.63-3.52 (m, 2H), 3.25-3.11 (m, 1H), 2.90-2.83 (m, 3H), 2.80-2.64 (m, 2H), 2.08-1.96 (m, 6H), 1.95-1.83 (m, 5H), 1.80-1.67 (m, 1H). LCMS M/Z (M+H) 552.

Example 328

1-(1-acetyl-4-piperidyl)-3-[7-(difluoromethyl)-6-(1-methylpyrazol-4-yl)-3,4-dihydro-2H-quinolin-1-yl]-N-methyl-6,7-dihydro-4H-pyrazolo[4,3-c]pyridine-5-carboxamide

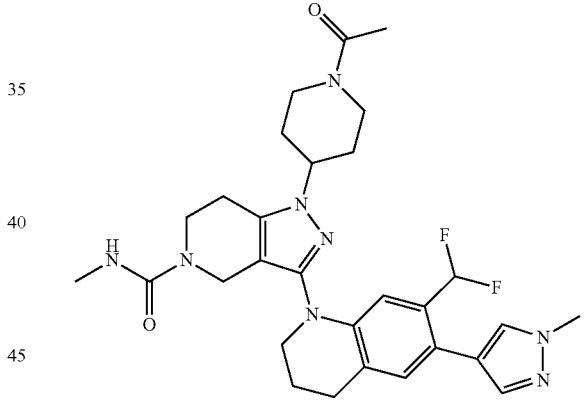

To a solution of 1-(4-(3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)ethanone (100 mg, 0.17 mmol) in DCM (3 mL) was added triethylamine (0.07 mL, 0.52 mmol) and N-methyl-1H-imidazole-1-carboxamide (26 mg, 0.21 mmol). The mixture was stirred at room temperature for 3 h. The mixture was diluted with DCM (50 mL), and washed with water (40 mL) and brine (40 mL). The organic layer was dried over anhydrous Na₂SO₄, filtered and concentrated in vacuo. The crude residue was purified by Prep-TLC (DCM/MeOH=20:1) to give the title compound (29 mg, 29%) as a white solid ¹H NMR (400 MHz, DMSO-d₆) δ 7.75 (s, 1H), 7.49 (s, 1H), 7.09 (s, 1H), 6.94-6.62 (m, 2H), 6.55 (d, J=4.4 Hz, 1H), 4.45-4.42 (m, 1H), 4.37-4.25 (m, 1H), 4.01 (s, 2H), 3.94-3.87 (m, 1H), 3.86 (s, 3H), 3.66-3.52 (m, 4H), 3.22-3.15 (m, 1H), 2.89-2.78 (m, 2H), 2.78-2.62 (m, 3H), 2.54 (d, J=4.4 Hz, 3H), 2.02 (s, 3H), 2.00-1.81 (m, 5H), 1.79-1.65 (m, 1H). LCMS M/Z (M+H) 567.

The Following Compound was Prepared in a Similar Fashion to Example 328

Examples 329

| Example | Compound Name | NMR | m/z |
|---|---|---|---|
| Example 329 | 1-(1-acetyl-4-piperidyl)-N-methyl-3-[4-methyl-6-(1-methylpyrazol-4-yl)-7-(trifluoromethyl)-2,3-dihydroquinoxalin-1-yl]-6,7-dihydro-4H-pyrazolo[4,3-c]pyridine-5-carboxamide | $^1$H NMR (400 MHz, CDCl$_3$) δ 7.57 (s, 1H), 7.45 (s, 1H), 6.77 (s, 1H), 6.52 (s, 1H), 4.78-4.70 (m, 1H), 4.40-4.30 (m, 1H), 4.17-4.07 (m, 1H), 4.04-3.93 (m, 6H), 3.84-3.76 (m, 4H), 3.49-3.47 (m, 2H), 3.26-3.20 (m, 1H), 3.00 (s, 3H), 2.81-2.71 (m, 6H), 2.23-1.90 (m, 7H) | 600 |

Example 330

N-methyl-3-[4-methyl-6-(1-methylpyrazol-4-yl)-7-(trifluoromethyl)-2,3-dihydroquinoxalin-1-yl]-1-[1-(oxetan-3-yl)-4-piperidyl]-6,7-dihydro-4H-pyrazolo[4,3-c]pyridine-5-carboxamide

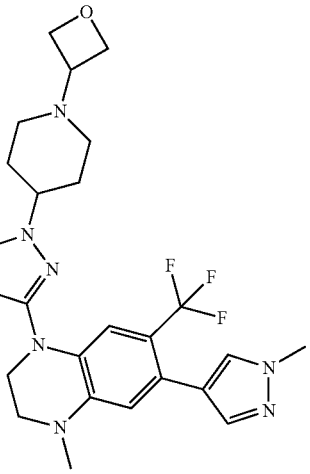

Step 1 tert-butyl 3-(4-methyl-6-(1-methyl-1H-pyrazol-4-yl)-7-(trifluoromethyl)-3,4-dihydroquinoxalin-1(2H)-yl)-1-(1-(oxetan-3-yl)piperidin-4-yl)-6,7-dihydro-1H-pyrazolo[4,3-c]pyridine-5(4H)-carboxylate

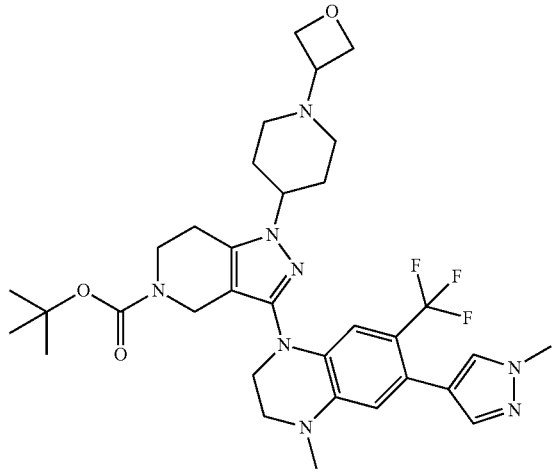 [SMILES: CN1CCN(c2nn(C3CCN(C4COC4)CC3)c3c2CN(C(=O)OC(C)(C)C)CC3)c2cc(C(F)(F)F)c(-c3cnn(C)c3)cc21]

To a solution of tert-butyl 3-bromo-1-(1-(oxetan-3-yl)piperidin-4-yl)-6,7-dihydro-1H-pyrazolo[4,3-c]pyridine-5(4H)-carboxylate (Intermediate V, 150 mg, 0.34 mmol), 4-methyl-6-(1-methylpyrazol-4-yl)-7-(trifluoromethyl)-2,3-dihydro-1H-quinoxaline (100 mg, 0.34 mmol) and t-BuONa (97 mg, 1.01 mmol) in 1,4-dioxane (4 mL) was added chloro(2-dicyclohexylphosphino-2',6'-di-i-propoxy-1,1'-biphenyl)(2'-amino-1,1'-biphenyl-2-yl)palladium(II) (26 mg, 0.03 mmol) and 2-dicyclohexylphosphino-2',6'-di-i-propoxy-1,1'-biphenyl (16 mg, 0.03 mmol). The mixture was heated to 120° C. for 16 h under a nitrogen atmosphere. After cooling the reaction to room temperature, the reaction was filtered and concentrated in vacuo. The crude residue was purified by silica gel chromatography (DCM/MeOH=50/1) to give the title compound (140 mg, 63%) as a yellow oil. LCMS M/Z (M+H) 657.

Step 2

1-methyl-7-(1-methyl-1H-pyrazol-4-yl)-4-(1-(1-(oxetan-3-yl)piperidin-4-yl)-3a,4,5,6,7,7a-hexahydro-1H-pyrazolo[4,3-c]pyridin-3-yl)-6-(trifluoromethyl)-1,2,3,4-tetrahydroquinoxaline

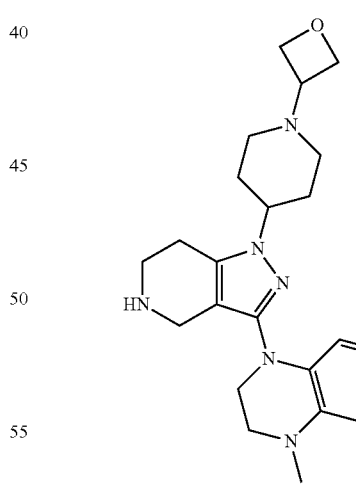

To a solution of tert-butyl 3-(4-methyl-6-(1-methyl-1H-pyrazol-4-yl)-7-(trifluoromethyl)-3,4-dihydroquinoxalin-1(2H)-yl)-1-(1-(oxetan-3-yl)piperidin-4-yl)-6,7-dihydro-1H-pyrazolo[4,3-c]pyridine-5(4H)-carboxylate (140 mg, 0.21 mmol) in DCM (2 mL) at 0° C. was added trifluoroacetic acid (0.32 mL, 4.26 mmol). The mixture was stirred at room temperature for 1 h. The reaction was quenched with sat. aq. NaHCO$_3$ (10 mL) and extracted with DCM (20 mL). The organic layer was dried over anhydrous Na$_2$SO$_4$, filtered and concentrated in vacuo to give the title compound (80 mg, crude) as a brown oil. LCMS M/Z (M+H) 557.

Step 3

N-methyl-3-[4-methyl-6-(1-methylpyrazol-4-yl)-7-(trifluoromethyl)-2,3-dihydroquinoxalin-1-yl]-1-[1-(oxetan-3-yl)-4-piperidyl]-6,7-dihydro-4H-pyrazolo[4,3-c]pyridine-5-carboxamide

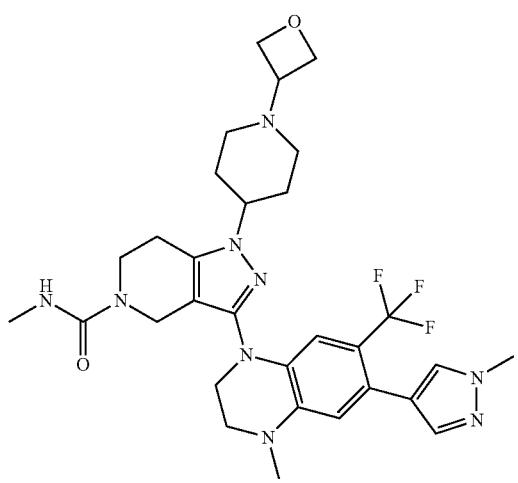

To a solution of 1-methyl-7-(1-methylpyrazol-4-yl)-4-[1-[1-(oxetan-3-yl)-4-piperidyl]-4,5,6,7-tetrahydropyrazolo[4,3-c]pyridin-3-yl]-6-(trifluoromethyl)-2,3-dihydroquinoxaline (80 mg, 0.14 mmol) and triethylamine (0.08 mL, 0.57 mmol) in DCM (2 mL) was added N-methyl-1H-imidazole-1-carboxamide (54 mg, 0.43 mmol). The mixture was stirred at room temperature for 16 h. Water (10 mL) was added and extracted with DCM (20 mL). The organic layer was dried over anhydrous $Na_2SO_4$, filtered and concentrated in vacuo. The crude residue was purified by reverse phase chromatography (acetonitrile 20-50%/0.05% $NH_4OH$ in water) to give the title compound (35 mg, 40%) as a white solid. $^1$H NMR (400 MHz, DMSO-$d_6$) δ 7.75 (s, 1H), 7.46 (s, 1H), 6.77 (s, 1H), 6.58-6.52 (m, 1H), 6.51 (s, 1H), 4.53 (t, J=6.4 Hz, 2H), 4.42 (t, J=6.4 Hz, 2H), 4.12-3.94 (m, 3H), 3.86 (s, 3H), 3.73-3.65 (m, 2H), 3.60-3.57 (m, 2H), 3.49-3.42 (m, 3H), 2.96 (s, 3H), 2.81-2.64 (m, 4H), 2.54-2.52 (m, 3H), 2.07-1.77 (m, 6H). LCMS M/Z (M+H) 614.

The Following Compound was Prepared in a Similar Fashion to Example 330

Example 332

3-[7-(difluoromethyl)-6-(1-methylpyrazol-4-yl)-3,4-dihydro-2H-quinolin-1-yl]-N-methyl-1,4,6,7-tetrahydropyrazolo[4,3-c]pyridine-5-carboxamide

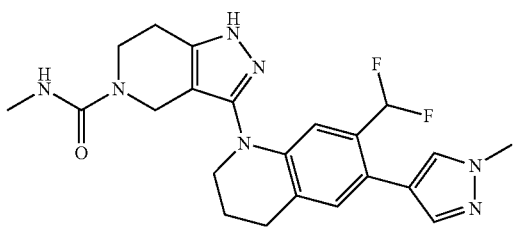

Step 1

7-(difluoromethyl)-6-(1-methyl-1H-pyrazol-4-yl)-1-(1-((2-(trimethylsilyl)ethoxy)methyl)-4,5,6,7-tetrahydro-1H-pyrazolo[4,3-c]pyridin-3-yl)-1,2,3,4-tetrahydroquinoline

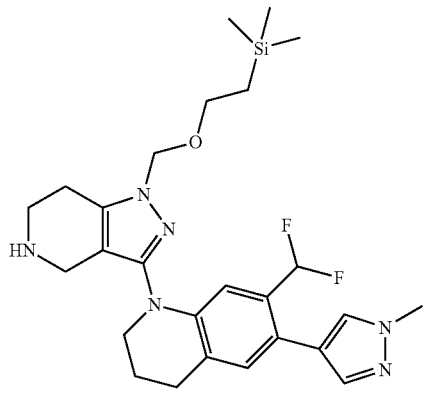 [SMILES: Cn1cc(-c2cc3c(cc2C(F)F)N(c2nn(COCC[Si](C)(C)C)c4c2CNCC4)CCC3)cn1]

A mixture of tert-butyl 3-(7-(difluoromethyl)-6-(1-methyl-1H-pyrazol-4-yl)-3,4-dihydroquinolin-1 (2H)-yl)-1-((2-(trimethylsilyl)ethoxy)methyl)-6,7-dihydro-1H-pyrazolo[4,3-c]pyridine-5(4H)-carboxylate (Intermediate T, 100 mg, 0.16 mmol) and formic acid (1.48 mL, 40 mmol) was stirred at 16° C. for 16 h. The reaction solution was concentrated in vacuo to give the title compound (80 mg, crude) as a yellow oil that required no further purification. LCMS M/Z (M+H) 515.

| Example 331 | 3-[7-chloro-6-(1-methylpyrazol-4-yl)-3,4-dihydro-2H-quinolin-1-yl]-N-methyl-1-[1-(oxetan-3-yl)-4-piperidyl]-6,7-dihydro-4H-pyrazolo[4,3-c]pyridine-5-carboxamide | $^1$H NMR (400 MHz, DMSO-$d_6$) δ 7.96 (s, 1H), 7.67 (s, 1H), 7.19 (s, 1H), 6.56-6.52 (m, 1H), 6.50 (s, 1H), 4.53 (t, J = 6.8 Hz, 2H), 4.42 (t, J = 6.4 Hz, 2H), 4.05-4.01 (m, 3H), 3.85 (s, 3H), 3.63-3.50 (m, 4H), 3.48-3.46 (m, 1H), 2.83-2.64 (m, 6H), 2.54 (d, J = 4.4 Hz., 3H), 2.03-1.78 (m, 8H). | 565 |
|---|---|---|---|

631

Step 2

3-(7-(difluoromethyl)-6-(1-methyl-1H-pyrazol-4-yl)-3,4-dihydroquinolin-1(2H)-yl)-N-methyl-1-((2-(trimethylsilyl)ethoxy)methyl)-6,7-dihydro-1H-pyrazolo[4,3-c]pyridine-5(4H)-carboxamide

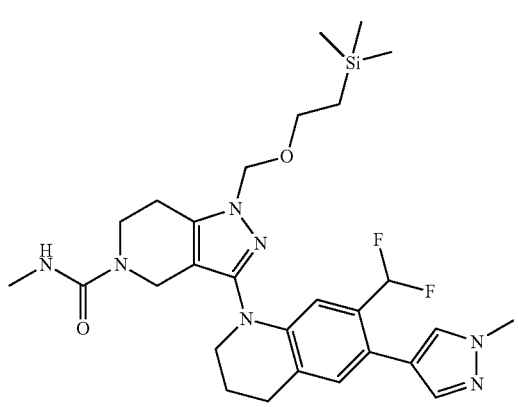

To a solution of 7-(difluoromethyl)-6-(1-methyl-1H-pyrazol-4-yl)-1-(1-((2-(trimethylsilyl)ethoxy)methyl)-4,5,6,7-tetrahydro-1H-pyrazolo[4,3-c]pyridin-3-yl)-1,2,3,4-tetrahydroquinoline (80 mg, 0.16 mmol) in DCM (15 mL) at 16° C. was added triethylamine (0.07 mL, 0.47 mmol) and N-methyl-1H-imidazole-1-carboxamide (39 mg, 0.31 mmol). The mixture was stirred at 16° C. for 16 h. The reaction solution was diluted with DCM (50 mL) and washed with brine (30 mL×3). The organic layer was dried over anhydrous Na$_2$SO$_4$, filtered and concentrated in vacuo. The crude residue was purified by Prep-TLC (DCM/MeOH=20:1) to give the title compound (40 mg, 45%) as a white solid. LCMS M/Z (M+H) 572.

Step 3

3-[7-(difluoromethyl)-6-(1-methylpyrazol-4-yl)-3,4-dihydro-2H-quinolin-1-yl]-N-methyl-1,4,6,7-tetrahydropyrazolo[4,3-c]pyridine-5-carboxamide

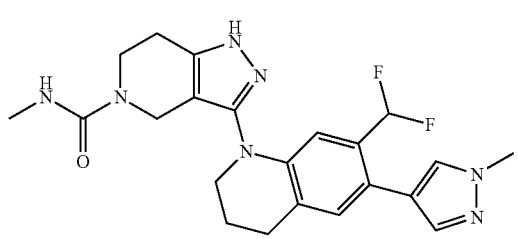

To a solution of 3-(7-(difluoromethyl)-6-(1-methyl-1H-pyrazol-4-yl)-3,4-dihydroquinolin-1(2H)-yl)-N-methyl-1-((2-(trimethylsilyl)ethoxy)methyl)-6,7-dihydro-1H-pyrazolo[4,3-c]pyridine-5(4H)-carboxamide (30 mg, 0.05 mmol) in DCM (10 mL) was added trifluoroacetic acid (1.5 mL, 17.54 mmol). The mixture was stirred at 16° C. for 4 h and concentrated in vacuo. The crude residue was purified by reverse phase chromatography (acetonitrile 15-45%/0.225% formic acid in water) to give the title compound (8 mg, 34%) as a white solid. $^1$H NMR (400 MHz, CDCl$_3$) δ 7.63 (s, 1H), 7.51 (s, 1H), 7.17 (s, 1H), 7.01 (s, 1H), 6.61 (t, J=55.6 Hz, 1H), 4.03-4.00 (m, 5H), 3.90 (s, 2H), 3.70 (t, J=5.6 Hz, 2H), 3.02 (t, J=4.0 Hz, 2H), 2.87-2.84 (m, 2H), 2.78 (s, 3H), 2.14-2.11 (m, 2H). LCMS M/Z (M+H) 442.

632

Example 333

1-[3-[7-(difluoromethyl)-6-(1-methylpyrazol-4-yl)-3,4-dihydro-2H-quinolin-1-yl]-1,4,6,7-tetrahydropyrazolo[4,3-c]pyridin-5-yl]ethanone

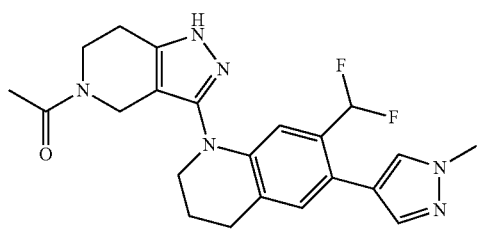 [SMILES: CC(=O)N1CCc2[nH]nc(N3CCCc4cc(-c5cnn(C)c5)c(C(F)F)cc43)c2C1]

Step 1

7-(difluoromethyl)-6-(1-methyl-1H-pyrazol-4-yl)-1-(4,5,6,7-tetrahydro-1H-pyrazolo[4,3-c]pyridin-3-yl)-1,2,3,4-tetrahydroquinoline

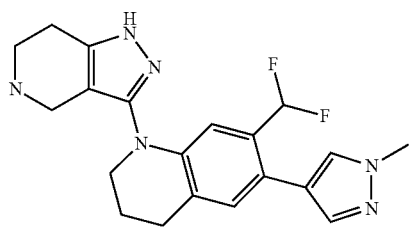 [SMILES: Cn1cc(-c2cc3c(cc2C(F)F)N(c2n[nH]c4c2CNCC4)CCC3)cn1]

To a solution of tert-butyl 3-(7-(difluoromethyl)-6-(1-methyl-1H-pyrazol-4-yl)-3,4-dihydroquinolin-(2H)-yl)-6,7-dihydro-1H-pyrazolo[4,3-c]pyridine-5(4H)-carboxylate (Intermediate U, 2.0 g, 4.13 mmol) in DCM (5 mL) at 0° C. was added trifluoroacetic acid (4.0 mL, 4.13 mmol). The mixture was stirred at 20° C. for 16 h and concentrated in vacuo to give the title compound (2.0 g, crude) as a brown oil that required no further purification. LCMS M/Z (M+H) 385.

Step 2

1-[3-[7-(difluoromethyl)-6-(1-methylpyrazol-4-yl)-3,4-dihydro-2H-quinolin-1-yl]-1,4,6,7-tetrahydropyrazolo[4,3-c]pyridin-5-yl]ethanone

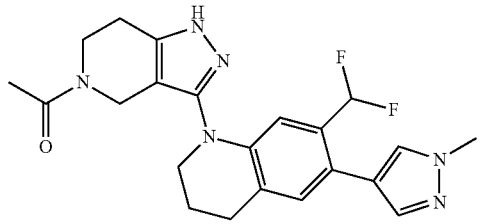 [SMILES: CC(=O)N1CCc2[nH]nc(N3CCCc4cc(-c5cnn(C)c5)c(C(F)F)cc43)c2C1]

To a solution of 7-(difluoromethyl)-6-(1-methyl-1H-pyrazol-4-yl)-1-(4,5,6,7-tetrahydro-1H-pyrazolo[4,3-c]pyridin-3-yl)-1,2,3,4-tetrahydroquinoline (120 mg, 0.31 mmol) in DCM (5 mL) at 0° C. was added triethylamine (0.09 mL, 0.62 mmol) and acetic anhydride (0.04 mL, 0.62 mmol). The mixture was stirred at 20° C. for 1 h. DCM (50 mL) was added and the mixture was washed with water (30 mL×3) and brine (30 mL). The organic layer was dried over anhydrous Na$_2$SO$_4$, filtered and concentrated in vacuo. The crude residue was purified by reverse phase chromatography (acetonitrile 26-56%/0.05% NH$_4$OH in water) to give the title compound (19 mg, 14%) as a white solid. $^1$H NMR (400 MHz, DMSO-d$_6$) δ 12.42-12.31 (m, 1H), 7.75 (s, 1H), 7.50 (s, 1H), 7.10 (s, 1H), 6.96-6.62 (m, 2H), 4.21-4.04 (m, 2H), 3.86 (s, 3H), 3.76-3.51 (m, 4H), 2.88-2.66 (m, 4H), 2.07-1.87 (m, 5H). LCMS M/Z (M+H) 427.

Example 334

3-[7-(difluoromethyl)-6-(1-methylpyrazol-4-yl)-3,4-dihydro-2H-quinolin-1-yl]]-N-methyl-1-[1-(2,2,2-trifluoroethyl)-4-piperidyl]-6,7-dihydro-4H-pyrazolo[4,3-c]pyridine-5-carboxamide

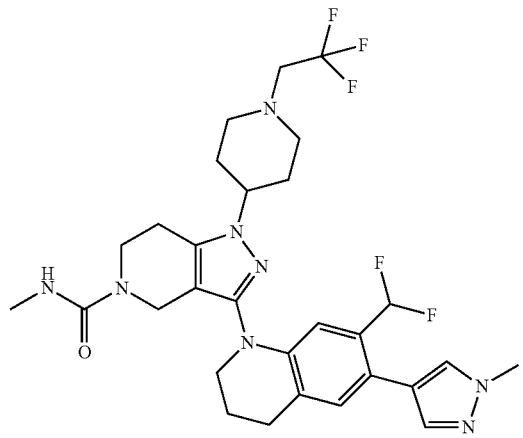

tert-butyl 1-(1-((benzyloxy)carbonyl)piperidin-4-yl)-3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridine-5(4H)-carboxylate

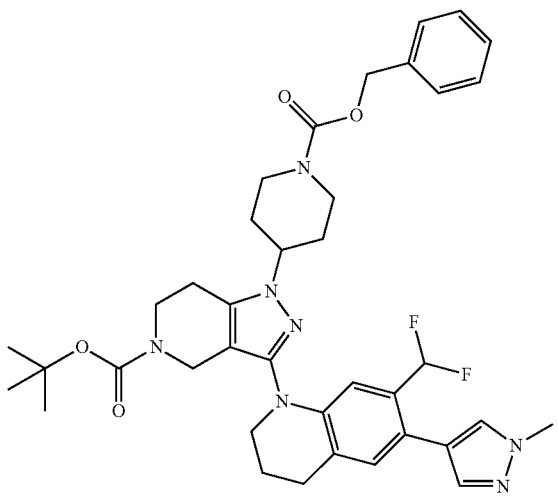 [SMILES: Cn1cc(-c2cc3c(cc2C(F)F)N(c2nn(C4CCN(C(=O)OCc5ccccc5)CC4)c4c2CN(C(=O)OC(C)(C)C)CC4)CCC3)cn1]

To a solution of tert-butyl 3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridine-5(4H)-carboxylate (Intermediate U, 700 mg, 1.44 mmol) in 1,4-dioxane (10 mL) was added benzyl 4-(2-tosylhydrazono)piperidine-1-carboxylate (696 mg, 1.73 mmol), Cs$_2$CO$_3$ (1.04 g, 3.18 mmol) and copper (II) acetylacetonate (38 mg, 0.14 mmol). The mixture was heated to 100° C. for 16 h under a nitrogen atmosphere. After cooling the reaction to room temperature, the mixture was filtered. The filtrate was concentrated in vacuo. The crude residue was purified by silica gel chromatography (DCM/MeOH=20:1) to give the title compound (650 mg, 65%) as a brown solid. LCMS M/Z (M+H) 702.

Step 2 tert-butyl 3-(7-(difluoromethyl)-6-(1-methyl-1H-pyrazol-4-yl)-3,4-dihydroquinolin-1(2H)-yl)-1-(piperidin-4-yl)-6,7-dihydro-1H-pyrazolo[4,3-c]pyridine-5(4H)-carboxylate

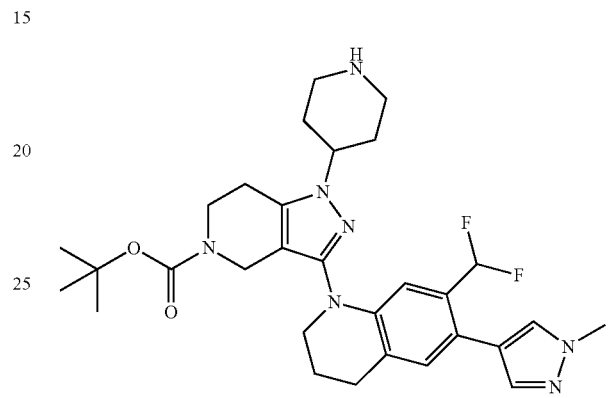

To a solution of tert-butyl 1-(1-((benzyloxy)carbonyl)piperidin-4-yl)-3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridine-5(4H)-carboxylate (650 mg, 0.93 mmol) in MeOH (10 mL) was added 10% Pd/C (50 mg). The mixture was stirred at 25° C. for 6 h under a hydrogen atmosphere (15 psi). The mixture was filtered and concentrated in vacuo to give the title compound (420 mg, 80%) as a white solid that required no further purification. LCMS M/Z (M+H) 568

Step 3 tert-butyl 3-(7-(difluoromethyl)-6-(1-methyl-1H-pyrazol-4-yl)-3,4-dihydroquinolin-1(2H)-yl)-1-(1-(2,2,2-trifluoroethyl)piperidin-4-yl)-6,7-dihydro-1H-pyrazolo[4,3-c]pyridine-5(4H)-carboxylate

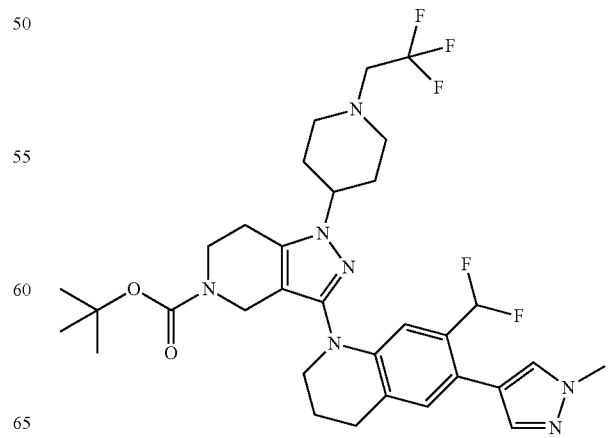

To a solution of tert-butyl 3-(7-(difluoromethyl)-6-(1-methyl-1H-pyrazol-4-yl)-3,4-dihydroquinolin-1(2H)-yl)-1-(piperidin-4-yl)-6,7-dihydro-1H-pyrazolo[4,3-c]pyridine-5(4H)-carboxylate (70.0 mg, 0.12 mmol) in MeCN (2 mL) was added triethylamine (0.052 mL, 0.37 mmol) and 2,2,2-trifluoroethyltrifluoromethanesulfonate (0.036 mL, 0.25 mmol). The mixture was stirred at 25° C. for 2 h. Water (10 mL) was added and the mixture was extracted with EtOAc (10 mL×3). The combined organic layers were dried over anhydrous Na₂SO₄, filtered and concentrated in vacuo to give the title compound (70 mg, crude) as a yellow solid that required no further purification. LCMS M/Z (M+H) 650.

Step 4

7-(difluoromethyl)-6-(1-methyl-1H-pyrazol-4-yl)-1-(1-(1-(2,2,2-trifluoroethyl)piperidin-4-yl)-4,5,6,7-tetrahydro-1H-pyrazolo[4,3-c]pyridin-3-yl)-1,2,3,4-tetrahydroquinoline

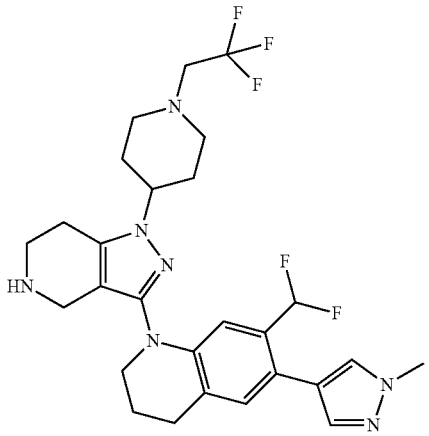 [SMILES: Cn1cc(-c2cc3c(cc2C(F)F)N(c2nn(C4CCN(CC(F)(F)F)CC4)c4c2CNCC4)CCC3)cn1]

To a solution of tert-butyl 3-(7-(difluoromethyl)-6-(1-methyl-1H-pyrazol-4-yl)-3,4-dihydroquinolin-1(2H)-yl)-1-(1-(2,2,2-trifluoroethyl)piperidin-4-yl)-6,7-dihydro-1H-pyrazolo[4,3-c]pyridine-5(4H)-carboxylate (70 mg, 0.11 mmol) in DCM (1 mL) at 0° C. was added trifluoroacetic acid (0.08 mL, 1.1 mmol). The mixture was stirred at 25° C. for 2 h and concentrated in vacuo to give the title compound (50 mg, crude) as a brown oil that required no further purification. LCMS M/Z (M+H) 550.

Step 5

3-[7-(difluoromethyl)-6-(1-methylpyrazol-4-yl)-3,4-dihydro-2H-quinolin-1-yl]-N-methyl-1-[1-(2,2,2-trifluoroethyl)-4-piperidyl]-6,7-dihydro-4H-pyrazolo[4,3-c]pyridine-5-carboxamide To a solution of 7-(difluoromethyl)-6-(1-methyl-1H-pyrazol-4-yl)-1-(1-(1-(2,2,2-trifluoroethyl)piperidin-4-yl)-4,5,6,7-tetrahydro-1H-pyrazolo[4,3-c]pyridin-3-yl)-1,2,3,4-tetrahydroquinoline (50 mg, 0.09 mmol) in DCM (3 mL) was added triethylamine (0.038 mL, 0.27 mmol) and N-methyl-1H-imidazole-1-carboxamide (23 mg, 0.18 mmol). The mixture was stirred at 25° C. for 3 h and concentrated in vacuo. The crude residue was purified by reverse phase chromatography (acetonitrile 30-60%/0.225% formic acid in water) to give the title compound (19 mg, 34%) as a white solid. ¹H NMR (400 MHz, CDCl₃) δ 7.55 (s, 1H), 7.42 (s, 1H), 7.05 (s, 1H), 6.86 (s, 1H), 6.55 (d, J=55.6 Hz, 1H), 4.39-4.38 (m, 1H), 3.96-3.80 (m, 6H), 3.79-3.72 (m, 4H), 3.13-3.04 (m, 4H), 2.88-2.87 (m, 2H), 2.79-2.75 (m, 5H), 2.58-2.57 (m, 2H), 2.31-2.29 (m, 2H), 2.08-2.07 (m, 2H), 1.91-1.88 (m, 2H). LCMS M/Z (M+H) 607.

The Following Compounds were Prepared in a Similar Fashion to Example 334

Examples 335-339

| Example | Compound Name | NMR | m/z |
|---|---|---|---|
| Example 335 | 1-[1-(2,2-difluoroethyl)-4-piperidyl]-3-[7-(difluoromethyl)-6-(1-methylpyrazol-4-yl)-3,4-dihydro-2H-quinolin-1-yl]-N-methyl-6,7-dihydro-4H-pyrazolo[4,3-c]pyridine-5-carboxamide | ¹H NMR (400 MHz, CDCl₃) δ 7.54 (s, 1H), 7.41(s, 1H), 7.04 (s, 1H), 6.86 (s, 1H), 6.55 (t, J = 55.6 Hz, 1H), 6.04-5.74 (m, 1H), 4.40-4.39 (m, 1H), 3.96-3.80 (m, 6H), 3.78-3.72 (m, 4H), 3.10-3.07 (m, 2H), 2.87-2.73 (m, 9H), 2.39-2.25 (m, 4H), 2.06-2.01 (m, 2H), 1.92-1.90 (m, 2H) | 589 |
| Example 336 | 3-[7-(difluoromethyl)-6-(1-methylpyrazol-4-yl)-3,4-dihydro-2H-quinolin-1-yl]-N-methyl-1-[1-(oxetan-3-yl)-4-piperidyl]-6,7- | ¹H NMR (400 MHz, CDCl₃) δ 7.54 (s, 1H), 7.42 (s, 1H), 7.05 (s, 1H), 6.86 (s, 1H), 6.55 (d, J = 55.6 Hz, 1H), 4.69-4.62 (m, 4H), 4.40-4.39 (s, 1H), 3.96-3.95 (m, 6H), 3.80-3.72 (m, 4H), 3.54-3.52 (m, 1H), 2.89-2.87 (m, 4H), 2.79-2.74 (m, 5H), | 581 |

| Example | Compound Name | NMR | m/z |
|---|---|---|---|
| | dihydro-4H-pyrazolo[4,3-c]pyridine-5-carboxamide | 2.08-2.05 (m, 2H), 1.99-1.93 (m, 6H) | |
| Example 337 | 3-[7-(difluoromethyl)-6-(1-methylpyrazol-4-yl)-3,4-dihydro-2H-quinolin-1-yl]-N-methyl-1-(1-methylsulfonyl-4-piperidyl)-6,7-dihydro-4H-pyrazolo[4,3-c]pyridine-5-carboxamide | $^1$H NMR (400 MHz, CDCl$_3$) δ 7.54 (s, 1H), 7.42 (s, 1H), 7.06 (s, 1H), 6.87 (s, 1H), 6.55 (t, J = 55.6 Hz, 1H), 4.44-4.37 (m, 1H), 4.13-4.03 (m, 1H), 3.99-3.91 (m, 7H), 3.84-3.76 (m, 2H), 3.74-3.70 (m, 2H), 2.97 (t, J = 11.2 Hz, 2H), 2.91-2.87 (m, 2H), 2.85 (s, 3H), 2.79 (d, J = 4.0 Hz, 3H), 2.78-2.72 (m, 2H), 2.38-2.24 (m, 2H), 2.11-2.01 (m, 4H) | 603 |
| Example 338 | (S,S)-3-[7-(difluoromethyl)-6-(1-methylpyrazol-4-yl)-3,4-dihydro-2H-quinolin-1-yl]-N-methyl-1-(2-methyltetrahydropyran-4-yl)-6,7-dihydro-4H-pyrazolo[4,3-c]pyridine-5-carboxamide | $^1$H NMR (400 MHz, CDCl$_3$) δ 7.54 (s, 1H), 7.42 (s, 1H), 7.04 (s, 1H), 6.86 (s, 1H), 6.55 (t, J = 55.6 Hz, 1H), 4.41-4.40 (m, 1H), 4.15-4.12 (m, 2H), 3.97-3.95 (m, 5H), 3.81-3.72 (m, 4H), 3.58-3.54 (m, 2H), 2.88-2.86 (m, 2H), 2.79-2.74 (m, 5H), 2.08-2.06 (m, 1H), 1.96-1.70 (m, 5H), 1.27 (d, J = 6.0 Hz, 3H) | 540 |
| Example 339 | (R,R)-3-[7-(difluoromethyl)-6-(1-methylpyrazol-4-yl)-3,4-dihydro-2H-quinolin-1-yl]-N-methyl-1-(2-methyltetrahydropyran-4-yl)-6,7-dihydro-4H-pyrazolo[4,3-c]pyridine-5-carboxamide | $^1$H NMR (400 MHz, CDCl$_3$) δ 7.54 (s, 1H), 7.41 (s, 1H), 7.04 (s, 1H), 6.86 (s, 1H), 6.54 (t, J = 55.6 Hz, 1H), 4.40-4.39 (m, 1H), 4.15-4.12 (m, 2H), 3.97-3.95 (m, 5H), 3.81-3.72 (m, 4H), 3.58-3.54 (m, 2H), 2.87-2.86 (m, 2H), 2.79-2.74 (m, 5H), 2.08-2.06 (m, 1H), 1.96-1,70 (m, 5H), 1.26 (d, J = 6.0 Hz, 3H). | 540 |

Example 340

3-[7-(difluoromethyl)-6-(1-methylpyrazol-4-yl)-3,4-dihydro-2H-quinolin-1-yl]-N-methyl-1-phenyl-6,7-dihydro-4H-pyrazolo[4,3-c]pyridine-5-carboxamide

Step 1 tert-butyl 3-(7-(difluoromethyl)-6-(1-methyl-1H-pyrazol-4-yl)-3,4-dihydroquinolin-1(2H)-yl)-1-phenyl-6,7-dihydro-1H-pyrazolo[4,3-c]pyridine-5(4H)-carboxylate

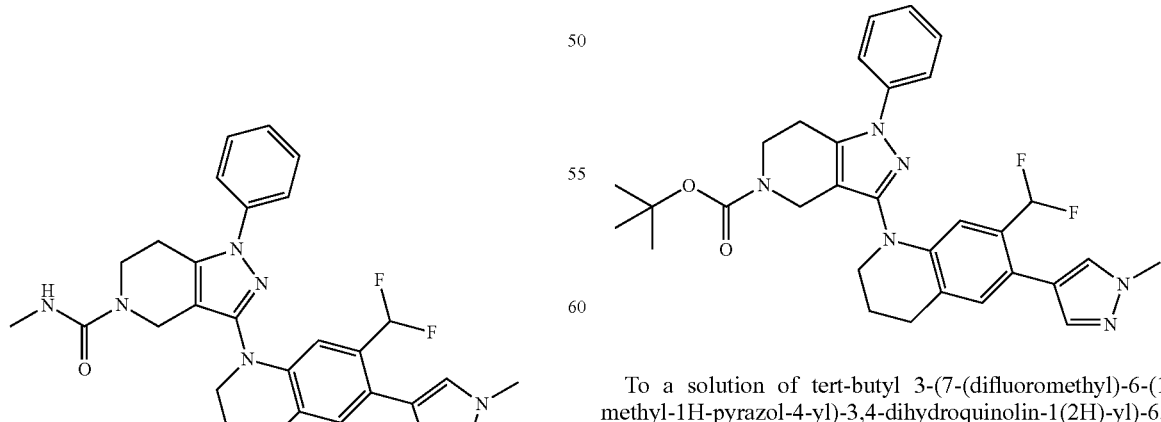

To a solution of tert-butyl 3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridine-5(4H)-carboxylate (Intermediates U, 200 mg, 0.41 mmol) in DCM (8 mL) was added phenylboronic acid (50 mg, 0.41 mmol), copper(II)

acetate (75 mg, 0.41 mmol) and triethylamine (0.139 mL, 1 mmol). The mixture was stirred at room temperature for 16 h under an oxygen atmosphere (15 psi). Water (10 mL) was added and extracted with EtOAc (15 mL×3). The combined organic layers were dried over anhydrous $Na_2SO_4$, filtered and concentrated in vacuo. The crude residue was purified by silica gel chromatography (petroleum ether/EtOAc=1:1) to give the title compound (135 mg, 58%) as colorless oil. LCMS M/Z (M+H) 561.

Step 2

7-(difluoromethyl)-6-(1-methyl-1H-pyrazol-4-yl)-1-(1-phenyl-4,5,6,7-tetrahydro-1H-pyrazolo[4,3-c]pyridin-3-yl)-1,2,3,4-tetrahydroquinoline

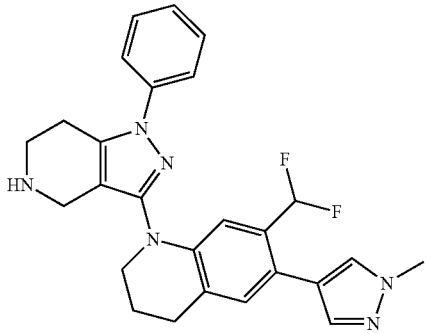

To a solution of tert-butyl 3-(7-(difluoromethyl)-6-(1-methyl-1H-pyrazol-4-yl)-3,4-dihydroquinolin-1(2H)-yl)-1-phenyl-6,7-dihydro-1H-pyrazolo[4,3-c]pyridine-5(4H)-carboxylate (135 mg, 0.24 mmol) in DCM (2 mL) at 0° C. was added trifluoroacetic acid (1.8 mL, 24.1 mmol). The mixture was stirred at 25° C. for 2 h and concentrated in vacuo to give the title compound (110 mg, crude) as a brown oil that required no further purification. LCMS M/Z (M+H) 461.

Step 3

3-[7-(difluoromethyl)-6-(1-methylpyrazol-4-yl)-3,4-dihydro-2H-quinolin-1-yl]-N-methyl-1-phenyl-6,7-dihydro-4H-pyrazolo[4,3-c]pyridine-5-carboxamide

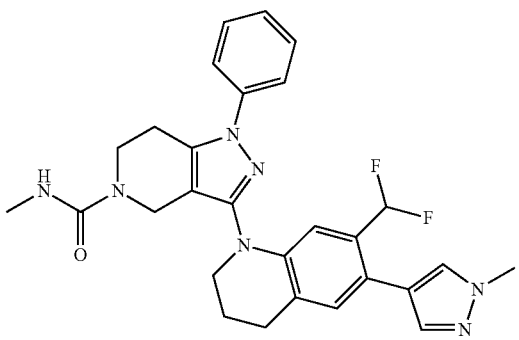

To a solution of 7-(difluoromethyl)-6-(1-methyl-1H-pyrazol-4-yl)-1-(1-phenyl-4,5,6,7-tetrahydro-1H-pyrazolo[4,3-c]pyridin-3-yl)-1,2,3,4-tetrahydroquinoline (110 mg, 0.24 mmol) in DCM (2 mL) was added triethylamine (0.1 mL, 0.72 mmol) and N-methyl-1H-imidazole-1-carboxamide (60 mg, 0.48 mmol). The mixture was stirred at 25° C. for 16 h and concentrated in vacuo. The crude residue was purified by reverse phase chromatography (acetonitrile 23-53%/0.225% formic acid in water) to give the title compound (37 mg, 29%) as a white solid. $^1$H NMR (400 MHz, $CDCl_3$) δ 7.57 (s, 1H), 7.52-7.44 (m, 5H), 7.36-7.29 (m, 1H), 7.09 (s, 1H), 7.00 (s, 1H), 6.73 (t, J=55.2 Hz, 1H), 4.47-4.39 (m, 1H), 4.05 (s, 2H), 3.98 (s, 3H), 3.87 (t, J=5.6 Hz, 2H), 3.77 (t, J=5.6 Hz, 2H), 2.93-2.89 (m, 4H), 2.82 (d, J=4.4 Hz, 3H), 2.13-2.09 (m, 2H). LCMS M/Z (M+H) 518.

The Following Compounds were Prepared in a Similar Fashion to Example 340

Examples 341-342

| Example | Compound Name | NMR | m/z |
|---|---|---|---|
| Example 341 | 3-[7-(difluoromethyl)-6-(1-methylpyrazol-4-yl)-3,4-dihydro-2H-quinolin-1-yl]-N-methyl-1-(3-pyridyl)-6,7-dihydro-4H-pyrazolo[4,3-c]pyridine-5-carboxamide | $^1$H NMR (400 MHz, DMSO-$d_6$) δ 8.84 (d, J = 2.4 Hz, 1H), 8.53 (d, J = 4.4 Hz, 1H), 8.01 (d, J = 8.4 Hz, 1H), 7.77 (s, 1H), 7.55-7.52 (m, 2H), 7.15 (s, 1H), 6.91 (s, 1H), 6.83 (t, J = 55.2 Hz, 1H), 6.62-6.57 (m, 1H), 4.07 (s, 2H), 3.86 (s, 3H), 3.70-3.68 (m, 2H), 3.59-3.57 (m, 2H), 2.92-2.86 (m, 4H), 2.54 (d, J = 4.4 Hz, 3H), 2.01-1.98 (m, 2H). | 519 |
| Example 342 | 3-[7-(difluoromethyl)-6-(1-methylpyrazol-4-yl)-3,4-dihydro-2H-quinolin-1-yl]-N-methyl-1-(4-pyridyl)-6,7-dihydro-4H-pyrazolo[4,3-c]pyridine-5-carboxamide | $^1$H NMR (400 MHz, $CDCl_3$) δ 8.66 (d, J = 6.0 Hz, 2H), 7.57 (s, 1H), 7.51 (d, J = 6.4 Hz, 2H), 7.45 (s, 1H), 7.12 (s, 1H), 7.00 (s, 1H), 6.60 (t, J = 55.6 Hz, 1H), 4.48-4.42 (m, 1H), 4.02 (s, 2H), 3.98 (s, 3H), 3.87 (t, J = 5.6 Hz, 2H), 3.78 (t, J = 5.6 Hz, 2H), 3.08-3.02 (m, 2H), 2.91-2.88 (m, 2H), 2.81 (d, J = 4.4 Hz, 3H), 2.14-2.07 (m, 2H) | 519 |

Examples 343 & 344

(R)-4-[5-acetyl-3-[7-(difluoromethyl)-6-(1-methyl-pyrazol-4-yl)-3,4-dihydro-2H-quinolin-1-yl]-6,7-dihydro-4H-pyrazolo[4,3-c]pyridin-1-yl]piperidin-2-one and (S)-4-[5-acetyl-3-[7-(difluoromethyl)-6-(1-methylpyrazol-4-yl)-3,4-dihydro-2H-quinolin-1-yl]-6,7-dihydro-4H-pyrazolo[4,3-c]pyridin-1-yl]piperidin-2-one

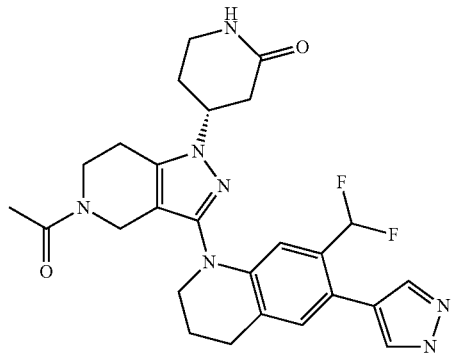

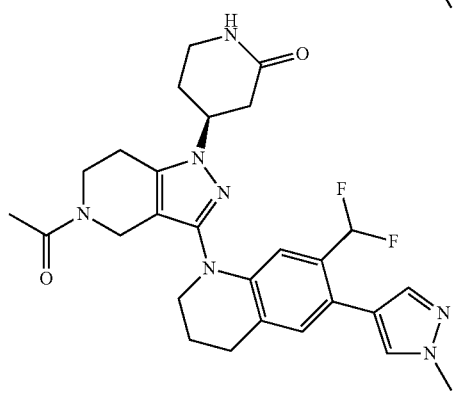

Step 1
tert-butyl 3-(7-(difluoromethyl)-6-(1-methyl-1H-pyrazol-4-yl)-3,4-dihydroquinolin-1(2H)-yl)-1-(2-oxo-1-((2-(trimethylsilyl)ethoxy)methyl)piperidin-4-yl)-6,7-dihydro-1H-pyrazolo[4,3-c]pyridine-5(4H)-carboxylate

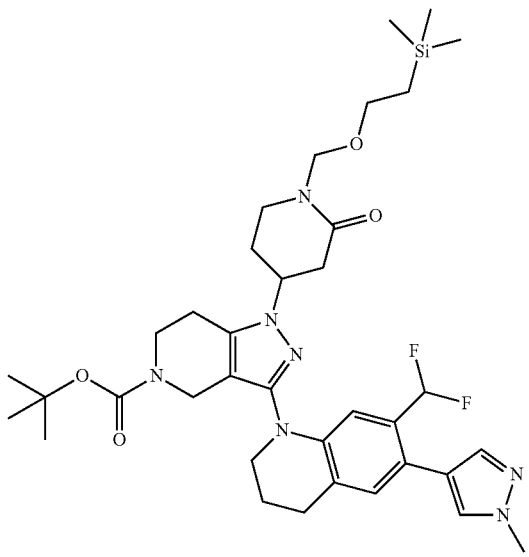 [SMILES: Cn1cc(-c2cc3c(cc2C(F)F)N(c2nn(C4CCN(COCC[Si](C)(C)C)C(=O)C4)c4c2CN(C(=O)OC(C)(C)C)CC4)CCC3)cn1]

To a solution of tert-butyl 3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridine-5(4H)-carboxylate (Intermediates U, 600 mg, 1.24 mmol) in MeCN (10 mL) was added 2,3,4,6,7,8,9,10-octahydropyrimido[1,2-a]azepine (942 mg, 6.19 mmol) and 1-(2-trimethylsilylethoxymethyl)-2,3-dihydropyridin-6-one (845 mg, 3.71 mmol). The mixture was heated to 100° C. for 48 h. The reaction solution was diluted with EtOAc (150 mL), washed with brine (50 mL×3), dried over anhydrous Na$_2$SO$_4$, filtered and concentrated in vacuo. The crude residue was purified by Prep-TLC (DCM/MeOH=20:1) to give the title compound (400 mg, 45%) as a colorless oil. LCMS M/Z (M+23) 734.

Step 2

4-(3-(7-(difluoromethyl)-6-(1-methyl-H-pyrazol-4-yl)-3,4-dihydroquinolin-1(2H)-yl)-4,5,6,7-tetrahydro-1H-pyrazolo[4,3-c]pyridin-1-yl)piperidin-2-one

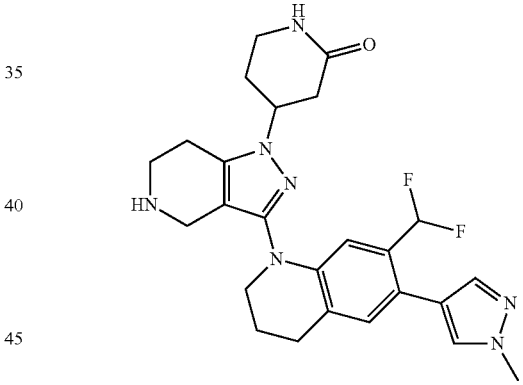

To a solution of tert-butyl 3-(7-(difluoromethyl)-6-(1-methyl-1H-pyrazol-4-yl)-3,4-dihydroquinolin-1(2H)-yl)-1-(2-oxo-1-((2-(trimethylsilyl)ethoxy)methyl)piperidin-4-yl)-6,7-dihydro-1H-pyrazolo[4,3-c]pyridine-5(4H)-carboxylate (100 mg, 0.14 mmol) in DCM (6 mL) was added trifluoroacetic acid (2 mL, 7.02 mmol). The mixture was stirred at 16° C. for 4 h and concentrated in vacuo. The crude residue was re-dissolved in MeOH (10 mL) and K$_2$CO$_3$ (86 mg, 0.63 mmol) was added. The mixture was stirred at 16° C. for 16 h. The reaction solution was filtered and concentrated in vacuo. The crude residue was purified by Prep-TLC (DCM/MeOH=20:1) to give the title compound (40 mg, 53%) as a white solid. LCMS M/Z (M+H) 482.

Step 3

(R)-4-[5-acetyl-3-[7-(difluoromethyl)-6-(1-methyl-pyrazol-4-yl)-3,4-dihydro-2H-quinolin-1-yl]-6,7-dihydro-4H-pyrazolo[4,3-c]pyridin-1-yl]piperidin-2-one and (S)-4-[5-acetyl-3-[7-(difluoromethyl)-6-(1-methylpyrazol-4-yl)-3,4-dihydro-2H-quinolin-1-yl]-6,7-dihydro-4H-pyrazolo[4,3-c]pyridin-1-yl]piperidin-2-one

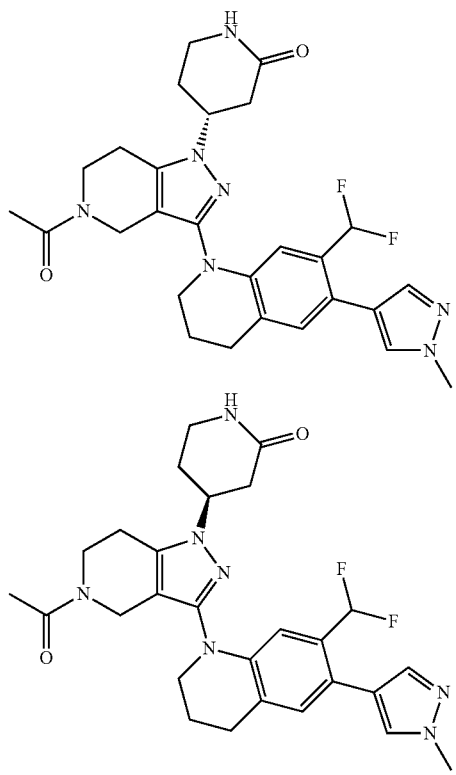

To a solution of 4-(3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-2-one (100 mg, 0.21 mmol) in DCM (10 mL) at 0° C. was added triethylamine (0.044 mL, 0.31 mmol) and acetic anhydride (0.02 mL, 0.21 mmol). The mixture was stirred at 0° C. for 1 h. The reaction solution was diluted with DCM (50 mL), washed with brine (30 mL×3), dried over anhydrous Na$_2$SO$_4$, filtered and concentrated in vacuo. The crude residue was purified by reverse phase chromatography (acetonitrile 15-45%/0.225% formic acid in water) to give racemic 4-[5-acetyl-3-[7-(difluoromethyl)-6-(1-methylpyrazol-4-yl)-3,4-dihydro-2H-quinolin-1-yl]-6,7-dihydro-4H-pyrazolo[4,3-c]pyridin-1-yl]piperidin-2-one (30 mg, 28%) as a white solid which was separated by using chiral SFC (AD(250 mm×30 mm, 10 um), I.D., 3 um Mobile phase: ethanol (Neu) in CO$_2$ from 5% to 40%; Flow rate: 80 mL/min) to give (R)-4-[5-acetyl-3-[7-(difluoromethyl)-6-(1-methylpyrazol-4-yl)-3,4-dihydro-2H-quinolin-1-yl]-6,7-dihydro-4H-pyrazolo[4,3-c]pyridin-1-yl]piperidin-2-one (4 mg, first peak) and (S)-4-[5-acetyl-3-[7-(difluoromethyl)-6-(1-methylpyrazol-4-yl)-3,4-dihydro-2H-quinolin-1-yl]-6,7-dihydro-4H-pyrazolo[4,3-c]pyridin-1-yl]piperidin-2-one (4 mg, second peak). Absolute configuration was arbitrarily assigned to each enantiomer. Example 343: $^1$H NMR (400 MHz, CDCl$_3$) δ 7.55-7.53 (m, 1H), 7.42-7.40 (m, 1H), 7.07-7.01 (m, 1H), 6.89-6.87 (m, 1H), 6.69-6.38 (m, 1H), 5.90-5.82 (m, 1H), 4.48-4.45 (m, 1H), 4.26-4.03 (m, 3H), 3.96 (s, 3H), 3.83-3.68 (m, 3H), 3.47-3.40 (m, 2H), 3.08-3.02 (m, 1H), 2.88-2.74 (m, 5H), 2.37-2.30 (m, 1H), 2.17-2.06 (m, 6H). LCMS M/Z (M+H) 524. Example 344: $^1$H NMR (400 MHz, CDCl$_3$) δ 7.55-7.53 (m, 1H), 7.42-7.40 (m, 1H), 7.07-7.01 (m, 1H), 6.88-6.87 (m, 1H), 6.69-6.38 (m, 1H), 5.98-5.89 (m, 1H), 4.48-4.45 (m, 1H), 4.26-4.03 (m, 3H), 3.96 (s, 3H), 3.82-3.68 (m, 3H), 3.50-3.40 (m, 2H), 3.08-3.01 (m, 1H), 2.88-2.74 (m, 5H), 2.37-2.31 (m, 1H), 2.17-2.06 (m, 6H). LCMS M/Z (M+H) 524.

Example 345

1-[1-[1-(2,2-difluoroethyl)-4-piperidyl]-3-[7-(difluoromethyl)-6-(1-methylpyrazol-4-yl)-3,4-dihydro-2H-quinolin-1-yl]-6,7-dihydro-4H-pyrazolo[4,3-c]pyridin-5-yl]ethanone

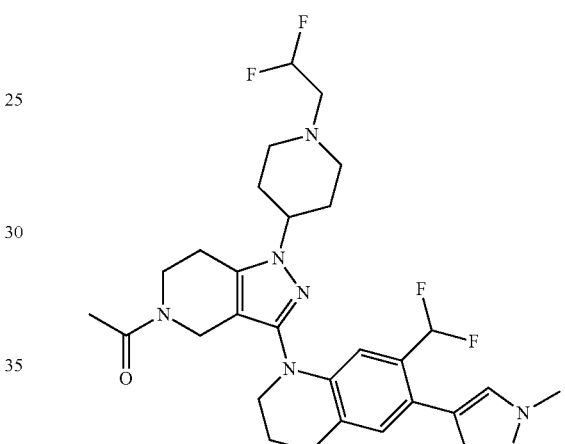

Step 1 tert-butyl 4-((methylsulfonyl)oxy)piperidine-1-carboxylate

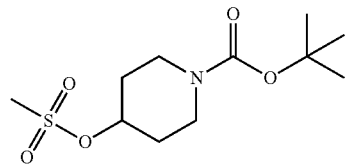 [SMILES: CC(C)(C)OC(=O)N1CCC(OS(C)(=O)=O)CC1]

To a solution of tert-butyl 4-hydroxypiperidine-1-carboxylate (5.0 g, 24.84 mmol) in DCM (40 mL) at 0° C. was added triethylamine (10.33 mL, 74.53 mmol) and methanesulfonyl chloride (2.6 mL, 33.44 mmol) dropwise. The mixture was stirred at room temperature for 12 h. The reaction was quenched with water (60 mL) and extracted with DCM (50 mL×2). The combined organic layers were dried over anhydrous Na$_2$SO$_4$, filtered and concentrated in vacuo to give the title compound (7.25 g, crude) as a light yellow solid that required no further purification. $^1$H NMR (400 MHz, CDCl$_3$) δ 4.93-4.82 (m, 1H), 3.75-3.62 (m, 2H), 3.40-3.23 (m, 2H), 3.04 (s, 3H), 2.00-1.90 (m, 2H), 1.87-1.76 (m, 2H), 1.46 (s, 9H).

Step 2 tert-butyl 4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidine-1-carboxylate

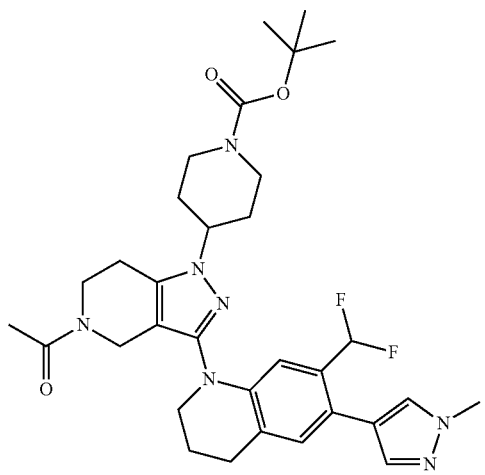 [SMILES: CC(=O)N1CCc2c(c(N3CCCc4cc(-c5cnn(C)c5)c(C(F)F)cc43)nn2C2CCN(C(=O)OC(C)(C)C)CC2)C1]

To a solution of 1-[3-[7-(difluoromethyl)-6-(1-methylpyrazol-4-yl)-3,4-dihydro-2H-quinolin-1-yl]-1,4,6,7-tetrahydropyrazolo[4,3-c]pyridin-5-yl]ethanone (Example 333, 850 mg, 2.0 mmol) in DMF (10 mL) was added Cs$_2$CO$_3$ (1.30 g, 3.99 mmol) and tert-butyl 4-((methylsulfonyl)oxy)piperidine-1-carboxylate (835 mg, 2.99 mmol). The mixture was heated to 80° C. for 12 h. After cooling the reaction to room temperature, the mixture was filtered and concentrated in vacuo. The crude residue was purified by reverse phase chromatography (acetonitrile 37-67%/0.05% NH$_4$OH in water) to give the title compound (210 mg, 17%) as a white solid. $^1$H NMR (400 MHz, CDCl$_3$) δ 7.55-7.53 (m, 1H), 7.42-7.40 (m, 1H), 7.06-7.00 (m, 1H), 6.86 (s, 1H), 6.68-6.37 (m, 1H), 4.38-4.12 (m, 3H), 4.08-3.99 (m, 1H), 3.96 (s, 3H), 3.95-3.89 (m, 2H), 3.75-3.67 (m, 3H), 2.89-2.70 (m, 6H), 2.17-2.03 (m, 7H), 1.92-1.88 (m, 2H), 1.48 (s, 9H). LCMS M/Z (M+H) 610.

Step 3

1-(3-(7-(difluoromethyl)-6-(1-methyl-1H-pyrazol-4-yl)-3,4-dihydroquinolin-1(2H)-yl)-1-(piperidin-4-yl)-6,7-dihydro-1H-pyrazolo[4,3-c]pyridin-5(4H)-yl)ethanone

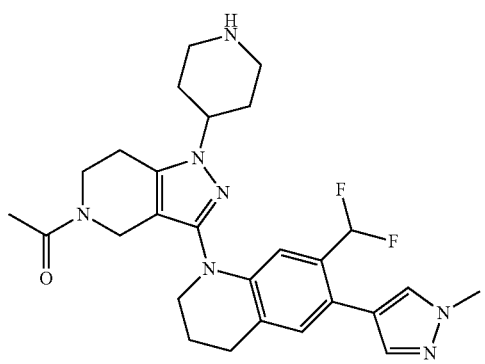 [SMILES: CC(=O)N1CCc2c(c(N3CCCc4cc(-c5cnn(C)c5)c(C(F)F)cc43)nn2C2CCNCC2)C1]

To a solution of tert-butyl 4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidine-1-carboxylate (80 mg, 0.13 mmol) in DCM (2 mL) at 0° C. was added trifluoroacetic acid (0.1 mL, 1.3 mmol). The mixture was stirred at room temperature for 2 h and concentrated in vacuo to give the title compound (73 mg, crude) as a brown oil that required no further purification. LCMS M/Z (M+H) 510.

Step 4

1-[1-[1-(2,2-difluoroethyl)-4-piperidyl]-3-[7-(difluoromethyl)-6-(1-methylpyrazol-4-yl)-3,4-dihydro-2H-quinolin-1-yl]-6,7-dihydro-4H-pyrazolo[4,3-c]pyridin-5-yl]ethanone

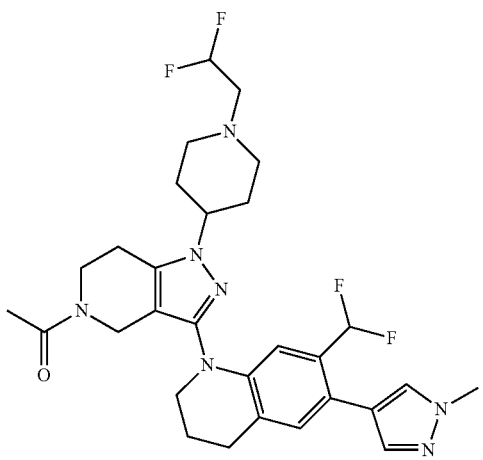 [SMILES: CC(=O)N1CCc2c(c(N3CCCc4cc(-c5cnn(C)c5)c(C(F)F)cc43)nn2C2CCN(CC(F)F)CC2)C1]

To a solution of 1-(3-(7-(difluoromethyl)-6-(1-methyl-1H-pyrazol-4-yl)-3,4-dihydroquinolin-1(2H)-yl)-1-(piperidin-4-yl)-6,7-dihydro-1H-pyrazolo[4,3-c]pyridin-5(4H)-yl)ethanone (73 mg, 0.14 mmol) in MeCN (2 mL) was added triethylamine (0.06 mL, 0.43 mmol) and 2,2-difluoroethyl trifluoromethanesulfonate (46 mg, 0.21 mmol). The mixture was stirred at room temperature for 3 h and concentrated in vacuo. The crude residue was purified by reverse phase chromatography (acetonitrile 30-60%/0.225% formic acid in water) to give the title compound (19 mg, 23%) as a white solid. $^1$H NMR (400 MHz, DMSO-d$_6$) δ 7.73 (s, 1H), 7.48 (s, 1H), 7.08 (s, 1H), 6.92-6.63 (m, 2H), 6.12 (t, J=56.0 Hz, 1H), 4.15-4.10 (m, 2H), 4.04-3.98 (m, 1H), 3.85 (s, 3H), 3.74-3.62 (m, 2H), 3.58-3.55 (m, 2H), 2.98-2.96 (m, 2H), 2.83-2.70 (m, 6H), 2.34-2.31 (m, 2H), 2.05-1.88 (m, 7H), 1.82-1.79 (m, 2H). LCMS M/Z (M+H) 574.

The Following Compound was Prepared in a Similar Fashion to Example 345

Examples 346

| Example | Compound Name | NMR | m/z |
|---|---|---|---|
| Example 346 | 1-[3-[7-(difluoromethyl)-6-(1-methylpyrazol-4-yl)-3,4-dihydro-2H-quinolin-1-yl]-1-[1-(2,2,2-trifluoroethyl)-4-piperidyl]-6,7-dihydro-4H-pyrazolo[4,3-c]pyridin-5-yl]ethanone | $^1$H NMR (400 MHz, DMSO-d$_6$) δ 7.70 (s, 1H), 7.47 (s, 1H), 7.10 (s, 1H), 6.82 (s, 1H), 6.75 (t, J = 55.6 Hz, 1H), 4.17-4.13 (m, 3H), 3.87 (s, 3H), 3.73-3.70 (m, 2H), 3.61 (t, J = 6.0 Hz, 2H), 3.47-3.38 (m, 2H), 3.17-3.13 (m, 2H), 2.89-2.64 (m, 6H), 2.35-1.87 (m, 9H) | 592 |

6.92-6.62 (m, 2H), 4.15-4.10 (m, 2H), 4.02-3.94 (m, 11H), 3.85 (s, 3H), 3.72-3.65 (m, 2H), 3.60-3.55 (m, 2H), 2.83-2.71 (m, 6H), 2.18 (s, 3H), 2.05-1.90 (m, 9H), 1.84-1.75 (m, 2H). LCMS M/Z (M+H) 524.

Example 347

1-[3-[7-(difluoromethyl)-6-(1-methylpyrazol-4-yl)-3,4-dihydro-2H-quinolin-1-yl]-1-(1-methyl-4-piperidyl)-6,7-dihydro-4H-pyrazolo[4,3-c]pyridin-5-yl]ethanone

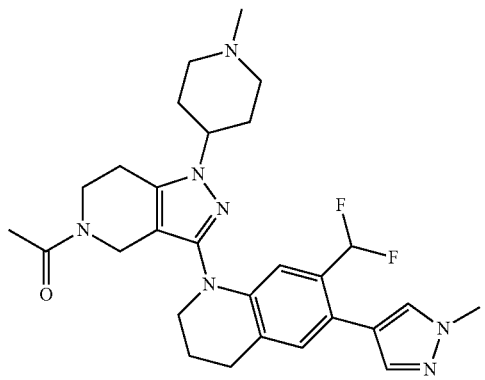 [SMILES: CC(=O)N1CCc2c(c(N3CCCc4cc(-c5cnn(C)c5)c(C(F)F)cc43)nn2C2CCN(C)CC2)C1]

To a solution of 1-(3-(7-(difluoromethyl)-6-(1-methyl-1H-pyrazol-4-yl)-3,4-dihydroquinolin-1(2H)-yl)-1-(piperidin-4-yl)-6,7-dihydro-1H-pyrazolo[4,3-c]pyridin-5(4H)-yl)ethanone (80 mg, 0.16 mmol) in DCE (2 mL) was added sodium cyanoborohydride (30 mg, 0.47 mmol), AcOH (0.05 mL, 0.87 mmol) and formaldehyde (37% in water, 0.035 mL, 0.47 mmol). The mixture was stirred at room temperature for 1 h. The reaction was quenched with sat. aq. NaHCO$_3$ (10 mL) and the mixture was extracted with DCM (10 mL×3). The combined organic layers were dried over anhydrous Na$_2$SO$_4$, filtered and concentrated in vacuo. The crude residue was purified by reverse phase chromatography (acetonitrile 24-54%/0.05% NH$_4$OH in water) to give the title compound (19 mg, 23%) as a white solid. $^1$H NMR (400 MHz, DMSO-d$_6$) δ 7.73 (s, 1H), 7.48 (s, 1H), 7.08 (s, 1H), Example 348

1-[1-(4,4-difluorocyclohexyl)-3-[7-(difluoromethyl)-6-(1-methylpyrazol-4-yl)-3,4-dihydro-2H-quinolin-1-yl]-6,7-dihydro-4H-pyrazolo[4,3-c]pyridin-5-yl]ethanone

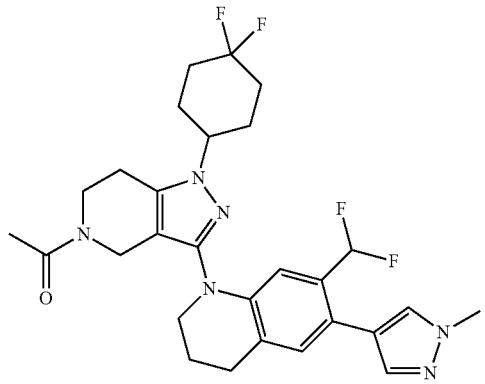 [SMILES: CC(=O)N1CCc2c(c(N3CCCc4cc(-c5cnn(C)c5)c(C(F)F)cc43)nn2C2CCC(F)(F)CC2)C1]

Step 1

4,4-difluorocyclohexyl methanesulfonate

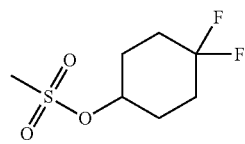

To a solution of 4,4-difluorocyclohexanol (800 mg, 5.88 mmol) in DCM (10 mL) at 0° C. was added triethylamine (2.44 mL, 17.63 mmol) and methanesulfonyl chloride (0.65 mL, 8.38 mmol) dropwise. The mixture was stirred at room temperature for 12 h. The reaction was quenched with water (30 mL) and the mixture was extracted with DCM (30 mL×2). The combined organic layers were dried over anhydrous Na$_2$SO$_4$, filtered and concentrated in vacuo to give the title compound (1.2 g, 95%) as a light red oil. $^1$H NMR (400 MHz, CDCl$_3$) δ 4.92-4.91 (m, 1H), 3.05 (s, 3H), 2.15-2.04 (m, 4H), 2.02-1.96 (m, 4H).

Step 2
1-[1-(4,4-difluorocyclohexyl)-3-[7-(difluoromethyl)-6-(1-methylpyrazol-4-yl)-3,4-dihydro-2H-quinolin-1-yl]-6,7-dihydro-4H-pyrazolo[4,3-c]pyridin-5-yl]ethanone

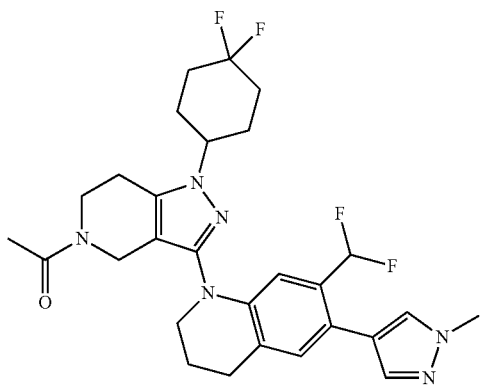 [SMILES: CC(=O)N1CCc2c(c(N3CCCc4cc(-c5cnn(C)c5)c(C(F)F)cc43)nn2C2CCC(F)(F)CC2)C1]

To a solution of 1-[3-[7-(difluoromethyl)-6-(1-methylpyrazol-4-yl)-3,4-dihydro-2H-quinolin-1-yl]-1,4,6,7-tetrahydropyrazolo[4,3-c]pyridin-5-yl]ethanone (Example 333, 100 mg, 0.23 mmol) in DMF (3 mL) was added $Cs_2CO_3$ (230 mg, 0.71 mmol) and 4,4-difluorocyclohexyl methanesulfonate (75 mg, 0.35 mmol). The mixture was heated to 80° C. for 16 h. After cooling the reaction to room temperature, the mixture was filtered. The filtrate was diluted with EtOAc (20 mL), washed with brine (20 mL×2). The organic layer was dried over anhydrous $Na_2SO_4$, filtered and concentrated in vacuo. The crude residue was purified by reverse phase chromatography (acetonitrile 37-67%/0.05% $NH_4OH$ in water) to give the title compound (23 mg, 18%) as a white solid. $^1$H NMR (400 MHz, $CDCl_3$) δ 7.55-7.53 (m, 1H), 7.42-7.40 (m, 1H), 7.06-7.01 (m, 1H), 6.86 (s, 1H), 6.68-6.38 (m, 1H), 4.29-4.12 (m, 2H), 4.10-4.01 (m, 1H), 3.96 (s, 3H), 3.93-3.66 (m, 4H), 2.93-2.61 (m, 4H), 2.41-2.25 (m, 4H), 2.17-1.81 (m, 9H). LCMS M/Z (M+H) 545.

The Following Compounds were Prepared in a Similar Fashion to Example 348

Examples 349-350

Examples 351 & 352

(S,S)-1-[3-[7-(difluoromethyl)-6-(1-methylpyrazol-4-yl)-3,4-dihydro-2H-quinolin-1-yl]-1-(4-hydroxy-cyclohexyl)-6,7-dihydro-4H-pyrazolo[4,3-c]pyridin-5-yl]ethanone and (R,R)-1-[3-[7-(difluoromethyl)-6-(1-methylpyrazol-4-yl)-3,4-dihydro-2H-quinolin-1-yl]-1-(4-hydroxycyclohexyl)-6,7-dihydro-4H-pyrazolo[4,3-c]pyridin-5-yl]ethanone

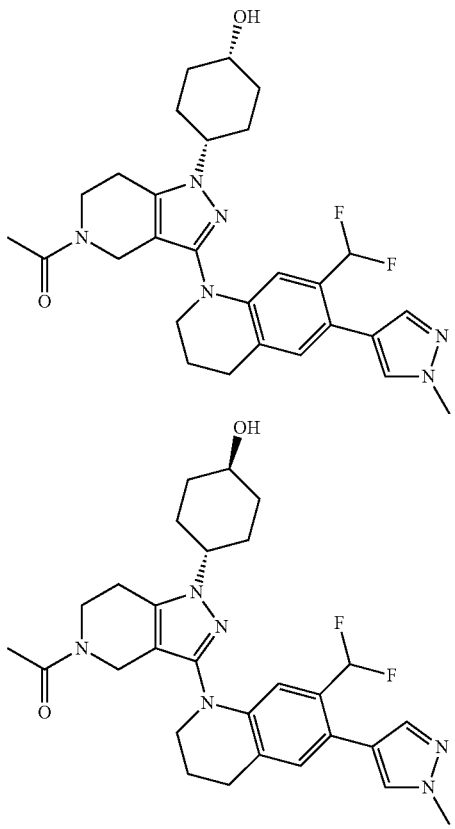

| Example | Compound Name | NMR | m/z |
|---|---|---|---|
| Example 349 | 1-[3-[7-(difluoromethyl)-6-(1-methylpyrazol-4-yl)-3,4-dihydro-2H-quinolin-1-yl]-1-(1-methylsulfonyl-4-piperidyl)-6,7-dihydro-4H-pyrazolo[4,3-c]pyridin-5-yl]ethanone | $^1$H NMR (400 MHz, $CDCl_3$) δ 7.57-7.54 (m, 1H), 7.44-7.39 (m, 1H), 7.07-7.01 (m, 1H), 6.90-6.87 (m, 1H), 6.71-6.37 (m, 1H), 4.28-4.13 (m, 2H), 4.10-4.02 (m, 1H), 3.99-3.91 (m, 6H), 3.75-3.69 (m, 3H), 3.02-2.92 (m, 2H), 2.90-2.83 (m, 5H), 2.81-2.71 (m, 2H), 2.39-2.24 (m, 2H), 2.17-2.05 (m, 7H) | 588 |
| Example 350 | 1-[3-[6-(1-methylpyrazol-4-yl)-7-(trifluoromethyl)-3,4-dihydro-2H-quinolin-1-yl]-1-(1-methylsulfonyl-4-piperidyl)-6,7-dihydro-4H-pyrazolo[4,3-c]pyridin-5-yl]ethanone | $^1$H NMR (400 MHz, DMSO-$d_6$) δ 7.71 (s, 1H), 7.42 (s, 1H), 7.10 (s, 1H), 6.97-6.93 (m, 1H), 4.25-4.16 (m, 3H), 3.84 (s, 3H), 3.74-3.55 (m, 6H), 2.89-2.73 (m, 9H), 2.07-1.95 (m, 9H) | 606 |

Step 1

4-(benzyloxy)cyclohexyl methanesulfonate

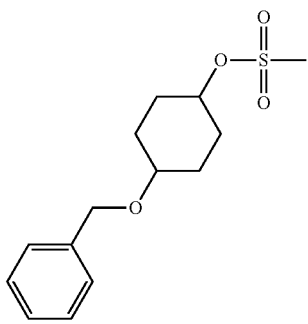 [SMILES: CS(=O)(=O)OC1CCC(OCc2ccccc2)CC1]

To a solution of 4-(benzyloxy)cyclohexanol (4 g, 19.4 mmol) and triethylamine (5.4 mL, 38.8 mmol) in DCM (20 mL) at 0° C. was added methanesulfonyl chloride (3.5 mL, 44.8 mmol). DCM (50 mL) was added and washed with water (40 mL×2). The organic phase was dried over anhydrous $Na_2SO_4$, filtered and concentrated in vacuo to give the title compound (5 g, crude) as a white solid that required no further purification. $^1$H-NMR (400 MHz, $CDCl_3$) δ 7.35-7.26 (m, 5H), 4.80-4.76 (m, 1H), 4.53 (s, 2H), 3.52-3.48 (m, 1H), 3.01 (s, 3H), 2.11-1.89 (m, 4H), 1.80-1.60 (m, 4H).

Step 2

1-(1-(4-(benzyloxy)cyclohexyl)-3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridin-5(4H)-yl)ethanone and 1-(2-(4-(benzyloxy)cyclohexyl)-3-(7-(difluoromethyl)-6-(1-methyl-1H-pyrazol-4-yl)-3,4-dihydroquinolin-1(2H)-yl)-6,7-dihydro-2H-pyrazolo[4,3-c]pyridin-5(4H)-yl)ethanone

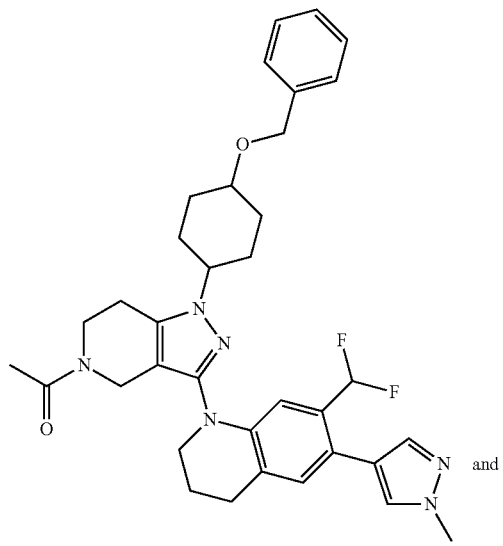

and

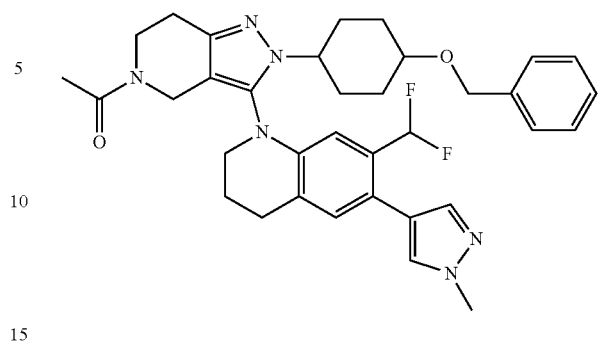

To a solution of 1-[3-[7-(difluoromethyl)-6-(1-methyl-pyrazol-4-yl)-3,4-dihydro-2H-quinolin-1-yl]-1,4,6,7-tetrahydropyrazolo[4,3-c]pyridin-5-yl]ethanone (Example 333, 400 mg, 0.9 mmol) in DMF was added $Cs_2CO_3$ (917 mg, 2.8 mmol) and 4-(benzyloxy)cyclohexyl methanesulfonate (320 mg, 1.13 mmol). The mixture was heated to 80° C. for 12 h. After cooling the reaction to room temperature, the mixture was filtered and concentrated in vacuo. The crude residue was purified by silica gel chromatography (petroleum ether/EtOAc=from 10:1 to 1:1) to give the mixture of title compounds (350 mg, ~3:1) as a white solid. LCMS M/Z (M+H) 615.

Step 3

(S,S)-1-[3-[7-(difluoromethyl)-6-(1-methylpyrazol-4-yl)-3,4-dihydro-2H-quinolin-1-yl]-1-(4-hydroxycyclohexyl)-6,7-dihydro-4H-pyrazolo[4,3-c]pyridin-5-yl]ethanone and (R,R)1-[3-[7-(difluoromethyl)-6-(1-methylpyrazol-4-yl)-3,4-dihydro-2H-quinolin-1-yl]-1-(4-hydroxycyclohexyl)-6,7-dihydro-4H-pyrazolo[4,3-c]pyridin-5-yl]ethanone

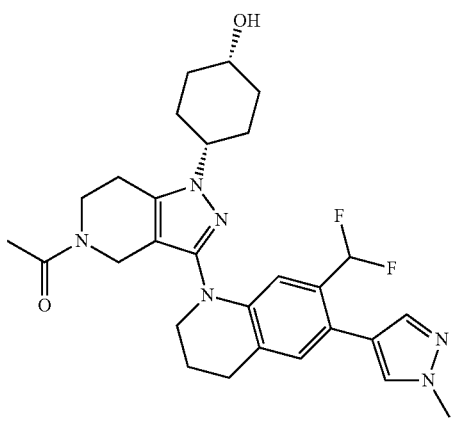

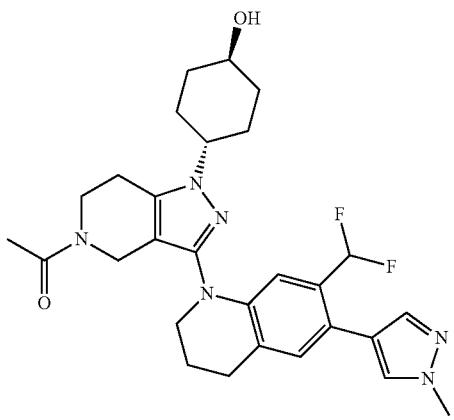

To a solution of 1-(1-(4-(benzyloxy)cyclohexyl)-3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridin-5(4H)-yl)ethanone and 1-(2-(4-(benzyloxy)cyclohexyl)-3-(7-(difluoromethyl)-6-(1-methyl-1H-pyrazol-4-yl)-3,4-dihydroquinolin-1(2H)-yl)-6,7-dihydro-2H-pyrazolo[4,3-c]pyridin-5 (4H)-yl)ethanone (200 mg, 0.3 mmol) in MeOH (10 mL) was added 10% Pd(OH)₂/C (50 mg). The mixture was stirred at room temperature for 9 days under a hydrogen atmosphere (15 psi). The mixture was filtered and concentrated in vacuo. The crude residue was purified by reverse phase chromatography (acetonitrile 20-50%/0.225% formic acid in water) to give (S,S)-1-[3-[7-(difluoromethyl)-6-(1-methylpyrazol-4-yl)-3,4-dihydro-2H-quinolin-1-yl]-1-(4-hydroxycyclohexyl)-6,7-dihydro-4H-pyrazolo[4,3-c]pyridin-5-yl]ethanone (16 mg, 78% purity) and (R,R)-1-[3-[7-(difluoromethyl)-6-(1-methylpyrazol-4-yl)-3,4-dihydro-2H-quinolin-1-yl]-1-(4-hydroxycyclohexyl)-6,7-dihydro-4H-pyrazolo[4,3-c]pyridin-5-yl]ethanone (26 mg, 51% purity). The impure compounds were further separated by using chiral SFC (OD (250 mm×30 mm, 10 um), Mobile phase: 30% ethanol (0.05% diethylamine) in CO₂, Flow rate: 80 mL/min) to give (S,S)-1-[3-[7-(difluoromethyl)-6-(1-methylpyrazol-4-yl)-3,4-dihydro-2H-quinolin-1-yl]-1-(4-hydroxycyclohexyl)-6,7-dihydro-4H-pyrazolo[4,3-c]pyridin-5-yl]ethanone (3 mg) as a white solid and (R,R)-1-[3-[7-(difluoromethyl)-6-(1-methylpyrazol-4-yl)-3,4-dihydro-2H-quinolin-1-yl]-1-(4-hydroxycyclohexyl)-6,7-dihydro-4H-pyrazolo[4,3-c]pyridin-5-yl]ethanone (10 mg) as a white solid, respectively. Example 351: ¹H NMR (400 MHz, CDCl₃) δ 7.55-7.53 (m, 1H), 7.42-7.39 (m, 1H), 7.08-6.96 (m, 1H), 6.87 (s, 1H), 6.69-6.36 (m, 1H), 4.27-4.12 (m, 2H), 4.11-4.08 (m, 1H), 4.03-3.87 (m, 5H), 3.78-3.68 (m, 2H), 2.94-2.80 (m, 3H), 2.77-2.75 (m, 1H), 2.40-2.30 (m, 2H), 2.21-1.94 (m, 7H), 1.81-1.78 (m, 2H), 1.72-1.69 (m, 2H). LCMS M/Z (M+H) 525. Example 352: ¹H NMR (400 MHz, CDCl₃) δ 7.55-7.52 (m, 1H), 7.42-7.39 (m, 1H), 7.07-6.96 (m, 1H), 6.87-6.85 (m, 1H), 6.69-6.35 (m, 1H), 4.31-4.10 (m, 2H), 4.01-3.85 (m, 5H), 3.81-3.65 (m, 4H), 2.92-2.72 (m, 4H), 2.22-2.03 (m, 7H), 2.02-1.93 (m, 2H), 1.65-1.61 (m, 2H), 1.53-1.40 (m, 2H). LCMS M/Z (M+H) 525.

Example 353

5-[1-(5-acetyl-1-tetrahydropyran-4-yl-6,7-dihydro-4H-pyrazolo[4,3-c]pyridin-3-yl)-7-chloro-3,4-dihydro-2H-quinolin-6-yl]-N-methyl-pyridine-2-carboxamide

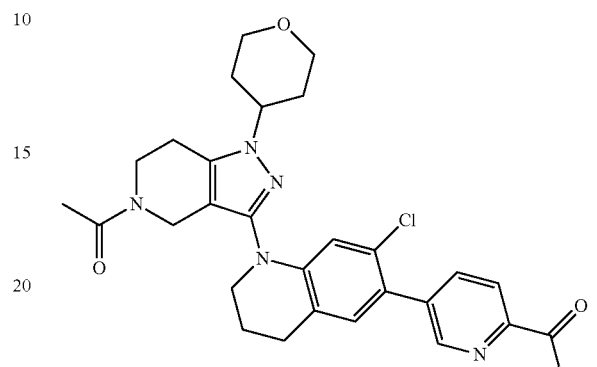

Step 1

1-(3-(7-chloro-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone

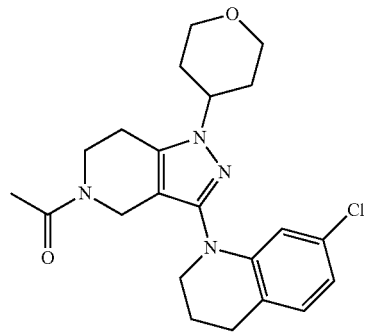 [SMILES: CC(=O)N1CCc2c(c(N3CCCc4ccc(Cl)cc43)nn2C2CCOCC2)C1]

To a solution of 1-(3-bromo-1-tetrahydropyran-4-yl-6,7-dihydro-4H-pyrazolo[4,3-c]pyridin-5-yl)ethanone (Intermediates I, 0.4 g, 1.2 mmol) in 1,4-dioxane (10 mL) was added 7-chloro-1,2,3,4-tetrahydroquinoline (482 mg, 3 mmol), chloro(2-dicyclohexylphosphino-2',6'-di-i-propoxy-1,1'-biphenyl)(2'-amino-1,1'-biphenyl-2-yl)palladium(II) (95 mg, 0.12 mmol), 2-dicyclohexylphosphino-2',6'-di-i-propoxy-1,1'-biphenyl (67 mg, 0.12 mmol) and t-BuONa (351 mg, 3.7 mmol). The mixture was heated to 120° C. for 12 h under a nitrogen atmosphere. After cooling the reaction to room temperature, the mixture was filtered and concentrated in vacuo. The crude residue was diluted with DCM (100 mL) and the mixture was washed with water (50 mL×3) and brine (50 mL). The organic layer was dried over anhydrous Na₂SO₄, filtered and concentrated in vacuo. The crude residue was purified by silica gel chromatography (DCM/MeOH=50:1) to give the title compound (320 mg, 63%) as a yellow solid. LCMS M/Z (M+H) 415.

Step 2

1-(3-(6-bromo-7-chloro-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone

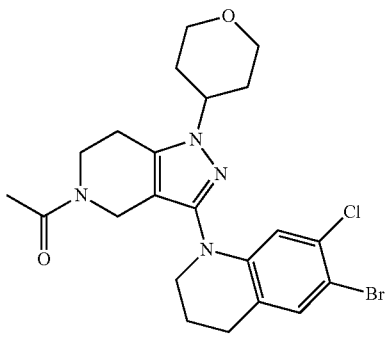 [SMILES: CC(=O)N1CCc2c(c(N3CCCc4cc(Br)c(Cl)cc43)nn2C2CCOCC2)C1]

To a solution of 1-(3-(7-chloro-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone (400 mg, 0.37 mmol) in DCM (5 mL) was added N-bromosuccinimide (65 mg, 0.37 mmol) portionwise. The mixture was stirred at 0° C. for 1 h. DCM (50 mL) was added and the mixture was washed with water (30 mL×3) and brine (30 mL). The organic layer was dried over anhydrous $Na_2SO_4$, filtered and concentrated in vacuo to give the title compound (480 mg, crude) as a yellow solid. LCMS M/Z (M+H) 495.

To a solution of 1-(3-(6-bromo-7-chloro-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone (100 mg, 0.2 mmol) in THF (5 mL) and water (1 mL) was added chloro(2-dicyclohexylphosphino-2',4',6'-tri-i-propyl-1,1'-biphenyl)(2'-amino-1,1'-biphenyl-2-yl) palladium(II) (16 mg, 0.02 mmol), 2-(dicyclohexylphosphino)-2',4',6'-triisopropylbiphenyl (10 mg, 0.02 mmol), N-methyl-5-(4,4,5,5-tetramethyl-1,3,2-dioxaborolan-2-yl)picolinamide (81 mg, 0.3 mmol) and $Na_2CO_3$ (65 mg, 0.6 mmol). The mixture was heated to 60° C. for 16 h under a nitrogen atmosphere. After cooling the reaction to room temperature, the mixture was filtered and concentrated in vacuo. DCM (50 mL) was added and the mixture was washed with water (30 mL×3) and brine (30 mL). The organic layer was dried over anhydrous $Na_2SO_4$, filtered and concentrated in vacuo. The crude residue was purified by reverse phase chromatography (acetonitrile 45-75%/0.05% $NH_4OH$ in water) to give the title compound (31 mg, 27%) as a yellow solid. $^1H$ NMR (400 MHz, DMSO-$d_6$) δ 8.81-8.79 (m, 1H), 8.67-8.62 (m, 1H), 8.08-7.97 (m, 2H), 7.19 (s, 1H), 6.64-6.55 (m, 1H), 4.36-4.27 (m, 1H), 4.26-4.19 (m, 2H), 3.98-3.95 (m, 2H), 3.81-3.70 (m, 2H), 3.63-3.55 (m, 2H), 3.49-3.43 (m, 2H), 2.91-2.76 (m, 7H), 2.11-1.92 (m, 7H), 1.86-1.83 (m, 2H). LCMS M/Z (M+H) 549.

The Following Compound was Prepared in a Similar Fashion to Example 353

Examples 354

| Example | Compound Name | NMR | m/z |
|---|---|---|---|
| Example 354 | 1-[3-[7-chloro-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone | $^1H$ NMR (400 MHz, DMSO-$d_6$) δ 7.96 (s, 1H), 7.68 (s, 1H), 7.20 (s, 1H), 6.54-6.46 (m, 1H), 4.35-4.23 (m, 1H), 4.21-4.13 (m, 2H), 3.97-3.94 (m, 2H), 3.85 (s, 3H), 3.80-3.68 (m, 2H), 3.58-3.51 (m, 2H), 3.48-3.42 (m, 2H), 2.91-2.71 (m, 4H), 2.12-1.90 (m, 7H), 1.84-1.81 (m, 2H) | 495 |

Step 3

5-[1-(5-acetyl-1-tetrahydropyran-4-yl-6,7-dihydro-4H-pyrazolo[4,3-c]pyridin-3-yl)-7-chloro-3,4-dihydro-2H-quinolin-6-yl]-N-methyl-pyridine-2-carboxamide

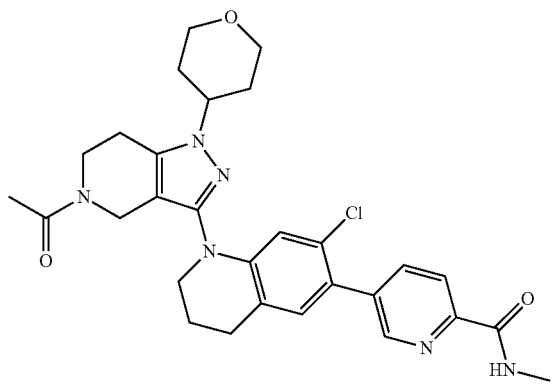 [SMILES: CNC(=O)c1ccc(-c2cc3c(cc2Cl)N(c2nn(C4CCOCC4)c4c2CN(C(C)=O)CC4)CCC3)cn1]

Example 355

1-[3-[6-(1-methylpyrazol-4-yl)-7-(oxetan-3-yl)-3,4-dihydro-2H-quinolin-1-yl]-1-tetrahydropyran-4-yl-6,7-dihydro-4H-pyrazolo[4,3-c]pyridin-5-yl]ethanone

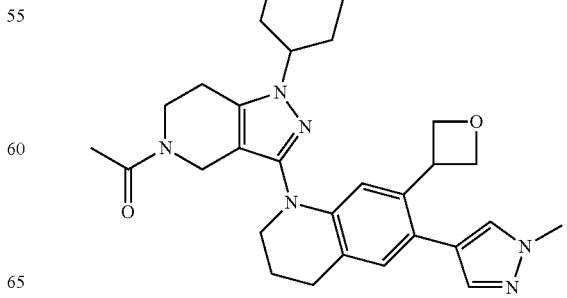

Step 1

1-(3-(6-(1-methyl-1H-pyrazol-4-yl)-7-(4,4,5,5-tetramethyl-1,3,2-dioxaborolan-2-yl)-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone

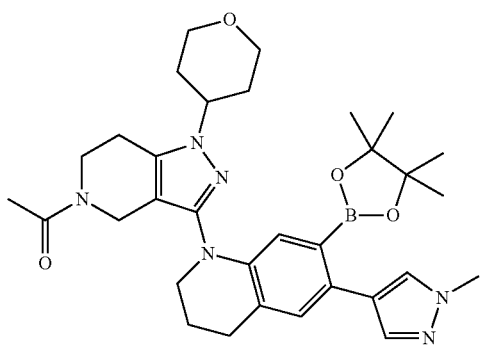 [SMILES: CC(=O)N1CCc2c(c(N3CCCc4cc(-c5cnn(C)c5)c(B5OC(C)(C)C(C)(C)O5)cc43)nn2C2CCOCC2)C1]

To a solution of 1-[3-[7-chloro-6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]ethanone (Example 354, 3.8 g, 7.68 mmol) in 1,4-dioxane (150 mL) was added chloro(2-dicyclohexylphosphino-2',4',6'-tri-i-propyl-1,1'-biphenyl)(2'-amino-1,1'-biphenyl-2-yl) palladium(II) (604 mg, 0.77 mmol), 2-(dicyclohexylphosphino)-2',4',6'-triisopropylbiphenyl (366 mg, 0.77 mmol), 4,4,4',4',5,5,5',5'-octamethyl-2,2'-bi(1,3,2-dioxaborolane) (5.85 g, 23.03 mmol) and potassium acetate (1.5 g, 15.35 mmol). The mixture was heated to 90° C. for 16 h under a nitrogen atmosphere. After cooling the reaction to room temperature, the mixture was filtered and concentrated in vacuo. EtOAc (150 mL) was added, washed with water (100 mL×3) and brine (100 mL). The organic layer was dried over anhydrous $Na_2SO_4$, filtered and concentrated in vacuo. The crude residue was purified by silica gel chromatography (DCM/MeOH=20:1) to give the title compound (1.64 g, 36%) as a brown solid. LCMS M/Z (M+H) 587.

Step 2

(1-(5-acetyl-1-(tetrahydro-2H-pyran-4-yl)-4,5,6,7-tetrahydro-1H-pyrazolo[4,3-c]pyridin-3-yl)-6-(1-methyl-1H-pyrazol-4-yl)-1,2,3,4-tetrahydroquinolin-7-yl)boronic acid

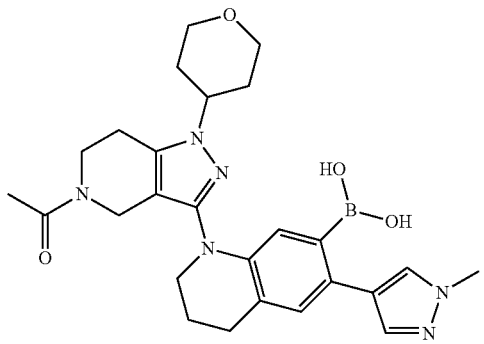 [SMILES: CC(=O)N1CCc2c(c(N3CCCc4cc(-c5cnn(C)c5)c(B(O)O)cc43)nn2C2CCOCC2)C1]

To a solution of 1-(3-(6-(1-methyl-1H-pyrazol-4-yl)-7-(4,4,5,5-tetramethyl-1,3,2-dioxaborolan-2-yl)-3,4-dihydroquinolin-1(2H)-yl)-1-(tetrahydro-2H-pyran-4-yl)-6,7-dihydro-1H-pyrazolo[4,3-c]pyridin-5(4H)-yl)ethanone (1.64 g, 2.8 mmol) in THF (30 mL) and water (15 mL) was added sodium periodate (1.79 g, 8.39 mmol) and acetic ammonia (0.65 g, 8.39 mmol). The mixture was stirred at room temperature for 48 h. Water (100 mL) was added and the mixture was extracted with DCM (80 mL×3). The combined organic layers were dried over anhydrous $Na_2SO_4$, filtered and concentrated in vacuo. The crude residue was purified by silica gel chromatography (DCM/MeOH=20:1) to give the title compound (560 mg, 40%) as a yellow solid. LCMS M/Z (M+H) 505.

Step 3

1-[3-[6-(1-methylpyrazol-4-yl)-7-(oxetan-3-yl)-3,4-dihydro-2H-quinolin-1-yl]-1-tetrahydropyran-4-yl-6,7-dihydro-4H-pyrazolo[4,3-c]pyridin-5-yl]ethanone

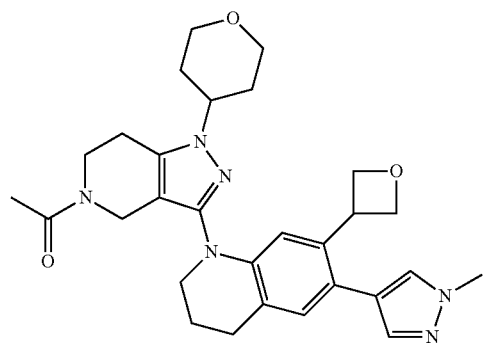 [SMILES: CC(=O)N1CCc2c(c(N3CCCc4cc(-c5cnn(C)c5)c(C5COC5)cc43)nn2C2CCOCC2)C1]

To a solution of (1-(5-acetyl-1-(tetrahydro-2H-pyran-4-yl)-4,5,6,7-tetrahydro-1H-pyrazolo[4,3-c]pyridin-3-yl)-6-(1-methyl-1H-pyrazol-4-yl)-1,2,3,4-tetrahydroquinolin-7-yl)boronic acid (250 mg, 0.50 mmol) in 1,4-dioxane (3 mL) was added 4-methoxy-N-(oxetan-3-ylideneamino)benzenesulfonamide (127 mg, 0.50 mmol) and cesium carbonate (200 mg, 0.61 mmol). The mixture was heated to 110° C. for 16 h under an argon atmosphere. After cooling the reaction to room temperature, the mixture was filtered and concentrated in vacuo. EtOAc (50 mL) was added and the mixture was washed with water (30 mL×3) and brine (30 mL). The organic layer was dried over anhydrous $Na_2SO_4$, filtered and concentrated in vacuo. The crude residue was purified by Prep-TLC (DCM/MeOH=20:1) to give the title compound (12 mg, 5%) as a yellow solid. $^1$H NMR (400 MHz, $CD_3OD$) δ 7.56-7.48 (m, 1H), 7.37 (s, 1H), 6.95-6.93 (m, 1H), 6.72-6.71 (m, 1H), 4.83-4.75 (m, 2H), 4.60-4.46 (m, 3H), 4.40-4.28 (m, 3H), 4.07-4.04 (m, 2H), 3.91-3.82 (m, 5H), 3.66-3.60 (m, 4H), 2.93-2.84 (m, 4H), 2.30-2.05 (m, 7H), 1.90-1.88 (m, 2H).

Examples 356 & 357

(R)-1-(5-acetyl-1-tetrahydropyran-4-yl-6,7-dihydro-4H-pyrazolo[4,3-c]pyridin-3-yl)-3-methyl-6-(1-methylpyrazol-4-yl)-3,4-dihydro-2H-quinoline-7-carbonitrile and (S)-1-(5-acetyl-1-tetrahydropyran-4-yl-6,7-dihydro-4H-pyrazolo[4,3-c]pyridin-3-yl)-3-methyl-6-(1-methylpyrazol-4-yl)-3,4-dihydro-2H-quinoline-7-carbonitrile

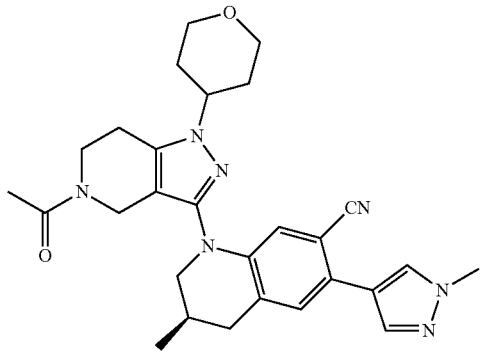

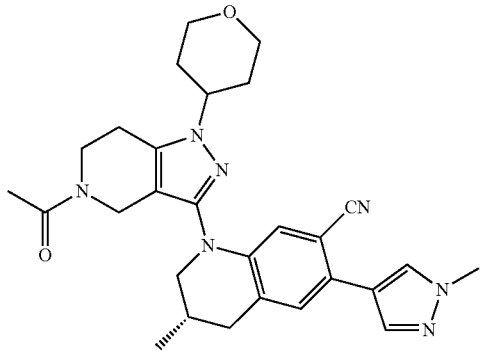

Racemic 1-(5-acetyl-1-tetrahydropyran-4-yl-6,7-dihydro-4H-pyrazolo[4,3-c]pyridin-3-yl)-3-methyl-6-(1-methylpyrazol-4-yl)-3,4-dihydro-2H-quinoline-7-carbonitrile (Example 85, 50 mg) was separated using HPLC-chiral normal phase (Chiralpak AD 250×30 mm I.D., 5 um; Mobile Phase A: Heptane; Mobile Phase B: Ethanol w/ 0.1% Formic Acid; Conditions: Isocratic at 20% B; Run; time: 30 minutes; Flow rate: 40 ml/min; Column oven: 40° C.; Wavelength: 254 nm) to afford (R)-1-(5-acetyl-1-tetrahydropyran-4-yl-6,7-dihydro-4H-pyrazolo[4,3-c]pyridin-3-yl)-3-methyl-6-(1-methylpyrazol-4-yl)-3,4-dihydro-2H-quinoline-7-carbonitrile (7.7 mg, first peak) and (S)-1-(5-acetyl-1-tetrahydropyran-4-yl-6,7-dihydro-4H-pyrazolo[4,3-c]pyridin-3-yl)-3-methyl-6-(1-methylpyrazol-4-yl)-3,4-dihydro-2H-quinoline-7-carbonitrile (6.2 mg, second peak). Absolute configuration was arbitrarily assigned to each enantiomer. Example 356: $^1$H NMR (400 MHz, DMSO-$d_6$) δ 8.06 (s, 1H), 7.79 (s, 1H), 7.35 (s, 1H), 6.73-6.67 (m, 1H), 4.34-4.26 (m, 1H), 4.19-4.16 (m, 2H), 3.97-3.94 (m, 2H), 3.87 (s, 3H), 3.73-3.71 (m, 2H), 3.58-3.48 (m, 2H), 3.35-3.15 (m, 2H), 2.88-2.74 (m, 2H), 2.56-2.54 (m, 2H), 2.08-1.95 (m, 6H), 1.84-1.81 (m, 2H), 1.04-1.02 (m, 3H). LCMS M/Z (M+H) 500. Example 357: $^1$H NMR (400 MHz, DMSO-$d_6$) δ 8.05 (s, 1H), 7.79 (s, 1H), 7.34 (s, 1H), 6.72-6.68 (m, 1H), 4.34-4.26 (m, 1H), 4.18-4.16 (m, 2H), 3.96-3.93 (m, 2H), 3.87 (s, 3H), 3.73-3.71 (m, 2H), 3.58-3.48 (m, 2H), 3.35-3.15 (m, 2H), 2.88-2.74 (m, 2H), 2.56-2.54 (m, 2H), 2.08-1.95 (m, 6H), 1.84-1.81 (m, 2H), 1.04-1.02 (m, 3H). LCMS M/Z (M+H) 500.

Examples 358 & 359

(R)-3-[7-(difluoromethyl)-4-methyl-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide and (S)-3-[7-(difluoromethyl)-4-methyl-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide

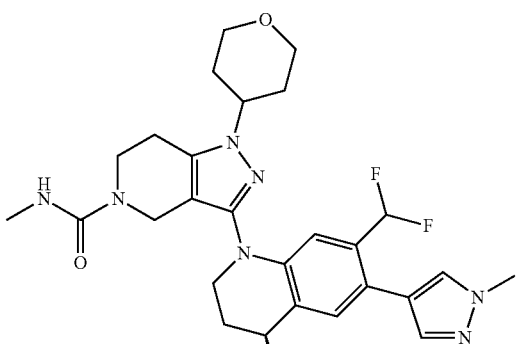

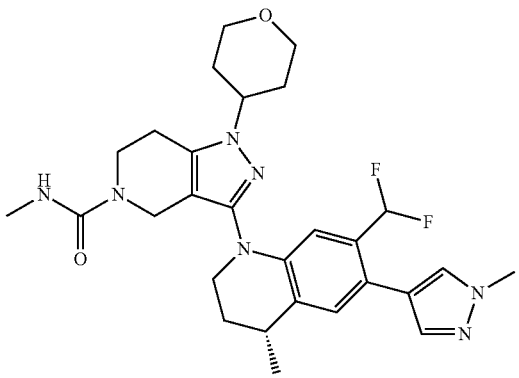

Racemic 3-[7-(difluoromethyl)-4-methyl-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide (Example 248, 50 mg) was separated using HPLC-chiral normal phase (Chiralpak AD 250×30 mm I.D., 5 um; Mobile Phase A: Heptane; Mobile Phase B: Ethanol w/0.1% Formic Acid; Conditions: Isocratic at 20% B; Run; time: 30 minutes; Flow rate: 40 ml/min; Column oven: 40° C.; Wavelength: 254 nm) to afford (R)-3-[7-(difluoromethyl)-4-methyl-6-(1-methylpyrazol-4-yl)-3,4- dihydro-2H-quinolin-1-yl]-N-methyl-1-tetrahydropyran-4-yl-6,7-dihydro-4H-pyrazolo[4,3-c]pyridine-5-carboxamide (13.7 mg, first peak) and (S)-3-[7-(difluoromethyl)-4-methyl-6-(1-methylpyrazol-4-yl)-3,4-dihydro-2H-quinolin-1-yl]-N-methyl-1-tetrahydropyran-4-yl-6,7-dihydro-4H-pyrazolo[4,3-c]pyridine-5-carboxamide (29.1 mg, second peak). Absolute configuration was arbitrarily assigned to each enantiomer. Example 358: $^1$H NMR (400 MHz, DMSO-$d_6$) δ 7.78 (s, 1H), 7.52 (s, 1H), 7.17 (s, 1H), 6.82 (s, 1H), 6.80 (t, J=55.6 Hz, 1H), 6.56-6.52 (m, 1H), 4.34-4.28 (m, 1H), 4.03-3.90 (m, 4H), 3.87 (s, 3H), 3.71-3.51 (m, 4H), 3.48-3.42 (m, 2H), 3.00-2.95 (m, 1H), 2.75-2.72 (m, 2H), 2.53 (d, J=4.0 Hz, 3H), 2.10-1.90 (m, 3H), 1.88-1.68 (m, 3H), 1.32 (d, J=6.8 Hz, 3H). LCMS M/Z (M+H) 540. Example 359: $^1$H NMR (400 MHz, DMSO-$d_6$) δ 7.77 (s, 1H), 7.51 (s, 1H), 7.17 (s, 1H), 6.82 (s, 1H), 6.79 (t, J=55.6 Hz, 1H), 6.56-6.53 (m, 1H), 4.33-4.28 (m, 1H), 4.03-3.90 (m, 4H), 3.87 (s, 3H), 3.71-3.51 (m, 4H), 3.48-3.42 (m, 2H), 3.00-2.95 (m, 1H), 2.75-2.72 (m, 2H), 2.54 (d, J=4.0 Hz, 3H), 2.10-1.90 (m, 3H), 1.88-1.68 (m, 3H), 1.32 (d, J=6.8 Hz, 3H). LCMS M/Z (M+H) 540.

Example 360

3-[7-(difluoromethyl)-6-(5-methyl-2-thienyl)-3,4-dihydro-2H-quinolin-1-yl]-N-methyl-1-tetrahydropyran-4-yl-6,7-dihydro-4H-pyrazolo[4,3-c]pyridine-5-carboxamide

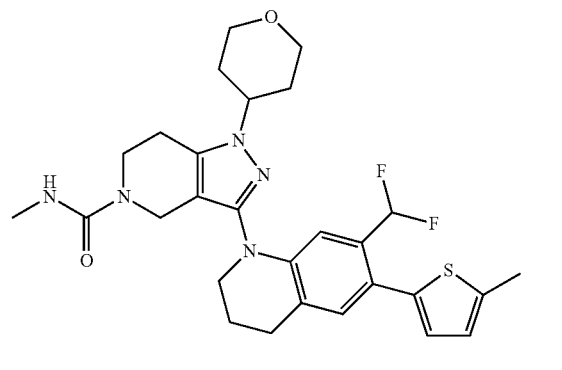

Step 1 tert-butyl 3-[7-(difluoromethyl)-6-(5-methyl-2-thienyl)-3,4-dihydro-2H-quinolin-1-yl]-1-tetrahydropyran-4-yl-6,7-dihydro-4H-pyrazolo[4,3-c]pyridine-5-carboxylate

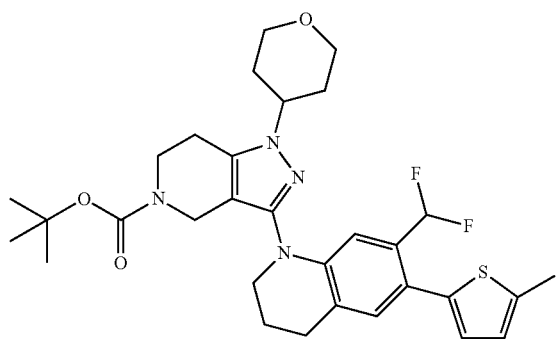 [SMILES: Cc1ccc(-c2cc3c(cc2C(F)F)N(c2nn(C4CCOCC4)c4c2CN(C(=O)OC(C)(C)C)CC4)CCC3)s1]

To a vial was added tert-butyl 3-[6-bromo-7-(difluoromethyl)-3,4,4a,8a-tetrahydro-2H-quinolin-1-yl]-1-tetrahydropyran-4-yl-6,7-dihydro-4H-pyrazolo[4,3-c]pyridine-5-carboxylate (Intermediate R, 35.0 mg, 0.0617 mmol), 4,4,5,5-tetramethyl-2-(5-methyl-2-thienyl)-1,3,2-dioxaborolane (20.7 mg, 0.0925 mmol), K$_2$CO$_3$ (39.3 mg, 0.185 mmol), 2-dicyclohexylphosphino-2',4',6'-triisopropylbiphenyl (1.7 mg, 0.0037 mmol) and (2-dicyclohexylphosphino-2',4',6'-triisopropyl-1,1'-biphenyl) [2-(2-aminoethyl)phenyl)]palladium(II) chloride (1.4 mg, 0.0018 mmol). THF (0.4 mL) and water (0.1 mL) were added and the mixture was sparged with an argon ballon before being heated to 100° C. for 16 h under argon atmosphere. After cooling the reaction to room temperature, DCM (1 mL) was added and the reaction was filtered through celite and concentrated in vacuo to give crude product that was purified by reverse phase preparative HPLC (acetonitrile 50-90%/0.1% formic acid in water) to give the title compound (25.1 mg, 70% yield) as a white solid. $^1$H NMR (400 MHz, DMSO-$d_6$) δ 7.11 (d, J=1.3 Hz, 1H), 6.99-6.56 (m, 4H), 4.35-4.23 (m, 1H), 4.06 (d, J=1.9 Hz, 2H), 4.00-3.90 (m, 2H), 3.67-3.55 (m, 4H), 3.49-3.41 (m, 2H), 2.88-2.81 (m, 2H), 2.79 (ddddd, J=5.1, 3.6, 3.1, 1.5, 1.0 Hz, 2H), 2.46 (d, J=1.0 Hz, 3H), 2.08-1.91 (m, 4H), 1.82 (d, J=12.7 Hz, 2H), 1.37 (s, 9H). LCMS M/Z (M+H) 585.

Step 2

7-(difluoromethyl)-6-(5-methyl-2-thienyl)-1-(1-tetrahydropyran-4-yl-4,5,6,7-tetrahydropyrazolo[4,3-c]pyridin-3-yl)-3,4-dihydro-2H-quinoline

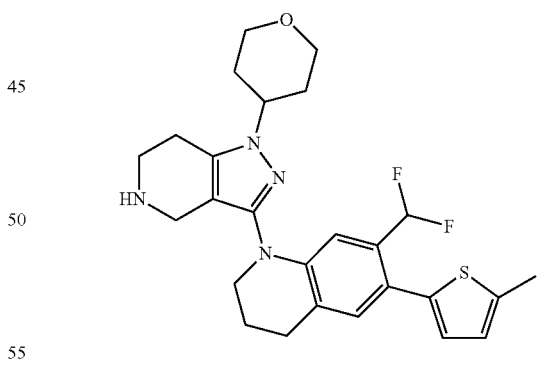

To a solution of tert-butyl 3-[7-(difluoromethyl)-6-(5-methyl-2-thienyl)-3,4-dihydro-2H-quinolin-1-yl]-1-tetrahydropyran-4-yl-6,7-dihydro-4H-pyrazolo[4,3-c]pyridine-5-carboxylate (25.1 mg, 0.0429 mmol) in DCM (1.0 mL) at 0° C. was added trifluoroacetic acid (0.5 mL) dropwise. The mixture was stirred at rt for 1.5 h, then concentrated in vacuo to give crude product that was used in the subsequent step without further purification. LCMS M/Z (M+H) 485.

Step 3

3-[7-(difluoromethyl)-6-(5-methyl-2-thienyl)-3,4-dihydro-2H-quinolin-1-yl]-N-methyl-1-tetrahydropyran-4-yl-6,7-dihydro-4H-pyrazolo[4,3-c]pyridine-5-carboxamide

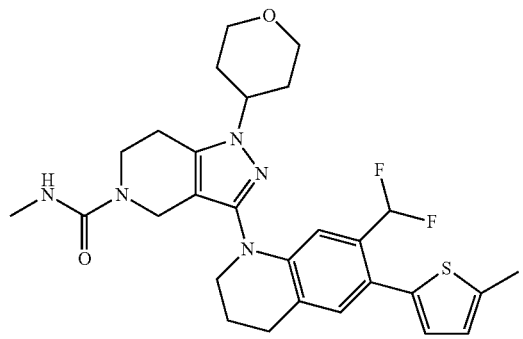

To a solution of 7-(difluoromethyl)-6-(5-methyl-2-thienyl)-1-(1-tetrahydropyran-4-yl-4,5,6,7-tetrahydropyrazolo[4,3-c]pyridin-3-yl)-3,4-dihydro-2H-quinoline in DCM (2 mL) was added TEA (23.9 μL, 0.172 mmol) and N-methyl-1H-imidazole-1-carboxamide (11.3 mg, 0.0859 mmol). The mixture was heated in a microwave reactor at 100° C. for 10 min then concentrated in vacuo to give crude product that was purified by reverse phase preparative HPLC (acetonitrile 30-70%/0.1% formic acid in water) to give the title compound (10.5 mg, 45% yield, 2 steps) as a white solid. $^1$H NMR (400 MHz, DMSO-$d_6$) δ 7.10 (s, 1H), 6.96-6.63 (m, 4H), 6.57-6.50 (m, 1H), 4.30 (td, J=11.1, 5.5 Hz, 1H), 4.04 (s, 2H), 4.00-3.88 (m, 2H), 3.65-3.55 (m, 4H), 3.45 (ddddd, J=11.7, 11.1, 2.0, 1.0, 0.5 Hz, 2H), 2.85 (s, 2H), 2.74 (s, 2H), 2.54 (d, J=4.2 Hz, 3H), 2.46 (d, J=1.0 Hz, 3H), 1.98 (dt, J=11.9, 6.0 Hz, 4H), 1.81 (d, J=11.2 Hz, 2H). LCMS M/Z (M+H) 542.

The Following Compounds were Prepared in a Similar Fashion to Example 360

Examples 361-367

| Example | Compound Name | NMR | m/z |
|---|---|---|---|
| Example 361 | 3-[6-(2-cyclopropylthiazol-5-yl)-7-(difluoromethyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 7.42 (s, 1H), 7.12 (d, J = 1.3 Hz, 1H), 6.97-6.65 (m, 2H), 6.54 (q, J = 4.3 Hz, 1H), 4.29 (td, J = 11.2, 5.5 Hz, 1H), 4.04 (s, 2H), 4.00-3.88 (m, 2H), 3.60 (ddddd, J = 4.6, 4.1, 3.1, 2.0, 1.5 Hz, 4H), 3.50-3.42 (m, 2H), 2.88-2.79 (m, 2H), 2.77-2.70 (m, 2H), 2.54 (d, J = 4.3 Hz, 3H), 2.39 (tt, J = 8.2, 4.8 Hz, 1H), 1.97 (ddt, J = 17.2, 12.0, 5.7 Hz, 4H), 1.81 (d, J = 12.6 Hz, 2H), 1.16-1.08 (m, 2H), 1.01-0.95 (m, 2H). | 569 |
| Example 362 | 3-[7-(difluoromethyl)-6-(2-thienyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 7.58 (dd, J = 5.2, 1.1 Hz, 1H), 7.15 (s, 1H), 7.12 (dd, J = 5.2, 3.5 Hz, 1H), 7.01 (dd, J = 3.5, 1.2 Hz, 1H), 6.90 (d, J = 19.1 Hz, 2H), 6.54 (q, J = 5.1, 4.6 Hz, 1H), 4.35-4.22 (m, 1H), 4.05 (s, 2H), 3.97-3.87 (m, 2H), 3.66-3.57 (m, 4H), 3.50-3.42 (m, 2H), 2.87 (t, J = 6.1 Hz, 2H), 2.75 (t, J = 5.7 Hz, 2H), 2.55 (d, J = 4.3 Hz, 3H), 2.08-1.89 (m, 4H), 1.82 (d, J = 12.0 Hz, 2H). | 528 |
| Example 363 | 3-[7-(difluoromethyl)-6-(2-methoxypyrimidin-5-yl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.52 (s, 2H), 7.07 (s, 1H), 6.94-6.60 (m, 2H), 6.60-6.49 (m, 1H), 4.36-4.23 (m, 1H), 4.10-4.01 (m, 2H), 4.00-3.85 (m, 5H), 3.61 (t, J = 5.3 Hz, 4H), 3.51-3.38 (m, 2H), 2.87 (t, J = 6.3 Hz, 2H), 2.75 (t, J = 5.7 Hz, 2H), 2.55 (d, J = 4.2 Hz, 3H), 2.08-1.88 (m, 4H), 1.86-1.76 (m, 2H). | 554 |
| Example 364 | 3-[6-(5-cyano-2-thienyl)-7-(difluoromethyl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 7.96 (d, J = 3.9 Hz, 1H), 7.23 (s, 1H), 7.17 (d, J = 3.9 Hz, 1H), 7.05-6.69 (m, 2H), 6.54 (d, J = 4.5 Hz, 1H), 4.37-4.23 (m, 1H), 4.05 (s, 2H), 4.00-3.89 (m, 2H), 3.66-3.55 (m, 4H), 3.49-3.39 (m, 2H), 2.87 (t, J = 6.5 Hz, 2H), 2.75 (t, J = 5.7 Hz, 2H), 2.55 (d, J = 4.1 Hz, 3H), 1.98 (dt, J = 11.7, 5.5 Hz, 4H), 1.83 (s, 2H). | 553 |
| Example 365 | 3-[6-(5-chloro-2-thienyl)-7-(difluoromethyl)-3,4-dihydro-2H-quinolin-1-yl]-N-methyl-1-tetrahydropyran-4-yl-6,7-dihydro-4H- | $^1$H NMR (400 MHz, DMSO-$d_6$) δ 7.16-7.10 (m, 2H), 6.99-6.68 (m, 3H), 6.53 (t, J = 4.4 Hz, 1H), 4.38-4.22 (m, 1H), 4.04 (s, 2H), 3.98-3.86 (m, 2H), 3.60 (td, J = 5.9, 3.3 Hz, 4H), 3.45 (td, J = 11.7, 2.0 Hz, 2H), 2.86 (t, J = 6.4 Hz, 2H), 2.75 (t, J = 5.8 Hz, 2H), 2.54 (d, J = | 562 |

| Example | Compound Name | NMR | m/z |
|---|---|---|---|
| | pyrazolo[4,3-c]pyridine-5-carboxamide | 4.2 Hz, 3H), 2.06-1.90 (m, 4H), 1.87-1.77 (m, 2H). | |
| Example 366 | 3-[7-(difluoromethyl)-6-[2-(dimethylamino)thiazol-5-yl]-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 7.07 (s, 1H), 6.96 (s, 1H), 6.95-6.64 (m, 2H), 6.57-6.49 (m, 1H), 4.34-4.24 (m, 1H), 4.03 (s, 2H), 4.00-3.90 (m, 2H), 3.59 (q, J = 5.9 Hz, 4H), 3.51-3.39 (m, 2H), 3.04 (s, 6H), 2.84 (t, J = 6.3 Hz, 2H), 2.76-2.70 (m, 2H), 2.54 (d, J = 4.3 Hz, 3H), 2.04-1.91 (m, 4H), 1.86-1.71 (m, 2H). | 572 |
| Example 367 | 3-[7-(difluoromethyl)-6-(2,4-dimethylthiazol-5-yl)-3,4-dihydro-2tf-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 7.00 (s, 1H), 6.85 (s, 1H), 6.72-6.37 (m, 2H), 4.37-4.22 (m, 1H), 4.07 (s, 2H), 3.94 (dd, J = 11.8, 4.3 Hz, 2H), 3.60 (q, J = 5.6 Hz, 4H), 3.45 (td, J = 11.9, 1.9 Hz, 2H), 2.84 (d, J = 6.6 Hz, 2H), 2.75 (t, J = 5.7 Hz, 2H), 2.61 (s, 3H), 2.55 (d, J = 4.2 Hz, 3H), 2.10 (s, 3H), 2.02-1.91 (m, 4H), 1.85-1.78 (m, 2H). | 557 |
| Example 368 | 3-[7-(difluoromethyl)-6-(2-methylthiazol-5-yl)-3,4-dihydro-2H-quinolin-1-yl]-N-methyl-1-tetrahydropyran-4-yl-6,7-dihydro-4H-pyrazolo[4,3-c]pyridine-5-carboxamide | $^1$H NMR (400 MHz, DMSO-d$_6$) δ 7.48 (s, 1H), 7.12 (s, 1H), 6.97-6.65 (m, 2H), 6.54 (q, J = 4.3 Hz, 1H), 4.29 (tt, J = 11.2, 4.4 Hz, 1H), 4.04 (s, 2H), 4.01-3.90 (m, 2H), 3.60 (dq, J = 5.9, 3.4 Hz, 4H), 3.51-3.43 (m, 2H), 2.85 (t, J = 6.4 Hz, 2H), 2.75 (t, J = 5.8 Hz, 2H), 2.66 (s, 3H), 2.54 (d, J = 4.2 Hz, 3H), 1.98 (ddd, J = 12.2, 7.5, 5.4 Hz, 4H), 1.81 (dd, J = 13.3, 4.2 Hz, 2H). | 543 |

Example 369

1-(5-acetyl-1-tetrahydropyran-4-yl-6,7-dihydro-4H-pyrazolo[4,3-c]pyridin-3-yl)-6-(2-methylthiazol-5-yl)-3,4-dihydro-2H-quinoline-7-carbonitrile

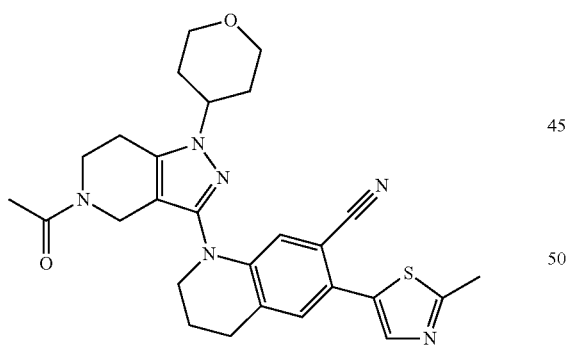

To a vial was added 1-(5-acetyl-1-tetrahydropyran-4-yl-6,7-dihydro-4H-pyrazolo[4,3-c]pyridin-3-yl)-6-bromo-3,4-dihydro-2H-quinoline-7-carbonitrile (Intermediate M, 15.0 mg, 0.0310 mmol), 2-methyl-5-(4,4,5,5-tetramethyl-1,3,2-dioxaborolan-2-yl)thiazole (10.6 mg, 0.0465 mmol), K$_3$PO$_4$ (19.2 mg, 0.0929 mmol), 2-dicyclohexylphosphino-2',4',6'-triisopropylbiphenyl (0.9 mg, 0.002 mmol), (2-dicyclohexylphosphino-2',4',6'-triisopropyl-1,1'-biphenyl)[2-(2-aminoethyl)phenyl)]palladium(II) chloride (0.7 mg, 0.001 mmol), then THF (0.4 mL) and water (0.1 mL). The mixture was sparged with an argon balloon, and then heated to 100° C. for 1 h under argon atmosphere. After cooling the reaction to room temperature, DCM (1 mL) was added and the reaction was filtered through celite and concentrated in vacuo to give crude product that was purified by reverse phase preparative HPLC (acetonitrile 20-60%/0.1% formic ammonium hydroxide in water) to give the title compound (5.7 mg, 37% yield) as a white solid. $^1$H NMR (400 MHz, DMSO-d$_6$) δ 7.85 (s, 1H), 7.37 (s, 1H), 6.77 (s, 1H), 4.31 (td, J=11.2, 5.5 Hz, 1H), 4.21 (d, J=10.9 Hz, 2H), 3.96 (d, J=12.7 Hz, 2H), 3.80-3.70 (m, 2H), 3.60 (dt, J=11.0, 5.4 Hz, 2H), 3.55-3.40 (m, 2H), 2.94-2.73 (m, 4H), 2.69 (s, 3H), 2.09 (s, 2H), 2.02-1.94 (m, 5H), 1.84 (d, J=13.0 Hz, 2H). LCMS M/Z (M+H) 503.2.

Example 370

2-methyl-5-[3-[6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]-1,3,4-thiadiazole

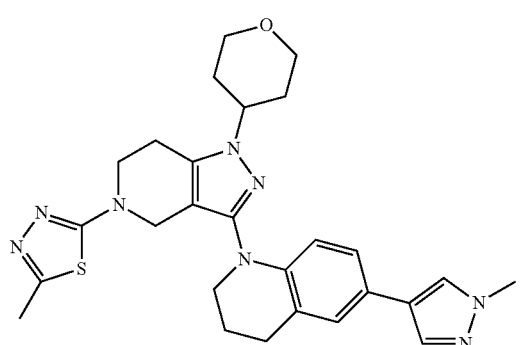

To a vial was added 6-(1-methylpyrazol-4-yl)-1-(1-tetrahydropyran-4-yl-4,5,6,7-tetrahydropyrazolo[4,3-c]pyridin- 3-yl)-3,4-dihydro-2H-quinoline (Intermediate XX, 30.3 mg, 0.0724 mmol), 2-bromo-5-methyl-1,3,4-thiadiazole (27.3 mg, 0.145 mmol), dichloro[1,3-bis(2,6-di-3-pentylphenyl)imidazol-2-ylidene](3-chloropyridyl)palladium(II) (12.1 mg, 0.0145 mmol), t-BuONa (13.9 mg, 0.145 mmol), then 1,4-dioxane (0.4 mL). The mixture was sparged with an argon balloon, and then heated to 120° C. for 16 h under argon atmosphere. After cooling the reaction to room temperature, DCM (1 mL) was added and the reaction was filtered through celite and concentrated in vacuo to give crude product that was purified by reverse phase preparative HPLC (acetonitrile 20-60%/0.1% ammonium hydroxide in water) to give the title compound (10.3 mg, 23% yield) as a white solid. $^1$H NMR (400 MHz, DMSO-$d_6$) δ 7.92 (d, J=0.8 Hz, 1H), 7.68 (d, J=0.8 Hz, 1H), 7.21 (d, J=2.1 Hz, 1H), 7.11 (dd, J=8.4, 2.2 Hz, 1H), 6.44 (d, J=8.4 Hz, 1H), 4.34-4.24 (m, 1H), 4.11 (s, 2H), 3.95 (d, J=11.6 Hz, 2H), 3.82 (d, J=1.3 Hz, 3H), 3.78 (t, J=5.8 Hz, 2H), 3.62-3.53 (m, 2H), 3.49-3.41 (m, 2H), 2.92 (t, J=5.9 Hz, 2H), 2.81 (t, J=6.2 Hz, 2H), 2.48 (s, 3H), 1.97 (tt, J=11.7, 5.2 Hz, 4H), 1.81 (d, J=12.3 Hz, 2H). LCMS M/Z (M+H) 517.

Example 371

2-methyl-5-[3-[6-(1-methylpyrazol-4-yl)-3,4-dihydro-2H-quinolin-1-yl]-1-tetrahydropyran-4-yl-6,7-dihydro-4H-pyrazolo[4,3-c]pyridin-5-yl]-1,3,4-oxadiazole

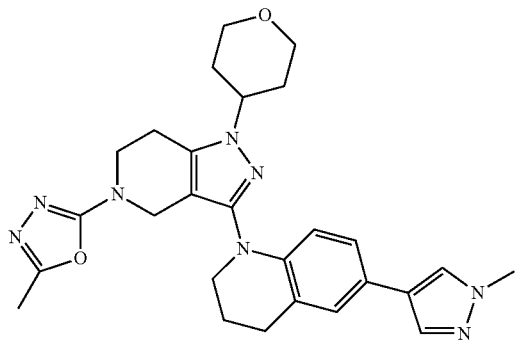 [SMILES: Cc1nnc(N2CCc3c(c(N4CCCc5cc(-c6cnn(C)c6)ccc54)nn3C3CCOCC3)C2)o1]

To a vial was added 6-(1-methylpyrazol-4-yl)-1-(1-tetrahydropyran-4-yl-4,5,6,7-tetrahydropyrazolo[4,3-c]pyridin-3-yl)-3,4-dihydro-2H-quinoline (Intermediate J, 30.3 mg, 0.0724 mmol), 2-bromo-5-methyl-1,3,4-oxadiazole (24.8 mg, 0.145 mmol), dichloro[1,3-bis(2,6-di-3-pentylphenyl)imidazol-2-ylidene](3-chloropyridyl)palladium(II) (12.1 mg, 0.0145 mmol), t-BuONa (13.9 mg, 0.145 mmol), then 1,4-dioxane (0.4 mL). The mixture was sparged with an argon balloon, and then heated to 120° C. for 16 h under argon atmosphere. After cooling the reaction to room temperature, DCM (1 mL) was added and the reaction was filtered through celite and concentrated in vacuo to give crude product which was purified by reverse phase preparative HPLC (acetonitrile 20-60%/0.1% ammonium hydroxide in water) to give the title compound (3.5 mg, 8% yield) as a white solid. $^1$H NMR (400 MHz, DMSO-$d_6$) δ 7.91 (d, J=0.8 Hz, 1H), 7.67 (d, J=0.8 Hz, 1H), 7.21 (d, J=2.1 Hz, 1H), 7.11 (dd, J=8.4, 2.2 Hz, 1H), 6.42 (d, J=8.4 Hz, 1H), 4.34-4.25 (m, 1H), 4.07 (s, 2H), 3.94 (d, J=4.2 Hz, 2H), 3.82 (s, 3H), 3.73 (t, J=5.8 Hz, 2H), 3.61-3.52 (m, 2H), 3.50-3.43 (m, 2H), 2.90 (t, J=4.5 Hz, 2H), 2.81 (t, J=6.4 Hz, 2H), 2.31 (s, 3H), 2.06-1.90 (m, 4H), 1.81 (dd, J=11.4, 2.4 Hz, 2H). LCMS M/Z (M+H) 501.

Example 372

1-(3-(7-(difluoromethyl)-6-(1-methyl-1H-pyrazol-4-yl)-3,4-dihydroquinolin-1(2H)-yl)-1-(4-(trifluoromethoxy)phenyl)-1,4,6,7-tetrahydro-5H-pyrazolo[4,3-c]pyridin-5-yl)ethan-1-one

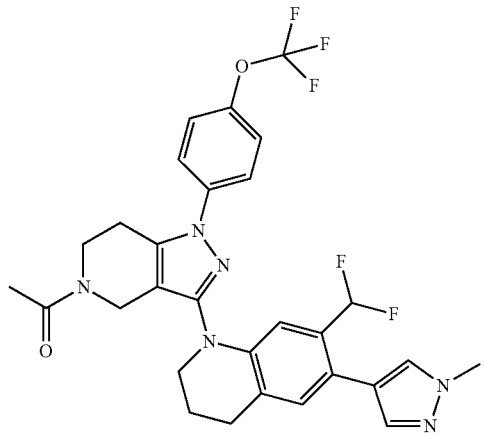 [SMILES: CC(=O)N1CCc2c(c(N3CCCc4cc(-c5cnn(C)c5)c(C(F)F)cc43)nn2-c2ccc(OC(F)(F)F)cc2)C1]

Step 1

1-(3-(7-(difluoromethyl)-6-(1-methyl-1H-pyrazol-4-yl)-3,4-dihydroquinolin-1(2H)-yl)-1,4,6,7-tetrahydro-5H-pyrazolo[4,3-c]pyridin-5-yl)ethan-1-one

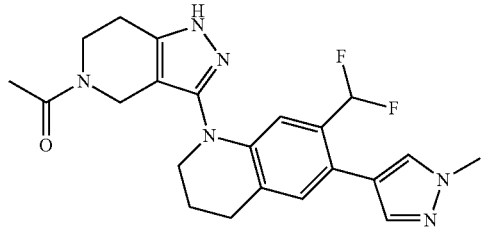 [SMILES: CC(=O)N1CCc2[nH]nc(N3CCCc4cc(-c5cnn(C)c5)c(C(F)F)cc43)c2C1]

To a stirred solution of tert-butyl 3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridine-5(4H)-carboxylate (Intermediate U, 500 mg, 1.03 mmol) in dichloromethane (5 mL) at 0° C. was added trifluoroacetic acid (1.56 g, 13.6 mmol) and the resulting solution was stirred for 2 h at room temperature. The crude mixture was concentrated in vacuo to remove the excess trifluoroacetic acid. The mixture was dissolved in acetonitrile (3.4 mL, 65 mmol) and a 5.25% solution of sodium bicarbonate in water (2.06 mL, 1.34 mmol) was added at room temperature before acetic anhydride (116 mg, 1.14 mmol) was added dropwise at 0° C. The reaction mixture was stirred at 0° C. for 1 h and the reaction mixture was slowly warmed up to room temperature and stirred for an additional 1 h. The reaction mixture was cooled down to 0° C. and acetic anhydride (116 mg, 1.14 mmol) was added dropwise at this temperature. Following the addition, the reaction mixture was slowly warmed up to room temperature and stirred for an additional 16 h. The mixture was concentrated in vacuo. Saturated aqueous NH$_4$Cl solution (60 mL) was added and the mixture was extracted with EtOAc (50 mL×3). The combined organic layers were dried over anhydrous MgSO$_4$, filtered and concentrated in vacuo. The crude residue was purified by silica gel chromatography (1% Et$_3$N in MeOH in iPrOAc=3:1) to afford a mixture of products containing the title compound (220 mg, 50%) as a white solid that was used without any further purification in the next step. LCMS M/Z (M+H) 427.

Step 2

1-(3-(7-(difluoromethyl)-6-(1-methyl-1H-pyrazol-4-yl)-3,4-dihydroquinolin-1(2H)-yl)-1-(4-(trifluoromethoxy)phenyl)-1,4,6,7-tetrahydro-5H-pyrazolo[4,3-c]pyridin-5-yl)ethan-1-one

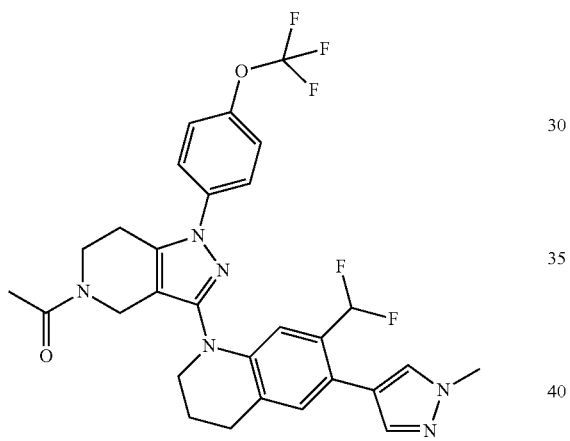

To a vial was added 1-(3-(7-(difluoromethyl)-6-(1-methyl-1H-pyrazol-4-yl)-3,4-dihydroquinolin-1(2H)-yl)-1,4,6,7-tetrahydro-5H-pyrazolo[4,3-c]pyridin-5-yl)ethan-1-one (30 mg, 0.070 mmol), (4-(trifluoromethoxy)phenyl) boronic acid (18 mg, 0.085 mmol) and copper(II) acetate (2.6 mg, 0.01407 mmol) in methanol (0.5 mL). The reaction mixture was stirred overnight at room temperature under air. The crude mixture was concentrated in vacuo and partioned between DCM (15 mL) and water (10 mL). The two phases were separated and the aqueous layer was washed with DCM (15 mL). The combined organic layers were dried over anhydrous MgSO$_4$, filtered and concentrated in vacuo. The crude residue was purified by reverse phase chromatography (acetonitrile 30-90%/0.1% NH$_4$OH in water) to give the title compound (7.3 mg, 18%) as a white solid. $^1$H NMR (400 MHz, DMSO-d$_6$) δ 7.83-7.69 (m, 3H), 7.52 (q, J=6.3, 4.8 Hz, 3H), 7.18 (d, J=3.2 Hz, 1H), 7.01-6.63 (m, 2H), 4.19 (d, J=25.8 Hz, 2H), 3.88 (d, J=1.7 Hz, 3H), 3.71 (dq, J=11.9, 6.1 Hz, 4H), 3.05 (t, J=5.7 Hz, 1H), 2.90 (d, J=21.1 Hz, 3H), 2.10 (s, 2H), 2.06-1.81 (m, 3H). LCMS M/Z (M+H) 587.

Examples 373 & 374

(S)-1-(3-(7-(difluoromethyl)-6-(1-methyl-1H-pyrazol-4-yl)-3,4-dihydroquinolin-1(2H)-yl)-1-(oxepan-4-yl)-1,4,6,7-tetrahydro-5H-pyrazolo[4,3-c]pyridin-5-yl)ethan-1-one and (R)-1-(3-(7-(difluoromethyl)-6-(1-methyl-1H-pyrazol-4-yl)-3,4-dihydroquinolin-1(2H)-yl)-1-(oxepan-4-yl)-1,4,6,7-tetrahydro-5H-pyrazolo[4,3-c]pyridin-5-yl)ethan-1-one

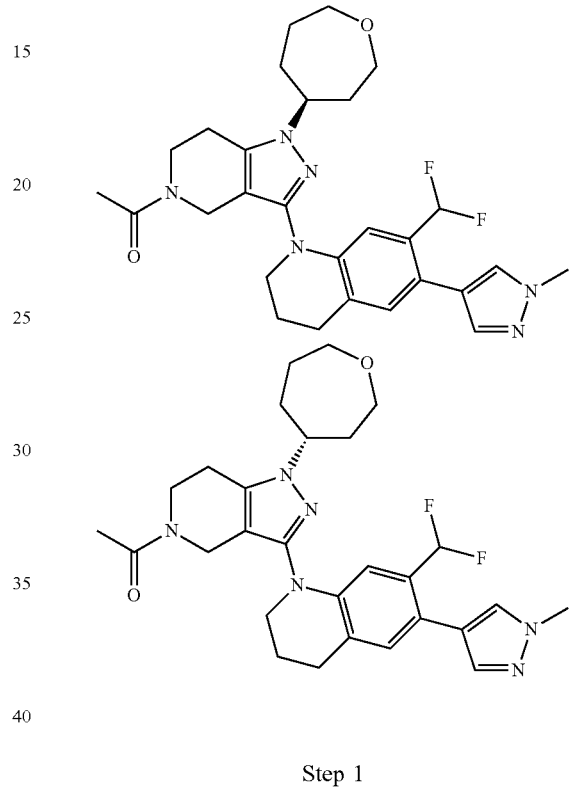

Step 1

4-methyl-N'-(oxepan-4-ylidene)benzenesulfonohydrazide

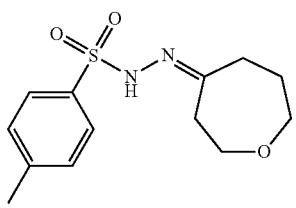 [SMILES: Cc1ccc(S(=O)(=O)N/N=C2/CCCOCC2)cc1]

To a stirred solution of oxepan-4-one (500 mg, 4.38 mmol) in methanol (10 mL) was added 4-methylbenzene sulfonhydrazide (841 mg, 4.38 mmol) and the reaction mixture was stirred at room temperature for 4 h. The mixture was concentrated in vacuo. The crude residue was washed with tert-butyl methyl ether (10 mL) to give the title compound (1.10 g, 90%) as white crystals. $^1$H NMR (400 MHz, CDCl$_3$) δ 7.87-7.80 (m, 2H), 7.30 (d, J=8.1 Hz, 2H), 7.13 (s, 1H), 3.83-3.75 (m, 1H), 3.75-3.68 (m, 2H), 3.68-3.62 (m, 1H), 2.69-2.52 (m, 2H), 2.42 (s, 3H), 2.47-2.33 (m, 2H), 1.89-1.79 (m, 1H), 1.74-1.63 (m, 1H). LCMS M/Z (M+H) 283.

Step 2 tert-butyl 3-(7-(difluoromethyl)-6-(1-methyl-1H-pyrazol-4-yl)-3,4-dihydroquinolin-1(2H)-yl)-1-(oxepan-4-yl)-1,4,6,7-tetrahydro-5H-pyrazolo[4,3-c]pyridine-5-carboxylate

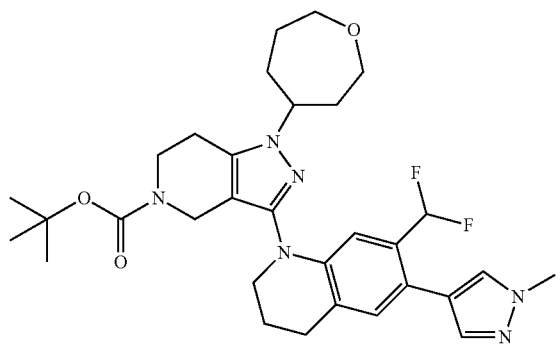 [SMILES: Cn1cc(-c2cc3c(cc2C(F)F)N(c2nn(C4CCCOCC4)c4c2CN(C(=O)OC(C)(C)C)CC4)CCC3)cn1]

To a stirred solution of tert-butyl 3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridine-5(4H)-carboxylate (Intermediate U, 25 mg, 0.052 mmol) was added 4-methyl-N'-(oxepan-4-ylidene)benzenesulfonohydrazide (29 mg, 0.10 mmol), copper(II) acetylacetonate (3 mg, 0.01 mmol) and cesium carbonate (59 mg, 0.18 mmol) in 1,4-dioxane (0.5 mL) and the reaction mixture was stirred at 100° C. for 16 h under a nitrogen atmosphere. The reaction mixture was diluted with DCM (5 mL), filtered through celite and concentrated in vacuo. The brown solid obtained was used without any further purification in the next step. LCMS M/Z (M+H) 583.

Step 3

(S)-1-(3-(7-(difluoromethyl)-6-(1-methyl-1H-pyrazol-4-yl)-3,4-dihydroquinolin-1(2H)-yl)-1-(oxepan-4-yl)-1,4,6,7-tetrahydro-5H-pyrazolo[4,3-c]pyridin-5-yl)ethan-1-one and (R)-1-(3-(7-(difluoromethyl)-6-(1-methyl-1H-pyrazol-4-yl)-3,4-dihydroquinolin-1(2H)-yl)-1-(oxepan-4-yl)-1,4,6,7-tetrahydro-5H-pyrazolo[4,3-c]pyridin-5-yl)ethan-1-one

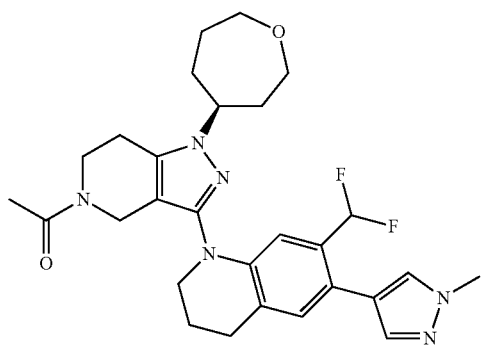

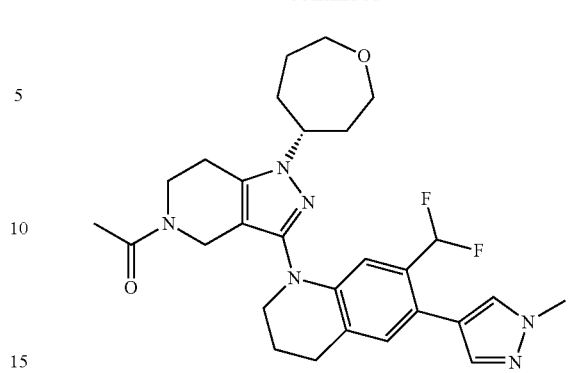

To a stirred solution of tert-butyl 3-(7-(difluoromethyl)-6-(1-methyl-1H-pyrazol-4-yl)-3,4-dihydroquinolin-1(2H)-yl)-1-(oxepan-4-yl)-1,4,6,7-tetrahydro-5H-pyrazolo[4,3-c]pyridine-5-carboxylate (crude mixture obtained from step 2) in dichloromethane (0.2 mL) at 0° C. was added trifluoroacetic acid (99 mg, 0.87 mmol) and the resulting solution was stirred for 2 h at room temperature. The crude mixture was concentrated in vacuo to remove the excess of trifluoroacetic acid. The black residue was redissolved in dichloromethane (0.2 mL). To this solution was added triethylamine (17 mg, 0.17 mmol) and acetic anhydride (13 mg, 0.12 mmol) and the reaction mixture was stirred at room temperature for an additional 3 h. The mixture was concentrated in vacuo. The crude residue was purified by reverse phase chromatography (acetonitrile 20-60%/0.1% formic acid in water) to give the racemic mixture of the title compounds. Then, the two enantiomers were separated by using chiral SFC (Chiralcel OJ 250×21.2 mm I.D., 5 µm; Supercritical CO$_2$/EtOH (0.1% NH$_3$H$_2$O)=80:20 at 70 mL/min) to give (S)-1-(3-(7-(difluoromethyl)-6-(1-methyl-1H-pyrazol-4-yl)-3,4-dihydroquinolin-1(2H)-yl)-1-(oxepan-4-yl)-1,4,6,7-tetrahydro-5H-pyrazolo[4,3-c]pyridin-5-yl)ethan-1-one (3.4 mg, first peak) and (R)-1-(3-(7-(difluoromethyl)-6-(1-methyl-1H-pyrazol-4-yl)-3,4-dihydroquinolin-1(2H)-yl)-1-(oxepan-4-yl)-1,4,6,7-tetrahydro-5H-pyrazolo[4,3-c]pyridin-5-yl)ethan-1-one (5.2 mg, second peak). Absolute configuration was arbitrarily assigned to each enantiomer. Example 251: $^1$H NMR (400 MHz, DMSO-d$_6$) δ 7.75 (s, 1H), 7.49 (s, 1H), 7.10 (d, J=2.7 Hz, 1H), 6.84-6.80 (m, 1H), 6.95-6.58 (m, 1H), 4.38-4.26 (m, 1H), 4.20-4.06 (m, 2H), 3.86 (s, 3H), 3.80-3.54 (m, 8H), 2.84 (q, J=5.8 Hz, 4H), 2.77-2.65 (m, 1H), 2.24-2.11 (m, 1H), 2.11-2.00 (m, 3H), 1.97 (d, J=6.5 Hz, 4H), 1.85-1.69 (m, 2H). LCMS M/Z (M+H) 525. Example 252: $^1$H NMR (400 MHz, DMSO-d$_6$) δ 7.75 (s, 1H), 7.49 (s, 1H), 7.10 (d, J=2.7 Hz, 1H), 6.84-6.80 (m, 1H), 6.95-6.58 (m, 1H), 4.38-4.26 (m, 1H), 4.20-4.06 (m, 2H), 3.86 (s, 3H), 3.80-3.54 (m, 8H), 2.84 (q, J=5.8 Hz, 4H), 2.77-2.65 (m, 1H), 2.24-2.11 (m, 1H), 2.11-2.00 (m, 3H), 1.97 (d, J=6.5 Hz, 4H), 1.85-1.69 (m, 2H). LCMS M/Z (M+H) 525.

Example 375

1-cyclohexyl-3-(7-(difluoromethyl)-6-(1-methyl-1H-pyrazol-4-yl)-3,4-dihydroquinolin-1(2H)-yl)-N-methyl-1,4,6,7-tetrahydro-5H-pyrazolo[4,3-c]pyridine-5-carboxamide

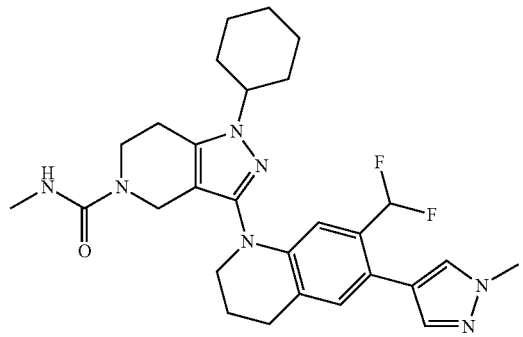

Step 1

N'-cyclohexylidene-4-methylbenzenesulfonohydrazide

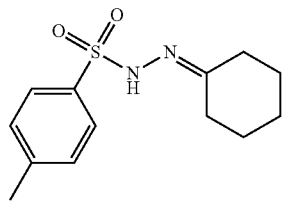 [SMILES: Cc1ccc(S(=O)(=O)NN=C2CCCCC2)cc1]

To a stirred solution of cyclohexanone (1.00 g, 10.2 mmol) in methanol (20 mL) was added 4-methylbenzene sulfonhydrazide (1.96 g, 10.2 mmol) and the reaction mixture was stirred at room temperature for 4 h. A white solid precipitated in the reaction mixture. The solution was cooled down to 0° C. The solid was filtered under vacuum to give the title compound (1.94 g, 72%) as white crystals. $^1$H NMR (400 MHz, CDCl$_3$) δ 7.87-7.79 (m, 2H), 7.29 (d, J=8.0 Hz, 2H), 7.06 (s, 1H), 2.42 (s, 3H), 2.28-2.16 (m, 4H), 1.69-1.51 (m, 6H). LCMS M/Z (M+H) 267.

Step 2 tert-butyl 1-cyclohexyl-3-(7-(difluoromethyl)-6-(1-methyl-1H-pyrazol-4-yl)-3,4-dihydroquinolin-1(2H)-yl)-1,4,6,7-tetrahydro-5H-pyrazolo[4,3-c]pyridine-5-carboxylate

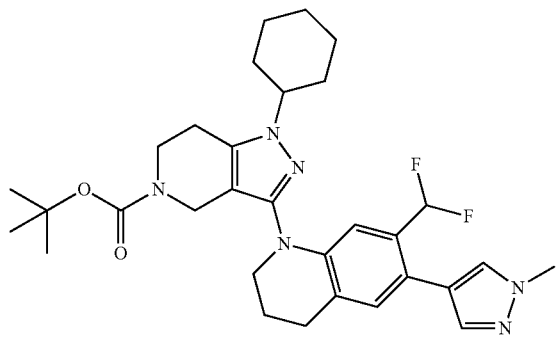 [SMILES: Cn1cc(-c2cc3c(cc2C(F)F)N(c2nn(C4CCCCC4)c4c2CN(C(=O)OC(C)(C)C)CC4)CCC3)cn1]

To a stirred solution of tert-butyl 3-(7-(difluoromethyl)-6-(1-methyl-1H-pyrazol-4-yl)-3,4-dihydroquinolin-1(2H)-yl)-6,7-dihydro-1H-pyrazolo[4,3-c]pyridine-5(4H)-carboxylate (Intermediate U, 60 mg, 0.12 mmol) was N'-cyclohexylidene-4-methylbenzenesulfonohydrazide (66 mg, 0.25 mmol), copper(II) acetylacetonate (7 mg, 0.025 mmol) and cesium carbonate (141 mg, 0.433 mmol) in 1,4-dioxane (1.2 mL) and the reaction mixture was stirred at 100° C. for 16 h under a nitrogen atmosphere. The reaction mixture was diluted with DCM (5 mL), filtered through celite and concentrated in vacuo. The brown solid obtained was used without any further purification in the next step. LCMS M/Z (M+H) 567.

Step 3

1-cyclohexyl-3-(7-(difluoromethyl)-6-(1-methyl-1H-pyrazol-4-yl)-3,4-dihydroquinolin-1(2H)-yl)-N-methyl-1,4,6,7-tetrahydro-5H-pyrazolo[4,3-c]pyridine-5-carboxamide

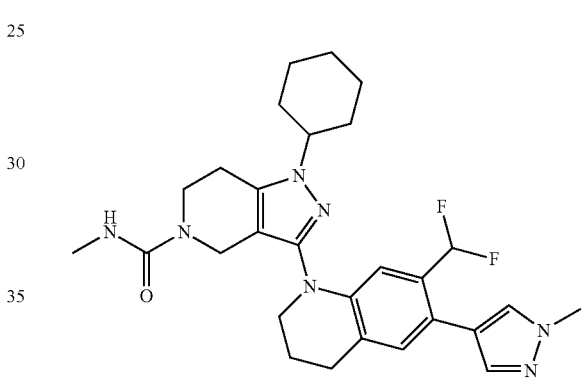

To a stirred solution of tert-butyl 3-(7-(difluoromethyl)-6-(1-methyl-1H-pyrazol-4-yl)-3,4-dihydroquinolin-1(2H)-yl)-1-(oxepan-4-yl)-1,4,6,7-tetrahydro-5H-pyrazolo[4,3-c]pyridine-5-carboxylate (crude mixture obtained from step 2) in dichloromethane (0.4 mL) at 0° C. was added trifluoroacetic acid (200 mg, 1.75 mmol) and the resulting solution was stirred for 2 h at room temperature. The crude mixture was concentrated in vacuo to remove the excess of trifluoroacetic acid The black residue was redissolved in dichloromethane (0.4 mL). To this solution was added triethylamine (35 mg, 0.34 mmol) and N-methyl-1H-imidazole-1-carboxamide (23 mg, 0.17 mmol). The reaction mixture was irradiated in a microwave at 100° C. for 10 min. The mixture was concentrated in vacuo. The crude residue was purified by reverse phase chromatography (acetonitrile 30-70%/0.1% NH$_4$OH in water) to give the title compounds (30 mg, 43% over 2 steps) as a white solid. $^1$H NMR (400 MHz, DMSO-d$_6$) δ 7.74 (s, 1H), 7.49 (d, J=0.8 Hz, 1H), 7.08 (s, 1H), 6.80 (s, 1H), 6.77 (t, J=55.3 Hz, 1H), 6.52 (q, J=4.3 Hz, 1H), 4.06-3.94 (m, 3H), 3.86 (s, 3H), 3.63-3.53 (m, 4H), 2.88-2.80 (m, 2H), 2.71 (t, J=5.8 Hz, 2H), 2.54 (d, J=4.2 Hz, 3H), 2.03-1.92 (m, 2H), 1.90-1.59 (m, 7H), 1.45-1.31 (m, 2H), 1.18 (q, J=13.3 Hz, 1H). LCMS M/Z (M+H) 524.

The Following Compounds were Prepared in a
Similar Fashion to Example 375

Examples 376-378

| Example | Compound Name | NMR | m/z |
|---|---|---|---|
| Example 376 | 1-(1-(cyanomethyl)piperidin-4-yl)-3-(7-(difluoromethyl)-6-(1-methyl-1H-pyrazol-4-yl)-3,4-dihydroquinolin-1(2H)-yl)-N-methyl-1,4,6,7-tetrahydro-5H-pyrazolo[4,3-c]pyridme-5-carboxamide | $^1$H NMR (400 MHz, DMSO-$d_6$) δ 7.74 (s, 1H), 7.49 (d, J = 0.8 Hz, 1H), 7.09 (s, 1H), 6.83 (s, 1H), 6.77 (t, J = 55.4 Hz, 1H), 6.53 (q, J = 4.3 Hz, 1H), 4.13-3.99 (m, 3H), 3.86 (s, 3H), 3.76 (s, 2H), 3.58 (q, J = 5.7 Hz, 4H), 2.93-2.80 (m, 4H), 2.73 (t, J = 5.7 Hz, 2H), 2.54 (d, J = 4.2 Hz, 3H), 2.41-2.30 (m, 2H), 2.10-1.92 (m, 4H), 1.92-1.84 (m, 2H). | 564 |
| Example 377 | 1-(1-(cyclopropanecarbonyl)piperidin-4-yl)-3-(7-(difluoromethyl)-6-(1-methyl-1H-pyrazol-4-yl)-3,4-dihydroquinolin-1(2H)-yl)-N-methyl-1,4,6,7-tetrahydro-5H-pyrazolo[4,3-c]pyridine-5-carboxamide | $^1$H NMR (400 MHz, DMSO-$d_6$, 36/38 H) δ 7.74 (s, 1H), 7.49 (s, 1H), 7.09 (s, 1H), 6.80 (s, 1H), 6.79 (t, J = 55.2 Hz, 1H), 6.53 (q, J = 4.3 Hz, 1H), 4.58-4.29 (m, 3H), 4.02 (s, 2H), 3.86 (s, 3H), 3.59 (dt, J = 14.0, 5.7 Hz, 4H), 2.83 (t, J = 6.4 Hz, 2H), 2.75 (t, J = 5.9 Hz, 2H), 2.54 (d, J = 4.2 Hz, 3H), 2.06-1.84 (m, 6H), 1.74 (s, 1H), 0.71 (tt, J = 7.9, 2.9 Hz, 4H). | 593 |
| Example 378 | 3-(7-(difluoromethyl)-6-(1-methyl-1H-pyrazol-4-yl)-3,4-dihydroquinolin-1(2H)-yl)-1-isopropyl-N-methyl-1,4,6,7-tetrahydro-5H-pyrazolo[4,3-c]pyridine-5-carboxamide | $^1$H NMR (400 MHz, DMSO-$d_6$) δ 7.74 (d, J = 0.8 Hz, 1H), 7.49 (d, J = 0.8 Hz, 1H), 7.09 (s, 1H), 6.83 (s, 1H), 6.77 (s, 1H), 6.53 (p, J = 4.4, 3.9 Hz, 1H), 4.39 (hept, J = 6.6 Hz, 1H), 4.02 (s, 2H), 3.86 (s, 3H), 3.58 (q, J = 5.8 Hz, 4H), 2.88-2.80 (m, 2H), 2.71 (t, J = 5.7 Hz, 2H), 2.54 (d, J = 4.2 Hz, 3H), 2.03-1.92 (m, 2H), 1.35 (d, J = 6.6 Hz, 6H). | 484 |

Example 379 & 380

(S)-3-(7-(difluoromethyl)-6-(1-methyl-1H-pyrazol-4-yl)-3,4-dihydroquinolin-1(2H)-yl)-N-methyl-1-(oxepan-4-yl)-1,4,6,7-tetrahydro-5H-pyrazolo[4,3-c]pyridine-5-carboxamide and (R)-3-(7-(difluoromethyl)-6-(1-methyl-1H-pyrazol-4-yl)-3,4-dihydroquinolin-1(2H)-yl)-N-methyl-1-(oxepan-4-yl)-1,4,6,7-tetrahydro-5H-pyrazolo[4,3-c]pyridine-5-carboxamide

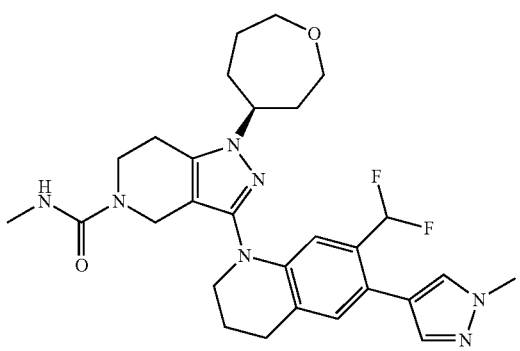

-continued

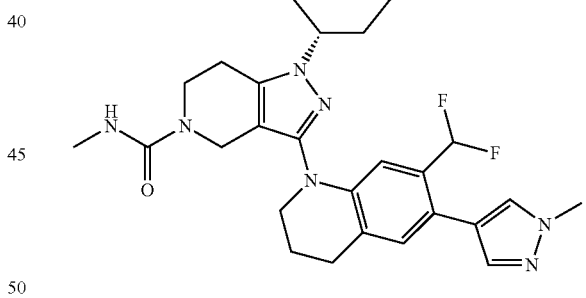

To a stirred solution of tert-butyl 3-(7-(difluoromethyl)-6-(1-methyl-1H-pyrazol-4-yl)-3,4-dihydroquinolin-1(2H)-yl)-1-(oxepan-4-yl)-1,4,6,7-tetrahydro-5H-pyrazolo[4,3-c]pyridine-5-carboxylate (crude mixture obtained from step 2 of Examples 373 & 374) in dichloromethane (0.2 mL) at 0° C. was added trifluoroacetic acid (99 mg, 0.87 mmol) and the resulting solution was stirred for 2 h at room temperature. The crude mixture was concentrated in vacuo to remove the excess trifluoroacetic acid. The black residue was redissolved in dichloromethane (0.2 mL). To this solution was added triethylamine (17 mg, 0.17 mmol) and N-methyl-1H-imidazole-1-carboxamide (11 mg, 0.083 mmol). The reaction mixture was irradiated in a microwave at 100° C. for 10 min. The mixture was concentrated in vacuo. The crude residue was purified by reverse phase chromatography (acetonitrile 20-60%/0.1% formic acid in water) to give the racemic mixture of the title compounds. Then, the two enantiomers were separated by using chiral SFC (Phenomenex Cellulose-3 250×21.2 mm I.D., 5 μm; Supercritical CO$_2$/EtOH (0.1% NH$_3$H$_2$O)=85:15 at 70 mL/min) to give (S)-3-(7-(difluoromethyl)-6-(1-methyl-1H-pyrazol-4-yl)-3,4-dihydroquinolin-1(2H)-yl)-N-methyl-1-(oxepan-4-yl)-1,4,6,7-tetrahydro-5H-pyrazolo[4,3-c]pyridine-5-carboxamide (6.5 mg, first peak) and (R)-3-(7-(difluoromethyl)-6-(1-methyl-1H-pyrazol-4-yl)-3,4-dihydroquinolin-1(2H)-yl)-N-methyl-1-(oxepan-4-yl)-1,4,6,7-tetrahydro-5H-pyrazolo[4,3-c]pyridine-5-carboxamide (6.0 mg, second peak). Absolute configuration was arbitrarily assigned to each enantiomer. Example 379: $^1$H NMR (400 MHz, DMSO-d$_6$) δ 7.74 (s, 1H), 7.49 (d, J=0.8 Hz, 1H), 7.09 (s, 1H), 6.82 (s, 1H), 6.77 (t, J=55.2 Hz, 1H), 6.52 (q, J=4.3 Hz, 1H), 4.32 (tt, J=9.3, 4.4 Hz, 1H), 4.02 (s, 2H), 3.86 (s, 3H), 3.80-3.69 (m, 2H), 3.69-3.52 (m, 6H), 2.88-2.80 (m, 2H), 2.72 (t, J=5.7 Hz, 2H), 2.54 (d, J=4.2 Hz, 3H), 2.21-1.86 (m, 6H), 1.85-1.66 (m, 2H). LCMS M/Z (M+H) 540. Example 380: $^1$H NMR (400 MHz, DMSO-d$_6$) δ 7.74 (s, 1H), 7.49 (d, J=0.8 Hz, 1H), 7.09 (s, 1H), 6.82 (s, 1H), 6.77 (t, J=55.2 Hz, 1H), 6.52 (q, J=4.3 Hz, 1H), 4.32 (tt, J=9.3, 4.4 Hz, 1H), 4.02 (s, 2H), 3.86 (s, 3H), 3.80-3.69 (m, 2H), 3.69-3.52 (m, 6H), 2.88-2.80 (m, 2H), 2.72 (t, J=5.7 Hz, 2H), 2.54 (d, J=4.2 Hz, 3H), 2.21-1.86 (m, 6H), 1.85-1.66 (m, 2H). LCMS M/Z (M+H) 540.

The Following Compounds were Prepared in a Similar Fashion to Example 379 & 380

Examples 381-386

| Example | Compound Name | NMR | m/z |
| --- | --- | --- | --- |
| Example 381 | (R)-1-(1-cyclopropylethyl)-3-(7-(difluoromethyl)-6-(1-methyl-1H-pyrazol-4-yl)-3,4-dihydroquinolin-1(2H)-yl)-N-methyl-1,4,6,7-tetrahydro-5H-pyrazolo[4,3-c]pyridine-5-carboxamide | $^1$H NMR (400 MHz, DMSO-d$_6$) δ 7.74 (s, 1H), 7.49 (d, J = 0.8 Hz, 1H), 7.08 (s, 1H), 6.86 (s, 1H), 6.77 (t, J = 55.2 Hz, 1H), 6.52 (q, J = 4.3 Hz, 1H), 4.12-3.96 (m, 2H), 3.86 (s, 3H), 3.70-3.47 (m, 5H), 2.84 (t, J = 6.1 Hz, 2H), 2.74-2.60 (m, 2H), 2.54 (d, J = 4.2 Hz, 3H), 1.99 (p, J = 6.3 Hz, 2H), 1.45 (d, J = 6.6 Hz, 3H), 1.26 (ddt, J = 13.3, 8.2, 4.4 Hz, 1H), 0.60-0.49 (m, 1H), 0.44-0.34 (m, 1H), 0.28 (dt, J = 4.8, 2.5 Hz, 2H). | 510 |
| Example 382 | (S)-1-(1-cyclopropylethyl)-3-(7-(difluoromethyl)-6-(1-methyl-1H-pyrazol-4-yl)-3,4-dihydroquinolin-1(2H)-yl)-N-methyl-1,4,6,7-tetrahydro-5H-pyrazolo[4,3-c]pyridine-5-carboxamide | $^1$H NMR (400 MHz, DMSO-d$_6$) δ 7.74 (s, 1H), 7.49 (d, J = 0.8 Hz, 1H), 7.08 (s, 1H), 6.86 (s, 1H), 6.77 (t, J = 55.2 Hz, 1H), 6.52 (q, J = 4.3 Hz, 1H), 4.12-3.96 (m, 2H), 3.86 (s, 3H), 3.70-3.47 (m, 5H), 2.84 (t, J = 6.1 Hz, 2H), 2.74-2.60 (m, 2H), 2.54 (d, J = 4.2 Hz, 3H), 1.99 (p, J = 6.3 Hz, 2H), 1.45 (d, J = 6.6 Hz, 3H), 1.26 (ddt, J = 13.3, 8.2, 4.4 Hz, 1H), 0.60-0.49 (m, 1H), 0.44-0.34 (m, 1H), 0.28 (dt, J = 4.8, 2.5 Hz, 2H). | 510 |
| Example 383 | 3-(7-(difluoromethyl)-6-(1-methyl-1H-pyrazol-4-yl)-3,4-dihydroquinolin-1(2H)-yl)-1-((Z)-4-methoxycyclohexyl)-N-methyl-1,4,6,7-tetrahydro-5H-pyrazolo[4,3-c]pyridine-5-carboxamide | $^1$H NMR (400 MHz, DMSO-d$_6$) δ 7.74 (s, 1H), 7.49 (s, 1H), 7.09 (s, 1H), 6.79 (s, 0H), 6.77 (t, J = 55.2 Hz, 1H), 6.76 (s, 1H), 6.52 (q, J = 4.4 Hz, 1H), 4.11-4.03 (m, 1H), 4.01 (s, 2H), 3.86 (s, 3H), 3.64-3.39 (m, 4H), 3.23-3.20 (m, 3H), 2.88-2.80 (m, 2H), 2.70 (t, J = 5.6 Hz, 2H), 2.54 (d, J = 4.3 Hz, 3H), 2.10-1.92 (m, 6H), 1.66-1.45 (m, 4H). | 554 |
| Example 384 | 3-(7-(difluoromethyl)-6-(1-methyl-1H-pyrazol-4-yl)-3,4-dihydroquinolin-1(2H)-yl)-1-((E)-4-methoxycyclohexyl)-N-methyl-1,4,6,7-tetrahydro-5H-pyrazolo[4,3-c]pyridine-5-carboxamide | $^1$H NMR (400 MHz, DMSO-d$_6$) δ 7.74 (s, 1H), 7.49 (d, J = 0.8 Hz, 1H), 7.09 (s, 1H), 6.79 (s, 1H), 6.77 (t, J = 55.2 Hz, 1H), 6.52 (q, J = 4.3 Hz, 1H), 4.11-4.01 (m, 1H), 4.01 (s, 2H), 3.86 (s, 3H), 3.57 (dt, J = 8.3, 5.6 Hz, 4H), 3.25 (s, 3H), 3.25-3.11 (m, 1H), 2.84 (t, J = 6.8 Hz, 2H), 2.71 (t, J = 5.7 Hz, 2H), 2.54 (d, J = 4.2 Hz, 3H), 2.12-2.04 (m, 2H), 2.01-1.93 (m, 2H), 1.93-1.74 (m, 4H), 1.29 (qd, J = 12.9, 4.0 Hz, 2H). | 554 |
| Example 385 | 1-((Z)-4-cyanocyclohexyl)-3-(7-(difluoromethyl)-6-(1-methyl-1H-pyrazol-4-yl)-3,4-dihydroquinolin-1(2H)-yl)-N-methyl-1,4,6,7-tetrahydro-5H-pyrazolo[4,3-c]pyridine-5-carboxamide | $^1$H NMR (400 MHz, DMSO-d$_6$) δ 7.75 (s, 1H), 7.49 (d, J = 0.8 Hz, 1H), 7.09 (s, 1H), 6.78 (s, 1H), 6.77 (t, J = 55.2 Hz, 1H), 6.53 (q, J = 4.3 Hz, 1H), 4.14-4.03 (m, 1H), 4.01 (s, 2H), 3.86 (s, 3H), 3.59 (td, J = 5.9, 2.8 Hz, 4H), 3.17 (q, J = 3.8 Hz, 1H), 2.85 (t, J = 6.3 Hz, 2H), 2.71 | 549 |

-continued

| Example | Compound Name | NMR | m/z |
|---|---|---|---|
| Example 386 | 1-((E)-4-cyanocyclohexyl)-3-(7-(difluoromethyl)-6-(1-methyl-1H-pyrazol-4-yl)-3,4-dihydroquinolin-1(2H)-yl)-N-methyl-1,4,6,7-tetrahydro-5H-pyrazolo[4,3-c]pyridine-5-carboxamide | (t, J = 5.7 Hz, 2H), 2.54 (d, J = 4.3 Hz, 3H), 1.99 (dd, J = 10.7, 4.4 Hz, 6H), 1.91 (dt, J = 13.7, 6.0 Hz, 2H), 1.81-1.69 (m, 2H). $^1$H NMR (400 MHz, DMSO-$d_6$) δ 7.74 (d, J = 0.8 Hz, 1H), 7.49 (d, J = 0.8 Hz, 1H), 7.09 (s, 1H), 6.77 (t, J = 55.2 Hz, 1H), 6.75 (s, 1H), 6.52 (q, J = 4.3 Hz, 1H), 4.09 (tt, J = 11.0, 4.2 Hz, 1H), 4.00 (s, 2H), 3.86 (s, 3H), 3.57 (dt, J = 11.3, 5.7 Hz, 4H), 2.87-2.76 (m, 3H), 2.76-2.65 (m, 2H), 2.53 (d, J = 4.2 Hz, 3H), 2.17-2.07 (m, 2H), 2.02-1.62 (m, 8H). | 549 |

Example 387

$IC_{50}$ Measurements for Inhibitors Using CBP TR-FRET Binding Assay

His/Flag epitope tagged CBP was cloned, expressed, and purified to homogeneity. CBP binding and inhibition was assessed by monitoring the engagement of a biotinylated small molecule compound with the target using the TR-FRET assay technology (Perkin-Elmer). Specifically, in a 384 well ProxiPlate CBP (4 nM final) was combined with biotin-ligand (60 nM final) in 50 mM HEPES (pH 7.5), 50 mM NaCl, 1 mM TCEP, 0.01% (w/v) BSA, and 0.008% (w/v) Brij-35 either in the presence of DMSO (final 0.2% DMSO) or compound dilution series in DMSO. After 10 minutes incubation at room temperature, a mixture Eu-W1024 Anti-6xHis antibody ("6xHis" disclosed as SEQ ID NO: 3) (Perkin Elmer AD0110) and SureLight™ Allophycocyanin-Streptavidin (APC-SA, Perkin Elmer CR130-100) were added to a final concentrations of 0.2 nMolar antibody and 50 nMolar APC-SA, respectively. After twenty minutes of equilibration, the plates were read on an Envision instrument and $IC_{50}$s calculated using a four parameter non-linear curve fit.

$IC_{50}$ measurements for inhibitors using BRD4 BD1 TR-FRET Binding Assay

His/Flag epitope-tagged BRD4 BD1 (bromo domain 1) was cloned, expressed, and purified to homogeneity. BRD4 BD1 binding and inhibition were assessed by monitoring the engagement of a biotinylated small molecule compound with the target using TR-FRET assay technology (PerkinElmer). Specifically, BRD4 BD1 (2.5 nM final) in 50 mM HEPES (pH 7.5), 50 mM NaCl, 1 mM TCEP, 0.01% (w/v) BSA, and 0.008% (w/v) Brij-35 was added to the wells of a 384-well white ProxiPlate containing DMSO alone or compound dilution series in DMSO (final 0.2% DMSO). After 10 minutes of incubation at room temperature, biotin-ligand (25 nM final) was added and allowed to incubate for an additional 10 minutes. Then a mixture of Eu-W1024 Anti-6xHis antibody ("6xHis" disclosed as SEQ ID NO: 3) (PerkinElmer AD0110) and SureLight™ Allophycocyanin-Streptavidin (APC-SA, PerkinElmer CR130-100) was added to final concentrations of 0.2 nM antibody and 100 nM APC-SA, respectively. After 40 minutes of equilibration under ambient conditions, the plates were read on an Envision plate reader, and $IC_{50}$ values were calculated using four-parameter, non-linear curve fitting.

MYC RPL19 QuantiGene Assay in MV-4-11 Cells

QuantiGene 2.0 Reagent system, Affymetrix: HUMAN MYCN; V-myc myelocytomatosis viral related oncogene, neuroblastoma derived (avian); NM_005378 SA-15008. 10,000 MV-4-11 cells (GNE in-house) were plated in 75 ul complete media: RPMI-1640 (GNE in-house), 10% FBS (Life Technologies, cat. no. 10082), 1% Pen-strep (GNE in-house), in 96 well clear flat bottom plates (Costar, cat. no. 3595). 25 ul compound was added for 4 hours at 37 deg C. in a 1:3 serial dilution 10-point dose response, with a final DMSO concentration=0.2%. The cells were then lysed according to the assay kit's protocol and frozen at −80 deg C. The following day, an appropriate volume of Working Probe Set was prepared by combining the following reagents in the order listed: Nuclease-free water, Lysis Mixture, Blocking Reagent, and 2.0 Probe Set (MYC or RPLI9). 20 ul of the working probe set was added into each assay well on the capture plate, and then 80 ul of the lysates were transferred into the assay plates. The capture plate was placed in a 55 deg C. incubator for overnight hybridization (16-20 hours). The following day, wash buffer was prepared according to manufacturer's recommendations. The capture plates were washed with 300 ul per well of 1× wash buffer three times. Then 100 ul Pre-Amplifier was added to the plate for a 60 minute incubation at 55 deg C. After the incubation, the capture plate was washed with 300 ul per well of 1× wash buffer three times, and 100 ul Amplifier was added to the plate for a 60 minute incubation at 55 deg C. The capture plate was again washed with 300 ul per well of 1× wash buffer three times, and 100 ul Label Probe was added to the plate for a 60 minute incubation at 50 deg C. Then the capture plate was washed with 300 ul per well of 1× wash buffer three times, and 100 ul 2.0 Substrate was added to each well of the plate. The plates were incubated at RT for 5 minutes in the dark and read on the Envision using the luminescence protocol, with an integration time set at 0.2 seconds.

Data for representative compounds of formula (I) from the three assays described above is provided in the following table (all units in μM).

| Example | CBP HTRF $IC_{50}$ (μM) | BRD4 HTRF $IC_{50}$ (μM) | Myc $IC_{50}$ (μM) |
|---|---|---|---|
| 1 | 1.181 | >20.0 | |
| 2 | 1.593 | >20.0 | |
| 3 | 1.575 | >20.0 | |
| 4 | 0.627 | >20.0 | |
| 5 | 0.994 | >20.0 | |
| 6 | 0.029 | >20.0 | 0.375 |
| 7 | 0.046 | >20.0 | |
| 8 | 0.050 | >20.0 | |

| Example | CBP HTRF IC$_{50}$ (μM) | BRD4 HTRF IC$_{50}$ (μM) | Myc IC$_{50}$ (μM) | Example | CBP HTRF IC$_{50}$ (μM) | BRD4 HTRF IC$_{50}$ (μM) | Myc IC$_{50}$ (μM) |
|---|---|---|---|---|---|---|---|
| 9 | 0.032 | >20.0 | 5.058 | 85 | 0.002 | 11.4 | |
| 10 | 0.025 | >20.0 | 2.130 | 86 | 0.030 | >20.0 | 6.103 |
| 11 | 0.051 | >20.0 | | 87 | 0.041 | >20.0 | 14.335 |
| 12 | 0.063 | 9.8 | | 88 | 0.031 | >20.0 | 0.354 |
| 13 | 0.048 | 16.7 | 1.237 | 89 | 0.057 | >20.0 | |
| 14 | 0.074 | >20.0 | | 90 | 0.276 | >20.0 | |
| 15 | 0.026 | >20.0 | 1.350 | 91 | 0.024 | >20.0 | 7.873 |
| 16 | 0.115 | >20.0 | | 92 | 0.026 | >20.0 | 0.937 |
| 17 | 0.014 | 8.8 | 1.141 | 93 | 0.025 | >20.0 | 1.249 |
| 18 | 0.050 | >20.0 | 1.555 | 94 | 2.190 | >20.0 | |
| 19 | 0.034 | >20.0 | 2.598 | 95 | 0.005 | >20.0 | 0.474 |
| 20 | 0.258 | >20.0 | | 96 | 0.511 | >20.0 | |
| 21 | 0.071 | >20.0 | | 97 | 0.014 | >20.0 | 0.149 |
| 22 | 0.115 | >20.0 | | 98 | 0.008 | >20.0 | 0.673 |
| 23 | 0.051 | 1.8 | 1.711 | 99 | 0.019 | >20.0 | 5.653 |
| 24 | 0.035 | >20.0 | 4.647 | 100 | 0.026 | >20.0 | 0.232 |
| 25 | 0.107 | >20.0 | | 101 | 0.021 | >20.0 | 0.110 |
| 26 | 0.064 | >20.0 | | 102 | 0.003 | 9.7 | 0.154 |
| 27 | 0.070 | >20.0 | | 103 | 0.006 | >20.0 | 0.224 |
| 28 | 0.063 | >20.0 | | 104 | 0.003 | 16.7 | 0.085 |
| 29 | 0.083 | >20.0 | | 105 | 0.012 | >20.0 | 0.364 |
| 30 | 0.043 | >20.0 | 18.449 | 106 | 0.031 | >20.0 | 2.148 |
| 31 | 0.033 | >20.0 | | 107 | 0.073 | >20.0 | |
| 32 | 0.021 | >20.0 | 7.043 | 108 | 0.034 | >20.0 | 5.167 |
| 33 | 0.009 | >20.0 | 1.583 | 109 | 0.071 | >20.0 | |
| 34 | 0.058 | >20.0 | | 110 | 0.019 | >20.0 | 8.932 |
| 35 | 0.023 | >20.0 | 0.202 | 111 | 0.018 | >20.0 | 4.246 |
| 36 | 0.039 | >20.0 | 1.857 | 112 | 0.058 | >20.0 | |
| 37 | 0.074 | >20.0 | | 113 | 0.023 | >20.0 | 0.250 |
| 38 | 0.089 | >20.0 | | 114 | 0.016 | >20.0 | 0.126 |
| 39 | 0.187 | >20.0 | | 115 | 0.019 | >20.0 | 2.622 |
| 40 | 0.424 | >20.0 | | 116 | 0.101 | >20.0 | |
| 41 | 0.065 | >20.0 | | 117 | 0.010 | >20.0 | 0.256 |
| 42 | 0.054 | >20.0 | | 118 | 0.022 | 16.0 | 0.809 |
| 43 | 0.091 | >20.0 | | 119 | 0.026 | >20.0 | 0.657 |
| 44 | 0.080 | >20.0 | | 120 | 0.021 | 18.4 | 1.500 |
| 45 | 0.237 | >20.0 | | 121 | 0.001 | 4.9 | 0.011 |
| 46 | 0.005 | 14.5 | 1.531 | 122 | 0.008 | 9.4 | 0.274 |
| 47 | 0.049 | 18.7 | 19.238 | 123 | 0.006 | 3.3 | 0.233 |
| 48 | 0.004 | 7.7 | 0.669 | 124 | 0.001 | 4.9 | 0.006 |
| 49 | 0.011 | 14.3 | 1.127 | 125 | 0.006 | 4.3 | 0.259 |
| 50 | 1.523 | >20.0 | | 126 | 0.006 | 8.6 | 0.087 |
| 51 | 0.007 | >20.0 | 0.729 | 127 | 0.006 | >20.0 | 0.693 |
| 52 | 0.020 | >20.0 | 3.277 | 128 | 0.001 | 8.8 | 0.027 |
| 53 | 0.011 | 18.0 | 0.721 | 129 | 0.002 | 10.6 | 0.028 |
| 54 | 0.010 | 15.2 | 9.556 | 130 | 0.009 | >20.0 | 0.323 |
| 55 | 0.023 | >20.0 | 0.254 | 131 | 0.005 | 19.7 | 0.051 |
| 56 | 0.020 | 18.1 | 1.845 | 132 | 0.015 | >20.0 | 0.737 |
| 57 | 0.008 | >20.0 | 0.037 | 133 | 0.005 | >20.0 | 0.047 |
| 58 | 0.004 | >20.0 | 0.199 | 134 | 0.005 | 9.2 | 0.957 |
| 59 | 0.004 | >20.0 | 0.188 | 135 | 0.041 | >20.0 | 1.073 |
| 60 | 0.001 | 7.4 | 0.089 | 136 | 0.0646 | >20.0 | |
| 61 | 0.003 | >20.0 | | 137 | 0.085 | >20.0 | |
| 62 | 0.003 | >20.0 | 0.598 | 138 | 0.069 | >20.0 | |
| 63 | 0.008 | >20.0 | 0.019 | 139 | 0.159 | >20.0 | |
| 64 | 0.007 | >20.0 | 0.334 | 140 | 0.686 | >20.0 | |
| 65 | 0.029 | 18.0 | 0.401 | 141 | 0.002 | 11.1 | 0.206 |
| 66 | 0.020 | 14.2 | 4.913 | 142 | 0.008 | 8.7 | 1.348 |
| 67 | 0.040 | >20.0 | 0.744 | 143 | 0.009 | 8.8 | 0.160 |
| 68 | 0.148 | 13.7 | | 144 | 0.017 | >20.0 | 1.021 |
| 69 | 0.070 | >20.0 | 4.860 | 145 | 0.005 | 1.9 | 0.055 |
| 70 | 0.024 | 17.2 | 1.341 | 146 | 0.001 | 1.9 | 0.051 |
| 71 | 0.016 | 18.2 | 0.582 | 147 | 0.004 | 7.9 | 0.135 |
| 72 | 0.025 | >20.0 | 0.681 | 148 | 0.001 | 2.3 | 0.023 |
| 73 | 0.035 | >20.0 | 1.567 | 149 | 0.001 | 2.9 | 0.004 |
| 74 | 0.041 | >20.0 | 1.474 | 150 | 0.017 | >20.0 | 14.416 |
| 75 | 0.008 | >20.0 | 0.411 | 151 | 0.058 | >20.0 | |
| 76 | 0.007 | >20.0 | 0.652 | 152 | 0.002 | 7.9 | 0.072 |
| 77 | 0.080 | >20.0 | | 153 | 0.0034 | >20.0 | 0.119 |
| 78 | 0.021 | 10.5 | 3.498 | 154 | 0.001 | 9.8 | 0.017 |
| 79 | 0.082 | >20.0 | | 155 | 0.001 | 10.9 | 0.014 |
| 80 | 0.020 | 12.1 | 4.749 | 156 | 0.004 | 14.3 | 0.706 |
| 81 | 0.024 | >20.0 | 0.280 | 157 | 0.001 | 5.4 | 0.015 |
| 82 | 0.019 | >20.0 | 1.338 | 158 | 0.002 | 11.5 | 0.046 |
| 83 | 0.024 | >20.0 | 0.830 | 159 | 0.001 | 11.2 | 0.016 |
| 84 | 0.006 | 16.5 | 0.088 | 160 | 0.003 | >20.0 | 0.150 |

| Example | CBP HTRF IC$_{50}$ (μM) | BRD4 HTRF IC$_{50}$ (μM) | Myc IC$_{50}$ (μM) | Example | CBP HTRF IC$_{50}$ (μM) | BRD4 HTRF IC$_{50}$ (μM) | Myc IC$_{50}$ (μM) |
|---|---|---|---|---|---|---|---|
| 161 | 0.001 | 4.3 | 0.009 | 237 | 2.886 | >20.0 | |
| 162 | 0.001 | 6.3 | 0.004 | 238 | 0.0011 | 4.7 | 0.028 |
| 163 | 0.001 | 5.8 | 0.005 | 239 | 0.0047 | 9.7 | 0.176 |
| 164 | 0.001 | 7.8 | 0.018 | 240 | 0.0020 | 7.8 | 0.035 |
| 165 | 0.001 | 8.9 | 0.013 | 241 | 0.0013 | 6.8 | 0.02 |
| 166 | 3.218 | 13.1 | | 242 | 0.0033 | 7.0 | 0.112 |
| 167 | 0.001 | 3.5 | 0.237 | 243 | 0.0007 | 1.9 | 0.016 |
| 168 | 0.025 | 6.5 | 0.478 | 244 | 0.0016 | 4.4 | 0.086 |
| 169 | 0.041 | 11.8 | 0.980 | 245 | 0.0011 | 3.9 | 0.011 |
| 170 | 0.011 | 1.5 | 0.499 | 246 | 0.0029 | 6.2 | 0.094 |
| 171 | 0.043 | 8.4 | 2.947 | 247 | 0.0011 | 1.3 | 0.018 |
| 172 | 0.128 | 14.4 | 1.691 | 248 | 0.0009 | 4.1 | 0.017 |
| 173 | 0.757 | >20.0 | | 249 | 0.0006 | 2.5 | 0.011 |
| 174 | 0.027 | 4.6 | 0.478 | 250 | 0.0008 | 3.7 | 0.006 |
| 175 | 0.068 | 13.5 | | 251 | 0.0007 | 3.8 | 0.006 |
| 176 | 0.038 | 5.8 | 0.523 | 252 | 0.0007 | 3.7 | 0.005 |
| 177 | 0.0688 | 7.6 | 0.892 | 253 | 0.0012 | 7.3 | 0.028 |
| 178 | 0.040 | 4.0 | 0.209 | 254 | 0.0007 | 3.8 | 0.004 |
| 179 | 0.015 | 2.0 | 2.457 | 255 | 0.0017 | 5.7 | 0.047 |
| 180 | 0.015 | 2.6 | 0.549 | 256 | 0.0010 | 2.2 | 0.011 |
| 181 | 0.025 | 3.7 | 0.188 | 257 | 0.0012 | 4.9 | 0.008 |
| 182 | 0.018 | 1.7 | 0.135 | 258 | 0.0011 | 2.0 | 0.011 |
| 183 | 0.016 | 2.1 | 0.667 | 259 | 0.0014 | 2.9 | 0.019 |
| 184 | 0.021 | 3.2 | 0.982 | 260 | 0.0025 | 4.7 | 0.039 |
| 185 | 0.025 | 5.0 | 0.565 | 261 | 0.0014 | 8.1 | 0.029 |
| 186 | 0.032 | 6.9 | 1.282 | 262 | 0.0008 | 7.5 | 0.005 |
| 187 | 0.025 | 3.6 | 0.284 | 263 | 0.0012 | 4.5 | 0.015 |
| 188 | 0.027 | 5.1 | 1.311 | 264 | 0.0013 | 2.8 | 0.016 |
| 189 | 0.026 | 4.3 | 1.760 | 265 | 0.0134 | >20.0 | 0.358 |
| 190 | 0.025 | 9.2 | 0.562 | 266 | 0.0009 | 4.6 | 0.004 |
| 191 | 0.016 | 7.2 | 0.329 | 267 | 0.0085 | >20.0 | 0.082 |
| 192 | 0.034 | 12.8 | 0.745 | 268 | 0.0010 | 4.0 | 0.007 |
| 193 | 0.219 | 12.0 | | 269 | 0.0013 | 1.5 | 0.007 |
| 194 | 0.031 | 7.0 | 0.915 | 270 | 0.0012 | 2.0 | 0.019 |
| 195 | 0.161 | 9.1 | | 271 | 0.0042 | >20.0 | 2.077 |
| 196 | 0.027 | 3.6 | 3.599 | 272 | 0.0010 | 3.6 | 0.006 |
| 197 | 0.023 | 3.9 | 1.575 | 273 | 0.0014 | 1.4 | 0.027 |
| 198 | 0.137 | 7.7 | | 274 | 0.0175 | >20.0 | |
| 199 | 0.222 | >20.0 | 1.792 | 275 | 0.0020 | 15.3 | 0.046 |
| 200 | 0.028 | 6.1 | 0.228 | 276 | 0.0017 | 7.7 | 0.013 |
| 201 | 0.020 | 13.9 | 1.434 | 277 | 0.0017 | 4.6 | 0.021 |
| 202 | 0.314 | >20.0 | | 278 | 0.0016 | 5.8 | 0.029 |
| 203 | 0.151 | >20.0 | | 279 | 0.0026 | >20.0 | 0.104 |
| 204 | 0.010 | >20.0 | >20.0 | 280 | 0.0052 | >20.0 | 0.057 |
| 205 | 0.067 | >20.0 | | 281 | 0.0036 | 19.3 | 0.062 |
| 206 | 0.119 | 9.9 | | 282 | 0.0014 | 13.0 | 0.019 |
| 207 | 0.041 | 4.1 | 1.219 | 283 | 0.0024 | 15.4 | 0.051 |
| 208 | 0.107 | >20.0 | | 284 | 0.0029 | 19.9 | 0.052 |
| 209 | 0.032 | 5.9 | 3.364 | 285 | 0.0014 | 7.3 | 0.040 |
| 210 | 0.044 | 2.5 | 0.564 | 286 | 0.0022 | 10.3 | 0.043 |
| 211 | 0.014 | >20.0 | >20.0 | 287 | 0.0080 | >20.0 | 0.069 |
| 212 | 0.041 | >20.0 | 4.497 | 288 | 0.0016 | 11.0 | 0.025 |
| 213 | 0.050 | 3.0 | | 289 | 0.0017 | 14.2 | 0.016 |
| 214 | 0.343 | >20.0 | | 290 | 0.0009 | 10.3 | 0.007 |
| 215 | 0.054 | 5.3 | 7.648 | 291 | 0.0014 | 11.8 | 0.027 |
| 216 | 0.069 | 7.8 | 1.284 | 292 | 0.0029 | 11.2 | 0.033 |
| 217 | 0.040 | 14.6 | 0.395 | 293 | 0.0039 | 11.9 | 0.073 |
| 218 | 0.010 | 5.1 | 0.551 | 294 | 0.0012 | 4.5 | 0.031 |
| 219 | 0.004 | >20.0 | 0.192 | 295 | 0.0014 | 2.8 | 0.027 |
| 220 | 0.041 | 7.0 | 3.840 | 296 | 0.0011 | 7.9 | 0.011 |
| 221 | 0.070 | 10.4 | | 297 | 0.0080 | 16.9 | 0.070 |
| 222 | 0.201 | >20.0 | | 298 | 0.0021 | 12.8 | 0.083 |
| 223 | 0.159 | >20.0 | | 299 | 0.0024 | >20.0 | 0.038 |
| 224 | 0.112 | >20.0 | >4.0 | 300 | 0.0021 | 17.2 | 0.053 |
| 225 | 0.055 | 19.3 | 0.535 | 301 | 0.0014 | 6.0 | 0.038 |
| 226 | 0.047 | 10.4 | 0.514 | 302 | 0.0041 | 12.9 | 0.032 |
| 227 | 2.125 | | | 303 | 0.0040 | 11.8 | 0.028 |
| 228 | 0.115 | >20.0 | >4.0 | 304 | 0.0028 | 11.8 | 0.086 |
| 229 | 0.461 | >20.0 | | 305 | 0.0017 | 7.0 | 0.030 |
| 230 | 0.005 | >20.0 | 0.236 | 306 | 0.0036 | 7.1 | 0.106 |
| 231 | 0.031 | >20.0 | | 307 | 0.0063 | 11.9 | 0.075 |
| 232 | 0.088 | >20.0 | | 308 | 0.0017 | 10.5 | 0.015 |
| 233 | 2.318 | 6.1 | | 309 | 0.0023 | >20.0 | 0.063 |
| 234 | 2.547 | >20.0 | | 310 | 0.0009 | 3.6 | 0.004 |
| 235 | 0.163 | >20.0 | | 311 | 0.0015 | 3.1 | 0.019 |
| 236 | 1.245 | >20.0 | | 312 | 0.0015 | >7.0 | 0.017 |

-continued

| Example | CBP HTRF IC$_{50}$ (μM) | BRD4 HTRF IC$_{50}$ (μM) | Myc IC$_{50}$ (μM) |
|---|---|---|---|
| 313 | 0.0015 | 3.5 | 0.015 |
| 314 | 0.0016 | 3.8 | 0.059 |
| 315 | 0.0027 | 4.2 | 0.022 |
| 316 | 0.0020 | 6.4 | 0.034 |
| 317 | 0.0017 | 2.6 | 0.017 |
| 318 | 0.0012 | 6.3 | 0.005 |
| 319 | 0.0008 | 4.2 | 0.008 |
| 320 | 0.0020 | 3.9 | 0.021 |
| 321 | 0.0010 | 2.4 | 0.011 |
| 322 | 0.0012 | 5.1 | 0.019 |
| 323 | 0.0012 | 5.4 | 0.021 |
| 324 | 0.0007 | 4.6 | 0.011 |
| 325 | 0.0010 | 8.1 | 0.017 |
| 326 | 0.0059 | 6.9 | 0.078 |
| 327 | 0.0007 | 3.8 | 0.006 |
| 328 | 0.0007 | 3.6 | 0.007 |
| 329 | 0.0009 | 3.9 | 0.007 |
| 330 | 0.0010 | 4.7 | 0.015 |
| 331 | 0.0010 | 3.7 | 0.018 |
| 332 | 0.0039 | >20.0 | 0.062 |
| 333 | 0.0037 | 15.9 | 0.063 |
| 334 | 0.0009 | 5.9 | 0.009 |
| 335 | 0.0009 | 3.4 | 0.005 |
| 336 | 0.0010 | 4.5 | 0.005 |
| 337 | 0.0010 | 4.9 | 0.012 |
| 338 | 0.0008 | 6.2 | 0.008 |
| 339 | 0.0008 | 5.2 | 0.006 |
| 340 | 0.0011 | 8.7 | 0.021 |
| 341 | 0.0030 | 16.2 | 0.038 |
| 342 | 0.0021 | 9.7 | 0.023 |
| 343 | 0.0070 | 10.6 | 0.285 |
| 344 | 0.0022 | 12.7 | 0.009 |
| 345 | 0.0010 | 3.4 | 0.013 |
| 346 | 0.0013 | 4.8 | 0.012 |
| 347 | 0.0020 | 4.2 | >1.0 |
| 348 | 0.0009 | 3.9 | 0.019 |
| 349 | 0.0008 | 3.6 | 0.026 |
| 350 | 0.0014 | 4.4 | 0.041 |
| 351 | 0.0011 | 3.6 | 0.008 |
| 352 | 0.0011 | 2.7 | 0.007 |
| 353 | 0.0023 | 5.3 | 0.029 |
| 354 | 0.0013 | 4.8 | 0.024 |
| 355 | 0.0060 | 4.0 | 0.070 |
| 356 | 0.0044 | >20.0 | 0.049 |
| 357 | 0.0061 | 19.2 | |
| 358 | 0.0007 | 3.6 | 0.010 |
| 359 | 0.0009 | 4.7 | 0.019 |
| 360 | 0.0011 | 3.6 | 0.113 |
| 361 | 0.0010 | 1.4 | 0.007 |
| 362 | 0.0009 | 4.8 | 0.056 |
| 363 | 0.0011 | 10.4 | 0.048 |
| 364 | 0.0010 | 2.8 | 0.095 |
| 365 | 0.0019 | 8.8 | 0.235 |
| 366 | 0.0013 | 1.2 | 0.008 |
| 367 | 0.0012 | 1.1 | 0.070 |
| 368 | 0.0011 | 2.8 | 0.006 |
| 369 | 0.0021 | 9.3 | 0.067 |
| 370 | 1.6582 | >20.0 | |
| 371 | 0.3836 | >20.0 | |
| 372 | 0.0108 | >20.0 | |
| 373 | 0.0012 | 4.9 | 0.023 |
| 374 | 0.0012 | 4.2 | 0.010 |
| 375 | 0.0010 | 4.1 | 0.008 |
| 376 | 0.0009 | 4.2 | 0.014 |
| 377 | 0.0007 | 3.5 | 0.006 |
| 378 | 0.0008 | 3.2 | 0.004 |
| 379 | 0.0009 | 4.2 | 0.006 |
| 380 | 0.0008 | 2.7 | 0.004 |
| 381 | 0.0010 | 1.7 | 0.006 |
| 382 | 0.0009 | 2.8 | 0.007 |
| 383 | 0.0009 | 4.0 | 0.006 |
| 384 | 0.0009 | 3.6 | 0.003 |
| 385 | 0.0009 | 3.0 | 0.016 |
| 386 | 0.0009 | 3.5 | 0.004 |

While a number of embodiments have been described, these examples may be altered to provide other embodiments that utilize the compounds and methods described herein. Therefore, the scope of this invention is to be defined by the appended claims rather than by the specific embodiments that have been represented by way of example.

Exemplification of Compounds of Formula (II)

As depicted in the Examples below, in certain exemplary embodiments, compounds of Formula (II) are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

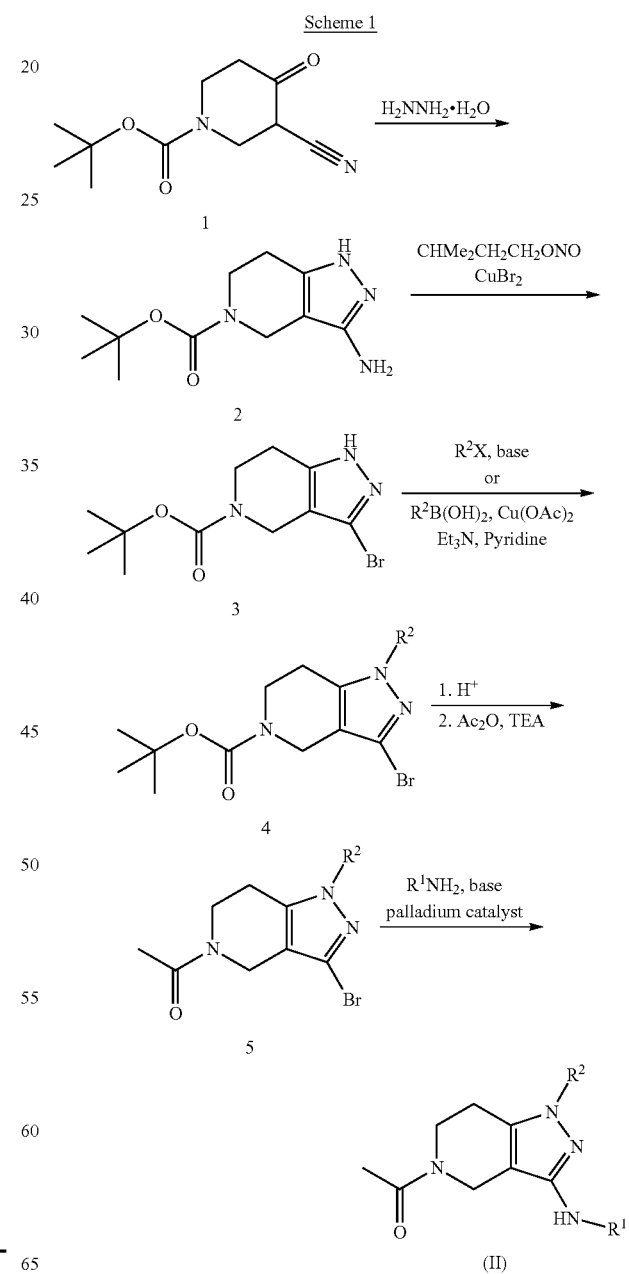

Compounds of Formula (II) may be prepared by general synthetic methods as shown in Scheme 1.

Reaction between α-cyanoketone (1) and hydrazine in a suitable solvent such as, but not limited to, ethanol at a temperature ranging from about room temperature to reflux temperature and for a time varying from about 30 minutes to about 2 hours can provide amino pyrazole (2). The bromo pyrazole (3) can be formed by diazotization of the amino pyrazole using a isoamylnitrite, sodium nitrite, or tert-butyl nitrite and copper(II) bromide in a suitable organic solvent such as, but not limited to, acetonitrile at a temperature of about 20° C. to about 60° C. for about 5 hours. The alkylation of pyrazole $N^1$ nitrogen to form compounds of formula (5) can be carried out using an alkyl iodide, bromide, mesylate or triflate in the presence of an inorganic base such as, but not limited to, sodium hydride or cesium carbonate, in a suitable solvent such as, but not limited to, N,N-dimethylformamide (DMF) or tetrahydrofuran (THF), and at a temperature ranging from about 0° C. to 120° C. and for a time varying from about 30 minutes to about 16 hours. Compounds of formula (3) can also be formed by treatment with alkyl boronic acids or boronate esters such as cyclopropylboronic acid in the presence of copper(II) acetate and an organic base such as, but not limited to, triethylamine or pyridine in a suitable solvent such as, but not limited to, THF at around 60° C. for 12 hours. Deprotection of N-tert-butoxycarbonyl (Boc) group using a protic acid such as, but not limited to, trifluoroacetic acid or hydrochloric acid followed by N-acetylation with acetic anhydride in the presence of an organic base such as, but not limited to, triethylamine can afford compounds of formula (5). Compounds of formula (5) can cross-couple with aryl, heteroaryl, alkyl or cycloalkyl amines under a palladium catalyst conditions such as, but not limited to, Ruphos pre-catalyst in combination with Brettphos/Ruphos ligand in the presence of inorganic base such as, but not limited to, sodium tert-butoxide or cesium carbonate in a suitable organic solvent such as, but not limited to, 1,4-dioxane at an elevated temperature to yield compounds of Formula (II).

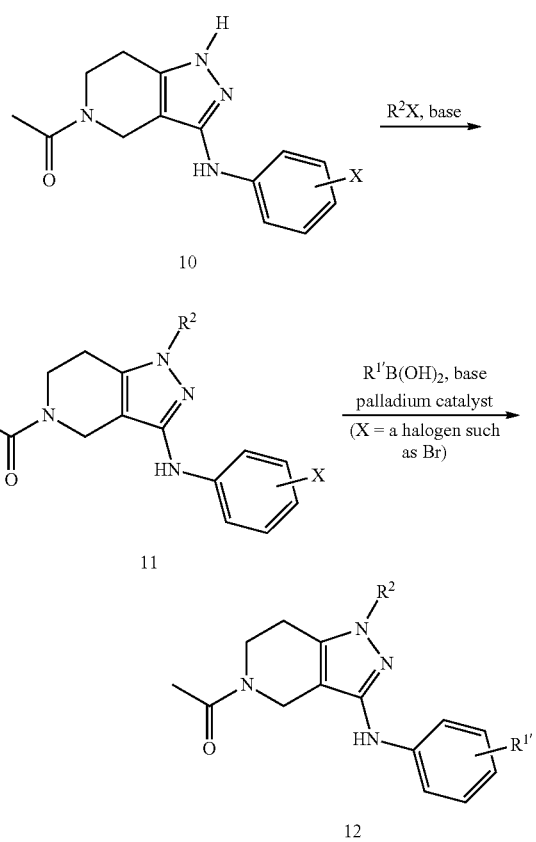

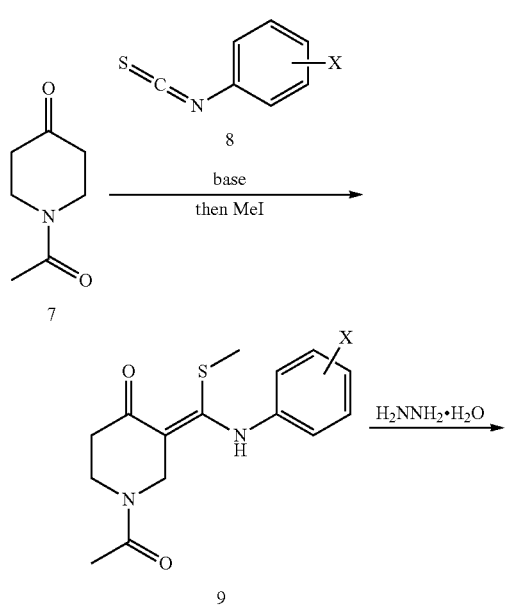

Compounds of formula (12) wherein $R^2$ has the values as shown in Formula II, may be prepared by general synthetic methods as shown in Scheme 2. It is to be understood that the "—$R^{1\prime}$" group as shown in Scheme 2 corresponds to the list of one or more substituents that may be optionally substituted on the $R^1$ group as shown in Formula II.

Reaction between a compound of formula (8) and ketone (7) in the presence of a base such as, but not limited to, potassium tert-butoxide in a suitable organic solvent such as, but not limited to, THF at about 20° C. for about 3 hours followed by addition of methyl iodide and stirring for approximately 1 hour can produce the compounds of formula (9). Reaction between a compound of formula (9) and hydrazine in a suitable solvent such as, but not limited to, ethanol at reflux temperature for about 2 hours can produce compounds of formula (10). Compounds of formula (11) can be produced by treatment with alkyl iodide, bromide, mesylate or triflate in the presence of an inorganic base such as, but not limited to, sodium hydride or cesium carbonate, in a suitable solvent such as, but not limited to, N,N-dimethylformamide (DMF) or tetrahydrofuran (THF) at a temperature ranging from about 0° C. to 120° C. and for a time varying from about 30 minutes to about 16 hours. Compounds of formula (11) can cross-couple with aryl/heteroaryl boronic acids or boronate esters under palladium catalyst conditions such as, but not limited to, Pd(dppf)Cl$_2$ in the presence of inorganic base such as, but not limited to, sodium carbonate in a suitable organic solvent such as, but not limited to, 1,4-dioxane at an elevated temperature to yield compounds of formula (12).

General Procedure for Intermediates A & B

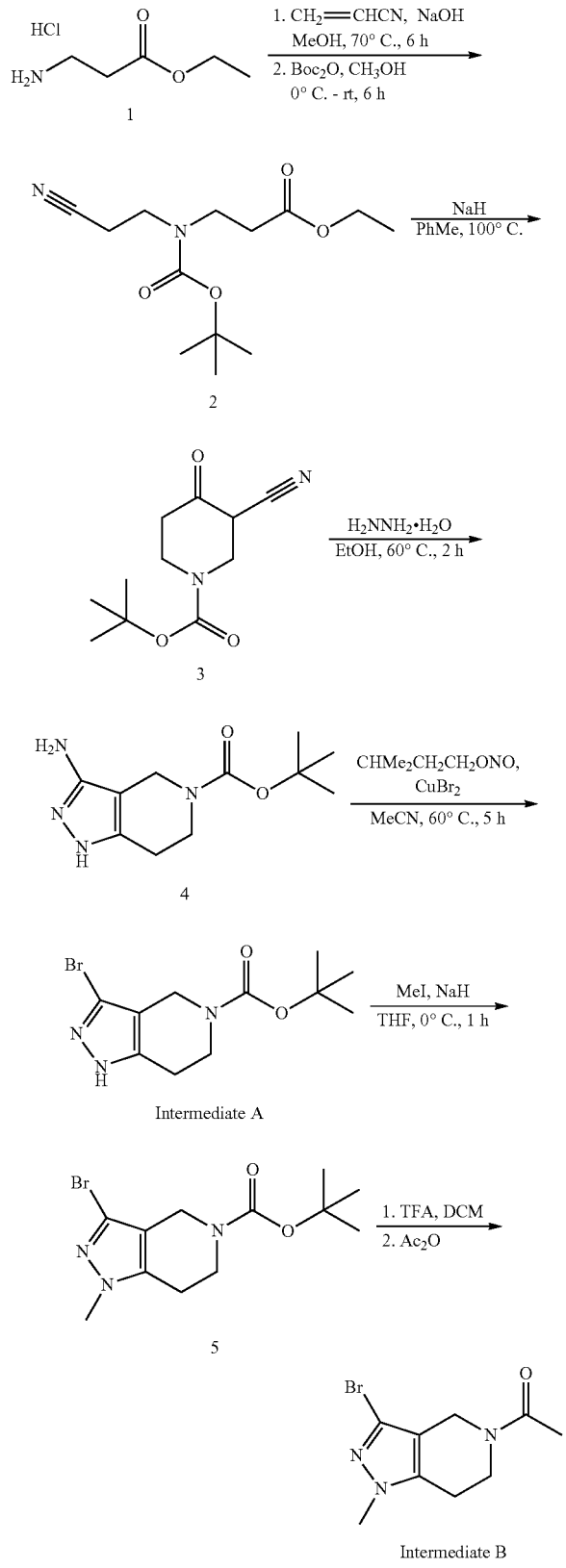

Step 1

3-((tert-butoxycarbonyl)(2-cyanoethyl)amino)propanoate

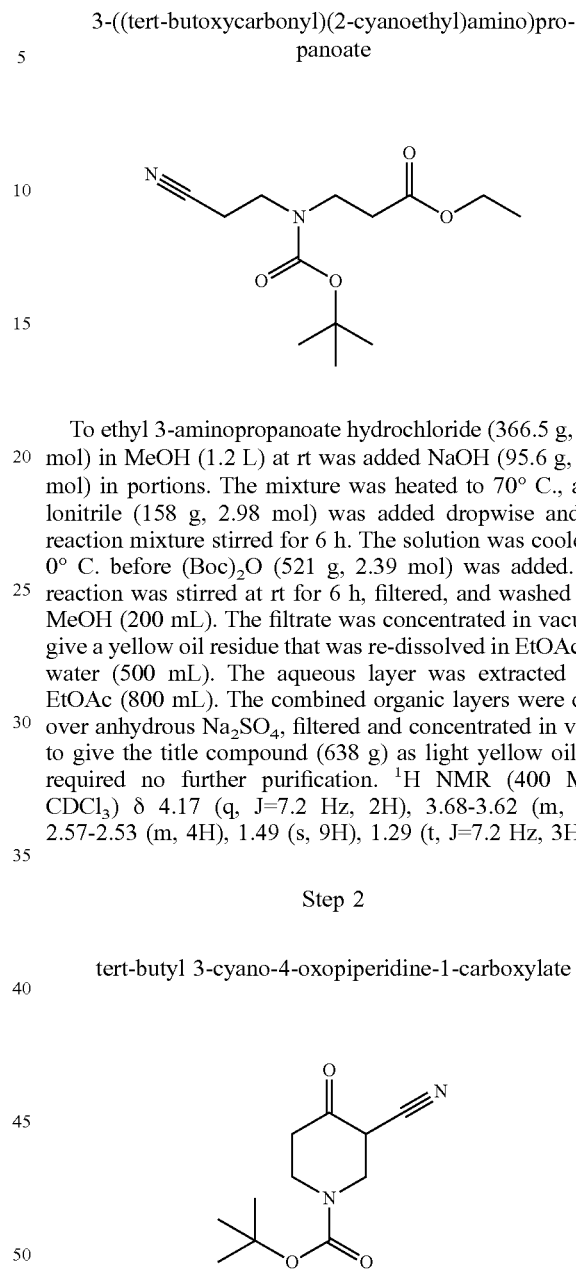

To ethyl 3-aminopropanoate hydrochloride (366.5 g, 2.39 mol) in MeOH (1.2 L) at rt was added NaOH (95.6 g, 2.39 mol) in portions. The mixture was heated to 70° C., acrylonitrile (158 g, 2.98 mol) was added dropwise and the reaction mixture stirred for 6 h. The solution was cooled to 0° C. before (Boc)$_2$O (521 g, 2.39 mol) was added. The reaction was stirred at rt for 6 h, filtered, and washed with MeOH (200 mL). The filtrate was concentrated in vacuo to give a yellow oil residue that was re-dissolved in EtOAc and water (500 mL). The aqueous layer was extracted with EtOAc (800 mL). The combined organic layers were dried over anhydrous Na$_2$SO$_4$, filtered and concentrated in vacuo to give the title compound (638 g) as light yellow oil that required no further purification. $^1$H NMR (400 MHz, CDCl$_3$) δ 4.17 (q, J=7.2 Hz, 2H), 3.68-3.62 (m, 4H), 2.57-2.53 (m, 4H), 1.49 (s, 9H), 1.29 (t, J=7.2 Hz, 3H).

Step 2 tert-butyl 3-cyano-4-oxopiperidine-1-carboxylate

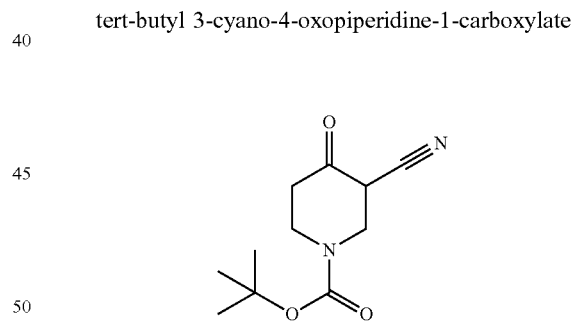

To toluene (2.7 L) at 25° C. was added NaH (80 g, 2.0 mol) portion-wise and the suspension was heated to 80° C. Ethyl 3-((tert-butoxycarbonyl)(2-cyanoethyl)amino)propanoate (270 g, crude) in anhydrous toluene (270 mL) was added dropwise. The mixture was heated to 100° C. and stirred for 5 h. The mixture was cooled to rt, quenched with sat. aq. ammonium chloride (800 mL) and washed with hexanes (800 mL). The aqueous phase was acidified with HCl (2 N) to pH 6 and then extracted with EtOAc (1 L×2). The combined organic layers were dried over anhydrous Na$_2$SO$_4$, filtered and concentrated in vacuo to give the title compound (310 g) as yellow oil that required no further purification. $^1$H NMR (400 MHz, CDCl$_3$) δ 4.17-4.14 (m, 1H), 3.59-3.56 (m, 2H), 3.43-3.41 (m, 2H), 2.70-2.66 (m, 2H), 1.51 (s, 9H).

Step 3 tert-butyl 3-amino-6,7-dihydro-1H-pyrazolo[4,3-c]pyridine-5(4H)-carboxylate

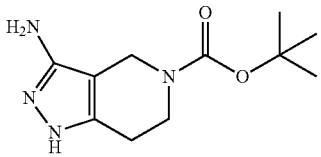 [SMILES: CC(C)(C)OC(=O)N1CCc2[nH]nc(N)c2C1]

A mixture of tert-butyl 3-cyano-4-oxopiperidine-1-carboxylate (310 g, 1.38 mol) and hydrazine mono-hydrate (140 mL, 2.08 mol) in EtOH (1.5 L) was heated to 60° C. for 2 h. The mixture was concentrated in vacuo to give the crude product that was dissolved in EtOAc (1 L) and washed with water (1 L×2). The organic layer was dried over anhydrous $Na_2SO_4$, filtered and concentrated in vacuo to afford the title compound (230 g, 70%) as a colorless solid. $^1$H NMR (400 MHz, $CD_3OD$) δ 4.28 (s, 2H), 3.66-3.63 (m, 2H), 2.62-2.59 (m, 2H), 1.49 (s, 9H).

Step 4 tert-butyl 3-bromo-6,7-dihydro-1H-pyrazolo[4,3-c]pyridine-5(4H)-carboxylate

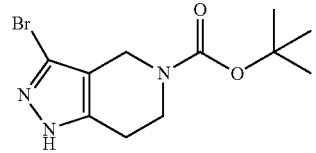 [SMILES: CC(C)(C)OC(=O)N1CCc2[nH]nc(Br)c2C1]

To a stirred mixture of tert-butyl 3-amino-6,7-dihydro-1H-pyrazolo[4,3-c]pyridine-5(4H)-carboxylate (120 g, 503.6 mmol), $CuBr_2$ (112.5 g, 503.6 mmol) and MeCN (1.2 L) at 0° C. was added isopentyl nitrite (76.7 g, 654.7 mmol) and the reaction mixture stirred for 20 min. The temperature was raised to 60° C. and the reaction mixture was stirred for an additional 5 h. After cooling the reaction to room temperature, the reaction mixture was quenched with water (1 L) and the mixture was extracted with EtOAc (1 L×2). The combined organic layers were dried over anhydrous $Na_2SO_4$, filtered and concentrated in vacuo to give the crude product that was purified by silica gel chromatography (petroleum ether/EtOAc=4:1) to afford the title compound (Intermediate A, 52 g, 34%) as light yellow solid. LCMS M/Z (M+H) 302.

Step 5 tert-butyl 3-bromo-1-methyl-6,7-dihydro-1H-pyrazolo[4,3-c]pyridine-5(4H)-carboxylate

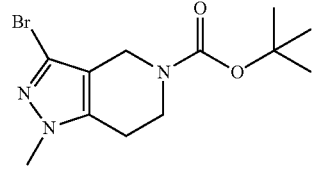 [SMILES: Cn1nc(Br)c2c1CCN(C(=O)OC(C)(C)C)C2]

To a stirred solution of tert-butyl 3-bromo-6,7-dihydro-1H-pyrazolo[4,3-c]pyridine-5(4H)-carboxylate (32 g, 105.9 mmol) in THF at 0° C. (350 mL) was added NaH (5.08 g, 127.1 mmol) and the mixture was stirred for 30 min. Methyliodide (18.05 g, 127.1 mmol) was added dropwise and the mixture stirred for an additional 2 h. The mixture was quenched with water and extracted with EtOAc (300 mL×2). The organic layer was dried over anhydrous $Na_2SO_4$, filtered and concentrated in vacuo. The crude residue was purified by silica gel chromatography (petroleum ether/EtOAc=8:1) to afford the title compound (16 g, 48%) as a colorless oil. $^1$H NMR (400 MHz, $CD_3OD$) δ 4.24 (s, 2H), 3.70 (s, 3H), 3.69-3.67 (m, 2H), 2.70-2.67 (m, 2H), 1.47 (s, 9H).

Step 6

1-(3-bromo-1-methyl-6,7-dihydro-1H-pyrazolo[4,3-c]pyridin-5(4H)-yl)ethanone

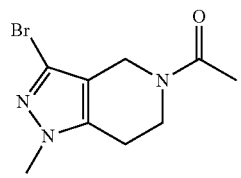

A mixture of tert-butyl 3-bromo-1-methyl-6,7-dihydro-1H-pyrazolo[4,3-c]pyridine-5(4H)-carboxylate (12 g, 38.0 mmol) and trifluoroacetic acid (40 mL) in DCM (80 mL) was stirred at room temperature for 2 h. The mixture was concentrated in vacuo and the residue was re-dissolved in DCM (120 mL). The mixture was cooled to 0° C. before TEA (12.1 g, 120 mmol) and acetic anhydride (5.3 g, 52 mmol) were added dropwise. The mixture stirred at room temperature for an additional 2 h before water (100 mL) was added. The organic layer was dried over anhydrous $Na_2SO_4$, filtered and concentrated in vacuo to give crude product which was purified by silica gel chromatography (DCM/MeOH=20:1) to afford the title compound (Intermediate B, 8.5 g, 87%) as colorless solid. $^1$H NMR (400 MHz, $CD_3OD$) δ 4.40-4.39 (m, 2H), 3.88-3.78 (m, 2H), 3.72 (s, 3H), 2.83-2.70 (m, 2H), 2.20-2.17 (m, 3H).

Example 1

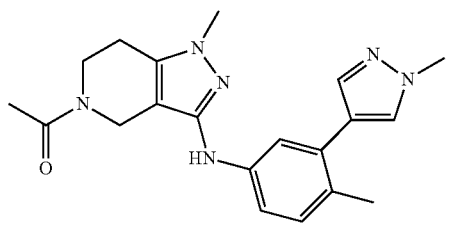 [SMILES: CC(=O)N1CCc2c(c(Nc3ccc(C)c(-c4cnn(C)c4)c3)nn2C)C1]

Step 1

1-methyl-4-(2-methyl-5-nitrophenyl)-1H-pyrazole

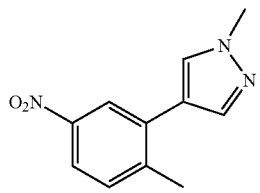 [SMILES: Cc1ccc([N+](=O)[O-])cc1-c1cnn(C)c1]

To a mixture of 2-bromo-1-methyl-4-nitrobenzene (860 mg, 4.0 mmol), (1-methyl-4-(4,4,5,5-tetramethyl-1,3,2-dioxaborolan-2-yl)-1H-pyrazole (998 mg, 4.8 mmol) and cesium carbonate (2.6 g, 8 mmol) in dioxane (20 ml)/$H_2O$ (4 ml) was added [1,1'-bis(diphenylphosphino)ferrocene]dichloropalladium(II), complex with dichloromethane (292 mg, 0.4 mmol). The mixture was heated to 90° C. for 10 hours under nitrogen atmosphere. After cooling to rt, the reaction mixture was concentrated in vacuo. The residue was purified by silica gel chromatography (petroleum ether/EtOAc=5:1 to 3:1) to give the title compound (860 mg, 99%) as a yellow solid.

Step 2

4-methyl-3-(1-methyl-1H-pyrazol-4-yl)aniline

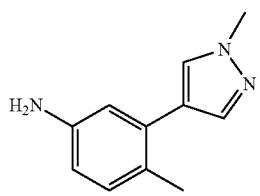

To a mixture of 1-methyl-4-(2-methyl-5-nitrophenyl)-1H-pyrazole (434 mg, 2 mmol) and $NH_4Cl$ (530 mg, 10 mmol) in MeOH (20 ml) was added Fe powder (560 mg, 10 mmol) and the reaction mixture was heated to 60° C. for 10 hours. After filtration, the filtrate was concentrated, washed with water and extracted with EtOAc. The combined organic layers were dried over anhydrous $Na_2SO_4$, filtered and concentrated in vacuo to give the title compound (370 mg, 98%) as a yellow solid that required no further purification.

Step 3

1-[1-methyl-3-[4-methyl-3-(1-methylpyrazol-4-yl)anilino]-6,7-dihydro-4H-pyrazolo[4,3-c]pyridin-5-yl]ethanone

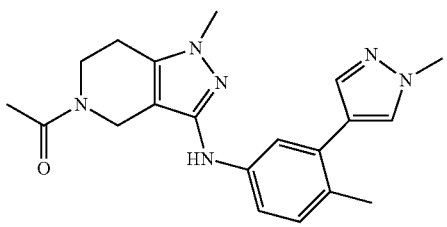 [SMILES: CC(=O)N1CCc2c(c(Nc3ccc(C)c(-c4cnn(C)c4)c3)nn2C)C1]

A mixture of 1-(3-bromo-1-methyl-6,7-dihydro-4H-pyrazolo[4,3-c]pyridin-5-yl)ethanone (Intermediate B, 200 mg, 0.77 mol), 4-methyl-3-(1-methylpyrazol-4-yl)aniline (145 mg, 0.77 mmol), 2-(dicyclohexylphosphino)3,6-dimethoxy-2',4',6'-triisopropyl-1,1'-biphenyl (42 mg, 0.08 mmol), Chloro-(2-Dicyclohexylphosphino-2',6'-diisopropoxy-1,1'-biphenyl)[2-(2-aminoethyl)phenyl]palladium(II) (63 mg, 0.08 mmol) and t-BuONa (223 mg, 2.32 mmol) in 1,4-dioxane (4 mL) was heated to 120° C. for 12 h. After cooling to rt, the reaction mixture was diluted with water (20 mL) and washed with DCM (20 mL×2). The combined organic layers were dried over anhydrous $Na_2SO_4$, filtered and concentrated in vacuo. The crude residue was purified reverse phase chromatography (acetonitrile 30-60%/0.1% $NH_4OH$ in water) to give the title compound (44 mg, 16%) as white solid. $^1$H NMR (400 MHz, $CD_3OD$) δ 7.72 (s, 1H), 7.58 (s, 1H), 7.14-7.04 (m, 2H), 6.95-6.92 (m, 1H), 4.37-4.35 (m, 2H), 3.93 (s, 3H), 3.86-3.79 (m, 2H), 3.65-3.64 (m, 3H), 2.81-2.69 (m, 2H), 2.29-2.28 (m, 3H), 2.20-2.09 (m, 3H). LCMS M/Z (M+H) 365.

The Following Examples 2-7 were Prepared in a Similar Fashion to Example 1

| Example | Compound Name and Structure | NMR | m/z |
|---|---|---|---|
| Example 2 | 1-[3-[2-fluoro-4-(1-methylpyrazol-4-yl)anilino]-1-methyl-6,7-dihydro-4H-pyrazolo[4,3-c]pyridin-5-yl]ethanone | $^1$H NMR (400 MHz, $CD_3OD$) δ 7.86 (d, J = 2.4 Hz, 1H), 7.73 (d, J = 2.0 Hz, 1H), 7.36-7.17 (m, 3H), 4.40-4.39 (m, 2H), 3.90 (s, 3H), 3.89-3.80 (m, 2H), 3.68 (s, 3H), 2.84-2.71 (m, 2H), 2.20-2.13 (m, 3H) | 369 |

-continued

| Example | Compound Name and Structure | NMR | m/z |
|---|---|---|---|
| Example 3 | 1-[3-[2-fluoro-3-(1-methylpyrazol-4-yl)anilino]-1-methyl-6,7-dihydro-4H-pyrazolo[4,3-c]pyridin-5-yl]ethanone | ¹H NMR (400 MHz, CD₃OD) δ 8.04 (s, 1H), 7.71 (s, 1H), 7.90 (s, 1H), 7.20-7.06 (m, 3H), 4.43 (s, 2H), 3.97 (s, 3H), 3.93-3.83 (m, 2H), 3.72-3.71 (m, 3H), 2.87-2.74 (m, 2H), 2.22-2.15 (m, 3H) | 369 |
| Example 4 | 1-[3-[2-fluoro-5-(1-methylpyrazol-4-yl)anilino]-1-methyl-6,7-dihydro-4H-pyrazolo[4,3-c]pyridin-5-yl]ethanone | ¹H NMR (400 MHz, CD₃OD) δ 7.86 (s, 1H), 7.71 (s, 1H), 7.53-7.38 (m, 1H), 7.39 (d, J = 8.0 Hz, 1H), 7.01-7.03 (m, 2H), 4.43-4.41 (m, 2H), 3.90 (s, 3H), 3.88-3.82 (m, 2H), 3.71 (s, 3H), 2.86-2.73 (m, 2H), 2.21-2.10 (m, 3H) | 369 |
| Example 5 | 1-[3-[3-fluoro-5-(1-methylpyrazol-4-yl)anilino]-1-methyl-6,7-dihydro-4H-pyrazolo[4,3-c]pyridin-5-yl]ethanone | ¹H NMR (400 MHz, CD₃OD) δ 7.92 (d, J = 2.8 Hz, 1H), 7.77 (s, 1H), 7.11-7.08 (m, 1H), 6.87 (dd, J = 8.0, 8.0 Hz, 1H), 6.70 (dd, J = 8.0, 8.0 Hz, 1H), 4.45-4.43 (m, 2H), 3.94 (s, 3H), 3.92-3.82 (m, 2H), 3.71 (s, 3H), 2.85-2.72 (m, 2H), 2.23-2.15 (m, 3H) | 369 |
| Example 6 | 1-[3-[4-fluoro-3-(1-methylpyrazol-4-yl)anilino]-1-methyl-6,7-dihydro-4H-pyrazolo[4,3-c]pyridin-5-yl]ethanone | ¹H NMR (400 MHz, CD₃OD) δ 7.92 (s, 1H), 7.78 (s, 1H), 7.39-7.37 (m, 1H), 7.00-6.95 (m, 2H), 4.38-4.36 (s, 2H), 3.92 (s, 3H), 3.85-3.78 (m, 2H), 3.64 (s, 3H), 2.79-2.66 (m, 2H), 2.18-2.10 (s, 3H) | 369 |
| Example 7 | 1-[3-[3-fluoro-4-(1-methylpyrazol-4-yl)anilino]-1-methyl-6,7-dihydro-4H-pyrazolo[4,3-c]pyridin-5-yl]ethanone | ¹H NMR (400 MHz, CD₃OD) δ 7.86 (s, 1H), 7.76 (s, 1H), 7.43-7.42 (m, 1H), 7.12 (dd, J = 9.6, 9.6 Hz, 1H), 6.95-6.91 (m, 1H), 4.42-4.41 (m, 2H), 3.92 (s, 3H), 3.91-3.79 (m, 2H), 3.68 (s, 3H), 2.82-2.69 (m, 2H), 2.20-2.15 (m, 3H) | 369 |

Example 8

1-(1-methyl-3-((1-methyl-1H-pyrazol-4-yl)amino)-6,7-dihydro-1H-pyrazolo[4,3-c]pyridin-5(4H)-yl)ethanone

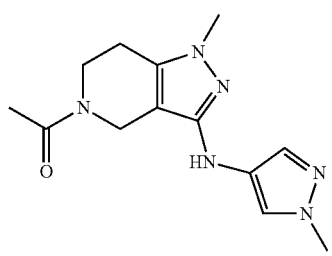 [SMILES: CC(=O)N1CCc2c(c(Nc3cnn(C)c3)nn2C)C1]

To a solution of 1-(3-bromo-1-methyl-6,7-dihydro-1H-pyrazolo[4,3-c]pyridin-5(4H)-yl)ethanone (Intermediate B, 200 mg, 0.77 mmol) in dioxane (8.0 mL) was added 1-methyl-1H-pyrazol-4-amine (90 mg, 0.93 mmol), tris(dibenzylideneacetone)dipalladium(0)-chloroform adduct (71.6 mg, 0.07 mmol), xantphos (41.2 mg, 0.07 mmol) and $Cs_2CO_3$ (504.9 mg, 1.55 mmol). The reaction mixture was purged with nitrogen atmosphere for 1 min and then stirred at 120° C. for 12 h. The mixture was concentrated in vacuo and the crude residue was purified by reverse phase chromatography (acetonitrile 1-28%/0.2% formic acid in water) to give the title compound (6.8 mg, 3%) as a white solid. $^1$H NMR (400 MHz, $CD_3OD$) δ 7.35-7.34 (m, 1H), 5.95-5.93 (m, 1H), 4.37-4.36 (m, 2H), 3.87-3.76 (m, 2H), 3.77 (s, 3H), 3.61 (s, 3H), 2.78-2.65 (m, 2H), 2.18-2.13 (m, 3H). LCMS M/Z (M+H) 275.

The Following Examples 9-16 were Prepared in a Similar Fashion to Step 3 of Example 1

| Example | Compound Name and Structure | NMR | m/z |
|---|---|---|---|
| Example 9 | 1-(3-((4-(1H-1,2,4-triazol-1-yl)phenyl)amino)-1-methyl-6,7-dihydro-1H-pyrazolo[4,3-c]pyridin-5(4H)-yl)ethanone | $^1$H NMR (400 MHz, $CD_3OD$) δ 8.90 (d, J = 2.8 Hz, 1H), 8.11 (d, J = 2.4 Hz, 1H), 7.57 (dd, J = 8.8. 7.2 Hz, 2H), 7.33 (dd, J = 11.2, 8.8 Hz, 2H), 4.42-4.41 (m, 2H), 3.90-3.79 (m, 2H), 3.68 (s, 3H), 2.82-2.69 (m, 2H), 2.20-2.15 (m, 3H) | 338 |
| Example 10 | 1-(3-((3-(1H-1,2,4-triazol-1-yl)phenyl)amino)-1-methyl-6,7-dihydro-1H-pyrazolo[4,3-c]pyridin-5(4H)-yl)ethanone | $^1$H NMR (400 MHz, $CD_3OD$) δ 9.00 (d, J = 3.6 Hz, 1H), 8.13 (d, J = 3.2 Hz, 1H), 7.66-7.62 (m, 1H), 7.35-7.31 (m, 1H), 7.17-7.14 (m, 1H), 4.43-4.41 (m, 2H), 3.90-3.79 (m, 2H), 3.69-3.68 (m, 3H), 2.83-2.70 (m, 2 H), 2.20-2.13 (m, 3H) | 338 |
| Example 11 | 1-[1-methyl-3-[(2-methylindazol-6-yl)amino]-6,7-dihydro-4H-pyrazolo[4,3-c]pyridin-5-yl]ethanone | $^1$H NMR (400 MHz, $CD_3OD$) δ 7.97 (d, J = 5.2 Hz, 1H), 7.50 (dd, J = 8.8,. 7.2 Hz, 1H), 7.31 (s, 1H), 6.90 (d, J = 7.6 Hz, 1H), 4.41-4.39 (m, 2H), 4.09 (s, 3H), 3.91-3.80 (m, 2H), 3.69 (s, 3H), 2.84-2.71 (m, 2H), 2.20-2.12 (m, 3H) | 325 |

-continued

| Example | Compound Name and Structure | NMR | m/z |
|---|---|---|---|
| Example 12 | 1-(1-methyl-3-((3-(oxazol-5-yl)phenyl)amino)-6,7-dihydro-1H-pyrazolo[4,3-c]pyridin-5(4H)-yl)ethanone | $^1$H NMR (400 MHz, CD$_3$OD) δ 8.23-8.22 (s, 1H), 7.54-7.51 (m, 1H), 7.43-7.42 (m, 1H), 7.28-7.24 (m, 1H), 7.15-7.12 (m, 2H), 4.41-4.40 (m, 2H), 3.90-3.80 (m, 2H), 3.69 (s, 3H), 2.83-2.70 (m, 2H), 2.20-2.13 (m, 3H) | 338 |
| Example 13 | 1-(1-methyl-3-((4-(oxazol-5-yl)phenyl)amino)-6,7-dihydro-1H-pyrazolo[4,3-c]pyridin-5(4H)-yl)ethanone | $^1$H NMR (400 MHz, CD$_3$OD) δ 8.15 (s, 1H), 7.57-7.53 (m, 2H), 7.30-7.21 (m, 3H), 4.41-4.40 (m, 2H), 3.90-3.80 (m, 2H), 3.69-3.68 (m, 3H), 2.83-2.70 (m, 2H), 2.20-2.14 (m, 3H) | 338 |
| Example 14 | 1-[1-methyl-3-[(1-methylindazol-6-yl)amino]-6,7-dihydro-4H-pyrazolo[4,3-c]pyridin-5-yl]ethanone | $^1$H NMR (400 MHz, CD$_3$OD) δ 7.77 (s, 1H), 7.51 (dd, J = 8.8, 6.0 Hz, 1H), 7.37-7.27 (s, 1H), 6.90 (d, J = 8.8 Hz, 1H), 4.42-4.41 (m, 2H), 3.92 (s, 3H), 3.91-3.79 (m, 2H), 3.39 (s, 3H), 2.82-2.71 (m, 2H), 2.19-2.12 (m, 3H) | 325 |
| Example 15 | 1-[1-methyl-3-[(2-methylindazol-5-yl)amino]-6,7-dihydro-4H-pyrazolo[4,3-c]pyridin-5-yl]ethanone | $^1$H NMR (400 MHz, CD$_3$OD) δ 7.89 (d, J = 7.2 Hz, 1H), 7.45-7.42 (m, 2H), 7.17 (d, J = 7.2 Hz, 1H), 4.38, 4.36 (m, 2H), 4.11 (s, 3H), 3.87-3.76 (m, 2H), 3.65 (s, 3H), 2.79-2.69 (m, 2H), 2.18-2.10 (m, 3H) | 325 |
| Example 16 | 1-[1-methyl-3-[(1-methylindazol-5-yl)amino]-6,7-dihydro-4H-pyrazolo[4,3-c]pyridin-5-yl]ethanone | $^1$H NMR (400 MHz, CD$_3$OD) δ 7.77 (d, J = 5.6 Hz, 1H), 7.53 (dd, J = 8.0, 8.0 Hz, 1H), 7.25 (d, J = 9.2 Hz, 1H), 4.35-4.33 (m, 2H), 3.98 (s, 3H), 3.85-3.75 (m, 2H), 3.63 (s, 3H), 2.78-2.67 (m, 2H), 2.17-2.08 (m, 3H) | 325 |

Example 17

3-[(5-acetyl-1-methyl-6,7-dihydro-4H-pyrazolo[4,3-c]pyridin-3-yl)amino]-N-isopropyl-5-(1-methylpyrazol-4-yl)benzamide

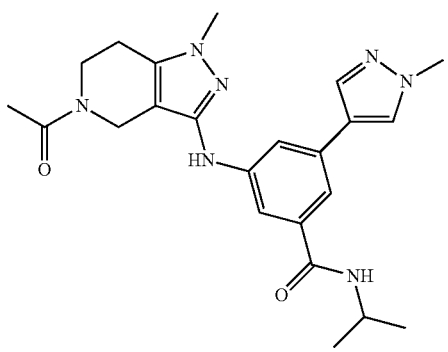 [SMILES: CC(=O)N1CCc2c(c(Nc3cc(C(=O)NC(C)C)cc(-c4cnn(C)c4)c3)nn2C)C1]

Step 1

3-bromo-N-isopropyl-5-nitrobenzamide

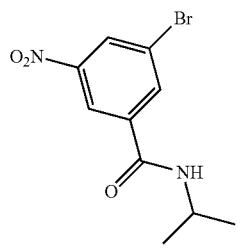 [SMILES: CC(C)NC(=O)c1cc(Br)cc([N+](=O)[O-])c1]

To a mixture of 3-bromo-5-nitrobenzoic acid (1.0 g, 4.1 mmol), propan-2-amine (0.29 g, 4.9 mmol and DIPEA (1.1 g, 8.2 mmol) in DCM (10.0 mL) was added HATU (1.6 g, 4.1 mmol). The mixture was stirred at rt for 12 h. The reaction mixture was filtered, concentrated in vacuo and the crude residue was purified by silica gel column chromatography (petroleum ether/EtOAc=1:1) to give the title compound (1.0 g, 86%) as a white solid.

Step 2

N-isopropyl-3-(1-methyl-1H-pyrazol-4-yl)-5-nitrobenzamide

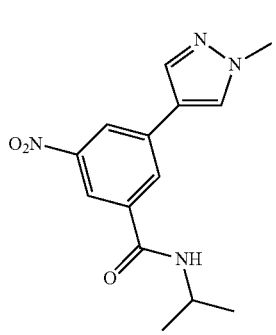 [SMILES: CC(C)NC(=O)c1cc(-c2cnn(C)c2)cc([N+](=O)[O-])c1]

[1,1'-bis(diphenylphosphino)ferrocene]dichloropalladium(II), complex with dichloromethane (0.13 g, 0.17 mmol) was added to a mixture of 3-bromo-N-isopropyl-5-nitrobenzamide (0.5 g, 1.7 mmol), 1-methyl-4-(4,4,5,5-tetramethyl-1,3,2-dioxaborolan-2-yl)-1H-pyrazole (0.43 g, 2.1 mmol) and Na$_2$CO$_3$ (0.37 g, 3.4 mmol) in 1,4-dioxane (5.0 mL) and water (1.3 mL). The mixture was stirred under nitrogen atmosphere at 120° C. for 12 h. The mixture was filtered, concentrated in vacuo and the residue was purified by silica gel column chromatography (petroleum ether/EtOAc=3:1 to 1:1) to give the title compound (0.30 g, 59%) as a light red solid.

Step 3

3-amino-N-isopropyl-5-(1-methyl-1H-pyrazol-4-yl)benzamide

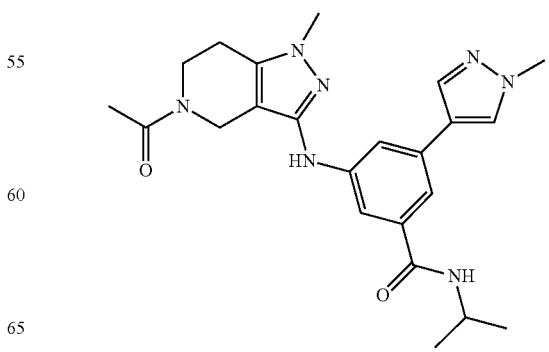

The title compound was prepared from N-isopropyl-3-(1-methyl-1H-pyrazol-4-yl)-5-nitrobenzamide in a similar fashion to Step 2 of Example 1. The residue was purified by silica gel chromatography (petroleum ether/EtOAc=1:1) to give the title compound (0.24 g, 90%) as a yellow solid. LCMS M/Z (M+H)=259.

Step 4

3-[(5-acetyl-1-methyl-6,7-dihydro-4H-pyrazolo[4,3-c]pyridin-3-yl)amino]-N-isopropyl-5-(1-methylpyrazol-4-yl)benzamide The title compound was prepared from 3-amino-N-isopropyl-5-(1-methyl-1H-pyrazol-4-yl)benzamide in a similar fashion to Step 3 of Example 1. The crude residue was purified by reverse phase chromatography (acetonitrile 32-62%/0.1% NH₄OH in water) to give the title compound in 12% yield. ¹H NMR (400 MHz, CD₃OD) δ 7.95 (d, J=3.2 Hz, 1H), 7.82 (d, J=3.6 Hz, 1H), 7.46-7.36 (m, 3H), 4.42-4.40 (m, 2H), 4.23-4.19 (m, 1H), 3.94 (s, 3H), 3.89-3.80 (m, 2H), 3.70 (s, 3H), 2.84-2.72 (m, 2H), 2.21-2.12 (m, 3H), 1.26 (d, J=6.4 Hz, 6H). LCMS M/Z (M+H) 436.

Example 18

3-[(5-acetyl-1-methyl-6,7-dihydro-4H-pyrazolo[4,3-c]pyridin-3-yl)amino]-N-isopropyl-5-methyl-benzamide

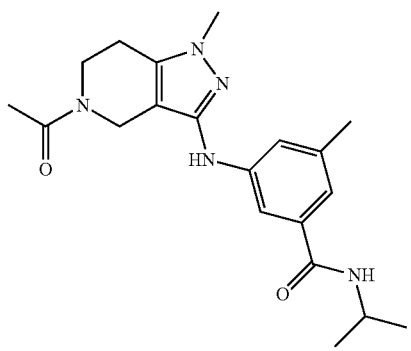 [SMILES: CC(=O)N1CCc2c(c(Nc3cc(C)cc(C(=O)NC(C)C)c3)nn2C)C1]

Step 1

N-isopropyl-3-methyl-5-nitrobenzamide

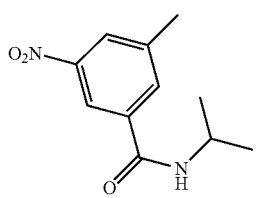 [SMILES: Cc1cc(C(=O)NC(C)C)cc([N+](=O)[O-])c1]

The title compound was prepared from 3-methyl-5-nitrobenzoic acid in a similar fashion to Step 1 of Example 17.

The residue was purified by silica gel chromatography (petroleum ether/EtOAc=5:1 to 3:1) to give the title compound (560 mg, 84%) as yellow oil.

Step 2

3-amino-N-isopropyl-5-methylbenzamide

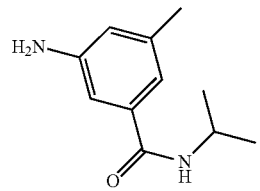

The title compound was prepared N-isopropyl-3-methyl-5-nitrobenzamide in a similar fashion to Step 2 of Example 1. No purification was required to give the title compound (400 mg, 83%) as a yellow solid.

Step 3

3-[(5-acetyl-1-methyl-6,7-dihydro-4H-pyrazolo[4,3-c]pyridin-3-yl)amino]-N-isopropyl-5-methyl-benzamide

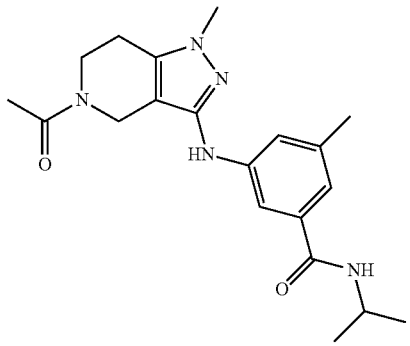 [SMILES: CC(=O)N1CCc2c(c(Nc3cc(C)cc(C(=O)NC(C)C)c3)nn2C)C1]

The title compound was prepared from 3-amino-N-isopropyl-5-methylbenzamide in a similar fashion to Step 3 of Example 1. The crude residue was purified by reverse phase chromatography (acetonitrile 30-60%/0.1% NH₄OH in water) to give the title compound in 22% yield. ¹H NMR (400 MHz, CD₃OD) δ 7.31 (d, J=7.6 Hz, 1H), 7.07-6.83 (m, 2H), 4.37-4.35 (m, 2H), 4.17-4.13 (m, 1H), 3.86-3.78 (m, 2H), 3.66 (s, 3H), 2.80-2.69 (m, 2H), 2.30 (s, 3H), 2.18-2.11 (m, 3H), 1.22 (d, J=6.4 Hz, 6H). LCMS M/Z (M+H) 369.

The Following Example 19 was Prepared in a Similar Fashion to Example 18

| Example | Compound Name and Structure | NMR | m/z |
|---|---|---|---|
| Example 19 | 3-[(5-acetyl-1-methyl-6,7-dihydro-4H-pyrazolo[4,3-c]pyridin-3-yl)amino]-5-chloro-N-isopropyl-benzamide | $^1$H NMR (400 MHz, CD$_3$OD) δ 7.45 (s, 1H), 7.39 (d, J = 6.8 Hz, 1H), 7.14 (d, J = 6.8 Hz, 1H), 4.42-4.40 (m, 2H), 4.18-4.16 (m, 1H), 3.89-3.80 (m, 2H), 3.69 (s, 3H), 2.83-2.70 (m, 2H), 2.21-2.15 (m, 3H), 1.23 (d, J = 6.8 Hz, 6H) | 390 |

Example 20

3-[(5-acetyl-1-methyl-6,7-dihydro-4H-pyrazolo[4,3-c]pyridin-3-yl)amino]-5-(1-methylpyrazol-4-yl)benzonitrile

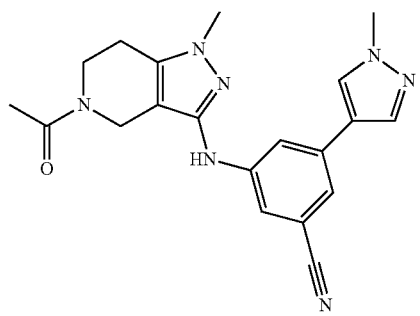 [SMILES: CC(=O)N1CCc2c(c(Nc3cc(C#N)cc(-c4cnn(C)c4)c3)nn2C)C1]

Step 1

3-amino-5-(1-methyl-1H-pyrazol-4-yl)benzonitrile

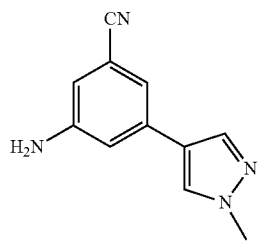

To a solution of 3-amino-5-bromo-benzonitrile (1.4 g, 7.1 mmol) in dioxane (8 mL)/water (2 mL) was added 1-methyl-4-(4,4,5,5-tetramethyl-1,3,2-dioxaborolan-2-yl) pyrazole (1.8 g, 8.5 mmol), [1,1'-bis(diphenylphosphino)ferrocene]dichloropalladium(II), complex with dichloromethane (0.5 g, 0.7 mmol) and Na$_2$CO$_3$ (1.5 g, 14.2 mmol). The reaction was heated to 120° C. for 16 h under nitrogen atmosphere. After cooling to room temperature, the reaction mixture was filtered and concentrated in vacuo. The residue was purified by silica gel chromatography (petroleum ether:EtOAc=10:1 to 1:2) to give the title compound (1.3 g, 92%) as a brown solid. LCMS M/Z (M+H) 199.

Step 2

3-[(5-acetyl-1-methyl-6,7-dihydro-4H-pyrazolo[4,3-c]pyridin-3-yl)amino]-5-(1-methylpyrazol-4-yl)benzonitrile

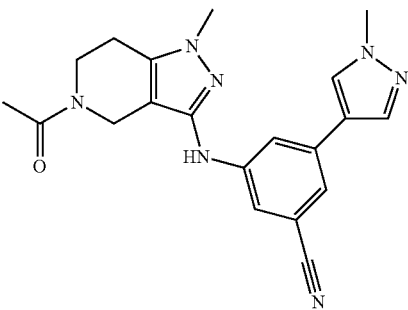 [SMILES: CC(=O)N1CCc2c(c(Nc3cc(C#N)cc(-c4cnn(C)c4)c3)nn2C)C1]

The title compound was prepared from 3-amino-5-(1-methyl-1H-pyrazol-4-yl)benzonitrile in a similar fashion to Step 3 of Example 1. The crude residue was purified by reverse phase chromatography (acetonitrile 35-65%/0.1% NH$_4$OH in water) to give the title compound in 17% yield. $^1$H NMR (400 MHz, CD$_3$OD) δ 8.00 (s, 1H), 7.83 (s, 1H), 7.64-7.60 (m, 1H), 7.47 (d, J=7.6 Hz, 1H), 7.31 (d, J=6.0 Hz, 1H), 4.47-4.45 (m, 2H), 3.95 (s, 3H), 3.93-3.82 (m, 2H), 3.73 (s, 3H), 2.84-2.74 (m, 2H), 2.23-2.17 (m, 3H). LCMS M/Z (M+H) 376.

The Following Examples 21-32 were Prepared in a Similar Fashion to Example 20

| Example | Compound Name and Structure | NMR | m/z |
|---|---|---|---|
| Example 21 | 1-[1-methyl-3-[3-methyl-5-(1-methylpyrazol-4-yl)anilino]-6,7-dihydro-4H-pyrazolo[4,3-c]pyridin-5-yl]ethanone | ¹H NMR (400 MHz, CD₃OD) δ 7.82 (d, J = 3.2 Hz, 1H), 7.69 (d, J = 2.4 Hz, 1H), 7.07-7.04 (m, 1H), 6.80-6.76 (m, 2H), 4.36-4.34 (m, 2H), 3.88 (s, 3H), 3.87-3.78 (m, 2H), 3.66 (s, 3H), 2.80-2.69 (m, 2H), 2.26 (s, 3H), 2.17-2.07 (m, 3H). | 365 |
| Example 22 | 1[3-[2,4-difluoro-5-(1-methylpyrazol-4-yl)panilino]-1-methyl-6,7-dihydro-4H-pyrazolo[4,3-c]pyridin-5-yl]ethanone | ¹H NMR (400 MHz, DMSO-d₆) δ 8.09-7.88 (m, 2H), 7.75-7.69 (m, 2H), 7.27-7.19 (m, 1H), 4.38-4.32 (m, 2H), 3.87 (s, 3H), 3.73-3.66 (m, 2H), 3.62 (s, 3H), 2.74-2.59 (m, 2H), 2.08-2.03 (m, 3H) | 387 |
| Example 23 | 1-[1-methyl-3-[[6-(1-methylpyrazol-4-yl)-3-pyridyl]amino]-6,7-dihydro-4H-pyrazolo[4,3-c]pyridin-5-yl]ethanone | ¹H NMR (400 MHz, CD₃OD) δ 8.21 (dd, J = 6.4, 2.0 Hz, 1H), 7.86 (d, J = 3.6 Hz, 1H), 7.73-7.70 (m, 2H), 6.98 (dd, J = 14.4, 4.8 Hz, 1H), 4.41-4.39 (m, 2H), 3.89 (s, 3H), 3.87-3.79 (m, 2H), 3.70 (s, 3H), 2.82-2.71 (m, 2H), 2.17-2.10 (m, 3H) | 352 |
| Example 24 | 2-[(5-acetyl-1-methyl-6,7-dihydro-4H-pyrazolo[4,3-c]pyridin-3-yl)amino]-6-(1-methylpyrazol-4-yl)benzonitrile | ¹H NMR (400 MHz, DMSO-d₆) δ 8.18 (s, 1H), 8.02-7.92 (m, 1H), 7.88 (s, 1H), 7.42-7.38 (m, 1H), 7.12 (d, J = 8.4 Hz, 1H), 6.97 (d, J = 7.6 Hz, 1H), 4.32-4.28 (s, 2H), 3.91 (s, 3H), 3.74-3.67 (m, 2H), 3.64 (s, 3H), 2.78-2.64 (m, 2H), 2.09-2.03 (m, 3H) | 376 |
| Example 25 | 1-(1-methyl-3-((3-(methylsulfonyl)phenyl)amino)- | ¹H NMR (400 MHz, DMSO-d₆) δ 8.62-8.57 (m, 1H), 7.85-7.81 (m, | 349 |

| Example | Compound Name and Structure | NMR | m/z |
|---|---|---|---|
| | 6,7-dihydro-1H-pyrazolo[4,3-c]pyridin-5(4H)-yl)ethanone | 1H), 7.77-7.71 (m, 1H), 7.41 (dd, J = 8.0, 8.0 Hz, 1H), 7.20 (dd, J = 6.4, 6.4 Hz, 1H), 4.33 (s, 2H), 3.71-3.64 (m, 2H), 3.60 (s, 3H), 3.13 (s, 3H), 2.72-2.59 (m, 2H), 2.07-2.05 (s, 3H) | |
| Example 26 | 1-(3-((2,4-difluoro-3-(1-methyl-1H-pyrazol-4-yl)phenyl)amino)-1-methyl-6,7-dihydro-1H-pyrazolo[4,3-c]pyridin-5(4H)-yl)ethanone | $^1$H NMR (400 MHz, DMSO-$d_6$) δ 8.13 (s, 1H), 7.81 (s, 1H), 7.60-7.42 (m, 1H), 7.03 (dd, J = 9.6, 9.6 Hz, 1H), 4.39-4.32 (s, 2H), 3.92 (s, 3H), 3.73-3.66 (m, 2H), 3.61 (s, 3H), 2.76-2.60 (m, 2H), 2.08-2.04 (m, 3H) | 387 |
| Example 27 | 1-(1-methyl-3-((6-(1-methyl-1H-pyrazol-4-yl)pyridin-2-yl)amino)-6,7-dihydro-1H-pyrazolo[4,3-c]pyridin-5(4H)-yl)ethanone | $^1$H NMR (400 MHz, CD$_3$OD) δ 8.01 (d, J = 4.4 Hz, 1H), 7.89 (s, 1H), 8.01 (dd, J = 8.0, 2.8 Hz, 1H), 6.99 (dd, J = 7.3, 2.9 Hz, 1H), 6.85-6.77 (m, 1H), 4.42-4.39 (m, 2H), 3.91 (s, 3H), 3.90-3.81 (m, 2H), 3.69 (s, 3H), 2.85-2.72 (m, 2H), 2.01-1.96 (m, 3H) | 352 |
| Example 28 | 1-(1-methyl-3-((2-(1-methyl-1H-pyrazol-4-yl)pyridin-4-yl)amino)-6,7-dihydro-1H-pyrazolo[4,3-c]pyridin-5(4H)-yl)ethanone | $^1$H NMR (400 MHz, CD$_3$OD) δ 8.11-8.03 (m, 1H), 8.02 (d, J = 3.2 Hz, 1H), 7.89 (d, J = 2.0 Hz, 1H), 7.39-7.34 (m, 1H), 6.98-6.95 (m, 1H), 4.45-4.43 (m, 2H), 3.93 (s, 3H), 3.92-3.79 (m, 2H), 3.72 (s, 3H), 2.83-2.70 (m, 2H), 2.20-2.14 (m, 3H) | 352 |
| Example 29 | 1-(1-methyl-3-((5-(1-methyl-1H-pyrazol-4-yl)pyridin-3-yl)amino)-6,7-dihydro-1H-pyrazolo[4,3-c]pyridin-5(4H)-yl)ethanone | $^1$H NMR (400 MHz, CD$_3$OD) δ 8.30 (d, J = 2.4 Hz, 1H), 8.14 (d, J = 4.4 Hz, 1H), 8.02 (d, J = 3.6 Hz, 1H), 7.94-7.87 (m, 1H), 7.84 (d, J = 2.4 Hz, 1H), 4.46-4.44 (m, 2H), 3.94 (s, 3H), 3.89-3.80 (m, 2H), 3.70 (s, | 352 |

| Example | Compound Name and Structure | NMR | m/z |
|---|---|---|---|
| | | 3H), 2.83-2.70 (m, 2H), 2.21-2.16 (m, 3H) | |
| Example 30 | 1-(1-methyl-3-((4-(1-methyl-1H-pyrazol-4-yl)pyridin-2-yl)amino)-6,7-dihydro-1H-pyrazolo[4,3-c]pyridin-5(4H)-yl)ethanone | $^1$H NMR (400 MHz, CD$_3$OD) δ 8.10 (s, 1H), 8.00-7.97 (m, 1H), 7.90 (s, 1H), 7.12-7.09 (m, 1H), 6.97 (d, J = 5.6 Hz, 1H), 4.42 (s, 2H), 3.94 (s, 3H), 3.89-3.81 (m, 2H), 3.72-3.71 (m, 3H), 2.85-2.72 (m, 2 H), 2.19-2.11 (m, 3H) | 352 |
| Example 31 | 1-(3-((3-chloro-5-(1-methyl-1H-pyrazol-4-yl)phenyl)amino)-1-methyl-6,7-dihydro-1H-pyrazolo[4,3-c]pyridin-5(4H)-yl)ethanone | $^1$H NMR (400 MHz, CD$_3$OD) δ 7.90 (d, J = 3.2 Hz, 1H), 7.75 (d, J = 2.2 Hz, 1H), 7.22-7.19 (m, 1H), 7.19 (s, 1H), 6.94 (d, J = 6.8 Hz, 1H), 4.42-4.40 (m, 2H), 3.92 (s, 3H), 3.95-3.70 (m, 2H), 3.69 (s, 3H), 2.83-2.70 (m, 2H), 2.21-2.13 (m, 3H) | 385 |
| Example 32 | 1-(1-methyl-3-((5-(1-methyl-1H-pyrazol-4-yl)pyridin-2-yl)amino)-6,7-dihydro-1H-pyrazolo[4,3-c]pyridin-5(4H)-yl)ethanone | $^1$H NMR (400 MHz, CD$_3$OD) δ 8.24 (dd, J = 6.4, 2.0 Hz, 1H), 7.89 (d, J = 3.2 Hz, 1H), 7.75-7.73 (m, 2H), 7.03-6.97 (m, 1H), 4.43-4.41 (m, 2H), 3.92 (s, 3H), 3.89 3.81 (m, 2H), 3.70-3.69 (m, 3H), 2.85-2.72 (m, 2H), 2.19-2.13 (m, 3H) | 352 |

Example 33

3-[(5-acetyl-1-methyl-6,7-dihydro-4H-pyrazolo[4,3-c]pyridin-3-yl)amino]-5-cyclopropyl-N-isopropyl-benzamide

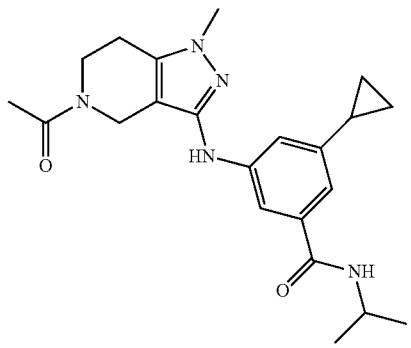 [SMILES: CC(=O)N1CCc2c(c(Nc3cc(C(=O)NC(C)C)cc(C4CC4)c3)nn2C)C1]

Step 1

3-cyclopropyl-N-isopropyl-5-nitrobenzamide

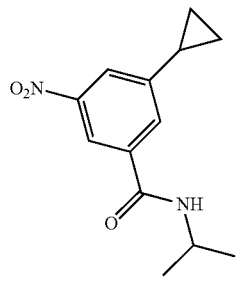

[1,1'-bis(diphenylphosphino)ferrocene]dichloropalladium(II), complex with dichloromethane (0.13 g, 0.17 mmol) was added to a mixture of 3-bromo-N-isopropyl-5-nitrobenzamide (0.5 g, 1.7 mmol), cyclopropylboronic acid (0.18 g, 2.1 mmol) and K$_2$CO$_3$ (0.48 g, 3.5 mmol) in 1,4-dioxane (5.0 mL) and water (1.3 mL). The reaction mixture was stirred under nitrogen atmosphere at 120° C. for 12 h before it was filtered. The filtrate was concentrated in vacuo and the residue was purified by silica gel chromatography (petroleum ether/EtOAc=3:1 to 1:1) to give the title compound (0.24 g, 55%) as a light red solid.

Step 2

3-amino-5-cyclopropyl-N-isopropylbenzamide

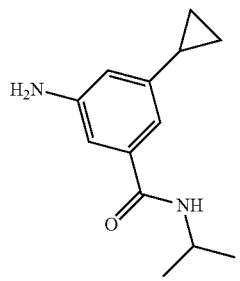 [SMILES: CC(C)NC(=O)c1cc(C2CC2)cc([N+](=O)[O-])c1]

The title compound was prepared from 3-cyclopropyl-N-isopropyl-5-nitrobenzamide in a similar fashion to Step 2 of Example 1. The residue was purified by silica gel column chromatography (petroleum ether/EtOAc=1:1) to give the title compound (0.18 g, 85%) as a yellow solid. LCMS M/Z (M+H) 219.

Step 3

3-[(5-acetyl-1-methyl-6,7-dihydro-4H-pyrazolo[4,3-c]pyridin-3-yl)amino]-5-cyclopropyl-N-isopropyl-benzamide

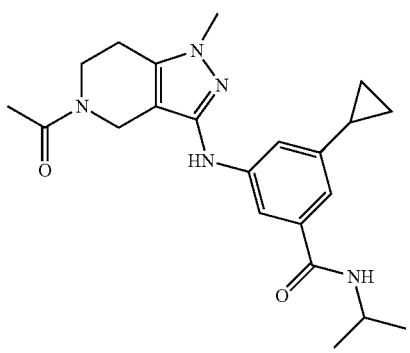 [SMILES: CC(=O)N1CCc2c(c(Nc3cc(C(=O)NC(C)C)cc(C4CC4)c3)nn2C)C1]

The title compound was prepared from 3-amino-5-cyclopropyl-N-isopropylbenzamide in a similar fashion to Step 3 of Example 1. The crude residue was purified by reverse phase chromatography (acetonitrile 35-65%/0.1% HCl in water) to give the title compound in 1% yield. $^1$H NMR (400 MHz, CD$_3$OD) δ 7.38-7.37 (m, 1H), 7.16-7.13 (m, 1H), 7.05-7.04 (m, 1H), 4.42-4.41 (m, 2H), 4.21-4.17 (m, 1H), 3.91-3.85 (m, 2H), 3.74-3.73 (m, 3H), 2.89-2.76 (m, 2H), 2.22-2.15 (m, 3H), 1.97-1.95 (m, 1H), 1.25 (d, J=6.8 Hz, 6H), 1.03-0.99 (m, 2H), 0.79-0.76 (m, 2H). LCMS M/Z (M+H) 396.

Example 34

1-[3-[2-fluoro-4-[1-methyl-3-(trifluoromethyl)pyrazol-4-yl]anilino]-1-methyl-6,7-dihydro-4H-pyrazolo[4,3-c]pyridin-5-yl]ethanone

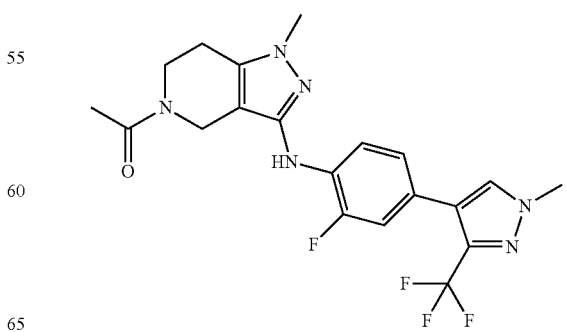

Step 1

2-fluoro-4-(1-methyl-3-(trifluoromethyl)-1H-pyrazol-4-yl)aniline

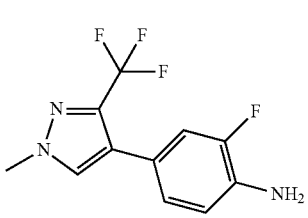 [SMILES: Cn1cc(-c2ccc(N)c(F)c2)c(C(F)(F)F)n1]

[1,1'-bis(diphenylphosphino)ferrocene]dichloropalladium(II), complex with dichloromethane (0.64 g, 0.87 mmol) was added to a mixture of 4-bromo-1-methyl-3-(trifluoromethyl)-1H-pyrazole (2.0 g, 8.7 mmol), 2-fluoro-4-(4,4,5,5-tetramethyl-1,3,2-dioxaborolan-2-yl)aniline (2.1 g, 8.7 mmol) and $Na_2CO_3$ (1.8 g, 17.4 mmol) in 1,4-dioxane (20 mL) and water (4 mL). The reaction mixture was stirred under nitrogen atmosphere at 120° C. for 12 h. After cooling to room temperature the reaction mixture was filtered, concentrated in vacuo and the residue was purified by silica gel chromatography (petroleum ether/EtOAc=3:1 to 1:1) to give the title compound (1.2 g, 55%) as a light yellow solid. LCMS M/Z (M+H) 260.

Step 2

1-[3-[2-fluoro-4-[1-methyl-3-(trifluoromethyl)pyrazol-4-yl]anilino]-1-methyl-6,7-dihydro-4H-pyrazolo[4,3-c]pyridin-5-yl]ethanone

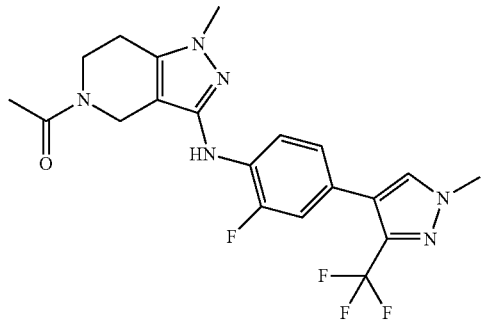 [SMILES: CC(=O)N1CCc2c(c(Nc3ccc(-c4cn(C)nc4C(F)(F)F)cc3F)nn2C)C1]

The title compound was prepared from 2-fluoro-4-(1-methyl-3-(trifluoromethyl)-1H-pyrazol-4-yl)aniline in a similar fashion to Step 3 of Example 1. The crude residue was purified by reverse phase chromatography (acetonitrile 44-74%/0.1% HCl in water) to give the title compound in 4% yield as a white solid. $^1$H NMR (400 MHz, $CD_3OD$) δ 7.81 (s, 1H), 7.39-7.13 (m, 1H), 7.12-7.04 (m, 2H), 4.41 (s, 2H), 3.95 (s, 3H), 3.88-3.79 (m, 2H), 3.68 (s, 3H), 2.83-2.71 (m, 2H), 2.19-2.13 (m, 3H). LCMS M/Z (M+H) 437.

The Following Example 35 was Prepared in a Similar Fashion to Example 34

| Example | Compound Name and Structure | NMR | m/z |
|---|---|---|---|
| Example 35 | 1-(1-methyl-3-(methyl(4-(1-methyl-3-(trifluoromethyl)-1H-pyrazol-4-yl)phenyl)amino)-6,7-dihydro-1H-pyrazolo[4,3-c]pyridin-5(4H)-yl)ethanone | $^1$H NMR (400 MHz, DMSO-$d_6$) δ 8.19 (s, 1H), 8.08 (s, 1H) 7.47-7.43 (m, 1H), 7.33 (d, J = 8.0 Hz, 1H), 7.24-7.19 (m, 1H), 6.74 (d, J = 7.2 Hz, 1H), 4.37-4.34 (s, 2H), 3.94 (s, 3H), 3.73-3.66 (m, 2H), 3.60-3.59 (m, 3H), 2.74-2.59 (m, 2H), 2.09-2.04 (m, 3H) | 441 [M + Na] |

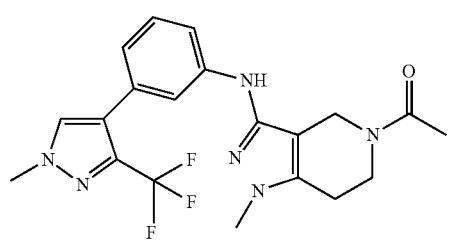

Example 36

1-(1-methyl-3-((6-(1-methyl-3-(trifluoromethyl)-1H-pyrazol-4-yl)pyridin-3-yl)amino)-6,7-dihydro-1H-pyrazolo[4,3-c]pyridin-5(4H)-yl)ethanone

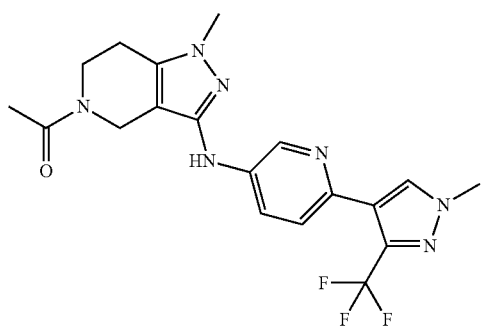 [SMILES: CC(=O)N1CCc2c(c(Nc3ccc(-c4cn(C)nc4C(F)(F)F)nc3)nn2C)C1]

Step 1

6-(1-methyl-3-(trifluoromethyl)-1H-pyrazol-4-yl)pyridin-3-amine

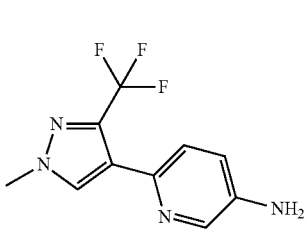 [SMILES: Cn1cc(-c2ccc(N)cn2)c(C(F)(F)F)n1]

[1,1'-bis(diphenylphosphino)ferrocene]dichloropalladium(II), complex with dichloromethane (39.7 mg, 0.054 mmol) was added to a mixture of 6-bromopyridin-3-amine (94.0 mg, 0.54 mmol), 1-methyl-4-(4,4,5,5-tetramethyl-1,3,2-dioxaborolan-2-yl)-3-(trifluoromethyl)-1H-pyrazole (150.0 mg, 0.54 mmol) and K$_2$CO$_3$ (149.0 mg, 1.1 mmol) in 1,4-dioxane (2.0 mL) and water (0.5 mL). The reaction mixture was stirred under nitrogen atmosphere at 120° C. for 12 h. The mixture was filtered, concentrated in vacuo and the residue was purified by silica gel chromatography (petroleum ether/EtOAc=3:1 to 1:1) to give the title compound (80 mg, 60%) as a red solid. LCMS M/Z (M+H)=243.

Step 2

1-(1-methyl-3-((6-(1-methyl-3-(trifluoromethyl)-1H-pyrazol-4-yl)pyridin-3-yl)amino)-6,7-dihydro-1H-pyrazolo[4,3-c]pyridin-5(4H)-yl)ethanone

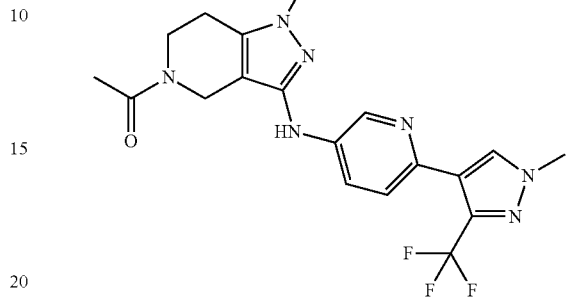

The title compound was prepared from 6-(1-methyl-3-(trifluoromethyl)-1H-pyrazol-4-yl)pyridin-3-amine in a similar fashion to Step 3 of Example 1. The crude residue was purified by reverse phase chromatography (acetonitrile 16-46%/0.1% formic acid in water) to give the title compound in 29% yield as a white. $^1$H NMR (400 MHz, DMSO-d$_6$) δ 8.66-8.64 (m, 1H), 8.49-8.45 (m, 1H), 8.23 (s, 1H), 7.92 (dd, J=8.8, 2.4 Hz, 1H), 7.37 (dd, J=8.8, 5.6 Hz, 1H), 4.38 (s, 2H), 3.94 (s, 3H), 3.74-3.66 (m, 2H), 3.62 (s, 3H), 2.74-2.59 (m, 2H), 2.10-2.07 (m, 3H). LCMS M/Z (M+H) 420.

General Procedure for Intermediate C

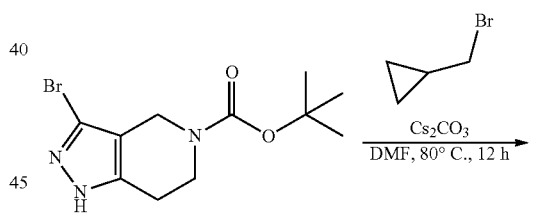

Intermediate A

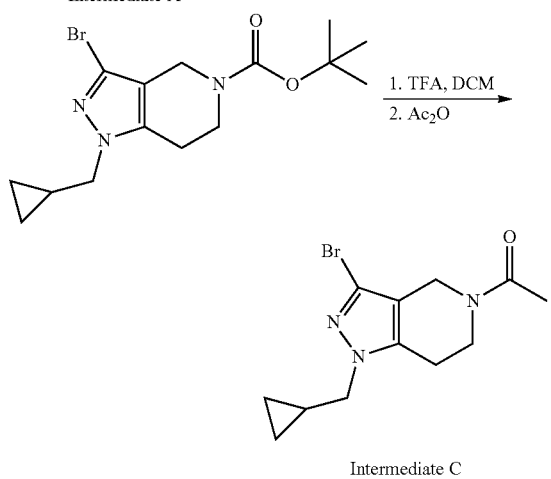

Intermediate C

Step 1 tert-butyl 3-bromo-1-(cyclopropylmethyl)-6,7-di-
hydro-1H-pyrazolo[4,3-c]pyridine-5(4H)-carboxy-
late

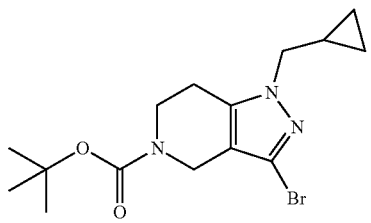 [SMILES: CC(C)(C)OC(=O)N1CCc2c(c(Br)nn2CC2CC2)C1]

To a stirred solution of tert-butyl 3-bromo-6,7-dihydro-1H-pyrazolo[4,3-c]pyridine-5(4H)-carboxylate (Intermediate A, 6.0 g, 19.8 mmol) in DMF (40 mL) was added $Cs_2CO_3$ (9.70 g, 29.8 mmol) and (bromomethyl)cyclopropane (4.0 g, 29.8 mmole). The reaction mixture was heated to 80° C. for 12 h. The mixture was diluted with EtOAc (200 mL), washed with brine (100 mL×3), dried over $Na_2SO_4$, filtered and concentrated in vacuo. The residue was purified by silica gel chromatography (eluent gradient from petroleum ether to petroleum ether/MTBE/THF=10:1:1) to give the title compound (3.0 g, 42%) as a white solid. $^1$H NMR (400 MHz, $CDCl_3$) δ 4.29 (s, 2H), 3.85 (d, J=3.4 Hz, 2H), 3.71 (t, J=5.2 Hz, 2H), 2.67 (t, J=5.2 Hz, 2H), 1.49 (s, 9H), 1.25-1.18 (m, 1H), 0.61-0.55 (m, 2H), 0.35-0.31 (m, 2H).

Step 1

1-(3-bromo-1-(cyclopropylmethyl)-6,7-dihydro-1H-
pyrazolo[4,3-c]pyridin-5(4H)-yl)ethanone

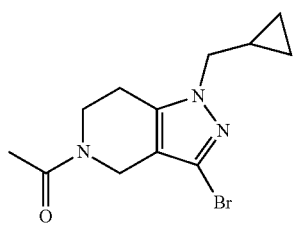 [SMILES: CC(=O)N1CCc2c(c(Br)nn2CC2CC2)C1]

A mixture of tert-butyl 3-bromo-1-(cyclopropylmethyl)-6,7-dihydro-1H-pyrazolo[4,3-c]pyridine-5(4H)-carboxylate (3.0 g, 8.4 mmol) and trifluoroacetic acid (30 mL) in DCM (30 mL) was stirred at room temperature for 2 h. The solvent was removed by evaporation and the crude product was re-dissolved in DCM (120 mL). The solution was cooled to 0° C. before TEA (2.49 g, 24.6 mmol) and acetic anhydride (1.26 g, 12.3 mmol) were added dropwise. The reaction mixture was stirred at room temperature for additional 2 h before it was quenched with water. The organic layer was dried over anhydrous $Na_2SO_4$, filtered and concentrated in vacuo to give crude product which was purified by silica gel chromatography (DCM/MeOH=20:1) to afford the title compound (2.40 g, 96%) as a white solid. $^1$H NMR (400 MHz, $CDCl_3$) δ 4.49-4.33 (m, 3H), 3.90-3.70 (m, 4H), 2.77-2.67 (m, 2H), 2.23-2.19 (m, 3H), 1.28-1.18 (m, 1H), 0.63-0.58 (m, 2H), 0.36-0.32 (m, 2H).

Example 37

1-[1-(cyclopropylmethyl)-3-[2-fluoro-3-(1-methyl-
pyrazol-4-yl)anilino]-6,7-dihydro-4H-pyrazolo[4,3-
c]pyridin-5-yl]ethanone

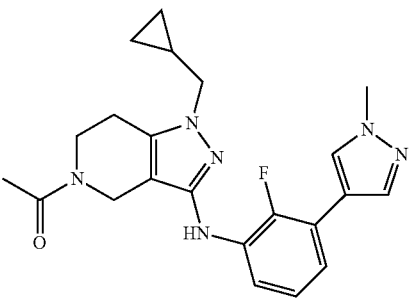 [SMILES: CC(=O)N1CCc2c(c(Nc3cccc(-c4cnn(C)c4)c3F)nn2CC2CC2)C1]

Step 1

4-(2-fluoro-3-nitrophenyl)-1-methyl-1H-pyrazole

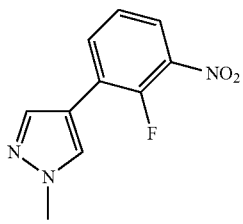 [SMILES: Cn1cc(-c2cccc([N+](=O)[O-])c2F)cn1]

The title compound was prepared from 1-bromo-2-fluoro-3-nitrobenzene in a similar fashion to Step 1 of Example 1. The residue was purified by silica gel chromatography (petroleum ether/EtOAc=5:1 to 3:1) to afford the title compound (9.5 g, 95%) as a yellow solid.

Step 2

2-fluoro-3-(1-methyl-1H-pyrazol-4-yl)aniline

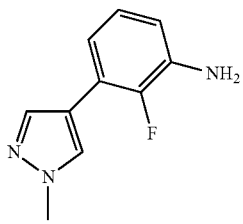

The title compound was prepared from 4-(2-fluoro-3-nitrophenyl)-1-methyl-1H-pyrazole in a similar fashion to Step 2 of Example 1. The residue was purified by silica gel chromatography (petroleum ether/EtOAc=1:1) to give the title compound (7.9 g, 96% yield) as a red solid. $^1$H NMR (400 MHz, DMSO-d$_6$) δ 7.99 (s, 1H), 7.76 (s, 1H), 6.81-6.58 (m, 3H), 5.08 (s, 2H), 3.84 (s, 3H).

Step 3

1-[1-(cyclopropylmethyl)-3-[2-fluoro-3-(1-methyl-pyrazol-4-yl)anilino]-6,7-dihydro-4H-pyrazolo[4,3-c]pyridin-5-yl]ethanone

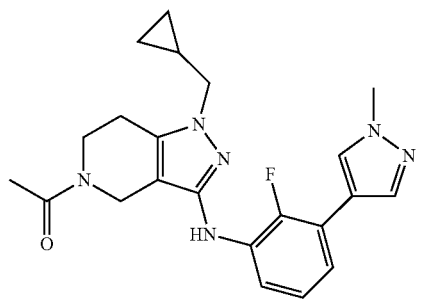 [SMILES: CC(=O)N1CCc2c(c(Nc3cccc(-c4cnn(C)c4)c3F)nn2CC2CC2)C1]

To a solution of 2-fluoro-3-(1-methyl-1H-pyrazol-4-yl)aniline (1.4 g, 7.0 mmol) and 1-(3-bromo-1-(cyclopropylmethyl)-6,7-dihydro-1H-pyrazolo[4,3-c]pyridin-5(4H)-yl)ethanone (1.8 g, 6.0 mmol) in 1,4-dioxane (40 mL) was added NaOtBu (1.9 g, 19.8 mmol), Chloro-(2-Dicyclohexylphosphino-2',6'-diisopropoxy-1,1'-biphenyl) [2-(2-aminoethyl)phenyl]palladium(I) (240 mg, 0.26 mmol) and 2-(dicyclohexylphosphino)3,6-dimethoxy-2',4',6'-triisopropyl-1,1'-biphenyl (160 mg, 0.24 mmol). The reaction mixture was heated to 120° C. for 12 h under N$_2$ atmosphere. The mixture was filtered and concentrated in vacuo. The crude residue was purified reverse phase chromatography (acetonitrile 30-60%/0.1% NH$_4$OH in water) to give the title compound (536 mg, 22%) as white solid. $^1$H NMR (400 MHz, CD$_3$OD) δ 8.00 (s, 1H), 7.85 (s, 1H), 7.17-6.91 (m, 3H), 4.44 (s, 2H), 3.93 (s, 3H), 3.90-3.75 (m, 4H), 2.89-2.71 (m, 2H), 2.22-2.08 (m, 3H), 1.27-1.22 (m, 1H), 0.60-0.49 (m, 2H), 0.40-0.31 (m, 2H). LCMS M/Z (M+H) 409.

The Following Examples 38-40 were Prepared in a Similar Fashion to Example 37

| Example | Compound Name and Structure | NMR | m/z |
|---|---|---|---|
| Example 38 | 1-(1-(cyclopropylmethyl)-3-((4-fluoro-3-(1-methyl-1H-pyrazol-4-yl)phenyl)amino)-6,7-dihydro-1H-pyrazolo[4,3-c]pyridin-5(4H)-yl)ethanone | $^1$H NMR (400 MHz, DMSO-d$_6$) δ 8.12-8.07 (m, 1H), 8.00 (s, 1H), 7.72-7.71 (m, 2H), 7.30-7.26 (m, 1H), 7.10-7.03 (m, 1H), 4.36 (s, 2H), 3.90 (s, 3H), 3.78 (d, J = 6.8 Hz, 2H), 3.74-3.66 (m, 2H), 2.74-2.62 (m, 2H), 2.11-2.07 (m, 3H), 1.25-1.11 (m, 1H), 0.51-0.49 (m, 2H), 0.36-0.35 (m, 2H) | 409 |
| Example 39 | 1-[1-(cyclopropylmethyl)-3-[4-methyl-3-(1-methylpyrazol-4-yl)anilino]-6,7-dihydro-4H-pyrazolo[4,3-c]pyridin-5-yl]ethanone | $^1$H NMR (400 MHz, CD$_3$OD) δ 7.75 (s, 1H), 7.61 (s, 1H), 7.22-7.17 (m, 1H), 7.09-7.08 (m, 1H), 7.06-6.95 (m, 1H), 3.95 (m, 2H), 3.88 (s, 3H), 3.84-3.79 (m, 4H), 2.85-2.74 (m, 2H), 2.31 (s, 3H), 2.30-2.12 (m, 3H), 1.24-1.21 (m, 1H), 0.59-0.56 (m, 2H), 0.39-0.37 (m, 2H) | 405 |
| Example 40 | 1-[1-(cyclopropylmethyl)-3-[2-fluoro-5-(1-methylpyrazol-4-yl)anilino]-6,7-dihydro- | $^1$H NMR (400 MHz, CD$_3$OD) δ 7.82 (s, 1H), 7.66 (s, 1H), 7.58-7.42 (m, 1H), 7.06-7.02 (m, 1H), 6.95-6.93 (m, 1H), 4.45 (s, 2H), 3.91 (s, 3H), 3.90-3.84 (m, 4H), 2.90-2.76 (m, 2H), 2.22- | 431 (M + Na) |

| Example | Compound Name and Structure | NMR | m/z |
|---|---|---|---|
| | 4H-pyrazolo[4,3-c]pyridin-5-yl]ethanone<br> | 2.13 (m, 3H), 1.27-1.23 (m, 1H), 0.62-0.60 (m, 2H), 0.43-0.41 (m, 2H) | |

Example 41

2-[[5-acetyl-1-(cyclopropylmethyl)-6,7-dihydro-4H-pyrazolo[4,3-c]pyridin-3-yl]amino]-6-(1-methyl-pyrazol-4-yl)benzonitrile

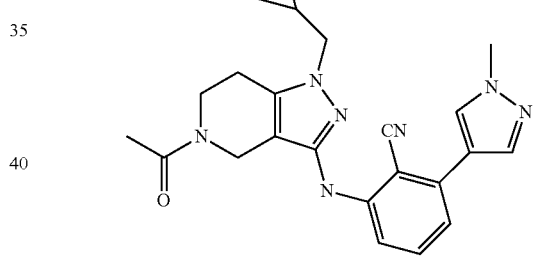

Step 1

2-amino-6-(1-methyl-1H-pyrazol-4-yl)benzonitrile

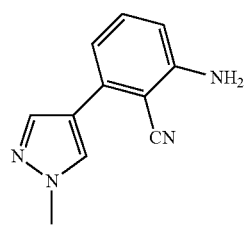

The title compound was prepared from 2-amino-6-bromobenzonitrile in a similar fashion to Step 1 of Example 20. The crude residue was purified by silica gel chromatography (petroleum ether:EtOAc=2:1) to give the title compound (900 mg, 89%) as a brown solid. $^1$H NMR (400 MHz, CDCl$_3$) δ 7.94 (s, 1H), 7.82 (s, 1H), 7.32-7.26 (m, 1H), 6.85 (d, J=7.2 Hz, 1H), 6.62 (d, J=8.4 Hz, 1H), 4.48 (s, 2H), 3.97 (s, 3H).

Step 2

2-[[5-acetyl-1-(cyclopropylmethyl)-6,7-dihydro-4H-pyrazolo[4,3-c]pyridin-3-yl]amino]-6-(1-methyl-pyrazol-4-yl)benzonitrile The title compound was prepared from 2-amino-6-(1-methyl-1H-pyrazol-4-yl)benzonitrile in a similar fashion to Step 3 of Example 1. The crude residue was purified by reverse phase chromatography (acetonitrile 25-55%/0.1% NH$_4$OH in water) to give the title compound in 8% yield as a white solid. $^1$H NMR (400 MHz, CD$_3$OD) δ 8.10 (s, 1H), 7.91 (s, 1H), 7.43-7.39 (m, 1H), 7.02-6.88 (m, 2H), 4.41-4.00 (m, 2H), 3.97 (s, 3H), 3.92-3.83 (m, 4H), 2.90-2.77 (m, 2H), 2.20-2.13 (m, 3H), 1.26-1.25 (m, 1H), 0.61-0.55 (m, 2H), 0.40-0.39 (m, 2H). LCMS M/Z (M+H) 416.

The Following Example 42 was Prepared in a Similar Fashion to Example 41

| Example | Compound Name and Structure | NMR | m/z |
|---|---|---|---|
| Example 42 | 1-(1-(cyclopropylmethyl)-3-((6-(1-methyl-1H-pyrazol-4-yl)pyridin-3-yl)amino)-6,7-dihydro-1H-pyrazolo[4,3-c]pyridin-5(4H)-yl)ethanone | $^1$H NMR (400 MHz, CD$_3$OD) δ 8.52 (d, J = 2.8 Hz, 1H), 7.99 (s, 1H), 7.90 (s, 1H), 7.83-7.76 (m, 1H), 7.51 (dd, J = 8.8, 4.8 Hz, 1H), 4.46 (s, 2H), 3.93 (s, 3H), 3.90-3.78 (m, 4H), 2.85-2.71 (m, 2H), 2.21-2.17 (m, 3H), 1.30- | 392 |

| Example | Compound Name and Structure | NMR | m/z |
|---|---|---|---|
| | | 1.20 (m, 1H), 0.61-0.54 (m, 2H), 0.42-0.35 (m, 2H) | |

Example 43

1-[1-(cyclopropylmethyl)-3-[(2-methylindazol-6-yl)amino]-6,7-dihydro-4H-pyrazolo[4,3-c]pyridin-5-yl]ethanone

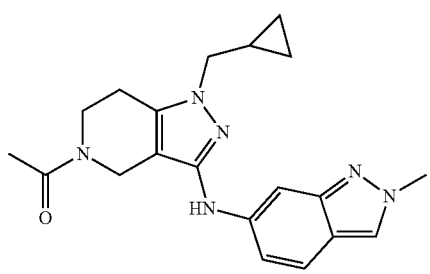 [SMILES: CC(=O)N1CCc2c(c(Nc3ccc4cn(C)nc4c3)nn2CC2CC2)C1]

The title compound was prepared from 2-methyl-2H-indazol-6-amine in a similar fashion to Step 3 of Example 37. The crude residue was purified by reverse phase chromatography (acetonitrile 20-50%/0.2% formic acid in water) to give the title compound in 8% yield as a white solid. $^1$H NMR (400 MHz, CD$_3$OD) δ 8.41 (d, J=6.4 Hz, 1H), 7.70-7.59 (m, 2H), 7.13 (dd, J=8.8, 4.8 Hz, 1H), 4.47 (s, 2H), 4.21 (s, 3H), 3.90-3.80 (m, 4H), 2.87-2.75 (m, 2H), 2.21-2.15 (m, 3H), 1.28-1.26 (m, 1H), 0.62-0.58 (m, 2H), 0.42-0.39 (m, 2H). LCMS M/Z (M+H) 365.

The Following Examples 44-47 were Prepared in a Similar Fashion to Example 43

| Example | Compound Name and Structure | NMR | m/z |
|---|---|---|---|
| Example 44 | 1-[3-anilino-1-(cyclopropylmethyl)-6,7-dihydro-4H-pyrazolo[4,3-c]pyridin-5-yl]ethanone | $^1$H NMR (400 MHz, CD$_3$OD) δ 7.20-7.08 (m, 4H), 6.78-6.73 (m, 1H), 4.38-4.37 (m, 2H), 3.87-3.78 (m, 4H), 2.84-2.71 (m, 2H), 2.20-2.12 (m, 3H), 1.25-1.20 (m, 1H), 0.58-0.55 (m, 2H), 0.39-0.35 (m, 2H) | 311 |
| Example 45 | 1-[1-(cyclopropylmethyl)-3-(tetralin-6-ylamino)-6,7-dihydro-4H-pyrazolo[4,3-c]pyridin-5-yl]ethanone | $^1$H NMR (400 MHz, CD$_3$OD) δ 6.89-6.80 (m, 3H), 3.88 (s, 21-1), 3.87-3.79 (m, 4H), 2.75-2.67 (n, 6H), 2.21-2.13 (m, 3H), 1.78 (n, 4H), 1.29-1.22 (m, 1H), 0.59-0.57 (n, 2H), 0.56-0.38 (m, 2H) | 365 |

-continued

| Example | Compound Name and Structure | NMR | m/z |
|---|---|---|---|
| Example 46 | 1-[1-(cyclopropylmethyl)-3-(3-methylsulfonylanilino)-6,7-dihydro-4H-pyrazolo[4,3-c]pyridin-5-yl]ethanone | $^1$H NMR (400 MHz, CD$_3$OD) δ 7.93-7.92 (m, 1H), 7.46-7.43 (m, 2H), 7.33-7.31 (m, 1H), 4.45 (s, 2H), 3.90-3.81 (m, 4H), 3.33 (s, 3H), 2.88-2.76 (m, 2H), 2.23-2.18 (m, 3H), 1.28-1.24 (m, 1H), 0.62-0.59 (m, 2H), 0.57-0.40 (m, 2H) | 389 |
| Example 47 | 1-[1-(cyclopropylmethyl)-3-[(5-methyl-3-pyridyl)amino]-6,7-dihydro-4H-pyrazolo[4,3-c]pyridin-5-yl]ethanone | $^1$H NMR (400 MHz, CD$_3$OD) δ 8.35 (s, 1H), 7.81 (s, 1H), 7.66-7.62 (m, 1H), 4.45 (s, 2H), 3.88-3.79 (m, 4H), 2.83 (t, J = 8.0 Hz, 1H), 2.73 (t, J = 8.0 Hz, 1H), 2.31 (s, 3H), 2.21-2.17 (m, 3H) | 326 |

Example 48

7-[[5-acetyl-1-(cyclopropylmethyl)-6,7-dihydro-4H-pyrazolo[4,3-c]pyridin-3-yl]amino]-2-methyl-3,4-dihydroisoquinolin-1-one

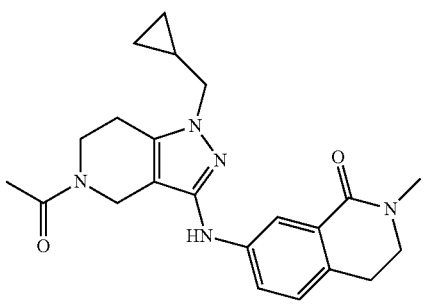 [SMILES: CC(=O)N1CCc2c(c(Nc3ccc4c(c3)C(=O)N(C)CC4)nn2CC2CC2)C1]

Step 1

2-methyl-3,4-dihydroisoquinolin-1(2H)-one

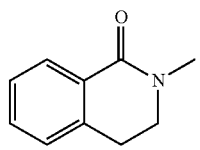

Sodium hydride (408 mg, 10.2 mmol) was added slowly to a stirring solution of 3,4-dihydroisoquinolin-1(2H)-one (1.00 g, 6.80 mmol) in THF (30 mL) at 0° C. The mixture stirred for 0.5 h before methyl iodide (1.45 mg, 10.2 mmol) was added and the mixture was heated to reflux for 16 hours. After cooling to room temperature, water (20 mL) was added and the mixture was extracted with EtOAc (20 mL×2). The combined organic layers were dried over anhydrous Na$_2$SO$_4$, filtered and concentrated in vacuo to give the crude product (1.2 g) as a yellow oil that required no further purification.

Step 2

2-methyl-7-nitro-3,4-dihydroisoquinolin-1(2H)-one

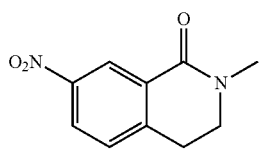

To a mixture of 2-methyl-3,4-dihydroisoquinolin-1(2H)-one (500 mg, 3.10 mmol) in concentrated H$_2$SO$_4$ (10 mL) at 0° C. was added potassium nitrate (2.89 mg, 3.10 mmol). The mixture was heated to 15° C. for 16 h. After cooling to room temperature, the mixture was quenched with ice water (25 mL) and extracted with EtOAc (30 mL). The combined organic layers were dried over anhydrous Na$_2$SO$_4$, filtered and concentrated in vacuo to give the title compound (500 mg, 27%) as yellow oil that required no further purification. $^1$H NMR (400 MHz, CDCl$_3$) δ 8.92 (d, J=2.4 Hz, 1H), 8.27 (dd, J=8.4, 2.4 Hz, 1H), 7.39 (d, J=8.4 Hz, 1H), 3.66 (t, J=6.8 Hz, 2H), 3.21 (s, 3H), 3.15 (d, J=6.8 Hz, 2H).

Step 3

7-amino-2-methyl-3,4-dihydroisoquinolin-1(2H)-one

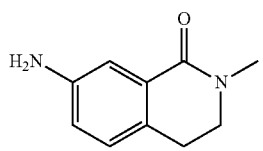

To a solution of 2-methyl-7-nitro-3,4-dihydroisoquinolin-1(2H)-one (500 mg, 2.43 mmol) in EtOAc (20 mL) was added Pd/C (300 mg). The mixture was stirred under hydrogen atmosphere (20 Psi) at room temperature for 16 hours. The mixture was filtered and the filtrate was concentrated in vacuo to give the title compound (400 mg, crude) as yellow oil, which required no further purification.

Step 4

7-[[5-acetyl-1-(cyclopropylmethyl)-6,7-dihydro-4H-pyrazolo[4,3-c]pyridin-3-yl]amino]-2-methyl-3,4-dihydroisoquinolin-1-one

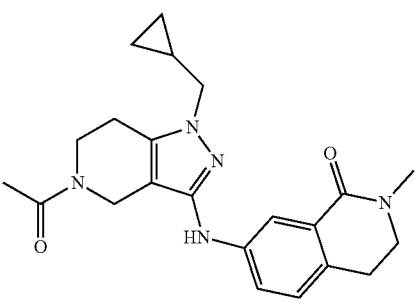 [SMILES: CC(=O)N1CCc2c(c(Nc3ccc4c(c3)C(=O)N(C)CC4)nn2CC2CC2)C1]

The title compound was prepared from 2-methyl-7-nitro-3,4-dihydroisoquinolin-1(2H)-one in a similar fashion to Step 3 of Example 37. The crude residue was purified by reverse phase chromatography (acetonitrile 20-50%/0.2% formic acid in water) to give the title compound in 4% yield as a white solid. $^1$H NMR (400 MHz, CDCl$_3$) δ 7.67-7.50 (m, 1H), 7.19-6.97 (m, 2H), 5.97-5.74 (m, 1H), 4.43-4.19 (m, 2H), 3.99-3.70 (m, 4H), 3.64-3.47 (m, 2H), 3.23-3.08 (m, 3H), 3.04-2.86 (m, 2H), 2.86-2.62 (m, 2H), 2.24-2.07 (m, 3H), 1.26-1.14 (m, 1H), 0.69-0.53 (m, 2H), 0.42-0.27 (m, 2H). LCMS M/Z (M+H) 394.

Example 49

3-[[5-acetyl-1-(cyclopropylmethyl)-6,7-dihydro-4H-pyrazolo[4,3-c]pyridin-3-yl]amino]-N-isopropyl-5-methyl-benzamide

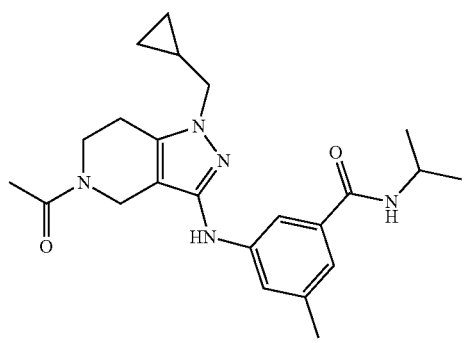 [SMILES: CC(=O)N1CCc2c(c(Nc3cc(C)cc(C(=O)NC(C)C)c3)nn2CC2CC2)C1]

The title compound was prepared from 3-amino-N-isopropyl-5-methylbenzamide (Step 2 of Example 18) in a similar fashion to Step 3 of Example 37. The crude residue was purified by reverse phase chromatography (acetonitrile 30-60%/0.2% formic acid in water) to give the title compound in 4% yield as a white solid. $^1$H NMR (400 MHz, CD$_3$OD) δ 7.4 (d, J=6.8 Hz, 1H), 7.09 (d, J=8.4 Hz, 1H), 7.02 (d, J=6.4 Hz, 1H), 4.16 (d, J=4.4 Hz, 2H), 4.23-4.12 (m, 1H), 3.92-3.79 (m, 4H), 2.86-2.69 (m, 2H), 2.34 (d, J=4.0 Hz, 3H), 2.25-2.18 (m, 3H), 1.29 (d, J=6.4 Hz, 3H), 1.25 (d, J=6.4 Hz, 3H), 0.62-0.51 (m, 2H), 0.42-0.37 (m, 2H). LCMS M/Z (M+H) 410.

General Procedure for Intermediate D

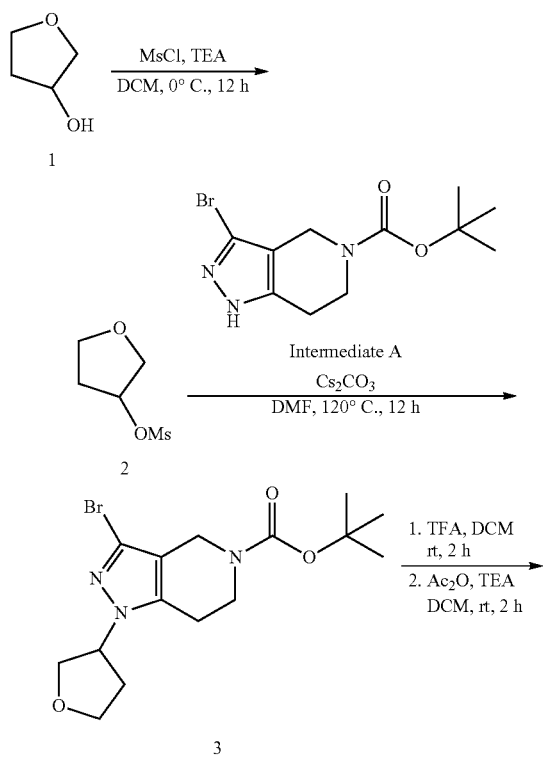

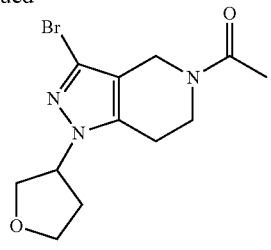

Intermediate D

Step 1 tetrahydrofuran-3-yl methanesulfonate

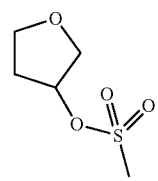

To a solution of tetrahydrofuran-3-ol (10 g, 113.5 mmol) in DCM (150 mL) was added MsCl (15.6 g, 136.2 mmol) and TEA (23 g, 227 mmol). The reaction mixture was stirred at room temperature for 18 h. Water (100 mL) was added and the mixture was extracted with DCM (100 mL×2). The combined organic layers was dried over anhydrous Na$_2$SO$_4$, filtered and concentrated in vacuo to give the title compound (16 g, 85%) as a brown oil. $^1$H NMR (400 MHz, CDCl$_3$) δ 5.27-5.25 (m, 1H), 4.00-3.83 (m, 4H), 3.01 (s, 3H), 2.23-2.18 (m, 2H).

Step 2 tert-butyl 3-bromo-1-(tetrahydrofuran-3-yl)-6,7-dihydro-1H-pyrazolo[4,3-c]pyridine-5(4H)-carboxylate

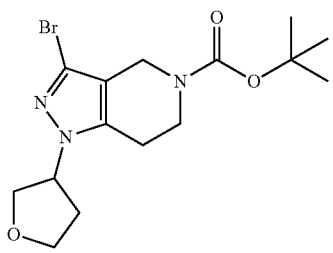 [SMILES: CC(C)(C)OC(=O)N1CCc2c(c(Br)nn2C2CCOC2)C1]

To a solution of tert-butyl 3-bromo-6,7-dihydro-1H-pyrazolo[4,3-c]pyridine-5(4H)-carboxylate (Intermediate A, 20.0 g, 66.0 mmol) in DMF (100 mL) was added Cs$_2$CO$_3$ (40.0 g, 123 mmol) and tetrahydrofuran-3-yl methanesulfonate (16.0 g, 98.0 mmol). The mixture was heated to 80° C. for 12 h. The solution was concentrated in vacuo and the crude residue was purified by silica gel chromatography (eluent from petroleum ether/EtOAc=10:1 to 3:1) to give the title compound (17 g, 69%) as a yellow oil. $^1$H NMR (400

MHz, CDCl₃) δ 4.78-4.69 (m, 1H), 4.26 (s, 2H), 4.18-3.86 (m, 4H), 3.72 (s, 2H), 2.72-2.62 (m, 2H), 2.44-2.22 (m, 2H), 1.48 (s, 9H).

Step 3

1-(3-bromo-1-(tetrahydrofuran-3-yl)-6,7-dihydro-1H-pyrazolo[4,3-c]pyridin-5(4H)-yl)ethanone

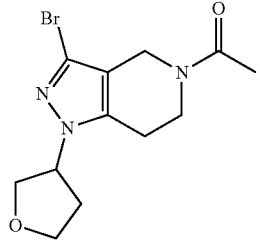 [SMILES: CC(=O)N1CCc2c(c(Br)nn2C2CCOC2)C1]

To a solution of tert-butyl 3-bromo-1-(tetrahydrofuran-3-yl)-6,7-dihydro-1H-pyrazolo[4,3-c]pyridine-5(4H)-carboxylate (17.0 g, 45.0 mmol) in DCM (60 mL) was added TFA (30 mL) dropwise. The reaction solution was stirred at room temperature for 2 h. The solvent was removed by evaporation and the crude product was re-dissolved in DMF (50 mL). The mixture was cooled to 0° C. before TEA (41.0 g, 40.5 mmol) and acetic anhydride (7.0 g, 68.0 mmol) were added dropwise. The ice bath was removed and the reaction was stirred at room temperature for additional 2 h. Water (50 mL) was added and the solution was extracted with EtOAc (150 mL×3). The combined organic layers were dried over anhydrous Na₂SO₄, filtered and concentrated in vacuo. The crude residue was purified by silica gel chromatography (DCM:MeOH=30:1) to give the title compound (12.0 g, 82%) as a white solid. ¹H NMR (400 MHz, DMSO-d₆) δ 4.96-4.92 (m 1H), 4.28 (s, 2H), 3.99-3.95 (m, 2H), 3.80-3.68 (m, 4H), 2.82-2.70 (m, 2H), 2.29-2.19 (m, 2H), 2.10-2.08 (m, 3H).

Example 50

1-[3-[2-fluoro-3-(1-methylpyrazol-4-yl)anilino]-1-tetrahydrofuran-3-yl-6,7-dihydro-4H-pyrazolo[4,3-c]pyridin-5-yl]ethanone

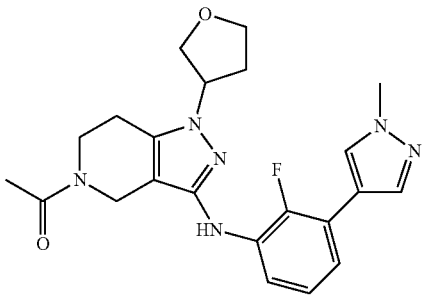 [SMILES: CC(=O)N1CCc2c(c(Nc3cccc(-c4cnn(C)c4)c3F)nn2C2CCOC2)C1]

To a solution of 1-(3-bromo-1-(tetrahydrofuran-3-yl)-6,7-dihydro-1H-pyrazolo[4,3-c]pyridin-5(4H)-yl)ethanone (Intermediate D, 300 mg, 0.96 mmol) in dioxane (8.0 mL) was added 2-fluoro-3-(1-methyl-1H-pyrazol-4-yl)aniline (Step 2 of Example 37, 183 mg, 0.96 mmol), chloro-(2-dicyclohexylphosphino-2',6'-diisopropoxy-1,1'-biphenyl)[2-(2-aminoethyl)phenyl]palladium(II) (81.7 mg, 0.10 mmol), 2-(dicyclohexylphosphino)3,6-dimethoxy-2',4',6'-triisopropyl-1,1'-biphenyl (53.6 mg, 0.10 mmol) and tBuONa (277 mg, 2.9 mmol). The reaction mixture was purged with nitrogen atmosphere for 1 min and then heated to 120° C. for 18 h. The mixture was concentrated in vacuo and the crude residue was purified by reverse phase chromatography (acetonitrile 25-55%/0.1% NH₄OH in water) to give the title compound (67 mg, 16%) as a white solid. ¹H NMR (400 MHz, DMSO-d₆) δ 8.09 (s, 1H), 7.85-7.77 (m, 2H), 7.57-7.38 (m, 1H), 7.04-6.95 (m, 2H), 4.89-4.82 (m, 1H), 4.39-4.32 (m, 2H), 4.02-3.95 (m, 2H), 3.90 (s, 3H), 3.85-3.68 (m, 4H), 2.79-2.63 (m, 2H), 2.33-2.22 (m, 2H), 2.08-2.05 (m, 3H). LCMS M/Z (M+H) 425.

The Following Examples 51-54 were Prepared in a Similar Fashion to Example 50

| Example | Compound Name and Structure | NMR | m/z |
| --- | --- | --- | --- |
| Example 51 | 1-(3-((2-fluoro-4-(1-methyl-1H-pyrazol-4-yl)phenyl)amino)-1-(tetrahydrofuran-3-yl)-6,7-dihydro-1H-pyrazolo[4,3-c]pyridin-5(4H)-yl)ethanone 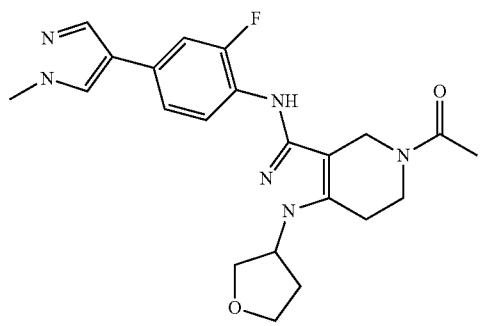 [SMILES: CN/C=C(\C=N)c1ccc(NC(=N)C2=C(NC3CCOC3)CCN(C(C)=O)C2)c(F)c1] | ¹H NMR (400 MHz, DMSO-d₆) δ 8.02 (s, 1H), 7.83-7.74 (m, 2H), 7.68 (dd, J = 8.0, 8.0 Hz, 1H), 7.36-7.33 (m, 1H), 7.21 (dd, J = 8.0, 8.0 Hz, 1H), 4.87-4.82 (m, 1H), 4.40-4.33 (m, 2H), 4.01 (t, J = 7.6 Hz, 2H), 3.84-3.77 (m, 5H), 3.72-3.67 (m, 2H), 2.78-2.66 (m, 2H), 2.26-2.22 (m, 2H), 2.08-2.05 (m, 3H) | 425 |

-continued

| Example | Compound Name and Structure | NMR | m/z |
|---|---|---|---|
| Example 52 | 1-[3-[3-fluoro-4-(1-methylpyrazol-4-yl)anilino]-1-tetrahydrofuran-3-yl-6,7-dihydro-4H-pyrazolo[4,3-c]pyridin-5-yl]ethanone | $^1$H NMR (400 MHz, CD$_3$OD) δ 7.88 (s, 1H), 7.78 (s, 1H), 7.46-7.41 (m, 1H), 7.33-7.30 (m,1H), 7.05 (d, J = 6.0 Hz, 114), 4.93-4.92 (m, 1H), 4.45-4.44 (m, 2H), 4.22-4.10 (m, 211), 3.99-3.82 (m, 7H), 2.85-2.75 (m, 2H), 2.38-2.34 (m, 2H), 2.22-2.18 (m, 3H) | 425 |
| Example 53 | 1-[3-[2,4-difluoro-5-(1-methylpyrazol-4-yl)anilino]-1-tetrahydrofuran-3-yl-6,7-dihydro-4H-pyrazolo[4,3-c]pyridin-5-yl]ethanone | $^1$H NMR (400 MHz, CD$_3$OD) δ 8.33-8.11 (m, 1H), 7.93 (d, J = 3.6 Hz, 1H), 7.77 (d, J = 8.0 Hz, 1H), 6.99-6.93 (m, 1H), 4.90-4.88 (m, 1H), 4.45-4.43 (m, 2H), 4.22-4.19 (m, 1H), 4.04 (d, J = 6.4 Hz, 2H), 3.91-3.78 (m, 6H), 2.85-2.72 (m, 2H), 2.37-2.29 (m, 2H), 2.19-2.13 (m, 3H) | 443 |
| Example 54 | 1-(3-bromo-1-(cyclopropylmethyl)-6,7-dihydro-1H-pyrazolo[4,3-c]pyridin-5(4H)-yl)ethanone | $^1$H NMR (400 MHz, CD$_3$OD) δ 8.31 (s, 1H), 8.18 (s, 1H), 7.42-7.33 (m, 1H), 7.14 (dd, J = 9.6, 9.6 Hz, 1H), 5.10 (s, 1H), 4.44-4.41 (m, 2H), 4.20-4.15 (m, 1H), 4.07-4.03 (m, 4H), 3.95-3.88 (m, 3H), 3.81-3.75 (m, 1H), 3.02-2.87 (m, 2H), 2.61-2.48 (m, 1H), 2.26 -2.15 (m, 4H) | 443 |

Example 55

1-(3-((2-fluoro-4-(1-methyl-3-(trifluoromethyl)-1H-pyrazol-4-yl)phenyl)amino)-1-(tetrahydrofuran-3-yl)-6,7-dihydro-1H-pyrazolo[4,3-c]pyridin-5(4H)-yl)ethanone

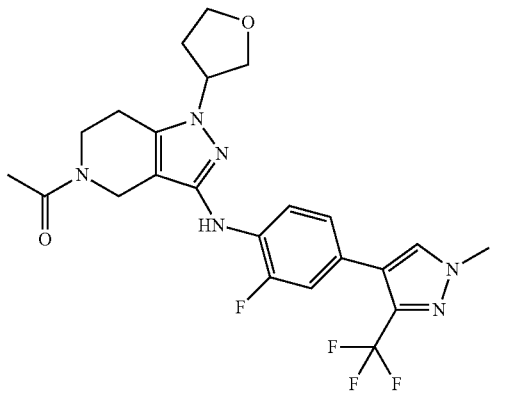 [SMILES: CC(=O)N1CCc2c(c(Nc3ccc(-c4cn(C)nc4C(F)(F)F)cc3F)nn2C2CCOC2)C1]

The title compound was prepared from 2-fluoro-4-(1-methyl-3-(trifluoromethyl)-1H-pyrazol-4-yl)aniline (Step 1 of Example 34) and Intermediate D in a similar fashion to Example 50. The crude residue was purified by reverse phase chromatography (acetonitrile 20-50%/0.2% formic acid in water) to give the title compound in 29% yield as a white solid. $^1$H NMR (400 MHz, DMSO-$d_6$) δ 8.11 (s, 1H), 7.99-7.92 (m, 1H), 7.85-7.68 (m, 1H), 7.17-7.12 (m, 1H), 7.06 (dd, J=8.0, 8.0 Hz, 1H), 4.92-4.80 (m, 1H), 4.41-4.35 (m, 2H), 4.03-3.80 (m, 5H), 3.87-3.75 (m, 2H), 3.73-3.68 (m, 2H), 2.79-2.67 (m, 2H), 2.27-2.23 (m, 2H), 2.09-2.05 (m, 3H). LCMS M/Z (M+H) 493.

The Following Examples 56-57 were Prepared in a Similar Fashion to Example 55

| Example | Compound Name and Structure | NMR | m/z |
|---|---|---|---|
| Example 56 | 1-[3-[4-[1-methyl-3-(trifluoromethyl)pyrazol-4-yl]anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.31-8.25 (m, 1H), 8.02 (s, 1H), 7.41 (dd, J = 8.8, 8.8 Hz, 2H), 7.20 (dd, J = 7.6, 7.6 Hz, 2H), 4.87-4.82 (m, 1H), 4.36 (s, 2H), 4.03-3.95 (m, 2H), 3.86 (s, 3H), 3.84-3.66 (m, 4H), 2.78-2.60 (m, 2H), 2.26-2.20 (m, 2H), 2.07 (s, 3H) | 475 |
| Example 57 | 1-[3-[[6-[1-methyl-3-(trifluoromethyl)pyrazol-4-yl]-3-pyridyl]amino]-1-tetrahydrofuran-3-yl-6,7-dihydro-4H-pyrazolo[4,3-c]pyridin-5-yl]ethanone | $^1$H NMR (400 MHz, CD$_3$OD) δ 8.67 (dd, J = 3.2, 3.2 Hz, 1H), 7.98-7.93 (m, 2H), 7.39 (dd, J = 7.6, 1.6 Hz, 1H), 4.93-4.90 (m, 1H), 4.48 (s, 2H), 4.20-4.00 (m, 2H), 3.99-3.95 (m, 5H), 3.89-3.81 (m, 2H), 2.85-2.75 (m, 2H), 2.39-2.33 (m, 2H), 2.22-2.18 (m, | 476 |

| Example | Compound Name and Structure | NMR | m/z |
|---|---|---|---|
| | | 3H) | |

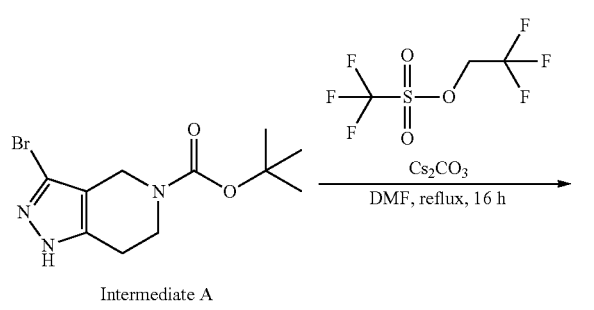

General Procedure for Intermediate E

Step 1 tert-butyl 3-bromo-1-(2,2,2-trifluoroethyl)-6,7-di-hydro-1H-pyrazolo[4,3-c]pyridine-5(4H)-carboxylate

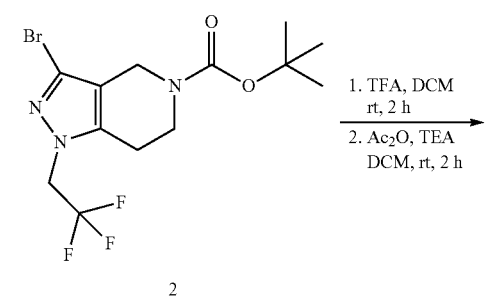

To a solution of tert-butyl 3-bromo-6,7-dihydro-1H-pyrazolo[4,3-c]pyridine-5(4H)-carboxylate (Intermediate A, 4.0 g, 13.2 mmol) and 2,2,2-trifluoroethyl trifluoromethanesulfonate (1.5 g, 19.9 mmole) in DMF (20 mL) was added $Cs_2CO_3$ (10.8 g, 33.1 mmol). The reaction mixture was stirred at 80° C. for 16 h. The mixture was diluted with EtOAc (200 mL), washed with brine (100 mL×3), dried over $Na_2SO_4$, filtered and concentrated in vacuo. The crude residue was purified by silica gel chromatography (eluent gradient from petroleum ether to petroleum ether/MTBE/THF=10:1:1) to give the title compound (1.4 g, 27%) as a white solid. $^1$H NMR (400 MHz, $CDCl_3$) δ 4.56 (q, J=8.4 Hz, 2H), 4.30 (s, 2H), 3.73 (s, 2H), 2.68 (s, 2H), 1.50 (s, 9H).

Step 2

1-(3-bromo-1-(2,2,2-trifluoroethyl)-6,7-dihydro-1H-pyrazolo[4,3-c]pyridin-5(4H)-yl)ethanone

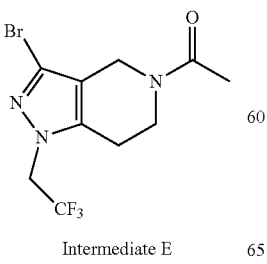

Intermediate E

To a solution of tert-butyl 3-bromo-1-(2,2,2-trifluoro-ethyl)-6,7-dihydro-1H-pyrazolo[4,3-c]pyridine-5(4H)-carboxylate (1.4 g, 3.6 mmol) in DCM (20 mL) was added TFA (20 mL). The reaction mixture was stirred at room temperature for 2 h. The solution was concentrated in vacuo and the resulting residue was dissolved in DMF (20 mL). TEA (1.05 g, 10.5 mmol) and Ac₂O (700 mg, 7.0 mmol) were added and reaction mixture was stirred at room temperature for 2 h. The mixture was diluted with EtOAc (200 mL), washed with brine (100 mL×3), dried over Na₂SO₄, filtered and concentrated in vacuo. The crude residue was purified by silica gel chromatography (eluent from DCM to DCM/MeOH=25:1) to give the title compound (1.0 g, 89%) as a white solid. LCMS M/Z (M+H)⁺=328 (Br⁸¹).

Example 58

1-(3-((2-fluoro-3-(1-methyl-1H-pyrazol-4-yl)phenyl)amino)-1-(2,2,2-trifluoroethyl)-6,7-dihydro-1H-pyrazolo[4,3-c]pyridin-5(4H)-yl)ethanone

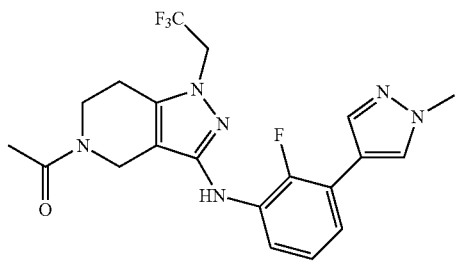 [SMILES: CC(=O)N1CCc2c(c(Nc3cccc(-c4cnn(C)c4)c3F)nn2CC(F)(F)F)C1]

To a solution of 1-(3-bromo-1-(2,2,2-trifluoroethyl)-6,7-dihydro-1H-pyrazolo[4,3-c]pyridin-5(4H)-yl)ethanone (Intermediate E, 400 mg, 0.9 mmol) and 2-fluoro-3-(1-methyl-1H-pyrazol-4-yl)aniline (Step 2 of Example 37, 260 mg, 1.4 mmol), tBuONa (220 mg, 1.4 mmol) in 1,4-dioxane (20 mL) was added chloro-(2-dicyclohexylphosphino-2',6'-diisopropoxy-1,1'-biphenyl)[2-(2-aminoethyl)phenyl]palladium (II) (50 mg, 0.05 mmol) and 2-(dicyclohexylphosphino)3,6-dimethoxy-2',4',6'-triisopropyl-1,1'-biphenyl (30 mg, 0.05 mmol). The reaction mixture was heated to 120° C. for 12 h under N₂ atmosphere. The mixture was filtered and concentrated. The crude residue was purified by reverse phase chromatography (acetonitrile 39-69%/0.1% HCl in water) to give the title compound (34 mg, 27%) yield as a white solid. ¹H NMR (400 MHz, CD₃OD) δ 8.38-8.30 (m, 2H), 7.54-7.42 (m, 1H), 7.24-7.10 (m, 2H), 4.81-4.74 (m, 2H), 4.48-4.46 (m, 2H), 4.10 (s, 3H), 3.81-3.90 (m, 2H), 2.88-2.73 (m, 2H), 2.21-2.16 (m, 3H). LCMS M/Z (M+H) 437.

General Procedure for Intermediate F

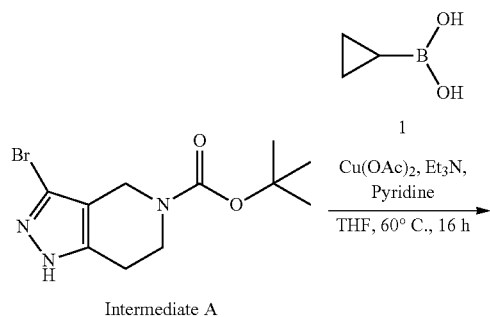

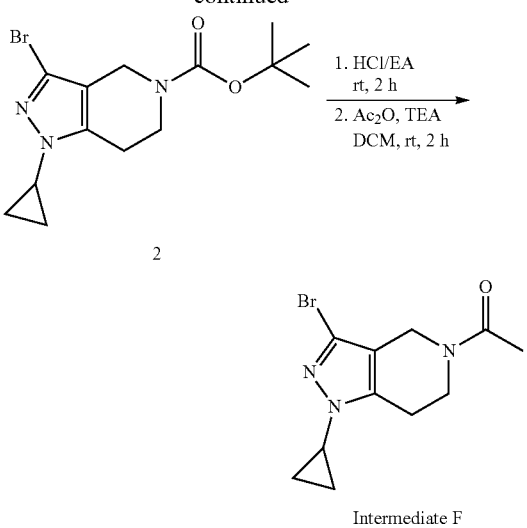

Step 1 tert-butyl 3-bromo-1-cyclopropyl-6,7-dihydro-1H-pyrazolo[4,3-c]pyridine-5(4H)-carboxylate

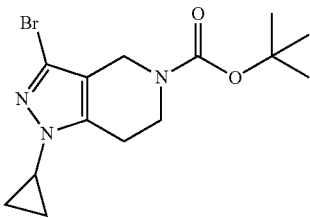 [SMILES: CC(C)(C)OC(=O)N1CCc2c(c(Br)nn2C2CC2)C1]

Cyclopropylboronic acid (568 mg, 6.62 mmol), copper acetate (903 mg, 4.96 mmol), pyridine (915 mg, 11.58 mmol) and triethylamine (835 mg, 8.27 mmol) were added successively to a solution of tert-butyl 3-bromo-6,7-dihydro-1H-pyrazolo[4,3-c]pyridine-5(4H)-carboxylate (Intermediate A, 500 mg, 127 mmol) in THF (10 mL) and the resulting mixture was heated to 60° C. for 12 h. The reaction mixture was filtered over celite, the filtrate was concentrated in vacuo and diluted with EtOAc (50 mL). The organic layer was washed with 1N HCl (10 mL), washed with brine (25 mL×2), dried over Na₂SO₄ and concentrated in vacuo. The crude residue was purified by silica gel chromatography (THF/methyl tertiary butyl ether/petroleum ether=1/1/20) to afford the title compound (140 mg, 24%) as a white solid. ¹H NMR (400 MHz, DMSO-d₆) δ 4.16 (s, 2H), 3.61 (t, J=5.6 Hz, 2H), 3.51-3.44 (m, 1H), 2.75 (t, J=5.6 Hz, 2H), 1.42 (s, 9H), 1.03-0.99 (m, 2H), 0.96-0.92 (m, 2H). LCMS M/Z (M+H) 344.

Step 2

1-(3-bromo-1-cyclopropyl-6,7-dihydro-1H-pyrazolo[4,3-c]pyridin-5(4H)-yl)ethanone

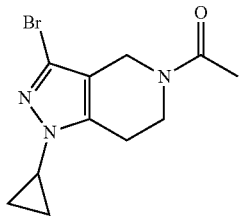 [SMILES: CC(=O)N1CCc2c(c(Br)nn2C2CC2)C1]

To tert-butyl 3-bromo-1-cyclopropyl-6,7-dihydro-1H-pyrazolo[4,3-c]pyridine-5(4H)-carboxylate (140 mg, 0.41 mmol) in EtOAc (5 mL) was added HCl (2 mL, 4 M in EtOAc). The reaction was stirred at room temperature for 2 h. The solvent was concentrated in vacuo and the crude product was re-dissolved in DCM (120 mL). The mixture was cooled to 0° C. and TEA (12.5 mg, 1.24 mmol) and acetic anhydride (84 mg, 0.82 mmol) were added dropwise. The mixture stirred at room temperature for an additional 2 h before water (25 mL) was added. The organic layer was dried over anhydrous Na$_2$SO$_4$, filtered and concentrated in vacuo to give the crude product that was purified by silica gel chromatography (petroleum ether/EtOAc=2/1) to afford the title compound (100 mg, 85%) as white solid. $^1$H NMR (400 MHz, DMSO-d$_6$) δ 4.26 (s, 2H), 3.74-3.67 (m, 2H), 3.49-3.43 (m, 1H), 2.85-2.71 (m, 2H), 2.09-2.07 (s, 3H), 1.03-0.99 (m, 2H), 0.97-0.92 (m, 2H).

Example 59

1-(1-cyclopropyl-3-((3-(1-methyl-1H-pyrazol-4-yl)phenyl)amino)-6,7-dihydro-1H-pyrazolo[4,3-c]pyridin-5(4H)-yl)ethanone

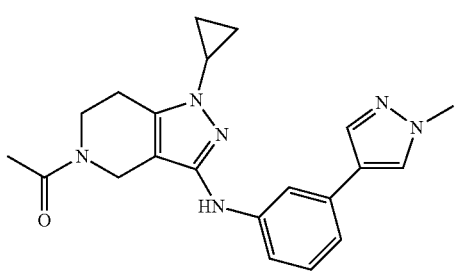 [SMILES: CC(=O)N1CCc2c(c(Nc3cccc(-c4cnn(C)c4)c3)nn2C2CC2)C1]

Step 1

Preparation of 3-(1-methyl-1H-pyrazol-4-yl)aniline

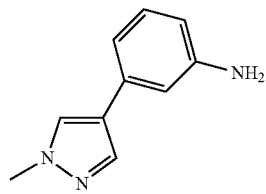

To a mixture of 3-bromoaniline (500 mg, 2.9 mmol), 1-methyl-4-(4,4,5,5-tetramethyl-1,3,2-dioxaborolan-2-yl)-1H-pyrazole (601 mg, 2.9 mmol) and Na$_2$CO$_3$ (613 mg, 5.8 mmol) in dioxane (4 mL)/H$_2$O (1 mL) was added [1,1'-bis(diphenylphosphino)ferrocene]dichloropalladium(II), complex with dichloromethane (219 mg, 0.3 mmol). The mixture was heated to 120° C. for 16 h under nitrogen atmosphere. After cooling to room temperature, the solvent was concentrated in vacuo. The crude residue was purified by silica gel chromatography (petroleum ether/EtOAc=5:1) to give the title compound (380 mg, 75%) as a white solid. LCMS M/Z (M+H) 174.

Step 2

1-(1-cyclopropyl-3-((3-(1-methyl-H-pyrazol-4-yl-H-pyrazol-4-yl)phenyl)amino)-6,7-dihydro-1H-pyrazolo[4,3-c]pyridin-5(4H)-yl)ethanone

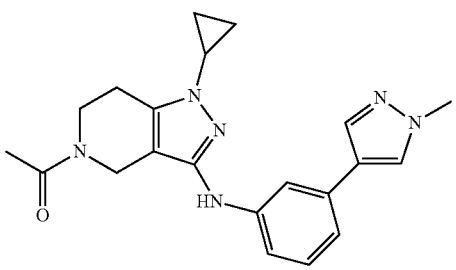 [SMILES: CC(=O)N1CCc2c(c(Nc3cccc(-c4cnn(C)c4)c3)nn2C2CC2)C1]

To a solution of 1-(3-bromo-1-cyclopropyl-6,7-dihydro-1H-pyrazolo[4,3-c]pyridin-5(4H)-yl)ethanone (200 mg, 0.70 mmol) in dioxane (8.0 mL) was added 3-(1-methyl-1H-pyrazol-4-yl) aniline (122 mg, 0.70 mmol), chloro-(2-dicyclohexylphosphino-2',6'-diisopropoxy-1,1'-biphenyl)[2-(2-aminoethyl)phenyl]palladium(II) (57.2 mg, 0.07 mmol), 2-(dicyclohexylphosphino)3,6-dimethoxy-2',4',6'-triisopropyl-1,1'-biphenyl (37.6 mg, 0.07 mmol) and t-BuONa (135 mg, 1.41 mmol). The reaction mixture was purged with nitrogen atmosphere for 1 min. The reaction mixture was heated to 120° C. for 16 h. After cooling to rt, the reaction mixture was diluted with water (20 mL) and washed with DCM (20 mL×2). The combined organic layers were dried over anhydrous Na$_2$SO$_4$, filtered and concentrated in vacuo. The crude residue was purified by reverse phase chromatography (acetonitrile 28-48%/0.1% NH$_4$OH in water) to give the title compound (77 mg, 30%) as white solid. $^1$H NMR (400 MHz, DMSO-d$_6$) δ 8.11-8.06 (m, 1H), 7.98-7.97 (m, 1H), 7.70-7.68 (m, 1H), 7.50 (s, 1H), 7.25-7.22 (m, 1H), 7.17-7.12 (m, 1H), 6.91-6.87 (m, 1H), 4.33 (s, 2H), 3.86 (s, 3H), 3.76-3.67 (m, 2H), 3.42-3.36 (m, 1H), 2.82-2.67 (m, 2H), 2.10-2.05 (m, 3H), 1.05-0.85 (m, 4H). LCMS M/Z (M+H) 377.

The Following Example 60 was Prepared in a Similar Fashion to Example 59

| Example | Compound Name and Structure | NMR | m/z |
|---|---|---|---|
| Example 60 | 1-(1-cyclopropyl-3-((4-(1-methyl-1H-pyrazol-4-yl)phenyl)amino)-6,7-dihydro-1H-pyrazolo[4,3-c]pyridin-5(4H)-yl)ethanone | $^1$H NMR (400 MHz, CD$_3$OD) δ 7.79, (s, 11), 7.68 (s, 1H), 7.35 (dd, J = 8.4, 6.8 Hz, 2H), 7.13 (dd, J = 8.4, 6.8 Hz, 2H), 4.36-4.34 (m, 2H), 3.88 (s, 3H), 3.85-3.78 (m, 2H), 3.38-3.32 (m, 1H), 2.88-2.78 (m, 2H), 2.18-2.10 (m, 3H) | 377 |

General Procedure for Intermediate G

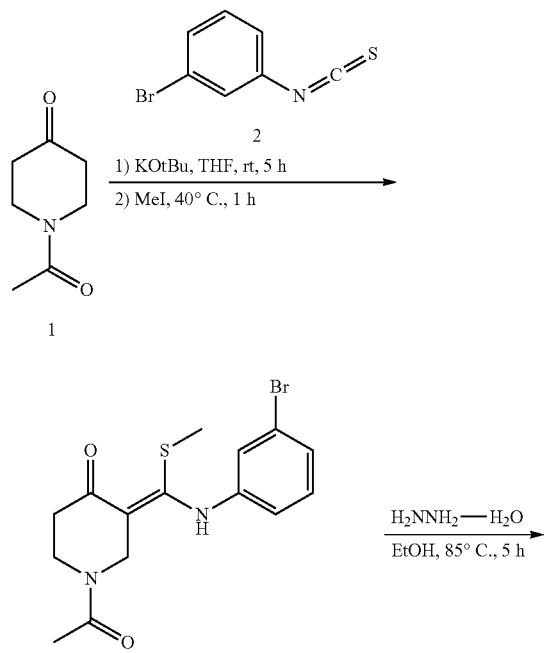

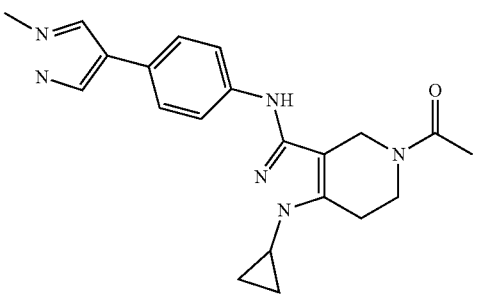 [SMILES: C/N=C/C(=C\N)c1ccc(NC(=N)C2=C(NC3CC3)CCN(C(C)=O)C2)cc1]

Step 1

(Z)-1-acetyl-3-(((3-bromophenyl)amino)(methylthio)methylene)piperidin-4-one

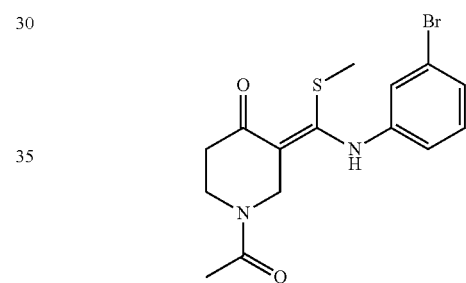

To a solution of 1-acetylpiperidin-4-one (10.0 g, 70.8 mmol) in anhydrous THF (100 mL) was added t-BuOK (9.5 g, 85.0 mmol) portionwise. The mixture was allowed to stir for 3 h at rt. A solution of 1-bromo-3-isothiocyanatobenzene (18.2 g, 85.0 mmol) in anhydrous THF (100 mL) was added dropwise at 40° C. and stirred for 2 h. Then MeI (30.2 g, 212.5 mmol) was added dropwise and the reaction was stirred for another 1 h. After cooling to room temperature, the mixture was poured into water (200 mL) and extracted with EtOAc (100 mL×3). The combined organic layers were dried over Na$_2$SO$_4$, filtered and concentrated in vacuo. The residue was purified by silica gel chromatography (petroleum ether/EtOAc=1/1) to afford the title compound (16.4 g, 63%) as yellow oil. LCMS M/Z (M+H) 371 (Br$^{81}$).

Step 2

1-(3-((3-bromophenyl)amino)-6,7-dihydro-1H-pyrazolo[4,3-c]pyridin-5(4H)-yl)ethanone

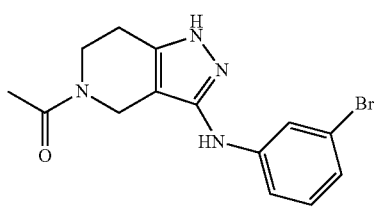 [SMILES: CC(=O)N1CCc2[nH]nc(Nc3cccc(Br)c3)c2C1]

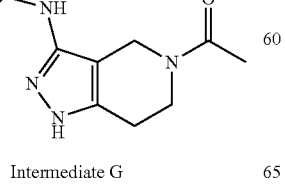

Intermediate G

To a solution of (Z)-1-acetyl-3-(((3-bromophenyl)amino)(methylthio)methylene)piperidin-4-one (13.4 g, 36.3 mmol) in EtOH (100 mL) was added hydrazine hydrate (1.8 g, 36.3 mmol). The mixture was heated to reflux for 2 h. The solvent was concentrated in vacuo to afford the title compound (11.4 g, 94%) as a yellow solid that required no further purification. LCMS M/Z (M+H) 337 (Br$^{81}$).

Example 61

1-(3-((3-bromophenyl)amino)-1-(cyclopropylmethyl)-6,7-dihydro-1H-pyrazolo[4,3-c]pyridin-5(4H)-yl)ethanone

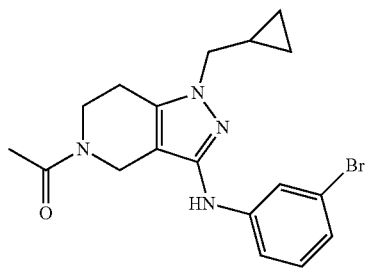 [SMILES: CC(=O)N1CCc2c(c(Nc3cccc(Br)c3)nn2CC2CC2)C1]

To a solution of 1-(3-((3-bromophenyl)amino)-6,7-dihydro-1H-pyrazolo[4,3-c]pyridin-5(4H)-yl)ethanone (Intermediate G, 6.0 g, 17.9 mmol) in DMF (30 mL) was added (bromomethyl)cyclopropane (3.6 g, 26.9 mmol) and Cs$_2$CO$_3$ (11.7 g, 35.8 mmol). The mixture was heated to 80° C. for 12 h. The mixture was diluted with EtOAc (100 mL) and washed with water (100 mL×3). The organic layer was separated, dried over Na$_2$SO$_4$ and concentrated in vacuo. The residue was purified by silica gel chromatography (DCM/MeOH=50/1 to 20/1) to afford the title compound (3.3 g, 47%) as a yellow solid. $^1$H NMR (400 MHz, DMSO-d$_6$) δ 8.36-8.31 (m, 1H), 7.75-7.73 (m, 1H), 7.32-7.29 (m, 1H), 7.11 (dd, J=15.2, 7.6 Hz, 1H), 6.86-6.83 (m, 1H), 4.35 (s, 2H), 3.78 (d, J=6.4 Hz, 2H), 3.74-3.66 (m, 2H), 2.74-2.61 (m, 2H), 2.10-2.07 (m, 3H), 1.23-1.09 (m, 1H), 0.50-0.49 (m, 2H), 0.36-0.32 (m, 2H). LCMS M/Z (M+H) 389.

Example 62

1-[1-(cyclopropylmethyl)-3-[3-[3-(hydroxymethyl)phenyl]anilino]-6,7-dihydro-4H-pyrazolo[4,3-c]pyridin-5-yl]ethanone

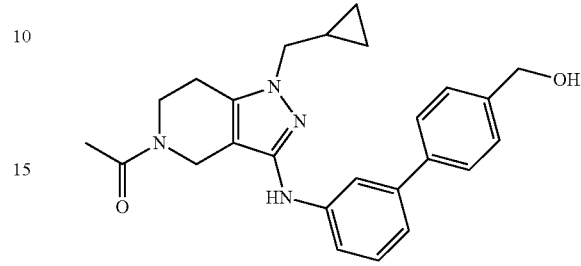

To a solution of 1-(3-((3-bromophenyl)amino)-1-(cyclopropylmethyl)-6,7-dihydro-1H-pyrazolo[4,3-c]pyridin-5(4H)-yl)ethanone (Example 61, 100 mg, 0.26 mmol) in dioxane (10 mL) and water (3 mL) was added (3-(hydroxymethyl)phenyl)boronic acid (47 mg, 0.31 mmol), Na$_2$CO$_3$ (55 mg, 0.52 mmol) and [1,1'-bis(diphenylphosphino)ferrocene]dichloropalladium(II), complex with dichloromethane (20 mg). The mixture was degassed with nitrogen and the mixture was heated to reflux for 2 h. The reaction mixture was concentrated in vacuo and the crude product was redissolved in EtOAc (50 mL). The organic layer was washed with brine, dried over Na$_2$SO$_4$, filtered and concentrated in vacuo. The crude residue was purified by reverse phase chromatography (acetonitrile 38-68%/0.1% NH$_4$OH in water) to give the title compound (29.3 mg, 29%) as white solid. $^1$H NMR (400 MHz, CD$_3$OD): 7.58-7.56 (m, 2H), 7.44-7.38 (m, 3H), 7.25-7.23 (m, 1H), 7.06-7.01 (m, 2H), 4.62 (s, 2H), 4.42-4.40 (m, 2H), 3.88-3.78 (m, 4H), 2.84-2.82 (m, 1H), 2.74-2.71 (m, 1H), 2.19-2.11 (m, 3H), 1.24-1.21 (m, 1H), 0.60-0.54 (m, 2H), 0.40-0.38 (m, 2H). LCMS M/Z (M+H) 417.

The Following Examples 63-73 were Prepared in a Similar Fashion to Example 62

| Example | Compound Name and Structure | NMR | m/z |
|---|---|---|---|
| Example 63 | 1-(1-(cyclopropylmethyl)-3-((3-(pyridin-3-yl)phenyl)amino)-6,7-dihydro-1H-pyrazolo[4,3-c]pyridin-5(4H)-yl)ethanone 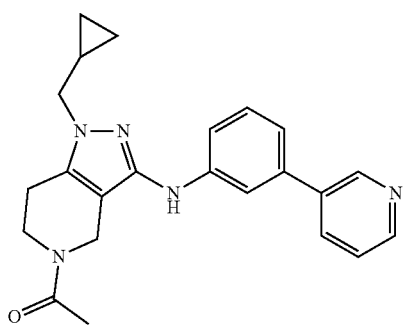 [SMILES: CC(=O)N1CCc2c(c(Nc3cccc(-c4cccnc4)c3)nn2CC2CC2)C1] | $^1$H NMR (400 MHz, CD$_3$OD) δ 8.77 (s, 1H), 8.49 (t, J = 2.4 Hz, 1H), 8.07 (d, J = 8.0 Hz, 1H), 7.59-7.48 (m, 2H), 7.32-7.18 (m, 1H), 7.09-7.06 (m, 1H), 7.05-7.03 (m, 1H), 4.43 (d, J = 6.0 Hz, 2H), 3.87-3.78 (m, 4H), 2.84-2.81 (m, 1H), 2.74-2.71 (m, 1H), 2.20-2.12 (m, 3H), 1.28-1.20 (m, 1H), 0.59-0.53 (m, 2H), 0.39-0.37 (m, 2H) | 388 |

-continued

| Example | Compound Name and Structure | NMR | m/z |
|---|---|---|---|
| Example 64 | 1-(1-(cyclopropylmethyl)-3-((3-(pyridin-4-yl)phenyl)amino)-6,7-dihydro-IH-pyrazolo[4,3-c]pyridin-5(4H)-yl)ethanone | $^1$H NMR (400 MHz, CD$_3$OD) δ 8.56-8.54 (m, 1H), 7.69-7.60 (m, 3H), 7.34-7.33 (m, 1H), 7.31-7.23 (m, 1H), 7.17-7.15 (m, 1H), 4.44 (d, J = 4.8 Hz, 2H), 3.90-3.82 (m, 4H), 2.86-2.85 (m, 1H), 2.83-2.75 (m, 1H), 2.21-2.14 (m, 3H), 1.26-1.24 (m, 1H), 0.59-0.57 (m, 2H), 0.41-0.39 (m, 2H) | 388 |
| Example 65 | 1-(1-(cyclopropylmethyl)-3-[3-[3-(1-hydroxyethyl)phenyl]anilino]-6,7-dihydro-4H-pyrazolo[4,3-c]pyridin-5-yl]ethanone | $^1$H NMR (400 MHz, CD$_3$OD) δ 7.60 (s, 1H), 7.50-7.42 (m, 2H), 7.40-7.28 (m, 2H), 7.26-7.18 (m, 1H), 7.11-6.97 (m, 2H), 4.91-4.89 (m, 1H), 4.42 (d, J =10.4 Hz, 2H), 3.89-3.78 (m, 4H), 2.84-2.83 (m, 1H), 2.82-2.17 (m, 1H), 2.20-2.10 (m, 3H), 1.48 (d, J = 6.4 Hz, 3H), 1.25-1.23 (m, 1H), 0.58-0.55 (m, 2H), 0.40-0.37 (m, 2H) | 431 |
| Example 66 | 1[1-(cyclopropylmethyl)-3-[3-[3-(1-hydroxy-1-methyl-ethyl)phenyl]anilino]-6,7-dihydro-4H-pyrazolo[4,3-c]pyridin-5-yl]ethanone | $^1$H NMR (400 MHz, CD$_3$OD) δ 7.73 (d, J = 1.2 Hz, 1H), 7.47-7.43 (m, 3H), 7.37-7.35 (m, 1H), 7.26-7.24 (m, 1H), 7.09-7.03 (m, 2H), 4.41 (d, J = 10.4 Hz, 2H), 3.88-3.78 (m, 4H), 2.84-2.81 (m, 1H), 2.74-2.71 (m, | 445 |

| Example | Compound Name and Structure | NMR | m/z |
|---|---|---|---|
| | | 1H), 2.19-2.10 (m, 3H), 1.57 (s, 6H), 1.25-1.20 (m, 1H), 0.58-0.54 (m, 2H), 0.39-0.36 (m, 2H) | |
| Example 67 | 1-(1-(cyclopropylmethyl)-3-((3-(1-methyl-1H-pyrazol-4-yl)phenyl)amino)-6,7-dihydro-1H-pyrazolo[4,3-c]pyridin-5(4H)-yl)ethanone | $^1$H NMR (400 MHz, CD$_3$OD) δ 7.85 (d, J = 2.4 Hz, 1H), 7.72 (d, J = 2.4 Hz, 1H), 7.35-7.30 (m, 1H), 7.18-7.13 (m, 1H), 3.96-6.92 (m, 2H), 4.40-4.38 (m, 2H), 3.90 (s, 3H), 3.89-3.80 (m, 4H), 2.84-2.81 (m, 1H), 2.74-2.72 (m, 1H), 2.19-2.11 (m, 3H), 1.24-1.21 (m, 1H), 0.60-0.54 (m, 2H), 0.40-0.38 (m, 2H) | 391 |
| Example 68 | 1-[1-(cyclopropylmethyl)-3-[3-(3-fluorophenyl)anilino]-6,7-dihydro-4H-pyrazolo[4,3-c]pyridin-5-yl]ethanone | $^1$H NMR (400 MHz, DMSO-d$_6$) δ 8.25-8.19 (m, 1H), 7.79 (s, 1H), 7.52-7.38 (m, 4H), 7.27 (dd, J = 15.6, 7.6 Hz, 1H), 7.20-7.16 (m, 1H), 7.04-7.01 (m, 1H), 4.38 (s, 2H), 3.78 (d, J = 6.8 Hz, 2H), 3.75-3.67 (m, 2H), 2.76-2.62 (m, 2H), 2.11-2.07 (m, 3H), 1.23-1.10 (m, 1H), 0.52-0.47 (m, 2H), 0.37-0.31 (m, 2H) | 405 |
| Example 69 | 1-[1-(cyclopropylmethyl)-3-[3-(2-fluorophenyl)anilino]-6,7-dihydro-4H-pyrazolo[4,3-c]pyridin-5-yl]ethanone | $^1$H NMR (400 MHz, DMSO-d$_6$) δ 8.22-8.16 (m, 1H), 7.62-7.60 (m, 1H), 7.51-7.47 (m, 1H), 7.43-7.37 (m, 2H), 7.31-7.23 (m, 3H), 6.86 (d, J = 7.0 Hz, 1H), 4.37 (s, 2H), 3.76 (d, J = | 405 |

| Example | Compound Name and Structure | NMR | m/z |
|---|---|---|---|
| | | 6.8 Hz, 2H), 3.73-3.66 (m, 2H), 2.76-2.61 (m, 2H), 2.10-2.06 (m, 3H), 1.19-1.11 (m, 1H), 0.50-0.44 (m, 2H), 0.34- 0.30 (m, 2H) | |
| Example 70 | 1-[1-(cyclopropylmethyl)-3-[3-(1H-pyrazol-4-yl)anilino]-6,7-dihydro-4H-pyrazolo[4,3-c]pyridin-5-yl]ethanone | $^1$H NMR (400 MHz, DMSO-d$_6$) δ 12.90 (s, 1H), 8.08-8.03 (m, 2H), 7.77 (s,1H), 7.61 (s, 1H), 7.22-7.20 (m, 1H), 7.14 (dd, J = 15.6, 7.6 Hz, 1H), 6.96-6.92, (m, 1H), 4.36 (s, 2H), 3.79 (d, J = 6.8 Hz, 2H), 3.75-3.67 (m, 2H), 2.76-2.61 (m, 2H), 2.10-2.07 (m, 3H), 1.22-1.18 (m, 1H), 0.51-0.48 (m, 2H), 0.38-0.35 (m, 2H) | 377 |
| Example 71 | 1-(1-(cyclopropylmethyl)-3-((3-(isoxazol-4-yl)phenyl)amino)-6,7-dihydro-1H-pyrazolo[4,3-c]pyridin-5(4H)-yl)ethanone | $^1$H NMR (400 MHz, DMSO-d$_6$) δ 9.30 (d, J = 6.4 Hz, 1H), 8.98 (d, J = 6.0 Hz, 1H), 8.25-8.19 (m, 1H), 7.60 (s, 1H), 7.38-7.32 (m, 1H), 7.23 (dd, J = 8.0, 8.0 Hz, 1H), 7.03-7.00 (m, 1H), 4.35 (s, 2H), 3.79 (d, J = 6.8 Hz, 2H), 3.73-3.67 (m, 2H), 2.75-2.63 (m, 2 H), 2.10-2.06 (m, 3H), 1.40-1.22 (m, 1H), 0.52-0.47 (m, 2H), 0.37-0.33 (m, 2H) | 338 |
| Example 72 | 1[1-(cyclopropylmethyl)-3-[3-(4-fluorophenyl)anilino]-6,7-dihydro-4H-pyrazolo[4,3-c]pyridin-5-yl]ethanone | $^1$H NMR (400 MHz, DMSO-d$_6$) δ 8.21-8.16 (m, 1H), 7.70 (s, 1H), 7.62-7.61 (m, 2H), 7.38 (dd, J = 7.8, 1.8 Hz, 1H), 7.31-7.23 (m, 3H), 6.98-6.95 (m, 1H), 4.37 (s, 2H), 3.78 (d, J = 6.8 Hz, 2H), 3.76-3.67 (m, 2H), 2.77-2.62 (m, 2H), 2.11-2.07 (m, 3H), 1.21-1.13 (m, 1H), 0.53-0.47 (m, 2H), 0.37-0.32 (m, 2H) | 405 |

| Example | Compound Name and Structure | NMR | m/z |
|---|---|---|---|
| Example 73 | 1-[1-(cyclopropylmethyl)-3-[3-(2-methylpyrazol-3-yl)anilino]-6,7-dihydro-4H-pyrazolo[4,3-c]pyridin-5-yl]ethanone | $^1$H NMR (400 MHz, CD$_3$OD) δ 7.47- 7.29 (m, 3H), 7.26 (dd, J = 7.2, 7.2 Hz, 1H), 6.85 (dd, J = 7.2, 7.2 Hz, 1H), 6.32 (d, J = 2.0 Hz, 1H), 4.42 (s, 2H), 3.86 (s, 3H), 3.84-3.78 (m, 4H), 2.83-2.71 (m, 2H), 2.19-2.13 (m, 3H), 1.22-1.18 (m, 1H), 0.55-0.52 (m, 2H), 0.37-0.33 (m, 2H) | 391 |

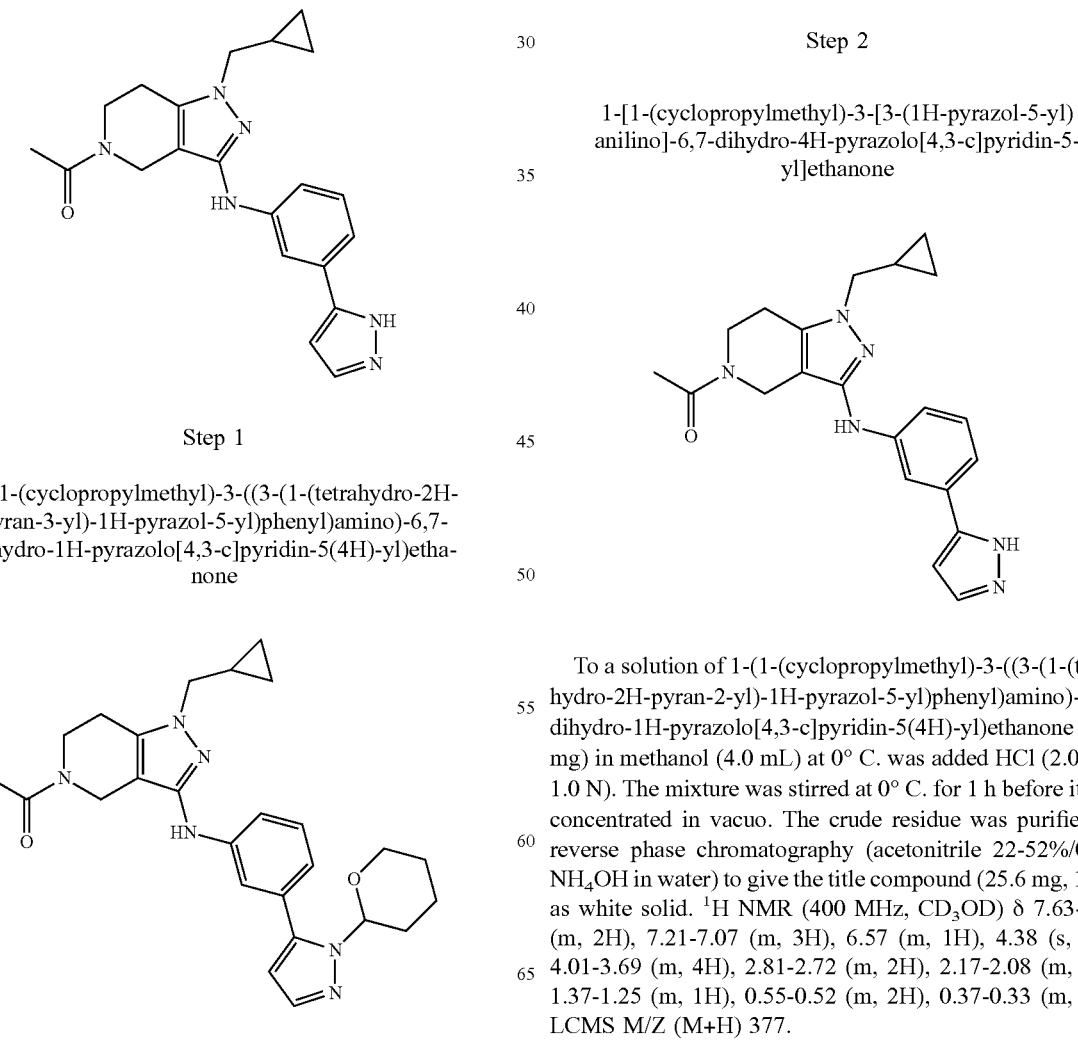

Example 74

1-[1-(cyclopropylmethyl)-3-[3-(1H-pyrazol-5-yl)anilino]-6,7-dihydro-4H-pyrazolo[4,3-c]pyridin-5-yl]ethanone

Step 1

1-(1-(cyclopropylmethyl)-3-((3-(1-(tetrahydro-2H-pyran-3-yl)-1H-pyrazol-5-yl)phenyl)amino)-6,7-dihydro-1H-pyrazolo[4,3-c]pyridin-5(4H)-yl)ethanone The title compound was prepared from 1-(tetrahydro-2H-pyran-2-yl)-5-(4,4,5,5-tetramethyl-1,3,2-dioxaborolan-2-yl)-1H-pyrazole in a similar fashion to Example 62. The residue was purified by silica gel chromatography (DCM/MeOH=50/1 to 20/1) to afford the title compound in 68% yield as a white solid. LCMS M/Z (M+Na) 483.

Step 2

1-[1-(cyclopropylmethyl)-3-[3-(1H-pyrazol-5-yl)anilino]-6,7-dihydro-4H-pyrazolo[4,3-c]pyridin-5-yl]ethanone To a solution of 1-(1-(cyclopropylmethyl)-3-((3-(1-(tetrahydro-2H-pyran-2-yl)-1H-pyrazol-5-yl)phenyl)amino)-6,7-dihydro-1H-pyrazolo[4,3-c]pyridin-5(4H)-yl)ethanone (400 mg) in methanol (4.0 mL) at 0° C. was added HCl (2.0 mL, 1.0 N). The mixture was stirred at 0° C. for 1 h before it was concentrated in vacuo. The crude residue was purified by reverse phase chromatography (acetonitrile 22-52%/0.1% NH$_4$OH in water) to give the title compound (25.6 mg, 12%) as white solid. $^1$H NMR (400 MHz, CD$_3$OD) δ 7.63-7.51 (m, 2H), 7.21-7.07 (m, 3H), 6.57 (m, 1H), 4.38 (s, 2H), 4.01-3.69 (m, 4H), 2.81-2.72 (m, 2H), 2.17-2.08 (m, 3H), 1.37-1.25 (m, 1H), 0.55-0.52 (m, 2H), 0.37-0.33 (m, 2H). LCMS M/Z (M+H) 377.

Example 75

1-[1-(cyclopropylmethyl)-3-[3-(1-methylpyrazol-3-yl)anilino]-6,7-dihydro-4H-pyrazolo[4,3-c]pyridin-5-yl]ethanone

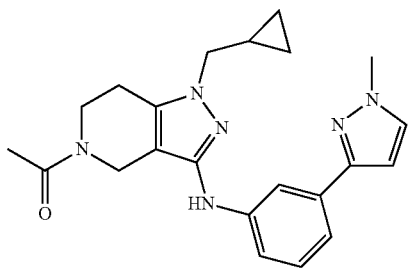 [SMILES: CC(=O)N1CCc2c(c(Nc3cccc(-c4ccn(C)n4)c3)nn2CC2CC2)C1]

Step 1

1-(1-(cyclopropylmethyl)-3-((3-(4,4,5,5-tetramethyl-1,3,2-dioxaborolan-2-yl)phenyl)amino)-6,7-dihydro-1H-pyrazolo[4,3-c]pyridin-5(4H)-yl)ethanone

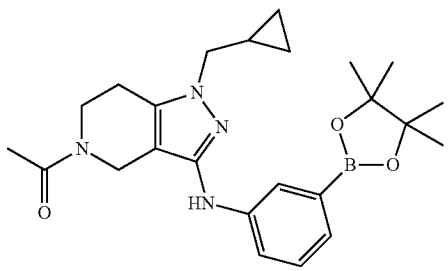 [SMILES: CC(=O)N1CCc2c(c(Nc3cccc(B4OC(C)(C)C(C)(C)O4)c3)nn2CC2CC2)C1]

To a solution of 1-(3-((3-bromophenyl)amino)-1-(cyclopropylmethyl)-6,7-dihydro-1H-pyrazolo[4,3-c]pyridin-5(4H)-yl)ethanone (Example 61, 600 mg, 1.54 mmol) in dioxane (20 mL) was added KOAc (300 mg, 3.06 mmol), [1,1'-bis(diphenylphosphino)ferrocene]dichloropalladium (II), complex with dichloromethane (110 mg, 0.15 mmol) and 4,4,4',4',5,5,5',5'-octamethyl-2,2'-bi(1,3,2-dioxaborolane) (600 mg, 2.31 mmol). The reaction mixture was purged with nitrogen atmosphere for 1 min and then heated to 110° C. for 18 h. The mixture was concentrated in vacuo and the crude residue was purified by silica gel chromatography (petroleum ether:EtOAc=1:1) to give the title compound (600 mg, 85%) as a brown oil.

Step 2

1-[1-(cyclopropylmethyl)-3-[3-(1-methylpyrazol-3-yl)anilino]-6,7-dihydro-4H-pyrazolo[4,3-c]pyridin-5-yl]ethanone

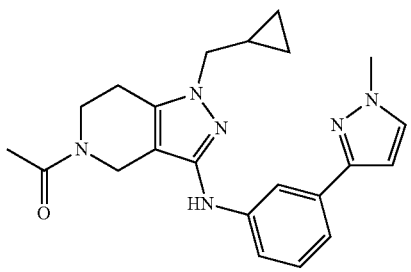 [SMILES: CC(=O)N1CCc2c(c(Nc3cccc(-c4ccn(C)n4)c3)nn2CC2CC2)C1]

To a solution of 1-(1-(cyclopropylmethyl)-3-((3-(4,4,5,5-tetramethyl-1,3,2-dioxaborolan-2-yl)phenyl)amino)-6,7-dihydro-1H-pyrazolo[4,3-c]pyridin-5(4H)-yl) ethanone (200 mg, 0.46 mmol) in dioxane (4 mL) and water (1 mL) was added $Na_2CO_3$ (98 mg, 0.92 mmol), [1,1'-bis(diphenylphosphino)ferrocene]dichloropalladium(II), complex with dichloromethane (34 mg, 0.05 mmol) and 3-bromo-1-methyl-1H-pyrazole (111 mg, 0.69 mmol). The reaction mixture was purged with nitrogen atmosphere for 1 min and heated to 110° C. for 18 h. The mixture was concentrated in vacuo and the crude residue was purified by silica gel chromatography (DCM:MeOH=10:1) to give the crude product (100 mg). The residue was further purified by reverse phase chromatography (acetonitrile 40-70%/0.1% $NH_4OH$ in water) to give the title compound (21.2 mg, 12%) as a white solid. $^1$H NMR (400 MHz, DMSO-$d_6$) δ 8.15-8.10 (m, 1H), 7.79-7.75 (m, 1H), 7.70 (s, 1H), 7.41-7.36 (m, 1H), 7.18-7.09 (m, 2H), 6.55-6.52 (m, 1H), 4.36-4.35 (m, 2H), 3.86 (s, 3H), 3.79-3.66 (m, 4H), 2.76-2.63 (m, 2H), 2.10-2.06 (m, 3H), 1.28-1.10 (m, 1H), 0.51-0.47 (m, 2H), 0.37-0.34 (m, 2H). LCMS M/Z (M+H) 391.

The Following Example 76 was Prepared in a Similar Fashion to Example 75

| Example | Compound Name and Structure | NMR | m/z |
|---|---|---|---|
| Example 76 | 1[1-(cyclopropylmethyl)-3]3-[3-(1-hydroxypropyl)phenyl]anilino]-6,7-dihydro-4H-pyrazolo[4,3-c]pyridin-5-yl]ethanone | $^1$H NMR (400 MHz, DMSO-$d_6$) δ 8.22-8.17 (m, 1H), 7.79 (s, 1H), 7.56 (s., 1H), 7.46 (d, J = 6.8 Hz, 1H), 7.39 (d, J = 6.8 Hz, 2H), 7.31-7.20 (m, 2H), 7.04-6.95 (m, 1H), 5.18 (d, J = 4.0 Hz, 1H), 4.51-4.50 (m, 1H), 4.38 (s, 2H), 3.82-3.64 (m, 4H), 2.76-2.60 (m, 2H), 2.11-2.07 (m, 3H), 1.71-1.59 (m, 2H),1.25-1.16 (m, 1H), 0.85 3H), 0.51-0.48 (rn, 2H), 0.35-0.30 (t, J = 7.2 Hz, (m, 2H) | 445 |

Example 77

1-(1-(cyclopropylmethyl)-3-((2',3',4',5'-tetrahydro[1,1'-biphenyl]-3-yl)amino)-6,7-dihydro-1H-pyrazolo[4,3-c]pyridin-5(4H)-yl)ethanone

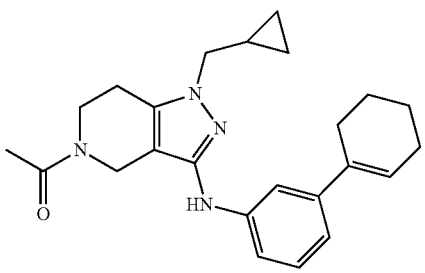 [SMILES: CC(=O)N1CCc2c(c(Nc3cccc(C4=CCCCC4)c3)nn2CC2CC2)C1]

To a solution of 1-(3-((3-bromophenyl)amino)-1-(cyclopropylmethyl)-6,7-dihydro-1H-pyrazolo[4,3-c]pyridin-5(4H)-yl)ethanone (Example 61, 100 mg, 0.26 mmol) in dioxane (5 mL) and water (1 mL) was added cyclohex-1-en-1-ylboronic acid (65 mg, 0.51 mmol), KOAc (50 mg, 0.51 mmol) and Pb(dppf)Cl$_2$ (20 mg, 0.03 mmol). The reaction mixture was heated to 120° C. for 12 h. The mixture was poured into water (20 mL) and extracted with EtOAc (3×30 mL). The combined organic layers were dried over anhydrous Na$_2$SO$_4$ and concentrated in vacuo. The crude residue was purified reverse phase chromatography (acetonitrile 46-76%/0.2% formic acid in water) to give the title compound (15 mg, 15%) as a white solid. $^1$H NMR (400 MHz, DMSO-d$_6$) δ 8.03-7.98 (m, 1H), 7.46 (s, 1H), 7.26 (d, J=8.0 Hz, 1H), 7.12-7.06 (m, 1H), 6.74 (d, J=6.8 Hz, 1H), 6.09 (s, 1H), 4.34 (s, 2H), 3.76 (d, J=6.4 Hz, 2H), 3.73-3.67 (m, 2H), 2.73-2.62 (m, 2H), 2.40-2.30 (m, 2H), 2.18-2.14 (m, 2H), 2.10-2.06 (m, 3H), 1.71-1.70 (m, 2H), 1.61-1.60 (m, 2H), 1.10-1.20 (m, 1H), 0.49-0.48 (m, 2H), 0.35-0.30 (m, 2H). LCMS M/Z (M+H) 391.

Example 78

1-(3-((3-cyclohexylphenyl)amino)-1-(cyclopropylmethyl)-6,7-dihydro-1H-pyrazolo[4,3-c]pyridin-5(4H)-yl)ethanone

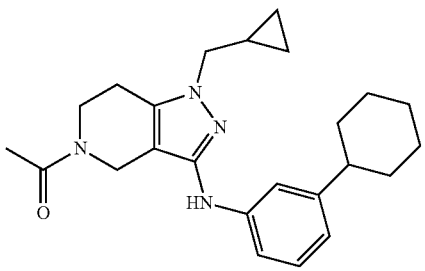 [SMILES: CC(=O)N1CCc2c(c(Nc3cccc(C4CCCCC4)c3)nn2CC2CC2)C1]

To a solution of 1-(1-(cyclopropylmethyl)-3-((2',3',4',5'-tetrahydro-[1,1'-biphenyl]-3-yl)amino)-6,7-dihydro-1H-pyrazolo[4,3-c]pyridin-5(4H)-yl)ethanone (Example 77, 100 mg, 0.26 mmol) in EtOH (10 mL) was added Pd/C (10%, 15 mg). The suspension was degassed under vacuum and purged with H$_2$ several times. The mixture was stirred under a H$_2$ balloon at 25° C. for 16 h. The suspension was filtered through a pad of Celite, washed with EtOH (50 mL×3) and the organic layer was concentrated in vacuo. The crude residue was purified by reverse phase chromatography (acetonitrile 46-76%/0.2% formic acid in water) to give the title compound (22 mg, 21%) as a white solid. $^1$H NMR (400 MHz, DMSO-d$_6$) δ 7.97-7.91 (m, 1H), 7.23 (s, 1H), 7.18 (d, J=8.4 Hz, 1H), 7.34 (dd, J=15.6, 7.6 Hz, 1H), 6.57-6.53 (m, 1H), 4.32 (s, 2H), 3.76 (d, J=6.4 Hz, 2H), 3.72-3.67 (m, 2H), 2.73-2.61 (m, 2H), 2.38-2.33 (m, 1H), 2.09-2.06 (m, 3H), 1.79-1.68 (m, 5H), 1.37-1.16 (m, 6H), 0.50-0.48 (m, 2H), 0.40-0.31 (m, 2H). LCMS M/Z (M+H) 393.

Example 79

1-(1-(cyclopropylmethyl)-3-((3-(pyridin-2-yl)phenyl)amino)-6,7-dihydro-1H-pyrazolo[4,3-c]pyridin-5(4H)-yl)ethanone

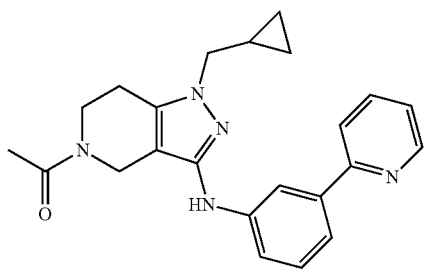 [SMILES: CC(=O)N1CCc2c(c(Nc3cccc(-c4ccccn4)c3)nn2CC2CC2)C1]

To a solution of 1-(3-((3-bromophenyl)amino)-1-(cyclopropylmethyl)-6,7-dihydro-1H-pyrazolo[4,3-c]pyridin-5(4H)-yl)ethanone (Example 61, 100 mg, 0.26 mmol) and 2-(tributylstannyl)pyridine (94 mg, 0.26 mmol) in toluene (10 mL) was added Pd(PPh$_3$)$_4$ (30 mg, 0.026 mmol). The reaction was heated to reflux for 12 h. The mixture was poured into water (20 mL) and extracted with EtOAc (30 mL×3). The combined organic layers were dried over anhydrous Na$_2$SO$_4$, filtered and concentrated in vacuo. The crude residue was purified by reverse phase chromatography (acetonitrile 18-48%/0.2% formic acid in water) to give the title compound (31 mg, 31%) as a white solid. $^1$H NMR (400 MHz, CD$_3$OD) δ 8.59-8.57 (m, 1H), 7.90-7.86 (m, 1H), 7.80 (d, J=8.0 Hz, 1H), 7.74-7.72 (m, 1H), 7.37-7.30 (m, 3H), 7.24-7.20 (m, 1H), 4.43-4.41 (m, 2H), 3.90-3.80 (m, 4H), 2.87-2.75 (m, 2H), 2.20-2.11 (m, 3H), 1.27-1.22 (m, 1H), 0.60-0.54 (m, 2H), 0.41-0.36 (m, 2H). LCMS M/Z (M+H) 388.

General Procedure for Intermediate H

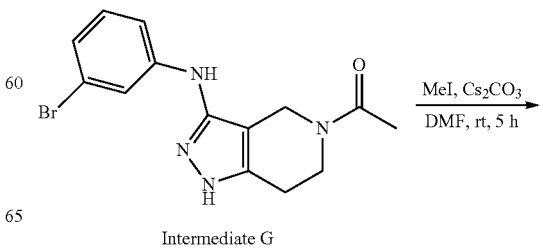

Intermediate G

-continued

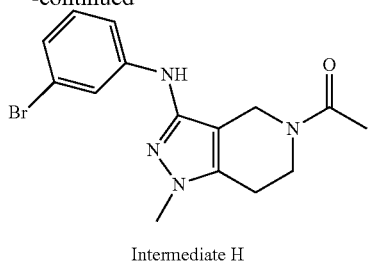

Intermediate H 1-(3-((3-bromophenyl)amino)-1-methyl-6,7-dihydro-1H-pyrazolo[4,3-c]pyridin-5(4H)-yl)ethanone

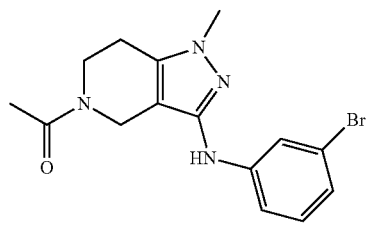 [SMILES: CC(=O)N1CCc2c(c(Nc3cccc(Br)c3)nn2C)C1]

To a solution of 1-(3-((3-bromophenyl)amino)-6,7-dihydro-1H-pyrazolo[4,3-c]pyridin-5(4H)-yl)ethanone (Intermediate G, 5.0 g, 15.5 mmol) in DMF (30 mL) was added iodomethane (3.8 g, 22.3 mmol) and $Cs_2CO_3$ (9.7 g, 29.8 mmol). The mixture was allowed to stir at room temperature for 5 h. The mixture was diluted with EtOAc (100 mL) and washed with water (100 mL×3). The organic layer was separated, dried over $Na_2SO_4$, filtered and concentrated in vacuo. The residue was purified by silica gel chromatography (DCM/MeOH=50/1 to 20/1) to afford the title compound (2.1 g, 40%) as a yellow solid. LCMS M/Z (M+H) 351 ($Br^{81}$).

Example 80

1-[1-methyl-3-(3-thiazol-5-yl-anilino)-6,7-dihydro-4H-pyrazolo[4,3-c]pyridin-5-yl]ethanone

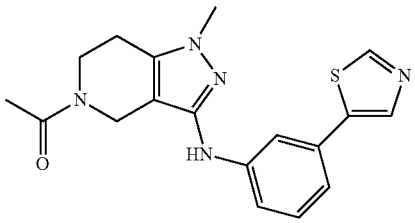 [SMILES: CC(=O)N1CCc2c(c(Nc3cccc(-c4cncs4)c3)nn2C)C1]

To a solution of 1-(3-((3-bromophenyl)amino)-1-methyl-6,7-dihydro-1H-pyrazolo[4,3-c]pyridin-5(4H)-yl)ethanone (Intermediate H, 100 mg, 0.28 mmol) in 1,4-dioxane (5.0 mL) and water (1.0 mL) was added 5-(4,4,5,5-tetramethyl-1,3,2-dioxaborolan-2-yl)thiazole (84 mg, 0.43 mmol), [1,1'-bis(diphenylphosphino)ferrocene]dichloropalladium(II), complex with dichloromethane (20.9 mg, 0.03 mmol) and $Na_2CO_3$ (60.7 mg, 0.57 mmol). The mixture was heated to 120° C. for 12 h. The reaction mixture was filtered and concentrated in vacuo. The crude residue was purified by reverse phase chromatography (acetonitrile 25-55%/0.2% formic acid in water) to give the title compound (5.5 mg, 5%) as a white solid. $^1$H NMR (400 MHz, $CD_3OD$) δ 8.91 (d, J=3.6 Hz, 1H), 8.09 (d, J=2.8 Hz, 1H), 7.51-7.48 (m, 1H), 7.26 (dd, J=14.0, 6.4 Hz, 1H), 7.17-7.13 (m, 1H), 7.08-7.05 (m, 1H), 4.42-4.41 (m, 2H), 3.90-3.80 (m, 2H), 3.69-3.68 (m, 3H), 2.83-2.70 (m, 2H), 2.21-2.13 (m, 3H). LCMS M/Z (M+H) 354.

The Following Examples 81-82 were Prepared in a Similar Fashion to Example 80

| Example | Compound Name and Structure | NMR | m/z |
|---|---|---|---|
| Example 81 | 1-[1-methyl-3-[3-(1-methylpyrazol-4-yl)anilino]-6,7-dihydro-4H-pyrazolo[4,3-c]pyridin-5-yl]ethanone | $^1$H NMR (400 MHz, $CD_3OD$) δ 7.88 (d, J = 2.8 Hz, 1H), 7.72 (d, J = 2.8 Hz, 1H), 7.22-7.19 (m, 1H), 6.95 (dd, J = 8.0, 8.0 Hz, 1H), 6.91-6.95 (m, 2H), 4.37-4.35 (m, 2H), 3.92 (s, 3H), 3.90-3.78 (m, 2H), 3.67 (s, 3H), 2.78-2.67 (m, 2H), 2.21-2.11 (m, 3H) | 351 |

| Example | Compound Name and Structure | NMR | m/z |
|---|---|---|---|
| Example 82 | 1-(3-((3-(1H-pyrazol-4-yl)phenyl)amino)-1-methyl-6,7-dihydro-1H-pyrazolo[4,3-c]pyridin-5(4H)-yl)ethanone | ¹H NMR (400 MHz, DMSO-d₆) δ 12.89 (s, 1H), 8.06-8.01 (m, 1H), 7.79 (s, 1H), 7.49 (s, 1H), 7.29-7.24 (m, 1H), 7.15 (dd, J = 15.6, 7.6 Hz, 1H), 6.95-6.92, (m, 1H), 4.34 (s, 2H), 3.74-3.66 (m, 2H), 3.61 (s, 3H), 2.73-2.59 (m, 2H), 2.10-2.05 (m, 3H) | 337 |

General Procedure for Intermediate I

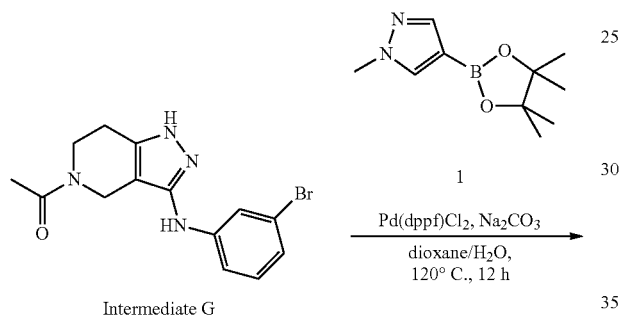

Intermediate I 1-(3-((3-(1-methyl-1H-pyrazol-4-yl)phenyl)amino)-6,7-dihydro-1H-pyrazolo[4,3-c]pyridin-5(4H)-yl)ethanone

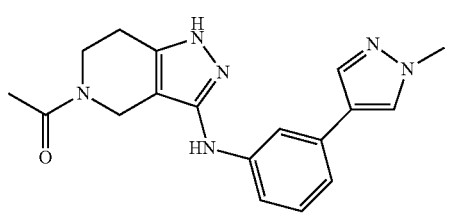 [SMILES: CC(=O)N1CCc2[nH]nc(Nc3cccc(-c4cnn(C)c4)c3)c2C1]

To a solution of 1-(3-((3-bromophenyl)amino)-6,7-dihydro-1H-pyrazolo[4,3-c]pyridin-5(4H)-yl)ethanone (Intermediate G, 1.0 g, 3.0 mmol) in 1,4-dioxane (10.0 mL) and water (2.5 mL) was added [1,1'-bis(diphenylphosphino)ferrocene]dichloropalladium(II), complex with dichloromethane (0.22 g, 0.30 mmol), 1-methyl-4-(4,4,5,5-tetramethyl-1,3,2-dioxaborolan-2-yl)-1H-pyrazole (0.74 g, 3.6 mmol) and Na₂CO₃ (0.63 g, 6.0 mmol). The mixture was stirred under N₂ atmosphere at 120° C. for 12 h. The reaction mixture was filtered, concentrated in vacuo and purified by silica gel chromatography (dichloromethane/methanol=20:1 to 3:1) to give the title compound (0.82 g, 82%) as a white solid.

Example 83

1-(3-((3-(1-methyl-1H-pyrazol-4-yl)phenyl)amino)-1-(2,2,2-trifluoroethyl)-6,7-dihydro-1H-pyrazolo[4,3-c]pyridin-5(4H)-yl)ethanone

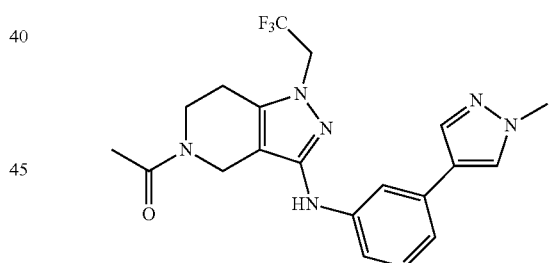

To a stirred solution of 1-(3-((3-(1-methyl-1H-pyrazol-4-yl)phenyl)amino)-6,7-dihydro-1H-pyrazolo[4,3-c]pyridin-5(4H)-yl)ethanone (Intermediate I, 0.3 g, 0.89 mmol) in DMF (5.0 mL) was added Cs₂CO₃ (0.58 g, 1.8 mmol) and 1,1,1-trifluoro-2-iodoethane (0.37 g, 1.8 mmol). The mixture was heated to 110° C. for 8 h. The mixture was quenched with water and extracted with EtOAc (50 mL×2). The combined organic layers were dried over anhydrous Na₂SO₄, filtered and concentrated in vacuo. The crude residue was purified reverse phase chromatography (acetonitrile 39-59%/0.1% NH₄OH in water) to give the title compound (6 mg, 2%) as a white solid. ¹H NMR (400 MHz, CD₃OD) δ 7.84 (s, 1H), 7.72 (s, 1H), 7.55 (d, J=13.2 Hz, 1H), 7.18-7.09 (m, 2H), 6.99-6.96 (m, 1H), 4.72 (q, J=8.8 Hz, 2H), 4.43-4.42 (m, 2H), 3.90 (s, 3H), 3.87-3.78 (m, 2H), 2.82-2.70 (m, 2H), 2.19-2.14 (m, 3H). LCMS M/Z (M+H) 419.

The Following Examples 84-86 were Prepared in a Similar Fashion to Example 83

| Example | Compound Name and Structure | NMR | m/z |
|---|---|---|---|
| Example 84 | 1-[3-[3-(1-methylpyrazol-4-yl)anilino]-1-(3,3,3-trifluoropropyl)-6,7-dihydro-4H-pyrazolo[4,3-c]pyridin-5-yl]ethanone | $^1$H NMR (400 MHz, CD$_3$OD) δ 7.84 (s, 1H), 7.71 (s, 1H), 7.38 (s, 1H), 7.19-7.14 (m, 1H), 6.96 (dd, J = 6.8, 6.8 Hz, 1H), 4.40-4.38 (m, 2H), 4.20 (t, J = 7.2 Hz, 2H), 3.90 (s, 3H), 3.87-3.79 (m, 2H), 2.80-2.70 (m, 4H), 2.19-2.11 (m, 3H) | 433 |
| Example 85 | 1-[1-[(2,2-difluorocyclopropyl)methyl]-3-[3-(1-methylpyrazol-4-yl)anilino]-6,7-dihydro-4H-pyrazolo[4,3-c]pyridin-5-yl]ethanone | $^1$H NMR(400 MHz, DMSO-d$_6$) δ 8.17-8.11 (m, 1 H), 7.98-7.96 (m, 1H), 7.72-7.70 (m, 1H), 7.62 (s, 1H), 7.24-7.22 (m, 1H), 7.18-7.11 (m, 1H), 6.95-6.85 (m, 1H), 4.36 (s, 2H), 4.13-3.94 (m, 2H), 3.86 (s, 3H), 3.79-3.65 (m, 2H), 2.76-2.59 (m, 2H), 2.22-2.11 (m, 1H), 2.10-2.07 (m, 3H), 1.70-1.65 (m, 1 H), 1.53-1.36 (m, 1 H) | 427 |
| Example 86 | 1-[3-[3-(1-methylpyrazol-4-yl)anilino]-1-(oxetan-3-ylmethyl)-6,7-dihydro-4H-pyrazolo[4,3-c]pyridin-5-yl]ethanone | $^1$H NMR (400 MHz, DMSO-d$_6$) δ 8.12-8.07 (m, 1H), 7.97 (d, J = 4.4 Hz, 1H), 7.69 (d, J = 4.8 Hz, 1H), 7.54 (s, 1H), 7.21-7.11 (m, 1H), 6.93-6.85 (m, 1H), 4.67 (dd, J = 7.6, 6.0 Hz, 2H), 4.49 (dd, J = 8.8, 6.4 Hz, 2H), 4.34 (s, 2H), 4.18 (d, J = 6.8 Hz, 2H), 3.86 (s, 3H), 3.77-3.64 (m, 2H), 2.7-2.58 (m, 2H), 2.10-2.06 (m, 3H) | 407 |

Example 87

1-(1-allyl-3-((3-(1-methyl-1H-pyrazol-4-yl)phenyl)amino)-6,7-dihydro-1H-pyrazolo[4,3-c]pyridin-5(4H)-yl)ethanone

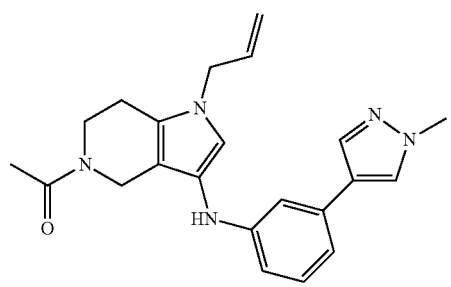 [SMILES: C=CCn1cc(Nc2cccc(-c3cnn(C)c3)c2)c2c1CCN(C(C)=O)C2]

To a solution of (1-(3-((3-(1-methyl-1H-pyrazol-4-yl)phenyl)amino)-6,7-dihydro-1H-pyrazolo[4,3-c]pyridin-5(4H)-yl)ethanone (Intermediate I, 300 mg, 0.89 mmol) in bromocyclopropane (5 mL) was added $Cs_2CO_3$ (1.45 g, 4.46 mmol). The reaction mixture was heated to 100° C. for 16 h in an autoclave. The mixture was concentrated in vacuo and the crude residue was purified by reverse phase chromatography (acetonitrile 32-62%/0.1% $NH_4OH$ in water) to give the title compound (13 mg, 4%) as a white solid. $^1H$ NMR (400 MHz, $CD_3OD$) δ 7.84 (s, 1H), 7.71 (s, 1H), 7.33 (d, J=14.8 Hz, 1H), 7.15 (dd, J=14.8, 8.0 Hz, 1H), 6.96-6.92 (m, 1H), 6.01-5.94 (m, 1H), 5.19 (d, J=10.0 Hz, 1H), 5.03 (d, J=17.2 Hz, 1H), 4.60-4.59 (m, 2H), 4.39 (d, J=9.2 Hz, 1H), 3.89 (s, 3H), 3.86-3.79 (m, 2H), 2.78-2.62 (m, 2H), 2.18-2.10 (m, 3H). LCMS M/Z (M+Na) 399.

General Procedure for Intermediate J

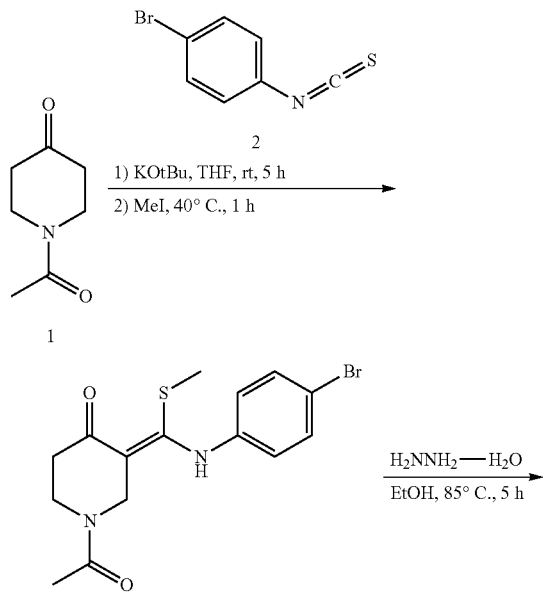

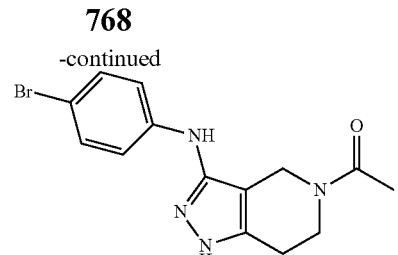

Intermediate J

Step 1

(Z)-1-acetyl-3-(((4-bromophenyl)amino)(methylthio)methylene)piperidin-4-one

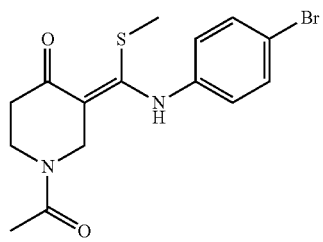 [SMILES: CS/C(Nc1ccc(Br)cc1)=C1/CN(C(C)=O)CCC1=O]

To a solution of 1-acetylpiperidin-4-one (15.0 g, 106.3 mmol) in anhydrous THF (100 mL) was added t-BuOK (14.3 g, 127.5 mmol) portionwise. The mixture was allowed to stir for 3 h before a solution of 1-bromo-4-isothiocyanatobenzene (27.3 g, 127.5 mmol) in anhydrous THF (100 mL) was added dropwise at 40° C. The mixture stirred for an additional 2 h at this temperature. Then MeI (45.3 g, 318.8 mmol) was added dropwise and the reaction was stirred for another 1 h. After cooling to room temperature, the mixture was poured into water (200 mL) and extracted with EtOAc (150 mL×3). The combined organic layers were dried over $Na_2SO_4$, filtered and concentrated in vacuo. The residue was purified by silica gel chromatography (petroleum ether/EtOAc=1/1) to afford the title compound (24.3 g, 62%) as a yellow solid. LCMS M/Z (M+H) 371 ($Br^{81}$).

Step 2

1-(3-((4-bromophenyl)amino)-6,7-dihydro-1H-pyrazolo[4,3-c]pyridin-5(4H)-yl)ethanone

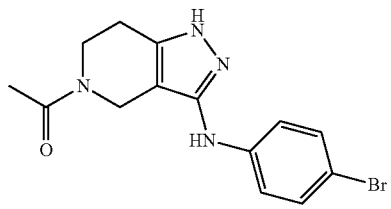 [SMILES: CC(=O)N1CCc2[nH]nc(Nc3ccc(Br)cc3)c2C1]

To a solution of 1-(3-((4-bromophenyl)amino)-6,7-dihydro-1H-pyrazolo[4,3-c]pyridin-5(4H)-yl)ethanone (24.3 g, 65.8 mmol) in EtOH (200 mL) was added hydrazine hydrate (3.3 g, 65.8 mmol). The mixture was heated to reflux for 2 h. The solvent was removed to afford the title compound (20.0 g, 91%) as a yellow solid. LCMS M/Z (M+H) 335.

Example 88

1-(3-((4-bromophenyl)amino)-1-(cyclopropylmethyl)-6,7-dihydro-1H-pyrazolo[4,3-c]pyridin-5(4H)-yl)ethanone

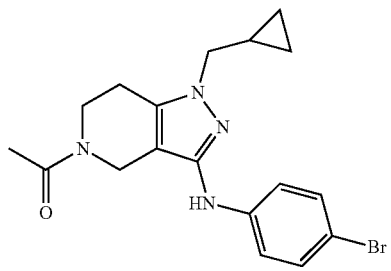 [SMILES: CC(=O)N1CCc2c(c(Nc3ccc(Br)cc3)nn2CC2CC2)C1]

To a solution of 1-(3-((4-bromophenyl)amino)-6,7-dihydro-1H-pyrazolo[4,3-c]pyridin-5(4H)-yl)ethanone (Intermediate J, 7.0 g, 20.9 mmol) in DMF (30 mL) was added (bromomethyl)cyclopropane (4.2 g, 31.3 mmol) and $Cs_2CO_3$ (13.6 g, 41.8 mmol). The mixture was heated to 80° C. for 12 h. The mixture was diluted with EtOAc (100 mL) and washed with water (100 mL×3). The organic layer was separated, dried over $Na_2SO_4$, filtered and concentrated in vacuo. The residue was purified by silica gel chromatography (DCM/MeOH=50/1 to 20/1, Rf=0.2) to afford the title compound as a yellow solid (4.0 g, 49%). $^1$H NMR (400 MHz, DMSO-$d_6$, T=80° C.) δ 7.97 (s, 1H), 7.34-7.28 (m, 4H), 4.35 (s, 2H), 3.80 (d, J=6.8 Hz, 2H), 3.71 (s, 2H), 2.72 (s, 2H), 2.09 (s, 3H), 1.27-1.17 (m, 1H), 0.54-0.49 (m, 2H), 0.35-0.33 (m, 2H). LCMS M/Z (M+H) 389.

Example 89

1-[1-(cyclopropylmethyl)-3-[4-(1-methylpyrazol-4-yl)anilino]-6,7-dihydro-4H-pyrazolo[4,3-c]pyridin-5-yl]ethanone

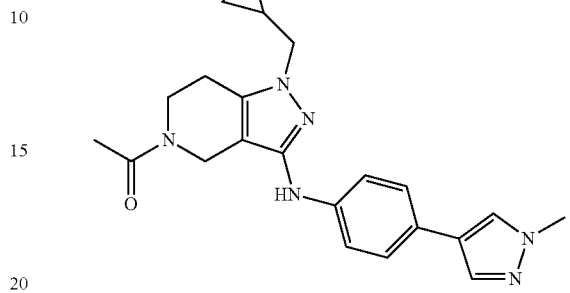

To a solution of 1-(3-((4-bromophenyl)amino)-1-(cyclopropylmethyl)-6,7-dihydro-1H-pyrazolo[4,3-c]pyridin-5(4H)-yl)ethanone (Example 88, 300 mg, 0.77 mmol) in dioxane (3.0 mL) and water (1.0 mL) was added 1-methyl-4-(4,4,5,5-tetramethyl-1,3,2-dioxaborolan-2-yl)-1H-pyrazole (192.4 mg, 0.92 mmol), [1,1'-bis(diphenylphosphino)ferrocene]-dichloropalladium(II), complex with dichloromethane (56.29 mg, 0.07 mmol) and $Na_2CO_3$ (161.7 mg, 1.5 mmol). The reaction was heated to 120° C. for 12 h. After cooling to room temperature, the reaction was filtered and concentrated in vacuo. The crude residue was purified by reverse phase chromatography (acetonitrile 32-62%/0.1% $NH_4OH$ in water) to give the title compound (61 mg, 20%) as a white solid. $^1$H NMR (400 MHz, $CD_3OD$) δ 7.54 (dd, J=6.4, 6.4 Hz, 2H), 7.82 (s, 1H), 7.71 (s, 1H), 7.38 (dd, J=8.0, 8.0 Hz, 2H), 7.15 (dd, J=8.8, 8.8 Hz, 2H), 4.42-4.40 (m, 2H), 3.92 (s, 3H), 3.90-3.80 (m, 4H), 2.86-2.73 (m, 2H), 2.22-2.15 (m, 3H), 1.26-1.25 (m, 1H), 0.62-0.56 (m, 2H), 0.40-0.39 (m, 2H). LCMS M/Z (M+H) 391.

The Following Examples 90-97 were Prepared in a Similar Fashion to Example 89

| Example | Compound Name and Structure | NMR | m/z |
|---|---|---|---|
| Example 90 | 1-(1-(cyclopropylmethyl)-3-((3'-(2-hydroxypropan-2-yl)-[1,1'-biphenyl]-4-yl)amino)-6,7-dihydro-1H-pyrazolo[4,3-c]pyridin-5(4H)-yl)ethanone | $^1$H NMR (400 MHz, $CD_3OD$) δ 7.72 (s, 1H), 7.52-7.48 (m, 2H), 7.42-7.41 (m, 1H), 7.36-7.34 (m, 2H), 7.22-7.20 (m, 2H), 4.41-4.40 (m, 2H), 3.92-3.81 (m, 4H), 2.86-2.84 (m, 1H), 2.77-2.74 (m, 1H), 2.22-2.16 (m, 3H), 1.59 (s, 6H), 1.24-1.21 (m, 1H), 0.61-0.58 (m, 2H), 0.41-0.40 (m, 2H) | 445 |

-continued

| Example | Compound Name and Structure | NMR | m/z |
|---|---|---|---|
| Example 91 | 1-(1-(cyclopropylmethyl)-3-((3'-(1-hydroxyethyl)-[1,1'-biphenyl]-4-yl)amino)-6,7-dihydro-1H-pyrazolo[4,3-c]pyridin-5(4H)-yl)ethanone | $^1$H NMR (400 MHz, CD$_3$OD): 7.57 (s, 1H), 7.50-7.43 (m, 3H). 7.35-7.33 (m, 1H), 7.26-7.18 (m, 3H), 4.42-4.41 (m, 2H), 3.88-3.79 (m, 4H), 2.85-2.82 (m, 1H), 2.75-2.72 (m, 1H), 2.20-2.14 (m, 3H), 1.48-1.47 (m, 3H), 1.25-1.24 (m, 1H), 0.59-0.56 (m, 2H), 0.39-0.38 (m, 2H) | 431 |
| Example 92 | 1-(1-(cyclopropylmethyl)-3-((3'-(hydroxymethyl)-[1,1'-biphenyl]-4-yl)amino)-6,7-dihydro-1H-pyrazolo[4,3-c]pyridin-5(4H)-yl)ethanone | $^1$H NMR (400 MHz, CD$_3$OD): 7.55 (s, 1H), 7.50-7.45 (m, 3H), 7.35-7.33 (m, 1H), 7.24-7.18 (m, 2H), 4.64-4.59 (m, 2H), 4.41-4.40 (m, 2H), 3.88-3.80 (m, 4H), 2.83-2.81 (m, 1H), 2.73-2.71 (m, 1H), 2.19-2.14 (m, 3H), 1.24-1.21 (m, 1H), 0.58-0.55 (m, 2H), 0.38-0.37 (m, 2H) | 417 |
| Example 93 | 1-(1-(cyclopropylmethyl)-3-((4-(pyridin-4-yl)phenyl)amino)-6,7-dihydro-1H-pyrazolo[4,3-c]pyridin-5(4H)-yl)ethanone | $^1$H NMR (400 MHz, DMSO-d$_6$) δ 8.64-8.62 (m, 2H), 8.28-8.26 (m, 2H), 7.95-7.93 (m, 2H), 7.43-7.40 (m, 1H), 7.37-7.34 (m, 1H), 3.90-3.80 (m, 4H), 2.90-2.75 (m, 2H), 2.23-2.12 (m, 3H) | 388 |

| Example | Compound Name and Structure | NMR | m/z |
|---|---|---|---|
| Example 94 | 1-(1-(cyclopropylmethyl)-3-((2'-fluoro-[1,1'-biphenyl]-4-yl)amino)-6,7-dihydro-1H-pyrazolo[4,3-c]pyridin-5(4H)-yl)ethanone | $^1$H NMR (400 MHz, DMSO-d$_6$) δ 8.29-8.24 (m, 1H), 7.51-7.47 (m, 3H), 7.41-7.37 (m, 2H), 7.33-7.29 (m, 1H), 7.27-7.23 (m, 2H), 4.38 (s, 2H), 3.80 (d, J = 6.8 Hz, 2H), 3.76-3.67 (m, 2H), 2.77-2.62 (m, 2 H), 2.11-2.08 (m, 3H), 1.23-1.15 (m, 1H), 0.52-0.47 (m, 2H), 0.36-0.32 (m, 2H) | 405 |
| Example 95 | 1-(1-(cyclopropylmethyl)-3-((3'-fluoro-[1,1'-biphenyl]-4-yl)amino)-6,7-dihydro-1H-pyrazolo[4,3-c]pyridin-5(4H)-yl)ethanone | $^1$H NMR (400 MHz, DMSO-d$_6$) δ 8.30-8.25 (m, 1H), 7.58-7.39 (m, 7H), 7.08-7.04 (m, 1H), 4.37 (s, 2H), 3.80 (d, J = 6.8 Hz, 2H), 3.76-3.67 (m, 2H), 2.76-2.62 (m, 2 H), 2.10-2.08 (m, 3H), 1.23-1.16 (m, 1H), 0.52-0.47 (m, 2H), 0.36-0.31 (m, 2H) | 405 |
| Example 96 | 1-(1-(cyclopropylmethyl)-3-((4-(1-methyl-1H-pyrazol-5-yl)phenyl)amino)-6,7-dihydro-1H-pyrazolo[4,3-c]pyridin-5(4H)-yl)ethanone | $^1$H NMR (400 MHz, DMSO-d$_6$) δ 8.34-8.30 (m, 1H), 7.51-7.48 (m, 2H), 7.39 (d, J = 1.6 Hz, 1H), 7.34-7.30 (m, 2H), 6.27 (d, J = 1.6 Hz, 1H), 4.37 (s, 2H), 3.82 (s, 3H), 3.74 (d, J = 5.2 Hz, 2H), 3.72-3.66 (m, 2H), 2.76-2.61 (m, 2 H), 2.10-2.08 (m, 3H), 1.25-1.15 (m, 1H), 0.51-0.47 (m, 2H), 0.35-0.33 (m, 2H) | 391 |

| Example | Compound Name and Structure | NMR | m/z |
|---|---|---|---|
| Example 97 | 1-(1-(cyclopropylmethyl)-3-[4-(4-fluorophenyl)anilino]-6,7-dihydro-4H-pyrazolo[4,3-c]pyridin-5-yl)ethanone | $^1$H NMR (400 MHz, CD$_3$OD) δ 7.54 (dd, J = 6.4, 6.4 Hz, 2H), 7.42 (dd, J = 8.4, 8.4 Hz, 2H), 7.20 (dd, J = 9.2, 9.2 Hz, 2H), 7.09 (dd, J = 2.0, 2.0 Hz, 2H), 4.40-4.39 (m, 2H), 3.87-3.78 (m, 4H), 2.83-2.71 (m, 2H), 2.19-2.13 (m, 3H), 1.24-1.23 (m, 1H), 0.59-0.54 (m, 2H), 0.38-0.37 (m, 2H) | 405 |

Example 98

1-(3-((4-(1H-pyrazol-4-yl)phenyl)amino)-1-(cyclopropylmethyl)-6,7-dihydro-1H-pyrazolo[4,3-c]pyridin-5(4H)-yl)ethanone

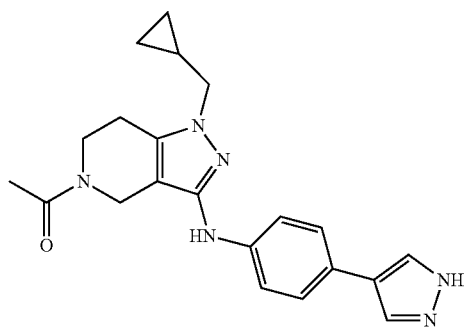 [SMILES: CC(=O)N1CCc2c(c(Nc3ccc(-c4cn[nH]c4)cc3)nn2CC2CC2)C1]

Step 1 tert-butyl 4-(4-((5-acetyl-1-(cyclopropylmethyl)-4,5,6,7-tetrahydro-1H-pyrazolo[4,3-c]pyridin-3-yl)amino)phenyl)-1H-pyrazole-1-carboxylate

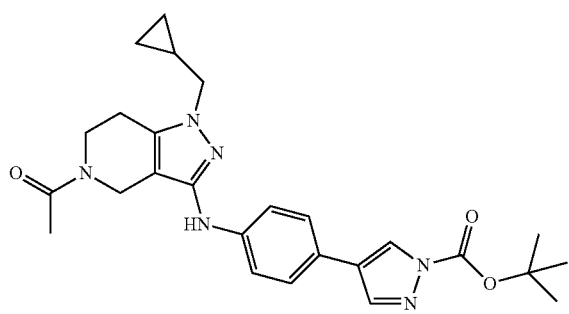 [SMILES: CC(=O)N1CCc2c(c(Nc3ccc(-c4cnn(C(=O)OC(C)(C)C)c4)cc3)nn2CC2CC2)C1]

The title compound was prepared in 80% yield from tert-butyl 4-(4,4,5,5-tetramethyl-1,3,2-dioxaborolan-2-yl)-1H-pyrazole-1-carboxylate in a similar fashion to Example 89.

Step 2

1-(3-((4-(1H-pyrazol-4-yl)phenyl)amino)-1-(cyclopropylmethyl)-6,7-dihydro-1H-pyrazolo[4,3-c]pyridin-5(4H)-yl)ethanone To a solution of tert-butyl 4-(4-((5-acetyl-1-(cyclopropylmethyl)-4,5,6,7-tetrahydro-1H-pyrazolo[4,3-c]pyridin-3-yl)amino)phenyl)-1H-pyrazole-1-carboxylate (500 mg, 0.24 mmol) in DCM (2 mL) was added TFA (2 mL) dropwise. The reaction was stirred at room temperature for 2 h. The mixture was concentrated in vacuo and the crude residue was purified by reverse phase chromatography (acetonitrile 18-48%/0.1% NH$_4$OH in water) to give the title compound (24 mg, 6%) as a white solid. $^1$H NMR (400 MHz, DMSO-d$_6$) δ 12.76 (s, 1H), 8.08-8.03 (m, 1H), 8.00 (s, 1H), 7.78 (s, 1H), 7.40-7.39 (m, 4H), 4.35 (s, 2H), 3.77 (d, J=7.2 Hz, 2H), 3.74-3.66 (m, 2H), 2.75-2.60 (m, 2H), 2.10-2.07 (m, 3H), 1.19-1.17 (m, 1H), 0.50-0.47 (m, 2H), 0.35-0.33 (m, 2H). LCMS M/Z (M+H) 377.

Example 99

1-(1-(cyclopropylmethyl)-3-((2',3',4',5'-tetrahydro-[1,1'-biphenyl]-4-yl)amino)-6,7-dihydro-1H-pyrazolo[4,3-c]pyridin-5(4H)-yl)ethanone

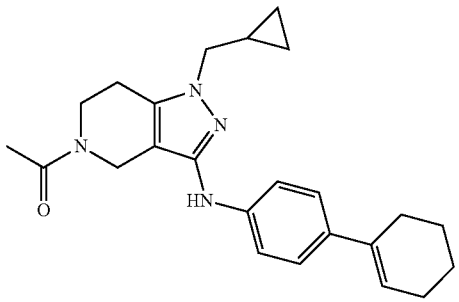 [SMILES: CC(=O)N1CCc2c(c(Nc3ccc(C4=CCCCC4)cc3)nn2CC2CC2)C1]

The title compound was prepared from 1-(3-((4-bromophenyl)amino)-1-(cyclopropylmethyl)-6,7-dihydro-1H-pyrazolo[4,3-c]pyridin-5(4H)-yl)ethanone (Example 88) in a similar fashion to Example 89. The crude residue was purified by reverse phase chromatography (acetonitrile 46-76%/0.2% formic acid in water) to give the title compound in 15% yield. $^1$H NMR (400 MHz, DMSO-$d_6$) δ 8.08-8.03 (m, 1H), 7.33 (d, J=8.8 Hz, 2H), 7.25-7.20 (m, 2H), 6.00 (s, 1H), 4.34 (s, 2H), 3.77 (d, J=6.8 Hz, 2H), 3.74-3.65 (m, 2H), 2.74-2.61 (m, 2H), 2.35-2.25 (m, 2H), 2.15-2.14 (m, 2H), 2.10-2.06 (m, 3H), 1.71-1.69 (m, 2H), 1.59-1.57 (m, 2H), 1.17-1.16 (m, 1H), 0.49-0.46 (m, 2H), 0.33-0.32 (m, 2H). LCMS M/Z (M+H) 391.

Example 100

1-(3-((4-cyclohexylphenyl)amino)-1-(cyclopropylmethyl)-6,7-dihydro-1H-pyrazolo[4,3-c]pyridin-5(4H)-yl)ethanone

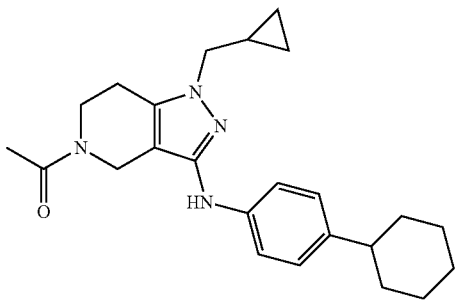 [SMILES: CC(=O)N1CCc2c(c(Nc3ccc(C4CCCCC4)cc3)nn2CC2CC2)C1]

The title compound was prepared from 1-(1-(cyclopropylmethyl)-3-((2',3',4',5'-tetrahydro-[1,1'-biphenyl]-4-yl)amino)-6,7-dihydro-1H-pyrazolo[4,3-c]pyridin-5 (4H)-yl) ethanone in a similar fashion to Example 78. The crude residue was purified by reverse phase chromatography (acetonitrile 52-82%/0.2% formic acid in water) to give the title compound in 15% yield. $^1$H NMR (400 MHz, DMSO-$d_6$) δ 7.91-7.86 (m, 1H), 7.28 (d, J=8.4 Hz, 2H), 7.03-6.99 (m, 2H), 4.33 (s, 2H), 3.76 (d, J=6.8 Hz, 2H), 3.72-3.65 (m, 2H), 2.74-2.61 (m, 2H), 2.34-2.33 (m, 2H), 2.10-2.09 (m, 3H), 1.76-1.67 (m, 5H), 1.37-1.16 (m, 6H), 0.49-0.46 (m, 2H), 0.33-0.30 (m, 2H). LCMS M/Z (M+H) 393.

Example 101

N-((4'-((5-acetyl-1-(cyclopropylmethyl)-4,5,6,7-tetrahydro-1H-pyrazolo[4,3-c]pyridin-3-yl)amino)-[1,1'-biphenyl]-3-yl)methyl)-3-methoxypropanamide

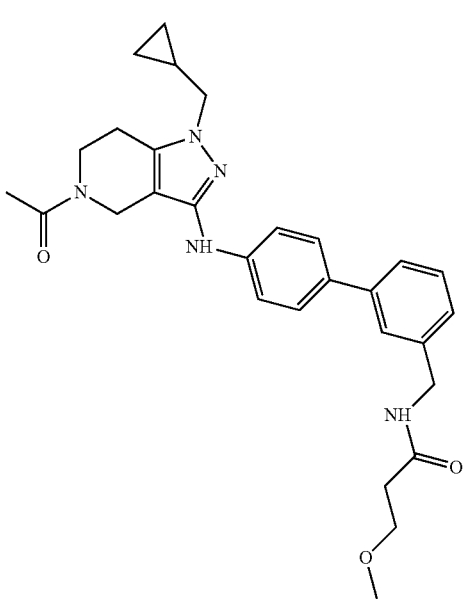 [SMILES: COCCC(=O)NCc1cccc(-c2ccc(Nc3nn(CC4CC4)c4c3CN(C(C)=O)CC4)cc2)c1]

Step 1

N-(3-bromobenzyl)-3-methoxypropanamide

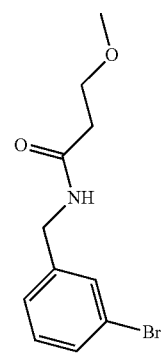

To a solution of (3-bromophenyl)methanamine (0.5 g, 2.69 mmol) in DCM (6 mL) at 0° C. was added 3-methoxypropanoic acid (0.28 g, 2.69 mmol), HATU (1.23 g, 3.22 mmol) and DIPEA (1.04 g, 8.10 mmol). The reaction was allowed to stir at room temperature for 16 h. The reaction mixture was washed with DCM (10 mL×3) and water (10 mL) and the combined organic layers were dried over anhydrous Na$_2$SO$_4$, filtered and concentrated in vacuo. The residue was purified by silica gel chromatography (petroleum ether/EtOAc=10:1-1:2) to afford the title compound (0.5 g, 68%) as a yellow oil. LCMS M/Z (M+H) 274.

Step 2

1-(1-(cyclopropylmethyl)-3-((4-(4,4,5,5-tetramethyl-1,3,2-dioxaborolan-2-yl)phenyl)amino)-6,7-dihydro-1H-pyrazolo[4,3-c]pyridin-5(4H)-yl)ethanone

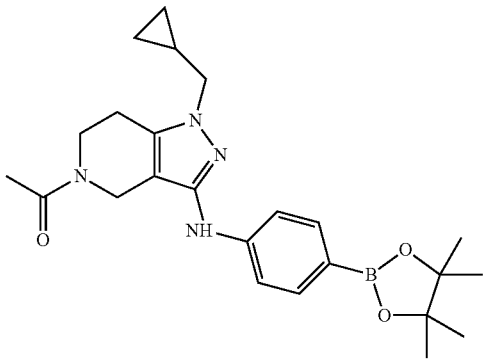 [SMILES: CC(=O)N1CCc2c(c(Nc3ccc(B4OC(C)(C)C(C)(C)O4)cc3)nn2CC2CC2)C1]

To a solution of 1-(3-((4-bromophenyl)amino)-1-(cyclopropylmethyl)-6,7-dihydro-1H-pyrazolo[4,3-c]pyridin-5(4H)-yl)ethanone (1 g, 2.57 mmol) in dioxane (5 mL), was added 4,4,4',4',5,5,5',5'-octamethyl-2,2'-bi(1,3,2-dioxaborolane) (0.78 g, 3.08 mmol), [1,1'-bis(diphenylphosphino)ferrocene]dichloropalladium(II), complex with dichloromethane (0.19 g, 0.26 mmol) and KOAc (0.50 g, 5.14 mmol). The reaction was heated to 120° C. for 16 h. After cooling to room temperature, the reaction was filtered and concentrated in vacuo. The residue was purified by silica gel chromatography (DCM:MeOH=0-5%) to afford the title compound (0.64 g, 57%) as a light yellow solid. LCMS M/Z (M+H) 437.

Step 3

N-((4'-((5-acetyl-1-(cyclopropylmethyl)-4,5,6,7-tetrahydro-1H-pyrazolo[4,3-c]pyridin-3-yl)amino)-[1,1'-biphenyl]-3-yl)methyl)-3-methoxypropanamide

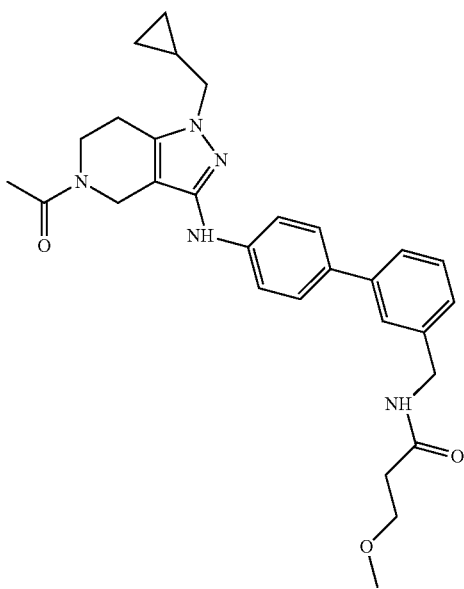 [SMILES: COCCC(=O)NCc1cccc(-c2ccc(Nc3nn(CC4CC4)c4c3CN(C(C)=O)CC4)cc2)c1]

To a solution of 1-(1-(cyclopropylmethyl)-3-((4-(4,4,5,5-tetramethyl-1,3,2-dioxaborolan-2-yl)phenyl)amino)-6,7-dihydro-1H-pyrazolo[4,3-c]pyridin-5(4H)-yl)ethanone (0.2 g, 0.46 mmol) in dioxane (2 mL) and water (0.5 mL) was added N-(3-bromobenzyl)-3-methoxypropanamide (0.15 g, 0.55 mmol), [1,1'-bis(diphenylphosphino)ferrocene]dichloropalladium(II), complex with dichloromethane (0.03 g, 0.05 mmol) and $Na_2CO_3$ (0.15 g, 1.38 mmol). The reaction was heated to 120° C. for 16 h. After cooling to room temperature, the reaction was filtered and concentrated in vacuo. The crude residue was purified by reverse phase chromatography (acetonitrile 20-50%/0.1% $NH_4OH$ in water) to give the title compound (47 mg, 20%) as a white solid. $^1H$ NMR (400 MHz, DMSO-$d_6$) δ 8.39 (s, 1H), 8.25-8.20 (m, 1H), 7.49-7.34 (m, 7H), 7.13 (d, J=5.6 1H), 4.37-4.33 (m, 4H), 3.80-3.68 (m, 6H), 3.23 (s, 3H), 2.75-2.63 (m, 2H), 2.40 (s, 2H), 2.11-2.08 (m, 3H), 1.26-1.10 (m, 1H), 0.57-0.40 (m, 2H), 0.36-0.25 (m, 2H). LCMS M/Z (M+Na) 524.

Example 102

1-[1-(cyclopropylmethyl)-3-[4-(1H-pyrazol-5-yl)anilino]-6,7-dihydro-4H-pyrazolo[4,3-c]pyridin-5-yl]ethanone

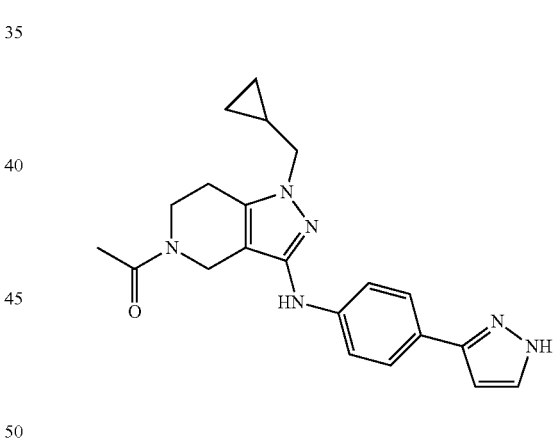

The title compound was prepared from 1-(3-((4-bromophenyl)amino)-1-(cyclopropylmethyl)-6,7-dihydro-1H-pyrazolo[4,3-c]pyridin-5(4H)-yl)ethanone in a similar fashion to Example 74. The crude residue was purified by reverse phase chromatography (acetonitrile 46-76%/0.1% $NH_4OH$ in water) to give the title compound in 6% yield. $^1H$ NMR (400 MHz, $CD_3OD$) δ 7.61-7.48 (m, 3H), 7.24-7.15 (m, 2H), 6.55-6.45 (m, 1H), 4.42-4.41 (m, 2H), 3.89-3.81 (m, 4H), 2.85-2.73 (m, 1H), 2.21-2.14 (m, 3H), 1.28-1.24 (m, 1H), 0.61-0.56 (m, 2H), 0.41-0.37 (m, 2H). LCMS M/Z (M+H) 337.

Example 103

1-[1-(cyclopropylmethyl)-3-[4-(1-methylpyrazol-3-yl)anilino]-6,7-dihydro-4H-pyrazolo[4,3-c]pyridin-5-yl]ethanone

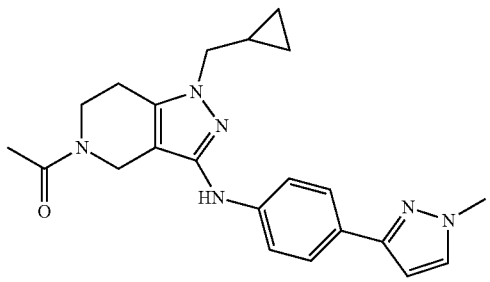 [SMILES: CC(=O)N1CCc2c(c(Nc3ccc(-c4ccn(C)n4)cc3)nn2CC2CC2)C1]

The title compound was prepared from 1-(3-((4-bromophenyl)amino)-1-(cyclopropylmethyl)-6,7-dihydro-1H-pyrazolo[4,3-c]pyridin-5(4H)-yl)ethanone in a similar fashion to Example 75. The crude residue was purified by reverse phase chromatography (acetonitrile 34-64%/0.1% NH$_4$OH in water) to give the title compound in 5% yield. $^1$H NMR (400 MHz, DMSO-d$_6$) δ 8.16-8.11 (m, 1H), 7.61-7.52 (m, 2H), 7.38 (d, J=8.8 Hz, 2H), 6.51 (d, J=2.0 Hz, 1H), 4.35 (s, 2H), 3.83 (s, 3H), 3.78 (d, J=6.8 Hz, 2H), 3.76-3.62 (m, 2H), 2.78-2.65 (m, 2H), 2.10-2.07 (m, 1H), 1.18-1.15 (m, 1H), 0.53-0.45 (m, 2H), 0.36-0.31 (m, 2H). LCMS M/Z (M+H) 391.

Example 104

1-(1-(cyclopropylmethyl)-3-((4-(pyridin-2-yl)phenyl)amino)-6,7-dihydro-1H-pyrazolo[4,3-c]pyridin-5(4H)-yl)ethanone

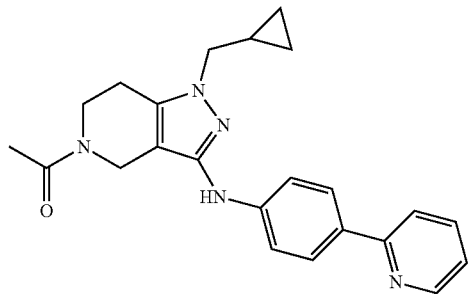 [SMILES: CC(=O)N1CCc2c(c(Nc3ccc(-c4ccccn4)cc3)nn2CC2CC2)C1]

The title compound was prepared from 1-(3-((4-bromophenyl)amino)-1-(cyclopropylmethyl)-6,7-dihydro-1H-pyrazolo[4,3-c]pyridin-5(4H)-yl)ethanone and 2-(tributylstannyl)pyridine in a similar fashion to Example 79. The crude residue was purified by reverse phase chromatography (acetonitrile 18-48%/0.1% NH$_4$OH in water) to give the title compound in 8% yield. $^1$H NMR (400 MHz, CD$_3$OD) δ 8.54-8.53 (m, 1H), 7.85-7.80 (m, 4H), 7.30-7.26 (m, 3H), 4.46-4.42 (m, 2H), 3.91-3.81 (m, 4H), 2.88-2.76 (m, 2H), 2.21-2.15 (m, 3H), 1.26-1.25 (m, 1H), 0.61-0.56 (m, 2H), 0.41-0.37 (m, 2H). LCMS M/Z (M+H) 338. (dd, J=8.8, 8.8 Hz, 2H), 7.20 (dd, J=7.6, 7.6 Hz, 2H), 4.87-4.82 (m, 1H), 4.36 (s, 2H), 4.03-3.95 (m, 2H), 3.86 (s, 3H), 3.84-3.66 (m, 4H), 2.78-2.60 (m, 2H), 2.26-2.20 (m, 2H), 2.07 (s, 3H). LCMS M/Z (M+H) 475.

General Procedure for Intermediate K

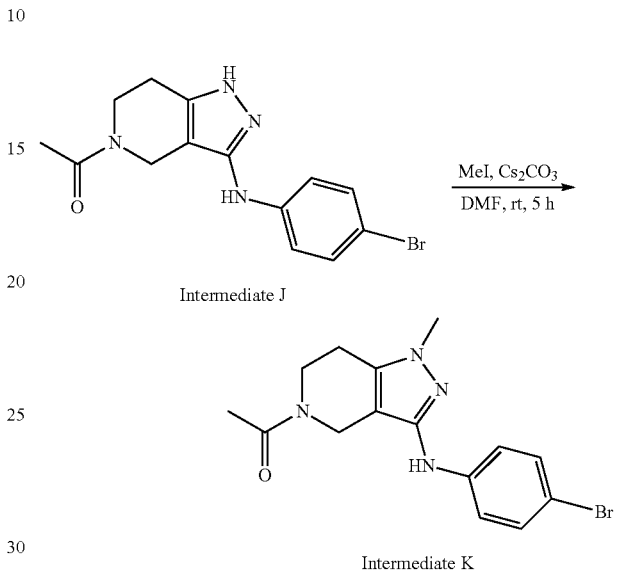

1-(3-((4-bromophenyl)amino)-1-methyl-6,7-dihydro-1H-pyrazolo[4,3-c]pyridin-5(4H)-yl)ethanone

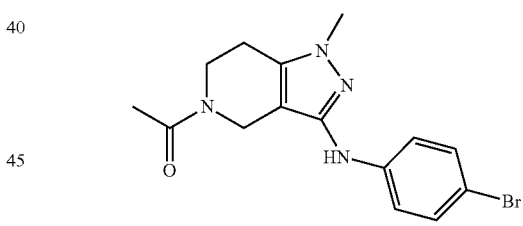

To a solution of 1-(3-((4-bromophenyl)amino)-6,7-dihydro-1H-pyrazolo[4,3-c]pyridin-5(4H)-yl)ethanone (Intermediate J, 5.0 g, 14.92 mmol) and Cs$_2$CO$_3$ (14.58 g, 44.75 mmol) in DMF (30 mL) was added iodomethane (3.18 g, 22.37 mmol) dropwise at 0° C. The reaction stirred at room temperature for 5 hours. The mixture was diluted with EtOAc (100 mL) and washed with brine (100 mL×3). The combined organic layers were dried over anhydrous Na$_2$SO$_4$, filtered and concentrated in vacuo. The residue was purified by silica gel chromatography (DCM/MeOH=100/1) to afford 1-(3-((4-bromophenyl)amino)-1-methyl-6,7-dihydro-1H-pyrazolo[4,3-c]pyridin-5(4H)-yl)ethanone (2.7 g, 51%) as a light yellow solid. $^1$H NMR (400 MHz, CD$_3$OD) δ 7.27-7.24 (m, 2H), 7.10-7.06 (m, 2H), 4.37-4.35 (m, 2H), 3.87-3.76 (m, 2H), 3.64-3.63 (m, 3H), 2.79-2.67 (m, 2H), 2.18-2.12 (m, 3H).

Example 105

1-(3-((4-(1,5-dimethyl-1H-pyrazol-4-yl)phenyl)amino)-1-methyl-6,7-dihydro-1H-pyrazolo[4,3-c]pyridin-5(4H)-yl)ethanone

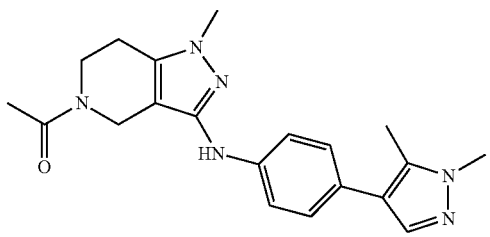 [SMILES: CC(=O)N1CCc2c(c(Nc3ccc(-c4cnn(C)c4C)cc3)nn2C)C1]

To a mixture of 1-(3-((4-bromophenyl)amino)-1-methyl-6,7-dihydro-1H-pyrazolo[4,3-c]pyridin-5(4H)-yl)ethanone (Intermediate K, 0.1 g, 0.29 mmol) and 1,5-dimethyl-4-(4,4,5,5-tetramethyl-1,3,2-dioxaborolan-2-yl)-1H-pyrazole (0.076 g, 0.34 mmol) was added [1,1'-bis(diphenylphosphino)ferrocene]dichloropalladium(II), complex with dichloromethane (0.021 g, 0.029 mmol) and $Na_2CO_3$ (0.061 g, 0.57 mmol) in 1,4-Dioxane/water (4:1, 5 mL). The reaction mixture was heated to 120° C. for 12 h. The reaction mixture was cooled to room temperature, filtered and concentrated in vacuo. The crude residue was purified by reverse phase chromatography (acetonitrile 27-57%/0.1% $NH_4OH$ in water) to give the title compound (0.022 g, 21%) as a white solid. $^1$H NMR (400 MHz, DMSO-$d_6$) δ 8.09-8.04 (s, 1H), 7.44-7.41 (m, 3H), 7.19 (dd, J=7.6, 7.6 Hz, 2H), 4.35 (s, 2H), 3.75-3.66 (m, 5H), 3.60 (s, 3H), 2.73-2.58 (m, 2H), 2.32 (s, 3H), 2.10-2.06 (s, 3H). LCMS M/Z (M+H) 387 [M+Na].

The Following Examples 106-114 were Prepared in a Similar Fashion to Example 105

| Example | Compound Name | NMR | m/z |
| --- | --- | --- | --- |
| Example 106 | 1-[3-[4-[3-(1-hydroxyethyl)phenyl]anilino]-1-methyl-6,7-dihydro-4H-pyrazolo[4,3-c]pyridin-5-yl]ethanone | $^1$H NMR (400 MHz, $CD_3OD$) δ 7.61 (s, 1H), 7.55-7.54 (m, 2H), 7.47-7.30 (m, 2H), 7.27-7.23 (m, 3H), 4.85-4.82 (m, 1H), 4.45-4.43 (s, 2H), 3.93-3.84 (m, 2H), 3.71 (s, 3H), 2.87-2.73 (m, 2H), 2.23-2.17 (m, 3H), 1.50 (d, J = 6.8 Hz, 3H) | 391 |
| Example 107 | 1-[3-[4-[3-(1-hydroxy-1-methyl-ethyl)phenyl]anilino]-1-methyl-6,7-dihydro-4H-pyrazolo[4,3-c]pyridin-5-yl]ethanone | $^1$H NMR (400 MHz, $CD_3OD$) δ 7.72 (s, 1H), 7.52-7.50 (m, 2H), 7.48-7.35 (m, 3H), 7.25-7.21 (m, 2H), 4.44-4.42 (m, 2H), 3.93-3.82 (m, 2H), 3.70 (s, 3H), 2.85-2.73 (m, 2H), 2.23-2.16 (m, 3H), 1.59 (s, 6H) | 405 |

| Example | Compound Name | NMR | m/z |
|---|---|---|---|
| Example 108 | 1-[1-methyl-3-[4-[1-(2,2,2-trifluoroethyl)pyrazol-4-yl]anilino]-6,7-dihydro-4H-pyrazolo[4,3-c]pyridin-5-yl]ethanone | $^1$H NMR (400 MHz, CDCl$_3$) δ 7.80-7.79 (m 1H), 7.66-7.64 (m, 1H), 7.38-7.34 (m, 2H), 7.12-6.96 (m, 2H), 5.71 (s, 1H), 4.76-4.70 (m, 2H), 4.43-4.24 (m, 2H), 3.93-3.70 (m, 2H), 2.22 (s, 1H), 2.76-2.68 (m, 2H), 2.20-2.10 (m, 3H) | 419 |
| Example 109 | 1-[1-methyl-3-[4-(2-methylpyrazol-3-yl)anilino]-6,7-dihydro-4H-pyrazolo[4,3-c]pyridin-5-yl]ethanone | $^1$H NMR (400 MHz, DMSO-d$_6$) δ 8.34-8.29 (m, 1H), 7.49 (dd, J = 8.4, 4.8 Hz, 2H), 7.40 (d, J = 1.6 Hz, 1 H), 7.33 (dd, J = 8.4, 8.4 Hz, 2H), 6.27 (s, 1H), 4.37 (s, 2H), 3.82 (s, 3H), 3.77-3.66 (m, 2H), 3.61 (s, 3H), 2.75-2.59 (m, 1H), 2.10-2.07 (m, 3H) | 351 |
| Example 110 | 1-[1-methyl-3-(4-thiazol-5-ylanilino)-6,7-dihydro-4H-pyrazolo[4,3-c]pyridin-5-yl]ethanone | $^1$H NMR (400 MHz, DMSO-d$_6$) δ 8.93 (s, 1H), 8.37-8.32 (m, 1H), 8.10 (s, 1H), 7.55-7.41 (m, 4H), 4.35-4.33 (s, 2H), 3.77-3.64 (m, 2 H), 3.61 (s, 3H), 2.76-2.58 (m, 1H), 2.10-2.06 (m, 3H) | 354 |
| Example 111 | 1-[3-[4-(1,3-dimethylpyrazol-4-yl)anilino]-1-methyl-6,7-dihydro-4H-pyrazolo[4,3-c]pyridin-5-yl]ethanone | $^1$H NMR (400 MHz, CD$_3$OD) δ 7.56-7.55 (m, 1H), 7.24-7.13 (m, 4H), 4.38-4.36 (m, 2H), 3.87-3.75 (m, 5H), 3.65-3.64 (m, 3H), 2.77-2.60 (m, 2H), 2.30 (s, 3H), 2.18-2.11 (s, 3H) | 365 |

-continued

| Example | Compound Name | NMR | m/z |
|---|---|---|---|
| Example 112 | 1-(1-methyl-3-((4-(1-methyl-3-(trifluoromethyl)-1H-pyrazol-4-yl)phenyl)amino)-6,7-dihydro-1H-pyrazolo[4,3-c]pyridin-5(4H)-yl)ethanone | $^1$H NMR (400 MHz, CD$_3$OD) δ 7.76 (s, 1H), 7.26-7.22 (m, 2H), 7.18-7.14 (m, 2H), 4.40-4.39 (m, 2H), 3.95 (s, 3H), 3.89-3.79 (m, 2H), 3.67-3.66 (m, 3H), 2.82-2.69 (m, 2H), 2.20-2.13 (m, 3H) | 419 |
| Example 113 | 1-(1-methyl-3-((4-(1,3,5-trimethyl-1H-pyrazol-4-yl)phenyl)amino)-6,7-dihydro-1H-pyrazolo[4,3-c]pyridin-5(4H)-yl)ethanone | $^1$H NMR (400 MHz, CD$_3$OD) δ 7.22-7.16 (m, 2H), 7.08-7.04 (m, 2H), 4.41 (s, 2H), 3.90-3.80 (m, 2H), 3.74 (s, 3H), 3.76-3.66 (m, 3H), 2.83-2.70 (m, 2H), 2.22-2.15 (m, 9H) | 379 |
| Example 114 | 1-(3-((4-(1-(difluoromethyl)-1H-pyrazol-4-yl)phenyl)amino)-1-methyl-6,7-dihydro-1H-pyrazolo[4,3-c]pyridin-5(4H)-yl)ethanone | $^1$H NMR (400 MHz, CD$_3$OD) δ 8.25 (d, J = 3.6 Hz, 1H), 7.99 (s, 1H), 7.47-7.43 (m, 2H), 7.46 (t, J = 60.0 Hz, 1H), 7.20-7.16 (m, 2H), 4.40-4.39 (m, 2H), 3.90-3.79 (m, 2H), 3.68-3.67 (s, 3H), 2.82-2.70 (m, 2H), 2.20-2.14 (m, 3H) | 387 |

Example 115

1-[3-[4-(2-fluorophenyl)anilino]-1-methyl-6,7-di-hydro-4H-pyrazolo[4,3-c]pyridin-5-yl]ethanone

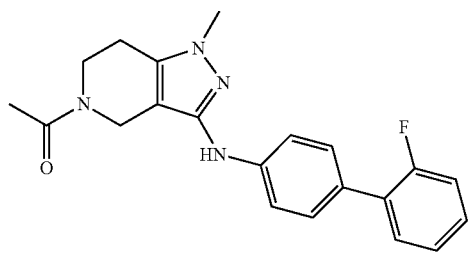 [SMILES: CC(=O)N1CCc2c(c(Nc3ccc(-c4ccccc4F)cc3)nn2C)C1]

To an 8 mL vial was added 1-[3-(4-bromoanilino)-1-methyl-6,7-dihydro-4H-pyrazolo[4,3-c]pyridin-5-yl]ethanone (Intermediate K, 35 mg, 0.10 mmol), (2-fluorophenyl)boronic acid (28 mg, 0.20 mmol), potassium phosphate tribasic (2.0 mol/L, 0.15 mL in water, 0.30 mmol), [1,1'-bis(diphenylphosphino)ferrocene]dichloropalladium(II) (4.2 mg, 0.005 mmol) and 1,4-dioxane (0.3 mL). The reaction was capped and shaken at 85° C. for 1 h, then cooled to room temperature and filtered through celite. The filtrate phase was separated and the organic layer was concentrated in vacuo. The residue was purified by reverse phase HPLC (acetonitrile 20-60%/0.1% $NH_4OH$ in water) to give the title compound (19 mg, 53%) as an off-white solid. $^1$H NMR (400 MHz, DMSO-$d_6$) δ 8.32-8.15 (m, 1H), 7.52-7.44 (m, 3H), 7.44-7.35 (m, 2H), 7.35-7.29 (m, 1H), 7.29-7.20 (m, 2H), 4.37 (s, 2H), 3.79-3.65 (m, 2H), 3.65-3.58 (m, 3H), 2.76-2.58 (m, 2H), 2.15-2.03 (m, 3H). LCMS M/Z (M+H) 365.

The Following Examples 116-151 were Prepared in a Similar Fashion to Example 115

| Example | Compound Name and Structure | NMR | m/z |
|---|---|---|---|
| Example 116 | 1-[3-[4-(3-fluorophenyl)anilino]-1-methyl-6,7-dihydro-4H-pyrazolo[4,3-c]pyridin-5-yl]ethanone | $^1$H NMR (400 MHz, DMSO-$d_6$) δ 8.33-8.19 (m, 1H), 7.62-7.51 (m, 2H), 7.51-7.37 (m, 5H), 7.12-6.98 (m, 1H), 4.36 (s, 2H), 3.76-3.65 (m, 2H), 3.65-3.59 (m, 3H), 2.77-2.56 (m, 2H), 2.16-2.05 (m, 3H) | 365 |
| Example 117 | 1-[1-methyl-3-[4-(m-tolyl)anilino]-6,7-dihydro-4H-pyrazolo[4,3-c]pyridin-5-yl]ethanone | $^1$H NMR (400 MHz, DMSO-$d_6$) δ 8.21-8.11 (m, 1H), 7.60-7.34 (m, 6H), 7.32-7.24 (m, 1H), 7.10-7.03 (m, 1H), 3.78-3.64 (m, 2H), 3.61 (d, J = 2.0 Hz, 3H), 2.78-2.57 (m, 2H), 2.35 (s, 3H), 2.13-2.03 (m, 3H) | 361 |

-continued

| Example | Compound Name and Structure | NMR | m/z |
|---|---|---|---|
| Example 118 | 1-[1-methyl-3-[4-(o-tolyl)anilino]-6,7-dihydro-4H-pyrazolo[4,3-c]pyridin-5-yl]ethanone | $^1$H NMR (400 MHz, DMSO-$d_6$) δ 8.18-8.07 (m, 1H), 7.60-7.40 (m, 2H), 7.28-7.11 (m, 6H), 4.37 (s, 2H), 3.79-3.65 (m, 2H), 3.63-3.58 (m, 3H), 2.77-2.58 (m, 2H), 2.26 (s, 3H), 2.13-2.06 (m, 3H) | 361 |
| Example 119 | 1-[1-methyl-3-[4-(3-pyridyl)anilino]-6,7-dihydro-4H-pyrazolo[4,3-c]pyridin-5-yl]ethanone | $^1$H NMR (400 MHz, DMSO-$d_6$) δ 8.88-8.80 (m, 1H), 8.50-8.42 (m, 1H), 8.33-8.21 (m, 1H), 8.04-7.93 (m, 1H), 7.62-7.47 (m, 4H), 7.44-7.31 (m, 1H), 4.42-4.30 (m, 2H), 3.79-3.65 (m, 3H), 3.60-3.57 (m, 1H), 2.79-2.56 (m, 3H), 2.13-2.01 (m, 3H) | 348 |
| Example 120 | 1-[1-methyl-3-[4-(p-tolyl)anilino]-6,7-dihydro-4H-pyrazolo[4,3-c]pyridin-5-yl]ethanone | $^1$H NMR (400 MHz, DMSO-$d_6$) δ 8.21-8.08 (m, 1H), 7.52-7.42 (m, 6H), 7.26-7.17 (m, 2H), 4.36 (s, 2H), 3.78-3.64 (m, 2H), 3.61 (d, J = 2.0 Hz, 3H), 2.77-2.57 (m, 2H), 2.31 (s, 3H), 2.13-2.03 (m, 3H) | 361 |
| Example 121 | 1-[1-methyl-3-[4-[4-(4-methylpiperazine-1-carbonyl)phenyl]anilino]-6,7-dihydro-4H-pyrazolo[4,3-c]pyridin-5-yl]ethanone | $^1$H NMR (400 MHz, DMSO-$d_6$) δ 8.29-8.20 (m, 1H), 7.70-7.63 (m, 2H), 7.60-7.52 (m, 2H), 7.51-7.45 (m, 2H), 7.43-7.38 (m, 2H), 4.37 (s, 2H), 3.77-3.65 (m, 2H), 3.64-3.60 (m, 3H), 2.77-2.58 (m, 2H), 2.52-2.47 (m, 4H), 2.40-2.26 (m, 4H), 2.20 (s, 3H), 2.13-2.05 (m, 3H) | 473 |

-continued

| Example | Compound Name and Structure | NMR | m/z |
|---|---|---|---|
| Example 122 | 3-[4-[(5-acetyl-1-methyl-6,7-dihydro-4H-pyrazolo[4,3-c]pyridin-3-yl)amino]phenyl]benzonitrile | $^1$H NMR (400 MHz, DMSO-d$_6$) δ 8.35-8.24 (m, 1H), 8.08-8.03 (m, 1H), 7.99-7.92 (m, 1H), 7.74-7.66 (m, 1H), 7.65-7.56 (m, 3H), 7.53-7.47 (m, 2H), 4.37 (d, J = 1.7 Hz, 2H), 3.77-3.65 (m, 2H), 3.62 (d, J = 2.0 Hz, 3H), 2.77-2.57 (m, 2H), 2.14-2.05 (m, 3H) | 372 |
| Example 123 | 1-[3-[4-(1-ethylpyrazol-4-yl)anilino]-1-methyl-6,7-dihydro-4H-pyrazolo[4,3-c]pyridin-5-yl]ethanone | $^1$H NMR (400 MHz, DMSO-d$_6$) δ 8.07-7.95 (m, 2H), 7.72-7.68 (m, 1H), 7.40-7.32 (m, 4H), 4.34 (s, 2H), 4.12 (q, J = 7.3 Hz, 2H), 3.77-3.64 (m, 2H), 3.63-3.57 (m, 3H), 2.75-2.56 (m, 2H), 2.12-2.04 (m, 3H), 1.39 (t, J = 7.3 Hz, 3H) | 365 |
| Example 124 | 1-[3-[4-(4-fluorophenyl)anilino]-1-methyl-6,7-dihydro-4H-pyrazolo[4,3-c]pyridin-5-yl]ethanone | $^1$H NMR (400 MHz, DMSO-d$_6$) δ 8.23-8.13 (m, 1H), 7.65-7.58 (m, 2H), 7.51-7.42 (m, 4H), 7.27-7.17 (m, 2H), 4.36 (s, 2H), 3.77-3.66 (m, 2H), 3.64-3.58 (m, 3H), 2.76-2.58 (m, 2H), 2.13-2.05 (m, 3H) | 365 |
| Example 125 | 1-[3-[4-(4-methoxyphenyl)anilino]-1-methyl-6,7-dihydro-4H-pyrazolo[4,3-c]pyridin-5-yl]ethanone | $^1$H NMR (400 MHz, DMSO-d$_6$) δ 8.16-8.06 (m, 1H), 7.55-7.49 (m, 2H), 7.46-7.42 (m, 4H), 7.00-6.94 (m, 2H), 4.36 (s, 2H), 3.77 (s, 3H), 3.76-3.65 (m, 2H), 3.63-3.59 (m, 3H), 2.76-2.57 (m, 2H), 2.12-2.04 (m, 3H) | 377 |

| Example | Compound Name and Structure | NMR | m/z |
|---|---|---|---|
| Example 126 | 4-[4-[(5-acetyl-1-methyl-6,7-dihydro-4H-pyrazolo[4,3-c]pyridin-3-yl)amino)phenyl]benzonitrile | $^1$H NMR (400 MHz, DMSO-d$_6$) δ 8.41-8.32 (m, 1H), 7.86-7.80 (m, 4H), 7.67-7.60 (m, 2H), 7.54-7.47 (m, 2H), 4.41-4.33 (m, 2H), 3.77-3.65 (m, 2H), 3.65-3.59 (m, 3H), 2.78-2.59 (m, 2H), 2.12-2.04 (m, 3H) | 372 |
| Example 127 | 1-[3-[4-(2-methoxyphenyl)anilino]-1-methyl-6,7-dihydro-4H-pyrazolo[4,3-c]pyridin-5-yl]ethanone | $^1$H NMR (400 MHz, DMSO-d$_6$) δ 8.18-8.01 (m, 1H), 7.46-7.36 (m, 2H), 7.34-7.20 (m, 4H), 7.08-7.02 (m, 1H), 7.02-6.94 (m, 1H), 4.36 (s, 2H), 3.80-3.64 (m, 5H), 3.64-3.56 (m, 3H), 2.79-2.56 (m, 2H), 2.13-2.03 (m, 3H) | 377 |
| Example 128 | 1-[3-[4-(3-methoxyphenyl)anilino]-1-methyl-6,7-dihydro-4H-pyrazolo[4,3-c]pyridin-5-yl]ethanone | $^1$H NMR (400 MHz, DMSO-d$_6$) δ 8.24-8.14 (m, 1H), 7.56-7.43 (m, 4H), 7.34-7.26 (m, 1H), 7.20-7.09 (m, 2H), 6.86-6.79 (m, 1H), 4.40-4.34 (m, 2H), 3.81 (s, 3H), 3.78-3.65 (m, 2H), 3.64-3.58 (m, 3H), 2.77-2.58 (m, 2H), 2.15-2.04 (m, 3H) | 377 |
| Example 129 | 1-[3-[4-(4-chlorophenyl)anilino]-1-methyl-6,7-dihydro-4H-pyrazolo[4,3-c]pyridin-5-yl]ethanone | $^1$H NMR (400 MHz, DMSO-d$_6$) δ 8.30-8.17 (m, 1H), 7.67-7.38 (m, 8H), 4.36 (s, 2H), 3.79-3.65 (m, 2H), 3.65-3.59 (m, 3H), 2.78-2.58 (m, 2H), 2.15-2.04 (m, 3H) | 381 |

-continued

| Example | Compound Name and Structure | NMR | m/z |
|---|---|---|---|
| Example 130 | 1-[3-[4-[4-(hydroxymethyl)phenyl]anilino]-1-methyl-6,7-dihydro-4H-pyrazolo[4,3-c]pyridin-5-yl]ethanone | $^1$H NMR(400 MHz, DMSO-d$_6$) δ 8.24-8.10 (m, 1H), 7.58-7.42 (m, 6H), 7.38-7.28 (m, 2H), 4.50 (d, J = 4.4 Hz, 2H), 4.36 (s, 2H), 3.78-3.65 (m, 2H), 3.63-3.56 (m, 3H), 2.76-2.57 (m, 2H), 2.13-2.04 (m, 3H) | 377 |
| Example 131 | 1-[3-[4-(3,5-difluorophenyl)anilino]-1-methyl-6,7-dihydro-4H-pyrazolo[4,3-c]pyridin-5-yl]ethanone | $^1$H NMR (400 MHz, DMSO-d$_6$) δ 8.38-8.27 (m, 1H), 7.65-7.45 (m, 5H), 7.39-7.30 (m, 2H), 7.10-7.01 (m, 1H), 4.37 (s, 2H), 3.79-3.65 (m, 2H), 3.65-3.57 (m, 3H), 2.78-2.58 (m, 2H), 2.15-2.03 (m, 3H) | 383 |
| Example 132 | 1-[3-[4-(3-chlorophenyl)anilino]-1-methyl-6,7-dihydro-4H-pyrazolo[4,3-c]pyridin-5-yl]ethanone | $^1$H NMR (400 MHz, DMSO-d$_6$) δ 8.31-8.21 (m, 1H), 7.65-7.38 (m, 7H), 7.33-7.27 (m, 1H), 4.36 (s, 2H), 3.78-3.65 (m, 2H), 3.65-3.59 (m, 3H), 2.77-2.57 (m, 2H), 2.13-2.04 (m, 3H) | 381 |
| Example 133 | 1-[3-[4-(3,4-difluorophenyl)anilino]-1-methyl-6,7-dihydro-4H-pyrazolo[4,3-c]pyridin-5-yl]ethanone | $^1$H NMR (400 MHz, DMSO-d$_6$) δ 8.30-8.19 (m, 1H), 7.70-7.60 (m, 1H), 7.57-7.41 (m, 6H), 4.36 (s, 2H), 3.77-3.65 (m, 2H), 3.65-3.58 (m, 3H), 2.77-2.57 (m, 2H), 2.13-2.04 (m, 3H) | 383 |

-continued

| Example | Compound Name and Structure | NMR | m/z |
|---|---|---|---|
| Example 134 | 1-[3-[4-(2,5-difluorophenyl)anilino]-1-methyl-6,7-dihydro-4H-pyrazolo[4,3-c]pyridin-5-yl]ethanone | $^1$H NMR (400 MHz, DMSO-d$_6$) δ 8.35-8.25 (m, 1H), 7.51-7.39 (m, 4H), 7.38-7.25 (m, 2H), 7.18-7.09 (m, 1H), 4.40-4.33 (m, 2H), 3.77-3.64 (m, 2H), 3.64 3.58 (m, 3H), 2.77-2.57 (m, 2H), 2.13-2.05 (m, 3H) | 383 |
| Example 135 | 4-[4-[(5-acetyl-1-methyl-6,7-dihydro-4H-pyrazolo[4,3-c]pyridin-3-yl)amino]phenyl]benzamide | $^1$H NMR (400 MHz, DMSO-d$_6$) δ 8.31-8.22 (m, 1H), 7.95-7.87 (m, 3H), 7.71-7.65 (m, 2H), 7.63-7.55 (m, 2H), 7.52-7.45 (m, 2H), 7.27 (s, 1H), 4.41-4.30 (m, 2H), 3.77-3.64 (m, 2H), 3.64-3.60 (m, 3H), 3.60-3.56 (m, 1H), 2.77-2.56 (m, 2H), 2.13-2.03 (m, 3H) | 390 |
| Example 136 | 1-[1-methyl-3-[4-[3-(trifluoromethyl)phenyl]anilino]-6,7-dihydro-4H-pyrazolo[4,3-c]pyridin-5-yl]ethanone | $^1$H NMR (400 MHz, DMSO-d$_6$) δ 8.33-8.24 (m, 1H), 7.94-7.85 (m, 2H), 7.67-7.57 (m, 4H), 7.53-7.47 (m, 2H), 4.37 (s, 2H), 3.78-3.64 (m, 2H), 3.65-3.60 (m, 3H), 2.78-2.57 (m, 2H), 2.14-2.04 (m, 3H) | 415 |
| Example 137 | 1-[3-[4-[3-(dimethylamino)phenyl]anilino]-1-methyl-6,7-dihydro-4H-pyrazolo[4,3-c]pyridin-5-yl]ethanone | $^1$H NMR (400 MHz, DMSO-d$_6$) δ 8.20-8.09 (m, 1H), 7.51-7.41 (m, 4H), 7.23-7.16 (m, 1H), 6.90-6.84 (m, 2H), 6.67-6.60 (m, 1H), 4.36 (s, 2H), 3.78-3.65 (m, 2H), 3.64-3.58 (m, 3H), 2.94 (s, 6H), 2.67 (d, J = 47.2, 5.8 Hz, 2H), 2.13-2.04 (m, 3H) | 390 |

-continued

| Example | Compound Name and Structure | NMR | m/z |
|---|---|---|---|
| Example 138 | 4-[4-[(5-acetyl-1-methyl-6,7-dihydro-4H-pyrazolo[4,3-c]pyridin-3-yl)amino]phenyl]-N,N-dimethyl-benzamide | $^1$H NMR (400 MHz, DMSO-d$_6$) δ 8.28-8.19 (m, 1H), 7.68-7.63 (m, 2H), 7.60-7.53 (m, 2H), 7.52-7.46 (m, 2H), 7.45-7.40 (m, 2H), 4.40-4.34 (m, 2H), 3.78-3.64 (m, 2H), 3.64-3.58 (m, 3H), 2.98 (s, 7H), 2.77-2.57 (m, 2H), 2.13-2.04 (m, 3H) | 419 |
| Example 139 | 1-[1-methyl-3-[4-[4-(trifluoromethyl)phenyl]anilino]-6,7-dihydro-4H-pyrazolo[4,3-c]pyridin-5-yl]ethanone | $^1$H NMR (400 MHz, DMSO-d$_6$) δ 8.36-8.27 (m, 1H), 7.85-7.79 (m, 2H), 7.77-7.70 (m, 2H), 7.64-7.57 (m, 2H), 7.54-7.47 (m, 2H), 4.37 (s, 2H), 3.79-3.66 (m, 2H), 3.65-3.58 (m, 3H), 2.79-2.58 (m, 2H), 2.14-2.05 (m, 3H) | 415 |
| Example 140 | 3-[4-[(5-acetyl-1-methyl-6,7-dihydro-4H-pyrazolo[4,3-c]pyridin-3-yl)amino]phenyl]-N,N-dimethyl-benzamide | $^1$H NMR (400 MHz, DMSO-d$_6$) δ 8.28-8.17 (m, 1H), 7.71-7.63 (m, 1H), 7.60-7.51 (m, 3H), 7.50-7.42 (m, 3H), 7.29-7.23 (m, 1H), 4.36 (s, 2H), 3.77-3.65 (m, 2H), 3.64-3.59 (m, 3H), 2.98 (d, J = 19.1 Hz, 6H), 2.76-2.58 (m, 2H), 2.08 (d, J = 13.2 Hz, 3H) | 419 |
| Example 141 | 1-[1-methyl-3-[4-[3-(trifluoromethoxy)phenyl]anilino]-6,7-dihydro-4H-pyrazolo[4,3-c]pyridin-5-yl]ethanone | $^1$H NMR (400 MHz, DMSO-d$_6$) δ 8.35-8.22 (m, 1H), 7.69-7.62 (m, 1H), 7.61-7.44 (m, 6H), 7.26-7.19 (m, 1H), 4.37 (s, 2H), 3.78-3.65 (m, 2H), 3.65-3.59 (m, 3H), 2.77-2.57 (m, 2H), 2.13-2.05 (m, 3H) | 431 |

-continued

| Example | Compound Name and Structure | NMR | m/z |
|---|---|---|---|
| Example 142 | 1-[1-methyl-3-[4-[4-(trifluoromethoxy)phenyl]anilino]-6,7-dihydro-4H-pyrazolo[4,3-c]pyridin-5-yl]ethanone | $^1$H NMR (400 MHz, DMSO-$d_6$) δ 8.29-8.19 (m, 1H), 7.74-7.67 (m, 2H), 7.56-7.45 (m, 4H), 7.41-7.34 (m, 2H), 4.40-4.32 (m, 2H), 3.77-3.65 (m, 2H), 3.64-3.59 (m, 3H), 2.77-2.57 (m, 2H), 2.12-2.05 (m, 3H) | 431 |
| Example 143 | N-[3-[4-[(5-acetyl-1-methyl-6,7-dihydro-4H-pyrazolo[4,3-c]pyridin-3-yl)amino]phenyl]phenyl]-methanesulfonamide | Not Determined | 440 |
| Example 144 | N-[4-[4-[(5-acetyl-1-methyl-6,7-dihydro-4H-pyrazolo[4,3-c]pyridin-3-yl)amino]phenyl]phenyl]-methanesulfonamide | $^1$H NMR (400 MHz, DMSO-$d_6$) δ 8.21-8.11 (m, 1H), 7.59-7.53 (m, 2H), 7.51-7.42 (m, 4H), 7.26-7.20 (m, 2H), 4.36 (s, 2H), 3.78-3.64 (m, 2H), 3.64-3.57 (m, 3H), 2.97 (s, 3H), 2.77-2.58 (m, 2H), 2.14-2.04 (m, 3H) | 440 |
| Example 145 | 5-[4-[(5-acetyl-1-methyl-6,7-dihydro-4H-pyrazolo[4,3-c]pyridin-3-yl)amino]phenyl]pyridine-2-carbonitrile | $^1$H NMR (400 MHz, DMSO-$d_6$) δ 9.08-9.03 (m, 1H), 8.50-8.41 (m, 1H), 8.28-8.20 (m, 1H), 8.05-7.99 (m, 1H), 7.77-7.69 (m, 2H), 7.59-7.50 (m, 2H), 4.37 (s, 2H), 3.71 (dt, J = 20.4, 5.8 Hz, 2H), 3.66-3.61 (m, 3H), 2.78-2.56 (m, 2H), 2.14-2.02 (m, 3H) | 373 |

| Example | Compound Name and Structure | NMR | m/z |
|---|---|---|---|
| Example 146 | 5-[4-[(5-acetyl-1-methyl-6,7-dihydro-4H-pyrazolo[4,3-c]pyridin-3-yl)amino]phenyl]pyridine-3-carbonitrile 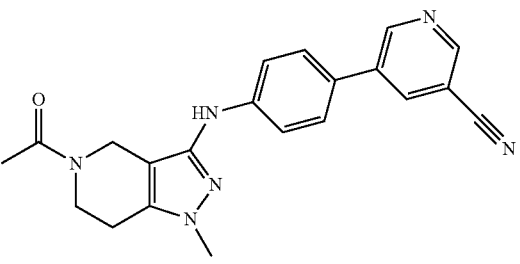 | $^1$H NMR (400 MHz, DMSO-d$_6$) δ 9.14 (t, J = 2.0 Hz, 1H), 8.86 (t, J = 2.0 Hz, 1H), 8.55-8.50 (m, 1H), 8.42-8.32 (m, 1H), 7.72-7.65 (m, 2H), 7.57-7.48 (m, 2H), 4.37 (s, 2H), 3.79-3.66 (m, 2H), 3.65-3.61 (m, 3H), 2.77-2.57 (m, 2H), 2.14-2.05 (m, 3H) | 373 |
| Example 147 | 1-[1-methyl-3-[4-[4-(morpholine-4-carbonyl)phenyl]anilino]-6,7-dihydro-4H-pyrazolo[4,3-c]pyridin-5-yl]ethanone 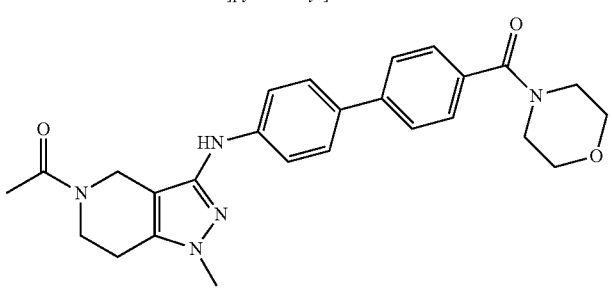 | $^1$H NMR (400 MHz, DMSO-d$_6$) δ 8.30-8.20 (m, 1H), 7.70-7.64 (m, 2H), 7.60-7.52 (m, 2H), 7.52-7.40 (m, 4H), 4.37 (s, 2H), 3.78-3.65 (m, 2H), 3.65-3.57 (m, 6H), 3.57-3.43 (m, 5H), 2.77-2.57 (m, 2H), 2.12-2.03 (m, 3H) | 460 |
| Example 148 | 5-[4-[(5-acetyl-1-methyl-6,7-dihydro-4H-pyrazolo[4,3-c]pyridin-3-yl)amino]phenyl]-N-methyl-pyridine-2-carboxamide 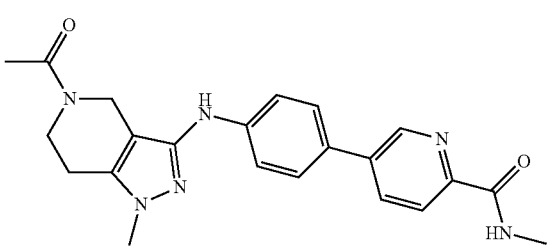 | $^1$H NMR (400 MHz, DMSO-d$_6$) δ 8.91-8.84 (m, 1H), 8.74-8.66 (m, 1H), 8.41-8.30 (m, 1H), 8.21-8.11 (m, 1H), 8.06-7.98 (m, 1H), 7.72-7.62 (m, 2H), 7.57-7.49 (m, 2H), 4.37 (s, 2H), 3.78-3.65 (m, 2H), 3.65-3.60 (m, 3H), 2.88-2.80 (m, 3H), 2.77-2.57 (m, 2H), 2.14-2.06 (m, 3H) | 405 |

| Example | Compound Name and Structure | NMR | m/z |
|---|---|---|---|
| Example 149 | 4-[4-[(5-acetyl-1-methyl-6,7-dihydro-4H-pyrazolo[4,3-c]pyridin-3-yl)amino]phenyl]-N-methyl-benzamide | $^1$H NMR (400 MHz, DMSO-$d_6$) δ 8.43-8.36 (m, 1H), 8.31-8.22 (m, 1H), 7.89-7.83 (m, 2H), 7.72-7.66 (m, 2H), 7.63-7.55 (m, 2H), 7.52-7.46 (m, 2H), 4.37 (s, 2H), 3.78-3.64 (m, 2H), 3.64-3.60 (m, 3H), 2.83-2.77 (m, 3H), 2.76-2.59 (m, 2H), 2.13-2.06 (m, 3H) | 404 |
| Example 150 | 3-[4-[(5-acetyl-1-methyl-6,7-dihydro-4H-pyrazolo[4,3-c]pyridin-3-yl)amino]phenyl]-N-methyl-benzamide | $^1$H NMR (400 MHz, DMSO-$d_6$) δ 8.54-8.45 (m, 1H), 8.29-8.18 (m, 1H), 8.07-8.02 (m, 1H), 7.79-7.68 (m, 2H), 7.63-7.53 (m, 2H), 7.53-7.44 (m, 3H), 4.36 (s, 2H), 3.78-3.65 (m, 2H), 3.64-3.60 (m, 3H), 2.81 (d, J = 4.5 Hz, 3H), 2.77-2.59 (m, 2H), 2.13-2.06 (m, 3H) | 404 |
| Example 151 | 1-[3-[4-[3-(hydroxymethyl)phenyl]anilino]-1-methyl-6,7-dihydro-4H-pyrazolo[4,3-c]pyridin-5-yl]ethanone | $^1$H NMR (400 MHz, DMSO-$d_6$) δ 8.24-8.11 (m, 1H), 7.57-7.42 (m, 6H), 7.38-7.31 (m, 1H), 7.24-7.17 (m, 1H), 5.21-5.12 (m, 1H), 4.59-4.51 (m, 2H), 4.36 (s, 2H), 3.78-3.65 (m, 2H), 3.65-3.59 (m, 3H), 2.77-2.55 (m, 2H), 2.08 (d, J = 13.4 Hz, 3H) | 377 |

Example 152

1-[1-methyl-3-[4-(4,5,6,7-tetrahydropyrazolo[1,5-a]pyridin-3-yl)anilino]-6,7-dihydro-4H-pyrazolo[4,3-c]pyridin-5-yl]ethanone

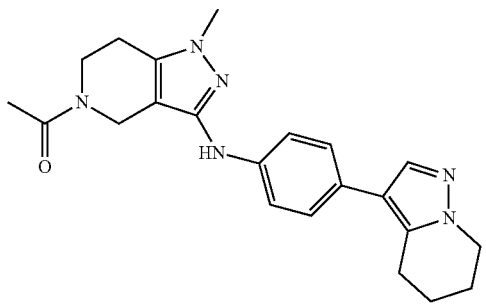 [SMILES: CC(=O)N1CCc2c(c(Nc3ccc(-c4cnn5c4CCCC5)cc3)nn2C)C1]

A microwave vial was charged with 1-[3-(4-bromoanilino)-1-methyl-6,7-dihydro-4H-pyrazolo[4,3-c]pyridin-5-yl]ethanone (Intermediate K, 30 mg, 0.08591 mmol), 3-(4,4,5,5-tetramethyl-1,3,2-dioxaborolan-2-yl)-4,5,6,7-tetrahydropyrazolo[1,5-a]pyridine (27.71 mg, 0.1117 mmol), SiliaCat DPP-Pd (17 mg, 0.004296 mmol) and potassium carbonate (23.75 mg, 0.1718 mmol). Methanol (2 mL) was added and the mixture was irradiated at 120° C. for min before being filtered. The solution was concentrated in vacuo to yield the crude residue that was purified by reverse phase HPLC to afford the title compound (20.4 mg, 59%) as a white solid. $^1$H NMR (400 MHz, DMSO-$d_6$) δ 8.09-7.95 (m, 1H), 7.57 (d, J=2.4 Hz, 1H), 7.45-7.19 (m, 3H), 4.34 (s, 2H), 4.07 (t, J=6.1 Hz, 2H), 3.78-3.63 (m, 2H), 3.59 (d, J=2.0 Hz, 3H), 2.87 (t, J=6.3 Hz, 2H), 2.77-2.55 (m, 2H), 2.13-2.02 (m, 3H), 2.02-1.91 (m, 2H), 1.88-1.76 (m, 2H). LCMS M/Z (M+H) 391.

The Following Examples 153-167 were Prepared in a Similar Fashion to Example 152

| Example | Compound Name and Structure | NMR | m/z |
|---|---|---|---|
| Example 153 | 1-[3-[4-(1-cyclopropylpyrazol-4-yl)anilino]-1-methyl-6,7-dihydro-4H-pyrazolo[4,3-c]pyridin-5-yl]ethanone | $^1$H NMR (400 MHz, DMSO-$d_6$) δ 8.08-7.95 (m, 2H), 7.74-7.66 (m, 1H), 7.36 (d, J = 3.3 Hz, 4H), 4.34 (s, 2H), 3.79-3.62 (m, 3H), 3.60 (d, J = 2.1 Hz, 3H), 2.80-2.55 (m, 3H), 2.07 (d, J = 14.8 Hz, 3H), 1.08-1.01 (m, 2H), 1.00-0.89 (m, 2H) | 377 |
| Example 154 | 1-[3-[4-(3-cyclopropyl-1-methyl-pyrazol-4-yl)anilino]-1-methyl-6,7-dihydro-4H-pyrazolo[4,3-c]pyridin-5-yl]ethanone | $^1$H NMR (400 MHz, DMSO-$d_6$) δ 8.10-7.97 (m, 1H), 7.66 (d, J = 2.2 Hz, 1H), 7.47-7.36 (m, 2H), 7.33 (dd, J = 8.8, 6.9 Hz, 2H), 4.35 (s, 2H), 3.78-3.55 (m, 8H), 2.77-2.56 (m, 2H), 2.08 (d, J = 14.0 Hz, 3H), 1.89 (tt, J = 8.3, 5.1 Hz, 1H), 0.90-0.79 (m, 2H), 0.79-0.71 (m, 2H) | 391 |

-continued

| Example | Compound Name and Structure | NMR | m/z |
|---|---|---|---|
| Example 155 | 1-[1-methyl-3-[4-(4-pyridyl)anilino]-6,7-dihydro-4H-pyrazolo[4,3-c]pyridin-5-yl]ethanone | Not Determined | 348 |
| Example 156 | 1-[1-methyl-3-(4-pyrimidin-5-ylanilino)-6,7-dihydro-4H-pyrazolo[4,3-c]pyridin-5-yl]ethanone | $^1$H NMR (400 MHz, DMSO-$d_6$) δ 9.08-9.04 (m, 3H), 8.40-8.31 (m, 1H), 7.70-7.63 (m, 2H), 7.58-7.51 (m, 2H), 4.37 (s, 2H), 3.78-3.57 (m, 5H), 2.79-2.58 (m, 2H), 2.14-2.03 (m, 3H) | 349 |
| Example 157 | 1-[3-[4-(6-amino-3-pyridyl)anilino]-1-methyl-6,7-dihydro-4H-pyrazolo[4,3-c]pyridin-5-yl]ethanone | $^1$H NMR (400 MHz, DMSO-$d_6$) δ 8.18-7.99 (m, 2H), 7.64-7.56 (m, 1H), 7.46-7.32 (m, 4H), 6.51-6.46 (m, 1H), 5.88-5.80 (m, 2H), 4.38-4.30 (m, 2H), 3.78-3.63 (m, 2H), 3.63-3.56 (m, 3H), 2.77-2.56 (m, 2H), 2.14-2.02 (m, 3H) | 363 |
| Example 158 | 1-[1-methyl-3-[4-(5-methylsulfonyl-3-pyridyl)anilino]-6,7-dihydro-4H-pyrazolo[4,3-c]pyridin-5-yl]ethanone | $^1$H NMR (400 MHz, DMSO-$d_6$) δ 9.20-9.15 (m, 1H), 8.95-8.89 (m, 1H), 8.47-8.39 (m, 1H), 7.76-7.68 (m, 1H), 7.59-7.51 (m, 2H), 7.40-7.32 (m, 1H), 7.21-7.10 (m, 1H), 4.41-4.30 (m, 2H), 3.81-3.55 (m, 6H), 3.38 (d, J = 0.8 Hz, 3H), 2.79-2.56 (m, 1H), 2.15-2.03 (m, 3H) | 427 |

| Example | Compound Name and Structure | NMR | m/z |
|---|---|---|---|
| Example 159 | 1-[3-[4-(2-isopropoxy-3-pyridyl)anilino]-1-methyl-6,7-dihydro-4H-pyrazolo[4,3-c]pyridin-5-yl]ethanone | $^1$H NMR (400 MHz, DMSO-d$_6$) δ 8.22-8.11 (m, 1H), 8.07-8.02 (m, 1H), 7.66 (dt, J = 7.3,1.5 Hz, 1H), 7.46-7.37 (m, 4H), 7.02-6.96 (m, 1H), 5.34 (hept, J = 6.1 Hz, 1H), 4.36 (d, J = 2.8 Hz, 2H), 3.81-3.65 (m, 2H), 3.61 (d, J = 1.9 Hz, 3H), 2.78-2.57 (m, 2H), 2.15-1.99 (m, 3H), 1.29 (d, J = 6.2 Hz, 6H) | 406 |
| Example 160 | 1-[1-methyl-3-[4-(6-methyl-3-pyridyl)anilino]-6,7-dihydro-4H-pyrazolo[4,3-c]pyridin-5-yl]ethanone | $^1$H NMR (400 MHz, DMSO-d$_6$) δ 8.70-8.66 (m, 1H), 8.27-8.17 (m, 1H), 7.86 (dt, J = 8.1, 2.2 Hz, 1H), 7.57-7.39 (m, 5H), 7.29-7.23 (m, 1H), 4.36 (s, 2H), 3.78-3.66 (m, 2H), 3.61 (d, J = 2.1 Hz, 3H), 2.78-2.58 (m, 2H), 2.47 (s, 3H), 2.13-2.04 (m, 3H) | 362 |
| Example 161 | 1-[1-methyl-3-[4-(2-methyl-3-pyridyl)anilino]-6,7-dihydro-4H-pyrazolo[4,3-c]pyridin-5-yl]ethanone | Not Determined | 362 |
| Example 162 | 1-[3-[4-(2,4-dimethylpyrazol-3-yl)anilino]-1-methyl-6,7-dihydro-4H-pyrazolo[4,3-c]pyridin-5-yl]ethanone | Not Determined | 365 |

-continued

| Example | Compound Name and Structure | NMR | m/z |
|---|---|---|---|
| Example 163 | N-[5-[4-[(5-acetyl-1-methyl-6,7-dihydro-4H-pyrazolo[4,3-c]pyridin-3-yl)amino]phenyl]-2-pyridyl]acetamide | $^1$H NMR (400 MHz, DMSO-d$_6$) δ 10.45 (s, 1H), 8.59-8.52 (m, 1H), 8.21 (d, J = 20.0 Hz, 1H), 8.09 (d, J = 8.7 Hz, 1H), 7.98 (dt, J = 8.7, 2.2 Hz, 1H), 7.58-7.43 (m, 4H), 4.36 (s, 2H), 3.71 (dt, J = 21.2, 5.8 Hz, 2H), 3.64-3.57 (m, 3H), 2.77-2.57 (m, 2H), 2.08 (d, J = 13.5 Hz, 6H) | 405 |
| Example 164 | 1-[3-[4-(1-isobutylpyrazol-4-yl)anilino]-1-methyl-6,7-dihydro-4H-pyrazolo[4,3-c]pyridin-5-yl]ethanone | $^1$H NMR (400 MHz, DMSO-d$_6$) δ 8.08-7.97 (m, 1H), 7.96-7.92 (m, 1H), 7.73-7.69 (m, 1H), 7.41-7.32 (m, 4H), 4.34 (s, 2H), 3.89 (d, J = 7.2 Hz, 2H), 3.79-3.63 (m, 2H), 3.60 (d, J = 2.0 Hz, 3H), 2.77-2.56 (m, 2H), 2.19-2.01 (m, 4H), 0.86 (d, J = 6.7 Hz, 6H) | 393 |
| Example 165 | 1-[3-[4-(6-hydroxy-3-pyridyl)anilino]-1-methyl-6,7-dihydro-4H-pyrazolo[4,3-c]pyridin-5-yl]ethanone | Not Determined | 364 |
| Example 166 | 1-[1-methyl-3-[4-(4-methyl-3-pyridyl)anilino]-6,7-dihydro-4H-pyrazolo[4,3-c]pyridin-5-yl]ethanone | Not Determined | 362 |

| Example | Compound Name and Structure | NMR | m/z |
|---|---|---|---|
| Example 167 | 1-[3-[4-(2,6-dimethyl-3-pyridyl)anilino]-1-methyl-6,7-dihydro-4H-pyrazolo[4,3-c]pyridin-5-yl]ethanone | Not Determined | 376 |

Example 168

1-[1-methyl-3-[4-[1-[2-(methylamino)ethyl]pyrazol-4-yl]anilino]-6,7-dihydro-4H-pyrazolo[4,3-c]pyridin-5-yl]ethanone

Step 1 tert-butyl (2-(4-(4,4,5,5-tetramethyl-1,3,2-dioxaborolan-2-yl)-1H-pyrazol-1-yl)ethyl)carbamate

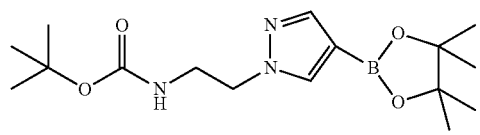 [SMILES: CC(C)(C)OC(=O)NCCn1cc(B2OC(C)(C)C(C)(C)O2)cn1]

To a solution of 4-(4,4,5,5-tetramethyl-1,3,2-dioxaborolan-2-yl)-1H-pyrazole (2 g, 10.3 mol) in MeCN (30 mL) was added tert-butyl(2-bromoethyl)carbamate (3.46 g, 15.5 mmol) and Cs$_2$CO$_3$ (10.1 g, 30.9 mmol). The mixture was heated to 60° C. for 12 h. After cooling to rt, the reaction was diluted in water (80 mL) and washed with EtOAc (80 mL×2). The combined organic layers were dried over anhydrous Na$_2$SO$_4$, filtered and concentrated in vacuo. The crude product was purified by silica gel chromatography (petroleum ether/EtOAc=8/1) to give the title compound (1.2 g, 35%) as a white solid.

Step 2 tert-butyl methyl(2-(4-(4,4,5,5-tetramethyl-1,3,2-dioxaborolan-2-yl)-1H-pyrazol-1-yl)ethyl)carbamate

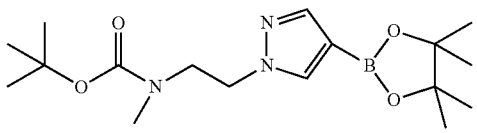 [SMILES: CN(CCn1cc(B2OC(C)(C)C(C)(C)O2)cn1)C(=O)OC(C)(C)C]

To a stirred of solution of tert-butyl (2-(4-(4,4,5,5-tetramethyl-1,3,2-dioxaborolan-2-yl)-1H-pyrazol-1-yl)ethyl)carbamate (500 mg, 1.48 mmol) in THF (10 mL) was added NaH (77 mg, 1.93 mmol) in an ice bath. After being stirred at 0° C. for 30 min, MeI (274 mg, 1.93 mmol) was added and the reaction mixture stirred at room temperature for 3 h. The reaction was quenched by water (20 ml) and extracted with EtOAc (20 mL×2). The combined organic layers were dried over Na$_2$SO$_4$, filtered and concentrated in vacuo. The crude product was purified by silica gel chromatography (petroleum ether:EtOAc=5:1) to afford the title compound (200 mg, 38%) as a white solid.

Step 3 tert-butyl (2-(4-(4-((5-acetyl-1-methyl-4,5,6,7-tetrahydro-1H-pyrazolo[4,3-c]pyridin-3-yl)amino)phenyl)-1H-pyrazol-1-yl)ethyl)(methyl)carbamate

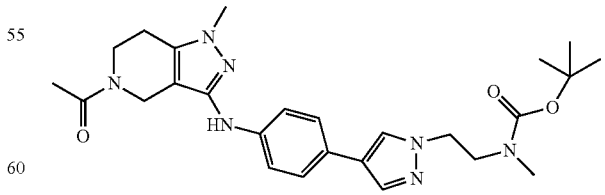

The title compound was prepared from 1-(3-((4-bromophenyl)amino)-1-methyl-6,7-dihydro-1H-pyrazolo[4,3-c]pyridin-5(4H)-yl)ethanone (Intermediate K, 201 mg, 0.57 mmol) and tert-butyl methyl(2-(4-(4,4,5,5-tetramethyl-1,3,2-dioxaborolan-2-yl)-1H-pyrazol-1-yl)ethyl)carbamate in a

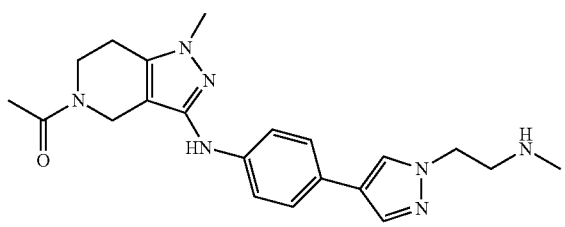 [SMILES: CNCCn1cc(-c2ccc(Nc3nn(C)c4c3CN(C(C)=O)CC4)cc2)cn1]

similar fashion to Example 105. The crude product was purified by silica gel chromatography (DCM/MeOH=20/1) to afford the title compound (110 mg, 39%) as a white solid.

Step 4

1-[1-methyl-3-[4-[1-[2-(methylamino)ethyl]pyrazol-4-yl]anilino]-6,7-dihydro-4H-pyrazolo[4,3-c]pyridin-5-yl]ethanone

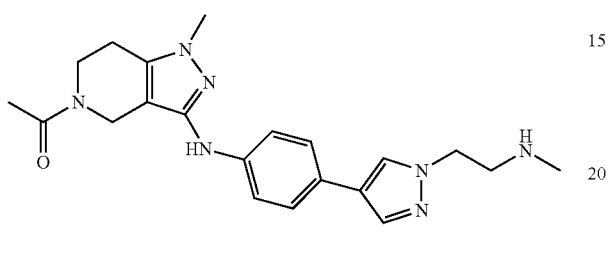

To a stirred solution of tert-butyl N-[2-[4-[4-[(5-acetyl-1-methyl-6,7-dihydro-4H-pyrazolo[4,3-c]pyridin-3-yl)amino]phenyl]pyrazol-1-yl]ethyl]-N-methyl-carbamate (100 mg, 0.2 mmol) in DCM (4 mL) was added TFA (2 mL) dropwise. The mixture was stirred at room temperature for 3 h. The mixture was concentrated in vacuo and the crude residue was purified by reverse phase chromatography (acetonitrile 27-57%/0.1% NH$_4$OH in water) to give the title compound (26 mg, 33%) as a white solid. $^1$H NMR (400 MHz, CD$_3$OD) δ 7.86 (d, J=3.6 Hz, 1H), 7.75 (d, J=2.0 Hz, 1H), 7.38 (dd, J=8.0, 8.0 Hz, 1H), 7.14 (dd, J=8.0, 8.0 Hz, 1H), 4.39-4.37 (m, 2H), 4.27 (t, J=6.0 Hz, 3H), 3.87-3.78 (m, 2H), 3.66 (s, 3H), 3.03 (t, J=6.0 Hz, 3H), 2.81-2.36 (m, 2H), 2.40 (s, 3H), 2.19-2.12 (m, 3H). LCMS M/Z (M+H) 394.

Example 169

1-[1-methyl-3-[4-(1H-pyrazol-3-yl)anilino]-6,7-dihydro-4H-pyrazolo[4,3-c]pyridin-5-yl]ethanone

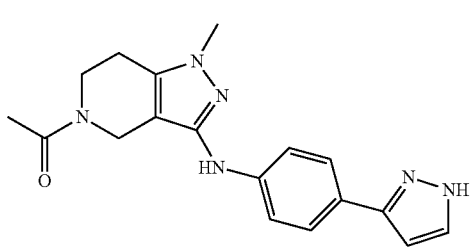 [SMILES: CC(=O)N1CCc2c(c(Nc3ccc(-c4cc[nH]n4)cc3)nn2C)C1]

The title compound was prepared from 1-(3-((4-bromophenyl)amino)-1-methyl-6,7-dihydro-1H-pyrazolo[4,3-c]pyridin-5(4H)-yl)ethanone in a similar fashion to Example 74. The crude residue was purified by reverse phase chromatography (acetonitrile 30-60%/0.1% NH$_4$OH in water) to give the title compound in 70% yield. $^1$H NMR (400 MHz, DMSO-d$_6$) δ 13.0 (s, 1H), 12.6 (s, 1H), 8.33-8.07 (m, 1H), 7.76-7.33 (m, 5H), 6.58-6.42 (m, 1H), 4.36 (s, 2H), 3.76-3.66 (m, 2H), 3.62 (s, 3H), 2.75-2.60 (m, 2H), 2.09-2.07 (m, 3H). LCMS M/Z (M+H) 337.

Example 170

1-[1-methyl-3-[4-(1-methylpyrazol-3-yl)anilino]-6,7-dihydro-4H-pyrazolo[4,3-c]pyridin-5-yl]ethanone

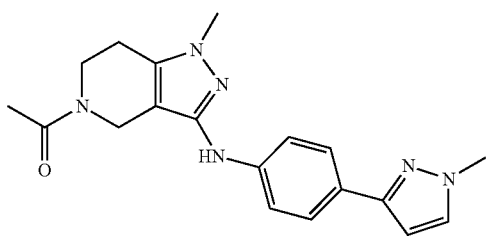 [SMILES: CC(=O)N1CCc2c(c(Nc3ccc(-c4ccn(C)n4)cc3)nn2C)C1]

The title compound was prepared from 1-(3-((4-bromophenyl)amino)-1-methyl-6,7-dihydro-1H-pyrazolo[4,3-c]pyridin-5(4H)-yl)ethanone in a similar fashion to Example 75. The crude residue was purified by reverse phase chromatography (acetonitrile 26-56%/0.1% NH$_4$OH in water) to give the title compound in 43% yield. $^1$H NMR (400 MHz, DMSO-d$_6$) δ 7.59 (dd, J=8.4, 6.0 Hz, 2H), 7.54 (dd, J=6.8, 6.0 Hz, 1H), 7.16 (dd, J=8.8, 5.2 Hz, 2H), 6.49 (dd, J=6.4, 2.4 Hz, 1H), 4.40-4.38 (m, 2H), 3.90 (s, 3H), 3.88-3.78 (m, 2H), 3.67 (s, 3H), 2.81-2.69 (m, 1H), 2.20-2.13 (m, 3H). LCMS M/Z (M+H) 351.

General Procedure for Intermediate L

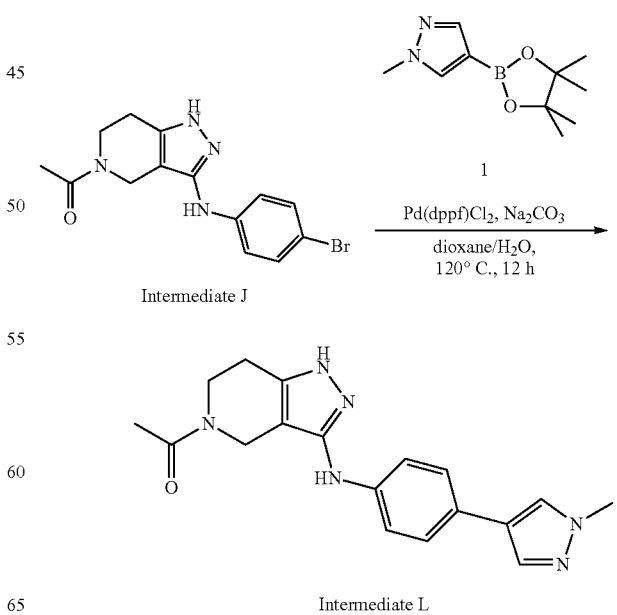

Intermediate J

Intermediate L

Step 1

1-(3-((4-(1-methyl-1H-pyrazol)amino)-6,7-dihydro-1H-pyrazolo[4,3-c]pyridin-5(4H)-yl)ethanone

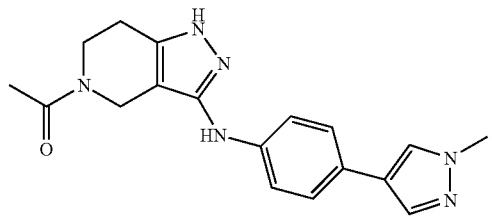 [SMILES: CC(=O)N1CCc2[nH]nc(Nc3ccc(-c4cnn(C)c4)cc3)c2C1]

To a solution of 1-[3-(4-bromoanilino)-1,4,6,7-tetrahydropyrazolo[4,3-c]pyridin-5-yl]ethanone (Intermediate J, 7.0 g, 20.88 mmol) in 1,4-dioxane (40.0 mL) and water (10.0 mL) was added 1-methyl-4-(4,4,5,5-tetramethyl-1,3,2-dioxaborolan-2-yl)pyrazole (5.21 g, 25.06 mmol), [1,1'-bis(diphenylphosphino)ferrocene]dichloropalladium(II), complex with dichloromethane (1.52 g, 2.09 mmol) and Na$_2$CO$_3$ (4.43 g, 41.77 mmol). The mixture was heated to 120° C. for 12 h. The reaction mixture was filtered, concentrated in vacuo and purified by silica gel chromatography (dichloromethane/methanol=50:1 to 10:1) to give the title compound (4.80 g, 65%) as a white solid. $^1$H NMR (400 MHz, CD$_3$OD) δ 7.80-7.79 (m, 1H), 7.69-7.68 (m, 1H), 7.38-7.34 (m, 2H), 7.12-6.97 (m, 2H), 4.40-4.39 (m, 2H), 3.89 (s, 3H), 3.88-3.77 (m, 2H), 2.82-2.69 (m, 2H), 2.19-2.12 (m, 3H). LCMS M/Z (M+H) 337.

Example 171

Preparation of 3-(5-acetyl-3-((4-(1-methyl-1H-pyrazol-4-yl)phenyl)amino)-4,5,6,7-tetrahydro-1H-pyrazolo[4,3-c]pyridin-1-yl)propanamide

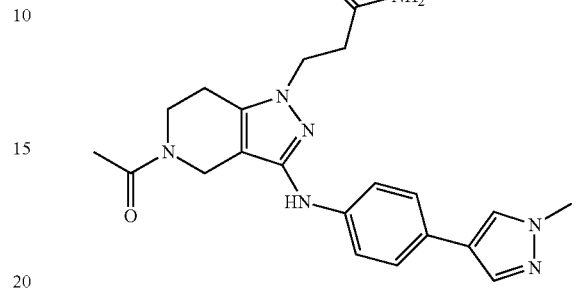

A mixture of 1-(3-((4-(1-methyl-1H-pyrazol-4-yl)phenyl)amino)-6,7-dihydro-1H-pyrazolo[4,3-c]pyridin-5(4H)-yl)ethanone (Intermediate L, 0.4 g, 1.19 mmol), 3-chloropropanamide (0.14 g, 1.31 mmol), Cs$_2$CO$_3$ (0.77 g, 2.38 mmol) in DMF (2 mL) was heated to 90° C. for 16 hours. The reaction mixture was washed with EtOAc (5 mL×3) and brine (5 mL). The combined organic layers were concentrated in vacuo and the crude residue was purified by reverse phase chromatography (acetonitrile 17-47%/0.1% NH$_4$OH in water) to give the title compound (38.3 mg, 8%) as a white solid. $^1$H NMR (400 MHz, DMSO-d$_6$) δ 8.10-8.06 (m, 1H), 7.95-7.89 (m, 1H), 7.70 (s, 1H), 7.45-7.33 (m, 4H), 6.95-6.87 (m, 1H), 6.64-6.59 (m, 1H), 4.33 (s, 1H), 4.11-4.03 (m, 3H), 3.83 (s, 3H), 3.71-3.65 (m, 2H), 2.74-2.67 (m, 2H), 2.57 (t, J=3.6 Hz, 2H), 2.08-2.06 (m, 3H). LCMS M/Z (M+H) 408.

The Following Examples 172-177 were Prepared in a Similar Fashion to Example 171

| Example | Compound Name and Structure | NMR | m/z |
| --- | --- | --- | --- |
| Example 172 | 1-(3-((4-(1-methyl-1H-pyrazol-4-yl)phenyl)amino)-1-(3,3,3-trifluoropropyl)-6,7-dihydro-1H-pyrazolo[4,3-c]pyridin-5(4H)-yl)ethanone 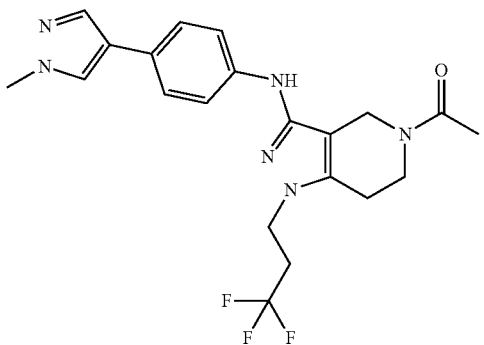 [SMILES: CN/C=C(\C=N)c1ccc(NC(=N)C2=C(NCCC(F)(F)F)CCN(C(C)=O)C2)cc1] | $^1$H NMR (400 MHz, DMSO-d$_6$) δ 8.15-8.10 (m, 1H), 7.93 (d, J = 2.4 Hz, 1H), 7.71 (d, J = 2.0 Hz, 1H), 7.41-7.34 (m, 4H), 4.43 (s, 2H), 4.13 (t, J = 6.8 Hz, 2H), 3.83 (s, 3H), 3.72-3.65 (m, 2H), 2.82-2.73 (m, 2H), 2.09-2.06 (m, 3H) | 433 |
| Example 173 | 1-(1-methyl-3-((4-(1-methyl-1H-pyrazol-4- | $^1$H NMR (400 MHz, DMSO-d$_6$) δ 8.08-8.04 (m, 1H), 7.93 (s, 1H), 7.70 (s, | 351 |

| Example | Compound Name and Structure | NMR | m/z |
|---|---|---|---|
| | yl)phenyl)amino)-6,7-dihydro-1H-pyrazolo[4,3-c]pyridin-5(4H)-yl)ethanone | 1H), 7.39-7.33 (m, 4H), 4.34 (s, 2H), 3.83 (s, 3H), 3.72-3.66 (m, 2H), 3.60 (s, 3H), 2.73-2.58 (m, 2H), 2.09-2.06 (m, 3H) | |
| Example 174 | 1-(3-((4-(1-methyl-1H-pyrazol-4-yl)phenyl)amino)-1-(2,2,2-trifluoroethyl)-6,7-dihydro-1H-pyrazolo[4,3-c]pyridin-5(4H)-yl)ethanone | $^1$H NMR (400MHz, DMSO-d$_6$) δ 8.27-8.22 (m, 1H), 7.95 (m, 1H), 7.72 (s, 1H), 7.46 (dd, J = 8.4, 8.4 Hz, 1H), 7.38 (dd, J = 8.4, 8.4 Hz, 1H), 4.89 (q, J = 9.2 Hz, 1H), 4.38 (s, 2H), 3.83 (s, 3H), 3.74-3.67 (m, 2H), 2.75-2.67 (m, 2H), 2.11-2.09 (m, 3H) | 419 |
| Example 175 | 1-(3-((4-(1-methyl-1H-pyrazol-4-yl)phenyl)amino)-1-(tetrahydrofuran-3-yl)-6,7-dihydro-1H-pyrazolo[4,3-c]pyridin-5(4H)-y)ethanone | $^1$H NMR (400 MHz, DMSO-d$_6$) δ 8.15-8.11 (m, 1H), 7.93 (s, 1H), 7.71 (s, 1H), 7.40-7.34 (m, 4H), 4.86-4.80 (m, 1H), 4.34 (s, 211), 4.03-4.00 (m, 2H), 3.86-3.81 (m, 5H), 3.73-3.67 (m, 2H), 2.76-2.64 (m, 2H), 2.26-2.21 (m, 2H), 2.09-2.06 (m, 3H) | 407 |
| Example 176 | 1-[1-[(2,2-difluorocyclopropyl)methyl]-3-[4-(1-methylpyrazol-4-yl)anilino]-6,7-dihydro-4H-pyrazolo[4,3-c]pyridin-5-yl]ethanone | $^1$H NMR (400 MHz, DMSO-d$_6$) δ 8.16-8.11 (m, 1H), 7.94 (s, 1H), 7.71 (s, 1H), 7.44-7.41 (m, 2H), 7.39-7.34 (m, 2H), 4.36 (s, 2H), 4.01 (d, J = 7.2 Hz, 2H), 3.83 (s, 3H), 3.76-3.65 (m, 2H), 2.74-2.59 (m, 2H), 2.41-2.20 (m, 1H), 2.10-2.07 (m, 3H), 1.68-1.65 (m, 1H), 1.45-1.35 (m, 1H) | 427 |

| Example | Compound Name and Structure | NMR | m/z |
|---|---|---|---|
| Example 177 | 1-[3-[4-(1-methylpyrazol-4-yl)anilino]-1-(oxetan-3-ylmethyl)-6,7-dihydro-4H-pyrazolo[4,3-c]pyridin-5-yl]ethanone 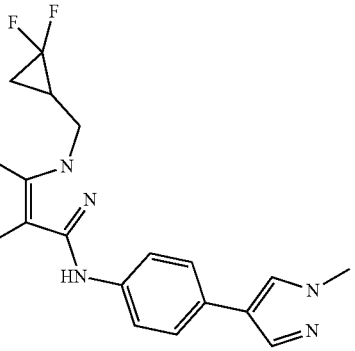 | $^1$H NMR (400 MHz, DMSO-d6) δ 8.12-8.07 (m, 1H), 7.94 (s, 1H), 7.71 (s, 1H), 7.41-7.34 (m, 4H), 4.66 (dd, J = 8.0, 6.0 Hz, 2H), 4.48 (dd, J = 9.6, 6.0 Hz, 2H), 4.34 (s, 2H), 4.17 (d, J = 7.2 Hz, 2H), 3.83 (s, 3H), 3.75-3.60 (m, 2H), 2.75-2.59 (m, 2H), 2.10-2.07 | 407 |

Examples 178 & 179

(S)-1-[3-[4-(1-methylpyrazol-4-yl)anilino]-1-tetrahydrofuran-3-yl-6,7-dihydro-4H-pyrazolo[4,3-c]pyridin-5-yl]ethanone and (R)-1-[3-[4-(1-methylpyrazol-4-yl)anilino]-1-tetrahydrofuran-3-yl-6,7-dihydro-4H-pyrazolo[4,3-c]pyridin-5-yl]ethanone

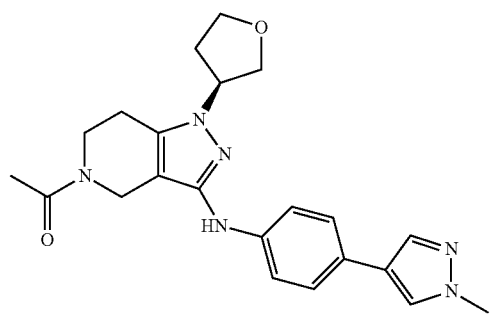

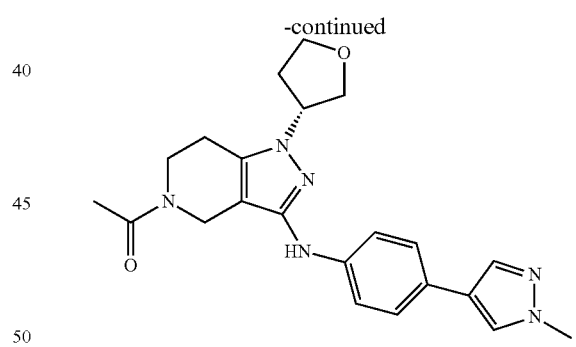

Racemic 1-[3-[4-(1-methylpyrazol-4-yl)anilino]-1-tetrahydrofuran-3-yl-6,7-dihydro-4H-pyrazolo[4,3-c]pyridin-5-yl]ethanone (35 mg) was separated using chiral SFC (Chiralpak AD 21.2×150 mm, 5 micron, mobile phase: carbon dioxide, methanol w/ 0.1% NH$_4$OH, method: isocratic at 45% B for 6 min, flow rate: 70 ml/min, pressure: 100 bar, temperature: 40° C., wavelength: 211 nm) to afford (S)-1-[3-[4-(1-methylpyrazol-4-yl)anilino]-1-tetrahydrofuran-3-yl-6,7-dihydro-4H-pyrazolo[4,3-c]pyridin-5-yl]ethanone (12.2 mg, first peak) and (R)-1-[3-[4-(1-methylpyrazol-4-yl)anilino]-1-tetrahydrofuran-3-yl-6,7-dihydro-4H-pyrazolo[4,3-c]pyridin-5-yl]ethanone (9.3 mg, second peak). Absolute configuration was arbitrarily assigned to each enantiomer.

Example 178: $^1$H NMR (400 MHz, DMSO-d$_6$) δ 8.17-8.07 (m, 1H), 7.96-7.92 (m, 1H), 7.73-7.70 (m, 1H), 7.42-7.33 (m, 4H), 4.88-4.78 (m, 1H), 4.34 (s, 2H), 4.08-3.96 (m, 2H), 3.90-3.63 (m, 7H), 2.82-2.60 (m, 2H), 2.35-2.19 (m, 2H), 2.13-2.05 (m, 3H). LCMS M/Z (M+H) 407. Example 179: ¹H NMR (400 MHz, DMSO-d₆) δ 8.16-8.08 (m, 1H), 7.95-7.92 (m, 1H), 7.73-7.69 (m, 1H), 7.42-7.33 (m, 4H), 4.89-4.78 (m, 1H), 4.34 (s, 2H), 4.07-3.96 (m, 2H), 3.90-3.64 (m, 7H), 2.80-2.60 (m, 2H), 2.29-2.17 (m, 2H), 2.13-2.03 (m, 3H). LCMS M/Z (M+H) 407.

Example 180

1-(3-((4-(1-methyl-1H-pyrazol-4-yl)phenyl)amino)-1-(2-(methylsulfonyl)ethyl)-6,7-dihydro-1H-pyrazolo[4,3-c]pyridin-5(4H)-yl)ethanone

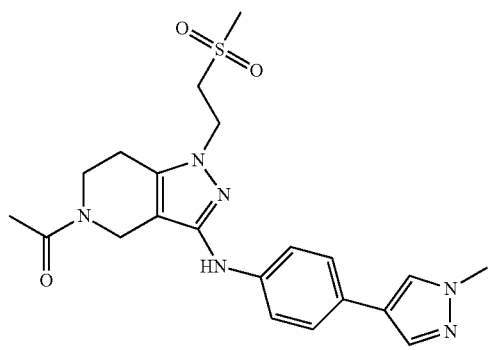 [SMILES: CC(=O)N1CCc2c(c(Nc3ccc(-c4cnn(C)c4)cc3)nn2CCS(C)(=O)=O)C1]

To a solution of 1-(3-((4-(1-methyl-1H-pyrazol-4-yl)phenyl)amino)-6,7-dihydro-1H-pyrazolo[4,3-c]pyridin-5(4H)-yl)ethanone (Intermediate L, 0.20 g, 0.595 mmol) and DBU (0.18 g, 1.19 mmol) in MeCN (2 mL) was added (methylsulfonyl)ethane (0.095 g, 0.892 mmol) and the reaction mixture was heated to 90° C. for 16 h. The reaction mixture was concentrated in vacuo and washed with EtOAc (5 mL×3) and brine (5 mL). The combined organic layers were dried over anhydrous MgSO₄ and concentrated in vacuo. The crude residue was purified by reverse phase chromatography (acetonitrile 5-35%/0.1% NH₄OH in water) to give the title compound (2 mg, 1%) as a white solid. ¹H NMR (400 MHz, DMSO-d₆) δ 8.19-8.14 (m, 1H), 7.93 (s, 1H), 7.70 (s, 1H), 7.42 (dd, J=8.4, 8.4 Hz, 2H), 7.37 (dd, J=8.4, 8.4 Hz, 2H), 4.35 (s, 2H), 4.30 (t, J=6.8 Hz, 2H), 3.83 (s, 3H), 3.72-3.66 (m, 2H), 3.63 (t, J=6.8 Hz, 2H), 2.89 (s, 3H), 2.77-2.66 (m, 2H), 2.10-2.07 (m, 3H). LCMS M/Z (M+H) 443.

Example 181

1-[1-[(2-fluorocyclopropyl)methyl]-3-[4-(1-methylpyrazol-4-yl)anilino]-6,7-dihydro-4H-pyrazolo[4,3-c]pyridin-5-yl]ethanone

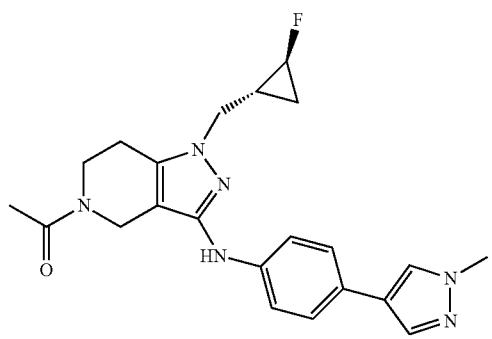 [SMILES: CC(=O)N1CCc2c(c(Nc3ccc(-c4cnn(C)c4)cc3)nn2C[C@H]2C[C@@H]2F)C1]

Step 1

((1R, 2S)-2-fluorocyclopropyl)methanol

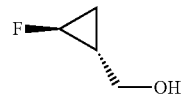

To a stirred solution of (1R, 2S)-ethyl 2-fluorocyclopropanecarboxylate (1 g, 7.57 mmol) in THF (20 mL) was added LiAlH₄ (862 mg, 22.7 mmol) in an ice bath and the mixture was stirred at room temperature for 12 h. The reaction was quenched with water (1 mL) and 1N NaOH (1 mL) and dried over anhydrous Na₂SO₄. The mixture was filtered and concentrated in vacuo to afford the title compound (0.8 g, crude) as a light yellow oil.

Step 2

((1R, 2S)-2-fluorocyclopropyl)methyl methanesulfonate

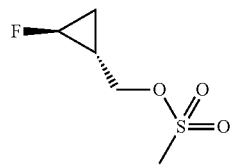

To a stirred solution of ((1R,2S)-2-fluorocyclopropyl)methanol (400 mg, 2.24 mol) and TEA (681 mg, 6.73 mmol) in DCM at 0° C. (8 mL) was added MsCl (379 mg, 3.37 mmol). The mixture was stirred at room temperature for 12 h. The reaction was quenched with water (20 mL), washed with DCM (20 mL×2) and the combined organic layers were dried over anhydrous Na₂SO₄. The solution was concentrated in vacuo to give the title compound (300 mg, 52%) as a light yellow oil.

Step 3

1-[1-[(2-fluorocyclopropyl)methyl]-3-[4-(1-methylpyrazol-4-yl)anilino]-6,7-dihydro-4H-pyrazolo[4,3-c]pyridin-5-yl]ethanone

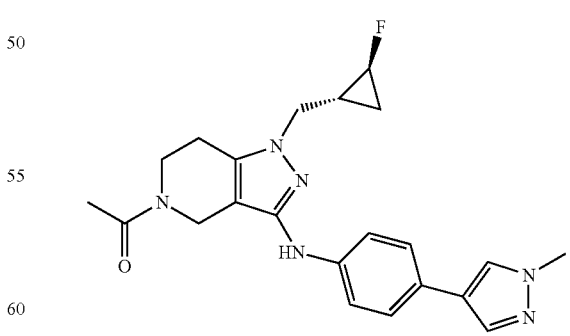

To a stirred solution of 1-(3-((4-(1-methyl-1H-pyrazol-4-yl)phenyl)amino)-6,7-dihydro-1H-pyrazolo[4,3-c]pyridin-5(4H)-yl)ethanone (Intermediate L, 200 mg, 0.59 mol) in DMF (5 mL), was added ((1R,2S)-2-fluorocyclopropyl)methyl methanesulfonate (150 mg, 0.89 mmol) and Cs₂CO₃

(581 mg, 1.81 mmol). The mixture was heated to 100° C. for 12 hours. After cooling to rt, the reaction mixture was diluted in water (40 mL) and washed with EtOAc (40 mL×2). The combined organic layers were dried over anhydrous $Na_2SO_4$, filtered and concentrated in vacuo. The crude residue was purified by reverse phase chromatography (acetonitrile 40-60%/0.2% formic acid in water) to give the title compound (15 mg, 6%) as a white solid. $^1$H NMR (400 MHz, $CD_3OD$) δ 7.81 (d, J=3.2 Hz, 1H), 7.71 (d, J=2.4 Hz, 1H), 7.41-7.37 (m, 2H), 7.21-7.17 (m, 2H), 4.71-4.55 (m, 1H), 4.42-4.41 (m, 2H), 3.91 (s, 3H), 3.87-3.80 (m, 4H), 2.84-2.72 (m, 2H), 2.21-2.15 (m, 3H), 1.73-1.69 (m, 1H), 1.13-1.07 (m, 1H), 0.74-1.69 (m, 1H). LCMS M/Z (M+H) 409.

Example 182

1-[1-[(1-methylcyclopropyl)methyl]-3-[4-(1-methyl-pyrazol-4-yl)anilino]-6,7-dihydro-4H-pyrazolo[4,3-c]pyridin-5-yl]ethanone

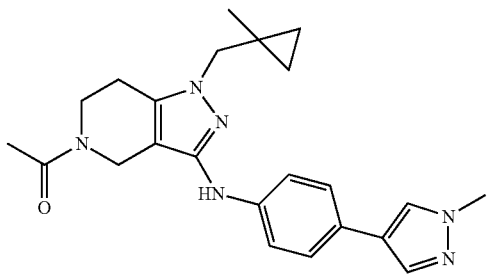 [SMILES: CC(=O)N1CCc2c(c(Nc3ccc(-c4cnn(C)c4)cc3)nn2CC2(C)CC2)C1]

The title compound was prepared from 1-(3-((4-(1-methyl-1H-pyrazol-4-yl)phenyl)amino)-6,7-dihydro-1H-pyrazolo[4,3-c]pyridin-5(4H)-yl)ethanone (Intermediate L) and (1-methylcyclopropyl)methyl methanesulfonate in a similar fashion to Example 183. The crude residue was purified by reverse phase chromatography (acetonitrile 40-60%/0.2% formic acid in water) to give the title compound in 6% yield. $^1$H NMR (400 MHz, $CD_3OD$) δ 7.83 (d, J=3.6 Hz, 1H), 7.72 (d, J=2.8 Hz, 1H), 7.41-4.37 (m, 2H), 7.19 (dd, J=8.0, 8.0 Hz, 2H), 4.43 (s, 2H), 3.92 (m, 3H), 3.90-3.82 (m, 4H), 2.87-2.75 (m, 2H), 2.23-2.17 (m, 3H), 1.05 (s, 3H), 0.66-0.64 (m, 2H), 0.44-0.41 (m, 2H). LCMS M/Z (M+H) 405.

Example 183

1-(1-allyl-3-((4-(1-methyl-1H-pyrazol-4-yl)phenyl)amino)-6,7-dihydro-1H-pyrazolo[4,3-c]pyridin-5(4H)-yl)ethanone

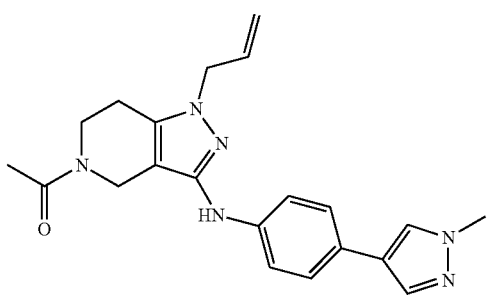 [SMILES: C=CCn1nc(Nc2ccc(-c3cnn(C)c3)cc2)c2c1CCN(C(C)=O)C2]

The title compound was prepared from 1-(3-((4-(1-methyl-1H-pyrazol-4-yl)phenyl)amino)-6,7-dihydro-1H-pyrazolo[4,3-c]pyridin-5(4H)-yl)ethanone (Intermediate L) and bromocyclopropane in a similar fashion to Example 87. The crude residue was purified by reverse phase chromatography (acetonitrile 27-57%/0.2% formic acid in water) to give the title compound in 4% yield. $^1$H NMR (400 MHz, $CD_3OD$) δ 7.81 (d, J=3.2 Hz, 1H), 7.70 (d, J=2.0 Hz, 1H), 7.39-7.35 (m, 2H), 7.17-7.13 (m, 2H), 6.02-5.95 (m, 1H), 5.19 (d, J=10.8 Hz, 1H), 5.03 (d, J=16.8 Hz, 1H), 4.60 (s, 2H), 4.40 (d, J=4.8 Hz, 2H), 3.90 (s, 3H), 3.87-3.78 (m, 2H), 2.80-2.67 (m, 2H), 2.20-2.14 (m, 3H). LCMS M/Z (M+H) 377.

Example 184

3-(5-acetyl-3-((4-(1-methyl-1H-pyrazol-4-yl)phenyl)amino)-4,5,6,7-tetrahydro-1H-pyrazolo[4,3-c]pyridin-1-yl)propanenitrile

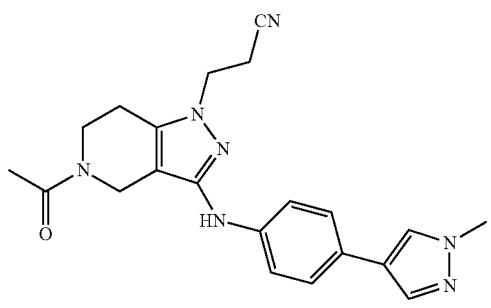 [SMILES: CC(=O)N1CCc2c(c(Nc3ccc(-c4cnn(C)c4)cc3)nn2CCC#N)C1]

The title compound was prepared from 1-(3-((4-(1-methyl-1H-pyrazol-4-yl)phenyl)amino)-6,7-dihydro-1H-pyrazolo[4,3-c]pyridin-5(4H)-yl)ethanone (Intermediate L) and acrylonitrile in a similar fashion to Example 182. The crude residue was purified by reverse phase chromatography (acetonitrile 1742%/0.05% HCl in water) to give the title compound in 5% yield. $^1$H NMR (400 MHz, DMSO-$d_6$) δ 8.07 (s, 1H), 7.86 (s, 1H), 7.45 (dd, J=8.4, 8.4 Hz, 2H), 7.39 (dd, J=8.4, 8.4 Hz, 2H), 4.41-4.36 (m, 2H), 4.17 (t, J=6.4 Hz, 2H), 3.87 (s, 3H), 3.73-3.68 (m, 2H), 2.77-2.66 (m, 2H), 2.09-2.07 (m, 3H). LCMS M/Z (M+H) 390.

Example 185

1-(3-((4-(1H-pyrazol-4-yl)phenyl)amino)-1-methyl-6,7-dihydro-1H-pyrazolo[4,3-c]pyridin-5(4H)-yl)ethanone

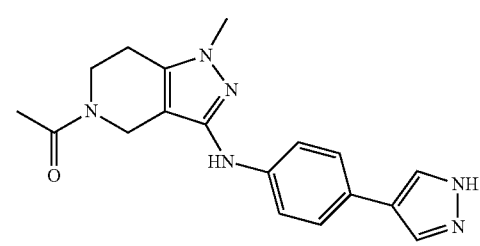 [SMILES: CC(=O)N1CCc2c(c(Nc3ccc(-c4cn[nH]c4)cc3)nn2C)C1]

Step 1 tert-butyl 4-(4-((5-acetyl-1-methyl-4,5,6,7-tetra-hydro-1H-pyrazolo[4,3-c]pyridin-3-yl)amino)phenyl)-1H-pyrazole-1-carboxylate

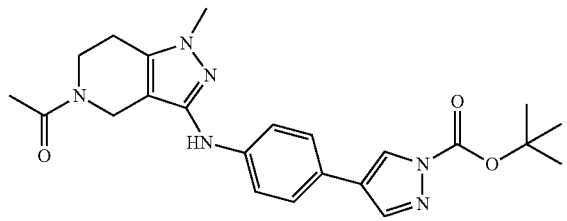 [SMILES: CC(=O)N1CCc2c(c(Nc3ccc(-c4cnn(C(=O)OC(C)(C)C)c4)cc3)nn2C)C1]

To a solution of 1-(3-((4-bromophenyl)amino)-1-methyl-6,7-dihydro-1H-pyrazolo[4,3-c]pyridin-5 (4H)-yl)ethanone (Intermediate K, 500 mg, 1.43 mmol) in dioxane (12 mL) and H$_2$O (3 mL) was added Na$_2$CO$_3$ (303 mg, 2.86 mmol), [1,1'-bis(diphenylphosphino)ferrocene]dichloropalladium (II), complex with dichloromethane (103 mg, 0.14 mmol) and tert-butyl 4-(4,4,5,5-tetramethyl-1,3,2-dioxaborolan-2-yl)-1H-pyrazole-1-carboxylate (630 mg, 2.14 mmol). After being purged with nitrogen atmosphere for 1 min, the reaction mixture was heated to 110° C. for 18 h. The mixture was evaporated to dryness and the crude compound was purified by silica gel chromatography (DCM:MeOH=20:1) to give the title compound (500 mg, 80% yield) as a brown solid.

Step 2

1-(3-((4-(1H-pyrazol-4-yl)phenyl)amino)-1-methyl-6,7-dihydro-1H-pyrazolo[4,3-c]pyridin-5(4H)-yl)ethanone

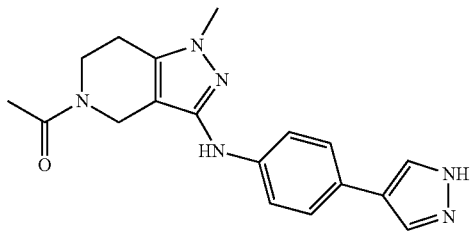 [SMILES: CC(=O)N1CCc2c(c(Nc3ccc(-c4cn[nH]c4)cc3)nn2C)C1]

To a solution of tert-butyl 4-(4-((5-acetyl-1-methyl-4,5,6,7-tetrahydro-1H-pyrazolo[4,3-c]pyridin-3-yl)amino) phenyl)-1H-pyrazole-1-carboxylate (500 mg, 0.24 mmol) in DCM (2 mL), was added TFA (2 mL) dropwise. The reaction mixture was stirred at room temperature for 2 h. The mixture was concentrated in vacuo and purified by reverse phase chromatography (acetonitrile 18-48%/0.1% NH$_4$OH in water) to give the title compound (24.2 mg, 6%) as a white solid. $^1$H NMR (400 MHz, DMSO-d$_6$) δ 12.76 (br s, 1H), 8.06-8.01 (m, 1H), 7.98 (br s, 1H), 7.79 (br s, 1H), 7.46-7.33 (m, 4H), 4.34 (s, 2H), 3.75-3.64 (m, 2H), 3.60 (s, 3H), 2.73-2.56 (m, 2H), 2.09-2.06 (m, 3H). LCMS M/Z (M+H) 337.

Example 186

1-[3-[4-[1-[2-(dimethylamino)ethyl]pyrazol-4-yl]anilino]-1-methyl-6,7-dihydro-4H-pyrazolo[4,3-c]pyridin-5-yl]ethanone

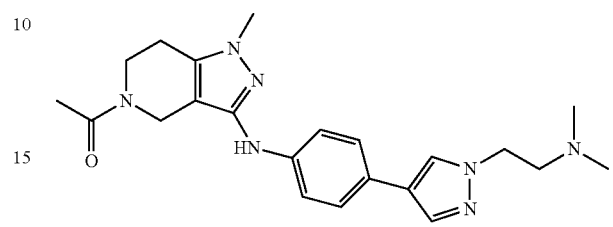

To a solution of 1-[1-methyl-3-[4-(1H-pyrazol-4-yl)anilino]-6,7-dihydro-4H-pyrazolo[4,3-c]pyridin-5-yl]ethanone (Example 187, 100 mg, 0.30 mmol) in DMF (2.0 mL) was added 2-bromo-N,N-dimethylethanamine (86 mg, 0.60 mmol) and Cs$_2$CO$_3$ (200 mg, 0.60 mmol). The reaction mixture was heated to 120° C. for 24 h. The crude residue was purified by reverse phase chromatography (acetonitrile 22-42%/0.1% NH$_4$OH in water) to give the title compound (41 mg, 34% yield) as a white solid. $^1$H NMR (400 MHz, DMSO-d$_6$) δ 8.07-8.03 (m, 1H), 7.97 (s, 1H), 7.70 (s, 1H), 7.39-7.32 (m, 4H), 4.34 (s, 2H), 4.17 (t, J=6.4 Hz, 2H), 3.74-3.60 (m, 1H), 2.73-2.63 (m, 2H), 2.17 (s, 6H), 2.09-2.06 (m, 3H). LCMS M/Z (M+H) 408.

Example 187

1-[3-[4-[1-(2-hydroxyethyl)pyrazol-4-yl]anilino]-1-methyl-6,7-dihydro-4H-pyrazolo[43-c]pyridin-5-yl]ethanone

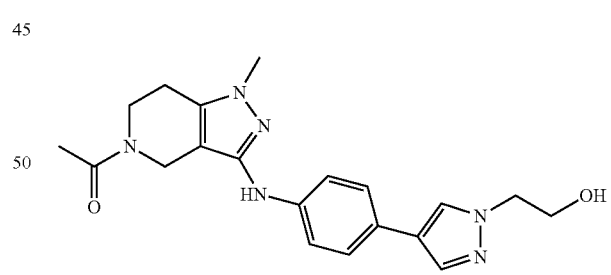

The title compound was prepared from 1-[1-methyl-3-[4-(H-pyrazol-4-yl)anilino]-6,7-dihydro-4H-pyrazolo[4,3-c]pyridin-5-yl]ethanone (Example 186) and 2-bromoethanol in a similar fashion to Example 188. The crude residue was purified by reverse phase chromatography (acetonitrile 21-41%/0.1% NH$_4$OH in water) to give the title compound in 6% yield. $^1$H NMR (400 MHz, DMSO-d$_6$) δ 7.87 (s, 1H), 7.74 (s, 1H), 7.40-7.33 (m, 2H), 7.15-7.11 (m, 2H), 4.39-4.37 (m, 2H), 4.23 (t, J=5.6 Hz, 2H), 3.93-3.85 (m, 4H), 3.66-3.65 (m, 3H), 2.81-2.68 (m, 2H), 2.19-2.12 (m, 3H). LCMS M/Z (M+H) 381.

General Procedure for Intermediate M

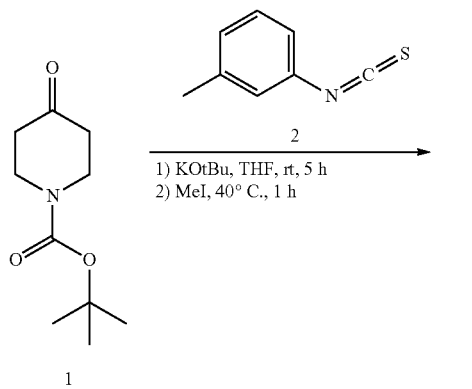

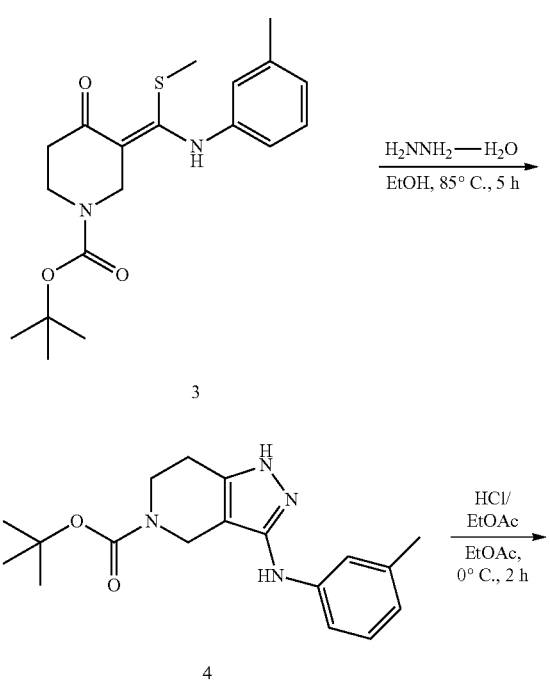

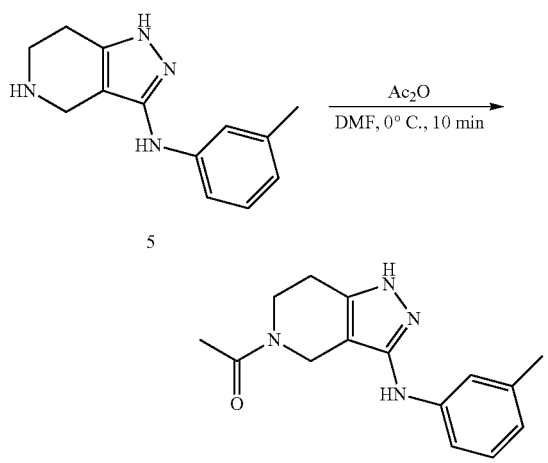

Step 1

(Z)-tert-butyl 3-((methylthio)(m-tolylamino)methylene)-4-oxopiperidine-1-carboxylate

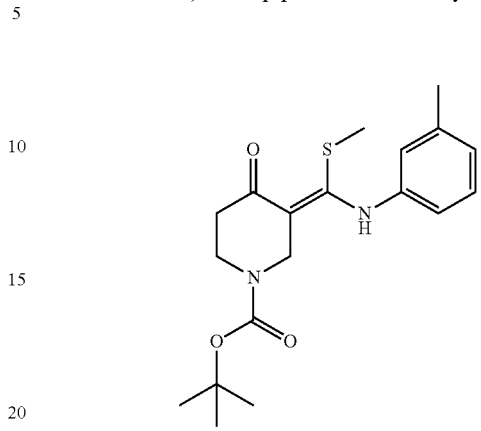

To a solution of tert-butyl 4-oxopiperidine-1-carboxylate (9.0 g, 45.17 mmol) in anhydrous THF (100 mL) was added t-BuOK (6.1 g, 54.20 mmol) portionwise. The reaction mixture was allowed to stir at room temperature for 5 h before being warmed to 40° C. A solution of 1-isothiocyanato-3-methylbenzene (8.1 g, 54.20 mmol) in anhydrous THF (50 mL) was added dropwise and stirred for an additional 2 h at this temperature before MeI (19.23 g, 135.51 mmol) was added dropwise. The reaction mixture was stirred for another 1 h. After cooling to room temperature, the mixture was poured into water (100 mL) and extracted with EtOAc (3×100 mL). The combined organic layers were dried over anhydrous $Na_2SO_4$, filtered and concentrated in vacuo. The residue was purified by silica gel chromatography (petroleum ether/EtOAc=10/1 to 5/1) to afford the title compound (9.5 g, 58%) as a yellow oil.

Step 2 tert-butyl 3-(m-tolylamino)-6,7-dihydro-1H-pyrazolo[4,3-c]pyridine-5(4H)-carboxylate

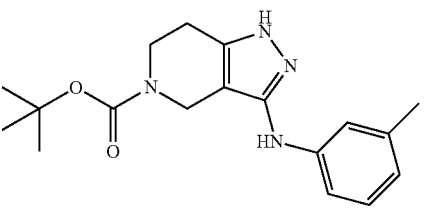 [SMILES: Cc1cccc(Nc2n[nH]c3c2CN(C(=O)OC(C)(C)C)CC3)c1]

To a solution of (Z)-tert-butyl 3-((methylthio)(m-tolylamino)methylene)-4-oxopiperidine-1-carboxylate (9.5 g, 26.21 mmol) in EtOH (50 mL) was added hydrazine hydrate (1.7 g, 28.83 mmol). The reaction was heated to reflux for 2 h. The solvent was removed and the residue was extracted with DCM (50 mL×3) and washed with water (50 mL). The combined organic layers were dried over anhydrous $Na_2SO_4$, filtered and concentrated in vacuo. The residue was purified by silica gel chromatography (petroleum ether/EtOAc=3/1 to 1/1) to afford the title compound (5.8 g, 67%) as a yellow solid.

Step 3

N-(m-tolyl)-4,5,6,7-tetrahydro-1H-pyrazolo[4,3-c]pyridin-3-amine

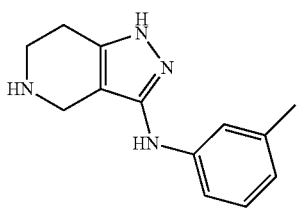 [SMILES: Cc1cccc(Nc2n[nH]c3c2CNCC3)c1]

To a solution of tert-butyl 3-(m-tolylamino)-6,7-dihydro-1H-pyrazolo[4,3-c]pyridine-5(4H)-carboxylate (5.8 g, 17.66 mmol) in EtOAc at 0° C. (30 mL) was added HCl/EtOAc (20 mL) dropwise. The reaction was allowed to stir at room temperature for 2 h. The mixture was concentrated in vacuo to afford the title compound (8.5 g, DCM:MeOH=20:1) as a yellow solid that required no further purification. LCMS M/Z (M+H) 229.

Step 4

1-(3-(m-tolylamino)-6,7-dihydro-1H-pyrazolo[4,3-c]pyridin-5(4H)-yl)ethanone

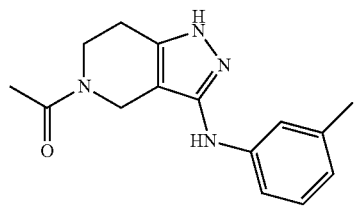 [SMILES: CC(=O)N1CCc2[nH]nc(Nc3cccc(C)c3)c2C1]

To a solution of N-(m-tolyl)-4,5,6,7-tetrahydro-1H-pyrazolo[4,3-c]pyridin-3-amine (8.5 g) and TEA (5.36 g, 52.96 mmol) in DMF (30 mL) at 0° C. was added a solution of Ac₂O (1.8 g, 17.65 mmol) in DMF (5 mL) dropwise. The reaction mixture was stirred at 0° C. for 10 min and quenched by the addition of brine (50 mL). The mixture was extracted with EtOAc (3×30 mL). The combined organic layers were dried over anhydrous Na₂SO₄ and concentrated in vacuo. The crude residue was purified by silica gel chromatography (DCM/MeOH=50/1 to 20/1) to afford the title compound (3.7 g, 77%, two steps) as a white solid. ¹H NMR (400 MHz, CD₃OD) δ 8.62-8.53 (m, 1H), 7.46-7.42 (m, 2H), 7.09 (dd, J=7.6, 7.6 Hz, 1H), 6.64-6.62 (m, 1H), 4.37-4.27 (m, 2H), 3.66-3.59 (m, 2H), 2.99-2.87 (m, 2H), 2.22 (s, 3H), 2.06 (s, 3H). LCMS M/Z (M+H) 271.

Example 188

1-(1-(2-methoxyethyl)-3-(m-tolylamino)-6,7-dihydro-1H-pyrazolo[4,3-c]pyridin-5(4H)-yl)ethanone

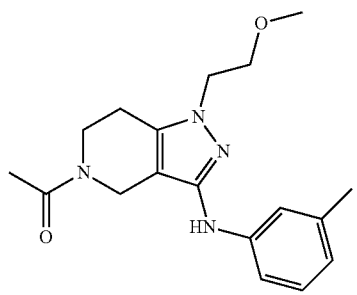 [SMILES: COCCn1nc(Nc2cccc(C)c2)c2c1CCN(C(C)=O)C2]

To a solution of 1-(3-(m-tolylamino)-6,7-dihydro-1H-pyrazolo[4,3-c]pyridin-5(4H)-yl)ethanone (Intermediate M, 200 mg, 0.74 mmol) and Cs₂CO₃ (481 mg, 1.48 mmol) in DMF (4 mL) was added chloro-2-methoxyethane (73.5 mg, 0.77 mmol). The mixture was heated to 80° C. for 2 h. The reaction mixture was filtered and concentrated in vacuo. The crude residue was purified by reverse phase chromatography (acetonitrile 1-28%/0.2% formic acid in water) to give the title compound (49 mg, 20%) as a white solid. ¹H NMR (400 MHz, T=80° C., DMSO-d₆) δ 7.67 (br s, 1H), 7.14-7.01 (m, 3H), 6.54 (d, J=7.2 Hz, 1H), 4.32 (s, 2H), 4.05-4.02 (m, 2H), 3.75-3.63 (m, 4H), 3.25 (s, 3H), 2.71 (br s, 2H), 2.23 (s, 3H), 2.08 (s, 3H). LCMS M/Z (M+H) 329.

The Following Examples 189-207 were Prepared in a Similar Fashion to Example 188

| Example | Compound Name and Structure | NMR | m/z |
|---|---|---|---|
| Example 189 | 1-(1-(oxazol-5-ylmethyl)-3-(m-tolylamino)-6,7-dihydro-1H-pyrazolo[4,3-c]pyridin-5(4H)-yl)ethanone 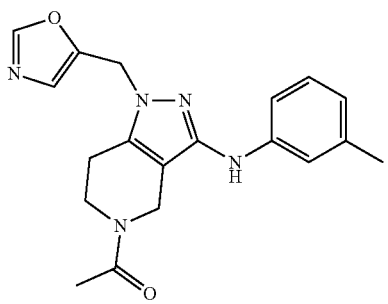 [SMILES: CC(=O)N1CCc2c(c(Nc3cccc(C)c3)nn2Cc2cnco2)C1] | ¹H NMR (400 MHz, T = 80° C., DMSO-d₆) δ 8.23 (s, 1H), 7.73 (br s, 1H), 7.12-7.10 (m, 3H), 7.05-7.01 (m, 1H), 6.54 (d, J = 6.8 Hz, 1H), 5.23 (s, 2H), 4.32 (s, 2H), 3.72 (br s, 2H), 2.76 (br s, 2H), 2.23 (s, 3H), 2.08 (s, 3H) | 352 |

-continued

| Example | Compound Name and Structure | NMR | m/z |
|---|---|---|---|
| Example 190 | 2-(5-acetyl-3-(m-tolylamino)-4,5,6,7-tetrahydro-1H-pyrazolo[4,3-c]pyridin-1-yl)-N-ethylacetamide | $^1$H NMR (400 MHz, T = 80° C., DMSO-$d_6$) δ 7.71 (br s, 2H), 7.15-7.01 (m, 3H), 6.54 (d, J = 7.8 Hz, 1H), 4.52 (s, 2H), 4.34 (s, 2H), 3.71 (br s, 2H), 3.17-3.11 (m, 2H), 2.70 (br s, 2H), 2.24 (s, 3H), 2.09 (s, 3H), 1.06 (t, J = 7.4 Hz, 3H) | 356 |
| Example 191 | 1-[3-(3-methylanilino)-1-(2-phenylethyl)-6,7-dihydro-4H-pyrazolo[4,3-c]pyridin-5-yl]ethanone | $^1$H NMR (400 MHz, DMSO-$d_6$) δ 7.72 (s, 1H), 7.21-7.11 (m, 4H), 7.10-6.94 (m, 1H), 6.55-6.52 (m, 1H), 6.38-6.31 (m, 2H), 4.11-4.02 (m, 4H), 3.71-3.63 (m, 2H), 3.15 (d, J = 5.2 Hz, 1H), 2.96 (t, J = 8.0 Hz, 2H), 2.67 (t, J = 8.0 Hz, 1H), 2.60-2.51 (m, 1H), 2.17 (s, 3H), 2.04 (s, 3H) | 375 |
| Example 192 | 1-(1-(2-(pyridin-2-yl)ethyl)-3-(m-tolylamino)-6,7-dihydro-1H-pyrazolo[4,3-c]pyridin-5(4H)-yl)ethanone | $^1$H NMR (400 MHz, DMSO-$d_6$) δ 8.5 (s, 1H), 7.90 (m, 1H), 7.70-7.60 (m, 1H), 7.25-7.06 (m, 6H), 6.53-6.45 (m, 1H), 4.34-4.21 (m, 4H), 3.64-3.52 (m, 2H), 3.19-3.11 (m, 2H), 2.47-2.42 (m, 1H), 2.38-2.31 (m, 1H), 2.22 (s, 3H), 2.04 (s, 3H) | 376 |

-continued

| Example | Compound Name and Structure | NMR | m/z |
|---|---|---|---|
| Example 193 | 1-[3-(3-methylanilino)-1-[2-(4-pyridyl)ethyl]-6,7-dihydro-4H-pyrazolo[4,3-c]pyridin-5-yl]ethanone | $^1$H NMR (400 MHz, DMSO-$d_6$) δ 8.42-8.41 (m, 2H), 7.99 (s, 1H), 7.07-7.01 (m, 5 H), 6.54- 6.51 (m, 1H), 4.28 (s, 2H), 4.16-4.13 (m, 2H), 3.60-3.50 (m, 2H), 3.05 (t, J = 6.8 Hz, 2H), 2.39-2.32 (m, 1H), 2.22 (s, 3H), 2.03 (s, 3H) | 376 |
| Example 194 | 2-(5-acetyl-3-(m-tolylamino)-4,5,6,7-tetrahydro-1H-pyrazolo[4,3-c]pyridin-1-yl)-N-methylacetamide | $^1$H NMR (400 MHz, T = 80° C., DMSO-$d_6$) δ 7.71 (br s, 1H), 7.61 (br s, 1H), 7.15-7.01 (m, 3H), 6.54 (d, J = 7.2 Hz, 1H), 4.52 (s, 2H), 4.33 (s, 2H), 3.70 (br s, 2H), 2.75-2.55 (m, 5 H), 2.23 (s, 3H), 2.08 (s, 3H) | 342 |
| Example 195 | 1-[3-(3-methylanilino)-1-(2-pyridylmethyl)-6,7-dihydro-4H-pyrazolo[4,3-c]pyridin-5-yl]ethanone | $^1$H NMR (400 MHz, T = 80° C., DMSO-$d_6$) δ 8.52-8.51 (m, 1H), 7.76 -7.68 (m, 2H), 7.28-7.27 (m, 1H), 7.15-6.99 (m, 4H), 6.52 (d, J = 7.2 Hz), 5.21 (s, 2H), 4.34 (s, 2H), 3.70 (br s, 2H), 2.71 (br s, 2H), 2.21 (s, 3H), 2.07 (s, 3H) | 362 |
| Example 196 | 1-[3-(3-methylanilino)-1-(3-pyridylmethyl)-6,7-dihydro-4H-pyrazolo[4,3-c]pyridin-5-yl]ethanone | $^1$H NMR (400 MHz, T = 80° C., DMSO-$d_6$) δ 8.48 (m, 2H), 8.14 (br s, 1H), 7.75 (br s, 1H), 7.62-7.61 (m, 1H), 7.36-7.33 (m, 1H), 7.11 (s, 2H), 7.04-7.00 (m, 1H), 6.53 (d, J = | 362 |

| Example | Compound Name and Structure | NMR | m/z |
|---|---|---|---|
| | | 7.2 Hz, 1H), 5.17 (s, 2H), 4.34 (s, 2H), 3.70 (br s, 2H), 2.72 (br s, 2H), 2.22 (s, 3H), 2.07 (s, 3H) | |
| Example 197 | 1-[3-(3-methylanilino)-1-(1-phenylethyl)-6,7-dihydro-4H-pyrazolo[4,3-c]pyridin-5-yl]ethanone | $^1$H NMR (400 MHz, T = 80° C., DMSO-$d_6$) δ 7.71 (br s, 1H), 7.34-7.24 (m, 5 H), 7.15-7.07 (m, 2H), 7.05-7.04 (m, 3H), 6.54 (d, J = 7.2 Hz, 1H), 5.43-5.38 (m, 1H), 4.38-4.26 (m, 2H), 3.65 (br s, 2H), 2.75 (br s, 2H), 2.24 (s, 3H), 2.05 (s, 3H), 1.80 (d, J = 6.8 Hz, 3H) | 375 |
| Example 198 | 1-[1-methyl-3-(3-methylanilino)-6,7-dihydro-4H-pyrazolo[4,3-c]pyridin-5-yl]ethanone | $^1$H NMR (400 MHz, T = 80° C., DMSO-$d_6$) δ 7.62 (br s, 1H), 7.12-7.01 (m, 3H), 6.53 (d, J = 7.2 Hz, 1H), 4.31 (s, 2H), 3.71 (br s, 2H), 3.60 (s, 3H), 2.67 (br s, 2H), 2.23 (s, 3H), 2.07 (br s, 3H) | 285 |
| Example 199 | 1-[1-ethyl-3-(3-methylanilino)-6,7-dihydro-4H-pyrazolo[4,3-c]pyridin-5-yl]ethanone | $^1$H NMR (400 MHz, T = 80° C., DMSO-$d_6$) δ 7.63 (br s, 1H), 7.12-7.01 (m, 3H), 6.53 (d, J = 7.2 Hz, 1H), 4.32 (s, 2H), 3.95-3.89 (m, 2H), 3.72 (br s, 2H), 2.71 (br s, 2H), 2.24 (s, 3H), 2.08 (br s, 3H), 1.32 (t, J = 7.4 Hz, 3H) | 299 |
| Example 200 | 1-[1-isopropyl-3-(3-methylanilino)-6,7-dihydro-4H-pyrazolo[4,3-c]pyridin-5-yl]ethanone | $^1$H NMR (400 MHz, T = 80° C., DMSO-$d_6$) δ 7.64 (br s, 1H), 7.08 (s, 2H), 7.05-7.01 (m, 1H), 6.52 (d, J = 7.2 Hz, 1H), 4.36-4.30 (m, 3H), 3.71 (br s, 2H), 2.73 (br s, 2H), 2.23 (s, | 313 |

-continued

| Example | Compound Name and Structure | NMR | m/z |
|---|---|---|---|
| | | 3H), 2.06 (br s, 3H), 1.38 (d, J = 6.8 Hz, 3H) | |
| Example 201 | 1-(1-(cyclopropylmethyl)-3-(m-tolylamino)-6,7-dihydro-1H-pyrazolo[4,3-c]pyridin-5(4H)-yl)ethanone | $^1$H NMR (400 MHz, T = 80° C., DMSO-d$_6$) δ 7.63 (br s, 1H), 7.12-7.11 (m, 2H), 7.05-7.01 (m, 1H), 6.53 (d, J = 7.6 Hz, 1H), 4.33 (s, 2H), 3.79 (d, J = 6.8 Hz, 1H), 3.71 (br s, 2H), 2.72 (br s, 2H), 2.24 (s, 3H), 2.08 (br s, 3H), 1.22-1.43 (m, 1H), 0.54-0.49 (m, 2H), 0.36-0.33 (m, 2H) | 325 |
| Example 202 | 1-[3-(3-methylanilino)-l-(4-pyridylmethyl)-6,7-dihydro-4H-pyrazolo[4,3-c]pyridin-5-yl]ethanone | $^1$H NMR (400 MHz, DMSO-d$_6$) δ 8.57-8.51 (m, 2H), 7.78 (s, 1H), 7.15-7.11 (m, 4H), 7.00-7.05 (m, 1H), 6.55-6.53 (m, 1H), 5.18 (s, 2H), 4.36 (s, 2H), 3.75-3.65 (m, 2H), 2.55-2.75 (m, 2H), 2.22 (s, 3H), 2.07 (s, 3H) | 362 |
| Example 203 | 1-[1-benzyl-3-(3-methylanilino)-6,7-dihydro-4H-pyrazolo]4,3-c]pyridin-5-yl]ethanone | $^1$H NMR (400 MHz, T = 80° C., DMSO-d$_6$) δ 7.70 (br s, 1H), 7.35-7.32 (m, 1H), 7.28-7.21 (m, 2H), 7.15-7.10 (m, 2H), 7.05-7.00 (s, 1H), 6.53 (d, J = 7.2 Hz, 1H), 5.13 (s, 2H), 4.33 (s, 2H), 3.69 (br s, 2H), 2.66 (br s, 2H), 2.22 (s, 3H), 2.06 (s, 3H) | 361 |
| Example 204 | 1[1-(2-hydroxyethyl)-3-(3-methylanilino)-dihydro-4H-pyrazolo[4,3-c]pyridin-5-yl]ethanone | $^1$H NMR (400 MHz, DMSO-d$_6$) δ 7.17-7.07 (m, 3H), 6.60 (dd, J = 7.2, 7.2 Hz, 1H), 4.34-4.30 (s, 2H), 3.97 (t, J = 4.8 Hz, 2H), 3.71-3.67 (m, | 315 |

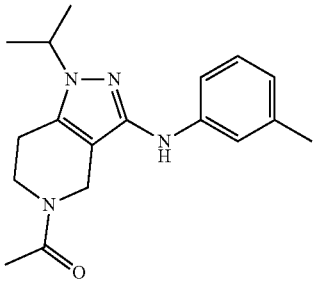 [SMILES: CC(=O)N1CCc2c(c(Nc3cccc(C)c3)nn2C(C)C)C1]

-continued

| Example | Compound Name and Structure | NMR | m/z |
|---|---|---|---|
| | | 4H), 2.78-2.65 (m, 2H), 2.23 (s, 3H), 2.09-2.05 (s, 3H) | |
| Example 205 | 3-[5-acetyl-3-(3-methylanilino)-6,7-dihydro-4H-pyrazolo[4,3-c]pyridin-1-yl]propanamide | $^1$H NMR (400 MHz, DMSO-d$_6$) δ 7.97-7.92 (m, 1H), 7.40 (s, 1H), 7.19 (d, J = 7.2 Hz, 1H), 7.11 (s, 1H) 7.07-7.01 (m, 1H), 6.86 (s, 1H), 6.52 (dd, J = 6.8, 6.8 Hz, 1H), 4.30 (s, 2H), 4.04 (t, J = 6.8 Hz, 2H), 3.70-3.64 (m, 2H), 2.74-2.62(m, 2H), 2.57 (t, J = 6.8 Hz, 2H), 2.23-2.22 (m, 3H), 2.09-2.05 (m, 3H) | 342 |
| Example 206 | 1-[1-(3-hydroxypropyl)-3-(3-methylanilino)-6,7-dihydro-4H-pyrazolo[4,3-c]pyridin-5-yl]ethanone | $^1$H NMR (400 MHz, DMSO-d$_6$) δ 7.16-7.06 (m, 3H), 6.59 (d, J = 7.2 Hz, 1H), 4.60-4.35 (m, 2H), 4.00-3.95 (m, 2H), 3.72-3.66 (m, 2H), 3.37 (t, J = 6.0 Hz, 2H), 2.76-2.63 (m, 2H), 2.23 (s, 3H), 2.09-2.05 (m, 3H), 1.88-1.83 (m, 2H) | 329 |
| Example 207 | 4-[5-acetyl-3-(3-methylanilino)-6,7-dihydro-4H-pyrazolo[4,3- | $^1$H NMR (400 MHz, DMSO-d$_6$) δ 8.02-7.97 (m, 1H), 7.17 (s, 2H), 7.07-7.01 (m, 1H), 6.53 (dd, J = 6.4, | 360 [M + Na] |

| Example | Compound Name and Structure | NMR | m/z |
|---|---|---|---|
| | c]pyridin-1-yl]butanenitrile | 6.4 Hz, 2H), 4.32 (s, 2H), 3.95 (t, J = 6.4 Hz, 2H), 3.74-3.66 (m, 2H), 2.74-2.52 (m, 2H), 2.51-2.49 (m, 2H), 2.23-2.22 (m, 3H), 2.09-2.05 (m, 3H), 2.02 (t, J = 6.8 Hz, 2H) | |

Example 208

1-[3-(3-methylanilino)-1-[(E)-pent-3-enyl]-6,7-dihydro-4H-pyrazolo[4,3-c]pyridin-5-yl]ethanone

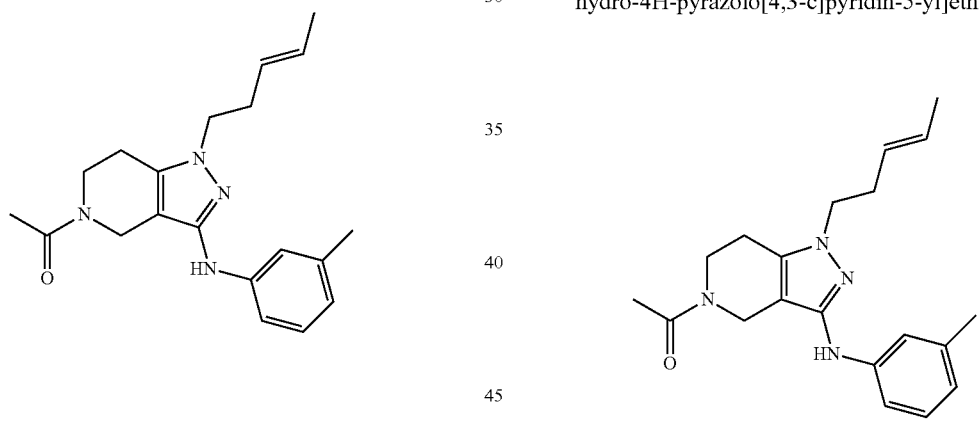

Step 1

1-cyclopropylethyl methanesulfonate

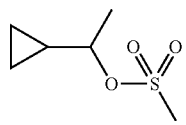

To a stirred solution of 1-cyclopropylethanol (5 g, 58.1 mmol) and TEA (17.6 g, 174.4 mmol) in DCM (100 mL) at 0° C. was added MsCl (8.02 g, 69.7 mmol). The reaction mixture was stirred at room temperature for 0.5 h. The mixture was diluted in DCM (100 mL), washed with 1 N HCl, washed with sat. aq. NaHCO$_3$ and washed with brine (120 mL). The combined organic layers were dried over anhydrous Na$_2$SO$_4$, filtered and concentrated in vacuo to give the title compound (6.5 g) as a colorless oil that required no further purification.

Step 2

1-[3-(3-methylanilino)-1-[(E)-pent-3-enyl]-6,7-dihydro-4H-pyrazolo[4,3-c]pyridin-5-yl]ethanone To a solution of 1-(3-(m-tolylamino)-6,7-dihydro-1H-pyrazolo[4,3-c]pyridin-5(4H)-yl)ethanone (Intermediate M, 200 mg, 0.74 mmol) in DMF (5 mL) was added 1-cyclopropylethyl methanesulfonate (607 mg, 3.70 mol) and K$_2$CO$_3$ (306 mg, 2.22 mmol). The mixture was heated to 100° C. for 16 hours under an autoclave. After cooling the reaction mixture to rt, the reaction mixture was diluted with water (30 mL) and washed with EtOAc (30 mL×2). The combined organic layers were dried over anhydrous Na$_2$SO$_4$, filtered and concentrated in vacuo. The crude residue was purified by reverse phase chromatography (acetonitrile 40-60%/0.2% formic acid in water) to give the title compound (11 mg, 4%) as a white solid. $^1$H NMR (400 MHz, CD$_3$OD) δ 7.10-7.14 (m, 1H), 6.92-6.87 (m, 2H), 6.61 (dd, J=6.8, 6.8 Hz, 1H), 5.46-5.43 (m, 2H), 4.37-4.36 (s, 2H), 3.98-3.95 (m, 2H), 3.88-3.79 (m, 2H), 2.82-2.71 (m, 2H), 2.46-2.44 (m, 2H), 2.28 (s, 3H), 2.21-2.13 (m, 3H), 1.64-1.57 (m, 3H). LCMS M/Z (M+H) 339.

Example 209

1-(1-((1-methylpiperidin-3-yl)methyl)-3-(m-tolylamino)-6,7-dihydro-1H-pyrazolo[4,3-c]pyridin-5(4H)-yl)ethanone

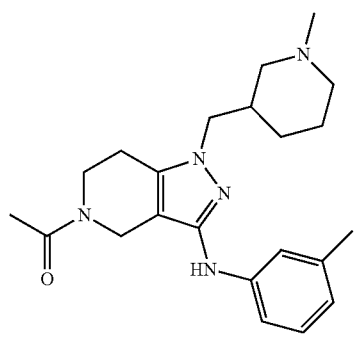 [SMILES: CC(=O)N1CCc2c(c(Nc3cccc(C)c3)nn2CC2CCCN(C)C2)C1]

Step 1 tert-butyl 3-((5-acetyl-3-(m-tolylamino)-4,5,6,7-tetrahydro-1H-pyrazolo[4,3-c]pyridin-1-yl)methyl)piperidine-1-carboxylate

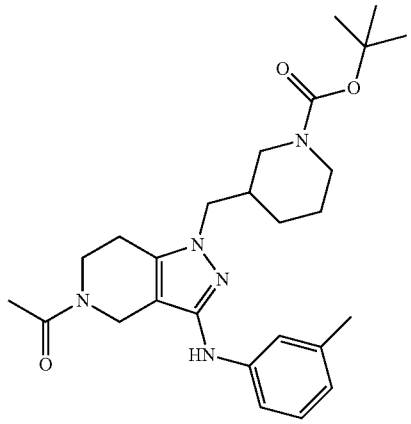 [SMILES: CC(=O)N1CCc2c(c(Nc3cccc(C)c3)nn2CC2CCCN(C(=O)OC(C)(C)C)C2)C1]

To a solution of 1-(3-(m-tolylamino)-6,7-dihydro-1H-pyrazolo[4,3-c]pyridin-5(4H)-yl)ethanone (Intermediate M, 150 mg, 0.56 mmol) in DMF (10 mL) was added tert-butyl 3-(bromomethyl)piperidine-1-carboxylate (169 mg, 0.61 mmol) and Cs$_2$CO$_3$ (362 mg, 1.11 mmol). The reaction mixture was heated to 80° C. for 2 h. The reaction mixture was diluted with EtOAc (30 mL) and washed with water (30 mL×3). The organic layer was separated, dried over Na$_2$SO$_4$ and concentrated in vacuo. The residue was purified by silica gel chromatography (petroleum ether/EtOAc (1/1)) to afford the title compound (200 mg, 77%).

Step 2

1-(1-(piperidin-3-ylmethyl)-3-(m-tolylamino)-6,7-dihydro-1H-pyrazolo[4,3-c]pyridin-5(4H)-yl)ethanone hydrochloride

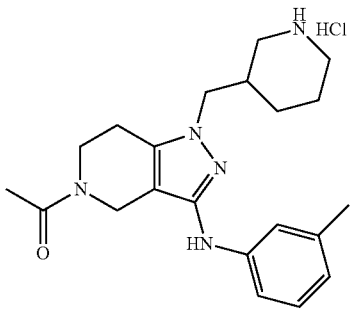 [SMILES: CC(=O)N1CCc2c(c(Nc3cccc(C)c3)nn2CC2CCCNC2)C1 ; Cl]

To a solution of tert-butyl 3-((5-acetyl-3-(m-tolylamino)-4,5,6,7-tetrahydro-1H-pyrazolo[4,3-c]pyridin-1-yl)methyl)piperidine-1-carboxylate (0.2 g, 0.428 mmol) in EtOAc (10 mL) was added HCl/EtOAc (2.0 ml). The mixture was allowed to stir at room temperature for 2 h. The solvent was concentrated in vacuo and the crude product required no further purification.

Step 3

1-(1-((1-methylpiperidin-3-yl)methyl)-3-(m-tolylamino)-6,7-dihydro-1H-pyrazolo[4,3-c]pyridin-5(4H)-yl)ethanone

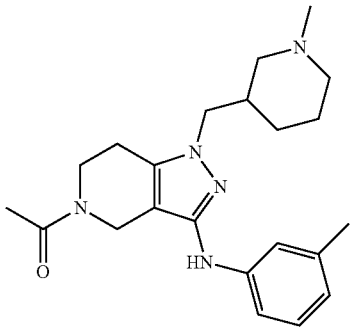 [SMILES: CC(=O)N1CCc2c(c(Nc3cccc(C)c3)nn2CC2CCCN(C)C2)C1]

To a solution of 1-(1-(piperidin-3-ylmethyl)-3-(m-tolylamino)-6,7-dihydro-1H-pyrazolo[4,3-c]pyridin-5(4H)-yl)ethanone hydrochloride in DCM (5.0 ml) was added HCHO (26 mg, 0.856 mmol) and Et$_3$N (0.5 ml). The mixture was heated to 30° C. for 1 h before NaBH(OAc)$_3$ (181 mg, 0.86 mmol) was added. The mixture stirred for an additional 1 h at 30° C. The reaction mixture was quenched by the addition of brine (10 ml) and the solution was extracted with DCM (20 ml×2) and washed with water (10 ml×3). The combined organic layers were dried over Na$_2$SO$_4$, filtered and concentrated in vacuo. The crude residue was purified by reverse phase chromatography (acetonitrile 30-60%/0.1% NH$_4$OH in water) to give the title compound (47 mg, 28%) as a white solid. $^1$H NMR (400 MHz, DMSO-d$_6$) δ 7.98 (s, 1H), 7.19-7.14 (m, 2H), 7.06-7.01 (m, 1H), 6.54-6.50 (m, 1H), 4.37-4.26 (m, 2H), 3.82-3.70 (m, 4H), 2.72-2.60 (m, 5H), 2.35-2.30 (m, 5H), 2.20-1.95 (m, 5H), 1.65-1.60 (m, 1H), 1.58-1.55 (m, 1H), 1.49-1.47 (m, 1H), 1.23-1.1 (m, 1H), 1.04-1.02 (m, 1H). LCMS M/Z (M+H) 382.

Example 210

1-(1-(1-(1-methyl-1H-pyrazol-3-yl)ethyl)-3-(m-tolylamino)-6,7-dihydro-1H-pyrazolo[4,3-c]pyridin-5(4H)-yl)ethanone

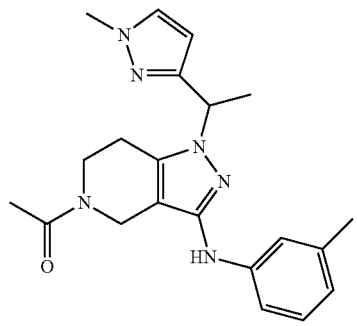 [SMILES: CC(=O)N1CCc2c(c(Nc3cccc(C)c3)nn2C(C)c2ccn(C)n2)C1]

Step 1

1-(1-methyl-1H-pyrazol-3-yl)ethanol

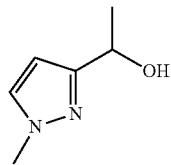

To a solution of 1-methylpyrazole-3-carbaldehyde (1 g, 9.1 mmol) in THF (5 mL) at 0° C. was added MeMgBr (4.54 ml, 13.62 mmol) dropwise. The reaction mixture was allowed to stir at room temperature for 12 h. The reaction was quenched with sat. aq. NH$_4$Cl (10 mL) and extracted with EtOAc (10 mL×3). The combined organic layers were dried over anhydrous Na$_2$SO$_4$ and concentrated in vacuo to afford the title compound (0.55 g) that required no further purification.

Step 2

3-(1-chloroethyl)-1-methyl-1H-pyrazole

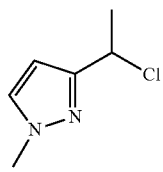

To a solution of 1-(1-methylpyrazol-3-yl)ethanol (0.55 g, 4.36 mmol) in DCM (10 ml) at 0° C. was added SOCl$_2$ (0.57 g, 4.80 mmol) dropwise and the reaction mixture was stirred at for 10 min. The reaction was quenched with brine (10 mL) and extracted with EtOAc (10 mL×3).

The combined organic layers were dried over anhydrous Na$_2$SO$_4$, filtered and concentrated in vacuo to afford the title compound (0.6 g) that required no further purification.

Step 3

1-(1-(1-(1-methyl-1H-pyrazol-3-yl)ethyl)-3-(m-tolylamino)-6,7-dihydro-1H-pyrazolo[4,3-c]pyridin-5(4H)-yl)ethanone

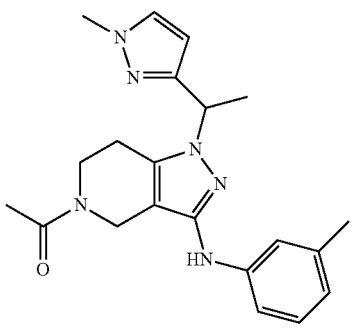 [SMILES: CC(=O)N1CCc2c(c(Nc3cccc(C)c3)nn2C(C)c2ccn(C)n2)C1]

The title compound was prepared from 1-(3-(m-tolylamino)-6,7-dihydro-1H-pyrazolo[4,3-c]pyridin-5(4H)-yl)ethanone (Intermediate M) and 3-(1-chloroethyl)-1-methyl-1H-pyrazole in a similar fashion to Example 188. The crude residue was purified by reverse phase chromatography (acetonitrile 31-61%/0.1% NH$_4$OH in water) to give the title compound in 4% yield. $^1$H NMR (400 MHz, DMSO-d$_6$) δ 7.98-7.93 (m, 1H), 7.56 (s, 1H), 7.14-7.11 (m, 2H), 7.02 (dd, J=7.6, 7.6 Hz, 1H), 6.51 (dd, J=6.0, 6.0 Hz, 1H), 6.04 (d, J=2.0 Hz, 1H), 5.34 (q, J=6.4 Hz, 1H), 4.37-4.20 (m, 2H), 3.77 (s, 3H), 3.73-3.62 (m, 2H), 2.79-2.64 (m, 2H), 2.22-2.21 (m, 3H), 2.08-2.04 (m, 3H), 1.72 (d, J=6.8 Hz, 3H). LCMS M/Z (M+H) 401 [M+Na].

Example 211

1-(1-(1-hydroxypropan-2-yl)-3-(m-tolylamino)-6,7-dihydro-1H-pyrazolo[4,3-c]pyridin-5(4H)-yl)ethanone

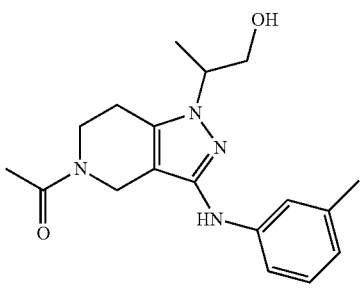 [SMILES: CC(=O)N1CCc2c(c(Nc3cccc(C)c3)nn2C(C)CO)C1]

Step 1 ethyl 2-(5-acetyl-3-(m-tolylamino)-4,5,6,7-tetrahydro-1H-pyrazolo[4,3-c]pyridin-1-yl)propanoate

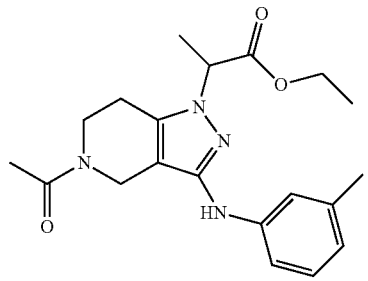 [SMILES: CCOC(=O)C(C)n1nc(Nc2cccc(C)c2)c2c1CCN(C(C)=O)C2]

The title compound was prepared from 1-(3-(m-tolylamino)-6,7-dihydro-1H-pyrazolo[4,3-c]pyridin-5(4H)-yl)ethanone (Intermediate M) and ethyl 2-bromopropanoate in a similar fashion to Example 188. The residue was purified by silica gel chromatography (DCM:MeOH=2%-50%) to afford the title compound (0.185 g, 27%) as a yellow oil. LCMS M/Z (M+Na) 393.

Step 2

1-(1-(1-hydroxypropan-2-yl)-3-(m-tolylamino)-6,7-dihydro-1H-pyrazolo[4,3-c]pyridin-5(4H)-yl)ethanone

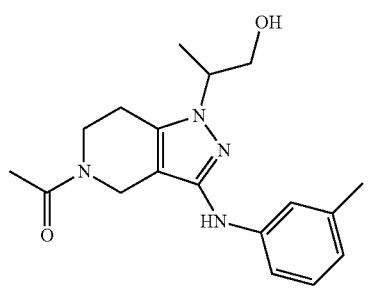 [SMILES: CC(=O)N1CCc2c(c(Nc3cccc(C)c3)nn2C(C)CO)C1]

To a solution of ethyl 2-(5-acetyl-3-(m-tolylamino)-4,5,6,7-tetrahydro-1H-pyrazolo[4,3-c]pyridine-1-yl)propanoate (0.23 g, 0.62 mmol) in MeOH (5 mL) at 0° C. was added NaBH$_4$ (0.094 mg, 2.48 mmol) portionwise and stirred at room temperature for 4 h. The reaction mixture was quenched by sat. aq. NH$_4$Cl (5 mL) and extracted with EtOAc (5 mL×3). The combined organic layers were dried over anhydrous Na$_2$SO$_4$ and concentrated in vacuo. The crude residue was purified by reverse phase chromatography (acetonitrile 20-50%/0.1% NH$_4$OH in water) to give the title compound (0.049 g, 22%) as a white solid. $^1$H NMR (400 MHz, DMSO-d$_6$) δ 7.98-7.93 (m, 1H), 7.16-7.10 (m, 2H), 7.06-7.00 (m, 1H), 6.51 (dd, J=6.8, 6.8 Hz, 1H), 4.83-4.75 (m, 1H), 4.36-4.28 (m, 2H), 4.12-4.11 (m, 1H), 3.67-3.65 (m, 2H), 3.60-3.54 (m, 2H), 2.76-2.63 (m, 2H), 2.23-2.21 (m, 3H), 2.09-2.05 (m, 3H), 1.33-1.31 (m, 3H). LCMS M/Z (M+H) 329.

Examples 212 & 213

(S)-1-(1-(1-hydroxypropan-2-yl)-3-(m-tolylamino)-6,7-dihydro-1H-pyrazolo[4,3-c]pyridin-5(4H)-yl)ethanone and (R)-1-(1-(1-hydroxy propan-2-yl)-3-(m-tolylamino)-6,7-dihydro-1H-pyrazolo[4,3-c]pyridin-5(4H)-yl)ethanone

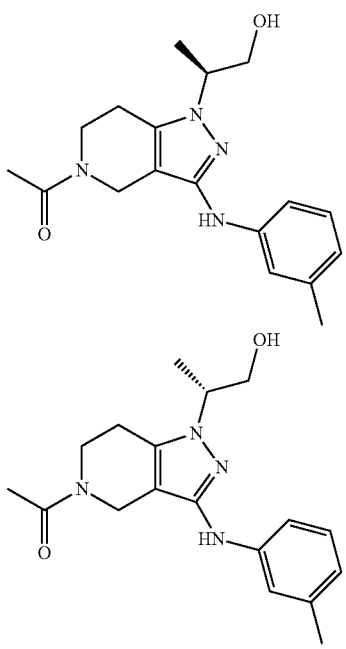

Racemic 1-(1-(1-hydroxypropan-2-yl)-3-(m-tolylamino)-6,7-dihydro-1H-pyrazolo[4,3-c]pyridin-5(4H)-yl)ethanone (45 mg) was separated using chiral SFC (SFC80; Chiralpak AD 250×30 mm I.D., 5 um; Supercritical CO$_2$/MEOH+NH$_3$.H$_2$O=55/45; 50 ml/min) to afford (S)-1-(1-(1-hydroxypropan-2-yl)-3-(m-tolylamino)-6,7-dihydro-1H-pyrazolo[4,3-c]pyridin-5(4H)-yl)ethanone (12.0 mg, first peak) and (R)-1-(1-(1-hydroxy propan-2-yl)-3-(m-tolylamino)-6,7-dihydro-1H-pyrazolo[4,3-c]pyridin-5(4H)-yl)ethanone (12.4 mg, second peak). Absolute configuration was arbitrarily assigned to each enantiomer. Example 212: $^1$H NMR (400 MHz, DMSO-d$_6$) δ 7.98-7.93 (m, 1H), 7.15-7.09 (m, 2H), 7.06-7.00 (m, 1H), 6.51 (dd, J=6.4, 6.4 Hz, 1H), 4.84-4.79 (m, 1H), 4.32-4.27 (m, 2H), 4.12-4.10 (m, 1H), 3.67-3.64 (m, 2H), 3.58-3.54 (m, 2H), 2.76-2.63 (m, 2H), 2.22-2.21 (m, 3H), 2.08-2.05 (m, 3H), 1.33-1.31 (m, 3H). LCMS M/Z (M+H) 329. Example 213: $^1$H NMR (400 MHz, DMSO-d$_6$) δ 7.97-7.92 (s, 1H), 7.15-7.09 (m, 2H), 7.05-6.99 (m, 1H), 6.50 (dd, J=6.4, 6.4 Hz, 1H), 4.83-4.80 (m, 1H), 4.31-4.27 (m, 2H), 4.12-4.10 (m, 1H), 3.66-3.58 (m, 2H), 3.57-3.53 (m, 2H), 2.75-2.62 (m, 2H), 2.22-2.21 (m, 3H), 2.08-2.04 (m, 3H), 1.33-1.30 (m, 3H). LCMS M/Z (M+H) 329.

Example 214

3-(5-acetyl-3-(m-tolylamino)-4,5,6,7-tetrahydro-1H-pyrazolo[4,3-c]pyridin-1-yl)propanenitrile

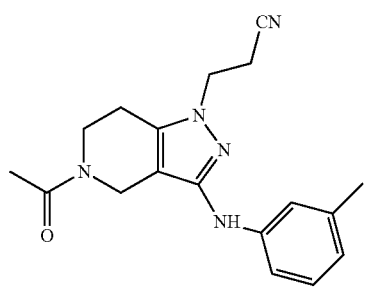 [SMILES: CC(=O)N1CCc2c(c(Nc3cccc(C)c3)nn2CCC#N)C1]

The title compound was prepared from 1-(3-(m-tolylamino)-6,7-dihydro-1H-pyrazolo[4,3-c]pyridin-5(4H)-yl)ethanone (Intermediate M) and acrylonitrile in a similar fashion to Example 180. The residue was purified by reverse phase chromatography (acetonitrile 35-65%/0.1% NH₄OH in water) to afford the title compound in 27% yield. ¹H NMR (400 MHz, DMSO-d₆) δ 8.07-8.01 (m, 1H), 7.22 (s, 2H), 7.06-7.01 (m, 1H), 6.53 (dd, J=6.8, 6.8 Hz, 2H), 4.33 (s, 2H), 4.16 (t, J=6.4 Hz, 2H), 3.74-3.66 (m, 2H), 2.96 (t, J=6.4 Hz, 2H), 2.76-2.65 (m, 2H), 2.23-2.22 (m, 3H), 2.09-2.06 (m, 3H). LCMS M/Z (M+H) 324.

Example 215

1-[3-(3-methylanilino)-1-[2-(3-piperidyl)ethyl]-6,7-dihydro-4H-pyrazolo[4,3-c]pyridin-5-yl]ethanone

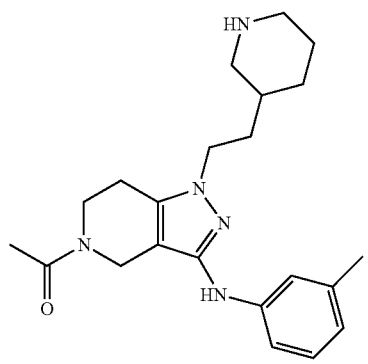 [SMILES: CC(=O)N1CCc2c(c(Nc3cccc(C)c3)nn2CCC2CCCNC2)C1]

The title compound was prepared from 1-(3-(m-tolylamino)-6,7-dihydro-1H-pyrazolo[4,3-c]pyridin-5(4H)-yl) ethanone (Intermediate M) and tert-butyl 3-(2-((methylsulfonyl)oxy)ethyl)piperidine-1-carboxylate in a similar fashion to Example 209. The residue was purified by reverse phase chromatography (acetonitrile 20-50%/0.1% HCl in water) to afford the title compound in 13% yield. ¹H NMR (400 MHz, DMSO-d₆) δ 7.25 (dd, J=7.6, 7.6 Hz, 1H), 7.11-6.86 (m, 3H), 4.38 (s, 2H), 4.19-4.11 (m, 2H), 3.96-3.82 (m, 2H), 3.38-3.28 (m, 2H), 3.01-2.61 (m, 4H), 2.33 (s, 3H), 2.20-2.13 (m, 3H), 2.01-1.60 (m, 6H), 1.40-1.19 (m, 1H). LCMS M/Z (M+H) 382.

Example 216

1-[3-(3-methylanilino)-1-[2-(1-methyl-3-piperidyl)ethyl]-6,7-dihydro-4H-pyrazolo[4,3-c]pyridin-5-yl]ethanone

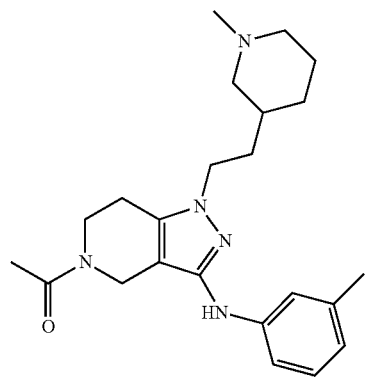 [SMILES: CC(=O)N1CCc2c(c(Nc3cccc(C)c3)nn2CCC2CCCN(C)C2)C1]

The title compound was prepared from 1-(3-(m-tolylamino)-6,7-dihydro-1H-pyrazolo[4,3-c]pyridin-5(4H)-yl) ethanone (Intermediate M) in a similar fashion to Example 209. The residue was purified by reverse phase chromatography (acetonitrile 20-50%/0.1% HCl in water) to afford the title compound in 20% yield. ¹H NMR (400 MHz, CD₃OD) δ 7.30 (dd, J=7.2, 3.6 Hz, 1H), 7.15-6.98 (m, 3H), 4.43 (s, 2H), 4.26-4.10 (m, 2H), 3.97-3.90 (m, 2H), 3.50-3.45 (m, 2H), 3.05-2.68 (m, 7H), 2.37 (s, 3H), 2.24-2.17 (m, 3H), 2.06-1.75 (m, 6H), 1.29-1.25 (m, 1H). LCMS M/Z (M+H) 396.

Example 217

1-(1-cyclopropyl-3-(m-tolylamino)-6,7-dihydro-1H-pyrazolo[4,3-c]pyridin-5(4H)-yl)ethanone

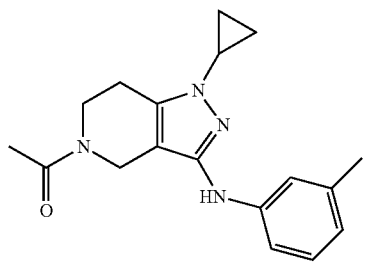 [SMILES: CC(=O)N1CCc2c(c(Nc3cccc(C)c3)nn2C2CC2)C1]

Step 1 tert-butyl 1-cyclopropyl-3-(m-tolylamino)-6,7-di-hydro-1H-pyrazolo[4,3-c]pyridine-5(4H)-carboxylate and tert-butyl 2-cyclopropyl-3-(phenylamino)-6,7-dihydro-2H-pyrazolo[4,3-c]pyridine-5(4H)-carboxylate

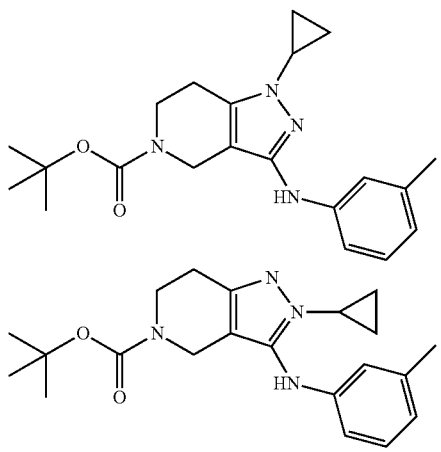

To a solution of (Z)-tert-butyl 3-((methylthio)(m-tolylamino)methylene)-4-oxopiperidine-1-carboxylate (0.2 g, 0.55 mmol) in ethanol (10 mL) was added cyclopropylhydrazine hydrochloride (77.5 mg, 0.71 mmol) and Et₃N (71 mg, 0.71 mmol). The mixture was heated to reflux for 2 h. The mixture was concentrated in vacuo and dissolved in EtOAc. The white solid was filtered and the filtrate was concentrated in vacuo to give crude mixture of the title compounds (0.2 g, 99%) as yellow oil.

Step 2

1-cyclopropyl-N-(m-tolyl)-4,5,6,7-tetrahydro-1H-pyrazolo[4,3-c]pyridin-3-amine hydrochloride and 2-cyclopropyl-N-(m-tolyl)-4,5,6,7-tetrahydro-2H-pyrazolo[4,3-c]pyridin-3-amine hydrochloride

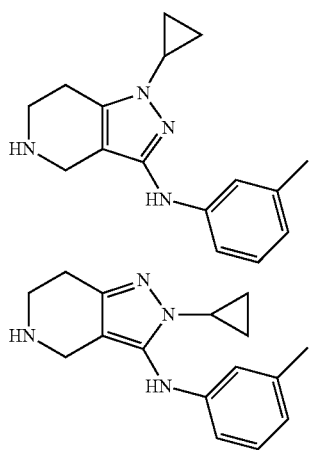

The mixture of tert-butyl 1-cyclopropyl-3-(m-tolylamino)-6,7-dihydro-1H-pyrazolo[4,3-c]pyridine-5(4H)-carboxylate and tert-butyl 2-cyclopropyl-3-(phenylamino)-6,7-dihydro-2H-pyrazolo[4,3-c]pyridine-5(4H)-carboxylate (0.2 g, 0.54 mmol) in EtOAc (2 mL) was treated with 4N HCl/EtOAc (10 mL) and stirred for 2 h at rt. The resulting mixture was concentrated in vacuo to afford the crude mixture of the title compounds (164 mg, 100%) as a light brown solid.

Step 3

1-(1-cyclopropyl-3-(m-tolylamino)-6,7-dihydro-1H-pyrazolo[4,3-c]pyridin-5(4H)-yl)ethanone

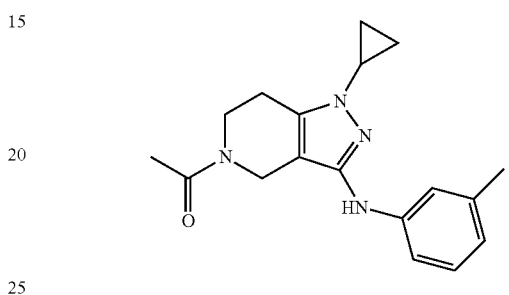

To a solution of 1-cyclopropyl-N-(m-tolyl)-4,5,6,7-tetrahydro-1H-pyrazolo[4,3-c]pyridin-3-amine hydrochloride and 2-cyclopropyl-N-(m-tolyl)-4,5,6,7-tetrahydro-2H-pyrazolo[4,3-c]pyridin-3-amine hydrochloride (164 mg, 0.54 mmol, from step 2) and Et₃N (166.9 mg, 1.65 mmol) in DMF (2 mL) at rt was added acetic anhydride (56.1 mg, 0.55 mmol). The mixture stirred for 2 h before being filtered. The filtrate was concentrated in vacuo the residue was purified by reverse phase chromatography (acetonitrile 40-70%/0.1% NH₄HCO₃ in water) to afford the title compound (5.8 mg, 35%) as a white solid. $^1$H NMR (400 MHz, T=80° C., DMSO-d₆) δ 7.63 (br s, 1H), 7.11-7.01 (m, 3H), 6.53 (d, J=7.2 Hz, 1H), 4.30 (s, 2H), 3.71 (br s, 2H), 3.36-3.34 (m, 1H), 2.78 (br s, 2H), 2.23 (s, 3H), 2.08 (s, 3H), 1.01-0.98 (m, 2H), 0.95-0.90 (m, 2H). LCMS M/Z (M+H) 311.

General Procedure for Intermediate N

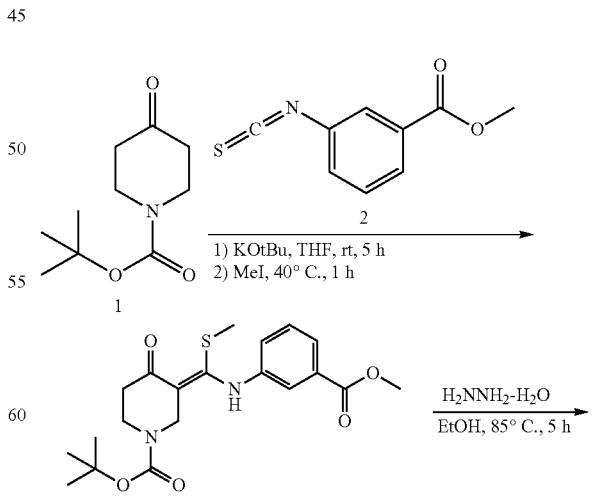

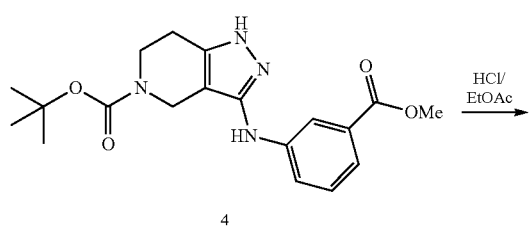

4

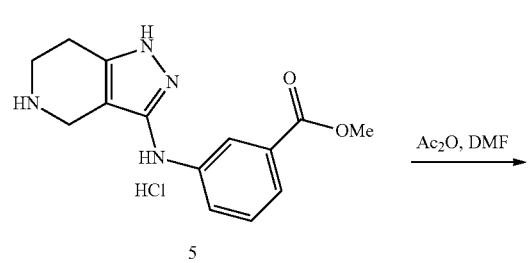

5

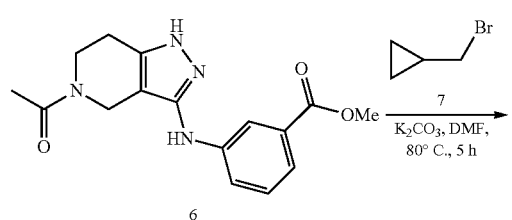

6

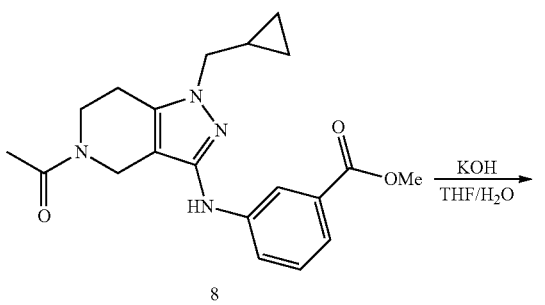

8

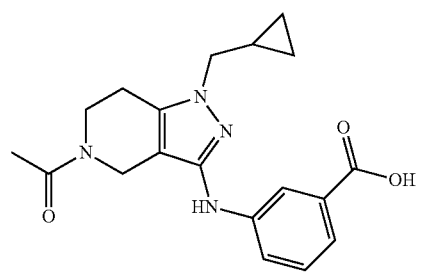

Intermediate N

Step 1

(Z)-tert-butyl 3-(((3-(methoxycarbonyl)phenyl)amino)(methylthio)methylene)-4-oxopiperidine-1-carboxylate

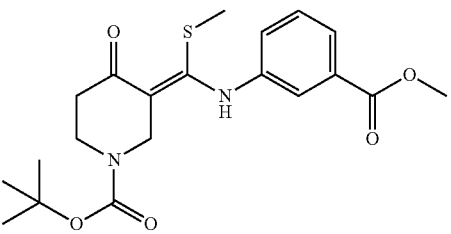 [SMILES: COC(=O)c1cccc(N/C(SC)=C2\CN(C(=O)OC(C)(C)C)CCC2=O)c1]

To a solution of tert-butyl 4-oxopiperidine-1-carboxylate (5.0 g, 25.09 mmol) in anhydrous THF (180 mL) was added t-BuOK (3.4 g, 30.3 mmol) portionwise. The mixture was stirred at room temperature for 3 h before the mixture was heated to 40° C. and 1-isothiocyanato-3-methylbenzene (5.8 g, 30.1 mmol) was added dropwise. After the addition, the reaction mixture was allowed to stir for 2 h at the same temperature before MeI (10.68 g, 75.2 mol) was added dropwise. After cooling to room temperature, the mixture was poured into water (500 mL) and extracted with EtOAc (200 mL×4). The combined organic layers were dried over anhydrous $Na_2SO_4$ and concentrated in vacuo to afford the title compound (10.0 g) as a brown oil.

Step 2 tert-butyl 3-((3-(methoxycarbonyl)phenyl)amino)-6,7-dihydro-1H-pyrazolo[4,3-c]pyridine-5(4H)-carboxylate

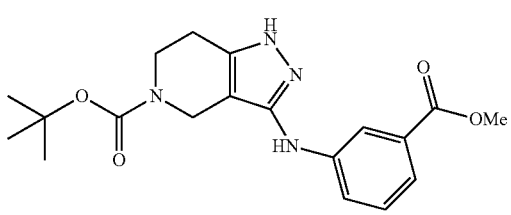 [SMILES: COC(=O)c1cccc(Nc2n[nH]c3c2CN(C(=O)OC(C)(C)C)CC3)c1]

To a solution of (Z)-tert-butyl 3-((methylthio)(m-tolylamino)methylene)-4-oxopiperidine-1-carboxylate (10.0 g, 24.6 mmol) in ethanol (250 mL) was added hydrazine hydrate (85% aq., 10 g). After the addition, the mixture was heated to reflux for 5 h. The mixture was concentrated in vacuo and the residue was purified by silica gel chromatography (petroleum ether:EtOAc=9:1) to afford the title compound (7.5 g, 82%) as light yellow oil.

Step 3 methyl 3-((4,5,6,7-tetrahydro-1H-pyrazolo[4,3-c]pyridin-3-yl)amino)benzoate hydrochloride

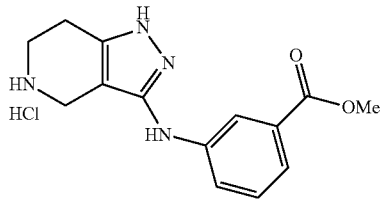 [SMILES: Cl ; COC(=O)c1cccc(Nc2n[nH]c3c2CNCC3)c1]

To a solution of tert-butyl 3-((3-(methoxycarbonyl)phenyl)amino)-6,7-dihydro-1H-pyrazolo[4,3-c]pyridine-5(4H)-carboxylate (6.1 g, 16.4 mmol) in EtOAc (60 mL) was added HCl/EtOAc (100 mL). The reaction mixture was stirred at room temperature for 1 h. The mixture was concentrated in vacuo to give the title compound (436 mg, crude) that required no further purification.

Step 4 methyl 3-((5-acetyl-4,5,6,7-tetrahydro-1H-pyrazolo[4,3-c]pyridin-3-yl)amino)benzoate

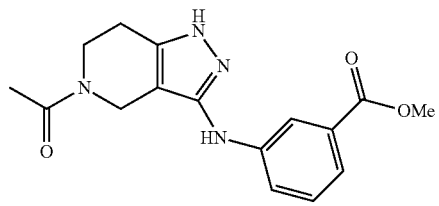 [SMILES: COC(=O)c1cccc(Nc2n[nH]c3c2CN(C(C)=O)CC3)c1]

To a solution of methyl 3-((4,5,6,7-tetrahydro-1H-pyrazolo[4,3-c]pyridin-3-yl) amino)benzoate hydrochloride (3.8 g, 12.3 mmol) and TEA (3.7 g, 36.9 mmol) in DMF (50 mL) was added acetic anhydride (1.3 g, 12.3 mmol). The mixture was heated to 32° C. for 2 h.

The reaction mixture was quenched by the addition of H$_2$O (50 mL) and extracted with EtOAc (50 mL×3). The combined organic layers were dried over anhydrous Na$_2$SO$_4$ and concentrated in vacuo to afford the title compound (3.0 g, 78%) that required no further purification.

Step 5 methyl 3-((5-acetyl-1-(cyclopropylmethyl)-4,5,6,7-tetrahydro-1H-pyrazolo[4,3-c]pyridin-3-yl)amino)benzoate

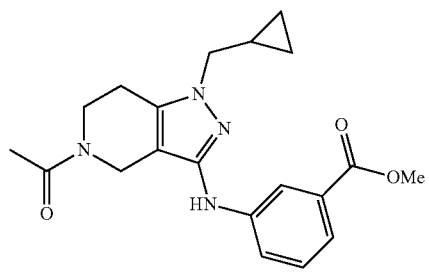 [SMILES: COC(=O)c1cccc(Nc2nn(CC3CC3)c3c2CN(C(C)=O)CC3)c1]

To a solution of methyl 3-((5-acetyl-4,5,6,7-tetrahydro-1H-pyrazolo[4,3-c]pyridin-3-yl) amino)benzoate (1.0 g, 3.18 mmol) and Cs$_2$CO$_3$ (2.1 g, 6.35 mmol) in DMF (40 mL) was added (bromomethyl)cyclopropane (0.5 g, 3.33 mmol). The mixture was heated to 80° C. for 8 h. The reaction mixture was quenched with H$_2$O (50 mL) and extracted with EtOAc (50 mL×3). The combined organic layers were dried over anhydrous Na$_2$SO$_4$ and concentrated in vacuo to give the title compound (1.1 g, 89%) that required no further purification.

Step 6

3-((5-acetyl-1-(cyclopropylmethyl)-4,5,6,7-tetrahydro-1H-pyrazolo[4,3-c]pyridin-3-yl)amino)benzoic Acid

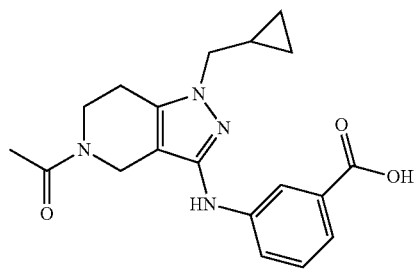 [SMILES: CC(=O)N1CCc2c(c(Nc3cccc(C(=O)O)c3)nn2CC2CC2)C1]

To a solution of KOH (0.8 g, 14.8 mmol) in MeOH/H$_2$O (2:1, 12 mL) was added methyl 3-((5-acetyl-1-(cyclopropylmethyl)-4,5,6,7-tetrahydro-1H-pyrazolo[4,3-c]pyridin-3-yl)amino)benzoate (0.8 g, 2.27 mmol) in THF (20 mL). The reaction mixture was heated to 32° C. for 2 h. The reaction mixture was quenched with H$_2$O (50 mL) and extracted with EtOAc (50 mL×3). The combined organic layers were dried over anhydrous Na$_2$SO$_4$ and concentrated in vacuo to give the title compound (410 mg, 53%) that required no further purification.

Example 218

3-((5-acetyl-1-(cyclopropylmethyl)-4,5,6,7-tetrahydro-1H-pyrazolo[4,3-c]pyridin-3-yl)amino)-N-isopropylbenzamide

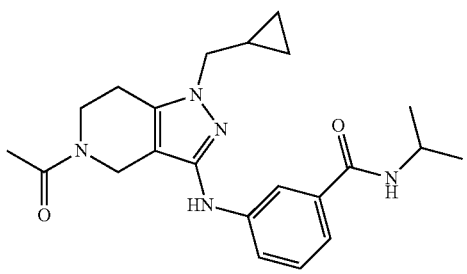 [SMILES: CC(=O)N1CCc2c(c(Nc3cccc(C(=O)NC(C)C)c3)nn2CC2CC2)C1]

To a mixture of 3-((5-acetyl-1-(cyclopropylmethyl)-4,5,6,7-tetrahydro-1H-pyrazolo[4,3-c]pyridin-3-yl)amino)benzoic acid (Intermediate N, 110 mg, 0.35 mmol), isopropylamine (84 mg, 1.40 mmol) and DIEA (136 mg, 1.05 mmol) in DMF (5 mL) was added HATU (133 mg, 0.35 mmol). The reaction mixture was heated to 32° C. for 8 h before being filtered and concentrated in vacuo. The residue was purified by reverse phase chromatography (acetonitrile 28-58%/0.2% formic acid in water) to afford the title compound compound (48 mg, 35%) as a white solid. $^1$H NMR (400 MHz, DMSO-d$_6$) δ 7.94 (s, 1H), 7.75-7.61 (m, 2H), 7.57-7.45 (m, 1H), 7.25-7.16 (m, 1H), 7.13 (d, J=7.6 Hz, 1H), 4.36 (s, 2H), 4.15-4.05 (m, 1H), 3.80 (d, J=6.8 Hz, 2H), 3.76-3.63 (m, 2H), 2.77-2.58 (m, 2H), 2.08 (s, 3H), 1.25-1.14 (m, 7H), 0.55-0.48 (m, 2H), 0.48-0.32 (m, 2H). LCMS M/Z (M+H) 396.

The Following Examples 219-222 were Prepared in a Similar Fashion to Example 218

| Example | Compound Name and Structure | NMR | m/z |
|---|---|---|---|
| Example 219 | 3-[[5-acetyl-1-(cyclopropylmethyl)-6,7-dihydro-4H-pyrazolo[4,3-e]pyridin-3-yl]amino]-N-methyl-benzamide | $^1$H NMR (400 MHz, DMSO-d$_6$) δ 8.05-7.90 (m, 1H), 7.69 (s, 2H), 7.58-7.45 (m, 1H), 7.25-7.11 (m, 1H), 7.12 (d, J = 7.6 Hz, 1H), 4.34 (s. 2H), 3.81 (d, J = 6.8 Hz, 2H), 3.75-3.65 (m, 2H), 2.78 (d, J = 4.4 Hz, 3H), 2.76-2.60 (m, 2H), 2.08 (s, 3H), 1.25-1.14 (m, 1H), 0.55-0.48 (m, 2H), 0.48-0.32 (m, 2H) | 368 |
| Example 220 | 3-[[5-acetyl-1-(cyclopropylmethyl)-6,7-dihydro-4H-pyrazolo[4,3-c]pyridin-3-yl]amino]-N,N-dimethyl-benzamide | $^1$H NMR (400 MHz, DMSO-d$_6$) δ 8.05-7.90 (m, 1H), 7.40-7.35 (m, 2H), 7.23-7.18 (m, 1H), 6.71 (d, J = 7.2 Hz, 1H), 4.36 (s, 2H), 3.80 (d, J = 6.8 Hz, 2H), 3.75-3.65 (m, 2H), 2.96 (s, 6H), 2.76-2.60 (m, 2H), 2.09 (s, 3H), 1.25-1.12 (m, 1H), 0.55-0.48 (m, 2H), 0.48-0.32 (m, 2H) | 382 |
| Example 221 | 3-[[5-acetyl-1-(cyclopropylmethyl)-6,7-dihydro-4H-pyrazolo[4,3-c]pyridin-3-yl]amino]-N-cyclopropyl-benzamide | $^1$H NMR (400 MHz, DMSO-d$_6$) δ 7.98 (s, 1H), 7.67 (s, 1H), 7.56-7.45 (m, 1H), 7.23-7.18 (m, 1H), 7.09 (d, J = 7.6 Hz, 1H), 4.34 (s. 2H), 3.82-3.78 (m, 2H), 3.75-3.65 (m, 2H), 2.92-2.70 (m, 1H), 2.69-2.60 (m, 2H), 2.08 (s, 3H), 1.25-1.15 (m, 1H), 0.75-0.65 (m, 2H), 0.60-0.55 (m, 2H), 0.54-0.45 (m, 2H), 0.39-0.30 (m, 2H) | 394 |
| Example 222 | 3-[[5-acetyl-1-(cyclopropylmethyl)-6,7- | $^1$H NMR (400 MHz, DMSO-d$_6$) δ 8.05-7.90 (m, 1H), 7.71 (s, 1H), | 412 |

| Example | Compound Name and Structure | NMR | m/z |
|---|---|---|---|
| | dihydro-4H-pyrazolo[4,3-c]pyridin-3-yl]amino]-N-(2-methoxyethyl)benzamide 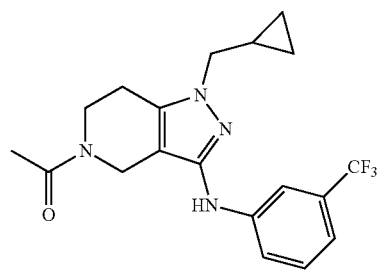 [SMILES: CC(=O)N1CCc2c(c(Nc3cccc(C(F)(F)F)c3)nn2CC2CC2)C1] | 7.55-7.45 (m, 1H), 7.23-7.18 (m, 1H), 7.14 (d, J = 8.0 Hz, 1H), 4.35 (s. 2H), 3.75-3.70 (m, 2H), 3.68-3.65 (m, 2H), 3.51-3.45 (m, 2H), 3.43-3.40 (m, 2H), 3.30 (s, 3H), 3.21 (s, 1H), 2.65-2.60 (m, 3H), 2.09 (s, 3H), 1.30-1.15 (m, 1H), 0.60-0.45 (m, 2H), 0.48-0.32 (m, 2H) | |

Example 223

1-(1-(cyclopropylmethyl)-3-((3-(trifluoromethyl)phenyl)amino)-6,7-dihydro-1H-pyrazolo[4,3-c]pyridin-5(4H)-yl)ethanone The title compound was prepared from tert-butyl 4-oxopiperidine-1-carboxylate and 1-isothiocyanato-3-(trifluoromethyl)benzene in a similar fashion to Intermediate N. The residue was purified by reverse phase chromatography (acetonitrile 53-63%/0.2% formic acid in water) to afford the title compound in 4% yield. $^1$H NMR (400 MHz, DMSO-d$_6$) δ 8.27 (s, 1H), 7.84 (s, 1H), 7.58 (d, J=8.4 Hz, 1H), 7.37 (t, J=8.0 Hz, 1H), 7.00 (d, J=7.6 Hz, 1H), 4.38 (s, 2H), 3.81 (d, J=6.4 Hz, 2H), 3.72 (s, 2H), 2.79-2.65 (m, 2H), 2.10 (s, 3H), 1.21-1.17 (m, 1H), 0.53-0.50 (m, 2H), 0.37-0.34 (m, 2H). LCMS M/Z (M+H) 379.

General Procedure for Intermediate O

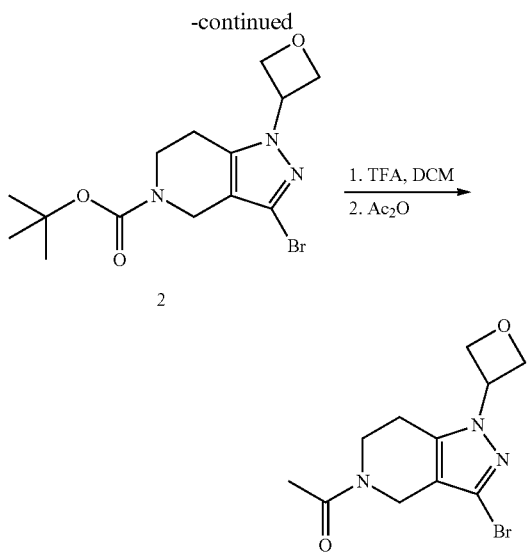

Step 1 tert-butyl 3-bromo-1-(oxetan-3-yl)-6,7-dihydro-1H-pyrazolo[4,3-c]pyridine-5(4H)-carboxylate To a solution of tert-butyl 3-bromo-6,7-dihydro-1H-pyrazolo[4,3-c]pyridine-5(4H)-carboxylate (Intermediate A, 40.0 g, 132 mmol) in DMF (500 mL) was added Cs$_2$CO$_3$ (87

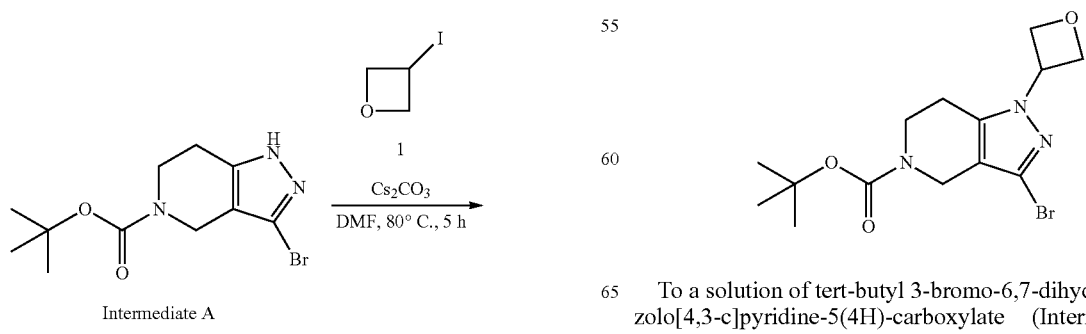

g, 264 mmol) and 3-iodooxetane (27 g, 146 mmol). The mixture was heated to 60° C. for 12 h before 3-iodooxetane (5 g, 27.0 mmol) was added and the mixture was stirred at 60° C. for an additional 6 h. After cooling the reaction to room temperature, the mixture was filtered, washed with EtOAc (500 mL) and concentrated in vacuo. The crude residue was purified by silica gel column chromatography (petroleum ether:tert-butyl methyl ether:THF=from 100:1:1 to 5:1:1) to give the title compound (30 g, 64%) as a white solid. $^1$H NMR (400 MHz, CDCl$_3$) δ 5.30-5.25 (m 1H), 5.18-5.14 (m, 2H), 4.95-4.91 (m, 2H), 4.28 (s, 2H), 3.73-3.66 (m, 2H), 2.64 (t, J=5.6 Hz, 2H), 1.48 (s, 9H).

Step 2

1-(3-bromo-1-(oxetan-3-yl)-6,7-dihydro-1H-pyrazolo[4,3-c]pyridin-5(4H)-yl)ethanone

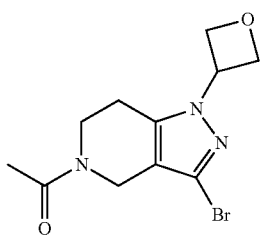 [SMILES: CC(=O)N1CCc2c(c(Br)nn2C2COC2)C1]

To a solution of tert-butyl 3-bromo-1-(oxetan-3-yl)-6,7-dihydro-1H-pyrazolo[4,3-c]pyridine-5(4H)-carboxylate (25.0 g, 70.0 mmol) in DCM (50 mL) was added trifluoroacetic acid (50 mL) dropwise at 0° C. The mixture was stirred at room temperature for 2 h. The mixture was concentrated in vacuo and the residue was re-dissolved in DCM (500 mL). The mixture was cooled to 0° C. before triethylamine (36.0 g, 350 mmol) and acetic anhydride (7.2 g, 70.0 mmol) were added dropwise. The mixture was stirred at room temperature for an additional 2 h. The reaction was quenched with water. The organic layer was dried over anhydrous Na$_2$SO$_4$, filtered and concentrated in vacuo. The crude residue was purified by silica gel chromatography (DCM/MeOH=80:1) to give the title compound (Intermediate O, 17.0 g, 81%) as a light yellow solid. $^1$H NMR (400 MHz, CDCl$_3$) δ 5.32-5.27 (m 1H), 5.16-5.13 (m, 2H), 4.95-4.91 (m, 2H), 4.47-4.31 (m, 2H), 3.88-3.70 (m, 2H), 2.75-2.63 (m, 2H), 2.17 (s, 3H).

Example 224

1-[3-[5-(difluoromethyl)-2-fluoro-4-(1-methylpyrazol-4-yl)anilino]-1-(oxetan-3-yl)-6,7-dihydro-4H-pyrazolo[4,3-c]pyridin-5-yl]ethanone

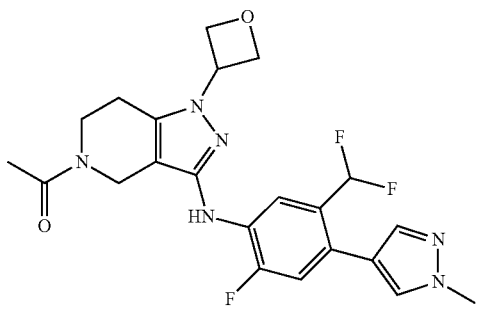 [SMILES: CC(=O)N1CCc2c(c(Nc3cc(C(F)F)c(-c4cnn(C)c4)cc3F)nn2C2COC2)C1]

Step 1

2-bromo-4-fluoro-5-nitrobenzaldehyde

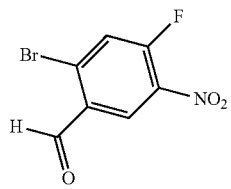 [SMILES: O=Cc1cc([N+](=O)[O-])c(F)cc1Br]

To a stirred solution of 2-bromo-4-fluoro-benzaldehyde (10 g, 49.3 mmol) in concentrated H$_2$SO$_4$ (100 mL) was added KNO$_3$ (5.5 g, 54.2 mmol) portionwise in an ice bath. The reaction mixture was stirred at 20° C. for 2 h. The reaction mixture was quenched by the addition of water (500 mL), and extracted with EtOAc (200 mL×2). The combined organic layers were dried over Na$_2$SO$_4$, filtered and concentrated in vacuo to give the title compound (12 g, 98%) as a yellow solid. $^1$H NMR (400 MHz, CDCl$_3$) δ 10.30 (s, 1H), 8.64 (d, J=8.0 Hz, 1H), 7.69 (d, J=9.6 Hz, 1H).

Step 2

1-bromo-2-(difluoromethyl)-5-fluoro-4-nitrobenzene

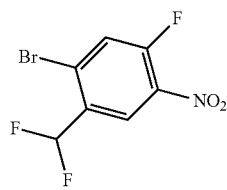 [SMILES: O=[N+]([O-])c1cc(C(F)F)c(Br)cc1F]

To a stirred solution of 2-bromo-4-fluoro-5-nitro-benzaldehyde (11 g, 44.4 mmol) in DCM (110 mL) was added diethylaminosulfur trifluoride (14.3 g, 88.7 mmol) in an ice bath. The reaction mixture was stirred at 20° C. for 12 h. The reaction mixture was quenched by water (100 mL), and extracted with DCM (100 mL×2). The combined organic layers were dried over Na$_2$SO$_4$, filtered and concentrated in vacuo. The crude residue was purified by silica gel column chromatography (petroleum ether/EtOAc=30:1) to give the title compound (7.2 g, 60%) as a light yellow solid. $^1$H NMR (400 MHz, CDCl$_3$) δ 8.40 (d, J=7.6 Hz, 1H), 7.65 (d, J=9.2 Hz, 1H), 6.89 (t, J=54.0 Hz, 1H).

Step 3

4-bromo-5-(difluoromethyl)-2-fluoroaniline

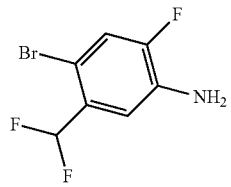 [SMILES: Nc1cc(C(F)F)c(Br)cc1F]

A mixture of 1-bromo-2-(difluoromethyl)-5-fluoro-4-nitro-benzene (7.2 g, 26.7 mmol), Fe powder (7.5 g, 133.3 mmol) and NH$_4$Cl (8.6 g, 160.0 mmol) in EtOH (80 mL) and water (20 mL) was heated to 80° C. for 4 h. After cooling to room temperature, the reaction mixture was filtered over a celite pad. The filtrate was diluted in water (100 mL) and extracted with EtOAc (100 mL×2). The combined organic layers were dried over anhydrous $Na_2SO_4$, filtered and concentrated in vacuo to give the title compound (3.8 g, 59%) as a light yellow solid. $^1$H NMR (400 MHz, DMSO-$d_6$) δ 7.43 (d, J=10.8 Hz, 1H), 7.08 (d, J=9.2 Hz, 1H), 6.97 (t, J=54.4 Hz, 1H), 5.69 (s, 2H).

Step 4

5-(difluoromethyl)-2-fluoro-4-(1-methyl-1H-pyrazol-4-yl)aniline

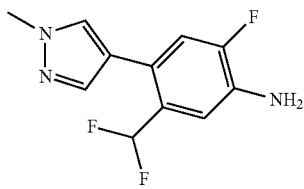 [SMILES: Cn1cc(-c2cc(F)c(N)cc2C(F)F)cn1]

A mixture of 4-bromo-5-(difluoromethyl)-2-fluoro-aniline (800 mg, 3.3 mmol), 1-methyl-4-(4,4,5,5-tetramethyl-1,3,2-dioxaborolan-2-yl)pyrazole (832 mg, 4 mmol), [1,1'-bis(diphenylphosphino)ferrocene]dichloropalladium(II) (244 mg, 0.33 mmol) and $Na_2CO_3$ (1.06 g, 10.00 mmol) in 1,4-dioxane (10 mL) and water (2 mL) was heated to 90° C. for 12 h under a nitrogen atmosphere. After cooling to room temperature, water (40 mL) was added and the mixture was extracted with EtOAc (40 mL×2). The combined organic layers were dried over anhydrous $Na_2SO_4$, filtered and concentrated in vacuo. The crude residue was purified by silica gel column chromatography (petroleum ether/EtOAc=5:1) to give the title compound (620 mg, 77%) as a light yellow solid. LCMS M/Z (M+H) 242.

Step 5

1-[3-[5-(difluoromethyl)-2-fluoro-4-(1-methylpyrazol-4-yl)anilino]-1-(oxetan-3-yl)-6,7-dihydro-4H-pyrazolo[4,3-c]pyridin-5-yl]ethanone

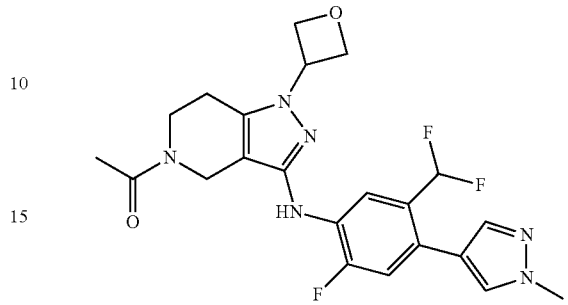

To a stirred solution of 5-(difluoromethyl)-2-fluoro-4-(1-methylpyrazol-4-yl)aniline (289 mg, 1.2 mmol) in 1,4-dioxane (3 mL) was added 1-(3-bromo-1-(oxetan-3-yl)-6,7-dihydro-1H-pyrazolo[4,3-c]pyridin-5(4H)-yl)ethanone (300 mg, 1.0 mmol), 2-(dicyclohexylphosphino)3,6-dimethoxy-2',4',6'-triisopropyl-1,1'-biphenyl (54 mg, 0.1 mmol), chloro (2-dicyclohexylphosphino-2',6'-di-i-propoxy-1,1'-biphenyl)[2-(2-aminoethylphenyl)]palladium(II), methyl-t-butylether adduct (82 mg, 0.1 mmol) and tBuONa (288 mg, 3 mmol). The reaction mixture was heated to 120° C. for 12 h under a nitrogen atmosphere. After cooling to room temperature, water (20 mL) was added and the mixture was extracted with DCM (20 mL×2). The combined organic layers were dried over anhydrous $Na_2SO_4$, filtered and concentrated in vacuo. The crude residue was purified by reverse phase chromatography (acetonitrile 28-58%/0.2% formic acid in water) to give the title compound (61 mg, 13%) as a white solid. $^1$H NMR (400 MHz, DMSO-$d_6$) δ 8.42-8.23 (m, 2H), 7.86 (s, 1H), 7.60 (s, 1H), 7.33-7.27 (m, 1H), 6.91 (t, J=54.8, 1H), 5.46-5.39 (m, 1H), 4.95-4.92 (m, 2H), 4.86-4.84 (m, 2H), 4.42-4.37 (m, 2H), 3.88 (s, 3H), 3.71-3.64 (m, 2H), 2.74-2.59 (m, 2H), 2.07-2.04 (m, 3H). LCMS M/Z (M+H) 461.

The Following Examples 225-231 were Prepared in a Similar Fashion to Example 224

| Example | Compound Name and Structure | NMR | m/z |
| --- | --- | --- | --- |
| Example 225 | 1-[3-[2,5-difluoro-4-[1-methyl-3-(trifluoromethyl)pyrazol-4-yl]anilino]-1-(oxetan-3-yl)-6,7-dihydro-4H-pyrazolo[4,3-c]pyridin-5-yl]ethanone | $^1$H NMR (400MHz, DMSO-$d_6$) δ 8.47-8.38 (m, 1H), 8.07 (s, 1H), 8.00-7.95 (m, 1H), 7.91-7.86 (m, 1H), 7.19-7.12 (m, 1H), 5.45-5.42 (m, 1H), 4.95-4.92 (m, 2H), 4.88-4.84 (m, 2H), 4.45-4.40 (m, 2H), 3.96 (s, 3H), 3.70-3.64 (m, 2H), 2.75-2.60 (m, 2H), 2.08-2.05 (m, 3H). | 497 |

| Example | Compound Name and Structure | NMR | m/z |
|---|---|---|---|
| Example 226 | 1-[3-[3-(difluoromethyl)-4-(1-methylpyrazol-4-yl)anilino]-1-(oxetan-3-yl)-6,7-dihydro-4H-pyrazolo[4,3-c]pyridin-5-yl]ethanone | $^1$H NMR (400 MHz, DMSO-d$_6$) δ 8.61-8.55 (m, 1H), 7.89-7.84 (m, 1H), 7.79 (s, 1H), 7.72-7.70 (m, 1H), 7.55 (s, 1H), 7.36-7.32 (m, 1H), 6.92 (t, J = 55.2, 1H), 5.43-5.40 (m, 1H), 5.00-4.97 (m, 2H), 4.86-4.82 (m, 2H), 4.37 (s, 2H), 3.88 (s, 3H), 3.73-3.66 (m, 2H), 2.73-2.59 (m, 2H), 2.09-2.07 (m, 3H) | 443 |
| Example 227 | 5-[[5-acetyl-1-(oxetan-3-yl)-6,7-dihydro-4H-pyrazolo[4,3-c]pyridin-3-yl]amino]-4-fluoro-2-(1-methylpyrazol-4-yl)benzonitrile | $^1$H NMR (400 MHz, DMSO-d$_6$) δ 8.53-8.34 (m, 2 H), 8.20 (s, 1H), 7.92 (s, 1H), 7.63-7.57 (m, 1H), 5.46-5.43 (m, 1H), 4.94-4.87 (m, 4H), 4.40-4.39 (m, 2H), 3.90 (s, 3H), 3.70-3.66 (m, 2H), 2.74-2.62 (m, 2H), 2.08-2.06 (m, 3H) | 436 |
| Example 228 | 5-[[5-acetyl-1-(oxetan-3-yl)-6,7-dihydro-4H-pyrazolo[4,3-c]pyridin-3-yl]amino]-4-fluoro-2-[1-methyl-3-(trifluoromethyl)pyrazol-4-yl]benzonitrile | $^1$H NMR (400 MHz, DMSO-d$_6$) δ 8.69-8.60 (m, 1H), 8.48-8.38 (m, 1H), 8.20 (s, 1H), 7.38-7.33 (m, 1H), 5.49-5.42 (m, 1H), 4.95-4.86 (m, 4H), 4.45-4.41 (m, 2H), 4.00 (s, 3H), 3.72-3.65 (m, 2H), 2.75-2.63 (m, 2H), 2.08-2.06 (m, 3H) | 504 |

-continued

| Example | Compound Name and Structure | NMR | m/z |
|---|---|---|---|
| Example 229 | 5-[[5-acetyl-1-(oxetan-3-yl)-6,7-dihydro-4H-pyrazolo[4,3-c]pyridin-3-yl]amino]-2-(1-methylpyrazol-4-yl)benzonitrile | $^1$H NMR (400 MHz, DMSO-d$_6$) δ 8.76-8.71 (m, 1H), 8.12 (s, 1H), 8.01-7.98 (m, 1H), 7.84 (s, 1H),7.77-7.76 (m, 1H), 7.59-7.56 (m, 1H), 5.46-5.41 (m, 1H), 5.00-4.95 (m, 2H), 4.88-4.84 (m, 2H), 4.39-4.38 (m, 2H), 3.90 (s, 3H), 3.73-3.66 (m, 2H), 2.74-2.60 (m, 2H), 2.09-2.07 (m, 3H) | 418 |
| Example 230 | 3-[[5-acetyl-1-(oxetan-3-yl)-6,7-dihydro-4H-pyrazolo[4,3-c]pyridin-3-yl]amino]-2-fluoro-6-(1-methylpyrazol-4-yl)benzonitrile | $^1$H NMR (400 MHz, DMSO-d$_6$) δ 8.47-8.39 (m, 1H), 8.32-8.19 (m, 1H), 8.16 (s, 1H), 7.88 (s, 1H), 7.46-7.42 (m, 1H), 5.47-5.40 (m, 1H), 4.95-4.92 (m, 2H), 4.87-4.83 (m, 2H), 4.42 -4.38 (m, 2H), 3.91 (s, 3H), 3.71-3.64 (m, 2H), 2.75-2.61 (m, 2H), 2.08-2.05 (m, 3H) | 436 |
| Example 231 | 1-[1-methyl-3-[[7-(1-methylpyrazol-4-yl)indan-5-yl]amino]-6,7-dihydro-4H-pyrazolo[4,3-c]pyridin-5-yl]ethanone | $^1$H NMR (400 MHz, DMSO-d$_6$) δ 7.89-7.85 (m, 2H), 7.62 (d, J = 4.8 Hz, 1H), 7.20-7.18 (m, 2H), 4.30 (s, 2H), 3.87 (s, 3H), 3.72-3.59 (m, 2H), 3.46 (s, 3H), 2.87-2.81 (m, 4H), 2.72-2.50 (m, 2H), 2.09-2.03 (m, 3H), 2.01-1.97 (m, 2H) | 391 |

Example 232

1-[3-[4-(1-methylpyrazol-4-yl)-2-methylsulfonyl-anilino]-1-tetrahydrofuran-3-yl-6,7-dihydro-4H-pyrazolo[4,3-c]pyridin-5-yl]ethanone

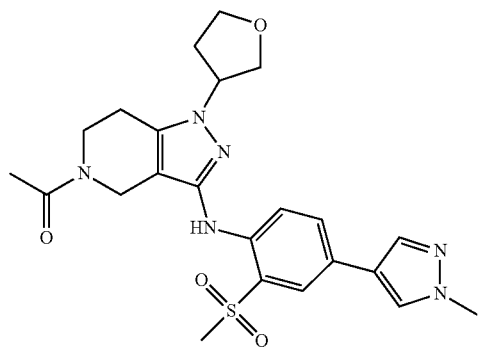 [SMILES: CC(=O)N1CCc2c(c(Nc3ccc(-c4cnn(C)c4)cc3S(C)(=O)=O)nn2C2CCOC2)C1]

Step 1

(5-bromo-2-nitrophenyl)(methyl)sulfane

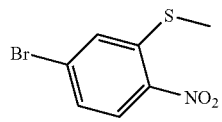

To a solution of 4-bromo-2-fluoro-1-nitrobenzene (5 g, 22.73 mmol) in DMF (100 mL) at 0° C. was added a solution of NaSMe (1.8 g, 25 mmol) in $H_2O$ (40 mL) dropwise. The reaction mixture was stirred at 0° C. for 1 h. The reaction mixture was filtered and washed with $H_2O$ (50 mL×3). The resulting yellow solid was dissolved in DCM (200 mL), drived over anhydrous $Na_2SO_4$, filtered and concentrated in vacuo to give the title compound (5.4 g, 96%) as a yellow solid.

Step 2

4-bromo-2-(methylsulfonyl)-1-nitrobenzene

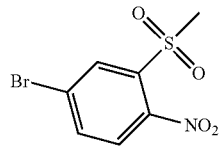

To a solution of (5-bromo-2-nitrophenyl)(methyl)sulfane (3 g, 12.09 mmol) in DCM (50 mL) at −10° C. was added mCPBA (85%, 8.59 g, 42.32 mmol). The reaction mixture was stirred at −10° C. for 10 min. The temperature was raised to 20° C. and the reaction mixture was stirred for an additional 2 h. A solution of sat. aq. $Na_2S_2O_3$ was added slowly until no peroxide existed (indicated by KI starch paper). The organic layer was separated and washed with sat. aq. $NaHCO_3$ (50 mL×2), derived over anhydrous $Na_2SO_4$, filtered and concentrated in vacuo to give the title compound (3.1 g, crude) as a yellow solid that required no further purification. $^1$H NMR (400 MHz, DMSO-$d_6$) δ 8.46 (d, J=2.0 Hz, 1H), 8.21-8.20 (m, 1H), 8.02 (d, J=8.4 Hz, 1H), 3.48 (s, 3H).

Step 3

4-bromo-2-(methylsulfonyl)aniline

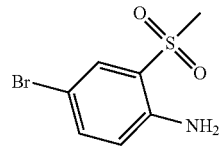

To a solution of 4-bromo-2-(methylsulfonyl)-1-nitrobenzene (1 g, 3.57 mmol) in MeOH (27 mL) was added $NH_4C_1$ (2.9 g, 53.55 mmol) and Zn powder (2.3 g, 35.70 mmol). The reaction mixture was stirred at room temperature for 1 h. After filtration, the filtrate was concentrated, washed with water and extracted with EtOAc. The combined organic layers were dried over anhydrous $Na_2SO_4$, filtered and concentrated in vacuo to give the title compound (0.8 g, 90%) as a brown solid. $^1$H NMR (400 MHz, DMSO-$d_6$) δ 7.43 (d, J=8.4 Hz, 1H), 7.11 (d, J=1.6 Hz, 1H), 6.86-6.83 (m, 1H), 6.28 (s, 2H), 3.11 (s, 3H).

Step 4

4-(1-methyl-1H-pyrazol-4-yl)-2-(methylsulfonyl)aniline

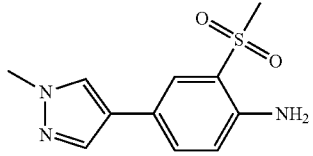 [SMILES: Cn1cc(-c2ccc(N)c(S(C)(=O)=O)c2)cn1]

To a solution of 4-bromo-2-(methylsulfonyl)aniline (0.8 g, 3.2 mmol) in dioxane (20 mL) and $H_2O$ (4 mL) was added 1-methyl-4-(4,4,5,5-tetramethyl-1,3,2-dioxaborolan-2-yl)-1H-pyrazole (666 mg, 3.2 mmol), [1,1'-bis(diphenylphosphino)ferrocene]dichloropalladium(II) (250 mg, 0.34 mmol) and $Na_2CO_3$ (678 mg, 6.4 mmol). The reaction mixture was heated to 120° C. for 12 h under a nitrogen atmosphere. After cooling to room temperature, the mixture was filtered and concentrated in vacuo. The residue was purified by silica gel column chromatography (DCM/MeOH=20:1) to give the title compound (600 mg, 75%) as a yellow solid.

Step 5

1-[3-[4-(1-methylpyrazol-4-yl)-2-methylsulfonyl-anilino]-1-tetrahydrofuran-3-yl-6,7-dihydro-4H-pyrazolo[4,3-c]pyridin-5-yl]ethanone

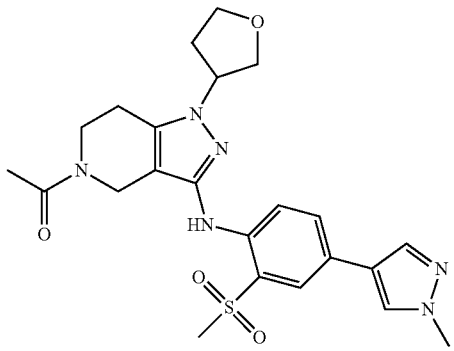 [SMILES: CC(=O)N1CCc2c(c(Nc3ccc(-c4cnn(C)c4)cc3S(C)(=O)=O)nn2C2CCOC2)C1]

To a solution of 1-(3-bromo-1-(tetrahydrofuran-3-yl)-6,7-dihydro-1H-pyrazolo[4,3-c]pyridin-5(4H)-yl)ethanone (Intermediate D, 188 mg, 0.60 mmol) in dioxane (10 mL) was added 4-(1-methyl-1H-pyrazol-4-yl)-2-(methylsulfonyl)aniline (150 mg, 0.60 mmol), chloro-(2-dicyclohexylphosphino-2',6'-diisopropoxy-1,1'-biphenyl)[2-(2-aminoethyl)phenyl]palladium(II) (50 mg, 0.06 mmol), 2-(dicyclohexylphosphino)3,6-dimethoxy-2',4',6'-triisopropyl-1,1'-biphenyl (32 mg, 0.06 mmol) and tBuONa (230 mg, 2.39 mmol). The reaction mixture was purged with nitrogen for 1 min and then heated to 120° C. for 18 h. After cooling to room temperature, the mixture was concentrated in vacuo. The crude residue was purified by silica gel column chromatography (DCM/MeOH=20:1) to give the crude product which was further purified by recrystallization (MeOH) to give the title compound (99 mg, 35%) as a white solid. $^1$H NMR (400 MHz, DMSO-$d_6$) δ 8.12-8.03 (m, 2H), 7.84-7.65 (m, 4H), 4.94-4.91 (m, 1H), 4.27 (s, 2H), 4.03-3.99 (m, 2H), 3.85-3.70 (m, 7H), 3.31 (s, 3H), 2.82-2.70 (m, 2H), 2.31-2.23 (m, 2H), 2.09-2.03 (m, 3H). LCMS M/Z (M+H) 485.

The Following Examples 233-240 were Prepared in a Similar Fashion to Example 232

| Example | Compound Name and Structure | NMR | m/z |
|---|---|---|---|
| Example 233 | 1-[3-(3-methylsulfonylanilino)-1-tetrahydrofuran-3-yl-6,7-dihydro-4H-pyrazolo[4,3-c]pyridin-5-yl]ethanone | $^1$H NMR (400 MHz, DMSO-$d_6$) δ 8.74-8.68 (m, 1H), 8.09-8.06 (m, 1H), 7.66-7.61 (m, 1H), 7.46-7.40 (m, 1H), 7.23-7.20 (m, 1H), 4.87-4.81 (m, 1H), 4.35 (s, 2H), 4.04-3.99 (m, 2H), 3.86-3.84 (m, 1H), 3.77-3.68 (m, 3H), 3.14 (s, 3H), 2.77-2.65 (m, 2H), 2.26-2.24 (m, 2H), 2.09-2.06 (m, 3H) | 405 |
| Example 234 | 2-[3-[(5-acetyl-1-tetrahydrofuran-3-yl-6,7-dihydro-4H-pyrazolo[4,3-c]pyridin-3-yl)amino]phenyl]-2-methyl-propanenitrile | $^1$H NMR (400MHz, DMSO-$d_6$) δ 8.39-8.30 (m, 1H), 7.77 (s, 1H), 7.32-7.26 (m, 1H), 7.24-7.18 (m, 1H), 6.87-6.78 (m, 1H), 4.88-4.78 (m, 1H), 4.36 (s, 2H), 4.07-3.96 (m, 2H), 3.88-3.65 (m, 4H), 2.78-2.62 (m, 2H), 2.31-2.20 (m, 2H), 2.10-2.07 (m, 3H), 1.70-1.58 (m, 6H). | 394 |
| Example 235 | 1-[3-(3-cyclopropylsulfonylanilino)-1-tetrahydrofuran-3-yl-6,7-dihydro-4H-pyrazolo[4,3-c]pyridin-5-yl]ethanone | $^1$H NMR (400 MHz, DMSO-$d_6$) δ 8.73-8.67 (m, 1H), 8.12-8.08 (m, 1H), 7.63-7.60 (m, 1H), 7.45-7.41 (m, 1H), 7.21-7.18 (m, 1H), 4.87-4.84 (m, 1H), 4.37 (s, 2H), 4.06-4.01 (m, 2H), 3.87- | 431 |

| Example | Compound Name and Structure | NMR | m/z |
|---|---|---|---|
| | | 3.68 (m, 4H), 2.78-2.66 (m, 3H), 2.28-2.23 (m, 2H), 2.10-2.07, (s, 3H), 1.09-1.02 (m, 4H) | |
| Example 236 | 1-[3-[2-isopropyl-4-(1-methylpyrazol-4-yl)anilino]-1-tetrahydrofuran-3-yl-6,7-dihydro-4H-pyrazolo[4,3-c]pyridin-5-yl]ethanone | ¹H NMR (400 MHz, DMSO-d₆) δ 8.00 (s, 1H), 7.73 (s, 1H), 7.33-7.32 (m, 1H), 7.18-7.13 (m, 1H), 7.12 (s, 1H), 7.04- 6.97 (m, 1H), 4.84- 4.81 (m, 1H), 4.16-4.13 (m, 2H), 3.99-3.95 (m, 2H), 3.83 (s, 3H), 3.81-3.66 (m, 4H), 2.78-2.66 (m, 2H), 2.27-2.20 (m, 2H), 2.08-1.97 (m, 3H), 1.23-1.16 (m, 6H) | 449 |
| Example 237 | 1-[3-[2-methyl-4-(1-methylpyrazol-4-yl)anilino]-1-tetrahydrofuran-3-yl-6,7-dihydro-4H-pyrazolo[4,3-c]pyridin-5-yl]ethanone | ¹H NMR (400 MHz, DMSO-d₆) δ 7.94 (s, 1H), 7.71 (s, 1H), 7.28 (s, 1H), 7.23-6.97 (m, 3H), 4.87-4.81 (m, 1H), 4.23-4.19 (m, 2H), 4.00-3.96 (m, 2H), 3.83 (s, 3H), 3.81-3.67 (m, 4H), 2.79-2.67 (m, 2H), 2.29-2.19 (m, 5H), 2.08-2.00 (m, 3H) | 421 |
| Example 238 | 1-[3-[2,5-difluoro-4-(1-methylpyrazol-4-yl)anilino]-1-tetrahydrofuran-3-yl-6,7-dihydro-4H-pyrazolo[4,3-c]pyridin-5-yl]ethanone | ¹H NMR (400 MHz, DMSO-d₆) δ 8.20-8.12 (m, 1H), 8.01 (s, 1H), 7.85-7.74 (m, 2H), 7.52-7.48 (m, 1H), 4.89-4.85 (m, 1H), 4.44-4.38 (m, 2H), 4.03-3.99 (m, 2H), 3.86 (s, 3H), 3.80-3.67 (m, | 443 |

| Example | Compound Name and Structure | NMR | m/z |
|---|---|---|---|
| | | 4H), 2.79-2.67 (m, 2H), 2.31-2.23 (m, 2H), 2.09-2.06 (m, 3H) | |
| Example 239 | 5-[(5-acetyl-1-tetrahydrofuran-3-yl-6,7-dihydro-4H-pyrazolo[4,3-c]pyridin-3-yl)amino]-4-fluoro-2-(1-methylpyrazol-4-yl)benzonitrile | ¹H NMR (400 MHz, DMSO-d₆) δ 8.43-8.34 (m, 2H), 8.17 (d, J = 2.4 Hz, 1H), 7.90 (d, J = 2.4 Hz, 1H), 7.56-7.53 (m, 1H), 4.91-4.84 (m, 1H), 4.43-4.38 (m, 2H), 4.03- 3.99 (m, 2H), 3.89 (s, 3H), 3.79-3.67 (m, 4H), 2.78-2.66 (m, 2H), 2.33-2.23 (m, 2H), 2.08-2.05 (m, 3H) | 450 |
| Example 240 | 3-[(5-acetyl-1-tetrahydrofuran-3-yl-6,7-dihydro-4H-pyrazolo[4,3-c]pyridin-3-yl)amino]-2-fluoro-6-(1-methylpyrazol-4-yl)benzonitrile | ¹H NMR (400MHz, DMSO-d₆) 8.38-8.30 (m, 1H), 8.17-8.02 (m, 2H), 7.87 (s, 1H), 7.41-7.37 (m, 1H), 4.91-4.85 (m, 1H), 4.41-4.36 (m, 2H), 4.00-3.98 (m, 2H), 3.90 (s, 3H), 3.84-3.79 (m, 2H), 3.77-3.68 (m, 2H), 2.79-2.67 (m, 2H), 2.28-2.22 (m, 2H), 2.09-2.06 (m, 3H). | 450 |
| Example 241 | 1-[3-[5-(difluoromethyl)-2-fluoro-4-(1-methylpyrazol-4-yl)anilino]-1-tetrahydrofuran-3-yl-6,7-dihydro-4H-pyrazolo[4,3-c]pyridin-5-yl]ethanone | ¹H NMR (400 MHz, DMSO-d₆) δ 8.40-8.28 (m, 1H), 8.22-8.14 (m, 1H), 7.84 (s, 1H), 7.59 (s, 1H), 7.230-7.24 (m, 1H), 6.89 (t, J = 54.8, 1H), 4.88-4.85 (m, 1H), 4.44-4.38 (m, 2H), 4.06-4.00 | 475 |

| Example | Compound Name and Structure | NMR | m/z |
|---|---|---|---|
| | 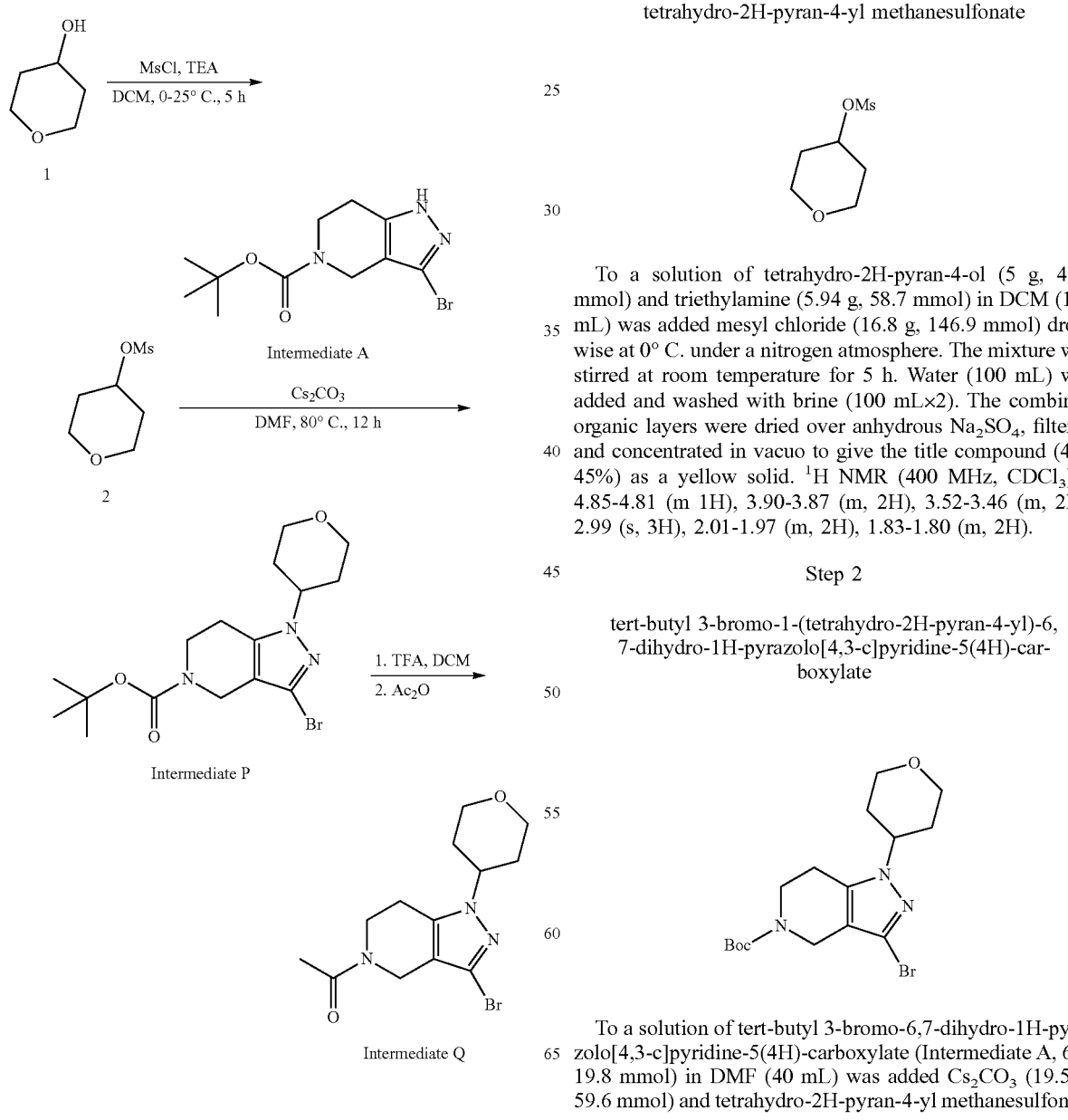 | (m, 2H), 3.88-3.84 (m, 4H), 3.78-3.66 (m, 3H), 2.79-2.67 (m, 2H), 2.29-2.25 (m, 2H), 2.09-2.06 (m, 3H) | |

General Procedure for Intermediates P & Q

Step 1 tetrahydro-2H-pyran-4-yl methanesulfonate

To a solution of tetrahydro-2H-pyran-4-ol (5 g, 49.0 mmol) and triethylamine (5.94 g, 58.7 mmol) in DCM (100 mL) was added mesyl chloride (16.8 g, 146.9 mmol) dropwise at 0° C. under a nitrogen atmosphere. The mixture was stirred at room temperature for 5 h. Water (100 mL) was added and washed with brine (100 mL×2). The combined organic layers were dried over anhydrous $Na_2SO_4$, filtered and concentrated in vacuo to give the title compound (4 g, 45%) as a yellow solid. $^1$H NMR (400 MHz, $CDCl_3$) δ 4.85-4.81 (m 1H), 3.90-3.87 (m, 2H), 3.52-3.46 (m, 2H), 2.99 (s, 3H), 2.01-1.97 (m, 2H), 1.83-1.80 (m, 2H).

Step 2 tert-butyl 3-bromo-1-(tetrahydro-2H-pyran-4-yl)-6,7-dihydro-1H-pyrazolo[4,3-c]pyridine-5(4H)-carboxylate To a solution of tert-butyl 3-bromo-6,7-dihydro-1H-pyrazolo[4,3-c]pyridine-5(4H)-carboxylate (Intermediate A, 6 g, 19.8 mmol) in DMF (40 mL) was added $Cs_2CO_3$ (19.5 g, 59.6 mmol) and tetrahydro-2H-pyran-4-yl methanesulfonate (3.9 g, 21.8 mmol). The mixture was heated to 80° C. for 12 h under a nitrogen atmosphere. After cooling the reaction to room temperature, the mixture was filtered. The mixture was diluted with EtOAc (100 mL) and washed with brine (100 mL×2). The organic layer was concentrated in vacuo. The crude residue was purified by silica gel chromatography (petroleum ether:tert-butyl methyl ether:THF=from 10:1:1 to 2:1:1) to give the title compound (Intermediate P, 3.2 g, 47%) as a clear oil. $^1$H NMR (400 MHz, DMSO-d$_6$) δ 4.35-4.25 (m, 1H), 4.17 (s, 2H), 3.95-3.93 (m, 2H), 3.62-3.57 (m, 2H), 3.42 (t, J=11.2 Hz, 2H), 2.74-2.73 (m, 2H), 1.98-1.89 (m, 2H), 1.80-1.77 (m, 2H), 1.41 (s, 9H).

Step 3

1-(3-bromo-1-(tetrahydro-2H-pyran-4-yl)-6,7-di-hydro-1H-pyrazolo[4,3-c]pyridin-5(4H)-yl)ethanone

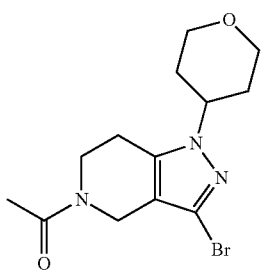 [SMILES: CC(=O)N1CCc2c(c(Br)nn2C2CCOCC2)C1]

To a solution of tert-butyl 3-bromo-1-(tetrahydro-2H-pyran-4-yl)-6,7-dihydro-1H-pyrazolo[4,3-c]pyridine-5 (4H)-carboxylate (Intermediate P, 3.2 g, 8.3 mmol) in DCM (20 mL) was added trifluoroacetic acid (20 mL) dropwise at 0° C. The mixture was stirred at room temperature for 2 h. The mixture was concentrated in vacuo and the residue was re-dissolved in DCM (30 mL). The mixture was cooled to 0° C. before triethylamine (2.1 g, 21 mmol) and acetic anhydride (0.93 g, 9.1 mmol) were added dropwise. The mixture was stirred at room temperature for an additional 0.5 h. The reaction was quenched with water (60 mL). The organic layer was dried over anhydrous Na$_2$SO$_4$, filtered and concentrated in vacuo. The crude residue was purified by silica gel chromatography (DCM/MeOH=50:1) to give the title compound (Intermediate Q, 2.1 g, 77%) as a light yellow solid. $^1$H NMR (400 MHz, DMSO-d$_6$) δ 4.33-4.29 (m, 1H), 4.28 (s 2H), 3.95-3.92 (m, 2H), 3.70-3.67 (m, 2H), 3.43-3.36 (m, 2H), 2.84-2.69 (m, 2H), 2.09-2.08 (m, 3H), 1.96-1.91 (m, 2H), 1.80-1.76 (m, 2H).

Example 242

1-[3-[5-(difluoromethyl)-2-fluoro-4-(1-methylpyrazol-4-yl)anilino]-1-tetrahydropyran-4-yl-6,7-dihydro-4H-pyrazolo[4,3-c]pyridin-5-yl]ethanone

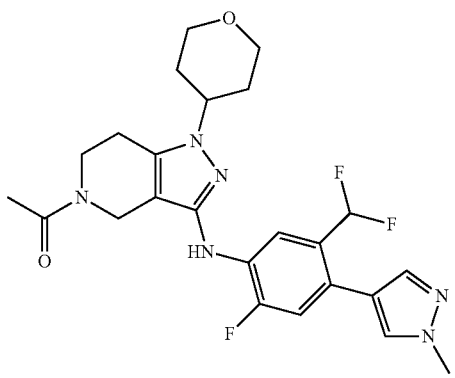 [SMILES: CC(=O)N1CCc2c(c(Nc3cc(C(F)F)c(-c4cnn(C)c4)cc3F)nn2C2CCOCC2)C1]

To a stirred solution of 5-(difluoromethyl)-2-fluoro-4-(1-methylpyrazol-4-yl)aniline (176 mg, 0.73 mmol) in 1,4-dioxane (4 mL) was added 1-(3-bromo-1-(tetrahydro-2H-pyran-4-yl)-6,7-dihydro-1H-pyrazolo[4,3-c]pyridin-5(4H)-yl)ethanone (Intermediate Q, 200 mg, 0.61 mmol), 2-(dicyclohexylphosphino)3,6-dimethoxy-2',4',6'-triisopropyl-1,1'-biphenyl (33 mg, 0.06 mmol), chloro(2-dicyclohexylphosphino-2',6'-di-i-propoxy-1,1'-biphenyl)[2-(2-aminoethylphenyl)]palladium(II), methyl-t-butylether adduct (50 mg, 0.06 mmol) and tBuONa (176 mg, 1.83 mmol). The reaction mixture was heated to 120° C. for 12 h under a nitrogen atmosphere. After cooling to room temperature, water (40 mL) was added, and extracted with DCM (40 mL×2). The combined organic layers were dried over anhydrous Na$_2$SO$_4$, filtered and concentrated in vacuo. The crude residue was purified by reverse phase chromatography (acetonitrile 38-68%/0.225% formic acid in water) to give the title compound (28 mg, 9%) as a white solid. $^1$H NMR (400 MHz, CD$_3$OD) δ 7.98-7.86 (m, 1H), 7.71 (s, 1H), 7.56 (s, 1H), 7.18-7.13 (m, 1H), 6.66 (t, J=55.6, 1H), 4.45-4.37 (m, 2H), 4.29-4.26 (m, 1H), 4.08-4.05 (m, 2H), 3.95 (s, 1H), 3.90-3.82 (m, 2H), 3.60-3.55 (m, 2H), 2.89-2.78 (m, 2H), 2.24-2.14 (m, 5H), 1.88-1.85 (m, 2H). LCMS M/Z (M+H) 489.

The Following Example 243 was Prepared in a Similar Fashion to Example 242

| Example | Compound Name and Structure | NMR | m/z |
|---|---|---|---|
| Example 243 | 1-[3-[4-[3-(difluoromethyl)-1-methyl-pyrazol-4-yl]-2-fluoro-anilino]-1-tetrahydropyran-4-yl-6,7-dihydro-4H-pyrazolo[4,3-c]pyridin-5-yl]ethanone | $^1$H NMR (400 MHz, DMSO-d$_6$) δ 8.06 (s, 1H), 7.90-7.70 (m, 2H), 7.26-7.14 (m, 1H), 7.04-6.91 (m, 2H), 4.41-4.35 (m, 2H), 4.25-4.22 (m, 1H), 3.97-3.94 (m, 2H), 3.88 (s, 3H), 3.73-3.66 (m, 2H), 3.48-3.42 (m, 2H), | 489 |

| Example | Compound Name and Structure | NMR | m/z |
|---|---|---|---|
| | 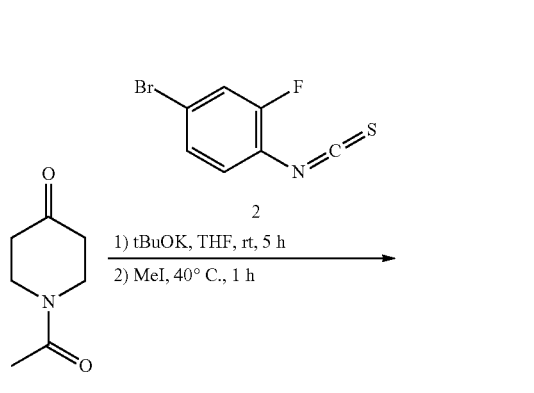 | 2.79-2.67 (m, 2H), 2.08-1.98 (m, 5H), 1.80-1.76 (m, 2H) | |

General Procedure for Intermediate R

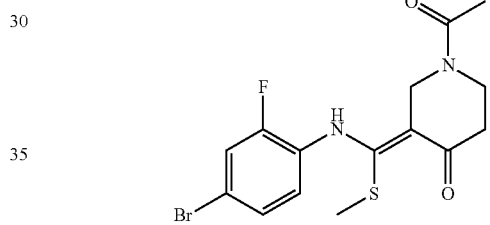

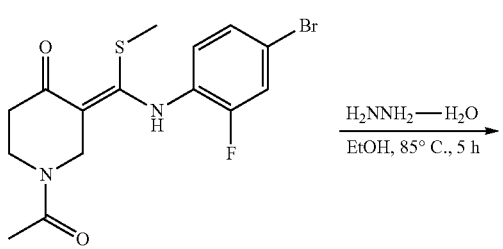

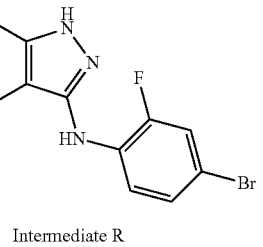

Intermediate R

Step 1

(Z)-1-acetyl-3-(((4-bromo-2-fluorophenyl)amino)(methylthio)methylene)piperidin-4-one

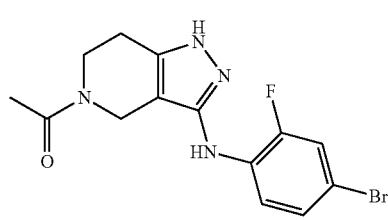 [SMILES: CC(=O)N1CCc2[nH]nc(Nc3ccc(Br)cc3F)c2C1]

To a stirred solution of 1-acetylpiperidin-4-one (6.08 g, 43.09 mmol) in THF (100 mL) at 0° C. was added tBuOK (4.83 g, 43.09 mmol). After stirring at room temperature for 30 min, 4-bromo-2-fluoro-1-isothiocyanato-benzene (10 g, 43.09 mmol) was added. The mixture was stirred at room temperature for an additional 3 h before MeI (7.34 g, 51.71 mmol) was added. The reaction mixture was heated to 40° C. for 1 h. The mixture was quenched with sat. aq. ammonium chloride (100 mL) and washed with EtOAc (100 mL×2). The combined organic layers were dried over anhydrous Na$_2$SO$_4$, filtered and concentrated in vacuo. The crude residue was purified by silica gel column chromatography (petroleum ether/EtOAc=1:1) to give the title compound (8.5 g, 51%) as a yellow oil.

Step 2

1-(3-((4-bromo-2-fluorophenyl)amino)-6,7-dihydro-1H-pyrazolo[4,3-c]pyridin-5(4H)-yl)ethanone A mixture of (Z)-1-acetyl-3-(((4-bromo-2-fluorophenyl)amino)(methylthio)methylene)piperidin-4-one (8.5 g, 21.95 mmol) and hydrazine monohydrate (1.65 g, 32.92 mmol) in EtOH (85 mL) was heated to 60° C. for 2 h. The reaction mixture was concentrated in vacuo to give the title compound (Intermediate R, 7.5 g, crude) as a white solid that required no further purification.

Example 244

1-[3-[2-fluoro-4-(1-methylpyrazol-4-yl)anilino]-1-(2-hydroxy-1,1-dimethyl-ethyl)-6,7-dihydro-4H-pyrazolo[4,3-c]pyridin-5-yl]ethanone

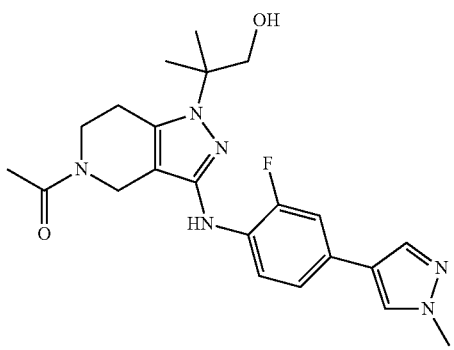 [SMILES: CC(=O)N1CCc2c(c(Nc3ccc(-c4cnn(C)c4)cc3F)nn2C(C)(C)CO)C1]

Step 1

1-(3-((2-fluoro-4-(1-methyl-1H-pyrazol-4-yl)phenyl)amino)-6,7-dihydro-1H-pyrazolo[4,3-c]pyridin-5(4H)-yl)ethanone

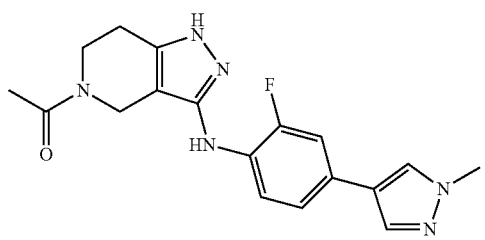 [SMILES: CC(=O)N1CCc2[nH]nc(Nc3ccc(-c4cnn(C)c4)cc3F)c2C1]

To a solution of 1-(3-((4-bromo-2-fluorophenyl)amino)-6,7-dihydro-1H-pyrazolo[4,3-c]pyridin-5(4H)-yl)ethanone (Intermediate R, 6 g, 16.99 mmol) in 1,4-dioxane (50 mL) and water (10 mL) was added 1-methyl-4-(4,4,5,5-tetramethyl-1,3,2-dioxaborolan-2-yl)pyrazole (4.24 g, 20.39 mmol), [1,1'-bis(diphenylphosphino)ferrocene]dichloropalladium(II) (1.24 g, 1.7 mmol) and Na$_2$CO$_3$ (3.6 g, 33.98 mmol). The reaction mixture was heated to 100° C. for 12 h under a nitrogen atmosphere. After cooling to room temperature, the mixture was filtered and concentrated in vacuo. The residue was purified by silica gel column chromatography (DCM/MeOH=30:1) to give the title compound (3.8 g, 63%) as a brown solid.

Step 2 ethyl 2-(5-acetyl-3-((2-fluoro-4-(1-methyl-1H-pyrazol-4-yl)phenyl)amino)-4,5,6,7-tetrahydro-1H-pyrazolo[4,3-c]pyridin-1-yl)-2-methylpropanoate

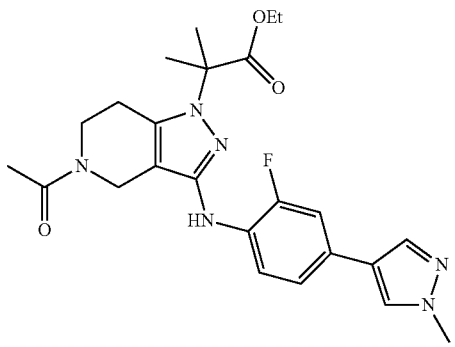 [SMILES: CCOC(=O)C(C)(C)n1nc(Nc2ccc(-c3cnn(C)c3)cc2F)c2c1CCN(C(C)=O)C2]

To a solution of 1-(3-((2-fluoro-4-(1-methyl-1H-pyrazol-4-yl)phenyl)amino)-6,7-dihydro-1H-pyrazolo[4,3-c]pyridin-5(4H)-yl)ethanone (500 mg, 1.4 mmol) and Cs$_2$CO$_3$ (600 mg, 1.8 mmol) in DMF (10 mL) was added ethyl 2-bromo-2-methylpropanoate (320 mg, 1.6 mmol).

The reaction mixture was heated to 80° C. for 16 h. After cooling to room temperature, EtOAc (50 mL) was added and the mixture was washed with brine (100 mL×2), dried over anhydrous Na$_2$SO$_4$, filtered and concentrated in vacuo. The crude residue was purified by silica gel column chromatography (DCM/MeOH=20:1) to give the title compound (150 mg, 25%) as a brown solid. LCMS M/Z (M+H) 469.

Step 3

1-[3-[2-fluoro-4-(1-methylpyrazol-4-yl)anilino]-1-(2-hydroxy-1,1-dimethyl-ethyl)-6,7-dihydro-4H-pyrazolo[4,3-c]pyridin-5-yl]ethanone

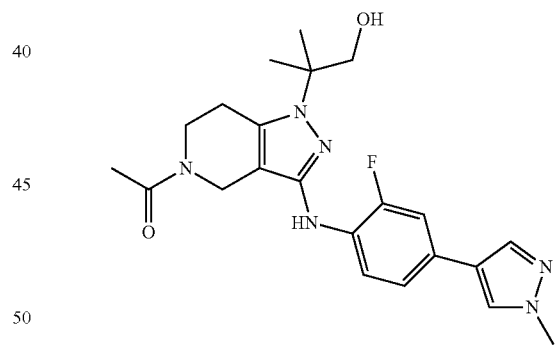

To a solution of ethyl 2-(5-acetyl-3-((2-fluoro-4-(1-methyl-1H-pyrazol-4-yl)phenyl)amino)-4,5,6,7-tetrahydro-1H-pyrazolo[4,3-c]pyridin-1-yl)-2-methylpropanoate (150 mg, 0.3 mmol) in MeOH (20 mL) was added LiBH$_4$ (150 mg, 7.0 mmol). The reaction mixture was heated to 60° C. for 16 h under nitrogen atmosphere. After cooling to room temperature, NaOH (1 M, 10 mL) was added and the mixture was extracted with EtOAc (20 mL×2). The combined organic layers were washed with brine (20 mL×2), dried over anhydrous Na$_2$SO$_4$, filtered and concentrated in vacuo. The crude residue was purified by silica gel column chromatography (DCM/MeOH=15:1) to give the title compound (50 mg, 40%) as a pale brown solid. $^1$H NMR (400 MHz, DMSO-d$_6$) δ 8.03 (s, 1H), 7.81-7.61 (m, 3H), 7.31-7.20 (m, 2H), 5.00 (s, 1H), 4.40-4.32 (m, 2H), 3.83 (s, 3H), 3.68-3.58 (m, 4H), 2.98-2.83 (m, 2H), 2.07-2.05 (m, 3H), 1.48 (s, 6H). LCMS M/Z (M+H) 427.

The Following Example 245 was Prepared in a Similar Fashion to Example 244

| Example | Compound Name and Structure | NMR | m/z |
|---|---|---|---|
| Example 245 | 1-[3-[4-(1,5-dimethylpyrazol-4-yl)-2-fluoro-anilino]-1-(oxetan-3-ylmethyl)-6,7-dihydro-4H-pyrazolo[4,3-c]pyridin-5-yl]ethanone 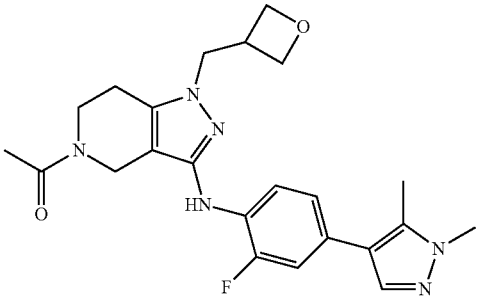 [SMILES: CC(=O)N1CCc2c(c(Nc3ccc(-c4cnn(C)c4C)cc3F)nn2CC2COC2)C1] | $^1$H NMR (400 MHz, DMSO-$d_6$) δ 7.86-7.72 (m, 2H), 7.51 (s, 1H), 7.17-7.03 (m, 2H), 4.67-4.63 (m, 2H), 4.46-4.43 (m, 2H), 4.41-4.34 (m, 2H), 4.19 (d, J = 7.2 Hz, 2H), 3.75 (s, 3H), 3.73-3.65 (m, 2H), 3.38-3.34 (m, 1H), 2.76-2.63 (m, 2H), 2.34 (s, 3H), 2.09-2.05 (m, 3H) | 439 |

General Procedure for Intermediate S

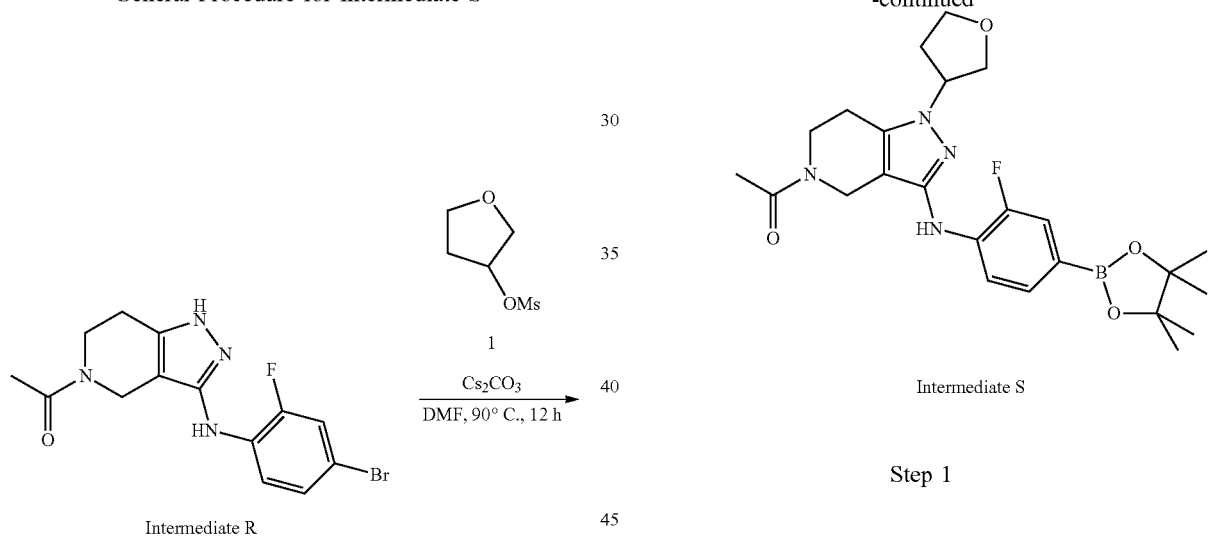

Step 1

1-(3-((4-bromo-2-fluorophenyl)amino)-1-(tetrahydrofuran-3-yl)-6,7-dihydro-1H-pyrazolo[4,3-c]pyridin-5(4H)-yl)ethanone

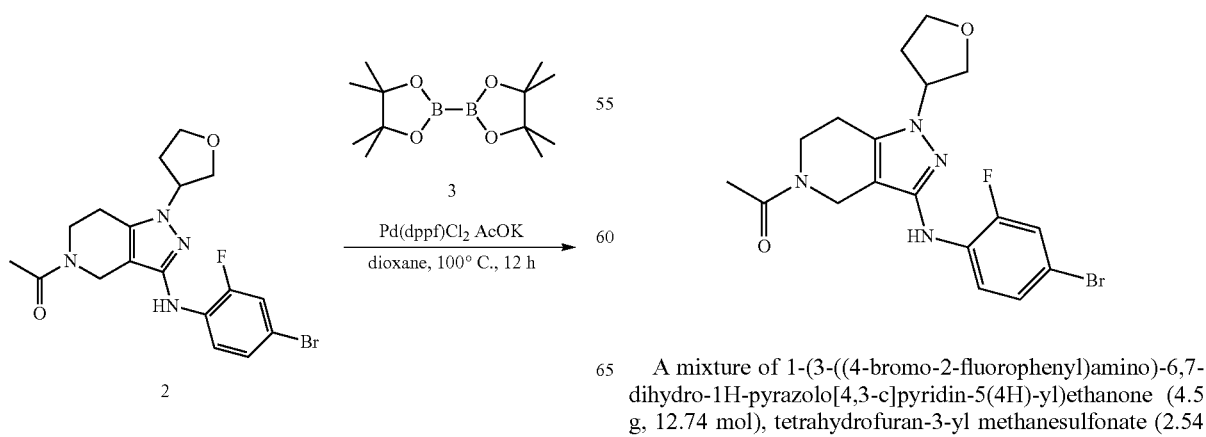

A mixture of 1-(3-((4-bromo-2-fluorophenyl)amino)-6,7-dihydro-1H-pyrazolo[4,3-c]pyridin-5(4H)-yl)ethanone (4.5 g, 12.74 mol), tetrahydrofuran-3-yl methanesulfonate (2.54 g, 15.29 mmol) and Cs$_2$CO$_3$ (8.31 g, 25.48 mmol) in DMF (45 mL) was heated to 90° C. for 12 h. After cooling to room temperature, water (50 mL) was added and the mixture was extracted with DCM (50 mL×2). The combined organic layers were dried over anhydrous Na$_2$SO$_4$, filtered and concentrated in vacuo. The crude residue was purified by silica gel column chromatography (DCM/MeOH=30:1) to give the title compound (3.5 g, 65%) as a yellow solid. $^1$H NMR (400 MHz, CD$_3$OD) δ 8.03-7.96 (m, 1H), 7.76-7.61 (m, 1H), 7.43-7.38 (m, 1H), 7.21-7.17 (m, 1H), 4.86-4.84 (m, 1H), 4.39-4.32 (m, 2H), 3.99-3.97 (m, 2H), 3.83-3.66 (m, 4H), 2.78-2.66 (m, 2H), 2.24-2.21 (m, 2H), 2.08-2.04 (m, 3H).

Step 2

1-(3-((2-fluoro-4-(4,4,5,5-tetramethyl-1,3,2-dioxaborolan-2-yl)phenyl)amino)-1-(tetrahydrofuran-3-yl)-6,7-dihydro-1H-pyrazolo[4,3-c]pyridin-5(4H)-yl)ethanone

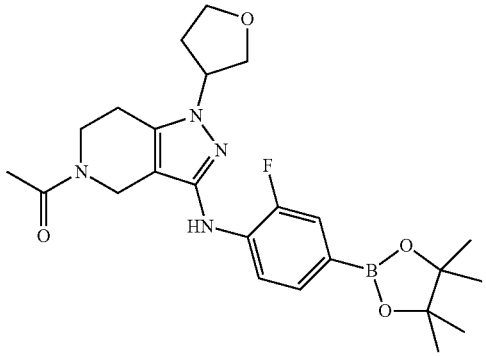 [SMILES: CC(=O)N1CCc2c(c(Nc3ccc(B4OC(C)(C)C(C)(C)O4)cc3F)nn2C2CCOC2)C1]

A mixture of 1-(3-((4-bromo-2-fluorophenyl)amino)-1-(tetrahydrofuran-3-yl)-6,7-dihydro-1H-pyrazolo[4,3-c]pyridin-5(4H)-yl)ethanone (2 g, 4.73 mmol), 4,4,5,5-tetramethyl-2-(4,4,5,5-tetramethyl-1,3,2-dioxaborolan-2-yl)-1,3,2-dioxaborolane (1.44 g, 5.67 mmol), [1,1'-bis(diphenylphosphino)ferrocene]dichloropalladium(II) (0.35 g, 0.47 mmol) and KOAc (1.39 g, 14.18 mmol) in 1,4-dioxane (20 mL) was purged with nitrogen for 1 min. The reaction mixture was heated to 100° C. for 12 h. After cooling to room temperature, water (40 mL) was added and the mixture was extracted with DCM (40 mL×2). The combined organic layers were dried over anhydrous Na$_2$SO$_4$, filtered and concentrated in vacuo. The crude residue was purified by silica gel column chromatography (DCM/MeOH=30:1) to give the title compound (Intermediate S, 1.5 g, 67%) as a yellow solid.

Example 246

1-[3-[4-[3-(difluoromethyl)-1H-pyrazol-4-yl]-2-fluoro-anilino]-1-tetrahydrofuran-3-yl-6,7-dihydro-4H-pyrazolo[4,3-c]pyridin-5-yl]ethanone

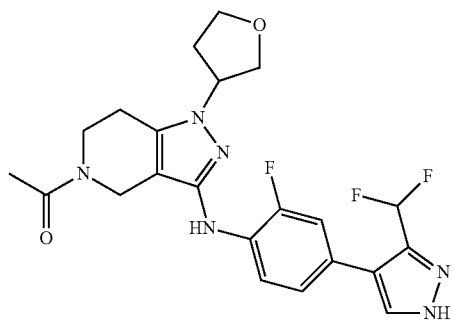 [SMILES: CC(=O)N1CCc2c(c(Nc3ccc(-c4c[nH]nc4C(F)F)cc3F)nn2C2CCOC2)C1]

Step 3

4-bromo-1-((2-(trimethylsilyl)ethoxy)methyl)-1H-pyrazole-3-carbaldehyde

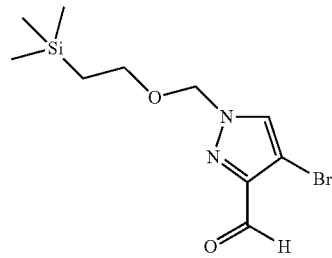 [SMILES: C[Si](C)(C)CCOCn1cc(Br)c(C=O)n1]

To a solution 4-bromo-1H-pyrazole-3-carbaldehyde (2.0 g, 11.4 mmol) in DMF (20 mL) at 0° C. was added sodium hydride (60%, 0.55 g, 13.7 mmol) and the mixture was stirred for 30 min before 2-(trimethylsilyl)ethoxymethyl chloride (2.4 mL, 13.7 mmol) was added and the mixture stirred at room temperature for an additional 16 h. The mixture was quenched with water (25 mL) and extracted with DCM (30 mL×3). The combined organic layers were dried over anhydrous Na$_2$SO$_4$, filtered and concentrated in vacuo. The crude residue was purified by silica gel column chromatography (petroleum ether/EtOAc=8:1) to give the title compound (1 g, 29%) as a yellow oil.

Step 4

4-bromo-3-(difluoromethyl)-1-((2-(trimethylsilyl)ethoxy)methyl)-1H-pyrazole

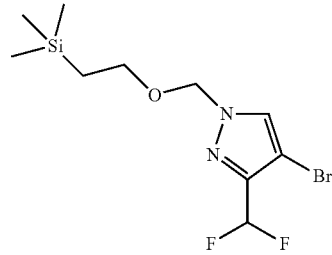 [SMILES: C[Si](C)(C)CCOCn1cc(Br)c(C(F)F)n1]

To a solution of 4-bromo-1-(2-trimethylsilylethoxymethyl)pyrazole-3-carbaldehyde (800 mg, 2.6 mmol) in DCM (8 mL) at 0° C. was added diethylaminosulfur trifluoride (0.87 mL, 6.6 mmol) and the mixture was stirred for 16 h at 0° C. The mixture was quenched with sat. aq. NaHCO₃ (10 mL) and the mixture was extracted with DCM (10 mL×3). The combined organic layers were dried over anhydrous Na₂SO₄, filtered and concentrated in vacuo. The crude residue was purified by silica gel column chromatography (petroleum ether/EtOAc=100:1 to 50:1) to give the title compound (560 mg, 65%) as a yellow oil.

Step 5

1-(3-((4-(3-(difluoromethyl)-1-((2-(trimethylsilyl)ethoxy)methyl)-1H-pyrazol-4-yl)-2-fluorophenyl)amino)-1-(tetrahydrofuran-3-yl)-6,7-dihydro-1H-pyrazolo[4,3-c]pyridin-5(4H)-yl)ethanone

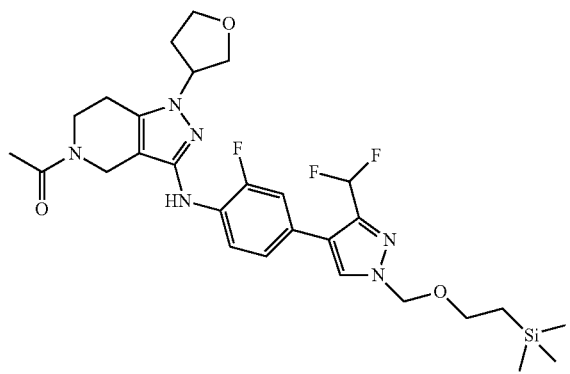 [SMILES: CC(=O)N1CCc2c(c(Nc3ccc(-c4cn(COCC[Si](C)(C)C)nc4C(F)F)cc3F)nn2C2CCOC2)C1]

To a solution of 1-(3-((2-fluoro-4-(4,4,5,5-tetramethyl-1,3,2-dioxaborolan-2-yl)phenyl)amino)-1-(tetrahydrofuran-3-yl)-6,7-dihydro-1H-pyrazolo[4,3-c]pyridin-5(4H)-yl)ethanone (Intermediate S, 300 mg, 0.64 mmol) in 1,4-dioxane (8 mL) and water (2 mL) was added 4-bromo-3-(difluoromethyl)-1-((2-(trimethylsilyl)ethoxy)methyl)-1H-pyrazole (251 mg, 0.77 mmol), [1,1'-bis(diphenylphosphino)ferrocene]dichloropalladium(II) (47 mg, 0.06 mmol) and Na₂CO₃ (207 mg, 1.9 mmol). The reaction mixture was heated to 120° C. for 16 h. After cooling to room temperature, the reaction mixture was filtered and concentrated in vacuo. The crude residue was purified by silica gel column chromatography (DCM/MeOH=50:1 to 20:1) to give the title compound (80 mg, 21%) as a yellow oil.

Step 6

1-[3-[4-[3-(difluoromethyl)-1H-pyrazol-4-yl]-2-fluoro-anilino]-1-tetrahydrofuran-3-yl-6,7-dihydro-4H-pyrazolo[4,3-c]pyridin-5-yl]ethanone

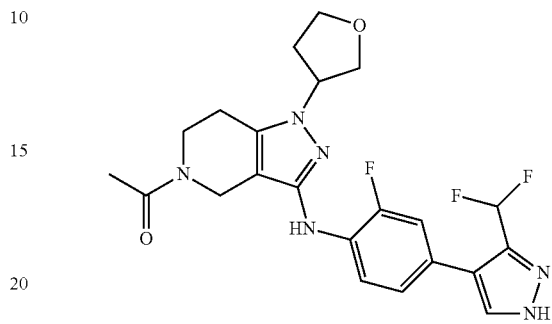

To a solution of 1-(3-((4-(3-(difluoromethyl)-1-((2-(trimethylsilyl)ethoxy)methyl)-1H-pyrazol-4-yl)-2-fluorophenyl)amino)-1-(tetrahydrofuran-3-yl)-6,7-dihydro-1H-pyrazolo[4,3-c]pyridin-5(4H)-yl)ethanone (150 mg, 0.25 mmol) in 1,4-dioxane (2 mL) was added HCl/dioxane (4 M, 4 mL) and the reaction mixture was stirred at 25° C. for 16 h. The mixture was concentrated in vacuo. Water (20 mL) was added and the mixture was made basic with sat. aq. NaHCO₃ to pH 7 and then extracted with DCM (10 mL×3). The combined organic layers were dried over anhydrous Na₂SO₄, filtered and concentrated in vacuo. The crude residue was purified by reverse phase chromatography (acetonitrile 23-53%/0.1% formic acid in water) to give the title compound (40 mg, 34%) as a colorless oil. $^{1}$H NMR (400 MHz, CD₃OD) δ 7.87 (s, 1H), 7.62-7.49 (m, 1H), 7.27-7.23 (m, 1H), 7.20-7.15 (m, 1H), 6.85 (t, J=54 Hz, 1H), 4.89-4.86 (m, 1H), 4.44-4.42 (m, 2H), 4.18-4.15 (m, 1H), 4.09-4.06 (m, 1H), 3.98-3.88 (m, 3H), 3.84-3.79 (m, 1H), 2.88-2.76 (m, 2H), 2.39-2.33 (m, 2H), 2.20-2.14 (m, 3H). LCMS M/Z (M+H) 461.

The Following Examples 247-249 were Prepared in a Similar Fashion to Example 246

| Example | Compound Name and Structure | NMR | m/z |
|---|---|---|---|
| Example 247 | 4-[4-[(5-acetyl-1-tetrahydrofuran-3-yl-6,7-dihydro-4H-pyrazolo[4,3-c]pyridin-3-yl)amino]-3-fluoro-phenyl]-1-methyl-pyrazole-3-carboxamide 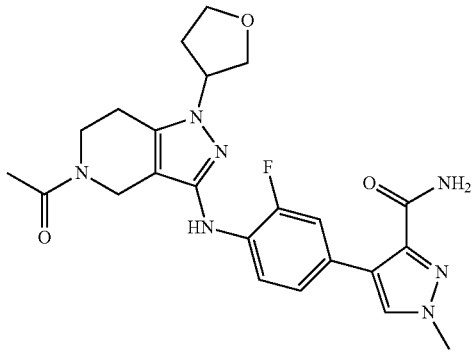 [SMILES: CC(=O)N1CCc2c(c(Nc3ccc(-c4cn(C)nc4C(N)=O)cc3F)nn2C2CCOC2)C1] | $^{1}$H NMR (400 MHz, DMSO-d₆) δ 7.98 (s, 1H), 7.85-7.64 (m, 2H), 7.52-7.45 (m, 2H), 7.23-7.20 (m, 2H), 4.87-4.84 (m, 1H), 4.41-4.35 (m, 2H), 4.03-3.99 (m, 2H), 3.87 (s, 3H), 3.84-3.80 (m, 2H), 3.76-3.67 (m, 2H), 2.78-2.66 (m, 2H), 2.28-2.23 (m, 2H), 2.09-2.05 (m, 3H) | 468 |

-continued

| Example | Compound Name and Structure | NMR | m/z |
|---|---|---|---|
| Example 248 | 1-[3-[2-fluoro-4-(1H-pyrazol-4-yl)anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 12.84 (s, 1H), 8.10 (s, 1H), 7.91-7.79 (m, 2H), 7.76-7.67 (m, 1H), 7.42-7.38 (m, 1H), 7.31-7.26 (m, 1H), 4.90-4.80 (m, 1H), 4.42-4.32 (m, 2H), 4.05-3.96 (m, 2H), 3.88-3.76 (m, 2H), 3.74-3.64 (m, 2H), 2.81-2.63 (m, 2H), 2.31-2.19 (m, 2H), 2.08-2.05 (m, 3H). | 411 |
| Example 249 | 1-[3-[4-(2,4-dimethyloxazol-5-yl)-2-fluoro-anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.11-7.99 (m, 1H), 7.93-7.72 (m, 1H), 7.34-7.18 (m, 2H), 4.91-4.82 (m, 1H), 4.44-4.31 (m, 2H), 4.06-3.95 (m, 2H), 3.88-3.76 (m, 2H), 3.74-3.66 (m, 2H), 2.81-2.65 (m, 2H), 2.39 (s, 3H), 2.32-2.22 (s, 5H), 2.09-2.05 (m, 3H). | 440 |

Example 250

1-[3-[N-benzyl-4-(1-methylpyrazol-4-yl)anilino]-1-[(3S)-tetrahydrofuran-3-yl]-6,7-dihydro-4H-pyrazolo[4,3-c]pyridin-5-yl]ethanone

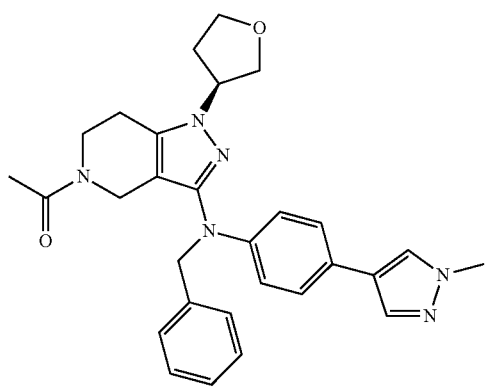 [SMILES: CC(=O)N1CCc2c(c(N(Cc3ccccc3)c3ccc(-c4cnn(C)c4)cc3)nn2[C@H]2CCOC2)C1]

To a solution (S)-1-[3-[4-(1-methylpyrazol-4-yl)anilino]-1-tetrahydrofuran-3-yl-6,7-dihydro-4H-pyrazolo[4,3-c]pyridin-5-yl]ethanone (Examples 178, 100 mg, 0.25 mmol) in DMF (2 mL) at 0° C. was added sodium hydride (60%, 20 mg, 0.49 mmol) and the mixture was stirred for 30 min. Benzyl bromide (51 mg, 0.3 mmol) was added and the mixture stirred at room temperature for an additional 2 h. The mixture was quenched with water (10 mL) and extracted with EtOAc (10 mL×3). The combined organic layers were dried over anhydrous $Na_2SO_4$, filtered and concentrated in vacuo. The crude residue was purified by reverse phase chromatography (acetonitrile 36-66%/0.1% $NH_4OH$ in water) to give the tittle compound (45 mg, 37%) as a white solid. $^1$H NMR (400 MHz, DMSO-$d_6$) δ 7.94 (s, 1H), 7.69 (s, 1H), 7.39-7.19 (m, 7H), 6.78-6.73 (m, 2H), 4.96 (s, 2H), 4.87-3.85 (m, 1H), 4.00-3.94 (m, 4H), 3.81-3.66 (m, 7H), 2.81-2.67 (m, 2H), 2.28-2.22 (m, 2H), 2.04-1.85 (m, 3H). LCMS M/Z (M+Na) 519.

The Following Example 251 was Prepared in a Similar Fashion to Example 250

| Example | Compound Name and Structure | NMR | m/z |
|---|---|---|---|
| Example 251 | 1-[3-[N-ethyl-4-(1-methylpyrazol-4-yl)anilino]-1-[(3S)-tetrahydrofuran-3-yl]-6,7-dihydro-4H-pyrazolo[4,3-c]pyridin-5-yl]ethanone<br>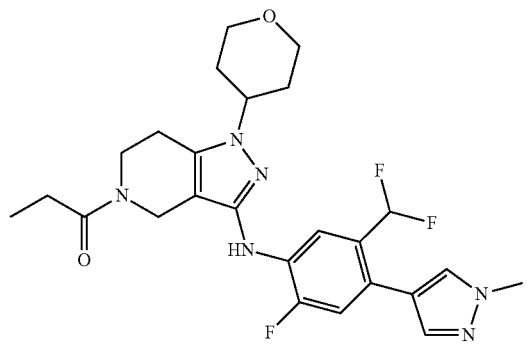 [SMILES: CCC(=O)N1CCc2c(c(Nc3cc(C(F)F)c(-c4cnn(C)c4)cc3F)nn2C2CCOCC2)C1] | $^1$H NMR (400 MHz, DMSO-$d_6$) δ 7.97 (s, 1H), 7.72 (s, 1H), 7.40-7.36 (m, 2H), 6.78-6.74 (m, 2H), 4.91-4.84 (m, 1H), 4.01-3.99 (m, 2H), 3.90 (s, 2H), 3.83 (s, 3H), 3.82-3.79 (m, 2H), 3.72-3.65 (m, 4H), 2.82-2.67 (m, 2H), 2.27-2.22 (m, 2H), 2.03-1.85 (m, 3H), 1.16-1.12 (m, 3H). | 435 |

Example 252

1-[3-[5-(difluoromethyl)-2-fluoro-4-(1-methylpyrazol-4-yl)anilino]-1-tetrahydropyran-4-yl-6,7-dihydro-4H-pyrazolo[4,3-c]pyridin-5-yl]propan-1-one

Step 1 tert-butyl 3-((5-(difluoromethyl)-2-fluoro-4-(1-methyl-1H-pyrazol-4-yl)phenyl)amino)-1-(tetrahydro-2H-pyran-4-yl)-6,7-dihydro-1H-pyrazolo[4,3-c]pyridine-5(4H)-carboxylate

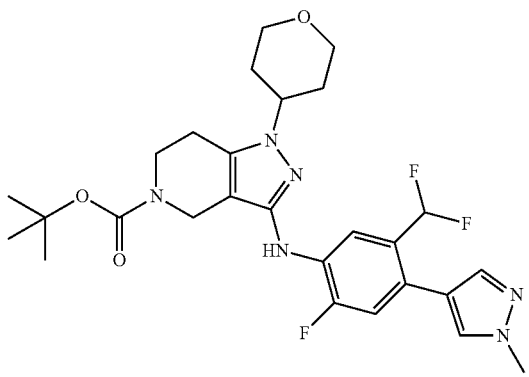 [SMILES: Cn1cc(-c2cc(F)c(Nc3nn(C4CCOCC4)c4c3CN(C(=O)OC(C)(C)C)CC4)cc2C(F)F)cn1]

To a stirred solution of 5-(difluoromethyl)-2-fluoro-4-(1-methylpyrazol-4-yl)aniline (500 mg, 2.1 mmol) in 1,4-dioxane (8 mL) was added tert-butyl 3-bromo-1-tetrahydropyran-4-yl-6,7-dihydro-4H-pyrazolo[4,3-c]pyridine-5-carboxylate (Intermediate P, 961 mg, 2.5 mmol), 2-(dicyclohexylphosphino)3,6-dimethoxy-2',4',6'-triisopropyl-1,1'-biphenyl (111 mg, 0.2 mmol), chloro(2-dicyclohexylphosphino-2',6'-di-i-propoxy-1,1'-biphenyl)(2'-amino-1,1'-biphenyl-2-yl)palladium(II) (161 mg, 0.2 mmol) and tBuONa (498 mg, 5.2 mmol). The reaction mixture was heated to 120° C. for 16 h under a nitrogen atmosphere. After cooling to room temperature, water (40 mL) was added and the mixture was extracted with EtOAc (40 mL×2). The combined organic layers were dried over anhydrous Na$_2$SO$_4$, filtered and concentrated in vacuo. The crude residue was purified by silica gel column chromatography (DCM/MeOH=50:1) to give the title compound (600 mg, 53%). LCMS M/Z (M+H) 548.

Step 2

N-(5-(difluoromethyl)-2-fluoro-4-(1-methyl-1H-pyrazol-4-yl)phenyl)-1-(tetrahydro-2H-pyran-4-yl)-4,5,6,7-tetrahydro-1H-pyrazolo[4,3-c]pyridin-3-amine

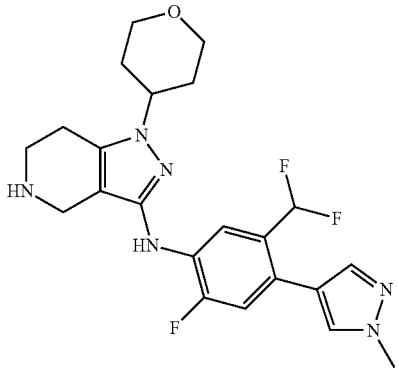 [SMILES: Cn1cc(-c2cc(F)c(Nc3nn(C4CCOCC4)c4c3CNCC4)cc2C(F)F)cn1]

To a stirred solution of tert-butyl 3-((5-(difluoromethyl)-2-fluoro-4-(1-methyl-1H-pyrazol-4-yl)phenyl)amino)-1-(tetrahydro-2H-pyran-4-yl)-6,7-dihydro-1H-pyrazolo[4,3-c]pyridine-5(4H)-carboxylate (150 mg, 0.2 mmol) in DCM (2 mL) at 0° C. was added a solution of trifluoroacetic acid (0.08 mL, 1.1 mmol) in DCM (2 mL). The mixture was stirred at 20° C. for 15 minutes and concentrated in vacuo to give the title compound (100 mg, crude) as a brown oil that required no further purification.

Step 3

1-[3-[5-(difluoromethyl)-2-fluoro-4-(1-methylpyrazol-4-yl)anilino]-1-tetrahydropyran-4-yl-6,7-dihydro-4H-pyrazolo[4,3-c]pyridin-5-yl]propan-1-one

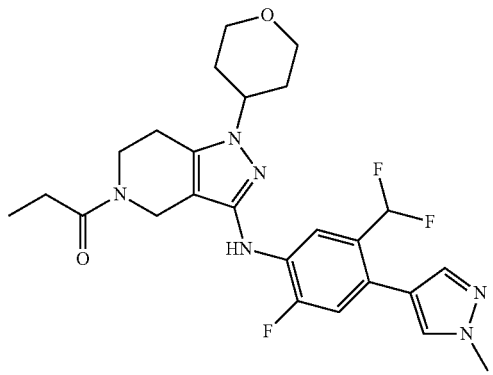 [SMILES: CCC(=O)N1CCc2c(c(Nc3cc(C(F)F)c(-c4cnn(C)c4)cc3F)nn2C2CCOCC2)C1]

To a stirred solution of N-(5-(difluoromethyl)-2-fluoro-4-(1-methyl-1H-pyrazol-4-yl)phenyl)-1-(tetrahydro-2H-pyran-4-yl)-4,5,6,7-tetrahydro-1H-pyrazolo[4,3-c]pyridin-3-amine (100 mg, 0.2 mmol) and N,N-diisopropylethylamine (0.12 mL, 0.7 mmol) in DCM (3 mL) at 0° C. was added a solution of propionyl chloride (0.02 mL, 0.25 mmol) in DCM (2 mL) dropwise. The reaction mixture was stirred at 20° C. for 10 minutes. Water (10 mL) was added and the mixture was extracted with DCM (10 mL×2). The combined organic layers were dried over anhydrous $Na_2SO_4$, filtered and concentrated in vacuo. The crude residue was purified by reverse phase chromatography (acetonitrile 30-60%/0.225% formic acid in water) to give the title compound (22 mg, 19%) as a white solid. $^1$H NMR (400 MHz, DMSO-$d_6$) δ 8.38-8.24 (m, 1H), 8.19-8.10 (m, 1H), 7.84 (s, 1H), 7.59 (d, J=2.2 Hz, 1H), 7.30-7.24 (m, 1H), 6.90 (t, J=54.8 Hz, 1H), 4.44-4.38 (m, 2H), 4.27-4.18 (m, 1H), 4.00-3.92 (m, 2H), 3.88 (s, 3H), 3.76-3.67 (m, 2H), 3.48-4.42 (m, 2H), 2.81-2.67 (m, 2H), 2.44-2.34 (m, 2H), 1.95-2.06 (m, 2H), 1.83-1.75 (m, 2H), 1.02-0.98 (m, 3H). LCMS M/Z (M+H) 503.

The Following Examples 253-255 were Prepared in a Similar Fashion to Example 252

| Example | Compound Name and Structure | NMR | m/z |
| --- | --- | --- | --- |
| Example 253 | 1-[3-[5-(difluoromethyl)-2-fluoro-4-(1-methylpyrazol-4-yl)anilino]-1-tetrahydropyran-4-yl-6,7-dihydro-4H-pyrazolo[4,3-c]pyridin-5-yl]butan-1-one | $^1$H-NMR (400 MHz, DMSO-$d_6$) δ 8.38-8.24 (m, 1H), 8.18-8.09 (m, 1H), 7.84 (s, 1H), 7.59 (d, J = 2.6 Hz, 1H), 7.30-7.24 (m, 1H), 6.89 (t, J = 55.2, 1H), 4.46-4.36 (m, 2H), 4.27-4.19 (m, 1H), 3.97-3.94 (m, 2H), 3.88 (s, 3H), 3.77-3.67 (m, 2H), 3.49-3.42 (m, 2H), 2.81-2.65 (m, 2H), 2.40-2.32 (m, 2H), 2.06-1.95 (m, 2H), 1.84-1.75 (m, 2H), 1.57-1.49 (m, 2H), 0.92-0.87 (m, 3H) | 517 |

-continued

| Example | Compound Name and Structure | NMR | m/z |
|---|---|---|---|
| Example 254 | 1-[3-[3-(difluoromethyl)-4-(1-methylpyrazol-4-yl)anilino]-1-tetrahydrofuran-3-yl-6,7-dihydro-4H-pyrazolo[4,3-c]pyridin-5-yl]propan-1-one | ¹H NMR (400 MHz, DMSO-d$_6$) δ 8.55-8.42 (m, 1H), 7.93-7.83 (m, 1H), 7.78 (s, 1H), 7.54-7.52 (m, 2H), 7.34-7.23 (m, 1H), 6.89 (t, J = 55.2, 1H), 4.88-4.79 (m, 1H), 4.38 (s., 2H), 4.09-3.98 (m, 2H), 3.88 (s, 3H), 3.86-3.67 (m, 4H), 2.80-2.62 (m, 2H), 2.47-2.35 (m, 2H), 2.25 (q, J = 7.2 Hz, 2H), 1.02 (t, J = 7.2 Hz, 3H) | 471 |
| Example 255 | 1-[3-[3-(difluoromethyl)-4-(1-methylpyrazol-4-yl)anilino]-1-tetrahydrofuran-3-yl-6,7-dihydro-4H-pyrazolo[4,3-c]pyridin-5-yl]butan-1-one | 1H NMR (400 MHz, DMSO-d$_6$) δ 8.53-8.42 (m, 1H), 7.93-7.83 (m, 1H), 7.78 (s, 1H), 7.58-7.51 (m, 2H), 7.32-7.25 (m, 1H), 6.89 (t, J = 54.8, 1H), 4.91-4.79 (m, 1H), 4.38 (s, 2H), 4.08-3.97 (m, 2H), 3.88 (s, 3H), 3.86-3.68 (m, 4H), 2.78-2.63 (m, 2H), 2.41-2.33 (m, 2H), 2.25 (q, J = 6.4 Hz, 2H), 1.60-1.48 (m, 2H), 0.93-0.86 (m, 3H) | 485 |

Example 256

3-[5-(difluoromethyl)-2-fluoro-4-(1-methylpyrazol-4-yl)anilino]-1-tetrahydropyran-4-yl-6,7-dihydro-4H-pyrazolo[4,3-c]pyridine-5-carboxamide

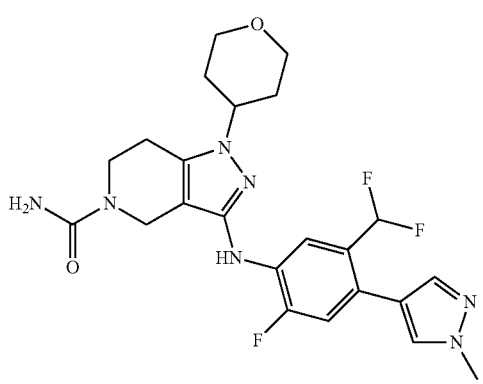 [SMILES: Cn1cc(-c2cc(F)c(Nc3nn(C4CCOCC4)c4c3CN(C(N)=O)CC4)cc2C(F)F)cn1]

To a solution of N-(5-(difluoromethyl)-2-fluoro-4-(1-methyl-1H-pyrazol-4-yl)phenyl)-1-(tetrahydro-2H-pyran-4-yl)-4,5,6,7-tetrahydro-1H-pyrazolo[4,3-c]pyridin-3-amine (100 mg, 0.2 mmol) in DCM (2 mL) was added trimethylsilyl isocyanate (46 mg, 0.4 mmol). The reaction mixture was stirred at 26° C. for 4 h and concentrated in vacuo. The crude residue was purified by reverse phase chromatography (acetonitrile 30-60%/0.2% formic acid in water) to give the title compound (11 mg, 11%) as a white solid. ¹H NMR (400 MHz, DMSO-d$_6$) δ 8.15 (d, J=8.8 Hz, 1H), 7.99 (s, 1H), 7.84 (s, 1H), 7.59 (s, 1H), 7.25 (d, J=12.4 Hz, 1H), 6.89 (t, J=54.8 Hz, 1H), 6.03 (s, 2H), 4.26-4.21 (m, 3H), 3.96-3.94 (m, 2H), 3.87 (s, 3H), 3.59-3.56 (m, 2H), 3.48-3.42 (m, 2H), 2.68-2.66 (m, 2H), 2.07-1.95 (m, 2H), 1.80-1.78 (m, 2H). LCMS M/Z (M+H) 490.

The Following Examples 257-259 were Prepared in
a Similar Fashion to Example 256

| Example | Compound Name and Structure | NMR | m/z |
|---|---|---|---|
| Example 257 | 3-[5-(difluoromethyl)-2-fluoro-4-(1-methylpyrazol-4-yl)anilino]-1-[(3S)-tetrahydrofuran-3-yl]-6,7-dihydro-4H-pyrazolo[4,3-c]pyridine-5-carboxamide | $^1$H NMR (400 MHz, DMSO-d$_6$) δ 8.20 (d, J = 8.8 Hz, 1H), 8.04 (s, 1H), 7.84 (s, 1H), 7.59 (s, 1H), 7.26 (d, J = 12.4 Hz, 1H), 6.89 (t, J = 54.8 Hz, 1H), 6.03 (s, 2H), 4.90-4.87 (m, 1H), 4.23 (s, 2H), 4.11-3.96 (m, 2H), 3.92-3.81 (m, 4H), 3.77-3.75 (m, 1H), 3.59-3.56 (m, 2H), 2.68-2.65 (m, 2H), 2.31-2.18 (m, 2H) | 476 |
| Example 258 | 3-[2-fluoro-4-(1-methylpyrazol-4-yl)anilino]-1-[(3S)-tetrahydrofuran-3-yl]-6,7-dihydro-4H-pyrazolo[4,3-c]pyridine-5-carboxamide | $^1$H NMR (400 MHz, DMSO-d$_6$) δ 8.02 (s, 1H), 7.78 (s, 1H), 7.65-7.61 (m, 2H), 7.37-7.33 (m, 1H), 7.23 (d, J = 8.4 Hz, 1H), 6.03 (s, 2H), 4.89-4.85 (m, 1H), 4.20 (s, 2H), 4.01-3.99 (m, 2H), 3.84 (s, 3H), 3.83-3.78 (m, 2H), 3.58-2.58 (m, 2H), 2.68-2.65 (m, 2H), 2.26-2.21 (m, 2 H) | 426 |
| Example 259 | 3-[2-fluoro-4-(1-methylpyrazol-4-yl)anilino]-1-tetrahydropyran-4-yl-6,7-dihydro-4H-pyrazolo[4,3-c]pyridine-5-carboxamide | $^1$H NMR (400 MHz, DMSO-d$_6$) δ 8.01 (s, 1H), 7.78 (s, 1H), 7.66-7.62 (m, 1H), 7.58 (s, 1H), 7.36-7.32 (m, 1H), 7.23 (d, J = 8.4 Hz, 1H), 6.01 (s, 2H), 4.31-4.13 (m, 3H), 3.97-3.94 (m, 2H), 3.83 (s, 3H), 3.59-3.56 (m, 2H). 3.48-3.43 (m, 2H), 2.69-2.63 (m, 2H), 2.07-2.01 (m, 2H), 1.79-1.76 (m, 2H) | 440 |

Example 260

3-[5-(difluoromethyl)-2-fluoro-4-(1-methylpyrazol-4-yl)anilino]-N-methyl-1-tetrahydropyran-4-yl-6,7-dihydro-4H-pyrazolo[4,3-c]pyridine-5-carboxamide

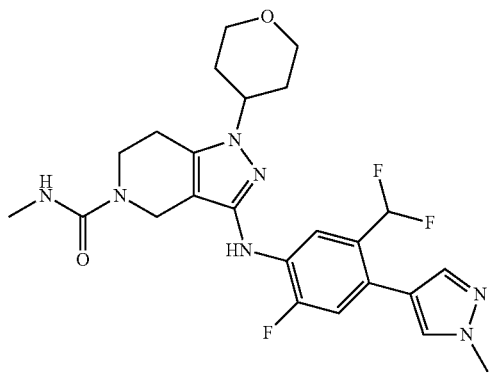

To a solution of N-(5-(difluoromethyl)-2-fluoro-4-(1-methyl-1H-pyrazol-4-yl)phenyl)-1-(tetrahydro-2H-pyran-4-yl)-4,5,6,7-tetrahydro-1H-pyrazolo[4,3-c]pyridin-3-amine (200 mg, 0.4 mmol) and pyridine (0.06 mL, 2.02 mmol) in DMF (2 mL) was added 4-nitrophenylchloroformate (244 mg, 1.21 mmol). The reaction mixture was stirred at 26° C. for 4 h. Methanamine in THF (2 M, 0.77 mL, 1.54 mmol) was added and the reaction mixture was heated to 60° C. for an additional 12 h. The mixture was concentrated in vacuo. The crude residue was purified by reverse phase chromatography (acetonitrile 26-56%/0.2% formic acid in water) to give the title compound (15 mg, 19%) as a white solid. $^1$H NMR (400 MHz, DMSO-$d_6$) δ 8.12 (d, J=9.2 Hz, 1H), 8.01 (s, 1H), 7.83 (s, 1H), 7.58 (s, 1H), 7.25 (d, J=12.8 Hz, 1H), 6.88 (t, J=54.8 Hz, 1H), 6.49 (d, J=4.4 Hz, 1H), 4.25-4.20 (m, 3H), 3.96-3.93 (m, 2H), 3.87 (s, 3H), 3.58-3.56 (m, 2H), 3.45-3.42 (m, 2H), 2.68-2.66 (m, 2H), 2.57-2.55 (m, 3H), 2.04-1.94 (m, 2H), 1.79-1.77 (m, 2H). LCMS M/Z (M+H) 504.

The Following Examples 261-272 were Prepared in a Similar Fashion to Example 260

| Example | Compound Name and Structure | NMR | m/z |
| --- | --- | --- | --- |
| Example 261 | 3-[5-(difluoromethyl)-2-fluoro-4-(1-methylpyrazol-4-yl)anilino]-N-methyl-1-[(3S)-tetrahydrofuran-3-yl]-6,7-dihydro-4H-pyrazolo[4,3-c]pyridine-5-carboxamide | $^1$H NMR (400 MHz, DMSO-$d_6$) δ 8.18 (d, J = 8.8 Hz, 1H), 8.06 (s, 1H), 7.84 (s, 1H), 7.59 (s, 1H), 7.26 (d, J = 12.8 Hz, 1H), 6.88 (t, J = 54.8 Hz, 1H), 6.50 (d, J = 4.5 Hz, 1H), 4.89-4.86 (m, 1H), 4.22 (s, 2H), 4.10-3.96 (m, 2H), 3.90-3.86 (m, 4H), 3.79-3.66 (m, 1H), 3.59-3.56 (m, 2H), 2.69-2.65 (m, 2H), 2.58-2.54 (m, 3H), 2.34-2.20 (m, 2H) | 490 |
| Example 262 | 3-[2-fluoro-4-(1-methylpyrazol-4-yl)anilino]-N-methyl-1-[(3S)-tetrahydrofuran-3-yl]-6,7-dihydro-4H-pyrazolo[4,3-c]pyridine-5-carboxamide | $^1$H NMR (400 MHz, DMSO-$d_6$) δ 7.99 (s, 1H), 7.75 (s, 1H), 7.61-7.54 (m, 2H), 7.33-7.30 (m, 1H), 7.20-7.17 (m, 1H), 6.46-6.45 (m, 1H), 4.84-4.82 (m, 1H), 4.15 (s, 2H), 3.97-3.95 (m, 2H), 3.80 (s, 3H), 3.76-3.74 (m, 2H), 3.55-3.52 (m, 2H), 2.64-2.62 (m, 2H), 2.54-2.52 (m, 3H), 2.22-2.17 (m, 2H) | 440 |

-continued

| Example | Compound Name and Structure | NMR | m/z |
|---------|------------------------------|-----|-----|
| Example 263 | 3-[2-fluoro-4-(1-methylpyrazol-4-yl)anilino]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.21-8.05 (m, 1H), 8.01 (s, 1H), 7.85-7.70 (m, 2H), 7.67-7.55 (m, 1H), 7.35 (d, J = 13.2 Hz, 1H), 7.26-7.23 (m, 1H), 6.49-6.48 (m, 1H), 4.32-4.18 (m, 3H), 3.97-3.95 (m, 2H), 3.84 (s, 3H), 3.73-3.63 (m, 1H), 3.58-3.42 (m, 3H), 2.80-2.66 (m, 2H), 2.57-2.55 (m, 3H), 2.04-2.00 (m, 2H), 1.79-1.75 (m, 2H) | 454 |
| Example 264 | 3-[2,3-difluoro-4-(1-methylpyrazol-4-yl)anilino]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.15-7.95 (m, 2H), 7.78 (s, 1H), 7.54-7.25 (m, 2H), 6.49-6.48 (m, 1H), 4.33-4.13 (m, 3H), 4.00-3.91 (m, 2H), 3.87 (s, 3H), 3.59-3.56 (m, 2H), 3.48-3.42 (m, 2H), 2.71-2.64 (m, 2H), 2.57-2.55 (m, 3H), 2.08-1.93 (m, 2H), 1.80-1.76 (m, 2H) | 472 |
| Example 265 | 3-[2-fluoro-4-[1-methyl-3-(trifluoromethyl)pyrazol-4-yl]anilino]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.10 (s, 1H), 7.79 (s, 1H), 7.64-7.59 (m, 1H), 7.13 (d, J = 13.2 Hz, 1H), 7.06 (d, J = 8.4 Hz, 1H), 6.50-6.47 (m, 1H), 4.28-4.21 (m, 1H), 4.19 (s, 2H), 3.99-3.94 (m, 2H), 3.93 (s, 3H), 3.59-3.57 (m, 2H), 3.48-3.42 (m, 2H), 2.72-2.63 (m, 2H), 2.57-2.55 (m, 3H), 2.05-1.96 (m, 2H), 1.84-1.73 (m, 2H). | 522 |

| Example | Compound Name and Structure | NMR | m/z |
|---|---|---|---|
| Example 266 | 3-[5-(difluoromethyl)-2-fluoro-4-(2-methoxy-4-pyridyl)anilino]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.23-8.21 (m, 2H), 8.15 (d, J = 8.8 Hz, 1H), 7.27 (d, J = 12.0 Hz, 1H), 6.98 (d, J = 4.4 Hz, 1H), 6.84 (t, J = 54.8 Hz, 1H), 6.78 (s, 1H), 6.50 (d, J = 4.0 Hz, 1H), 4.31-4.17 (m, 3H), 3.97-3.94 (m, 2H), 3.89 (s, 3H), 3.64-3.54 (m, 2H), 3.51-3.42 (m, 2H), 2.75-2.65 (m, 2H), 2.57-2.56 (m, 3H), 2.08-1.93 (m, 2H), 1.82-1.78 (m, 2H) | 531 |
| Example 267 | 3-[4-(1,5-dimethylpyrazol-4-yl)-2-fluoro-anilino]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 7.68-7.64 (m, 1H), 7.60 (s, 1H), 7.51 (s, 1H), 7.14 (d, J = 13.2 Hz, 1H), 7.06 (d, J = 8.4 Hz, 1H), 6.49-6.47 (m, 1H), 4.22-4.19 (m, 3H), 3.97-3.95 (m, 2H), 3.76 (s, 3H), 3.58-3.57 (m, 2H), 3.48-3.42 (m, 2H), 2.67-2.57 (m, 2H), 2.56-2.50 (m, 3H), 2.35 (s, 3H), 2.04-2.01 (m, 2H), 2.00-1.76 (m, 2H) | 468 |
| Example 268 | 3-[2,5-difluoro-4-(1-methylpyrazol-4-yl)anilino]-N-methyl-1-tetrahydropyran-4-yl-6,7-dihydro-4H-pyrazolo[4,3-c]pyridine-5-carboxamide | $^1$H NMR (400 MHz, DMSO-$d_6$) δ 8.00 (s, 1H), 7.93 (s, 1H), 7.81 (s, 1H), 7.63-6.59 (m, 1H), 7.52-7.47 (m, 1H), 6.48 (s, 1H), 4.25-4.18 (m, 3H), 3.98-3.95 (m, 2H), 3.87 (s, 3H), 3.58-3.57 (m, 2H), 3.49-3.43 (m, 2H), 2.67-2.60 (m, 2H), 2.58-2.57 (m, 3H), 2.05-1.97 (m, 2H), 1.81-1.78 (m, 2H). | 472 |

| Example | Compound Name and Structure | NMR | m/z |
|---|---|---|---|
| Example 269 | 3-[5-cyano-2-fluoro-4-(1-methylpyrazol-4-yl)anilino]-N-methyl-1-tetrahydropyran-4-yl-6,7-dihydro-4H-pyrazolo[4,3-c]pyridine-5-carboxamide | ¹H-NMR (400 MHz, CDCl₃) δ 8.01 (s, 1H), 7.96 (d, J = 8.4 Hz, 1H), 7.82 (s, 1H), 7.32 (s, 1H), 7.29 (d, J = 12.4 Hz, 1H), 5.91-5.89 (m, 1H), 4.56-4.54 (m, 1H), 4.26 (s, 2H), 4.22-4.17 (m, 3H), 4.02 (s, 3H), 3.84-3.82 (m, 2H), 3.61-3.55 (m, 2H), 2.90 (d, J = 4.4 Hz, 3H), 2.83-2.80 (m, 2H), 2.36-2.23 (m, 2H), 1.92-1.89 (m, 2H) | 479 |
| Example 270 | 3-((2-fluoro-3-(1-methyl-1H-pyrazol-4-yl)phenyl)amino)-N-methyl-1-(tetrahydro-2H-pyran-4-yl)-6,7-dihydro-1H-pyrazolo[4,3-c]pyridine-5(4H)-carboxamide | ¹H NMR (400 MHz, CDCl₃) δ 7.85 (s, 1H), 7.76 (s, 1H), 7.26-7.24 (m, 1H), 6.96-7.05 (m, 2H), 5.88-5.87 (m, 1H), 4.50-4.49 (m, 1H), 4.15-4.11 (m, 5H), 3.98 (s, 3H), 3.82-3.79 (m, 2H), 3.56-3.50 (m, 2H), 2.82 (d, J = 4.8 Hz, 3H), 2.76-2.73 (m, 2H), 2.34-2.29 (m, 2H), 1.87-1.83 (m, 2H). | 454 |
| Example 271 | 3-((3-(N,N-dimethylsulfamoyl)-5-(1-methyl-1H-pyrazol-4-yl)phenyl)amino)-N-methyl-1-(tetrahydro-2H-pyran-4-yl)-6,7-dihydro-1H-pyrazolo[4,3-c]pyridine-5(4H)-carboxamide | ¹H NMR (400 MHz, DMSO-d₆) δ 8.62 (s, 1H), 8.18 (s, 1H), 7.85-7.70 (m, 3H), 7.16 (s, 1H), 6.55-6.54 (m, 1H), 4.25-4.22 (m, 3H), 3.97-3.95 (m, 2H), 3.87 (s, 3H), 3.58-3.56 (m, 2H), 3.49-3.43 (m, 2H), 2.67-2.65 (m, 8H), 2.58 (d, J = 4.8 Hz, 3H), 2.09-1.91 (m, 2H), 1.81-1.75 (m, 2H). | 543 |

| Example | Compound Name and Structure | NMR | m/z |
|---|---|---|---|
| Example 272 | 3-((5-(difluoromethyl)-2-fluoro-4-(6-(methylcarbamoyl)pyridin-3-yl)phenyl)amino)-N-methyl-1-(tetrahydro-2H-pyran-4-yl)-6,7-dihydro-1H-pyrazolo[4,3-c]pyridine-5(4H)-carboxamide | $^1$H NMR (400 MHz, DMSO-$d_6$) δ 8.87-8.84 (m, 1H), 8.60 (s, 1H), 8.24 (s, 1H), 8.17 (d, J = 9.2 Hz, 1H), 8.09 (d, J = 8.0 Hz, 1H), 7.97-7.95 (m, 1H), 7.35 (d, J = 12.0 Hz, 1H), 6.82 (t, J = 54.8 Hz, 1H), 6.52-6.48 (m, 1H), 4.38-4.16 (m, 3H), 3.98-3.95 (m, 2H), 3.60-3.58 (m, 2H), 3.50-3.44 (m, 2H), 2.85 (d, J = 4.4 Hz, 3H), 2.71-2.62 (m, 2H), 2.58 (d, J = 4.0 Hz, 3H), 2.09-1.94 (m, 2H), 1.83-1.78 (m, 2H). | 558 |

Example 273

3-[5-(difluoromethyl)-2-fluoro-4-(1-methylpyrazol-4-yl)anilino]-1-(1,1-dioxothian-4-yl)-N-methyl-6,7-dihydro-4H-pyrazolo[4,3-c]pyridine-5-carboxamide

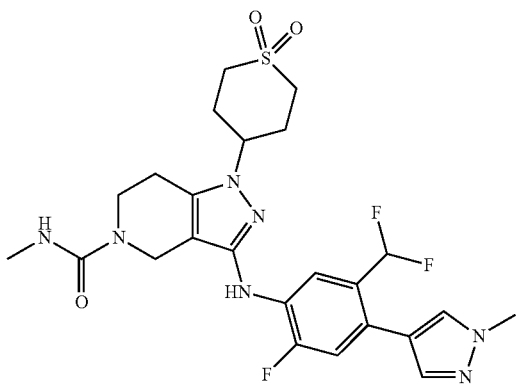

Step 1 tetrahydro-2H-thiopyran-4-yl methanesulfonate

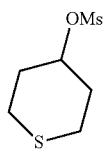 [SMILES: CS(=O)(=O)OC1CCSCC1]

To a solution of tetrahydrothiopyran-4-ol (10 g, 84.6 mmol) and triethylamine (35.4 mL, 253.8 mmol) in DCM (150 mL) at 0° C. was added methanesulfonyl chloride (10.7 mL, 138.8 mmol) dropwise. The reaction was stirred at 25° C. for 16 h. Water (100 mL) was added and the mixture was extracted with DCM (100 mL×2). The combined organic layers were dried over anhydrous Na$_2$SO$_4$, filtered and concentrated in vacuo to give the title compound (17 g, crude) as an orange oil that required no further purification. $^1$H NMR (400 MHz, DMSO-$d_6$) δ 4.73-4.69 (m, 1H), 3.19 (s, 3H), 2.76-2.63 (m, 4H), 2.17-2.16 (m, 2H), 1.87-1.84 (m, 2H).

Step 2 tert-butyl 3-bromo-1-(tetrahydro-2H-thiopyran-4-yl)-6,7-dihydro-1H-pyrazolo[4,3-c]pyridine-5(4H)-carboxylate

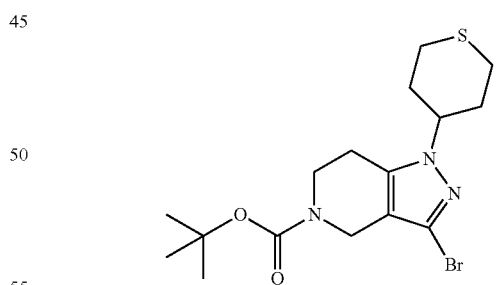

A mixture of tert-butyl 3-bromo-1,4,6,7-tetrahydropyrazolo[4,3-c]pyridine-5-carboxylate (10 g, 33 mmol), tetrahydrothiopyran-4-yl methanesulfonate (8.4 g, 43 mmol) and Cs$_2$CO$_3$ (27 g, 83 mmol) in DMF (50 mL) was heated to 80° C. for 16 h. The reaction mixture was diluted with EtOAc (300 mL), washed with brine (200 mL×3), dried over anhydrous Na$_2$SO$_4$, filtered and concentrated in vacuo. The residue was purified by silica gel column chromatography (eluent gradient from petroleum ether to petroleum ether/MTBE/THF=10:1:1) to give the title compound (5.9 g, 44%) as a white solid. $^1$H NMR (400 MHz, DMSO-$d_6$) δ 4.17 (s, 2H), 4.15-4.09 (m, 1H), 3.61-3.59 (m, 2H), 2.83-2.77 (m, 2H), 2.71-2.68 (m, 4H), 2.13-2.10 (m, 2H), 2.03-1.93 (m, 2H), 1.41 (s, 9H).

Step 3 tert-butyl 3-bromo-1-(1,1-dioxidotetrahydro-2H-thiopyran-4-yl)-6,7-dihydro-1H-pyrazolo[4,3-c]pyridine-5(4H)-carboxylate

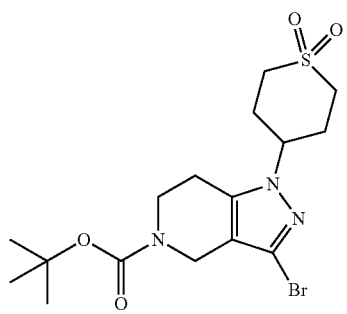 [SMILES: CC(C)(C)OC(=O)N1CCc2c(c(Br)nn2C2CCS(=O)(=O)CC2)C1]

To a solution of tert-butyl 3-bromo-1-tetrahydrothiopyran-4-yl-6,7-dihydro-4H-pyrazolo[4,3-c]pyridine-5-carboxylate (2 g, 5.0 mmol) in THF (8 mL) and water (2 mL) at 25° C. was added potassium peroxymonosulfate (5.8 g, 9.4 mmol). The reaction was stirred at 25° C. for 2 h. Water (20 mL) was added and the mixture was extracted with DCM (20 mL×3). The combined organic layers were dried over anhydrous Na$_2$SO$_4$, filtered and concentrated in vacuo to give the title compound (2.1 g, 99%) as a white solid that required no further purification. LCMS M/Z (M+H) 434.

Step 4 tert-butyl 3-((5-(difluoromethyl)-2-fluoro-4-(1-methyl-1H-pyrazol-4-yl)phenyl)amino)-1-(1,1-dioxidotetrahydro-2H-thiopyran-4-yl)-6,7-dihydro-1H-pyrazolo[4,3-c]pyridine-5(4H)-carboxylate

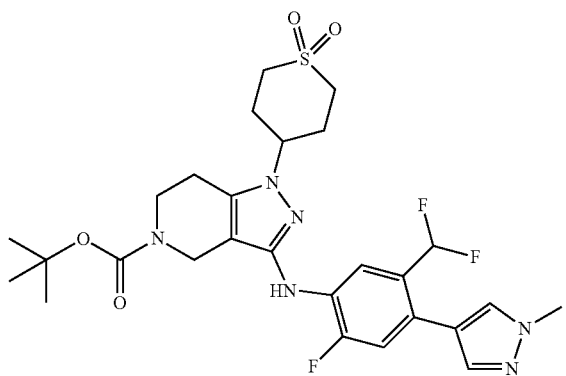 [SMILES: Cn1cc(-c2cc(F)c(Nc3nn(C4CCS(=O)(=O)CC4)c4c3CN(C(=O)OC(C)(C)C)CC4)cc2C(F)F)cn1]

To a solution of tert-butyl 3-bromo-1-(1,1-dioxothian-4-yl)-6,7-dihydro-4H-pyrazolo[4,3-c]pyridine-5-carboxylate (200 mg, 0.46 mmol) in 1,4-dioxane (2 mL) was added 5-(difluoromethyl)-2-fluoro-4-(1-methylpyrazol-4-yl)aniline (133 mg, 0.55 mmol), chloro(2-dicyclohexylphosphino-2',6'-di-i-propoxy-1,1'-biphenyl)(2'-amino-1,1'-biphenyl-2-yl)palladium(II) (36 mg, 0.05 mmol), tBuONa (133 mg, 1.4 mmol) and 2-(dicyclohexylphosphino)3,6-dimethoxy-2',4',6'-triisopropyl-1,1'-biphenyl (25 mg, 0.05 The reaction was heated to 120° C. for 16 h under a nitrogen atmosphere. After cooling to room temperature, the reaction was filtered and the filtrate was concentrated in vacuo. The crude residue was purified by silica gel column chromatography (DCM/MeOH=20:1) to give the title compound (148 mg, 54%) as a light yellow solid. LCMS M/Z (M+H) 595.

Step 4

4-(3-((5-(difluoromethyl)-2-fluoro-4-(1-methyl-1H-pyrazol-4-yl)phenyl)amino)-4,5,6,7-tetrahydro-1H-pyrazolo[4,3-c]pyridin-1-yl)tetrahydro-2H-thiopyran 1,1-dioxide

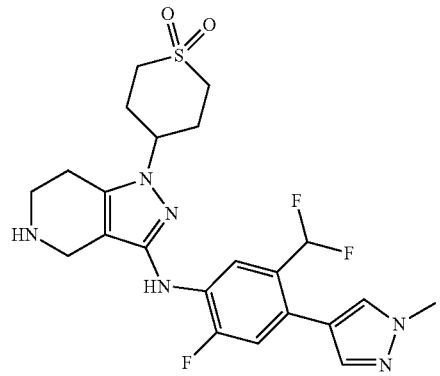 [SMILES: Cn1cc(-c2cc(F)c(Nc3nn(C4CCS(=O)(=O)CC4)c4c3CNCC4)cc2C(F)F)cn1]

A solution of tert-butyl 3-[5-(difluoromethyl)-2-fluoro-4-(1-methylpyrazol-4-yl)anilino]-1-(1,1-dioxothian-4-yl)-6,7-dihydro-4H-pyrazolo[4,3-c]pyridine-5-carboxylate (130 mg, 0.22 mmol) in DCM (1 mL) and trifluoroacetic acid (1 mL) was stirred at 25° C. for 1 h. The reaction was concentrated in vacuo to give the title compound (70 mg, crude) as a yellow oil that required no further purification. LCMS M/Z (M+H) 495.

Step 5

3-[5-(difluoromethyl)-2-fluoro-4-(1-methylpyrazol-4-yl)anilino]-1-(1,1-dioxothian-4-yl)-N-methyl-6,7-dihydro-4H-pyrazolo[4,3-c]pyridine-5-carboxamide

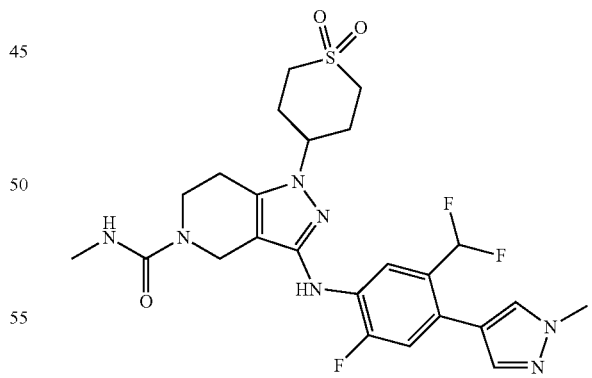

To a solution of N-[5-(difluoromethyl)-2-fluoro-4-(1-methylpyrazol-4-yl)phenyl]-1-(1,1-dioxothian-4-yl)-4,5,6,7-tetrahydropyrazolo[4,3-c]pyridin-3-amine (70 mg, 0.14 mmol), triethylamine (0.08 mL, 0.57 mmol) in DCM (1 mL) was added N-methylimidazole-1-carboxamide (21 mg, 0.17 mmol). The reaction was stirred at 25° C. for 16 h. Water (2 mL) was added and the mixture was extracted with DCM (2 mL×3). The combined organic layers were dried over anhydrous Na$_2$SO$_4$, filtered and concentrated in vacuo. The crude residue was purified by silica gel column chromatography (DCM/MeOH=20:1) to give the title compound (33 mg, 41%) as a white solid. $^1$H NMR (400 MHz, CDCl$_3$) δ 7.76 (d, J=8.4 Hz, 1H), 7.57 (s, 1H), 7.47 (s, 1H), 7.09 (d, J=12.0 Hz, 1H), 6.60 (t, J=55.2, 1H), 5.91 (s, 1H), 4.50-4.49 (m, 1H), 4.32-4.30 (m, 1H), 4.18 (s, 2H), 3.98 (s, 3H), 3.81-3.71 (m, 4H), 3.07-3.04 (m, 2H), 2.84 (d, J=4.4 Hz, 3H), 2.74-2.72 (m, 2H), 2.56-2.53 (m, 4H). LCMS M/Z (M+H) 552.

The Following Example 274 was Prepared in a Similar Fashion to Example 273

| Example | Compound Name and Structure | NMR | m/z |
|---|---|---|---|
| Example 274 | 1-(1-acetyl-4-piperidyl)-3-[5-(difluoromethyl)-2-fluoro-4-(1-methylpyrazol-4-yl)anilino]-N-methyl-6,7-dihydro-4H-pyrazolo[4,3-c]pyridine-5-carboxamide 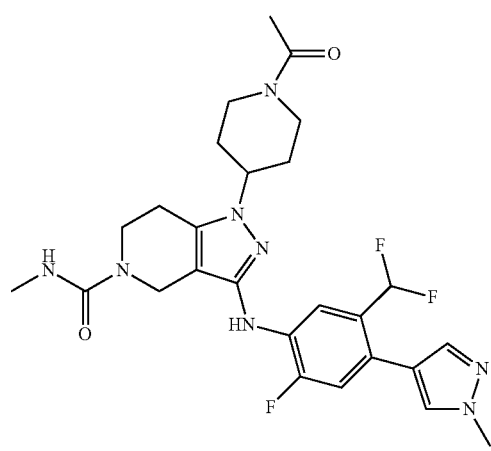 | $^1$H NMR (400 MHz, DMSO-d$_6$) δ 8.04 (d, J = 8.8 Hz, 1H), 8.01 (s, 1H), 7.84 (s, 1H), 7.59 (s, 1H), 7.25 (d, J = 12.4 Hz, 1H), 6.88 (t, J = 54.8, 1H), 6.50 (d, J = 4.0 Hz, 1H), 4.44-4.41 (m, 1H), 4.33-4.24 (m, 1H), 4.21 (s, 2H), 3.96-3.89 (m, 1H), 3.87 (s, 3H), 3.63-3.54 (m, 2H), 3.24-3.17 (m, 1H), 2.75-2.65 (m, 3H), 2.56 (d, J = 4.0 Hz, 3H), 2.02 (s, 3H), 1.90-1.77 (m, 4H). | 545 |

General Procedure for Intermediate T

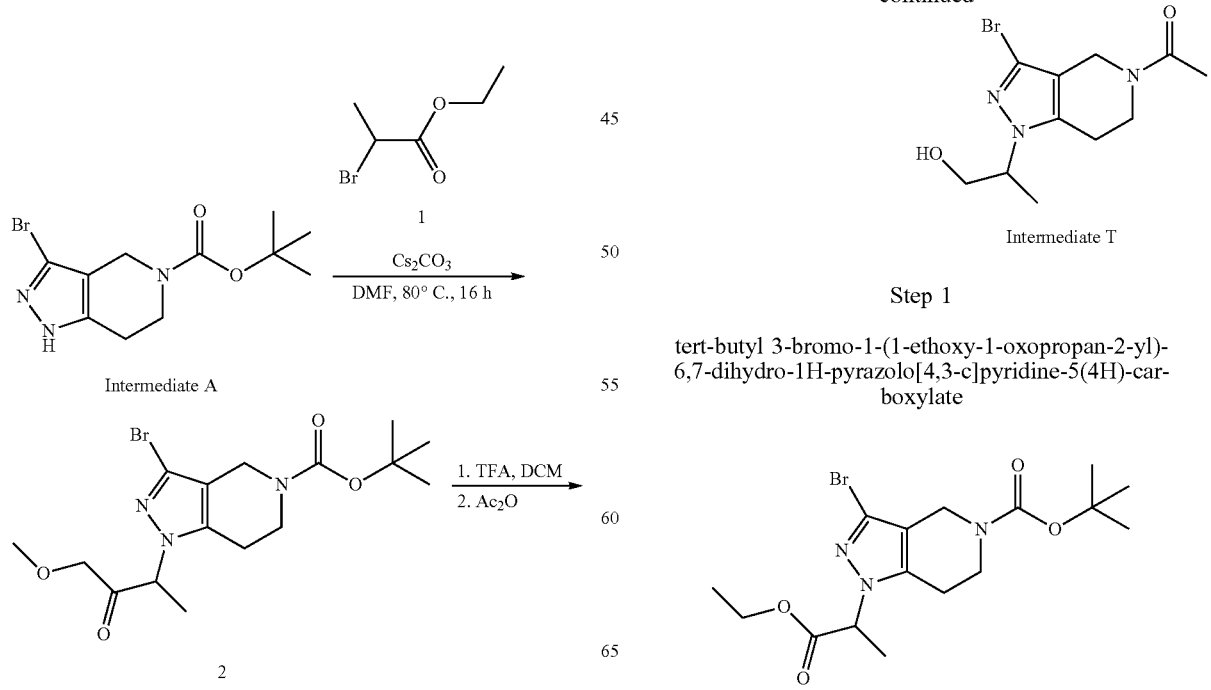

Step 1 tert-butyl 3-bromo-1-(1-ethoxy-1-oxopropan-2-yl)-6,7-dihydro-1H-pyrazolo[4,3-c]pyridine-5(4H)-carboxylate To a solution of tert-butyl 3-bromo-6,7-dihydro-1H-pyrazolo[4,3-c]pyridine-5(4H)-carboxylate (20.0 g, 66.19 mmol) in dioxane (100 mL), was added ethyl 2-bromopropanoate (13.18 g, 72.81 mmol) and Cs$_2$CO$_3$ (64.7 g, 198.57 mmol). The reaction mixture was heated to 120° C. for 16 h. After cooling to room temperature, water (100 mL) was added and the mixture was extracted with EtOAc (100 mL×3). The combined organic layers were dried over anhydrous Na$_2$SO$_4$, filtered and concentrated in vacuo. The crude residue was purified by silica gel chromatography (eluent gradient from petroleum ether/MTBE/THF=10:1:1 to 2:1:1) to give the title compound (7.3 g, 27%) as clear oil. $^1$H NMR (400 MHz, DMSO-d$_6$) δ 5.20 (q, J=7.2 Hz, 1H), 4.22-4.08 (m, 4H), 3.67-3.53 (m, 2H), 2.73-2.59 (m, 2H), 1.61 (d, J=7.2 Hz, 3H), 1.42 (s, 9H), 1.14 (t, J=7.2 Hz, 3H).

Step 2 ethyl 2-(5-acetyl-3-bromo-4,5,6,7-tetrahydro-1H-pyrazolo[4,3-c]pyridin-1-yl)propanoate

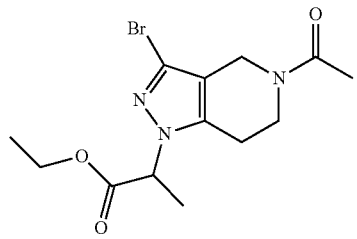 [SMILES: CCOC(=O)C(C)n1nc(Br)c2c1CCN(C(C)=O)C2]

To a solution of tert-butyl 3-bromo-1-(1-ethoxy-1-oxopropan-2-yl)-6,7-dihydro-1H-pyrazolo[4,3-c]pyridine-5(4H)-carboxylate (1.9 g, 4.7 mmol) in DCM (10 mL) at 0° C. was added trifluoroacetic acid (10 mL) dropwise. The mixture was stirred at room temperature for 2 h. The mixture was concentrated in vacuo and the residue was re-dissolved in DMF (10 mL). The mixture was cooled to 0° C. before triethylamine (2.7 g, 26.4 mmol) and acetic anhydride (0.68 g, 6.62 mmol) were added dropwise. The mixture was stirred at room temperature for an additional 0.5 h. The reaction was quenched with water (50 mL) and extracted with EtOAc (50 mL×3. The combined organic layers were dried over anhydrous Na$_2$SO$_4$, filtered and concentrated in vacuo. The crude residue was purified by silica gel chromatography (DCM/MeOH=50:1) to give the title compound (1.3 g, 57%) as clear oil. LCMS M/Z (M+H) 344.

Step 3

1-(3-bromo-1-(1-hydroxypropan-2-yl)-6,7-dihydro-1H-pyrazolo[4,3-c]pyridin-5(4H)-yl)ethanone

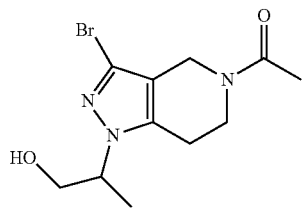 [SMILES: CC(=O)N1CCc2c(c(Br)nn2C(C)CO)C1]

To a solution of ethyl 2-(5-acetyl-3-bromo-4,5,6,7-tetrahydro-1H-pyrazolo[4,3-c]pyridin-1-yl)propanoate (1.3 g, 3.78 mmol) in MeOH (10 mL) at 0° C. was added NaBH$_4$ (0.71 g, 18.9 mmol). The reaction mixture was stirred at room temperature for 2 h. The reaction was quenched with brine (10 mL) and extracted with EtOAc (10 mL×3). The combined organic layers were dried over anhydrous Na$_2$SO$_4$, filtered and concentrated in vacuo. The crude residue was purified by silica gel chromatography (DCM/MeOH=20:1) to give the title compound (0.8 g, 70%) as a white solid. $^1$H NMR (400 MHz, DMSO-d$_6$) δ 4.92-4.87 (m, 1H), 4.34-4.19 (m, 3H), 3.74-3.65 (m, 2H), 3.55-3.51 (m, 2H), 2.80-2.66 (m, 2H), 2.09-2.88 (m, 3H), 1.30 (d, J=6.8 Hz, 3H).

Example 275

1-[3-[3-fluoro-4-(1-methylpyrazol-4-yl)anilino]-1-(2-hydroxy-1-methyl-ethyl)-6,7-dihydro-4H-pyrazolo[4,3-c]pyridin-5-yl]ethanone

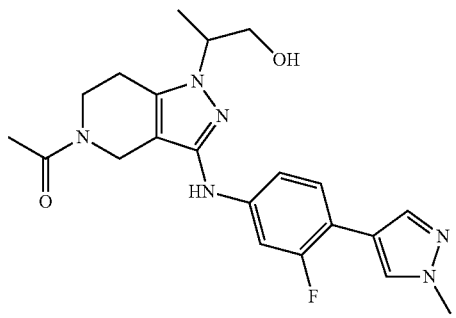 [SMILES: CC(=O)N1CCc2c(c(Nc3ccc(-c4cnn(C)c4)c(F)c3)nn2C(C)CO)C1]

To a solution of 1-(3-bromo-1-(1-hydroxypropan-2-yl)-6,7-dihydro-1H-pyrazolo[4,3-c]pyridin-5(4H)-yl)ethanone (0.25 g, 0.80 mmol) in 1,4-dioxane (3 mL) was added 2-fluoro-4-(1-methylpyrazol-4-yl) aniline (0.18 g, 0.95 mmol), chloro(2-dicyclohexylphosphino-2',6'-di-i-propoxy-1,1'-biphenyl)[2-(2-aminoethylphenyl)]palladium(II), methyl-t-butylether adduct (0.07 g, 0.08 mmol), tBuONa (0.23 g, 2.39 mmol) and 2-(dicyclohexylphosphino)3,6-dimethoxy-2',4',6'-triisopropyl-1,1'-biphenyl (0.04 g, 0.08 mmol). The reaction was heated to 120° C. for 16 h under a nitrogen atmosphere. After cooling to room temperature, the reaction was filtered and the filtrate was concentrated in vacuo. The crude residue was purified by reverse phase chromatography (acetonitrile 26-56%/0.2% formic acid in water) to give the title compound (24 mg, 6%) as a white solid. $^1$H NMR (400 MHz, DMSO-d$_6$) δ 8.40-8.36 (m, 1H), 7.93 (s, 1H), 7.36 (s, 1H), 7.47-7.41 (m, 2H), 7.13-7.08 (m, 1H), 4.85-4.82 (m, 1H), 4.38-4.29 (m, 2H), 4.18-4.10 (m, 1H), 3.85 (s, 3H), 3.67-3.38 (m, 4H), 2.75-2.63 (m, 2H), 2.09-2.07 (m, 3H), 1.34-1.32 (m, 3H).

The Following Example 276 was Prepared in a Similar Fashion to Example 275

| Example | Compound Name and Structure | NMR | m/z |
|---|---|---|---|
| Example 276 | 1-[1-(2-hydroxy-1-methyl-ethyl)-3-[4-[1-methyl-3-(trifluoromethyl)pyrazol-4-yl]anilino]-6,7-dihydro-4H-pyrazolo[4,3-c]pyridin-5-yl]ethanone 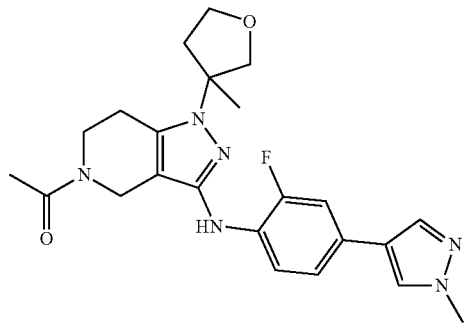 [SMILES: CC(=O)N1CCc2c(c(Nc3ccc(-c4cnn(C)c4)cc3F)nn2C2(C)CCOC2)C1] | $^{1}$H NMR (400 MHz, DMSO-$d_6$) δ 8.29-8.16 (m, 1H), 8.01 (s, 1H), 7.47-7.34 (m, 2H), 7.26-7.14 (m, 2H), 4.88-4.77 (m, 1H), 4.45-4.26 (m, 2H), 4.19-4.04 (m, 1H), 3.93 (s, 3H), 3.83-3.49 (m, 4H), 2.81-2.60 (m, 2H), 2.10-2.07 (m, 3 H), 1.34-1.32 (m, 3H). | 463 |

Example 277

1-[3-[2-fluoro-4-(1-methylpyrazol-4-yl)anilino]-1-(3-methyltetrahydrofuran-3-yl)-6,7-dihydro-4H-pyrazolo[4,3-c]pyridin-5-yl]ethanone

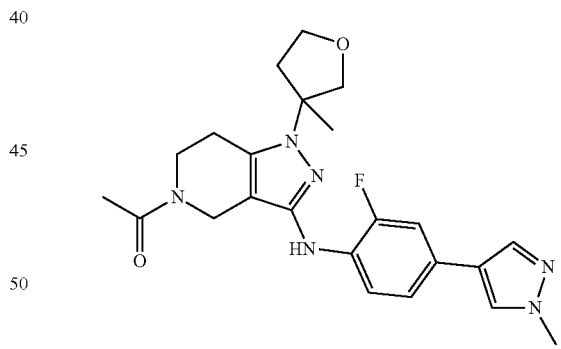

Step 1

1-(3-((2-fluoro-4-(1-methyl-1H-pyrazol-4-yl)phenyl)amino)-1-(3-((phenylsulfonyl)methyl)tetrahydrofuran-3-yl)-6,7-dihydro-1H-pyrazolo[4,3-c]pyridin-5(4H)-yl)ethanone

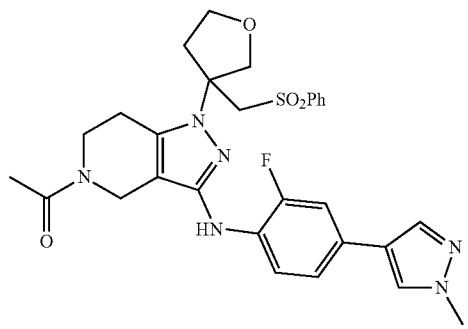

To a solution of 1-(3-((2-fluoro-4-(1-methyl-1H-pyrazol-4-yl)phenyl)amino)-6,7-dihydro-1H-pyrazolo[4,3-c]pyridin-5(4H)-yl)ethanone (400 mg, 1.13 mmol) and $Cs_2CO_3$ (368 mg, 1.13 mmol) in DMF (4 mL) was added (E)-3-((phenylsulfonyl)methylene)tetrahydrofuran (506 mg, 2.26 mmol). The reaction mixture was stirred at 20° C. for 12 h. Water (20 mL) was added and the mixture was extracted with DCM (20 mL×2). The combined organic layers were dried over anhydrous $Na_2SO_4$, filtered and concentrated in vacuo. The crude residue was purified by silica gel chromatography (DCM/MeOH=20:1) to give the title compound (100 mg, 15%) as a light yellow solid. LCMS M/Z (M+H) 579.

Step 2

1-[3-[2-fluoro-4-(1-methylpyrazol-4-yl)anilino]-1-(3-methyltetrahydrofuran-3-yl)-6,7-dihydro-4H-pyrazolo[4,3-c]pyridin-5-yl]ethanone To a solution of 1-(3-((2-fluoro-4-(1-methyl-1H-pyrazol-4-yl)phenyl)amino)-1-(3-((phenylsulfonyl)methyl)tetrahydrofuran-3-yl)-6,7-dihydro-1H-pyrazol[4,3-c]pyridin-5(4H)-yl)ethanone (90 mg, 0.16 mmol) in MeOH (2 mL) was added Mg (19 mg, 0.78 mmol) and $HgCl_2$ (8 mg, 0.03 mmol). The reaction mixture was stirred at 20° C. under ultrasound for 20 min and stirred at 20° C. for an additional 12 h. Water (40 mL) was added and the mixture was extracted with DCM (40 mL×2). The combined organic layers were dried over anhydrous $Na_2SO_4$, filtered and concentrated in vacuo. The crude residue was purified by reverse phase chromatography (acetonitrile 33-63%/0.2% formic acid in water) to give the title compound (10 mg, 15%) as a white solid. $^{1}$H NMR (400 MHz, DMSO-$d_6$) δ

7.85 (s, 1H), 7.31 (s, 1H), 7.57-7.45 (m, 1H), 7.28-7.20 (m, 2H), 4.47-4.30 (m, 3H), 4.04-3.97 (m, 3H), 3.90 (s, 3H), 3.82-3.75 (m, 2H), 2.95-2.84 (m, 2H), 2.72-2.71 (m, 1H), 2.33-2.30 (m, 1H), 2.20-2.14 (m, 3H), 1.55-1.54 (m, 3H). LCMS M/Z (M+H) 439.

The Following Examples 278-300, 301-302, 303-304, and 305-310 were Prepared in a Similar Fashion to Example 50, 224, 244, and 246, Respectively

| Example | Compound Name and Structure | NMR | m/z |
| --- | --- | --- | --- |
| Example 278 | 1-[3-[2,3-difluoro-4-(1-methylpyrazol-4-yl)anilino]-1-tetrahydrofuran-3-yl-6,7-dihydro-4H-pyrazolo[4,3-c]pyridin-5-yl]ethanone | $^{1}$H NMR (400 MHz, CD$_3$OD) δ 7.91 (s, 1H), 7.78 (s, 1H), 7.42-7.19 (m, 2H), 4.94-4.87 (m, 1H), 4.44-4.42 (m, 2H), 4.16-4.08 (m, 2H), 3.96-3.81 (m, 4H), 3.93 (s, 3H), 2.87-2.76 (m, 2H), 2.42-2.33 (m, 2H), 2.20-2.15 (m, 3H) | 443 |
| Example 279 | 1-[3-[2,6-difluoro-3-(1-methylpyrazol-4-yl)anilino]-1-tetrahydrofuran-3-yl-6,7-dihydro-4H-pyrazolo[4,3-c]pyridin-5-yl]ethanone | $^{1}$H NMR (400 MHz, CD$_3$OD) δ 7.92 (s, 1H), 7.79 (s, 1H), 7.21-7.17 (m, 1H), 6.96-6.89 (m, 1H), 4.86-4.75 (m, 1H), 4.33-4.32 (m, 2H), 4.04-3.99 (m, 2H), 3.91 (s, 3H), 3.86-3.76 (m, 4H), 2.83-2.72 (m, 2H), 2.29-2.21 (m, 2H), 2.17-2.08 (m, 3H) | 443 |
| Example 280 | (S)-1-[3-[2,6-difluoro-3-(1-methylpyrazol-4-yl)anilino]-1-tetrahydrofuran-3-yl-6,7-dihydro-4H-pyrazolo[4,3-c]pyridin-5-yl]ethanone | $^{1}$H NMR (400 MHz, CD$_3$OD) δ 8.05 (s, 1H), 7.81 (s, 1H), 7.65-7.60 (m, 1H), 7.29-7.23 (m, 1H), 7.07-7.01 (m, 1H), 4.79-4.76 (m, 1H), 4.30-4.23 (m, 2H), 3.95-3.83 (m, 2H), 3.87 (s, 3H), 3.73-3.65 (m, 4H), 2.74-2.63 (m, 2H), 2.22-2.10 (m, 2H), 2.07-2.01 (m, 3H) | 443 |

-continued

| Example | Compound Name and Structure | NMR | m/z |
|---|---|---|---|
| Example 281 | (R)-1-[3-[2,6-difluoro-3-(1-methylpyrazol-4-yl)anilino]-1-tetrahydrofuran-3-yl-6,7-dihydro-4H-pyrazolo[4,3-c]pyridin-5-yl]ethanone | $^1$H NMR (400 MHz, CD$_3$OD) δ 8.05 (s, 1H), 7.81 (s, 1H), 7.65-7.60 (m, 1H), 7.29-7.23 (m, 1H), 7.06-7.01 (m, 1H), 4.79-4.74 (m, 1H), 4.30-4.23 (m, 2H), 3.91-3.83 (m, 2H), 3.87 (s, 3H), 3.73-3.63 (m, 4H), 2.76-2.63 (m, 2H), 2.18-2.09 (m, 2H), 2.07-2.01 (m, 3H) | 443 |
| Example 282 | 1-[3-[3-(1-methylpyrazol-4-yl)-5-(trifluoromethyl)anilino]-1-tetrahydrofuran-3-yl-6,7-dihydro-4H-pyrazolo[4,3-c]pyridin-5-yl]ethanone | $^1$H NMR (400 MHz, DMSO-d$_6$) δ 8.68-8.63 (m, 1H), 8.17-8.16 (m, 1H), 7.96 (s, 1H), 7.83-7.82 (m, 1H), 7.68-7.67 (m, 1H), 7.22-7.20 (m, 1H), 4.90-4.85 (m, 1H), 4.39 (s, 2H), 4.06-4.00 (m, 2H), 3.89-3.79 (m, 2H), 3.87 (s, 3H), 3.73-3.68 (m, 2H), 2.79-2.67 (m, 2H), 2.29-2.23 (m, 2H), 2.10-2.08 (m, 3H) | 475 |
| Example 283 | 1-[3-[4-(1,5-dimethylpyrazol-4-yl]-2-fluoro-anilino]-1-tetrahydrofuran-3-yl-6,7-dihydro-4H-pyrazolo[4,3-c]pyridin-5-yl]ethanone | $^1$H NMR (400 MHz, CD$_3$OD) δ 7.87-7.83 (m, 1H), 7.77-7.71 (m, 1H), 7.51 (s, 1H), 7.15-7.13 (m, 1H), 7.12-7.03 (m, 1H), 4.88-4.82 (m, 1H), 4.40-4.34 (m, 2H), 4.02-3.98 (m, 2H), 3.84-3.67 (m, 4H), 3.75 (s, 3H), 2.78-2.66 (m, 2H), 2.34 (s, 3H), 2.26-2.22 (m, 2H), 2.08-2.05 (m, 3H) | 439 |

-continued

| Example | Compound Name and Structure | NMR | m/z |
|---------|----------------------------|-----|-----|
| Example 284 | (S)-1-[3-[4-(1,5-dimethylpyrazol-4-yl)-2-fluoro-anilino]-1-tetrahydrofuran-3-yl-6,7-dihydro-4H-pyrazolo[4,3-c]pyridin-5-yl]ethanone | $^1$H NMR (400 MHz, DMSO-d$_6$) δ 7.87-7.83 (m, 1H), 7.77-7.71 (m, 1H), 7.51 (s, 1H), 7.15-7.13 (m, 1H), 7.12-7.03 (m, 1H), 4.88-4.82 (m, 1H), 4.40-4.34 (m, 2H), 4.02-3.98 (m, 2H), 3.84-3.67 (m, 4H), 3.75 (s, 3H), 2.78-2.66 (m, 2H), 2.34 (s, 3H), 2.26-2.22 (m, 2H), 2.09-2.05 (m, 3H) | 439 |
| Example 285 | (R)-1-[3-[4-(1,5-dimethylpyrazol-4-yl)-2-fluoro-anilino]-1-tetrahydrofuran-3-yl-6,7-dihydro-4H-pyrazolo[4,3-c]pyridin-5-yl]ethanone | $^1$H NMR (400 MHz, CD$_3$OD) δ 7.88-7.83 (m, 1H), 7.77-7.71 (m, 1H), 7.52 (s, 1H), 7.18-7.13 (m, 1H), 7.08-7.03 (m, 1H), 4.88-4.84 (m, 1H), 4.41-4.35 (m, 2H), 4.03-3.99 (m, 2H), 3.84-3.67 (m, 4H), 3.76 (s, 3H), 2.78-2.66 (m, 2H), 2.35 (s, 3H), 2.28-2.23 (m, 2H), 2.09-2.06 (m, 3H) | 439 |
| Example 286 | 1-[3-[2-fluoro-4-(1-methyltriazol-4-yl)anilino]-1-tetrahydrofuran-3-yl-6,7-dihydro-4H-pyrazolo[4,3-c]pyridin-5-yl]ethanone | $^1$H NMR (400 MHz, DMSO-d$_6$) δ 8.38 (s, 1H), 7.99-7.93 (m, 1H), 7.88-7.67 (m, 1H), 7.60-7.47 (m, 2H), 4.90-4.83 (m, 1H), 4.41-4.34 (m, 2H), 4.06 (s, 3H), 4.03-3.96 (m, 2H), 3.85-3.66 (m, 4H), 2.79-2.64 (m, 2H), 2.40-2.17 (m, 2H), 2.09-2.05 (m, 3H) | 426 |

-continued

| Example | Compound Name and Structure | NMR | m/z |
| --- | --- | --- | --- |
| Example 287 | 1-[3-[2,3-difluoro-5-(1-methylpyrazol-4-yl)anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.26-8.17 (m, 1H), 8.01 (s, 1H), 8.00-7.85 (m, 1H), 7.72 (s, 1H), 6.98-6.93 (m, 1H), 4.93-4.88 (m, 1H), 4.43-4.37 (m, 2H), 4.04-4.01 (m, 2H), 3.88-3.84 (m, 2H), 3.86 (s, 3H), 3.83-3.69 (m, 2H), 2.81-2.68 (m, 2H), 2.30-2.21 (m, 2H), 2.10-2.05 (m, 3H) | 443 |
| Example 288 | 1-[3-[4-fluoro-3-(1-methylpyrazol-4-yl)anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.22-8.17 (m, 1H), 8.00-7.94 (m, 2H), 7.74-7.73 (m, 1H), 7.17-7.15 (m, 1H), 7.08-7.03 (m, 1H), 4.90-4.80 (m, 1H), 4.36 (s, 2H), 4.06-4.01 (m, 2H), 3.89 (s, 3H), 3.86-3.84 (m, 2H), 3.74-3.69 (m, 2H), 2.77-2.65 (m, 2H), 2.28-2.21 (m, 2H), 2,10-2.07 (m, 3H) | 425 |
| Example 289 | 1-[3-[3-(difluoromethyl)-4-(1-methylpyrazol-4-yl)anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.51-8.46 (m, 1H), 7.91-7.90 (m, 1H), 7.78 (s, 1H), 7.55-7.53 (m, 2H), 7.31-7.27 (m, 1H), 6.89 (t, J = 56.0 Hz, 1H), 4.88-4.85 (m, 1H), 4.37 (s, 2H), 4.05-4.02 (m, 2H), 3.90-3.68 (m, 4H), 3.88 (s, 3H), 2.78-2.66 (m, 2H), 2.27-2.23 (m, 2H), 2.10-2.08 (m, 3H) | 457 |

-continued

| Example | Compound Name and Structure | NMR | m/z |
|---|---|---|---|
| Example 290 | 1-[3-[2-fluoro-4-(2-methyltriazol-4-yl)anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.13 (s, 1H), 8.12-8.06 (m, 1H), 7.99-7.73 (m, 1H), 7.58-7.48 (m, 2H), 4.90-4.84 (m, 1H), 4.41-4.35 (m, 2H), 4.15 (s, 3H), 4.03-4.00 (m, 2H), 3.85-3.78 (m, 2H), 3.73-3.68 (m, 2H), 2.80-2.67 (m, 2H), 2.29-2.09 (m, 2H), 2.07-2.05 (m, 3H) | 426 |
| Example 291 | 1-[3-[3-fluoro-5-(1-methylpyrazol-4-yl)anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.49-8.45 (m, 1H), 8.05-8.03 (m, 1H), 7.75-7.74 (m, 1H), 7.46-7.42 (m, 1H), 7.14-7.10 (m, 1H), 6.75-6.71 (m, 1H), 4.89-4.83 (m, 1H), 4.36 (s, 2H). 4.07-3.99 (m, 2H), 3.90-3.80 (m, 2H), 3.85 (s, 3H), 3.75-3.67 (m, 2H), 2.78-2.66 (m, 2H), 2.32-2.20 (m, 2H), 2.10-2.07 (m, 3H) | 425 |
| Example 292 | 1-[3-[2-fluoro-5-(1-methylpyrazol-4-yl)anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.25-8.05 (m, 1H), 7.95 (s, 1H), 7.91-7.84 (m, 1H), 7.66 (s, 1H), 7.11-7.06 (m, 1H), 6.91-6.88 (m, 1H), 4.90-4.86 (m, 1H), 4.43-4.36 (m, 2H), 4.03-3.99 (m, 2H), 3.88-3.83(m, 2H), 3.85 (s, 3H), 3.71-3.68 (m, 2H), 2.79-2.67 (m, 2H), 2.32-2.31 (m, 2H), 2.09-2.04 (m, 3H) | 425 |

-continued

| Example | Compound Name and Structure | NMR | m/z |
|---|---|---|---|
| Example 293 | 1-[3-[2-chloro-4-(1-methylpyrazol-4-yl)anilino]-1-tetrahydrofuran-3-yl-6,7-dihydro-4H-pyrazolo[4,3-c]pyridin-5-yl]ethanone | $^1$H NMR (400 MHz, DMSO-d$_6$) δ 8.05 (s, 1H), 7.79 (s, 1H), 7.56 (s, 1H), 7.51-7.29 (m, 3H), 4.92-4.82 (m, 1H), 4.35-4.28 (m, 2H), 4.03-3.96 (m, 2H), 3.83 (s, 3H), 3.80-3.68 (m, 4H), 2.80-2.68 (m, 2 H), 2.33-2.22 (m, 2H), 2.09-2.04 (m, 3H) | 441 |
| Example 294 | 1-[3-[3-chloro-4-(1-methylpyrazol-4-yl)anilino]-1-tetrahydrofuran-3-yl-6,7-dihydro-4H-pyrazolo[4,3-c]pyridin-5-yl]ethanone | $^1$H NMR (400 MHz, DMSO-d$_6$) δ 8.46-8.42 (m, 1H), 8.00 (s, 1H), 7.71 (s, 1H), 7.69 (s, 1H), 7.40-7.29 (m, 2H), 4.88-4.82 (m, 1H), 4.36 (s, 2H), 4.05-4.01 (m, 2H), 3.88-3.67 (m, 4H), 3.86 (s, 3H), 2.77-2.65 (m, 2H), 2.28-2.24 (m, 2H), 2.10-2.07 (m, 3H) | 441 |
| Example 295 | 1-[3-[4-[1-methyl-5-(trifluoromethyl)pyrazol-4-yl]anilino]-1-tetrahydrofuran-3-yl-6,7-dihydro-4H-pyrazolo[4,3-c]pyridin-5-yl]ethanone | $^1$H NMR (400 MHz, DMSO-d$_6$) δ 8.34-8.30 (m, 1H), 7.65 (s, 1H), 7.45-7.42 (m, 2H), 7.19-7.15 (m, 2H), 4.86-4.83 (m, 1H), 4.36 (s, 2H), 4.05-3.99 (m, 5H), 3.88-3.67 (m, 4H), 2.79-2.66 (m, 2H), 2.25-2.22 (m, 2H), 2.10-2.07 (m, 3H) | 475 |

| Example | Compound Name and Structure | NMR | m/z |
|---|---|---|---|
| Example 296 | 1-[3-[3,4-difluoro-5-(1-methylpyrazol-4-yl)anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.45-8.41 (m, 1H), 8.07-8.06 (m, 1H), 7.76-7.75 (m, 1H), 7.60-7.57 (m, 1H), 7.34-7.29 (m, 1H), 4.89-4.85 (m, 1H), 4.37 (s, 2H), 4.05-4.00 (m, 2H), 3.90 (s, 3H), 3.88-3.85 (m, 2H), 3.84-3.67 (m, 2H), 2.78-2.64 (m, 2H), 2.27-2.20 (m, 2H), 2.10-2.07 (m, 3H) | 443 |
| Example 297 | (R)-1-[3-[2-fluoro-4-[1-methyl-3-(trifluoromethyl)pyrazol-4-yl]anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.11 (s, 1H), 8.00-7.93 (m, 1H), 7.86-7.69 (m, 1H), 7.16-7.13 (m, 1H), 7.12-7.04 (m, 1H), 4.90-4.85 (m, 1H), 4.41-4.35 (m, 2H), 4.03-3.99 (m, 2H), 3.93 (s, 3H), 3.84-3.68 (m, 4H), 2.80-2.67 (m, 2H), 2.27-2.23 (m, 2H), 2.09-2.05 (m, 3H) | 493 |
| Example 298 | (S)-1-[3-[2-fluoro-4-[1-methyl-3-(trifluoromethyl)pyrazol-4-yl]anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.11 (s, 1H), 7.99-7.93 (m, 1H), 7.86-7.69 (m, 1H), 7.16-7.12 (m, 1H), 7.08-7.04 (m, 1H), 4.89-4.83 (m, 1H), 4.41-4.35 (m, 2H), 4.03-3.98 (m, 2H), 3.93 (s, 3H), 3.84-3.68 (m, 4H), 2.79-2.67 (m, 2H), 2.28-2.23 (m, 2H), 2.09-2.05 (m, 3H) | 493 |

| Example | Compound Name and Structure | NMR | m/z |
|---|---|---|---|
| Example 299 | 1-[3-[2-fluoro-4-(1-methylpyrazol-4-yl)anilino]-1-[(3R)-tetrahydrofuran-3-yl]-6,7-dihydro-4H-pyrazolo[4,3-c]pyridin-5-yl]ethanone | $^1$H NMR (400 MHz, DMSO-$d_6$) δ 8.03 (s, 1H), 7.83-7.67 (m, 3H), 7.39-7.34 (m, 1H), 7.26-7.21 (m, 1H), 4.87-4.77 (m, 1H), 4.41-4.34 (m, 2H), 4.02-3.97 (m, 2H), 3.83 (s, 3H), 3.81-3.67 (m, 4H), 2.77-2.66 (m, 2H), 2.26-2.22 (m, 2H), 2.08-2.05 (m, 3H) | 425 |
| Example 300 | 1-[3-[2-fluoro-4-(1-methylpyrazol-4-yl)anilino]-1-[(3S)-tetrahydrofuran-3-yl]-6,7-dihydro-4H-pyrazolo[4,3-c]pyridin-5-yl]ethanone | $^1$H NMR (400 MHz, DMSO-$d_6$) δ 8.03 (s, 1H), 7.83-7.68 (m, 3H), 7.36-7.33 (m, 1H), 7.32-7.21 (m, 1H), 4.88-4.84 (m, 1H), 4.40-4.33 (m, 2H), 4.03-3.99 (m, 2H), 3.84-3.67 (m, 7H), 2.79-2.64 (m, 2H), 2.26-2.21 (m, 2H), 2.08-2.05 (m, 3H) | 425 |
| Example 301 | 1-[3-[2-fluoro-4-[1-methyl-3-(trifluoromethyl)pyrazol-4-yl]anilino]-1-(oxetan-3-yl)-6,7-dihydro-4H-pyrazolo[4,3-c]pyridin-5-yl]ethanone | $^1$H NMR (400 MHz, DMSO-$d_6$) δ 8.12 (s, 1H), 8.01-7.84 (m, 2H), 7.20-7.09 (m, 2H), 5.44-5.38 (m, 1H), 4.96-4.93 (m, 2H), 4.85-4.83 (m, 2H), 4.42-4.36 (m, 2H), 3.94 (s, 3H), 3.71-3.64 (m, 2H), 2.73-2.60 (m, 2H), 2.08-2.05 (m, 3H) | 479 |

| Example | Compound Name and Structure | NMR | m/z |
|---------|---------------------------|-----|-----|
| Example 302 | 1-[3-[2-fluoro-4-(1-methylpyrazol-4-yl)anilino]-1-(oxetan-3-yl)-6,7-dihydro-4H-pyrazolo[4,3-c]pyridin-5-yl]ethanone | $^1$H NMR (400 MHz, DMSO-$d_6$) δ 8.04 (s, 1H), 7.97-7.90 (m, 1H), 7.88-7.79 (m, 2H), 7.40-7.36 (m, 1H), 7.35-7.26 (m, 1H), 5.44-5.37 (m, 1H), 4.96-4.93 (m, 2H), 4.86-4.81 (m, 2H), 4.41-4.34 (m, 2H), 3.84 (s, 3H), 3.71-3.63 (m, 2H), 2.71-2.58 (m, 2H), 2.07-2.05 (m, 3H) | 411 |
| Example 303 | 1-[3-[2-fluoro-4-[1-methyl-3-(trifluoromethyl)pyrazol-4-yl]anilino]-1-(oxetan-3-ylmethyl)-6,7-dihydro-4H-pyrazolo[4,3-c]pyridin-5-yl]ethanone | $^1$H NMR (400 MHz, DMSO-$d_6$) δ 8.10 (s, 1H), 7.96-7.85 (m, 2H), 7.17-7.04 (m, 2H), 4.67-4.64 (m, 2H), 4.46-4.36 (m, 4H), 4.21-4.19 (m, 2H), 3.93 (s, 3H), 3.72-3.67 (m, 2H), 3.41-3.39 (m, 1H), 2.76-2.64 (m, 2H), 2.09-2.06 (m, 3H) | 493 |
| Example 304 | 1-[3-[2-fluoro-4-(1-methylpyrazol-4-yl)anilino]-1-tetrahydropyran-4-yl-6,7-dihydro-4H-pyrazolo[4,3-c]pyridin-5-yl]ethanone | $^1$H NMR (400 MHz, DMSO-$d_6$) δ 8.01 (s, 1H), 7.87-7.67 (m, 3H), 7.37-7.32 (m, 1H), 7.26-7.21 (m, 1H), 4.40-4.32 (m, 2H), 4.25-4.16 (m, 1H), 3.96-3.94 (m, 2H), 3.83 (s, 3H), 3.72-3.66 (m, 2H), 3.45-3.38 (m, 2H), 2.78-2.66 (m, 2H), 2.08-1.99 (m, 5H), 1.78-1.75 (m, 2H) | 439 |

-continued

| Example | Compound Name and Structure | NMR | m/z |
|---|---|---|---|
| Example 305 | 1-[3-[4-[3-(difluoromethyl)-1-methyl-pyrazol-4-yl]-2-fluoro-anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.07 (s, 1H), 7.95-7.88 (m, 1H), 7.86-7.69 (m, 1H), 7.27-7.15 (m, 2H), 7.05 (t, J = 53.6 Hz, 1H), 4.89-4.83 (m, 1H), 4.41-4.35 (m, 2H), 4.03-3.97 (m, 2H), 3.89-3.66 (m, 7H), 2.79-2.68 (m, 2H), 2.28-2.23 (m, 2H), 2.09-2.05 (m, 3H) | 475 |
| Example 306 | (S)-1-[3-[4-[3-(difluoromethyl)-1-methyl-pyrazol-4-yl]-2-fluoro-anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.08 (s, 1H), 7.96-7.89 (m, 1H), 7.86-7.69 (m, 1H), 7.27-7.15 (m, 2H), 7.05 (t, J = 53.6 Hz, 1H), 4.87-4.83 (m, 1H), 4.41-4.35 (m, 2H), 4.03-3.97 (m, 2H), 3.89 (s, 3H), 3.88-3.66 (m, 4H), 2.79-2.68 (m, 2H), 2.28-2.23 (m, 2H), 2.09-2.06 (m, 3H) | 475 |
| Example 307 | (R)-1-[3-[4-[3-(difluoromethyl)-1-methyl-pyrazol-4-yl]-2-fluoro-anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 8.07 (s, 1H), 7.95-7.88 (m, 1H), 7.86-7.69 (m, 1H), 7.27-7.15 (m, 2H), 7.05 (t, J = 53.6 Hz, 1H), 4.89-4.83 (m, 1H), 4.41-4.35 (m, 2H), 4.03-3.97 (m, 2H), 3.89 (s, 3H), 3.88-3.66 (m, 4H), 2.79-2.66 (m, 2H), 2.28-2.23 (m, 2H), 2.09-2.05 (m, 3H) | 475 |

| Example | Compound Name and Structure | NMR | m/z |
|---|---|---|---|
| Example 308 | 4-[4-[(5-acetyl-1-tetrahydrofuran-3-yl-6,7-dihydro-4H-pyrazolo[4,3-c]pyridin-3-yl)amino]-3-fluoro-phenyl]-1-methyl-pyrazole-3-carbonitrile | $^1$H NMR (400 MHz, DMSO-$d_6$) δ 8.32 (s, 1H), 8.09-8.02 (m, 1H), 7.90-7.75 (m, 1H), 7.44-7.31 (m, 2H), 4.89-4.85 (m, 1H), 4.42-4.35 (m, 2H), 4.03-3.99 (m, 2H), 3.96 (s, 3H), 3.85-3.68 (m, 4H), 2.79-2.67 (m, 2H), 2.29-2.22 (m, 2H), 2.09-2.05 (m, 3H). | 450 |
| Example 309 | 1-[3-[4-(1,3-dimethylpyrazol-4-yl)-2-fluoro-anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 7.85-7.76 (m, 3H), 7.19-7.06 (m, 2H), 4.89-4.82 (m, 1H), 4.41-4.43 (m, 2H), 4.03-3.99 (m, 2H), 3.84-3.67 (m, 4H), 3.75 (s, 3H), 2.79-2.65 (m, 2H), 2.24-2.22 (m, 5H), 2.09-2.05 (m, 3H) | 439 |
| Example 310 | 1-[3-[2-fluoro-4-[3-(trifluoromethyl)-1H-pyrazol-4-yl]anilino]-1-tetrahydrofuran-3-yl-6,7-dihydro-4H-pyrazolo[4,3-c]pyridin-5-yl]ethanone | $^1$H NMR (400 MHz, DMSO-$d_6$) δ 13.67 (s, 1H), 8.16 (s, 1H), 7.97-7.13 (m, 2H), 7.21-7.07 (m, 2H), 4.88-4.82 (m, 1H), 4.41-4.35 (m, 2H), 4.01-3.84 (m, 2H), 3.83-3.68 (m, 4H), 2.79-2.67 (m, 2H), 2.25-2.23 (m, 2H), 2.09-2.05 (s, 3H) | 479 |

Example 311

The inhibitory activity of representative compounds of Formula (II) against CBP/EP300 can be evaluated using known methods or using one of the following assay protocols.

IC$_{50}$ Measurements for Inhibitors Using CBP TR-FRET Binding Assay

His/Flag epitope tagged CBP was cloned, expressed, and purified to homogeneity. CBP binding and inhibition was assessed by monitoring the engagement of a biotinylated small molecule compound with the target using the TR-FRET assay technology (Perkin-Elmer). Specifically, in a 384 well ProxiPlate CBP (4 nM final) was combined with biotin-ligand (60 nM final) in 50 mM HEPES (pH 7.5), 50 mM NaCl, 1 mM TCEP, 0.01% (w/v) BSA, and 0.008% (w/v) Brij-35 either in the presence of DMSO (final 0.2% DMSO) or compound dilution series in DMSO. After 10 minutes incubation at room temperature, a mixture Eu-W1024 Anti-6×His antibody ("6×His" disclosed as SEQ ID NO: 3) (Perkin Elmer AD0110) and SureLight™ Allophycocyanin-Streptavidin (APC-SA, Perkin Elmer CR130-100) were added to a final concentrations of 0.2 nMolar antibody and 50 nMolar APC-SA, respectively. After twenty minutes of equilibration, the plates were read on an Envision instrument and $IC_{50}$s calculated using a four parameter non-linear curve fit.

$IC_{50}$ Measurements for Inhibitors Using BRD4 AlphaLisa Binding Assay

His/Flag epitope tagged BRD4 $BD1_{42-168}$ was cloned, expressed, and purified to. BRD4 binding and inhibition was assessed by monitoring the engagement of biotinylated H4-tetraacetyl peptide (New England Peptide, NEP2069-1/13) with the target using the AlphaLisa technology (Perkin-Elmer). Specifically, in a 384 well ProxiPlate BRD4(BD1) (30 nM final) was combined with peptide (200 nM final) in 40 mM HEPES (pH 7.0), 40 mM NaCl, 1 mM DTT, 0.01% (w/v) BSA, and 0.008% (w/v) Brij-35 either in the presence of DMSO (final 1.2% DMSO) or compound dilution series in DMSO. After 20 minutes incubation at room temperature Alpha streptavidin donor beads and AlphaLisa anti-Flag acceptor beads were added to a final concentration of 10 ug/mL each. After three hours equilibration plates were read on an Envision instrument and $IC_{50}$s calculated using a four parameter non-linear curve fit.

MYC_RPL19 QuantiGene Assay in MV-4-11 Cells

QuantiGene 2.0 Reagent system, Affymetrix: HUMAN MYCN; V-myc myelocytomatosis viral related oncogene, neuroblastoma derived (avian); NM_005378 SA-15008. 10,000 MV-4-11 cells (GNE in-house) were plated in 75 ul complete media: RPMI-1640 (GNE in-house), 10% FBS (Life Technologies, cat. no. 10082), 1% Pen-strep (GNE in-house), in 96 well clear flat bottom plates (Costar, cat. no. 3595). 25 ul compound was added for 4 hours at 37 deg C. in a 1:3 serial dilution 10-point dose response, with a final DMSO concentration=0.2%. The cells were then lysed according to the assay kit's protocol and frozen at −80 deg C. The following day, an appropriate volume of Working Probe Set was prepared by combining the following reagents in the order listed: Nuclease-free water, Lysis Mixture, Blocking Reagent, and 2.0 Probe Set (MYC or RPL19). 20 ul of the working probe set was added into each assay well on the capture plate, and then 80 ul of the lysates were transferred into the assay plates. The capture plate was placed in a 55 deg C. incubator for overnight hybridization (16-20 hours). The following day, wash buffer was prepared according to manufacturer's recommendations. The capture plates were washed with 300 ul per well of 1× wash buffer three times. Then 100 ul Pre-Amplifier was added to the plate for a 60 minute incubation at 55 deg C. After the incubation, the capture plate was washed with 300 ul per well of 1× wash buffer three times, and 100 ul Amplifier was added to the plate for a 60 minute incubation at 55 deg C. The capture plate was again washed with 300 ul per well of 1× wash buffer three times, and 100 ul Label Probe was added to the plate for a 60 minute incubation at 50 deg C. Then the capture plate was washed with 300 ul per well of 1× wash buffer three times, and 100 ul 2.0 Substrate was added to each well of the plate. The plates were incubated at RT for 5 minutes in the dark and read on the Envision using the luminescence protocol, with an integration time set at 0.2 seconds.

Data for representative compounds of formula (II) from the three assays described above is provided in the following table (all units in µM).

| Example | CBP HTRF IC50 (µM) | BRD4 Alpha IC50 (µM) | Myc IC50 (µM) |
|---|---|---|---|
| 1 | 0.06 | 7.32 | 0.88 |
| 2 | 0.06 | 12.50 | 0.70 |
| 3 | 0.12 | 7.73 | |
| 4 | 0.03 | 10.24 | 0.98 |
| 5 | 0.02 | 4.98 | 0.68 |
| 6 | 0.02 | 4.77 | 0.65 |
| 7 | 0.02 | 6.22 | 0.29 |
| 8 | 1.43 | >19.74 | |
| 9 | 0.10 | 15.57 | 0.14 |
| 10 | 0.14 | 11.94 | 2.32 |
| 11 | 0.06 | 15.58 | 0.74 |
| 12 | 0.03 | | |
| 13 | 0.04 | 3.33 | 0.68 |
| 14 | 0.04 | 6.72 | 0.35 |
| 15 | 0.27 | 17.62 | |
| 16 | 0.19 | 18.14 | |
| 17 | 0.02 | 2.93 | 0.29 |
| 18 | 0.05 | 9.41 | 0.73 |
| 19 | 0.15 | >19.74 | |
| 20 | 0.02 | 3.82 | 0.33 |
| 21 | 0.01 | 2.87 | 0.24 |
| 22 | 0.02 | 7.80 | 0.34 |
| 23 | 0.16 | >19.74 | |
| 24 | 0.13 | 10.37 | 1.06 |
| 25 | 0.04 | 4.29 | 0.63 |
| 26 | 0.13 | 14.63 | 1.79 |
| 27 | 0.30 | >19.74 | |
| 28 | 0.17 | >19.74 | |
| 29 | 0.04 | 4.89 | 2.39 |
| 30 | 0.07 | 15.86 | |
| 31 | 0.02 | 2.70 | 0.24 |
| 32 | 0.15 | >19.74 | 2.46 |
| 33 | >20.00 | | |
| 34 | 0.01 | 3.52 | 0.60 |
| 35 | 0.01 | 1.98 | 0.15 |
| 36 | 0.02 | 2.46 | 0.39 |
| 37 | 0.04 | 2.84 | 0.46 |
| 38 | 0.01 | 2.52 | |
| 39 | 0.03 | 3.06 | 0.36 |
| 40 | 0.01 | 2.77 | 0.61 |
| 41 | 0.06 | 4.59 | 0.49 |
| 42 | 0.03 | 3.29 | 0.23 |
| 43 | 0.04 | | |
| 44 | 0.15 | 11.08 | |
| 45 | 0.03 | | |
| 46 | 0.04 | | |
| 47 | 0.14 | 7.15 | |
| 48 | 0.05 | 6.62 | |
| 49 | 0.03 | | |
| 50 | 0.04 | 2.65 | 0.65 |
| 51 | 0.03 | 10.51 | 0.41 |
| 52 | 0.01 | 3.69 | 0.24 |
| 53 | 0.02 | 4.05 | 0.63 |
| 54 | 0.09 | 13.97 | 1.81 |
| 55 | 0.01 | 1.79 | 0.14 |
| 56 | 0.01 | 1.60 | 0.08 |
| 57 | 0.01 | 2.49 | 0.28 |
| 58 | 0.04 | 3.50 | 0.70 |
| 59 | 0.01 | 1.69 | 0.13 |
| 60 | 0.01 | 2.34 | 0.15 |
| 61 | 0.03 | 5.60 | 0.59 |
| 62 | 0.01 | 1.02 | 0.31 |
| 63 | 0.02 | 1.16 | 0.47 |
| 64 | 0.01 | 0.84 | 0.24 |
| 65 | 0.01 | 1.25 | 0.80 |
| 66 | 0.01 | 0.89 | 1.12 |
| 67 | 0.01 | 2.11 | 0.23 |
| 68 | 0.02 | 2.20 | 1.24 |
| 69 | 0.03 | 1.97 | 1.29 |

| Example | CBP HTRF IC50 (μM) | BRD4 Alpha IC50 (μM) | Myc IC50 (μM) | Example | CBP HTRF IC50 (μM) | BRD4 Alpha IC50 (μM) | Myc IC50 (μM) |
|---|---|---|---|---|---|---|---|
| 70 | 0.01 | 2.63 | 0.22 | 146 | 0.03 | 5.32 | |
| 71 | 0.02 | | | 147 | 0.16 | 4.77 | |
| 72 | 0.02 | 2.49 | 1.39 | 148 | 0.12 | 3.85 | |
| 73 | 0.03 | 3.05 | 0.63 | 149 | 0.11 | 2.74 | |
| 74 | 0.02 | 2.47 | 0.47 | 150 | 0.11 | 3.52 | |
| 75 | 0.02 | 2.64 | 0.44 | 151 | 0.03 | 10.27 | 0.87 |
| 76 | 0.01 | 0.90 | 1.04 | 152 | 0.02 | 3.66 | 0.38 |
| 77 | 0.01 | 1.51 | | 153 | 0.03 | 5.36 | 0.64 |
| 78 | 0.02 | 2.36 | | 154 | 0.02 | 1.36 | 0.37 |
| 79 | 0.02 | 2.02 | 0.77 | 155 | 0.03 | | |
| 80 | 0.02 | 2.34 | | 156 | 0.07 | >19.74 | 2.29 |
| 81 | 0.02 | 5.29 | 0.50 | 157 | 0.03 | 4.52 | 0.69 |
| 82 | 0.03 | 5.38 | | 158 | 0.06 | 7.77 | 1.86 |
| 83 | 0.02 | | | 159 | 0.03 | 2.63 | 1.89 |
| 84 | 0.02 | 2.65 | 0.39 | 160 | 0.02 | 3.68 | 0.41 |
| 85 | 0.01 | 2.41 | 0.45 | 161 | 0.03 | | |
| 86 | 0.02 | 2.72 | 0.44 | 162 | 0.03 | | |
| 87 | 0.02 | | | 163 | 0.02 | 4.14 | 0.44 |
| 88 | 0.05 | 11.02 | 0.63 | 164 | 0.04 | 5.10 | 1.07 |
| 89 | 0.02 | 3.27 | 0.23 | 165 | 0.08 | | |
| 90 | 0.03 | 2.90 | 0.55 | 166 | 0.08 | | |
| 91 | 0.03 | 2.86 | 0.50 | 167 | 0.04 | | |
| 92 | 0.02 | 3.99 | 0.35 | 168 | 0.11 | 10.22 | |
| 93 | 0.04 | 4.33 | 0.36 | 169 | 0.06 | 11.72 | 1.05 |
| 94 | 0.02 | 3.54 | 0.38 | 170 | 0.04 | 8.25 | 0.52 |
| 95 | 0.04 | 3.57 | 1.04 | 171 | 0.06 | 15.94 | 4.55 |
| 96 | 0.03 | 3.69 | 0.45 | 172 | 0.04 | | 0.44 |
| 97 | 0.04 | 3.19 | 0.71 | 173 | 0.04 | 6.47 | 0.63 |
| 98 | 0.02 | 4.42 | 0.20 | 174 | 0.03 | 2.92 | 0.44 |
| 99 | 0.05 | 7.22 | 1.42 | 175 | 0.03 | 8.09 | 0.89 |
| 100 | 0.04 | 4.25 | 2.30 | 176 | 0.03 | 3.85 | 0.60 |
| 101 | 0.02 | 1.93 | 0.39 | 177 | 0.04 | 6.66 | 0.36 |
| 102 | 0.02 | | | 178 | 0.03 | 5.18 | 0.61 |
| 103 | 0.02 | 3.78 | 0.24 | 179 | 0.02 | 2.54 | 0.42 |
| 104 | 0.02 | 4.49 | 0.42 | 180 | 0.15 | | |
| 105 | 0.03 | 6.45 | 0.30 | 181 | 0.03 | 3.98 | 0.31 |
| 106 | 0.06 | 5.04 | 1.09 | 182 | 0.02 | | |
| 107 | 0.05 | 5.06 | 1.13 | 183 | 0.02 | 4.06 | |
| 108 | 0.05 | 9.06 | 1.09 | 184 | 0.08 | 9.65 | |
| 109 | 0.08 | 7.87 | 1.11 | 185 | 0.05 | 11.42 | 0.86 |
| 110 | 0.05 | | 0.63 | 186 | 0.12 | 6.75 | |
| 111 | 0.03 | 5.59 | 0.116 | 187 | 0.08 | 12.33 | |
| 112 | 0.01 | 2.20 | 0.18 | 188 | 0.36 | 19.38 | |
| 113 | 0.10 | 10.48 | 1.88 | 189 | 0.20 | 5.48 | 0.81 |
| 114 | 0.07 | 8.16 | 1.20 | 190 | 0.87 | 28.37 | |
| 115 | 0.02 | 6.98 | 0.63 | 191 | 3.38 | | |
| 116 | 0.02 | 6.02 | 1.08 | 192 | 1.65 | >19.74 | |
| 117 | 0.09 | 3.99 | | 193 | 1.25 | | |
| 118 | 0.11 | 5.48 | | 194 | 0.93 | >19.74 | |
| 119 | 0.04 | 7.50 | 1.03 | 195 | 0.28 | | 3.45 |
| 120 | 0.11 | 4.34 | | 196 | 0.29 | | 2.72 |
| 121 | 0.20 | 3.76 | | 197 | 0.22 | 4.07 | 1.17 |
| 122 | 0.15 | 5.32 | | 198 | 0.26 | 25.68 | 2.74 |
| 123 | 0.05 | 6.32 | 0.99 | 199 | 0.18 | 14.07 | 2.89 |
| 124 | 0.17 | 5.48 | | 200 | 0.05 | 15.81 | 1.48 |
| 125 | 0.10 | 3.53 | | 201 | 0.13 | 9.08 | 2.38 |
| 126 | 0.12 | 5.34 | | 202 | 0.22 | 5.19 | |
| 127 | 0.15 | 6.53 | | 203 | 0.17 | 2.63 | |
| 128 | 0.10 | 4.30 | | 204 | 0.31 | >19.74 | |
| 129 | 0.16 | 5.59 | | 205 | 0.16 | >19.74 | |
| 130 | 0.11 | 7.74 | | 206 | 0.16 | 13.08 | |
| 131 | 0.15 | 6.83 | | 207 | 0.27 | >19.74 | |
| 132 | 0.09 | 4.19 | | 208 | 0.30 | 11.65 | |
| 133 | 0.11 | 6.33 | | 209 | 0.88 | 6.05 | |
| 134 | 0.15 | 5.47 | | 210 | 0.12 | 8.46 | |
| 135 | 0.18 | 4.66 | | 211 | 0.22 | >19.74 | |
| 136 | 0.16 | 4.24 | | 212 | 0.23 | >19.74 | |
| 137 | 0.11 | 2.12 | | 213 | 0.21 | 18.65 | |
| 138 | 0.16 | 6.38 | | 214 | 0.22 | 14.56 | |
| 139 | 0.16 | 5.27 | | 215 | 0.22 | 5.88 | |
| 140 | 0.19 | 6.08 | | 216 | 0.20 | 6.89 | |
| 141 | 0.17 | 6.20 | | 217 | 0.13 | 13.60 | 1.30 |
| 142 | 0.09 | 5.25 | | 218 | 0.02 | 5.25 | 0.50 |
| 143 | 0.08 | 3.43 | | 219 | 0.08 | >10.53 | 0.79 |
| 144 | 0.09 | 4.72 | | 220 | 0.29 | 9.72 | 1.72 |
| 145 | 0.10 | 4.40 | | 221 | 0.03 | 6.18 | 0.41 |

-continued

| Example | CBP HTRF IC50 (µM) | BRD4 Alpha IC50 (µM) | Myc IC50 (µM) |
|---|---|---|---|
| 222 | 3.28 | >19.74 | |
| 223 | 0.02 | 5.11 | 0.50 |
| 224 | 0.007 | 3.46 | 0.69 |
| 225 | 0.021 | 5.32 | 1.65 |
| 226 | 0.010 | 2.90 | 0.10 |
| 227 | 0.024 | 8.41 | 0.51 |
| 228 | 0.082 | 7.58 | |
| 229 | 0.022 | 4.40 | 1.33 |
| 230 | 0.072 | >6.67 | |
| 231 | 0.017 | 2.61 | 0.03 |
| 232 | 0.067 | 15.03 | |
| 233 | 0.063 | 2.13 | |
| 234 | 0.018 | 2.72 | 0.38 |
| 235 | 0.034 | 2.18 | 0.91 |
| 236 | 0.031 | 5.90 | 0.78 |
| 237 | 0.022 | 11.06 | 0.37 |
| 238 | 0.021 | 3.19 | 0.39 |
| 239 | 0.015 | 5.07 | 0.44 |
| 240 | 0.035 | 5.01 | 2.84 |
| 241 | 0.007 | 2.14 | 0.02 |
| 242 | 0.002 | 2.48 | 0.20 |
| 243 | 0.013 | 2.99 | 2.75 |
| 244 | 0.074 | 6.66 | |
| 245 | 0.031 | 5.93 | 3.47 |
| 246 | 0.016 | 4.27 | 0.49 |
| 247 | 0.141 | 9.08 | |
| 248 | 0.028 | 5.80 | 1.09 |
| 249 | 0.032 | 2.78 | 4.09 |
| 250 | 0.159 | >20 | |
| 251 | 0.202 | >20 | |
| 252 | 0.004 | 4.81 | 0.18 |
| 253 | 0.239 | >20 | |
| 254 | 0.017 | 2.52 | 1.15 |
| 255 | 0.854 | >20 | |
| 256 | 0.002 | >20 | 0.07 |
| 257 | 0.003 | >20 | 0.10 |
| 258 | 0.061 | >20 | |
| 259 | 0.032 | >20 | 4.72 |
| 260 | 0.001 | 11.69 | 0.03 |
| 261 | 0.003 | 14.47 | 0.07 |
| 262 | 0.016 | >20 | 1.21 |
| 263 | 0.028 | >20 | 1.88 |
| 264 | 0.015 | >20 | 0.95 |
| 265 | 0.005 | 15.42 | 0.21 |
| 266 | 0.002 | 3.85 | 0.05 |
| 267 | 0.011 | >20 | 0.60 |
| 268 | 0.004 | 12.24 | >10 |
| 269 | 0.005 | 17.99 | 0.22 |
| 270 | 0.077 | 12.52 | |
| 271 | 0.003 | 7.07 | 0.09 |
| 272 | 0.002 | 14.66 | 0.03 |
| 273 | 0.002 | 7.88 | 0.10 |
| 274 | 0.001 | 8.86 | 0.02 |
| 275 | 0.020 | 4.89 | 0.27 |
| 276 | 0.015 | 1.68 | 0.18 |
| 277 | 0.035 | | 0.08 |
| 278 | 0.021 | 6.49 | 0.37 |
| 279 | 0.020 | 8.26 | 0.34 |
| 280 | 0.032 | 8.01 | 0.46 |
| 281 | 0.022 | 8.26 | 0.33 |
| 282 | 0.010 | 0.76 | 0.11 |
| 283 | 0.023 | 5.01 | 0.078 |
| 284 | 0.019 | 4.93 | 0.36 |
| 285 | 0.035 | 4.09 | 0.58 |
| 286 | 0.038 | 8.55 | 1.06 |
| 287 | 0.023 | 4.56 | 0.67 |
| 288 | 0.019 | 2.33 | 0.57 |
| 289 | 0.008 | 1.54 | 0.04 |
| 290 | 0.045 | 8.67 | 1.16 |
| 291 | 0.027 | 1.99 | 0.61 |
| 292 | 0.025 | 3.40 | 0.56 |
| 293 | 0.026 | 4.13 | 0.35 |
| 294 | 0.015 | 1.20 | 0.13 |
| 295 | 0.013 | 1.98 | 0.16 |
| 296 | 0.020 | 1.93 | 0.48 |
| 297 | 0.010 | 1.69 | 0.13 |
| 298 | 0.015 | 2.34 | 0.15 |
| 299 | 0.040 | 6.25 | 0.77 |
| 300 | 0.022 | 5.49 | 1.2 |
| 301 | 0.012 | 5.33 | 0.24 |
| 302 | 0.039 | 8.25 | 0.56 |
| 303 | 0.019 | 3.67 | 0.25 |
| 304 | 0.021 | 8.87 | 0.19 |
| 305 | 0.023 | 3.06 | 0.093 |
| 306 | 0.018 | 2.08 | 0.21 |
| 307 | 0.020 | 2.45 | 0.54 |
| 308 | 0.016 | 4.00 | 0.43 |
| 309 | 0.032 | 3.62 | 0.40 |
| 310 | 0.010 | 2.91 | 0.26 |

Exemplification of CBP/EP300 Inhibitors for the Treatment of Fibrotic Disease

The results of the fibrosis experiments described herein are shown in FIGS. 1-14.

Cell Culture:

Collagen 1-coated 384-well plates (BD Biosciences cat #356667) were seeded with Normal Human Lung Fibroblasts (Lonza cat#CC-2512) at 2000 cells per well in 50 µl DMEM (Genentech) containing 0.5% fetal bovine serum (Sigma cat#F2442). After 16 hours, the indicated compounds were added to cells at final concentrations ranging from 10 µM to 0.005 nM in an 8-fold dilution series. After one hour, TGF beta (Genentech) was added to cells to a final concentration of 10 ng/ml. All treatments were performed in duplicate.

Animal Study:

Bleomycin was administered to mice via subcutaneous implantation of an osmotic pump (Alzet cat#1007D). After bleomycin administration, mice were treated with compounds by oral gavage. Mice received either MCT vehicle (0.5% w/v methylcellulose, 0.2% w/v polysorbate 80), G0272 in MCT at 5 mg/kg twice daily, G0272 in MCT at 15 mg/kg twice daily, G5049 in MCT at 5 mg/kg twice daily, G5049 in MCT at 15 mg/kg twice daily, G3486 in MCT at 15 mg/kg twice daily, or G3486 in MCT at 45 mg/kg twice daily. To label newly synthesized collagen, mice were injected intraperitoneally with 35 ml/kg heavy water (Sigma Aldrich, cat#151882) in two doses and heavy water was provided in drinking water. At study termination, blood samples were collected by retro-orbital bleed under isoflurane anesthesia and mice were euthanized. Upper right lung lobes were placed in glass vials and snap frozen in liquid nitrogen for mass spectrometry. The lower right lung lobe was placed in RNAlater for expression analysis, and frozen at −20° C.

Lung Hydroxyproline Determination:

Lungs were thawed, dried overnight at 80° C., then hydrolyzed at 110° C. overnight in 6N HCl. The remainder of this paragraph was performed by KineMed, Emeryville Calif.). A 100 µl aliquot of tissue hydrolysate received a spike containing 1 µg $^2H_3$-labeled hydroxyproline (D3-OHP; trans-4-Hydroxy-L-proline-2,5,5-d3; CDN), and then dried under vacuum and re-suspended in a solution of 50% acetonitrile, 50 mM $K_2HPO_4$ and pentafluorobenzyl bromide before incubation. Derivatives were extracted into ethyl acetate, and the top layer was removed and dried by vacuum centrifugation. In order to acetylate the hydroxyl moiety of hydroxyproline, samples were incubated with a solution of acetonitrile, N-Methyl-N-[tert-butyl-dimethylsilyl]trifluoroacetamide and methylimidizole. This material was extracted in petroleum ether and dried with $Na_2SO_4$. The derivatized hydroxyproline was analyzed by GC/MS, performed in the negative chemical ionization mode. Selected ion monitoring was performed on ions with mass-to-charge ratios (m/z) 445, 446, 447, and 448 which include all of the carbon-hydrogen bonds from hydroxyproline. Incorporation of $^2H$ into hydroxyproline was calculated as the molar fraction of molecules with one excess mass unit above the natural abundance fraction (EM1). Fractional collagen synthesis (f) was calculated as the ratio of the EM1 value in protein-bound hydroxyproline to the maximal value possible at the body water enrichment present. This method has previously been described (Gardner, J. L., et al., Measurement of liver collagen synthesis by heavy water labeling: effects of profibrotic toxicants and antifibrotic interventions. *Am J Physiol Gastrointest Liver Physiol*, 2007. 292 (6): p. G1695-705). Additionally, hydroxyproline content in each tissue sample was determined by comparing the abundance in the m3 448 m/z channel representing the D3-OHP internal standard in each sample with that the m0 445 m/z ion. A set of standards with known OHP/D3-OHP concentration ratios was analyzed alongside the samples. $^2H_2O$ enrichment in plasma was determined using a previously described method (Previs S F, Hazey J W, Diraison F, Beylot M, David F, Brunengraber H (1996) Assay of the deuterium enrichment of water via acetylene. *J Mass Spectrom* 31:639-642.). Briefly body water is evaporated from plasma by overnight incubation at 80° C. Samples are then mixed in 10M NaOH and acetone followed by a second overnight incubation. This material was extracted in hexane and dried with $Na_2SO_4$ prior to GCMS analysis.

RNA Isolation:

For cultured cells, after 24 hours of treatment with TGF beta and CBP/p300 inhibitor, mRNA was isolated with the Turbocapture 384 mRNA kit (Qiagen cat#72271) according to the manufacturers' instructions and eluted with 30 µl elution buffer. For lungs, tissues were thawed, removed from RNAlater, homogenized in GentleMACS M tubes (Miltenyi Biotec cat#130-093-236) and RNA extracted with the RNeasy 96 kit (Qiagen cat#74182) according to the manufacturers instructions.

Expression Analysis:

First-strand cDNA was synthesized using 14 µl mRNA for cultured cells and 150 ng RNA for lung. The High Capacity cDNA Reverse Transcription Kit (Life Technologies cat#4368814) was used according to the manufacturers protocol. Specific target amplification was performed using 1.25 µl cDNA, Taqman assays (Life Technologies cat#4331182) at a final concentration of 0.2x, and Taqman Preamp Master Mix (Life Technologies cat#4488593) and subsequently diluted according to the protocol for Fluidigm qPCR (Fluidigm Corp). Samples and assays were mixed with loading buffers and loaded onto 192.24 IFCs (Fluidigm cat#100-6266) according to the manufacturers instructions. Reactions were mixed using the IFC controller RX (Fluidigm) then amplified and measured using the Biomark system (Fluidigm). For cultured cells, relative expression of each target gene was determined using the ΔCt method, normalizing to the Ct for HPRT1 using Excel software (Microsoft). To generate heat maps, TGF beta-mediated expression increase for each gene in the presence of CBP/p300 inhibitor was divided by the increase in the absence of CBP/p300 inhibitor using Excel (i.e. $(2^{-\Delta Ct,\ SMI+TGFb} - 2^{-\Delta Ct,\ SMI,\ no\ TGFb})/(2^{-\Delta Ct,\ TGFb} - 2^{-\Delta Ct,\ no\ TGFb})$). Line graphs of $2^{-\Delta Ct}$ values were generated using Prism software (Graphpad). For lung, relative expression of each target gene was determined using the ΔΔCt method, normalizing to the Ct for GAPDH and the vehicle control group. Heat maps were generated with Excel software (Microsoft).

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A compound of formula (I) or formula (II):

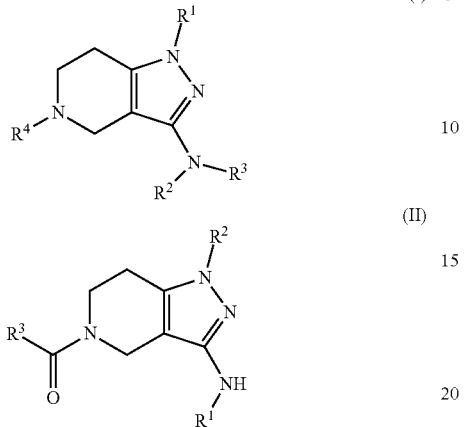

or a salt thereof, wherein:

R$^1$ of Formula (I) is C$_{1-12}$alkyl, C$_{2-12}$alkenyl, C$_{2-12}$alkynyl, 3-12 membered carbocycle, and 3-12 membered heterocycle, wherein each C$_{1-12}$alkyl, C$_{2-12}$alkenyl, C$_{2-12}$alkynyl, 3-12 membered carbocycle, and 3-12 membered heterocycle of R$^1$ is optionally substituted with one or more groups R$^b$;

R$^2$ of Formula (I) is selected from C$_6$-C$_{20}$ aryl, C$_1$-C$_{20}$ heteroaryl, —(C$_6$-C$_{20}$ aryl)(C$_1$-C$_{20}$ heteroaryl), —(C$_1$-C$_{20}$ heteroaryl)-(C$_6$-C$_{20}$ aryl), and —(C$_1$-C$_{20}$ heteroaryl)-(C$_1$-C$_{20}$ heteroaryl), wherein each C$_6$-C$_{20}$ aryl, C$_1$-C$_{20}$ heteroaryl, —(C$_6$-C$_{20}$ aryl)-(C$_1$-C$_{20}$ heteroaryl) and —(C$_1$-C$_{20}$ heteroaryl)-(C$_1$-C$_{20}$ heteroaryl) is independently optionally substituted with one or more substituent groups independently selected from R$^c$, oxo, —F, —Cl, —Br, —I, —NO$_2$, —N(R$^a$)$_2$, —CN, —C(O)—N(R$^a$)$_2$, —S(O)—N(R$^a$)$_2$, —S(O)$_2$—N(R$^a$)$_2$, —O—R$^a$, —S—R$^a$, —O—C(O)—R$^a$, —O—C(O)—O—R$^a$, —C(O)—R$^a$, —C(O)—O—R$^a$, —S(O)—R$^a$, —S(O)$_2$—R$^a$, —O—C(O)—N(R$^a$)$_2$, —N(R$^a$)—C(O)—OR$^a$, —N(R$^a$)—C(O)—N(R$^a$)$_2$, —N(R$^a$)—C(O)—R$^a$, —N(R$^a$)—S(O)—R$^a$, —N(R$^a$)—S(O)$_2$—R$^a$, —N(R$^a$)—S(O)—N(R$^a$)$_2$, and —N(R$^a$)—S(O)$_2$—N(R$^a$)$_2$;

R$^3$ of Formula (I) is C$_{1-12}$alkyl, C$_{2-12}$alkenyl, C$_{2-12}$alkynyl, 3-12 membered carbocycle, and 3-12 membered heterocycle, wherein each C$_{1-12}$alkyl, C$_{2-12}$alkenyl, C$_{2-12}$alkynyl, 3-12 membered carbocycle, and 3-12 membered heterocycle of R$^3$ is optionally substituted with one or more groups R$^e$; or R$^2$ and R$^3$ of Formula (I) taken together with the nitrogen to which they are attached form a 3-12 membered heterocycle that is optionally substituted with one or more groups R$^e$;

R$^4$ of Formula (I) is C$_{1-4}$alkyl, C$_{2-4}$alkenyl, C$_{2-4}$alkynyl, 3-5 membered carbocycle, 3-5 membered heterocycle, —C(O)—N(R$^h$)$_2$, —S(O)—N(R$^h$)$_2$, —S(O)$_2$—N(R$^h$)$_2$, —C(O)—R$^h$, —C(O)—O—R$^h$, —S(O)—R$^h$, or —S(O)$_2$—R$^h$, wherein any C$_{1-4}$alkyl, C$_{2-4}$alkenyl, C$_{2-4}$alkynyl, 3-5 membered carbocycle, and 3-5 membered heterocycle is optionally substituted with one or more substituent groups independently selected from —F, —Cl, —Br, —I, 3-5 membered carbocycle, —C(O)—N(R$^h$)$_2$, —S(O)—N(R$^h$)$_2$, —S(O)$_2$—N(R$^h$)$_2$, —O—R$^h$, —S—R$^h$, —O—C(O)—R$^h$, —O—C(O)—O—R$^h$, —C(O)—R$^h$, —C(O)—O—R$^h$, —S(O)—R$^h$, —S(O)$_2$—R$^h$, —O—C(O)—N(R$^h$)$_2$, —N(R$^h$)—C(O)—OR$^h$, —N(R$^h$)—C(O)—N(R$^h$)$_2$, —N(R$^h$)—C(O)—R$^a$, —N(R$^h$)—S(O)—R$^h$, —N(R$^h$)—S(O)$_2$—R$^h$, —N(R$^h$)—S(O)—N(R$^h$)$_2$, and —N(R$^h$)—S(O)$_2$—N(R$^h$)$_2$;

each R$^a$ of Formula (I) is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, and heterocyclyl is optionally substituted with one or more groups independently selected from oxo, halo, amino, hydroxyl, C$_{1-6}$alkoxy, carbocyclyl, heterocyclyl, and C$_1$-C$_6$ alkyl that is optionally substituted with one or more groups independently selected from oxo and halo; or two R$^a$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^b$ of Formula (I) is independently selected from oxo, C$_{1-6}$alkyl, C$_{2-6}$alkenyl, C$_{2-6}$alkynyl, carbocyclyl, heterocyclyl, aryl, heteroaryl, —F, —Cl, —Br, —I, —NO$_2$, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—O—R$^c$, —O—C(O)—O—R$^c$, —C(O)—R$^c$, —C(O)—O—R$^c$, —S(O)—R$^c$, —S(O)$_2$—R$^c$, —O—C(O)—N(R$^c$)$_2$, —N(R$^c$)—C(O)—OR$^c$, —N(R$^c$)—C(O)—N(R$^c$)$_2$, —N(R$^c$)—C(O)—R$^c$, —N(R$^c$)—S(O)—R$^c$, —N(R$^c$)—S(O)$_2$—R$^c$, —N(R$^c$)—S(O)—N(R$^c$)$_2$, and —N(R$^c$)—S(O)$_2$—N(R$^c$)$_2$, wherein any C$_{1-6}$alkyl, C$_{2-6}$alkenyl, C$_{2-6}$alkynyl, carbocyclyl, heterocyclyl, aryl, and heteroaryl is optionally substituted with one or more groups independently selected from oxo, halo, —NO$_2$, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—R$^c$, —C(O)—R$^c$, —S(O)—R$^c$, —S(O)$_2$—R$^c$, —C(O)—N(R$^c$)$_2$, —N(R$^c$)—C(O)—R$^c$, —N(R$^c$)—S(O)—R$^c$, —N(R$^c$)—S(O)$_2$—R$^c$ and C$_{1-6}$alkyl that is optionally substituted with one or more groups independently selected from oxo and halo;

each R$^c$ of Formula (I) is independently selected from hydrogen, C$_{1-6}$alkyl, C$_{2-6}$alkenyl, C$_{2-6}$alkynyl, carbocyclyl, and heterocyclyl, wherein any C$_{1-6}$alkyl, C$_{2-6}$alkenyl, C$_{2-6}$alkynyl, carbocyclyl, and heterocyclyl is optionally substituted with one or more groups independently selected from oxo, carbocyclyl, heterocyclyl, halo, —NO$_2$, —N(R$^d$)$_2$, —CN, —C(O)—N(R$^d$)$_2$, —S(O)—N(R$^d$)$_2$, —S(O)$_2$—N(R$^d$)$_2$, —O—R$^d$, —S—R$^d$, —O—C(O)—R$^d$, —C(O)—R$^d$, —C(O)—O—R$^d$, —S(O)—R$^d$, —S(O)$_2$—R$^d$, —C(O)—N(R$^d$)$_2$, —N(R$^d$)—C(O)—R$^d$, —N(R$^d$)—S(O)—R$^d$, N(R$^d$)—S(O)$_2$—R$^d$, and C$_{1-6}$alkyl, which carbocyclyl and C$_{1-6}$alkyl are optionally substituted with one or more groups independently selected from oxo, halo, C$_{1-6}$alkyl, cyano, —N(R$^d$)$_2$, —O—R$^d$, heterocyclyl, and carbocyclyl that is optionally substituted with one or more groups independently selected from halo, and C$_{1-6}$alkyl;

each R$^d$ of Formula (I) is independently selected from hydrogen, C$_{1-6}$alkyl, C$_{2-6}$alkenyl, C$_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from oxo, halo, amino, hydroxyl, $C_{1-6}$alkoxy, carbocyclyl, heterocyclyl, and $C_1$-$C_6$alkyl that is optionally substituted with one or more groups independently selected from oxo and halo; or two $R^d$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^e$ of Formula (I) is independently selected from oxo, $C_{1-6}$alkyl, $C_{2-6}$alkenyl, $C_{2-6}$alkynyl, carbocyclyl, heterocyclyl, aryl, heteroaryl, —F, —Cl, —Br, —I, —$NO_2$, —$N(R^f)_2$, —CN, —C(O)—$N(R^f)_2$, —S(O)—$N(R^f)_2$, —$S(O)_2$—$N(R^f)_2$, —O—$R^f$, —S—$R^f$, —O—C(O)—$R^f$, —O—C(O)—O—$R^f$, —C(O)—$R^f$, —C(O)—O—$R^f$, —S(O)—$R^f$, —$S(O)_2$—$R^f$, —O—C(O)—$N(R^f)_2$, —$N(R^f)$—C(O)—$OR^f$, —$N(R^f)$—C(O)—$N(R^f)_2$, —$N(R^f)$—C(O)—$R^f$, —$N(R^f)$—S(O)—$R^f$, —$N(R^f)$—$S(O)_2$—$R^f$, —$N(R^f)$—S(O)—$N(R^f)_2$, and —$N(R^f)$—$S(O)_2$—$N(R^f)_2$, wherein any $C_{1-6}$alkyl, $C_{2-6}$alkenyl, $C_{2-6}$alkynyl, carbocyclyl, heterocyclyl, aryl, and heteroaryl is optionally substituted with one or more groups independently selected from oxo, halo, —$NO_2$, —$N(R^f)_2$, —CN, —C(O)—$N(R^f)_2$, —S(O)—$N(R^f)_2$, —$S(O)_2$—$N(R^f)_2$, —O—$R^f$, —S—$R^f$, —O—C(O)—$R^f$, —C(O)—$R^f$, —C(O)—O—$R^f$, —S(O)—$R^f$, —$S(O)_2$—$R^f$, —C(O)—$N(R^f)_2$, —$N(R^f)$—C(O)—$R^f$, —$N(R^f)$—S(O)—$R^f$, —$N(R^f)$—$S(O)_2$—$R^f$, carbocycle, and $C_{1-6}$alkyl that is optionally substituted with one or more groups independently selected from oxo and halo;

each $R^f$ of Formula (I) is independently selected from hydrogen, $C_{1-6}$alkyl, $C_{2-6}$alkenyl, $C_{2-6}$alkynyl, carbocyclyl, and heterocyclyl, wherein any $C_{1-6}$alkyl, $C_{2-6}$alkenyl, $C_{2-6}$alkynyl, carbocyclyl, and heterocyclyl is optionally substituted with one or more groups independently selected from oxo, carbocyclyl, heterocyclyl, halo, —$NO_2$, —$N(R^g)_2$, —CN, —C(O)—$N(R^g)_2$, —S(O)—$N(R^g)_2$, —$S(O)_2$—$N(R^g)_2$, —O—$R^g$, —S—$R^g$, —O—C(O)—$R^g$, —C(O)—$R^g$, —C(O)—O—$R^g$, —S(O)—$R^g$, —$S(O)_2$—$R^g$, —C(O)—$N(R^g)_2$, —$N(R^g)$—C(O)—$R^g$, —$N(R^g)$—S(O)—$R^g$, $N(R^g)$—$S(O)_2$—$R^g$, and $C_{1-6}$alkyl, which carbocyclyl and $C_{1-6}$alkyl are optionally substituted with one or more groups independently selected from oxo, halo, $C_{1-6}$alkyl, cyano, —$N(R^g)_2$, —O—$R^g$, heterocyclyl, and carbocyclyl that is optionally substituted with one or more groups independently selected from halo, and $C_{1-6}$alkyl;

each $R^g$ of Formula (I) is independently selected from hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from oxo, halo, amino, hydroxyl, $C_{1-6}$alkoxy, carbocyclyl, heterocyclyl, and $C_1$-$C_6$alkyl that is optionally substituted with one or more groups independently selected from oxo and halo; or two $R^g$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^h$ of Formula (I) is independently selected from hydrogen, $C_{1-4}$alkyl, $C_{2-4}$alkenyl, $C_{2-4}$alkynyl, and $C_{2-5}$cycloalkyl, wherein each $C_{1-4}$alkyl, $C_{2-4}$alkenyl, $C_{2-4}$alkynyl, and $C_{2-5}$cycloalkyl is optionally substituted with one or more groups independently selected from oxo, halo, amino, hydroxyl, $C_{1-3}$alkoxy, and $C_1$-$C_3$ alkyl that is optionally substituted with one or more groups independently selected from halo; and $R^1$ of Formula (II) is selected from $C_6$-$C_{20}$ aryl, $C_1$-$C_{20}$ heteroaryl, —($C_6$-$C_{20}$ aryl)-($C_1$-$C_{20}$ heteroaryl), and —($C_1$-$C_{20}$ heteroaryl)-($C_1$-$C_{20}$ heteroaryl), wherein each $C_6$-$C_{20}$ aryl, $C_1$-$C_{20}$ heteroaryl, —($C_6$-$C_{20}$ aryl)-($C_1$-$C_{20}$ heteroaryl) and —($C_1$-$C_{20}$ heteroaryl)-($C_1$-$C_{20}$ heteroaryl) is independently optionally substituted with one or more substituent groups independently selected from $R^c$, oxo, —F, —Cl, —Br, —I, —$NO_2$, —$N(R^a)_2$, —CN, —C(O)—$N(R^a)_2$, —S(O)—$N(R^a)_2$, —$S(O)_2$—$N(R^a)_2$, —O—$R^a$, —S—$R^a$, —O—C(O)—$R^a$, —O—C(O)—O—$R^a$, —C(O)—$R^a$, —C(O)—O—$R^a$, —S(O)—$R^a$, —$S(O)_2$—$R^a$, —O—C(O)—$N(R^a)_2$, —$N(R^a)$—C(O)—$OR^a$, —$N(R^a)$—C(O)—$N(R^a)_2$, —$N(R^a)$—C(O)—$R^a$, —$N(R^a)$—S(O)—$R^a$, —$N(R^a)$—$S(O)_2$—$R^a$, —$N(R^a)$—S(O)—$N(R^a)_2$, and —$N(R^a)$—$S(O)_2$—$N(R^a)_2$;

$R^2$ of Formula (II) is $C_{1-12}$alkyl, $C_{2-12}$alkenyl, $C_{2-12}$alkynyl, 3-12 membered carbocycle, and 3-12 membered heterocycle, wherein each $C_{1-12}$alkyl, $C_{2-12}$alkenyl, $C_{2-12}$alkynyl, 3-12 membered carbocycle, and 3-12 membered heterocycle of $R^2$ is optionally substituted with one or more groups $R^b$;

$R^3$ of Formula (II) is $C_{1-4}$alkyl, $C_{2-4}$alkenyl, $C_{2-4}$alkynyl, 3-5 membered carbocycle, 3-5 membered heterocycle, —C(O)—$N(R^e)_2$, —S(O)—$N(R^e)_2$, —$S(O)_2$—$N(R^e)_2$, —C(O)—$R^e$, —C(O)—O—$R^e$, —S(O)—$R^e$, or —$S(O)_2$—$R^e$, wherein any $C_{1-4}$alkyl, $C_{2-4}$alkenyl, $C_{2-4}$alkynyl, 3-5 membered carbocycle, and 3-5 membered heterocycle is optionally substituted with one or more substituent groups independently selected from —F, —Cl, —Br, —I, 3-5 membered carbocycle, —C(O)—$N(R^e)_2$, —S(O)—$N(R^e)_2$, —$S(O)_2$—$N(R^e)_2$, —O—$R^e$, —S—$R^e$, —O—C(O)—$R^e$, —O—C(O)—O—$R^e$, —C(O)—$R^e$, —C(O)—O—$R^e$, —S(O)—$R^e$, —$S(O)_2$—$R^e$, —O—C(O)—$N(R^e)_2$, —$N(R^e)$—C(O)—$OR^e$, —$N(R^e)$—C(O)—$N(R^e)_2$, —$N(R^e)$—C(O)—$R^e$, —$N(R^e)$—S(O)—$R^e$, —$N(R^e)$—$S(O)_2$—$R^e$, —$N(R^e)$—S(O)—$N(R^e)_2$, and —$N(R^e)$—$S(O)_2$—$N(R^e)_2$;

each $R^a$ of Formula (II) is independently selected from hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from oxo, halo, amino, hydroxyl, $C_{1-6}$alkoxy, carbocyclyl, heterocyclyl, and $C_1$-$C_6$ alkyl that is optionally substituted with one or more groups independently selected from oxo and halo; or two $R^a$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^b$ of Formula (II) is independently selected from oxo, $C_{1-6}$alkyl, $C_{2-6}$alkenyl, $C_{2-6}$alkynyl, carbocyclyl, heterocyclyl, aryl, heteroaryl, —F, —Cl, —Br, —I, —$NO_2$, —$N(R^c)_2$, —CN, —C(O)—$N(R^c)_2$, —S(O)—$N(R^c)_2$, —$S(O)_2$—$N(R^c)_2$, —O—$R^c$, —S—$R^c$, —O—C(O)—O—$R^c$, —C(O)—$R^c$, —C(O)—O—$R^c$, —S(O)—$R^c$, —$S(O)_2$—$R^c$, —O—C(O)—$N(R^c)_2$, —$N(R^c)$—C(O)—$OR^c$, —$N(R^c)$—C(O)—$N(R^c)_2$, —$N(R^c)$—C(O)—$R^c$, —$N(R^c)$—S(O)—$R^c$, —$N(R^c)$—$S(O)_2$—$R^c$, —$N(R^c)$—S(O)—$N(R^c)_2$, and —$N(R^c)$—$S(O)_2$—$N(R^c)_2$, wherein any $C_{1-6}$alkyl, $C_{2-6}$alkenyl, $C_{2-6}$alkynyl, carbocyclyl, heterocyclyl, aryl, and heteroaryl is optionally substituted with one or more groups independently selected from oxo, halo, —$NO_2$, —$N(R^c)_2$, —CN, —C(O)—$N(R^c)_2$, —S(O)—$N(R^c)_2$, —$S(O)_2$—$N(R^c)_2$, —O—$R^c$, —S—$R^c$, —O—C(O)—$R^c$, —C(O)—$R^c$, —C(O)—O—$R^c$, —S(O)—$R^c$, —$S(O)_2$—$R^c$, —C(O)—$N(R^c)_2$, —$N(R^c)$—C(O)—$R^c$, —$N(R^c)$—S(O)—$R^c$, —$N(R^c)$—$S(O)_2$—$R^c$ and $C_{1-6}$alkyl that is optionally substituted with one or more groups independently selected from oxo and halo;

each $R^c$ of Formula (II) is independently selected from hydrogen, $C_{1-6}$alkyl, $C_{2-6}$alkenyl, $C_{2-6}$alkynyl, carbocyclyl, and heterocyclyl, wherein any $C_{1-6}$alkyl, $C_{2-6}$alkenyl, $C_{2-6}$alkynyl, carbocyclyl, and heterocyclyl is optionally substituted with one or more groups independently selected from oxo, carbocyclyl, heterocyclyl, halo, —$NO_2$, —$N(R^d)_2$, —CN, —C(O)—$N(R^d)_2$, —S(O)—$N(R^d)_2$, —$S(O)_2$—$N(R^d)_2$, —O—$R^d$, —O—C(O)—$R^d$, —C(O)—$R^d$, —C(O)—O—$R^d$, —S(O)—$R^d$, —$S(O)_2$—$R^d$, —C(O)—$N(R^d)_2$, —$N(R^d)$—C(O)—$R^d$, —$N(R^d)$—S(O)—$R^d$, $N(R^d)$—$S(O)_2$—$R^d$, and $C_{1-6}$alkyl, which carbocyclyl and $C_{1-6}$alkyl are optionally substituted with one or more groups independently selected from oxo, halo, $C_{1-6}$alkyl, cyano, —$N(R^d)_2$, —O—$R^d$, heterocyclyl, and carbocyclyl that is optionally substituted with one or more groups independently selected from halo, and $C_{1-6}$alkyl;

each $R^d$ of Formula (II) is independently selected from hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from oxo, halo, amino, hydroxyl, $C_{1-6}$alkoxy, carbocyclyl, heterocyclyl, and $C_1$-$C_6$ alkyl that is optionally substituted with one or more groups independently selected from oxo and halo; or two $R^d$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo; and each $R^e$ of Formula (II) is independently selected from hydrogen, $C_{1-4}$alkyl, $C_{2-4}$alkenyl, $C_{2-4}$alkynyl, and $C_{2-5}$cycloalkyl, wherein each $C_{1-4}$alkyl, $C_{2-4}$alkenyl, $C_{2-4}$alkynyl, and $C_{2-5}$cycloalkyl is optionally substituted with one or more groups independently selected from oxo, halo, amino, hydroxyl, $C_{1-3}$alkoxy, and $C_1$-$C_3$ alkyl that is optionally substituted with one or more groups independently selected from halo; provided that $R^1$ is not unsubstituted phenyl, when $R^2$ is carboxymethyl or 2-carboxyethyl.

2. The compound of claim 1, where the compound is of formula (I):

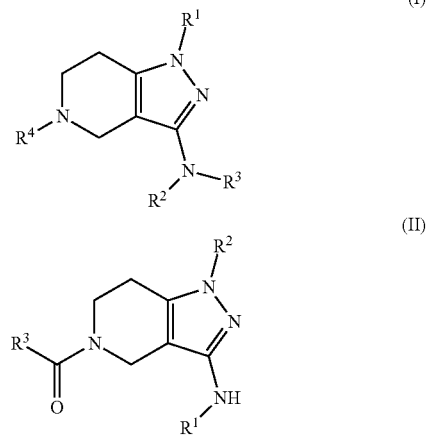

or a salt thereof, wherein:

$R^1$ is $C_{1-12}$alkyl, $C_{2-12}$alkenyl, $C_{2-12}$alkynyl, 3-12 membered carbocycle, and 3-12 membered heterocycle, wherein each $C_{1-12}$alkyl, $C_{2-12}$alkenyl, $C_{2-12}$alkynyl, 3-12 membered carbocycle, and 3-12 membered heterocycle of $R^1$ is optionally substituted with one or more groups $R^b$;

$R^2$ is selected from $C_6$-$C_{20}$ aryl, $C_1$-$C_{20}$ heteroaryl, —($C_6$-$C_{20}$ aryl)-($C_1$-$C_{20}$ heteroaryl), —($C_1$-$C_{20}$ heteroaryl)-($C_6$-$C_{20}$ aryl), and —($C_1$-$C_{20}$ heteroaryl)-($C_1$-$C_{20}$ heteroaryl), wherein each $C_6$-$C_{20}$ aryl, $C_1$-$C_{20}$ heteroaryl, —($C_6$-$C_{20}$ aryl)-($C_1$-$C_{20}$ heteroaryl) and —($C_1$-$C_{20}$ heteroaryl)-($C_1$-$C_{20}$ heteroaryl) is independently optionally substituted with one or more substituent groups independently selected from $R^c$, oxo, —F, —Cl, —Br, —I, —$NO_2$, —$N(R^a)_2$, —CN, —C(O)—$N(R^a)_2$, —S(O)—$N(R^a)_2$, —$S(O)_2$—$N(R^a)_2$, —O—$R^a$, —S—$R^a$, —O—C(O)—$R^a$, —O—C(O)—O—$R^a$, —C(O)—$R^a$, —C(O)—O—$R^a$, —S(O)—$R^a$, —$S(O)_2$—$R^a$, —O—C(O)—$N(R^a)_2$, —$N(R^a)$—C(O)—$OR^a$, —$N(R^a)$—C(O)—$N(R^a)_2$, —$N(R^a)$—C(O)—$R^a$, —$N(R^a)$—S(O)—$R^a$, —$N(R^a)$—$S(O)_2$—$R^a$, —$N(R^a)$—S(O)—$N(R^a)_2$, and —$N(R^a)$—$S(O)_2$—$N(R^a)_2$;

$R^3$ is $C_{1-12}$alkyl, $C_{2-12}$alkenyl, $C_{2-12}$alkynyl, 3-12 membered carbocycle, and 3-12 membered heterocycle, wherein each $C_{1-12}$alkyl, $C_{2-12}$alkenyl, $C_{2-12}$alkynyl, 3-12 membered carbocycle, and 3-12 membered heterocycle of $R^3$ is optionally substituted with one or more groups $R^e$; or $R^2$ and $R^3$ taken together with the nitrogen to which they are attached form a 3-12 membered heterocycle that is optionally substituted with one or more groups $R^e$;

$R^4$ is $C_{1-4}$alkyl, $C_{2-4}$alkenyl, $C_{2-4}$alkynyl, 3-5 membered carbocycle, 3-5 membered heterocycle, —C(O)—$N(R^h)_2$, —S(O)—$N(R^h)_2$, —$S(O)_2$—$N(R^h)_2$, —C(O)—$R^h$, —C(O)—O—$R^h$, —S(O)—$R^h$, or —$S(O)_2$—$R^h$, wherein any $C_{1-4}$alkyl, $C_{2-4}$alkenyl, $C_{2-4}$alkynyl, 3-5 membered carbocycle, and 3-5 membered heterocycle is optionally substituted with one or more substituent groups independently selected from —F, —Cl, —Br, —I, 3-5 membered carbocycle, —C(O)—N(R$^h$)$_2$, —S(O)—N(R$^h$)$_2$, —S(O)$_2$—N(R$^h$)$_2$, —O—R$^h$, —S—R$^h$, —O—C(O)—R$^h$, —O—C(O)—O—R$^h$, —C(O)—R$^h$, —C(O)—O—R$^h$, —S(O)—R$^h$, —S(O)$_2$—R$^h$, —O—C(O)—N(R$^h$)$_2$, —N(R$^h$)—C(O)—OR$^h$, —N(R$^h$)—C(O)—N(R$^h$)$_2$, —N(R$^h$)—C(O)—R$^a$, —N(R$^h$)—S(O)—R$^h$, —N(R$^h$)—S(O)$_2$—R$^h$, —N(R$^h$)—S(O)—N(R$^h$)$_2$, and —N(R$^h$)—S(O)$_2$—N(R$^h$)$_2$;

each R$^a$ is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, and heterocyclyl is optionally substituted with one or more groups independently selected from oxo, halo, amino, hydroxyl, C$_{1-6}$alkoxy, carbocyclyl, heterocyclyl, and C$_1$-C$_6$ alkyl that is optionally substituted with one or more groups independently selected from oxo and halo; or two R$^a$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^b$ is independently selected from oxo, C$_{1-6}$alkyl, C$_{2-6}$alkenyl, C$_{2-6}$alkynyl, carbocyclyl, heterocyclyl, aryl, heteroaryl, —F, —Cl, —Br, —I, —NO$_2$, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—R$^c$, —O—C(O)—O—R$^c$, —C(O)—R$^c$, —C(O)—O—R$^c$, —S(O)—R$^c$, —S(O)$_2$—R$^c$, —O—C(O)—N(R$^c$)$_2$, —N(R$^c$)—C(O)—OR$^c$, —N(R$^c$)—C(O)—N(R$^c$)$_2$, —N(R$^c$)—C(O)—R$^c$, —N(R$^c$)—S(O)—R$^c$, —N(R$^c$)—S(O)$_2$—R$^c$, —N(R$^c$)—S(O)—N(R$^c$)$_2$, and —N(R)—S(O)$_2$—N(R$^c$)$_2$, wherein any C$_{1-6}$alkyl, C$_{2-6}$alkenyl, C$_{2-6}$alkynyl, carbocyclyl, heterocyclyl, aryl, and heteroaryl is optionally substituted with one or more groups independently selected from oxo, halo, —NO$_2$, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—R$^c$, —C(O)—R$^c$, —C(O)—O—R$^c$, —S(O)—R$^c$, —S(O)$_2$—R$^c$, —C(O)—N(R$^c$)$_2$, —N(R$^c$)—C(O)—R$^c$, —N(R$^c$)—S(O)—R$^c$, —N(R$^c$)—S(O)$_2$—R$^c$ and C$_{1-6}$alkyl that is optionally substituted with one or more groups independently selected from oxo and halo;

each R$^c$ is independently selected from hydrogen, C$_{1-6}$alkyl, C$_{2-6}$alkenyl, C$_{2-6}$alkynyl, carbocyclyl, and heterocyclyl, wherein any C$_{1-6}$alkyl, C$_{2-6}$alkenyl, C$_{2-6}$alkynyl, carbocyclyl, and heterocyclyl is optionally substituted with one or more groups independently selected from oxo, carbocyclyl, heterocyclyl, halo, —NO$_2$, —N(R$^d$)$_2$, —CN, —C(O)—N(R$^d$)$_2$, —S(O)—N(R$^d$)$_2$, —S(O)$_2$—N(R$^d$)$_2$, —O—R$^d$, —S—R$^d$, —O—C(O)—R$^d$, —C(O)—R$^d$, —C(O)— O—R$^d$, —S(O)—R$^d$, —S(O)$_2$—R$^d$, —C(O)—N(R$^d$)$_2$, —N(R$^d$)—C(O)—R$^d$, —N(R$^d$)—S(O)—R$^d$, N(R$^d$)—S(O)$_2$—R$^d$, and C$_{1-6}$alkyl, which carbocyclyl and C$_{1-6}$alkyl are optionally substituted with one or more groups independently selected from oxo, halo, C$_{1-6}$alkyl, cyano, —N(R$^d$)$_2$, —O—R$^d$, heterocyclyl, and carbocyclyl that is optionally substituted with one or more groups independently selected from halo, and C$_{1-6}$alkyl;

each R$^d$ is independently selected from hydrogen, C$_{1-6}$alkyl, C$_{2-6}$alkenyl, C$_{2-6}$alkynyl, C$_{1-6}$alkoxy, carbocyclyl, and heterocyclyl, wherein each C$_{1-6}$alkyl, C$_{2-6}$alkenyl, C$_{2-6}$alkynyl, C$_{1-6}$alkoxy, carbocyclyl, and heterocyclyl is optionally substituted with one or more groups independently selected from oxo, halo, amino, hydroxyl, C$_{1-6}$alkoxy, carbocyclyl, heterocyclyl, and C$_1$-C$_6$ alkyl that is optionally substituted with one or more groups independently selected from oxo and halo; or two R$^d$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^e$ is independently selected from oxo, C$_{1-6}$alkyl, C$_{2-6}$alkenyl, C$_{2-6}$alkynyl, carbocyclyl, heterocyclyl, aryl, heteroaryl, —F, —Cl, —Br, —I, —NO$_2$, —N(R$^f$)$_2$, —CN, —C(O)—N(R$^f$)$_2$, —S(O)—N(R$^f$)$_2$, —S(O)$_2$—N(R$^f$)$_2$, —O—R$^f$, —S—R$^f$, —O—C(O)—R$^f$, —O—C(O)—O—R$^f$, —C(O)—R$^f$, —C(O)—O—R$^f$, —S(O)—R$^f$, —S(O)$_2$—R$^f$, —O—C(O)—N(R$^f$)$_2$, —N(R$^f$)—C(O)—OR$^f$, —N(R$^f$)—C(O)—N(R$^f$)$_2$, —N(R$^f$)—C(O)—R$^f$, —N(R$^f$)—S(O)—R$^f$, —N(R$^f$)—S(O)$_2$—R$^f$, —N(R$^f$)—S(O)—N(R$^f$)$_2$, and —N(R$^f$)—S(O)$_2$—N(R$^f$)$_2$, wherein any C$_{1-6}$alkyl, C$_{2-6}$alkenyl, C$_{2-6}$alkynyl, carbocyclyl, heterocyclyl, aryl, and heteroaryl is optionally substituted with one or more groups independently selected from oxo, halo, —NO$_2$, —N(R$^f$)$_2$, —CN, —C(O)—N(R$^f$)$_2$, —S(O)—N(R$^f$)$_2$, —S(O)$_2$—N(R$^f$)$_2$, —O—R$^f$, —S—R$^f$, —O—C(O)—R$^f$, —C(O)—R$^f$, —C(O)—O—R$^f$, —S(O)—R$^f$, —S(O)$_2$—R$^f$, —C(O)—N(R$^f$)$_2$, —N(R$^f$)—C(O)—R$^f$, —N(R$^f$)—S(O)—R$^f$, —N(R$^f$)—S(O)$_2$—R$^f$, carbocycle, and C$_{1-6}$alkyl that is optionally substituted with one or more groups independently selected from oxo and halo;

each R$^f$ is independently selected from hydrogen, C$_{1-6}$alkyl, C$_{2-6}$alkenyl, C$_{2-6}$alkynyl, carbocyclyl, and heterocyclyl, wherein any C$_{1-6}$alkyl, C$_{2-6}$alkenyl, C$_{2-6}$alkynyl, carbocyclyl, and heterocyclyl is optionally substituted with one or more groups independently selected from oxo, carbocyclyl, heterocyclyl, halo, —NO$_2$, —N(R$^g$)$_2$, —CN, —C(O)—N(R$^g$)$_2$, —S(O)—N(R$^g$)$_2$, —S(O)$_2$—N(R$^g$)$_2$, —O—R$^g$, —S—R$^g$, —O—C(O)—R$^g$, —C(O)—R$^g$, —C(O)— O—R$^g$, —S(O)—R$^g$, —S(O)$_2$—R$^g$, —C(O)—N(R$^g$)$_2$, —N(R$^g$)—C(O)—R$^g$, —N(R$^g$)—S(O)—R$^g$, N(R$^g$)—S(O)$_2$—R$^g$, and C$_{1-6}$alkyl, which carbocyclyl and C$_{1-6}$alkyl are optionally substituted with one or more groups independently selected from oxo, halo, C$_{1-6}$alkyl, cyano, —N(R$^g$)$_2$, —O—R$^g$, heterocyclyl, and carbocyclyl that is optionally substituted with one or more groups independently selected from halo, and C$_{1-6}$alkyl;

each R$^g$ is independently selected from hydrogen, C$_{1-6}$alkyl, C$_{2-6}$alkenyl, C$_{2-6}$alkynyl, C$_{1-6}$alkoxy, carbocyclyl, and heterocyclyl, wherein each C$_{1-6}$alkyl, C$_{2-6}$alkenyl, C$_{2-6}$alkynyl, C$_{1-6}$alkoxy, carbocyclyl, and heterocyclyl is optionally substituted with one or more groups independently selected from oxo, halo, amino, hydroxyl, C$_{1-6}$alkoxy, carbocyclyl, heterocyclyl, and $C_1$-$C_6$ alkyl that is optionally substituted with one or more groups independently selected from oxo and halo; or two $R^g$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo; and each $R^h$ is independently selected from hydrogen, $C_{1-4}$alkyl, $C_{2-4}$alkenyl, $C_{2-4}$alkynyl, and $C_{2-5}$cycloalkyl, wherein each $C_{1-4}$alkyl, $C_{2-4}$alkenyl, $C_{2-4}$alkynyl, and $C_{2-5}$cycloalkyl is optionally substituted with one or more groups independently selected from oxo, halo, amino, hydroxyl, $C_{1-3}$alkoxy, and $C_1$-$C_3$ alkyl that is optionally substituted with one or more groups independently selected from halo.

3. The compound of claim 2 wherein $R^1$ is:

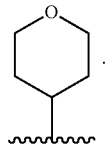

4. The compound of claim 2 wherein $R^2$ is phenyl optionally substituted with one or more substituent groups independently selected from $R^e$, and $R^3$ is methyl or phenyl, wherein each methyl and phenyl of $R^3$ is optionally substituted with one or more groups $R^e$.

5. The compound of claim 2 wherein $R^2$ and $R^3$ taken together with the nitrogen to which they are attached form a 9- or 10-membered bicyclic heterocycle that is optionally substituted with one or more groups $R^e$.

6. The compound of claim 2 wherein $R^2$ and $R^3$ taken together with the nitrogen to which they are attached form a 9- or 10-membered bicyclic heterocycle that is optionally substituted with one or more groups $R^e$; and wherein the 9- or 10-membered bicyclic heterocycle comprises at least one aromatic ring.

7. The compound of claim 2 wherein —NR²R³ taken together is selected from the group consisting of:

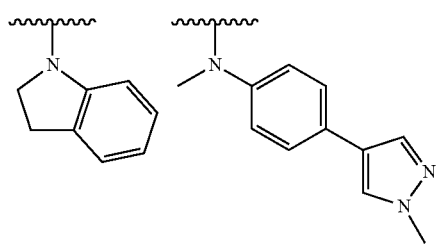

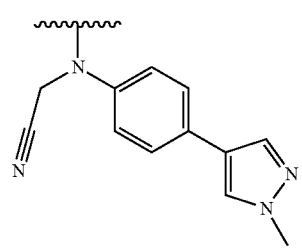

-continued

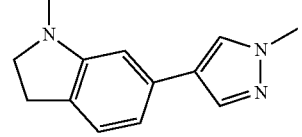

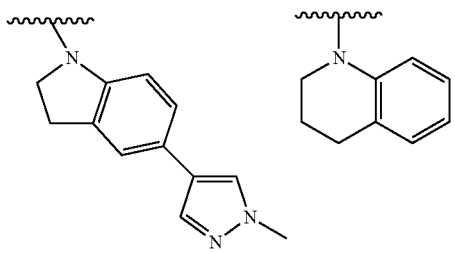

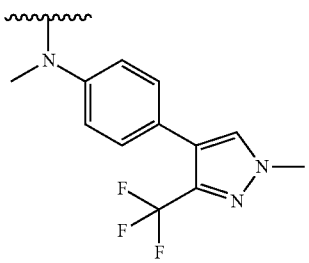

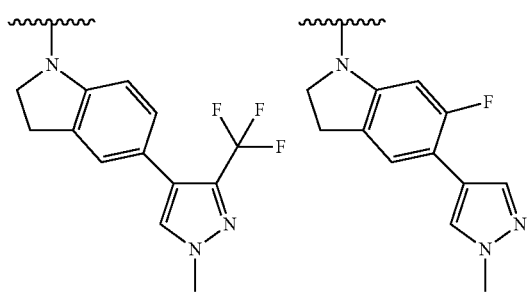

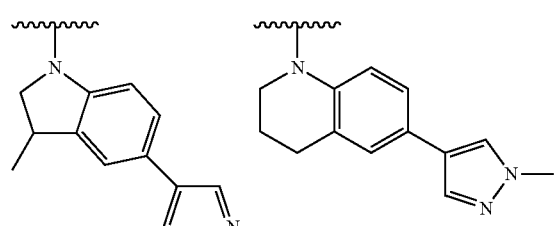

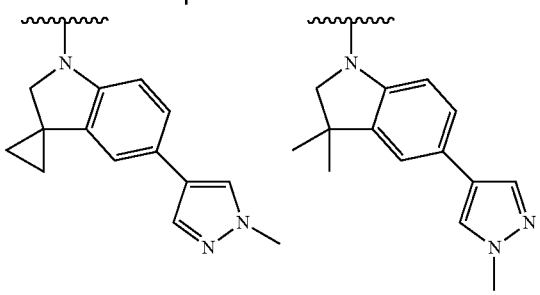

969
-continued
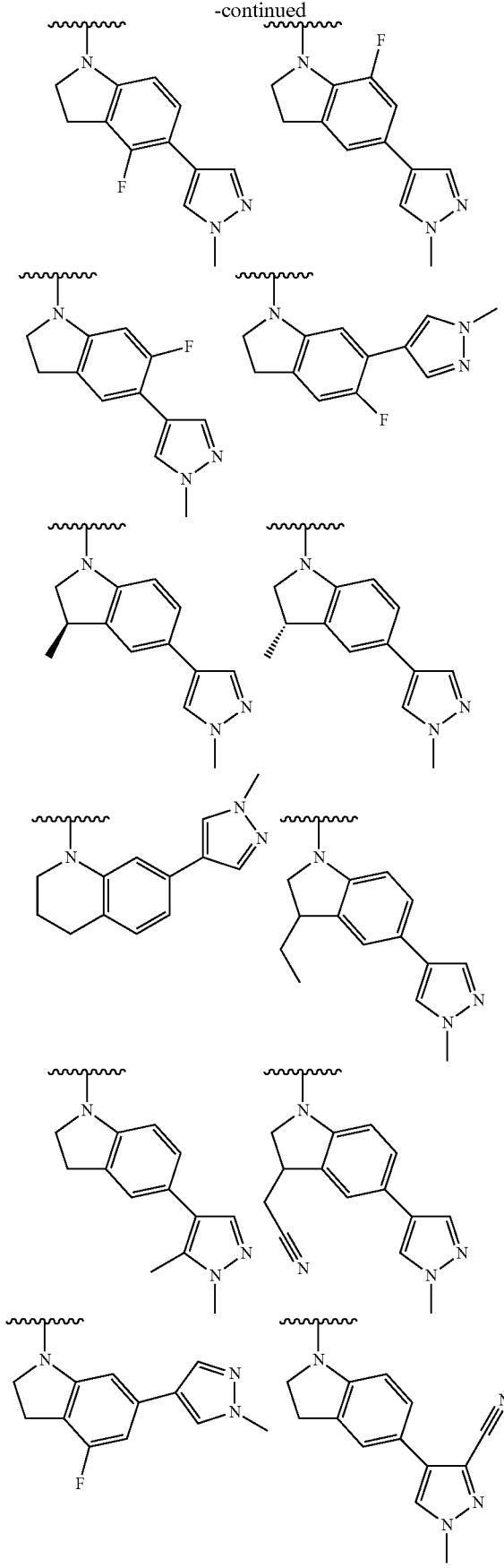
970
-continued
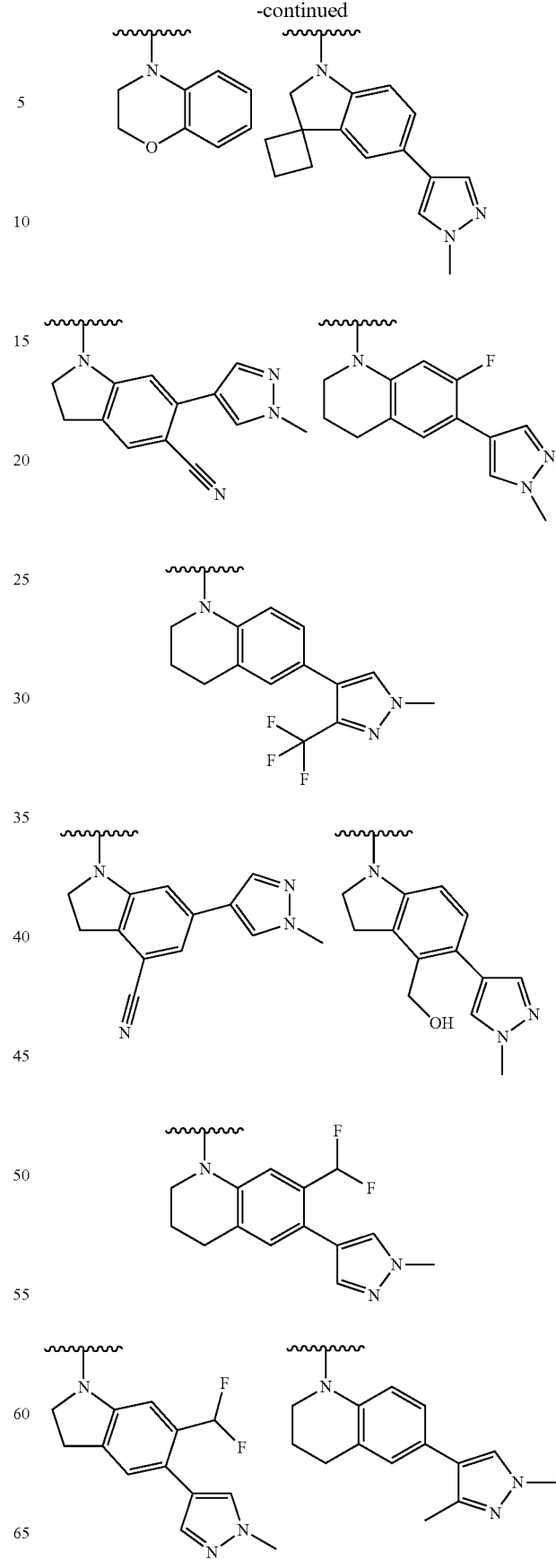

971
-continued
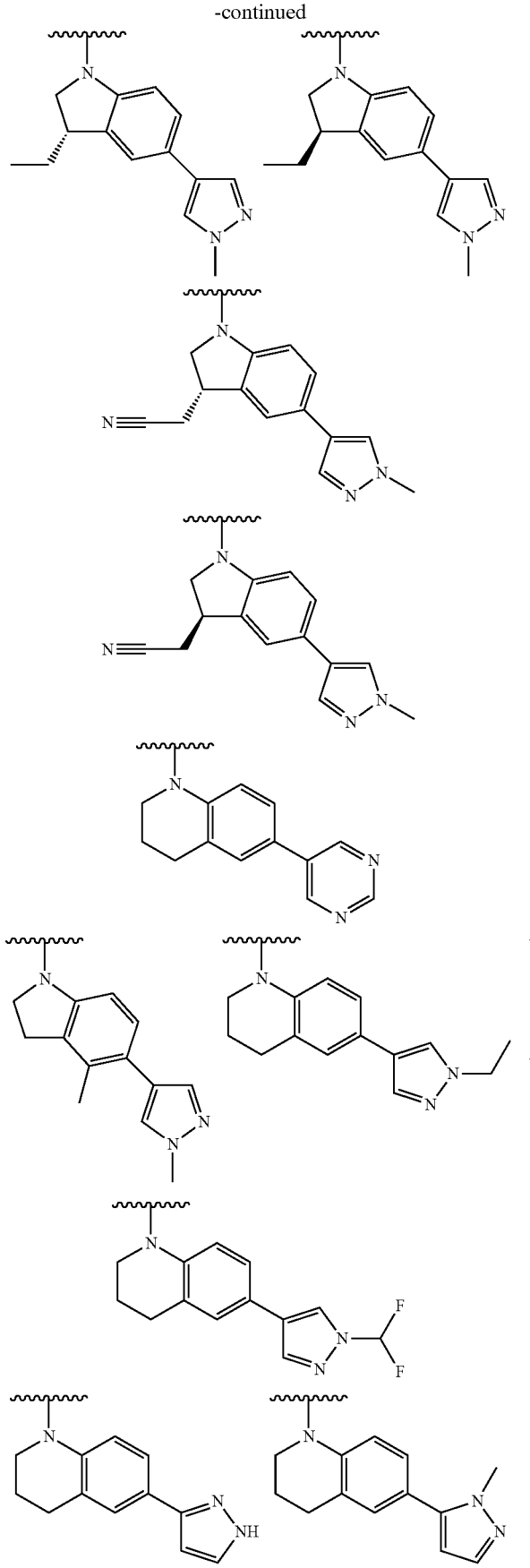
972
-continued
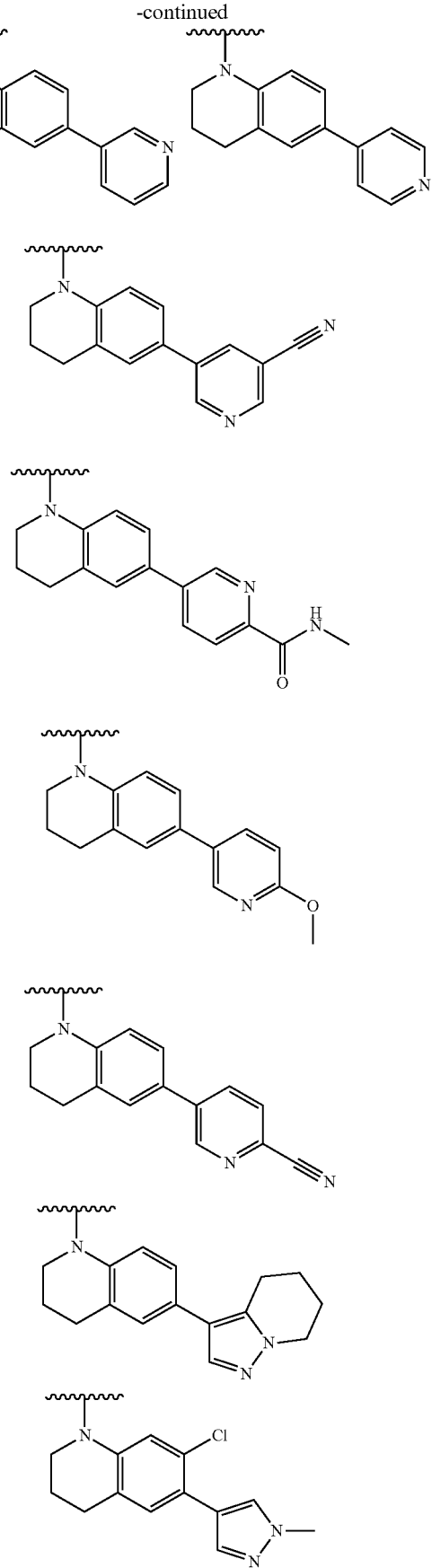

973
-continued
974
-continued
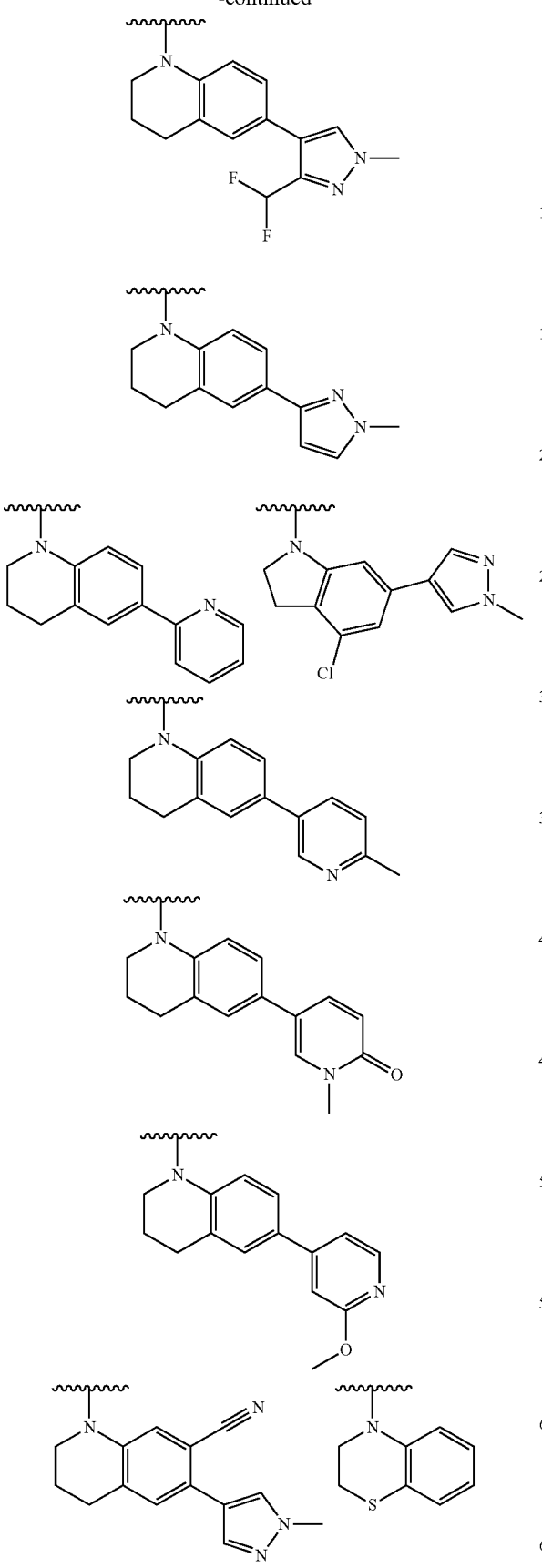
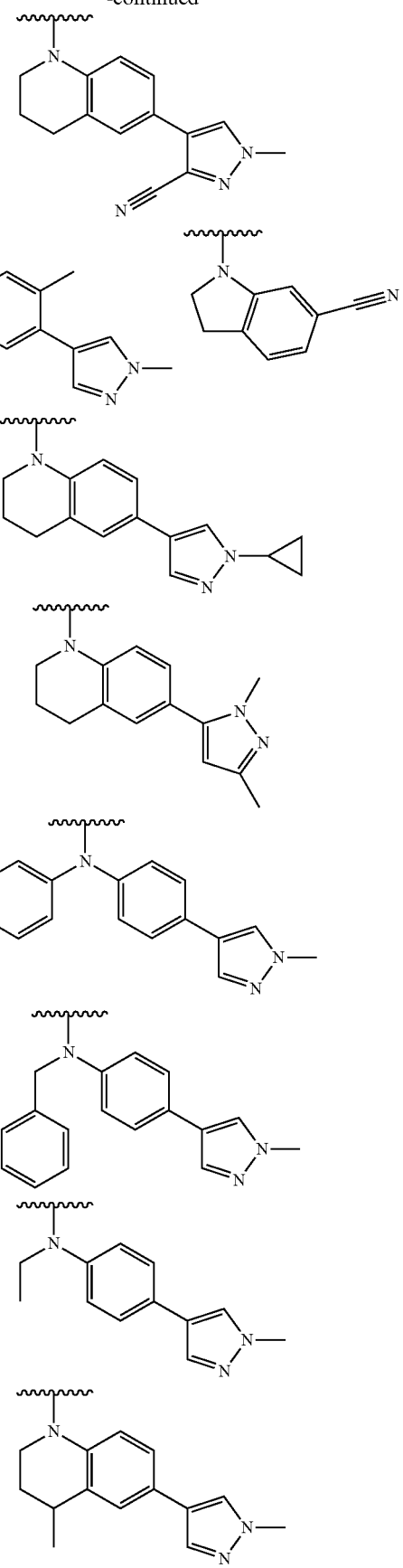

975
-continued
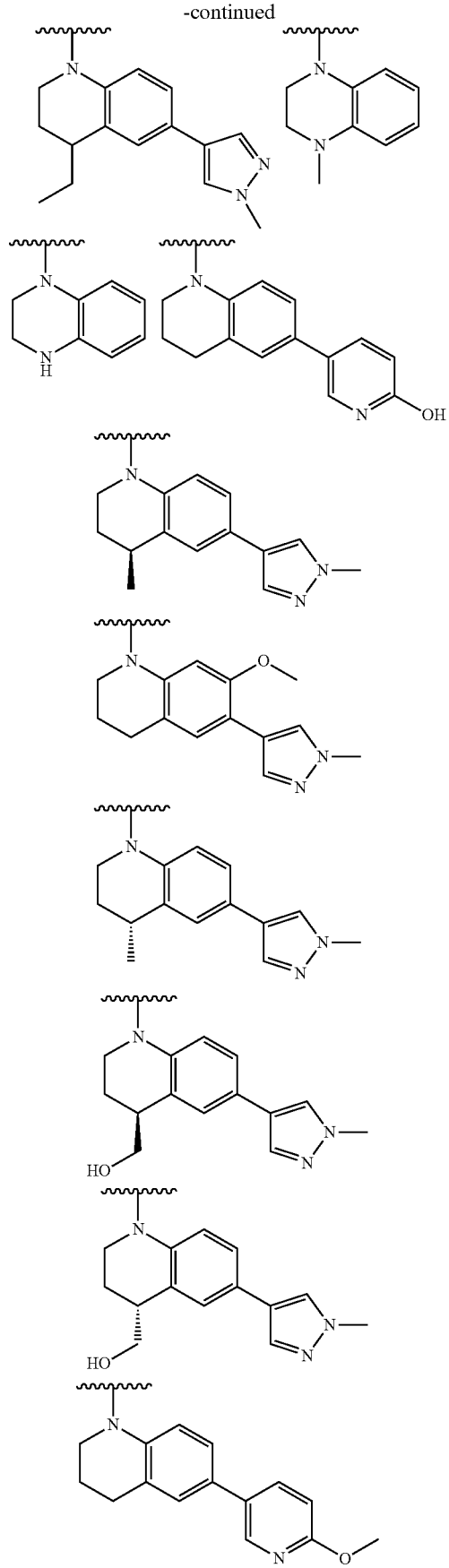
976
-continued
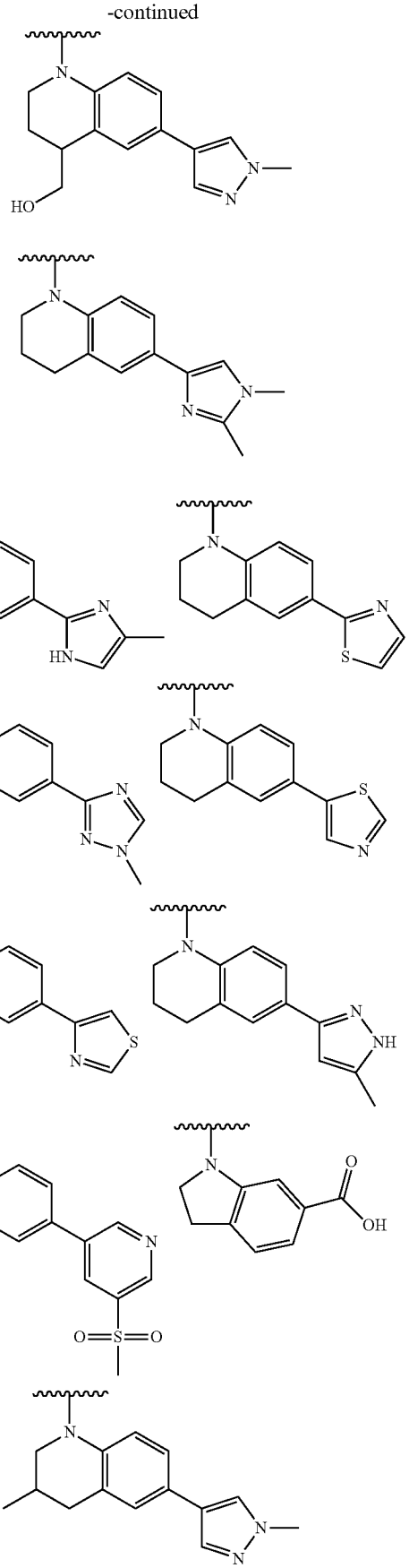

977
-continued
978
-continued
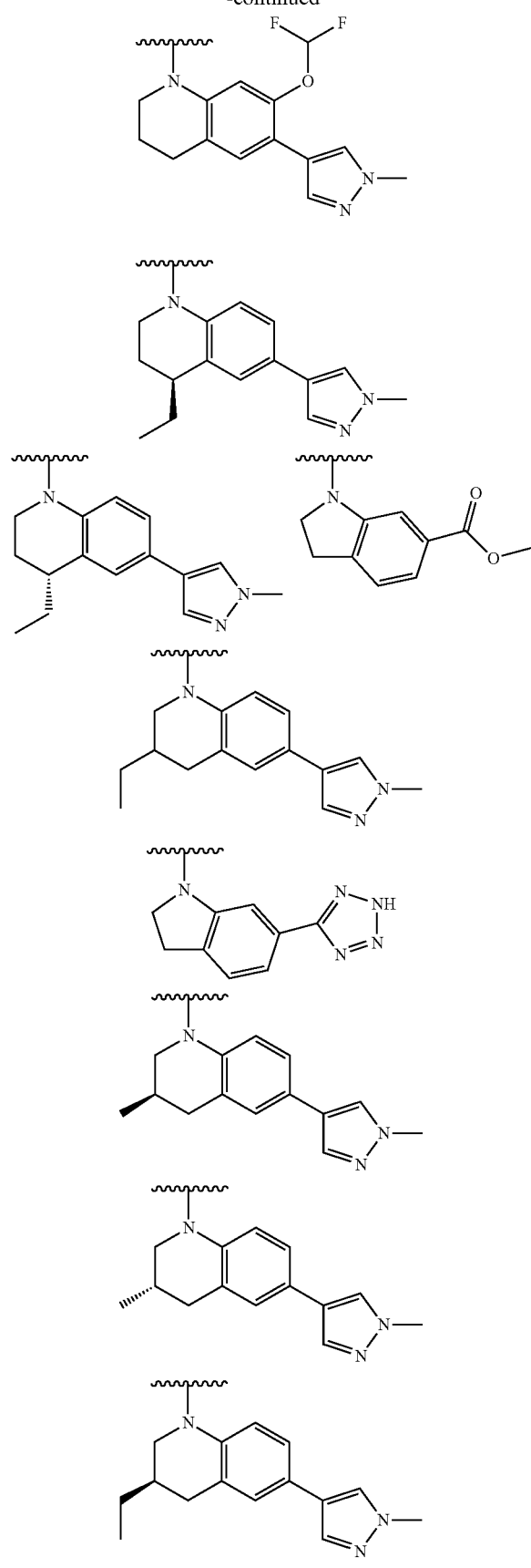
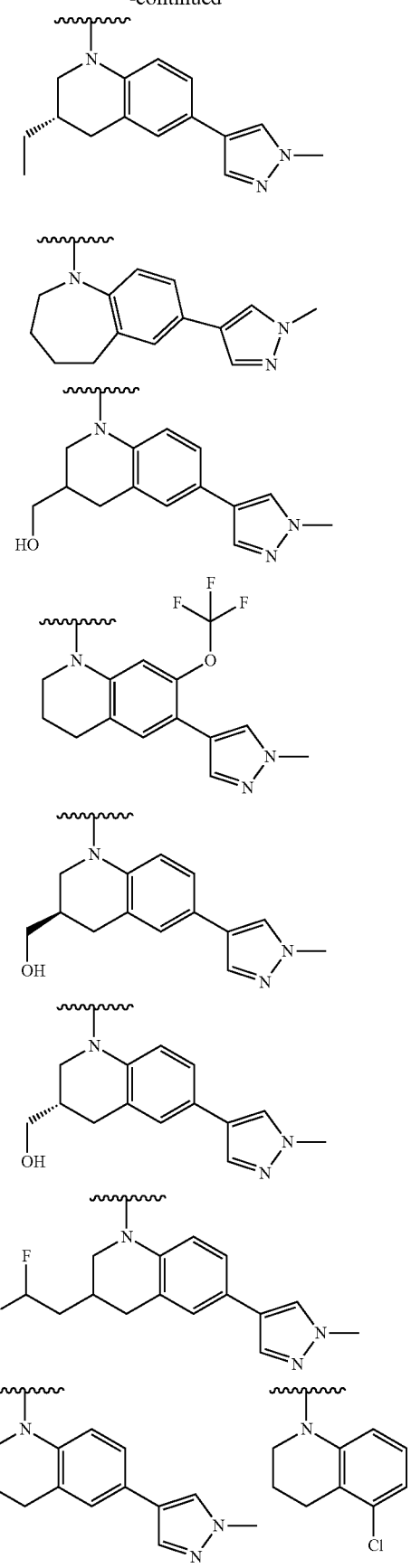

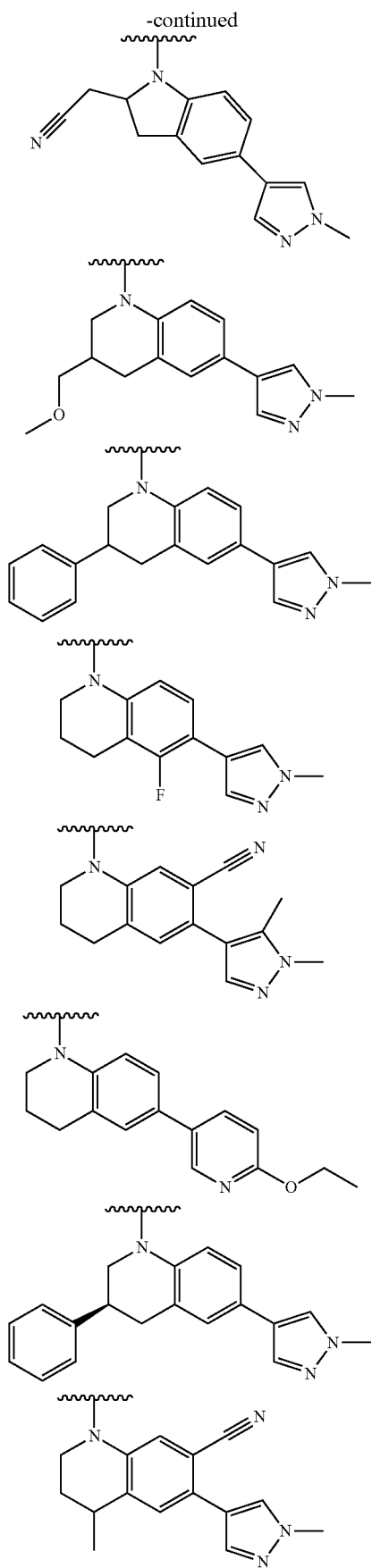
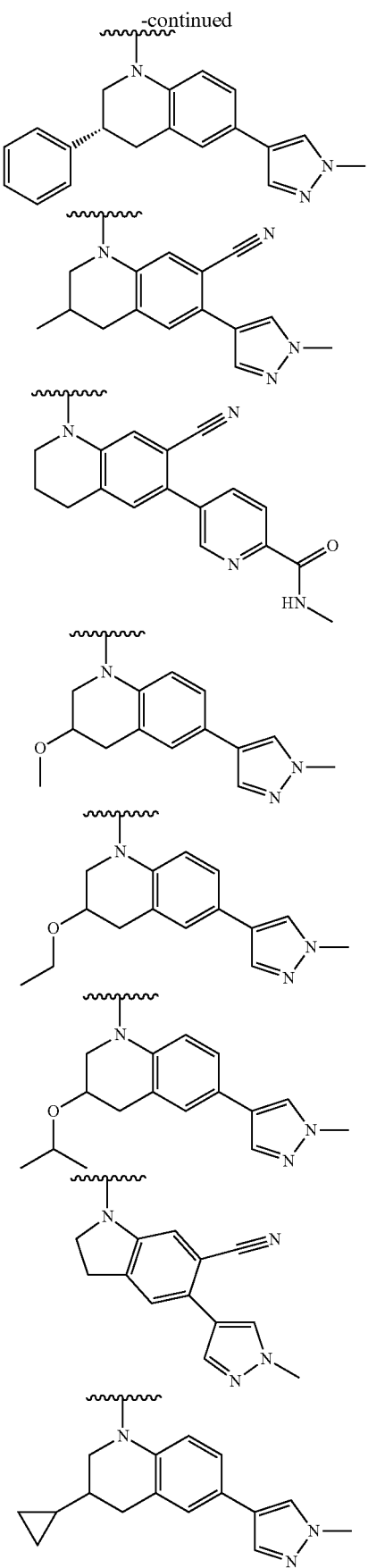

981
-continued
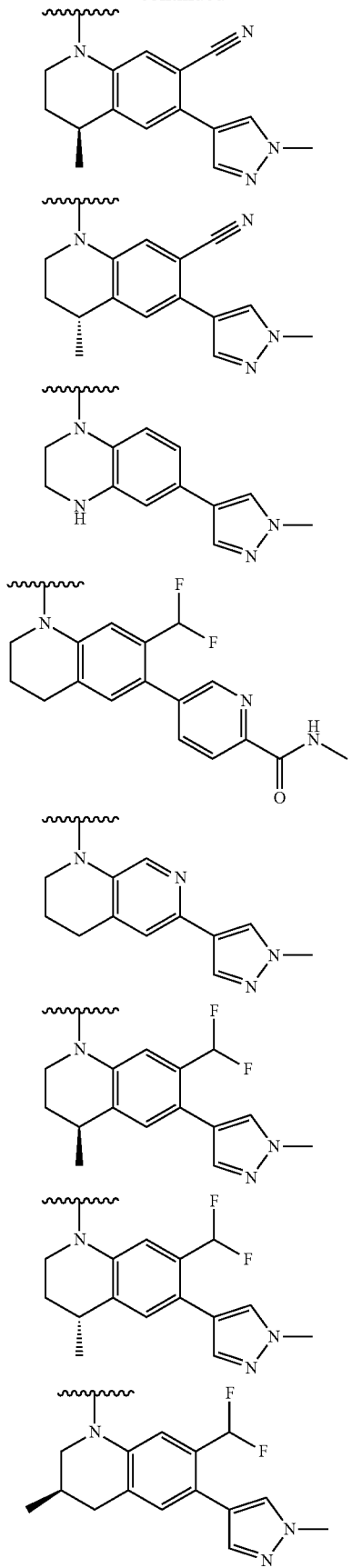
982
-continued
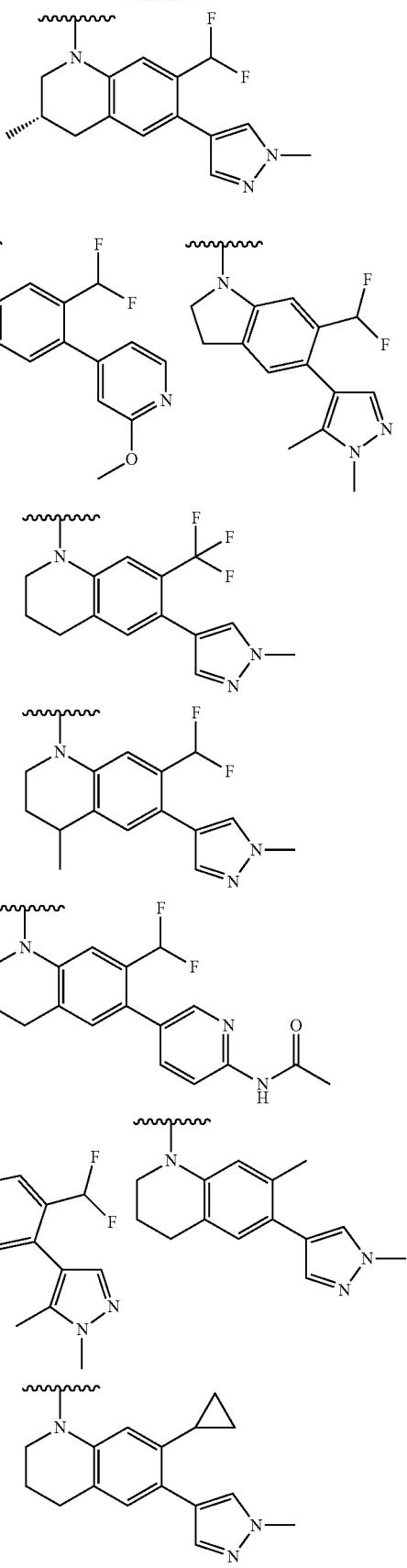

983
-continued
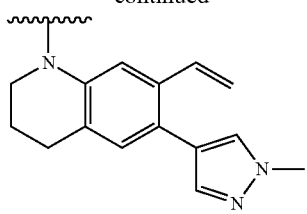
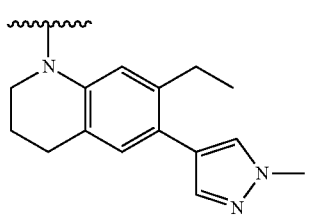
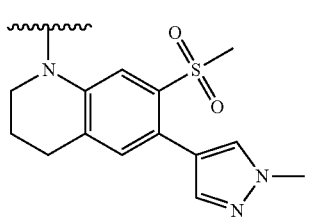
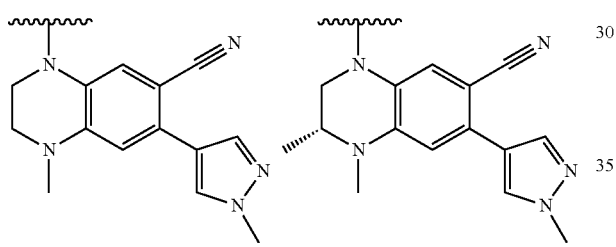
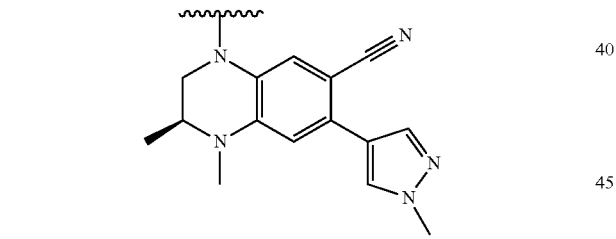
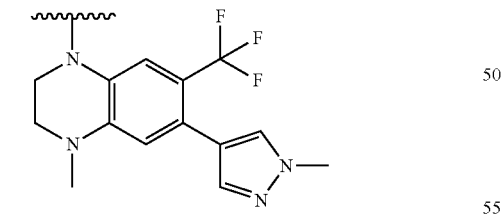
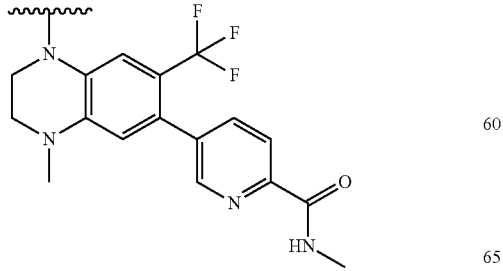
984
-continued
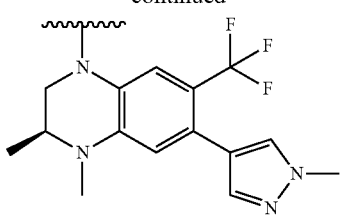
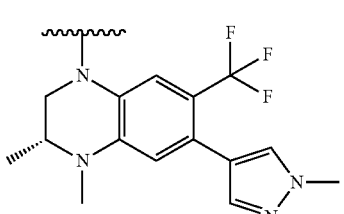
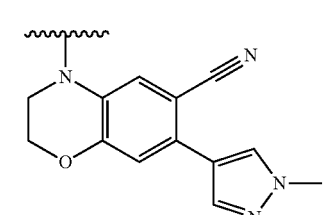
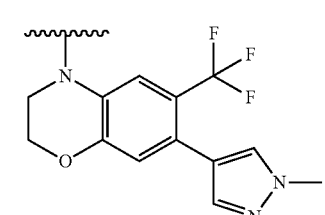
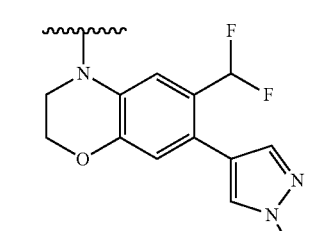
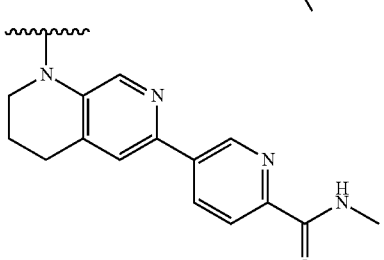
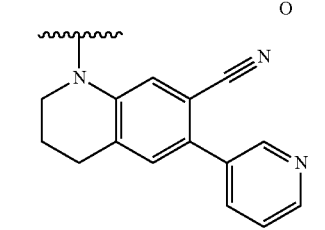

985
-continued
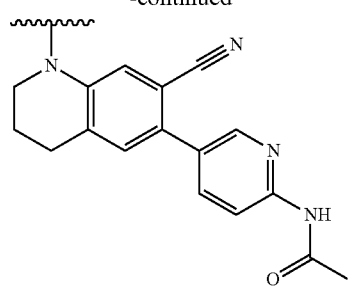
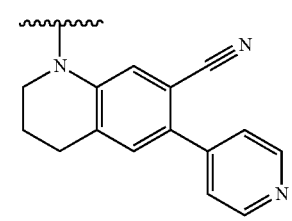
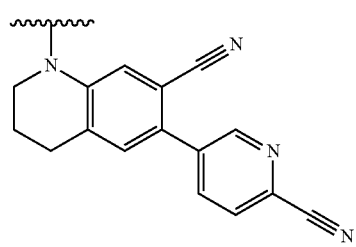
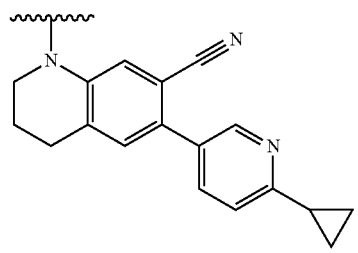
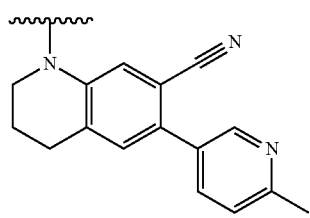
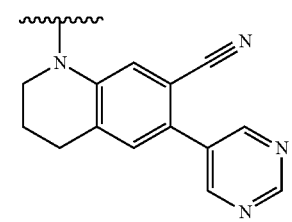
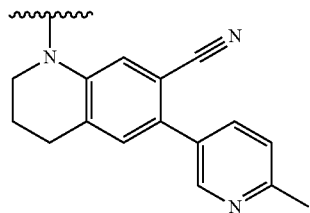
986
-continued
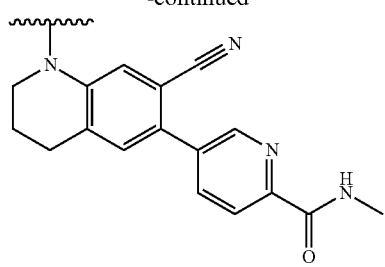
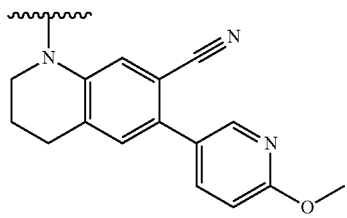
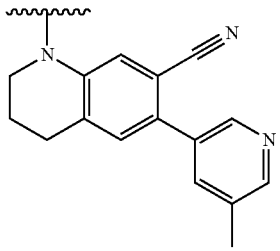
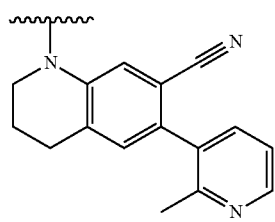
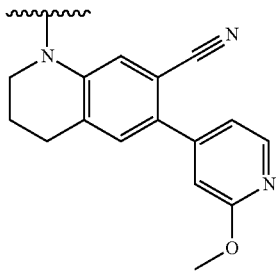
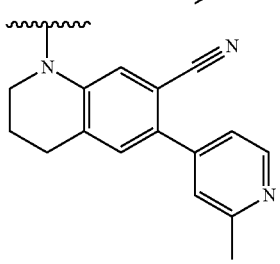
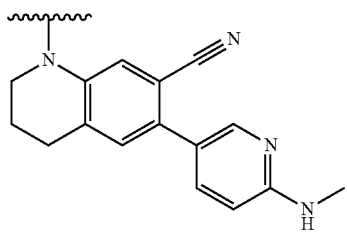

987
-continued
988
-continued
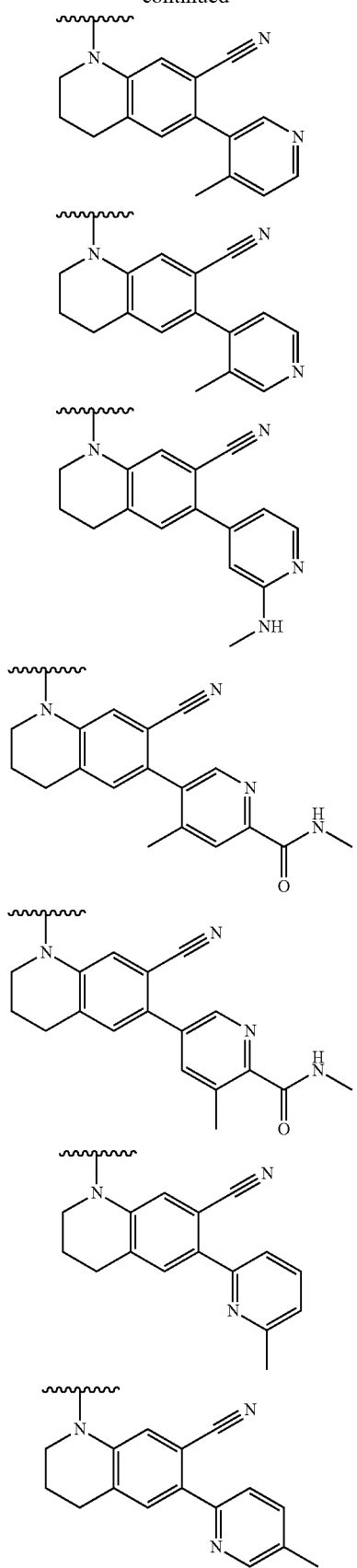
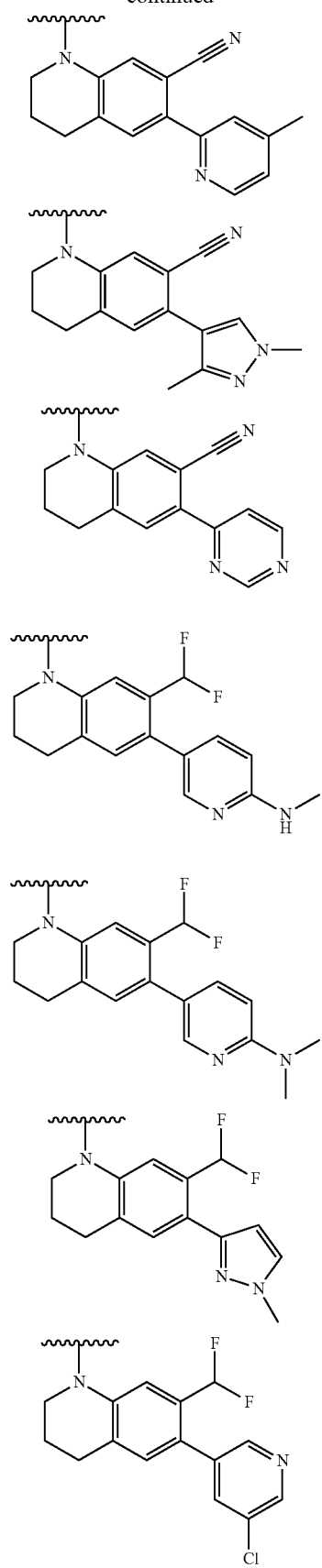

989
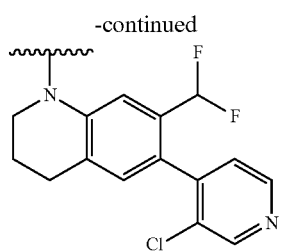
990
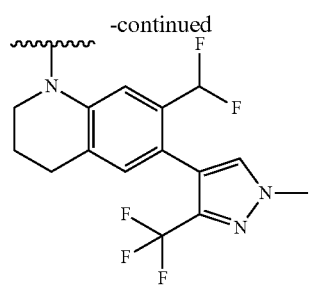
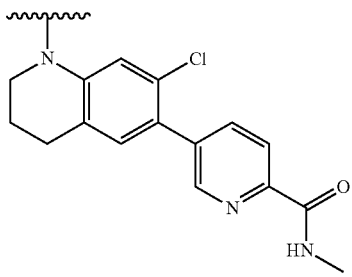
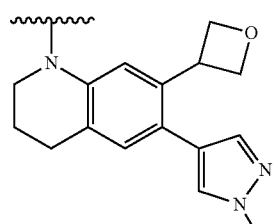
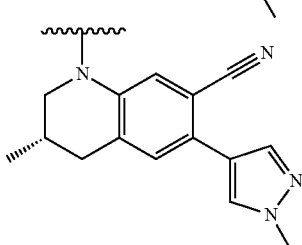
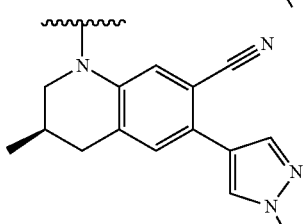
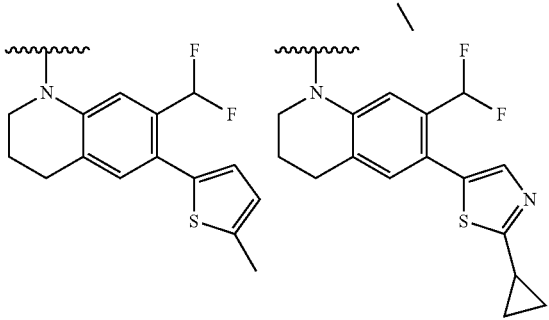
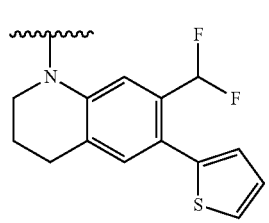

-continued

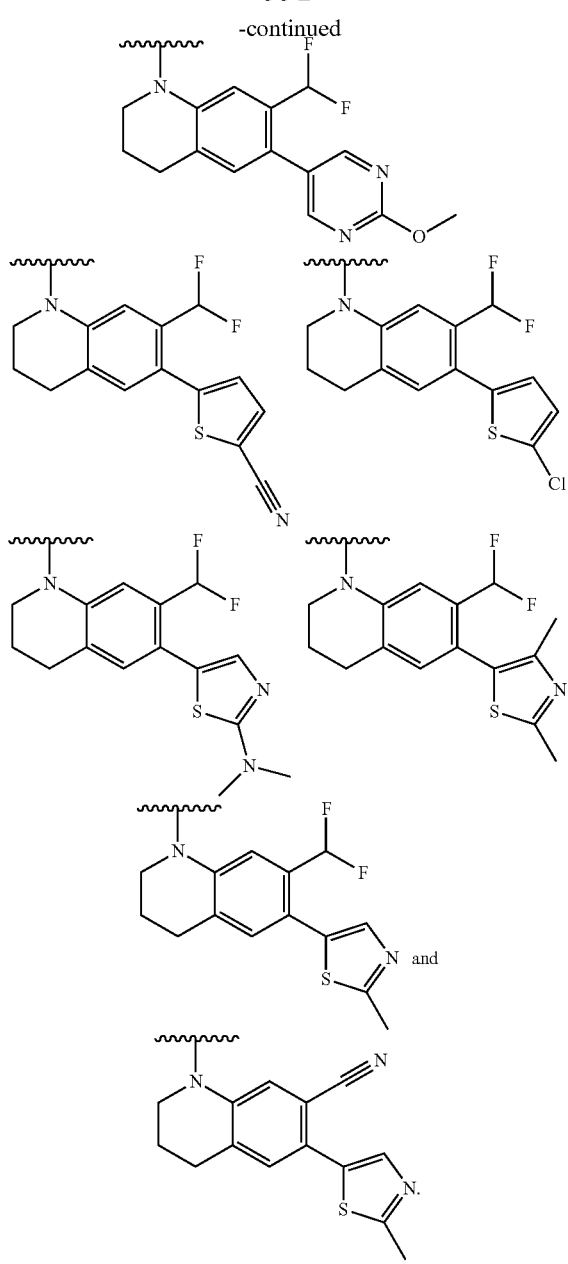

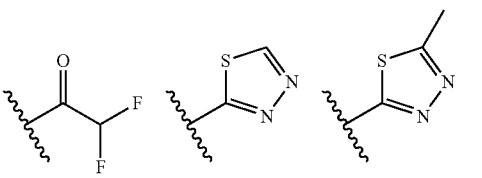

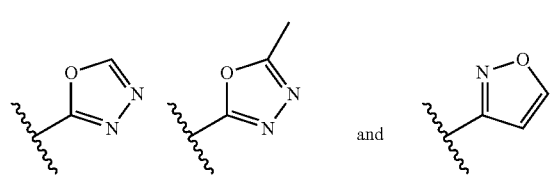

9. The compound of claim 2 wherein:

R[1] is methyl, oxetanyl, tetrahydrofuranyl, tetrahydropyranyl, dioxothiolanyl, piperidyl, or pyrrolidinyl, wherein each methyl, oxetanyl, tetrahydrofuranyl, tetrahydropyranyl, dioxothiolanyl, piperidyl, or pyrrolidinyl of R[1] is optionally substituted with one or more groups R[b];

—NR[2]R[3] taken together is selected from the group consisting of:

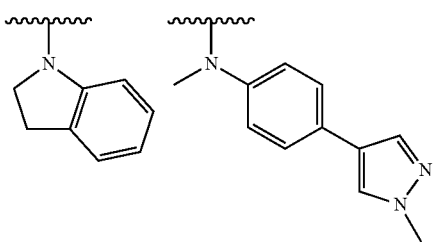

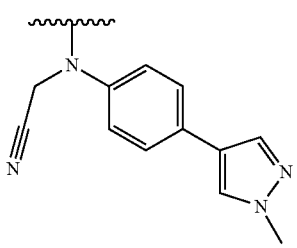

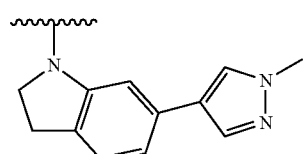

8. The compound of claim 2 wherein R[4] is selected from the group consisting of:

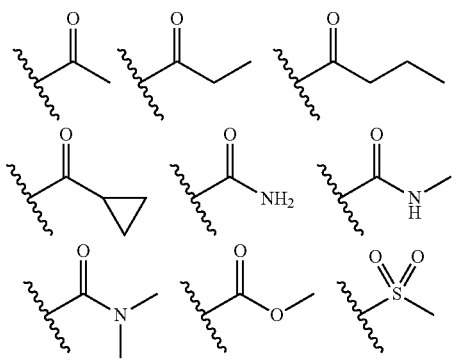

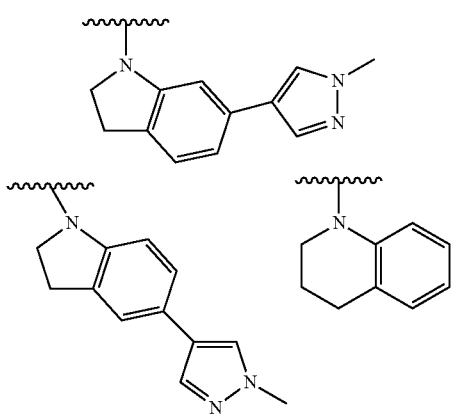

993
-continued
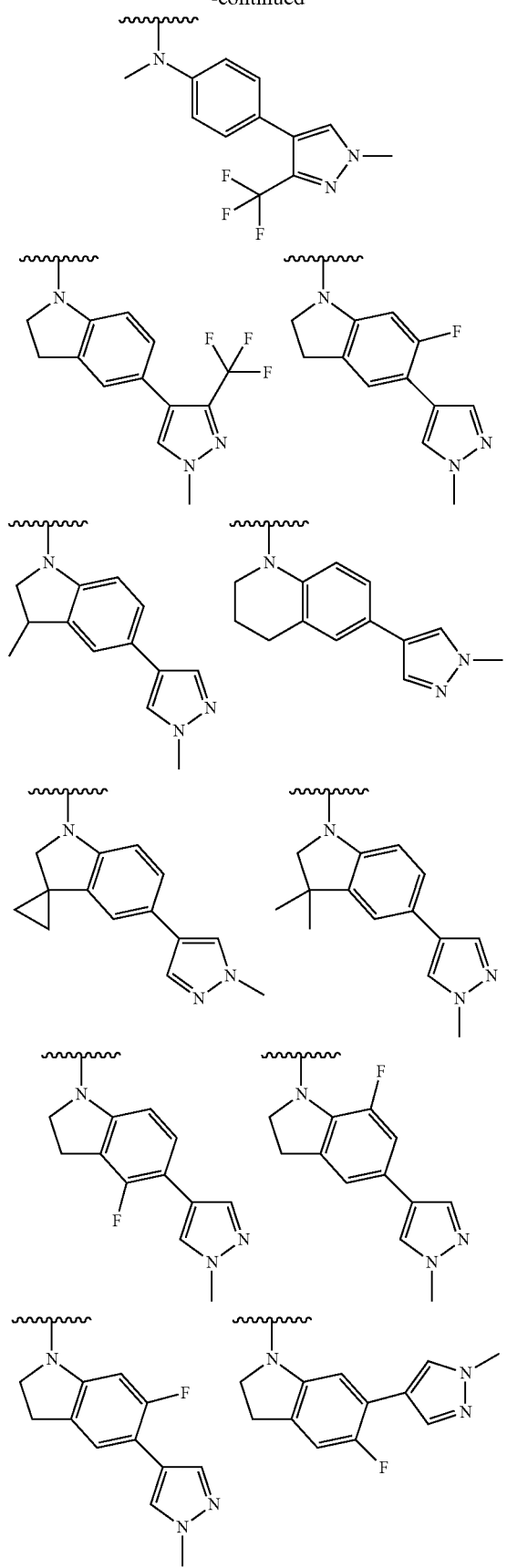
994
-continued
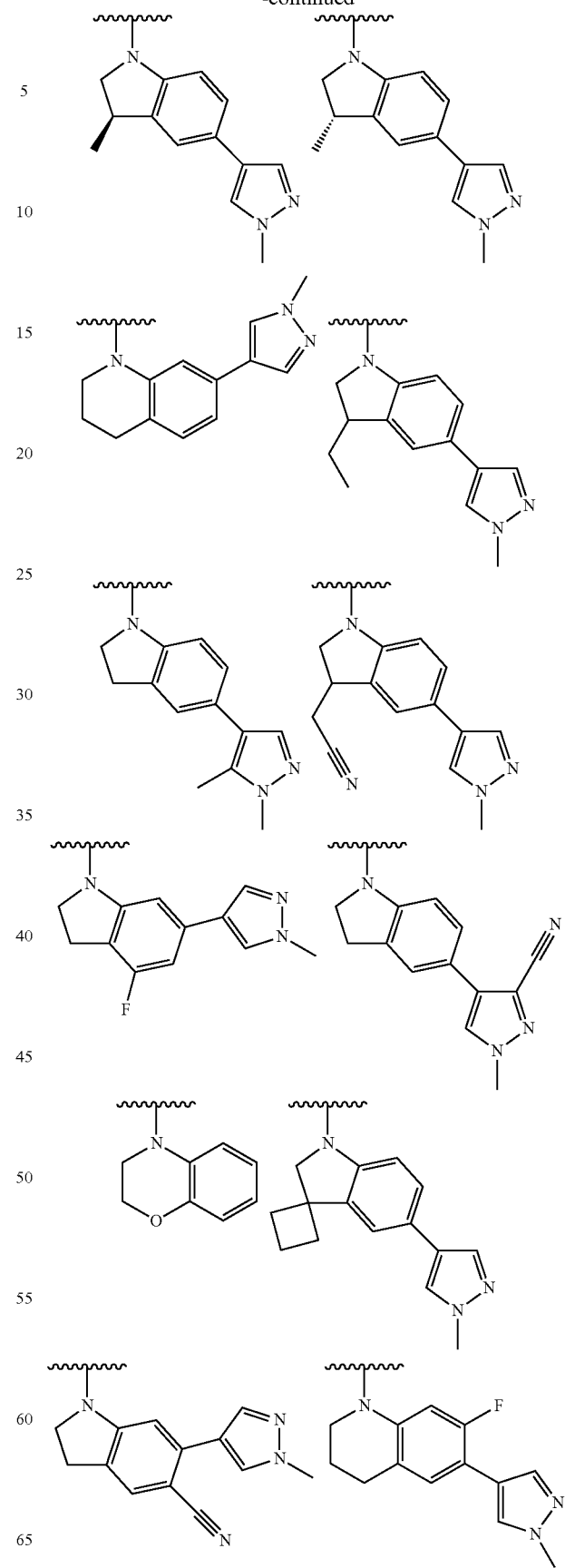

995
-continued
996
-continued
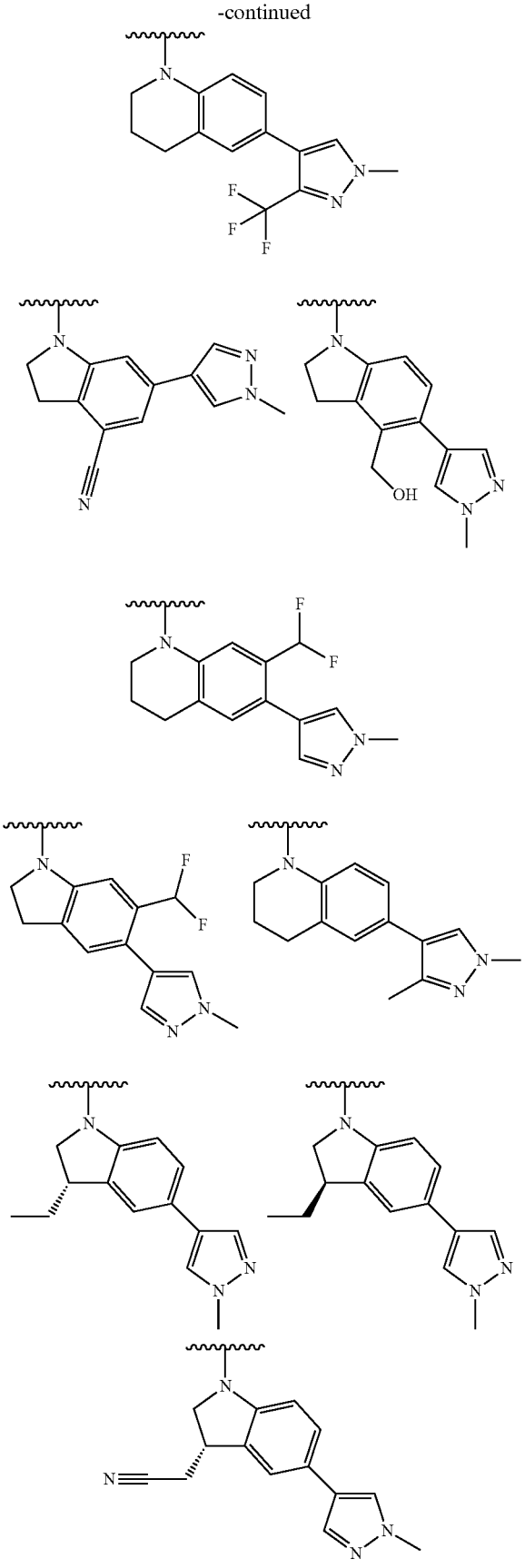
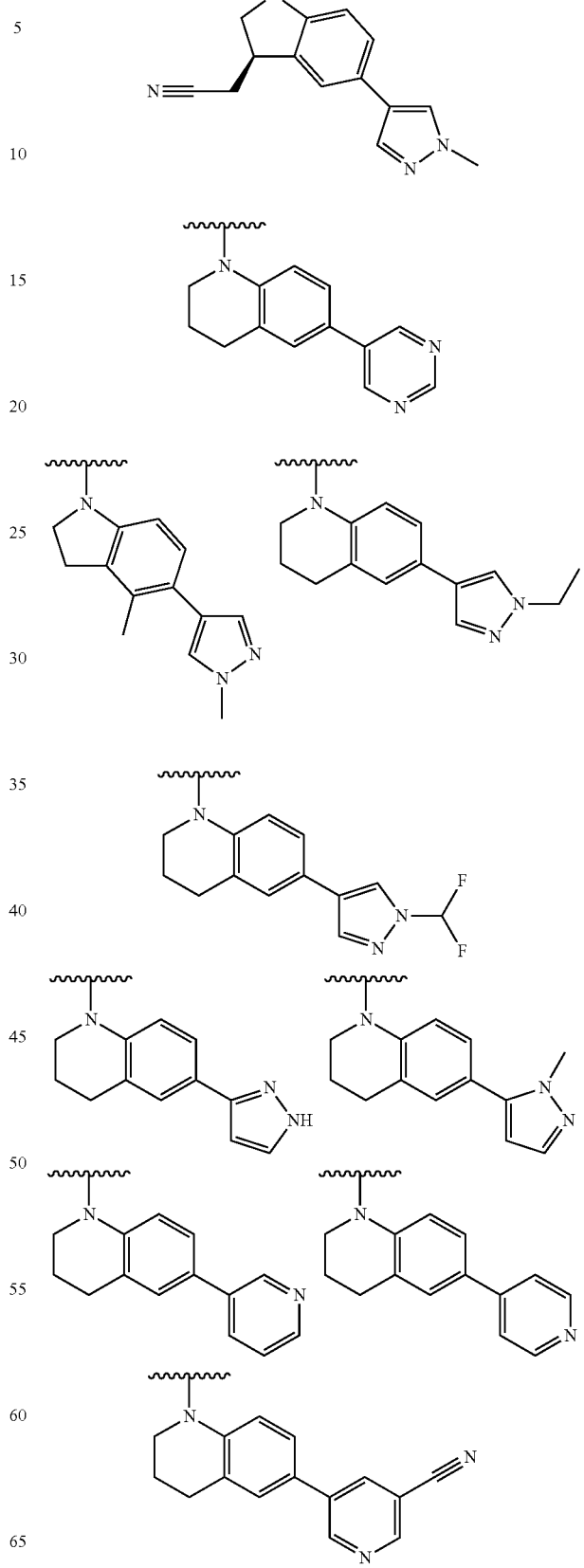

997
-continued
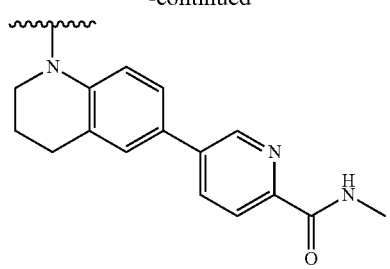
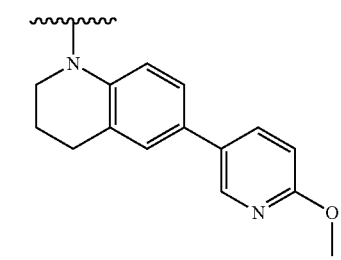
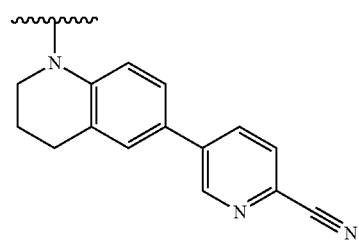
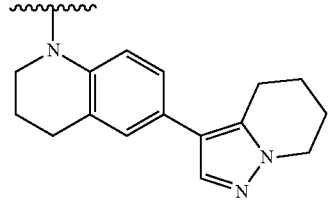
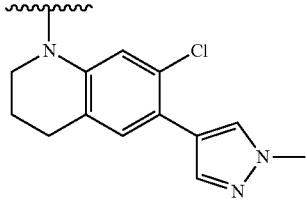
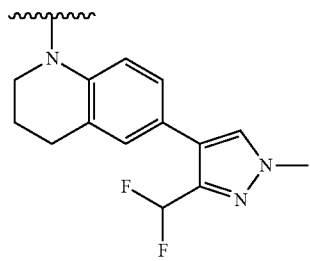
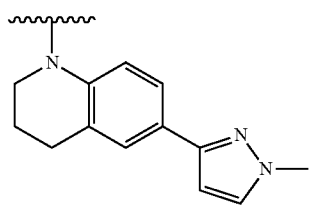
998
-continued
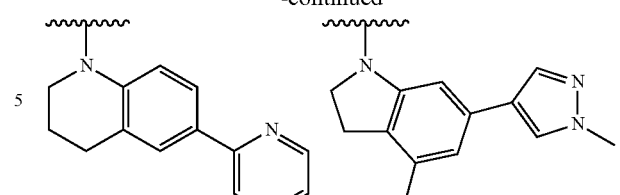
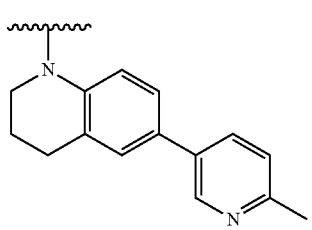
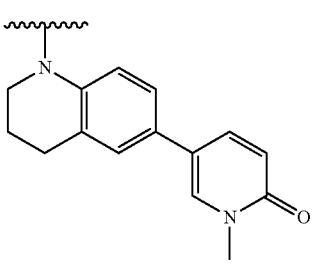
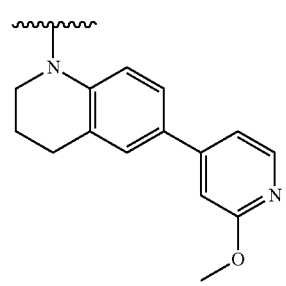
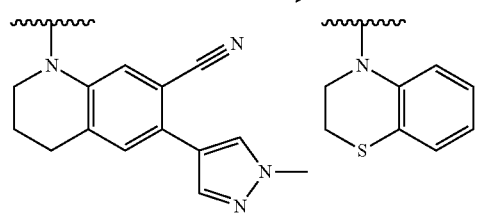
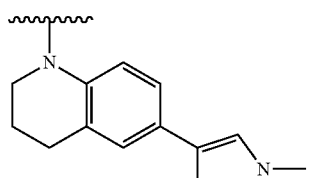
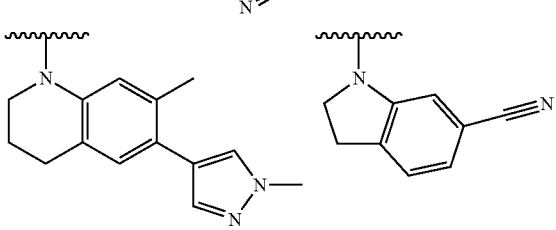

| 999 | 1000 |
|---|---|
| -continued | -continued |
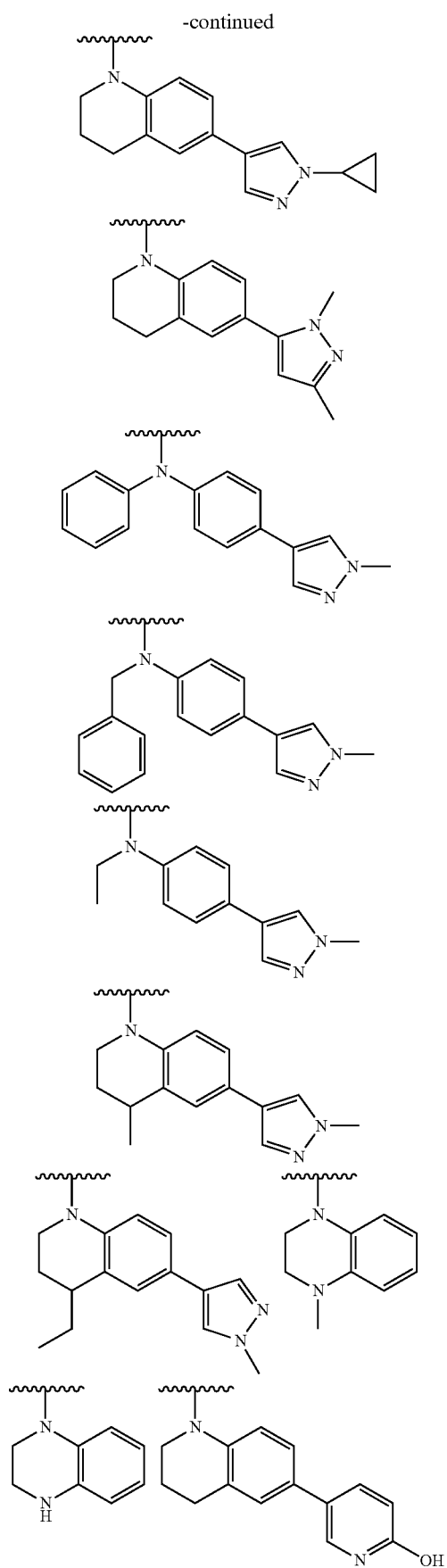
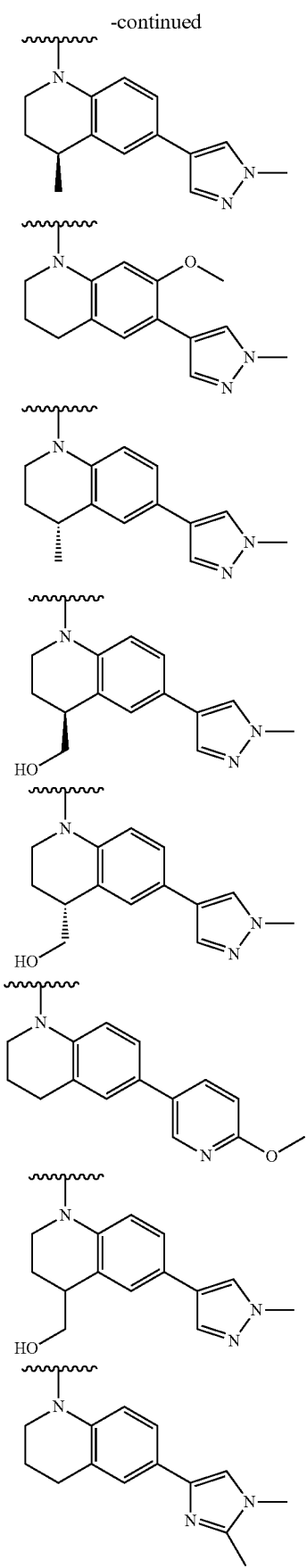

1001
-continued
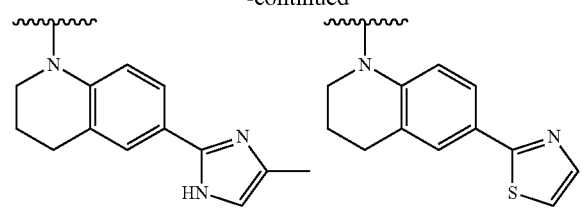
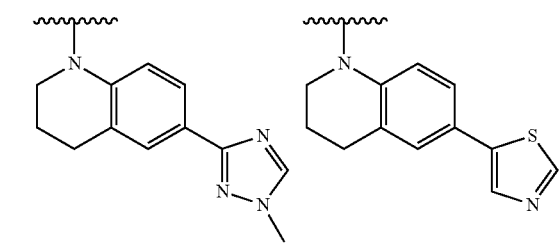
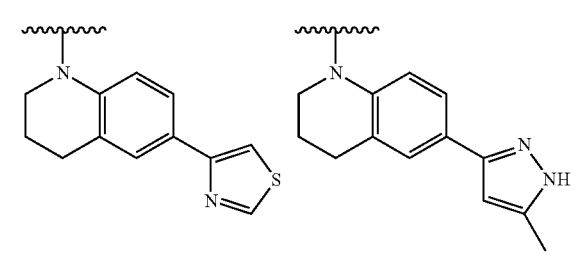
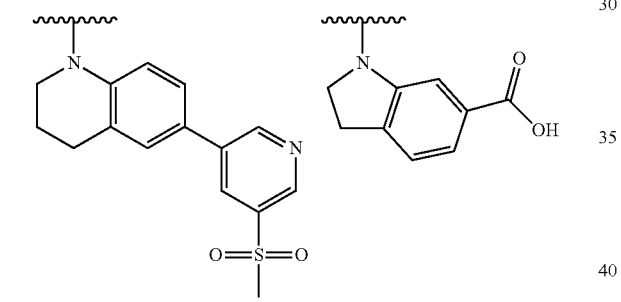
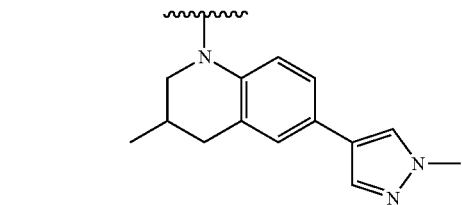
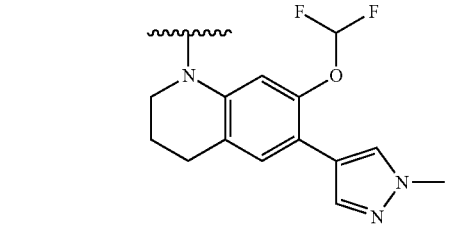
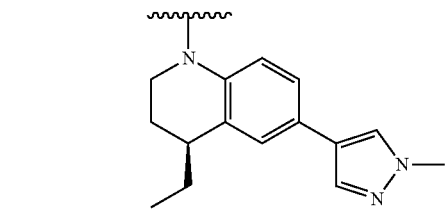
1002
-continued
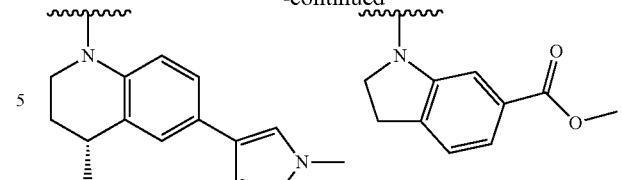
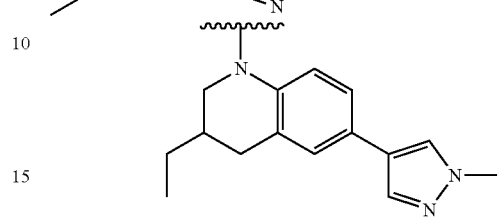
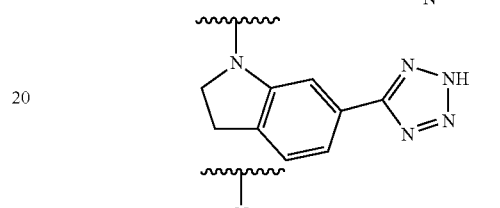
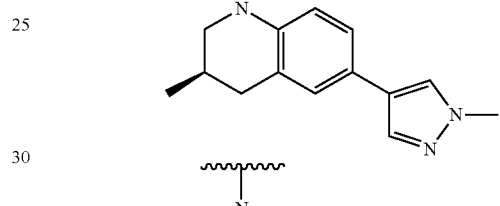
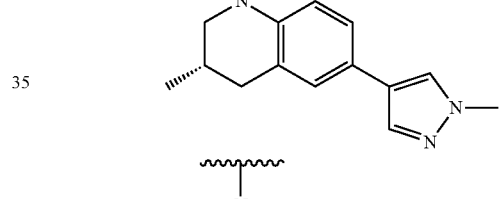
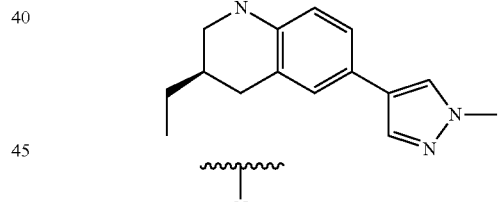
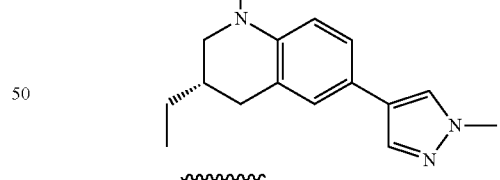
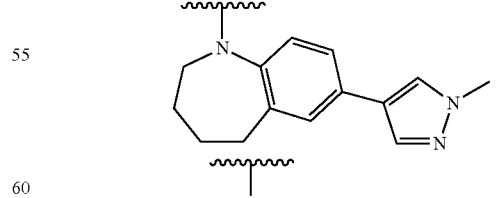
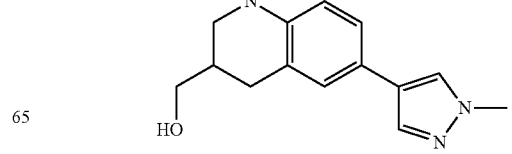

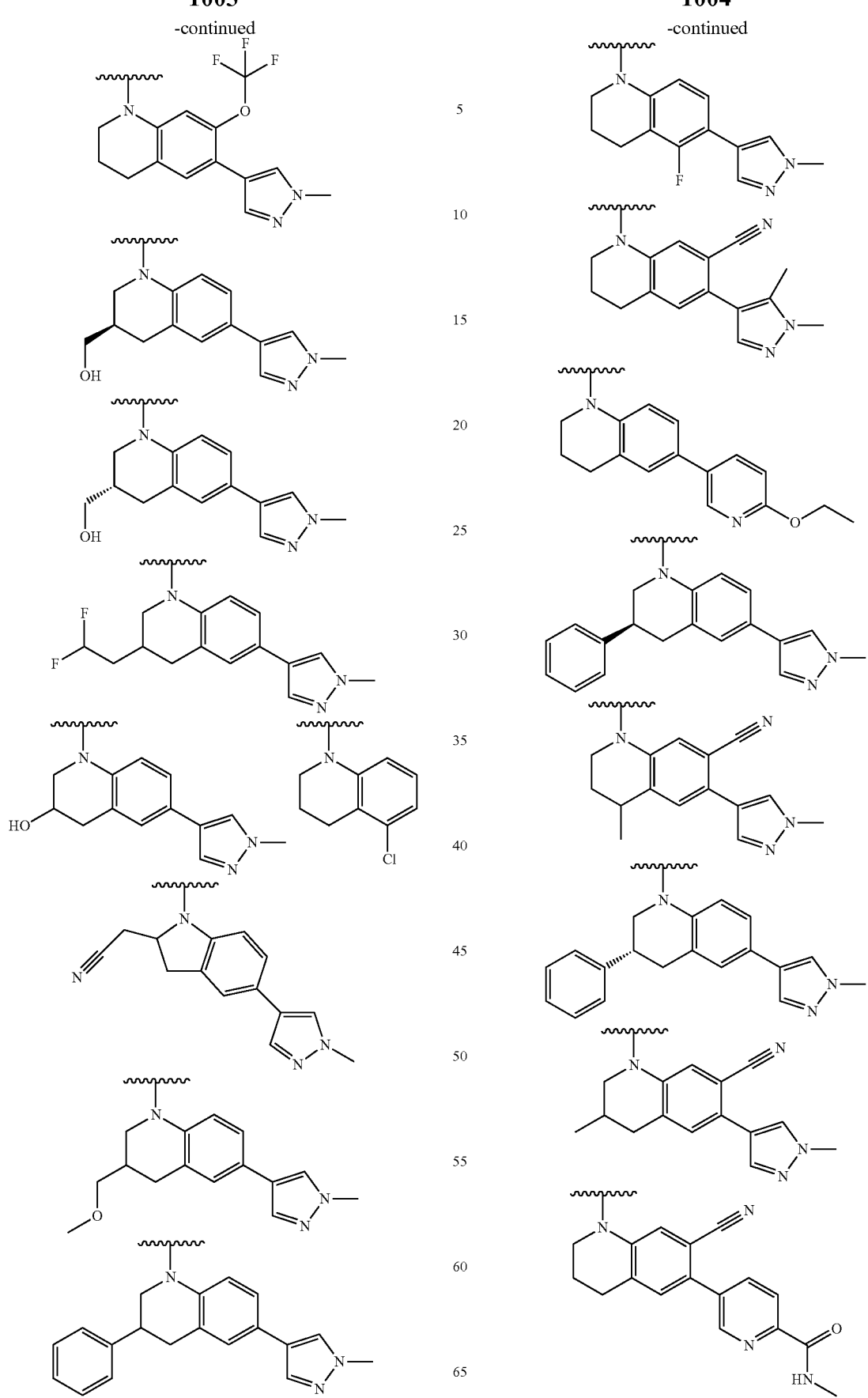

1005
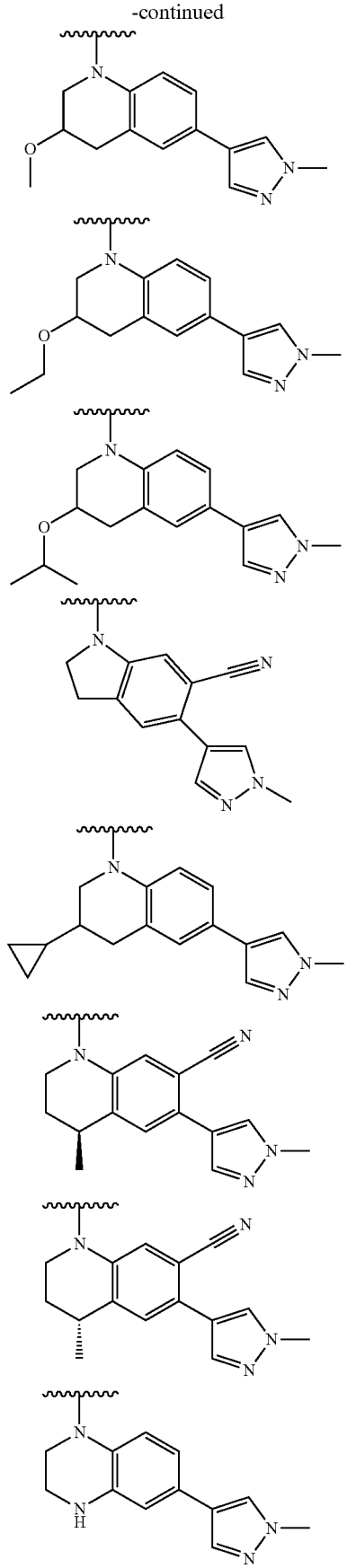
1006
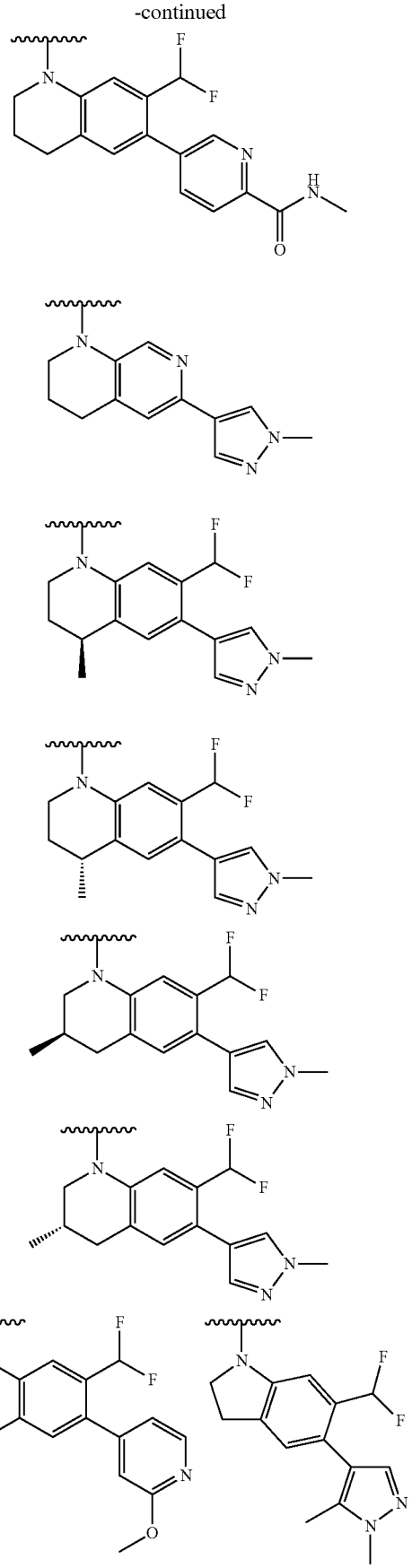

1007
-continued
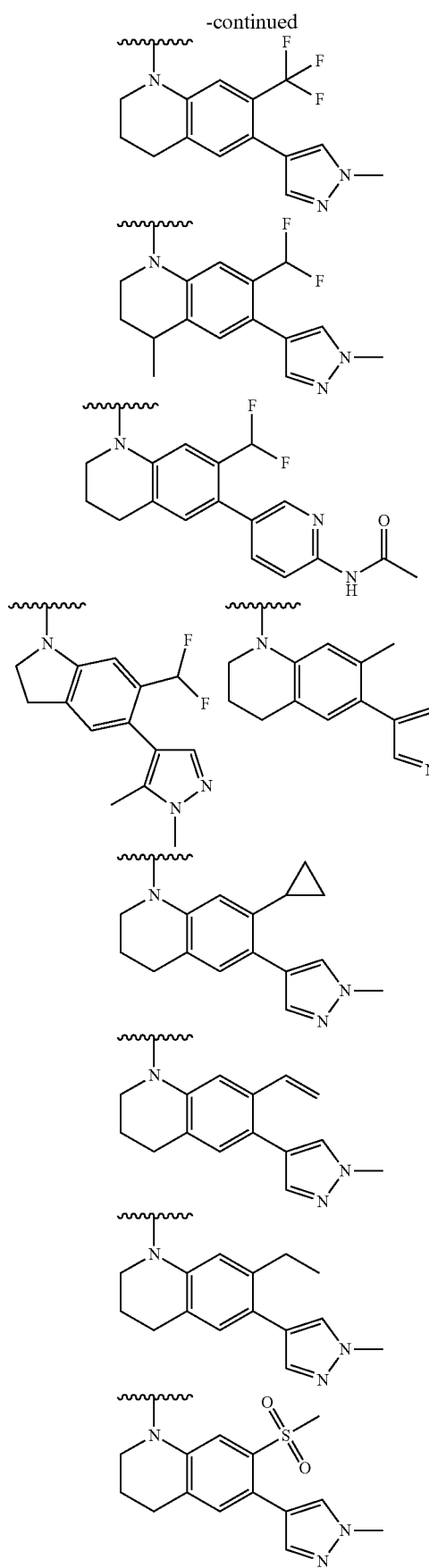
1008
-continued
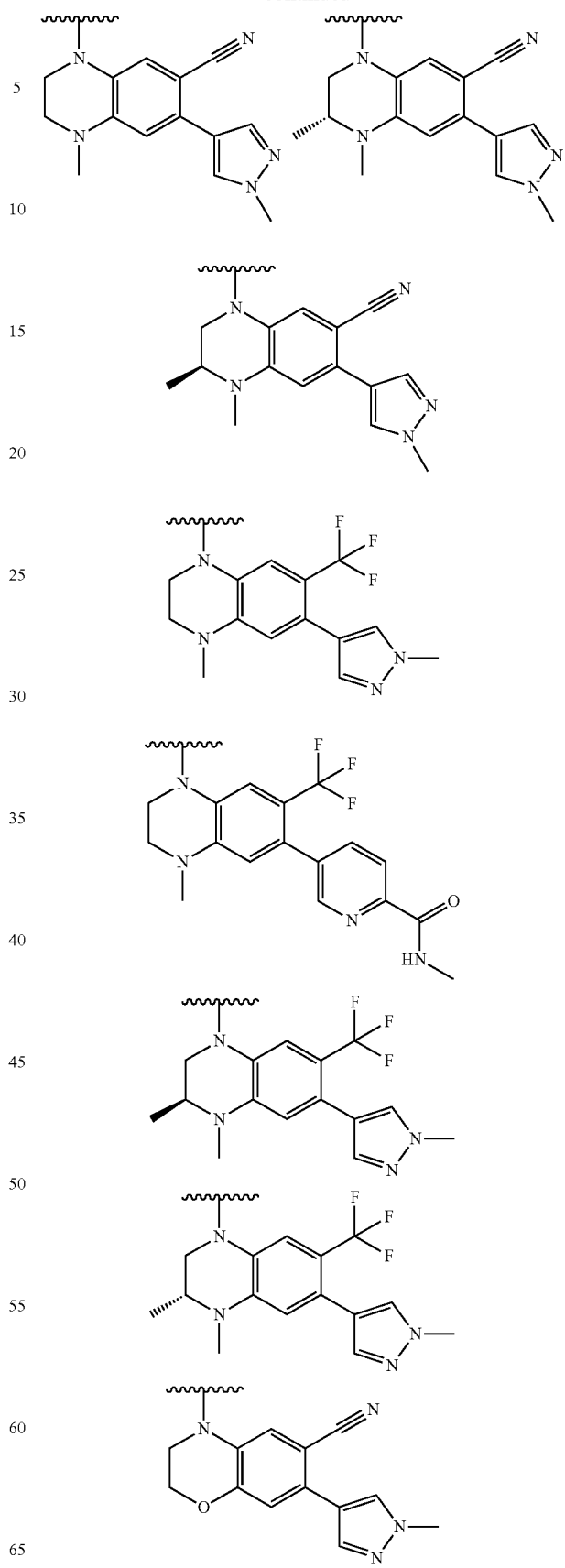

1009
-continued
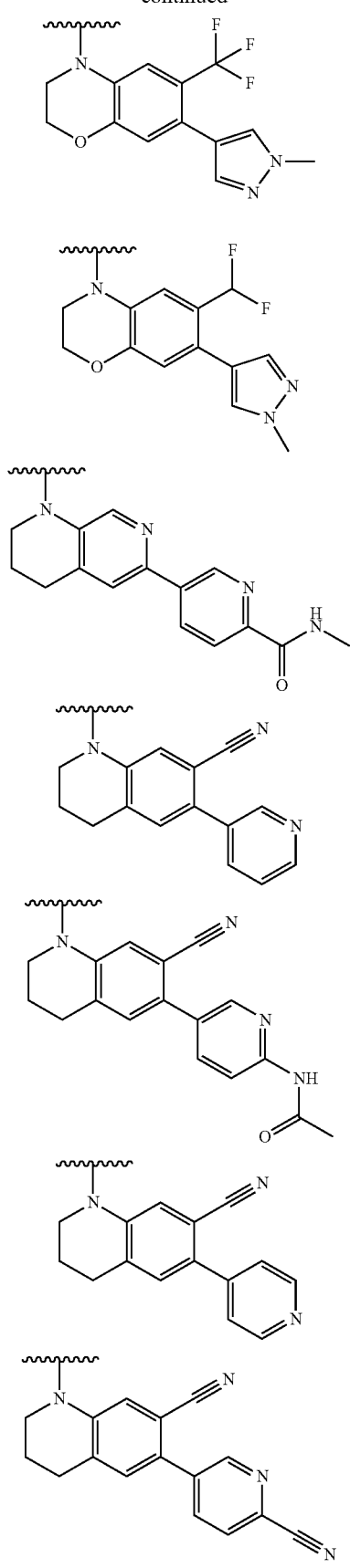
1010
-continued
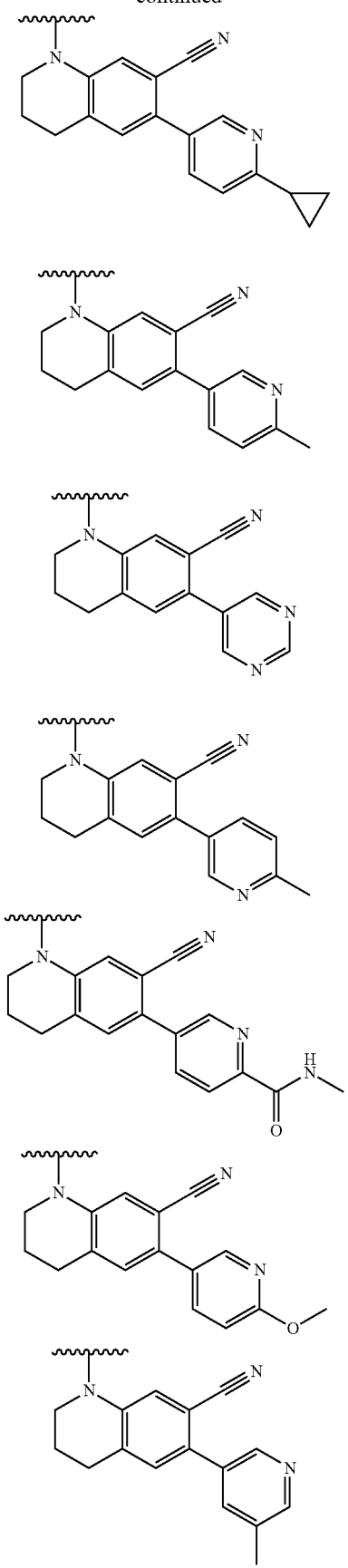

1011
-continued
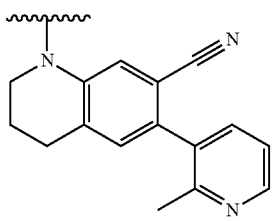
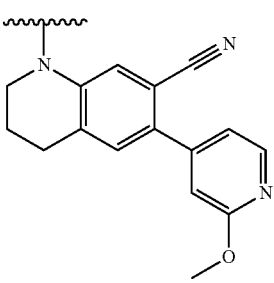
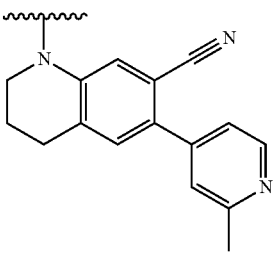
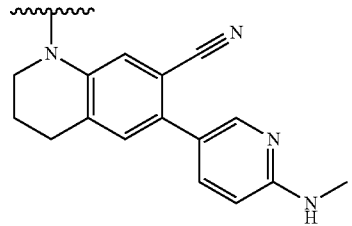
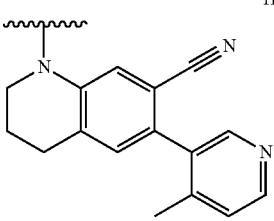
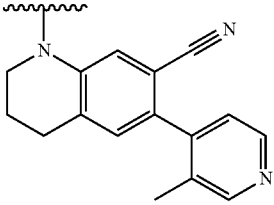
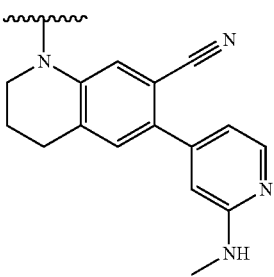
1012
-continued
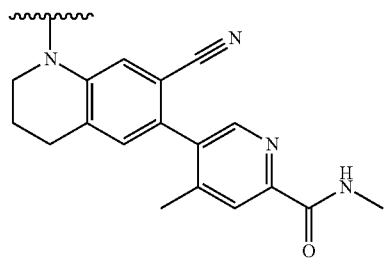
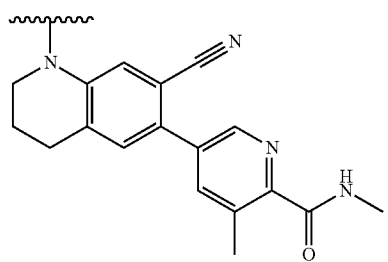
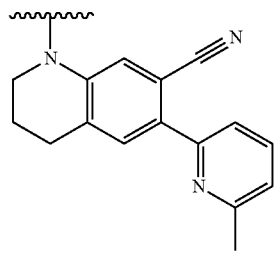
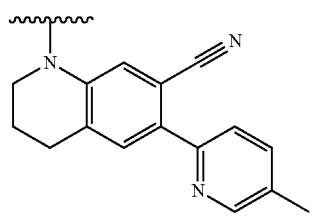
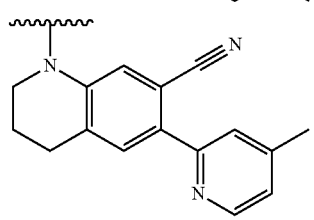
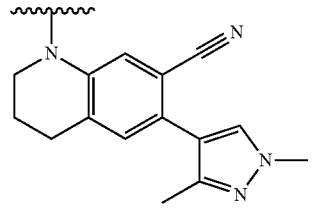
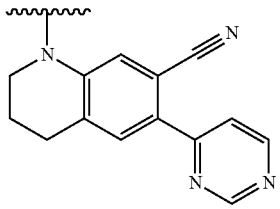

1013
-continued
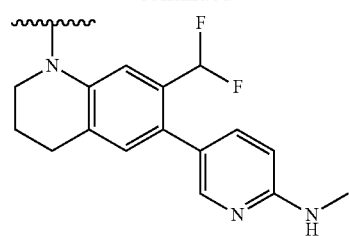
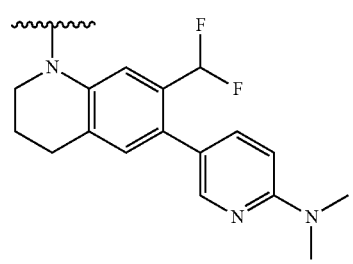
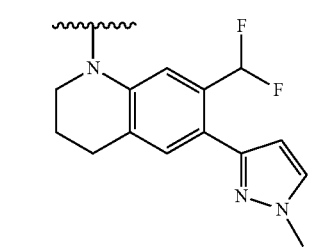
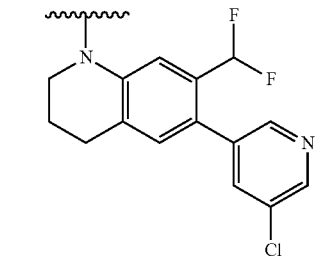
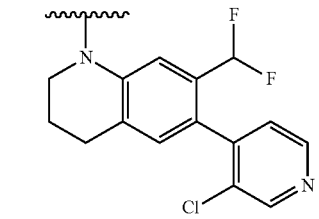
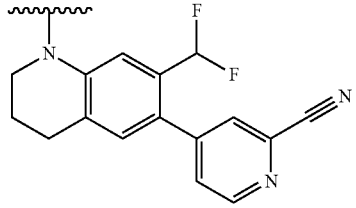
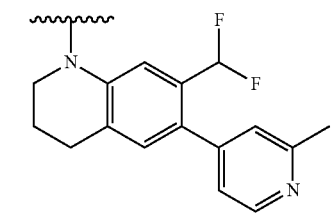
1014
-continued
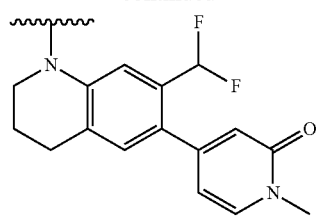
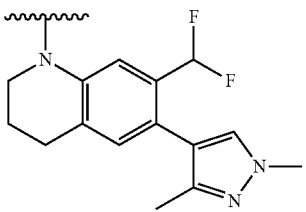
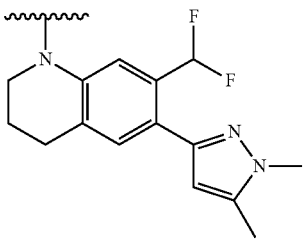
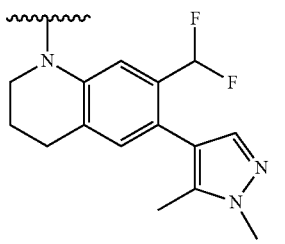
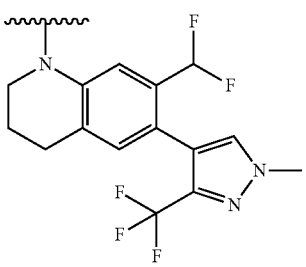
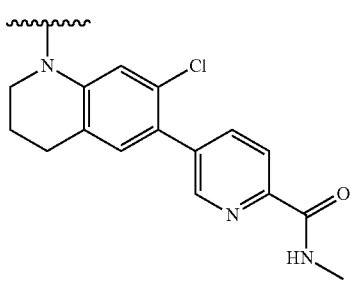
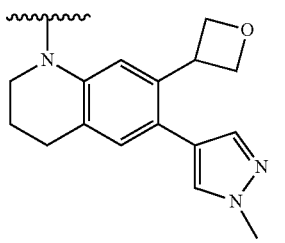

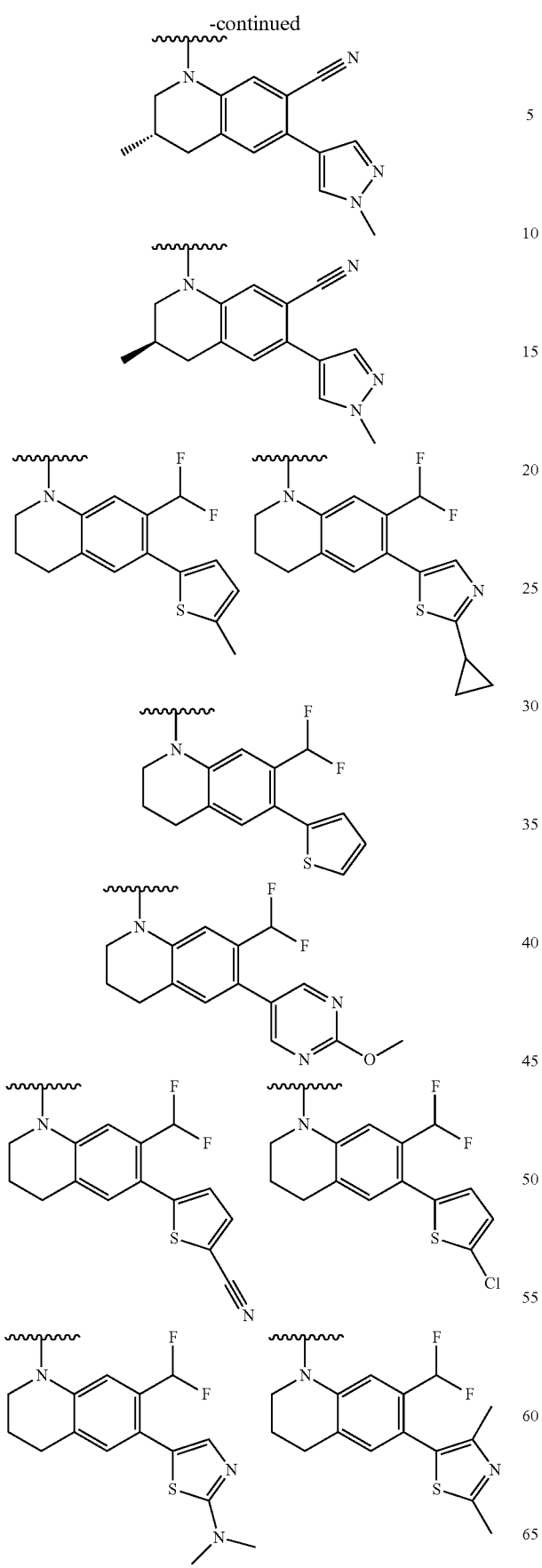
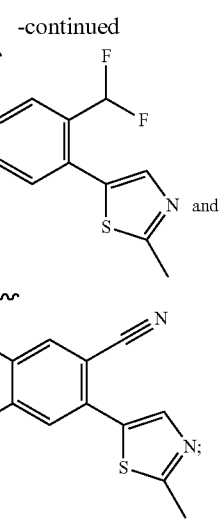
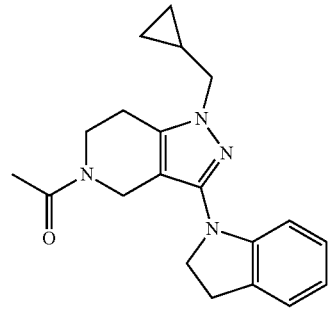
and
R[4] is acetyl, aminocarbonyl, methylaminocarbonyl, dimethylaminocarbonyl, methoxycarbonyl, propanoyl, cyclopropylcarbonyl, methyl sulfonyl, butanoyl, difluoroacetyl, thiadiazole or isoxazole.
10. The compound of claim 2 selected from the group consisting of:
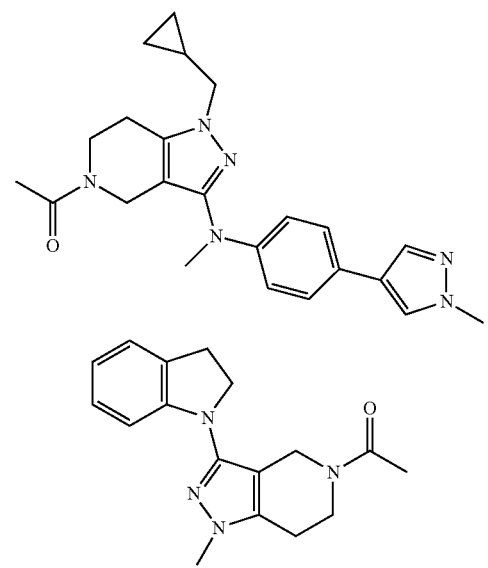

1017
-continued
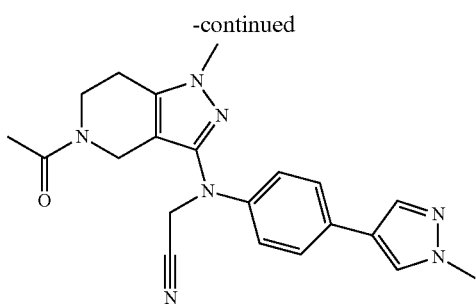
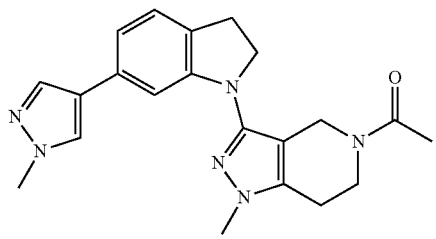
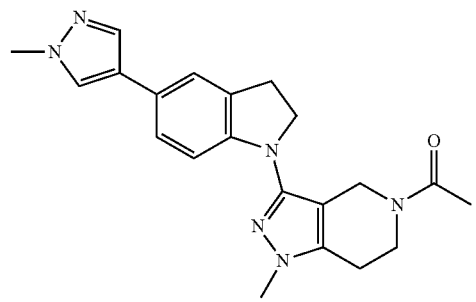
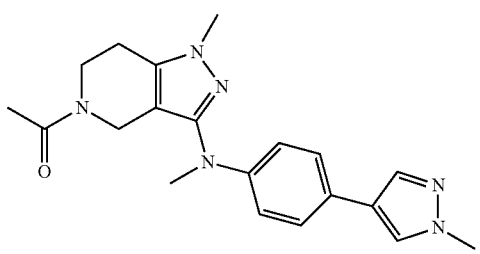
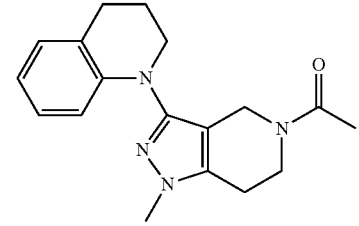
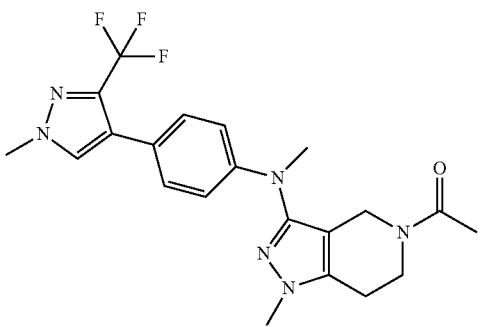
1018
-continued
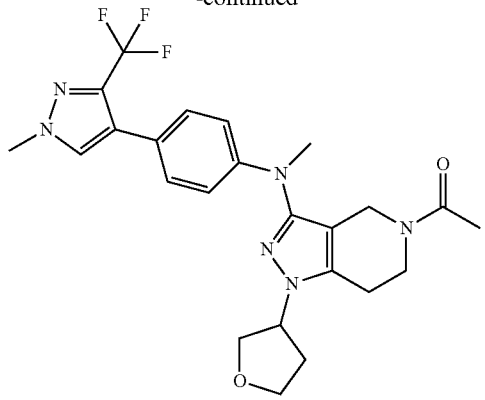
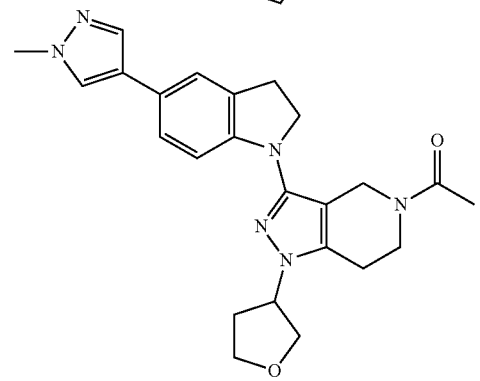
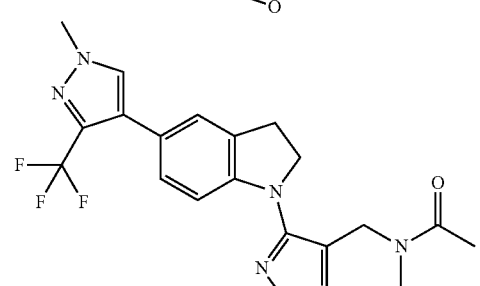
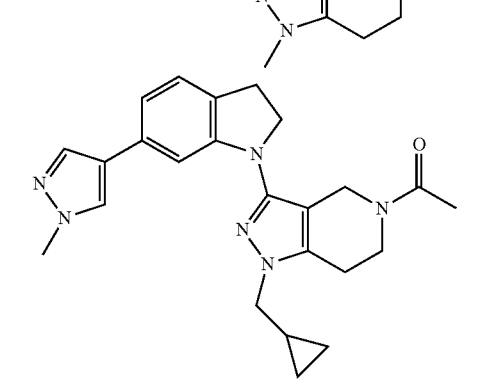
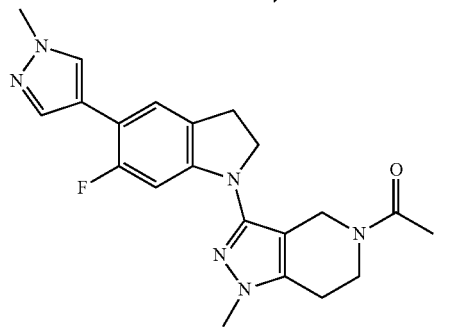

1019
-continued
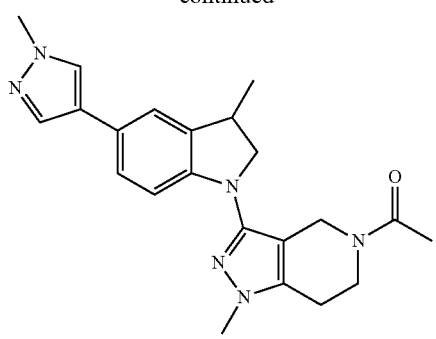
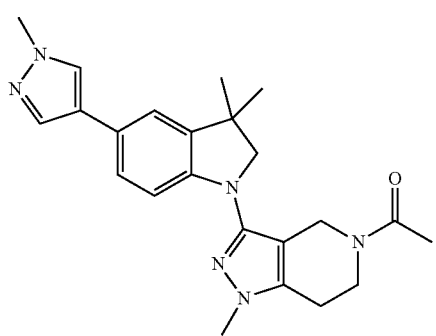
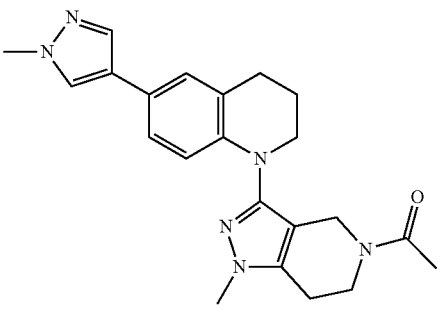
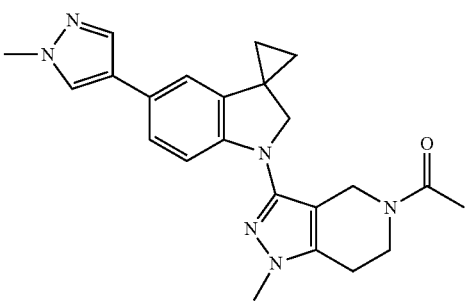
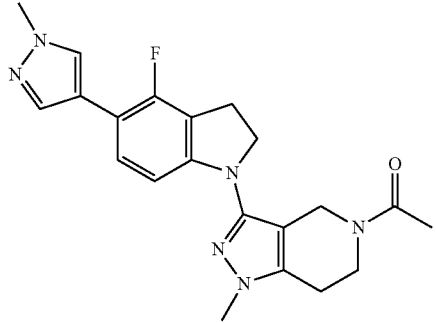
1020
-continued
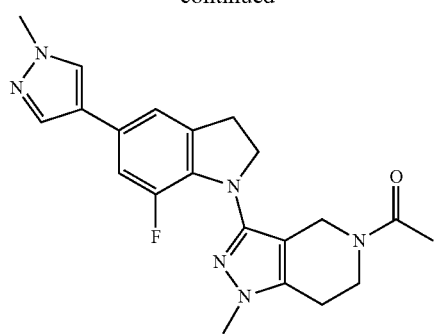
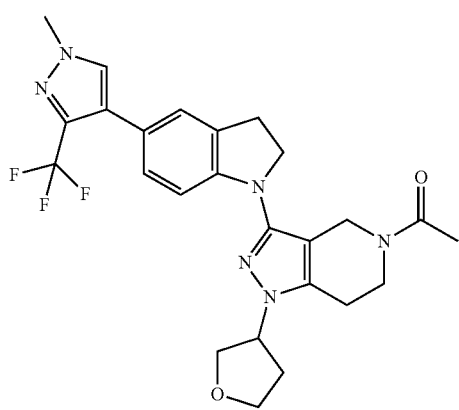
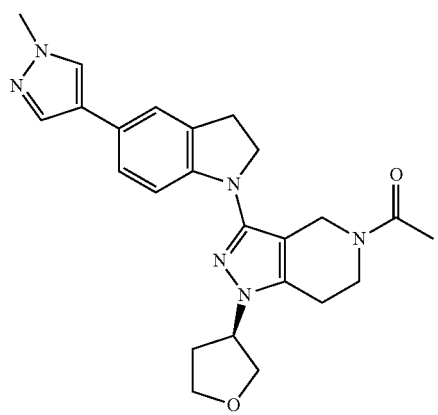
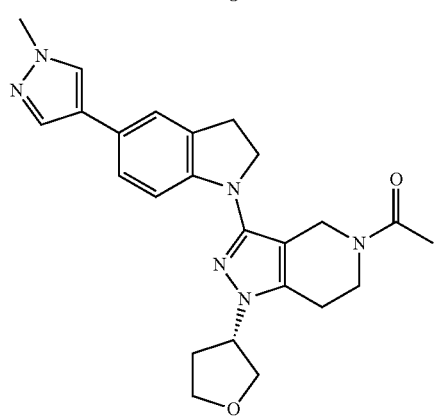

1021
-continued
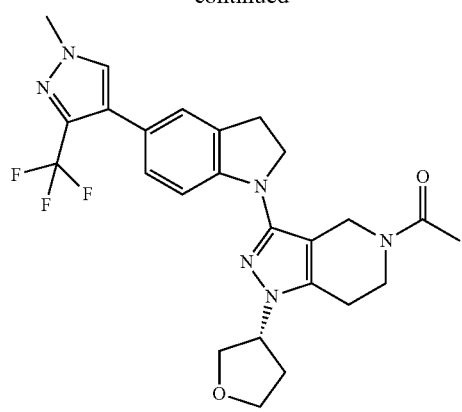
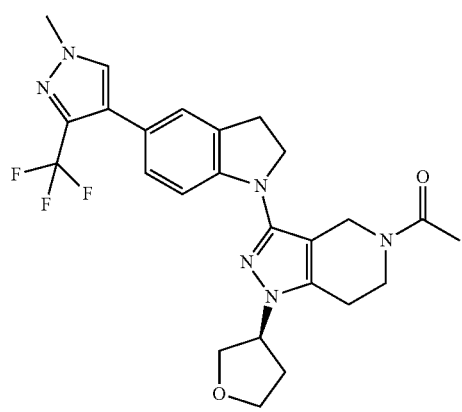
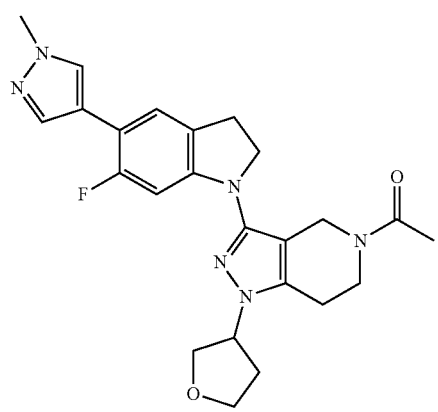
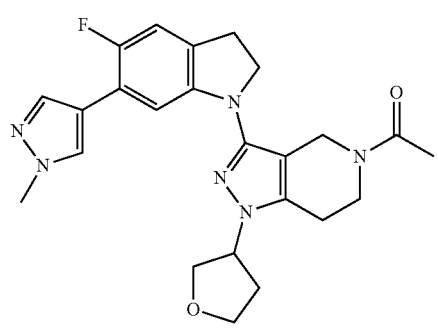
1022
-continued
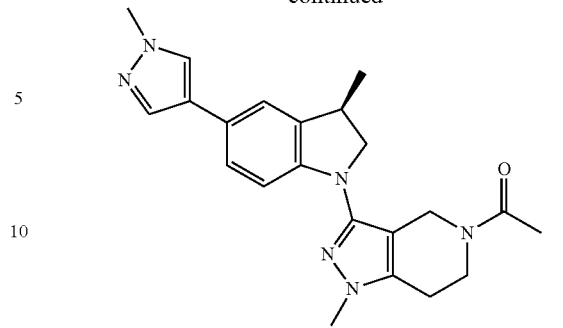
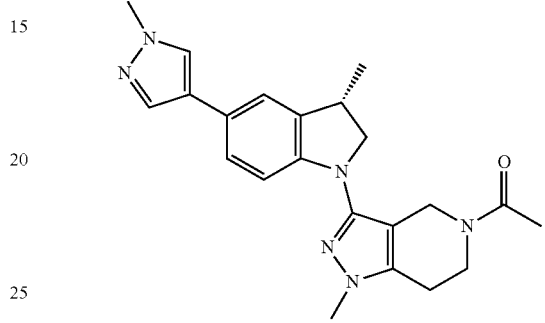
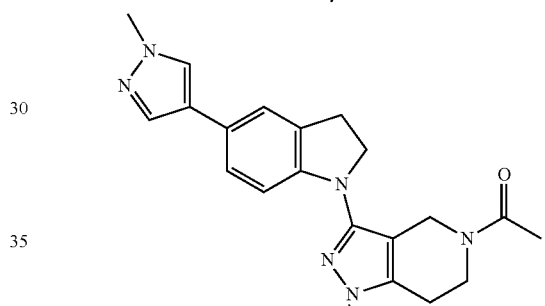
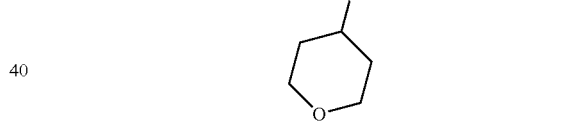
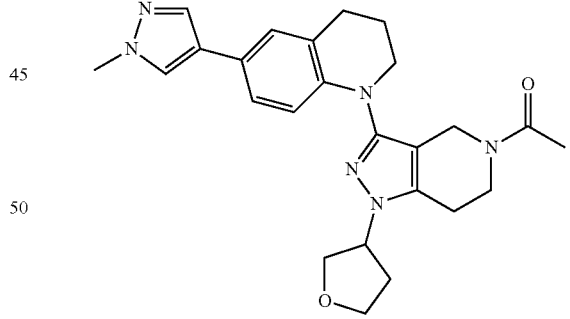
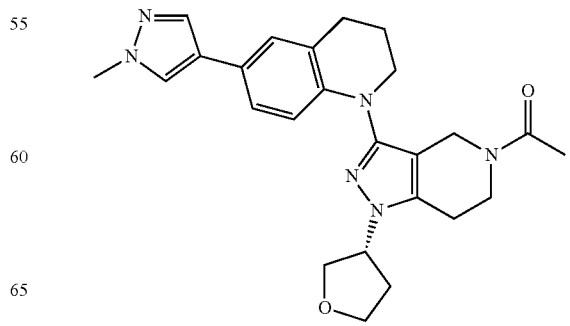

1023
-continued
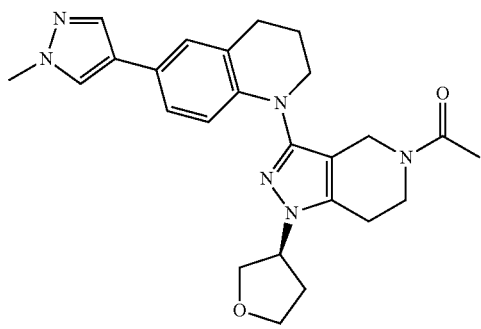
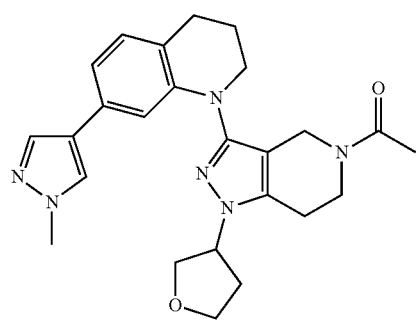
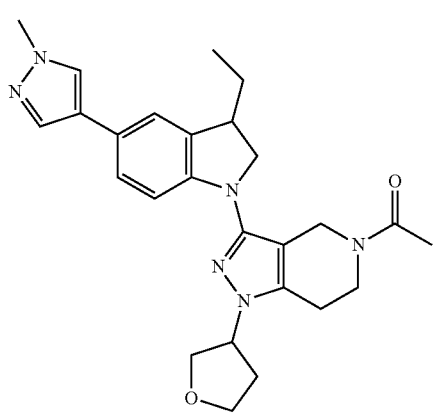
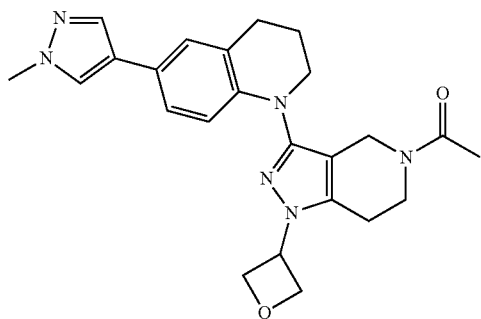
1024
-continued
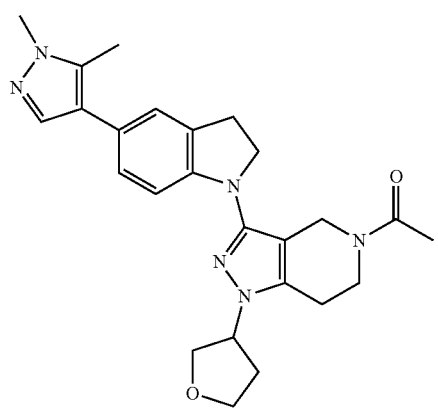
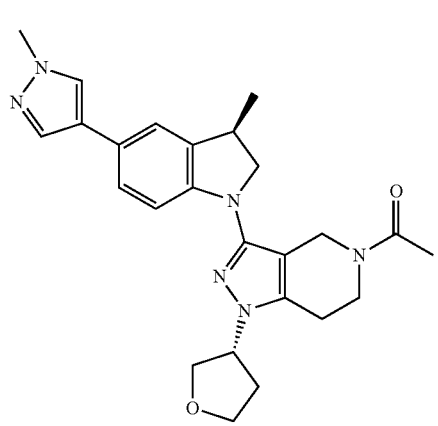
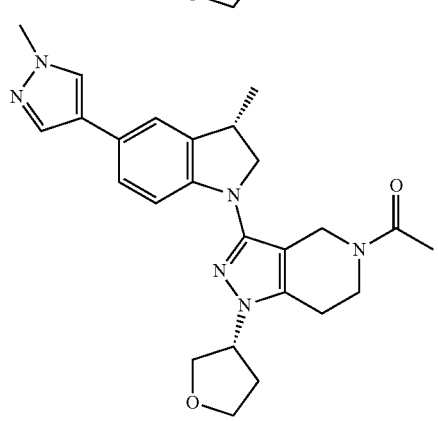
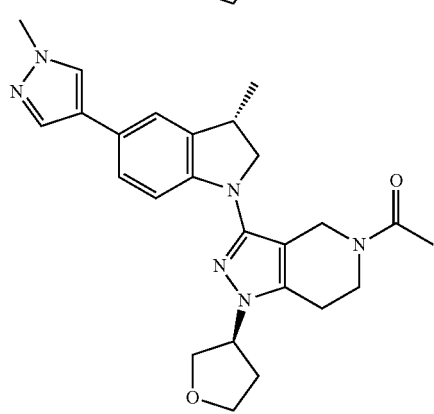

1025
-continued
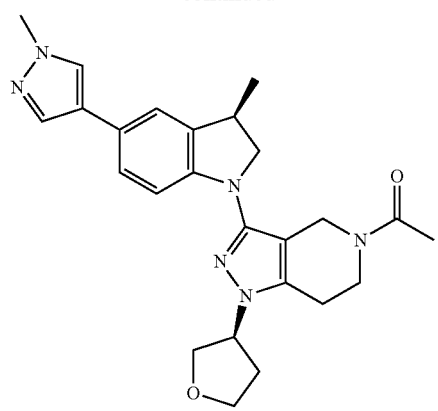
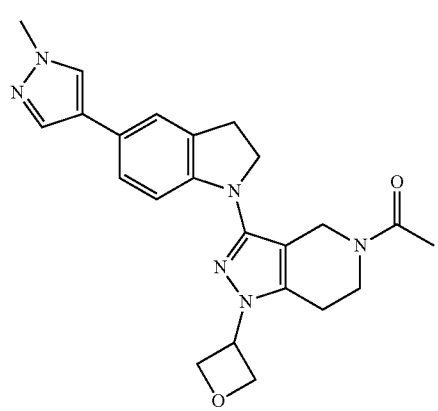
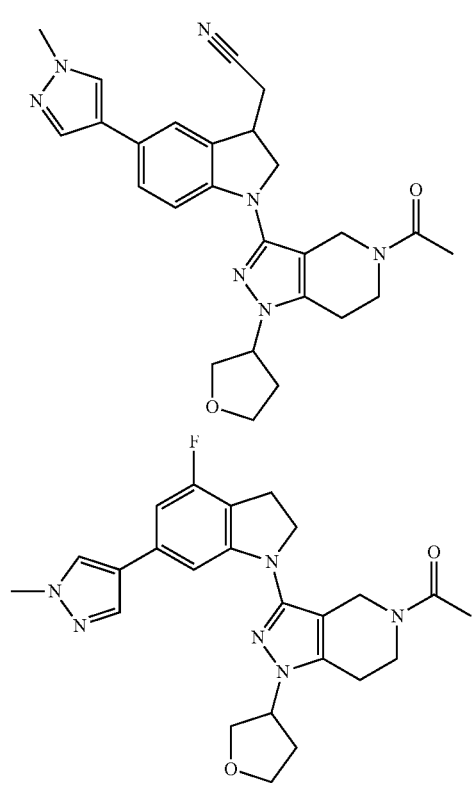
1026
-continued
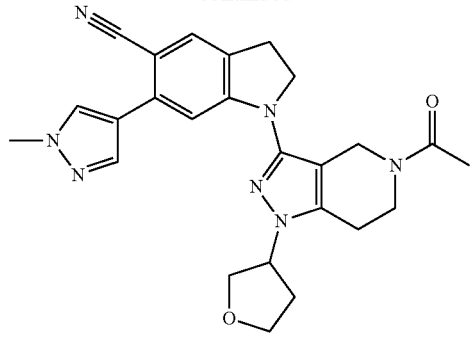
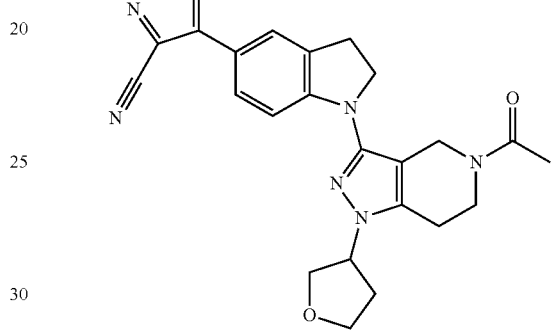
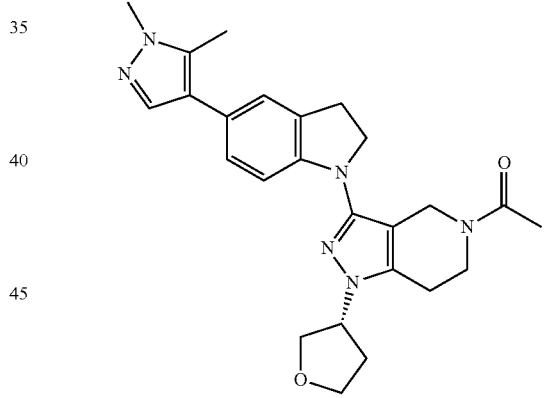
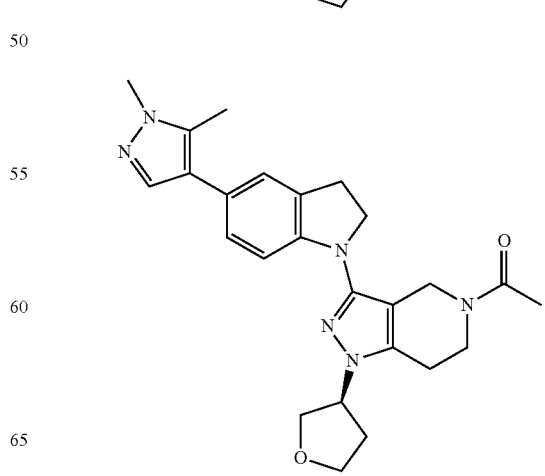

1027
-continued
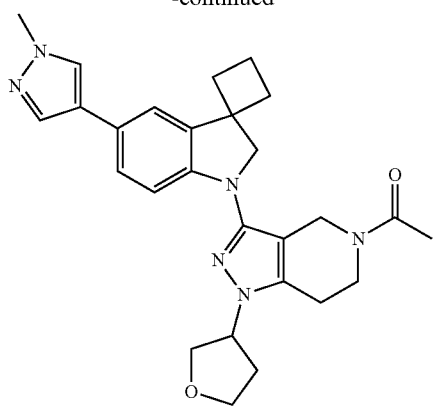
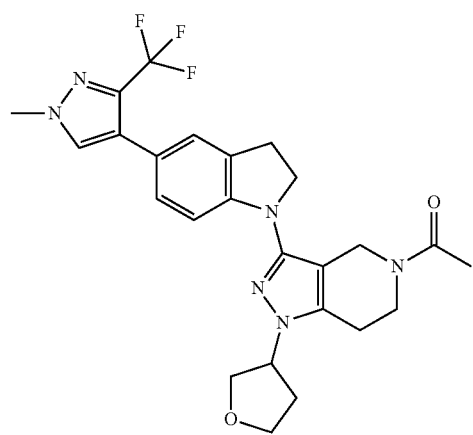
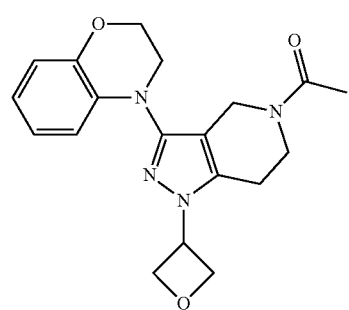
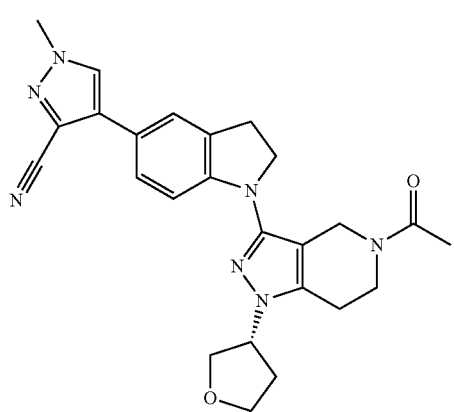
1028
-continued
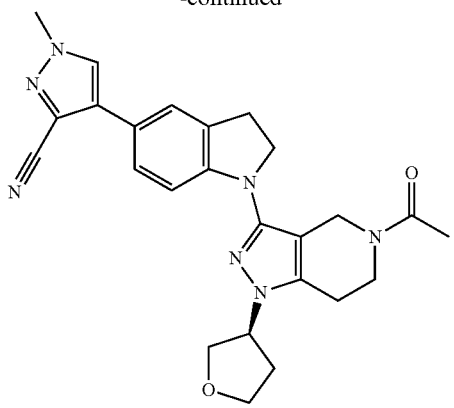
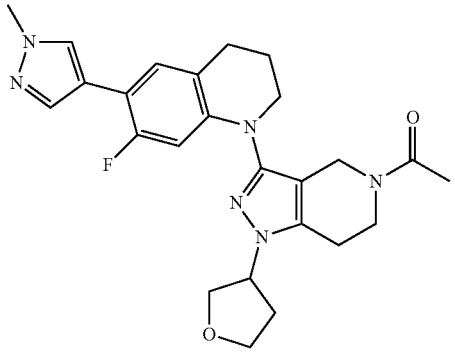
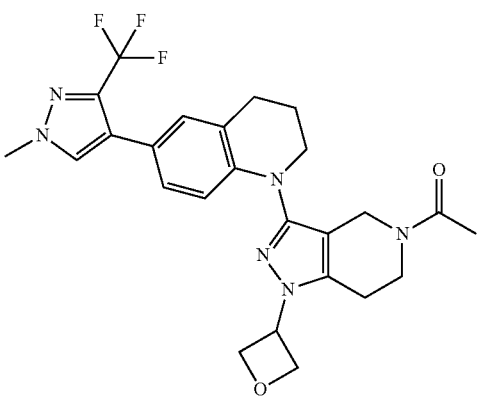
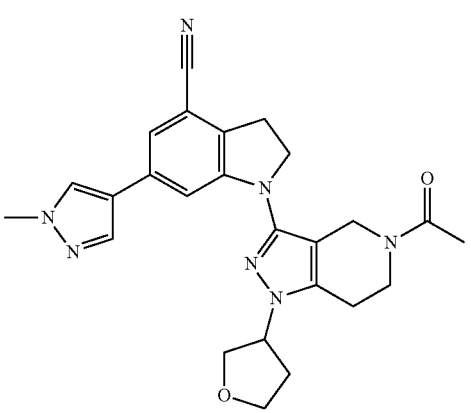

1029
-continued
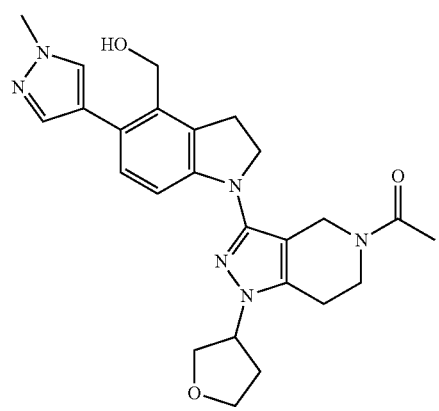
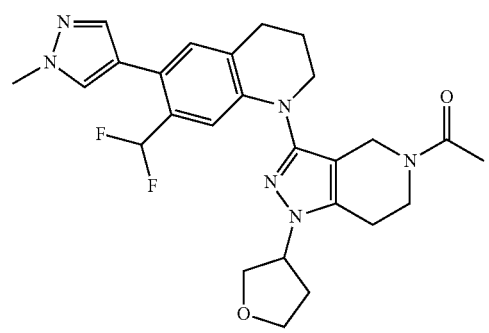
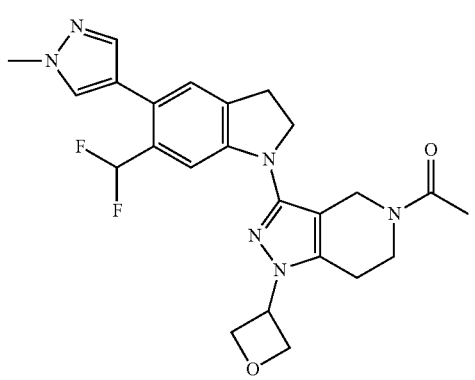
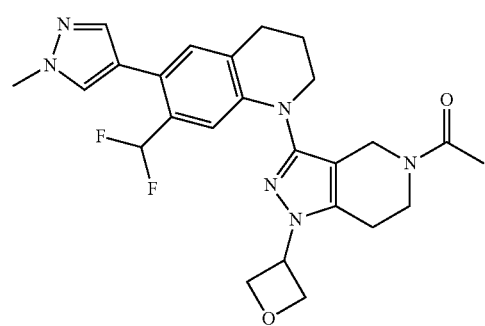
1030
-continued
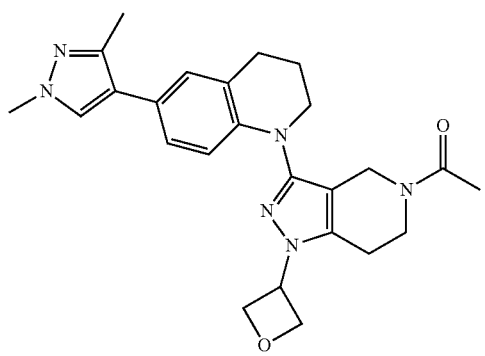
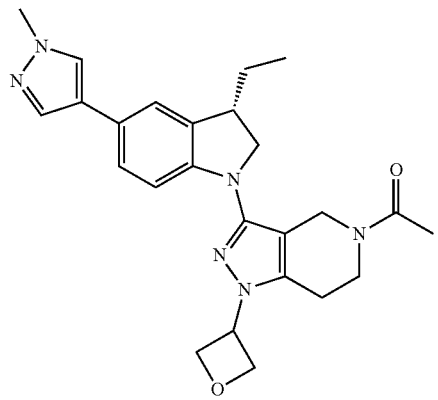
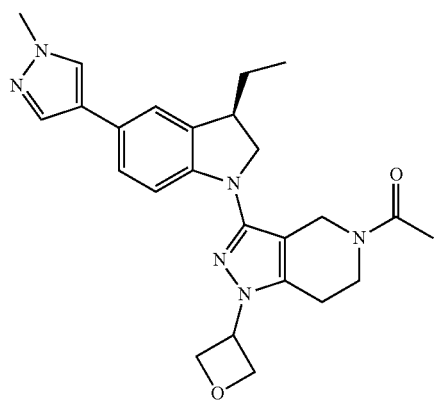
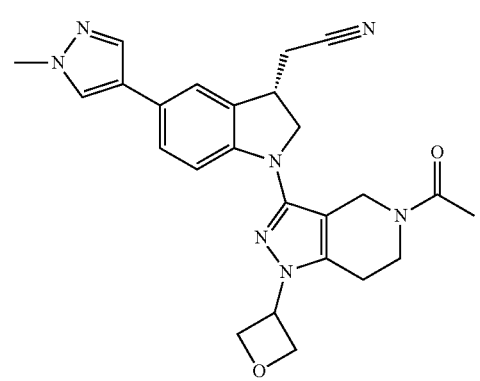

1031
-continued
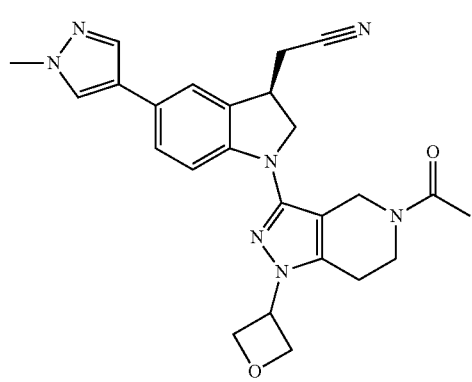
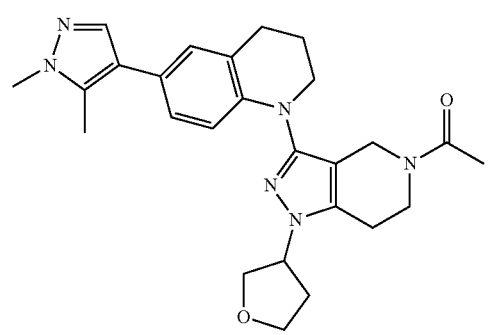
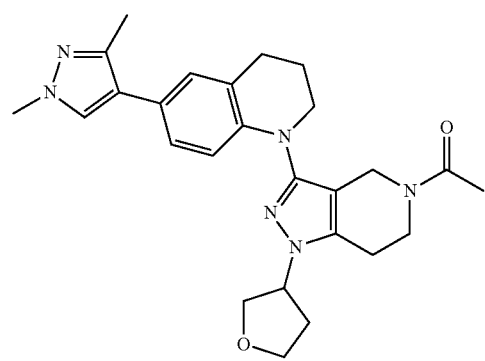
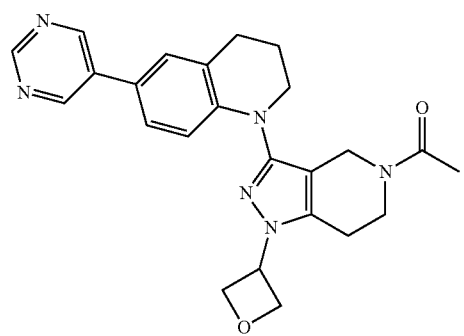
1032
-continued
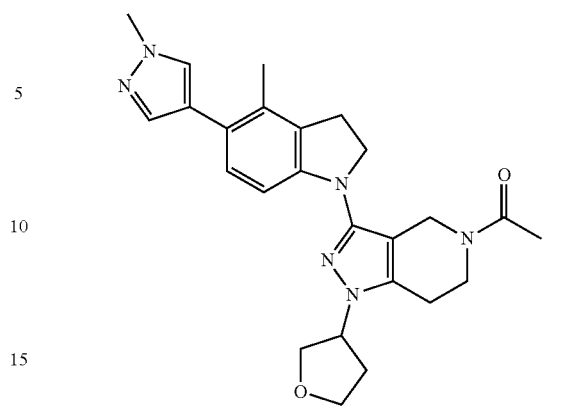
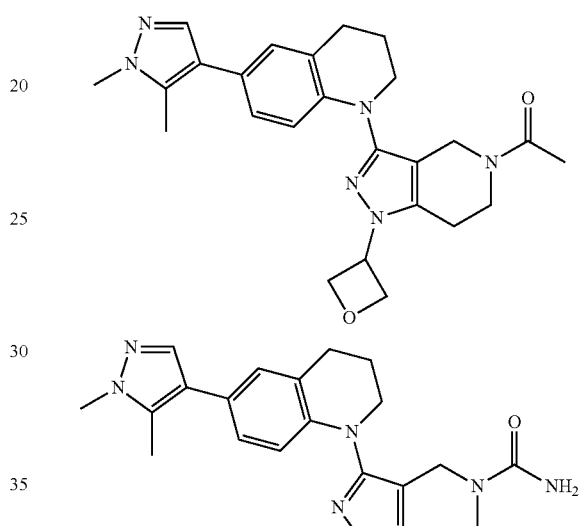
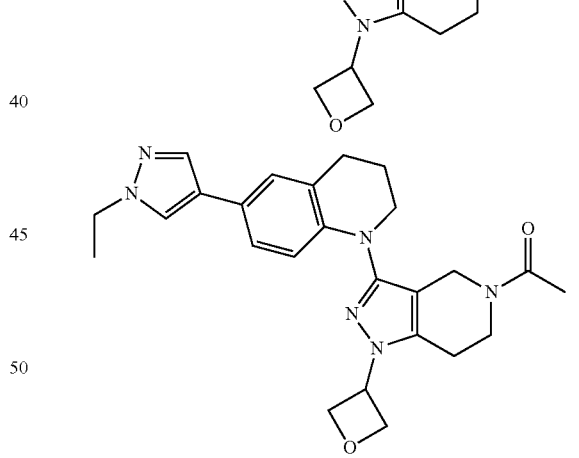
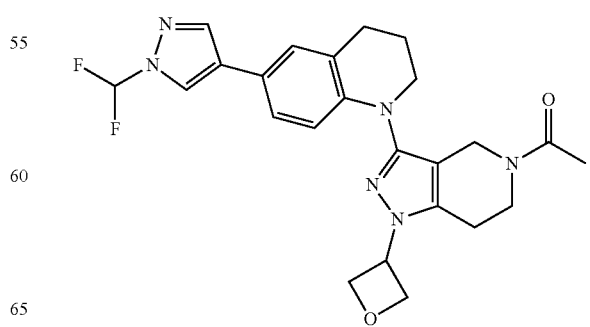

1033
-continued
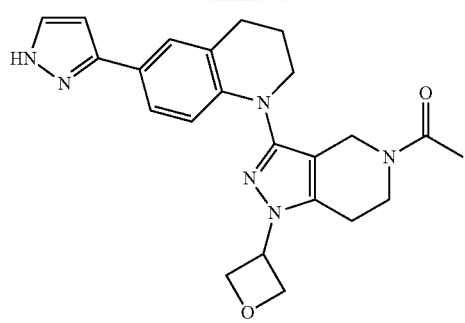
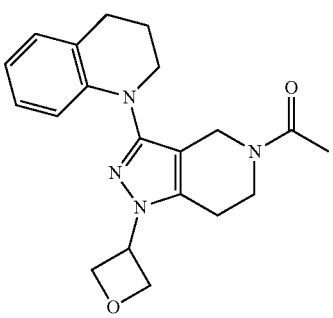
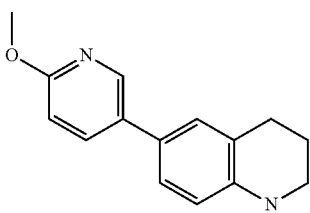
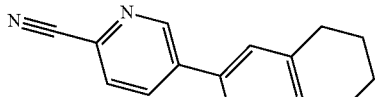
1034
-continued
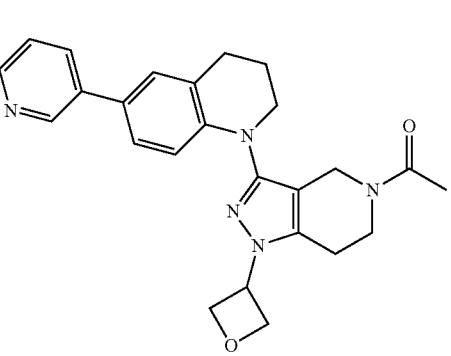
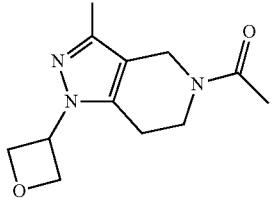
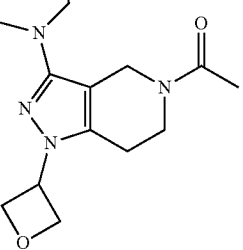

1035
-continued
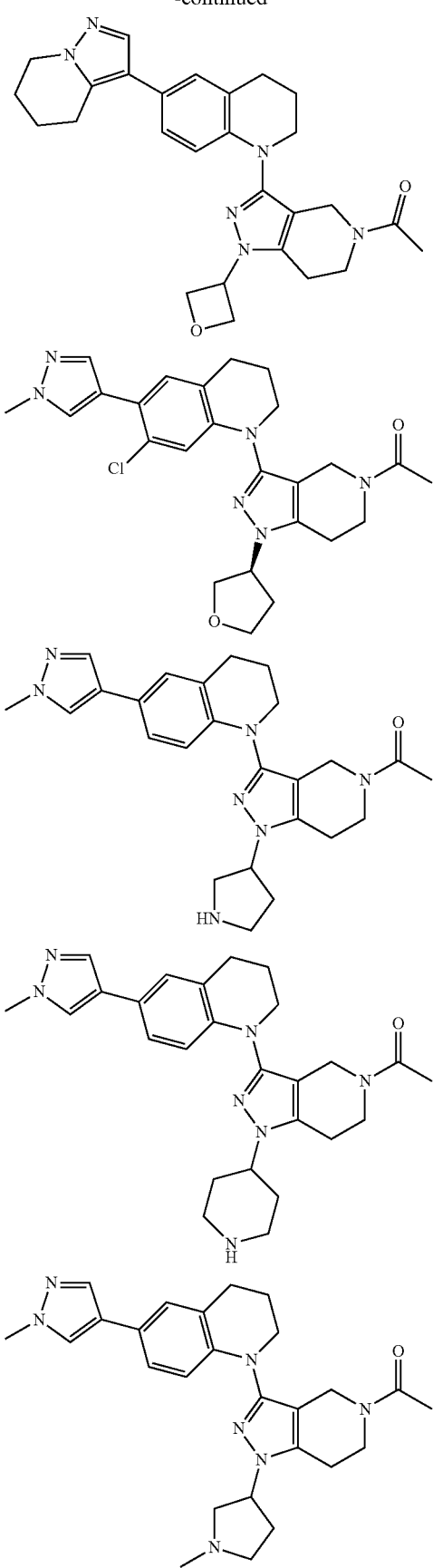
1036
-continued
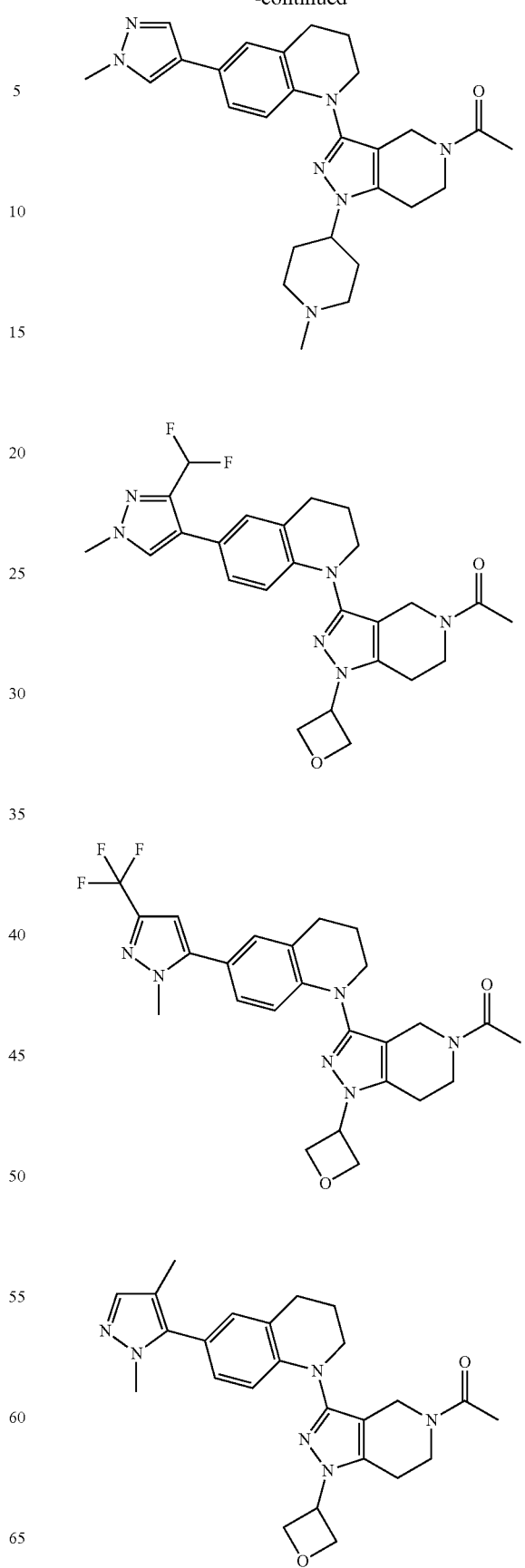

1037
-continued
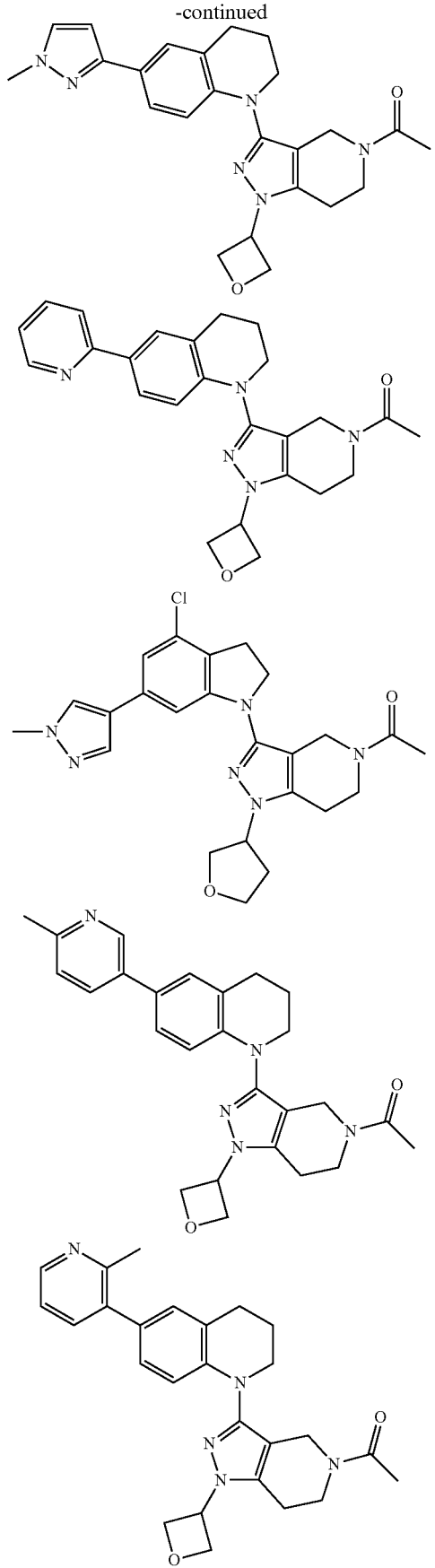
1038
-continued
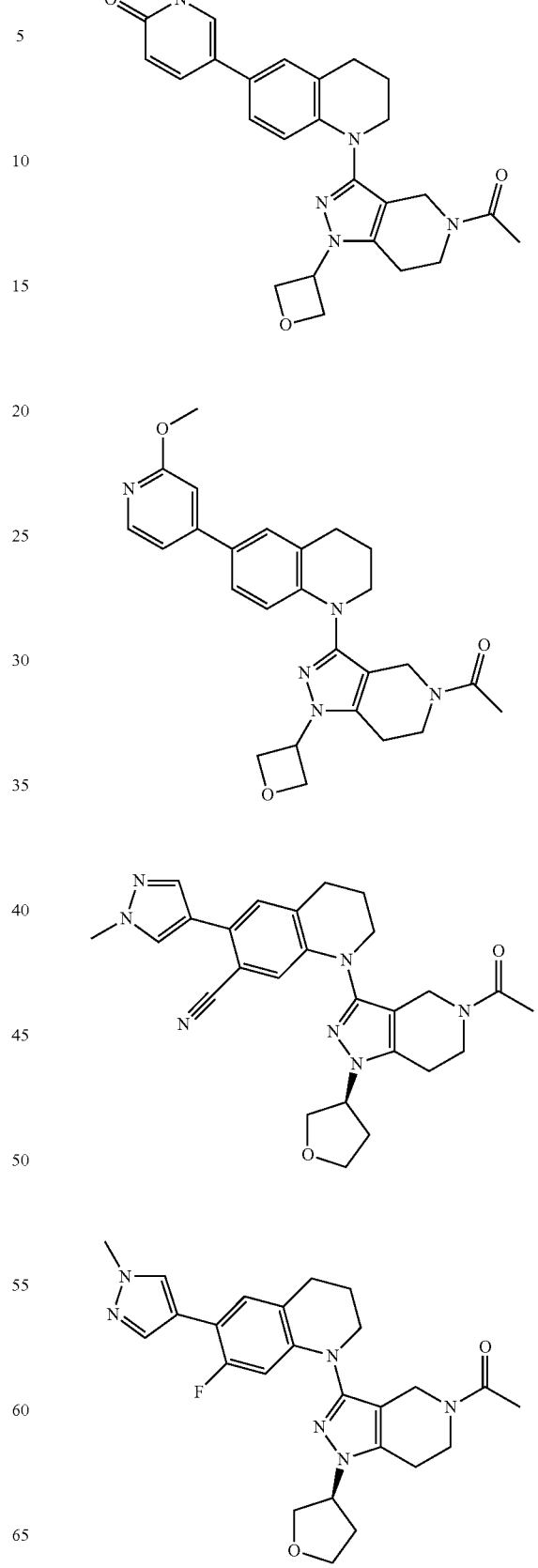

1039
-continued
1040
-continued
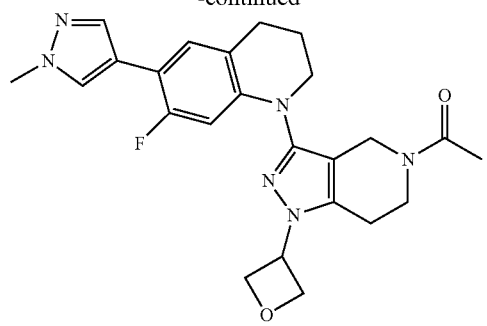
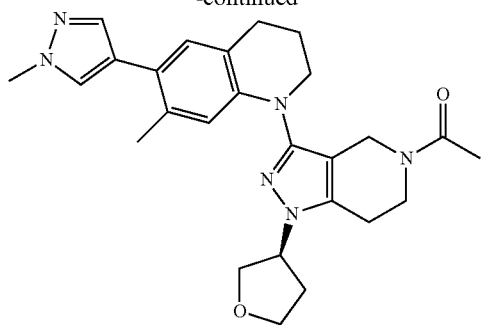
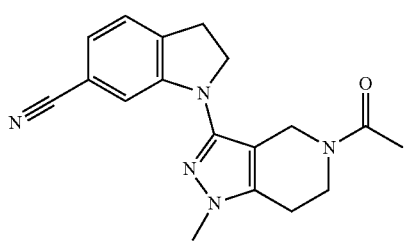
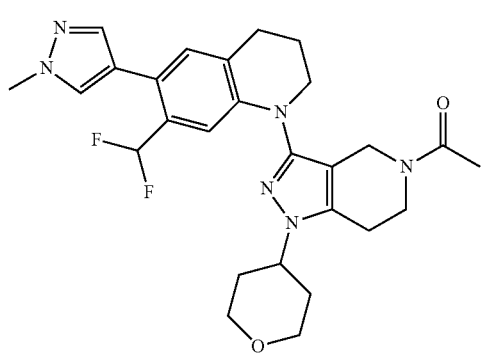
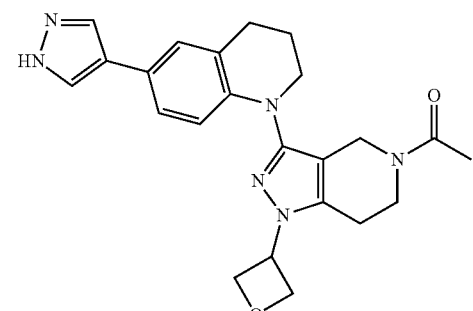
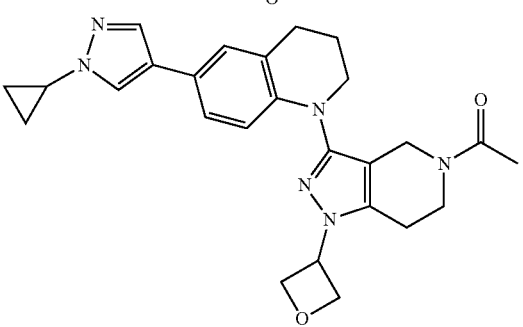

1041
-continued
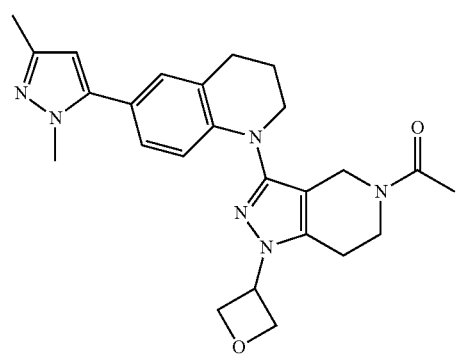
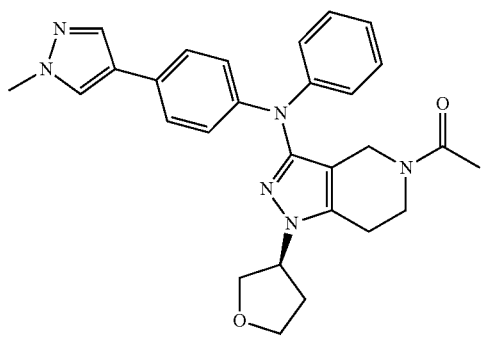
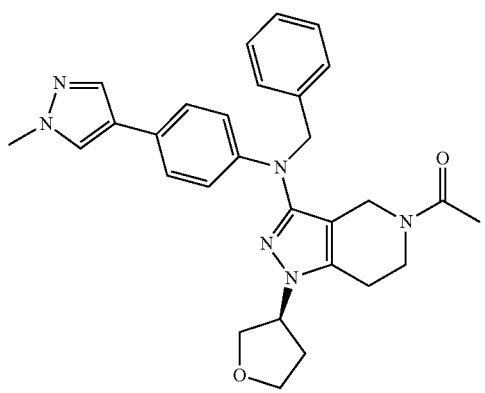
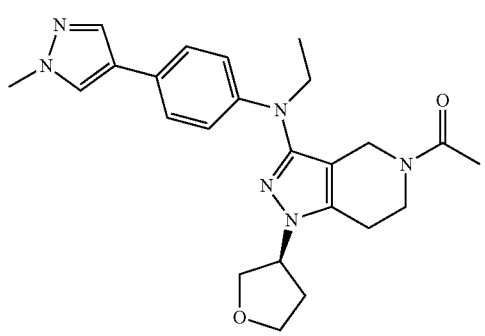
1042
-continued
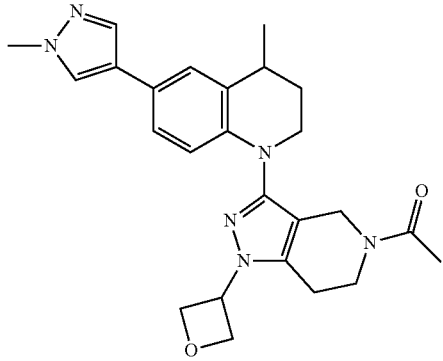
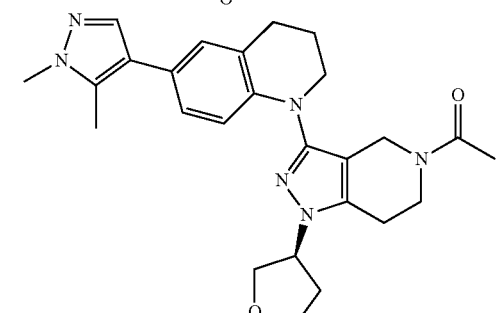
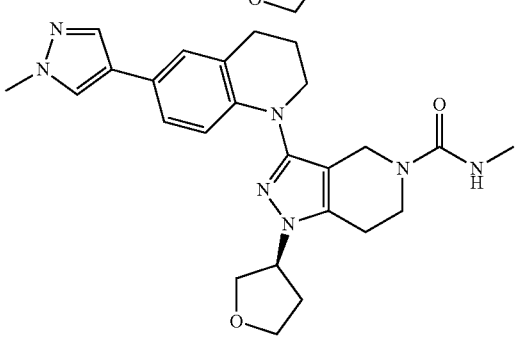
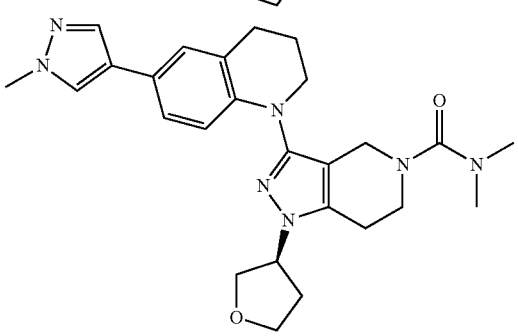
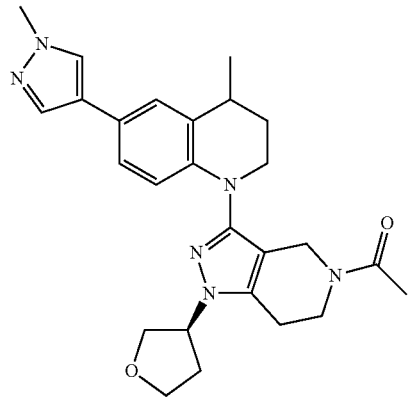

1043
-continued
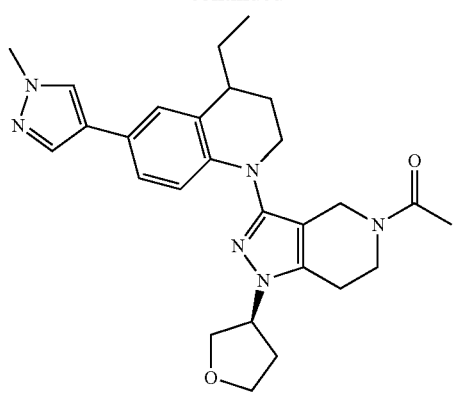
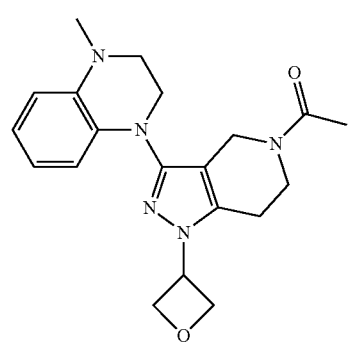
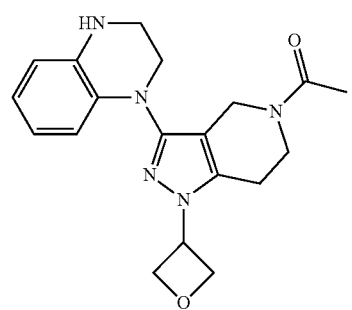
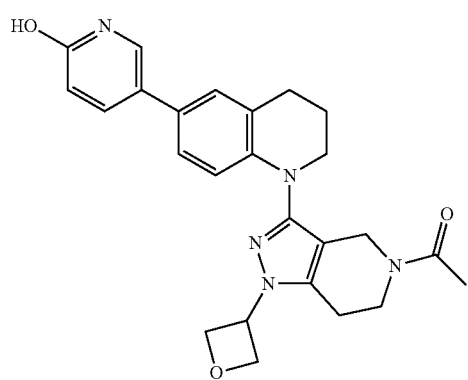
1044
-continued
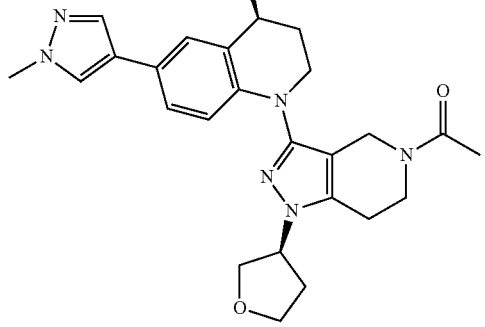
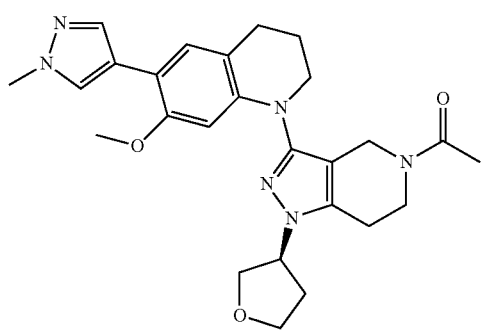
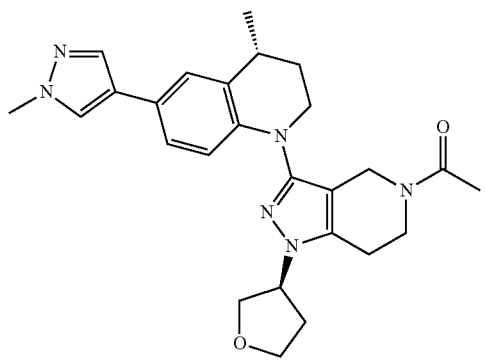
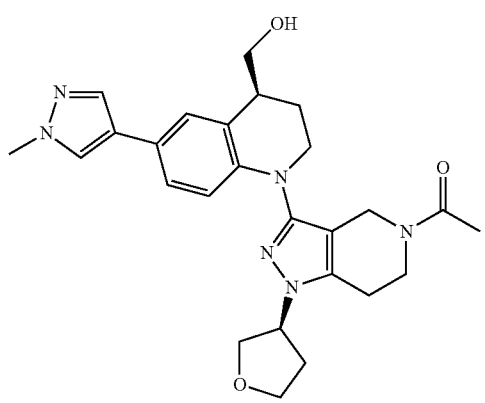

1045
-continued
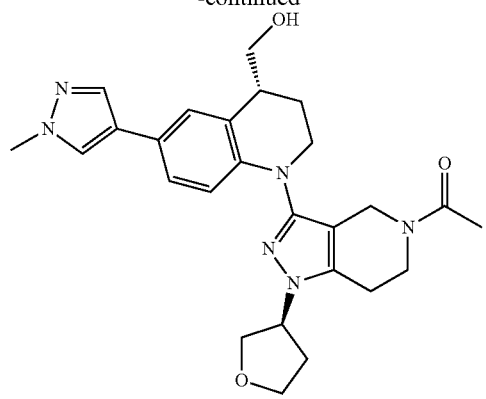
1046
-continued
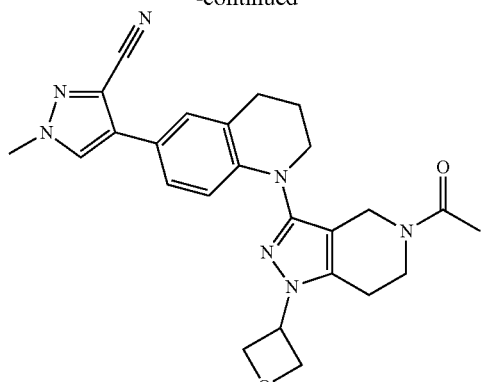
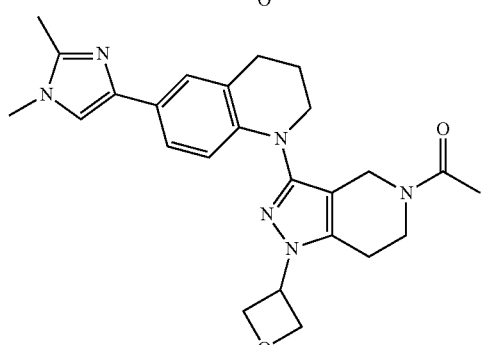
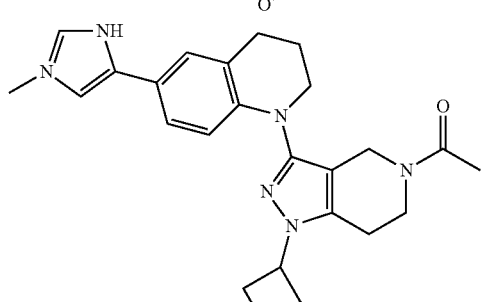
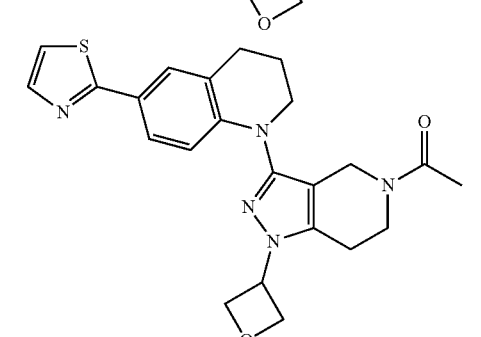
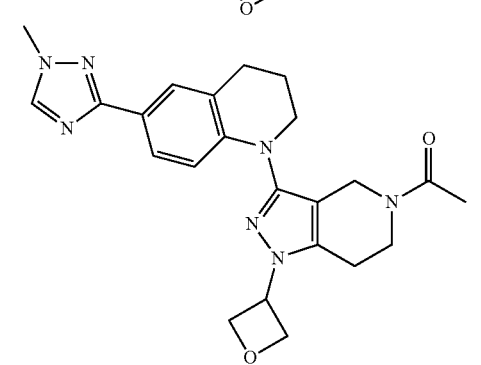

1047
-continued
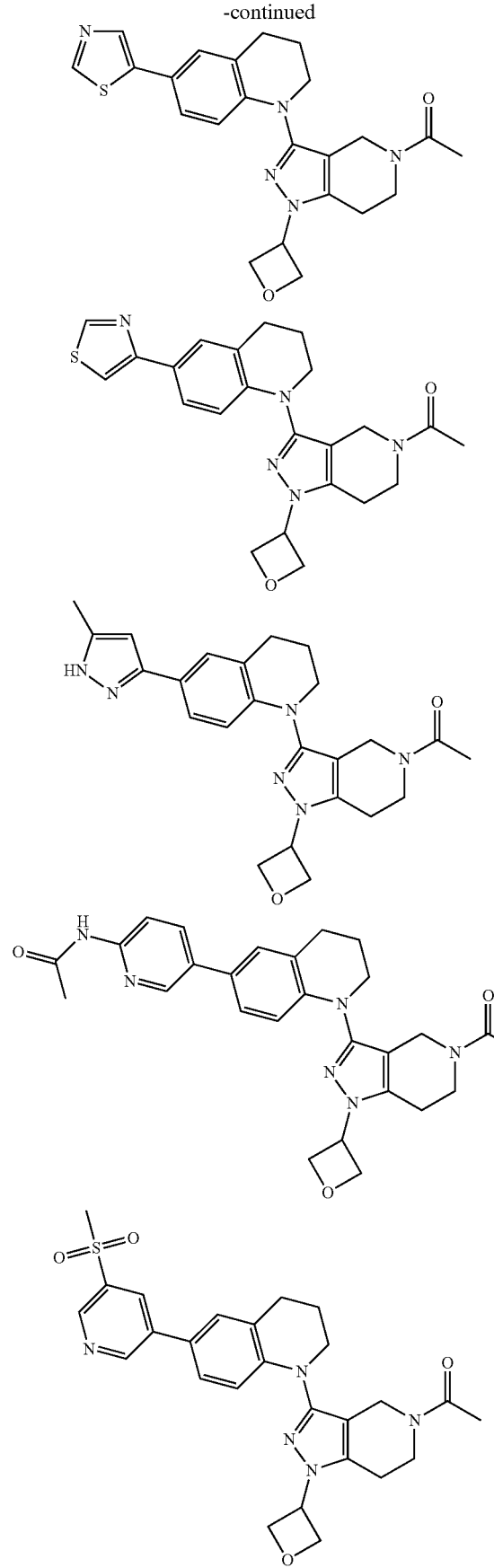
1048
-continued
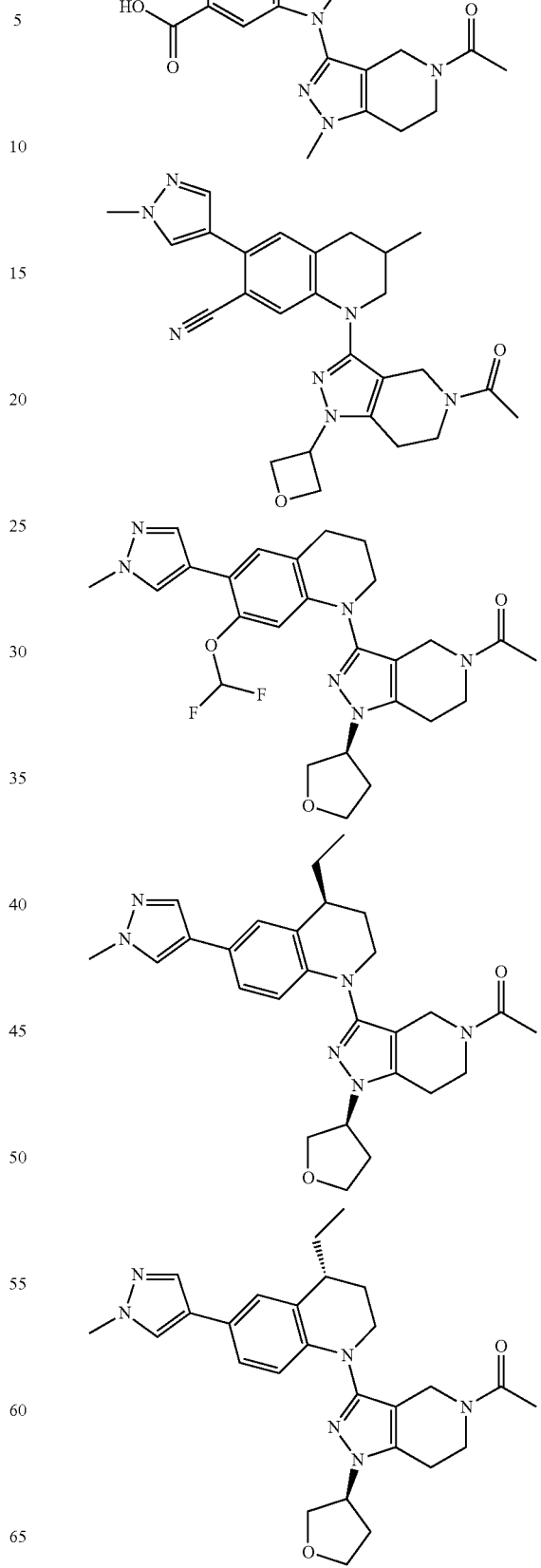

1049
-continued
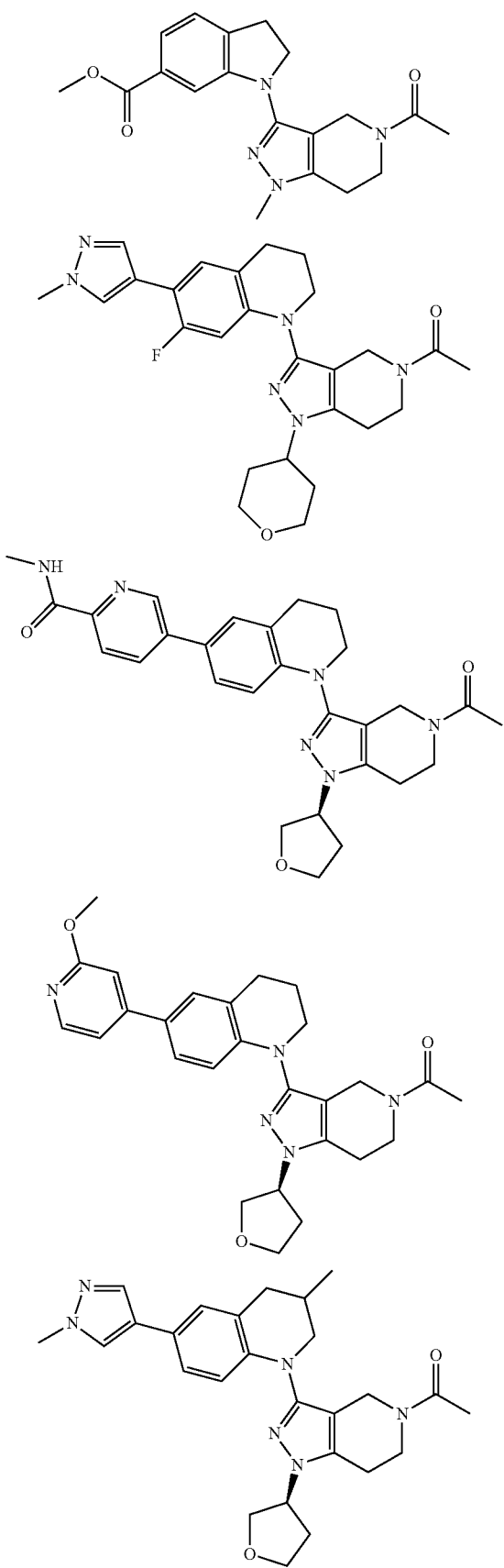
1050
-continued
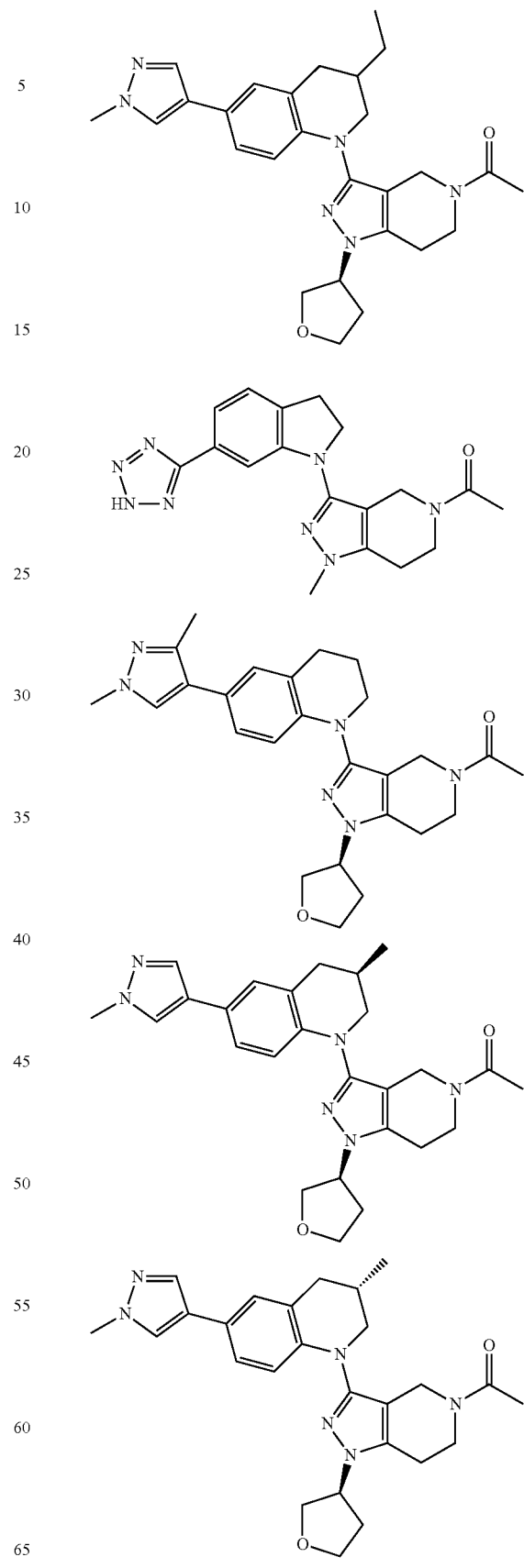

1051
-continued
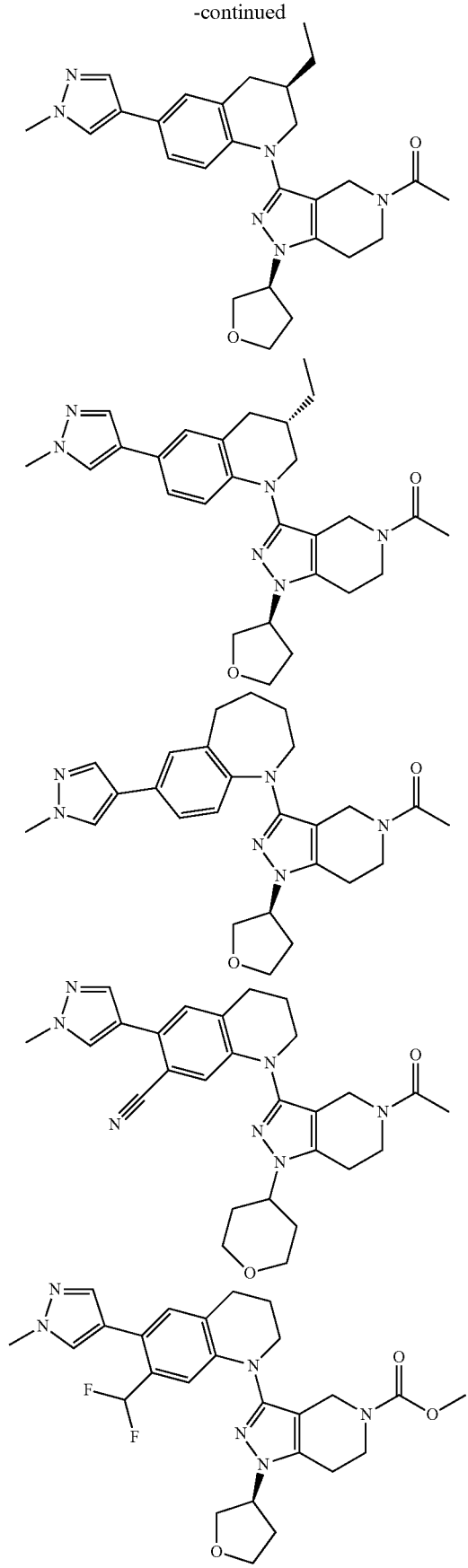
1052
-continued
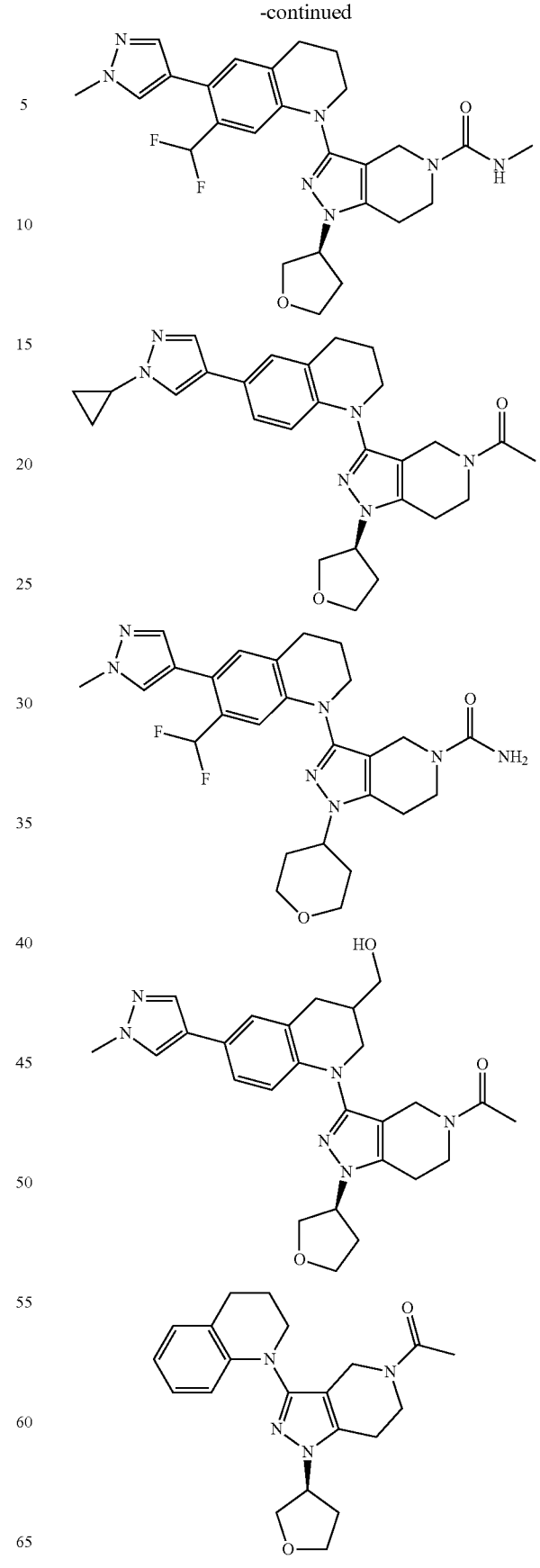

1053
-continued
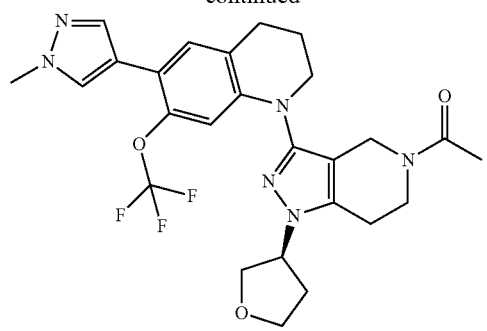
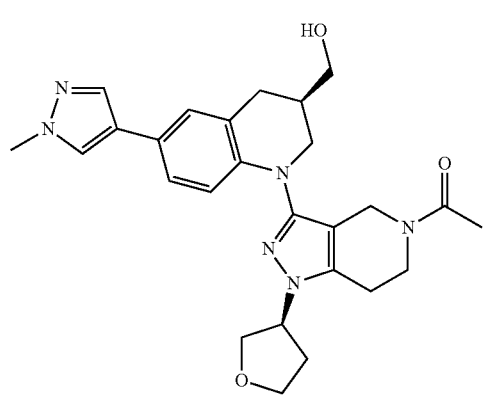
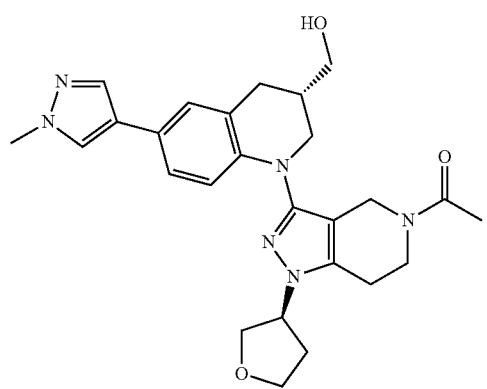
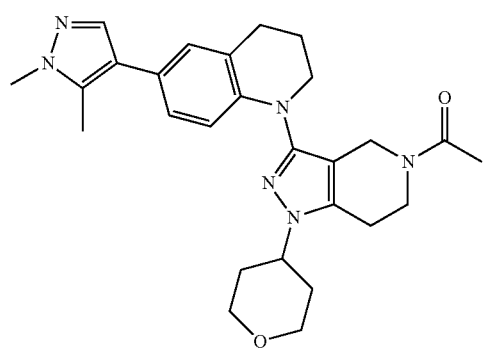
1054
-continued
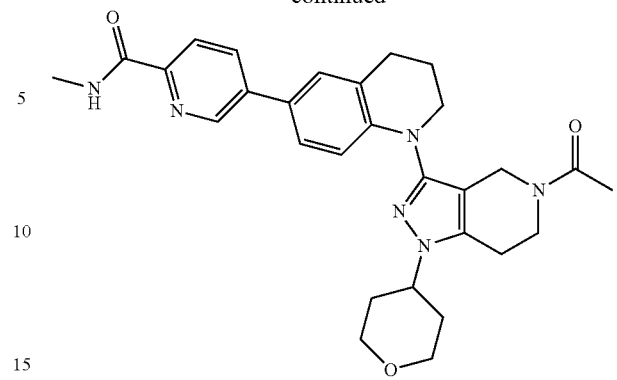
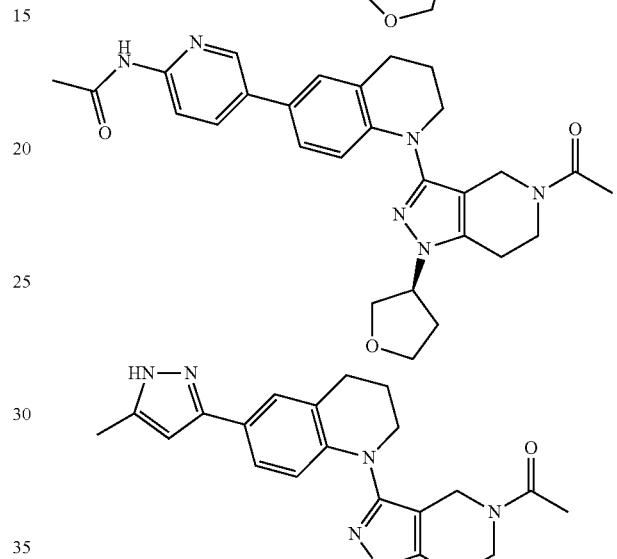
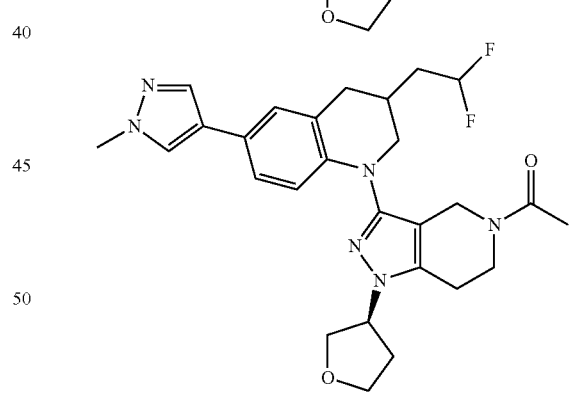
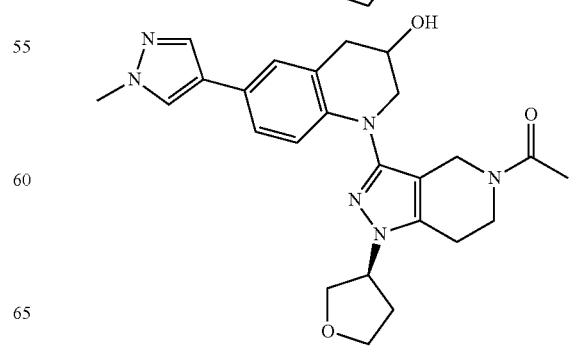

1055
-continued
1056
-continued
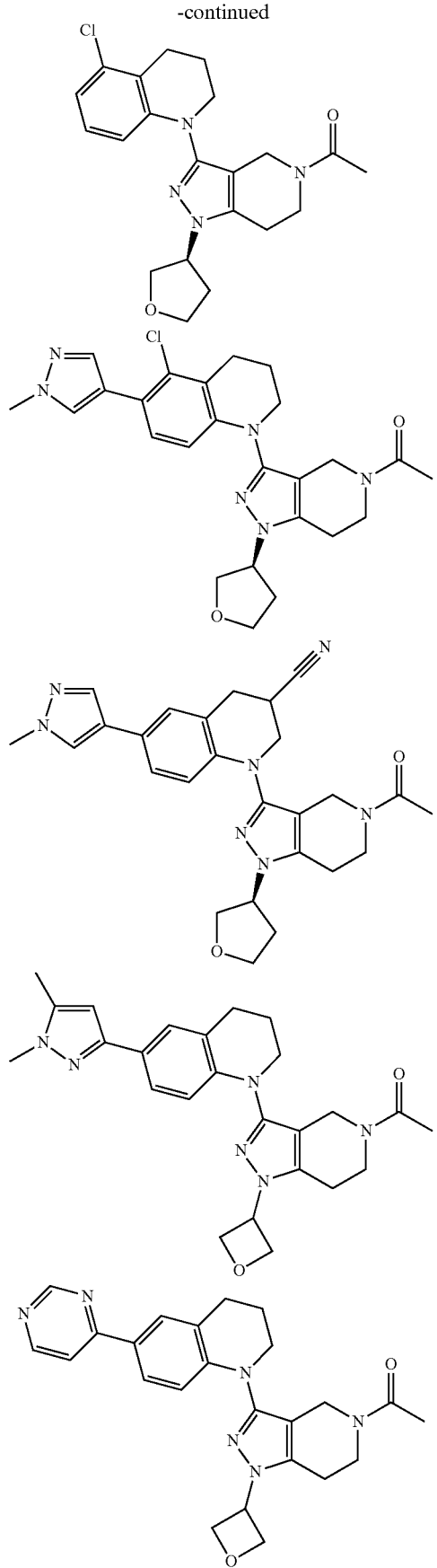
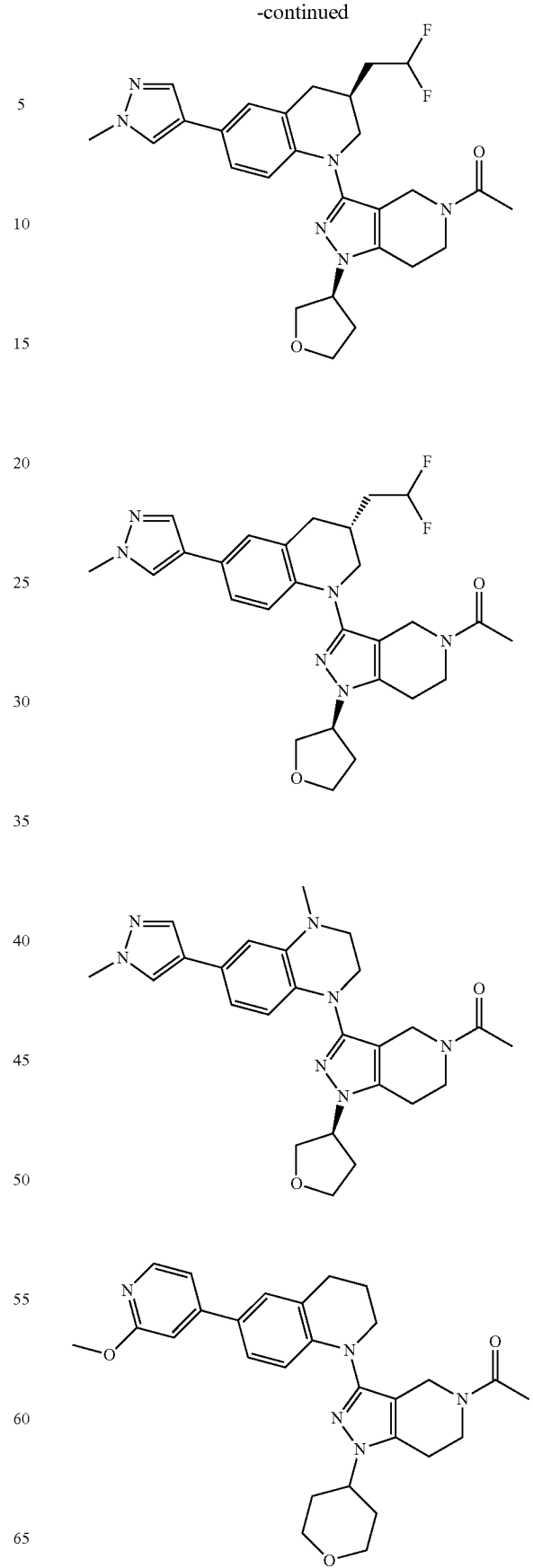

1057
-continued
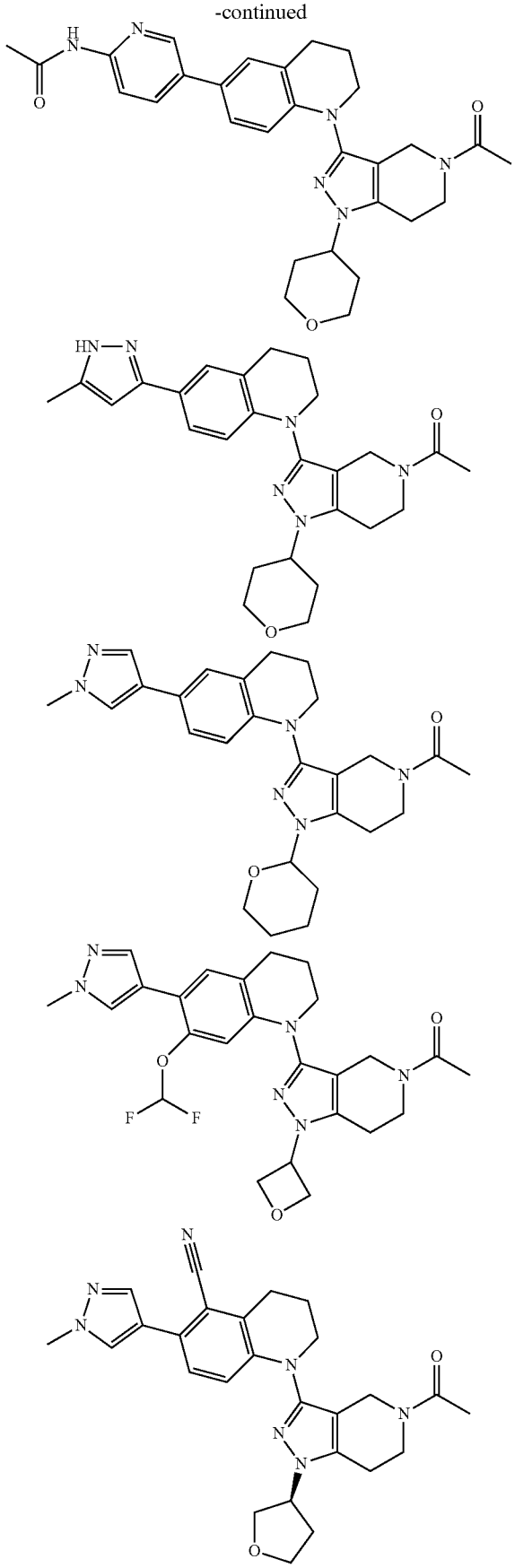
1058
-continued
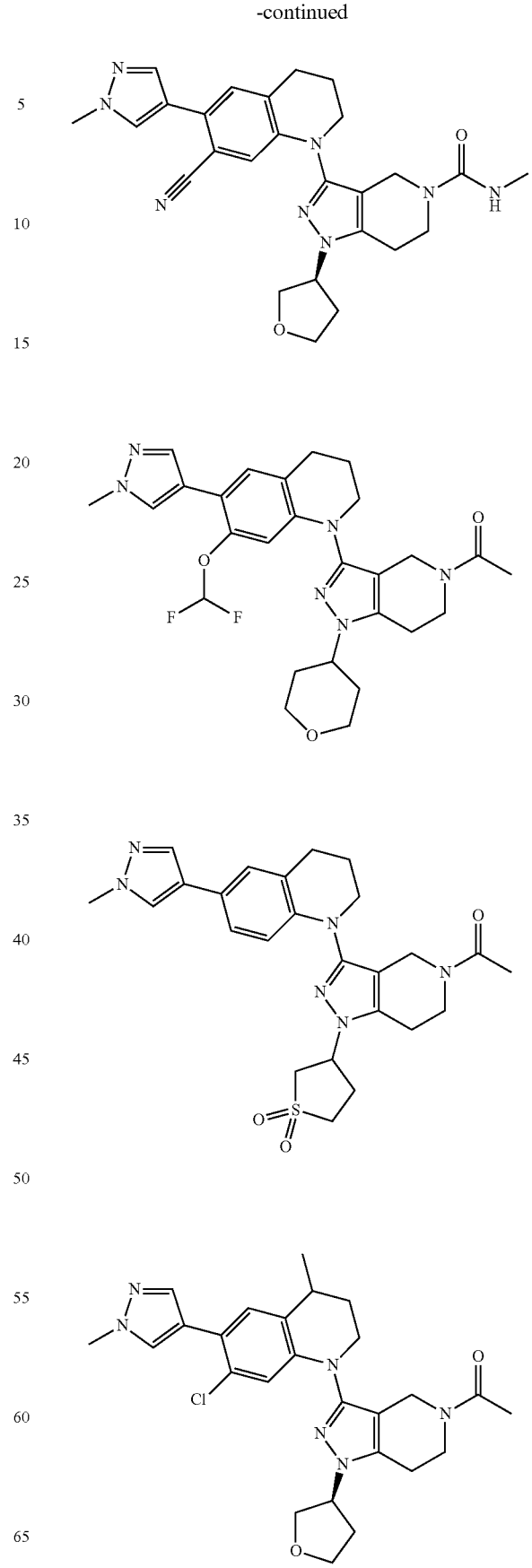

1059
-continued
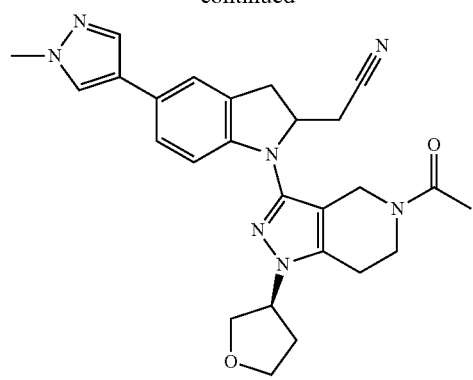
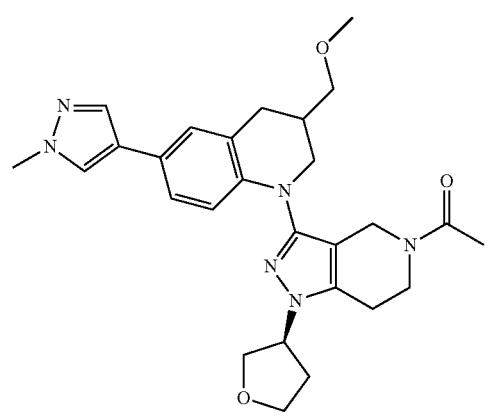
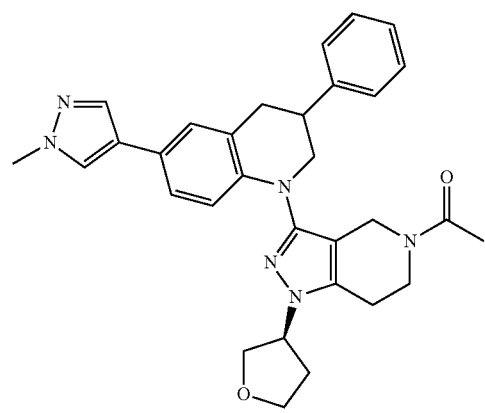
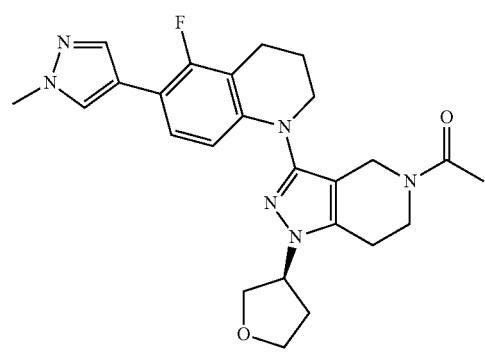
1060
-continued
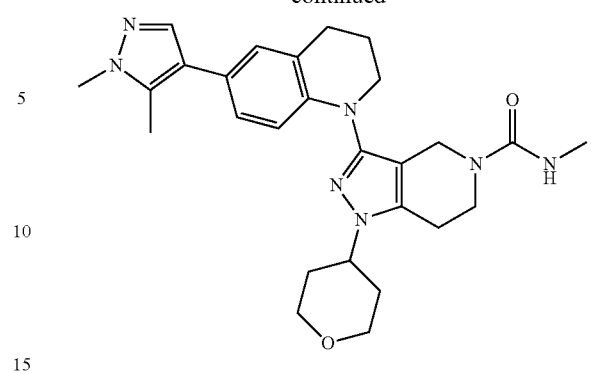
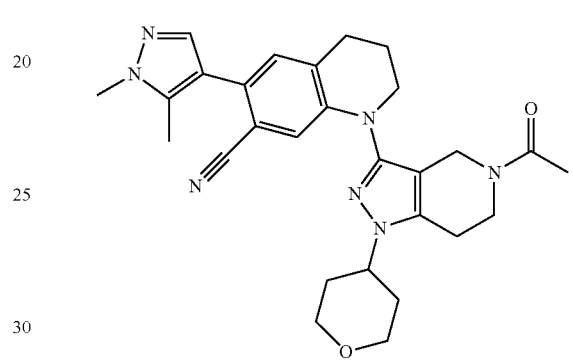
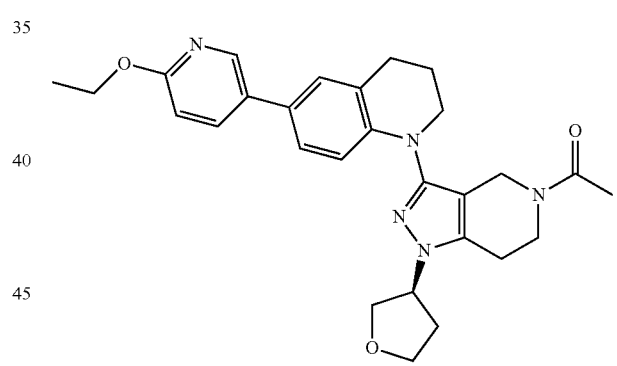
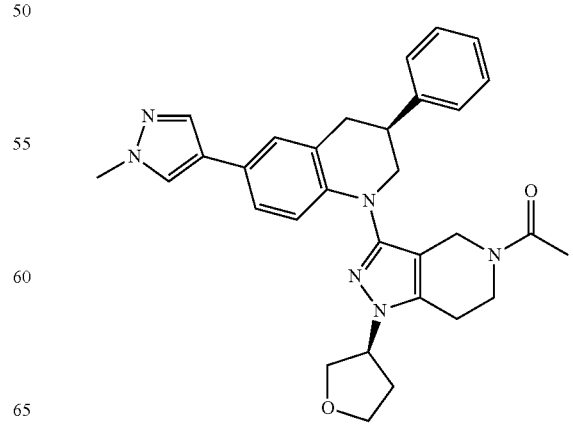

| 1061 | 1062 |
|---|---|
| -continued | -continued |
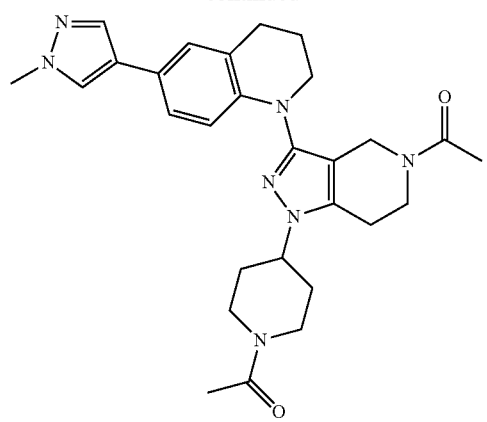
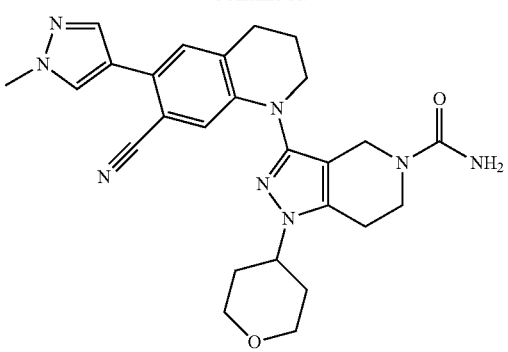
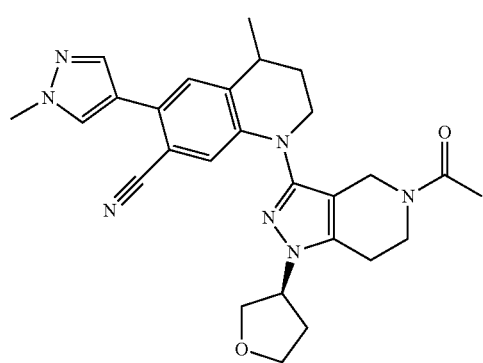
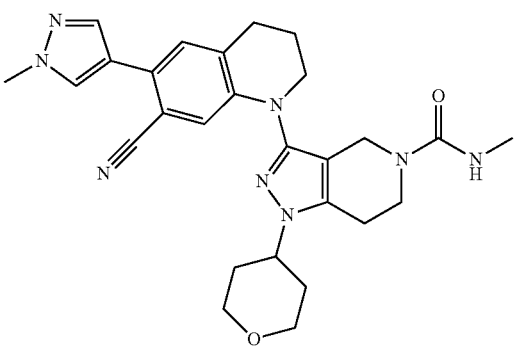
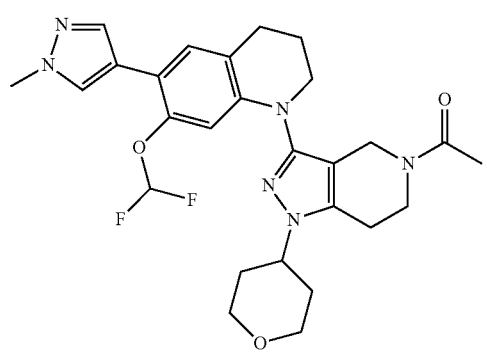
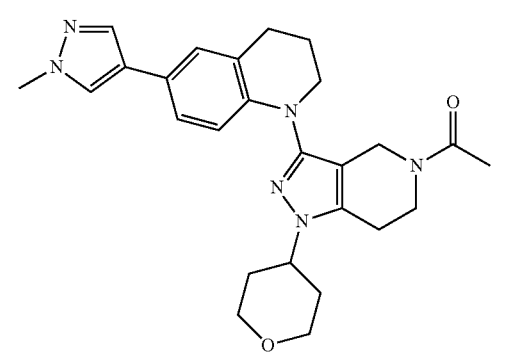
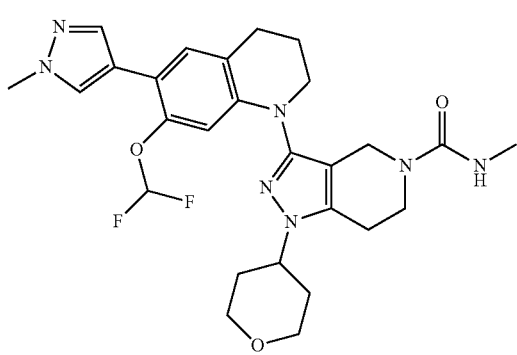
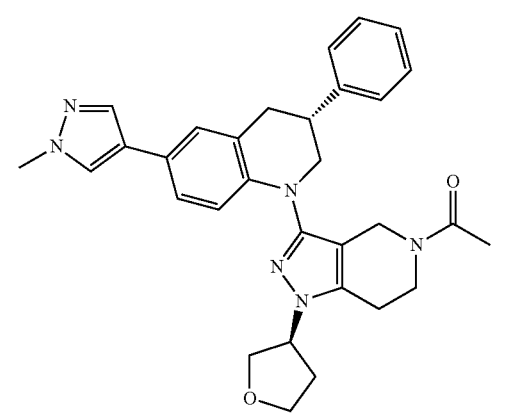

1063
-continued
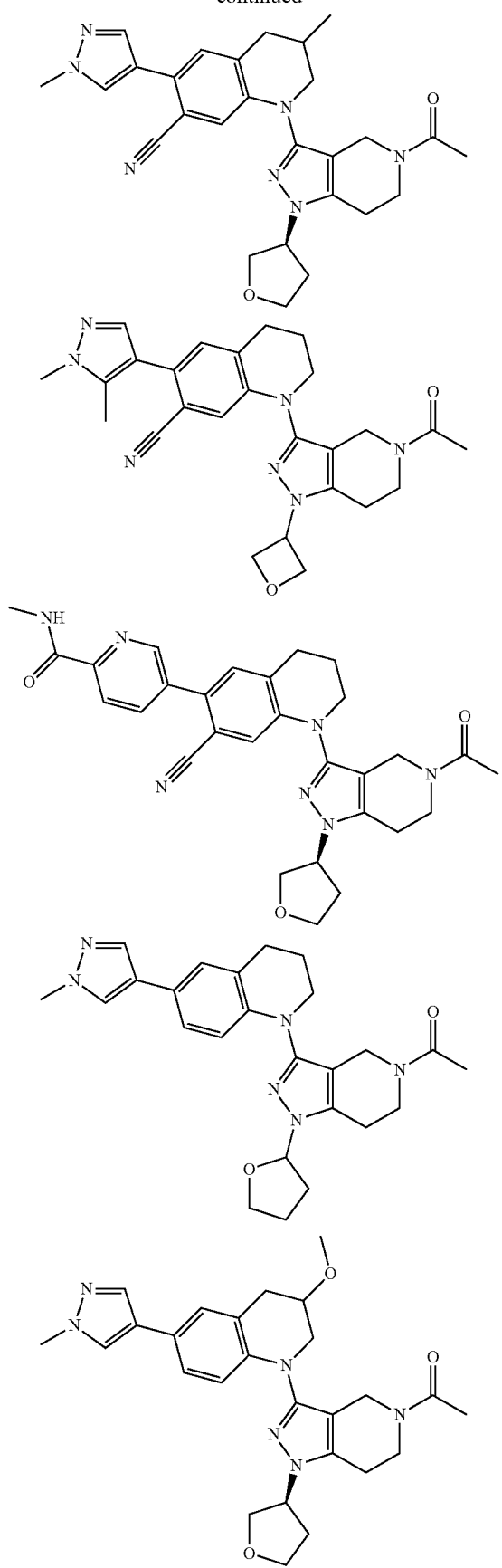
1064
-continued
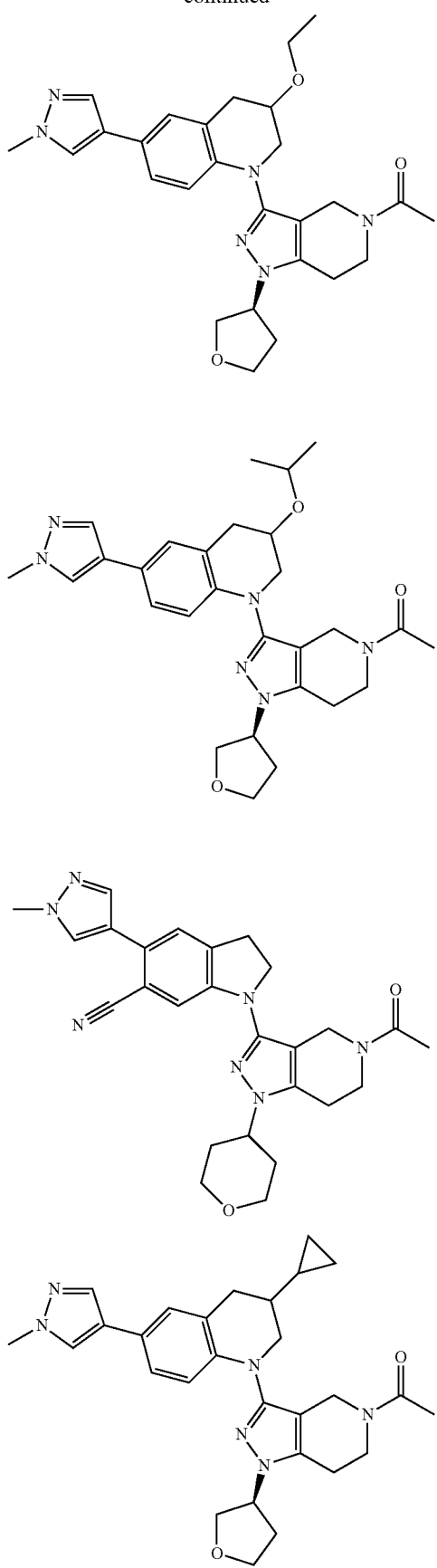

1065
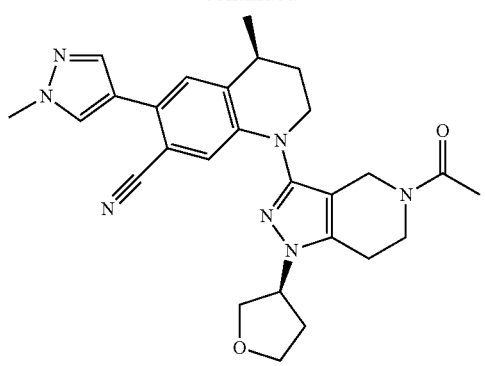
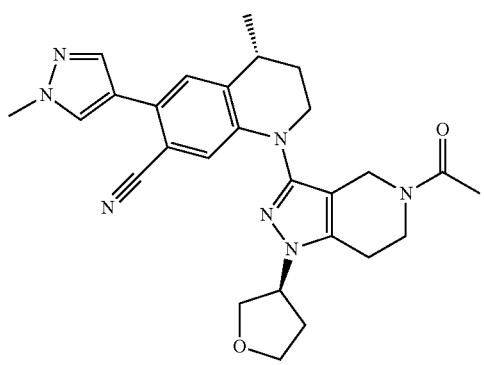
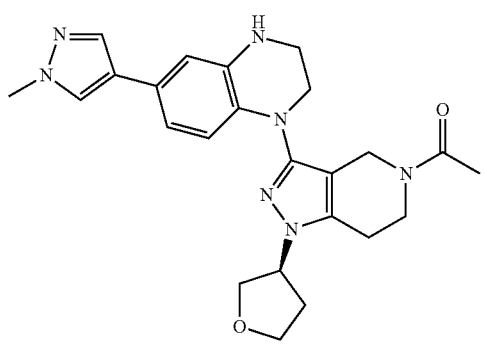
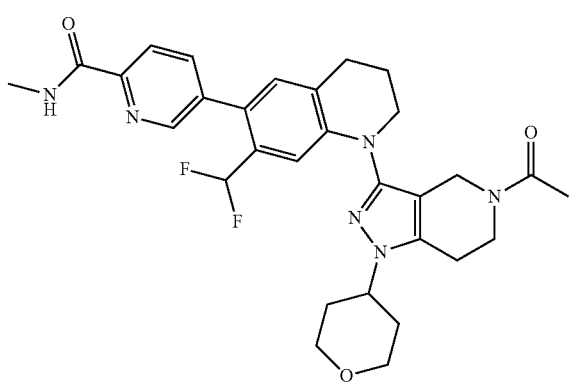
1066
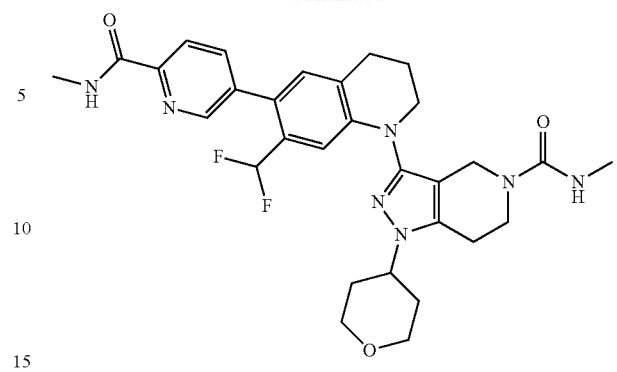
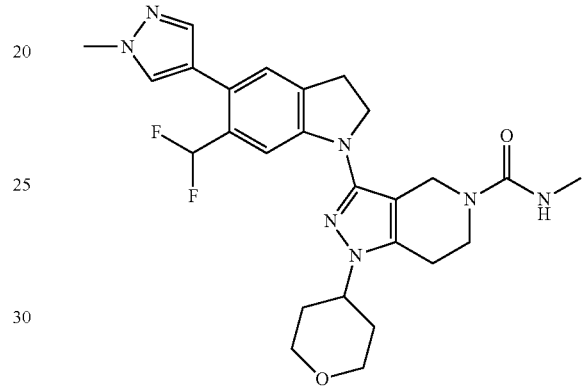
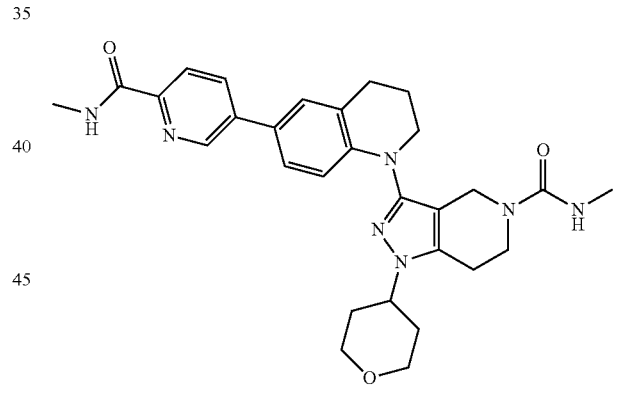
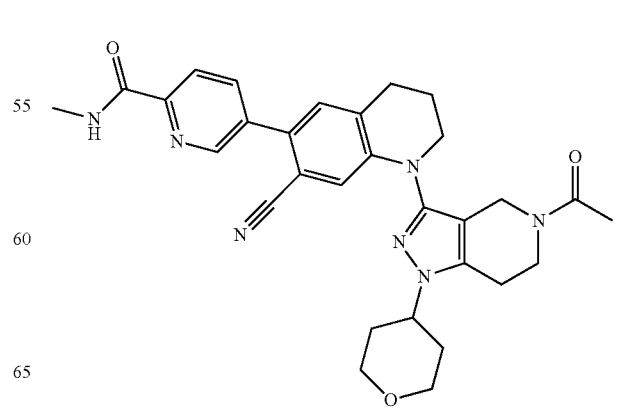

1067
-continued
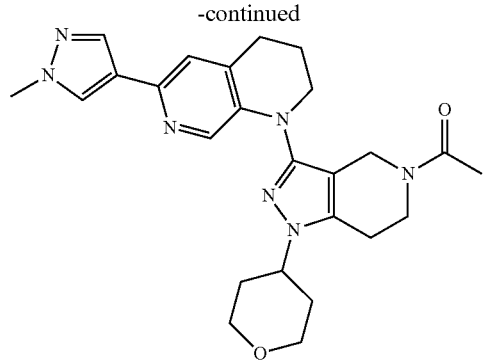
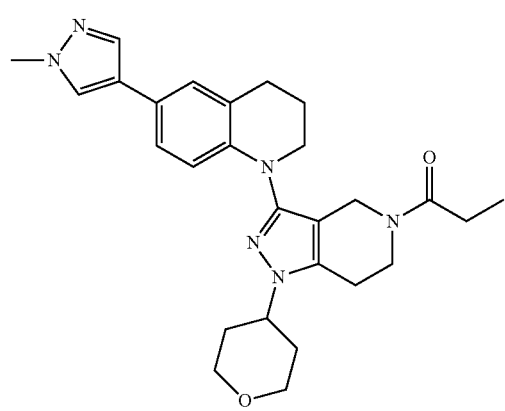
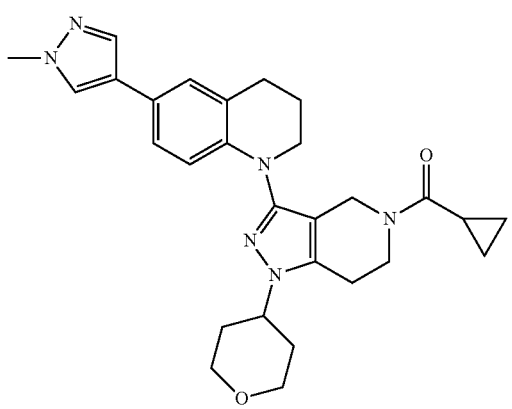
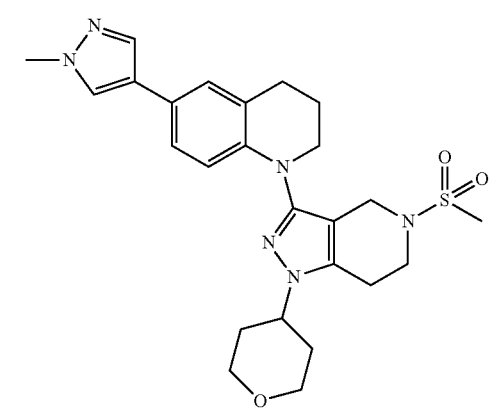
1068
-continued
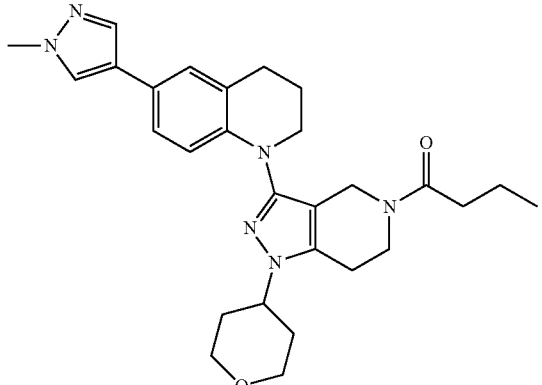
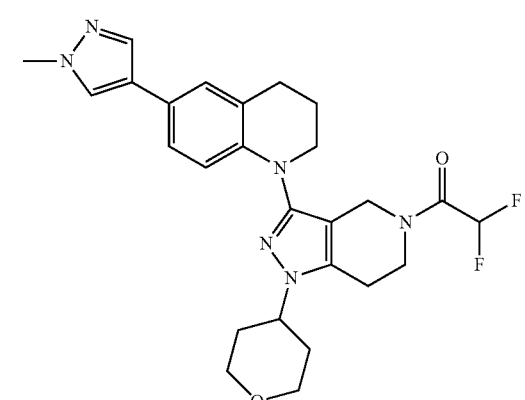
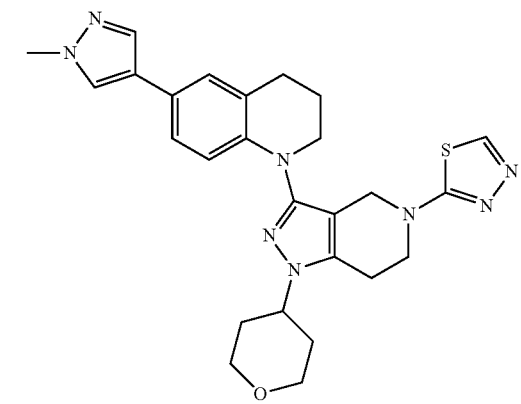
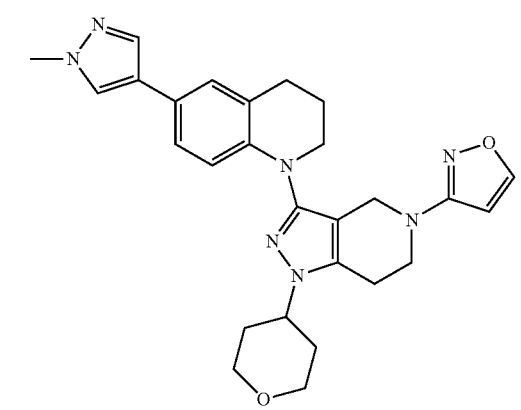

1069
-continued
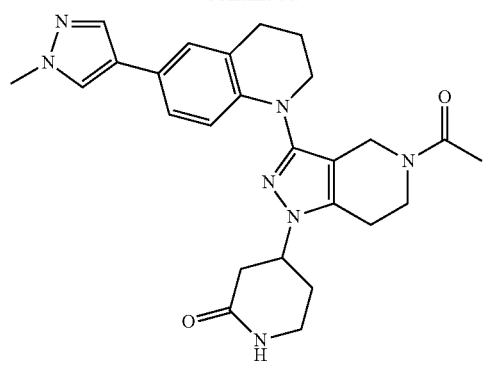
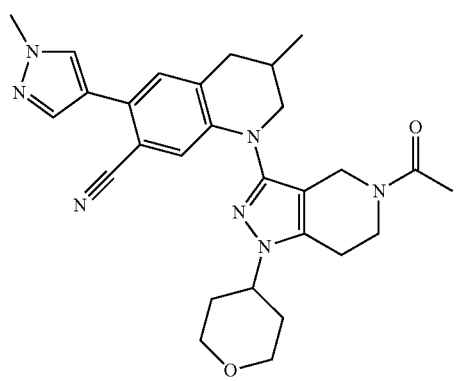
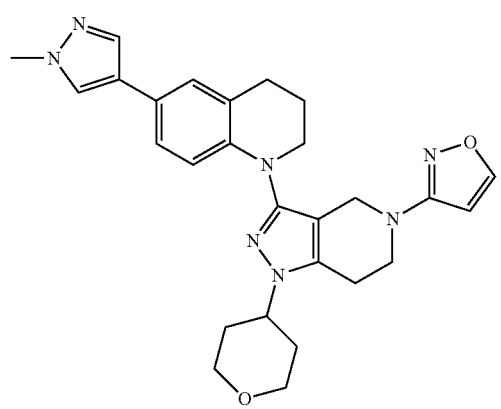
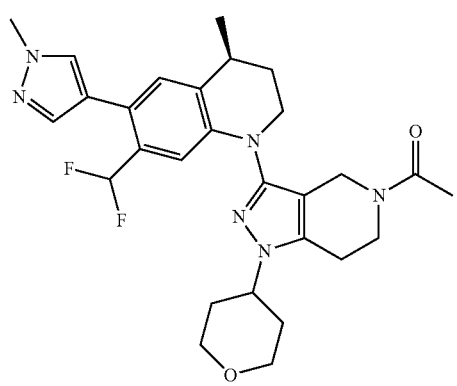
1070
-continued
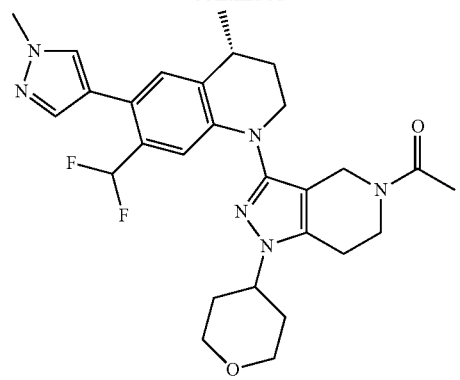
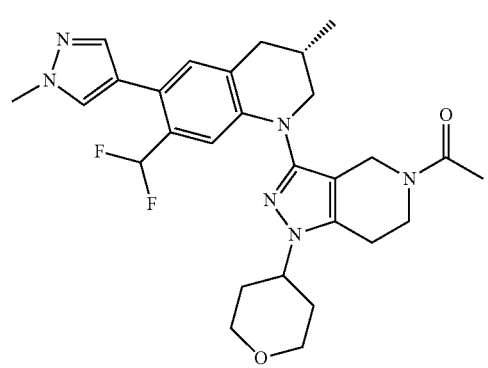
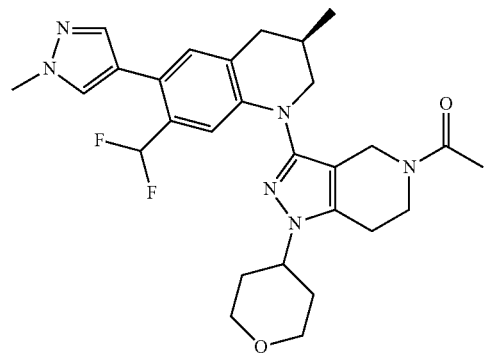
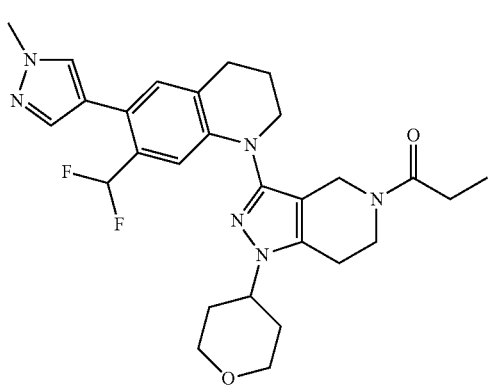

1071
-continued
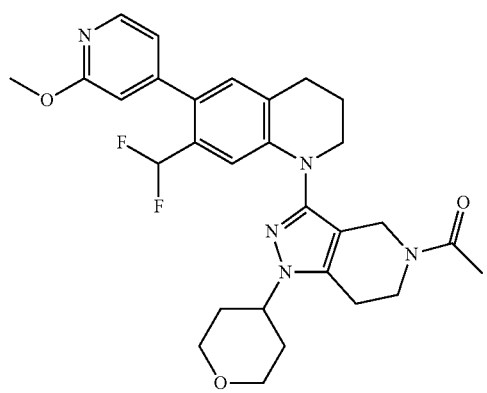
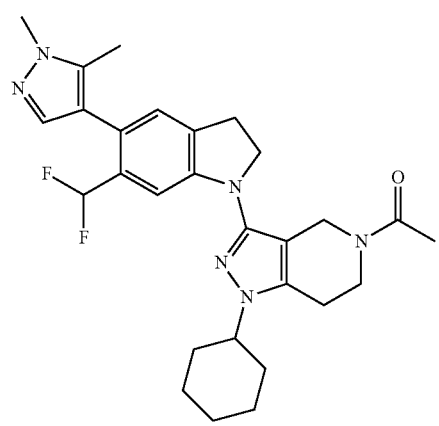
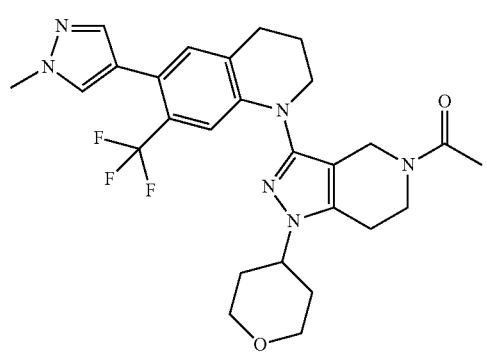
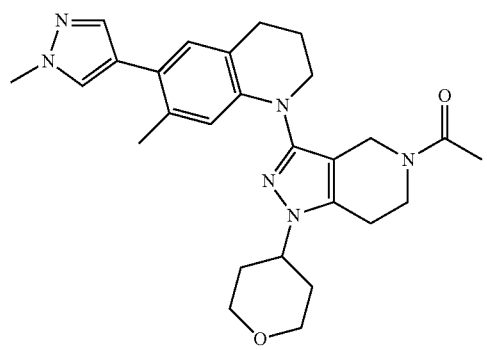
1072
-continued
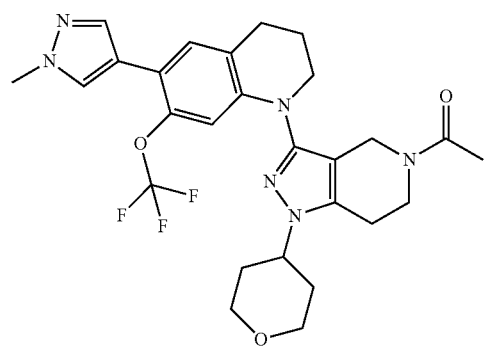
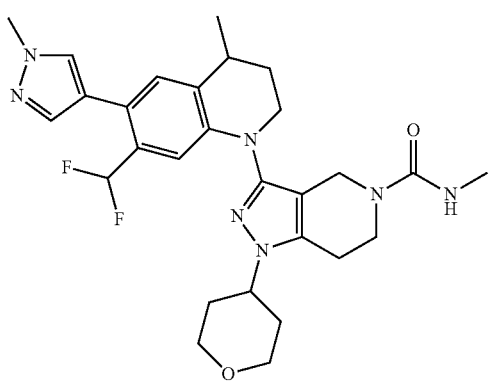
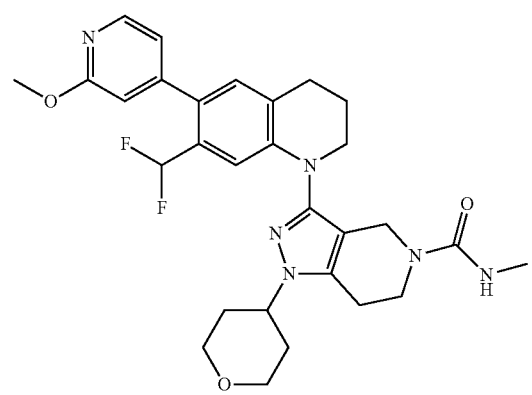
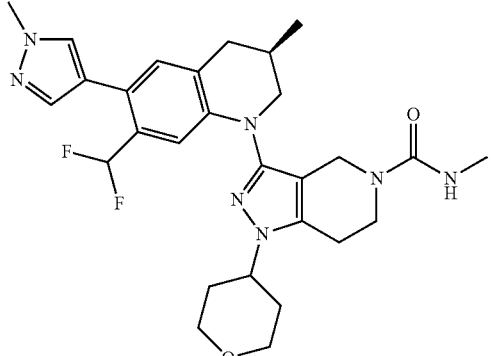

1073
-continued
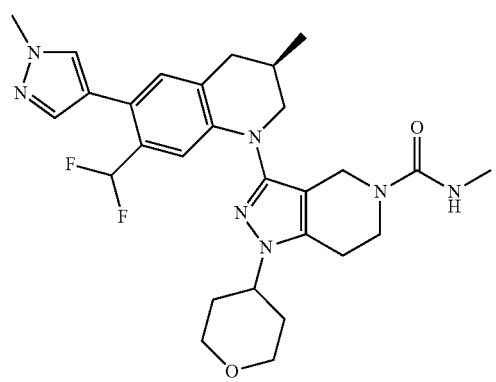
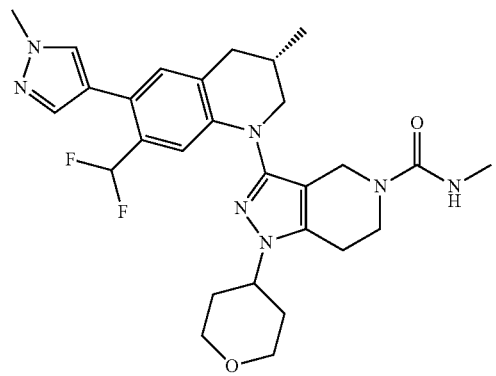
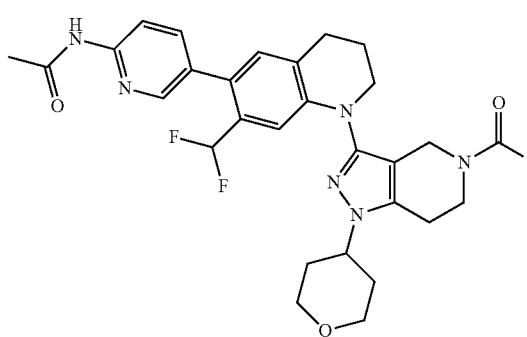
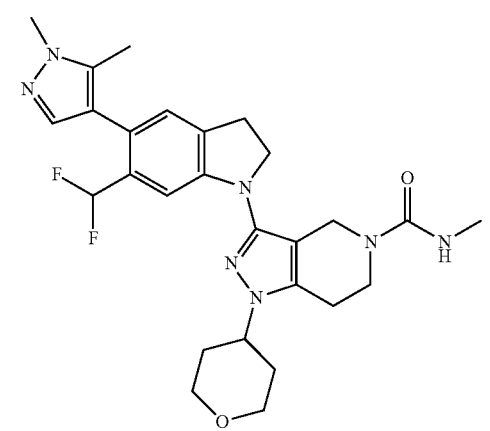
1074
-continued
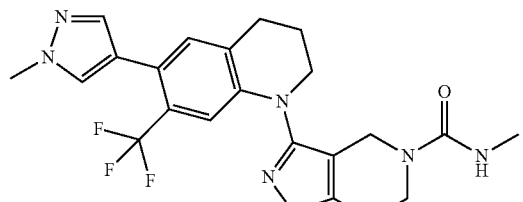
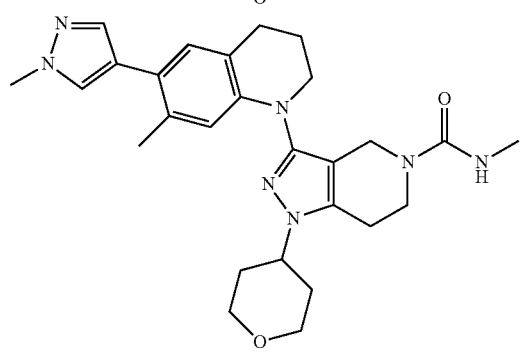
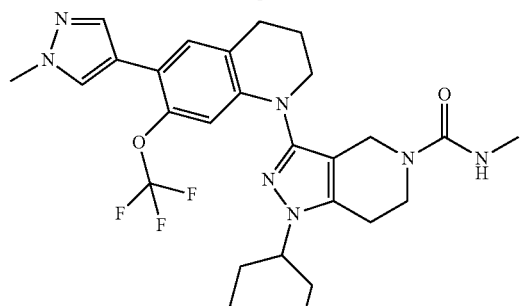
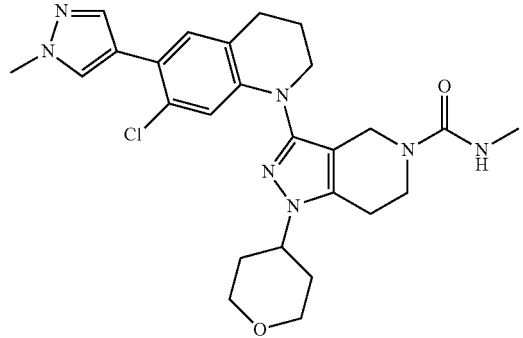
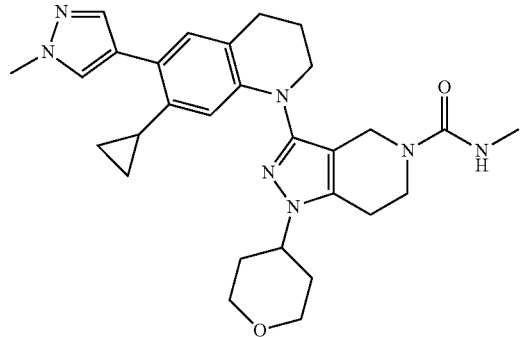

1075
-continued
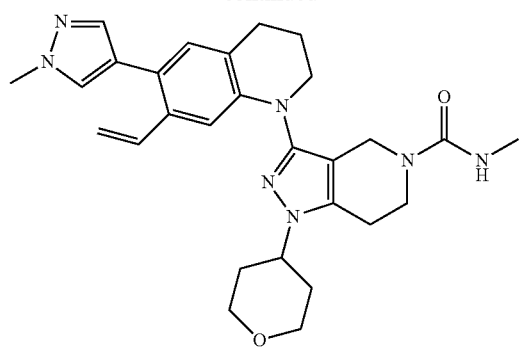
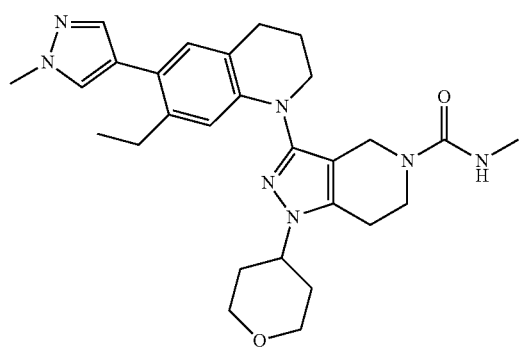
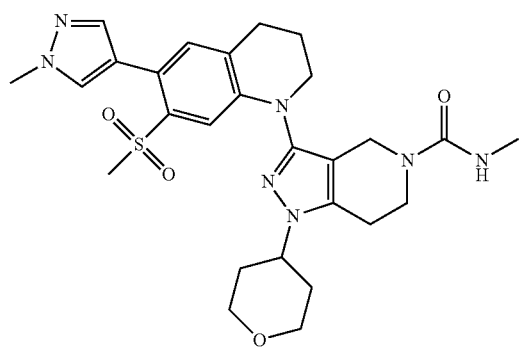
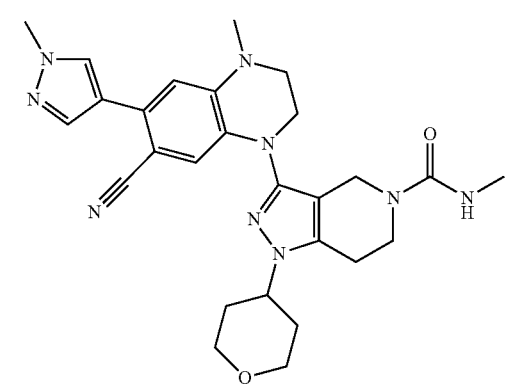
1076
-continued
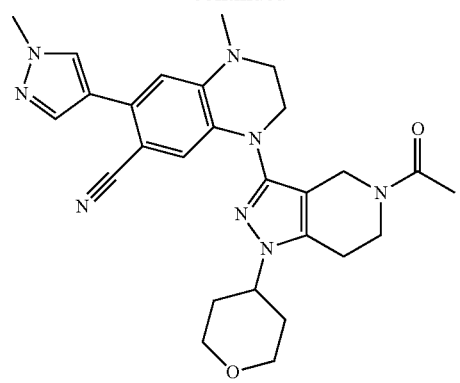
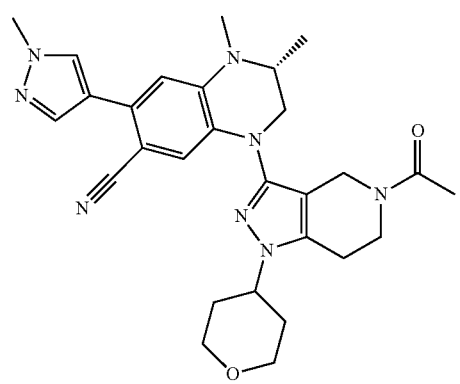
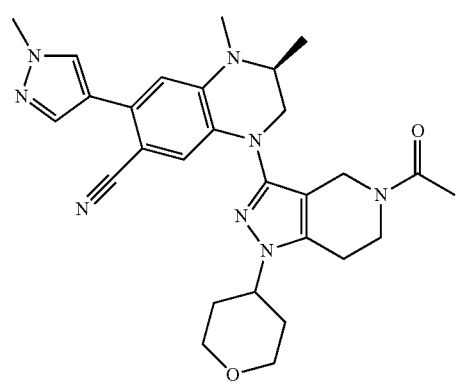
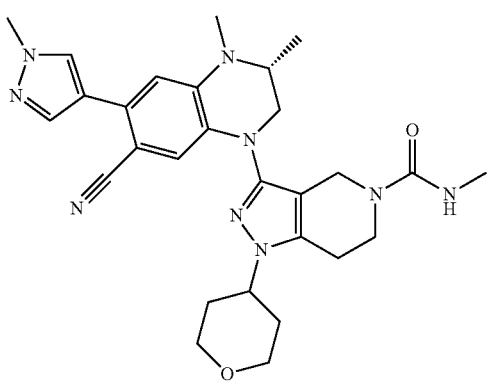

1077
-continued
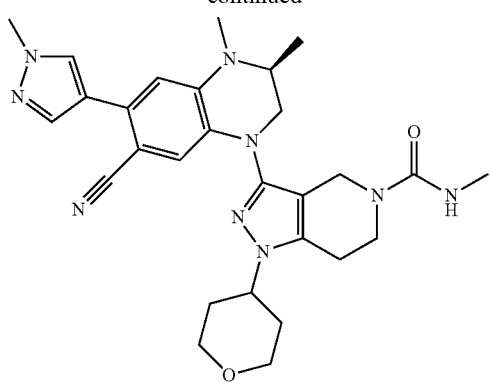
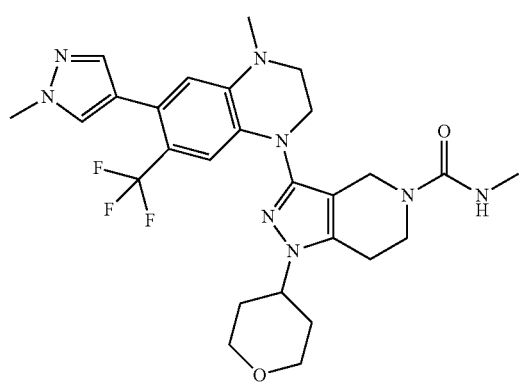
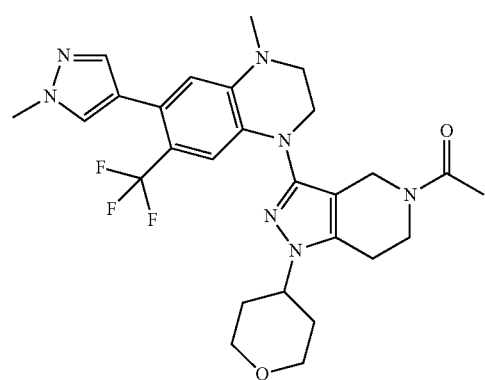
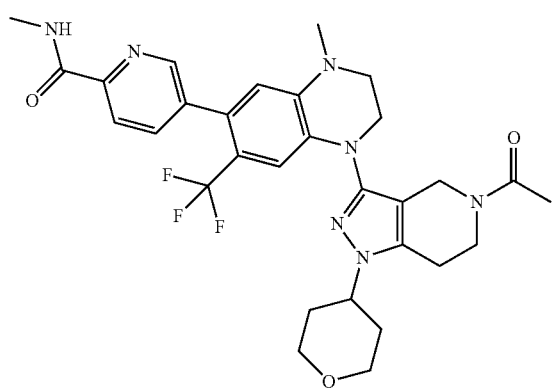
1078
-continued
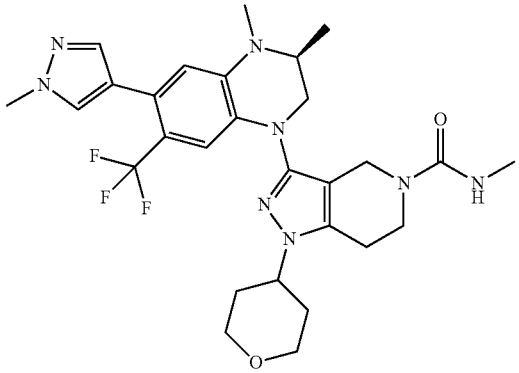
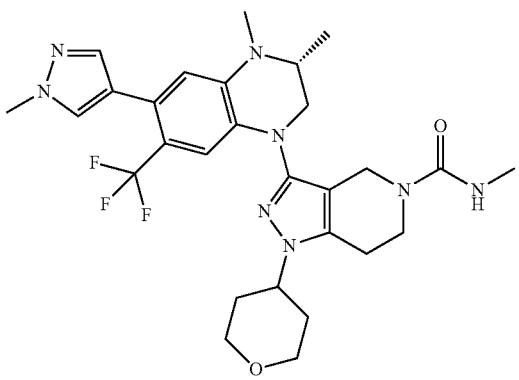
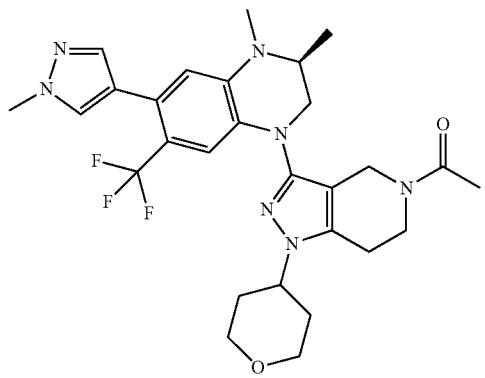
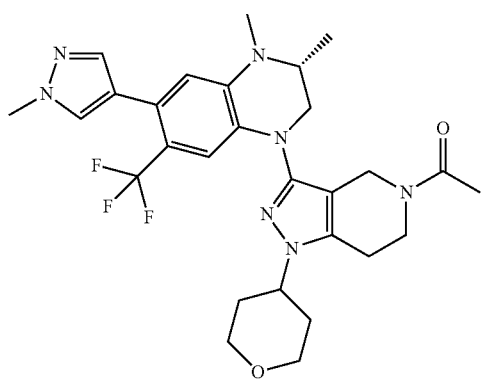

| 1079 | 1080 |
|---|---|
| -continued | -continued |
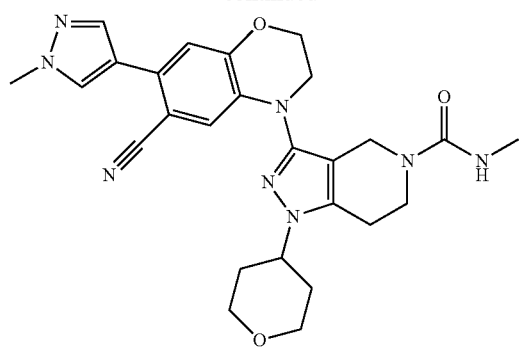
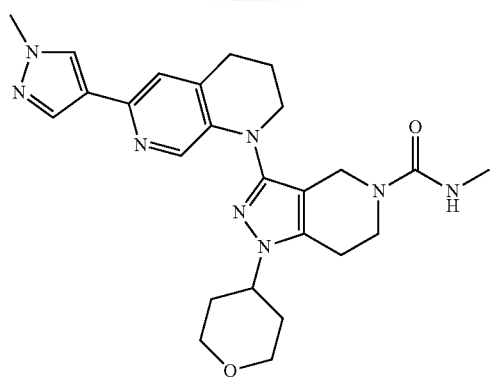
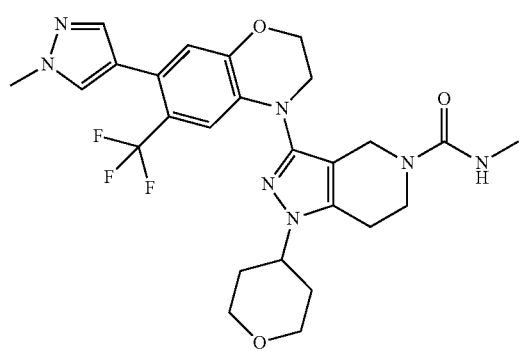
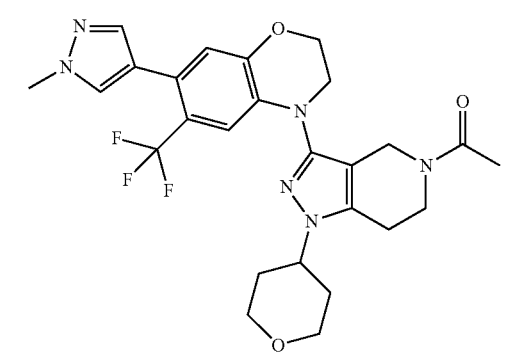
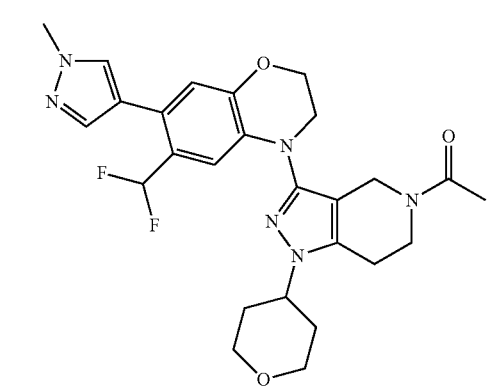
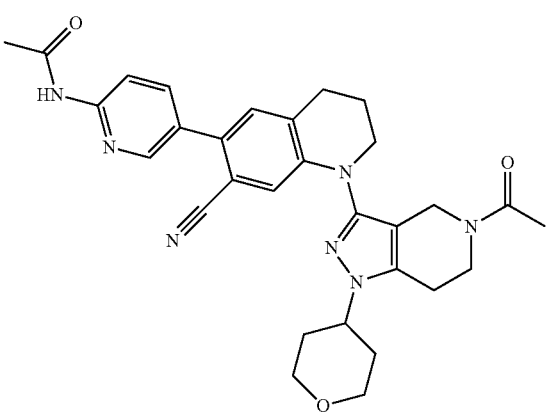

| 1081 | 1082 |
|---|---|
| -continued | -continued |
| 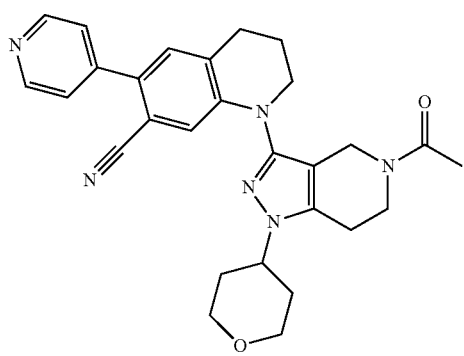 | 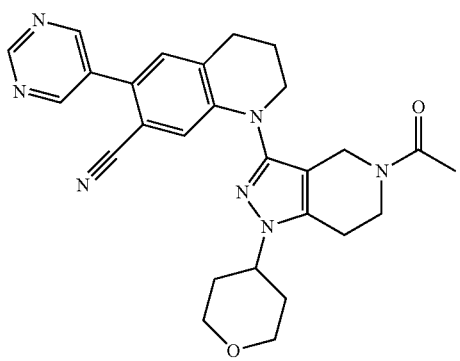 |
| 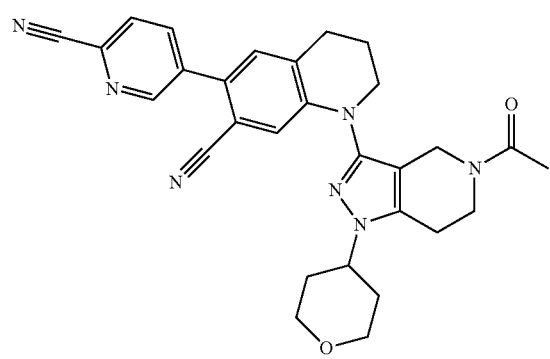 | 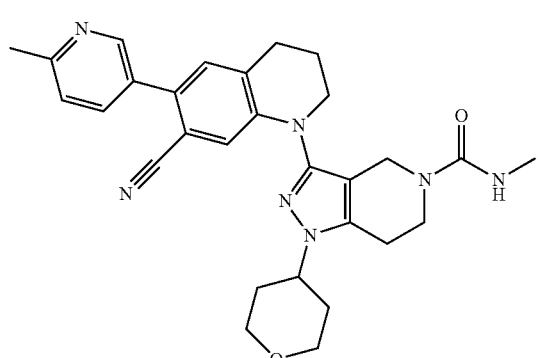 |
| 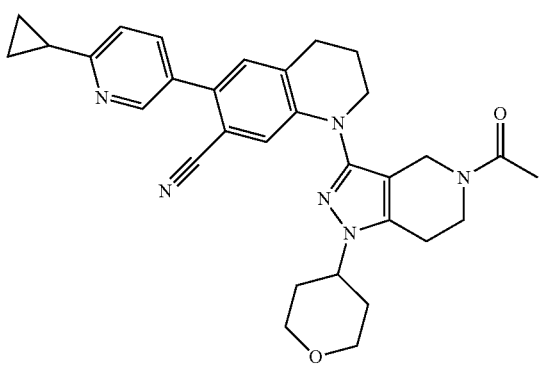 | 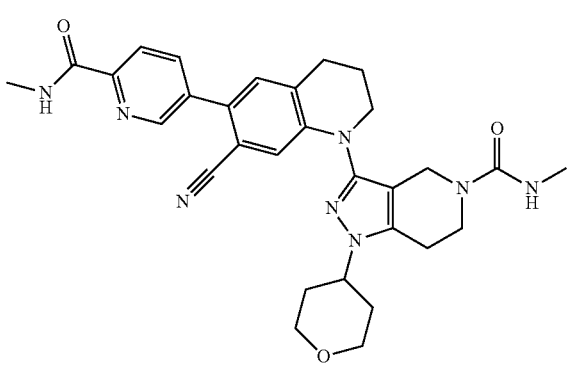 |
| 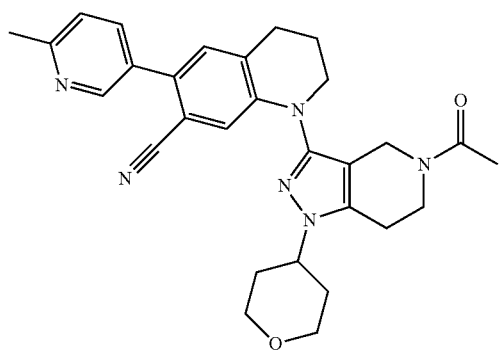 | 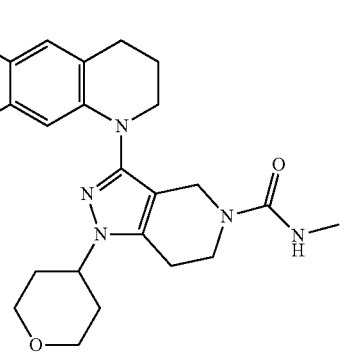 |

1083
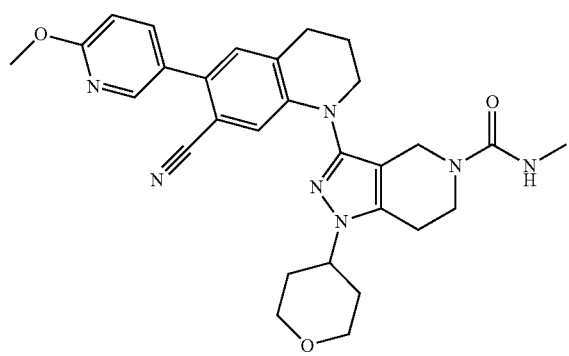
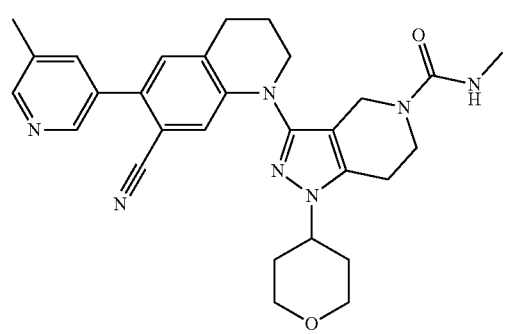
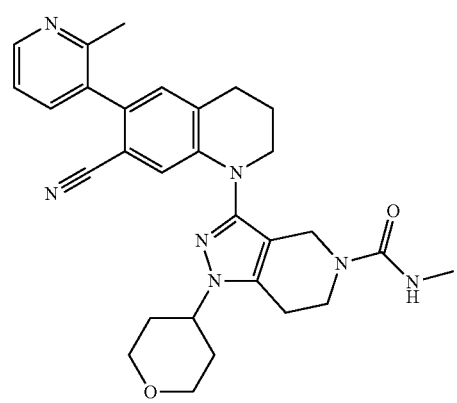
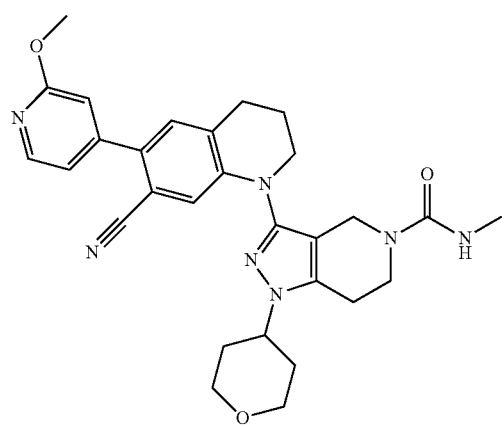
1084
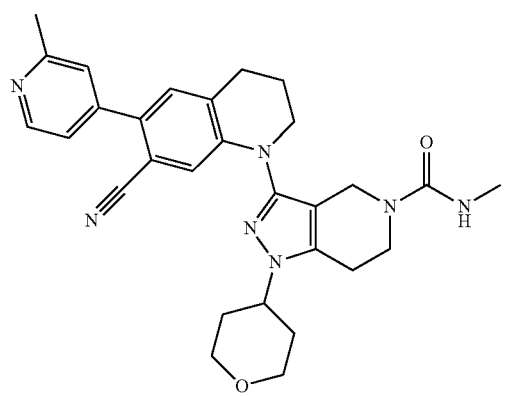
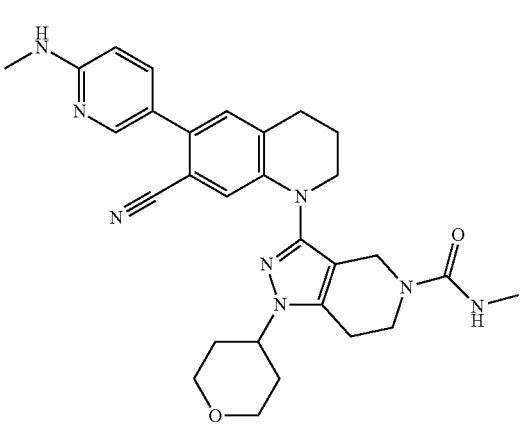
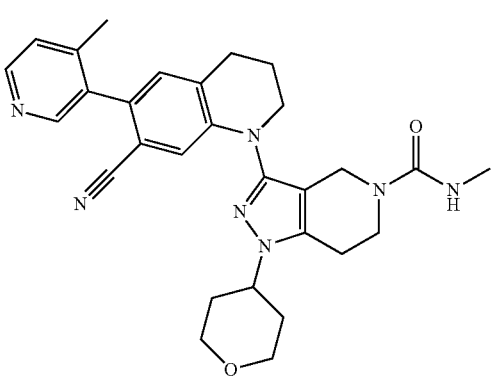
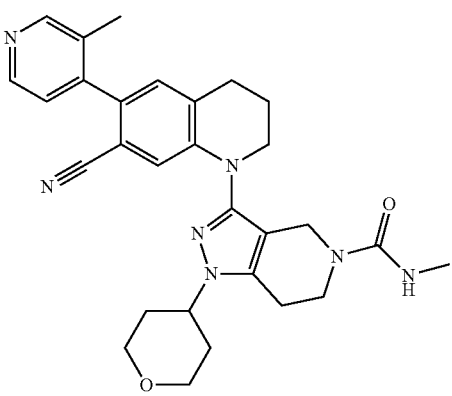

1085
-continued
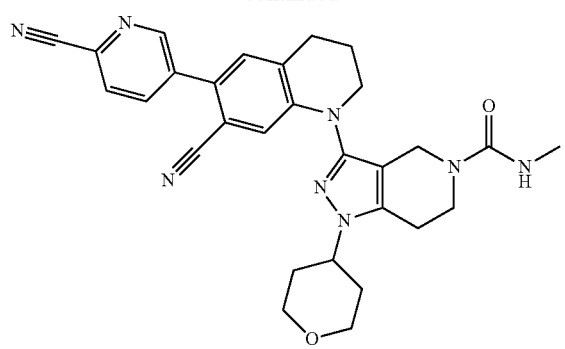
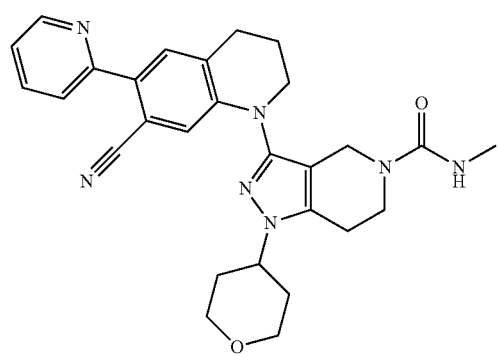
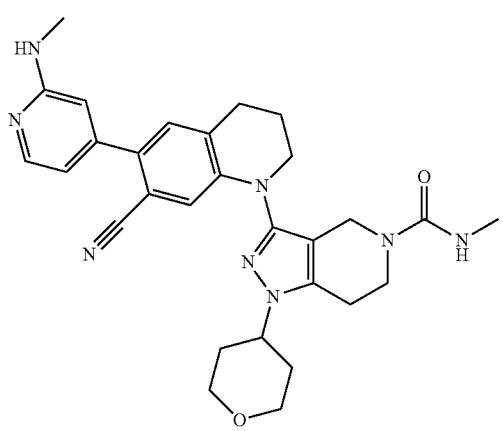
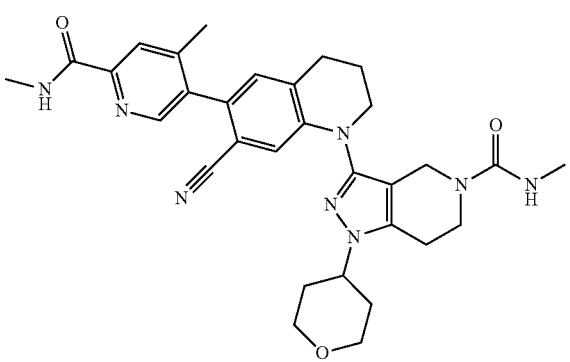
1086
-continued
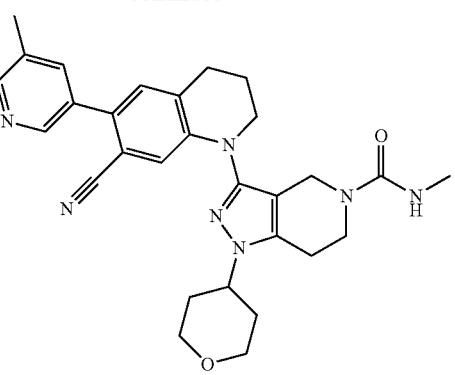
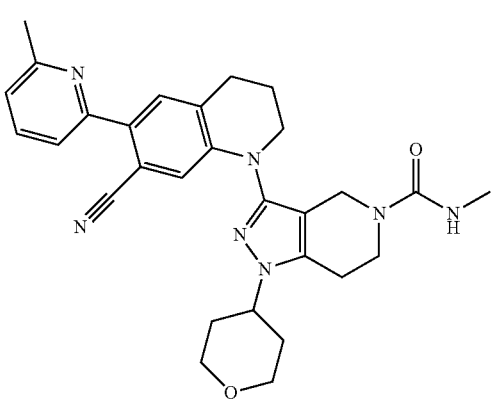
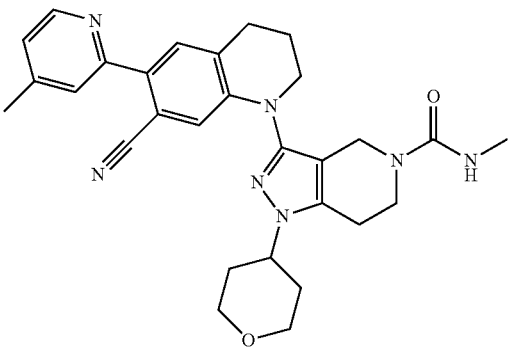
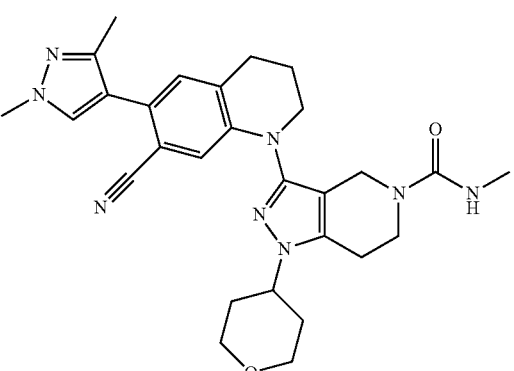

1087
-continued
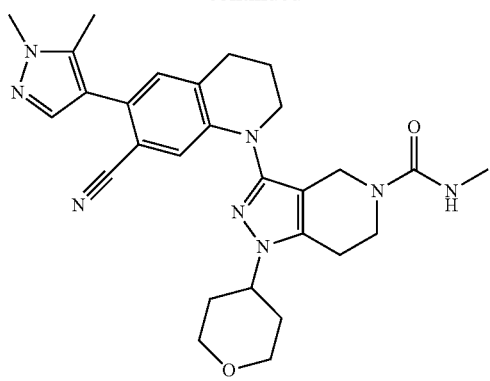
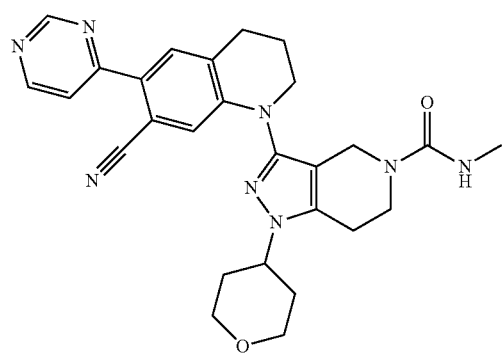
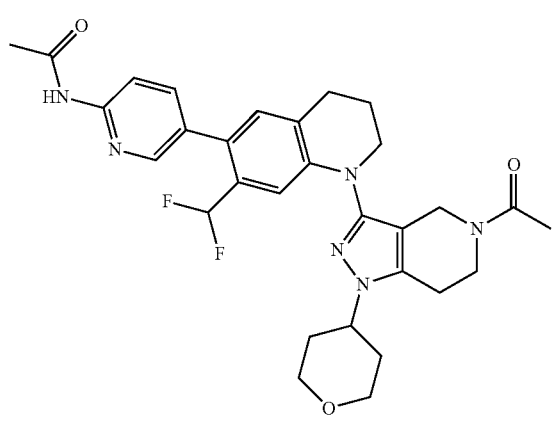
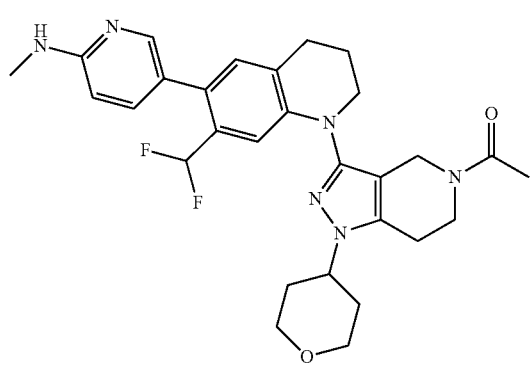
1088
-continued
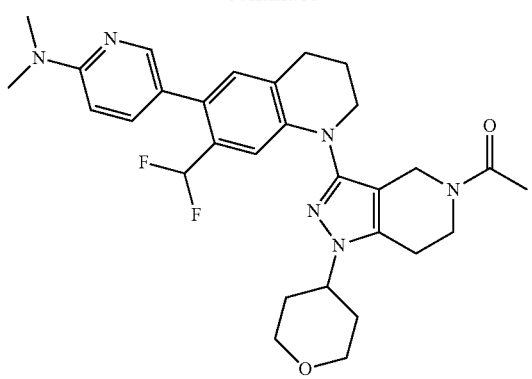
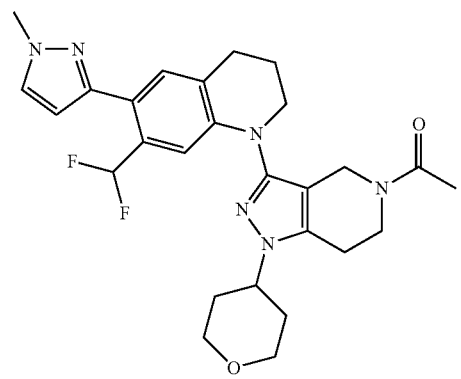
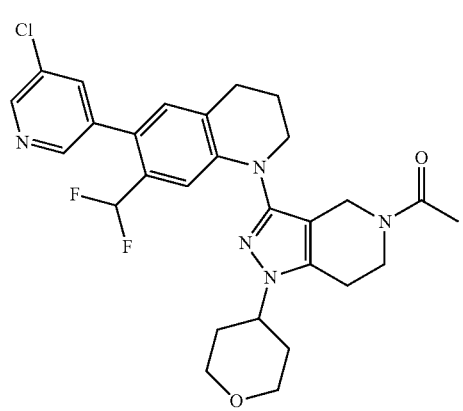
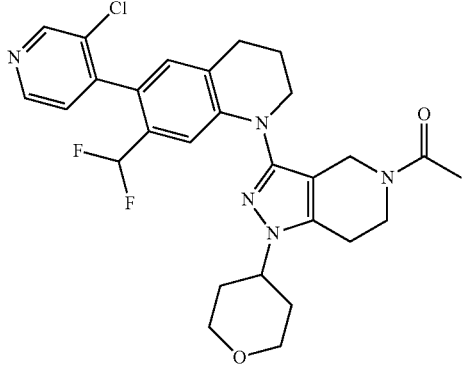

| 1089 -continued | 1090 -continued |
|---|---|
| 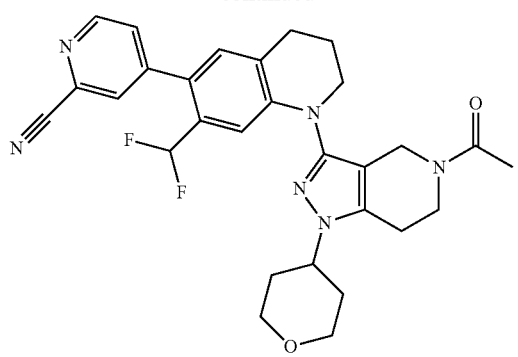 | 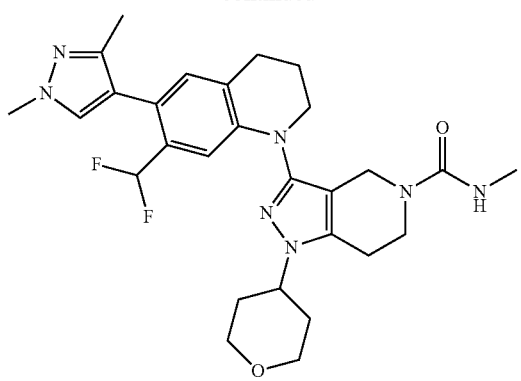 |
| 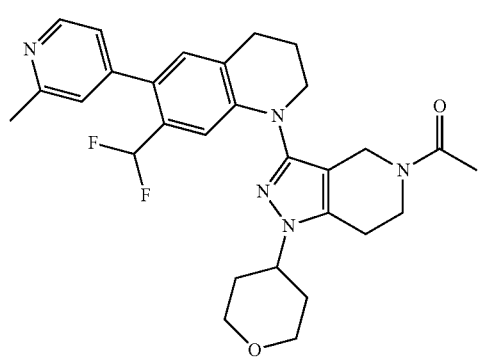 | 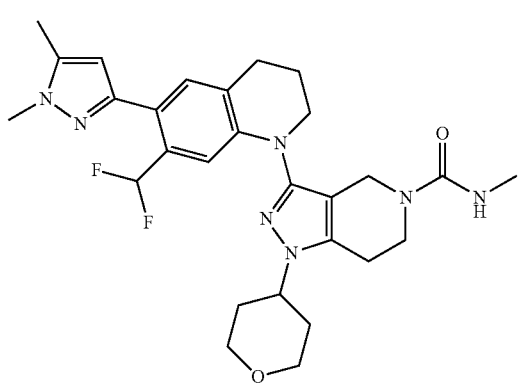 |
| 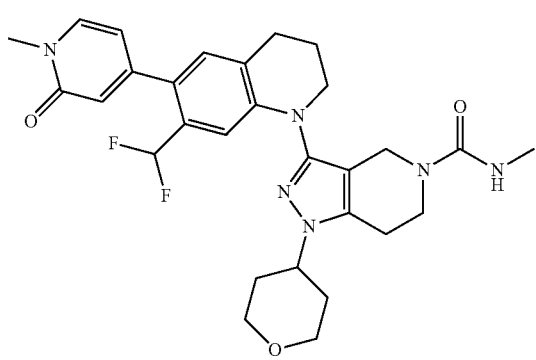 | 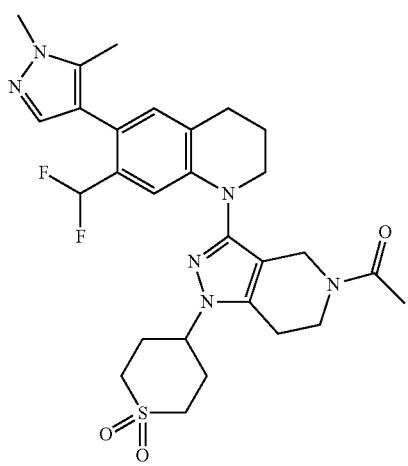 |
| 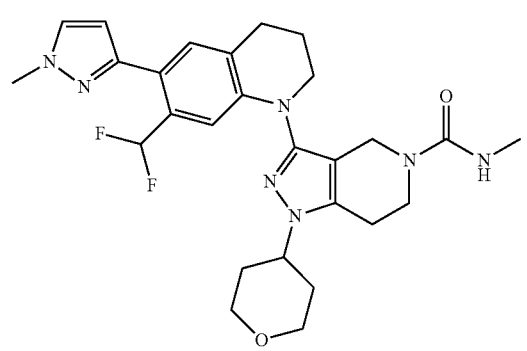 | 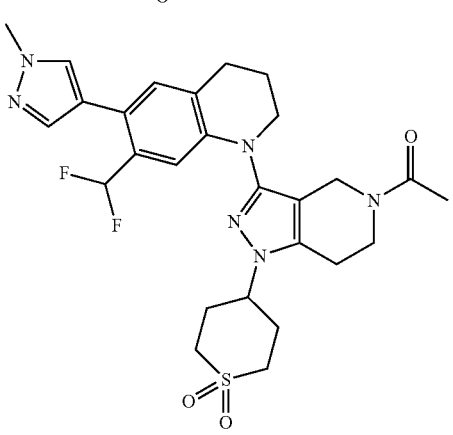 |

1091
-continued
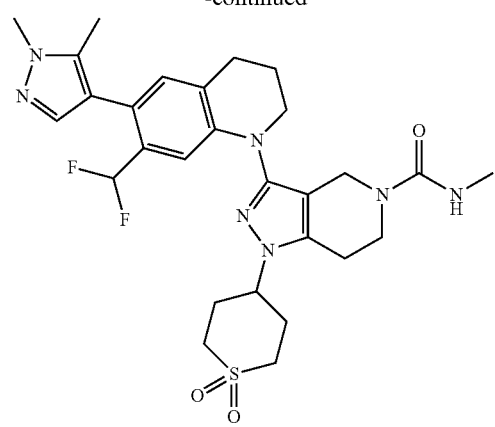
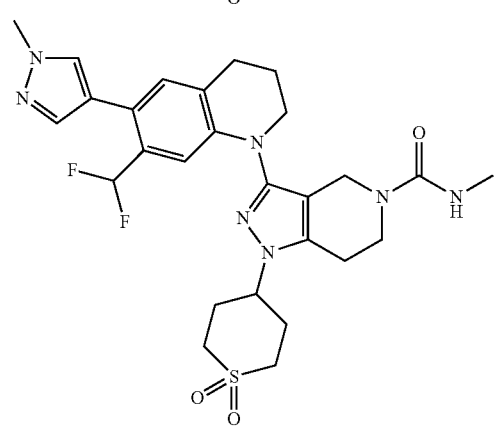
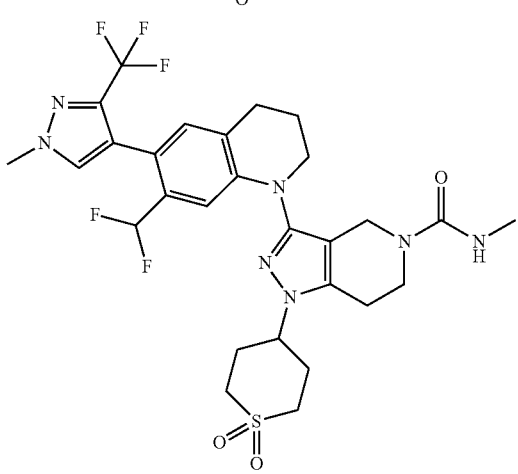
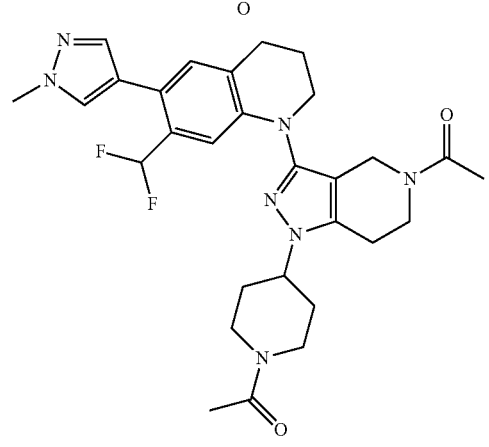
1092
-continued
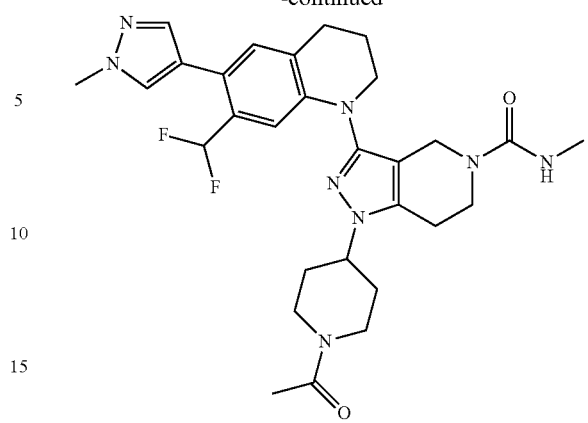
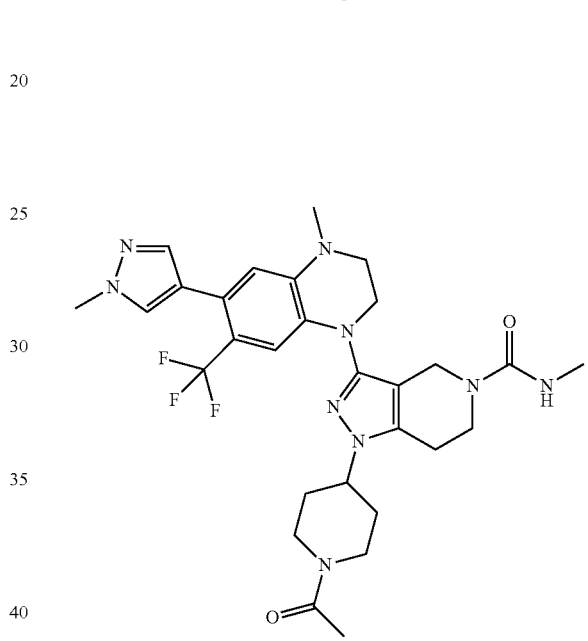
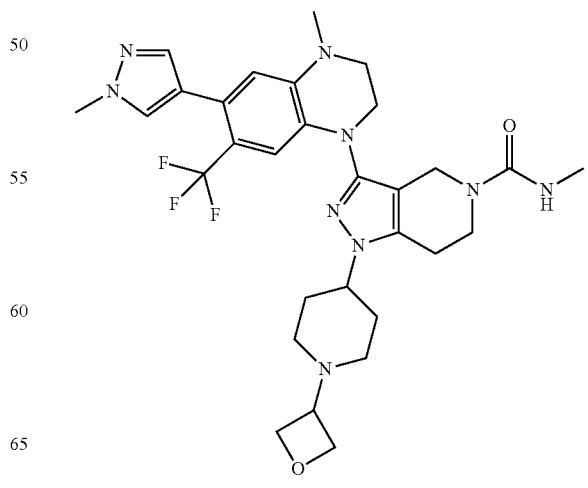

1093
-continued
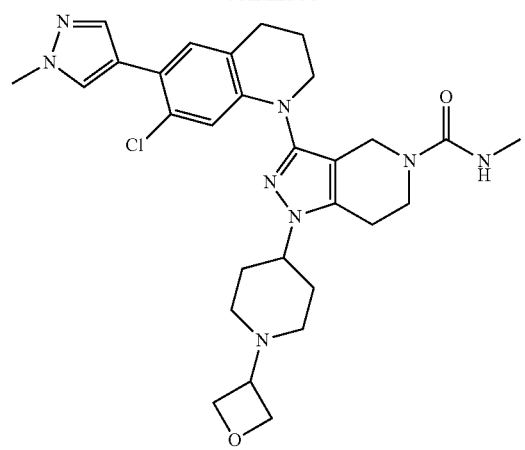
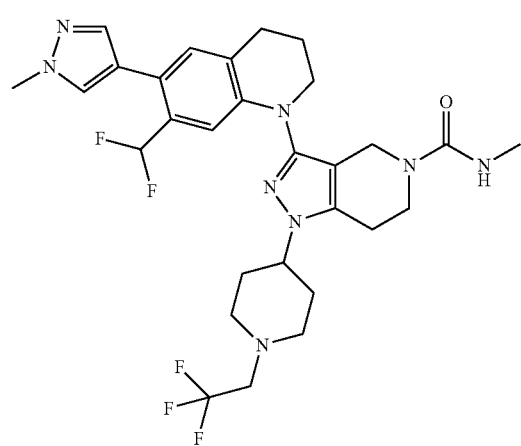
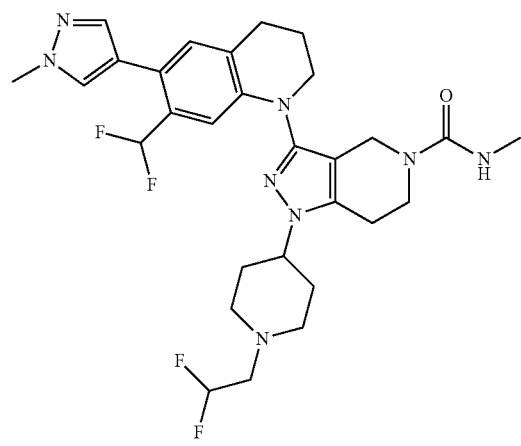
1094
-continued
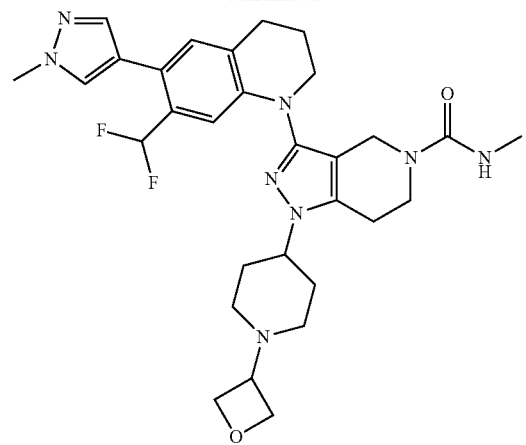
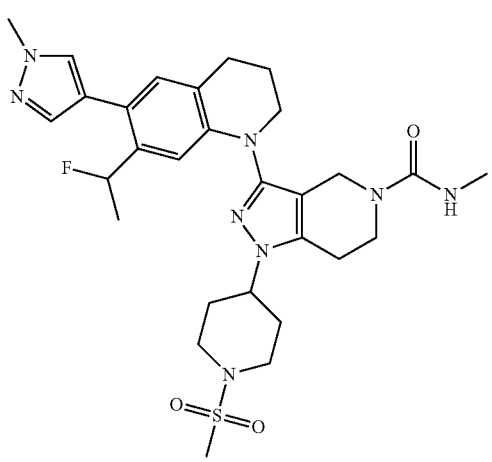
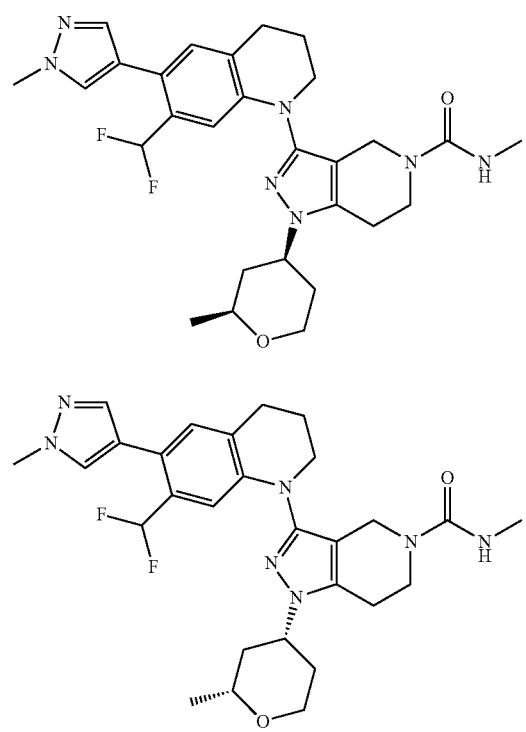

1095
-continued
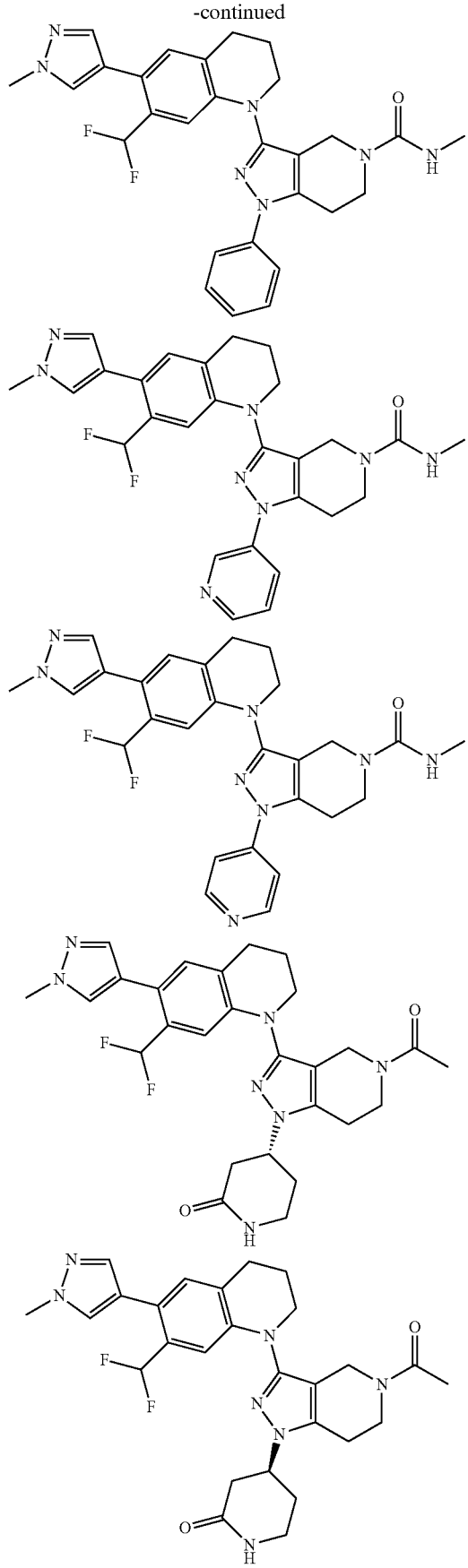
1096
-continued
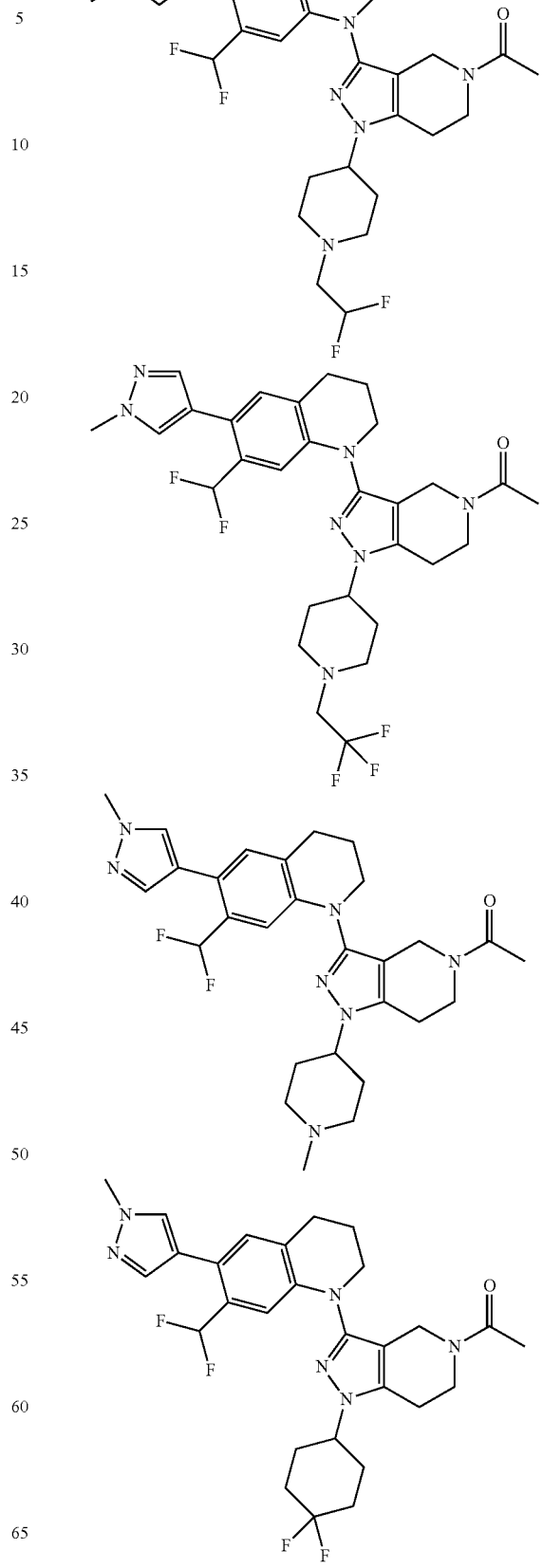

1097
-continued
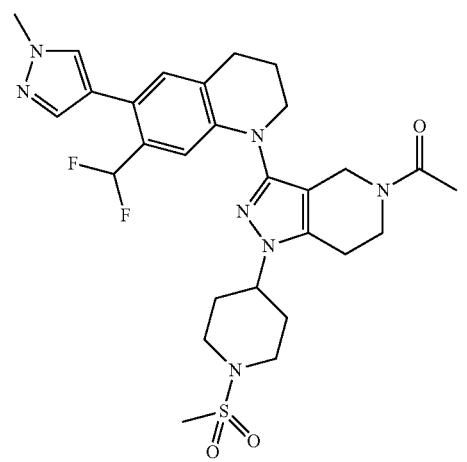
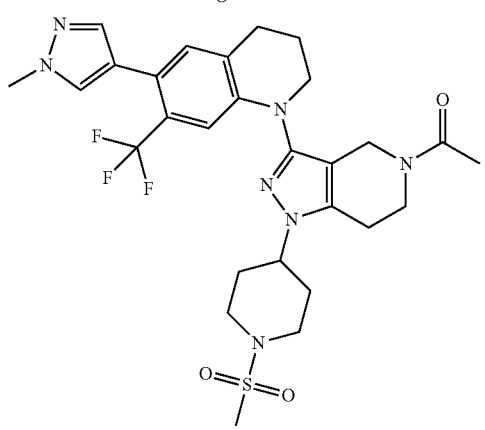
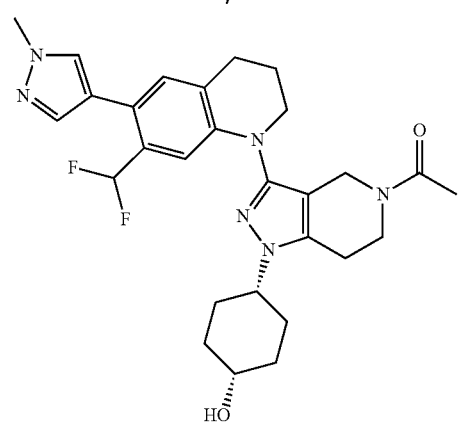
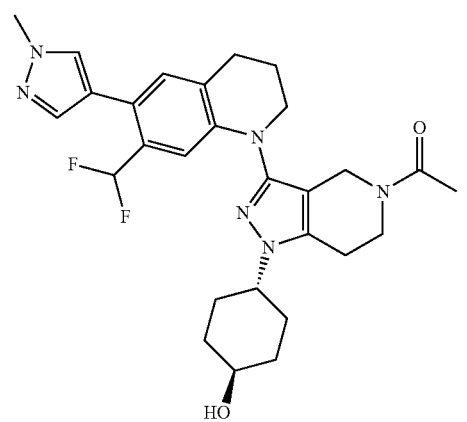
1098
-continued
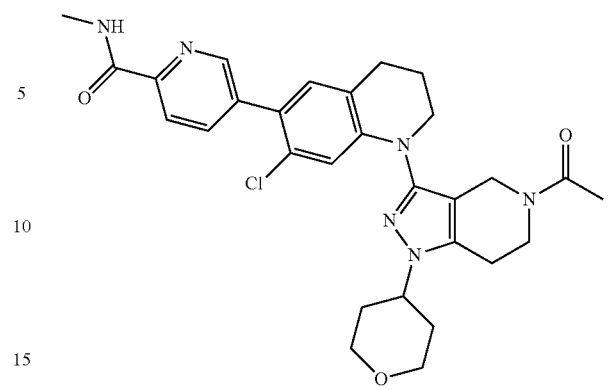
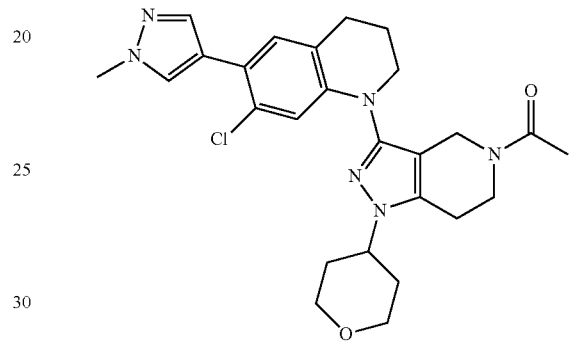
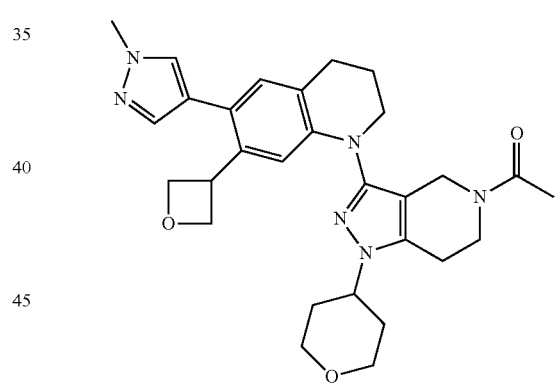
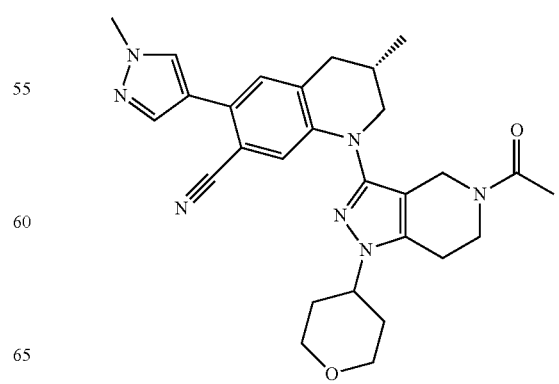

1099
-continued
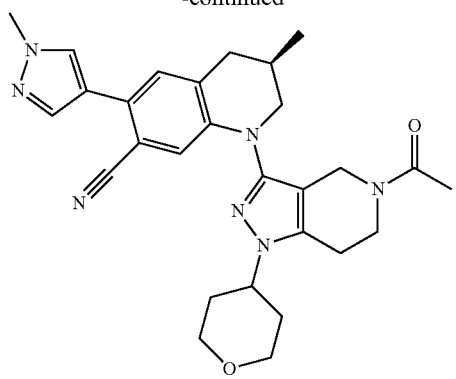
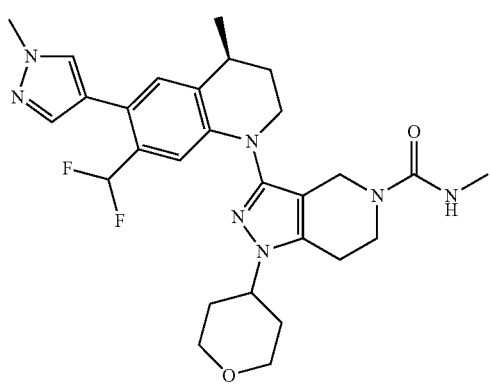
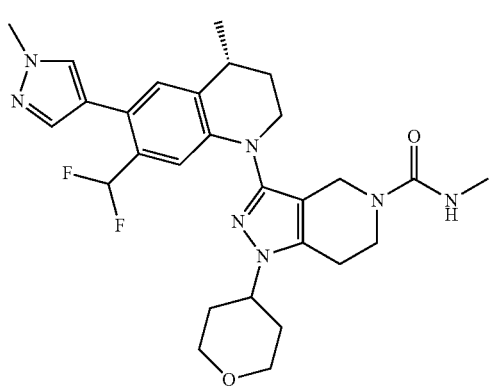
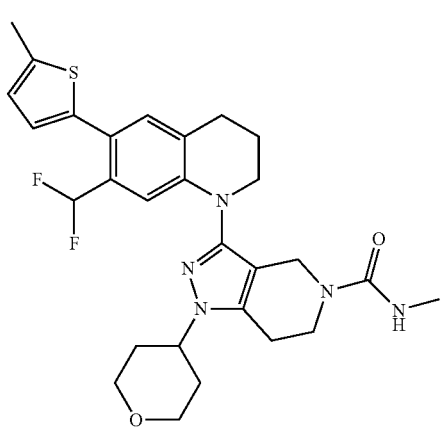
1100
-continued
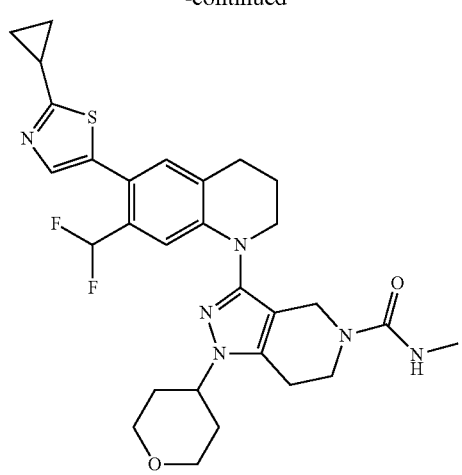
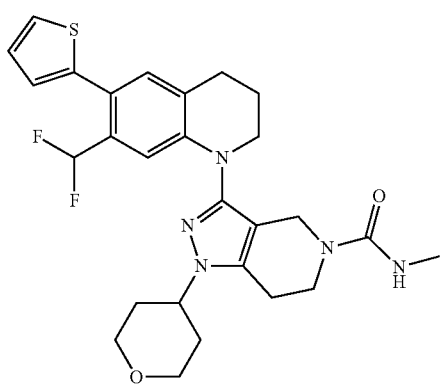
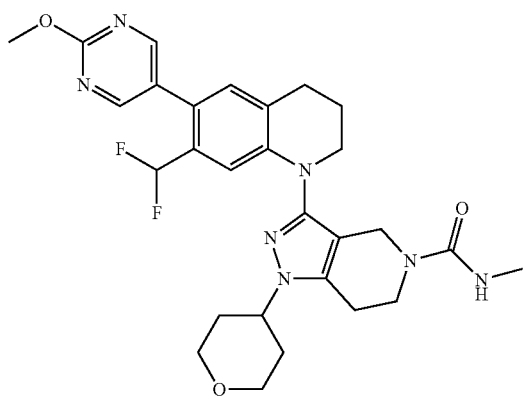
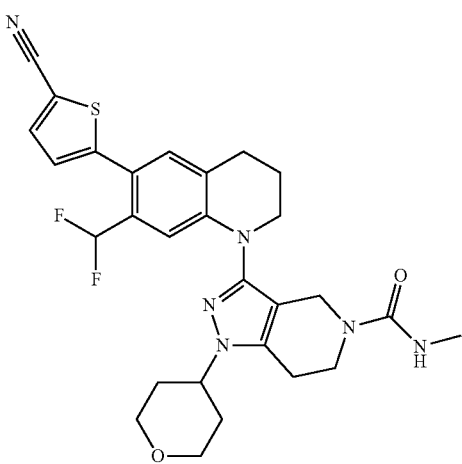

1101
-continued
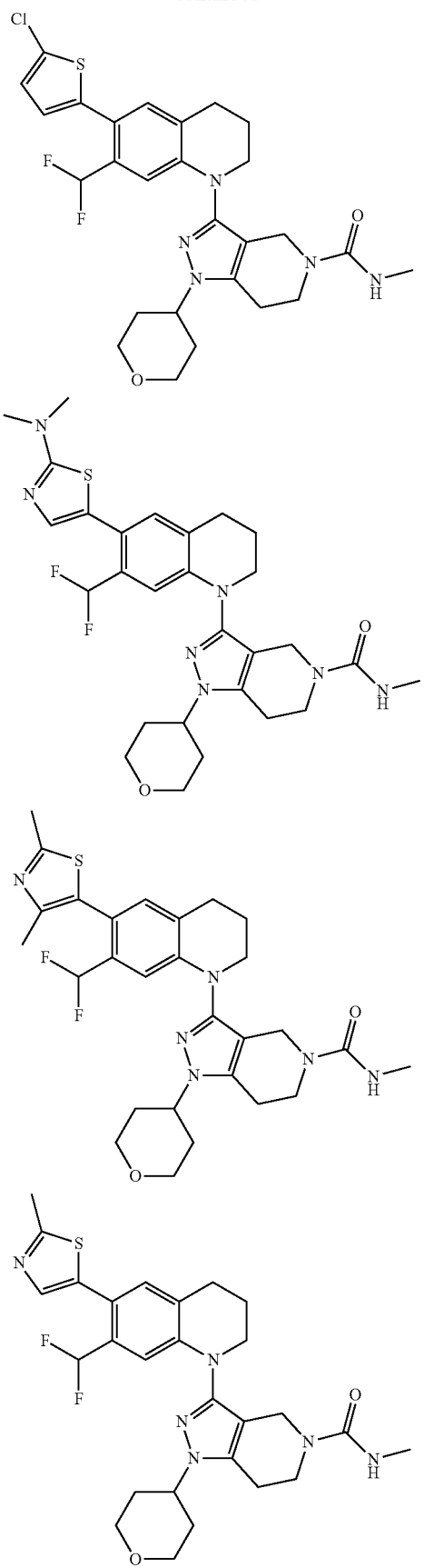
1102
-continued
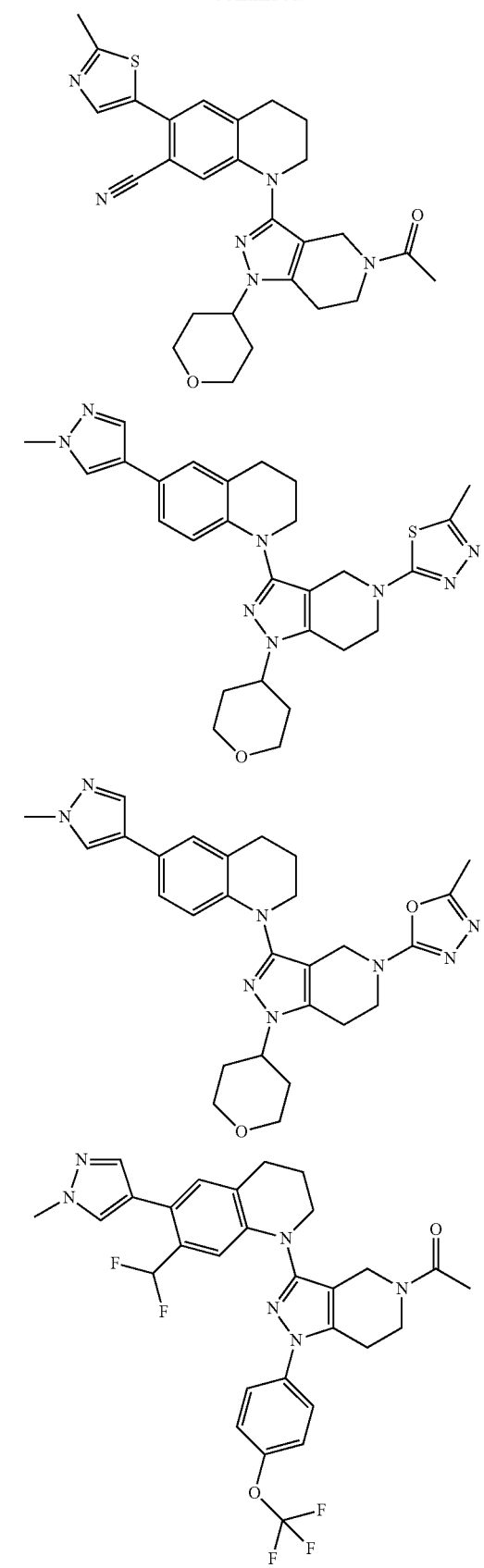

1103
-continued
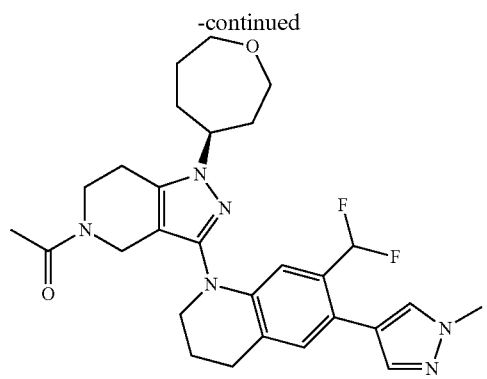
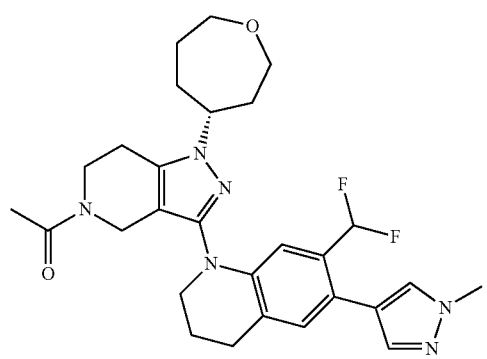
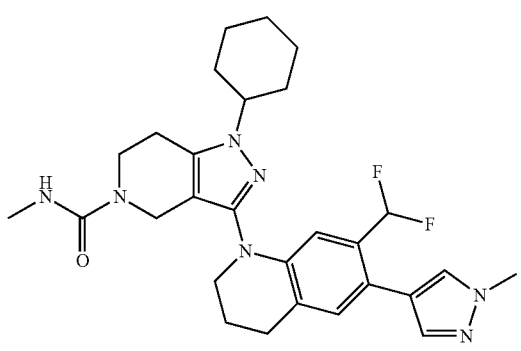
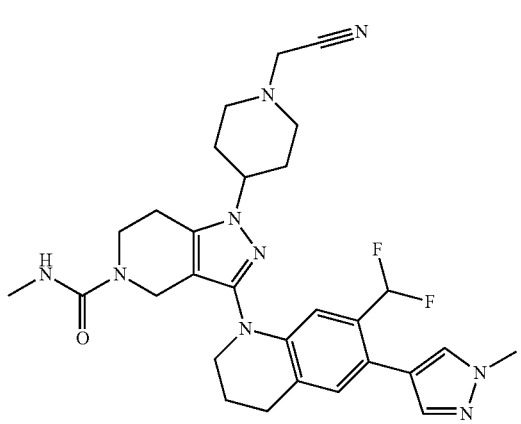
1104
-continued
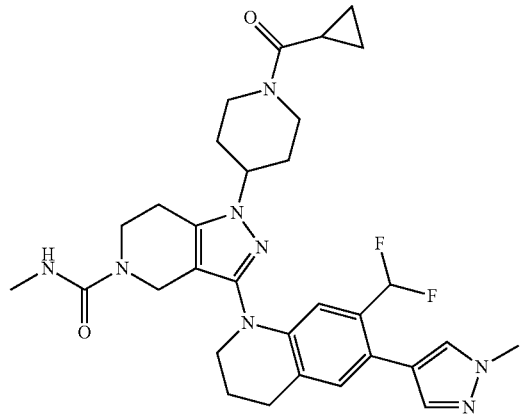
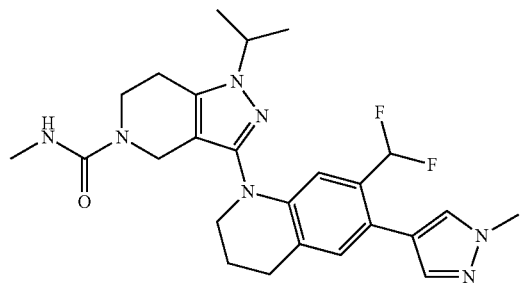
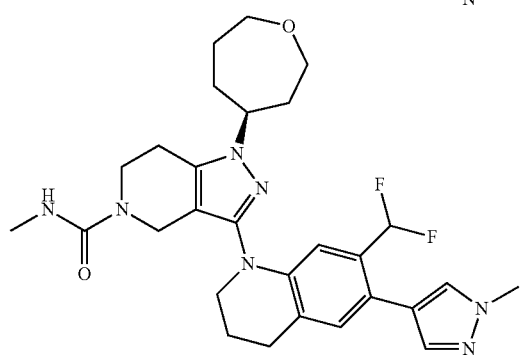
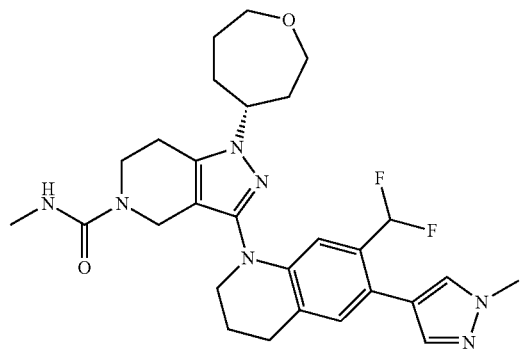
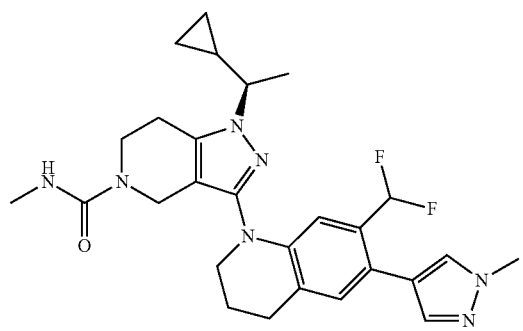

1105
-continued

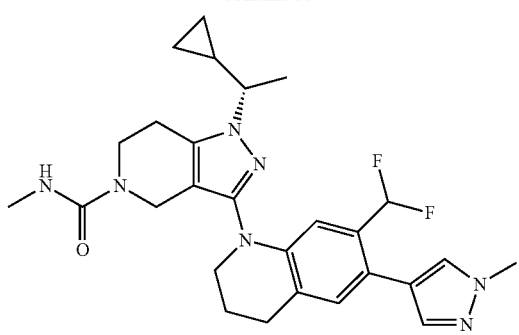

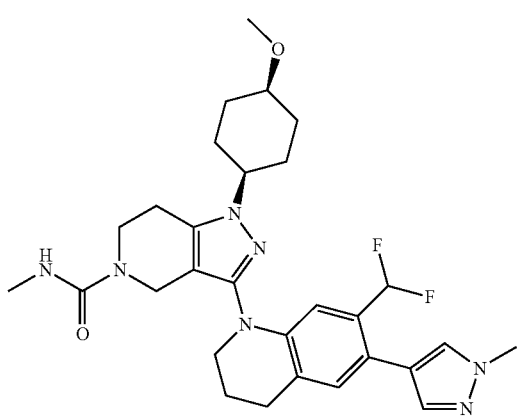

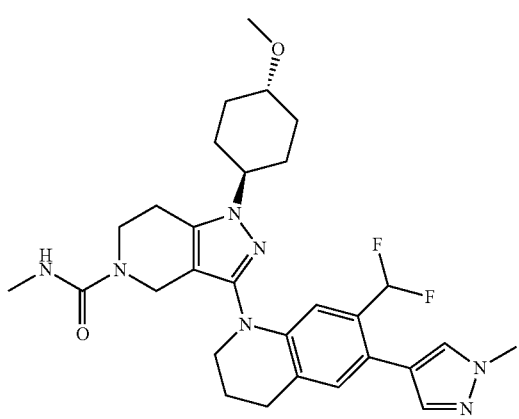

1106
-continued

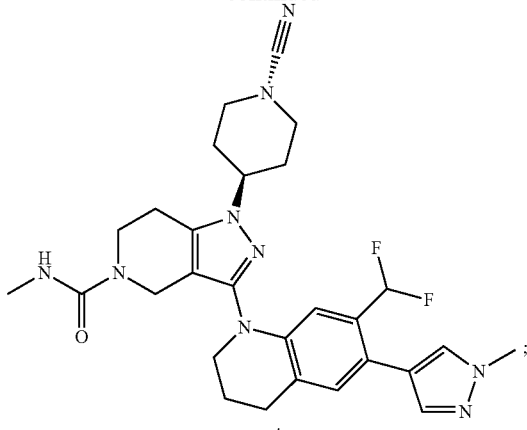

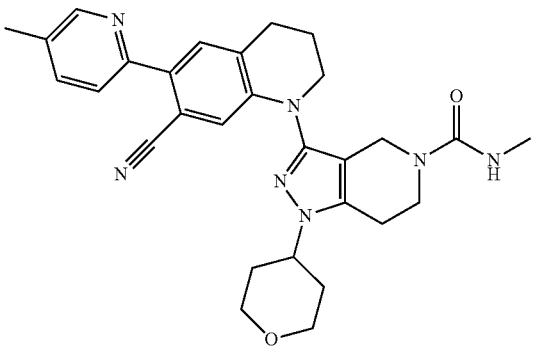

and salts thereof.

11. The compound of claim 1, wherein the compound is of formula (II):

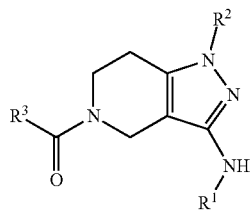

(II)

or a salt thereof, wherein:
R$^1$ is selected from C$_6$-C$_{20}$ aryl, C$_1$-C$_{20}$ heteroaryl, —(C$_6$-C$_{20}$ aryl)-(C$_1$-C$_{20}$ heteroaryl), and —(C$_1$-C$_{20}$ heteroaryl)-(C$_1$-C$_{20}$ heteroaryl), wherein each C$_6$-C$_{20}$ aryl, C$_1$-C$_{20}$ heteroaryl, —(C$_6$-C$_{20}$ aryl)-(C$_1$-C$_{20}$ heteroaryl) and —(C$_1$-C$_{20}$ heteroaryl)-(C$_1$-C$_{20}$ heteroaryl) is independently optionally substituted with one or more substituent groups independently selected from R$^c$, oxo, —F, —Cl, —Br, —I, —NO$_2$, —N(R$^a$)$_2$, —CN, —C(O)—N(R$^a$)$_2$, —S(O)—N(R$^a$)$_2$, —S(O)$_2$, —N(R$^a$)$_2$, —O—R$^a$, —S—R$^a$, —O—C(O)—R$^a$, —O—C(O)—O—R$^a$, —C(O)—R$^a$, —C(O)—O—R$^a$, —S(O)—R$^a$, —S(O)$_2$—R$^a$, —O—C(O)—N(R$^a$)$_2$, —N(R$^a$)—C(O)—OR$^a$, —N(R$^a$)—C(O)—N(R$^a$)$_2$, —N(R$^a$)—C(O)—R$^a$, —N(R$^a$)—S(O)—R$^a$, —N(R$^a$)—S(O)$_2$—R$^a$ and —N(R$^a$)—S(O)$_2$—N(R$^a$)$_2$;
R$^2$ is C$_{1-12}$alkyl, C$_{2-12}$alkenyl, C$_{2-12}$alkynyl, 3-12 membered carbocycle, and 3-12 membered heterocycle, wherein each $C_{1-12}$alkyl, $C_{2-12}$alkenyl, $C_{2-12}$alkynyl, 3-12 membered carbocycle, and 3-12 membered heterocycle of $R^2$ is optionally substituted with one or more groups $R^b$;

$R^3$ is $C_{1-4}$alkyl, $C_{2-4}$alkenyl, $C_{2-4}$alkynyl, 3-5 membered carbocycle, 3-5 membered heterocycle, —C(O)—N($R^e$)$_2$, —S(O)—N($R^e$)$_2$, —S(O)$_2$—N($R^e$)$_2$, —C(O)—$R^e$, —C(O)—O—$R^e$, —S(O)—$R^e$, or —S(O)$_2$—$R^e$, wherein any $C_{1-4}$alkyl, $C_{2-4}$alkenyl, $C_{2-4}$alkynyl, 3-5 membered carbocycle, and 3-5 membered heterocycle is optionally substituted with one or more substituent groups independently selected from —F, —Cl, —Br, —I, 3-5 membered carbocycle, —C(O)—N($R^e$)$_2$, —S(O)—N($R^e$)$_2$, —S(O)$_2$—N($R^e$)$_2$, —O—$R^e$, —S—$R^e$, —O—C(O)—$R^e$, —O—C(O)—O—$R^e$, —C(O)—$R^e$, —C(O)—O—$R^e$, —S(O)—$R^e$, —S(O)$_2$—$R^e$, —O—C(O)—N($R^e$)$_2$, —N($R^e$)—C(O)—O$R^e$, —N($R^e$)—C(O)—N($R^e$)$_2$, —N($R^e$)—C(O)—$R^e$, —N($R^e$)—S(O)—$R^e$, —N($R^e$)—S(O)$_2$—$R^e$, —N($R^e$)—S(O)—N($R^e$)$_2$, and —N($R^e$)—S(O)$_2$—N($R^e$)$_2$;

each $R^a$ is independently selected from hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from oxo, halo, amino, hydroxyl, $C_{1-6}$alkoxy, carbocyclyl, heterocyclyl, and $C_1$-$C_6$ alkyl that is optionally substituted with one or more groups independently selected from oxo and halo; or two IV are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^b$ is independently selected from oxo, $C_{1-6}$alkyl, $C_{2-6}$alkenyl, $C_{2-6}$alkynyl, carbocyclyl, heterocyclyl, aryl, heteroaryl, —F, —Cl, —Br, —I, —NO$_2$, —N($R^c$)$_2$, —CN, —C(O)—N($R^c$)$_2$, —S(O)—N($R^c$)$_2$, —S(O)$_2$—N($R^c$)$_2$, —O—C(O)—O—$R^c$, —C(O)—$R^c$, —C(O)—O—$R^c$, —S(O)—$R^c$, —S(O)$_2R^c$, —O—C(O)—N($R^c$)$_2$, —N($R^c$)—C(O)—O$R^c$, —N($R^c$)—C(O)—N($R^c$)$_2$, —N($R^c$)—C(O)—$R^c$, —N($R^c$)—S(O)—$R^c$, —N($R^c$)—S(O)$_2$—$R^c$, —N($R^c$)—S(O)—N($R^c$)$_2$, and —N($R^c$)—S(O)$_2$—N($R^c$)$_2$, wherein any $C_{1-6}$alkyl, $C_{2-6}$alkenyl, $C_{2-6}$alkynyl, carbocyclyl, heterocyclyl, aryl, and heteroaryl is optionally substituted with one or more groups independently selected from oxo, halo, —NO$_2$, —N($R^c$)$_2$, —CN, —C(O)—N($R^c$)$_2$, —S(O)—N($R^c$)$_2$, —S(O)$_2$—N($R^c$)$_2$, —S—$R^c$, —O—C(O)—$R^c$, —C(O)—$R^c$, —S(O)—$R^c$, —S(O)$_2R^c$—, —C(O)—N($R^c$)$_2$, —N($R^c$)—C(O)—$R^c$, —N($R^c$)—S(O)—$R^c$, —N($R^c$)—S(O)$_2$—$R^c$ and $C_{1-6}$alkyl that is optionally substituted with one or more groups independently selected from oxo and halo;

each $R^c$ is independently selected from hydrogen, $C_{1-6}$alkyl, $C_{2-6}$alkenyl, $C_{2-6}$alkynyl, carbocyclyl, and heterocyclyl, wherein any $C_{1-6}$alkyl, $C_{2-6}$alkenyl, $C_{2-6}$alkynyl, carbocyclyl, and heterocyclyl is optionally substituted with one or more groups independently selected from oxo, carbocyclyl, heterocyclyl, halo, —NO$_2$, —N($R^d$)$_2$, —CN, —C(O)—N($R^d$)$_2$, —S(O)—N($R^d$)$_2$, —S(O)$_2$—N($R^d$)$_2$, —O—$R^d$, —S—$R^d$, —O—C(O)—$R^d$, —C(O)—$R^d$, —C(O)—O—$R^d$, —S(O)—$R^d$, —S(O)$_2$—$R^d$, —C(O)—N($R^d$)$_2$, —N($R^d$)—C(O)—$R^d$, —N($R^d$)—S(O)—$R^d$, N($R^d$)—S(O)$_2$—$R^d$, and $C_{1-6}$alkyl, which carbocyclyl and $C_{1-6}$alkyl are optionally substituted with one or more groups independently selected from oxo, halo, $C_{1-6}$alkyl, cyano, —N($R^d$)$_2$, —O—$R^d$, heterocyclyl, and carbocyclyl that is optionally substituted with one or more groups independently selected from halo, and $C_{1-6}$alkyl;

each $R^d$ is independently selected from hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from oxo, halo, amino, hydroxyl, $C_{1-6}$alkoxy, carbocyclyl, heterocyclyl, and $C_1$-$C_6$ alkyl that is optionally substituted with one or more groups independently selected from oxo and halo; or two $R^d$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo; and each $R^e$ is independently selected from hydrogen, $C_{1-4}$alkyl, $C_{2-4}$alkenyl, $C_{2-4}$alkynyl, and $C_{2-5}$cycloalkyl, wherein each $C_{1-4}$alkyl, $C_{2-4}$alkenyl, $C_{2-4}$alkynyl, and $C_{2-5}$cycloalkyl is optionally substituted with one or more groups independently selected from oxo, halo, amino, hydroxyl, $C_{1-3}$alkoxy, and $C_1$-$C_3$ alkyl that is optionally substituted with one or more groups independently selected from halo; provided that $R^1$ is not unsubstituted phenyl, when $R^2$ is carboxymethyl or 2-carboxyethyl.

12. The compound of claim 11 wherein $R^1$ is selected from:

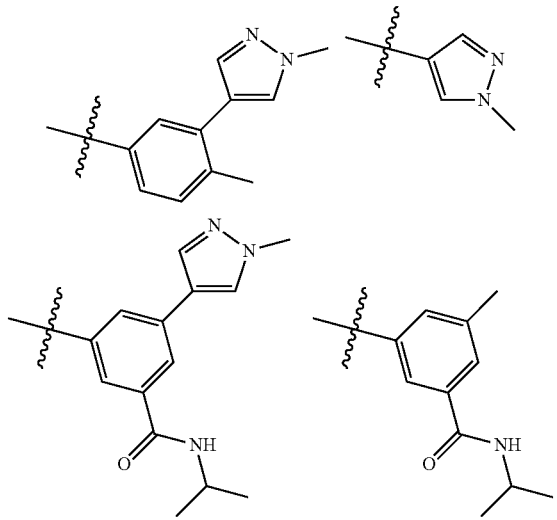

1109
-continued
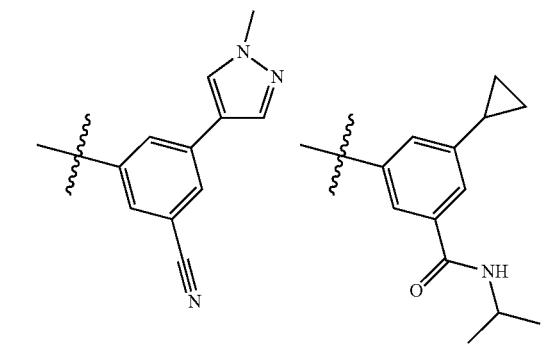
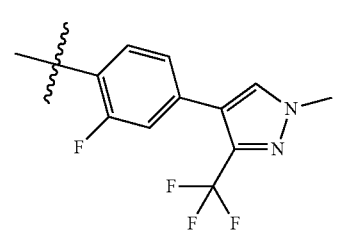
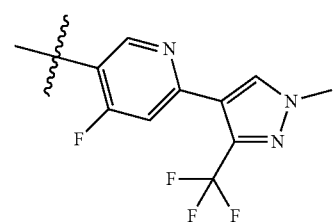
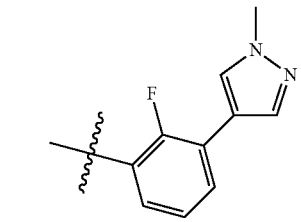
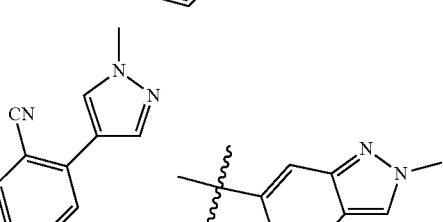
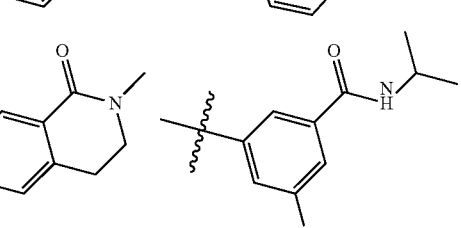
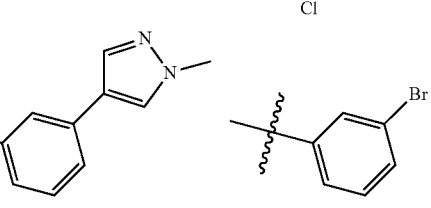
1110
-continued
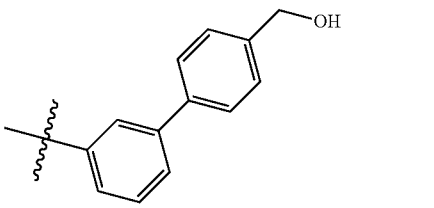
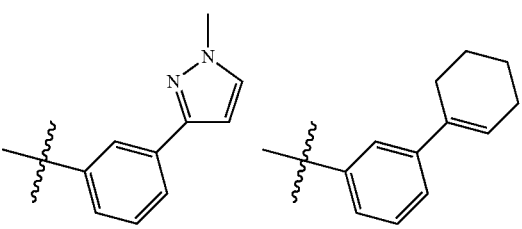
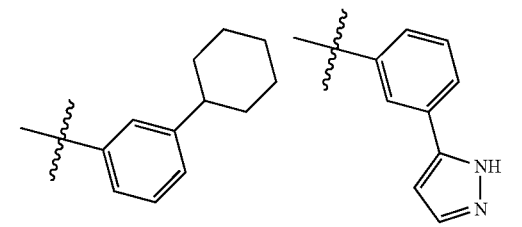
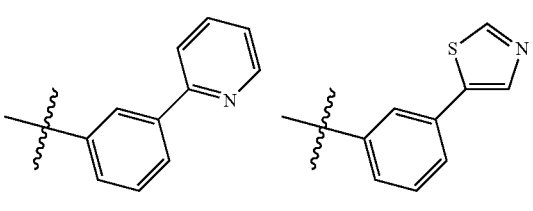
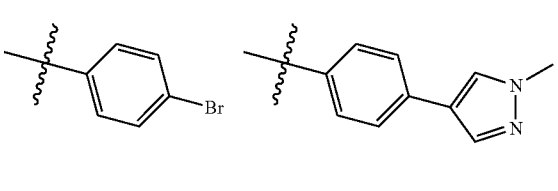
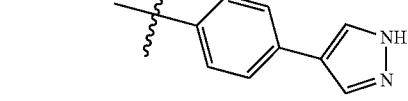
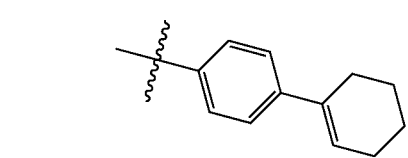
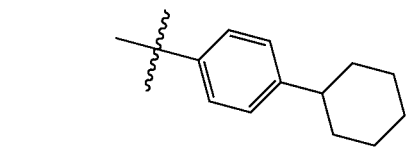

1111
-continued
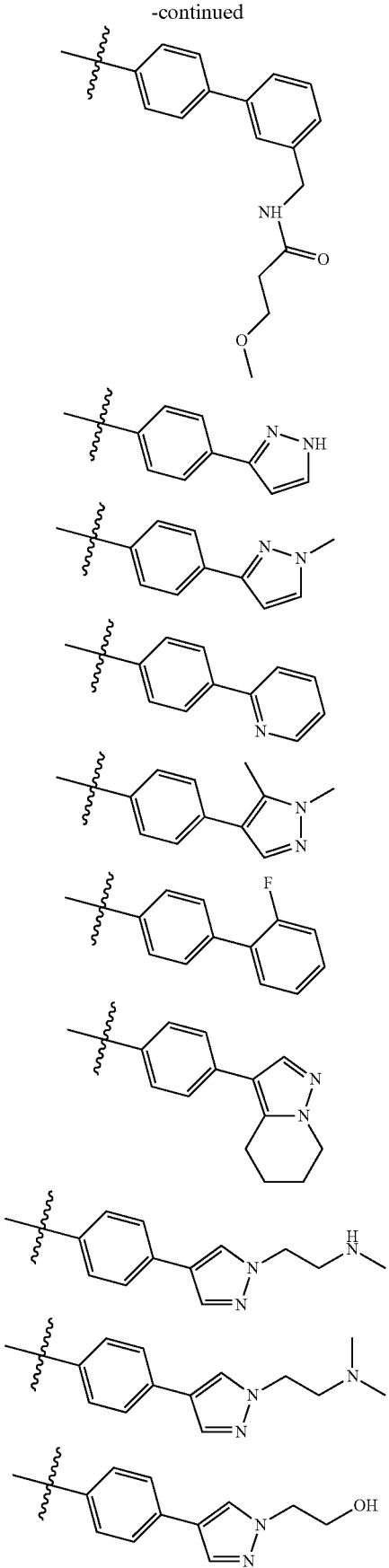
1112
-continued
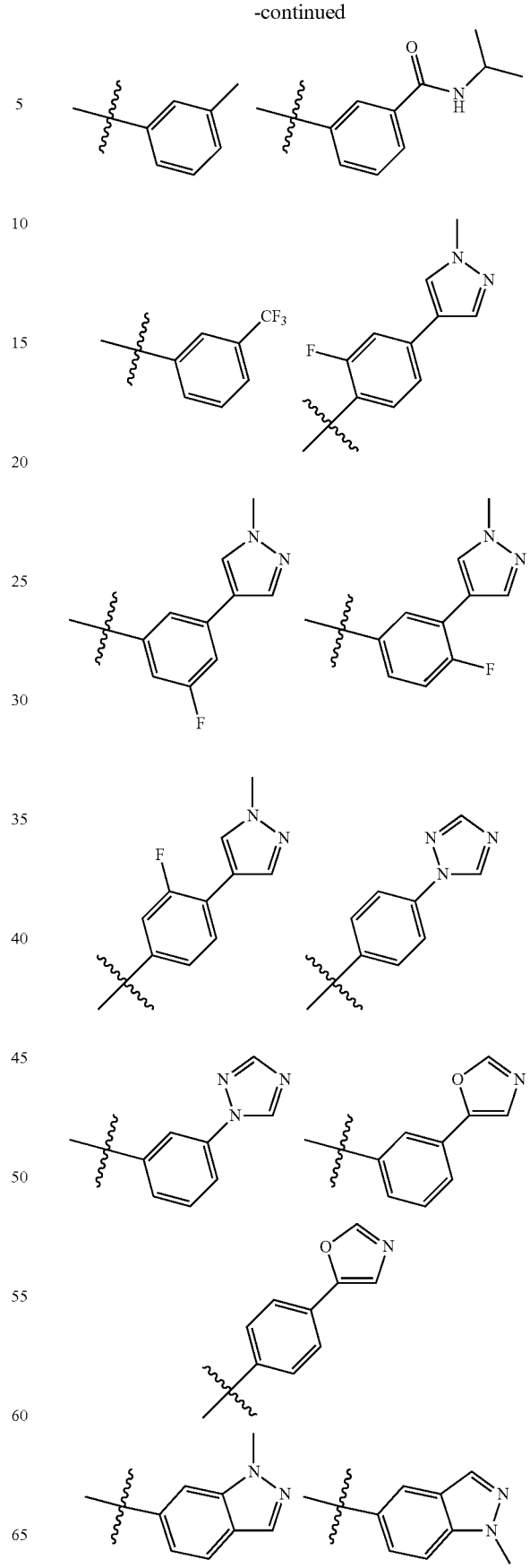

-continued
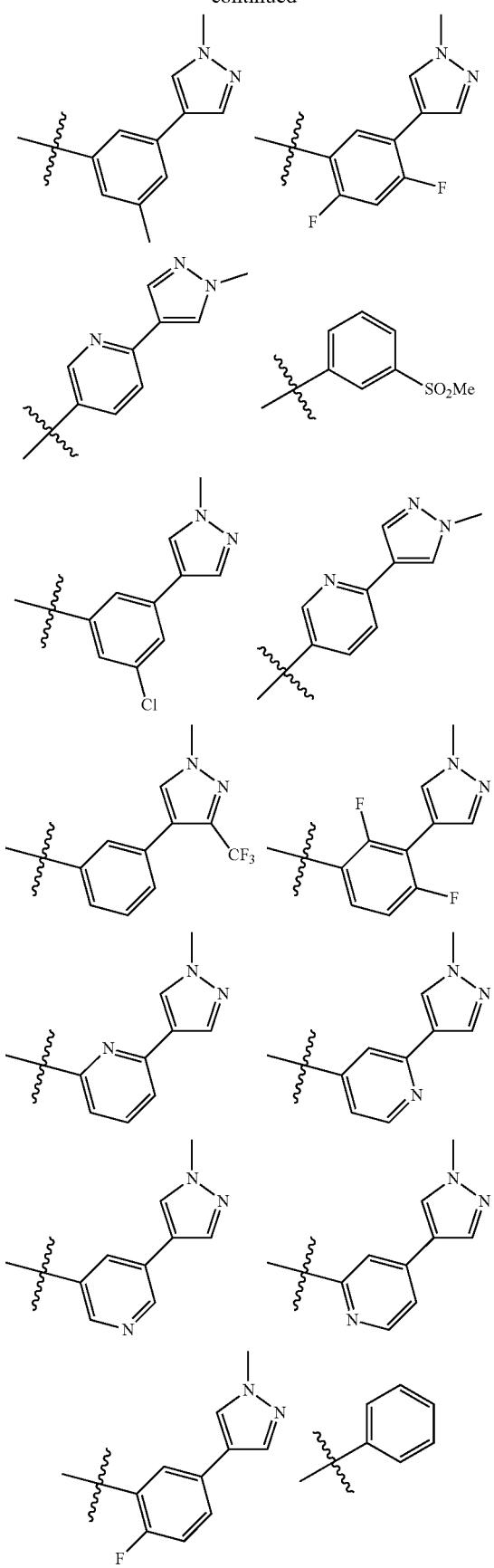
-continued
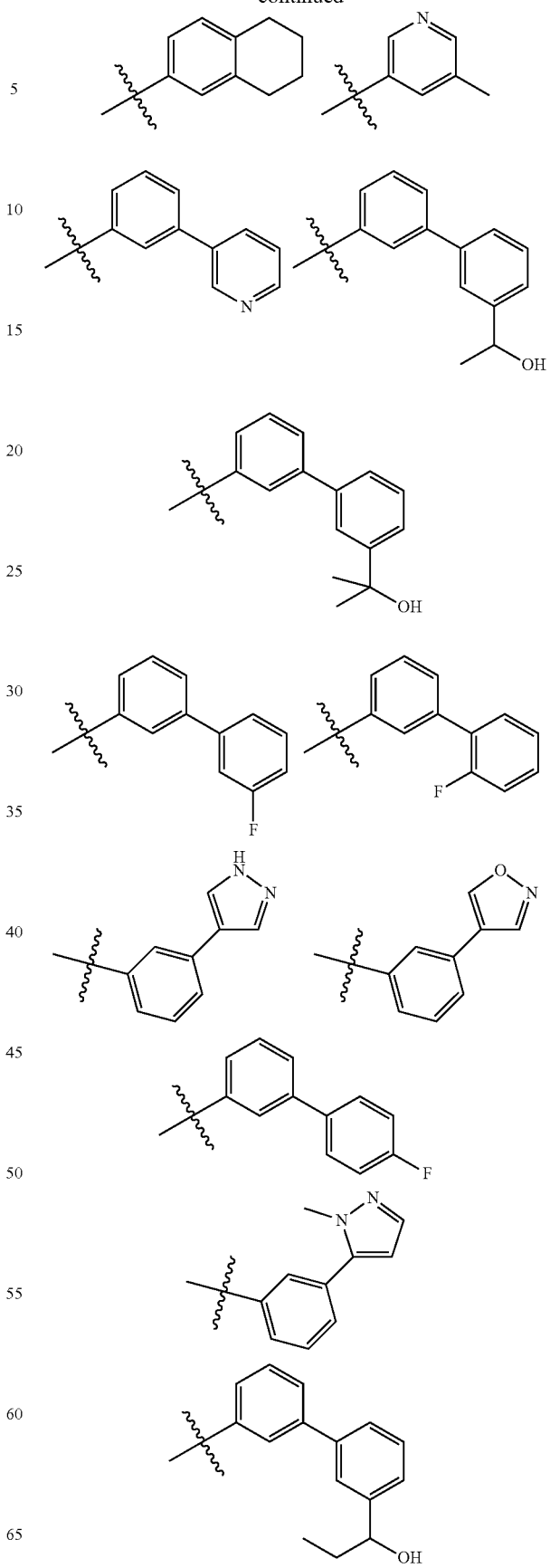

1115
-continued
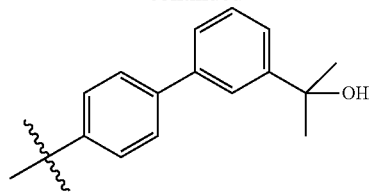
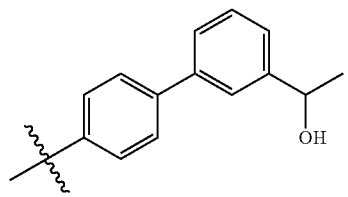
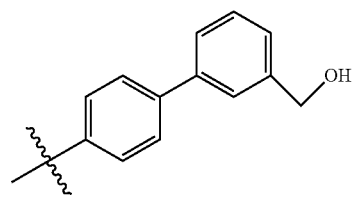
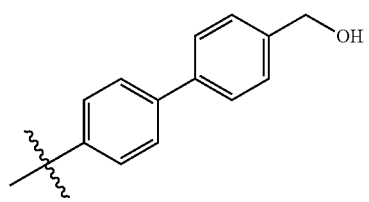
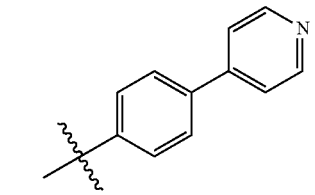
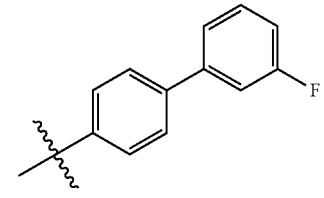
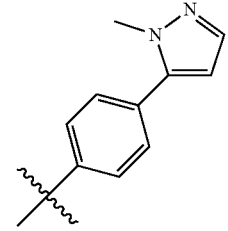
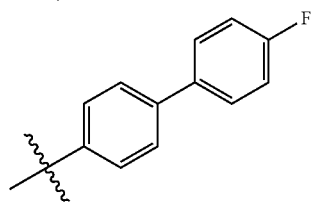
1116
-continued
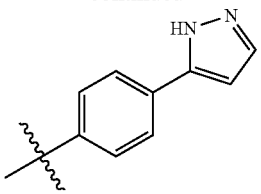
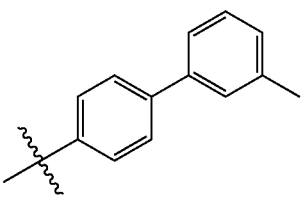
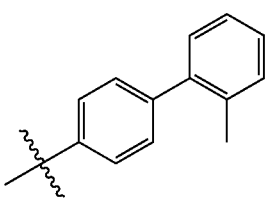
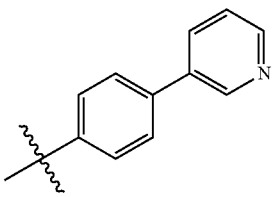
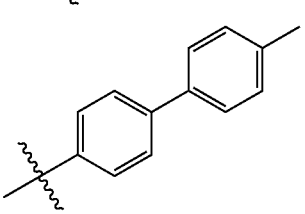
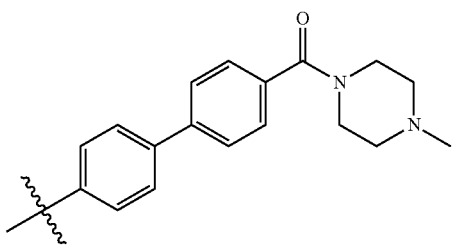
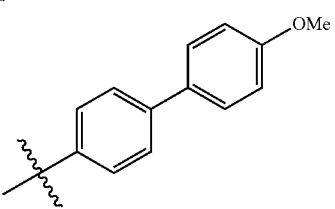
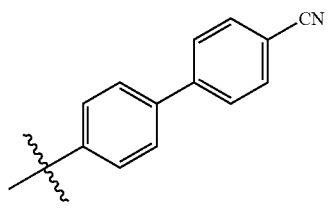

| 1117 -continued | 1118 -continued |
|---|---|
| 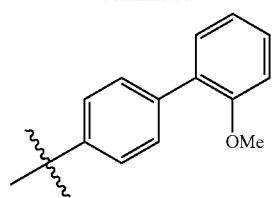 | 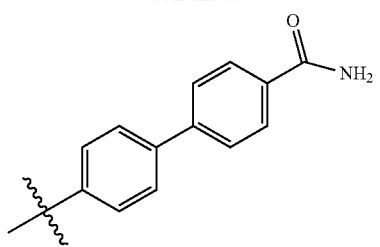 |
| 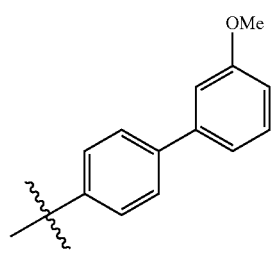 | 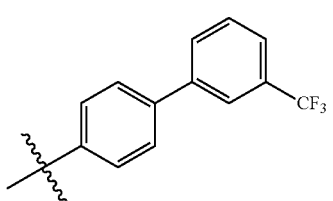 |
| 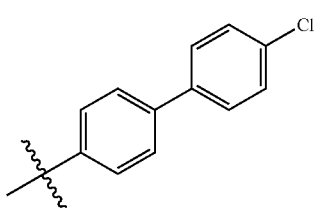 | 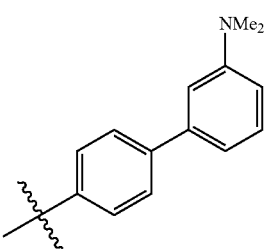 |
| 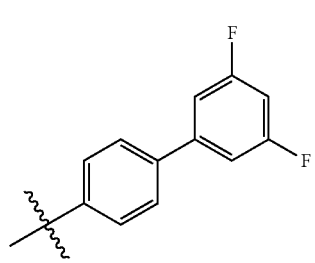 | 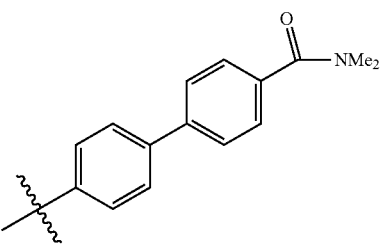 |
| 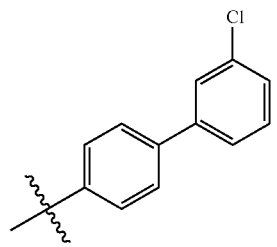 | 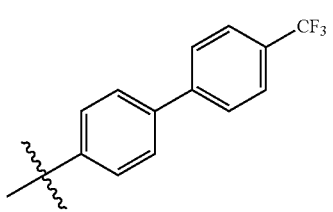 |
| 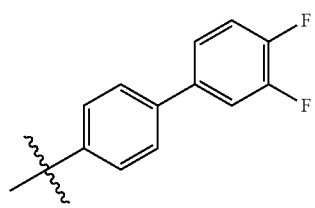 | 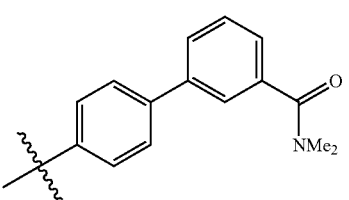 |
| 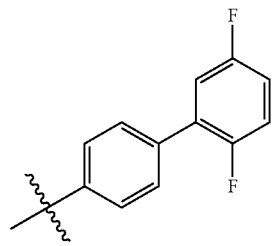 | 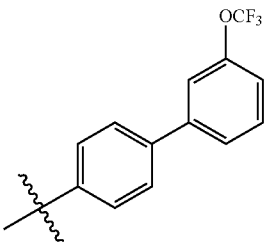 |

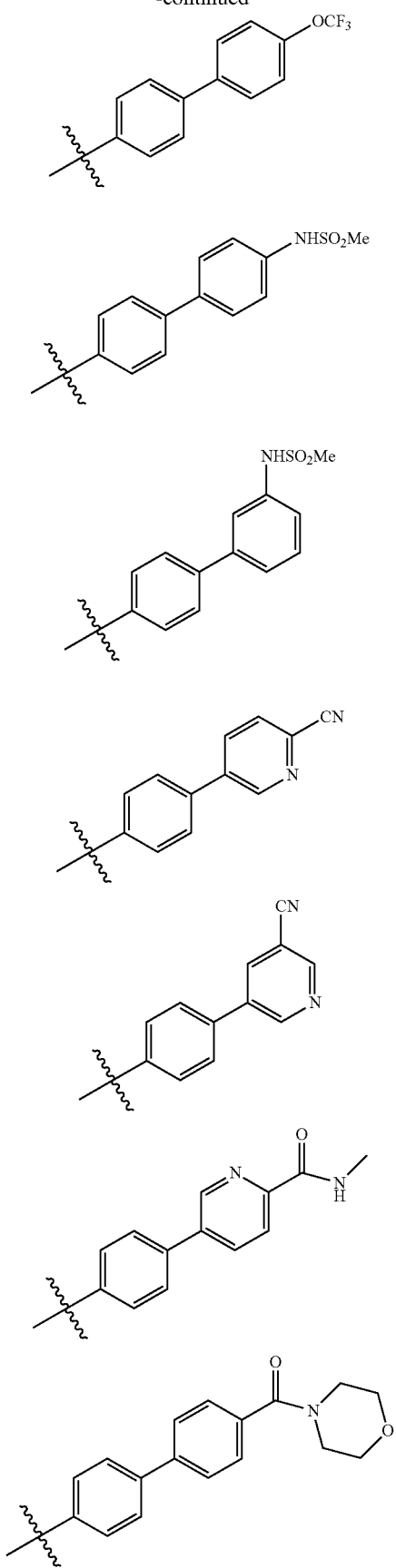
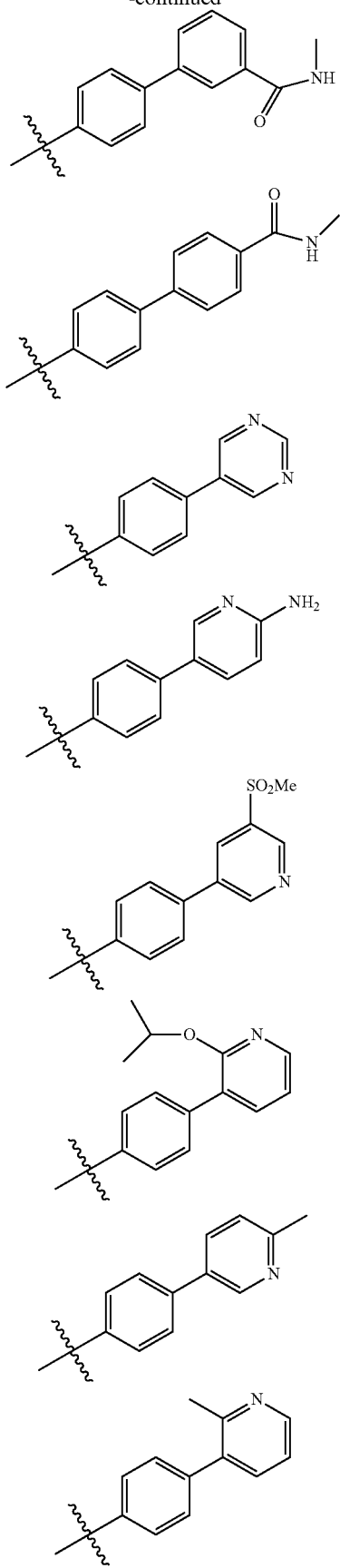

1121
-continued
1122
-continued
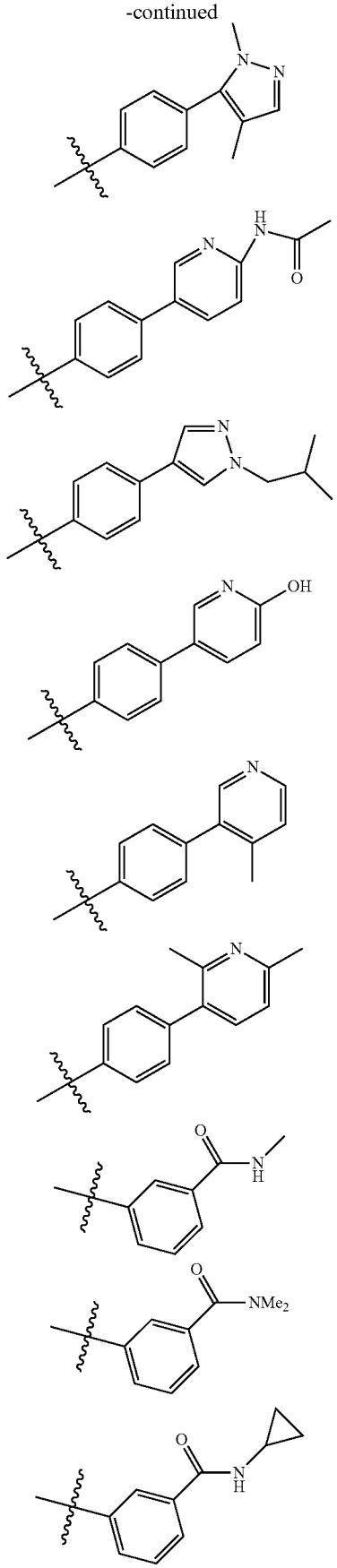
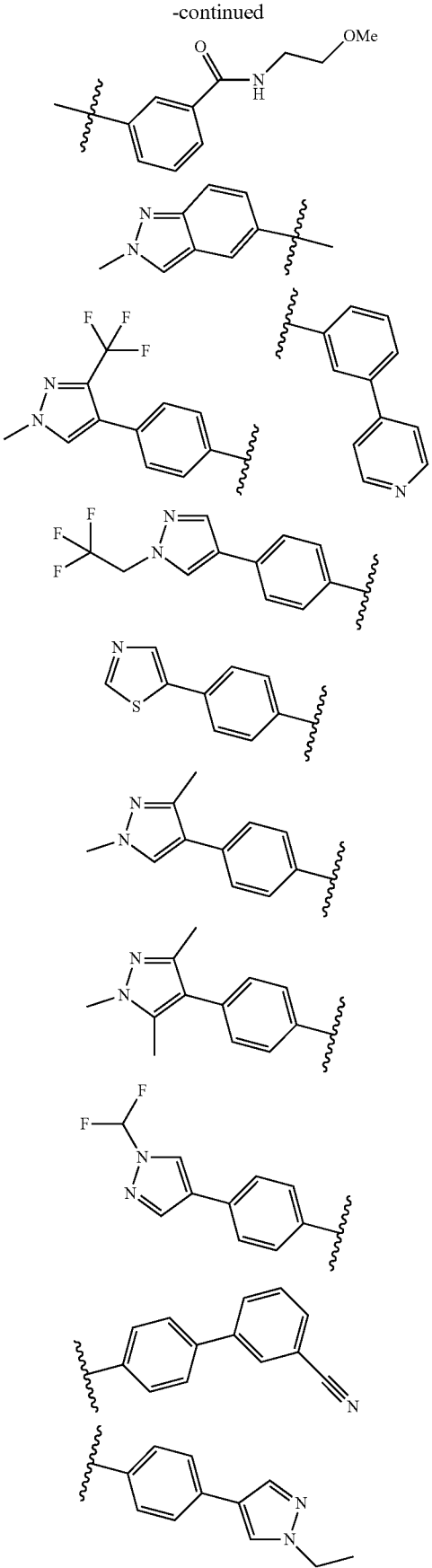

1123
-continued
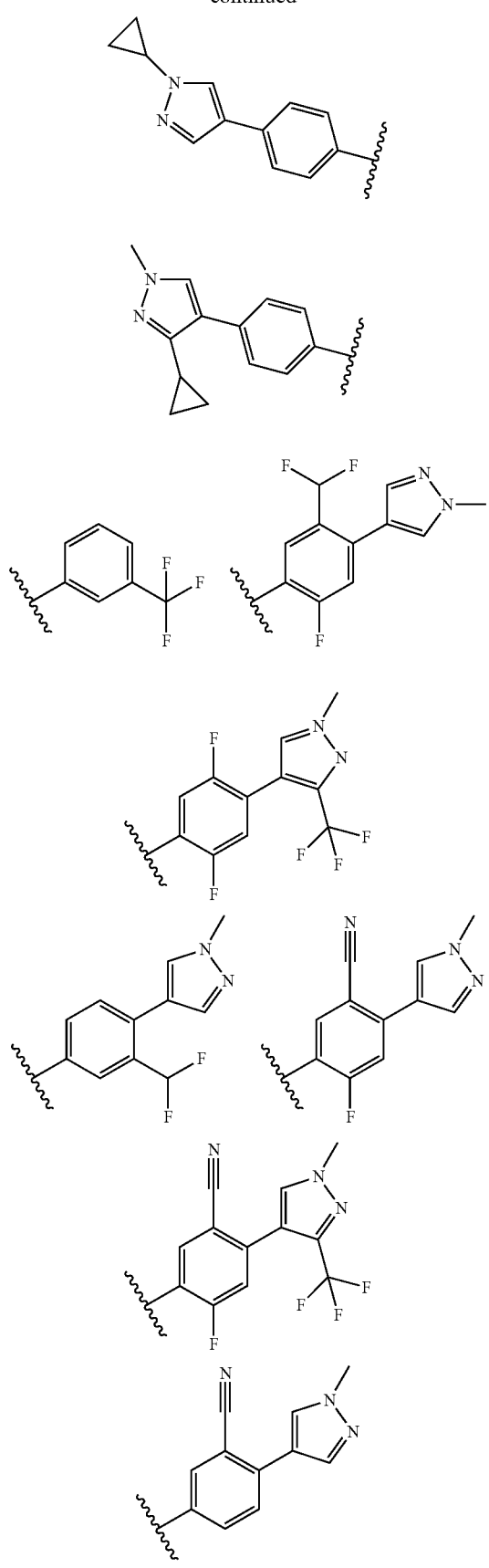
1124
-continued
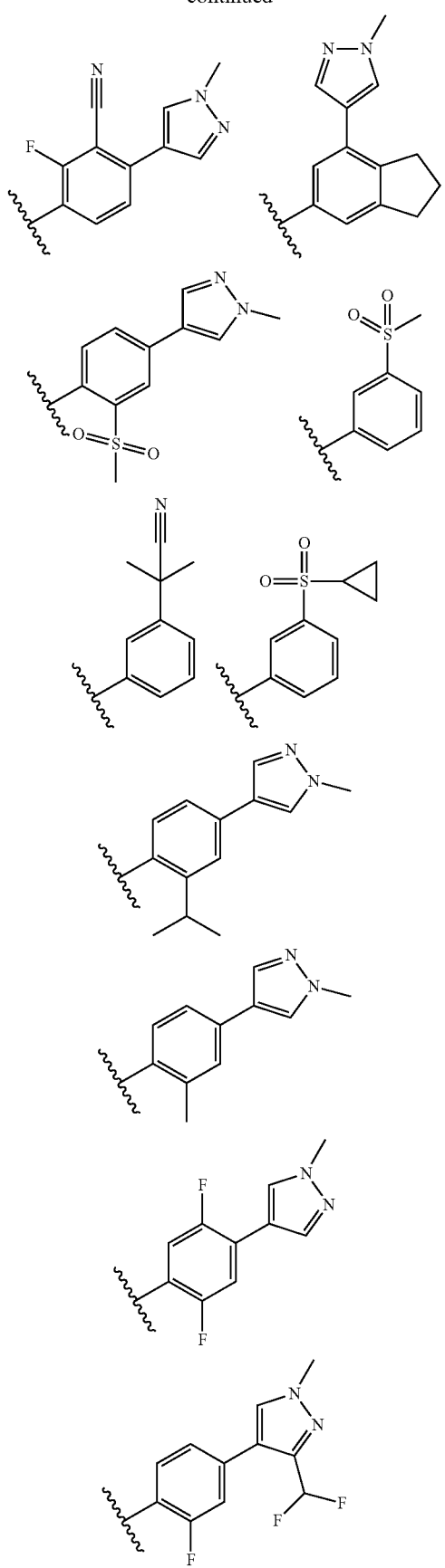

1125
-continued
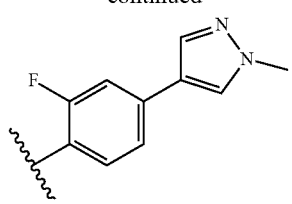
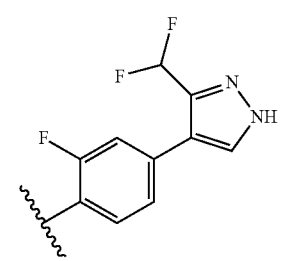
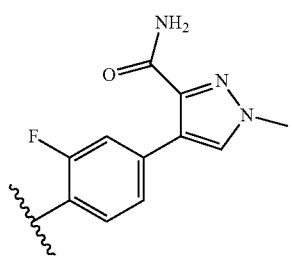
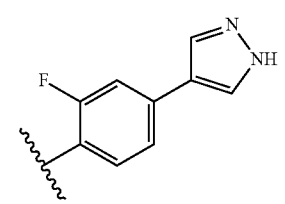
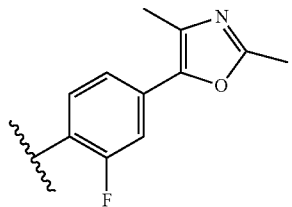
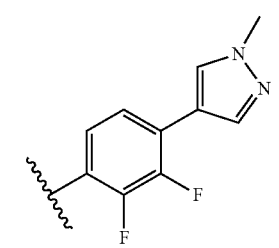
1126
-continued
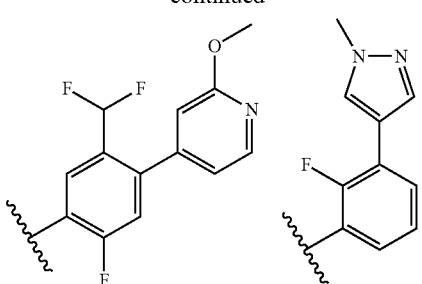
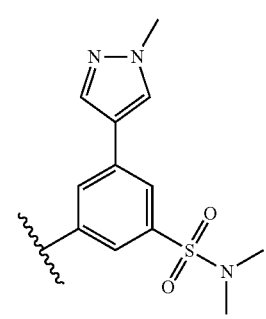
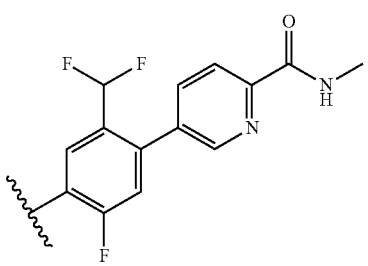
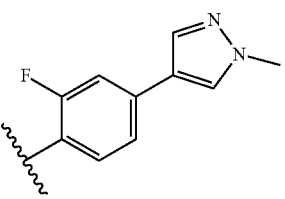
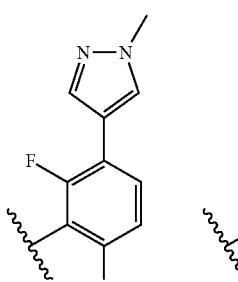
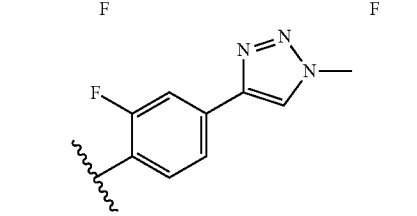

1127
-continued
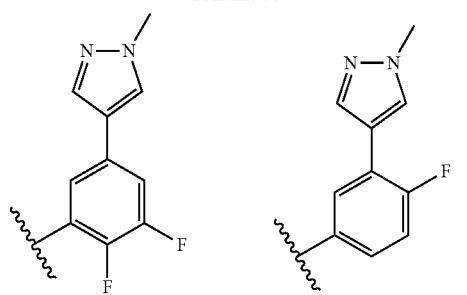
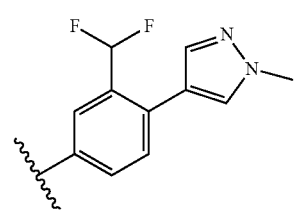
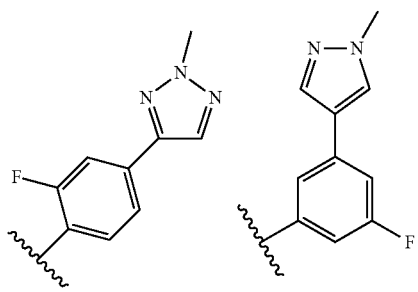
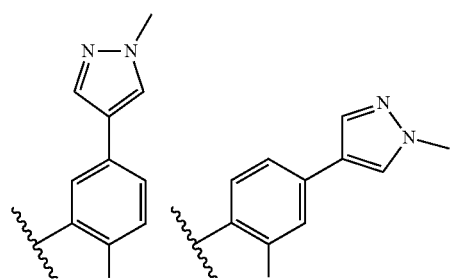
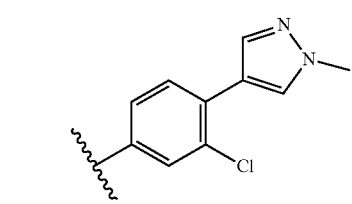
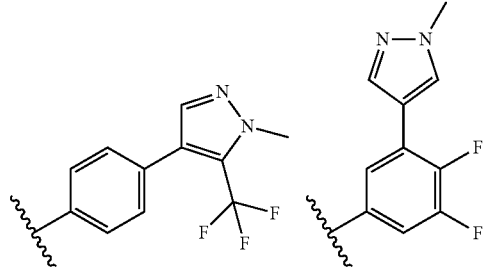
1128
-continued
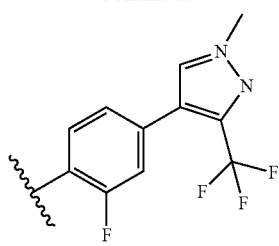
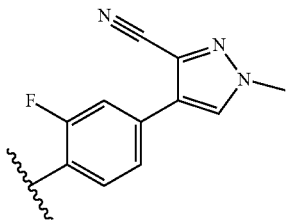
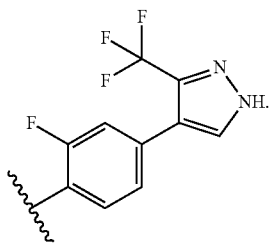
and
13. The compound of claim 11 wherein R² is:
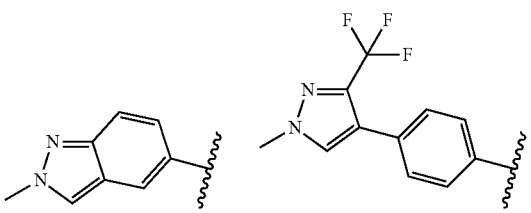
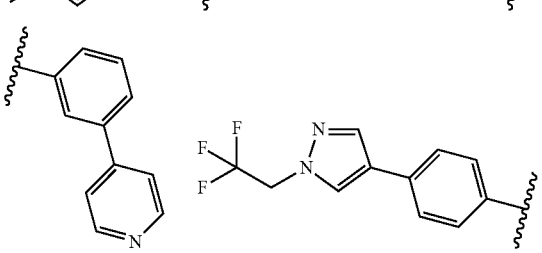
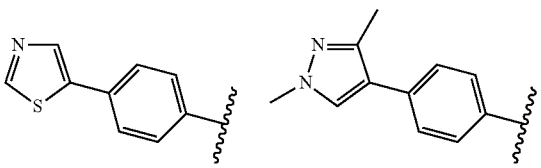
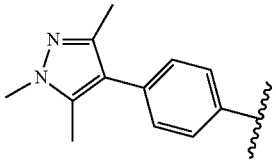

1129
-continued
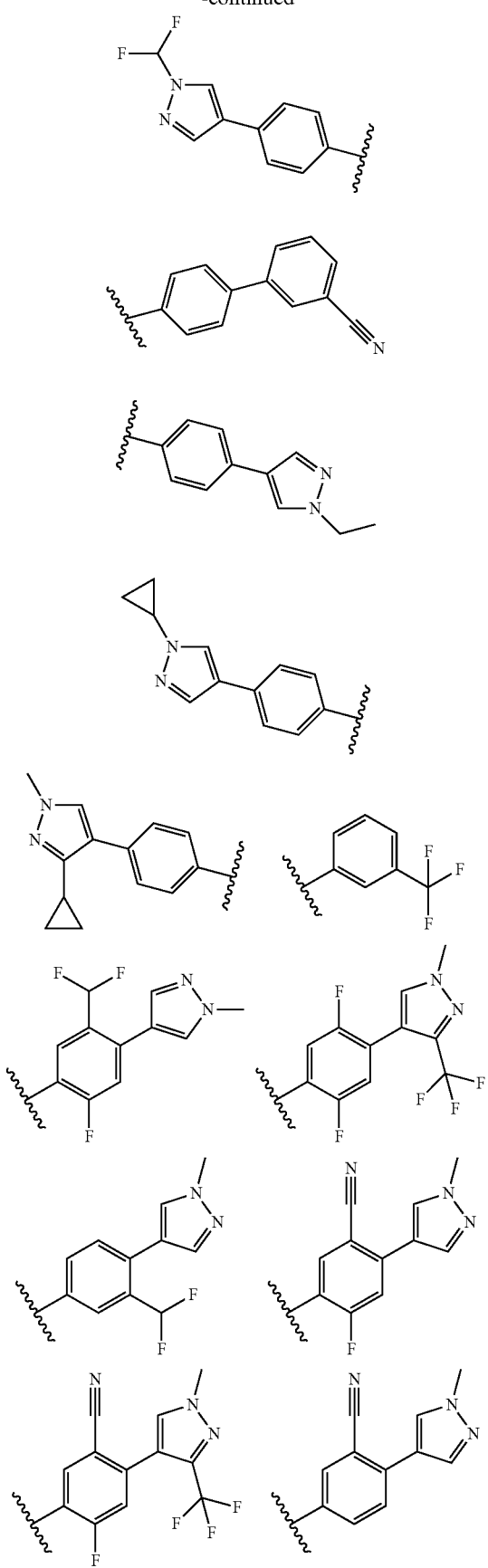
1130
-continued
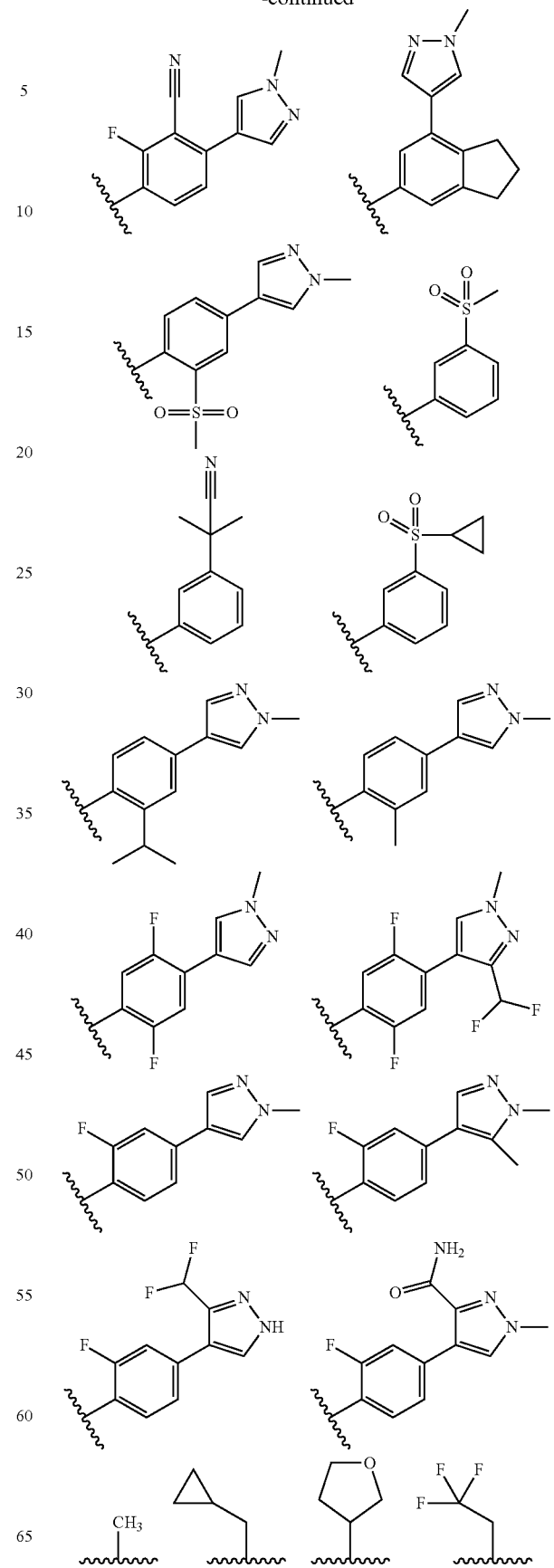

-continued
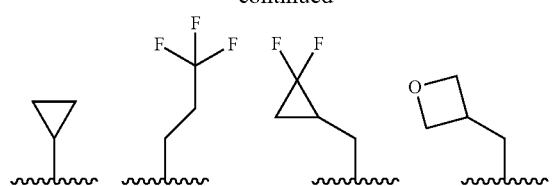
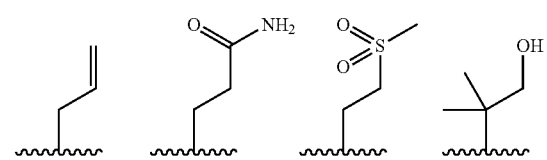
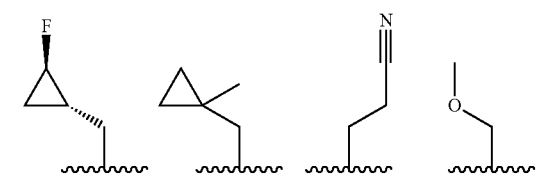
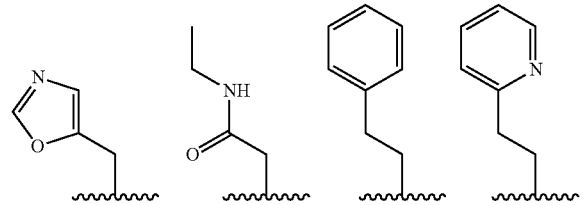
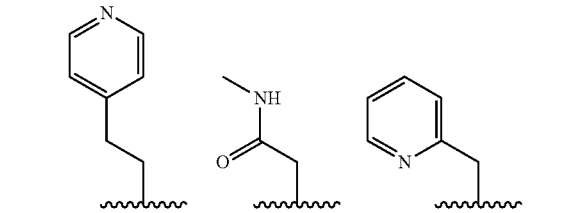
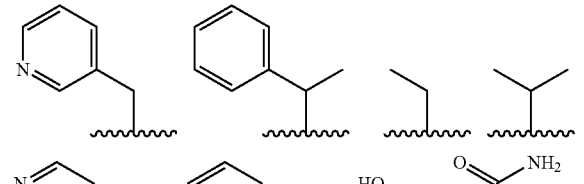
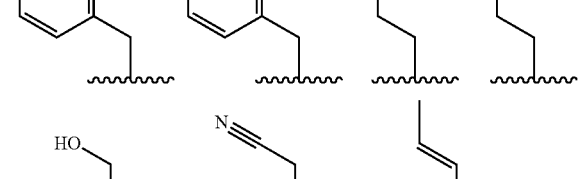
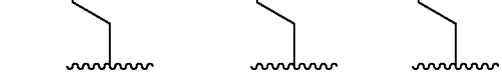
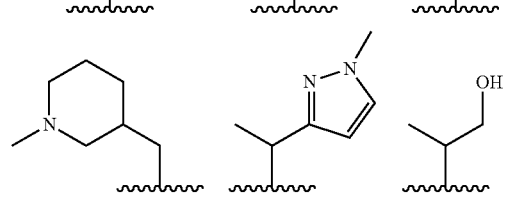
-continued
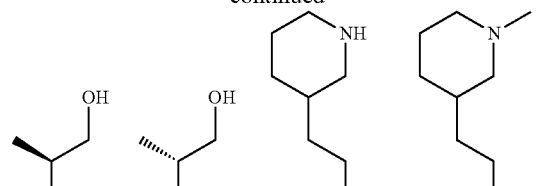
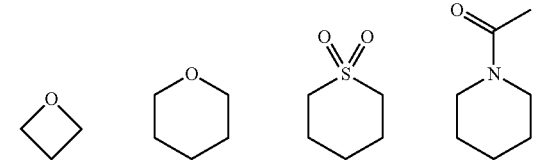
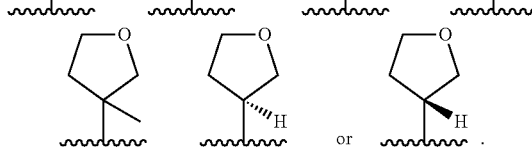
14. The compound of claim 11 wherein $R^3$ is selected from the group consisting of:
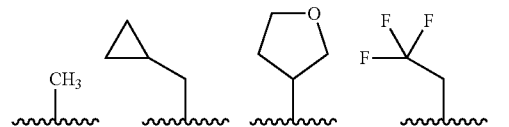
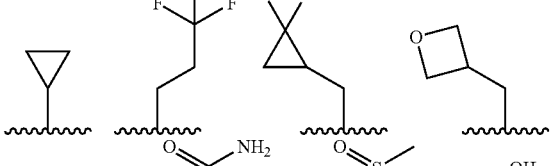
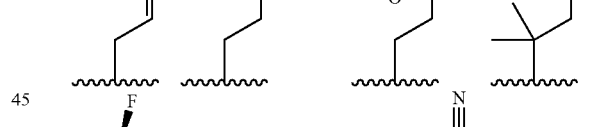
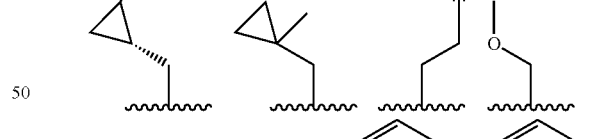
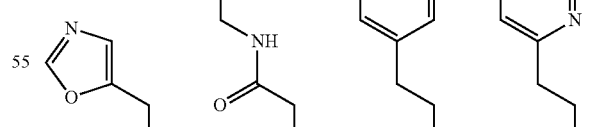
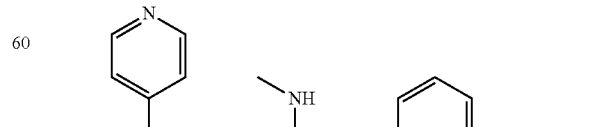
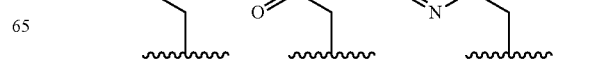

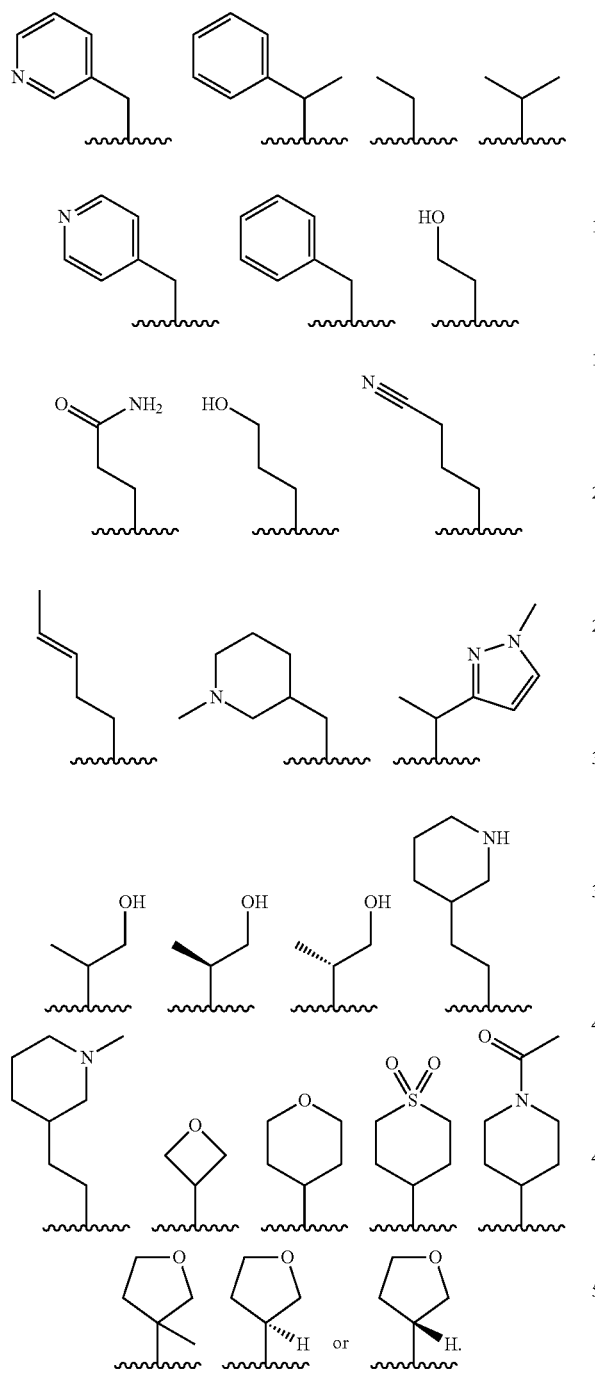
15. The compound of claim 11 selected from:
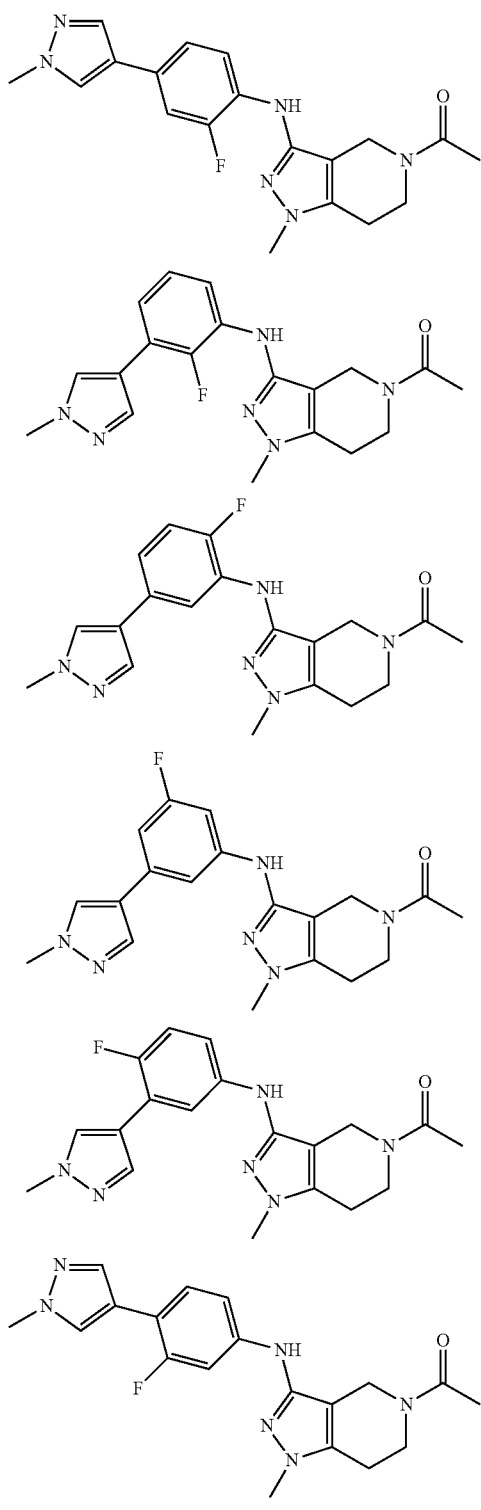
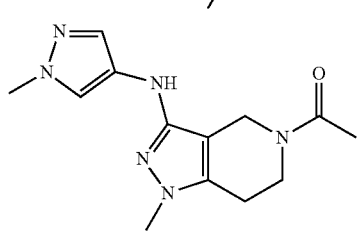

1135
-continued
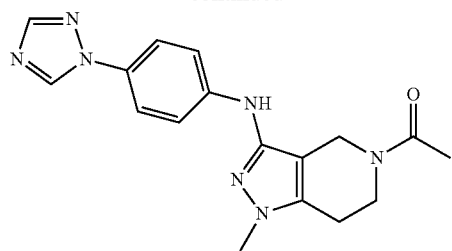
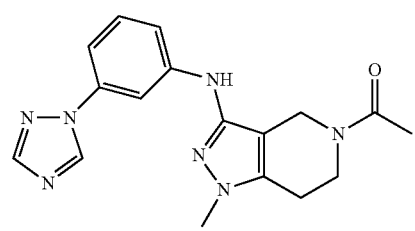
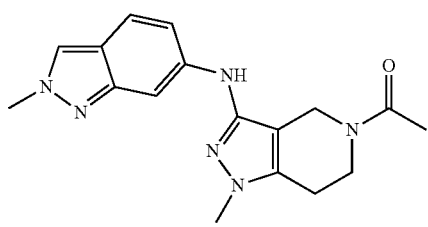
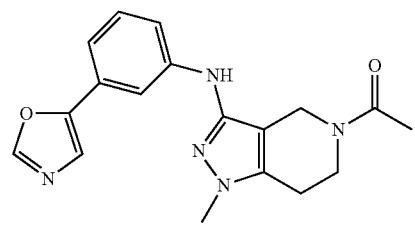
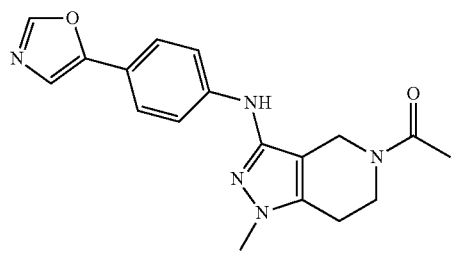
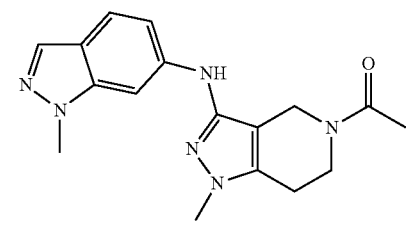
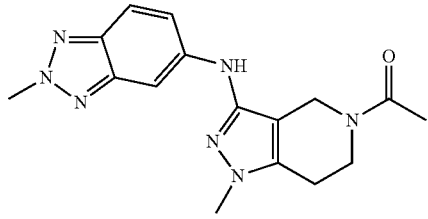
1136
-continued
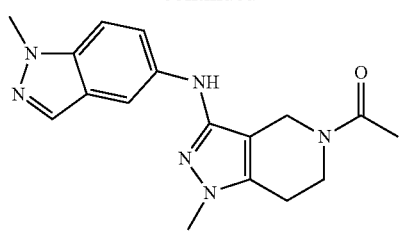
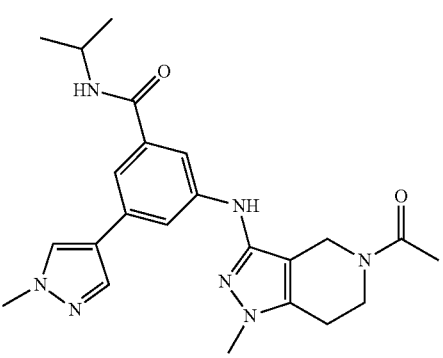
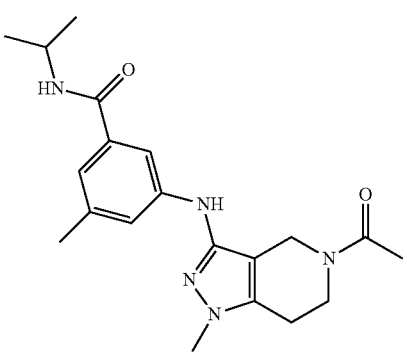
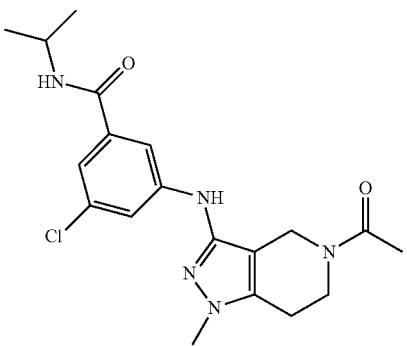
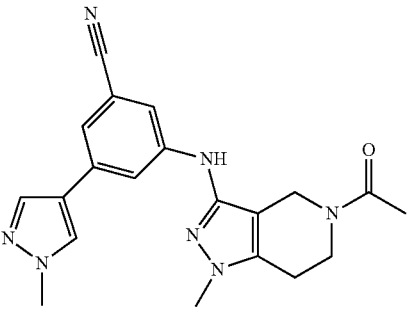

1137
-continued
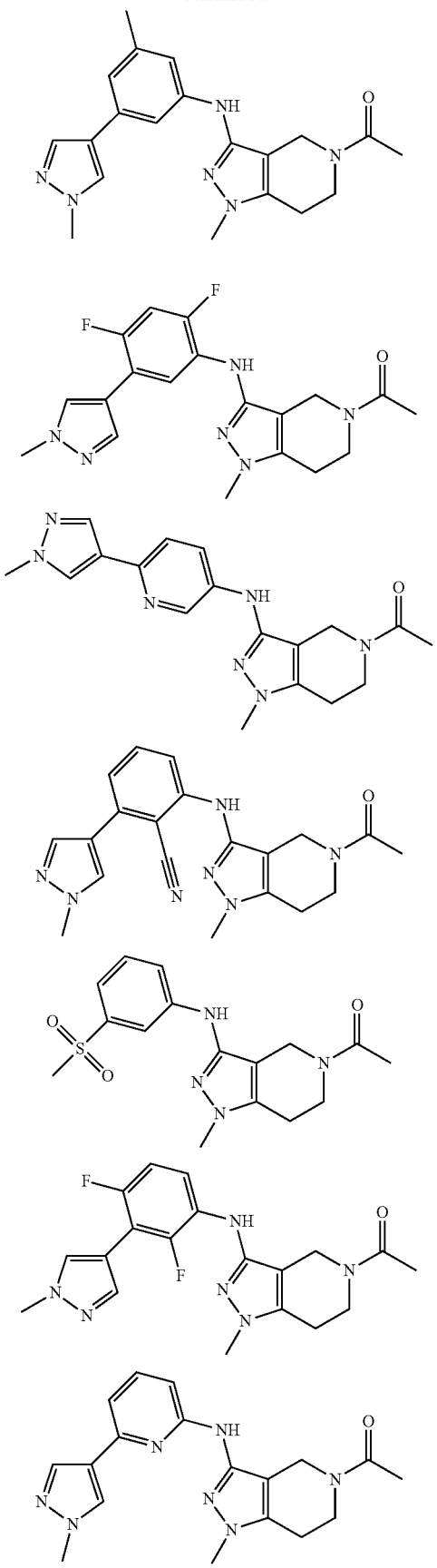
1138
-continued
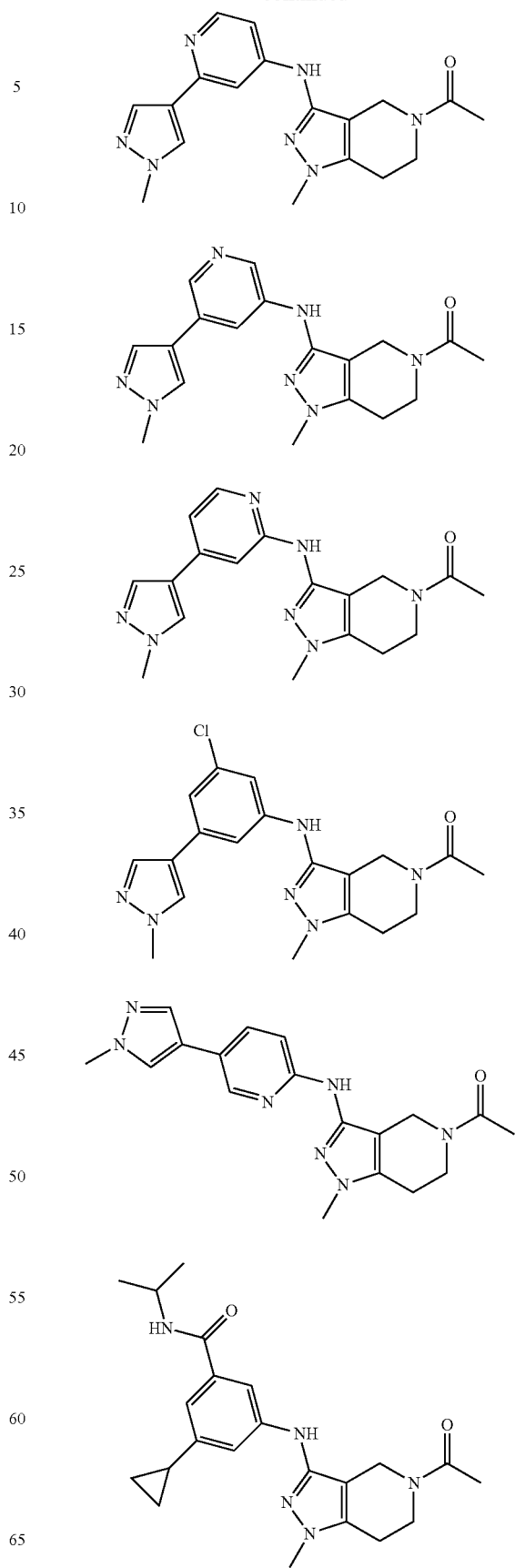

1139
-continued
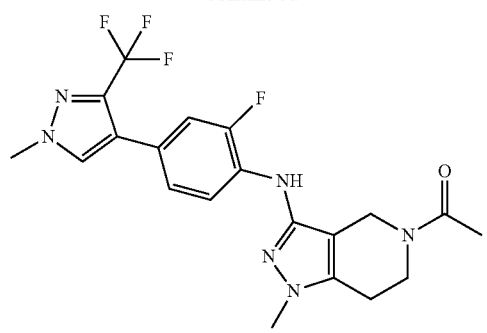
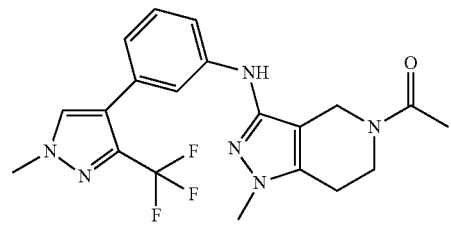
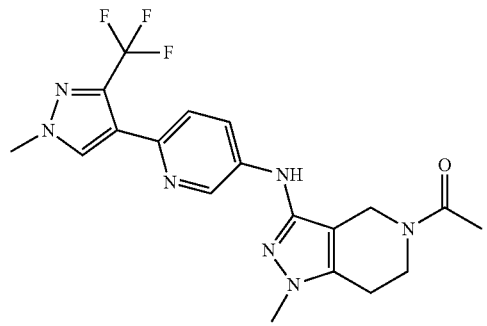
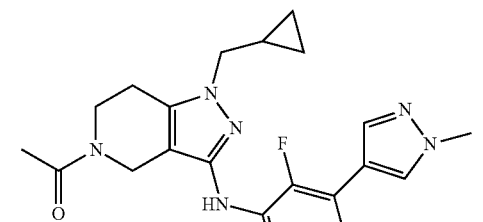
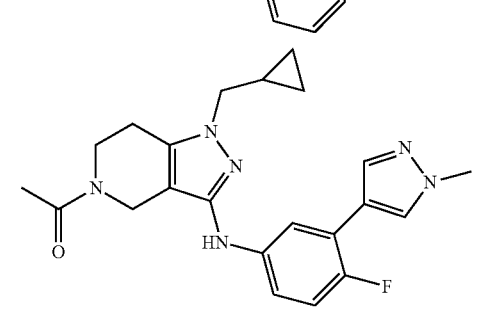
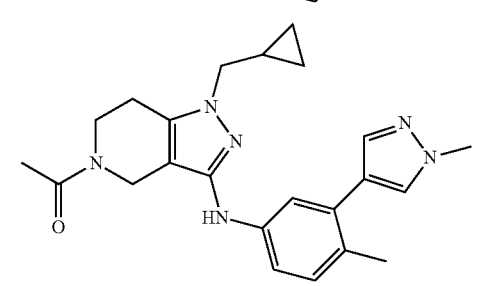
1140
-continued
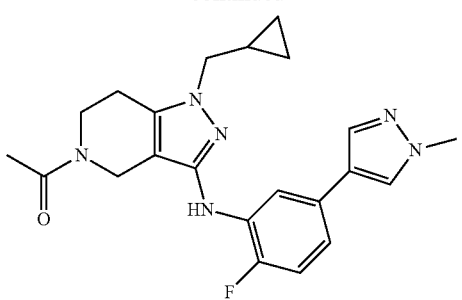
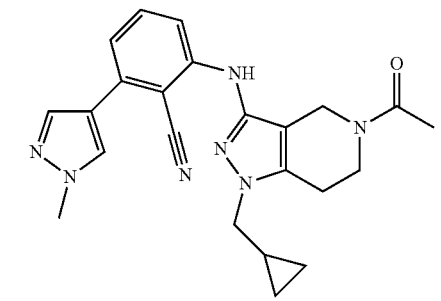
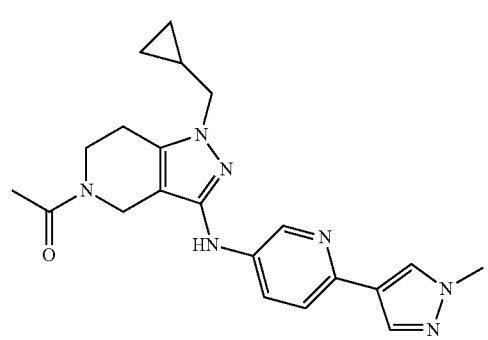
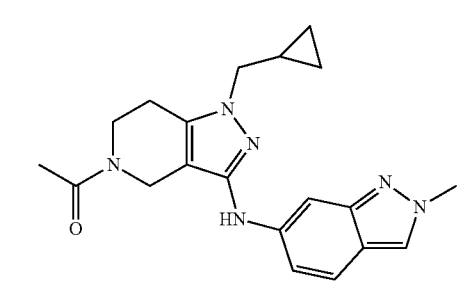
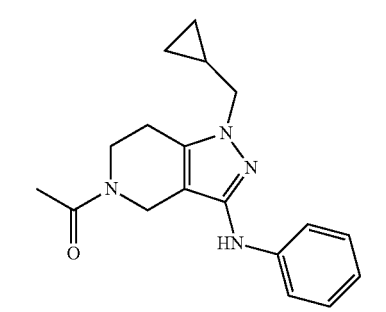

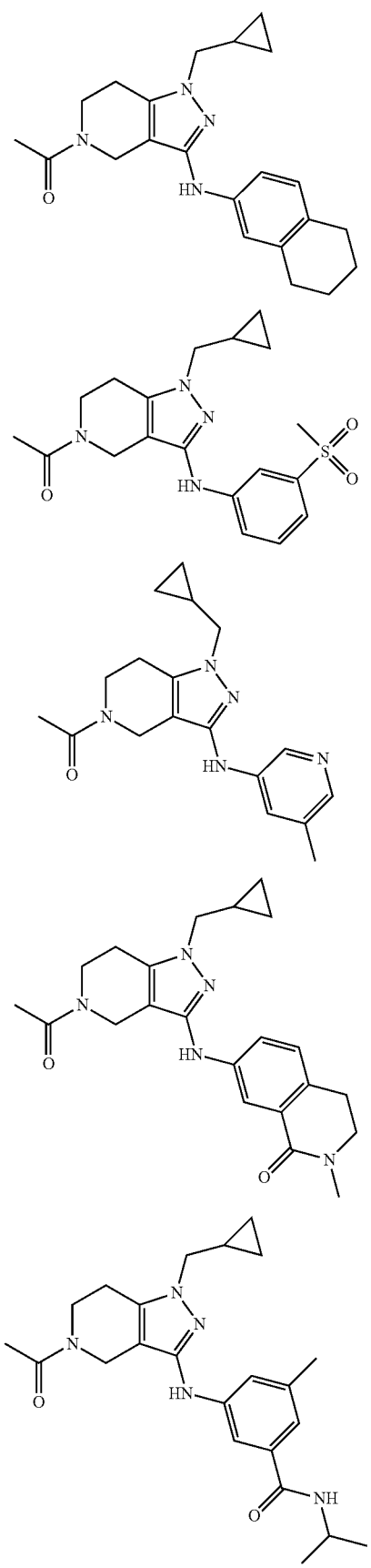
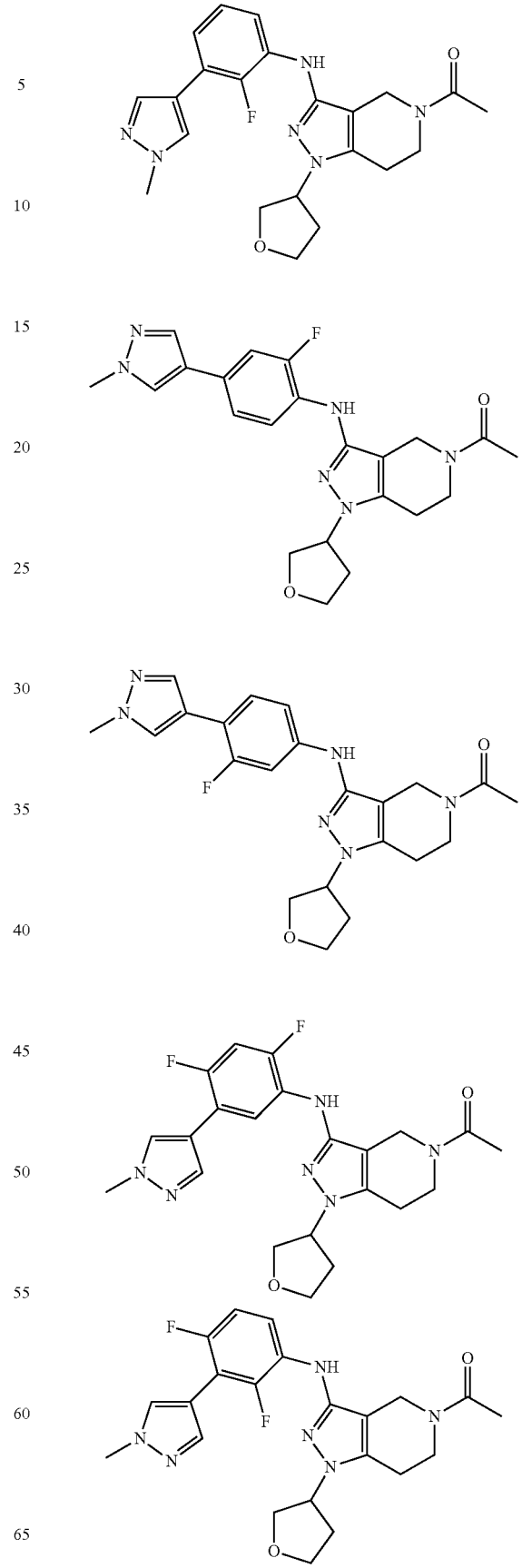

1143
-continued
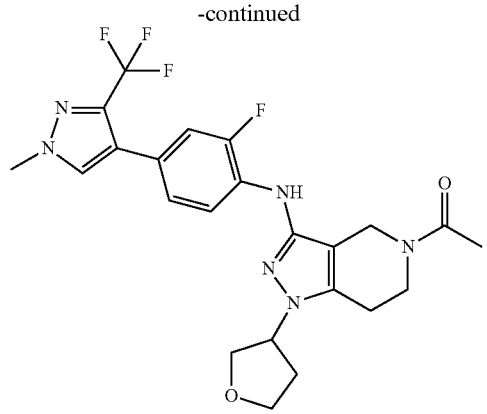
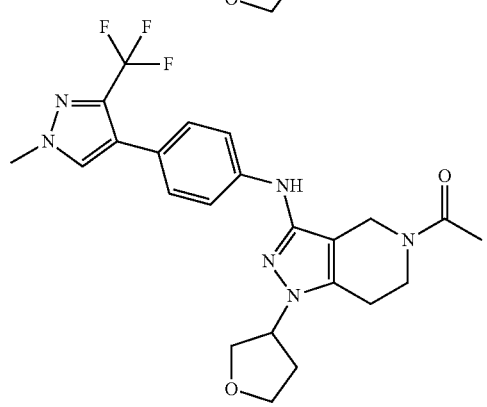
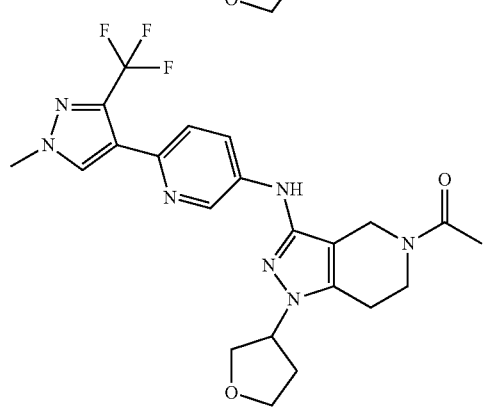
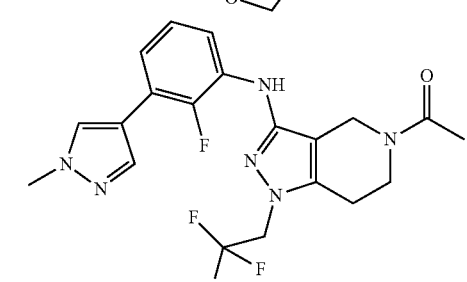
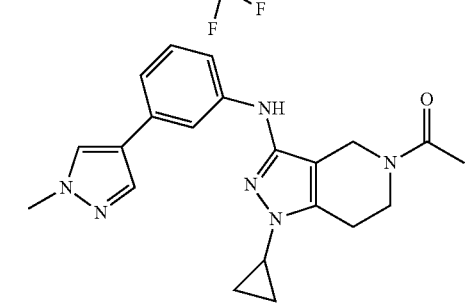
1144
-continued
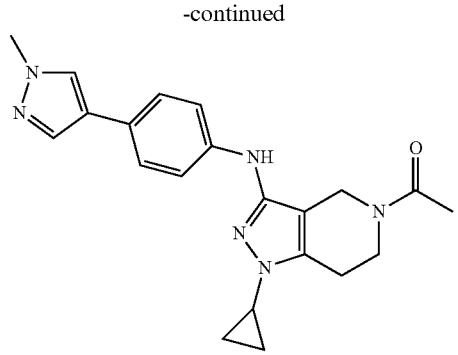
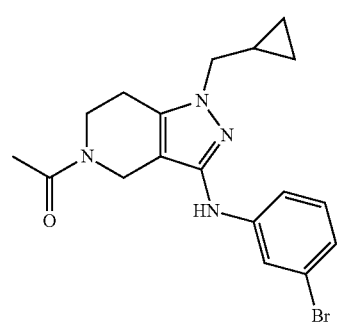
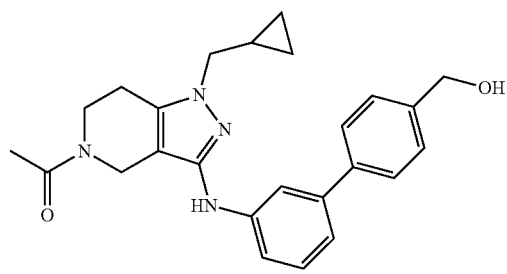
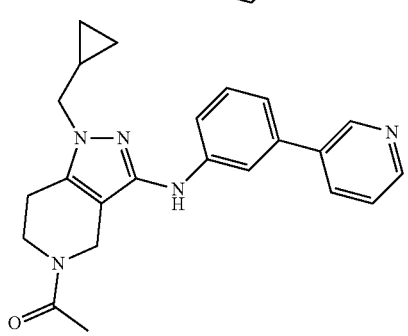
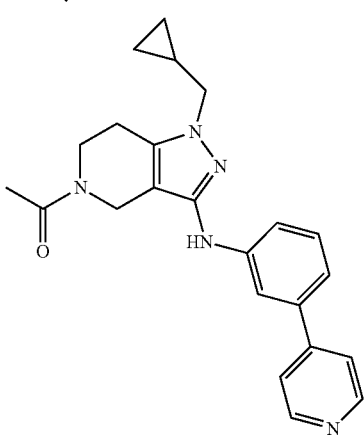

1145
-continued
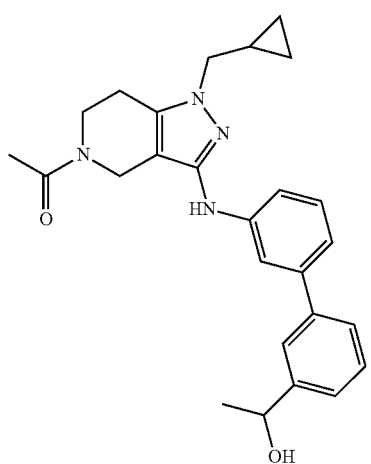
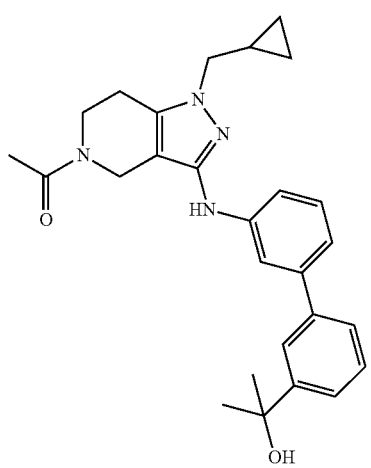
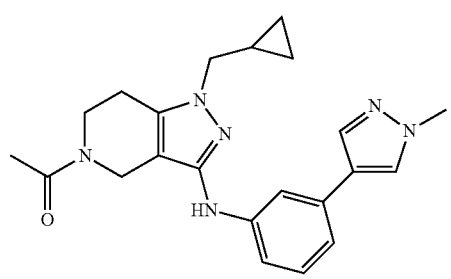
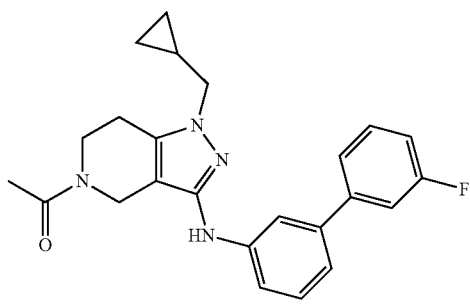
1146
-continued
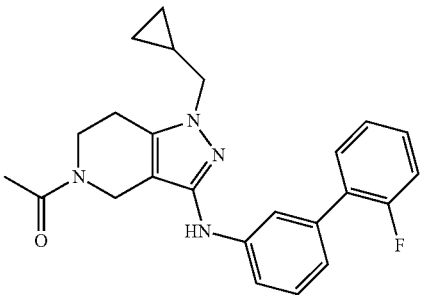
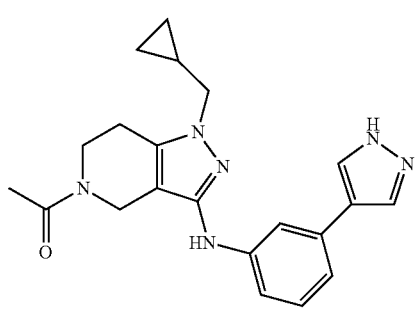
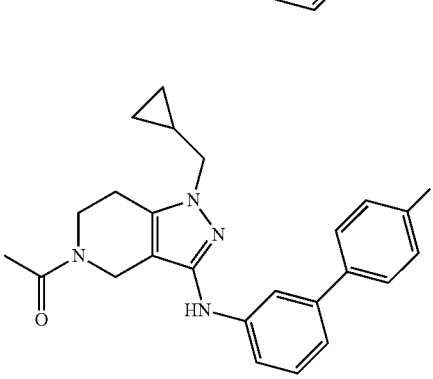
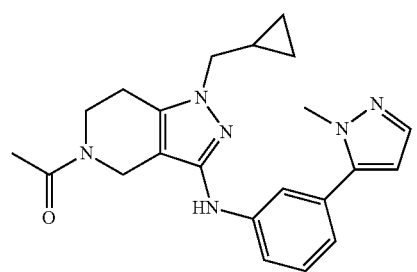

1147
-continued
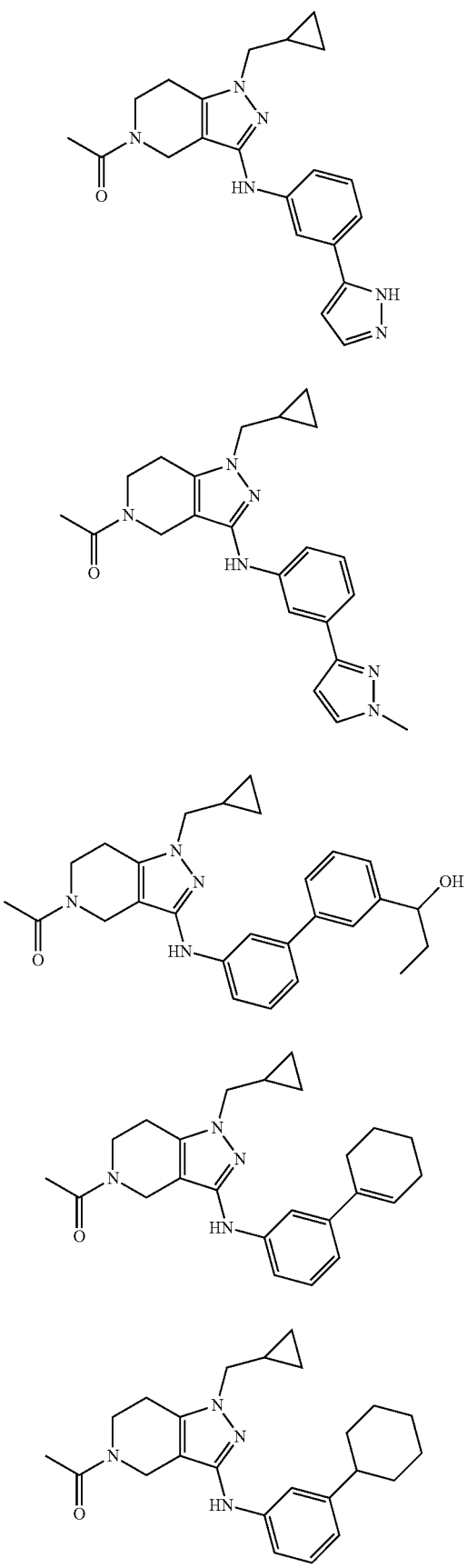
1148
-continued
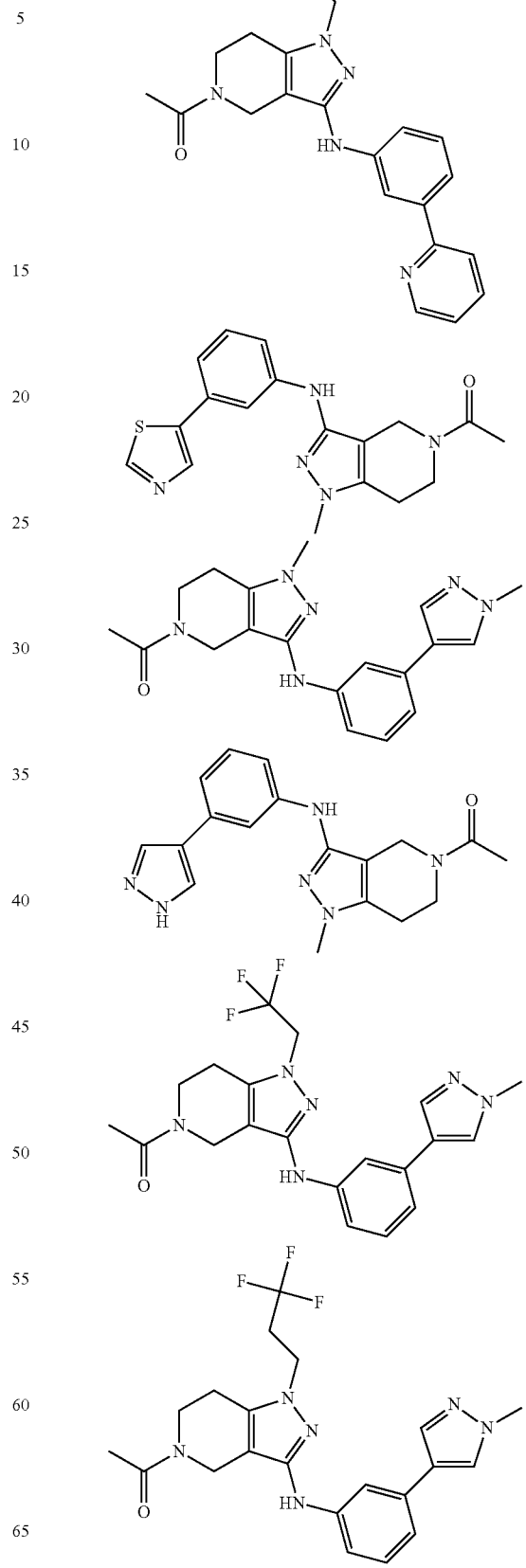

1149
-continued
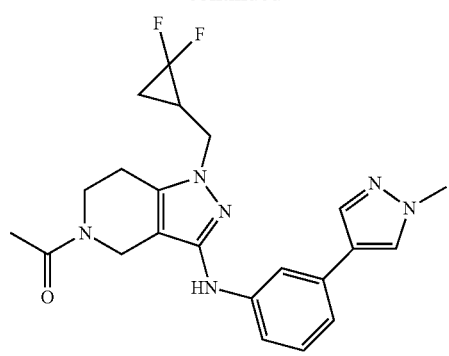
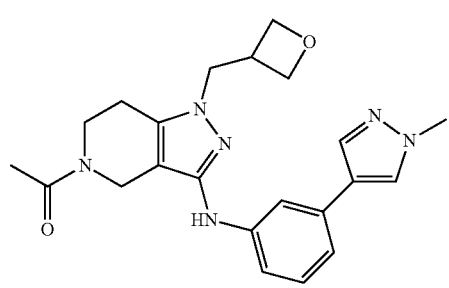
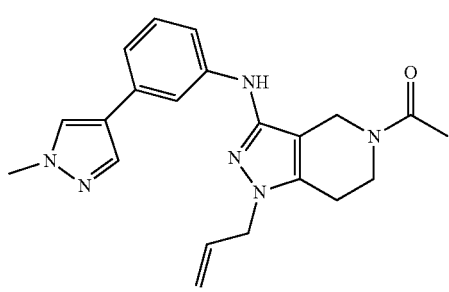
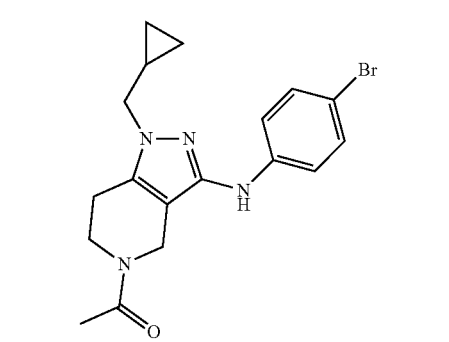
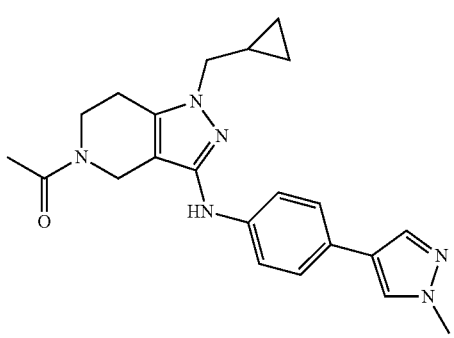
1150
-continued
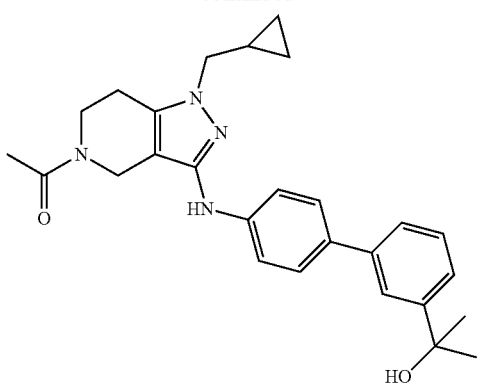
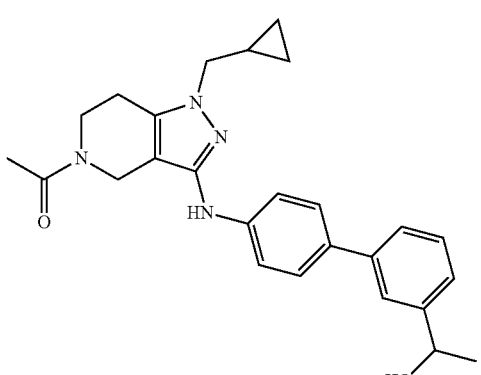
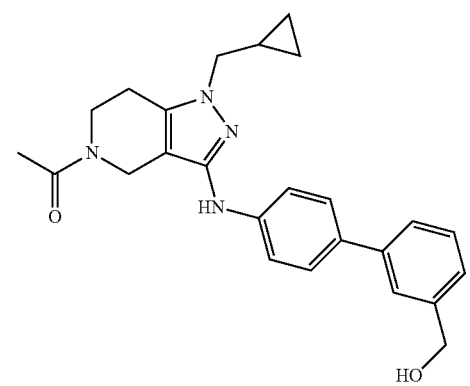
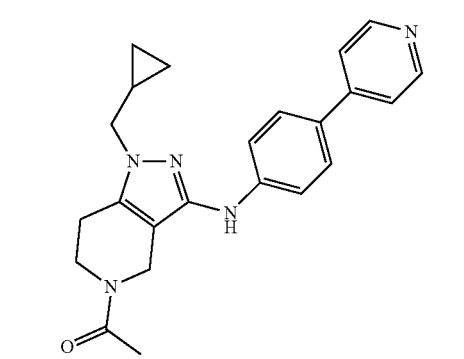

1151
-continued
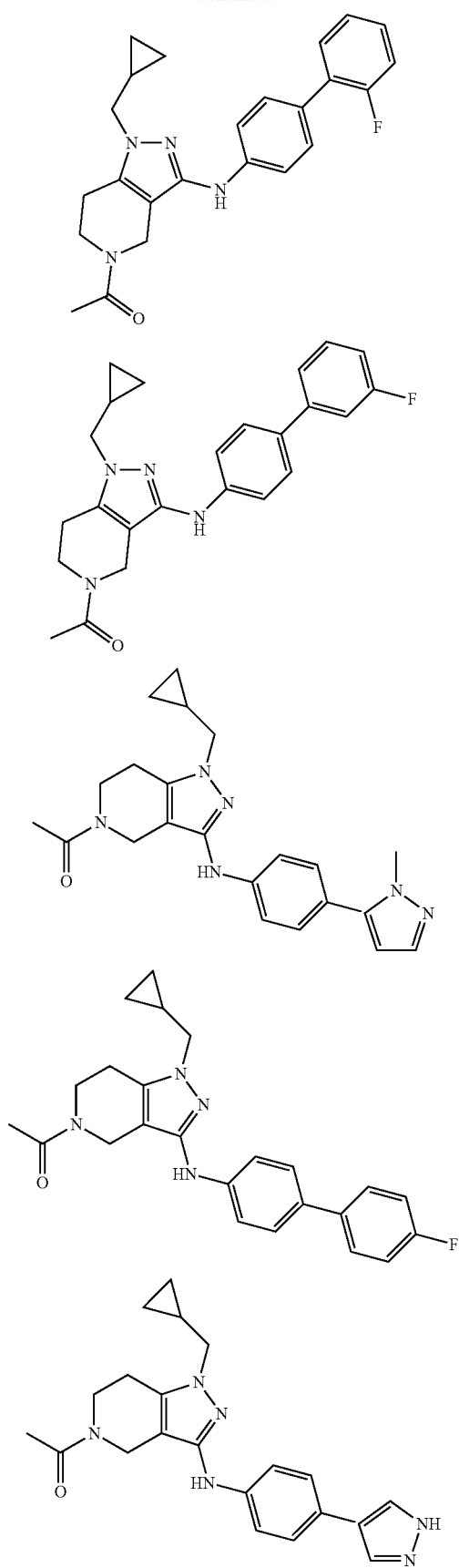
1152
-continued
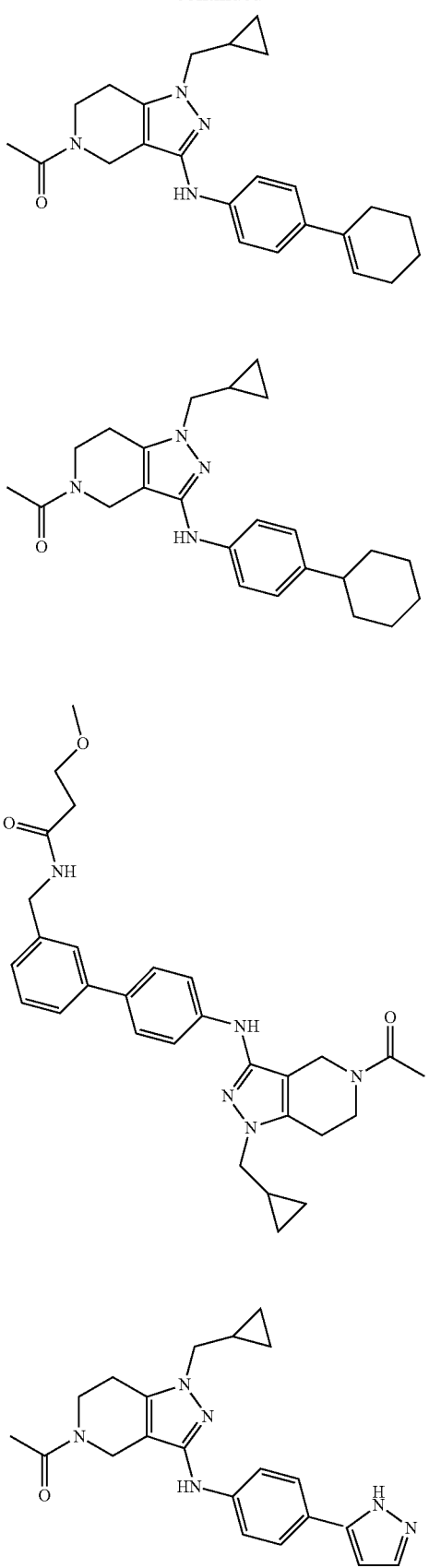

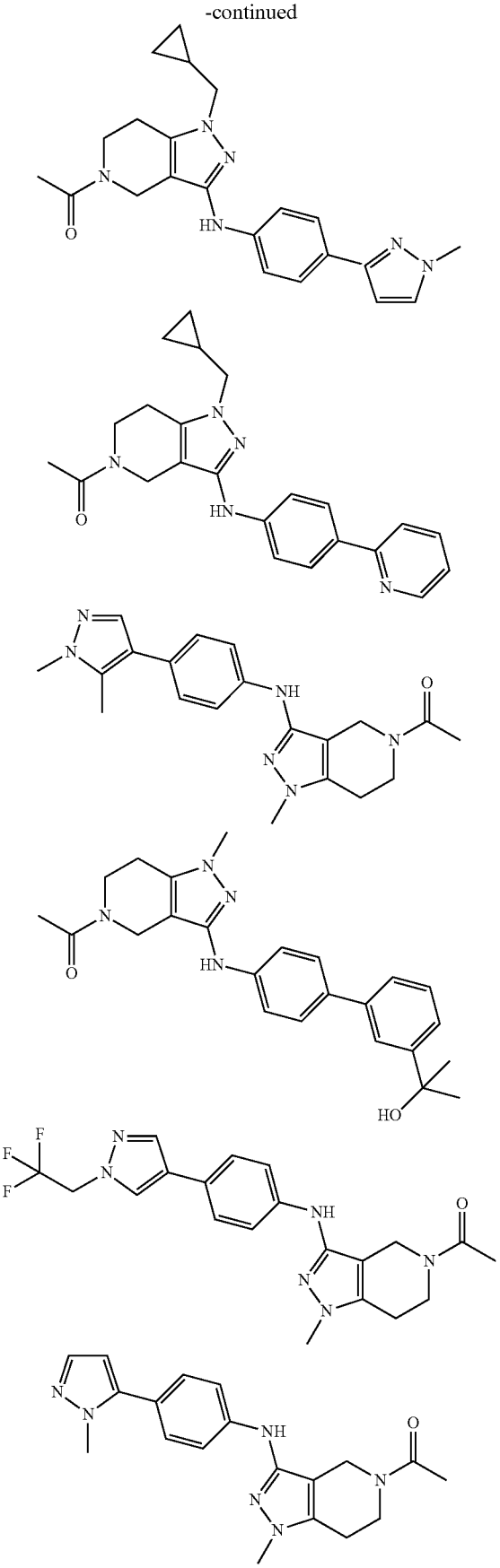
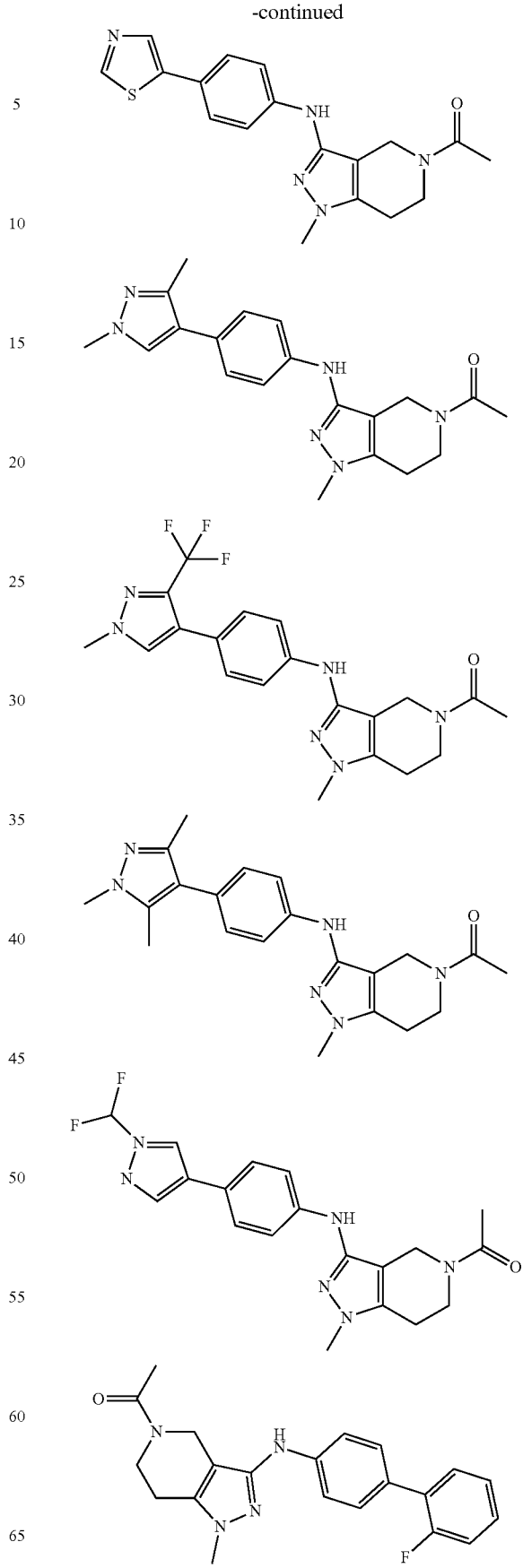

1155 1156
-continued -continued
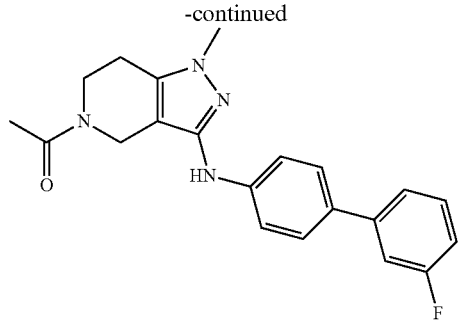
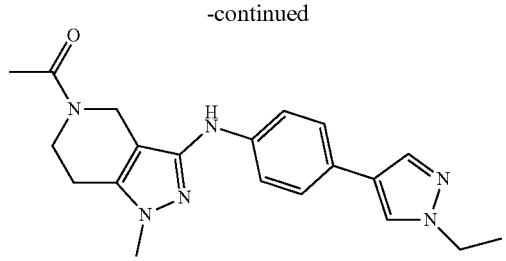
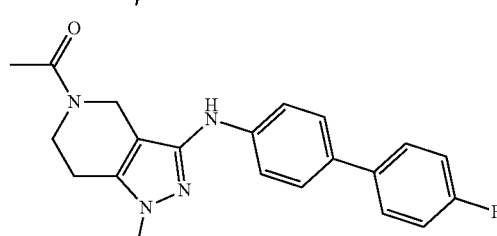
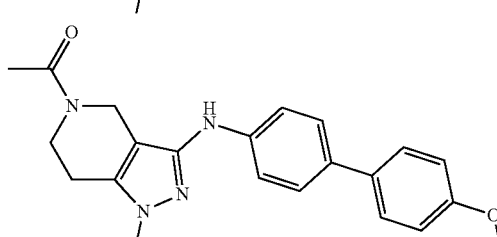
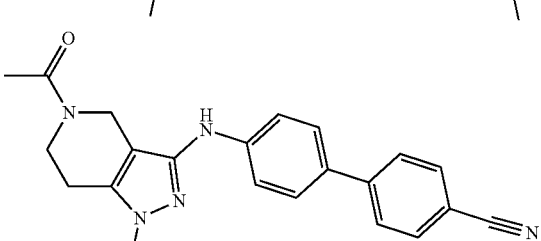
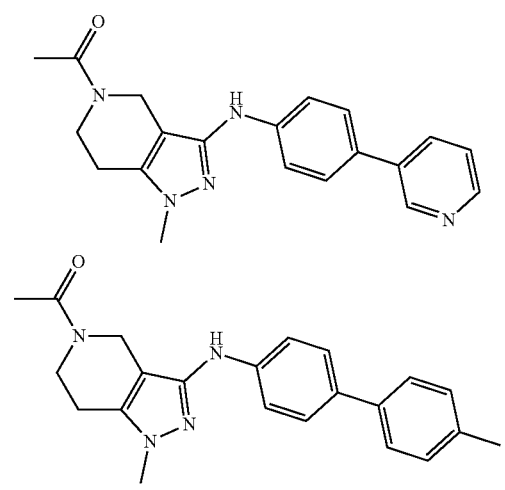
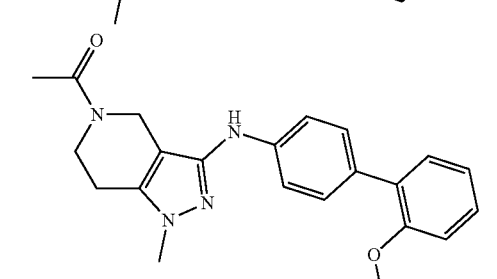
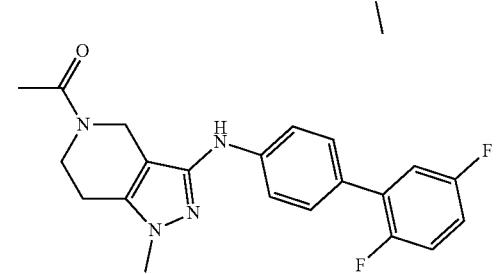
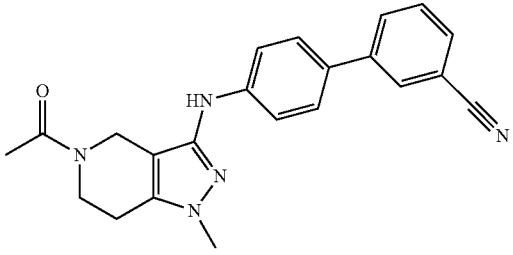
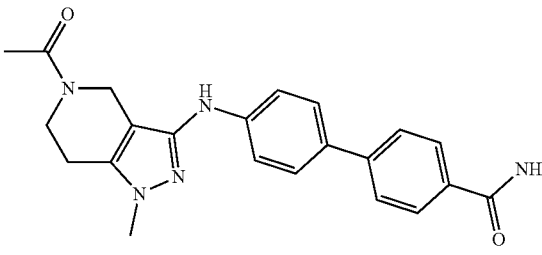

1157
-continued
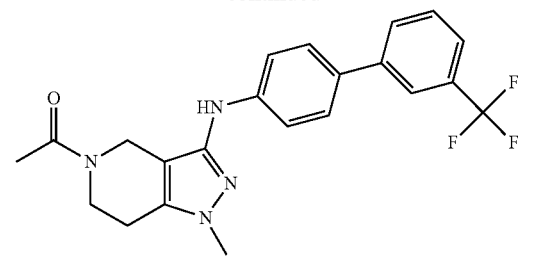
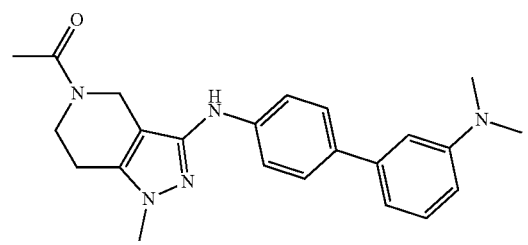
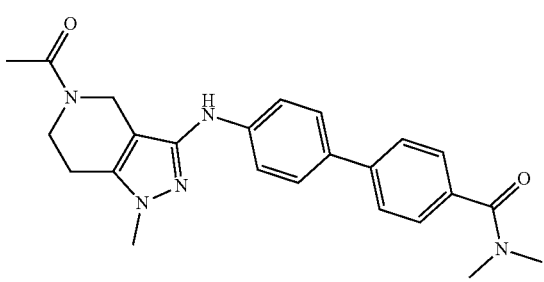
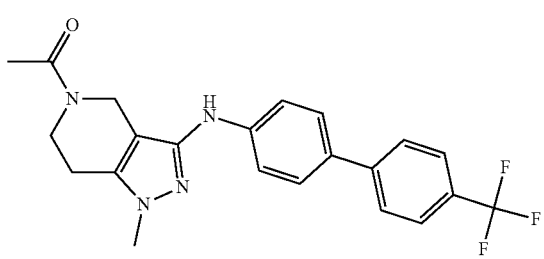
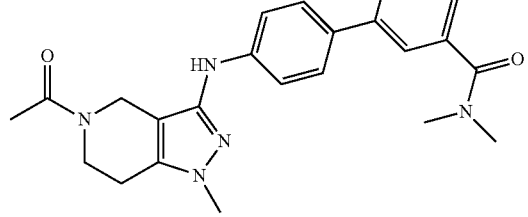
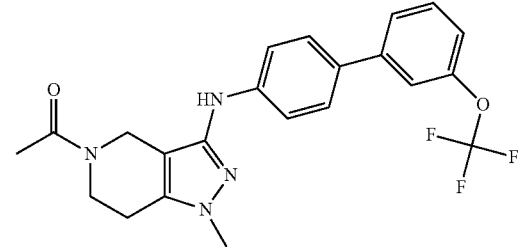
1158
-continued
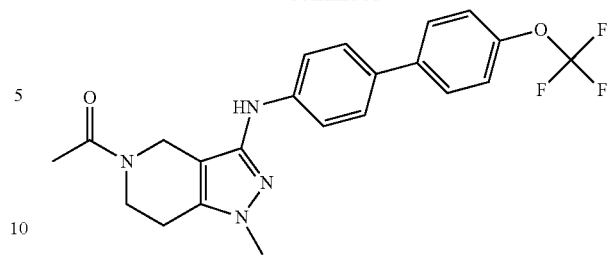
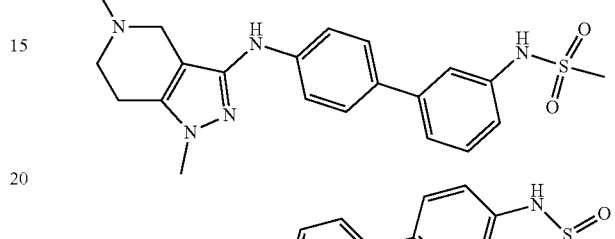
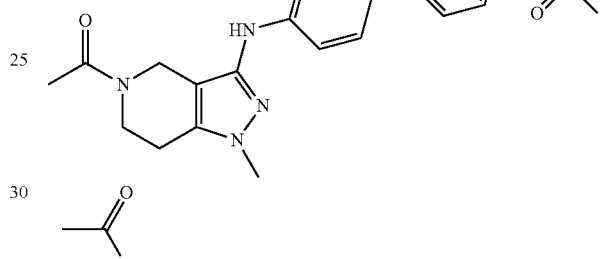
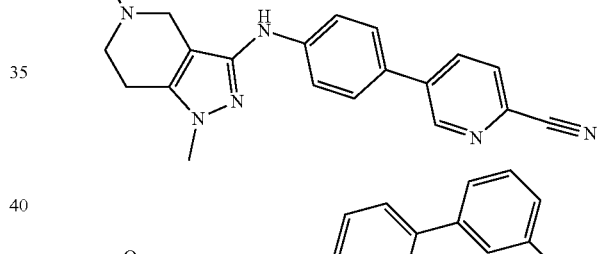
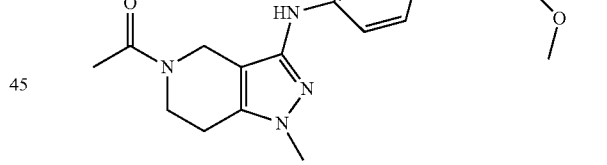
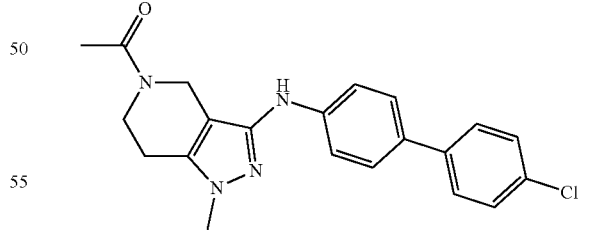
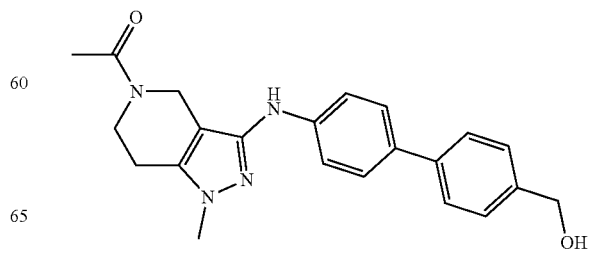

1159
-continued
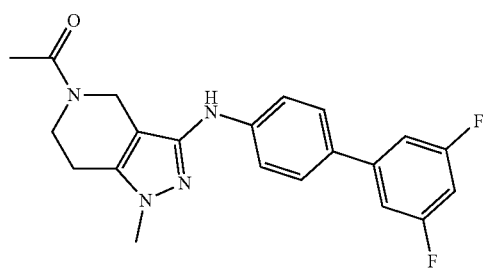
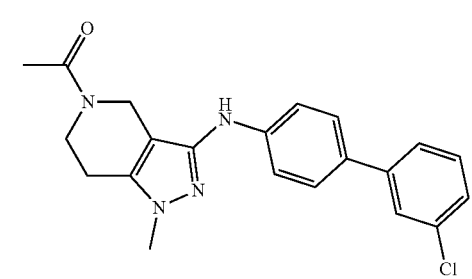
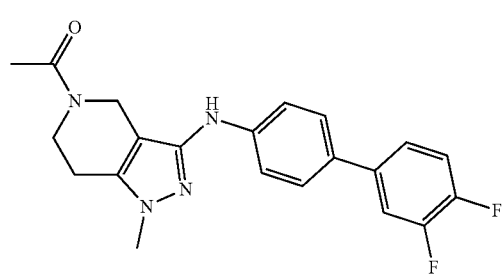
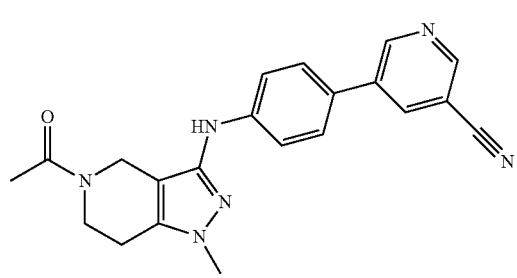
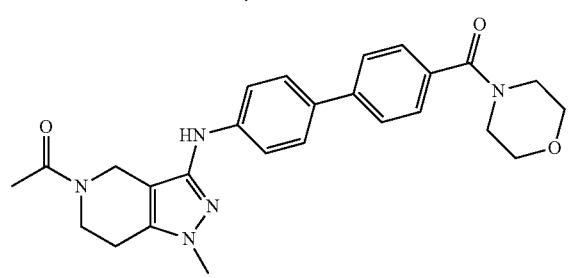
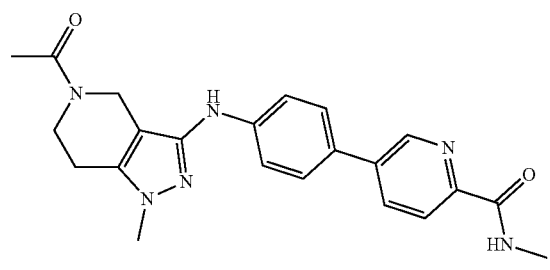
1160
-continued
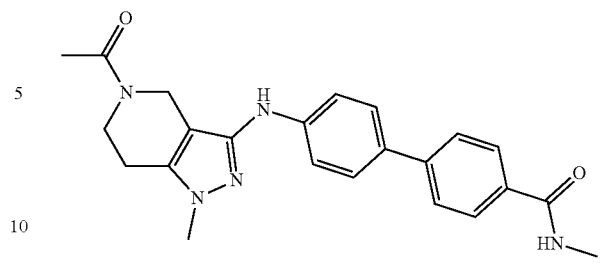
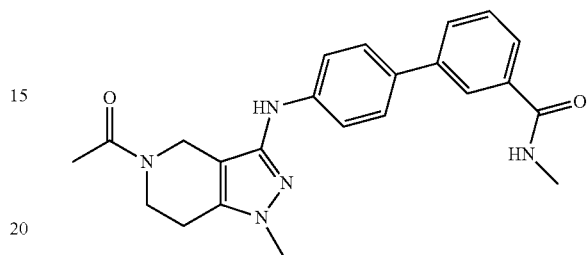
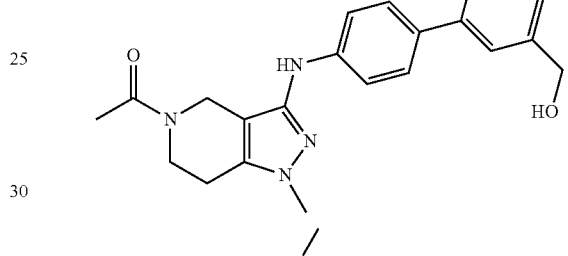
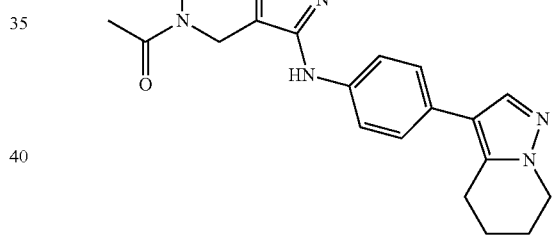
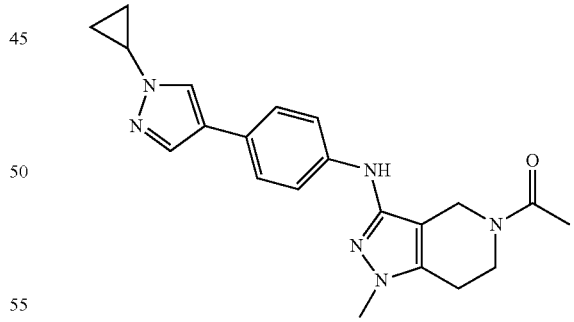
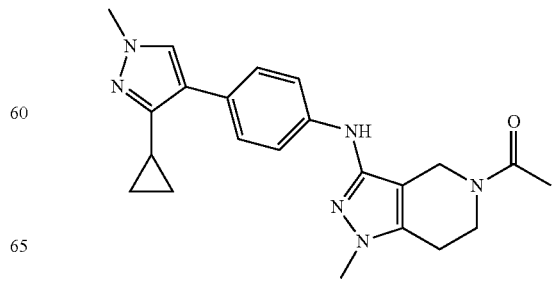

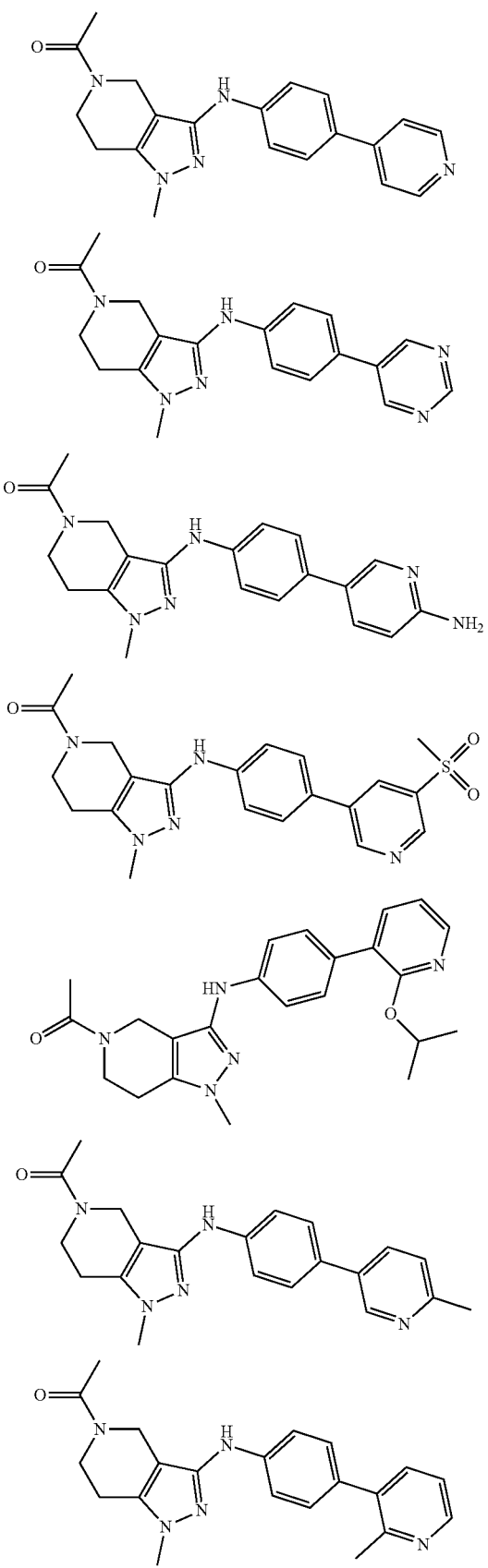
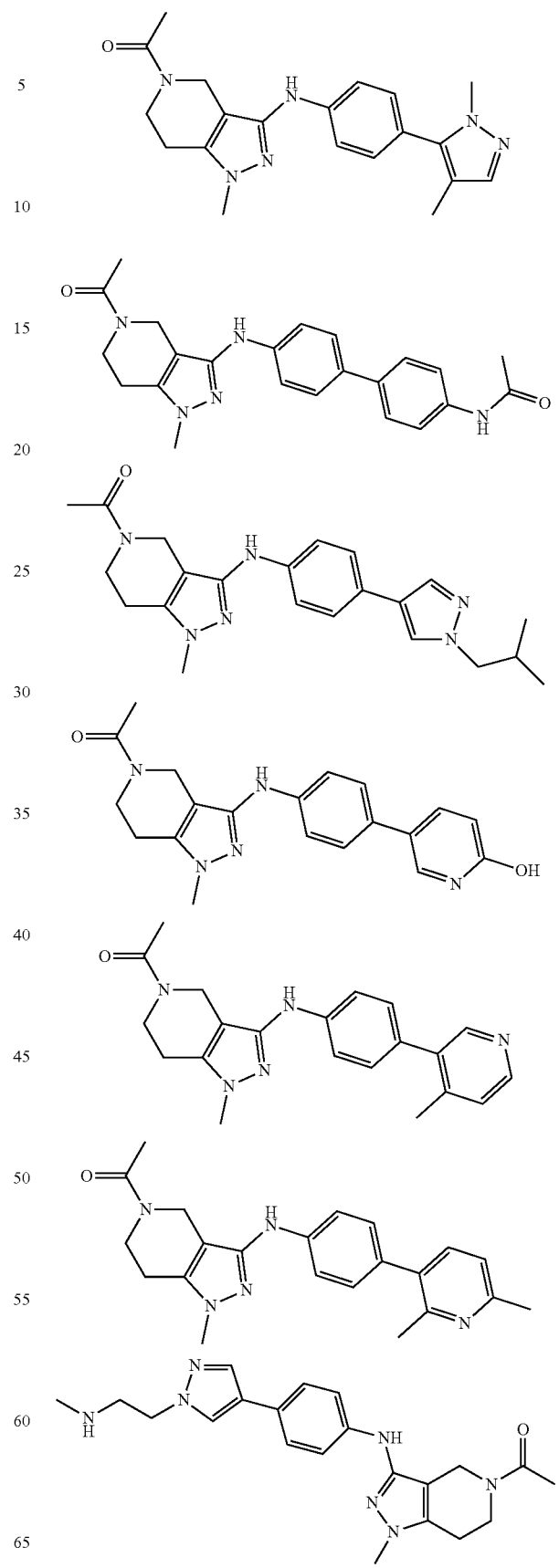

1163
-continued
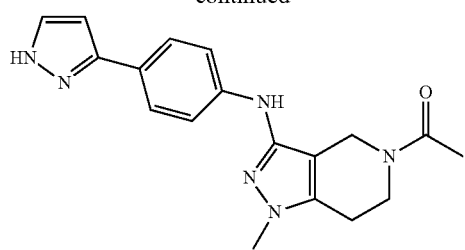
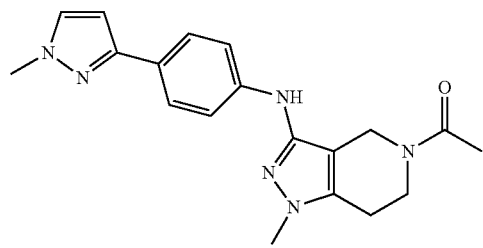
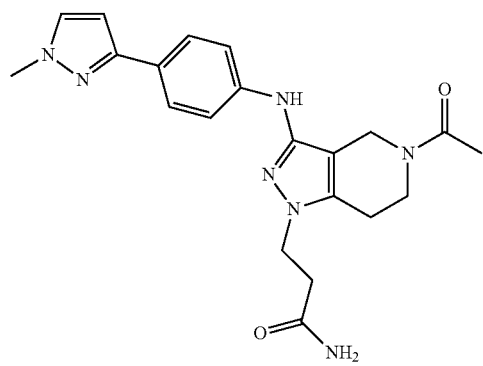
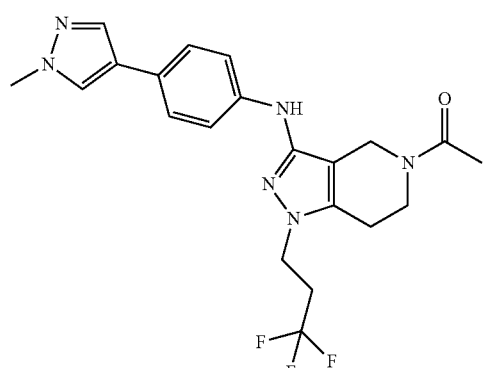
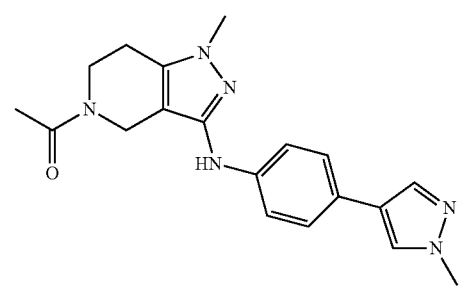
1164
-continued
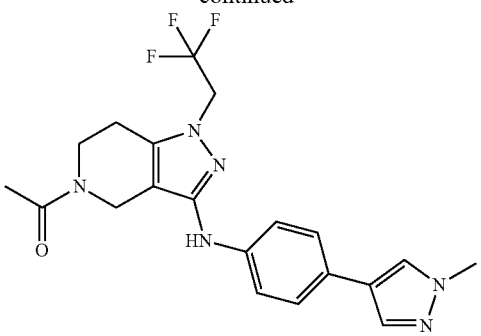
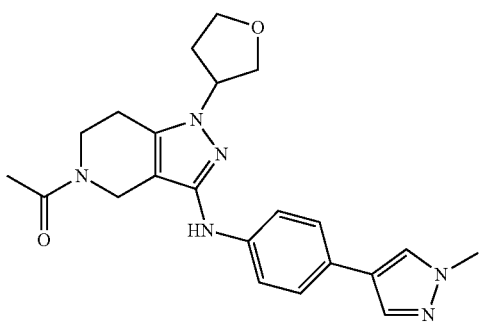
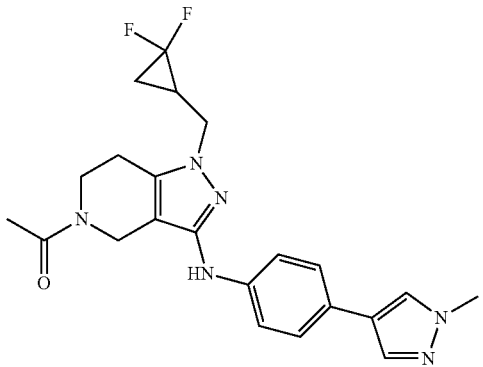
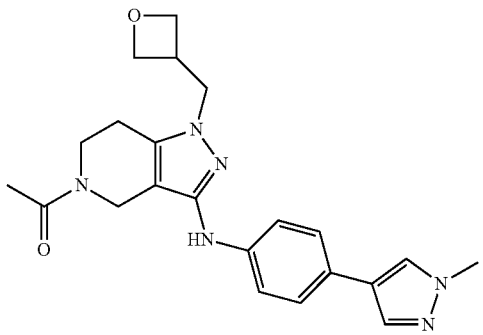
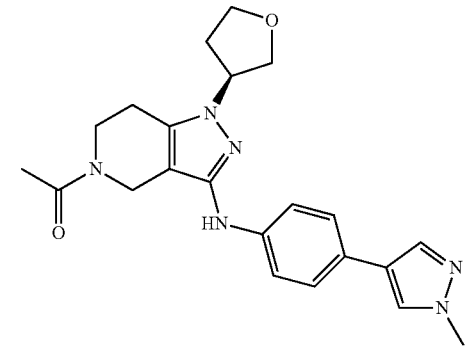

1165
-continued
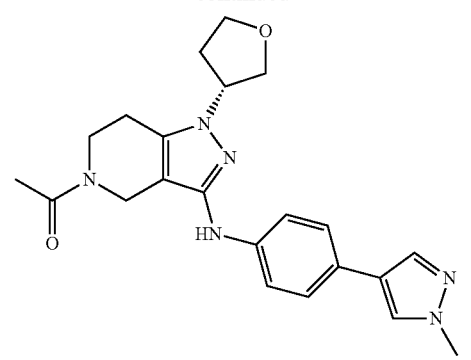
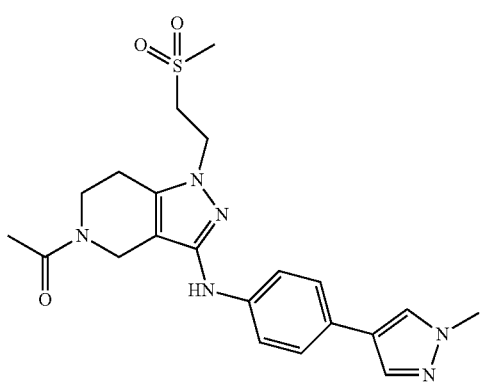
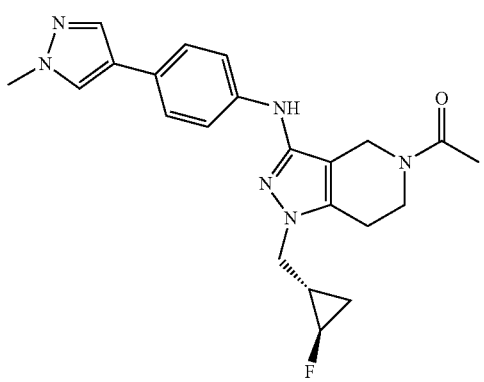
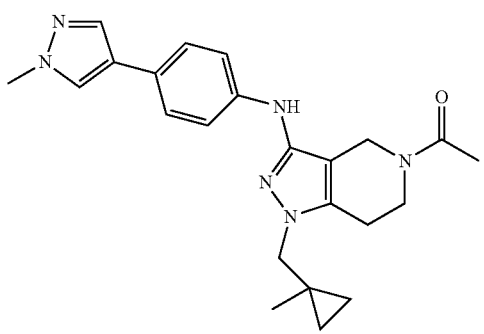
1166
-continued
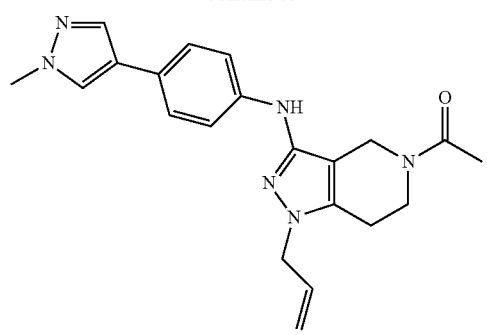
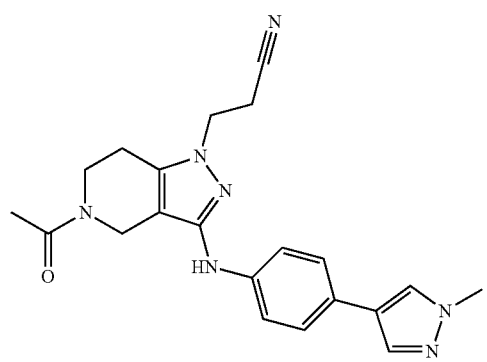
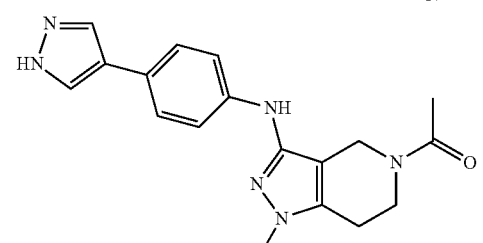
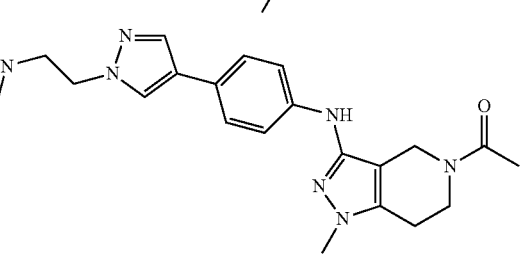
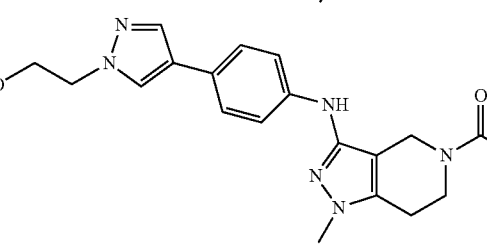
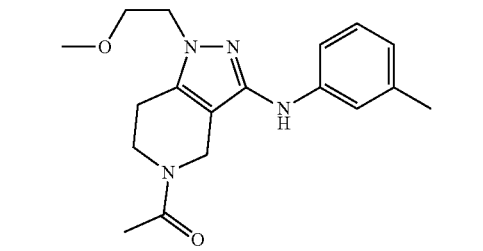

1167
-continued
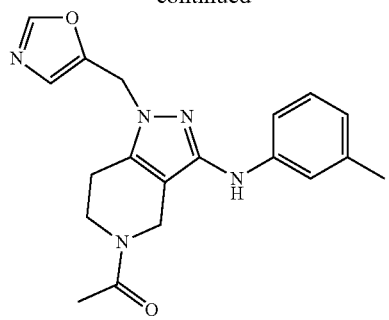
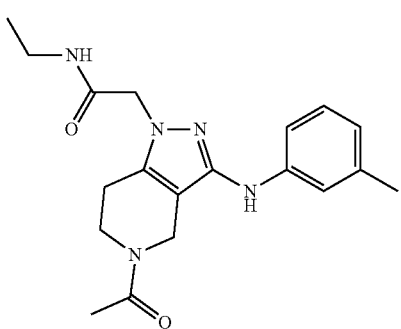
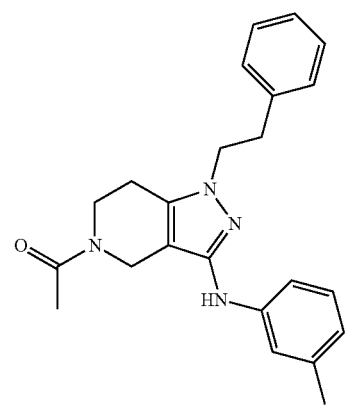
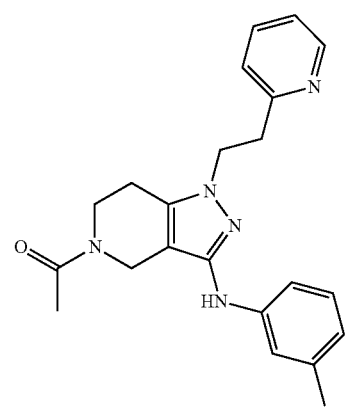
1168
-continued
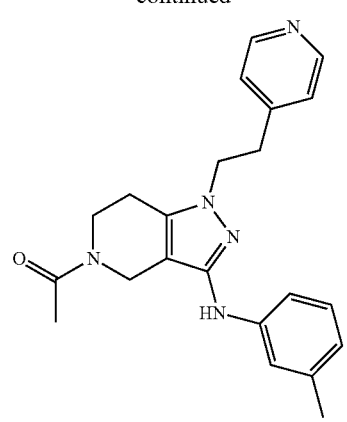
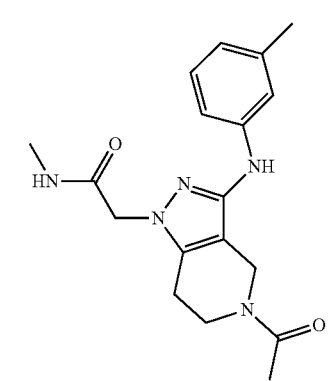
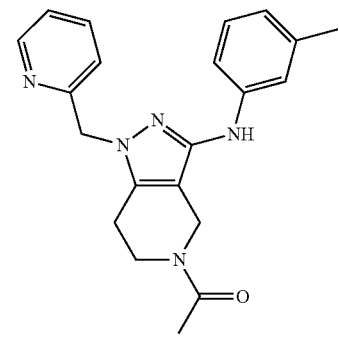
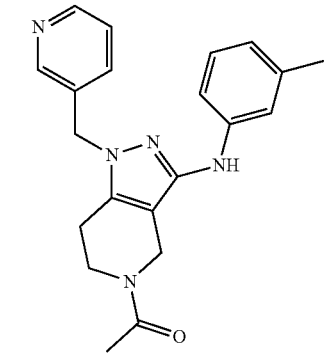

1169
-continued
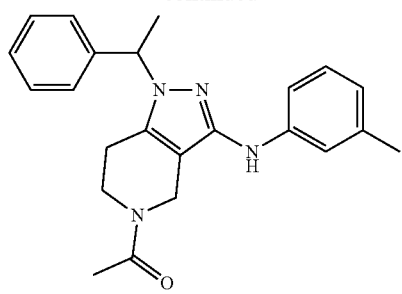
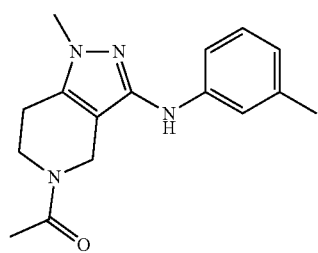
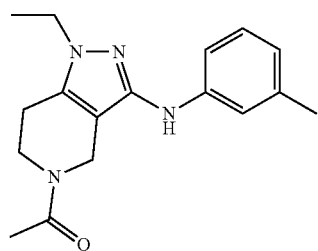
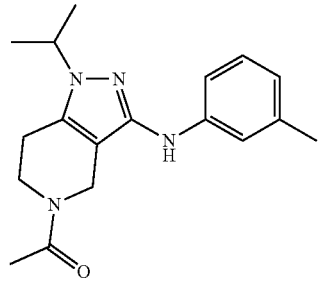
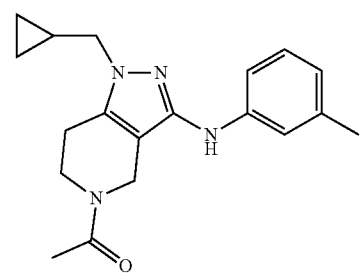
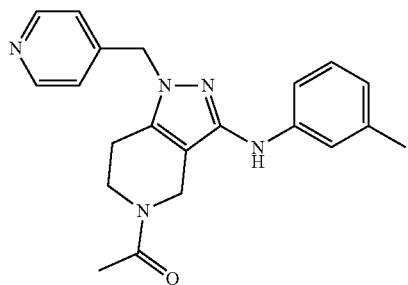
1170
-continued
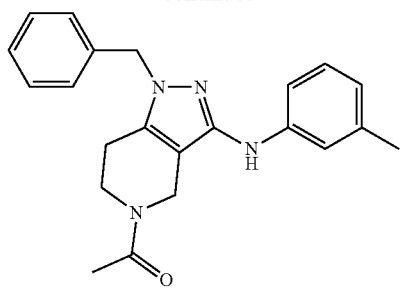
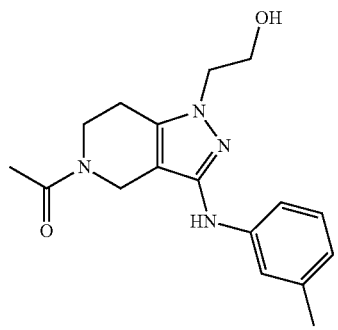
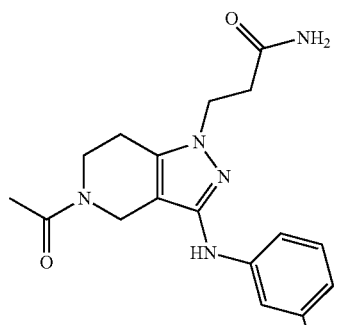
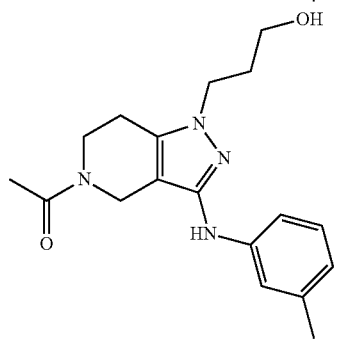
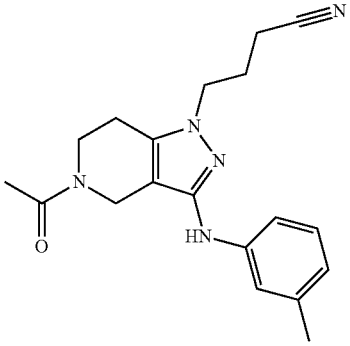

1171
-continued
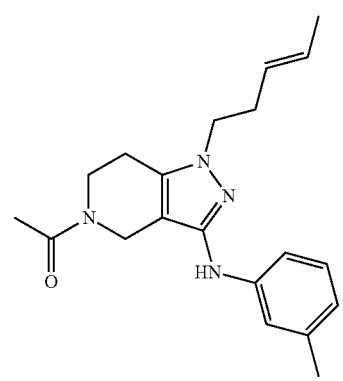
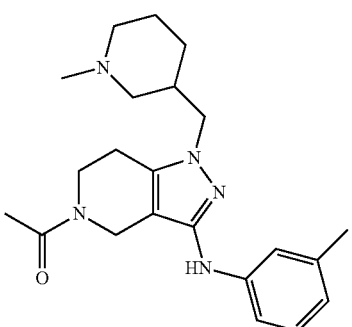
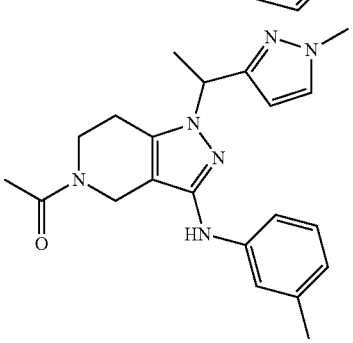
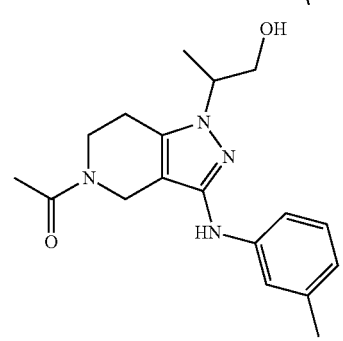
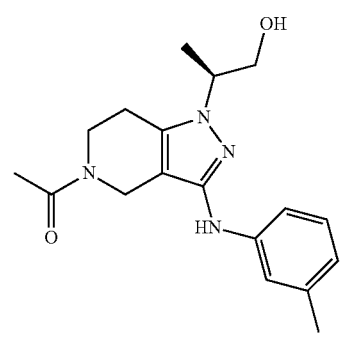
1172
-continued
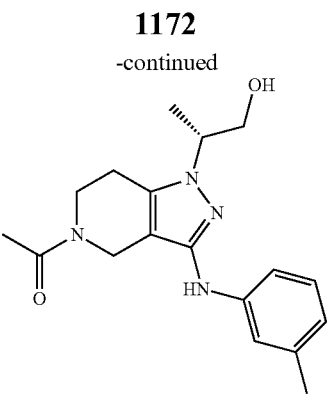
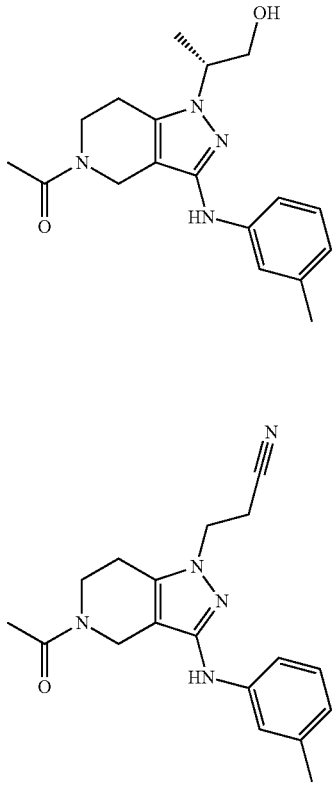
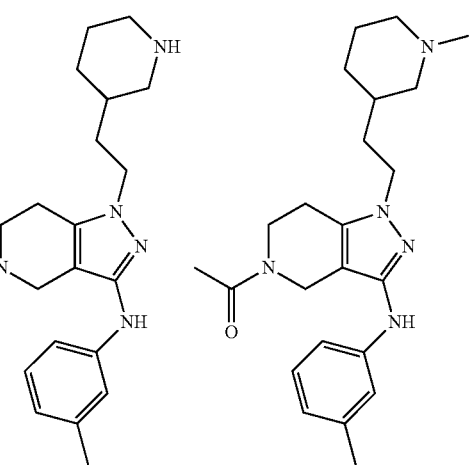
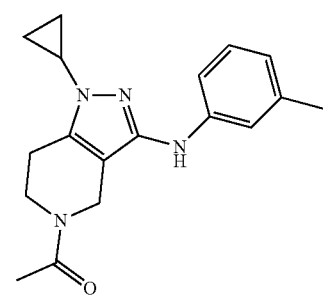

1173
-continued
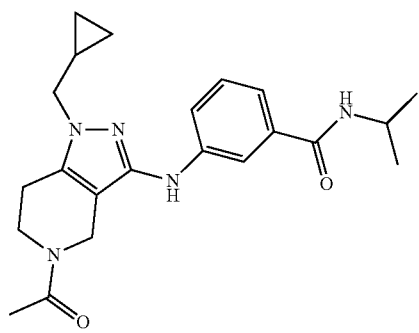
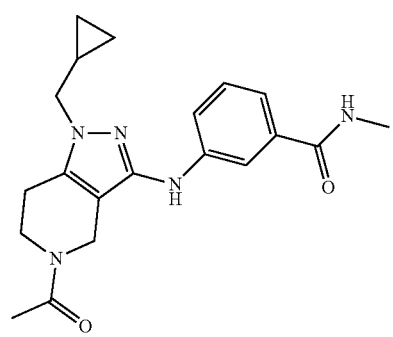
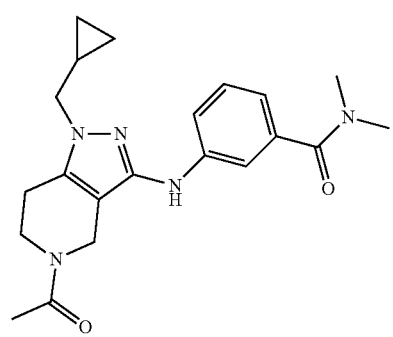
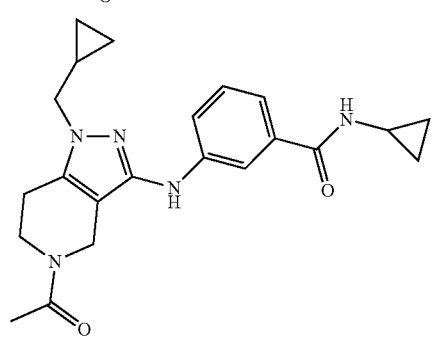
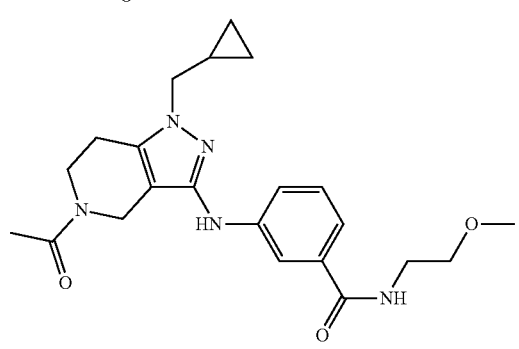
1174
-continued
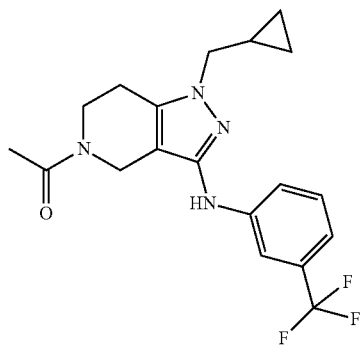
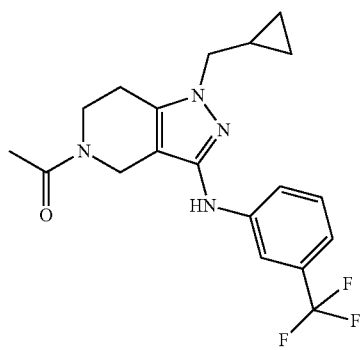
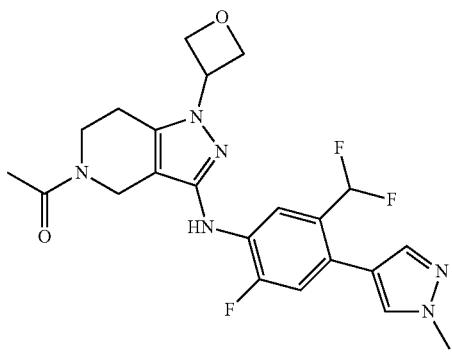
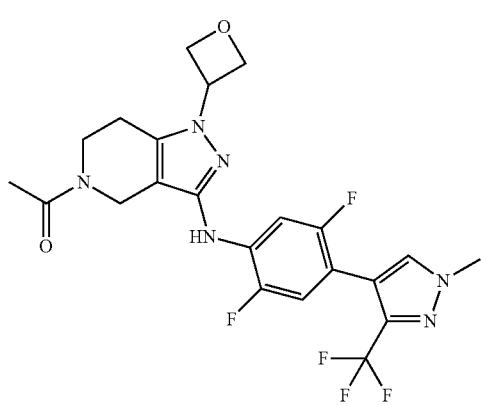

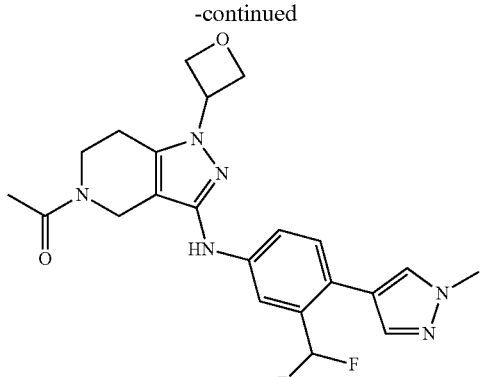
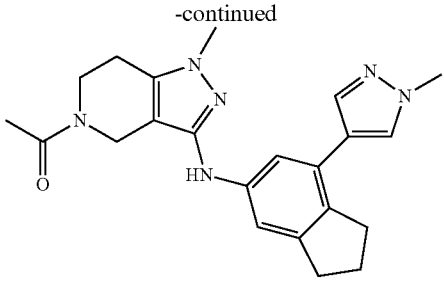
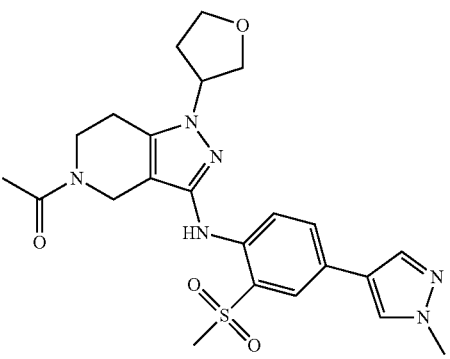
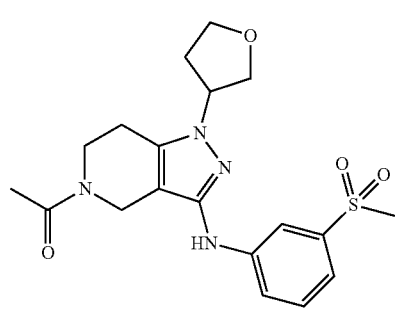
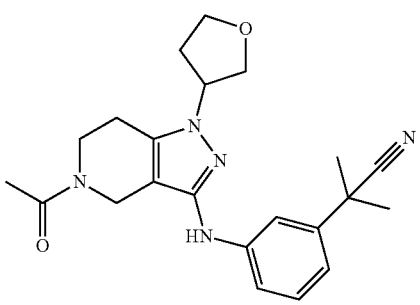
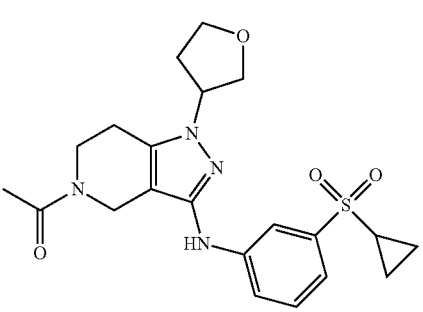

1177
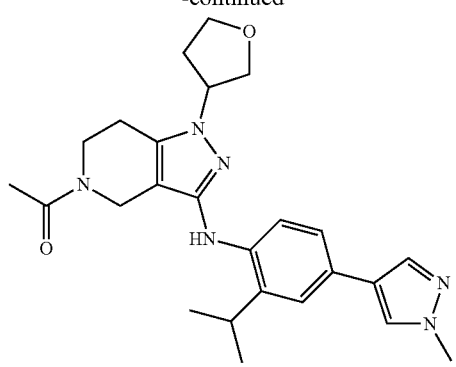
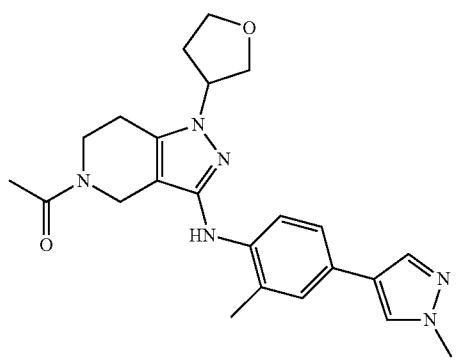
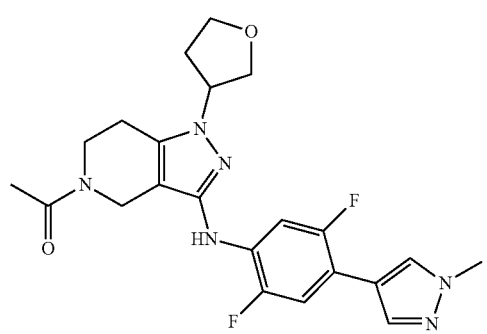
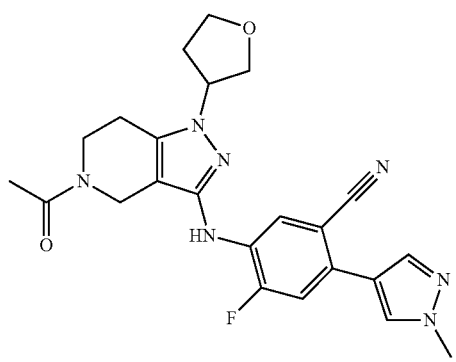
1178
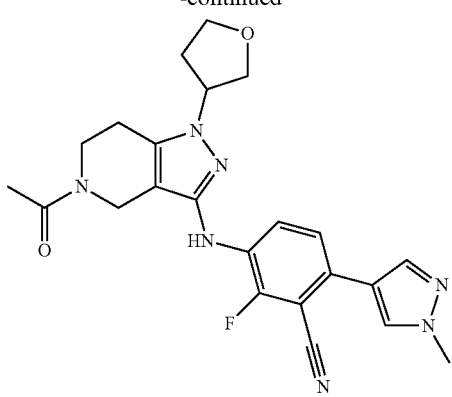
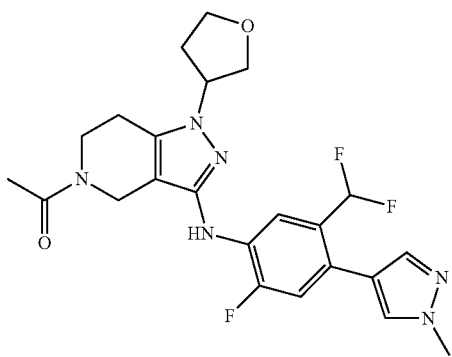
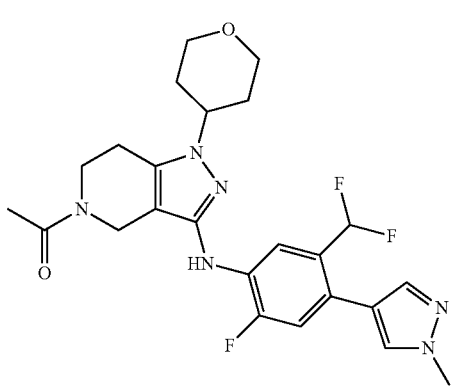
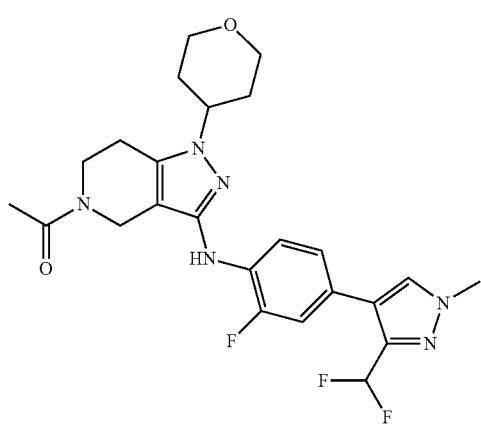

1179
-continued
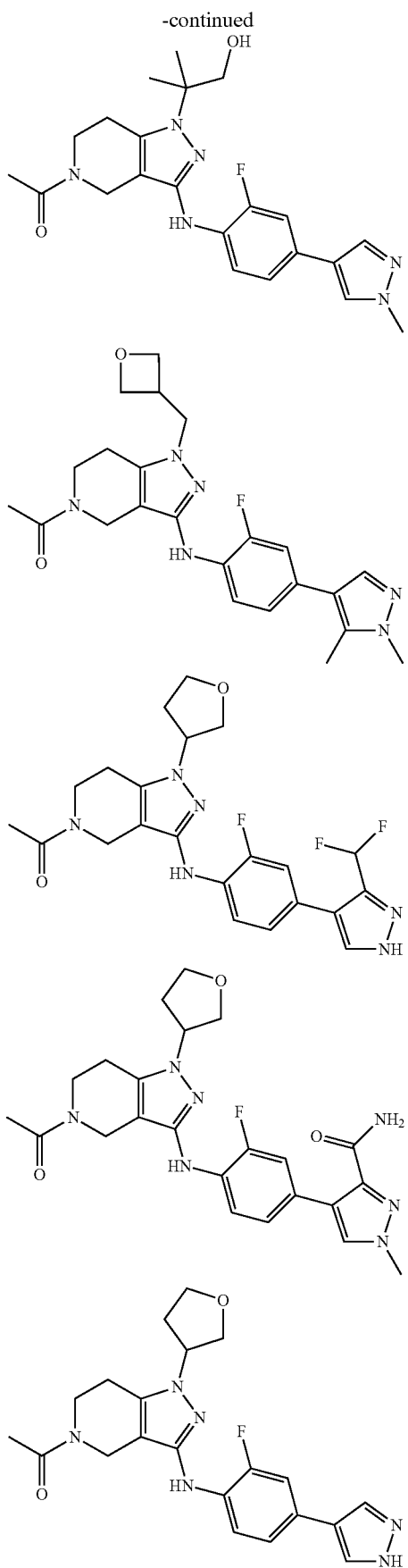
1180
-continued
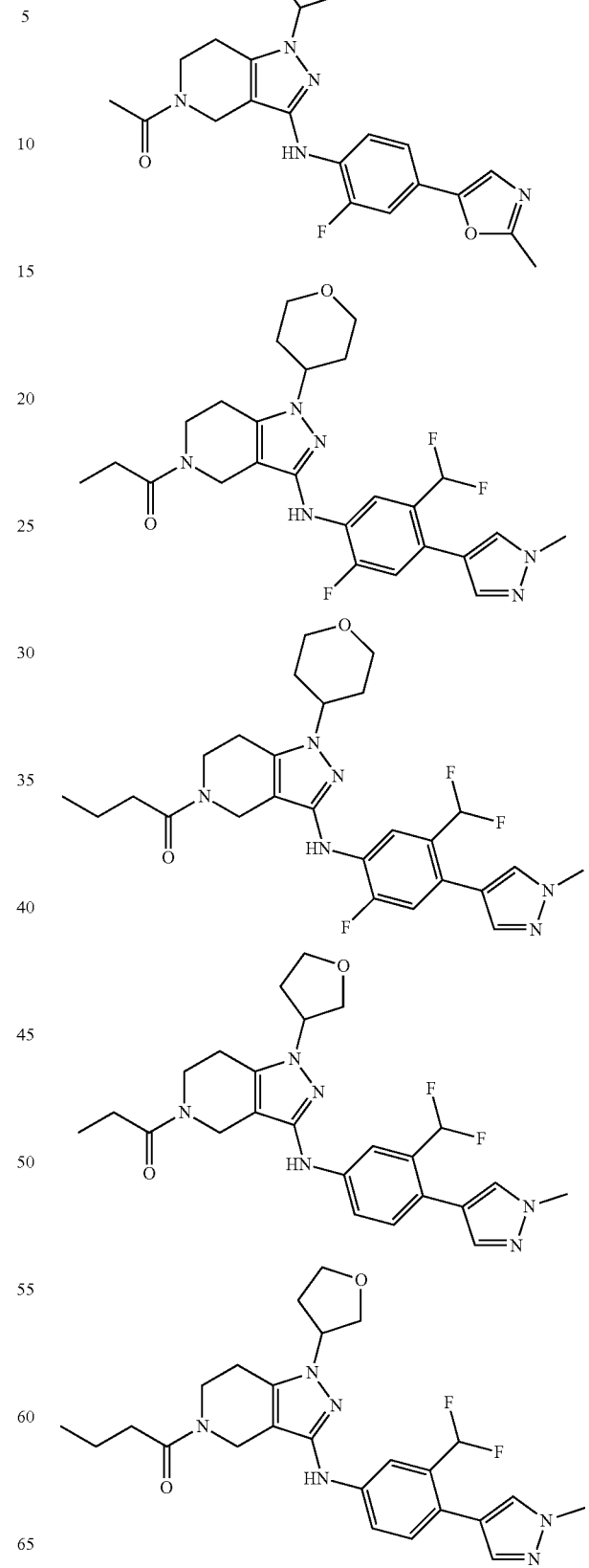

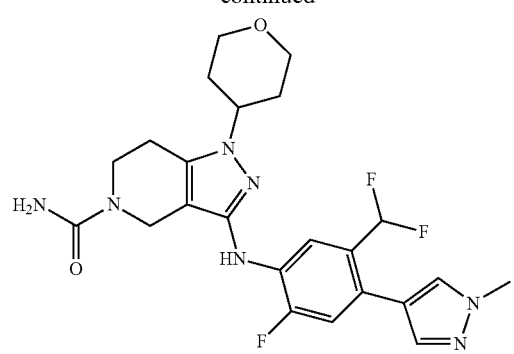
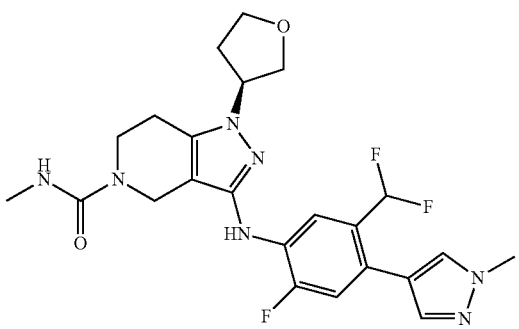
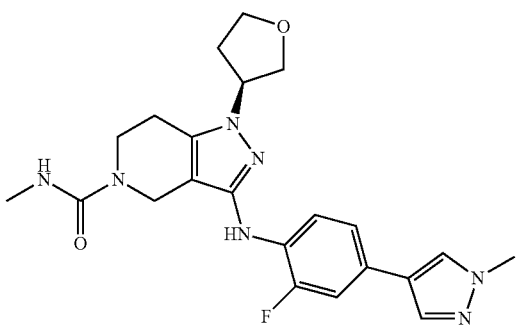
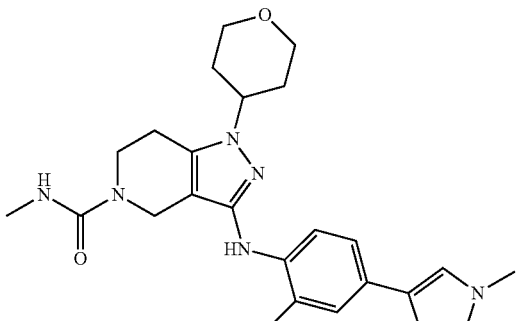
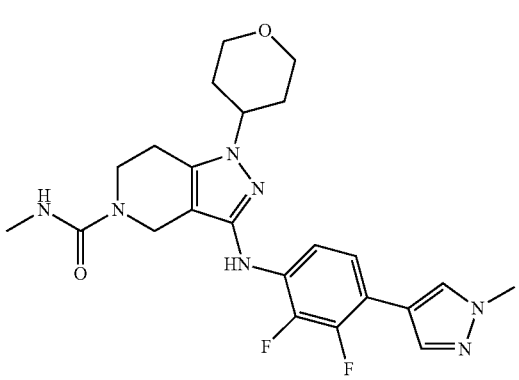

-continued
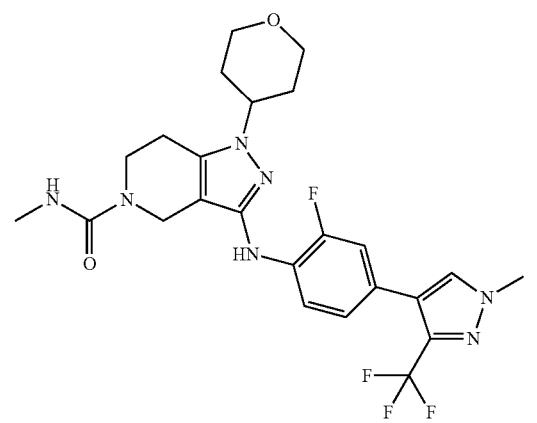
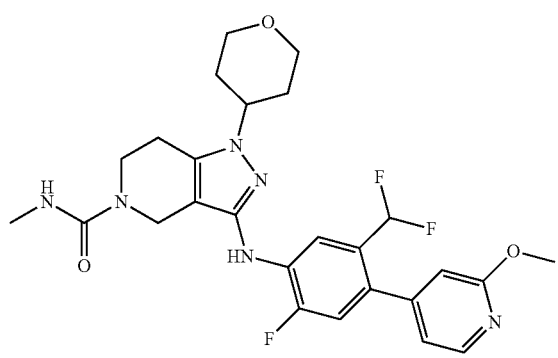
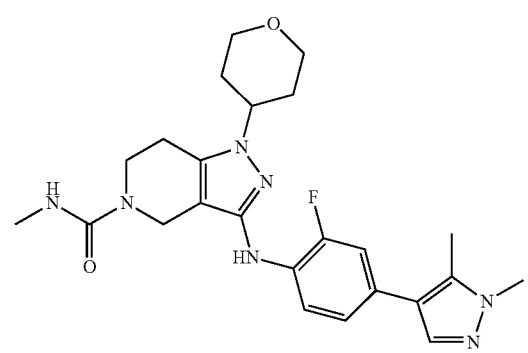
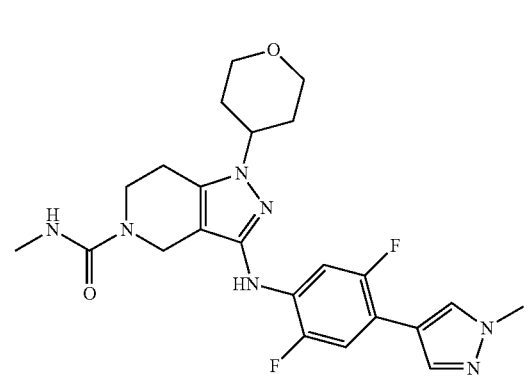
-continued
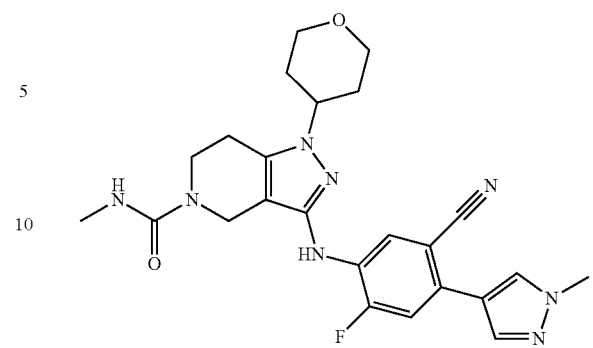
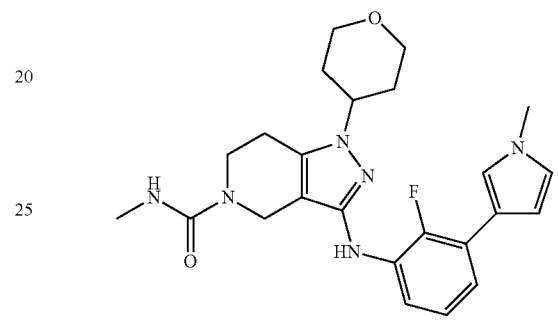
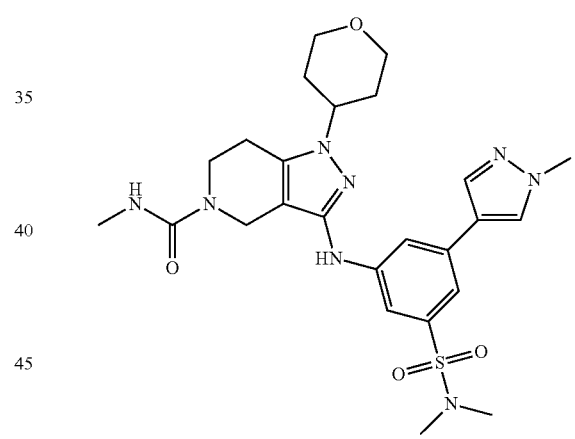
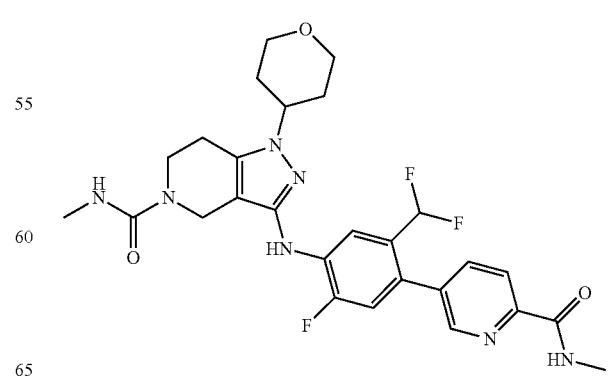

1185
-continued
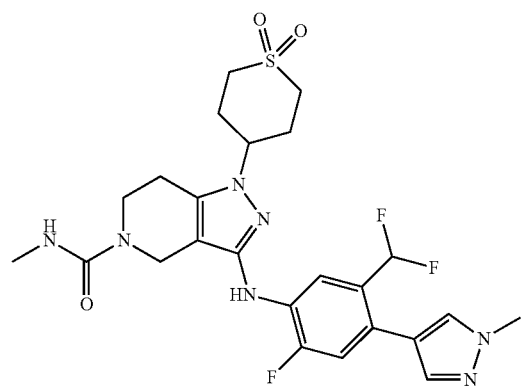
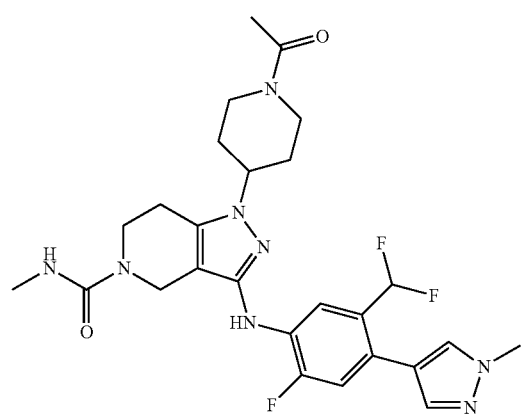
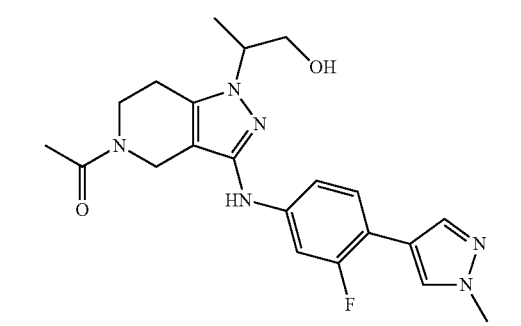
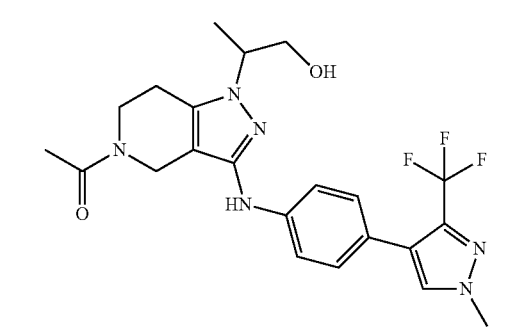
1186
-continued
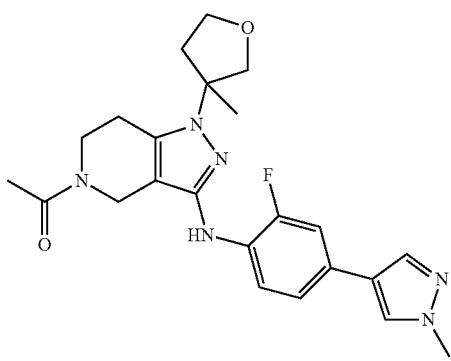
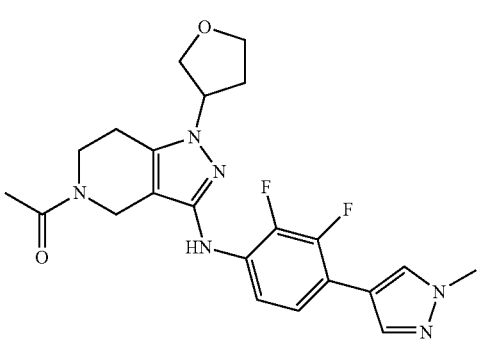 [SMILES: CC(=O)N1CCc2c(c(Nc3ccc(-c4cnn(C)c4)c(F)c3F)nn2C2CCOC2)C1]
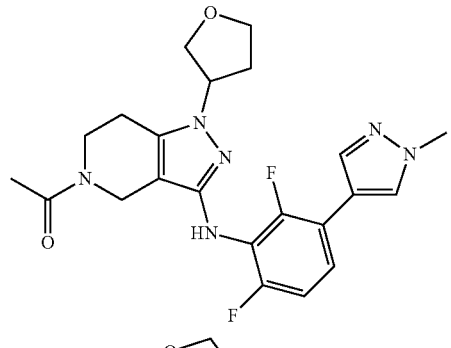
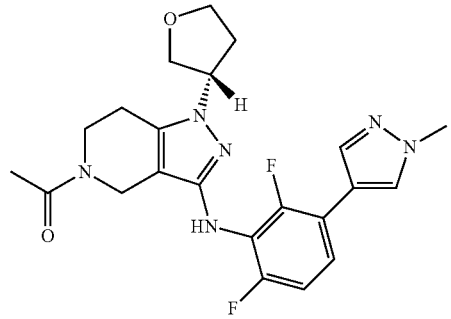 [SMILES: CC(=O)N1CCc2c(c(Nc3c(F)ccc(-c4cnn(C)c4)c3F)nn2[C@@H]2CCOC2)C1]
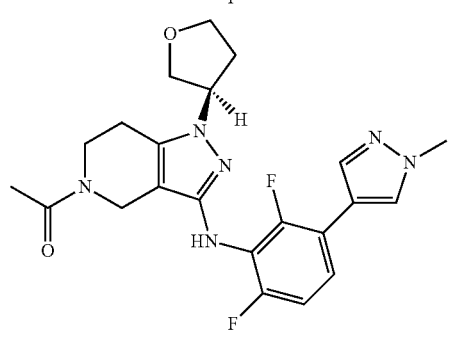

1187
-continued
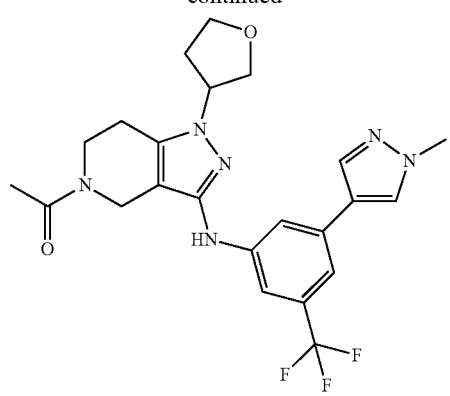
1188
-continued
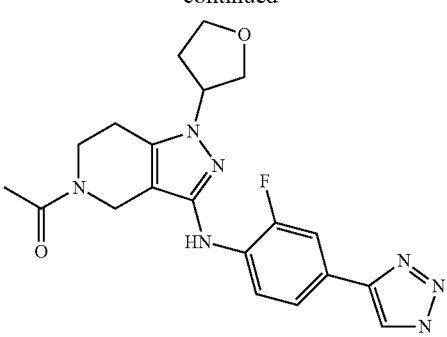
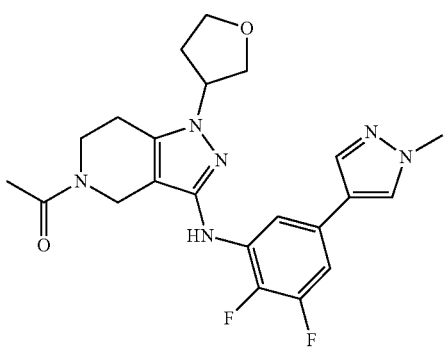 [SMILES: CC(=O)N1CCc2c(c(Nc3cc(-c4cnn(C)c4)cc(F)c3F)nn2C2CCOC2)C1]
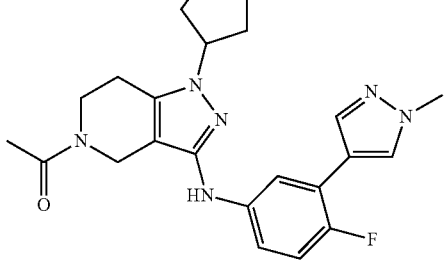
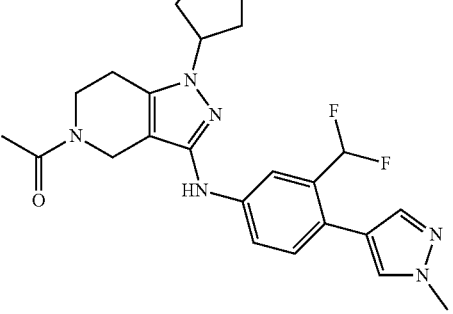
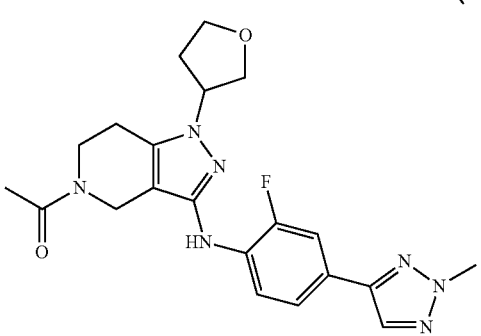

| 1189 | 1190 |
|---|---|
| -continued | -continued |
| 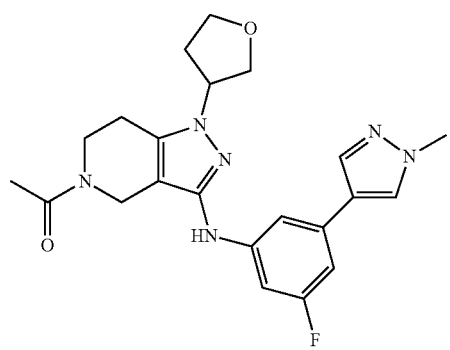 [SMILES: CC(=O)N1CCc2c(c(Nc3cc(F)cc(-c4cnn(C)c4)c3)nn2C2CCOC2)C1] | 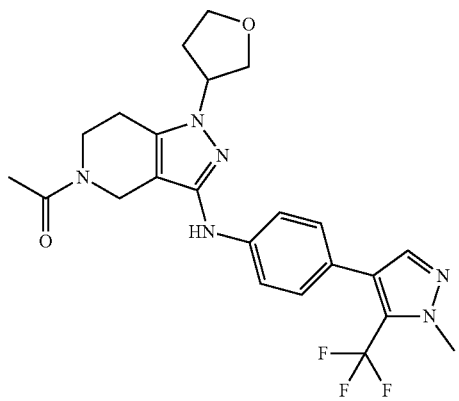 |
| 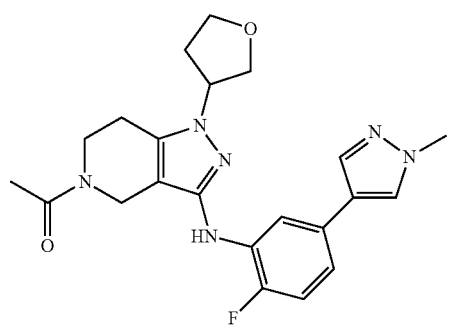 [SMILES: CC(=O)N1CCc2c(c(Nc3cc(-c4cnn(C)c4)ccc3F)nn2C2CCOC2)C1] | 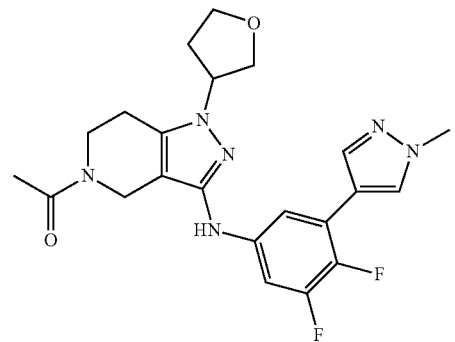 [SMILES: CC(=O)N1CCc2c(c(Nc3cc(F)c(F)c(-c4cnn(C)c4)c3)nn2C2CCOC2)C1] |
| 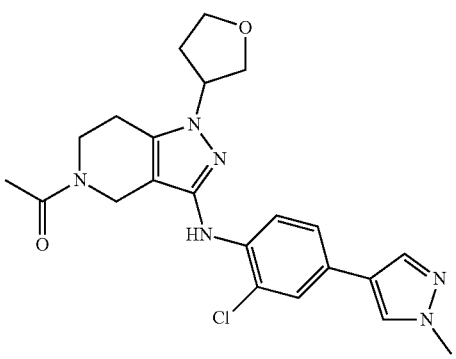 | 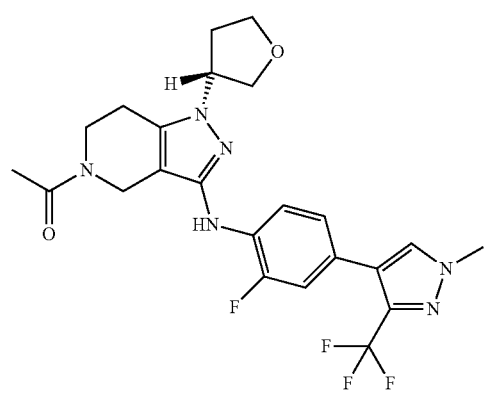 [SMILES: CC(=O)N1CCc2c(c(Nc3ccc(-c4cn(C)nc4C(F)(F)F)cc3F)nn2[C@@H]2CCOC2)C1] |
| 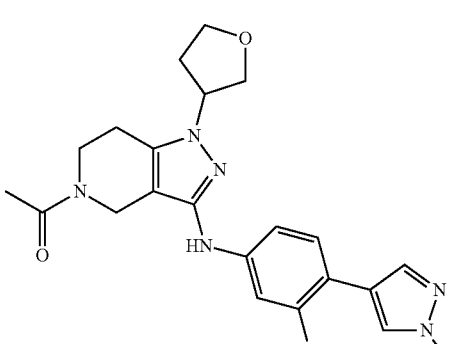 | 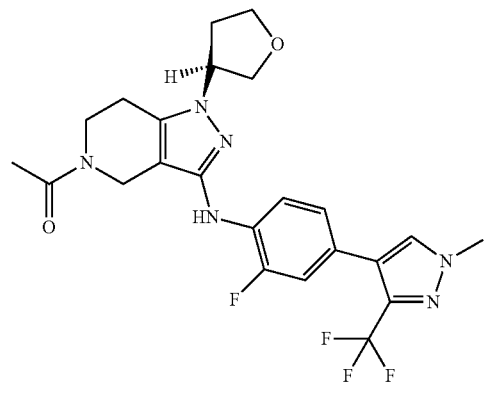 [SMILES: CC(=O)N1CCc2c(c(Nc3ccc(-c4cn(C)nc4C(F)(F)F)cc3F)nn2[C@H]2CCOC2)C1] |

| 1191 | 1192 |
|---|---|
| -continued | -continued |
| 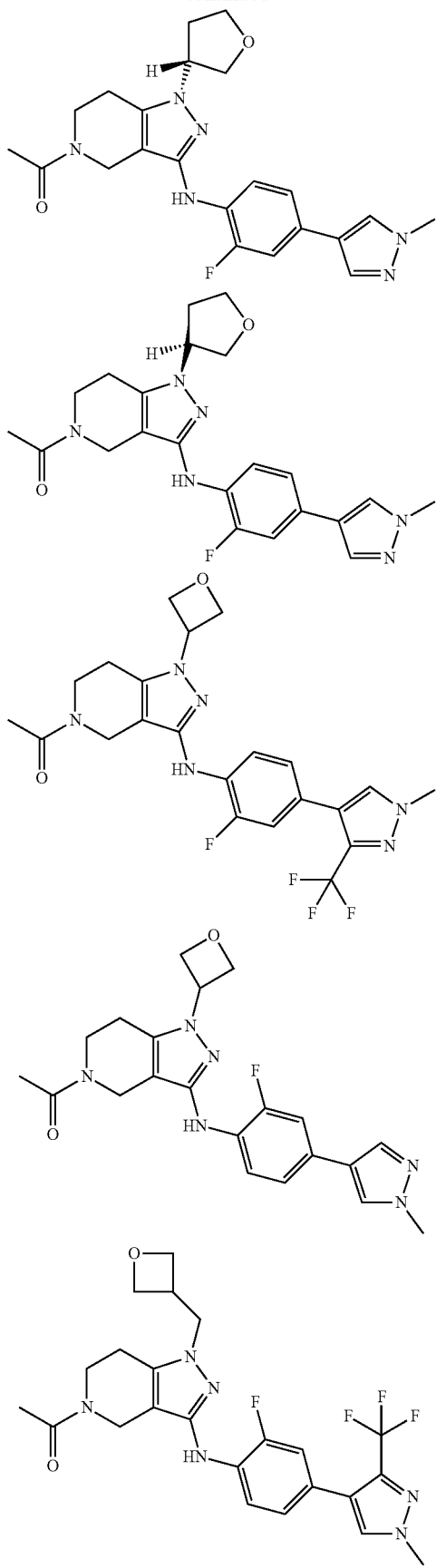 | 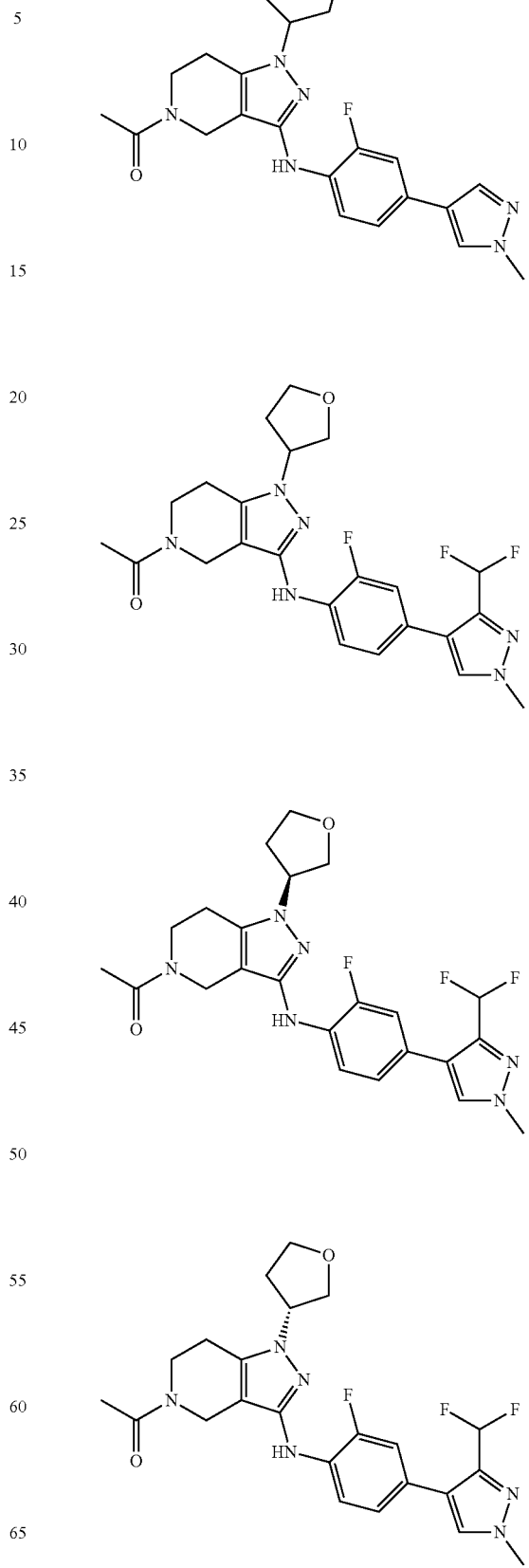 |

-continued

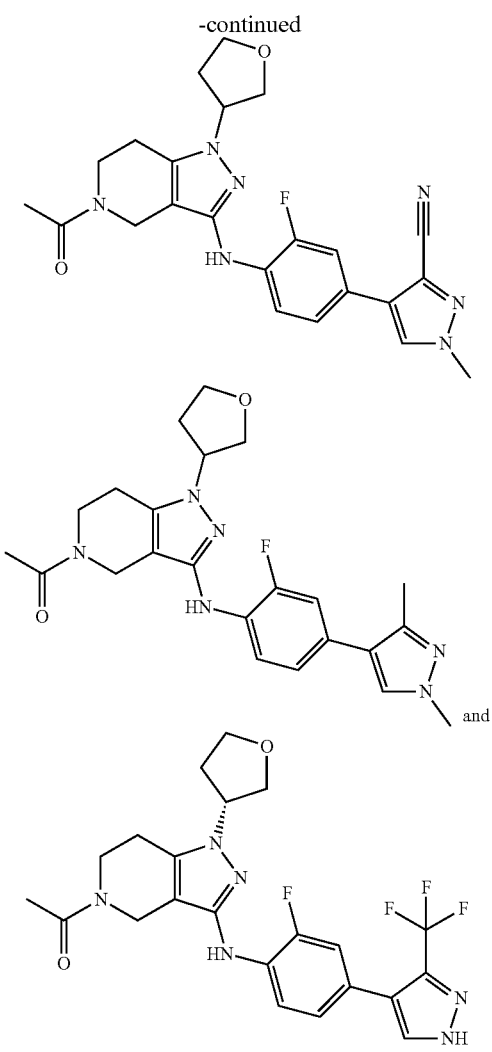

and salts thereof.

16. A composition comprising a compound of formula (I) or formula (II) as described in claim 1 or a pharmaceutically acceptable salt thereof, and a pharmaceutically acceptable adjuvant, carrier, or vehicle.

17. A method for treating a CBP and/or EP300-mediated disorder in an animal comprising administering a compound of formula (I) or formula (II), or a pharmaceutically acceptable salt thereof as described in claim 1, to the animal, wherein the treating does not include preventing the disorder.

18. A method of increasing efficacy of a cancer treatment comprising a cytotoxic agent in an animal comprising administering to the animal an effective amount of a compound of formula (I) or formula (II) or a pharmaceutically acceptable salt thereof as described in claim 1.

19. A method of extending the duration of response to a cancer therapy in an animal, comprising administering to an animal undergoing the cancer therapy a compound of formula (I) or formula (II) or a pharmaceutically acceptable salt thereof, as described in claim 1, wherein the duration of response to the cancer therapy when the compound of formula (I) or formula (II) or the pharmaceutically acceptable salt thereof is administered is extended over the duration of response to the cancer therapy in the absence of the administration of the compound of formula (I) or formula (II) or the pharmaceutically acceptable salt thereof.

20. A method of treating cancer in an individual comprising administering to the individual (a) a compound of formula (I) or formula (II) or a pharmaceutically acceptable salt thereof as described in claim 1, and (b) a cytotoxic agent, wherein the treating does not include preventing the cancer.

* * * * *

UNITED STATES PATENT AND TRADEMARK OFFICE
CERTIFICATE OF CORRECTION

PATENT NO. : 9,763,922 B2
APPLICATION NO. : 14/952821
DATED : September 19, 2017
INVENTOR(S) : Marc Adler et al.

Page 1 of 2

It is certified that error appears in the above-identified patent and that said Letters Patent is hereby corrected as shown below:

In the Claims

Column 959, Line 32, Claim 1, delete "—($C_6$-$C_{20}$ aryl)($C_1$-$C_{20}$ heteroaryl)," and insert -- —($C_6$-$C_{20}$ aryl)-($C_1$-$C_{20}$ heteroaryl), --;

Column 960, Line 30, Claim 1, delete "—O—C(O)—O—$R^c$," and insert -- —O—C(O)—$R^c$, --;

Column 960, Line 43, Claim 1, delete "—C(O)—$R^c$," and insert -- —C(O)—$R^c$, —C(O)—O—$R^c$ --;

Column 963, Line 8, Claim 1, delete "—S—$R^c$," and insert -- —S—$R^c$, —O—C(O)—$R^c$, --;

Column 963, Lines 33-34, Claim 1, delete "—O—$R^d$," and insert -- —O—$R^d$, —S—$R^d$, --;

Column 964, Lines 16-25, Claim 2, delete the following compound:

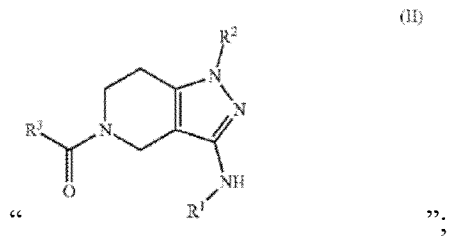

"　　　";

Column 965, Lines 40-41, Claim 2, delete "—N(R)—S(O)$_2$—N($R^c$)$_2$" and insert -- —N($R^c$)—S(O)$_2$—N($R^c$)$_2$ --;

Column 1016, Line 25, Claim 9, delete "methyl sulfonyl" and insert -- methylsulfonyl --;

Column 1106, Lines 64, Claim 11, delete "—N($R^a$)—S(O)$_2$—$R^a$ and" and insert -- —N($R^a$)—S(O)$_2$—$R^a$, —N($R^a$)—S(O)—N($R^a$)$_2$, and --;

Signed and Sealed this
Fourteenth Day of August, 2018

Andrei Iancu
*Director of the United States Patent and Trademark Office*

Column 1107, Line 32, Claim 11, delete "two IV" and insert -- two $R^a$ --;

Column 1107, Line 42, Claim 11, delete "—S(O)$_2$—N(R$^c$)$_2$," and insert -- —S(O)$_2$—N(R$^c$)$_2$, —O—R$^c$, —S—R$^c$, —O—C(O)—R$^c$, --;

Column 1107, Line 53, Claim 11, delete "—S—R$^c$," and insert -- —O—R$^c$, —S—R$^c$, --;

Column 1107, Line 54, Claim 11, delete "—C(O)—R$^c$," and insert -- —C(O)—R$^c$, —C(O)—O—R$^c$, --.